US008859259B2

(12) United States Patent
Rude

(10) Patent No.: US 8,859,259 B2
(45) Date of Patent: Oct. 14, 2014

(54) SURFACTANT AND CLEANING COMPOSITIONS COMPRISING MICROBIALLY PRODUCED BRANCHED FATTY ALCOHOLS

(75) Inventor: Mathew Rude, South San Francisco, CA (US)

(73) Assignee: LS9, Inc., South San Francisco, CA (US)

(*) Notice: Subject to any disclaimer, the term of this patent is extended or adjusted under 35 U.S.C. 154(b) by 181 days.

(21) Appl. No.: 13/026,871

(22) Filed: Feb. 14, 2011

(65) Prior Publication Data

US 2011/0206630 A1 Aug. 25, 2011

Related U.S. Application Data

(60) Provisional application No. 61/304,448, filed on Feb. 14, 2010, provisional application No. 61/324,310, filed on Apr. 15, 2010.

(51) Int. Cl.

| | |
|---|---|
| ***C12N 1/20*** | (2006.01) |
| ***C12N 1/00*** | (2006.01) |
| ***C12P 1/00*** | (2006.01) |
| ***C11D 1/66*** | (2006.01) |
| ***C07C 31/125*** | (2006.01) |
| ***C11D 1/75*** | (2006.01) |
| ***C11D 1/62*** | (2006.01) |
| ***C11D 3/20*** | (2006.01) |
| ***C07C 33/025*** | (2006.01) |
| ***C11D 1/28*** | (2006.01) |
| ***C11D 1/34*** | (2006.01) |
| ***C12P 7/04*** | (2006.01) |
| ***C11D 1/72*** | (2006.01) |
| ***C11D 1/29*** | (2006.01) |

(52) U.S. Cl.

CPC . *C12P 7/04* (2013.01); *C11D 1/662* (2013.01); *C07C 31/125* (2013.01); *C11D 1/75* (2013.01); *C11D 1/62* (2013.01); *C11D 3/202* (2013.01); *C07C 33/025* (2013.01); *C11D 1/28* (2013.01); *C11D 1/345* (2013.01); *C11D 1/72* (2013.01); *C11D 1/29* (2013.01)

USPC ........................... 435/252.3; 435/243; 435/41

(58) Field of Classification Search

None

See application file for complete search history.

(56) References Cited

U.S. PATENT DOCUMENTS

| | | | |
|---|---|---|---|
| 5,233,109 | A | 8/1993 | Chow |
| 5,807,893 | A | 9/1998 | Voelker et al. |
| 7,056,714 | B2 | 6/2006 | Rosazza et al. |
| 7,118,896 | B2 | 10/2006 | Kalscheuer et al. |
| 7,273,966 | B2 | 9/2007 | Voelker et al. |
| 7,425,433 | B2 | 9/2008 | Rosazza et al. |
| 7,491,854 | B2 | 2/2009 | Binder |
| 7,608,700 | B2 | 10/2009 | Klaenhammer et al. |
| 7,968,321 | B1 * | 6/2011 | Green et al. .................. 435/161 |
| 2003/0040474 | A1 | 2/2003 | Kapeller-Libermann et al. |
| 2003/0097686 | A1 | 5/2003 | Knauf et al. |
| 2003/0129601 | A1 | 7/2003 | Cole |
| 2004/0009576 | A1 | 1/2004 | Kalscheuer et al. |
| 2004/0180400 | A1 | 9/2004 | Rosazza et al. |
| 2004/0197896 | A1 | 10/2004 | Cole |
| 2005/0250135 | A1 | 11/2005 | Klaenhammer et al. |
| 2006/0014977 | A1 | 1/2006 | Miller et al. |
| 2007/0251141 | A1 | 11/2007 | Bist et al. |
| 2007/0261138 | A1 | 11/2007 | Graham et al. |
| 2007/0270319 | A1 | 11/2007 | Seggelkow et al. |
| 2007/0281345 | A1 | 12/2007 | Binder |
| 2008/0161595 | A1 | 7/2008 | Huang et al. |
| 2008/0295388 | A1 | 12/2008 | Bazzani et al. |
| 2009/0084025 | A1 | 4/2009 | Bhatia et al. |
| 2010/0071259 | A1 | 3/2010 | Hu et al. |
| 2010/0105955 | A1 | 4/2010 | Alibhai et al. |
| 2010/0105963 | A1 | 4/2010 | Hu |
| 2010/0154293 | A1 | 6/2010 | Hom et al. |
| 2010/0242345 | A1 | 9/2010 | Keasling et al. |
| 2010/0251601 | A1 | 10/2010 | Hu et al. |

FOREIGN PATENT DOCUMENTS

| | | | |
|---|---|---|---|
| DE | 10 2004 052115 | A1 | 4/2006 |
| WO | WO 2007/003736 | A1 | 1/2007 |
| WO | WO 2007/136762 | A2 | 11/2007 |
| WO | WO 2008/119082 | A2 | 10/2008 |
| WO | WO 2009/042950 | A1 | 4/2009 |
| WO | WO 2009/140695 | A1 | 11/2009 |
| WO | WO 2009/140696 | A2 | 11/2009 |
| WO | WO 2010/042664 | A2 | 6/2010 |
| WO | WO 2010/062480 | A2 | 6/2010 |
| WO | WO 2010/075483 | A2 | 7/2010 |
| WO | WO 2011/062987 | A2 | 5/2011 |

OTHER PUBLICATIONS

Alper, et al., "Engineering for biofuels: exploiting innate microbial capacity or importing biosynthetic potential?", *NRM 7*: 715-723 (2009).

Antoni, et al., "Biofuels from microbes", *Appl. Microbiol. Biotechnol.*, 77: 23-35 (2007).

Atsumi et al., "Metabolic engineering for advanced biofuels production from *Escherichia coli", Current Opin.Biotech*, 19:414-419 (2008).

Atsumi et al., "Metabolic engineering of *Escherichia coli* for 1-butanol production", *Metabolic Enginering* 10:305-311 (2008).

Atsumi et al., "Non-fermentative pathways for synthesis of branched-chain higher alcohols as biofuels", *Nature*, 451: 86-89 (2008).

Barnes, Jr. et al., "Studies on the Mechanism of Fatty Acid Synthesis. XIX. Preparation and General Properties of Palmityl Thioesterase", *J. Biol. Chem.*, 243(11):2955-2962 (1968).

(Continued)

*Primary Examiner* — Anne Gussow

*Assistant Examiner* — Channing S Mahatan

(74) *Attorney, Agent, or Firm* — REG Life Sciences LLC

(57) ABSTRACT

The invention provides a surfactant and/or a cleaning composition comprising a microbially produced branched fatty alcohol or a derivative thereof. The invention also provides a household cleaning composition and a personal or pet care cleaning composition comprising a microbially produced branched fatty alcohol or a derivative thereof.

4 Claims, 189 Drawing Sheets

(56) References Cited

OTHER PUBLICATIONS

Birge et al., "Acyl Carrier Protein. XVI.Intermediate Reactions of Unsaturated Fatty Acid Synthesis in Escerichia Coli and Studies of fab B Mutants", *J.Biol.Chem.* 247(16): 4921-4929 (1972).
Black et al., "Cloning, Sequencing, and Expression of the fadD Gene of *Escherichia Coli* Encoding Acyl Coenzyme A Synthetase," *J. Biol. Chem.* 267(35): 25513-25520 (1992).
Black, P., "Primary Sequence of the *Escherichia coli* fadL Gene Encoding an Outer Membrane Protein Required for Long-Chain Fatty Acid Transport", *J. Bacteriololgy* 173(2): 435-442 (1991).
Black et al., "Mutational Analysis of a Fatty Acyl-Coenzyme A Synthetase Signature Motif Identifies Seven Amino Acid Residues That Modulate Fatty Acid Substrate Specificity", *J. Biol. Chem.* 272(8) 4896-4903 (1997).
Blanchard et al., "Overexpression and Kinetic Characterization of the Carboxyltransferase Component of Acetyl-CoA Carboxylase", *J.Biol.Chem.* 273(30): 19140-19145 (1998).
Bunch et al., "The IdhA Gene Encoding the Fermentative Lactate Dehydrogenase of *Escherichia coli," Microbiology*, 143(1): 187-95 (1997).
Cahoon et al., "Modification of the Fatty Acid Composition of *Escherichia coli*by Coexpression of a Plant Acyl-Acyl Carrier Protein Desaturase and Ferredoxin", J.Bacteriology 178(3): 936-936 (1996).
Cahoon et al., "Redesign of soluble fatty acid desaturases from plants for altered substrate specificity and double bond position", *Proc. Natl. Acad. Sci.*94: 4872-4877 (1997).
Cahoon et al., "A Determinant of Substrate Specificity Predicted from the Acyl-Acyl Carrier Protein Desaturase of Developing Cat's Claw Seed", *Plant Physiol* 117: 593-598 (1998).
Campbell et al., "The Enigmatic *Escherichia coli fadE* Gene is *yafH" J. Bacteriol.*, 184(13): 3759-3764 (2002).
Campbell et al., "A New *Escherichia coli* metabolic competency: growth on fatty acids by a novel anaerobic β-oxidation pathway," *Mol. Microbiol.*, 47(3): 793-805 (2003).
Campbell et al., "*Escherichia coli* FadR Positively Regulates Transcription of the fabB Fatty Acid Biosynthetic Gene", *J.Bacteriology* 183(20): 5982-5990 (2001).
Canonaco et al., "Metabolic flux response to phosphoglucose isomerase knock-out in *Escherichia coli* and impact of overexpression of the soluble transhydrogenase UdhA", *FEMS Microbiology Letters* 204: 247-252 (2001).
Carlson et al., "Fundamental *Escherichia coli* Biochemical Pathways for Biomass and Energy Production: Creation of Overall Flux States", *Biotech & Bioengineering* 86(2): 149-162 (2004).
Caviglia et al., "Rat Long Chain Acyl-CoA Synthetase 5, but Not 1,2,3, or 4, Complements *Escherichia coli fadD," J. Biol. Chem.*, 279(12): 11163-11169 (2004).
Chan et al., "Current understanding of fatty acid biosynthesis and the acyl carrier protein", *Biochem. J.* 430: 1-19 (2010).
Cheng et al., "Mammalian Wax Biosynthesis, II. Expression Cloning of Wax Synthase cDNAs Encoding a Member of the Acyltransferase Enzyme Family," *J. Biol. Chem.*, 279(36): 37798-37807 (2004).
Cho et al., "Defective Export of a Periplasmic Enzyme Disrupts Regulation of Fatty Acid Synthesis," *J. Biol. Chem.*, 270: 4216-4219 (1995).
Cho et al., "*Escherichia coli* Thioesterase I, Molecular Cloning and Sequencing of the Structural Gene and Identification as a Periplasmic Enzyme", *J.Biol.Chem* 268(13:5): 9238-9245 (1993).
Cho et al., "Transcriptional regulation of the fad regulon genes of *Escherichia coli* by ArcA", *Microbiology* 152: 2207-2219 (2006).
Coleman et al., "Enzymes of triacylglycerol synthesis and their regulation" *Progress in Lipid Research* 43:134-176.
Cronan et al., "Bacterial Fatty Acid Synthesis and Its Relationships with Polyketide Synthetic Pathways", *Methods Enzymology* 459(17):1-41 (2009).
Davis et al., "Inhibition of *Escherichia coli* Acetyl Coenzyme A Carboxylase by Acyl-Acyl Carrier Protein" *J. of Bacteriology* 183(4): 1499-1503 (2001).
Davis et al., "Overproduction of Acetyl-CoA Carboxylase Activity Increases the Rate of Fatty Acid Biosynthesis in *Escherichia coli" J.Biol.Chem* 275(37:15) 28593-28598 (2000).
Dehesh et al., "KAS IV: A 3-ketoacyl-ACP synthase from *Cuphea* sp. is a medium chain specific condensing enzyme", *The Plant Journal* 15(3):383-390 (1998).
Dehesh et al., "Production of high levels of 8:0 and 10:0 fatty acids in transgenic canola by overexpression of *Ch FatB2*, a thioesterase cDNA from *Cuphea hookeriana" The Plant Journal* 9(2): 167-172 (1996).
Delay et al., "In Vivo Functional Analyses of the Type II Acyl Carrier Proteins of Fatty Acid Biosynthesis", *J.Biol.Chem.* 282: 20319-20328 (2007).
Dellomonaco et al., "Engineered Respiro-Fermentative Metabolism for the Production of Biofuels and Biochemicals from Fatty Acid-Rich Feedstocks", *Applied & Environmental Microbiology* 76(15): 5067-5078 (2010).
Demendoza et al., "Thermal Regulation of Membrane Fluidity in *Escherichia coli*. Effects of Overproduction of P-Ketoacylacyl Carrier Protein Synthase 1", *J.Biol.Chem.* 258(4):2098-2101 (1983).
Denoya et al., "A Second Branched-Chain α-Keto Acid Dehydrogenase Gene Cluster (bkdFGH) from *Streptomyces avermitillis*: Its Relationship to Avermectin Biosynthesis and the Construction of a *bkdF* Mutant Suitable for the Production of Novel Antiparasitic Avermectins," *J. Bacteriol.*, 177(12): 3504-3511 (1995).
Deveaux et al., "Genetic and Biochemical Characterization of a Mutation (*fatA*) That Allows *trans* Unsaturated Fatty Acids to Replace the Essential *cis* Unsaturated Fatty Acids of *Escherichia coli" J.Bacteriology* 171(3):1562-1568 (1989).
Doan et al., "Functional expression of five *Arabidopsis* fatty acyl-CoA reductase genes in *Escherichia coli" J. Plant Physiology* 166:787-796 (2009).
Domergue et al., "Acyl Carriers Used as Substrates by the Desaturases and Elongases Involved in Very Long-chain Polyunsaturated Fatty Acids Biosynthesis Reconstituted in Yeast" *J.Biol.Chem* 278(37):35115-35126 (2003).
Dormann et al., "Specificities of the Acyl-Acyl Carrier Protein (ACP) Thioesterase and Glycerol-3-Phosphate Acyltransferase for Octadecenoyl-ACP Isomers (Identification of a Petroselinoyl-ACP Thioesterase in Umbelliferae)", *Plant Physiol.* 104: 839-844 (1994).
Farewell et al., "Role of the *Escherichia coli* FadR Regulator in Stasis Survival and Growth Phase-Dependent Expression of the *uspA, fad,* and *fab* Genes", *J. of Bacteriology* 178(22): 6443-6450 (1996).
Feddersen et al. "Transcriptional regulation of phospholipid biosynthesis in *Saccharomyces*" Biochem. J., 407: 219-230 (2007).
Fehler et al., "Biosynthesis of Hydrocarbons in *Anabaena variabilis*. Incorporation of [*methyl*-$^{14}$C]- and [*methyl*-$^{2}H_3$]Methionine into 7- and 8-Methylheptadecanes", *Biochemistry*, 9(2): 418-422 (1970).
Feng et al., "A New Member of the *Escherichia coli* fad Regulon: Transcriptional Regulation of *fadM* (*ybaW*)", *J. of Bacteriology* 191(20): 6320-6328 (2009).
Feng et al., "Overlapping Repressor Binding Sites Result in Additive Regulation of *Escherichia coli* FadH by FadR and ArcA" *J. of Bacteriology* 192(17):4289-4299 (2010).
Feng et al., "*Escherichia coli* Unsaturated Fatty Acid Synthesis: Complex Transcription of the fabA Gene and in Vivo Identification of the Essential Reaction Catalyzed by FabB", *J.Biol.Chem.* 284(43): 29526-29535 (2009).
Fischer et al., "Selection and optimization of microbial hosts for biofuels production" *Metabolic Engineering* 1:295-304.
Flaman et al., "Site-directed Mutagenesis of Acyl Carrier Protein (ACP) Reveals Amino Acid Residues Involved in ACP Structure and Acyl-ACP Synthetase Activity", *J.Biol.Chem.* 276(38): 35934-35939 (2001).
Fujita et al., "Regulation of fatty acid metabolism in bacteria", *Mol. Microbiology* 66(4): 829-839 (2007).
Ghisla et al., Acyl-CoA dehydrogenases—A mechanistic overview, *Eur. J. Biochem.* 271: 494-508 (2004).
Hamilton-Kemp et al., "Production of the Long-Chain Alcohols Octanol, Decanol, and Dodecanol by *Escherichia coli", Current Microbiology* 51: 82-86 (2005).

(56) References Cited

OTHER PUBLICATIONS

Han et al., "A Novel Alternate Anaplerotic Pathway to the Glyoxylate Cycle in Streptomycetes," *J. Bacteriol.*, 179(16): 5157-5164 (1997).
Han et al., "Fed-Batch Cultivation of an Oxygen-Dependent Inducible Promoter System, the nar Promoter in *Escherichia coli* with an Inactivated nar Operon", *Biotech. & Bioengineering* 59(4): 400-406 (1998).
Hantke, K., "Ferrous iron transport mutants in *Escherichia coli* K12", *FEMS Microbiology Letters* 44: 53-57 (1987).
Heath et al., "Regulation of Malonyl-CoA Metabolism by Acyl-Acyl Carrier Protein and β-Ketoacyl-Acyl Carrier Protein Synthases in *Escherichia coli", J.Biol.Chem.* 270(26):15531-15538 (1995).
Heath et al., "Regulation of Fatty Acid Elongation and Initiation by Acyl-Acyl Carrier Protein in *Escherichia coli", J.Biol.Chem.* vol. 271(4): 1833-1836 (1996).
Heath et al., "Inhibition of β-Ketoacyl-Acyl Carrier Protein Synthase III (FabH) by Acyl-Acyl Carrier Protein in *Escherichia coli", J.Biol. Chem.* 271(18): 10996-11000 (1996).
Heath et al., "Roles of the FabA and FabZ β-Hydroxyacyl-Acyl Carrier Protein Dehydratases in *Escherichia coli* Fatty Acid Biosynthesis", *J.Biol.Chem.* 271(44): 27795-27801 (1996).
Henry et al., "*Escherichia coli* Transcription Factor That Both Activates Fatty Acid Synthesis and Represses Fatty Acid Degradation", *J. Mol. Bio E.* 222: 843-849 (1991).
Hu et al., Microalgal triacylglycerols as feedstocks for biofuel production: perspectives and advances, *The Plant Journal* 54: 621-639 (2008).
Huber et al., "Branched-Chain Fatty Acids Produced by Mutants of *Streptomyces fradiae*, Putative Precursors of the Lactone Ring of Tylosin", *Antimicrob.Agents.Chemother.* 34(8):1535-1541 (1990).
Huber et al., "Synthesis of Transportation Fuels from Biomass: Chemistry, Catalysts, and Engineering", *Chem.Rev.* 106: 1-55 (2006).
Hunt et al., "Characterization of an Acyl-CoA Thioesterase That Functions as a Major Regulator of Peroxisomal Lipid Metabolism" *J.Biol.Chem.* 277(2):1128-1138 (2002).
Inui, et al. "Fatty acid synthesis in mitochondria of *Euglena gracilis" Eur. J. Biochem.* 142(1): 121-126 (1984).
Jarobe, et al., "Development of ethanologenic Bacteria", Adv. Biochem.Engin./Biotechnol. 108: 237-261 (2007).
Jayakumar et al., "Cloning and expression of the multifunctional human fatty acid synthase and its subdomains in *Escherichia coli",PNAS* 93: 14509-14514 (1996).
Jiang, et al., "Inhibition of Fatty Acid Synthesis in *Escherichia coli* in the Absence of Phospholipid Synthesis and Release of Inhibition by Thioesterase Action" *J. Bacteriology* 176(10): 2814-2821 (1994).
Juttner et al., "The Reducing Capacities of *Cyanobacteria* for Aldehydes and Ketones," *Appl. Microbiol. and Biotechnol.*, 25:52-54 (1986).
Juttner et al. "Environmental Factors Affecting the Formation of Mesityloxide Dimethylallyic Alcohol and Other Volatile Compounds Excreted by *Anabaena cylindrica," J. Gen. Microbiol.*, 129: 407-412 (1983).
Kalscheuer et al., "Microdiesel: *Escherichia coli* engineered for fuel production", *Microbiol.* 152(9): 2529-2536 (2006).
Kalscheuer et al., "Neutral Lipid Biosynthesis in Engineered *Escherichia coli*: Jojoba Oil-Like Wax Esters and Fatty Acid Butyl Esters", *Appl.Environ.Microbiol.* 72(2): 1373-1379 (2006).
Kalscheuer et al., "A Novel Bifunctional Wax Ester Synthase/Acyl-CoA:Diacylglycerol Acyltransferase Mediates Wax Ester & Triacylglycerol Biosynthesis in *Acinetobacter calcoaceticus* ADP1," *J. Biol. Chem.*, 278(10): 8075-8082 (2003).
Kameda et al., "Further purification, characterization and salt activation of acyl-CoA synthetase from *Escherichia coli", Biochimica et Biophysica Acta* 840: 29-36(1985).
Keasling et al., "Metabolic engineering delivers next-generation biofuels", *Nature Biotechology* 26(3):298-299 (2008).
Knoll et al., "Biochemical Studies of Three *Saccharomyces Cerevisiae* Acyl-CoA Synthetases, Faalp, Faa2p, and Faa3p," *J. Biol. Chem.*, 269(23): 16348-16356 (1994).
Knothe, G., "Dependence of Biodiesel Fuel Properties on the Structure of Fatty Acid Alkyl Esters," *Fuel Process. Technol.*, 86: 1059-1070 (2005).
Knothe et al., "Kinematic viscosity of biodiesel fuel components and related compounds. Influence of compound structure and comparison to petrodiesel fuel components", *Fuel* 84:1059-1065 (2005).
Knudsen et al,. "Transacylation as a chain-termination mechanism in fatty acid synthesis by mammalian fatty acid synthetase. Synthesis of medium-chain-length ($C_8$—$C_{12}$) acyl-CoA esters by goat mammary-gland fatty acid synthetase", *Biochem. J.* 202: 139-143 (1982).
Koffas, M.A.G., "Expanding the repertoire of biofuel alternatives through metabolic pathway evolution", *PNAS* 106(4): 965-966 (2009).
Kumari et al., "Regulation of Acetyl Coenzyme A Synthetase in *Escherichia coli", J. Bacteriology* 182(15): 4173-4179 (2000).
Lang et al., "Preparation and characterization of bio-diesels from various bio-oils", *Bioresource Tech.* 80: 53-62 (2001).
Lee et al., "Enhanced preference for π-bond containing substrates is correlated to Pro110 in the substrate-binding tunnel of *Escherichia coli* thioesterase I/protease I/lysophospholipase $L_1$" *Biochim. et Biophys. Acta*, 1774: 959-967 (2007).
Lee et al., "Metabolic engineering of microorganisms for biofuels production: from bugs to synthetic biology to fuels", *Current Opinion in Biotechnology* 19: 556-563 (2008).
Lennen et al., "A Process for Microbial Hydrocarbon Synthesis: Overproduction of Fatty Acids in *Escherichia coli* and Catalytic Conversion to Alkane", *Biotech.Bioengineering* 106(2):193-202 (2010).
Li et al., "The Gene Encoding the Biotin Carboxylase Subunit of *Escherichia coli* Acetyl-CoA carboxylase", *J.Biol.Chem.* 267(2): 855-863 (1992).
Li et al., "Alteration of the Fatty Acid Profile of *Streptomyces coelicolor* by Replacement of the Initiation Enzyme 3-Ketoacyl Acyl Carrier Protein Synthase III (FabH)," *J. Bacteriol.*, 187(11): 3795-3799 (2005).
Li et al., "Growth Rate Regulation of *Escherichia coli* Acetyl Coenzyme A Carboxylase, Which Catalyzes the First Committed Step of Lipid Biosynthesis", *J. of Bacteriology* 175(2): 332-340 (1993).
Li et al., "Purification, Characterization, and Properties of an Aryl Aldehyde Oxidoreductase from *Nocardia* Sp. Strain NRRL 5646," *J. Bacteriol.*, 179(11): 3482-3487 (1997).
Link et al., "Methods for Generating Precise Deletions and Insertions in the Genome of Wild-Type *Escherichia coli*: Application to Open Reading Frame Characterization", *J.Bacteriology* 179(20): 6228-6237 (1997).
Lu et al., "Overproduction of free fatty acids in *E. Coli*: Implications for biodiesel production", *Metabolic Engineering* 10: 333-339 (2008).
Lykidis et al., "Genomic Prospecting for Microbial Biodiesel Production," LBLN-301E, No. 10: 1-39 (2008).
Mackey et al., "Detection of Rhythmic Bioluminescense from Luciferase Reporters in Cyanobacteria," *Meth. Mol.Biol.* 362: 115-129 (2007).
Magnuson et al., "Regulation of Fatty Acid Biosynthesis in *Escherichia coli" Microbiol.Reviews* 57(3): 522-542 (1993).
Marr, et al., "Effect of Temperature on the Composition of Fatty Acids in *Escherichia Coli", J.Bacteriology* 84: 1260-1267 (1962).
Massengo-Tiasse et al., "*Vibrio cholerae* FabV Defines a New Class of Enoyl-Acyl Carrier Protein Reductase", *J.Biol.Chem.* 283(3): 1308-1316 (2008).
Mayer et al., "Identification of amino acid residues involved in substrate specificity of plant acyl-ACP thioesterases using a bioinformatics-guided approach" *BMC Plant Biology* 7(1) (2007).
Metz et al., "Purification of a Jojoba Embryo Fatty Acyl-Coenzyme A Reductase and Expression of Its cDNA in High Erucic Acid Rapeseed", *Plant Physiol.* 122: 635-644 (2000).
Metzgar et al., "*Acinetobacter sp.* ADP1: an ideal model organism for genetic analysis and genome engineering", *Nucleic Acid Res.* 32(19):5780-5790 (2004).
Mohan et al., "An *Escherichia coli* Gene (*FabZ*) Encoding (3*R*)-Hydroxymyristoyl Acyl Carrier Protein Dehydrase. Relation to fubA and Suppression of Mutations in Lipid A Biosynthesis", *J.Biol.Chem* 269(52): 32896-32903 (1994).

(56) References Cited

OTHER PUBLICATIONS

Morgan-Kiss et al, "*The Escherichia coli fadK* (*ydiD*) Gene Encodes an Anerobically Regulated Short Chain Acyl-CoA Synthetase," *J. Biol. Chem.*, 279(36): 37324-37333 (2004).

Morgan-Kiss et al., "The *Lactococcus lactis* FabF Fatty Acid Synthetic Enzyme can Functionally Replace both the FabB and FabF Proteins of *Escherichia coli* and the FabH Protein of *Lactococcus lactis*," Arch. Microbiol. 190: 427-437 (2008).

Muthusamy et al., "Biosurfactants: Properties, commercial production and application", *Current Science* 94(6): 736-747 (2008).

Naccarato et al., "In Vivo and In Vitro Biosynthesis of Free Fatty Alcohols in *Escherichia coli* K-12," *Lipids*, 9(6): 419-428 (1973).

Nagao et al., "Microbial Conversion of Vegetable Oil to Rare Unsaturated Fatty Acids and Fatty Alcohols by an *Aeromonas hydrophila* Isolate", *J.Amer.Oil Chem.Soc.* 86(12): 1189-1197 (2009).

NCBI Reference Sequence YP_889972.1, Putative Long-Chain Fatty-Acid-CoA Ligase [*Mycobacterium smegmatis* Str. MC2 155](2006).

Nunn et al., "Transport of long-chain fatty acids by *Escherichia coli*: Mapping and characterization of mutants in the *fadL* gene" *PNAS* 75(7): 3377-3381 (1978).

Nunn et al., "Role for fadR in Unsaturated Fatty Acid Biosynthesis in *Escherichia coli"*, *J.Bacteriol.* 154(2):554-560 (1983).

Palaniappan et al., Enhancement and Selective Production of Phoslactomycin B, a Protein Phosphatase IIa Inhibitor, though Identification and Engineering of the Corresponding Biosynthetic Gene Cluster, *J. Biol. Chem.* 278(37): 35552-35557 (2003).

Partial ISR from the International Search Authority of the European Patent Office, for PCT/US2009/058788, mailed May 11, 2009 4 pages.

Peng et al., "Effect of *fadR* gene knockout on the metabolism of *Escherichia coli* based on analyses of protein expressions, enzyme activities and intracellular metabolite concentrations" *Enzyme and Microbial Tech.* 38: 512-520 (2006).

Perez et al., "*Escherichia coli* YqhD Exhibits Aldehyde Reductase Activity and Protects from the Harmful Effect of Lipid Peroxidation-derived Aldehydes" *J.Biol.Chem.* 283(12): 7346-7353 (2008).

Phung et al., "Genes for Fatty Acid Biosynthesis in the *Cyanobacterium synechococcus* sp. Strain PCC 7942," Abstracts of the General Meeting of the American Society of Microbiology, 524 (1995).

Pillai et al., "Functional characterization of β-ketoacyl-ACP reductase (FabG) from *Plasmodium falciparum" Biochem and Biophysical Research Comm.* 303: 387-392 (2003).

Qiu et al., "Crystal structure and substrate specificity of the β-ketoacyl-acyl carrier protein synthase III (FabH) from *Staphylococcus aureus", Protein Science* 14: 2087-2094 (2005).

Qiu, Yuan-Zheng et al., "Metabolic Engineering of *Aeromonas hydrophila* for the Enhanced Production of poly(3-hydroxybutyrate-co-3-hydroxyhexanoate),"*Appl. Microbiol. Biotechnol.*, 69: 537-532 (2006).

Rafi et al., "Structure of Acyl Carrier Protein Bound to Fabl, the FASII Enoyl Reductase from *Escherichia Coli" J.Biol.Chem.* 281(51): 39285-39293 (2006).

Rawlings et al., "Biosynthesis of fatty acids and related metabolites", *Natural Product Reports* 15: 275-308 (1998).

Ray et al., "Activation of long chain fatty acids with acyl carrier protein: Demonstration of a new enzyme, acyl-acyl carrier protein synthetase, in *Escherichia coli" PNAS* 73(12):4374-4378 (1976).

Rehm et al., "Heterologous expression of the acyl—acyl carrier protein thioesterase gene from the plant *Umbellularia californica* mediates polyhydroxyalkanoate biosynthesis in recombinant *Escherichia coli", Applied Microbiology and Biotechnology* 55: 205-209 (2001).

Reiser et al., "Isolation of Mutants of *Acinetobacter calcoaceticus* Deficient in Wax Ester Synthesis of Complementation of One Mutation with a Gene Encoding a Fatty Acyl Coenzyme A Reductase", *J. Bacteriol.*, 179(9): 2969-2975 (1997).

Ren et al., "FabG, an NADPH-Dependent 3-Ketoacyl Reductase of *Pseudomonas aeruginosa*, Provides Precursors for Medium-Chain-Length Poly-3-Hydroxyalkanoate Biosynthesis in *Escherichia coli", J. Bacteriol.*182(10):2978-2981 (2000).

Rock et al., "Acyl-Acyl Carrier Protein Synthetase from *Escherichia co/i" Meth.Enzymol.* 71: 163-168 (1981).

Rock et al., "Increased Unsaturated Fatty Acid Production Associated with a Surpressor of the *fabA6*(Ts) Mutation in *Escherichia coli*," J. Bacteriol., 178(18): 5382-5387 (1996).

Rude et al., "Terminal Olefin (1-Alkene) Biosynthesis by a Novel P450 Fatty Acid Decarboxylase from *Jeotgalicoccus* Species", *Appl. Environ.Microbiol.* 77(5): 1718-1727 (2011).

Rude et al., "New microbial fuels: a biotech perspective", *Current Opinion in Microbiology* 12: 274-281 (2009).

Sabirova et al., "Mutation in a "*tesB*-Like" Hydroxyacyl-Coenzyme A-Specific Thioesterase Gene Causes Hyperproduction of Extracellular Polyhydroxyalkanoates by *Alcanivorax borkumensis* SK2", *J. Bacteriology* 188(23): 8452-8459 (2006).

Saito et al., "Crystal structure of enoyl—acyl carrier protein reductase (FabK) from *Streptococcus pneumoniae* reveals the binding mode of an inhibitor", *Protein Science* 17: 691-699 ((2008).

Salas et al., "Characterization of substrate specificity of plant FatA and FatB acyl-ACP thioesterases", *Archives of Biochem. and Biophysics* 403: 25-34 (2002).

Sanchez et al., "Effect of Overexpression of a Soluble Pyridine Nucleotide Transhydrogenase (UdhA) on the Production of Poly(3-hydroxybutyrate) in *Escherichia coli", Biotechnol.Prog.* 22: 420-425 (2006).

Schirmer et al., "Microbial Biosynthesis of Alkanes", *Science* 329:559-562 (2010).

Seguel et al., "Tracing Sewage in the Marine Environment: altered signatures in Concepcion Bay, Chile", *Water Research* 35(17): 4166-4174 (2001).

Spencer et al., "Thioesterases I and II of *Escherichia coli.* Hydrolysis of Native Acyl-Acyl Carrier Protein Thioesters," *J. Biol.Chem.*, 253(17): 5922-5926 (1978).

Stöveken et al., "The Wax Ester Synthase/Acyl Coenzyme A:Diacylglycerol Acyltransferase from *Acinetobacter* sp. Strain ADP1: Characterization of a Novel Type of Acyltransferase", *J.Bacteriology* 187(4):1369-1376 (2005).

Subrahmanyam et al., "Overproduction of a Functional Fatty Acid Biosynthetic Enzyme Blocks Fatty Acid Synthesis in *Escherichia coli" J.Bacteriology* 180(17):4596-4602 (1998).

Sulzenbacher et al., "Crystal Structure of *E. coli* Alcohol Dehydrogenase YqhD: Evidence of a Covalently Modified NADP Coenzyme" *J.Mol.Biol.* 342: 489-502 (2004).

Thomason et al., "Identification of the *Escherichia coli* K-12 ybhE Gene as pgl, Encoding 6-Phosphogluconolactonase" *J.Bacteriology* 186(24): 8248-8253 (2004).

Thorpe et al., "Structure and mechanism of action of the Acyl-CoA dehydrogenases1", *FASEB J.* 9: 718-725 (1995).

Tong et al., "Acetyl-Coenzyme A Carboxylases: Versatile Targets for Drug Discovery", *J.Cellular Biochem.* 99: 1476-1488 (2006).

Toomey et al., "Studies on the Mechanism of Fatty Acid Synthesis XVI. Preparation and General Properties of Acyl-Malonyl Acyl Carrier Proteincondensing Enzyme From *Escherichia Coli", J.Biol. Chem.* 241(5):1159-1165 (1996).

Tsay et al., "Isolation and Characterization of the β-Ketoacyl-acyl Carrier Protein Synthase I11 Gene (*fabH*) from *Escherichia coli* K-12", *J.Biol.Chem.* 267(10): 6807-6814 (1992).

UniProt accession No. Q325A2 "Subname: Full=Acyl-CoA thioesterase I" (2005), 1 page.

UniProt accession No. Q54764; XP002545841 "Subname: Full=Putative Uncharacterized Protein" (1996), 1 page.

UniProt accession No. Q54765; XP002564231 "Subname: Full=Putative Uncharacterized Protein SEC0028" (1996), 1 page.

Vadali et al., "Cofactor engineering of intracellular CoA/acetyl-CoA and its effect on metabolic flux redistribution in *Escherichia coli" Metabolic Engineering* 6: 133-139 (2004).

Van Den Berg et al., "The FadL family: unusual transporters for unusual substrates", *Curr.Opin.Struct.Biol.* 15: 401-407 (2005).

Vanderhoeven et al., "Biosynthesis and Elongation of Short- and Medium-Chain-Length Fatty Acids", Plant Physiology 122: 275-282 (2000).

(56) References Cited

OTHER PUBLICATIONS

Voelker et al. "Alteration of the Specificity and Regulation of Fatty Acid Synthesis of *Escherichia coli* by Expression of a Plant Medium-Chain Acyl-Acyl Carrier Protein Thioesterase," *J. Bacteriol.*, 176(23): 7320-7327 (1994).
Yomano et al.,Re-Engineering *Escherichia coli* for Ethanol Production, *Biotechnol. Lett.*, 30: 2097-2103 (2008).
Yoo et al., "Determination of the native form of FadD, the *Escherichia coli* fatty acyl-CoA synthetase, and characterization of limited proteolysis by outer membrane protease OmpT", *Biochem. J.* 360: 699-706 (2001)).
Zhang, et al. "The FabR (YijC) Transcription Factor Regulates Unsaturated Fatty Acid Biosynthesis in *Escherichia coli," J. Biol. Chem.*, 277(18): 15558-15565 (2002).
Zhang et al., "Inhibiting Bacterial Fatty Acid Synthesis", *J.Biol. Chem.* 281(26): 17541-17544 (2006).
Zhang et al., "Structural Basis for Catalytic and Inhibitory Mechanisms of β-Hydroxyacyl-acyl Carrier Protein Dehydratase (FabZ)", *J.Biol.Chem.* 283(9):5370-5379 (2008).
Zhang, et al. "Molecular effect of FadD on the regulation and metabolism of fatty acid in *Escherichia coli," FEMS Microbiol. Lett.*, 259(2): 249-253 (2006).
Zhang, et al., "Expanding metabolism for biosynthesis of nonnatural alcohols", *PNAS* 105(52): 20653-20658 (2008).
Zheng et al., "Evaluation of Different Biomass Materials as Feedstock for Fermentable Sugar Production", Appl.Biochem.Biotech. 137-140: 423-436 (2007).
Zhu et al., "Functions of the *Clostridium acetobutylicium* FabF and FabZ proteins in unsaturated fatty acid biosynthesis", *BMC Microbiology* 9:119 (2009).
Zimhony et al., "Characterization of *Mycobacterium smegmatis* Expressing the *Mycobacterium tuberculosis* Fatty Acid Synthase I (*fas1*) Gene", *J.Bacteriology* 186(13): 4051-4055 (2004).
ISR and WO from PCT/US2007/011923, mailed Feb. 22, 2008, 23 pages.
ISR and WO from PCT/US2008/058788, mailed Jan. 27, 2009, 26 pages.
ISR and WO from PCT/US2008/057127, mailed Jan. 27, 2009, 13 pages.
ISR and WO from PCT/US2009/059903, mailed Jun. 2, 2010, 14 pages.
ISR and WO from PCT/US09/069356, mailed Jul. 29, 2010, 16 pages.
ISR and WO from PCT/US2009/044409, mailed Jan. 29, 2010, 10 pages.
ISR and WO from PCT/US2010/050026, mailed Jan. 6, 2011, 9 pages.
Choi et al., "β-Ketoacyl-acyl Carrier Protein Synthase III (FabH) Is a Determining Factor in Branched-Chain Fatty Acid Biosynthesis" *J. of Bacteriology* 182(2): 365-370 (2000).
Conway et al., "Cloning and Sequencing of the Alcohol Dehydrogenase II Gene from Zymomonas mobilis" J. of Bacteriology 169(6): 2591-2597 (1987).
Database EMBL (online): "Synechococcus, PCC7942 Ribosomal Protein S1 of 30S Ribosome (rpls): ORF271, ORF231, ORF341, Carboxyltransferase alpha subunit (accA) ORF245, ORF227, and GTP cyclohydrolase I (folE) genes, complete cds, and ORF205 gene, partial cds," XP002564232 (1996).
Fleischman et al., Accession No. ABK71854, YP_889972.1/ Gl:4535433 (2006).
He et al., "*Nocardia* sp. Carboxylic Acid Reductase: Cloning, Expression and Characterization of a New Aldehyde Oxidoreductase Family," Appl. and Environ. Microbiol., 70(3): 1874-1881 (2004).
Leonard et al., "A *Cuphea* β-ketoacyl-ACP synthase shifts the synthesis of fatty acids towards shorter chains in *Arabidopsis* seeds expressing *Cuphea* FatB thioesterases", *Plant Journal* 13(5): 621-628 (1998).
Li et al., "The carboxylic acid reduction pathway in *Nocardia*. Purification and characterization of the aldehyde reductase", J. of Industrial Microbiology & Biotechnology 25: 328-332 (2000).
Marrakchi et al.,"Mechanistic Diversity and Regulation of Type II Fatty Acid Synthesis," Biochem. Soc. Trans.30(6): 1050-1055 (2002).
NCBI Reference Sequence Gl:49532534, Putative Alcohol Dehydrogenase [*Acinetobacter* sp. ADP1] (2004).

* cited by examiner

FIG. 2A

BKD E1 alpha subunit homologs

*Bacillus subtilis 168:* ZP_03592172

```
  1 mstnrhqalg ltdqeavdmy rtmllarkid ermwllnrsg kipfviscqg qeaaqvgaaf
 61 aldremdyvl pyyrdmgvvl afgmtakdlm msgfakaadp nsggrqmpgh fgqkknrivt
121 gsspvttqvp havgialagr mekkdiaafv tfgegssnqg dfheganfaa vhklpvifmc
181 ennkyaisvp ydkqvaceni sdraigygmp gvtvngndpl evyqavkear erarrgegpt
241 lietisyrlt phssddddss yrgreeveea kksdplltyq aylketglls deieqtmlde
301 imaivneatd eaenapyaap esaldyvyak (SEQ ID NO:1)
```

```
  1 ctacttcgca taaacataat caagcgctga ctcaggagct gcatatgggg cgttctccgc
 61 ttcatccgtc gcttcattta cgattgccat aatttcatcc agcatggttt gttctatctc
121 atcggacagc aggcctgttt cctttaagta agcttgataa gtaagcaggg gatcactttt
181 tttcgcttcc tctacttctt cacggcctct gtagctgctg tcatcgtcat cactggaatg
241 tggtgtaagg cggtaagaaa tcgtttcaat taatgtcggg ccttctcctc tgcgtgccct
301 ttcgcgtgct tctttaaccg cttgataaac ttccagcgga tcatttccat tcacagttac
361 gccaggcatc ccatagccta tggcacggtc ggaaatgttc tcacatgcga cttgcttatc
421 gtaaggcact gagattgcgt atttgttgtt ttcacacatg aaaataaccg gcagcttatg
481 gacagcggca aagtttgccc cttcatggaa atcgccttgg tttgaagacc cttccccgaa
541 tgtaacaaag gctgcgatat ccttttttctc catacgtccc gcaagcgcaa taccgactgc
601 gtgcggcact tgcgttgtaa ccggagatga tcccgtcaca atgcggtttt tcttttgtcc
661 gaaatgtccc ggcatctggc ggcctcctga gttcggatct gctgcttttg caaacccgga
721 catcattaag tcctttgctg tcatgccaaa cgcgagcacg acacccatgt ctctgtagta
781 cggcaataca taatccattt cacggtcaag tgcgaaagcc gctcctacct gtgctgcttc
841 ctgtccttga caagagatta caaatggaat tttgccagaa cggtttaaca gccacattct
901 ttcatcgatt tttcttgcta acagcatggt tctatacata tcaacggctt cctgatcagt
961 cagccctagt gcttgatgtc ggtttgtact cat (SEQ ID NO:2)
```

*Streptomyces avermitilis MA-4860:* NP_825553

```
  1 mtvestaark prrsagtksa aakrtspgak kspsttgaeh eliqlltpdg rrvknpeyda
 61 yvaditpeel rglyrdmvls rrfdaeatsl qrqgelglwa smlgqeaaqi gsgratrddd
121 yvfptyrehg vawcrgvdpt nllgmfrgvn nggwdpnsnn fhlytivigs qtlhatgyam
181 giakdgadsa viayfgdgas sqgdvaesft fsavynapvv ffcqnnqwai septekqtrv
241 plyqraqgyg fpgvrvdgnd vlaclavtkw alerarrgeg ptlveaftyr mgahttsddp
301 tkyradeere aweakdpilr lrtyleasnh adegffaele vesealgrrv revvrampdp
361 dhfaifenvy adghalvdee raqfaayqas fttepdggsa agqggn (SEQ ID NO:3)
```

```
  1 gtgaccgtgg agagcactgc cgcgcgaaag ccgcgacgca gcgccggtac gaagagcgcc
 61 gcagccaagc gcaccagccc cggcgccaag aagtcaccga gcacgaccgg cgccgagcac
121 gagctgattc agctgctcac gcccgacggc cggcgggtga agaaccccga gtacgacgcg
181 tacgtcgcgg acatcacccc cgaagagctg cgcggtctgt accgggacat ggtgctgagc
241 cgccgcttcg acgcagaggc cacctccctg caacgccagg gcgagctggg cctgtgggcc
301 tcgatgctcg ggcaggaggc cgcccagatc ggctcgggcc gggccacccg tgacgacgac
361 tacgtcttcc cgacctaccg cgagcacggc gtcgcctggt gccgcggggt cgaccccacc
421 aacctgctcg gcatgttccg cggcgtgaac aacggcggct gggatcccaa cagcaacaac
481 ttccacctct acacgatcgt catcggctcg cagacgctgc acgccaccgg ctacgccatg
```

FIG. 2A cont'd 541 ggtatcgcca aggacggcgc cgactcggcc gtgatcgcgt acttcggtga cggcgcctcc
601 agccagggtg acgtcgccga atcgttcacc ttctccgcgg tctacaacgc ccctgtcgtc
661 ttcttctgcc agaacaacca gtgggcgatc tccgagccca ccgagaagca gacccgcgtc
721 ccgctctacc agcgcgcgca gggctacggc ttcccgggcg tccgcgtcga cggcaacgac
781 gtactggcct gcctcgccgt caccaagtgg gccctcgagc gggcccgccg gggcgagggg
841 cccacgttgg tcgaggcgtt cacgtaccgc atgggcgcgc acaccacctc cgacgacccg
901 accaagtacc gggccgacga ggagcgcgag gcgtgggagg cgaaggaccc gatcctgcgt
961 ctgcgcacgt atctcgaggc ctcaaaccac gcggacgagg gattcttcgc ggaactcgag
1021 gtggagagcg aggcgttggg aaggcgagtg cgcgaagtgg tgcgtgccat gccggacccg
1081 gaccacttcg ccatcttcga gaacgtgtac gcggacgggc atgcgctcgt cgacgaggag
1141 cgggcgcagt tcgccgccta ccaggcgtcg ttcacgacgg agcctgacgg cggctccgcc
1201 gcgggacagg ggggtaactg a (SEQ ID NO:4)

*Pseudomonas putida F1:* YP_001266795

1 mneyaplrlh vpeptgrpgc qtdfsylrln dagqarkpai dvdaadtadl syslvrvlde
61 qgdaqgpwae didpqilrqg mramlktrif dsrmvvaqrq kkmsfymqsl geeaigsgqa
121 lalnrtdmcf ptyrqqsilm ardvslvemi cqllsnerdp lkgrqlpimy svreagffti
181 sgnlatqfvq avgwamasai kgdtkiasaw igdgataesd fhtaltfahv yrapvilnvv
241 nnqwaistfq aiaggesttf agrgvgcgia slrvdgndfv avyaasrwaa erarrglgps
301 liewvtyrag phstsddpsk yrpaddwshf plgdpiarlk qhlikighws eeehqavtae
361 leaaviaaqk eaeqygtlan ghipsaasmf edvykempeh lrrqrqelgv (SEQ ID
NO:5)

1 tcaaaccccc agttcctggc gttgacggcg caggtgttcg ggcatctcct tgtacacatc
61 ctcgaacatc gaggcggcgc tcgggatgtg cccgttagcc agggtgccgt actgctcggc
121 ttctttctgt gcggcaatca ccgcagcttc gagctcggcc gtgacggctt ggtgttcttc
181 ttcggaccag tggccgatct tgatcaggtg ctgcttcagg cgggcgatcg ggtcacccag
241 cgggaagtgg ctccagtcat cggcagggcg gtacttggag gggtcgtccg acgtcgagtg
301 cgggccggca cggtaggtga cccactcgat caggcttggg cccaggccgc ggcgggcgcg
361 ctcggcagcc cagcgcgagg cggcgtacac ggcgacgaag tcgttgccgt caacccgcag
421 cgaggcaatg ccgcagccca cgccacggcc ggcgaaggtg gtcgactcgc caccggcgat
481 ggcctggaag gtagaaatcg cccactggtt gttgaccaca ttgaggatca ccggggcgcg
541 gtaaacgtgg gcaaaggtga gggcggtgtg gaagtccgac tcggcggtgg ctccgtcacc
601 gatccacgcc gaagcaatct tggtatcgcc cttgatcgcc gaggccatgg cccagccgac
661 tgcctgcacg aactgggtcg ccaggttgcc gctgatggtg aagaagccgg cttcgcgcac
721 cgagtacatg atcggcaact ggcggccctt gagggggtcg cgctcgttgg acagcagttg
781 gcagatcatc tcgaccagcg atacgtcgcg ggccatcagg atgctttgct ggcggtaggt
841 cgggaagcac atgtcggtgc ggttcagcgc cagcgcctgg ccactgccga tggcttcttc
901 gcccaggctt tgcatgtaga aggacatctt cttctggcgc tgggcaacca ccatgcggct
961 gtcgaagatc cgcgtcttga gcatggcgcg catgccttga cgaaggatct gtgggtcgat
1021 gtcttcggcc caggggcctt gcgcatcacc ttgctcgtcg agcacgcgga ccaggctgta
1081 ggacaggtcg gcagtgtcgg cagcatcgac atcgatcgcg ggtttacggg cttgacctgc
1141 atcgttgagg cgcaggtagg aaaaatcggt ctggcagcct ggccggccgg tgggctcggg
1201 cacatgcaaa cgcagggggg cgtactcgtt cat (SEQ ID NO:6)

*Listeria monocytogenes 08-5578:* YP_003413622

1 mtlkeaglte dklikmyetm lmarrlderm wllnrsgkip ftisgqgqet aqigaafafd
61 ldkdyalpyy rdlavvlafg mtakdimlsa fakaedpnsg grqmpahfgq ksnrivtqss
121 pvttqfphaa giglaakmag deiaiyastg egssnqgdfh eginfasvhk lpvvfvihnn

FIG. 2A cont'd

```
181 qyaisvpask qyaaeklsdr aigygipger vdgtnmgevy aafkraadra rngegptlie
241 tvsyrftphs sddddssyrs reevneakgk dpltifqtel leegylteek iaeiekniak
301 evneatdyae saayaepess llyvydeean s (SEQ ID NO:7)

  1 atgactttaa aagaagcagg tttaacagaa gataaattaa ttaaaatgta tgaaacaatg
 61 ctaatggcaa gaagactaga cgagcgtatg tggttgctga accgttctgg gaaaattcct
121 ttcaccattt ctggacaagg acaagaaacg gcacaaattg gcgcagcgtt tgcctttgat
181 ttagataaag attacgcatt accatattac cgtgatttag cggtggtgtt agcatttggg
241 atgacagcga aagatattat gttatccgcg ttcgctaaag cagaggatcc aaactctggt
301 ggacgtcaaa tgccagctca ttttggtcaa aaatcaaatc gcatcgtgac acaaagttca
361 ccagtaacaa cgcagttccc gcatgcagca ggtattggtc ttgcagcgaa aatggccggt
421 gatgagattg caatttatgc ttcaacgggt gaaggatctt ctaaccaagg agatttccat
481 gaaggaatca acttcgcatc tgtacataag ttgccagttg ttttcgtgat tcacaataac
541 caatatgcca tttccgttcc agcatcgaaa caatatgctg cagaaaaact atccgaccga
601 gcaatcggtt atggtatccc aggggaacgt gtggatggca caaatatggg tgaagtatac
661 gcggcattta aacgtgcagc agatcgtgca agaaacggcg agggccccac tttaattgaa
721 acagtttctt accgattcac accgcactct tctgatgatg atgacagcag ttatcgttcc
781 agagaagaag tgaacgaagc aaaaggaaaa gatccactga caattttcca aacagaatta
841 ctcgaagaag gttacttaac agaagaaaaa atcgctgaaa tcgaaaaaaa tattgcaaaa
901 gaagttaacg aagcaaccga ttacgcggaa agtgcagcat acgctgaacc agaatcatct
961 ttactttatg tatatgatga agaagcgaat agctga (SEQ ID NO:8)
```

*Streptomyces avermitilis MA-4860*: NP_825539

```
  1 mtvmeqrgay rptpppawgp rtdpapllpd alphrvlgte aaaeadplll rrlyaelvrg
 61 rryntqatal tkqgrlavyp sstgqeacev aaalvleerd wlfpsyrdtl aavargldpv
121 qaltllrgdw htgydprehr iaplctplat qlphavglah aarlkgddvv alalvgdggt
181 segdfhealn faavwqapvv flvqnngfai svplakqtaa pslahkavgy gmpgrlvdgn
241 daaavhevls davaharagg gptlveavty ridahtnadd atryrgdsev eawrahdpia
301 llehelterg lldedgiraa redaeamaad lrarmnqdpa ldpmdlfahv yaeptpqlre
361 qeaqiraela aeadgpqgvg r (SEQ ID NO:9)

   1 atgacggtca tggagcagcg gggcgcttac cggcccacac cgccgcccgc ctggcagccc
  61 cgcaccgacc ccgcgccact gctgcccgac gcgctgcccc accgcgtcct gggcaccgag
 121 gcggccgcgg aggccgaccc gctactgctg cgccgcctgt acgcggagct ggtgcgcggc
 181 cgccgctaca acacgcaggc cacggctctc accaagcagg gccggctcgc cgtctacccg
 241 tcgagcacgg gccaggaggc ctgcgaggtc gccgccgcgc tcgtgctgga ggagcgcgac
 301 tggctcttcc ccagctaccg ggacaccctc gccgccgtcg cccgcggcct cgatcccgtc
 361 caggcgctca ccctcctgcg cggcgactgg cacaccgggt acgacccccg tgagcaccgc
 421 atcgcgcccc tgtgcacccc tctcgcgacc cagctcccgc acgccgtcgg cctcgcgcac
 481 gccgcccgcc tcaagggcga cgacgtggtc gcgctcgccc tggtcggcga cggcggcacc
 541 agcgagggcg acttccacga ggcactgaac ttcgccgccg tctggcaggc gccggtcgtc
 601 ttcctcgtgc agaacaacgg cttcgccatc tccgtcccgc tcgccaagca gaccgccgcc
 661 ccgtcgctgg cccacaaggc cgtcggctac gggatgccgg gccgcctggt cgacggcaac
 721 gacgcggcgg ccgtgcacga ggtcctcagc gacgccgtgg cccacgcgcg cgcgggaggg
 781 gggccgacgc tcgtggaggc ggtgacctac cgcatcgacg cccacaccaa cgccgacgac
 841 gcgacgcgct accgggggga ctccgaggtg gaggcctggc gcgcgcacga cccgatcgcg
 901 ctcctggagc acgagttgac cgaacgcggg ctgctcgacg aggacggcat ccgggccgcc
 961 cgcgaggacg ccgaggcgat ggccgcggac ctgcgcgcac gcatgaacca ggatccggcc
1021 ctggacccca tggacctgtt cgcccatgtg tatgccgagc ccaccccccca gctgcgggag
1081 caggaagccc agttgcgggc cgagctggca gcggaggccg acgggcccca aggagtcggc
```

FIG. 2A cont'd 1141 cgatga (SEQ ID NO:10)

*Micrococcus luteus NCTC 2655*: YP_002956766

```
  1 mtlvdhtrpt ggqsagsppp agpaeavmlq vldtegrrrp qpeldpwied vdaaalaaly
 61 rqmavvrrld veathlqrqg elalwppllg qeaaqvgsav alrpddfvfp syrengvall
121 rgvpaldllr vwrgstfssw dpnetrvatq qiligaqalh avgyamgvqr dqadvativy
181 fgdgatsqgd vneamvfsas yqapvvffcq nnhwaisepv rlqtrrsiad rpwgfgipsm
241 rvdgndvlav laatraaver aadgggptfv eavtyrmgph ttaddptryr ddaeleawka
301 rdpltrveah lrtldvdvda vlaqaqaead elaaevrral ealeedgadr lfdeiyaeph
361 qelerqrreh alylqqfdde eaga (SEQ ID NO:11)
```

```
   1 gtgaccctcg tggaccacac ccgtcccacc ggcggacagt ccgccggctc tccgcccccg
  61 gcgggcccgg ccgaggccgt gatgctccag gtgctcgaca cggagggccg ccgccgtccg
 121 cagccggagc tcgacccgtg gatcgaggac gtcgacgccg ccgccctcgc cgcgctgtac
 181 cgccagatgg ccgtggtccg tcgcctcgac gtcgaggcca cgcacctgca gcgtcagggc
 241 gagctggccc tgtggccgcc gctgctgggc caggaggccg cccaggtggg ctccgccgtc
 301 gcgctgcgcc cggacgactt cgtcttcccg tcctaccgcg agaacggcgt ggccctgctg
 361 cgcggcgtcc ccgcgctgga cctgctgcgg gtgtggcgcg gctccacgtt ctcgagctgg
 421 gacccgaacg agacgcgggt ggccacccag cagatcatca tcggcgcgca ggccctgcac
 481 gccgtcggct acgcgatggg cgtccagcgg gaccaggcgg acgtcgccac gatcgtctac
 541 ttcggcgacg gcgccacgag ccagggcgac gtcaacgagg ccatggtctt cagcgcctcc
 601 taccaggcgc ccgtggtgtt cttctgccag aacaaccact gggccatctc cgagcccgtg
 661 cgcctgcaga cccgccgcag catcgcggac cgcccgtggg gcttcggcat cccgtcgatg
 721 cgcgtggacg gcaacgacgt cctggccgtg ctcgccgcaa cccgcgccgc cgtcgagcgc
 781 gcggccgacg gggcggcccc cacgttcgtc gaggccgtca cctaccgcat gggtccacac
 841 accaccgcgg acgaccccac ccgctaccgg gacgacgccg agctcgaggc ctggaaggcc
 901 cgtgacccgc tgacccgcgt ggaggcgcac ctgcgcaccc tcgacgtgga cgtggacgcc
 961 gtgcttgcac aggcccaggc cgaggccgac gagctggcag cggaggtccg ccgtgccctc
1021 gaggcgctcg aggaggacgg cgcggacagg ctcttcgacg agatctacgc ggagccccac
1081 caggagctcg agcggcagcg ccgcgagcac gccctctacc tgcagcagtt cgacgacgag
1141 gaggcgggcg cgtga (SEQ ID NO:12)
```

*Staphylococcus aureus A8819*: ZP_06816445

```
  1 midykslgls eedlkviykw mdlgrkider lwllnragki pfvvsgqgqe atqigmayal
 61 eegditapyy rdlafvtymg isaydtflsa fgkkddvnsg gkqmpshfss raknilsqss
121 pvatqiphav gaalalkmdg kkkiatatvg egssnqgdfh eglnfagvhk lpfvcviinn
181 kyaisvpdsl qyaaeklsdr algygihgeq vdgndplamy kamkeardra isgqgstlie
241 avtsrmtahs sddddqyrtk eerealkkad cnekfkkell sagiiddawl aeieaehkdi
301 inkatkaaed apypsveeay afvyeegsln (SEQ ID NO:13)
```

```
  1 ttagttaaga ctcccttctt cgtacacaaa tgcataggct tcttcgacac ttggatatgg
 61 cgcgtcttca gcagcctttg tcgctttatt gatgatgtct ttatgctccg cttctatttc
121 tgccaaccaa gcatcatcga taatgccagc tgaaagcaac tctttttga acttttcatt
181 gcagtcagct tttttaagcg cttcacgctc ttctttcgta cgatattggt cgtcatcatc
241 tgatgaatga gctgtcatac gacttgttac tgcttcaatc aaagttgaac cttgaccaga
301 aatagctcga tctcttgctt ctttcatcgc tttatacatt gctaatggat cattaccatc
361 tacttgttca ccatgtatac cgtaaccaag tgctctatcc gataattttt cagctgcgta
421 ttgtaatgaa tcaggtactg aaattgcata tttattattt ataatgacac atacaaaagg
481 aagtttgtgt acacccgcga agtttaaacc ttcatggaag tcaccttggt ttgagctacc
```

FIG. 2A cont'd 541 ttcaccaaca gttgctgttg caatttcttt cttaccatcc atttttaaag ctaaagcagc
601 accaacagca tggggtattt gagttgctac cggtgaactt tgagacaaaa tattcttagc
661 tctactacta aagtgtgatg gcatttgttt tccaccagag ttaacatcgt ctttctttcc
721 aaacgctgat aaaaacgtat catacgctga gatacccata taagtaacga aagctagatc
781 tctataataa ggcgctgtaa tatcaccttc ttctaatgcg tatgccatcc caatctgagt
841 tgcttcttgt ccttgaccac ttacaacaaa tggaatttta cctgcacggt tcaataacca
901 cagtctttca tctatttttc tacctaaatc catccattta tatattactt ttaggtcttc
961 ttcgctaagg cctaatgatt tataatcaat cat (SEQ ID NO:14)

*Streptococcus mutans UA159*: NP_720600

1 markilevii amlskkqyld mflkmqrird vdtklnklvr rgfvqgmthf svgeeaasvg
61 aiqgltdqdi ifsnhrghgq tiakgidipa mfaelagkat gsskgrggsm hlanlekgny
121 gtngivgggy alavgaaltq qydntgnivv afsgdsatne gsfhesvnla avwnlpviff
181 iinnrygist dinystkish lylradaygi pghyvedgnd viavyekmqe vidyvrsgng
241 palvevesyr wfghstadag ayrtkeevda wkakdpikky rtyltenkia tdeeldmiek
301 evaqeiedav kfaqdspepe lsvafedvwv d (SEQ ID NO:15)

1 atggcaagaa aaattttgga ggtcattata gcaatgttat ctaaaaaaca atatttggat
61 atgtttttaa aaatgcagcg tatccgtgat gtcgatacaa aactcaataa attagttcgt
121 cgtggtttcg tacaaggtat gacacacttt tcagtaggag aagaggcggc ttcggttggt
181 gcgattcaag gcttgactga tcaggatatt atcttttcaa atcaccgtgg acatggtcaa
241 accattgcaa aagggattga cattcctgct atgtttgcag aattagccgg taaggcaacg
301 ggttcttcaa aaggtcgtgg tggttctatg cacttggcaa atcttgaaaa aggaaactat
361 gggaccaatg gtattgttgg cgggggttat gccttagcag tcggtgctgc tttgacacag
421 caatatgaca atacgggaaa tattgttgtc gccttttcag gagactcggc aactaatgaa
481 ggctctttcc atgagtctgt taatttggca gctgtctgga atttaccggt tatcttcttt
541 attattaata atcgttatgg tatctcaaca gatatcaatt attctactaa gatttcacat
601 ctttatttac gtgctgatgc ttatggtatt cctggacatt atgttgaaga tggtaatgat
661 gtcattgcag tttatgaaaa aatgcaggaa gtcattgatt atgtgcgttc aggaaatggg
721 ccagctcttg ttgaagtgga atcttatcgt tggttcggac attctactgc tgatgcagga
781 gcttaccgta caaaagaaga agtagatgct tggaaagcta aagatcctct caagaaatac
841 cgcacttatc taacagaaaa taagattgca acagatgagg aacttgatat gattgaaaaa
901 gaagtcgcac aggaaattga ggatgcagtg aaatttgccc aagatagccc tgaaccagag
961 ctttctgtag cttttgaaga tgtttgggta gattag (SEQ ID NO:16)

(S,Q)-(x)2-G-(Q,E)-E-A-(x)3-(G,A)-x-(G,A)-x-(V,A)-(L,T) [SEQ ID NO:17]
D-(x)2-(L,F)-P-x-Y-R [SEQ ID NO:18]
(S,T)-Q-(x)2-(H,Q)-A-(T,V)-G-x-A-(A,G) [SEQ ID NO:19]
(K,G)-x-(T,D)-(x)2-(A,V)-x-(A,V)-(x)2-G-(E,D)-G-(x)4-(G,S)-D-(F,V) [SEQ ID NO:20]
F-(A,S)-(H,A)-V-(x)2-(L,A)-P-V-x-(L,F)-(x)3-N-N-(x)2-A-I-S [SEQ ID NO:21]
(K,R)-(G,A)-x-G-(C,Y)-(F,G)-x-(A,P)-(S,G)-(x)2-V-D-G-N-D [SEQ ID NO:22]
(H,R)-A-R-(A,R)-G-x-G-P-x-L-x-E-(x)2-(S,T)-Y-R-(x)3-H-(x)3-D-D-(x)3-Y-R [SEQ ID NO:23]
wherein, the amino acid residues in each of the brackets indicate alternative amino acid residues at the particular position, each x indicates any amino acid residue, and each n in "x(n)" indicates the number of x residues in a contiguous stretch of amino acid residues.

FIG. 2B

BKD E1 beta subunit homologs

*Bacillus subtillis 168:* ZP_03592171

```
  1 msvmsyidai nlamkeemer dsrvfvlged vgrkggvfka taglyeqfge ervmdtplae
 61 saiagvgiga amygmrpiae mqfadfimpa vnqiiseaak iryrsnndws cpivvrapyg
121 ggvhgalyhs qsveaifanq pglkivmpst pydakgllka avrdedpvlf fehkrayrli
181 kgevpaddyv lpigkadvkr egdditvity glcvhfalqa aerlekdgis ahvvdlrtvy
241 pldkeaiiea asktgkvllv tedtkegsim sevaaiiseh clfdldapik rlagpdipam
301 pyaptmekyf mvnpdkveaa mrelaef (SEQ ID NO:24)
```

```
  1 ttaaaactcc gctaattctc tcatcgccgc ttccacttta tcagggttga ccataaagta
 61 tttttccatt gtcggcgcat aaggcatagc cggaatatca ggacctgcaa gccgtttgat
121 cggcgcgtct aagtcgaaca gacaatgctc ggatataatt gcggctactt cgctcatgat
181 gctgccttct tttgtatctt ctgtgaccaa aagaaccttt ccagttttgg acgcagcttc
241 gatgatggct tctttatcaa gcgggtaaac tgttcttaaa tccaccacat gcgctgaaat
301 gccatctttt tcgagacgtt ctgcagcttg taaggcgaag tggacacaca ggccgtatgt
361 gatcactgtg atgtcgtcgc cttccctttt tacgtccgcc ttgccgattg gcaggacata
421 atcatcagcc ggaacctcgc cctttatcag acggtatgcc cgcttgtgct caaaaaacag
481 cacggggtct tcgtcacgaa ctgcggcttt taagagccct ttcgcgtcat atggtgttga
541 tggcatgaca attttcagtc cgggctggtt ggcgaaaatt gcctcgactg attgagaatg
601 atacagggct ccgtgcacgc ctccgccgta tggcgctctg acgacaatcg gacagctcca
661 gtcattgttg ctgcggtagc ggattttagc cgcttcagaa ataatttggt tgactgccgg
721 cataatgaaa tcagcaaact gcatttcagc aatcggtctc attccgtaca ttgccgctcc
781 gataccgact cctgcgattg cagattcagc aagcggcgta tccataacgc gctcttcccc
841 aaattgttca tagagtcccg ctgtcgcttt aaacacaccg ccttttcttc ctacatcttc
901 cccaaggacg aaaacgcgag aatctcgttc catttcttct ttcatcgcca aattgattgc
961 atcaatatat gacattactg acat (SEQ ID NO:25)
```

*Streptomyces avermitilis MA-4860:* NP_825554

```
  1 maekmaiaka ineslrkale sdpkvlimge dvgklggvfr vtdglqkdfg eervidtpla
 61 esgivgtaig lalrgyrpvv eiqfdgfvfp aydqivtqla kmharalgki klpvvvripy
121 gggigavehh sespealfah vaglkvvsps nasdaywmmq qaiqsddpvi ffepkrrywd
181 kgevnveaip dplhkarvvr egtdltlaay gpmvkvcqea aaaaeeegks levvdlrsms
241 pidfdavqas vektrrlvvv heapvflgtg aeiaariter cfyhleapvl rvggyhapyp
301 parleeeylp gldrvldavd rslay (SEQ ID NO:26)
```

```
  1 atggccgaga agatggcgat cgccaaggcg atcaacgagt cgctgcgcaa ggccctggag
 61 tccgacccca aggttctgat catgggtgag gacgtcggca agctcggtgg cgtcttccgc
121 gtcaccgacg gcctgcagaa ggacttcggc gaggagcggg tcatcgacac cccgctcgcc
181 gagtcgggca tcgtcggcac ggcgatcggt ctcgccctgc gcggctaccg cccggtggtg
241 gagatccagt tcgacggctt cgtcttcccg gcgtacgacc agatcgtcac gcagctcgcg
301 aagatgcacg cgcgggcgct cggcaagatc aagctccccg ttgtcgtccg catcccgtac
361 ggcggcggca tcggcgccgt cgagcaccac tccgagtccc ccgaggcgct cttcgcgcac
421 gtggcgggcc tcaaggtggt ctccccgtcc aacgcgtcgg acgcgtactg gatgatgcag
481 caggccatcc agagcgacga cccggtgatc ttcttcgagc cgaagcggcg ctactgggac
541 aagggcgagg tcaacgtcga ggcgatcccc gacccgctgc acaaggcccg tgtggtgcgt
```

FIG. 2B cont'd 601 gagggcaccg acctgacgct cgccgcgtac ggccccgatgg tgaaggtctg ccaggaggcc
661 gcggccgccg ccgaggagga gggcaagtcc ctggaggtcg tcgacctgcg ctccatgtcg
721 ccgatcgact tcgacgccgt ccaggcctcc gtcgagaaga cccgccgtct ggtcgtggtg
781 cacgaggcgc cggtgttcct gggcacgggc gcggagatcg ccgccccgcat cacggagcgc
841 tgcttctacc acctggaggc acccgtgctg agggtcggcg gctaccacgc cccgtatccg
901 ccggcgcgtc tggaagagga gtaccttccg ggccttgacc gggtgctcga tgccgtcgac
961 cgctcgctgg cgtactga (SEQ ID NO:27)

*Pseudomonas putida F1*: YP_001266795

1 mneyaplrlh vpeptgrpgc qtdfsylrln dagqarkpai dvdaadtadl syslvrvlde
61 qgdaqgpwae didpqilrqg mramlktrif dsrmvvaqrq kkmsfymqsl geeaigsgqa
121 lalnrtdmcf ptyrqgsilm ardvslvemi cqllsnerdp lkgrqlpimy svreagffti
181 sgnlatqfvq avgwamasai kgdtkiasaw igdgataesd fhtaltfahv yrapvilnvv
241 nnqwaistfq aiaggesttf agrgvgcgia slrvdgndfv avyaasrwaa erarrglgps
301 liewvtyrag phstsddpsk yrpaddwshf plgdpiarlk qhlikighws eeehqavtae
361 leaaviaaqk eaeqygtlan ghipsaasmf edvykempeh lrrqrqelgv (SEQ ID NO:28)

1 tcaaaccccc agttcctggc gttgacggcg caggtgttcg ggcatctcct tgtacacatc
61 ctcgaacatc gaggcggcgc tcgggatgtg cccgttagcc agggtgccgt actgctcggc
121 ttctttctgt gcggcaatca ccgcagcttc gagctcggcc gtgacggctt ggtgttcttc
181 ttcggaccag tggccgatct tgatcaggtg ctgcttcagg cgggcgatcg ggtcacccag
241 cgggaagtgg ctccagtcat cggcagggcg gtacttggag ggtcgtccg acgtcgagtg
301 cgggccggca cggtaggtga cccactcgat caggcttggg cccaggccgc ggcgggcgcg
361 ctcggcagcc cagcgcgagg cggcgtacac ggcgacgaag tcgttgccgt caacccgcag
421 cgaggcaatg ccgcagccca cgccacggcc ggcgaaggtg gtcgactcgc caccggcgat
481 ggcctggaag gtagaaatcg cccactggtt gttgaccaca ttgaggatca ccggggcgcg
541 gtaaacgtgg gcaaaggtga gggcggtgtc gaagtccgac tcggcggtgg ctccgtcacc
601 gatccacgcc gaagcaatct tggtatcgcc cttgatcgcc gaggccatgg cccagccgac
661 tgcctgcacg aactgggtcg ccaggttgcc gctgatggtg aagaagccgg cttcgcgcac
721 cgagtacatg atcggcaact ggcggccctt gagggggtcg cgctcgttgg acagcagttg
781 gcagatcatc tcgaccagcg atacgtcgcg ggccatcagg atgctttgct ggcggtaggt
841 cgggaagcac atgtcggtgc ggttcagcgc cagcgcctgg ccactgccga tggcttcttc
901 gcccaggctt tgcatgtaga aggacatctt cttctggcgc tgggcaacca ccatgcggct
961 gtcgaagatc cgcgtcttga gcatggcgcg catgccctga cgaaggatct gtgggtcgat
1021 gtcttcggcc caggggcctt gcgcatcacc ttgctcgtcg agcacgcgga ccaggctgta
1081 ggacaggtcg gcagtgtcgg cagcatcgac atcgatcgcg ggtttacggg cttgacctgc
1141 atcgttgagg cgcaggtagg aaaaatcggt ctggcagcct ggccggccgg tgggctcggg
1201 cacatgcaaa cgcagggggg cgtactcgtt cat (SEQ ID NO:29)

*Listeria monocytogenes 08-5578*: YP_003413623

1 mpvisyidai tmalkeemer ddkvfilged vgkkggvfka taglydefge drvldtplae
61 saiagvgiga amygyrpvae mqfadfimpa vnqiiseaar iryrsnndws cpmvirapfg
121 ggvhgalyhs qsvekvffgq pglkivvpss pydakgllka airdndpvlf fehkrayrll
181 kgevpetdyi vpigeanvvr egdditvity glavqfaqqa aerlaaegve ahildlrtiy
241 pldqeaiiea tkktgkvllv tednkqgsii sevaaiiseh clfdldapia rlagpdtpam
301 pfaptmekhf minpdkvada mkelaef (SEQ ID NO:30)

1 atgccagtca tttcatatat tgatgcaata accatggcgc ttaaagaaga aatggagcgc

FIG. 2B cont'd

```
 61 gatgataaag tatttatttt aggagaagat gttgggaaaa aaggtggcgt atttaaagcg
121 actgctggtc tatatgacga atttggtgaa gacagagtac ttgatacacc acttgctgaa
181 tctgccattg ccggagttgg aattggcgcg gcgatgtatg gctaccgccc agttgcagaa
241 atgcaatttg ctgactttat tatgccagct gtcaaccaaa tcatttcaga agctgccaga
301 attcggtacc gttctaataa cgattggtct tgtccaatgg ttattcgcgc accttttggc
361 ggcggggtac acggggcact ttaccattca caatctgttg aaaaagtgtt tttcggacaa
421 cctggtttga aaatcgttgt tccttcttca ccatatgatg caaaagggct tttaaaagcg
481 gcgattcgcg ataatgatcc agtgcttttc tttgagcata aacgtgcgta ccgcttgcta
541 aaaggcgaag tgccagaaac tgattatatc gttccaatcg gcgaagcaaa tgttgttcgt
601 gaaggtgatg atattacagt aattacttac ggacttgcgg ttcaatttgc ccaacaagca
661 gcagaacgtt tagcagcgga aggcgtagaa gcacatattc ttgatttacg gacaatctat
721 ccactagacc aagaagcaat tattgaagca acgaaaaaaa caggtaaagt acttcttgta
781 acggaagata acaaacaagg aagtattatc agtgaagtgg cagcaatcat ttcggagcat
841 tgtttatttg acttagacgc accgattgct agactcgcag gacctgatac cccagcgatg
901 ccttttgctc caacaatgga aaaacatttt atgatcaatc cagataaagt ggcggatgca
961 atgaaagaat tagcggaatt ttag (SEQ ID NO:31)
```

*Streptomyces avermitilis MA-4860*: NP_825540

```
  1 mttvalkpat maqaltralr damaadpavh vmgedvgtlg gvfrvtdgla kefgedrctd
 61 tplaeagilg tavgmamygl rpvvemqfda faypafeqli shvarmrnrt rgamplpiti
121 rvpygggigg vehhsdssea yymatpglhv vtpatvaday gllraaiasd dpvvflepkr
181 lywskdswnp depgtvepig ravvrrsgrs atlitygpsl pvcleaaeaa raegwdlevv
241 dlrslvpfdd etvcasvrrt gravvvhesg gyggpggeia aritercfhh leapvlrvag
301 fdipypppml erhhlpgvdr ildavgrlqw eags (SEQ ID NO:32)
```

```
  1 atgaccaccg ttgccctcaa gccggccacc atggcgcagg cactcacacg cgcgttgcgt
 61 gacgccatgg ccgccgaccc cgccgtccac gtgatgggcg aggacgtcgg cacgctcggc
121 ggggtcttcc gggtcaccga cgggctcgcc aaggagttcg gcgaggaccg ctgcacggac
181 acgccgctcg ccgaggcagg catcctcggc acggccgtcg gcatggcgat gtacgggctg
241 cggccggtcg tcgagatgca gttcgacgcg ttcgcgtacc cggcgttcga gcagctcatc
301 agccatgtcg cgcggatgcg caaccgcacc cgcgggggcga tgccgctgcc gatcaccatc
361 cgtgtcccct acggcggcgg aatcggcgga gtcgaacacc acagcgactc ctccgaggcg
421 tactacatgg cgactccggg gctccatgtc gtcacgcccg ccacggtcgc cgacgcgtac
481 gggctgctgc gcgccgccat cgcctccgac gacccggtcg tcttcctgga gcccaagcgg
541 ctgtactggt cgaaggactc ctggaacccg gacgagccgg ggaccgttga accgataggc
601 cgcgcggtgg tgcggcgctc gggccggagc gccacgctca tcacgtacgg gccttccctg
661 cccgtctgcc tggaggcggc cgaggcggcc cgggccgagg gctgggacct cgaagtcgtc
721 gatctgcgct ccctggtgcc cttcgacgac gagacggtgt gcgcgtcggt gcgccggacc
781 ggacgcgccg tcgtcgtgca cgagtcgggt ggttacggcg gcccgggcgg ggagatcgcc
841 gcgcggatca ccgagcgctg cttccaccat ctggaggcgc cggtgctgcg cgtcgccggg
901 ttcgacatcc cgtatccgcc gccgatgctg gagcgccatc atctgcccgg tgtcgaccgg
961 atcctggacg cggtggggcg gcttcagtgg gaggcgggga gctga (SEQ ID NO:33)
```

*Micrococcus luteus NCTC 2655*: YP_002956767

```
  1 msermtfgra inrglhrala ddpkvllmge digalggvfr itdglqaefg edrvldtpla
 61 esgivgtaig lamrgyrpvv eiqfdgfvyp afdqivanla klrartrgav pmpvtiripf
121 gggigspehh sespeayflh taglrvvsps spqegydlir aaiasedpvv ylepkrryhd
181 kgdvdlgvai ppmsparilr egrdatlvay gpivktalqa aevaaeegve vevvdirsls
241 pldtglvess vrrtgrlvva heasrtgglg aelvatvaer afhwleappv rvtgmdvpyp
```

FIG. 2B cont'd 301 psklehlhlp dldrildgld ralgrpnsld svdafaapet aeqflaaqna geetr (SEQ ID NO:34)

1 gtgagcgagc gcatgacctt cggccgtgcg atcaaccgcg gcctgcaccg tgccctggcc
61 gacgacccca aggtcctgct catgggcgag gacatcggcg ccctcggcgg cgtgttccgc
121 atcaccgacg gcctgcaggc cgagttcggc gaggaccggg tgctcgacac cccgctggcc
181 gagtccggca tcgtgggcac ggccatcggc ctggcgatgc gcggctaccg gcccgtcgtc
241 gagatccagt tcgacggctt cgtgtacccg gcgttcgacc agatcgtggc gaacctggcc
301 aagctgcgcg cccgcacccg cggcgccgtg ccgatgccgg tgaccatccg catccccttc
361 ggcggcggca tcggctcccc ggagcaccac tccgagtcgc ccgaggccta cttcctgcac
421 accgcgggtc tgcgcgtggt ctccccgtcc tccccgcagg aggggtacga cctcatccgc
481 gccgcgatcg cctcggagga cccggtggtc tacctcgagc ccaagcgtcg ctaccacgac
541 aagggcgacg tggacctggg cgtcgcgatc ccgccgatga gcccggcccg catcctgcgc
601 gagggccgtg acgccacgct cgtggcctac ggcccgctcg tgaagaccgc cctgcaggcc
661 gccgaggtgg cggccgagga gggtgtcgag gtcgaggtgg tcgacctgcg cagcctgtcc
721 ccgctggaca ccggcctcgt cgagtcctcg gtgcggcgca ccggtcggct cgtcgtggcg
781 cacgaggcct cccgcacggg cggcctcggc gccgagctcg tggccacggt ggccgagcgc
841 gcgttccatt ggctcgaggc cccgccggtg cgcgtcaccg gcatggacgt gccctacccg
901 ccgtccaagc tcgagcacct gcacctgccg gacctcgacc gcatcctcga cggcctggac
961 cgtgctctgg gccggccgaa ttcgctggac tccgtggacg cgttcgccgc ccccgagacc
1021 gccgagcagt tcctcgccgc ccagaacgcc ggggaggaga cccgatga (SEQ ID NO:35)

*Staphylococcus aureus A8819*: ZP_06816444

1 maklsyleai rqaqdlalqq nkdvfilged vgkkggvfgt tqglqqqyge drvidtplae
61 snivgtaiga amvgkrpiae iqfadfilpa tnqiiseaak mryrsnndwq cpitirapfg
121 ggvhgglyhs qsiesifass pgltivipst pydakgllis siesndpvly fehkkayrfl
181 keevpeeyyt vplgkadvkr egedltvfcy glmvnyclqa adilaadgin vevvdlrtvy
241 pldketiidr akntgkvllv tednlegsim sevsaiiaeh clfdldtpim rlaapdvpsm
301 pfspvlenei mmnpekilnk mrelaef (SEQ ID NO:36)

1 ctagaattct gctaattcac gcattttatt taagattttt tctggattca tcataatttc
61 attttctaat acaggagaaa atggcataga tggtacatct ggagcagcta aacgcatgat
121 tggtgtatct aaatcgaaca agcaatgctc tgcaataatc gctgacactt ctgacataat
181 actaccttct aaattatctt cagttacaag taaaacttta cctgtatttt tagcacgatc
241 aataattgtt tctttatcta atggataaac agttcgtaaa tcaacgactt caacgttgat
301 accgtctgca gctaaaatat ccgctgcttg taaacaataa ttgaccatta atccataaca
361 aaatactgtt aaatcttcac cttcacgttt aacatctgct tttcctaaag gtacagtgta
421 atattcttct ggcacttctt cctttaagaa acgataagct tttttatgct caaagtacaa
481 tactggatca tttgattcga tagatgataa taaaagccct ttagcatcat acggtgtgga
541 aggaataaca attgttaaac ctggtgatga agcaaatata ctttcaatac tttgtgaatg
601 atatagtcct ccgtgaacac cgccaccaaa tggtgcacga atcgttaatg ggcattgcca
661 atcattattt gaacgataac gcattttcgc agcttcacta ataatttgat ttgtcgcagg
721 taaaataaaa tctgcaaatt gaatttctgc aattggtctt ttacctacca tagctgcacc
781 aatggcagtt ccaacaatat ttgactcagc taatggcgta tcgataactc tgtcttcacc
841 atattgttgt tgtagtcctt gagtagtacc aaatacgcca ccttttttac caacatcttc
901 accaagaata aacacatctt tattttgttg taatgctaag tcttgtgcct ggcgtatcgc
961 ctctaaataa gataatttag ccat (SEQ ID NO:37)

FIG. 2B cont'd

*Streptococcus mutans UA159*: NP_720601

```
  1 mrrkrymset kvvalreain lamseemrkd ekiilmgedv giyggdfgts vgmlaefgek
 61 rvkdtpisea aiagsavgaa qtglrpivdl tfmdfvtiam daivnqgaka nymfggglkt
121 pvtfrvasgs gigsaaqhsq sleawlthip gikvvapgtv ndakallksa irdnnivifm
181 epkalygkke evnldpdfyi plgkgeikre gtdvtivsyg rmlervlkaa eevaaedisv
241 evvdprtlip ldkdliinsv kktgkvilvn dayktggfig eiasvitese afdyldapvl
301 rlasedvpvp yshvletail pdvakikeai ykqvrkr (SEQ ID NO:38)
```

```
  1 atgaggagaa agagatatat gtcagaaaca aaagtagtag ccttacggga agctatcaat
 61 cttgctatga gcgaggaaat gcgtaaggac gaaaaaatta ttttgatggg tgaagatgtc
121 ggtatttatg gtggtgactt tggaacttct gttggtatgc tggctgaatt tggtgaaaag
181 cgtgttaaag ataccccctat ttcagaagca gccattgcag gatctgcagt aggtgccgct
241 caaactggac ttcgtcctat tgttgatttg acctttatgg actttgtgac tattgccatg
301 gatgctattg ttaatcaagg tgctaaagcc aattatatgt ttggcggcgg acttaaaacg
361 cctgtaacct ttcgtgtggc ctcaggctca ggtatcggct cagcagcgca gcattctcag
421 tcactagaag cttggttaac tcatattccg ggaatcaagg tggttgcgcc tggcacagtc
481 aatgatgcta aagccttgct caaatctgct attcgtgata ataatatcgt tattttcatg
541 gaaccaaaag cgctttatgg caaaaaagaa gaggtcaatt tagatcctga tttttatatt
601 ccgcttggta aaggcgaaat taagcgcgag ggaacagatg ttaccattgt gtcttatggt
661 cgtatgctgg aacgcgttct caaagccgct gaggaagtgg cggctgaaga tatcagtgtt
721 gaagttgttg acccgcgtac ccttattccg cttgataaag acttaattat taattctgtg
781 aaaaagacgg gtaaggttat cctagttaat gatgcttata aaacaggtgg tttcattggt
841 gaaatagcat cagtgattac tgaaagcgaa gcatttgatt atttagatgc accagtgctt
901 cgtctcgctt ctgaggatgt gcctgttccc tattctcatg ttctcgaaac agccatttta
961 ccagatgtgg caaaaattaa agaagctatc tataaacaag tcaggaaaag atag (SEQ
ID NO:39)
```

V-x-(V,I)-x-G-(Q,E)-D-V-G-(x)2-G-G-V-F-(R,K)-x-T-x-G-I [SEQ ID NO:40]
(Y,F)-G-(E,K)-x-R-(C,V)-x-D-(A,T)-P-(L,I)-(A,S)-E-(A,S)-(A,G)-I [SEQ ID NO:41]
G-T-(A,E)-x-(R,Y)-G-x-R-P-(I,V)-(A,V)-E-x-Q-F [SEQ ID NO:42]
P-(C,Y)-G-G-(V,I)-x-(A,G)-(x)3-H-S-x-S-x-E-A-x-(F,Y) [SEQ ID NO:43]
(E,D)-D-P-V-x-(F,Y)-x-E-(H,P)-K-R-x-Y [SEQ ID NO:44]
(H,E)-V-(I,V)-D-L-R-(T,S)-(x)2-P-x-D [SEQ ID NO:45]
E-x-C-(L,F)-x-(D,H)-L-(D,E)-A-P-(x)2-R-(L,V)-x-G-x-(H,D)-P [SEQ ID NO:46]

wherein, the amino acid residues in each of the brackets indicate alternative amino acid residues at the particular position, each x indicates any amino acid residue, and each n in "x(n)" indicates the number of x residues in a contiguous stretch of amino acid residues.

FIG. 2C

BKD E2 subunit homologs

*Bacillus subtillis 168*: ZP_03592170

```
  1 maieqmtmpq lgesvtegti skwlvapgdk vnkydpiaev mtdkvnaevp ssftgtitel
 61 vgeeggtlqv gemickiete ganpaeqkqe qpaaseaaen pvaksagaad qpnkkryspa
```

FIG. 2C cont'd

```
 121 vlrlagehgi dldqvtgtga ggritrkdiq rlietggvqe qnpeelktaa papksaskpe
 181 pkeetsypas aagdkeipvt gvrkaiasnm krskteipha wtmmevdvtn mvayrnsikd
 241 sfkktegfnl tffaffvkav aqalkefpqm nsmwagdkii qkkdinisia vatedslfvp
 301 viknadekti kgiakditgl akkvrdgklt addmqggtft vnntgsfgsv qsmgiinypq
 361 aailqvesiv krpvvmdngm iavrdmvnlc lsldhrvldg lvcgrflgrv kqilesidek
 421 tsvy (SEQ ID NO:47)

   1 ttagtaaaca gatgtcttct cgtcaatcga ttctaaaatt tgtttcactc gtccgaggaa
  61 tcgtccgcac acgagaccgt caagcactct gtgatctaat gacaggcaca gattaaccat
 121 gtctctgaca gcaatcatgc cattgtccat gacaaccggg cgtttgacga tggattctac
 181 ttgaagaatc gcagcctgag ggtagttgat aatgcccatc gactgaacag acccgaacga
 241 acctgtgttg ttgacggtaa acgtgcctcc ctgcatgtca tctgcagtga gttttccgtc
 301 tcttactttt ttagctaggc cggtaatgtc tttcgcaatg cctttaattg tttttttcatc
 361 agcgttttta atcaccggaa caaataaaga atcctctgtg gcaactgcaa ttgaaatatt
 421 gatatccttt ttctgaataa ttttgtcccc cgcccacatg ctattcattt gcgggaattc
 481 ttttaacgcc tgagcgaccg cttttacaaa aaaggcgaag aacgttaaat taaagccttc
 541 tgtcttctta aaagaatctt ttatactgtt gcgatatgca accatatttg tgacgtcgac
 601 ttccatcatc gtccaagcat gcggaatttc tgttttgctt cgcttcatat tggaagcaat
 661 tgcttttctt acacctgtga cagggatttc tttatcaccg gctgcagacg caggatatga
 721 cgtctcttct tttggctcag gttttgatgc agacttcggt gcaggagctg ctgttttcag
 781 ctcctcagga ttctgttctt gcacgccgcc tgtttcaatt aagcgctgaa tatcttttcg
 841 tgtgatgcgc ccgccggcac cagttcctgt cacttgatcg aggtcaatgc cgtgctctcc
 901 ggccaaacgg agaacagctg gcgagtagcg ctttttattg ggctgatcgg ctgctccagc
 961 actttttgca acaggttctc cagcggcttc tgatgctgct ggctgttctt gtttttgttc
1021 agccggattc gcgccttctg tttcaatttt gcaaatcatt tctccgactt gcagggtttg
1081 gccttcttct cccacaagct ctgttatcgt accagtaaaa gaagacggaa cctctgcatt
1141 taccttatct gtcatgactt ccgcgatcgg atcgtatttg ttcactttat caccgggggc
1201 gacaagccat ttgctgatcg tcccctctgt tacgctttct ccaagctgcg gcatcgtcat
1261 ttgttcaatt gccat (SEQ ID NO:48)
```

*Streptomyces avermitilis MA-4860*: NP_825555

```
   1 mteasvrefk mpdvgeglte aeilkwyvqp gdtvtdgqvv cevetakaav elpipydgvv
  61 relrfpegtt vdvgqviiav dvagdapvae ipvpaqeapv qeepkpegrk pvlvgygvae
 121 sstkrrprks apasepaaeg tyfaatvlqg iqgelnghga vkqrplakpp vrklakdlgv
 181 dlatitpsgp dgvitredvh aavappppap qpvqtpaapa papvaaydta retrvpvkgv
 241 rkataaamvg saftaphvte fvtvdvtrtm klveelkqdk eftglrvnpl lliakallva
 301 ikrnpdinas wdeanqeivl khyvnlgiaa atprglivpn ikdahaktlp qlaeslgelv
 361 staregktsp tamqggtvti tnvgvfgvdt gtpilnpges ailavgaikl qpwvhkgkvk
 421 prqvttlals fdhrlvdgel gskvladvaa ileqpkrlit wa (SEQ ID NO:49)

   1 atgactgagg cgtccgtgcg tgagttcaag atgcccgatg tgggtgaggg actcaccgag
  61 gccgagatcc tcaagtggta cgtccagccc ggcgacaccg tcaccgacgg ccaggtcgtc
 121 tgcgaggtcg agaccgcgaa ggcggccgtg gaactcccca ttccgtacga cggtgtcgta
 181 cgcgaactcc gtttccccga ggggacgacg gtggacgtgg gacaggtgat catcgcggtg
 241 gacgtggccg gcgacgcacc ggtggcggag atccccgtgc ccgcgcagga ggctccggtc
 301 caggaggagc ccaagcccga gggccgcaag cccgtcctcg tgggctacgg ggtggccgag
 361 tcctccacca agcgccgtcc gcgcaagagc gcgccggcga gcgagcccgc tgcggagggc
 421 acgtacttcg cagcgaccgt tctccagggc atccagggcg agctgaacgg acacggcgcg
 481 gtgaagcagc gtccgctggc gaagccgccg gtgcgcaagc tggccaagga cctgggcgtc
 541 gacctcgcga cgatcacgcc gtcgggcccc gacggcgtca tcacgcgcga ggacgtgcac
```

FIG. 2C cont'd

```
 601 gcggcggtgg cgccaccgcc gccggcaccc cagcccgtgc agacgcccgc tgcccggccc
 661 ccggcgccgg tggccgcgta cgacacggct cgtgagaccc gtgtccccgt caagggcgtc
 721 cgcaaggcga cggcggcggc gatggtcggc tcggcgttca cggcgccgca cgtcacggag
 781 ttcgtgacgg tggacgtgac gcgcacgatg aagctggtcg aggagctgaa gcaggacaag
 841 gagttcaccg gcctgcgggt gaacccgctg ctcctcatcg ccaaggcgct cctggtcgcg
 901 atcaagcgga acccggacat caacgcgtcc tgggacgagg cgaaccagga gatcgtcctc
 961 aagcactatg tgaacctggg catcgcggcg gccaccccgc gcggtctgat cgtcccgaac
1021 atcaaggacg cccacgccaa gacgctgccg caactggccg agtcactggg tgagttggtg
1081 tcgacggccc gcgagggcaa gacgtccccg acggccatgc agggcggcac ggtcacgatc
1141 acgaacgtcg gcgtcttcgg cgtcgacacg ggcacgccga tcctcaaccc cggcgagtcc
1201 gcgatcctcg cggtcggcgc gatcaagctc cagccgtggg tccacaaggg caaggtcaag
1261 ccccgacagg tcaccacgct ggcgctcagc ttcgaccatc gcctggtcga cggcgagctg
1321 ggctccaagg tgctggccga cgtggcggcg atcctggagc agccgaagcg gctgatcacc
1381 tgggcctag (SEQ ID NO:50)
```

*Pseudomonas putida F1*: YP_001266793

```
  1 mgthvikmpd igegiaqvel vewfvkvgdi iaedqvvadv mtdkatveip spvsgkvlal
 61 ggqpgevmav gselirieve gsgnhvdvpq pkpveapaap iaakpepqkd vkpavyqapa
121 nheaapivpr qpgdkplasp avrkraldag ielryvhgsg pagrilhedl dafmskpqsn
181 aggapdgyak rtdseqvpvi girrkiaqrm qdakrrvahf syveeidvta lealrqqlns
241 khgdsrgklt llpflvralv valrdfpqin atyddeaqii trhgavhvgi atqgdnglmv
301 pvlrhaeags lwanageisr lanaarnnka sreelsgsti tltslgalgg ivstpvvntp
361 evaivgvnrm verpvvidgq ivvrkmmnls ssfdhrvvdg mdaalfiqav rglleqpacl
421 fve (SEQ ID NO:51)
```

```
   1 tcactccacg aacaggcagg cgggttgttc gagcaggcca cgcacggcct ggatgaacag
  61 ggcggcgtcc atgccatcga ccacgcggtg gtcgaacgag ctggacaggt tcatcatctt
 121 gcgcacgacg atctggccat caatcaccac cggtcgttcg accatgcggt tgaccccgac
 181 gattgccact tccgggtgt tgaccaccgg cgtgctgaca atgccaccca aggcgccgag
 241 gctggtcagg gtgatggtcg agccggacag ctcctcgcgg ctggccttgt tgttacgtgc
 301 agcgttggcc aggcgcgaaa tctcgccggc attggcccac aggctgcccg cttcggcgtg
 361 gcgcagcacg ggtaccatca ggccgttgtc accctgggtg gcaatgccca catgcaccgc
 421 gccatggcgg gtgatgatct gcgcttcgtc gtcgtaggtc gcgttgatct gcgggaagtc
 481 acgcagcgcc acgacgaggg cgcgcaccag gaatggcagc aaggtcagtt tgccgcggct
 541 gtcgccgtgc ttgctgttga gttgctggcg cagggcttcc agggcggtga cgtcgatttc
 601 ctcgacataa ctgaagtgcg cgacccggcg tttggcgtcc tgcatgcgct gggcgatctt
 661 gcggcgcagg ccgatcaccg gcacctgctc gctgtcggtg cgcttggcat aaccatcagg
 721 tgcttgcccg gcattgcttt gcggcttgct catgaaggcg tcgaggtctt cgtgcagaat
 781 gcgcccggcc gggccgctac catgcacata acgcagttcg ataccggcgt ccagggcgcg
 841 tttgcgcacg gccggcgagg ccagcggctt gtcgcccggc tggcgcggca cgatgggcgc
 901 agcttcgtgg ttggcgggcg cctggtacac ggcgggtttt acgtctttct gcggttccgg
 961 cttggctgca atcggggcgg ccggggcctc taccggtttt ggctgaggca cgtccacatg
1021 gttgccgctg ccttccactt cgatgcggat cagttcgcta ccgaccgcca tcacttcccc
1081 gggctggcca cccagggcca acaccttgcc gctgaccggc gaggggattt ccacggtggc
1141 cttgtcggtc atgacgtcgg ccaccacctg gtcctcggcg atgatgtcgc cgaccttgac
1201 gaaccattcc accaactcga cctgcgcgat gccttcgcca atgtccggca tcttgatgac
1261 gtgcgtgccc at (SEQ ID NO:52)
```

FIG. 2C cont'd

*Listeria monocytogenes 08-5578*: YP_003413624

```
  1 mavekitmpk lgesvtegti sswivkpgdt vekydaiaev ltdkvtaeip ssfsgtikei
 61 laeedetlev gevictiete eassssepvve aeqtepktpe kqetkqvkla eapasgrfsp
121 aviriagenn idistvegtg kggritrkdl lqviengpva pkreevksap qekeatpnpv
181 rsaagdreip ingvrkaiak hmsvskqeip hawmmvevda tglvryrntv kdsfkkeegy
241 sltyfaffik avaqalkefp qlnstwagdk iiehaninis iaiaagdlly vpviknadek
301 sikgiareis elagkarngk lsqadmeggt ftvnstgsfg svqsmgiinh pqaailqves
361 ivkrpviidd miavrdmvnl clsidhrild gllagkflqa ikanvekisk entaly (SEQ
ID NO:53)
```

```
   1 gtggcagttg aaaaaatcac catgcccaaa ttaggggaaa gtgtaacaga aggaacgatt
  61 agttcatggt tagttaaacc aggcgataca gtagaaaaat atgatgctat cgcggaagtt
 121 ttaacagata aagtaacagc tgaaatccca tcatccttta gtggcactat caaagaaatt
 181 ttagcagagg aagatgaaac actagaagta ggcgaagtta tttgtaccat cgaaacagaa
 241 gaggctagta gttcagagcc tgtagttgaa gcagaacaaa cagaaccaaa aactccagaa
 301 aaacaagaaa caaaacaagt gaaattagca gaagcaccag ccagtggaag attttcacca
 361 gcggtactgc gtattgctgg agaaaacaat attgatttat caaccgtaga aggcacaggt
 421 aaaggtggcc gaattacaag aaaagattta cttcaagtaa ttgaaaatgg tccagtagct
 481 ccgaaacgcg aggaagtgaa gtctgctcca caagaaaaag aagcgacgcc aaatcctgta
 541 cgttcagcag caggtgacag agaaatccca atcaatggtg taagaaaagc gattgctaaa
 601 catatgagcg tgagtaaaca agaaattccg catgcttgga tgatggtgga agtagatgca
 661 actggtcttg ttcgctatcg taatacagtt aaagacagct ttaaaaaaga agaaggttat
 721 tcattaactt atttcgcctt tttcatcaaa gccgttgcac aagcattgaa agaattcccg
 781 caacttaaca gcacgtgggc aggcgataaa attattgagc atgcgaatat caatatttcg
 841 attgcgattg cagctggcga tttattgtat gtgccagtta ttaaaaatgc ggacgaaaaa
 901 tccattaaag gtattgctcg cgaaataagt gaactagctg gaaaagcgcg taatggtaaa
 961 ctgagccaag ccgatatgga aggtgggact ttcactgtaa atagtactgg ttcatttggc
1021 tctgttcaat caatggggat tattaaccac ccacaagccg ctattcttca agtggaatcc
1081 attgttaagc gcccagtcat tattgacgat atgattgctg tacgagatat ggtcaaccta
1141 tgtctatcca tcgatcatcg tattttagac ggcttactag caggtaaatt cttacaagca
1201 attaaagcca atgtcgaaaa gatttctaaa gaaaatacag cgttgtatta a (SEQ ID
NO:54)
```

*Streptomyces avermitilis MA-4860*: NP_825541

```
  1 maqvlefklp dlgeglteae ivrwlvqvgd vvaidqpvve vetakamvev pcpyggvvta
 61 rfgeegtelp vgspiltvav gapssvpaas slsgatsass assvssddge ssgnvivgyg
121 tsaaparrrr vrpgqaapvv tataaaaatr vaapersdgp vpvisplvrr larengldlr
181 alagsgpdgl ilrsdveqal raaptpaptp tmppaptpap tpaaaprgtr iplrgvrgav
241 adklsrsrre ipdatcwvda datalmharv amnatggpki slialllaric taalarfpel
301 nstvdmdare vvrldqvhlg faaqterglv vpvvrdahar daeslsaefa rlteaartgt
361 ltpgeltggt ftlnnygvfg vdgstpiinh peaamlgvgr iipkpwvheg elavrqvvql
421 sltfdhrvcd ggtaggflry vadcveqpav llrtl (SEQ ID NO:55)
```

```
  1 atggcccagg tgctcgagtt caagctcccc gacctcgggg agggcctgac cgaggccgag
 61 atcgtccgct ggctggtgca ggtcggcgac gtcgtggcga tcgaccagcc ggtcgtcgag
121 gtggagacgg ccaaggcgat ggtcgaggtg ccgtgcccct acgggggcgt ggtcaccgcc
181 cgcttcggcg aggagggcac ggaactgccc gtgggctcac cgctgttgac ggtggctgtc
241 ggagctccgt cctcggtgcc cgcggcgtcc tcgctgtccg ggcgacatc ggcgtcctcc
301 gcgtcctcgg tgtcatcgga cgacggcgag tcgtccggca acgtcctggt cggatacggc
```

FIG. 2C cont'd 361 acgtcggccg cgcccgcgcg ccggcggagg gtgcggccgg gccaggcggc acccgtggtg
421 acggcaactg ccgccgcggc cgccacgcgc gtggcggctc ccgagcggag cgacggcccc
481 gtgcccgtga tctccccgct ggtccgcagg ctcgcccggg agaacggcct ggatctgcgg
541 gcgctggcgg gctccgggcc cgacgggctg atcctgaggt cggacgtcga gcaggcgctg
601 cgcgccgcgc ccactcctgc ccccaccccg accatgcctc cggctcccac tcctgccccc
661 acccccgccg cggcaccccg cggcacccgc atccccctcc gaggggtccg cggtgccgtc
721 gccgacaaac tctcccgcag ccggcgtgag atccccgacg cgacctgctg ggtggacgcc
781 gacgccacgg cactcatgca cgcgcgcgtg gcgatgaacg cgaccggcgg cccgaagatc
841 tccctcatcg cgctgctcgc caggatctgc accgccgcac tggcccgctt ccccgagctc
901 aactccaccg tcgacatgga cgcccgcgag gtcgtacggc tcgaccaggt gcacctgggc
961 ttcgccgcgc agaccgaacg gggctcgtc gtcccggtcg tgcgggacgc gcacgcgcgg
1021 gacgccgagt cgctcagcgc cgagttcgcg cggctgaccg aggccgcccg gaccggcacc
1081 ctcacacccg gggaactgac cggcggcacc ttcacgttga acaactacgg ggtgttcggc
1141 gtcgacggtt ccacgccgat catcaaccac cccgaggcgg ccatgctggg cgtcggccgc
1201 atcatcccca agccgtgggt gcacgagggc gagctggcgg tgcggcaggt cgtccagctc
1261 tcgctcacct tcgaccaccg ggtgtgcgac ggcggcacgg caggcggttt cctgcgctac
1321 gtggcggact gcgtggaaca gccggcggtg ctgctgcgca ccctgtag (SEQ ID
NO:56)

*Micrococcus luteus NCTC 2655*: YP_002956767

1 msermtfgra inrglhrala ddpkvllmge digalggvfr itdglqaefg edrvldtpla
61 esgivgtaig lamrgyrpvv eiqfdgfvyp afdqivanla klrartrgav pmpvtiripf
121 gggigspehh sespeayflh taglrvvsps spqegydlir aaiasedpvv ylepkrryhd
181 kgdvdlgvai ppmsparilr egrdatlvay gplvktalqa aevaaeegve vevvdlrsls
241 pldtglvess vrrtgrlvva heasrtgglg aelvatvaer afhwleappv rvtgmdvpyp
301 psklehlhlp dldrildgld ralgrpnsld svdafaapet aeqflaaqna geetr (SEQ
ID NO:57)

1 gtgagcgagc gcatgacctt cggccgtgcg atcaaccgcg gcctgcaccg tgccctggcc
61 gacgacccca aggtcctgct catgggcgag gacatcggcg ccctcggcgg cgtgttccgc
121 atcaccgacg gcctgcaggc cgagttcggc gaggaccggg tgctcgacac cccgctggcc
181 gagtccggca tcgtgggcac ggccatcggc ctggcgatgc gcggctaccg gcccgtcgtc
241 gagatccagt tcgacggctt cgtgtacccg gcgttcgacc agatcgtggc gaacctggcc
301 aagctgcgcg cccgcacccg cggcgccgtg ccgatgccgg tgaccatccg catccccttc
361 ggcggcggca tcggctcccc ggagcaccac tccgagtcgc ccgaggccta cttcctgcac
421 accgcgggtc tgcgcgtggt ctccccgtcc tccccgcagg aggggtacga cctcatccgc
481 gccgcgatcg cctcggagga cccggtggtc tacctcgagc ccaagcgtcg ctaccacgac
541 aagggcgacg tggacctggg cgtcgcgatc ccgccgatga gcccggcccg catcctgcgc
601 gagggccgtg acgccacgct cgtggcctac ggcccgctcg tgaagaccgc cctgcaggcc
661 gccgaggtgg cggccgagga gggtgtcgag gtcgaggtgg tcgacctgcg cagcctgtcc
721 ccgctggaca ccggcctcgt cgagtcctcg gtgcggcgca ccggtcggct cgtcgtggcg
781 cacgaggcct cccgcacggg cggcctcggc gccgagctcg tggccacggt ggccgagcgc
841 gcgttccatt ggctcgaggc ccccgccggtg cgcgtcaccg gcatggacgt gccctacccg
901 ccgtccaagc tcgagcacct gcacctgccg gacctcgacc gcatcctcga cggcctggac
961 cgtgctctgg gccggccgaa ttcgctggac tccgtggacg cgttcgccgc ccccgagacc
1021 gccgagcagt tcctcgccgc ccagaacgcc ggggaggaga cccgatga (SEQ ID
NO:58)

FIG. 2C cont'd

*Staphylococcus aureus A8819*: ZP_06816443

```
  1 meitmpklge svhegtieqw lvsvgdhide yeplcevitd kvtaevpsti sgtiteilve
 61 agqtvaidti ickietadek tnetteeiqa kvdehtqkst kkasatveqt ftakqnqprn
121 ngrfspvvfk lasehdidls qvvgsgfegr vtkkdimsvi enggttaqsd kqvqtkstsv
181 dtssnqssed nsenstipvn gvrkaiaqnm vnsvteipha wmmievdatn lvntrnhykn
241 sfknkegynl tffaffvkav adalkaypll nsswqgneiv lhkdinisia vadenklyvp
301 vikhadeksi kgiareintl atkarnkqlt tedmqggtft vnntgtfgsv ssmgiinhpq
361 aailqvesiv kkpvvindmi airsmvnlci sidhrildgl qtgkfmnhik qrieqytlen
421 tniy (SEQ ID NO:59)
```

```
   1 ctaatatata tttgtatttt ctaaagtata ctgttcgata cgctgtttaa tatgattcat
  61 aaatttacca gtttgtaaac catctaaaat gcgatgatct attgaaatac ataaatttac
 121 catacttcga attgcaatca tatcattaat tactactggc tttttaacga ttgattctac
 181 ttgtaatatc gctgcttgag ggtgatttat aatccccatt gatgatactg aaccaaatgt
 241 accagtatta ttaactgtaa atgttccacc ttgcatatct tcagttgtca attgcttatt
 301 acgcgctttt gttgctaaag tattaatttc tctagctata cctttgattg acttttcgtc
 361 tgcatgctta atcacaggta cgtataattt attttcatca gcaacagcaa ttgaaatatt
 421 aatgtcttta tgtaagacaa tttcatttcc ttgccagcta ctatttaata aaggatatgc
 481 ttttaaagca tctgctacag cttttacaaa gaaagcaaag aacgttagat tatatccttc
 541 tttatttta aagctgtttt tataatgatt tctcgtattc acaagatttg tagcatctac
 601 ttcaatcatc atccatgcat gtggaatctc tgttacacta ttaaccatat tttgcgcaat
 661 tgctttacgc acaccattta ctggtattgt gctgttttca ctattgtctt cagatgattg
 721 gttacttgat gtatctactg atgttgattt tgtttgaact tgtttgtcag attgagctgt
 781 ggtaccacca ttttcaataa ctgacattat atccttctta gttacacgac cttcaaatcc
 841 actacctaca acttgtgata aatcaatgtc atgctctgaa gcgagtttaa atacaacagg
 901 tgaaaagcga ccattattac gaggttgatt ttgtttagca gtaaatgtct gttccactgt
 961 tgcactagct tttttagtag atttctgagt atgctcatcc acttttgctt gtatctcttc
1021 agttgtttca tttgtctttt catcagcagt ttcaatttta cagataattg tatcaatagc
1081 tactgtctgc cccgcttcaa ctaaaatttc tgtaattgtt cctgatatcg tggaagggac
1141 ttcagctgtc actttatctg taataacttc acataatggt tcatattcat caatatgatc
1201 accaacagaa actaaccatt gttcaatggt accttcatga acactctcac ctaacttagg
1261 cattgttatt tccat (SEQ ID NO:60)
```

*Streptococcus mutans UA159*: NP_720602.1

```
  1 maveiimpkl gvdmqegeii ewkkqegdev kegeilleim sdktnmeiea edsgvllkiv
 61 kgngqvvpvt evigyigqag evleiadvpa stvpkensaa paektkamss ptvaaapqgk
121 iratpaarka ardlgvnlnq vsgtgakgrv hkedvesfka aqpkatplar kiaidkgidl
181 asvsgtgfgg kiikedilnl feaaqpvndv sdpakeaaal pegvevikms amrkavaksm
241 vnsyltaptf tlnydidmte mialrkklid pimektgfkv sftdliglav vktlmkpehr
301 ylnaslinda teielhqfvn lgiavgldeg llvpvvhgad kmslsdfvia skdvikkaqt
361 gklkatemsg stfsitnlgm fgtktfnpii nqpnsailqv gatiqtptvv dgeikirpim
421 alcltidhrl vdgmngakfm vdlkklmenp ftlli (SEQ ID NO:61)
```

```
  1 atggcagtcg aaattattat gcctaaactt ggtgttgata tgcaggaagg cgaaatcatc
 61 gagtggaaaa aacaagaagg tgatgaggtc aaagaagggg agatcctcct tgagattatg
121 tctgacaaga ccaatatgga aatcgaagct gaggattcag gtgtcctgct taagattgtt
181 aaaggaaatg gtcaagttgt tcctgtaact gaggtcattg gttatattgg tcaagcaggt
241 gaagttcttg aaatagctga tgttcctgca agtacagttc ctaaagaaaa tagtgcagca
```

FIG. 2C cont'd

```
 301 cctgctgaaa aaacaaaagc aatgtcttct ccgacagttg cagcagcccc tcaaggaaag
 361 attcgagcaa caccagcagc tcgtaaggcg gctcgtgatc tgggagttaa cctgaatcag
 421 gtttcaggga caggcgctaa aggccgtgtt cacaaggaag atgttgaaag ctttaaagca
 481 gctcagccta aagcaacacc attagctagg aaaattgcta tagataaagg tattgatcta
 541 gccagtgtct caggaacagg ttttggcggc aaaattatca aggaagatat tttaaatctg
 601 tttgaggcag ctcagcctgt taatgatgtg tcagatcctg ctaaagaagc agctgcctta
 661 ccagagggtg ttgaagtcat taagatgtct gccatgcgta aggcagtggc taaaagcatg
 721 gtcaattctt acctgacagc tccaactttt actctcaatt atgacattga catgactgag
 781 atgattgcgt tgcgtaaaaa gttaattgat cctatcatgg aaaaaacagg ttttaaagtt
 841 agcttcacag atttgattgg tctggcagtc gtaaaaacct taatgaaacc agaacatcgt
 901 tacctcaatg cttcactcat taatgacgcg actgagattg aacttcatca atttgttaac
 961 cttggtatcg ccgttggact tgatgaagga ctgttagtac ctgttgttca tggtgcagat
1021 aagatgagct tgtcagattt tgttatagct tcaaaggatg tcattaagaa agctcagacc
1081 ggtaaattaa aagccactga aatgtctggt tcaacctttt ccattacaaa cttggggatg
1141 tttggcacta agactttcaa ccccattatc aatcagccaa attcggctat tttgggtgta
1201 ggagcaacta tccaaacgcc aactgttgtg gatggtgaaa ttaagattcg tccaatcatg
1261 gcactgtgct tgaccatcga tcaccgcttg gttgatggca tgaacggcgc taagttcatg
1321 gttgatctta aaaaactgat ggaaaatcca tttacattat tgatttga (SEQ ID
NO:62)
```

P-x-V-(L,R)-x-(R,L)-A-(x)3-G-x-(D,E)-L [SEQ ID NO:63]
(G,P)-(S,T)-G-(A,P)-x-G-x-I [SEQ ID NO:64]
(V,I)-P-(L,V)-x-G-(L,V)-R-x-(A,K)A-(x)2-(L,M)-(x)2-(A,S) [SEQ ID NO:65]
G-(G,S)-T-x-T-(x)2-(N,S)-x-G-x-(F,L)-G [SEQ ID NO:66]
N-x-P-E-x-A-(I,M)-(L,V)-x-V-(x)2-(I,M)-(x)3-P-x-V [SEQ ID NO:67]
L-x-(L,S)-(S,T)-F-(D,L)-H-R-(V,L)-x-D-G [SEQ ID NO:68]

wherein, the amino acid residues in each of the brackets indicate alternative amino acid residues at the particular position, each x indicates any amino acid residue, and each n in "x(n)" indicates the number of x residues in a contiguous stretch of amino acid residues.

FIG. 2D

BKD E3 subunit homologs

*Bacillus subtillis 168*: ZP_03592173

```
  1 mateydvvii gggtggyvaa iraaqlglkt avvekeklgg tclhkgcips kallrsaevy
 61 rtareadqfg vetagvslnf ekvqqrkgav vdklaagvnh lmkkgkidvy tgygrilgps
121 ifsplpgtis vergngeend mlipkqviia tgsrprmlpg levdgksvlt sdealqmeel
181 pqsiiivggg vigiewasml hdfgvkvtvi eyadriipte dleiskemes likkkgiqfi
241 tgakvlpdtm tktsddisiq aekdgetvty saekmlvsig rqaniegigl entdivteng
301 misvnescqt keshiyaigd viggiqlahv ashegiiave hfaglnphpi dptlvpkciy
361 sspeaasvgl tedeakangh nvkigkfpfm aigkalvyge sdgfvkivad rdtddilgvh
421 migphvtdmi seaglakvld atpwevgqti spasnaf (SEQ ID NO:69)
```

```
  1 tcagaaagcg ttggatgcgg gtgaaatcgt ttgcccgacc tccccacggtg ttgcgtccag
 61 cactttggca agacccgctt cagaaatcat gtcggtgaca tgcgggccaa tcatatgaac
121 gccgagaata tcatctgtat ctcggtcagc cacgatttg acaaaaccgt cgctttcacc
181 gtatacaagc gcttttccaa tcgccataaa tgggaacttg ccgattttga cattatgccc
```

FIG. 2D cont'd 241 gttcgccttt gcttcgtctt cggttaagcc gacactggca gcttcagggc ttgagtaaat
301 gcacttcggc acaagcgtcg gatcaagcgg atgcggattg agacctgcaa aatgctcaac
361 agcaataatt ccctcatgtg aagcaacgtg agctaactgc aggccaccga ttacgtctcc
421 gattgcataa atatgagatt ccttcgtttg gcagctttca ttgactgaaa tcatgccatt
481 ttcagtaaca atatcggtgt tctctaggcc gatgccttcg atatttgcct gtctgccgat
541 ggaaacaagc atttctcag cagaataggt aacggtttct ccgtcttttt ccgcttgtat
601 gctgatatcg tctgatgttt ttgtcattgt gtcaggcagc acttttgccc ctgttatgaa
661 ctggatgcct tttttcttaa gaagactttc catttctttt gaaatctcta gatcttcagt
721 cggcaatatg cgatccgcgt attcaataac cgttacctta acgccaaaat catgaagcat
781 agacgcccat tcgataccga taaccctcc gccgacaatg atgattgact gtggcagctc
841 ctccatttgg agcgcctcat ctgaagtcag tacagactta ccgtccactt caagacccgg
901 aagcattctc ggtcttgatc ctgttgcaat gatcacttgt ttcgggatca gcatgtcatt
961 ttcttcgcca tttccccgct caacagaaat tgttcccggc agcggagaga agattgacgg
1021 tccaaggata cgtccatatc cggtgtacac gtcaattttt cctttttca ttaaatgatt
1081 tacacccgct gcaagcttat caacaacggc ttgcttacgc tgctgcactt tttcaaagtt
1141 gagggacacg ccagccgttt ccactccgaa ttgatcggct tcacgagctg tccggtatac
1201 ctctgcgctt ctaagcagcg ctttactcgg gatacagcct ttatgcagac atgttccccc
1261 gagtttttcc ttttccacaa cggctgtttt taagccgagc tgagcggctc tgatggccgc
1321 aacataaccg ccggtaccgc cgcccagaat gactacgtca tactcagttg ccat (SEQ ID NO:70)

*Streptomyces avermitilis MA-4860*: NP_827200

1 mandastvfd lvilgggsgg yaaalrgaql gldvaliekd kvggtclhrg ciptkallha
61 geiadqares eqfgvkatfe gidvpavhky kdgvisglyk glqgliasrk vtyiegegrl
121 ssptsvdvng qrvqgrhvll atgsvpkslp glaidgnrii ssdhalvldr vpesaivlgg
181 gvigvefasa wksfgadvtv ieglkhlvpv edensskIle rafrkrgikf nlgtffskae
241 ytqngvkvtl adgkefeaev llvavgrgpv sqglgyeegg vamdrgyvlv deymrtnvpt
301 isavgdlvpt lqlahvgfae gilvaerlag lktvpidydg vprvtychpe vasvgiteak
361 akeiygadkv valkynlagn gkskilntag eiklvqvkdg avvgvhmvgd rmgeqvgeaq
421 liynwealpa evaqlihahp tqneamgeah lalagkplhs hd (SEQ ID NO:71)

1 tcagtcgtgc gagtgcagcg gcttgcccgc gagggccagg tgggcctcgc ccatcgcttc
61 gttctgcgtc gggtgggcgt ggatgagctg ggcgacctcg gccggcagcg cctcccagtt
121 gtagatcagc tgggcttcgc cgacctgctc gcccatacgg tcaccgacca tgtggacgcc
181 gaccacggca ccgtccttca cctggacgag cttgatctcg cccgcggtgt tgaggatctt
241 gctcttgccg ttgcccgcca ggttgtactt cagagcgacg accttgtccg cgccgtagat
301 ctccttggcc ttggcctcgg tgatgcccac ggaggcgacc tcggggtggc agtacgtcac
361 ccgcggcacg ccgtcgtagt cgatcgggac ggtcttcaga ccggccagac gctccgccac
421 caggatgccc tcggcgaagc cgacgtgcgc gagctggagc gtcgggacca ggtcaccgac
481 ggcggagatg gtcgggacgt tcgtccgcat gtactcgtcg accaggacgt agccgcggtc
541 catggcgacg ccctgctcct cgtagccgag gccctgccag accgggccgc ggccgacggc
601 gacgagcagg acctcggcct cgaactcctt gccgtcggcg agggtgacct tgacaccgtt
661 ctgggtgtac tcggccttcg agaagaaggt gcccaggttg aacttgatgc cgcgcttgcg
721 gaacgcgcgc tcaagaagct tggaggagtt ctcgtcctcg accgggacga ggtgcttgag
781 gccctcgatc accgtcacgt cggctccgaa ggacttccac gcggaggcga actcgacgcc
841 gatgacgccg ccgccgagca cgatcgcgga ctccgggacg cggtccagga ccagcgcgtg
901 gtcggaggag atgatgcggt tgccgtcgat cgccaggccc ggcagcgact tcggcacgga
961 gccggtcgcc aggagcacgt ggcggccctg gacgcgctgg ccgttcacgt cgacggaggt
1021 cggggaggac agacggccct caccctcgat gtacgtcacc ttgcgggagg cgatcagccc
1081 ctgcagaccc ttgtacaggc ccgagatgac cccgtccttg tacttgtgga cggccggtac
1141 gtcgatgccc tcgaaggtgg ccttgacgcc gaactgctcg ctctcgcggg cctggtcggc

FIG. 2D cont'd 1201 gatctcgccc gcgtgcagca gcgccttggt ggggatgcac ccacggtgca ggcaggtacc
1261 gccgaccttg tccttctcga tcagggcgac gtccaggccc agctgcgctc cgcgcagggc
1321 cgcggcgtaa ccaccgctac caccgccgag gatcactagg tcgaaaacgg tgctggcgtc
1381 gttcgccac (SEQ ID NO:72)

*Pseudomonas putida F1:* YP_001266792

1 mqqiiqttll iigggpggyv aairagqlgi ptvlveqqal ggtclnigci pskalihvae
61 qfhqasrfte psplgisvas prldiggqsvt wkdgivdrlt tgvaallkkh gvkvvhgwak
121 vldgkqvevd ggriqcehll latgstsvel pmlplggpvi sstealapka lpqhlvvvgg
181 gyiglelgia yrklgaqvsv veareriIpt ydseltapva eslkklgial hlghsvegye
241 ngcllasdgk ggqlrieadq vlvavgrrpr tkgfnlecld lkmngtaiai derchtsmhn
301 vwaigdvage pmlahramaq gemvaeiiag karrfepaai aavcftdpev vvvgktpeqa
361 sqqaldciva qfpfaangra msiesksgfv rvvarrdnhl ivgwqavgva vselstafaq
421 slemgacled vagtihahpt lqeavqeaal ralghalhi (SEQ ID NO:73)

1 tcagatatgc aaggcgtggc ccaacgcgcg tagggcggct tcttgcaccg cttcacccaa
61 cgtggggtgg gcatgaatgg tgccggccac atcttccagg cacgcgccca tctccagcga
121 ttgggcaaac gcggtggaca gctcggagac cgccacgcca accgcctgcc aacccacgat
181 caggtggttg tcacggcgcg ccaccacccg cacgaaaccg cttttcgact ccaggctcat
241 ggcccggcca ttggcggcaa acgggaactg cgcgacgatg cagtccaggg cctgctggct
301 ggcttgttcc ggggtcttgc cgaccaccac cacttccggg tcggtaaagc acacggcggc
361 aatcgctgcc ggctcgaagc gtcgggcctt gccggcgatg atttcggcga ccatctcgcc
421 ttgggccatg gcccggtgcg ccagcatcgg ttcgccagcg acgtcgccaa tggcccagac
481 gttgtgcatg ctggtatgac agcgctcgtc gatggcaatg gcggtgccgt tcatcttcag
541 gtccaggcat tccaggttga agcccttggt gcgtggccgg cggcccacgg ccaccagtac
601 ctgatcggct tcaagacgca gttgcccacc cttgccgtcg ctggccagca ggcagccatt
661 ttcgtagccc tcgacgctgt ggcccaggtg caacgcgatg cccagtttct tcagcgactc
721 ggccaccggg gcggtcaatt cgctgtcgta ggtcggcagg atgcgttcgc gcgcttccac
781 cacactcacc tgtgcaccca gcttgcgata ggcaatgccc agctccaggc cgatatagcc
841 accgccgacc accaccaggt gttgcggcag ggctttcggc gccagggctt cggtcgagga
901 aatcaccggg ccacccagcg gcagcatcgg cagttcgaca ctggtggaac cggtcgccag
961 caacagatgc tcgcactgga tacgctggcc atcgacctcg acctgcttgc cgtccagtac
1021 cttggcccag ccatgcacca ctttcacccc gtgctttttc agcaaggcgg caacaccggt
1081 ggtcagacgg tcgacaatgc cgtccttcca ggtgacgctc tggccgatgt ccaggcgcgg
1141 cgaagccacg ctgatgccca gcggcgaggg ttcggtaaag cgcgaggctt ggtgaaactg
1201 ctcggccacg tggatcagcg ccttggacgg gatgcagccg atgttcaggc aggtgccgcc
1261 cagtgcctgg ccttccacca gtacggtagg aatgcccagt tgcccggcgc ggatggctgc
1321 tacatagccg ccagggccgc cgccgatgat caacagggta gtctggataa tctgttgcat
(SEQ ID NO:74)

*Listeria monocytogenes 08-5578*: YP_003413621

1 makeydvvil gggtggyvaa iqaakngqkv avvekgkvgg tclhrgcipt kallrsaevl
61 qtvkkasefg isvegtagin flqaqerkqa ivdqlekgih qlfkqgkidl fvgtgtilgp
121 sifsptagti svefedgsen emlipknlii atgskprtls gltideehvl ssdgalnlet
181 lpksiiivgg gvigmewasm mhdfgvevtv leyadrilpt edkevakela rlykkkklnm
241 htsaevqaas ykktdtgvei kaiikgeeqt ftadkilvsv grsattenig lqntdiaten
301 gfiqvndfyq tkeshiyaig dciptiqlah vameegtiaa nhiagkaaek ldydlvprci
361 ytsteiasvg iteeqakerg hevkkgkfff rgigkalvyg esdgfikiia dkktddilgv

FIG. 2D cont'd 421 smigphvtdm iseaalaqvl natpwevgnt ihphptlses freaalavdg naihg (SEQ ID NO:75)

```
   1 gtggcaaaag aatatgatgt agttattctt ggcggaggaa ctggcggtta cgttgcagca
  61 attcaagcag ctaagaatgg ccagaaagta gccgtcgttg aaaaagggaa agttggagga
 121 acgtgtcttc accgtgggtg tattccaacg aaagcgttat tacgttcagc ggaagttcta
 181 caaacggtaa aaaaagcaag tgaatttggt atttctgtag aaggaactgc cggaatcaat
 241 tttttacaag cacaagaacg aaaacaagca atagtagatc aattagaaaa aggtattcac
 301 caattattta aacaagggaa aattgacttg tttgttggaa cgggaactat tttgggacca
 361 tcaatttttt caccaacagc tggaacaatt tcagttgaat tcgaagatgg ttctgaaaat
 421 gaaatgctaa ttcctaaaaa cttaattatc gcaactgggt ccaaaccgcg cacattaagc
 481 ggtttaacaa tcgatgagga acatgtttta tcatctgacg gcgcgcttaa cctagaaact
 541 ttaccaaaat caattattat tgttggcggt ggggttatcg gaatggaatg ggcttcgatg
 601 atgcatgatt tcggtgtaga agttacggtg ctagaatatg cagaccgaat tttgccaaca
 661 gaagataaag aagtggccaa agaattagca agactttata aaaagaaaaa attaaacatg
 721 catacatctg ctgaagttca agcagctagt tataaaaaaa cagatactgg tgtggaaatt
 781 aaagcaatca ttaaaggcga agagcagact ttcacagcag ataaaattct tgtttcagtt
 841 ggtcgttctg ctactacaga aaacatcggc ttacaaaata cagatatcgc gaccgaaaac
 901 ggctttatcc aagtaaatga tttttaccaa acaaaagaaa gtcacatcta tgcgattgga
 961 gactgcattc caacgattca actcgcgcac gttgcaatgg aagaaggaac aattgcagcc
1021 aaccatattg ccggaaaagc agccgaaaaa cttgactacg acttagttcc ccgctgtatt
1081 tatacttcta cagaaatcgc aagtgtcggt atcacagaag aacaagcaaa agaacggggt
1141 catgaagtga aaaaaggcaa attcttcttc cgtggtatcg ggaaagcgct cgtttacgga
1201 gaatcagatg gcttcattaa aattattgca gataaaaaaa cagacgatat cttaggcgtg
1261 agcatgattg gaccacacgt tacggacatg attagcgaag ccgctttagc acaagtttta
1321 aatgcaacgc cgtgggaagt gggcaacacg attcacccgc acccaacttt atcagaaagt
1381 tttagagaag ctgcccttgc tgtggatggc aatgcaattc acggttaa (SEQ ID
NO:76)
```

*Streptomyces avermitilis MA-4860*: NP_823330

```
   1 menmntpdvi vigggtggys aalraaalgl tvvlaerdkv ggtclhrgci pskamlhaae
  61 lvdgiaeare rwgvkatldd idwpalvatr ddivtrnhrg veahlaharv rvvrgsarlt
 121 gprsvrvega pddlpggagd ftarrgivla tgsrprtlpg lvpdgrrvvt sddalfapgl
 181 prsvlviggg aigveyasfh rsmgaevtlv eaadrivple dvdvsrhltr glkkrgidvr
 241 agarlldael leagvrarvr tvrgeirtle aerllvavgr apvtdgldla aaglatderg
 301 fvtpsdwdrl etavpgihvv gdllpppslg lahasfaegl svaetlaglp sapvdyaavp
 361 rvtysspqta svglgeaear arghevdvnt mpltavakgm vhgrggmvkv vaeegggqvl
 421 gvhlvgphvs emiaesqliv gwdaqpsdva rhihahptls eavgetfltl agrglhqq
(SEQ ID NO:77)
```

```
   1 gtggagaaca tgaacacacc ggacgtcatc gtcatcggag gcggcaccgg cggctacagc
  61 gccgccctgc gcgccgccgc cctcggtctg accgtggtgc tcgccgagcg ggacaaggtc
 121 ggcggaacct gtctgcaccg tggctgcatt ccgagcaagg cgatgctgca cgccgcagaa
 181 ctggtcgacg gcatcgccga ggcgcgcgag cgctgggggg tgaaggccac gctggacgac
 241 atcgactggc ctgcgctcgt cgccacgcgc gacgacatag tgacgcgcaa ccaccgcggc
 301 gtggaggcgc acctcgccca cgcgcgcgtg cgcgtcgtcc ggggcagtgc ccggctgacc
 361 ggtccgcgca gcgtccgcgt cgagggtgct ccggacgacc tgccgggcgg cgcgggcgac
 421 ttcaccgcgc gccggggcat cgtcctggcg accggctcac ggccgcgtac gctcccgggg
 481 ctcgtgccgg acgggcggcg cgtggtgacg agcgacgacg cgctgttcgc gcccggcctc
 541 ccccgctccg tgctggtcct gggcggcggt gcgatcgggg tcgagtacgc ctcgttccac
 601 cgctccatgg gtgcggaggt cactctcgtc gaggccgccg accggatcgt gccgctcgaa
```

FIG. 2D cont'd

```
 661 gacgtcgacg tcagccgtca tctgacgcgc ggtctgaaga agcgcggcat cgatgtgcgg
 721 gcgggggcgc ggctgctcga cgccgaactc ctggaggcgg gggtacgcgc gcgcgtacgc
 781 accgtgcggg gcgagatccg cacactggag gccgagcggc tcctggtggc ggtcgggcgg
 841 gcgccggtca ccgacgggct ggacctggcc gccgcgggcc tggcgacgga cgagcggggt
 901 tttgtgacgc cgtccgactg ggaccgtctg gagaccgcgg tgcccggcat ccacgtggtg
 961 ggcgacctgc tgccaccgcc gtccctggga ctggcccacg cgtcgttcgc cgagggcctg
1021 tcggtggccg agacgctggc cgggctgccg tccgcgcccg tggactacgc ggccgtgccc
1081 cgggtcacgt actcgtcgcc gcagaccgcc tccgtggggc tgggcgaggc ggaggcacgc
1141 gcgcgtggac acgaggtgga cgtcaacacg atgccgctga ccgccgtcgc caagggcatg
1201 gtccacggcc ggggcgggat ggtgaaggtc gtcgccgagg agggcggcgg gcaggtgctc
1261 ggcgtgcatc tggtgggccc ccacgtgtcc gagatgatcg ccgagagcca gctgatcgtc
1321 ggctgggacg cacagccctc cgacgtggcc cggcacatcc acgcgcaccc cacgctgtcc
1381 gaggcggtcg gcgaaacgtt tctcacgctc gcgggacggg ggctgcatca gcagtga
(SEQ ID NO:78)
```

*Micrococcus luteus NCTC 2655*: YP_002956656

```
  1 mteenstfip sltiigggpg gyeaamvaak lgarvtlver qgvggaavlt dvvpsktlia
 61 aadsmrrvga svdlgvdlgg aevhadmgrv ghrilnlahe qssdiragle rvgvrvidgv
121 grvvgphevs vralddadag aepeiitsda ilvavgaspr elptavpdge rifnwkqvyn
181 ikelpehiiv vgsgvtgaef asaynrlgak vtlvssrdrv lpgedadaae ilekvfegng
241 lrvvsrsrae svertetgvr vhlsgegaed tpsiegshal vavggvpnta glglddvgvk
301 ladsghvlvd gvsrtsvpsi yaagdctgkl alasvaamqg riavahllgd alkplrphll
361 asniftspei atvgvsqaqv dsgqyqadvl rldfhtnpra kmsgaeegfv kifarqgsgt
421 viggvvvspr aseliyalal avthklhvdd ladtftvyps msgsiaeaar rlhvrv (SEQ
ID NO:79)
```

```
   1 gtgaccgagg aaaacagcac cttcatcccg tccctgacca tcatcggcgg cggccccggc
  61 ggctacgagg ccgccatggt ggccgcgaag ctgggcgccc gcgtgaccct ggtcgagcgc
 121 caggggggtgg gcggcgcggc cgtcctcacg gacgtggtcc cctccaagac gctgatcgcc
 181 gccgccgact cgatgcgccg cgtgggcgcc tccgtggacc tgggggtcga cctcggcggg
 241 gccgaggtcc acgcggacat gggccgggtc ggccaccgca tcctgaacct ggcccacgag
 301 cagtcctcgg acatccgcgc gggcctcgag cgggtcggtg tccgggtgat cgacggcgtg
 361 ggccgcgtcg tcggccccca cgaggtgtcc gtccgcgccc tcgacgacgc cgacgccggc
 421 gccgagcccg agatcatcac ctcggacgcg atcctcgtgg ccgtcggcgc gagtccccgg
 481 gagctgccca ccgccgtccc ggacggcgag cggatcttca actggaagca ggtctacaac
 541 ctcaaggagc tgcccgagca cctgatcgtc gtgggctccg gcgtcaccgg cgccgagttc
 601 gcctcggcct acaaccgcct cggcgccaag gtcaccctcg tctcctcgcg cgaccgcgtg
 661 ctccccggcg aggacgccga cgccgcagag ctgctcgaga aggtcttcga gggcaacggc
 721 ctcagggttg tctcccgctc ccgggccgag tcggtcgagc ggaccgagac cggcgtgcgc
 781 gtgcacctct ccggcgaggg ggccgaagac accccgtcga tcgagggctc ccacgcgctg
 841 gtggccgtcg gcggcgtgcc gaacacggcg ggcctcggcc tcgacgacgt gggcgtgaag
 901 ctggccgact ccggccacgt gctcgtggac ggcgtctccc gcacgtccgt gccgagcatc
 961 tacgcggcgg gcgactgcac gggcaagctc gccctcgcct cggtggcggc catgcagggg
1021 cgcatcgccg tggcccacct gctcggcgac gccctcaagc cgctgcgccc gcacctgctg
1081 gcctcgaaca tcttcacctc gccggagatc gccaccgtgg gcgtctcgca ggcgcaggtg
1141 gactccggcc agtaccaggc ggacgtgctg cgactggact tccacaccaa ccccgcgcc
1201 aagatgtccg gcgcggagga ggggttcgtg aagatcttcg cgcgtcaggg ctccggcacc
1261 gtgatcggcg gcgtggtggt ctcgccgcgc gcctccgagc tgatctacgc gctcgcgctc
1321 gcggtcacgc acaagttgca cgtggacgac ctcgcggaca ccttcaccgt gtacccgtcc
```

FIG. 2D cont'd 1381 atgtccgggt cgatcgcgga ggcggcgcgc cgcctccatg tgcgggtgtg a (SEQ ID NO:80)

*Staphylococcus aureus A8819*: ZP_06816446

```
  1 msekqydlvv lgggtagyva airasqlgkk vaiverqlig gtcihkgcip tksllksaev
 61 fqtvkqaamf gvdvkdanvn fenmlarked iinqmyqgvk hlmqhnhidi yngtgrilgt
121 sifspqsgti sveyedgesd llpnqfvlia tgsspaelpf lsfdhdkils sddilslktl
181 pssigiiggg vigmefaslm idlgvdvtvi eagerilpte skqasqllkk slsargvkfy
241 egiklsendi nvnedgvtfe issdiikvdk vllsigrkpn tsdiglnntk ikistsghil
301 tnefqqtedk hiyaagdcig klqlahvgsk egvvavdhmf egnpipvnyn mmpkciysqp
361 eiasiglnie qakaegmkvk sfkvpfkaig kavidshdan egysemvidq steeivginm
421 igphvtelin easllqfmng salelglttth ahpsisevlm elglkaesra ihv (SEQ ID
NO:81)
```

```
   1 ttatacgtga atagctctac tttctgcttt caatcctaat tccatcaaca cttcagagat
  61 ggaaggatgt gcgtgtgttg ttagtcctaa ttctaatgcc gagccattca tgaactgtaa
 121 cagtgatgcc tcattaatca attctgttac atgtggacca atcatattaa tacccacaat
 181 ttcttcagtt gattgatcaa tcaccatttc gctatacct tcgtttgcgt catggctatc
 241 aatcactgct ttaccaattg ctttaaatgg tactttaaaa cttttaactt tcattccctc
 301 tgcctttgct tgttcaatgt ttaaaccgat agaagcaatt tcaggttgtg aataaataca
 361 cttaggcatc atgttatagt ttactgggat tgggttcccc tcaaacatat gatcaacagc
 421 cacaacacct tcttttgatc caacatgtgc caattgtaat ttccctatac aatcaccagc
 481 tgcataaata tgtttatctt cagtttgttg aaattcgttc gttaaaatat gtcctgatgt
 541 agaaagtttt attttagtgt tgtttaaacc aatatctgat gtgttaggtt ttctaccaat
 601 cgatagcaac actttatcta ctttaattat gtctgaagaa atttcaaacg taacaccatc
 661 ttcgttaaca tttatatcat tttcagaaag ttttattccc tcatagaatt taacaccacg
 721 tgctgacaat gatttttta atagttgtga agcttgttta ctttcagttg gtaaaattct
 781 ttcacctgct tctataactg ttacgtcaac acctaaatct atcatcaatg atgcaaattc
 841 cattccgata acaccaccac caataatacc aatacttgat ggtaacgtct ttaatgataa
 901 tatatcatcg ctagataaaa ttttatcatg atcaaatgat aagaatggca actctgcagg
 961 cgaagaacca gttgcaatta atacaaattg gttgggtaat aagtctgatt caccatcttc
1021 atattcgaca gaaattgtgc cactttgagg tgaaaatata gatgtaccta gaatacgtcc
1081 cgtgccatta taaatgtcaa tgtgattgtg ttgcattaaa tgctttacac cttgatacat
1141 ttgattaata atgtcttctt ttcgtgccaa catattttca aaattaacat tagcatcttt
1201 gacatcaacg ccaaacattg ctgcctgttt tactgtttga aatacttcag cagatttaag
1261 cagcgattta gtaggaatac aacctttatg gagacaagta cctcctaata gttgtcgttc
1321 tactattgcc actttcttac ctaattgaga cgcacgtatc gcagcaacat atcctgcagt
1381 acctccaccg agaacgacta aatcatattg tttctctgac at (SEQ ID NO:82)
```

*Streptococcus mutans UA159*: NP_720603

```
  1 maveiimpkl gvdmgegeii ewkkqegdev kegdilleim sdktnmeiea edsgvllkiv
 61 kgngqvvpvt evigyigsag etietnaapa asaddlkaag levpdtlges aapaaqktpl
121 addeydmivv gggpagyyaa irgaqlggkv aiveksefgg tclnkgcipt ktylknaeil
181 dgikiaagrg infastnyti dmdktvafkd tvvktltsgv qgllkankvt ifnglggvnp
241 dktvtvgset ikghniilat gskvsrinip gidsplvlts ddildlreip ksiavmgggv
301 vgielglvya sygtevtvie madriipamd kevslelqki lskkgmnikt svgvaeivea
361 nnqltlklnd gsevvaekal lsigrvpqls glenlnlele rgrikvddyq etsisgiyap
421 gdvngrkmla haayrmgeva aenaiwgnvr kanlkytpaa vythpevamc giteeqarqe
481 ygnvlvgkss fsgngraias neaqgfvkvv adakyheilg vhiigpaaae mineastime
```

FIG. 2D cont'd

```
541 neltvdellr sihghptfse vmyeafadvl geaihnppkr r (SEQ ID NO:83)

   1 atggcagtcg aaattattat gcctaaactc ggtgttgata tgcaggaagg cgaaatcatc
  61 gagtggaaaa aacaagaagg tgatgaggtc aaagaagggg atatcctcct tgaaatcatg
 121 tctgacaaga ccaatatgga aattgaagct gaggattcag gtgtcctgct caaaattgtt
 181 aaaggaaatg gtcaagttgt ccctgtgact gaggtcattg gttatattgg ttctgctggt
 241 gaaacgattg aaacaaatgc agcgccagca gcttcagctg atgatctcaa agcagcgggt
 301 cttgaagttc ctgatacttt aggcgagtca gcagcaccag cagctcaaaa aactccgctt
 361 gctgatgatg agtatgatat gattgtcgtt ggtggtggtc ctgctggtta ttatgctgct
 421 attcgcggtg cacaattggg cggcaaggtt gctatcgtcg aaaaatcaga atttggaggg
 481 acttgtttaa ataaaggctg cattccaact aaaacttatc ttaagaatgc tgaaatcctt
 541 gatggcatca aaattgcagc gggtcgcggt attaattttg cttcaaccaa ctataccatt
 601 gacatggaca aaacggttgc ctttaaagat accgttgtta aaacattgac aagtggggtt
 661 cagggtcttc ttaaagccaa taaagtgact attttcaatg gtctcggtca ggttaatcct
 721 gataagacag tgactgtcgg ttcggaaacg attaaaggac ataatattat ccttgcaaca
 781 ggttcaaaag tgtctcgtat taatattccg ggaattgatt cacctcttgt tttaacatcg
 841 gatgatattc ttgatcttcg tgaaattcca aagtcacttg ctgttatggg cggtggtgtt
 901 gtcggcattg aactcggtct tgtttacgct tcctatggta cagaagtgac tgttattgaa
 961 atggctgatc gcattattcc tgctatggac aaggaagtat cgcttgaact gcaaaaaatt
1021 ctatccaaga aaggaatgaa cattaagact tctgttggtg tggctgaaat tgttgaagct
1081 aacaatcaat taacgctgaa actcaatgac ggctctgaag ttgtggctga aaaggccctg
1141 ctttctattg gtcgtgtccc acaattaagc ggtttagaaa atcttaatct ggaacttgaa
1201 cgcggtcgca tcaaagtgga cgattatcag gaaacctcta tttcaggtat ttatgccccg
1261 ggtgatgtta atggaagaaa gatgttagcg catgctgcct atcgtatggg tgaagtagct
1321 gccgaaaatg ctatctgggg aaatgttcgt aaggctaacc tgaaatatac accagcagct
1381 gtttacaccc atccagaggt tgctatgtgc ggtattactg aagaacaagc ccgtcaagaa
1441 tatggaaacg tcttagttgg gaaatcctct ttttcaggaa atggacgtgc gatcgcttct
1501 aatgaagcac aaggatttgt caaagttgtc gcagatgcta aataccatga aattcttgga
1561 gtccatatta ttggaccagc agctgctgag atgattaatg aagcctcaac gattatggaa
1621 aatgagttga cggttgatga gctgctacgt tctattcatg gccatcctac cttctcggag
1681 gttatgtatg aagcctttgc agacgtcctt ggcgaagcta tccataaccc gccaaagcgt
1741 cgttaa (SEQ ID NO:84)
```

(I,V)-G-G-(A,T)-(S,C)-(V,L)-(x)2-(G,D)-C-(V,I)-P-(T,S)-K-(A,T)-(M,L)-(I,L) [SEQ ID NO:85]
(L,I)-A-T-G-(G,S)-x-(S,P)-(x)2-L-(A,P)-(D,G)-(x)3-(D,L)-G [SEQ ID NO:86]
(V,I)-x-G-(G,S)-G-x-(I,T)-G-x-E-x-(A,G) [SEQ ID NO:87]
T-(x)6-(A,V)-x-G-D-(x)2-(P,G) [SEQ ID NO:88]
(I,V)-(G,A)-(x)2-(F,I)-(T,H)-x-(Y,H)-P-(S,T)-(Q,L) [SEQ ID NO:89]

wherein, the amino acid residues in each of the brackets indicate alternative amino acid residues at the particular position, each x indicates any amino acid residue, and each n in "x(n)" indicates the number of x residues in a contiguous stretch of amino acid residues.

FIG. 2E

Beta ketoacyl-ACP synthase homologs

*E. coli beta ketoacyl-ACP synthase FabH*

FIG. 2E cont'd

>gi|157160617|ref|YP_001457935.1| 3-oxoacyl-(acyl carrier protein) synthase III
MYTKIIGTGSYLPEQVRTNADLEKMVDTSDEWIVTRTGIRERHIAAQNETVSTMGFEAATRAIEMAGIEK
DQIGLIVVATTSATHAFPSAACQIQSMLGIKGCPAFDVAAACAGFTYALSVADQYVKSGAVKYALVVGSD
VLARTCDPTDRGTIIIFGDGAGAAVLAASEEPGIISTHLHADGSYGELLTLPNADRVNPENSIHLTMAGN
EVFKVAVTELAHIVDETLAANNLDRSQLDWLVPHQANLRIISATAKKLGMSMDNVVVTLDRHGNTSAASV
PCALDEAVRDGRIKPGQLVLLEAFGGGFTWGSALVRF (SEQ ID NO:90)

>gi|157159467:1212439-1213392, complete genome
ATGTATACGAAGATTATTGGTACTGGCAGCTATCTGCCCGAACAAGTGCGGACAAACGCCGATTTGGAAA
AAATGGTGGACACCTCTGACGAGTGGATTGTCACTCGTACCGGTATCCGCGAACGCCACATTGCCGCGCA
AAACGAAACCGTTTCAACCATGGGCTTTGAAGCGGCGACACGCGCAATTGAGATGGCGGGCATTGAGAAA
GACCAGATTGGCCTGATCGTTGTGGCAACGACTTCTGCTACGCACGCTTTCCCGAGCGCAGCTTGTCAGA
TTCAAAGCATGCTGGGCATTAAAGGTTGCCCGGCATTTGACGTTGCAGCAGCCTGCGCAGGTTTCACCTA
TGCATTAAGCGTAGCCGATCAATACGTGAAATCTGGGGCGGTGAAGTATGCTCTGGTCGTCGGTTCCGAT
GTACTGGCGCGCACCTGCGATCCAACCGATCGTGGGACTATTATTATTTTTGGCGATGGCGCGGGCGCTG
CGGTGCTGGCTGCCTCTGAAGAGCCGGGAATCATCTCCACCCATCTGCATGCCGACGGTAGCTATGGTGA
GTTGCTGACGCTGCCTAATGCTGACCGTGTGAATCCAGAGAATTCAATTCATCTGACGATGGCGGGCAAC
GAAGTCTTCAAGGTTGCGGTAACGGAACTGGCGCACATCGTTGATGAGACGCTGGCGGCAAATAATCTTG
ACCGTTCTCAACTGGACTGGCTGGTTCCGCATCAGGCTAACCTGCGTATTATCAGTGCAACGGCGAAAAA
ACTCGGTATGTCTATGGACAATGTCGTGGTGACGCTGGATCGCCACGGTAATACCTCTGCGGCCTCTGTC
CCGTGCGCGCTGGATGAAGCTGTACGCGACGGGCGCATTAAGCCGGGGCAGTTGGTTCTGCTTGAAGCCT
TTGGCGGTGGATTCACCTGGGGCTCCGCGCTGGTTCGTTTCTAG (SEQ ID NO:91)

>gi|209918346|ref|YP_002292430.1| 3-oxoacyl-(acyl carrier protein) synthase III
MYTKIIGTGSYLPEQVRTNADLEKMVDTSDEWIVTRTGIRERHIAAPNETVSTMGFEAATRAIEMAGIEK
DQIGLIVVATTSATHAFPSAACQIQSMLGIKGCPAFDVAAACAGFTYALSVADQYVKSGAVKYALVVGSD
VLARTCDPTDRGTIIIFGDGAGAAVLAASEEPGIISTHLHADGSYGELLTLPNADRVNPENSIHLTMAGN
EVFKVAVTELAHIVDETLTANNLDRSQLDWLVPHQANLRIISATAKKLGMSMDNVVVTLDRHGNTSAASV
PCALDEAVRDGRIKPGQLVLLEAFGGGFTWGSALVRF (SEQ ID NO:92)

>gi|209917191:1231590-1232543, complete genome
ATGTATACGAAGATTATTGGTACTGGCAGCTATCTGCCCGAACAAGTGCGGACAAACGCCGATTTGGAAA
AAATGGTGGACACCTCTGACGAGTGGATTGTCACTCGTACCGGTATCCGCGAACGCCACATTGCCGCGCC
AAACGAAACCGTTTCAACCATGGGCTTTGAAGCGGCGACACGCGCAATTGAGATGGCGGGCATTGAGAAA
GACCAGATTGGCCTGATCGTTGTGGCAACGACTTCTGCTACGCACGCTTTCCCGAGCGCAGCTTGTCAGA
TTCAAAGCATGTTGGGCATTAAAGGTTGCCCGGCATTTGACGTTGCAGCAGCCTGCGCAGGTTTCACCTA
TGCATTAAGCGTAGCCGATCAATACGTGAAATCTGGGGCGGTGAAGTATGCTCTGGTCGTCGGTTCCGAT
GTACTGGCGCGCACCTGCGATCCAACCGATCGTGGGACTATTATTATTTTTGGCGATGGCGCGGGCGCTG
CGGTGCTGGCTGCCTCTGAAGAGCCGGGAATCATCTCCACCCATCTGCATGCCGACGGTAGTTATGGTGA
ATTGCTGACGCTGCCAAACGCCGACCGCGTGAATCCAGAGAATTCAATTCATCTGACGATGGCGGGCAAC
GAAGTCTTCAAGGTTGCGGTAACGGAACTGGCGCACATCGTTGATGAGACGCTGACGGCGAATAATCTTG
ACCGTTCTCAACTGGACTGGCTGGTTCCGCATCAGGCTAACCTGCGTATTATCAGTGCAACGGCGAAAAA
ACTCGGTATGTCGATGGACAATGTCGTGGTGACGCTGGATCGCCACGGTAATACCTCTGCGGCCTCTGTC
CCGTGCGCGCTGGATGAAGCTGTACGCGACGGGCGCATTAAGCCGGGGCAGTTGGTTCTGCTTGAAGCCT
TTGGCGGTGGATTCACCTGGGGCTCCGCGCTGGTTCGTTTCTAG (SEQ ID NO:93)

FIG. 2E cont'd

*B. subtilis beta ketoacyl-ACP synthase FabH homolog*

>gi|16078198|ref|NP_389015.1| 3-oxoacyl-(acyl carrier protein) synthase III
MKAGILGVGRYIPEKVLTNHDLEKMVETSDEWIRTRTGIEERRIAADDVFSSHMAVAAAKNALEQAEVAA
EDLDMILVATVTPDQSFPTVSCMIQEQLGAKKACAMDISAACAGFMYGVVIGKQFIESGTYKHVLVVGVE
KLSSITDWEDRNTAVLFGDGAGAAVVGPVSDDRGILSFELGADGTGGQHLYLNEKRHTIMNGREVFKFAV
RQMGESCVNVIEKAGLSKEDVDFLIPHQANIRIMEAARERLELPVEKMSKIVHKYGNTSAASIPISLVEE
LEAGKIKDGDVVVMVGFGGGLTWGAIAIRWGR (SEQ ID NO:94)

>gi|255767013:1208222-1209160, complete genome
ATGAAAGCTGGAATACTTGGTGTTGGACGTTACATTCCTGAGAAGGTTTTAACAAATCATGATCTTGAAA
AAATGGTTGAAACTTCTGACGAGTGGATTCGTACAAGAACAGGAATAGAAGAAAGAAGAATCGCAGCAGA
TGATGTGTTTTCATCACATATGGCTGTTGCAGCAGCGAAAAATGCGCTGGAACAAGCTGAAGTGGCTGCT
GAGGATCTGGATATGATCTTGGTTGCAACTGTTACACCTGATCAGTCATTCCCTACGGTCTCTTGTATGA
TTCAAGAACAACTCGGCGCGAAGAAAGCGTGTGCTATGGATATCAGCGCGGCTTGTGCGGGCTTCATGTA
CGGGGTTGTAACCGGTAAACAATTTATTGAATCCGGAACCTACAAGCATGTTCTAGTTGTTGGTGTAGAG
AAGCTCTCAAGCATTACCGACTGGGAAGACCGCAATACAGCCGTTCTGTTTGGAGACGGAGCAGGCGCTG
CGGTAGTCGGGCCAGTCAGTGATGACAGAGGAATCCTTTCATTTGAACTAGGAGCCGACGGCACAGGCGG
TCAGCACTTGTATCTGAATGAAAAACGACATACAATCATGAATGGACGAGAAGTTTTCAAATTTGCAGTC
CGCCAAATGGGAGAATCATGCGTAAATGTCATTGAAAAAGCCGGACTTTCAAAAGAGGATGTCGACTTTT
TGATTCCGCATCAGGCGAACATCCGTATCATGGAAGCTGCTCGCGAGCGTTTAGAGCTTCCTGTCGAAAA
GATGTCTAAAACTGTTCATAAATATGGAAATACTTCTGCCGCATCCATTCCGATCTCTCTTGTAGAAGAA
TTGGAAGCCGGTAAAATCAAAGACGGCGATGTGGTCGTTATGGTAGGGTTCGGCGGAGGACTAACATGGG
GCGCCATTGCAATCCGCTGGGGCCGATAA (SEQ ID NO:95)

*S. avermitilis beta ketoacyl-ACP synthase FabH homolog*

>gi|29828832|ref|NP_823466.1| 3-oxoacyl-(acyl carrier protein)
synthase III
MSGGRAAVITGIGGYVPPDLVTNDDLAQRLDTSDAWIRSRTGIAERRVIAPGTATSDLAVEAGLRALKSA
GDEHVDAVVLATTTPDQPCPATAPQVAARLGLGQVPAFDVAAVCSGFLFGLATASGLIAAGVADKVLLVA
ADAFTTIINPEDRTTAVIFADGAGAVVLRAGAADEPGAVGPLVLGSDGELSHLIEVPAGGSRQRSSGPTT
DPDDQYFRMLGRDTYRHAVERMTDASQRAAELADWRIDDVDRFAAHQANARILDSVAERLGVPAERQLTN
IARVGNTGAASIPLLLSQAAAAGRLGAGHRVLLTAFGGGLSWGAGTLVWPEVQPV (SEQ ID NO:96)

>gi|162960844:2791730-2792737, complete genome
ATGAGCGGCGGACGCGCGGCGGTGATCACCGGGATCGGGGGCTATGTGCCTCCCGATCTGGTGACCAACG
ACGATCTGGCCCAGCGGCTCGACACCTCCGACGCGTGGATCCGCTCGCGCACCGGGATCGCCGAGCGGCA
TGTGATCGCGCCCGGCACCGCGACCTCCGACCTGGCGGTGGAGGCCGGACTGCGGGCCCTGAAGTCGGCG
GGCGACGAGCACGTGGACGCGGTCGTCCTGGCCACCACGACGCCCGACCAGCCCTGCCCGGCGACCGCCC
CGCAGGTGGCCGCACGGCTGGGACTCGGGCAGGTGCCGGCGTTCGACGTGGCCGCCGTCTGCTCCGGCTT
CCTGTTCGGCCTCGCCACCGCGTCCGGGCTGATCGCGGCCGGGGTGGCGGACAAGGTCCTGCTGGTCGCC
GCCGACGCGTTCACCACGATCATCAACCCCGAGGACCGCACCACGGCCGTCATCTTCGCGGACGGCGCGG
GCGCGGTGGTGCTGCGCGCGGGCGCCGCCGACGAGCCGGGGGCCGTCGGCCCGCTGGTGCTCGGCAGCGA
CGGCGAGCTGAGCCATCTCATCGAGGTGCCGGCGGGCGGCTCGCGCCAGCGCTCGTCCGGCCCCACGACC
GACCCGGACGACCAGTACTTCCGGATGCTCGGCCGGGACACCTACCGGCACGCGGTGGAGCGGATGACCG
ATGCGTCCCAGCGGGCGGCCGAACTGGCCGACTGGCGGATCGACGACGTCGACCGGTTCGCGGCGCACCA

FIG. 2E cont'd

GGCCAACGCCCGCATCCTCGACTCGGTCGCGGAACGTCTCGGGGTCCCCGCCGAACGGCAGTTGACCAAC
ATCGCCCGGGTCGGCAACACCGGCGCCGCCTCGATCCCGCTGCTTCTGTCGCAGGCGGCCGCGGCCGGCC
GGCTCGGCGCCGGGCACCGGGTGCTCCTGACCGCGTTCGGCGGGGGCCTGTCCTGGGGCGCGGGGACTCT
GGTCTGGCCGGAGGTCCAGCCGGTCTGA (SEQ ID NO:97)

*Straphylococcus aureus beta ketoacyl-ACP synthase homolog*

>gi|227557016|ref|ZP_03987063.1| 3-oxoacyl-(acyl carrier protein) synthase III
MNVGIKGFGAYAPEKIIDNAYFEQFLDTSDEWISKMTGIKERHWADDDQDTSDLAYEASVKAIADAGIQP
EDIDMIIVATATGDMPFPTVANMLQERLGTGKVASMDQLAACSGFMYSMITAKQYVQSGDYHNILVVGAD
KLSKITDLTDRSTAVLFGDGAGAVIIGEVSEGRGIISYEMGSDGTGGKHLYLDKDTGKLKMNGREVFKFA
VRIMGDASTRVVEKANLTSDDIDLFIPHQANIRIMESARERLGISKDKMSVSVNKYGNTSAASIPLSIDQ
ELKNGKLKDDDTIVLVGFGGGLTWGAMTIKWGK (SEQ ID NO:98)

>gi|225008537:8085-9026, whole genome shotgun sequence
CTATTTTCCCCATTTTATTGTCATTGCGCCCCAAGTTAGGCCGCCACCGAATCCGACAAGAACAATTGTA
TCATCATCTTTGAGTTTACCATTTTTTAATTCTTGATCGATACTTAAAGGTATTGACGCAGCTGAAGTAT
TTCCATATTTATTTACAGAAACACTCATTTTGTCTTTTGAAATACCTAAGCGTTCTCTAGCTGATTCCAT
AATTCTAATATTAGCTTGATGAGGAATAAATAAATCTATATCATCTGATGTTAAATTCGCTTTTTCAACT
ACACGTGTTGATGCATCACCCATAATTCTAACAGCAAATTTAAATACTTCTCGACCATTCATTTTCAGTT
TACCAGTATCTTTATCTAAATATAAATGTTTACCACCTGTGCCATCAGAACCCATTTCATAACTTATAAT
ACCTCTGCCTTCTGAAACTTCACCGATGATAACCGCACCTGCACCATCTCCAAATAGAACTGCAGTAGAA
CGGTCAGTTAAATCTGTTATTTTAGATAATTTATCTGCACCGACAACTAAAATATTATGATAATCTCCAG
ATTGAACATATTGTTTAGCTGTAATCATTGAATACATAAATCCAGAACATGCTGCAAGTTGATCCATAGA
GGCAACTTTGCCCGTCCCTAAACGTTCTTGTAACATATTTGCGACAGTTGGAAATGGCATATCTCCAGTT
GCTGTGGCAACAATTATCATATCTATATCTTCGGGCTGAATACCAGCGTCAGCGATTGCTTTTACACTTG
CTTCATATGCTAAATCTGAAGTATCTTGATCGTCATCTGCCCAATGTCTTTCTTTAATTCCAGTCATCTT
AGAAATCCATTCATCAGATGTATCTAAAAATTGCTCAAAATAGGCATTGTCAATAATCTTTTCTGGTGCA
TATGCACCAAAACCTTTAATACCCACGTTCAT (SEQ ID NO:99)

*Streptococcus mutans beta ketoacyl-ACP synthase homolog*

>gi|24380116|ref|NP_722071.1| 3-oxoacyl-(acyl carrier protein) synthase III
MTFAKISQAAYYVPSQVVTNDDLSKIMDTSDEWITSRTGIRERRISQSEDTSDLASQVAKELLKKASLKA
KEIDFIIVATITPDAMMPSTAACVQAKIGAVNAFAFDLTAACSGFIFALSAAEKMIKSGQYQKGLVIGAE
VLSKIIDWSDRTTAVLFGDGAGGVLLEADSSEHFLFESIHSDGSRGESLTSGEHAVSSPFSQVDKKDNCF
LKMDGRAIFDFAIRDVSKSISMLIRKSDMPVEAIDYFLLHQANIRILDKMAKKIGADREKFPANMMKYGN
TSAASIPILLAECVENGTIELNGSHTVLLSGFGGGLTWGSLIVKI (SEQ ID NO:100)

>gi|24378532:c1650584-1649607, complete genome
ATGACTTTTGCAAAGATTAGTCAAGCAGCATATTATGTACCATCACAGGTTGTCACCAATGATGATTTAT
CTAAAATAATGGATACCAGTGATGAATGGATTACAAGTCGTACGGGAATAAGAGAGCGCCGTATTAGTCA
ATCCGAAGATACCAGTGACTTAGCCAGTCAGGTGGCCAAAGAACTTTTAAAAAAAGCCTCATTAAAGGCG

FIG. 2E cont'd

AAAGAGATTGATTTTATTATTGTTGCTACAATTACTCCGGATGCAATGATGCCATCAACAGCTGCTTGTG
TCCAAGCGAAAATTGGTGCAGTGAATGCTTTTGCTTTCGATTTAACTGCCGCCTGCAGTGGATTTATTTT
TGCACTTTCAGCTGCGGAAAAAATGATTAAATCCGGTCAGTACCAGAAAGGTTTAGTTATCGGTGCAGAA
GTTCTATCTAAAATCATCGATTGGTCGGATCGAACAACAGCTGTTCTTTTTGGAGATGGAGCTGGCGGTG
TTCTTTTAGAAGCAGATTCTTCTGAACATTTTTTATTTGAATCTATTCATTCAGATGGCAGTCGTGGTGA
AAGTTTGACATCAGGTGAACACGCTGTTTCGTCACCCTTTTCACAGGTTGATAAAAAAGATAACTGTTTT
CTAAAAATGGATGGTCGAGCTATATTTGACTTTGCTATTCGTGATGTGTCAAAAAGTATTTCGATGCTCA
TTAGGAAGTCAGATATGCCTGTAGAAGCGATTGATTATTTCTTATTACATCAGGCTAATATTCGTATTTT
GGATAAAATGGCTAAAAAAATTGGCGCTGATAGAGAAAAATTTCCTGCTAATATGATGAAGTATGGTAAT
ACCAGTGCAGCAAGTATTCCTATTTTATTAGCCGAATGTGTCGAAAATGGAACTATAGAGCTAAATGGTT
CACACACTGTTCTCCTGAGCGGGTTCGGTGGGGGTTTGACATGGGGCAGTTTAATTGTTAAAATTTAG
(SEQ ID NO:101)

*Lactococcus lactis beta ketoacyl-ACP synthase homolog*

>gi|15672753|ref|NP_266927.1| 3-oxoacyl-(acyl carrier protein)
synthase III
MTFAKITQVAHYVPENVVSNDDLSKIMDTNDEWIYSRTGIKNRHISTGENTSDLAAKVAKQLISDSNLSP
ETIDFIIVATVTPDSLMPSTAARVQAQVGAVNAFAYDLTAACSGFVFALSTAEKLISSGAYQRGLVIGAE
VFSKVIDWSDRSTAVLFGDGAAGVLIEAGASQPLIIAEKMQTDGSRGNSLLSSYADIQTPFASVSYESSN
LSMEGRAIFDFAVRDVPKNIQATLEKANLSAEEVDYYLLHQANSRILDKMAKKLGVTRQKFLQNMQEYGN
TSAASIPILLSESVKNGIFSLDGQTKVVLTGFGGGLTWGTAIINL (SEQ ID NO:102)

>gi|15671982:781227-782204, complete genome
ATGACTTTTGCGAAAATTACGCAAGTGGCACACTATGTGCCTGAAAATGTGGTATCTAATGATGACTTGT
CCAAAATAATGGATACTAATGATGAATGGATTTACAGTCGGACAGGGATTAAAAATCGCCATATTTCAAC
TGGAGAGAACACCTCAGACTTAGCAGCTAAAGTTGCTAAGCAGTTGATTAGCGATTCAAATTTAAGCCCA
GAAACGATTGACTTCATCATTGTTGCTACAGTAACTCCGGACTCATTGATGCCTTCAACCGCGGCACGGG
TTCAAGCTCAAGTAGGAGCAGTTAATGCTTTTGCTTACGATTTGACTGCGGCTTGTTCAGGCTTTGTCTT
TGCTCTATCAACAGCGGAAAAATTAATTTCCTCAGGAGCATATCAACGAGGGCTTGTCATTGGCGCAGAA
GTCTTTTCAAAAGTAATTGATTGGTCAGACCGATCAACTGCTGTTCTTTTCGGAGATGGAGCTGCTGGTG
TGCTTATTGAAGCTGGCGCGAGTCAACCTCTGATTATTGCTGAAAAAATGCAAACAGATGGAAGTCGTGG
GAACAGTTTACTTTCTAGTTATGCTGACATCCAAACTCCATTTGCCTCTGTTTCATACGAAAGTTCAAAC
TTGAGTATGGAAGGGCGAGCAATTTTTGATTTTGCCGTACGTGATGTTCCTAAAAATATCCAGGCAACTT
TAGAAAAAGCTAATTTGTCTGCTGAAGAAGTAGATTATTATCTCCTTCATCAAGCGAATTCAAGAATCCT
TGATAAAATGGCTAAAAAGCTTGGTGTGACGCGCCAAAAGTTCCTTCAAAATATGCAAGAATATGGTAAC
ACATCGGCAGCAAGTATCCCTATATTGTTGTCAGAATCCGTAAAAAATGGTATATTTAGTTTGGACGGTC
AAACAAAAGTCGTCTTGACAGGATTTGGCGGTGGCCTCACTTGGGGTACAGCAATTATTAATTTATAA
(SEQ ID NO:103)

*Leginonella pneumophila beta ketoacyl-ACP synthase homolog*

>gi|54294279|ref|YP_126694.1| 3-oxoacyl-[acyl-carrier-protein]
synthase III
MKNAVISGTGSYSPERQMTNAELETMLDTSDEWIVTRTGISSRSVAQEHETTSYMASRAAEQALEASGLD

FIG. 2E cont'd

AEEIDLILVATCTPDYFFPSVACHVQHALGIKRPIPAFDIGAACSGFVYAMDVAKQYIATGAAKHVLVVG
SESMSRAVDWTDRSICVLFGDGAGAVVLSASDRQGIMGSVLHSAYDSDKLLVLRNSTFEQDRATIGMRGN
EVFKIAVNIMGNIVDEVLEASHLKKSDIDWLIPHQANIRIIQAIAKKLSLPMSHVIVTIGNQGNTSAASI
PLALDYSIKNNQIKRDEILLIESFGGGMTWGAMVIRY (SEQ ID NO:104)

>gi|54292964:1500631-1501584, complete genome
ATGAAAAATGCTGTTATTAGTGGCACTGGAAGTTACTCTCCAGAGAGACAAATGACTAATGCTGAACTGG
AAACCATGCTTGATACTAGCGATGAATGGATAGTTACCAGGACTGGTATTAGTAGTCGTAGTGTTGCTCA
AGAACATGAAACAACATCTTATATGGCCTCCAGAGCAGCAGAGCAAGCACTAGAGGCATCAGGCCTTGAT
GCTGAAGAAATTGATTTGATATTAGTAGCAACATGTACCCCGGATTATTTTTTCCTAGCGTTGCCTGTC
ACGTACAACATGCTTTAGGAATCAAAAGACCTATTCCGGCTTTTGACATTGGAGCTGCATGCAGCGGTTT
TGTTTATGCGATGGATGTAGCGAAACAATACATTGCTACAGGGGCTGCCAAACACGTTCTTGTCGTAGGC
AGCGAGAGCATGTCAAGAGCGGTAGATTGGACTGATCGTTCTATTTGTGTCTTATTCGGAGATGGCGCAG
GCGCTGTTGTTTTAAGCGCAAGTGATCGCCAAGGGATTATGGGTAGTGTTTTACATTCTGCCTATGACTC
TGATAAATTACTAGTCCTTCGTAATTCAACTTTTGAACAAGATCGTGCAACGATTGGAATGCGAGGTAAT
GAGGTATTTAAAATTGCTGTTAATATTATGGGTAATATTGTTGATGAAGTGTTAGAAGCAAGTCATTTAA
AAAAATCTGATATTGATTGGCTGATACCTCATCAAGCCAATATACGCATTATACAAGCCATAGCTAAAAA
ATTATCTCTTCCTATGTCACATGTTATTGTTACAATTGGTAACCAAGGCAACACATCGGCTGCTTCTATT
CCCTTAGCACTTGATTATTCTATTAAAAATAATCAGATTAAAAGGGATGAAATATTATTAATTGAATCCT
TTGGTGGTGGAATGACCTGGGGCGCTATGGTTATTCGTTACTAA (SEQ ID NO:105)

*Listeria monocytogenes beta ketoacyl-ACP synthase homolog*

>gi|217963636|ref|YP_002349314.1| 3-oxoacyl-(acyl-carrier-protein)
synthase 3 protein 1 (3-oxoacyl-(acyl-carrier-protein) synthase III
protein 1) (Beta-ketoacyl-ACP synthase III 1) (KAS III 1) (bFabH1)
MNAGILGVGKYVPEKIVTNFDLEKIMDTSDEWIRTRTGIEERRIARDDEYTHDLAYEAAKVAIENAGLTP
DDIDLFIVATVTQEATFPSVANIIQDRLGATNAAGMDVEAACAGFTFGVVTAAQFIKTGAYKNIVVVGAD
KLSKITNWDDRATAVLFGDGAGAVVMGPVSDDHGLLSFDLGSDGSGGKYLNLDENKKIYMNGREVFRFAV
RQMGEASLRVLERAGLEKEELDLLIPHQANIRIMEASRERLNLPEEKLMKTVHKYGNTSSSSIALALVDA
VEEGRIKDNDNVLLVGFGGGLTWGALIIRWGK (SEQ ID NO:106)

>gi|217963303:342983-343921, complete genome
ATGAACGCAGGAATTTTAGGAGTAGGTAAATACGTACCTGAAAAAATAGTAACAAATTTTGATTTAGAAA
AAATAATGGATACATCCGATGAGTGGATTCGTACTCGAACTGGTATTGAAGAAAGAAGAATTGCTCGTGA
TGACGAATATACGCACGACTTAGCATACGAAGCAGCAAAGGTAGCTATTGAGAATGCTGGGCTTACACCA
GATGACATTGACTTATTTATTGTTGCCACTGTGACGCAGGAAGCGACTTTTCCATCCGTTGCGAATATTA
TTCAAGACCGTTTAGGAGCAACAAATGCTGCGGGTATGGACGTGGAAGCGGCATGTGCCGGTTTTACTTT
TGGCGTAGTAACTGCAGCACAATTTATTAAAACAGGGGCATACAAGAATATCGTCGTAGTTGGTGCGGAT
AAATTATCTAAAATCACTAACTGGGATGATCGCGCAACAGCCGTATTATTTGGTGATGGAGCGGGAGCCG
TTGTTATGGGTCCGGTTTCTGATGACCATGGACTACTTTCGTTTGACTTAGGCTCAGATGGATCTGGCGG
CAAATACTTGAACTTAGATGAAAATAAGAAGATTTATATGAATGGACGTGAAGTGTTCCGTTTTGCAGTT
CGCCAAATGGGAGAAGCTTCGTTACGAGTACTTGAACGTGCTGGACTTGAAAAAGAAGAATTGGATTTAC
TAATTCCTCACCAAGCAAATATCCGTATCATGGAAGCTTCTCGCGAGCGTTTGAATTTACCGGAAGAAAA
ACTGATGAAAACAGTGCATAAATACGGTAATACTTCGTCATCTTCTATTGCTCTTGCGCTAGTTGATGCA

FIG. 2E cont'd

GTCGAAGAAGGACGCATTAAAGATAATGACAATGTCCTGCTTGTTGGCTTTGGCGGCGGACTAACATGGG
GCGCCCTAATCATTCGTTGGGGTAAGTAA (SEQ ID NO:107)

*Bacillus subtilis subsp. subtilis str. 168, beta ketoacyl-ACP synthase homolog*

3-oxoacyl-(acyl carrier protein) synthase III: ZP_03590702, GI:221308855

```
  1 mskakitaig tyapsrrltn adlekivdts dewivqrtgm rerriadehq ftsdlcieav
 61 knlksrykgt lddvdmilva tttsdyafps tacrvqeyfg westgaldin atcagltygl
121 hlanglitsg lhqkilviag etlskvtdyt drttcvlfgd aagallverd eetpgflasv
181 qgtsgnggdi lyraglrnei ngvqlvgsgk mvqngrevyk waartvpgef erllhkagls
241 sddldwfvph sanlrmiesi cektpfpiek tltsvehygn tssvsivial dlavkagklk
301 kdqivllfgf gggltytgll ikwgm (SEQ ID NO:108)
```

```
  1 atgtcaaaag caaaaattac agctatcggc acctatgcgc cgagcagacg tttaaccaat
 61 gcagatttag aaaagatcgt tgatacctct gatgaatgga tcgttcagcg cacaggaatg
121 agagaacgcc ggattgcgga tgaacatcaa tttacctctg atttatgcat agaagcggtg
181 aagaatctca agagccgtta taaaggaacg cttgatgatg tcgatatgat cctcgttgcc
241 acaaccacat ccgattacgc ctttccgagt acggcatgcc gcgtacagga atatttcggc
301 tgggaaagca ccggcgcgct ggatattaat gcgacatgcg ccgggctgac atacggcctc
361 catttggcaa atggattgat cacatctggc cttcatcaaa aaattctcgt catcgccgga
421 gagacgttat caaaggtaac cgattatacc gatcgaacga catgcgtact gttcggcgat
481 gccgcgggtg cgctgttagt agaacgagat gaagagacgc cgggatttct tgcgtctgta
541 caaggaacaa gcgggaacgg cggcgatatt ttgtatcgtg ccggactgcg aaatgaaata
601 aacggtgtgc agcttgtcgg ttccggaaaa atggtgcaaa acggacgcga ggtatataaa
661 tgggccgcaa gaaccgtccc tggcgaattt gaacggcttt tacataaagc aggactcagc
721 tccgatgatc tcgattggtt tgttcctcac agcgccaact tgcgcatgat cgagtcaatt
781 tgtgaaaaaa caccgttccc gattgaaaaa acgctcacta gtgttgagca ctacggaaac
841 acgtcttcgg tttcaattgt tttggcgctc gatctcgcag tgaaagccgg gaagctgaaa
901 aaagatcaaa tcgttttgct tttcgggttt ggcggcggat taacctatac aggattgctt
961 attaaatggg ggatgtaa (SEQ ID NO:109)
```

*Myxococcus xanthus DK 1622, beta ketoacyl-ACP synthase homolog* putative 3-oxoacyl-(acyl-carrier-protein) synthase GI:108763242, YP_628497

```
  1 mryaqilstg ryvpekvltn advekilgek vdewlqqnvg irerhmmadd qatsdlcvga
 61 arqaleragt kpeeldliii atdtpdylsp atasvvqakl gavnagtydl ncacagwvta
121 ldvgsktiaa ddsyqrilvv gaygmsryin wkdkktatlf adgagavvlg agdtpgfmga
181 kllangeyhd algvytggtn rpataeslel tggkpavqfv rkfpatfnte rwpmlldqll
241 krqnlklddv kqfvftqlnl rtieatmkil gqpmekahyt mdkwgytgsa cipmtlddav
301 vqgkvqrgdl valcasgggl amasalyrwt a (SEQ ID NO:110)
```

```
  1 atgcgatacg cccagattct ctccactggc cgctacgtcc ccgagaaggt cctcaccaac
 61 gctgacgtcg agaagattct cggtgagaag gtggatgagt ggctccagca gaacgtgggc
121 attcgcgaac gccacatgat ggcggatgac caggccacct ccgacctctg cgtgggcgcc
181 gcccgccagg cgctggagcg cgcgggcacg aagccggagg aactggacct catcatcatc
241 gccaccgata ccccggacta tctcagcccc gccacggcct ccgtggtgca ggcgaagctg
301 ggcgcggtga acgccggcac ctacgacctc aactgcgcgt gcgcgggctg ggtgacggcg
```

FIG. 2E cont'd

```
361 ctggacgtgg gctcgaagac gattgccgcg gatgacagct accagcgcat cctcgtcgtg
421 ggcgcctacg gcatgtcgcg ctacatcaac tggaaggaca agaagaccgc caccctgttc
481 gcggacggcg cgggcgcggt cgtgctgggc gcgggtgaca cgcccggctt catgggcgcg
541 aagctgctgg ccaacggcga gtaccacgac gcgctggctg tctacaccgg cggtacgaac
601 cgcccggcca ccgcggagtc gctggagctc acgggcggca agcccgcggt gcagttcgtc
661 cgcaagttcc cggcgacgtt caacaccgag cgctggccca tgctgctgga ccagctcctc
721 aagcggcaga acctgaagct ggacgacgtg aagcagttcg tcttcacgca gctcaacctg
781 cgcaccatcg aagccaccat gaagatcctg ggccagccga tggagaaggc ccactacacc
841 atggacaagt ggggctacac cggttcggcc tgcatcccga tgacgctgga tgacgcggtg
901 gtgcagggca aggtgcagcg cggcgacctg gtggccctgt gtgccagcgg cggcgggctc
961 gccatggcct ccgccctcta ccgctggacg gcctga (SEQ ID NO:111)
```

*Stenotrophomonas maltophilia R551-3, beta ketoacyl-ACP synthase homolog*

3-oxoacyl-(acyl-carrier-protein) synthase III GI:119876006, ZP_01643059

```
  1 mskriysria gtgsylpekv ltnadlekmv etsdewiqsr tgirerhiaa egettsdigy
 61 naalraleaa gidasqidmi vvgtttpdli fpstacliqa kigvagcpaf dvnaacsgfv
121 falgvadkfi rsgdcryvlv igaetltrmv dwndrttcvl fgdgagavvl kadeetgils
181 thlhsdgskk eilwnpvgvs tgfkgganqg gtinmkgndv fkyavkalds vvdetlaang
241 ldksdldwli phqanlriie atakrldmsm eqvvvtvdqh gntssgsvpl aldaavrsgk
301 vergqlllle afgggftwgs allry (SEQ ID NO:112)

  1 atgagcaagc ggatctattc gaggatcgcg ggcaccggta gctatttgcc ggaaaaagtc
 61 ctgaccaacg ccgacctgga aaaaatggtc gaaacctcgg atgagtggat ccagtcgcgc
121 accggcattc gtgaacggca catcgcggcc gaaggcgaaa ccaccagcga tctcggctac
181 aacgccgcgc tgcgcgcact tgaagcggcc ggcatcgacg cttcgcagct cgacatgatc
241 gtggtcggta cgaccacccc tgaccttatt ttcccgtcca ccgcgtgcct gatccaggcc
301 aagctcggtg tggccggatg ccccgccttc gacgtcaacg cggcctgttc gggtttcgtg
361 ttcgcgctgg gcgtggccga caaattcatc cgttccggcg actgccggta cgtgctggtg
421 atcggcgccg aaacgctgac ccgcatggtt gactggaacg atcgcaccac ctgcgtgctg
481 ttcggtgatg gtgccggcgc cgtcgtgctc aaggccgacg aagagaccgg catcctcagc
541 acccacctgc attccgatgg cagcaagaag gagctgttgt ggaacccggt gggtgtctcg
601 accggtttca agggcggcgc caacggtggt ggcactatca acatgaaggg caacgatgtg
661 ttcaagtacg ccgtcaaggc gctggactcg gtcgtggacg agaccttggc tgcgaacggc
721 ctggacaagt ccgacctgga ttggctgatt ccgcaccagg ccaacctacg catcatcgaa
781 gccacggcca agcgcctgga catgtcgatg gaacaggtcg tggtcacggt tgatcagcac
841 ggcaacacct cgtccggctc ggtgccgctg gcgctggacg ctgcagtgcg atcgggcaag
901 gtcgagcgcg gccagctgct gttgctggaa gccttcggcg gcggcttcac ctggggttcg
961 gccctgctgc gctattga (SEQ ID NO:113)
```

Bacteroides vulgatus ATCC 8482, *beta ketoacyl-ACP synthase homolog*

3-oxoacyl-(acyl carrier protein) synthase III, YP_001297789, GI:150003045

```
  1 mekinavitg vggyvpdyvl tneeisrmvd tndewimtri gvkerrilne eglgtsymar
 61 kaakqlmqkt asnpddidav ivatttpdyh fpstasilcd kiglknafaf dlqaacgfl
121 ylmetaasli asgrhkkiii vgadkmssmv nyqdratcpi fgdgaaacmv eattedygim
181 dsilrtdgkg lpflhmkagg svcppsyftv dhkmhylyqe grtvfkyavs nmsditatia
241 eknglnkdni dwviphqanl riidavasrl evplekvmin iqrygntsga tlplclwdye
```

FIG. 2E cont'd

```
301 kqlkkgdnli ftafgagfty gavyvkwgyd gskr (SEQ ID NO:114)

  1 atggaaaaaa taaatgcagt aataacagga gtcggtggat atgtaccaga ttatgtcttg
 61 actaacgaag agatttcaag aatggtagat accaatgatg aatggattat gactcgaatc
121 ggagttaaag aaagacgtat tctgaatgaa gaaggattag gtacatcgta tatggcgcgt
181 aaggctgcca aacaactgat gcagaaaaca gcttctaatc cggatgacat tgatgcagta
241 atcgtagcaa ctactactcc tgactatcat ttcccttcca ctgcttctat cctgtgtgat
301 aagctgggat tgaaaaatgc atttgcattt gatttgcagg ctgcctgctg cggctttttg
361 tatttaatgg aaactgctgc ttcacttatc gcatcgggaa gacataaaaa gattattatt
421 gtcggtgcag ataagatgtc atctatggta aactaccagg atcgtgcaac ttgccctatc
481 tttggtgatg gtgcagcagc atgtatggtg gaagctacta cagaagatta tggtattatg
541 gattctattc ttcgtacaga tggtaaggga cttccttttc ttcacatgaa agccggtggt
601 tctgtatgtc ctccttctta tttcactgtt gatcataaga tgcattatct ttatcaggaa
661 ggaagaacag tatttaaata tgctgtttcc aatatgtcgg atattacagc gactattgcc
721 gaaaagaatg gtttgaataa agataatatc gactgggtaa ttcctcatca ggctaatctg
781 cgtattattg atgcggtagc ctctcgcttg gaagttccct tggaaaaggt aatgattaat
841 attcagcgat atggtaatac cagtggtgct acacttccgt tgtgtctttg ggattacgaa
901 aagcagctga agaaaggaga taacctgata tttacagctt tcggcgcagg ttttacctat
961 ggagccgttt atgtgaaatg ggttacgat ggtagtaaga gataa (SEQ ID NO:115)
```

<u>Clostridium acetobutylicum ATCC 824, *beta ketoacyl-ACP synthase homolog*</u>

3-oxoacyl-(acyl carrier protein) synthase III, NP_350161, GI:15896812

```
  1 mnsveiigtg syvpekivtn edmskivdts dewissrtgi kerrisinen tsdlgakaal
 61 raiedsnikp eeidliivat tspdsytpsv acivqekiga knaacfdina actgfifaln
121 tasqfiktge yktalvvgte vlskildwqd rgtcvlfgdg agaviirggd engiikaclg
181 sdgtgkdflh cpatnvinpf sdekglassk ismngrevfk favkvmvssv kkviedsgln
241 iedidyivph qaniriiefa akklglsmdk ffinlqnygn tsgatiplai demnkkgllk
301 rgakivvvgf gggltwgsmv lkwtk (SEQ ID NO:116)

  1 gtgaatagtg ttgagattat agggactgga agctatgtcc cagaaaaaat agttactaat
 61 gaagatatgt ctaagatagt tgatactagt gatgagtgga tatcatcaag aacaggtata
121 aaggaaagaa gaatatctat aaacgaaaat acatcagatt taggtgctaa agctgcctta
181 agggcaatag aggactcaaa cataaaacca gaagaaatag atttaataat agttgcaact
241 acaagtccag actcatatac tccatccgta gcttgtattg ttcaggagaa gataggtgcc
301 aaaaatgctg cctgttttga tttgaatgcg gcatgtactg gatttatatt tgctcttaat
361 acggcatctc agtttataaa aacaggagag tataaaacag ctcttgtagt aggaacagag
421 gtactatcaa agatacttga ttggcaagat agaggtacat gtgtactttt tggagatggt
481 gcaggtgcgg taattataag aggcggagat gaaaacggaa ttattaaagc atgtcttggt
541 tcagatggta cgggaaaaga cttcttgcat tgtccagcga ctaatgtgat aaatccattt
601 tcggatgaaa aaggtttagc aagcagtaag atttctatga atggaagaga agtctttaaa
661 tttgcagtta aggtaatggt aagctcagtt aaaaaggtta tagaagatag tggactaaat
721 atagaagaca ttgattatat agtacctcat caggctaaca ttagaataat agagtttgca
781 gctaaaaaac ttggattaag tatggacaaa tttttttataa acctacaaaa ctatggaaat
841 acatctggag cgactatacc actggcaata gatgaaatga ataaaaaagg cttgcttaaa
901 agaggtgcta aaatagttgt agttggtttt ggtggaggac ttacttgggg ttccatggtt
961 cttaaatgga ctaaataa (SEQ ID NO:117)
```

<u>Flavobacterium johnsoniae UW101, *beta ketoacyl-ACP synthase homolog*</u>

FIG. 2E cont'd

3-oxoacyl-(acyl carrier protein) synthase III, YP_001193000, GI:146298409

```
  1 mntitaaita vggyvpdfvl snkvletmvd tndewittrt gikerrilkd adkgtsylai
 61 qaaqdliaka nidpleidmv imatatpdmm vastgvyvat eigavnafay dlqaacssfl
121 ygmstaaayv qsgrykkvll igadkmssiv dytdratcii fgdgagavlf epnyeglglq
181 deylrsdgvg rdflkipagg slipasedtv knrqhnimqd gktvfkyavt nmadaselil
241 qrnnltnqdv dwlvphqank riidatagrl eleeskvlvn ierygnttsg tlpivlsdfe
301 nqfkkgdnii laafgggftw gsiylkwayd kk (SEQ ID NO:118)
```

```
  1 atgaatacaa tcacagccgc aattaccgct gttggaggct acgttccaga ctttgtgctt
 61 tcaaacaaag tgttggaaac aatggtagat accaatgacg aatggattac cactcgtaca
121 ggaattaaag aaagaagaat tcttaaagat gctgataaag gtacatctta ccttgccata
181 caagcagcac aggatttaat agcaaaagct aatattgatc ctcttgaaat tgatatggtt
241 attatggcaa ctgcaacacc agatatgatg gtagcttcaa caggagttta tgttgcaaca
301 gaaattggag ctgttaatgc atttgcatac gatttgcagg cagcttgttc aagtttctta
361 tacggaatgt ctactgctgc ggcttatgta caatctggaa gatataaaaa agttctttta
421 attggtgccg ataaaatgtc atcaattgta gattacacag acagagcaac ttgtattatt
481 tttggtgatg gagcaggggc agttttgttt gagccaaatt acgaaggtct tggtctgcaa
541 gacgaatatt taagaagtga tggtgtagga cgcgattttc ttaaaatacc agctggagga
601 tctttaattc cagcttcaga agatactgta aaaaacagac aacacaatat tatgcaggat
661 ggtaaaacag tttttaaata tgctgtaacc aatatggctg atgccagcga actaatcttg
721 caaagaaaca atttaactaa tcaggatgtt gattggttag tgcctcacca ggcaaacaaa
781 cgcatcatcg atgcaactgc aggaagacta gagttagaag agtctaaagt actagttaat
841 atcgaaagat atggtaatac aacttcagga acattacctt tggtattaag cgattttgaa
901 aatcaattca aaaaaggaga taatattatt ttagcagcat ttggaggtgg attcacttgg
961 ggatctattt acctaaaatg ggcttacgat aagaaataa (SEQ ID NO:119)
```

<u>**Micrococcus luteus NCTC 2665, *beta ketoacyl-ACP synthase homolog***</u>

3-oxoacyl-(acyl-carrier-protein) synthase III, YP_002957006, GI:239917448

```
  1 mtvtlkqher paasrivavg ayrpanlvpn edligpidss dewirqrtgi vtrqrataee
 61 tvpvmavgaa realeraglq gsdldavivs tvtfphatps aaalvaheig atpapaydvs
121 aacagycygv aqadalvrsg tarhvlvvgv erlsdvvdpt drsisfllgd gagavivaas
181 depgispsvw gsdgerwsti smthsqlelr daveharttg dasaitgaeg mlwptlrqdg
241 psvfrwavws makvareald aagvepedla afiphqanmr iidefakqik lpesvvvard
301 iadagntsaa siplamhrll eenpelsggi alqigfgagl vygaqvvrlp (SEQ ID
NO:120)
```

```
  1 atgaccgtca ccctgaagca gcacgagcgc cccgcggcca gccgcatcgt ggccgtgggc
 61 gcctaccgcc cggcgaacct ggtcccgaac gaggacctca tcggccccat cgactcgtcg
121 gacgagtgga tccgccagcg caccggcatc gtcacacgcc agcgcgccac ggcggaggag
181 accgtgcccg tcatggccgt gggcgccgcc cgggaggccc tcgagcgggc cggcctgcag
241 ggctcggacc tggacgccgt gatcgtctcg accgtcacct tcccgcacgc cacccccctcg
301 gccgcggccc tcgtggcgca cgagatcggc gccaccccgg cgcccgccta cgacgtctcc
361 gccgcgtgcg ccggctactg ctacggcgtg gcccaggccg acgcgctcgt gcgctccggc
421 accgcgcggc acgtgctcgt ggtcggcgtc gagcgcctct ccgacgtcgt ggatcccacg
481 gaccgctcca tctccttcct gctgggcgac ggcgcgggcg ccgtgatcgt cgcggcctcg
541 gacgagccgg gcatctcccc ctcggtgtgg ggctcggacg gggagcgctg gtccacgatc
601 tccatgacgc actcgcagct ggagctgcgc gatgccgtgg agcacgcccg caccacgggc
```

FIG. 2E cont'd

```
 661 gacgcctcgg cgatcaccgg cgcagagggg atgctctggc ccacgctgcg ccaggacggg
 721 ccctccgtct tccgttgggc cgtgtggtcg atggcgaagg tggcccgcga ggcccttgac
 781 gccgcgggcg tggagcccga ggacctcgcc gcgttcatcc cgcaccaggc caacatgcgg
 841 atcatcgacg agttcgccaa gcagctgaag ctgccggagt ccgtcgtcgt ggcccgggac
 901 atcgcggacg ccggcaacac gtcggccgcg tccatcccgc tggccatgca ccggctgctg
 961 gaggagaacc ccgagctctc cggcggtctg gccctgcaga tcggcttcgg tgccgggctg
1021 gtctacggcg cccaggtggt ccgcctcccc tga (SEQ ID NO:121)
```

D-T-(N,S)D-(A,E)-W-I-(x)2-(M,R)-T-G-I-x-(N,E)-R-(R,H)    [SEQ ID NO:122]
(S,A)-x-D-(x)2-A-(A,V)-C-(A,S)-G-F-(x)3-(M,L)-(x)2-A    [SEQ ID NO:123]
D-R-x-T-(A,I)-(I,V)-x-F-(A,G)-D-G-A-(A,G)-(G,A)-(A,V)    [SEQ ID NO:124]
H-Q-A-N-x-R-I-(M,L)    [SEQ ID NO:125]
G-N-T-(G,S)-A-A-S-(V,I)-P-(x)2-(I,L)-(x)6-G    [SEQ ID NO:126]
(I,V)-x-L-(x)2-F-G-G-G-(L,F)-(T,S)-W-G (SEQ ID NO:7281)    [SEQ ID NO:127]

FIG. 3A-BKD E1 Alpha Subunit Homologs

| Acc. No. | Organism | ID%Pp | ID%Bs | ID%Sc | ID%Sa | ID%Sa2 | ID%Sc2 |
|---|---|---|---|---|---|---|---|
| gi\|16079461\|ref\|NP_390285.1\| | Bacillus subtilis | 34.5 | 100 | 39.4 | 40.8 | 0.0 | 55.6 |
| gi\|154686664\|ref\|YP_001421825.1\| | B. amyloliquefaciens | 35.1 | 88.8 | 38.6 | 40.8 | 0.0 | 54.6 |
| gi\|52080943\|ref\|YP_079734.1\| | B.licheniformis | 32.1 | 84.8 | 35.8 | 36.7 | 0.0 | 54.0 |
| gi\|152976567\|ref\|YP_001376084.1\| | Bacillus cereus | 33.3 | 83.5 | 37.7 | 40.4 | 0.0 | 54.3 |
| gi\|157692911\|ref\|YP_001487373.1\| | Bacillus pumilus | 32.7 | 83.0 | 40.4 | 40.0 | 0.0 | 57.6 |
| gi\|194016754\|ref\|ZP_03055367.1\| | Bacillus pumilus | 32.4 | 82.4 | 39.7 | 38.0 | 0.0 | 57.2 |
| gi\|228998952\|ref\|ZP_04158534.1\| | Bacillus mycoides | 33.0 | 82.3 | 39.0 | 40.1 | 0.0 | 55.8 |
| gi\|228992907\|ref\|ZP_04152831.1\| | B. pseudomycoides | 32.7 | 82.0 | 38.6 | 39.7 | 0.0 | 55.8 |
| gi\|42783280\|ref\|NP_980527.1\| | Bacillus cereus | 33.3 | 81.9 | 38.3 | 39.4 | 0.0 | 56.1 |
| gi\|30264237\|ref\|NP_846614.1\| | B.thuringiensis, B. cereus, B. anthracis | 33.3 | 81.9 | 38.3 | 39.4 | 0.0 | 56.1 |
| gi\|167633774\|ref\|ZP_02392098.1\| | Bacillus anthracis | 33.3 | 81.9 | 38.3 | 39.4 | 0.0 | 55.8 |
| gi\|229157743\|ref\|ZP_04285818.1\| | Bacillus cereus | 33.7 | 81.6 | 38.3 | 39.4 | 0.0 | 55.8 |
| gi\|228935483\|ref\|ZP_04098301.1\| | B. thuringiensis | 33.7 | 81.6 | 38.0 | 39.4 | 0.0 | 56.1 |
| gi\|229086734\|ref\|ZP_04218900.1\| | Bacillus cereus | 33.0 | 81.3 | 37.8 | 38.8 | 0.0 | 55.8 |
| gi\|206971161\|ref\|ZP_03232112.1\| | Bacillus cereus | 33.0 | 81.3 | 37.6 | 38.6 | 0.0 | 56.1 |
| gi\|229013373\|ref\|ZP_04170513.1\| | Bacillus mycoides | 33.0 | 81.3 | 37.4 | 38.5 | 0.0 | 55.8 |
| gi\|228922915\|ref\|ZP_04086210.1\| | B.thuringiensis | 33.0 | 81.0 | 38.0 | 39.0 | 0.0 | 55.8 |
| gi\|228909998\|ref\|ZP_04073818.1\| | B.cereus, B. thuringiensis | 33.0 | 81.0 | 37.8 | 38.5 | 0.0 | 55.8 |
| gi\|218233774\|ref\|YP_002368965.1\| | B. cereus, B.thuringiensis | 33.0 | 81.0 | 38.0 | 39.0 | 0.0 | 55.8 |
| gi\|149181878\|ref\|ZP_01860367.1\| | Bacillus sp. | 31.6 | 80.9 | 36.8 | 37.1 | 0.0 | 53.7 |
| gi\|75761046\|ref\|ZP_00741046.1\| | B. thuringiensis | 31.9 | 80.9 | 40.6 | 43.8 | 0.0 | 61.7 |
| gi\|163941912\|ref\|YP_001646796.1\| | B. cereus, B.wei-henstephanensis | 33.0 | 80.7 | 37.8 | 38.8 | 0.0 | 56.1 |
| gi\|30022243\|ref\|NP_833874.1\| | Bacillus cereus | 32.7 | 80.4 | 38.4 | 39.4 | 0.0 | 55.8 |
| gi\|89099272\|ref\|ZP_01172150.1\| | Bacillus sp. | 33.2 | 78.8 | 36.8 | 37.5 | 0.0 | 54.0 |
| gi\|255332688\|ref\|ZP_05373687.1\| | Geobacillus sp. | 32.2 | 78.5 | 38.7 | 38.3 | 0.0 | 55.7 |
| gi\|239827651\|ref\|YP_002950275.1\| | Geobacillus sp. | 32.9 | 78.2 | 40.4 | 39.0 | 0.0 | 55.4 |
| gi\|212638803\|ref\|YP_002315323.1\| | A.flavithermus | 31.4 | 77.6 | 38.9 | 38.8 | 0.0 | 53.9 |
| gi\|15615326\|ref\|NP_243629.1\| | Bacillus halodurans | 34.7 | 77.6 | 37.9 | 37.9 | 0.0 | 54.1 |
| gi\|229498330\|ref\|ZP_04392026.1\| | Geobacillus sp | 33.3 | 75.8 | 39.9 | 40.8 | 0.0 | 55.5 |
| gi\|56420913\|ref\|YP_148231.1\| | G.kaustophilus | 32.9 | 75.5 | 39.9 | 40.8 | 0.0 | 55.8 |

FIG. 3A-BKD cont'd

FIG. 3A-BKD E1 Alpha Subunit Homologs

| | | | | | | | |
|---|---|---|---|---|---|---|---|
| gi\|138895948\|ref\|YP_001126401.1\| | Geobacillus sp. | 32.8 | 75.5 | 39.9 | 41.1 | 0.0 | 55.8 |
| gi\|229543916\|ref\|ZP_04432975.1\| | Bacillus coagulans | 34.6 | 75.2 | 40.1 | 39.4 | 0.0 | 54.7 |
| gi\|56964216\|ref\|YP_175947.1\| | Bacillus clausii | 34.8 | 74.8 | 38.2 | 38.7 | 0.0 | 54.3 |
| gi\|23099321\|ref\|NP_692787.1\| | O.iheyensis | 34.6 | 73.8 | 35.7 | 36.7 | 0.0 | 54.7 |
| gi\|255030621\|ref\|ZP_05302572.1\| | L.monocytogenes | 36.1 | 73.2 | 38.0 | 38.4 | 0.0 | 57.2 |
| gi\|254994509\|ref\|ZP_05276699.1\| | L.monocytogenes | 36.1 | 71.8 | 38.0 | 38.0 | 0.0 | 57.0 |
| gi\|283567958\|gb\|EFC18381.1\| | B.cellulosilyticus | 32.7 | 71.5 | 35.7 | 35.0 | 0.0 | 56.7 |
| gi\|226311956\|ref\|YP_002771850.1\| | Brevibacillus brevis | 32.3 | 69.7 | 34.9 | 38.9 | 0.0 | 58.5 |
| gi\|229916238\|ref\|YP_002884884.1\| | Exiguobacterium sp. | 32.5 | 68.6 | 36.7 | 37.0 | 0.0 | 52.5 |
| gi\|46907598\|ref\|YP_013987.1\| | L.monocytogenes | 32.8 | 68.3 | 36.1 | 35.8 | 0.0 | 56.7 |
| gi\|16800477\|ref\|NP_470745.1\| | Listeria innocua | 33.0 | 68.3 | 36.4 | 36.1 | 0.0 | 57.1 |
| gi\|217964482\|ref\|YP_002350160.1\| | L.monocytogenes | 33.3 | 68.3 | 36.1 | 36.6 | 0.0 | 57.1 |
| gi\|254824569\|ref\|ZP_05229570.1\| | L.monocytogenes | 33.0 | 68.3 | 36.1 | 35.8 | 0.0 | 56.7 |
| gi\|255522413\|ref\|ZP_05389650.1\| | L.monocytogenes | 33.0 | 68.3 | 36.0 | 35.7 | 0.0 | 57.3 |
| gi\|229556639\|ref\|ZP_04444428.1\| | Listeria grayi | 34.1 | 68.3 | 35.2 | 36.2 | 0.0 | 54.7 |
| gi\|126653078\|ref\|ZP_01725213.1\| | Bacillus sp. | 34.9 | 68.3 | 36.3 | 35.8 | 0.0 | 54.9 |
| gi\|254827632\|ref\|ZP_05232319.1\| | L. monocytogenes | 33.3 | 68.0 | 35.8 | 36.6 | 0.0 | 56.7 |
| gi\|16803412\|ref\|NP_464897.1\| | L.monocytogenes | 33.0 | 68.0 | 36.1 | 36.9 | 0.0 | 56.4 |
| gi\|254873036\|ref\|ZP_05245746.1\| | L.monocytogenes | 33.7 | 68.0 | 36.1 | 36.6 | 0.0 | 57.4 |
| gi\|116872803\|ref\|YP_849584.1\| | L.welshimeri serovar | 32.1 | 68.0 | 35.8 | 35.9 | 0.0 | 56.7 |
| gi\|47093759\|ref\|ZP_00231509.1\| | L.monocytogenes | 32.7 | 68.0 | 35.8 | 35.4 | 0.0 | 56.7 |
| gi\|169828954\|ref\|YP_001699112.1\| | L.sphaericus | 34.9 | 68.0 | 36.3 | 35.8 | 0.0 | 54.9 |
| gi\|163763748\|ref\|ZP_02170808.1\| | B.selenitireducens | 34.8 | 67.9 | 35.0 | 35.6 | 0.0 | 54.9 |
| gi\|22773771\|gb\|AAN05020.1\| | L.monocytogenes | 32.7 | 67.3 | 36.0 | 37.1 | 0.0 | 56.0 |
| gi\|172056956\|ref\|YP_001813416.1\| | E.sibiricum | 33.2 | 65.6 | 34.8 | 35.4 | 0.0 | 54.8 |
| gi\|251796332\|ref\|YP_003011063.1\| | Paenibacillus sp. | 34.2 | 65.5 | 37.4 | 37.5 | 0.0 | 54.2 |
| gi\|261405972\|ref\|YP_003242213.1\| | Geobacillus sp. | 35.4 | 65.2 | 37.5 | 38.1 | 0.0 | 53.7 |
| gi\|253576335\|ref\|ZP_04853665.1\| | Paenibacillus sp. | 36.4 | 64.6 | 40.7 | 40.0 | 0.0 | 55.0 |
| gi\|167465151\|ref\|ZP_02330240.1\| | Paenibacillus larvae | 35.1 | 61.1 | 38.6 | 39.7 | 0.0 | 53.0 |
| gi\|51893300\|ref\|YP_075991.1\| | S. thermophilum | 34.6 | 59.3 | 41.2 | 38.0 | 0.0 | 53.6 |
| gi\|269929377\|ref\|YP_003321698.1\| | S. thermophilus | 35.0 | 56.7 | 35.2 | 35.5 | 0.0 | 56.5 |

FIG. 3A-BKD cont'd

FIG. 3A-BKD E1 Alpha Subunit Homologs

| | | | | | | | |
|---|---|---|---|---|---|---|---|
| gi\|163847255\|ref\|YP_001635299.1\| | Chloroflexus sp. | 35.3 | 56.7 | 36.6 | 35.9 | 0.0 | 51.4 |
| gi\|108805282\|ref\|YP_645219.1\| | R.xylanophilus | 35.7 | 56.4 | 39.5 | 39.3 | 0.0 | 56.8 |
| gi\|73662547\|ref\|YP_301328.1\| | S. saprophyticus | 31.8 | 56.0 | 32.9 | 32.7 | 0.0 | 51.5 |
| gi\|219848985\|ref\|YP_002463418.1\| | C.aggregans | 36.0 | 55.8 | 35.4 | 35.0 | 0.0 | 51.7 |
| gi\|269925214\|ref\|YP_003321837.1\| | T. terrenum | 36.3 | 55.3 | 36.9 | 42.5 | 0.0 | 54.6 |
| gi\|159899110\|ref\|YP_001545357.1\| | H.aurantiacus | 34.6 | 55.1 | 35.8 | 35.5 | 0.0 | 54.2 |
| gi\|242373817\|ref\|ZP_04819391.1\| | S.epidermidis | 31.7 | 55.1 | 32.5 | 34.1 | 0.0 | 53.2 |
| gi\|27468116\|ref\|NP_764753.1\| | S.epidermidis | 32.1 | 53.9 | 32.6 | 34.0 | 0.0 | 57.6 |
| gi\|57866998\|ref\|YP_188655.1\| | S. epidermidis | 32.1 | 53.9 | 32.6 | 34.0 | 0.0 | 57.6 |
| gi\|242242786\|ref\|ZP_04797231.1\| | S. epidermidis | 31.8 | 53.9 | 32.6 | 34.0 | 0.0 | 57.6 |
| gi\|82751122\|ref\|YP_416863.1\| | S.aureus | 31.3 | 53.8 | 33.8 | 33.4 | 0.0 | 54.9 |
| gi\|283470796\|emb\|CAQ50007.1\| | S. aureus | 31.9 | 53.6 | 33.8 | 34.1 | 0.0 | 55.3 |
| gi\|258423171\|ref\|ZP_05686064.1\| | S.aureus | 31.9 | 53.6 | 33.1 | 33.4 | 0.0 | 55.3 |
| gi\|282916788\|ref\|ZP_06324546.1\| | S.aureus | 31.9 | 53.6 | 33.4 | 33.8 | 0.0 | 55.3 |
| gi\|239637673\|ref\|ZP_04678645.1\| | S. warneri | 30.1 | 53.5 | 32.0 | 33.2 | 0.0 | 56.4 |
| gi\|49483767\|ref\|YP_040991.1\| | S.aureus | 31.3 | 53.3 | 33.8 | 33.4 | 0.0 | 55.3 |
| gi\|15924507\|ref\|NP_372041.1\| | S.aureus | 31.6 | 53.3 | 33.8 | 33.4 | 0.0 | 55.3 |
| gi\|57650474\|ref\|YP_186403.1\| | S.aureus | 31.6 | 53.3 | 33.4 | 33.1 | 0.0 | 54.9 |
| gi\|70726399\|ref\|YP_253313.1\| | S. haemolyticus | 30.7 | 52.9 | 32.1 | 32.5 | 0.0 | 54.2 |
| gi\|253732171\|ref\|ZP_04866336.1\| | S.aureus | 31.3 | 52.9 | 33.4 | 33.1 | 0.0 | 54.9 |
| gi\|283790431\|gb\|EFC29248.1\| | S.aureus | | 52.9 | | 33.1 | 0.0 | 54.9 |
| gi\|256762591\|ref\|ZP_05503171.1\| | E.faecalis | 28.9 | 52.6 | 31.6 | 31.0 | 0.0 | 52.9 |
| gi\|223043306\|ref\|ZP_03613353.1\| | S.capitis | 30.9 | 52.6 | 32.6 | 33.2 | 0.0 | 52.2 |
| gi\|257082459\|ref\|ZP_05576820.1\| | E.faecalis | 28.8 | 52.3 | 31.3 | 31.9 | 0.0 | 52.6 |
| gi\|255975754\|ref\|ZP_05426340.1\| | E.faecalis | 28.9 | 52.3 | 31.3 | 31.9 | 0.0 | 52.6 |
| gi\|29376214\|ref\|NP_815368.1\| | E. faecalis | 28.9 | 52.3 | 31.3 | 31.9 | 0.0 | 52.6 |
| gi\|257422519\|ref\|ZP_05599509.1\| | E.faecalis | 28.8 | 52.3 | 31.3 | 31.9 | 0.0 | 51.9 |
| gi\|227553461\|ref\|ZP_03983510.1\| | E.faecalis | 28.9 | 52.0 | 31.3 | 31.9 | 0.0 | 52.6 |
| gi\|5901696\|gb\|AAD55377.1\|AF149712_5 | E. faecalis | 29.1 | 52.0 | 31.3 | 31.9 | 0.0 | 52.6 |
| gi\|257089976\|ref\|ZP_05584337.1\| | E.faecalis | 29.2 | 52.0 | 30.9 | 31.6 | 0.0 | 54.3 |
| gi\|229545729\|ref\|ZP_04434454.1\| | E.faecalis | 29.2 | 52.0 | 31.3 | 31.9 | 0.0 | 52.6 |

FIG. 3A-BKD cont'd

FIG. 3A-BKD E1 Alpha Subunit Homologs

| | | | | | | | |
|---|---|---|---|---|---|---|---|
| gi\|227518846\|ref\|ZP_03948895.1\| | E.faecalis | 28.8 | 52.0 | 31.6 | 32.2 | 0.0 | 52.6 |
| gi\|238856493\|ref\|ZP_04646759.1\| | E.faecalis | 29.2 | 52.0 | 31.3 | 31.9 | 0.0 | 52.6 |
| gi\|255972702\|ref\|ZP_05423288.1\| | E.faecalis | 28.9 | 52.0 | 30.1 | 30.7 | 0.0 | 52.3 |
| gi\|228475951\|ref\|ZP_04060659.1\| | S. hominis | 31.7 | 52.0 | 32.5 | 33.4 | 0.0 | 56.2 |
| gi\|224476626\|ref\|YP_002634232.1\| | S.carnosus | 32.6 | 52.0 | 32.2 | 33.8 | 0.0 | 51.6 |
| gi\|229549919\|ref\|ZP_04438644.1\| | E. faecalis | 28.5 | 51.9 | 30.2 | 30.8 | 0.0 | 52.3 |
| gi\|257419387\|ref\|ZP_05596381.1\| | E. faecalis | 28.9 | 51.7 | 31.6 | 31.6 | 0.0 | 52.0 |
| gi\|256803208\|ref\|ZP_05532832.1\| | S. viridochromogenes | 35.1 | 41.7 | 81.9 | 85.6 | 0.0 | 55.8 |
| gi\|29830919\|ref\|NP_825553.1\| | S.avermitilis | 34.3 | 40.8 | 80.7 | 100 | 0.0 | 54.1 |
| gi\|256815059\|ref\|ZP_05540074.1\| | S.griseoflavus | 34.1 | 40.3 | 80.7 | 85.5 | 0.0 | 55.7 |
| gi\|254402699\|ref\|ZP_05017648.1\| | S.sviceus | 34.8 | 40.1 | 80.0 | 89.0 | 0.0 | 55.3 |
| gi\|260648470\|emb\|CBG71581.1\| | S. scabiei | 36.3 | 40.1 | 82.2 | 84.9 | 0.0 | 54.0 |
| gi\|87199993\|ref\|YP_497250.1\| | N.aromaticivorans | 58.1 | 39.9 | 39.8 | 37.6 | 0.0 | 49.0 |
| gi\|239942620\|ref\|ZP_04694557.1\| | S.roseosporus | 34.8 | 39.9 | 42.1 | 40.5 | 0.0 | 89.9 |
| gi\|239930115\|ref\|ZP_04687068.1\| | S.ghanaensis | 34.2 | 39.9 | 81.0 | 84.1 | 0.0 | 54.8 |
| gi\|254383354\|ref\|ZP_04998706.1\| | Streptomyces sp. | 33.3 | 39.7 | 77.8 | 82.5 | 0.0 | 55.8 |
| gi\|21222227\|ref\|NP_628006.1\| | S.lividans, S. coelicolor | 35.5 | 39.4 | 100 | 79.8 | 0.0 | 54.2 |
| gi\|256395302\|ref\|YP_003116866.1\| | C. acidiphila | 39.2 | 39.2 | 42.9 | 43.9 | 0.0 | 75.2 |
| gi\|256768472\|ref\|ZP_05507646.1\| | Streptomyces sp. | 37.7 | 38.6 | 78.5 | 80.9 | 0.0 | 53.7 |
| gi\|269957992\|ref\|YP_003327781.1\| | X.cellulosilytica | 36.4 | 38.6 | 55.9 | 57.1 | 0.0 | 57.7 |
| gi\|254420646\|ref\|ZP_05034370.1\| | Brevundimonas sp. | 58.5 | 38.4 | 36.6 | 34.5 | 0.0 | 51.3 |
| gi\|239980725\|ref\|ZP_04703249.1\| | Streptomyces albus | 34.3 | 38.4 | 83.8 | 87.5 | 0.0 | 56.6 |
| gi\|239942602\|ref\|ZP_04694539.1\| | S.roseosporus | 35.5 | 38.3 | 80.7 | 83.0 | 0.0 | 56.4 |
| gi\|182437558\|ref\|YP_001825277.1\| | Streptomyces sp. | 34.9 | 38.3 | 81.5 | 81.7 | 0.0 | 56.1 |
| gi\|239980739\|ref\|ZP_04703263.1\| | Streptomyces albus | 32.1 | 38.3 | 40.8 | 41.4 | 0.0 | 88.6 |
| gi\|239930129\|ref\|ZP_04687082.1\| | S.ghanaensis | 34.0 | 38.3 | 41.4 | 41.4 | 0.0 | 93.7 |
| gi\|282863885\|ref\|ZP_06272943.1\| | Streptomyces sp. | 35.5 | 38.2 | 75.2 | 83.0 | 0.0 | 57.2 |
| gi\|85373858\|ref\|YP_457920.1\| | E.litoralis | 56.8 | 38.0 | 33.4 | 35.8 | 0.0 | 48.9 |
| gi\|256768490\|ref\|ZP_05507664.1\| | Streptomyces sp. | 35.3 | 38.0 | 41.9 | 41.9 | 0.0 | 91.4 |
| gi\|134101992\|ref\|YP_001107653.1\| | S. erythraea | 34.0 | 38.0 | 40.8 | 40.2 | 0.0 | 81.0 |
| gi\|111018575\|ref\|YP_701547.1\| | Rhodococcus jostii | 36.1 | 38.0 | 58.1 | 59.6 | 0.0 | 55.5 |

FIG. 3A-BKD cont'd

FIG. 3A-BKD E1 Alpha Subunit Homologs

| | | | | | | | |
|---|---|---|---|---|---|---|---|
| gi\|229489965\|ref\|ZP_04383818.1\| | R.erythropolis | 32.6 | 38.0 | 53.2 | 53.6 | 0.0 | 56.8 |
| gi\|256671550\|ref\|ZP_05482503.1\| | Streptomyces sp. | 34.6 | 38.0 | 43.0 | 42.5 | 0.0 | 74.1 |
| gi\|260648483\|emb\|CBG71594.1\| | S. scabiei | 34.6 | 37.9 | 39.4 | 39.7 | 0.0 | 97.9 |
| gi\|239917208\|ref\|YP_002956766.1\| | Micrococcus luteus | 31.9 | 37.9 | 50.0 | 50.0 | 0.0 | 59.4 |
| gi\|260453180\|ref\|ZP_05801587.1\| | S.flavogriseus | 37.0 | 37.8 | 76.7 | 82.8 | 0.0 | 56.6 |
| gi\|239934270\|ref\|ZP_04691223.1\| | S.ghanaensis | 35.5 | 37.8 | 72.3 | 70.7 | 0.0 | 54.9 |
| gi\|269922275\|ref\|ZP_06171182.1\| | B.subvibrioides | 59.8 | 37.8 | 36.5 | 37.1 | 0.0 | 50.3 |
| gi\|111222645\|ref\|YP_713439.1\| | Frankia alni | 32.4 | 37.6 | 43.2 | 40.0 | 0.0 | 79.1 |
| gi\|148555060\|ref\|YP_001262642.1\| | S. wittichii | 59.3 | 37.6 | 37.6 | 36.9 | 0.0 | 48.9 |
| gi\|149186676\|ref\|ZP_01864987.1\| | Erythrobacter sp. | 55.9 | 37.5 | 32.4 | 34.6 | 0.0 | 50.2 |
| gi\|226360692\|ref\|YP_002778470.1\| | R. opacus | 34.5 | 37.4 | 57.9 | 58.7 | 0.0 | 56.6 |
| gi\|260453166\|ref\|ZP_05801573.1\| | S.flavogriseus | 35.0 | 37.3 | 42.1 | 41.3 | 0.0 | 90.6 |
| gi\|282863270\|ref\|ZP_06272329.1\| | Streptomyces sp. | 35.2 | 37.2 | 41.2 | 38.3 | 0.0 | 90.9 |
| gi\|256379012\|ref\|YP_003102672.1\| | A.mirum | 36.0 | 37.1 | 40.5 | 39.0 | 0.0 | 70.8 |
| gi\|85708446\|ref\|ZP_01039512.1\| | Erythrobacter sp. | 56.6 | 37.1 | 36.7 | 34.9 | 0.0 | 50.0 |
| gi\|260652579\|emb\|CBG75712.1\| | S.scabiei | 37.2 | 37.1 | 42.9 | 42.6 | 0.0 | 74.6 |
| gi\|227823512\|ref\|YP_002827485.1\| | Rhizobium sp. | 61.1 | 37.0 | 36.1 | 35.5 | 0.0 | 49.8 |
| gi\|260907141\|ref\|ZP_05915463.1\| | B.linens | 37.6 | 37.0 | 44.4 | 43.6 | 0.0 | 66.8 |
| gi\|254402712\|ref\|ZP_05017661.1\| | S.sviceus | 33.4 | 37.0 | 39.9 | 39.7 | 0.0 | 94.2 |
| gi\|254396773\|ref\|ZP_05011830.1\| | S.pristinaespiralis | 35.1 | 37.0 | 80.1 | 81.8 | 0.0 | 56.9 |
| gi\|86738781\|ref\|YP_479181.1\| | Frankia sp. | 34.1 | 36.9 | 54.4 | 59.0 | 0.0 | 56.1 |
| gi\|254383335\|ref\|ZP_04998687.1\| | Streptomyces sp. | 33.7 | 36.9 | 42.9 | 42.5 | 0.0 | 88.6 |
| gi\|226307479\|ref\|YP_002767439.1\| | R.erythropolis | 32.6 | 36.9 | 54.3 | 54.4 | 0.0 | 56.9 |
| gi\|182437541\|ref\|YP_001825260.1\| | Streptomyces sp. | 36.3 | 36.9 | 42.1 | 40.1 | 0.0 | 90.2 |
| gi\|256786661\|ref\|ZP_05525092.1\| | S.lividans | 33.2 | 36.8 | 41.1 | 40.6 | 0.0 | 93.7 |
| gi\|32141217\|ref\|NP_733618.1\| | S. coelicolor A3(2) | 33.0 | 36.8 | 41.3 | 40.7 | 0.0 | 93.7 |
| gi\|167645834\|ref\|YP_001683497.1\| | Caulobacter sp. | 56.8 | 36.7 | 36.5 | 36.0 | 0.0 | 52.2 |
| gi\|229208222\|ref\|ZP_04334667.1\| | N.dassonvillei | 36.5 | 36.6 | 42.5 | 42.6 | 0.0 | 72.4 |
| gi\|254392373\|ref\|ZP_05007556.1\| | S.clavuligerus | 33.2 | 36.6 | 41.2 | 39.7 | 0.0 | 88.5 |
| gi\|84495444\|ref\|ZP_00994563.1\| | Janibacter sp. | 35.4 | 36.5 | 61.5 | 60.3 | 0.0 | 55.8 |
| gi\|254376094\|ref\|ZP_04991569.1\| | Streptomyces sp. | 36.8 | 36.4 | 79.6 | 82.7 | 0.0 | 56.6 |

FIG. 3A-BKD cont'd

FIG. 3A-BKD E1 Alpha Subunit Homologs

| | | | | | | | |
|---|---|---|---|---|---|---|---|
| gi\|111020369\|ref\|YP_703341.1\| | Rhodococcus jostii | 33.4 | 36.4 | 58.5 | 56.1 | 0.0 | 56.7 |
| gi\|158318984\|ref\|YP_001511492.1\| | Frankia sp. | 36.1 | 36.4 | 59.4 | 57.3 | 0.0 | 55.9 |
| gi\|88855175\|ref\|ZP_01129840.1\| | marine actinobacterium | 33.7 | 36.3 | 49.3 | 49.9 | 0.0 | 56.3 |
| gi\|270499466\|ref\|ZP_06216405.1\| | M.aurantiaca | 32.5 | 36.3 | 53.2 | 53.2 | 0.0 | 55.6 |
| gi\|158314329\|ref\|YP_001506837.1\| | Frankia sp. | 35.8 | 36.3 | 51.7 | 49.7 | 0.0 | 56.7 |
| gi\|89902318\|ref\|YP_524789.1\| | R.ferrireducens | 73.4 | 36.2 | 35.8 | 33.8 | 0.0 | 48.4 |
| gi\|257069656\|ref\|YP_003155911.1\| | B.faecium | 33.2 | 36.2 | 55.7 | 55.2 | 0.0 | 56.8 |
| gi\|94496507\|ref\|ZP_01303084.1\| | Sphingomonas sp. | 60.3 | 36.2 | 38.3 | 36.3 | 0.0 | 50.7 |
| gi\|150398024\|ref\|YP_001328491.1\| | S.medicae | 60.9 | 36.2 | 35.2 | 34.3 | 0.0 | 50.6 |
| gi\|15966685\|ref\|NP_387038.1\| | S.meliloti | 61.4 | 36.2 | 35.2 | 34.8 | 0.0 | 50.6 |
| gi\|163839326\|ref\|YP_001623731.1\| | R.salmoninarum | 34.8 | 36.1 | 54.1 | 56.9 | 0.0 | 56.1 |
| gi\|256777794\|ref\|ZP_05516257.1\| | S.hygroscopicus | 34.7 | 36.1 | 40.3 | 39.9 | 0.0 | 91.2 |
| gi\|256678037\|ref\|ZP_05488348.1\| | Streptomyces sp. | 35.5 | 36.1 | 80.2 | 76.4 | 0.0 | 56.8 |
| gi\|229866854\|ref\|ZP_04486462.1\| | S.nassauensis | 31.0 | 36.0 | 59.1 | 59.7 | 0.0 | 54.8 |
| gi\|111219576\|ref\|YP_710370.1\| | Frankia alni | 35.8 | 36.0 | 55.2 | 62.5 | 0.0 | 54.9 |
| gi\|270501763\|ref\|ZP_06218680.1\| | M.aurantiaca | 32.8 | 35.9 | 66.2 | 63.4 | 0.0 | 56.1 |
| gi\|262398718\|emb\|CBH31046.1\| | S.pristinaespiralis | 37.6 | 35.9 | 44.7 | 45.0 | 0.0 | 73.1 |
| gi\|254399543\|ref\|ZP_05014538.1\| | S.pristinaespiralis | 37.6 | 35.9 | 44.7 | 45.0 | 0.0 | 73.1 |
| gi\|256803194\|ref\|ZP_05532818.1\| | S. viridochromogenes | 33.2 | 35.9 | 40.8 | 41.2 | 0.0 | 93.2 |
| gi\|134100487\|ref\|YP_001106148.1\| | S. erythraea | 37.0 | 35.9 | 42.6 | 40.1 | 0.0 | 75.4 |
| gi\|226362326\|ref\|YP_002780104.1\| | R.opacus | 38.1 | 35.8 | 44.8 | 43.8 | 0.0 | 76.1 |
| gi\|220913649\|ref\|YP_002488958.1\| | A.chlorophenolicus | 35.3 | 35.8 | 38.8 | 40.4 | 0.0 | 74.7 |
| gi\|256824332\|ref\|YP_003148292.1\| | K.sedentarius | 35.9 | 35.8 | 41.7 | 42.2 | 0.0 | 70.5 |
| gi\|280964586\|ref\|ZP_06239105.1\| | Frankia sp. | 33.5 | 35.8 | 59.6 | 59.5 | 0.0 | 56.8 |
| gi\|239918260\|ref\|YP_002957818.1\| | Micrococcus luteus | 33.4 | 35.7 | 40.4 | 38.5 | 0.0 | 72.6 |
| gi\|54022988\|ref\|YP_117230.1\| | Nocardia farcinica | 31.9 | 35.7 | 55.5 | 55.9 | 0.0 | 55.8 |
| gi\|256777779\|ref\|ZP_05516242.1\| | S.hygroscopicus | 34.6 | 35.7 | 74.9 | 81.1 | 0.0 | 54.5 |
| gi\|169631991\|ref\|YP_001705640.1\| | M.abscessus | 36.2 | 35.7 | 54.4 | 54.2 | 0.0 | 57.7 |
| gi\|111020310\|ref\|YP_703282.1\| | Rhodococcus jostii | 38.7 | 35.7 | 42.4 | 43.8 | 0.0 | 76.5 |
| gi\|148553705\|ref\|YP_001261287.1\| | S.wittichii | 57.8 | 35.6 | 34.8 | 34.2 | 0.0 | 51.5 |
| gi\|103486817\|ref\|YP_616378.1\| | S.alaskensis | 57.4 | 35.6 | 35.2 | 35.1 | 0.0 | 49.6 |

FIG. 3A-BKD cont'd

FIG. 3A-BKD E1 Alpha Subunit Homologs

| | | | | | | | |
|---|---|---|---|---|---|---|---|
| gi\|239814017\|ref\|YP_002942927.1\| | V.paradoxus | 74.8 | 35.6 | 33.9 | 33.4 | 0.0 | 47.4 |
| gi\|256380962\|ref\|YP_003104622.1\| | A.mirum | 34.0 | 35.6 | 61.1 | 58.1 | 0.0 | 55.1 |
| gi\|256059277\|ref\|ZP_05449479.1\| | Brucella neotomae | 60.4 | 35.5 | 35.0 | 35.5 | 0.0 | 49.2 |
| gi\|148557918\|ref\|YP_001257490.1\| | Brucella ovis | 60.6 | 35.5 | 34.5 | 35.5 | 0.0 | 49.7 |
| gi\|225686316\|ref\|YP_002734288.1\| | Brucella melitensis | 60.4 | 35.5 | 35.0 | 36.0 | 0.0 | 50.0 |
| gi\|17989093\|ref\|NP_541726.1\| | B.melitensis, B. abortus, B. suis | 60.6 | 35.5 | 35.0 | 36.0 | 0.0 | 49.7 |
| gi\|256029642\|ref\|ZP_05443256.1\| | B.ceti, B.pinnipedialis | 60.6 | 35.5 | 34.7 | 35.8 | 0.0 | 49.8 |
| gi\|254711726\|ref\|ZP_05173537.1\| | B.pinnipedialis | 60.6 | 35.5 | 34.7 | 35.8 | 0.0 | 49.8 |
| gi\|153010872\|ref\|YP_001372086.1\| | O.anthropi | 60.9 | 35.5 | 35.6 | 35.5 | 0.0 | 49.7 |
| gi\|23500271\|ref\|NP_699711.1\| | Brucella suis | 60.1 | 35.5 | 34.7 | 34.5 | 0.0 | 49.4 |
| gi\|254702903\|ref\|ZP_05164731.1\| | Brucella suis | 60.1 | 35.5 | 34.7 | 34.5 | 0.0 | 49.4 |
| gi\|256015303\|ref\|YP_003105312.1\| | Brucella microti | 60.6 | 35.5 | 35.0 | 36.0 | 0.0 | 49.4 |
| gi\|163844682\|ref\|YP_001622337.1\| | Brucella suis | 60.4 | 35.5 | 34.7 | 35.5 | 0.0 | 49.4 |
| gi\|227377013\|ref\|ZP_03860475.1\| | Kribbella flavida | 33.1 | 35.5 | 43.0 | 41.1 | 0.0 | 72.8 |
| gi\|254406257\|ref\|ZP_05021172.1\| | S.sviceus | 39.2 | 35.5 | 42.7 | 41.6 | 0.0 | 73.1 |
| gi\|72160584\|ref\|YP_288241.1\| | Thermobifida fusca | 33.9 | 35.4 | 61.6 | 62.7 | 0.0 | 56.3 |
| gi\|62317615\|ref\|YP_223468.1\| | B.abortus, B.melitensis | 59.4 | 35.3 | 34.8 | 35.8 | 0.0 | 50.2 |
| gi\|254705975\|ref\|ZP_05167803.1\| | B.pinnipedialis | 61.4 | 35.3 | 36.9 | 38.5 | 0.0 | 51.9 |
| gi\|261313408\|ref\|ZP_05952605.1\| | B. pinnipedialis | 61.4 | 35.3 | 36.9 | 38.5 | 0.0 | 51.9 |
| gi\|237817164\|ref\|ZP_04596156.1\| | B. abortus | 59.4 | 35.3 | 34.3 | 35.8 | 0.0 | 50.2 |
| gi\|254390345\|ref\|ZP_05005562.1\| | S.clavuligerus | 35.3 | 35.3 | 73.8 | 76.8 | 0.0 | 56.5 |
| gi\|256389325\|ref\|YP_003110889.1\| | C. acidiphila | 34.4 | 35.3 | 69.8 | 69.5 | 0.0 | 54.9 |
| gi\|158313434\|ref\|YP_001505942.1\| | Frankia sp. | 35.2 | 35.3 | 44.7 | 44.4 | 0.0 | 75.8 |
| gi\|169627996\|ref\|YP_001701645.1\| | M.abscessus | 37.3 | 35.3 | 40.6 | 39.5 | 0.0 | 71.7 |
| gi\|260167270\|ref\|ZP_05754081.1\| | Brucella sp. | 60.4 | 35.2 | 34.5 | 35.5 | 0.0 | 49.5 |
| gi\|161620586\|ref\|YP_001594472.1\| | B. suis, B. canis | 59.9 | 35.2 | 34.7 | 34.5 | 0.0 | 49.4 |
| gi\|225628956\|ref\|ZP_03786990.1\| | Brucella ceti | 60.4 | 35.2 | 34.5 | 34.9 | 0.0 | 49.5 |
| gi\|239833851\|ref\|ZP_04682179.1\| | O.intermedium | 60.6 | 35.2 | 34.8 | 34.2 | 0.0 | 49.2 |
| gi\|209546465\|ref\|YP_002278383.1\| | R. leguminosarum | 62.3 | 35.2 | 35.0 | 34.8 | 0.0 | 50.3 |
| gi\|86360115\|ref\|YP_472004.1\| | Rhizobium etli | 62.1 | 35.2 | 34.2 | 35.1 | 0.0 | 50.2 |
| gi\|254293976\|ref\|YP_003059999.1\| | Hirschia baltica | 54.1 | 35.1 | 34.9 | 33.1 | 0.0 | 46.2 |

FIG. 3A-BKD cont'd

FIG. 3A-BKD E1 Alpha Subunit Homologs

| | | | | | | | |
|---|---|---|---|---|---|---|---|
| gi\|257057823\|ref\|YP_003135655.1\| | S.aviridis | 34.6 | 35.0 | 59.1 | 59.8 | 0.0 | 54.3 |
| gi\|29830905\|ref\|NP_825539.1\| | S. avermitilis | 33.2 | 34.9 | 40.4 | 39.8 | 0.0 | 100 |
| gi\|116671738\|ref\|YP_832671.1\| | Arthrobacter sp. | 36.3 | 34.9 | 40.6 | 41.5 | 0.0 | 76.3 |
| gi\|86741184\|ref\|YP_481584.1\| | Frankia sp. | 33.0 | 34.9 | 40.7 | 37.6 | 0.0 | 80.3 |
| gi\|27381442\|ref\|NP_772971.1\| | B. japonicum | 62.9 | 34.9 | 33.3 | 33.2 | 0.0 | 49.2 |
| gi\|254712340\|ref\|ZP_05174151.1\| | Brucella ceti | 59.9 | 34.9 | 34.0 | 34.4 | 0.0 | 49.7 |
| gi\|116254745\|ref\|YP_770581.1\| | R.leguminosarum | 61.9 | 34.9 | 35.0 | 35.7 | 0.0 | 50.9 |
| gi\|269124598\|ref\|YP_003297968.1\| | T. curvata | 34.5 | 34.9 | 63.5 | 64.2 | 0.0 | 59.2 |
| gi\|220914551\|ref\|YP_002489860.1\| | A.chlorophenolicus | 35.9 | 34.8 | 57.5 | 60.3 | 0.0 | 55.7 |
| gi\|270498440\|ref\|ZP_06215384.1\| | M. aurantiaca | 36.1 | 34.8 | 40.5 | 41.9 | 0.0 | 71.1 |
| gi\|227406261\|ref\|ZP_03889498.1\| | G.obscurus | 33.9 | 34.8 | 62.1 | 62.4 | 0.0 | 58.6 |
| gi\|116669942\|ref\|YP_830875.1\| | Arthrobacter sp. | 34.1 | 34.8 | 53.3 | 54.6 | 0.0 | 58.5 |
| gi\|271970152\|ref\|YP_003344348.1\| | S. roseum | 35.7 | 34.8 | 69.5 | 68.6 | 0.0 | 57.9 |
| gi\|163796017\|ref\|ZP_02189980.1\| | alpha proteobacterium | 61.2 | 34.8 | 36.6 | 35.1 | 0.0 | 50.2 |
| gi\|260469853\|ref\|ZP_05814002.1\| | M.opportunistum | 61.0 | 34.8 | 33.2 | 36.6 | 0.0 | 49.4 |
| gi\|159185754\|ref\|NP_357136.2\| | A.tumefaciens | 60.6 | 34.8 | 36.8 | 35.6 | 0.0 | 50.6 |
| gi\|229822444\|ref\|YP_002883970.1\| | B.cavernae | 35.9 | 34.7 | 60.0 | 60.4 | 0.0 | 54.7 |
| gi\|254176370\|ref\|ZP_04883028.1\| | Burkholderia mallei | 79.5 | 34.7 | 34.1 | 32.7 | 0.0 | 45.6 |
| gi\|238562318\|ref\|ZP_04610013.1\| | Burkholderia mallei | 79.8 | 34.7 | 34.1 | 32.7 | 0.0 | 45.6 |
| gi\|217424130\|ref\|ZP_03455629.1\| | B pseudomallei | 80.0 | 34.7 | 34.1 | 32.7 | 0.0 | 46.2 |
| gi\|53723291\|ref\|YP_112276.1\| | B.pseudomallei | 80.0 | 34.7 | 34.1 | 32.7 | 0.0 | 46.2 |
| gi\|53716061\|ref\|YP_106531.1\| | Burkholderia mallei | 79.8 | 34.7 | 34.1 | 32.7 | 0.0 | 45.6 |
| gi\|167829832\|ref\|ZP_02461303.1\| | B.pseudomallei | 80.0 | 34.7 | 34.1 | 32.7 | 0.0 | 46.2 |
| gi\|90420470\|ref\|ZP_01228377.1\| | A.manganoxydans | 62.6 | 34.6 | 33.3 | 32.9 | 0.0 | 50.6 |
| gi\|51699504\|dbj\|BAD38879.1\| | S.carzinostaticus | 35.3 | 34.6 | 62.5 | 63.7 | 0.0 | 56.7 |
| gi\|269796852\|ref\|YP_003316307.1\| | S.keddieii | 36.6 | 34.6 | 60.5 | 60.6 | 0.0 | 55.3 |
| gi\|152968231\|ref\|YP_001364015.1\| | K.radiotolerans | 33.9 | 34.6 | 53.7 | 54.9 | 0.0 | 61.1 |
| gi\|117927244\|ref\|YP_871795.1\| | A.cellulolyticus | 37.7 | 34.6 | 59.2 | 59.7 | 0.0 | 58.2 |
| gi\|241554279\|ref\|YP_002979492.1\| | R.leguminosarum | 61.9 | 34.5 | 34.7 | 35.4 | 0.0 | 50.5 |
| gi\|126740932\|ref\|ZP_01756616.1\| | Roseobacter sp. | 61.1 | 34.5 | 39.5 | 38.2 | 0.0 | 49.1 |
| gi\|260904557\|ref\|ZP_05912879.1\| | B.linens | 32.7 | 34.5 | 57.4 | 59.9 | 0.0 | 55.1 |

FIG. 3A-BKD cont'd

FIG. 3A-BKD E1 Alpha Subunit Homologs

| | | | | | | | |
|---|---|---|---|---|---|---|---|
| gi\|238023732\|ref\|YP_002907964.1\| | B.giumae | 77.3 | 34.5 | 32.6 | 31.0 | 0.0 | 47.7 |
| gi\|26991090\|ref\|NP_746515.1\| | P.putida | 99.8 | 34.5 | 35.5 | 34.3 | 0.0 | 48.5 |
| gi\|148546693\|ref\|YP_001266795.1\| | P.putida | 100 | 34.5 | 35.5 | 34.3 | 0.0 | 48.5 |
| gi\|1352616\|sp\|P09060.2\|ODBA_PSEPU | P.putida | 98.8 | 34.5 | 35.2 | 36.1 | 0.0 | 48.5 |
| gi\|167034957\|ref\|YP_001670188.1\| | P. putida | 98.5 | 34.5 | 35.2 | 34.1 | 0.0 | 48.5 |
| gi\|167840924\|ref\|ZP_02467608.1\| | B.thailandensis | 80.0 | 34.5 | 35.5 | 33.7 | 0.0 | 48.1 |
| gi\|167574075\|ref\|ZP_02366949.1\| | B.okiahomensis | 79.8 | 34.5 | 34.1 | 31.9 | 0.0 | 48.1 |
| gi\|167567002\|ref\|ZP_02359918.1\| | B.okiahomensis | 79.8 | 34.5 | 34.1 | 31.9 | 0.0 | 48.1 |
| gi\|28493757\|ref\|NP_787918.1\| | T.whipplei | 28.6 | 34.4 | 45.1 | 43.7 | 0.0 | 53.4 |
| gi\|262186845\|ref\|ZP_06046196.1\| | A.marinum | 32.3 | 34.4 | 57.8 | 56.9 | 0.0 | 56.3 |
| gi\|163839304\|ref\|YP_001623709.1\| | R.salmoninarum | 34.4 | 34.4 | 55.1 | 50.9 | 0.0 | 60.1 |
| gi\|121597380\|ref\|YP_990635.1\| | Burkholderia mallei | 79.5 | 34.3 | 34.3 | 32.9 | 0.0 | 45.3 |
| gi\|145592675\|ref\|YP_001156972.1\| | Salinispora tropica | 32.4 | 34.3 | 63.4 | 60.9 | 0.0 | 56.0 |
| gi\|259417175\|ref\|ZP_05741094.1\| | Silicibacter sp. | 63.1 | 34.2 | 41.2 | 40.2 | 0.0 | 46.0 |
| gi\|84683575\|ref\|ZP_01011478.1\| | R.bacterium | 60.2 | 34.2 | 39.7 | 35.4 | 0.0 | 47.4 |
| gi\|170722905\|ref\|YP_001750593.1\| | P. putida | 97.6 | 34.1 | 35.0 | 35.5 | 0.0 | 48.5 |
| gi\|104782857\|ref\|YP_609355.1\| | P.entomophila | 93.9 | 34.1 | 35.6 | 35.5 | 0.0 | 48.4 |
| gi\|83717236\|ref\|YP_440491.1\| | B.thailandensis | 80.7 | 34.1 | 34.5 | 33.4 | 0.0 | 48.4 |
| gi\|13473769\|ref\|NP_105337.1\| | Mesorhizobium loti | 60.7 | 34.1 | 32.6 | 34.5 | 0.0 | 49.7 |
| gi\|238059377\|ref\|ZP_04604086.1\| | Micromonospora sp. | 37.6 | 34.1 | 40.5 | 41.4 | 0.0 | 72.1 |
| gi\|238062017\|ref\|ZP_04606726.1\| | Micromonospora sp. | 32.0 | 34.1 | 66.4 | 63.1 | 0.0 | 56.8 |
| gi\|159035782\|ref\|YP_001535035.1\| | S.arenicola | 32.2 | 34.1 | 62.8 | 60.4 | 0.0 | 55.7 |
| gi\|229209343\|ref\|ZP_04335774.1\| | N.dassonvillei | 33.7 | 34.0 | 65.9 | 66.5 | 0.0 | 57.5 |
| gi\|258655410\|ref\|YP_003204566.1\| | N.multipartita | 30.6 | 34.0 | 55.3 | 54.9 | 0.0 | 53.6 |
| gi\|184199990\|ref\|YP_001854197.1\| | Kocuria rhizophila | 32.8 | 34.0 | 51.4 | 49.3 | 0.0 | 52.3 |
| gi\|119961173\|ref\|YP_949570.1\| | A.aurescens | 38.0 | 34.0 | 57.8 | 58.2 | 0.0 | 57.5 |
| gi\|163857824\|ref\|YP_001632122.1\| | Bordetella petrii, | 80.5 | 34.0 | 35.1 | 33.3 | 0.0 | 47.2 |
| gi\|229822332\|ref\|YP_002883858.1\| | B. cavernae | 37.9 | 34.0 | 59.0 | 59.1 | 0.0 | 59.4 |
| gi\|83859626\|ref\|ZP_00953146.1\| | O.alexandrii | 56.1 | 33.9 | 35.0 | 37.3 | 0.0 | 49.6 |
| gi\|116672570\|ref\|YP_833503.1\| | Arthrobacter sp. | 36.0 | 33.9 | 55.3 | 56.9 | 0.0 | 55.1 |
| gi\|220912169\|ref\|YP_002487478.1\| | A.chiorophenolicus | 35.2 | 33.9 | 54.7 | 52.6 | 0.0 | 56.6 |

FIG. 3A-BKD cont'd

FIG. 3A-BKD E1 Alpha Subunit Homologs

| | | | | | | | |
|---|---|---|---|---|---|---|---|
| gi\|119718728\|ref\|YP_925693.1\| | Nocardioides sp. | 32.6 | 33.8 | 63.3 | 62.9 | 0.0 | 54.1 |
| gi\|5822330\|pdb\|1QS0\|A | | 95.8 | 33.8 | 37.2 | 36.1 | 0.0 | 47.4 |
| gi\|91786184\|ref\|YP_547136.1\| | Polaromonas sp. | 75.8 | 33.8 | 34.2 | 31.4 | 0.0 | 48.7 |
| gi\|145594629\|ref\|YP_001158926.1\| | Salinispora tropica | 35.0 | 33.8 | 42.7 | 41.9 | 0.0 | 74.9 |
| gi\|163841387\|ref\|YP_001625792.1\| | R.salmoninarum | 36.9 | 33.6 | 40.5 | 40.1 | 0.0 | 74.8 |
| gi\|227378206\|ref\|ZP_03861666.1\| | Kribbella flavida | 35.3 | 33.6 | 62.4 | 62.1 | 0.0 | 52.4 |
| gi\|269956884\|ref\|YP_003326673.1\| | X.cellulosilytica | 32.4 | 33.6 | 50.5 | 50.0 | 0.0 | 53.7 |
| gi\|255326067\|ref\|ZP_05367154.1\| | Rothia mucilaginosa | 33.4 | 33.6 | 47.5 | 48.5 | 0.0 | 52.8 |
| gi\|229491144\|ref\|ZP_04384972.1\| | R.erythropolis | 35.7 | 33.6 | 39.9 | 39.1 | 0.0 | 76.3 |
| gi\|99082618\|ref\|YP_614772.1\| | Ruegeria sp. | 63.3 | 33.6 | 39.3 | 39.9 | 0.0 | 46.0 |
| gi\|159037836\|ref\|YP_001537089.1\| | S.arenicola | 33.0 | 33.5 | 40.4 | 40.2 | 0.0 | 71.0 |
| gi\|229591396\|ref\|YP_002873515.1\| | P.fluorescens | 87.3 | 33.4 | 34.6 | 33.7 | 0.0 | 48.5 |
| gi\|283457296\|ref\|YP_003361869.1\| | Rothia mucilaginosa | 31.2 | 33.3 | 47.7 | 49.1 | 0.0 | 51.7 |
| gi\|114569255\|ref\|YP_755935.1\| | Maricaulis maris | 58.3 | 33.2 | 34.7 | 34.4 | 0.0 | 50.0 |
| gi\|119960563\|ref\|YP_947289.1\| | A.aurescens | 32.8 | 33.2 | 54.0 | 52.6 | 0.0 | 58.5 |
| gi\|256833676\|ref\|YP_003162403.1\| | Jonesia denitrificans | 37.1 | 33.2 | 58.1 | 56.0 | 0.0 | 50.1 |
| gi\|254467417\|ref\|ZP_05080827.1\| | R. bacterium | 59.8 | 33.2 | 38.4 | 37.3 | 0.0 | 45.3 |
| gi\|226309471\|ref\|YP_002769433.1\| | R.erythropolis | 35.4 | 33.2 | 39.6 | 38.8 | 0.0 | 76.2 |
| gi\|255292432\|dbj\|BAH89550.1\| | uncultured bacterium | 56.9 | 33.1 | 35.9 | 35.3 | 0.0 | 47.0 |
| gi\|111223679\|ref\|YP_714473.1\| | Frankia alni | 30.8 | 33.1 | 51.9 | 50.9 | 0.0 | 54.2 |
| gi\|70729902\|ref\|YP_259641.1\| | P.fluorescens | 88.5 | 33.1 | 32.9 | 31.7 | 0.0 | 48.2 |
| gi\|77459685\|ref\|YP_349192.1\| | P.fluorescens | 87.0 | 33.1 | 32.2 | 31.9 | 0.0 | 49.0 |
| gi\|50955932\|ref\|YP_063220.1\| | Leifsonia xyli | 32.4 | 33.1 | 53.2 | 52.6 | 0.0 | 52.7 |
| gi\|119387480\|ref\|YP_918514.1\| | P.denitrificans | 61.7 | 33.0 | 35.9 | 36.7 | 0.0 | 48.8 |
| gi\|152985298\|ref\|YP_001348354.1\| | P.aeruginosa | 78.5 | 33.0 | 35.4 | 33.0 | 0.0 | 49.1 |
| gi\|229243578\|ref\|ZP_04367775.1\| | C.flavigena | 37.4 | 32.9 | 59.8 | 61.3 | 0.0 | 53.4 |
| gi\|148274128\|ref\|YP_001223689.1\| | C.michiganensis | 32.8 | 32.9 | 55.3 | 53.3 | 0.0 | 57.5 |
| gi\|256782140\|ref\|ZP_05520603.1\| | S.hygroscopicus | 33.2 | 32.8 | 53.3 | 51.7 | 0.0 | 54.1 |
| gi\|254283946\|ref\|ZP_04958914.1\| | gamma proteobacterium | 55.0 | 32.7 | 32.9 | 34.0 | 0.0 | 49.1 |
| gi\|184201771\|ref\|YP_001855978.1\| | Kocuria rhizophila | 34.9 | 32.7 | 39.3 | 39.7 | 0.0 | 70.4 |
| gi\|256824125\|ref\|YP_003148085.1\| | K.sedentarius | 30.2 | 32.6 | 59.4 | 55.5 | 0.0 | 57.8 |

FIG. 3A-BKD cont'd

FIG. 3A-BKD E1 Alpha Subunit Homologs

| | | | | | | | |
|---|---|---|---|---|---|---|---|
| gi\|256673218\|ref\|ZP_05484171.1\| | Streptomyces sp. | 32.8 | 32.6 | 56.2 | 55.7 | 0.0 | 54.0 |
| gi\|170783367\|ref\|YP_001711701.1\| | C.michiganensis | 34.5 | 32.6 | 56.1 | 53.6 | 0.0 | 57.5 |
| gi\|134103716\|ref\|YP_001109377.1\| | S. erythraea | 31.0 | 32.5 | 58.3 | 57.6 | 0.0 | 54.8 |
| gi\|171320119\|ref\|ZP_02909184.1\| | B.ambifaria | 79.5 | 32.4 | 33.9 | 34.4 | 0.0 | 49.5 |
| gi\|15597443\|ref\|NP_250937.1\| | P. aeruginosa | 78.8 | 32.4 | 35.4 | 33.0 | 0.0 | 49.1 |
| gi\|78065831\|ref\|YP_368600.1\| | Burkholderia sp. | 80.9 | 32.2 | 34.4 | 33.3 | 0.0 | 49.5 |
| gi\|170699377\|ref\|ZP_02890423.1\| | B.ambifaria | 80.2 | 32.2 | 34.4 | 34.4 | 0.0 | 49.5 |
| gi\|107022318\|ref\|YP_620645.1\| | B.cenocepacia | 80.4 | 32.2 | 34.1 | 33.1 | 0.0 | 49.5 |
| gi\|172060189\|ref\|YP_001807841.1\| | B.ambifaria | 80.4 | 32.2 | 34.4 | 34.4 | 0.0 | 49.5 |
| gi\|115351176\|ref\|YP_773015.1\| | B.ambifaria | 80.4 | 31.9 | 34.4 | 34.4 | 0.0 | 49.5 |
| gi\|88854469\|ref\|ZP_01129136.1\| | marine actinobacterium | 30.6 | 31.7 | 52.4 | 51.0 | 0.0 | 58.5 |
| gi\|254396792\|ref\|ZP_05011849.1\| | S.pristinaespiralis | 34.3 | | 41.9 | 37.4 | 0.0 | 91.7 |
| gi\|7480529\|pir\|\|T36512 | | | | | 40.6 | 0.0 | 93.5 |
| gi\|16079461\|ref\|NP_390285.1\| | Bacilius subtilis | 34.5 | 100.0 | 39.4 | 40.8 | 0.0 | 55.6 |
| gi\|154686664\|ref\|YP_001421825.1\| | B.amyloliquefaciens | 35.1 | 88.8 | 38.6 | 40.8 | 0.0 | 54.6 |
| gi\|52080943\|ref\|YP_079734.1\| | B.licheniformis | 32.1 | 84.8 | 35.8 | 36.7 | 0.0 | 54.0 |
| gi\|152976567\|ref\|YP_001376084.1\| | Bacillus cereus | 33.3 | 83.5 | 37.7 | 40.4 | 0.0 | 54.3 |
| gi\|157692911\|ref\|YP_001487373.1\| | Bacillus pumilus | 32.7 | 83.0 | 40.4 | 40.0 | 0.0 | 57.6 |
| gi\|194016754\|ref\|ZP_03055367.1\| | Bacillus pumilus | 32.4 | 82.4 | 39.7 | 38.0 | 0.0 | 57.2 |
| gi\|228998952\|ref\|ZP_04158534.1\| | Bacillus mycoides | 33.0 | 82.3 | 39.0 | 40.1 | 0.0 | 55.8 |
| gi\|228992907\|ref\|ZP_04152831.1\| | B.pseudomycoides | 32.7 | 82.0 | 38.6 | 39.7 | 0.0 | 55.8 |
| gi\|42783280\|ref\|NP_980527.1\| | Bacillus cereus | 33.3 | 81.9 | 38.3 | 39.4 | 0.0 | 56.1 |
| gi\|30264237\|ref\|NP_846614.1\| | B. thuringiensis, B. cereus, B. anthracis | 33.3 | 81.9 | 38.3 | 39.4 | 0.0 | 56.1 |
| gi\|167633774\|ref\|ZP_02392098.1\| | Bacillus anthracis | 33.3 | 81.9 | 38.3 | 39.4 | 0.0 | 55.8 |

FIG. 3B – BKD E1beta Subunit Homologs

| Acc. No. | Organism | ID%Pp | ID%Bs | ID%Sc | ID%Sa2 | ID%Sa | ID%Sc2 |
|---|---|---|---|---|---|---|---|
| gi\|16079460\|ref\|NP_390284.1\| | Bacillus subtilis | 41.9 | 100 | 41.0 | 42.9 | 43.5 | 42.0 |
| gi\|154686663\|ref\|YP_001421824.1\| | B.amyloliquefaciens | 41.1 | 95.7 | 40.6 | 42.0 | 43.4 | 42.1 |
| gi\|157692910\|ref\|YP_001487372.1\| | Bacillus pumilus | 40.5 | 92.7 | 41.7 | 41.7 | 42.9 | 41.6 |
| gi\|52080942\|ref\|YP_079733.1\| | Bacillus licheniformis | 41.2 | 92.4 | 41.2 | 41.9 | 44.7 | 43.0 |
| gi\|47569678\|ref\|ZP_00240353.1\| | Bacillus cereus | 41.6 | 90.5 | 41.2 | 42.6 | 43.8 | 42.9 |
| gi\|205374101\|ref\|ZP_03226901.1\| | Bacillus coahuilensis | 42.0 | 90.2 | 40.2 | 40.2 | 45.1 | 42.3 |
| gi\|89099273\|ref\|ZP_01172151.1\| | Bacillus sp. | 40.5 | 90.2 | 41.4 | 42.0 | 43.2 | 41.6 |
| gi\|228992906\|ref\|ZP_04152830.1\| | B.pseudomycoides, B. mycoides | 41.6 | 90.2 | 41.5 | 42.3 | 44.2 | 43.2 |
| gi\|30264236\|ref\|NP_846613.1\| | B.thuringiensis, B. cereus, B. anthracis | 41.6 | 90.2 | 41.5 | 42.3 | 44.2 | 43.2 |
| gi\|225866143\|ref\|YP_002751521.1\| | Bacillus cereus | 41.3 | 89.9 | 41.5 | 42.3 | 44.2 | 43.2 |
| gi\|228916797\|ref\|ZP_04080362.1\| | Bacillus thuringiensis | 41.6 | 89.9 | 41.2 | 42.0 | 44.3 | 43.3 |
| gi\|152976566\|ref\|YP_001376083.1\| | B.cereus, B.cytotoxicus | 41.9 | 89.6 | 41.2 | 42.0 | 43.8 | 42.9 |
| gi\|218899325\|ref\|YP_002447736.1\| | Bacillus cereus | 41.9 | 89.6 | 41.5 | 42.3 | 43.5 | 42.9 |
| gi\|229031609\|ref\|ZP_04187797.1\| | Bacillus cereus | 42.5 | 89.6 | 42.1 | 42.3 | 44.2 | 43.5 |
| gi\|126653079\|ref\|ZP_01725214.1\| | Bacillus sp. | 41.9 | 89.3 | 41.0 | 41.4 | 43.2 | 42.3 |
| gi\|30022242\|ref\|NP_833873.1\| | B. cereus, B. thuringiensis. | 41.9 | 89.3 | 41.8 | 42.0 | 43.8 | 43.2 |
| gi\|229168905\|ref\|ZP_04296622.1\| | Bacillus cereus | 42.2 | 89.2 | 41.8 | 41.8 | 43.8 | 43.2 |
| gi\|138895947\|ref\|YP_001126400.1\| | Geobacillus sp. | 41.4 | 89.0 | 41.2 | 41.9 | 43.5 | 41.3 |
| gi\|212638804\|ref\|YP_002315324.1\| | A. flavithermus | 41.5 | 89.0 | 42.5 | 43.1 | 44.5 | 42.3 |
| gi\|169828953\|ref\|YP_001699111.1\| | L.sphaericus | 41.9 | 89.0 | 41.8 | 41.4 | 43.2 | 42.3 |
| gi\|239827650\|ref\|YP_002950274.1\| | Geobacillus sp. | 42.0 | 89.0 | 41.5 | 42.1 | 43.8 | 41.6 |
| gi\|229075868\|ref\|ZP_04208844.1\| | Bacillus cereus | 41.6 | 89.0 | 42.1 | 42.3 | 44.2 | 43.5 |
| gi\|163941911\|ref\|YP_001646795.1\| | B.mycoides, B.cereus | 41.9 | 89.0 | 41.8 | 42.0 | 43.8 | 43.2 |
| gi\|229174837\|ref\|ZP_04302357.1\| | Bacillus cereus | 41.9 | 89.0 | 41.8 | 42.0 | 43.8 | 43.2 |
| gi\|56420912\|ref\|YP_148230.1\| | Geobacillus sp. | 41.4 | 88.7 | 40.9 | 41.6 | 43.5 | 41.3 |
| gi\|75761045\|ref\|ZP_00741045.1\| | B. thuringiensis | 42.5 | 88.7 | 41.8 | 42.0 | 43.8 | 43.2 |
| gi\|255332689\|ref\|ZP_05373688.1\| | Geobacillus sp. | 42.3 | 88.1 | 42.8 | 42.8 | 44.8 | 43.2 |
| gi\|149181879\|ref\|ZP_01860368.1\| | Bacillus sp. | 41.6 | 87.5 | 42.3 | 42.3 | 44.2 | 42.3 |
| gi\|23099320\|ref\|NP_692786.1\| | O.iheyensis | 42.4 | 87.5 | 41.4 | 41.7 | 45.9 | 45.0 |
| gi\|15615325\|ref\|NP_243628.1\| | Bacillus halodurans | 44.0 | 86.5 | 42.4 | 43.5 | 45.0 | 44.0 |

FIG. 3B-BKD cont'd

FIG. 3B – BKD E1beta Subunit Homologs

| | | | | | | | |
|---|---|---|---|---|---|---|---|
| gi\|229543917\|ref\|ZP_04432976.1\| | Bacillus coagulans | 41.3 | 86.2 | 41.5 | 43.8 | 44.2 | 42.9 |
| gi\|283567959\|gb\|EFC18382.1\| | B.cellulosilyticus | 44.1 | 83.5 | 41.4 | 42.1 | 45.6 | 45.3 |
| gi\|255029290\|ref\|ZP_05301241.1\| | L.monocytogenes | 43.9 | 81.8 | 42.5 | 42.2 | 45.2 | 43.9 |
| gi\|229556638\|ref\|ZP_04444427.1\| | Listeria grayi | 42.6 | 81.7 | 42.1 | 42.3 | 42.9 | 41.3 |
| gi\|46907599\|ref\|YP_013988.1\| | L.monocytogenes | 41.8 | 81.7 | 42.5 | 42.2 | 44.5 | 43.2 |
| gi\|47095956\|ref\|ZP_00233559.1\| | L. monocytogenes | 42.1 | 81.7 | 42.8 | 42.5 | 44.5 | 43.2 |
| gi\|56964215\|ref\|YP_175946.1\| | B. clausii KSM-K16 | 43.2 | 81.7 | 43.5 | 44.8 | 47.5 | 46.9 |
| gi\|254932312\|ref\|ZP_05265671.1\| | L.monocytogenes | 41.9 | 81.3 | 42.5 | 42.2 | 44.5 | 43.2 |
| gi\|116872804\|ref\|YP_849585.1\| | L.welshimeri serovar | 42.1 | 81.3 | 42.5 | 42.2 | 44.2 | 43.5 |
| gi\|16800478\|ref\|NP_470746.1\| | L.monocytogenes | 41.8 | 81.3 | 42.5 | 42.2 | 44.2 | 43.2 |
| gi\|16803413\|ref\|NP_464898.1\| | L.monocytogenes | 41.8 | 81.3 | 42.5 | 42.2 | 44.2 | 42.9 |
| gi\|226311957\|ref\|YP_002771851.1\| | Brevibacillus brevis | 44.5 | 81.0 | 43.3 | 44.0 | 46.0 | 45.7 |
| gi\|22773772\|gb\|AAN05021.1\| | L.monocytogenes | 41.8 | 81.0 | 42.2 | 41.9 | 44.2 | 42.9 |
| gi\|172056957\|ref\|YP_001813417.1\| | E.sibiricum | 44.1 | 78.4 | 40.8 | 43.0 | 43.2 | 42.0 |
| gi\|163763749\|ref\|ZP_02170809.1\| | B.selenitireducens | 40.6 | 78.0 | 43.0 | 42.5 | 46.8 | 45.8 |
| gi\|229916237\|ref\|YP_002884883.1\| | Exiguobacterium sp. | 43.8 | 74.3 | 42.4 | 44.2 | 44.4 | 45.2 |
| gi\|261405973\|ref\|YP_003242214.1\| | Geobacillus sp. | 43.3 | 71.6 | 40.4 | 41.0 | 42.1 | 41.2 |
| gi\|253576336\|ref\|ZP_04853666.1\| | Paenibacillus sp. | 42.8 | 71.3 | 39.8 | 40.6 | 41.5 | 41.2 |
| gi\|228475965\|ref\|ZP_04060673.1\| | S.hominis | 46.3 | 70.0 | 41.7 | 42.3 | 42.5 | 42.1 |
| gi\|70726400\|ref\|YP_253314.1\| | S.haemolyticus | 44.7 | 69.4 | 42.3 | 42.0 | 42.1 | 42.1 |
| gi\|73662548\|ref\|YP_301329.1\| | S.saprophyticus | 42.5 | 68.8 | 43.2 | 41.9 | 44.4 | 44.1 |
| gi\|239637674\|ref\|ZP_04678646.1\| | S.warneri | 44.0 | 68.2 | 43.8 | 42.2 | 41.6 | 41.0 |
| gi\|251796333\|ref\|YP_003011064.1\| | Paenibacillus sp. | 42.4 | 68.2 | 39.9 | 40.5 | 42.0 | 41.6 |
| gi\|223043178\|ref\|ZP_03613225.1\| | S. capitis | 42.5 | 67.9 | 42.6 | 42.3 | 41.5 | 40.9 |
| gi\|242373816\|ref\|ZP_04819390.1\| | S.epidermidis | 42.2 | 67.6 | 43.2 | 42.3 | 41.5 | 40.9 |
| gi\|253732170\|ref\|ZP_04866335.1\| | S.aureus | 44.1 | 67.3 | 43.8 | 42.3 | 42.5 | 42.5 |
| gi\|15924506\|ref\|NP_372040.1\| | S. aureus | 41.3 | 67.0 | 43.8 | 42.3 | 42.1 | 42.1 |
| gi\|224476625\|ref\|YP_002634231.1\| | S.carnosus | 47.1 | 67.0 | 44.8 | 43.2 | 42.4 | 42.7 |
| gi\|49483766\|ref\|YP_040990.1\| | S.aureus | 44.1 | 67.0 | | 42.3 | 42.1 | 42.1 |
| gi\|57650473\|ref\|YP_186402.1\| | S.aureus | 44.4 | 67.0 | 43.5 | 42.0 | 42.1 | 42.1 |
| gi\|167465152\|ref\|ZP_02330241.1\| | Paenibacillus larvae | 42.8 | 67.0 | 42.4 | 42.0 | 41.3 | 39.8 |

FIG. 3B-BKD cont'd

FIG. 3B – BKD E1beta Subunit Homologs

| | | | | | | | |
|---|---|---|---|---|---|---|---|
| gi\|148268001\|ref\|YP_001246944.1\| | S. aureus | 41.0 | 66.7 | 43.5 | 42.0 | 41.8 | 41.8 |
| gi\|258423170\|ref\|ZP_05686063.1\| | S.aureus | 44.1 | 66.7 | 43.8 | 42.3 | 42.1 | 42.1 |
| gi\|283470795\|emb\|CAQ50006.1\| | S.aureus | 44.4 | 66.7 | 43.8 | 42.3 | 42.1 | 42.1 |
| gi\|221137826\|ref\|ZP_03562628.1\| | S.aureus | 44.4 | 66.7 | 43.5 | 42.0 | 42.1 | 42.1 |
| gi\|282916787\|ref\|ZP_06324545.1\| | S.aureus | 44.4 | 66.4 | 43.8 | 42.3 | 42.1 | 42.1 |
| gi\|82751121\|ref\|YP_416862.1\| | S.aureus | 44.4 | 66.4 | 43.7 | 42.2 | 42.1 | 42.1 |
| gi\|27468115\|ref\|NP_764752.1\| | S.epidermidis | 44.4 | 66.4 | 41.7 | 40.7 | 40.9 | 40.9 |
| gi\|283770593\|ref\|ZP_06343485.1\| | S.aureus | 44.1 | 66.1 | | 42.0 | 41.8 | 41.8 |
| gi\|242242785\|ref\|ZP_04797230.1\| | S.epidermidis | 43.8 | 66.1 | 41.4 | 40.4 | 40.9 | 40.9 |
| gi\|57866997\|ref\|YP_188654.1\| | S.epidermidis | 44.1 | 66.1 | 41.7 | 40.7 | 40.9 | 40.9 |
| gi\|51893299\|ref\|YP_075990.1\| | S.thermophilum | 43.2 | 66.1 | 44.9 | 44.9 | 44.4 | 43.2 |
| gi\|227553460\|ref\|ZP_03983509.1\| | E.faecalis | 43.3 | 60.9 | 41.8 | 42.7 | 45.8 | 43.9 |
| gi\|257089975\|ref\|ZP_05584336.1\| | E.faecalis | 42.6 | 60.4 | 40.9 | 42.1 | 44.4 | 42.7 |
| gi\|255975755\|ref\|ZP_05426341.1\| | E.faecalis | 42.6 | 60.4 | 40.9 | 42.1 | 44.8 | 43.0 |
| gi\|29376213\|ref\|NP_815367.1\| | E.faecalis | 41.8 | 60.4 | 41.3 | 42.1 | 44.8 | 43.0 |
| gi\|256619154\|ref\|ZP_05476000.1\| | E.faecalis | 41.8 | 60.4 | 41.3 | 42.1 | 44.8 | 43.0 |
| gi\|257082460\|ref\|ZP_05576821.1\| | E.faecalis | 41.8 | 60.4 | 41.3 | 42.1 | 44.8 | 43.0 |
| gi\|239631470\|ref\|ZP_04674501.1\| | L.paracasei | 42.6 | 60.1 | 40.8 | 41.0 | 42.2 | 40.4 |
| gi\|191638440\|ref\|YP_001987606.1\| | Lactobacillus casei | 42.6 | 60.1 | 40.8 | 41.8 | 42.2 | 40.4 |
| gi\|227535070\|ref\|ZP_03965119.1\| | L.paracasei | 42.3 | 59.8 | 40.5 | 41.5 | 41.9 | 40.1 |
| gi\|116494930\|ref\|YP_806664.1\| | Lactobacillus casei | 42.3 | 59.8 | 40.5 | 41.5 | 41.9 | 40.1 |
| gi\|148656538\|ref\|YP_001276743.1\| | Roseiflexus sp. | 45.6 | 59.3 | 44.6 | 45.3 | 47.5 | 46.3 |
| gi\|163847254\|ref\|YP_001635298.1\| | Chloroflexus sp. | 44.1 | 59.0 | 45.8 | 44.9 | 47.0 | 46.4 |
| gi\|159899111\|ref\|YP_001545358.1\| | H.aurantiacus | 44.4 | 58.7 | 47.4 | 47.0 | 48.8 | 47.2 |
| gi\|219848986\|ref\|YP_002463419.1\| | C.aggregans | 43.8 | 58.4 | 47.1 | 46.2 | 47.7 | 47.0 |
| gi\|269929376\|ref\|YP_003321697.1\| | S.thermophilus | 43.5 | 57.9 | 46.1 | 46.2 | 46.1 | 44.9 |
| gi\|269925215\|ref\|YP_003321838.1\| | T.terrenum | 43.7 | 57.6 | 45.0 | 45.4 | 43.6 | 43.0 |
| gi\|156743005\|ref\|YP_001433134.1\| | R.castenholzii | 47.2 | 56.9 | 43.9 | 45.7 | 47.9 | 46.2 |
| gi\|153004856\|ref\|YP_001379181.1\| | Anaeromyxobacter sp. | 54.5 | 50.8 | 54.0 | 54.3 | 52.8 | 52.8 |
| gi\|86158250\|ref\|YP_465035.1\| | A.dehalogenans | 55.1 | 49.2 | 54.3 | 53.7 | 53.5 | 53.5 |
| gi\|197122440\|ref\|YP_002134391.1\| | Anaeromyxobacter sp. | 55.1 | 48.9 | 54.3 | 53.7 | 53.2 | 53.8 |

FIG. 3B – BKD E1beta Subunit Homologs

| | | | | | | | |
|---|---|---|---|---|---|---|---|
| gi\|241554278\|ref\|YP_002979491.1\| | R. leguminosarum | 74.3 | 47.9 | 47.7 | 49.4 | 49.5 | 47.4 |
| gi\|86360116\|ref\|YP_472005.1\| | Rhizobium etli | 75.1 | 47.7 | 47.6 | 48.9 | 49.4 | 47.3 |
| gi\|116254746\|ref\|YP_770582.1\| | R.leguminosarum | 74.8 | 47.7 | 47.3 | 48.6 | 49.7 | 47.6 |
| gi\|254720465\|ref\|ZP_05182276.1\| | Brucella sp. | 74.6 | 47.4 | 50.6 | 50.5 | 47.1 | 46.6 |
| gi\|15966686\|ref\|NP_387039.1\| | S. meliloti | 74.8 | 47.1 | 45.6 | 46.9 | 48.5 | 46.3 |
| gi\|148558303\|ref\|YP_001257491.1\| | Brucella ovis | 74.9 | 47.1 | 50.6 | 50.5 | 47.7 | 46.6 |
| gi\|225628957\|ref\|ZP_03786991.1\| | B.ceti, B.pinnipedialis | 74.6 | 47.1 | 50.3 | 50.2 | 47.4 | 46.3 |
| gi\|23500272\|ref\|NP_699712.1\| | B. suis, B. neoto-mae, B. microti, B. canis | 74.9 | 47.1 | 50.6 | 50.5 | 47.7 | 46.6 |
| gi\|254712341\|ref\|ZP_05174152.1\| | B.ceti | 74.3 | 47.1 | 50.3 | 50.2 | 47.4 | 45.6 |
| gi\|239833852\|ref\|ZP_04682180.1\| | O.intermedium | 76.1 | 47.1 | 49.8 | 50.3 | 47.1 | 46.5 |
| gi\|150398025\|ref\|YP_001328492.1\| | S.medicae | 74.5 | 46.8 | 45.0 | 46.3 | 48.5 | 46.2 |
| gi\|17989092\|ref\|NP_541725.1\| | Brucella melitensis | 74.6 | 46.8 | 50.6 | 50.5 | 47.4 | 46.3 |
| gi\|153010873\|ref\|YP_001372087.1\| | O.anthropi | 76.1 | 46.8 | 50.6 | 51.1 | 48.0 | 46.8 |
| gi\|62317614\|ref\|YP_223467.1\| | Brucella abortus | 74.3 | 46.8 | 50.3 | 50.2 | 47.4 | 46.0 |
| gi\|254695583\|ref\|ZP_05157411.1\| | Brucella abortus | 74.0 | 46.8 | 50.3 | 50.2 | 47.4 | 46.0 |
| gi\|90420469\|ref\|ZP_01228376.1\| | A.manganoxydans | 75.4 | 46.8 | 48.8 | 50.5 | 48.2 | 47.9 |
| gi\|209546466\|ref\|YP_002278384.1\| | R.leguminosarum | 74.6 | 46.7 | 47.1 | 48.8 | 48.6 | 46.5 |
| gi\|15891465\|ref\|NP_357137.1\| | A.tumefaciens | 78.1 | 46.5 | 47.0 | 48.0 | 47.0 | 46.0 |
| gi\|218461751\|ref\|ZP_03501842.1\| | Rhizobium etli | 74.8 | 46.5 | 46.1 | 47.4 | 48.7 | 46.6 |
| gi\|225686317\|ref\|YP_002734289.1\| | Brucella melitensis | 74.3 | 46.5 | 50.3 | 50.2 | 47.1 | 46.0 |
| gi\|163844683\|ref\|YP_001622338.1\| | Brucella suis | 74.3 | 46.5 | 50.0 | 49.8 | 46.5 | 46.0 |
| gi\|119387481\|ref\|YP_918515.1\| | P.denitrificans | 71.0 | 46.5 | 47.0 | 48.0 | 48.5 | 47.9 |
| gi\|83859625\|ref\|ZP_00953145.1\| | O.alexandrii | 63.1 | 46.5 | 44.3 | 46.4 | 44.3 | 43.1 |
| gi\|255292431\|dbj\|BAH89549.1\| | uncultured bacterium | 68.1 | 45.9 | 47.0 | 48.1 | 45.2 | 44.9 |
| gi\|227823513\|ref\|YP_002827486.1\| | Rhizobium sp. | 74.2 | 45.6 | 45.3 | 46.0 | 48.3 | 47.2 |
| gi\|84683576\|ref\|ZP_01011479.1\| | R.bacterium | 65.8 | 45.6 | 46.7 | 48.8 | 47.3 | 46.0 |
| gi\|148555059\|ref\|YP_001262641.1\| | S.wittichii | 72.7 | 45.6 | 44.4 | 46.4 | 46.5 | 45.6 |
| gi\|218661697\|ref\|ZP_03517627.1\| | Rhizobium etli | 72.4 | 45.5 | 46.1 | 47.4 | 49.7 | 47.4 |
| gi\|87199992\|ref\|YP_497249.1\| | N. aromaticivorans | 70.5 | 45.4 | 46.9 | 48.1 | 48.1 | 47.5 |
| gi\|99082617\|ref\|YP_614771.1\| | Ruegeria sp. | 77.2 | 45.2 | 47.3 | 48.4 | 46.9 | 46.6 |
| gi\|260469852\|ref\|ZP_05814001.1\| | M.opportunistum | 75.8 | 45.1 | 46.0 | 47.3 | 46.2 | 45.0 |

FIG. 3B-BKD cont'd

FIG. 3B-BKD cont'd

FIG. 3B – BKD E1beta Subunit Homologs

| | | | | | | | |
|---|---|---|---|---|---|---|---|
| gi\|254283254\|ref\|ZP_04958222.1\| | g.proteobacterium | 68.2 | 45.1 | 46.0 | 46.7 | 46.0 | 43.9 |
| gi\|163796018\|ref\|ZP_02189981.1\| | alpha proteobacterium | 76.9 | 44.8 | 46.2 | 46.9 | 47.4 | 48.5 |
| gi\|254392374\|ref\|ZP_05007557.1\| | S.clavuligerus | 47.5 | 44.8 | 55.5 | 56.3 | 91.8 | 90.0 |
| gi\|254467413\|ref\|ZP_05080823.1\| | R. bacterium | 75.7 | 44.7 | 48.4 | 49.6 | 45.8 | 46.1 |
| gi\|13473768\|ref\|NP_105336.1\| | Mesorhizobium loti | 75.6 | 44.7 | 46.2 | 48.1 | 45.9 | 44.6 |
| gi\|254293977\|ref\|YP_003060000.1\| | Hirschia baltica | 67.3 | 44.7 | 47.3 | 47.8 | 42.3 | 41.1 |
| gi\|256379011\|ref\|YP_003102671.1\| | A.mirum | 47.9 | 44.7 | 57.3 | 58.8 | 73.8 | 73.5 |
| gi\|85373859\|ref\|YP_457921.1\| | Erythrobacter litoralis | 67.0 | 44.5 | 44.8 | 46.9 | 44.5 | 43.3 |
| gi\|259418093\|ref\|ZP_05742012.1\| | Silicibacter sp. | 77.5 | 44.4 | 47.9 | 49.0 | 47.7 | 46.7 |
| gi\|114569256\|ref\|YP_755936.1\| | Maricaulis maris | 62.5 | 44.4 | 45.3 | 46.0 | 44.9 | 43.9 |
| gi\|229208221\|ref\|ZP_04334666.1\| | N.dassonvillei | 43.6 | 44.2 | 56.5 | 55.8 | 74.2 | 72.5 |
| gi\|148553704\|ref\|YP_001261286.1\| | S.wittichii | 70.3 | 44.2 | 46.6 | 49.0 | 47.4 | 47.0 |
| gi\|85708447\|ref\|ZP_01039513.1\| | Erythrobacter sp. | 67.0 | 44.2 | 44.1 | 46.0 | 44.8 | 43.9 |
| gi\|254396790\|ref\|ZP_05011847.1\| | S.pristinaespiralis | 47.2 | 44.2 | 56.3 | 57.7 | 91.3 | 90.4 |
| gi\|282863269\|ref\|ZP_06272328.1\| | Streptomyces sp. | 48.1 | 44.2 | 55.3 | 56.9 | 90.5 | 89.2 |
| gi\|260453167\|ref\|ZP_05801574.1\| | S.flavogriseus | 47.8 | 44.2 | 54.3 | 56.2 | 90.2 | 89.6 |
| gi\|182437542\|ref\|YP_001825261.1\| | S.griseus | 46.4 | 44.2 | 55.0 | 56.8 | 89.9 | 86.3 |
| gi\|239814018\|ref\|YP_002942928.1\| | V.paradoxus | 82.3 | 44.2 | 46.2 | 46.9 | 46.7 | 47.0 |
| gi\|256395301\|ref\|YP_003116865.1\| | C.acidiphila | 46.6 | 44.1 | 58.6 | 59.1 | 75.2 | 74.5 |
| gi\|256380961\|ref\|YP_003104621.1\| | A.mirum | 44.4 | 44.0 | 68.3 | 69.7 | 54.7 | 53.8 |
| gi\|238023733\|ref\|YP_002907965.1\| | Burkholderia glumae | 85.9 | 44.0 | 44.6 | 45.3 | 46.9 | 47.2 |
| gi\|271970151\|ref\|YP_003344347.1\| | S.roseum | 48.5 | 43.9 | 74.1 | 75.0 | 56.4 | 55.2 |
| gi\|227377012\|ref\|ZP_03860474.1\| | Kribbella flavida | 43.9 | 43.9 | 55.5 | 56.2 | 70.9 | 71.2 |
| gi\|238059376\|ref\|ZP_04604085.1\| | Micromonospora sp. | 46.1 | 43.9 | 57.0 | 56.7 | 72.9 | 72.3 |
| gi\|254418895\|ref\|ZP_05032619.1\| | Brevundimonas sp. | 66.7 | 43.9 | 49.3 | 50.0 | 48.4 | 48.2 |
| gi\|134103717\|ref\|YP_001109378.1\| | S.erythraea | 43.4 | 43.9 | 67.8 | 69.1 | 54.5 | 54.5 |
| gi\|239980738\|ref\|ZP_04703262.1\| | Streptomyces albus | 47.2 | 43.9 | 56.9 | 57.7 | 88.9 | 88.0 |
| gi\|134100488\|ref\|YP_001106149.1\| | S.erythraea | 48.6 | 43.9 | 59.4 | 59.7 | 72.3 | 71.5 |
| gi\|27381443\|ref\|NP_772972.1\| | B.japonicum | 75.1 | 43.9 | 47.0 | 46.6 | 47.1 | 46.8 |
| gi\|260648482\|emb\|CBG71593.1\| | Streptomyces scabiei | 46.1 | 43.8 | 56.2 | 58.0 | 94.9 | 91.9 |
| gi\|282874094\|ref\|ZP_06283042.1\| | Streptomyces sp. | 46.1 | 43.8 | 55.0 | 56.8 | 89.6 | 86.6 |

FIG. 3B-BKD cont'd

FIG. 3B – BKD E1beta Subunit Homologs

| | | | | | | | |
|---|---|---|---|---|---|---|---|
| gi\|239942619\|ref\|ZP_04694556.1\| | S.roseosporus | 46.1 | 43.8 | 55.0 | 56.8 | 89.7 | 89.1 |
| gi\|145594630\|ref\|YP_001158927.1\| | Salinispora tropica | 44.8 | 43.8 | 55.7 | 55.3 | 70.8 | 69.8 |
| gi\|103486816\|ref\|YP_616377.1\| | S.alaskensis | 69.6 | 43.8 | 42.8 | 44.6 | 44.5 | 43.2 |
| gi\|120405039\|ref\|YP_954868.1\| | M.vanbaalenii | 48.6 | 43.7 | 55.8 | 57.4 | 59.9 | 59.6 |
| gi\|270498439\|ref\|ZP_06215383.1\| | M.aurantiaca | 45.5 | 43.7 | 54.7 | 55.3 | 71.7 | 70.7 |
| gi\|94496506\|ref\|ZP_01303083.1\| | Sphingomonas sp. | 68.2 | 43.6 | 43.3 | 44.8 | 45.3 | 44.7 |
| gi\|227378205\|ref\|ZP_03861665.1\| | Kribbella flavida | 45.3 | 43.6 | 74.6 | 72.2 | 54.9 | 53.6 |
| gi\|254390346\|ref\|ZP_05005563.1\| | S.clavuligerus | 46.4 | 43.6 | 85.0 | 87.6 | 58.5 | 57.7 |
| gi\|126740934\|ref\|ZP_01756618.1\| | Roseobacter sp. | 74.9 | 43.6 | 48.8 | 49.0 | 48.5 | 48.2 |
| gi\|29830906\|ref\|NP_825540.1\| | S.avermitilis | 46.4 | 43.5 | 55.4 | 57.1 | 100 | 93.7 |
| gi\|256824331\|ref\|YP_003148291.1\| | K.sedentarius | 42.9 | 43.5 | 55.3 | 55.0 | 68.9 | 69.1 |
| gi\|169627995\|ref\|YP_001701644.1\| | M.abscessus | 44.4 | 43.5 | 57.1 | 56.8 | 70.2 | 69.3 |
| gi\|239942601\|ref\|ZP_04694538.1\| | S.roseosporus | 45.2 | 43.5 | 85.6 | 89.5 | 55.1 | 54.6 |
| gi\|54022989\|ref\|YP_117231.1\| | Nocardia farcinica | 47.5 | 43.4 | 70.6 | 69.4 | 61.3 | 60.4 |
| gi\|118472225\|ref\|YP_888971.1\| | M.smegmatis | 45.7 | 43.4 | 55.6 | 57.2 | 59.7 | 59.7 |
| gi\|229822443\|ref\|YP_002883969.1\| | B.cavernae | 43.5 | 43.4 | 71.8 | 71.2 | 53.1 | 52.2 |
| gi\|91786185\|ref\|YP_547137.1\| | Polaromonas sp. | 84.4 | 43.4 | 45.7 | 47.5 | 46.8 | 46.8 |
| gi\|149186675\|ref\|ZP_01864986.1\| | Erythrobacter sp. | 62.4 | 43.3 | 44.4 | 44.1 | 43.7 | 42.9 |
| gi\|269922273\|ref\|ZP_06171180.1\| | B.subvibrioides | 66.1 | 43.3 | 49.7 | 50.9 | 48.5 | 48.5 |
| gi\|229242947\|ref\|ZP_04367276.1\| | C. flavigena | 47.1 | 43.3 | 70.5 | 70.8 | 56.8 | 56.1 |
| gi\|51699505\|dbj\|BAD38880.1\| | S.carzinostaticus | 46.3 | 43.3 | 82.8 | 82.7 | 57.9 | 57.3 |
| gi\|280964327\|ref\|ZP_06238852.1\| | Frankia sp. | 48.4 | 43.2 | 64.7 | 63.8 | 60.9 | 60.3 |
| gi\|256815074\|ref\|ZP_05540089.1\| | S.griseoflavus | 46.6 | 43.2 | 54.9 | 56.6 | 93.7 | 94.3 |
| gi\|624140\|gb\|AAA66073.1\| | S.avermitilis | 45.8 | 43.2 | 53.8 | 55.5 | 97.3 | 91.0 |
| gi\|158313433\|ref\|YP_001505941.1\| | Frankia sp. | 46.5 | 43.2 | 56.1 | 56.4 | 82.1 | 81.5 |
| gi\|229591397\|ref\|YP_002873516.1\| | P.fluorescens | 90.9 | 43.2 | 43.7 | 44.6 | 47.0 | 46.4 |
| gi\|86741183\|ref\|YP_481583.1\| | Frankia sp. | 44.7 | 43.0 | 54.3 | 55.8 | 79.6 | 79.7 |
| gi\|229209342\|ref\|ZP_04335773.1\| | N.dassonvillei | 46.0 | 42.9 | 69.8 | 68.3 | 56.7 | 56.7 |
| gi\|111020309\|ref\|YP_703281.1\| | Rhodococcus jostii | 45.9 | 42.9 | 57.1 | 55.5 | 68.9 | 68.3 |
| gi\|227406262\|ref\|ZP_03889499.1\| | G.obscurus | 45.8 | 42.9 | 70.9 | 69.8 | 56.7 | 55.8 |
| gi\|254383336\|ref\|ZP_04998688.1\| | Streptomyces sp. | 49.4 | 42.9 | 54.8 | 55.9 | 88.3 | 85.5 |

FIG. 3B-BKD cont'd

FIG. 3B – BKD E1beta Subunit Homologs

| | | | | | | | |
|---|---|---|---|---|---|---|---|
| gi\|254402711\|ref\|ZP_05017660.1\| | S. sviceus | 46.4 | 42.9 | 55.6 | 57.1 | 95.8 | 92.5 |
| gi\|256803195\|ref\|ZP_05532819.1\| | S. viridochromogenes | 45.5 | 42.9 | 55.2 | 57.2 | 95.8 | 94.9 |
| gi\|29830920\|ref\|NP_825554.1\| | S.avermitilis | 46.2 | 42.9 | 91.4 | 100 | 57.1 | 57.4 |
| gi\|77459686\|ref\|YP_349193.1\| | P. fluorescens | 92.9 | 42.9 | 43.7 | 44.6 | 46.7 | 45.8 |
| gi\|255326066\|ref\|ZP_05367153.1\| | Rothia mucilaginosa | 41.6 | 42.8 | 63.5 | 62.5 | 51.9 | 51.9 |
| gi\|78065832\|ref\|YP_368601.1\| | Burkholderia sp. | 88.3 | 42.8 | 45.7 | 45.5 | 46.2 | 46.9 |
| gi\|269957991\|ref\|YP_003327780.1\| | X.cellulosilytica | 44.0 | 42.8 | 69.3 | 68.7 | 56.3 | 56.0 |
| gi\|256768489\|ref\|ZP_05507663.1\| | Streptomyces sp. | 48.1 | 42.8 | 56.0 | 57.3 | 87.3 | 86.7 |
| gi\|256671551\|ref\|ZP_05482504.1\| | Streptomyces sp. | 47.8 | 42.7 | 56.9 | 57.5 | 66.7 | 66.5 |
| gi\|257057824\|ref\|YP_003135656.1\| | S. viridis | 44.9 | 42.7 | 64.7 | 65.6 | 55.1 | 54.7 |
| gi\|229243579\|ref\|ZP_04367776.1\| | C.flavigena | 44.8 | 42.7 | 68.7 | 68.6 | 55.3 | 54.7 |
| gi\|84495443\|ref\|ZP_00994562.1\| | Janibacter sp. | 45.9 | 42.7 | 69.2 | 70.9 | 52.5 | 52.8 |
| gi\|226362325\|ref\|YP_002780103.1\| | R.opacus | 46.2 | 42.6 | 57.9 | 56.3 | 70.2 | 69.9 |
| gi\|256782141\|ref\|ZP_05520604.1\| | S.hygroscopicus | 45.9 | 42.6 | 65.5 | 64.6 | 55.7 | 57.0 |
| gi\|159035781\|ref\|YP_001535034.1\| | Salinispora arenicola | 46.2 | 42.6 | 67.5 | 67.9 | 57.2 | 56.3 |
| gi\|270501762\|ref\|ZP_06218679.1\| | M.aurantiaca | 47.7 | 42.6 | 69.9 | 69.1 | 55.7 | 54.5 |
| gi\|182437559\|ref\|YP_001825278.1\| | S.griseus | 44.9 | 42.6 | 86.2 | 90.4 | 56.0 | 55.6 |
| gi\|282873843\|ref\|ZP_06282803.1\| | Streptomyces sp. | 44.9 | 42.6 | 86.5 | 90.7 | 56.0 | 55.6 |
| gi\|260652580\|emb\|CBG75713.1\| | Streptomyces scabiei | 44.5 | 42.6 | 57.3 | 58.3 | 70.8 | 71.0 |
| gi\|239930128\|ref\|ZP_04687081.1\| | S.ghanaensis | 45.8 | 42.6 | 55.9 | 57.9 | 94.6 | 95.8 |
| gi\|70729901\|ref\|YP_259640.1\| | P. fluorescens | 90.6 | 42.6 | 44.3 | 45.2 | 45.8 | 45.5 |
| gi\|119963718\|ref\|YP_949569.1\| | A.aurescens | 43.0 | 42.6 | 70.3 | 70.4 | 52.2 | 50.3 |
| gi\|260648469\|emb\|CBG71580.1\| | Streptomyces scabiei | 45.4 | 42.5 | 91.6 | 90.1 | 57.0 | 56.2 |
| gi\|283457297\|ref\|YP_003361870.1\| | Rothia mucilaginosa | 41.6 | 42.5 | 63.5 | 62.5 | 52.2 | 52.2 |
| gi\|89902317\|ref\|YP_524788.1\| | R.ferrireducens | 83.0 | 42.5 | 46.3 | 46.4 | 47.5 | 46.6 |
| gi\|163857823\|ref\|YP_001632121.1\| | Bordetella petrii, | 88.7 | 42.5 | 44.1 | 44.8 | 47.2 | 46.9 |
| gi\|256824126\|ref\|YP_003148086.1\| | K.sedentarius | 45.3 | 42.5 | 67.9 | 68.6 | 54.7 | 54.5 |
| gi\|86738780\|ref\|YP_479180.1\| | Frankia sp. | 46.1 | 42.5 | 65.9 | 67.2 | 57.6 | 58.2 |
| gi\|111219575\|ref\|YP_710369.1\| | Frankia alni | 46.1 | 42.5 | 66.5 | 67.2 | 60.7 | 60.1 |
| gi\|254376095\|ref\|ZP_04991570.1\| | Streptomyces | 44.9 | 42.5 | 87.0 | 90.8 | 57.6 | 57.2 |
| gi\|258655409\|ref\|YP_003204565.1\| | N.multipartita | 45.7 | 42.4 | 62.1 | 62.5 | 55.1 | 52.6 |

FIG. 3B-BKD cont'd

FIG. 3B – BKD E1beta Subunit Homologs

| | | | | | | | |
|---|---|---|---|---|---|---|---|
| gi\|254402698\|ref\|ZP_05017647.1\| | S.sviceus | 45.9 | 42.3 | 92.6 | 92.3 | 56.0 | 55.8 |
| gi\|256768471\|ref\|ZP_05507645.1\| | Streptomyces sp. | 44.9 | 42.3 | 87.4 | 91.6 | 56.9 | 56.2 |
| gi\|159037837\|ref\|YP_001537090.1\| | Salinispora arenicola | 46.0 | 42.3 | 56.2 | 55.9 | 70.8 | 69.8 |
| gi\|148546692\|ref\|YP_001266794.1\| | Pseudomonas putida | 100 | 42.3 | 45.4 | 46.4 | 46.7 | 46.7 |
| gi\|167034958\|ref\|YP_001670189.1\| | Pseudomonas putida | 99.4 | 42.3 | 45.1 | 46.1 | 46.7 | 46.7 |
| gi\|226199320\|ref\|ZP_03794880.1\| | B. pseudomallei | 89.1 | 42.3 | 45.1 | 45.5 | 48.0 | 47.1 |
| gi\|134281704\|ref\|ZP_01768411.1\| | B.pseudomallei | 88.9 | 42.2 | 46.4 | 46.6 | 48.7 | 47.8 |
| gi\|167574074\|ref\|ZP_02366948.1\| | B.oklahomensis | 88.1 | 42.2 | 44.1 | 45.2 | 47.1 | 46.5 |
| gi\|217424194\|ref\|ZP_03455693.1\| | B. pseudomallei | 88.4 | 42.2 | 45.2 | 45.2 | 48.1 | 47.2 |
| gi\|237510322\|ref\|ZP_04523037.1\| | Burkholderia mallei | 88.4 | 42.2 | 45.2 | 45.2 | 48.1 | 47.2 |
| gi\|167567001\|ref\|ZP_02359917.1\| | B.oklahomensis | 88.4 | 42.2 | 44.1 | 45.2 | 46.8 | 46.2 |
| gi\|53716062\|ref\|YP_106530.1\| | B.pseudomallei | 88.4 | 42.2 | 45.2 | 45.2 | 48.1 | 47.2 |
| gi\|126444265\|ref\|YP_001064183.1\| | B.pseudomallei | 88.4 | 42.2 | 45.2 | 45.2 | 48.1 | 47.2 |
| gi\|83716737\|ref\|YP_440490.1\| | B.thailandensis | 89.0 | 42.2 | 45.2 | 45.6 | 48.1 | 47.2 |
| gi\|107022319\|ref\|YP_620646.1\| | B.cenocepacia | 87.7 | 42.2 | 45.2 | 44.9 | 46.6 | 46.6 |
| gi\|206559590\|ref\|YP_002230351.1\| | B. cenocepacia | 88.6 | 42.2 | 45.4 | 45.3 | 46.9 | 46.9 |
| gi\|254245805\|ref\|ZP_04939126.1\| | B. cenocepacia | 87.4 | 42.2 | 45.2 | 44.9 | 46.6 | 46.6 |
| gi\|167589511\|ref\|ZP_02381899.1\| | B.ubonensis | 85.9 | 42.2 | 45.2 | 45.7 | 48.1 | 47.8 |
| gi\|171320118\|ref\|ZP_02909183.1\| | B.ambifaria | 86.8 | 42.2 | 46.0 | 46.0 | 46.9 | 45.9 |
| gi\|115351177\|ref\|YP_773016.1\| | B.ambifaria | 86.5 | 42.2 | 46.0 | 46.0 | 46.9 | 45.9 |
| gi\|76818778\|ref\|YP_336567.1\| | B.pseudomallei | 89.2 | 42.2 | 45.1 | 45.3 | 48.2 | 47.3 |
| gi\|167579156\|ref\|ZP_02372030.1\| | B.thailandensis | 89.0 | 42.2 | 45.4 | 45.6 | 48.2 | 47.3 |
| gi\|72160585\|ref\|YP_288242.1\| | Thermobifida fusca | 47.4 | 42.2 | 69.9 | 69.5 | 57.7 | 56.4 |
| gi\|256678038\|ref\|ZP_05488349.1\| | Streptomyces sp. | 44.9 | 42.1 | 87.0 | 90.8 | 57.6 | 57.2 |
| gi\|167645835\|ref\|YP_001683498.1\| | Caulobacter sp. | 68.6 | 42.1 | 46.0 | 47.3 | 45.9 | 45.9 |
| gi\|111222644\|ref\|YP_713438.1\| | Frankia alni | 45.1 | 42.1 | 55.6 | 56.6 | 81.8 | 81.8 |
| gi\|254406256\|ref\|ZP_05021171.1\| | S.sviceus | 45.2 | 42.1 | 55.3 | 54.7 | 69.0 | 69.0 |
| gi\|111018576\|ref\|YP_701548.1\| | Rhodococcus jostii | 46.5 | 42.0 | 69.9 | 69.5 | 57.3 | 56.0 |
| gi\|148274127\|ref\|YP_001223688.1\| | C.michiganensis | 41.8 | 42.0 | 65.9 | 65.0 | 53.9 | 52.7 |
| gi\|152968230\|ref\|YP_001364014.1\| | K.radiotolerans | 45.4 | 42.0 | 70.3 | 70.0 | 57.3 | 56.0 |
| gi\|260453181\|ref\|ZP_05801588.1\| | St. flavogriseus | 45.8 | 42.0 | 87.4 | 91.4 | 55.7 | 54.9 |

FIG. 3B-BKD cont'd

FIG. 3B – BKD E1beta Subunit Homologs

| | | | | | | | |
|---|---|---|---|---|---|---|---|
| gi\|229491148\|ref\|ZP_04384976.1\| | R.erythropolis | 45.1 | 42.0 | 56.2 | 54.6 | 70.5 | 69.3 |
| gi\|256803209\|ref\|ZP_05532833.1\| | S.viridochromogenes | 46.4 | 42.0 | 92.0 | 91.7 | 54.7 | 54.6 |
| gi\|256777778\|ref\|ZP_05516241.1\| | S.hygroscopicus | 44.9 | 42.0 | 88.3 | 88.3 | 55.2 | 54.6 |
| gi\|145592674\|ref\|YP_001156971.1\| | Salinispora tropica | 46.5 | 42.0 | 68.4 | 68.5 | 56.9 | 56.0 |
| gi\|229866853\|ref\|ZP_04486461.1\| | S.nassauensis | 44.8 | 42.0 | 69.1 | 69.5 | 53.9 | 53.7 |
| gi\|790515\|gb\|AAA65615.1\| | Pseudomonas putida | 99.1 | 42.0 | 44.8 | 45.8 | 46.4 | 46.4 |
| gi\|170722906\|ref\|YP_001750594.1\| | Pseudomonas putida | 97.2 | 42.0 | 46.3 | 47.3 | 47.3 | 47.3 |
| gi\|21222240\|ref\|NP_628019.1\| | S.coelicolor | 46.1 | 42.0 | 55.2 | 57.4 | 93.7 | 100 |
| gi\|256786662\|ref\|ZP_05525093.1\| | S.lividans | 46.1 | 42.0 | 55.6 | 57.4 | 93.4 | 99.7 |
| gi\|26991091\|ref\|NP_746516.1\| | Pseudomonas putida | 100 | 41.9 | 45.1 | 46.2 | 46.3 | 46.3 |
| gi\|104782858\|ref\|YP_609356.1\| | Pentomophila | 96.0 | 41.9 | 44.0 | 46.2 | 47.5 | 48.1 |
| gi\|167840923\|ref\|ZP_02467607.1\| | B.thailandensis | 89.3 | 41.9 | 44.7 | 44.9 | 47.2 | 46.3 |
| gi\|111020368\|ref\|YP_703340.1\| | Rhodococcus jostii | 44.7 | 41.9 | 68.1 | 67.1 | 57.4 | 56.5 |
| gi\|229490028\|ref\|ZP_04383881.1\| | R.erythropolis | 50.3 | 41.9 | 67.9 | 67.0 | 56.1 | 57.1 |
| gi\|170699376\|ref\|ZP_02890422.1\| | B.ambifaria | 86.2 | 41.9 | 45.7 | 45.5 | 46.6 | 46.9 |
| gi\|256833675\|ref\|YP_003162402.1\| | Jonesia denitrificans | 45.2 | 41.9 | 65.3 | 65.4 | 53.8 | 53.8 |
| gi\|260907140\|ref\|ZP_05915462.1\| | Brevibacterium linens | 46.8 | 41.9 | 55.0 | 54.6 | 61.8 | 62.4 |
| gi\|226309470\|ref\|YP_002769432.1\| | R.erythropolis | 45.4 | 41.8 | 55.8 | 54.3 | 70.5 | 69.3 |
| gi\|116672569\|ref\|YP_833502.1\| | Arthrobacter sp. | 42.0 | 41.8 | 67.4 | 66.5 | 50.3 | 50.5 |
| gi\|170783366\|ref\|YP_001711700.1\| | C.michiganensis | 42.0 | 41.8 | 66.7 | 65.4 | 53.6 | 52.4 |
| gi\|220914550\|ref\|YP_002489859.1\| | A.chlorophenolicus | 42.0 | 41.8 | 69.5 | 68.3 | 52.2 | 50.6 |
| gi\|108800591\|ref\|YP_640788.1\| | Mycobacterium sp. | 45.7 | 41.8 | 59.2 | 58.6 | 60.2 | 59.4 |
| gi\|239980724\|ref\|ZP_04703248.1\| | Streptomyces albus | 45.5 | 41.7 | 89.0 | 88.6 | 57.1 | 56.2 |
| gi\|134101993\|ref\|YP_001107654.1\| | S.erythraea | 44.6 | 41.7 | 56.4 | 57.3 | 81.0 | 79.9 |
| gi\|238062016\|ref\|ZP_04606725.1\| | Micromonospora sp. | 46.2 | 41.7 | 70.5 | 69.7 | 56.8 | 55.6 |
| gi\|184201772\|ref\|YP_001855979.1\| | Kocuria rhizophila | 39.3 | 41.7 | 51.5 | 51.8 | 65.0 | 65.3 |
| gi\|254383355\|ref\|ZP_04998707.1\| | Streptomyces sp. | 45.2 | 41.7 | 86.8 | 92.6 | 55.9 | 55.9 |
| gi\|129047\|sp\|P09061.1\|ODBB_PSEPU | Pseudomonas putida | 99.1 | 41.6 | 44.5 | 45.6 | 46.0 | 46.0 |
| gi\|88855174\|ref\|ZP_01129839.1\| | marine actinobacterium | 45.5 | 41.6 | 62.9 | 61.7 | 56.9 | 57.9 |
| gi\|262398720\|emb\|CBH31047.1\| | S.pristinaespiralis | 47.0 | 41.6 | 56.6 | 56.6 | 73.1 | 72.8 |
| gi\|270499467\|ref\|ZP_06216406.1\| | M. aurantiaca | 47.5 | 41.6 | 67.7 | 68.0 | 57.1 | 57.4 |

FIG. 3B-BKD cont'd

FIG. 3B – BKD E1beta Subunit Homologs

| | | | | | | | |
|---|---|---|---|---|---|---|---|
| gi\|220912170\|ref\|YP_002487479.1\| | A.chlorophenolicus | 46.4 | 41.6 | 63.3 | 63.3 | 57.3 | 56.4 |
| gi\|152988941\|ref\|YP_001348353.1\| | P.aeruginosa | 86.2 | 41.5 | 43.3 | 45.1 | 47.2 | 45.4 |
| gi\|15597444\|ref\|NP_250938.1\| | P.aeruginosa | 86.5 | 41.5 | 43.3 | 45.1 | 47.2 | 45.4 |
| gi\|169631990\|ref\|YP_001705639.1\| | M.abscessus | 47.3 | 41.5 | 70.7 | 69.5 | 59.1 | 58.5 |
| gi\|282863884\|ref\|ZP_06272942.1\| | Streptomyces sp. | 45.7 | 41.5 | 87.4 | 92.0 | 55.7 | 55.4 |
| gi\|194267456\|gb\|ACF35711.1\| | R.fascians | 46.4 | 41.5 | 67.9 | 67.0 | 58.1 | 56.8 |
| gi\|226307480\|ref\|YP_002767440.1\| | R.erythropolis | 49.6 | 41.5 | 67.7 | 67.7 | 56.1 | 57.1 |
| gi\|254396772\|ref\|ZP_05011829.1\| | S.pristinaespiralis | 46.9 | 41.4 | 88.0 | 90.1 | 56.9 | 56.8 |
| gi\|5822331\|pdb\|1QS0\|B | | 96.4 | 41.4 | 45.0 | 46.1 | 46.1 | 46.1 |
| gi\|239934269\|ref\|ZP_04691222.1\| | S.ghanaensis | 44.1 | 41.4 | 92.6 | 91.7 | 56.3 | 56.2 |
| gi\|256673219\|ref\|ZP_05484172.1\| | S. sp. AA4 | 43.0 | 41.3 | 65.6 | 66.0 | 51.7 | 51.8 |
| gi\|220913648\|ref\|YP_002488957.1\| | A.chlorophenolicus | 43.3 | 41.3 | 54.8 | 54.4 | 65.9 | 65.6 |
| gi\|226360693\|ref\|YP_002778471.1\| | R. opacus | 46.5 | 41.3 | 68.4 | 68.5 | 57.2 | 56.0 |
| gi\|254240689\|ref\|ZP_04934011.1\| | P. aeruginosa | 86.2 | 41.2 | 43.3 | 45.1 | 47.2 | 45.4 |
| gi\|163839327\|ref\|YP_001623732.1\| | R.salmoninarum | 39.9 | 41.1 | 64.5 | 64.8 | 47.5 | 47.2 |
| gi\|21222226\|ref\|NP_628005.1\| | S.coelicolor | 45.1 | 41.0 | 100 | 91.4 | 55.4 | 55.2 |
| gi\|256786679\|ref\|ZP_05525110.1\| | S.lividans | 44.6 | 41.0 | 99.7 | 91.7 | 55.4 | 55.2 |
| gi\|256815058\|ref\|ZP_05540073.1\| | S.griseoflavus | 45.9 | 41.0 | 93.5 | 91.1 | 56.6 | 56.5 |
| gi\|239930114\|ref\|ZP_04687067.1\| | S.ghanaensis | 44.4 | 41.0 | 92.9 | 92.0 | 56.0 | 55.8 |
| gi\|117927243\|ref\|YP_871794.1\| | A.cellulolyticus | 48.1 | 41.0 | 73.2 | 72.6 | 57.1 | 56.8 |
| gi\|116669943\|ref\|YP_830876.1\| | Arthrobacter sp. | 47.0 | 41.0 | 64.2 | 65.0 | 56.1 | 54.9 |
| gi\|213960999\|ref\|ZP_03389279.1\| | P.acnes | 44.5 | 41.0 | 61.2 | 60.6 | 55.3 | 55.3 |
| gi\|50843532\|ref\|YP_056759.1\| | P.acnes | 44.5 | 41.0 | 61.5 | 60.9 | 55.6 | 55.9 |
| gi\|229822332\|ref\|YP_002883858.1\| | B.cavernae | 47.0 | 40.9 | 62.9 | 63.6 | 56.1 | 56.1 |
| gi\|280964587\|ref\|ZP_06239106.1\| | Frankia sp. | 45.1 | 40.9 | 62.3 | 60.9 | 54.9 | 55.5 |
| gi\|239918259\|ref\|YP_002957817.1\| | Micrococcus luteus | 41.8 | 40.8 | 52.0 | 51.4 | 62.0 | 59.9 |
| gi\|158318985\|ref\|YP_001511493.1\| | Frankia sp. | 47.2 | 40.7 | 67.1 | 67.1 | 58.2 | 58.6 |
| gi\|256389324\|ref\|YP_003110888.1\| | C.acidiphila | 43.6 | 40.6 | 74.4 | 72.8 | 54.9 | 54.3 |
| gi\|282854855\|ref\|ZP_06264189.1\| | P.acnes | 44.2 | 40.6 | 61.2 | 60.6 | 55.3 | 55.6 |
| gi\|269124599\|ref\|YP_003297969.1\| | T. curvata | 48.3 | 40.2 | 75.9 | 75.3 | 56.3 | 55.3 |
| gi\|116671737\|ref\|YP_832670.1\| | Arthrobacter sp. | 42.4 | 40.2 | 54.8 | 54.7 | 66.9 | 65.8 |

FIG. 3B-BKD cont'd

FIG. 3B – BKD E1beta Subunit Homologs

| | | | | | | | |
|---|---|---|---|---|---|---|---|
| gi\|119718727\|ref\|YP_925692.1\| | Nocardioides sp. | 46.2 | 40.1 | 70.5 | 69.9 | 54.8 | 55.3 |
| gi\|163841386\|ref\|YP_001625791.1\| | R.salmoninarum | 40.2 | 39.9 | 55.3 | 54.3 | 64.8 | 65.8 |
| gi\|163839305\|ref\|YP_001623710.1\| | R.salmoninarum | 44.3 | 39.9 | 62.0 | 61.4 | 54.2 | 54.2 |
| gi\|88854468\|ref\|ZP_01129135.1\| | marine actinobacterium | 41.9 | 39.8 | 64.1 | 64.3 | 51.9 | 51.3 |
| gi\|229208762\|ref\|ZP_04335202.1\| | N.dassonvillei | 44.7 | 39.8 | 56.8 | 55.2 | 56.9 | 55.5 |
| gi\|119962700\|ref\|YP_948855.1\| | A.aurescens | 41.7 | 39.8 | 54.8 | 53.8 | 65.1 | 66.1 |
| gi\|269956885\|ref\|YP_003326674.1\| | X.cellulosilytica | 45.9 | 39.7 | 60.6 | 61.2 | 58.1 | 58.1 |
| gi\|239917209\|ref\|YP_002956767.1\| | Micrococcus luteus | 45.8 | 39.7 | 62.2 | 61.1 | 57.5 | 57.2 |
| gi\|257067261\|ref\|YP_003153516.1\| | B.faecium | 46.4 | 39.5 | 60.3 | 60.8 | 59.4 | 58.8 |
| gi\|50955931\|ref\|YP_063219.1\| | Leifsonia xyli | 42.2 | 39.3 | 64.4 | 64.7 | 53.0 | 51.6 |
| gi\|184199991\|ref\|YP_001854198.1\| | Kocuria rhizophila | 42.3 | 39.3 | 66.1 | 66.1 | 52.7 | 51.9 |
| gi\|119960874\|ref\|YP_947290.1\| | A.aurescens | 45.2 | 39.1 | 63.1 | 62.8 | 54.5 | 53.7 |
| gi\|257069655\|ref\|YP_003155910.1\| | B.faecium | 41.9 | 38.8 | 67.6 | 65.5 | 57.3 | 56.1 |
| gi\|260904558\|ref\|ZP_05912880.1\| | Brevibacterium linens | 43.0 | 38.7 | 68.3 | 67.9 | 50.2 | 49.8 |
| gi\|28493756\|ref\|NP_787917.1\| | Tropheryma whippiei | 44.2 | 37.9 | 56.7 | 55.8 | 49.1 | 48.4 |
| gi\|218672962\|ref\|ZP_03522631.1\| | Rhizobium etli | 65.4 | 37.1 | 40.5 | 42.1 | 41.3 | 39.8 |
| gi\|269796851\|ref\|YP_003316306.1\| | Sanguibacter keddieii | 42.5 | 37.1 | 63.0 | 62.5 | 49.6 | 49.2 |
| gi\|16079460\|ref\|NP_390284.1\| | Bacillus subtilis | 41.9 | 100 | 41.0 | 42.9 | 43.5 | 42.0 |
| gi\|154686663\|ref\|YP_001421824.1\| | B.amyloliquefaciens | 41.1 | 95.7 | 40.6 | 42.0 | 43.4 | 42.1 |
| gi\|157692910\|ref\|YP_001487372.1\| | Bacillus pumilus | 40.5 | 92.7 | 41.7 | 41.7 | 42.9 | 41.6 |
| gi\|52080942\|ref\|YP_079733.1\| | Bacillus licheniformis | 41.2 | 92.4 | 41.2 | 41.9 | 44.7 | 43.0 |
| gi\|47569678\|ref\|ZP_00240353.1\| | Bacillus cereus | 41.6 | 90.5 | 41.2 | 42.6 | 43.8 | 42.9 |
| gi\|205374101\|ref\|ZP_03226901.1\| | Bacillus coahuilensis | 42.0 | 90.2 | 40.2 | 40.2 | 45.1 | 42.3 |
| gi\|89099273\|ref\|ZP_01172151.1\| | Bacillus sp. | 40.5 | 90.2 | 41.4 | 42.0 | 43.2 | 41.6 |

FIG. 3C – BKD E2 Subunit Homologs

| Acc. No. | Organism | ID%Pp | ID%Bs | ID%Sc | ID%Sa2 | ID%Sa | ID%Sc2 |
|---|---|---|---|---|---|---|---|
| gi\|16079459\|ref\|NP_390283.1\| | Bacillus subtilis | 30.8 | 100 | 31.3 | 31.3 | 32.2 | 30.0 |
| gi\|154686662\|ref\|YP_001421823.1\| | B.amyloliquefaciens | 30.4 | 77.6 | 30.1 | 31.5 | 29.4 | 34.1 |
| gi\|229006481\|ref\|ZP_04164132.1\| | Bacillus mycoides | | 74.4 | | | | |
| gi\|52080941\|ref\|YP_079732.1\| | Bacillus licheniformis | 31.2 | 74.3 | 30.1 | 31.1 | 31.1 | 34.9 |
| gi\|157692909\|ref\|YP_001487371.1\| | Bacillus pumilus | 30.4 | 73.5 | 31.3 | 30.9 | 30.0 | 29.9 |
| gi\|194017047\|ref\|ZP_03055660.1\| | Bacillus pumilus | 30.8 | 73.0 | 30.9 | 31.0 | 30.8 | 29.5 |
| gi\|229140893\|ref\|ZP_04269438.1\| | Bacillus cereus | | 71.3 | | | 31.6 | 32.2 |
| gi\|239827649\|ref\|YP_002950273.1\| | Geobacillus sp. | 32.0 | 70.9 | 31.2 | 33.5 | 32.2 | 31.6 |
| gi\|89099275\|ref\|ZP_01172153.1\| | Bacillus sp. | 31.3 | 70.1 | 29.8 | 30.4 | 30.4 | 29.5 |
| gi\|205374102\|ref\|ZP_03226902.1\| | Bacillus coahuilensis | 31.0 | 70.0 | 30.2 | 32.1 | 29.4 | 28.6 |
| gi\|162330296\|ref\|YP_001126399.2\| | Geobacillus sp., G. thermodenitrificans | 31.3 | 69.9 | 31.7 | 32.6 | 30.9 | 30.8 |
| gi\|134267459\|gb\|ABO67654.1\| | G.thermodenitrificans | 31.6 | 69.6 | 32.1 | 33.0 | 31.2 | 31.1 |
| gi\|229031808\|ref\|ZP_04187796.1\| | Bacillus cereus | 31.8 | 69.5 | 32.4 | 33.5 | 30.8 | 30.0 |
| gi\|149181880\|ref\|ZP_01860369.1\| | Bacillus sp. | 30.4 | 69.5 | 29.4 | 30.3 | 29.9 | 29.8 |
| gi\|228902674\|ref\|ZP_04066822.1\| | Bacillus thuringiensis | 31.9 | 69.0 | 32.6 | 31.9 | 30.2 | 31.1 |
| gi\|228922913\|ref\|ZP_04086208.1\| | Bacillus thuringiensis | 31.6 | 69.0 | 32.4 | 31.6 | 30.2 | 30.7 |
| gi\|228998950\|ref\|ZP_04158532.1\| | Bacillus mycoides | 32.1 | 69.0 | 31.1 | 32.6 | 31.5 | 29.6 |
| gi\|229098630\|ref\|ZP_04229570.1\| | Bacillus cereus | 31.8 | 68.9 | 32.2 | 32.8 | 30.0 | 29.6 |
| gi\|228916796\|ref\|ZP_04080361.1\| | Bacillus thuringiensis | 31.6 | 68.9 | 32.4 | 33.0 | 30.5 | 29.8 |
| gi\|228992905\|ref\|ZP_04152829.1\| | B.pseudomycoides | 32.1 | 68.9 | 31.3 | 32.8 | 31.8 | 30.0 |
| gi\|229104765\|ref\|ZP_04235426.1\| | Bacillus cereus | 31.9 | 68.8 | 32.2 | 33.5 | 30.5 | 29.6 |
| gi\|229075867\|ref\|ZP_04208843.1\| | Bacillus cereus | 32.0 | 68.8 | 32.2 | 33.5 | 30.5 | 29.6 |
| gi\|222097607\|ref\|YP_002531664.1\| | Bacillus cereus | 31.3 | 68.7 | 33.3 | 33.7 | 30.7 | 30.3 |
| gi\|196034915\|ref\|ZP_03102322.1\| | B.cereus, B. thuringiensis | 31.4 | 68.5 | 32.1 | 33.3 | 30.3 | 29.4 |
| gi\|228967202\|ref\|ZP_04128238.1\| | Bacillus thuringiensis | 31.9 | 68.5 | 32.6 | 32.9 | 30.2 | 29.6 |
| gi\|228909996\|ref\|ZP_04073816.1\| | Bacillus thuringiensis | 31.6 | 68.5 | 32.6 | 32.9 | 30.2 | 30.0 |
| gi\|218899324\|ref\|YP_002447735.1\| | Bacillus cereus | 31.3 | 68.4 | 33.1 | 33.1 | 30.4 | 29.9 |
| gi\|42783278\|ref\|NP_980525.1\| | Bacillus cereus | 32.1 | 68.4 | 32.3 | 33.1 | 30.6 | 29.5 |
| gi\|228935481\|ref\|ZP_04098299.1\| | Bacillus thuringiensis | 31.6 | 68.4 | 32.3 | 33.5 | 30.6 | 30.3 |
| gi\|229061842\|ref\|ZP_04199173.1\| | Bacillus cereus | 32.2 | 68.3 | 32.4 | 33.5 | 30.4 | 30.0 |

FIG. 3C – BKD E2 Subunit Homologs

| | | | | | | | |
|---|---|---|---|---|---|---|---|
| gi\|229013371\|ref\|ZP_04170511.1\| | Bacillus mycoides | 32.2 | 68.3 | 32.2 | 33.5 | 30.4 | 30.0 |
| gi\|229019373\|ref\|ZP_04176197.1\| | Bacillus cereus | 31.9 | 68.3 | 32.4 | 33.5 | 30.4 | 30.0 |
| gi\|163941910\|ref\|YP_001646794.1\| | B. weihenstephanensis | 32.2 | 68.3 | 32.8 | 33.3 | 30.2 | 29.7 |
| gi\|254721759\|ref\|ZP_05183548.1\| | Bacillus anthracis | 31.2 | 68.3 | 32.3 | 32.4 | 29.9 | 29.7 |
| gi\|228941322\|ref\|ZP_04103875.1\| | Bacillus thuringiensis | 31.8 | 68.3 | 32.5 | 32.8 | 30.1 | 29.6 |
| gi\|152976565\|ref\|YP_001376082.1\| | Bacillus cereus | 31.4 | 68.3 | 32.6 | 33.4 | 30.9 | 30.3 |
| gi\|228954446\|ref\|ZP_04116471.1\| | B.thuringiensis, B. cereus | 31.6 | 68.2 | 32.3 | 33.3 | 30.1 | 30.6 |
| gi\|206971304\|ref\|ZP_03232255.1\| | Bacillus cereus | 31.8 | 68.2 | 32.5 | 33.5 | 30.3 | 30.6 |
| gi\|229163095\|ref\|ZP_04291051.1\| | Bacillus cereus | 31.5 | 68.2 | 32.6 | 33.3 | 30.2 | 30.0 |
| gi\|229134974\|ref\|ZP_04263780.1\| | Bacillus cereus | 31.9 | 68.1 | 32.0 | 32.9 | 30.0 | 29.1 |
| gi\|30264235\|ref\|NP_846612.1\| | Bacillus anthracis | 31.4 | 68.1 | 32.3 | 33.1 | 30.1 | 30.1 |
| gi\|228929206\|ref\|ZP_04092233.1\| | Bacillus thuringiensis | 31.4 | 68.1 | 32.3 | 33.1 | 30.1 | 30.1 |
| gi\|118479353\|ref\|YP_896504.1\| | Bacillus thuringiensis | 30.8 | 68.0 | 32.7 | 31.8 | 29.9 | 29.4 |
| gi\|229157741\|ref\|ZP_04285816.1\| | Bacillus cereus | 31.6 | 67.9 | 32.3 | 33.7 | 30.8 | 30.3 |
| gi\|228987352\|ref\|ZP_04147472.1\| | Bacillus thuringiensis | 31.6 | 67.9 | 32.7 | 33.7 | 30.8 | 30.3 |
| gi\|30022241\|ref\|NP_833872.1\| | B. cereus, B. thuringiensis | 32.0 | 67.9 | 32.5 | 33.5 | 30.3 | 30.4 |
| gi\|196041650\|ref\|ZP_03108942.1\| | Bacillus cereus | 31.6 | 67.9 | 32.3 | 33.5 | 30.6 | 30.1 |
| gi\|49480916\|ref\|YP_038222.1\| | Bacillus thuringiensis | 31.6 | 67.9 | 32.3 | 33.5 | 30.6 | 30.1 |
| gi\|52141336\|ref\|YP_085492.1\| | Bacillus cereus | 31.6 | 67.9 | 32.3 | 33.5 | 30.6 | 30.3 |
| gi\|47569677\|ref\|ZP_00240352.1\| | Bacillus cereus | 31.6 | 67.9 | 32.1 | 33.5 | 30.6 | 30.1 |
| gi\|225866142\|ref\|YP_002751520.1\| | Bacillus cereus | 30.8 | 67.9 | 32.7 | 31.8 | 29.9 | 31.9 |
| gi\|212638805\|ref\|YP_002315325.1\| | A.flavithermus | 31.6 | 66.4 | 29.4 | 30.8 | 29.2 | 34.9 |
| gi\|229498328\|ref\|ZP_04392024.1\| | Geobacillus sp. | 30.6 | 66.3 | 30.6 | | 29.4 | 30.2 |
| gi\|56420911\|ref\|YP_148229.1\| | Geobacillus kaustophilus | 30.4 | 66.2 | 31.5 | 31.6 | 30.4 | 30.7 |
| gi\|255332690\|ref\|ZP_05373689.1\| | Geobacillus sp. | 30.5 | 66.2 | 31.4 | 31.9 | 30.1 | 30.4 |
| gi\|229543918\|ref\|ZP_04432977.1\| | Bacillus coagulans | 30.0 | 64.6 | 30.1 | 32.3 | 33.1 | 30.6 |
| gi\|169828952\|ref\|YP_001699110.1\| | Lysinibacillus sphaericus | 31.2 | 64.3 | 30.5 | 31.0 | 30.1 | 29.1 |
| gi\|15615324\|ref\|NP_243627.1\| | Bacillus halodurans | 31.4 | 64.2 | 32.1 | 33.3 | 30.7 | 30.4 |
| gi\|254827634\|ref\|ZP_05232321.1\| | Listeria monocytogenes | 31.9 | 64.0 | 30.9 | 31.3 | 31.1 | 30.8 |
| gi\|224499949\|ref\|ZP_03668298.1\| | Listeria monocytogenes | 31.9 | 64.0 | 30.9 | 31.7 | 31.1 | 30.6 |
| gi\|16803414\|ref\|NP_464899.1\| | Listeria monocytogenes, | 31.6 | 63.7 | 30.9 | 31.5 | 30.5 | 30.6 |

FIG. 3C-BKD cont'd

FIG. 3C-BKD cont'd

FIG. 3C – BKD E2 Subunit Homologs

| | | | | | | | |
|---|---|---|---|---|---|---|---|
| gi\|47095957\|ref\|ZP_00233560.1\| | Listeria monocytogenes | 31.6 | 63.7 | 30.5 | 31.4 | 31.1 | 30.8 |
| gi\|22773773\|gb\|AAN05022.1\| | Listeria monocytogenes | 31.9 | 63.7 | 30.9 | 31.7 | 31.3 | 30.7 |
| gi\|229556637\|ref\|ZP_04444426.1\| | Listeria grayi | 31.8 | 63.7 | 29.4 | 31.3 | 32.1 | 30.9 |
| gi\|46907600\|ref\|YP_013989.1\| | Listeria monocytogenes | 31.9 | 63.3 | 30.3 | 30.7 | 31.9 | 29.7 |
| gi\|254852579\|ref\|ZP_05241927.1\| | Listeria monocytogenes | 31.8 | 63.2 | 30.6 | 31.3 | 31.5 | 30.4 |
| gi\|217964480\|ref\|YP_002350158.1\| | Listeria monocytogenes | 31.8 | 63.2 | 30.8 | 31.3 | 31.7 | 30.6 |
| gi\|254873034\|ref\|ZP_05245744.1\| | Listeria monocytogenes | 31.8 | 63.0 | 30.8 | 31.3 | 31.7 | 30.4 |
| gi\|16800479\|ref\|NP_470747.1\| | Listeria innocua | 31.5 | 62.9 | 30.4 | 31.1 | 32.2 | 30.1 |
| gi\|116872805\|ref\|YP_849586.1\| | Listeria welshimeri serovar | 30.6 | 62.8 | 29.3 | 29.2 | 31.6 | 29.8 |
| gi\|126653080\|ref\|ZP_01725215.1\| | Bacillus sp. | 32.0 | 62.6 | 31.4 | 31.5 | 30.7 | 29.5 |
| gi\|23099319\|ref\|NP_692785.1\| | Oceanobacillus iheyensis | 31.1 | 61.4 | 35.0 | 30.1 | 31.5 | 35.0 |
| gi\|255522415\|ref\|ZP_05389652.1\| | Listeria monocytogenes | | 60.2 | | | | |
| gi\|56964214\|ref\|YP_175945.1\| | Bacillus clausii | 31.0 | 59.7 | 32.2 | 33.3 | 32.5 | 36.6 |
| gi\|172056958\|ref\|YP_001813418.1\| | E.sibiricum | 30.3 | 59.2 | 31.2 | 31.3 | 30.3 | 30.4 |
| gi\|226311958\|ref\|YP_002771852.1\| | Brevibacillus brevis | 34.0 | 58.8 | 33.5 | 32.3 | 31.3 | 31.4 |
| gi\|163763750\|ref\|ZP_02170810.1\| | Bacillus selenitireducens | 31.9 | 58.3 | 30.8 | 31.4 | 30.7 | 35.5 |
| gi\|283567960\|gb\|EFC18383.1\| | Bacillus cellulosilyticus | 31.5 | 57.9 | 29.5 | 29.8 | 29.9 | 33.4 |
| gi\|283470794\|emb\|CAQ50005.1\| | Staphylococcus aureus | 30.5 | 54.8 | 28.2 | 28.0 | 27.6 | 28.8 |
| gi\|57650472\|ref\|YP_186401.1\| | Staphylococcus aureus | 30.8 | 54.8 | 28.9 | 28.9 | 27.8 | 28.8 |
| gi\|88195322\|ref\|YP_500126.1\| | Staphylococcus aureus | 30.8 | 54.8 | 28.7 | 28.7 | 27.8 | 28.8 |
| gi\|269941006\|emb\|CBI49390.1\| | Staphylococcus aureus | 30.5 | 54.8 | 28.7 | 28.7 | 27.8 | 28.8 |
| gi\|21283197\|ref\|NP_646285.1\| | Staphylococcus aureus | 30.8 | 54.8 | 28.7 | 28.3 | 27.8 | 28.8 |
| gi\|253732169\|ref\|ZP_04866334.1\| | Staphylococcus aureus | 30.3 | 54.8 | 28.4 | 28.7 | 27.6 | 28.5 |
| gi\|242242784\|ref\|ZP_04797229.1\| | S.epidermidis | 29.2 | 54.7 | 29.0 | 29.3 | 28.3 | 28.6 |
| gi\|87160233\|ref\|YP_494160.1\| | Staphylococcus aureus | 30.5 | 54.5 | 28.7 | 28.7 | 28.0 | 28.5 |
| gi\|15924505\|ref\|NP_372039.1\| | Staphylococcus aureus | 30.8 | 54.5 | 28.7 | 28.3 | 27.8 | 28.8 |
| gi\|239637675\|ref\|ZP_04678647.1\| | Staphylococcus warneri | 30.9 | 54.5 | 27.6 | 28.3 | 28.7 | 26.7 |
| gi\|282916786\|ref\|ZP_06324544.1\| | Staphylococcus aureus | 31.2 | 54.4 | 28.4 | 28.3 | 28.7 | 28.8 |
| gi\|82751120\|ref\|YP_416861.1\| | Staphylococcus aureus | 30.8 | 54.3 | 28.4 | 27.8 | 27.6 | 28.5 |
| gi\|258423169\|ref\|ZP_05686062.1\| | Staphylococcus aureus | 30.3 | 54.3 | 28.4 | 28.3 | 28.5 | 29.0 |
| gi\|49483765\|ref\|YP_040989.1\| | Staphylococcus aureus | | 54.3 | 28.4 | 28.3 | 27.4 | 28.8 |

FIG. 3C-BKD cont'd

FIG. 3C – BKD E2 Subunit Homologs

| | | | | | | | |
|---|---|---|---|---|---|---|---|
| gi\|27468114\|ref\|NP_764751.1\| | S. epidermidis | 28.9 | 54.2 | 28.6 | 28.7 | 28.1 | 28.1 |
| gi\|228476022\|ref\|ZP_04060730.1\| | Staphylococcus hominis | 29.0 | 54.1 | 27.3 | 27.0 | 28.3 | 27.1 |
| gi\|282919292\|ref\|ZP_06327027.1\| | Staphylococcus aureus | 30.5 | 54.1 | 28.4 | 28.3 | 27.4 | 28.8 |
| gi\|57866996\|ref\|YP_188653.1\| | S.epidermidis | 28.6 | 54.0 | 28.3 | 29.0 | 27.8 | 28.3 |
| gi\|224476624\|ref\|YP_002634230.1\| | Staphylococcus carnosus | 30.8 | 53.9 | | | 28.2 | 26.2 |
| gi\|229916236\|ref\|YP_002884882.1\| | Exiguobacterium sp. | 31.8 | 53.7 | 30.6 | 30.2 | 30.9 | 31.0 |
| gi\|73662549\|ref\|YP_301330.1\| | S.saprophyticus | 30.0 | 53.2 | 29.2 | 29.8 | 30.2 | 29.2 |
| gi\|242373815\|ref\|ZP_04819389.1\| | S.epidermidis | 29.5 | 52.8 | 28.1 | 27.5 | 28.2 | 28.7 |
| gi\|70726401\|ref\|YP_253315.1\| | S. haemolyticus | 30.5 | 52.2 | 27.9 | 28.3 | 28.8 | 27.7 |
| gi\|253576337\|ref\|ZP_04853667.1\| | Paenibacillus sp. | | 52.1 | | | 26.1 | |
| gi\|223043226\|ref\|ZP_03613273.1\| | Staphylococcus capitis | 29.8 | 52.0 | 27.6 | 27.2 | 28.0 | 27.5 |
| gi\|191638439\|ref\|YP_001987605.1\| | Lactobacillus casei | | 50.1 | | | | 31.6 |
| gi\|261405974\|ref\|YP_003242215.1\| | Geobacillus sp. | | 50.0 | | | | |
| gi\|116494929\|ref\|YP_806663.1\| | Lactobacillus casei | | 49.5 | | | | |
| gi\|167465153\|ref\|ZP_02330242.1\| | Paenibacillus larvae | 28.6 | 49.4 | 28.5 | 29.2 | 29.0 | 27.6 |
| gi\|257085093\|ref\|ZP_05579454.1\| | Enterococcus faecalis | | 49.4 | 30.9 | 31.3 | 30.5 | 35.1 |
| gi\|227535071\|ref\|ZP_03965120.1\| | Lactobacillus paracasei | | 49.3 | | | | |
| gi\|256762589\|ref\|ZP_05503169.1\| | Enterococcus faecalis | 29.7 | 49.1 | 31.9 | 31.5 | 30.8 | 34.9 |
| gi\|256959069\|ref\|ZP_05563240.1\| | Enterococcus faecalis | | 49.0 | 30.6 | 31.5 | 30.1 | 34.9 |
| gi\|255975756\|ref\|ZP_05426342.1\| | Enterococcus faecalis | | 49.0 | 30.4 | 31.5 | 29.9 | 34.9 |
| gi\|229545732\|ref\|ZP_04434457.1\| | Enterococcus faecalis | | 49.0 | 30.6 | 31.5 | 30.1 | 34.9 |
| gi\|257082461\|ref\|ZP_05576822.1\| | Enterococcus faecalis | | 49.0 | 30.6 | 31.1 | 30.5 | 34.9 |
| gi\|29376212\|ref\|NP_815366.1\| | Enterococcus faecalis | | 48.7 | 30.6 | 31.3 | 30.3 | 34.9 |
| gi\|257422521\|ref\|ZP_05599511.1\| | Enterococcus faecalis | | 48.7 | 30.9 | 31.9 | 30.5 | 34.5 |
| gi\|257089974\|ref\|ZP_05584335.1\| | Enterococcus faecalis | | 48.5 | 30.6 | 30.4 | 30.8 | 34.9 |
| gi\|5901698\|gb\|AAD55379.1\|AF149712_7 | Enterococcus faecalis | | 48.5 | 30.2 | 30.2 | 29.2 | 35.1 |
| gi\|269925216\|ref\|YP_003321839.1\| | T.terrenum | 30.4 | 47.5 | 31.2 | 30.8 | 29.7 | 26.3 |
| gi\|108805280\|ref\|YP_645217.1\| | Rubrobacter xylanophilus | 31.8 | 46.0 | 32.0 | 32.0 | 31.1 | 33.1 |
| gi\|269929375\|ref\|YP_003321696.1\| | S.thermophilus | 31.3 | 46.0 | 30.5 | 30.5 | 28.2 | 27.9 |
| gi\|169627994\|ref\|YP_001701643.1\| | M.abscessus | 33.5 | 35.0 | 36.4 | 37.0 | 49.8 | 46.7 |
| gi\|169631989\|ref\|YP_001705638.1\| | M.abscessus | 32.2 | 34.7 | 49.8 | 49.1 | 39.6 | |

FIG. 3C-BKD cont'd

FIG. 3C – BKD E2 Subunit Homologs

| | | | | | | | |
|---|---|---|---|---|---|---|---|
| gi\|163841385\|ref\|YP_001625790.1\| | R.salmoninarum | 32.5 | 34.6 | 37.9 | 37.1 | 52.6 | 48.8 |
| gi\|91786186\|ref\|YP_547138.1\| | Polaromonas sp. | 61.8 | 34.6 | 33.9 | 33.0 | 37.0 | 40.4 |
| gi\|209546467\|ref\|YP_002278385.1\| | R.leguminosarum | 52.5 | 34.1 | 30.4 | 31.0 | 36.7 | 37.8 |
| gi\|227377011\|ref\|ZP_03860473.1\| | Kribbella flavida | 29.3 | 33.7 | 35.8 | 34.9 | 50.6 | 50.7 |
| gi\|239814019\|ref\|YP_002942929.1\| | Variovorax paradoxus | 60.0 | 33.6 | | | 39.0 | 39.3 |
| gi\|226362324\|ref\|YP_002780102.1\| | Rhodococcus opacus | 34.1 | 33.4 | 40.0 | 40.1 | 53.8 | 50.9 |
| gi\|163839328\|ref\|YP_001623733.1\| | R.salmoninarum | 32.4 | 33.3 | 47.1 | 48.1 | 37.9 | 35.6 |
| gi\|227823514\|ref\|YP_002827487.1\| | Rhizobium sp. | 52.5 | 33.3 | 31.4 | 31.3 | 33.6 | 33.5 |
| gi\|84683577\|ref\|ZP_01011480.1\| | R.bacterium | 49.1 | 33.3 | 32.4 | 33.0 | 33.1 | 30.3 |
| gi\|229491207\|ref\|ZP_04385035.1\| | Rhodococcus erythropolis | 33.6 | 33.3 | 36.7 | 37.0 | 50.7 | 49.3 |
| gi\|226309469\|ref\|YP_002769431.1\| | Rhodococcus erythropolis | 34.1 | 33.3 | 36.7 | 36.6 | 51.2 | 49.7 |
| gi\|134101994\|ref\|YP_001107655.1\| | S.erythraea | 35.5 | 33.2 | 38.6 | 36.8 | 58.5 | 53.8 |
| gi\|15966687\|ref\|NP_387040.1\| | Sinorhizobium meliloti | 53.1 | 33.1 | 31.4 | 31.1 | 34.1 | 35.8 |
| gi\|150398026\|ref\|YP_001328493.1\| | Sinorhizobium medicae | 53.5 | 33.0 | 32.7 | 30.6 | 34.9 | 36.4 |
| gi\|111020367\|ref\|YP_703339.1\| | Rhodococcus jostii | 33.4 | 33.0 | 53.6 | 53.8 | 36.7 | 37.1 |
| gi\|255292430\|dbj\|BAH89548.1\| | uncultured bacterium | 53.8 | 33.0 | 33.0 | 32.5 | 35.6 | 33.3 |
| gi\|282863883\|ref\|ZP_06272941.1\| | Streptomyces sp. | 31.1 | 32.8 | 77.4 | 76.8 | 38.8 | 37.5 |
| gi\|238059375\|ref\|ZP_04604084.1\| | Micromonospora sp. | 34.3 | 32.8 | 40.2 | 40.0 | 55.5 | 54.0 |
| gi\|111020308\|ref\|YP_703280.1\| | Rhodococcus jostii | 33.4 | 32.7 | 39.8 | 39.6 | 54.8 | 52.5 |
| gi\|226360694\|ref\|YP_002778472.1\| | Rhodococcus opacus | 34.8 | 32.7 | 51.0 | 50.1 | 40.1 | 38.8 |
| gi\|241554277\|ref\|YP_002979490.1\| | R.leguminosarum | 52.7 | 32.7 | 32.8 | 31.5 | 36.3 | 36.1 |
| gi\|148553703\|ref\|YP_001261285.1\| | Sphingomonas wittichii | 53.9 | 32.6 | 31.7 | | 33.6 | 35.7 |
| gi\|163796019\|ref\|ZP_02189982.1\| | alpha proteobacterium | 55.3 | 32.5 | 31.8 | 32.8 | 36.1 | 34.0 |
| gi\|86360117\|ref\|YP_472006.1\| | Rhizobium etli | 53.4 | 32.5 | 32.7 | 30.4 | 39.9 | 37.8 |
| gi\|159185753\|ref\|NP_357138.2\| | A.tumefaciens | 52.1 | 32.4 | 34.2 | 34.4 | 33.6 | 34.2 |
| gi\|256673220\|ref\|ZP_05484173.1\| | Streptomyces sp. | 36.8 | 32.3 | 56.8 | 56.2 | 40.1 | 39.4 |
| gi\|260648481\|emb\|CBG71592.1\| | S. scabiei 87.22 | 35.0 | 32.3 | 39.7 | 39.9 | 80.1 | 74.7 |
| gi\|254402710\|ref\|ZP_05017659.1\| | Streptomyces sviceus | 34.8 | 32.3 | 40.7 | 39.0 | 78.9 | 73.5 |
| gi\|239930113\|ref\|ZP_04687066.1\| | S.ghanaensis | 31.7 | 32.2 | 80.4 | 79.1 | 41.2 | 40.6 |
| gi\|134100489\|ref\|YP_001106150.1\| | S.erythraea | 31.4 | 32.1 | 36.8 | 36.8 | 57.4 | 52.6 |
| gi\|116254747\|ref\|YP_770583.1\| | R.leguminosarum | 52.5 | 32.1 | | | 39.2 | 36.5 |

FIG. 3C-BKD cont'd

FIG. 3C – BKD E2 Subunit Homologs

| | | | | | | | |
|---|---|---|---|---|---|---|---|
| gi\|99082616\|ref\|YP_614770.1\| | Ruegeria sp. | 55.4 | 32.0 | 30.6 | 30.6 | 32.8 | 31.5 |
| gi\|256379010\|ref\|YP_003102670.1\| | Actinosynnema mirum | 31.3 | 31.9 | 37.0 | 35.4 | 58.1 | 55.6 |
| gi\|13473767\|ref\|NP_105335.1\| | Mesorhizobium loti | 53.0 | 31.9 | 32.8 | 32.2 | 35.3 | 33.2 |
| gi\|259417576\|ref\|ZP_05741495.1\| | Silicibacter sp. | 54.7 | 31.9 | 30.1 | 30.7 | 32.5 | 32.1 |
| gi\|229591398\|ref\|YP_002873517.1\| | P.fluorescens | 74.8 | 31.9 | 33.0 | 33.1 | 36.9 | 33.9 |
| gi\|239934268\|ref\|ZP_04691221.1\| | S.ghanaensis | 33.1 | 31.9 | 69.4 | 71.5 | 40.6 | 37.5 |
| gi\|260453182\|ref\|ZP_05801589.1\| | S.flavogriseus | 31.4 | 31.8 | 76.5 | 78.8 | 39.7 | 37.6 |
| gi\|239833853\|ref\|ZP_04682181.1\| | O.intermedium | 54.7 | 31.7 | 30.5 | 32.0 | 33.3 | 33.0 |
| gi\|152984679\|ref\|YP_001348352.1\| | P.aeruginosa | 70.5 | 31.7 | 30.8 | | 35.3 | 36.4 |
| gi\|239917210\|ref\|YP_002956768.1\| | Micrococcus luteus | 32.9 | 31.6 | 49.4 | 46.3 | 38.7 | 40.7 |
| gi\|170722907\|ref\|YP_001750595.1\| | Pseudomonas putida | 91.7 | 31.5 | 31.5 | 31.7 | 34.4 | 34.8 |
| gi\|107101695\|ref\|ZP_01365613.1\| | P. aeruginosa | 71.3 | 31.4 | 31.3 | 29.9 | 35.3 | 40.0 |
| gi\|256782142\|ref\|ZP_05520605.1\| | S.hygroscopicus | 31.5 | 31.4 | 49.6 | 51.6 | 36.2 | 36.0 |
| gi\|260469851\|ref\|ZP_05814000.1\| | M.opportunistum | 53.6 | 31.4 | 32.6 | 31.9 | 35.2 | 33.9 |
| gi\|206559591\|ref\|YP_002230352.1\| | Burkholderia cenocepacia | 64.4 | 31.3 | 32.8 | 30.6 | 34.1 | 35.9 |
| gi\|254720464\|ref\|ZP_05182275.1\| | Brucella sp. | 55.3 | 31.2 | 30.7 | 31.8 | 32.7 | 33.0 |
| gi\|104782859\|ref\|YP_609357.1\| | P.entomophila | 89.9 | 31.1 | 32.6 | 31.4 | 33.7 | 33.7 |
| gi\|17989091\|ref\|NP_541724.1\| | Brucella melitensis | 55.0 | 31.1 | 30.8 | 31.9 | 32.7 | 33.0 |
| gi\|23500273\|ref\|NP_699713.1\| | B. suis, B. pinnipedialis, B. neotomae, B.ceti | 55.2 | 31.1 | 30.8 | 31.9 | 32.7 | 33.0 |
| gi\|161620588\|ref\|YP_001594474.1\| | Brucella suis | 55.0 | 31.1 | 30.6 | 32.2 | 32.7 | 32.8 |
| gi\|148558405\|ref\|YP_001257492.1\| | Brucella ovis | 53.4 | 31.1 | 30.8 | 32.4 | 32.5 | 33.0 |
| gi\|254695584\|ref\|ZP_05157412.1\| | Brucella abortus | 54.7 | 31.1 | 30.8 | 31.9 | 32.7 | 33.0 |
| gi\|227378204\|ref\|ZP_03861664.1\| | Kribbella flavida | | 31.1 | 55.2 | 55.1 | 35.7 | 36.0 |
| gi\|116050196\|ref\|YP_790987.1\| | P.aeruginosa | 70.3 | 31.1 | | | 34.1 | 36.0 |
| gi\|107022320\|ref\|YP_620647.1\| | Burkholderia cenocepacia | 65.3 | 31.0 | 33.6 | 31.2 | 36.2 | 36.5 |
| gi\|170732568\|ref\|YP_001764515.1\| | Burkholderia cenocepacia | 63.5 | 31.0 | 31.8 | 31.5 | 34.6 | 39.7 |
| gi\|153010874\|ref\|YP_001372088.1\| | Ochrobactrum anthropi | 52.2 | 31.0 | 31.2 | 31.1 | 32.7 | 32.6 |
| gi\|145594631\|ref\|YP_001158928.1\| | Salinispora tropica | 35.6 | 31.0 | 40.3 | 39.8 | 55.3 | 54.9 |
| gi\|256671552\|ref\|ZP_05482505.1\| | Streptomyces sp. | 32.8 | 30.9 | 38.6 | 37.4 | 55.6 | 52.6 |
| gi\|62317613\|ref\|YP_223466.1\| | B. abortus, B.melitensis | 54.7 | 30.9 | 30.8 | 31.9 | 32.7 | 33.0 |
| gi\|94496505\|ref\|ZP_01303082.1\| | Sphingomonas sp. | 53.1 | 30.9 | 31.2 | 32.0 | 35.0 | 34.4 |

FIG. 3C-BKD cont'd

FIG. 3C – BKD E2 Subunit Homologs

| | | | | | | | |
|---|---|---|---|---|---|---|---|
| gi\|218891777\|ref\|YP_002440644.1\| | P. aeruginosa | 71.3 | 30.8 | 31.3 | 29.7 | 35.1 | 40.0 |
| gi\|15597445\|ref\|NP_250939.1\| | P.aeruginosa | 71.0 | 30.8 | 31.6 | 29.9 | 35.3 | 40.3 |
| gi\|167034959\|ref\|YP_001670190.1\| | Pseudomonas putida | 96.2 | 30.8 | 34.0 | 32.7 | 34.5 | 34.3 |
| gi\|126740935\|ref\|ZP_01756619.1\| | Roseobacter sp. | 57.4 | 30.8 | | | | 33.8 |
| gi\|89902316\|ref\|YP_524787.1\| | Rhodoferax ferrireducens | 57.8 | 30.7 | | 31.4 | 34.1 | 36.7 |
| gi\|254293978\|ref\|YP_003060001.1\| | Hirschia baltica | 50.1 | 30.6 | 30.9 | 31.8 | 31.7 | 29.7 |
| gi\|129044\|sp\|P09062.1\|ODB2_PSEPU | Pseudomonas putida | 97.4 | 30.6 | 32.7 | 31.9 | 34.8 | 32.2 |
| gi\|26991092\|ref\|NP_746517.1\| | Pseudomonas putida | 100 | 30.6 | 33.1 | 31.3 | 34.5 | 35.7 |
| gi\|269922272\|ref\|ZP_06171179.1\| | B. subvibrioides | 53.9 | 30.6 | 34.1 | 32.8 | 37.8 | 36.1 |
| gi\|257057825\|ref\|YP_003135657.1\| | S.viridis | 31.4 | 30.6 | 51.8 | 50.8 | 43.1 | 42.3 |
| gi\|254419195\|ref\|ZP_05032919.1\| | Brevundimonas sp. | 54.7 | 30.5 | 34.4 | 34.6 | 38.3 | 37.6 |
| gi\|115351178\|ref\|YP_773017.1\| | Burkholderia ambifaria | 64.2 | 30.5 | 31.0 | 29.9 | 36.0 | 36.4 |
| gi\|167645836\|ref\|YP_001683499.1\| | Caulobacter sp. | 51.9 | 30.4 | 29.5 | | 34.8 | 34.2 |
| gi\|85373860\|ref\|YP_457922.1\| | Erythrobacter litoralis | 51.7 | 30.3 | | | 35.2 | 35.4 |
| gi\|27381444\|ref\|NP_772973.1\| | B.japonicum | 52.5 | 30.2 | 33.1 | 32.1 | 35.1 | 32.9 |
| gi\|77459687\|ref\|YP_349194.1\| | P. fluorescens | 74.1 | 30.1 | 32.1 | 33.2 | 33.2 | 33.9 |
| gi\|256380960\|ref\|YP_003104620.1\| | Actinosynnema mirum | 38.8 | 30.1 | 56.1 | 55.2 | 40.5 | 39.5 |
| gi\|78065833\|ref\|YP_368602.1\| | Burkholderia sp. | 62.7 | 30.0 | 32.7 | 31.9 | 35.5 | 37.6 |
| gi\|163857822\|ref\|YP_001632120.1\| | Bordetella petrii. | 63.7 | 29.9 | 33.3 | 33.9 | 37.0 | 38.5 |
| gi\|172060191\|ref\|YP_001807843.1\| | Burkholderia ambifaria | 64.0 | 29.8 | 31.2 | 30.7 | 34.5 | 37.0 |
| gi\|119387482\|ref\|YP_918516.1\| | Paracoccus denitrificans | 52.5 | 29.8 | | | 37.6 | 35.6 |
| gi\|83859624\|ref\|ZP_00953144.1\| | Oceanicaulis alexandrii | 48.3 | 29.7 | 32.3 | 31.4 | 32.8 | 34.4 |
| gi\|171320117\|ref\|ZP_02909182.1\| | Burkholderia ambifaria | 63.4 | 29.7 | 30.9 | 30.5 | 35.8 | 37.1 |
| gi\|86741182\|ref\|YP_481582.1\| | Frankia sp. | 36.4 | 29.6 | 36.7 | 35.0 | 58.6 | 53.5 |
| gi\|254383337\|ref\|ZP_04998689.1\| | Streptomyces sp. | 35.6 | 29.6 | 42.1 | 41.5 | 72.6 | 68.0 |
| gi\|70729900\|ref\|YP_259639.1\| | P. fluorescens | 70.0 | 29.5 | 35.2 | 35.4 | 32.8 | 36.4 |
| gi\|239930127\|ref\|ZP_04687080.1\| | S.ghanaensis | 31.9 | 29.2 | 39.0 | 39.0 | 75.9 | 74.2 |
| gi\|88854467\|ref\|ZP_01129134.1\| | marine actinobacterium | 29.4 | 29.2 | 48.3 | 46.6 | 36.1 | 36.0 |
| gi\|256803196\|ref\|ZP_05532820.1\| | S. viridochromogenes | 34.0 | 28.9 | 38.9 | 38.4 | 77.1 | 74.5 |
| gi\|90420468\|ref\|ZP_01228375.1\| | A. manganoxydans | 50.6 | 28.7 | 31.2 | 29.7 | 35.7 | 36.2 |
| gi\|238023734\|ref\|YP_002907966.1\| | Burkholderia glumae | 60.7 | 28.3 | 32.3 | 30.5 | 37.3 | 37.4 |

FIG. 3C – BKD E2 Subunit Homologs

| | | | | | | | |
|---|---|---|---|---|---|---|---|
| gi\|148555058\|ref\|YP_001262640.1\| | Sphingomonas wittichii | 51.0 | 27.9 | 32.8 | 31.4 | 34.3 | 33.4 |
| gi\|256678028\|ref\|ZP_05488339.1\| | Streptomyces sp. | | | 39.9 | 39.1 | 73.3 | 73.4 |
| gi\|256678039\|ref\|ZP_05488350.1\| | Streptomyces sp. | | | 70.3 | 70.6 | 38.7 | 38.8 |
| gi\|229243580\|ref\|ZP_04367777.1\| | Cellulomonas flavigena | | | 54.7 | 54.7 | 37.7 | 39.6 |
| gi\|158313432\|ref\|YP_001505940.1\| | Frankia sp. | 34.4 | | 35.7 | 35.4 | 55.0 | 56.7 |
| gi\|254402697\|ref\|ZP_05017646.1\| | Streptomyces sviceus | 31.6 | | 78.9 | 79.3 | 40.2 | 38.5 |
| gi\|111222643\|ref\|YP_713437.1\| | Frankia alni | 36.6 | | 35.3 | 35.3 | 54.8 | 53.9 |
| gi\|29830907\|ref\|NP_825541.1\| | Streptomyces avermitilis | 35.0 | | 37.6 | 39.5 | 100 | 75.2 |
| gi\|29830921\|ref\|NP_825555.1\| | Streptomyces avermitilis | 31.0 | | 82.0 | 100 | 38.4 | 38.6 |
| gi\|237507870\|ref\|ZP_04520585.1\| | B.pseudomallei | 72.1 | | 31.9 | 34.3 | 37.4 | 36.1 |
| gi\|271970150\|ref\|YP_003344346.1\| | Streptosporan-gium roseum | 31.2 | | 53.8 | 54.1 | 36.8 | 37.7 |
| gi\|281415549\|ref\|ZP_06247291.1\| | Micrococcus luteus | 30.8 | | 34.8 | 34.8 | 45.1 | 46.0 |
| gi\|239918258\|ref\|YP_002957816.1\| | Micrococcus luteus | 30.8 | | 34.8 | 34.8 | 45.1 | 45.8 |
| gi\|51699506\|dbj\|BAD38881.1\| | S.carzinostaticus | 33.7 | | 61.7 | 60.0 | 39.7 | 38.6 |
| gi\|260453168\|ref\|ZP_05801575.1\| | S.flavogriseus | 34.8 | | 39.2 | 39.1 | 70.9 | 68.6 |
| gi\|239942618\|ref\|ZP_04694555.1\| | S. roseosporus | 35.2 | | 39.5 | 38.2 | 72.4 | 69.3 |
| gi\|239942600\|ref\|ZP_04694537.1\| | S. roseosporus | | | 75.6 | 76.2 | 37.3 | 37.3 |
| gi\|167590839\|ref\|ZP_02383227.1\| | B. ubonensis Bu | 69.3 | | | | 37.8 | 39.0 |
| gi\|229209341\|ref\|ZP_04335772.1\| | N. dassonvillei | 31.4 | | 60.3 | 60.3 | 38.4 | 36.5 |
| gi\|167924438\|ref\|ZP_02511529.1\| | B.pseudomallei | 72.1 | | 34.7 | | 37.4 | 39.0 |
| gi\|111018577\|ref\|YP_701549.1\| | Rhodococcus jostii | 32.5 | | 50.8 | 51.5 | 39.7 | 36.9 |
| gi\|254392375\|ref\|ZP_05007556.1\| | S.clavuligerus | | | 36.5 | 37.4 | 67.1 | 68.3 |
| gi\|269796850\|ref\|YP_003316305.1\| | Sanguibacter keddieii | | | 64.9 | 64.9 | 37.9 | 40.3 |
| gi\|167579155\|ref\|ZP_02372029.1\| | B.thailandensis | 70.8 | | | | 36.4 | 38.4 |
| gi\|163839306\|ref\|YP_001623711.1\| | R.salmoninarum | 31.3 | | 51.1 | 52.7 | 36.0 | 35.3 |
| gi\|117927242\|ref\|YP_871793.1\| | A.cellulolyticus | | | 46.7 | 45.5 | 36.0 | 36.4 |
| gi\|255326065\|ref\|ZP_05367152.1\| | Rothia mucilaginosa | | | 45.7 | 45.0 | 35.2 | 34.9 |
| gi\|229822442\|ref\|YP_002883968.1\| | Beutenbergia cavernae | | | 52.5 | 64.1 | 36.2 | 37.6 |
| gi\|119718726\|ref\|YP_925691.1\| | Nocardioides sp. | | | 58.7 | 50.4 | 39.2 | 38.5 |
| gi\|86738779\|ref\|YP_479179.1\| | Frankia sp. | | | 43.7 | 42.5 | 38.7 | 42.3 |
| gi\|50955930\|ref\|YP_063218.1\| | Leifsonia xyli | 31.0 | | 52.1 | 50.5 | 36.8 | 37.4 |

FIG. 3C-BKD cont'd

FIG. 3C-BKD cont'd

FIG. 3C – BKD E2 Subunit Homologs

| | | | | | | | |
|---|---|---|---|---|---|---|---|
| gi\|85708448\|ref\|ZP_01039514.1\| | Erythrobacter sp. | 51.6 | | 31.5 | | 33.6 | 36.5 |
| gi\|256833674\|ref\|YP_003162401.1\| | Jonesia denitrificans | | | 49.3 | 50.7 | 34.9 | 35.3 |
| gi\|167574072\|ref\|ZP_02366946.1\| | B.oklahomensis | 72.6 | | | | 36.7 | 38.0 |
| gi\|256815072\|ref\|ZP_05540087.1\| | S.griseoflavus | 35.3 | | 39.8 | 39.4 | 80.9 | 85.1 |
| gi\|256815056\|ref\|ZP_05540071.1\| | S.griseoflavus | | | 92.2 | 92.3 | 40.9 | 40.4 |
| gi\|167821483\|ref\|ZP_02453163.1\| | B.pseudomallei | 72.3 | | | | 37.4 | 39.1 |
| gi\|103486815\|ref\|YP_616376.1\| | Sphingopyxis alaskensis | 48.2 | | | | 31.6 | 34.1 |
| gi\|167829829\|ref\|ZP_02461300.1\| | B.pseudomallei | 72.2 | | | | 37.5 | 39.1 |
| gi\|270498438\|ref\|ZP_06215382.1\| | M.aurantiaca | 34.2 | | 36.7 | 36.3 | 59.7 | 51.4 |
| gi\|270499468\|ref\|ZP_06216407.1\| | M.aurantiaca | 31.1 | | 52.1 | 53.2 | 36.4 | 36.5 |
| gi\|270501761\|ref\|ZP_06218678.1\| | M. aurantiaca | | | 53.0 | 54.6 | 37.4 | 37.2 |
| gi\|239980736\|ref\|ZP_04703260.1\| | Streptomyces albus | 41.2 | | 40.3 | 40.3 | 83.7 | 83.7 |
| gi\|239980722\|ref\|ZP_04703246.1\| | Streptomyces albus | | | 75.4 | 74.9 | 36.9 | 36.4 |
| gi\|76818033\|ref\|YP_336566.1\| | B.pseudomallei | 72.1 | | 32.5 | | | 36.5 |
| gi\|114569257\|ref\|YP_755937.1\| | Maricaulis maris | 50.6 | | | | 32.0 | 33.0 |
| gi\|256803210\|ref\|ZP_05532834.1\| | S. viridochromogenes | 31.0 | | 84.4 | 78.8 | 40.5 | 39.6 |
| gi\|53716063\|ref\|YP_106529.1\| | Burkholderia mallei | 71.8 | | 32.7 | | | 36.5 |
| gi\|21222225\|ref\|NP_628004.1\| | S. coelicolor A3(2) | | | 100 | 80.8 | 37.8 | 39.1 |
| gi\|21222239\|ref\|NP_628018.1\| | S. coelicolor A3(2) | 35.4 | | 39.1 | 37.7 | 74.6 | 100 |
| gi\|126445162\|ref\|YP_001064182.1\| | B.pseudomallei | 71.8 | | 32.1 | 34.7 | 37.4 | 35.9 |
| gi\|256395300\|ref\|YP_003116864.1\| | Catenulispora acidiphila | 37.3 | | 39.5 | 38.5 | 63.9 | 64.5 |
| gi\|256389323\|ref\|YP_003110887.1\| | Catenulispora acidiphila | | | 53.7 | 53.8 | 33.6 | 33.7 |
| gi\|126456596\|ref\|YP_001077094.1\| | B.pseudomallei | 71.8 | | 32.3 | 34.7 | | 36.1 |
| gi\|167908243\|ref\|ZP_02495448.1\| | B.pseudomallei | 71.7 | | 35.4 | 34.7 | 37.4 | 39.0 |
| gi\|53723289\|ref\|YP_112274.1\| | B.pseudomallei | 72.1 | | 32.5 | | | 36.5 |
| gi\|83716049\|ref\|YP_440489.1\| | B.thailandensis | 57.8 | | 31.3 | | 36.4 | 35.7 |
| gi\|256777791\|ref\|ZP_05516254.1\| | S. hygroscopicus | 37.4 | | 37.6 | 37.8 | 67.8 | 71.3 |
| gi\|134281660\|ref\|ZP_01768367.1\| | B. pseudomallei | 72.1 | | 32.0 | | 37.4 | 36.3 |
| gi\|88855173\|ref\|ZP_01129838.1\| | marine actinobacterium | 29.3 | | 47.3 | 47.2 | 36.1 | 38.6 |
| gi\|256786681\|ref\|ZP_05525112.1\| | Streptomyces lividans | | | 100 | 88.5 | 39.0 | 37.6 |
| gi\|256786663\|ref\|ZP_05525094.1\| | Streptomyces lividans | 33.2 | | 38.8 | 38.2 | 74.2 | 98.2 |

FIG. 3C – BKD E2 Subunit Homologs

| | | | | | | | |
|---|---|---|---|---|---|---|---|
| gi\|116671736\|ref\|YP_832669.1\| | Arthrobacter sp. | 30.2 | | 34.5 | 35.9 | 47.6 | 47.9 |
| gi\|116669944\|ref\|YP_830877.1\| | Arthrobacter sp. | 29.4 | | 50.8 | 51.0 | 37.7 | 38.0 |
| gi\|116672568\|ref\|YP_833501.1\| | Arthrobacter sp. | | | 44.6 | 45.6 | 35.6 | 34.9 |
| gi\|218661696\|ref\|ZP_03517626.1\| | Rhizobium etli | 57.5 | | | | 40.1 | 37.8 |
| gi\|159035780\|ref\|YP_001535033.1\| | Salinispora arenicola | | | 53.7 | 51.5 | 39.7 | 37.1 |
| gi\|159037838\|ref\|YP_001537091.1\| | Salinispora arenicola | 34.9 | | 40.3 | 41.0 | 54.1 | 53.2 |
| gi\|254396789\|ref\|ZP_05011846.1\| | S.pristinaespiralis | | | | | 87.4 | 87.4 |
| gi\|254396771\|ref\|ZP_05011828.1\| | S.pristinaespiralis | | | 76.7 | 80.5 | 40.9 | 41.9 |
| gi\|238562316\|ref\|ZP_00440605.2\| | Burkholderia mallei | 71.8 | | 32.7 | | | 36.5 |
| gi\|182437560\|ref\|YP_001825279.1\| | Streptomyces griseus | 30.7 | | 78.9 | 76.3 | 38.1 | 37.2 |
| gi\|182437543\|ref\|YP_001825262.1\| | Streptomyces griseus | 36.9 | | 40.3 | 39.1 | 68.3 | 77.6 |
| gi\|87199991\|ref\|YP_497248.1\| | N.aromaticivorans | 50.1 | | | | 33.3 | 35.6 |
| gi\|269124600\|ref\|YP_003297970.1\| | T.curvata | | | 47.8 | 62.6 | 40.5 | 41.8 |
| gi\|170783365\|ref\|YP_001711699.1\| | C.michiganensis | | | 49.3 | 49.3 | 38.0 | 39.4 |
| gi\|283457298\|ref\|YP_003361871.1\| | Rothia mucilaginosa | | | 54.2 | 44.6 | 35.2 | 34.9 |
| gi\|254284315\|ref\|ZP_04959283.1\| | gamma proteobacterium | 47.1 | | 28.3 | 29.3 | 29.3 | 30.8 |
| gi\|254376096\|ref\|ZP_04991571.1\| | Streptomyces sp. | | | 71.7 | 71.9 | 37.8 | 38.9 |
| gi\|282873842\|ref\|ZP_06282802.1\| | Streptomyces sp. | 30.9 | | 78.7 | 76.1 | 38.3 | 37.4 |
| gi\|282874093\|ref\|ZP_06283041.1\| | Streptomyces sp. | 37.5 | | 39.0 | 36.5 | 69.3 | 67.3 |
| gi\|254187048\|ref\|ZP_04893563.1\| | B.pseudomallei | 72.1 | | 32.2 | | | 36.5 |
| gi\|119963490\|ref\|YP_947291.1\| | Arthrobr aurescens | 32.3 | | 50.2 | 49.1 | 38.4 | 37.1 |
| gi\|119964146\|ref\|YP_948854.1\| | Arthrobacter aurescens | 30.8 | | 37.2 | 36.9 | 49.5 | 48.3 |
| gi\|119962336\|ref\|YP_949568.1\| | Arthrobacter aurescens | | | 46.7 | 44.9 | 33.1 | 32.3 |
| gi\|254383356\|ref\|ZP_04998708.1\| | Streptomyces sp. | | | 69.9 | 67.6 | 38.9 | 38.1 |
| gi\|269957990\|ref\|YP_003327779.1\| | X.cellulosilytica | | | 52.7 | | 39.3 | 37.1 |
| gi\|220913647\|ref\|YP_002488956.1\| | A.chlorophenolicus | 30.5 | | 35.7 | 36.9 | 47.3 | 48.0 |
| gi\|220912171\|ref\|YP_002487480.1\| | A.chlorophenolicus | 30.8 | | 52.1 | 53.8 | 38.7 | 38.3 |
| gi\|220914549\|ref\|YP_002489858.1\| | A.chlorophenolicus | | | 45.8 | 45.9 | 35.6 | 33.5 |
| gi\|167567000\|ref\|ZP_02359916.1\| | B.oklahomensis | 72.6 | | | | 36.3 | 38.0 |
| gi\|167851292\|ref\|ZP_02476800.1\| | B. pseudomallei | 72.1 | | | | 37.5 | 39.1 |
| gi\|167840921\|ref\|ZP_02467605.1\| | B. thailandensis | 72.7 | | | | 35.8 | 38.4 |

FIG. 3C-BKD cont'd

FIG. 3C-BKD cont'd

FIG. 3C – BKD E2 Subunit Homologs

| | | | | | | | |
|---|---|---|---|---|---|---|---|
| gi\|260904559\|ref\|ZP_05912881.1\| | Brevibacterium linens | | | 52.0 | 49.8 | 38.2 | 36.2 |
| gi\|170701859\|ref\|ZP_02892789.1\| | Burkholderia ambifaria | 68.7 | | | | 37.5 | 38.7 |
| gi\|229866852\|ref\|ZP_04486460.1\| | S.nassauensis | | | 54.2 | 54.0 | 36.3 | 34.9 |
| gi\|184201773\|ref\|YP_001855980.1\| | Kocuria rhizophila | 30.3 | | 36.3 | 34.8 | 45.6 | 55.2 |
| gi\|134103718\|ref\|YP_001109379.1\| | S.erythraea | | | 55.6 | 52.2 | 37.8 | 35.6 |
| gi\|148274126\|ref\|YP_001223687.1\| | C.michiganensis | | | 49.7 | 49.0 | 37.3 | 38.3 |
| gi\|167916582\|ref\|ZP_02503673.1\| | B.pseudomallei | 71.6 | | | | 36.5 | 38.5 |
| gi\|256824330\|ref\|YP_003148290.1\| | Kytococcus sedentarius | | | 37.3 | 34.5 | 43.7 | 53.0 |
| gi\|256824127\|ref\|YP_003148087.1\| | Kytococcus sedentarius | | | 52.0 | 53.7 | 36.3 | 35.7 |
| gi\|217424294\|ref\|ZP_03455793.1\| | B.pseudomallei | 71.8 | | | | | 36.8 |
| gi\|257069654\|ref\|YP_003155909.1\| | Brachybacterium faecium | | | 48.3 | 47.1 | 35.1 | 35.1 |
| gi\|256768470\|ref\|ZP_05507644.1\| | Streptomyces sp. | 28.4 | | 69.4 | 66.8 | 37.0 | 37.8 |
| gi\|256768487\|ref\|ZP_05507661.1\| | Streptomyces sp. | 36.8 | | 38.9 | 39.4 | 76.7 | 74.7 |
| gi\|145592673\|ref\|YP_001156970.1\| | Salinispora tropica | | | 53.9 | 52.1 | 38.6 | 38.0 |
| gi\|282863268\|ref\|ZP_06272327.1\| | Streptomyces sp. | | | 39.1 | 37.4 | 70.2 | 69.3 |
| gi\|167744279\|ref\|ZP_02417053.1\| | B.pseudomallei | 72.1 | | | | 37.2 | 38.9 |
| gi\|152968229\|ref\|YP_001364013.1\| | K.radiotolerans | 31.0 | | 53.9 | 54.9 | 35.9 | 35.2 |
| gi\|167725356\|ref\|ZP_02408592.1\| | B.pseudomallei | 72.8 | | | | 40.4 | 41.6 |
| gi\|72160586\|ref\|YP_288243.1\| | Thermobifida fusca | 32.5 | | 57.3 | 58.7 | 37.7 | 37.4 |
| gi\|227406263\|ref\|ZP_03889500.1\| | Geodermatophilus obscurus | 30.5 | | 55.1 | 53.5 | 39.2 | 41.4 |
| gi\|260648468\|emb\|CBG71579.1\| | Streptomyces scabiei | 30.8 | | 76.8 | 81.0 | 39.4 | 38.5 |
| gi\|260652581\|emb\|CBG75714.1\| | Streptomyces scabiei | 35.6 | | 40.6 | 41.7 | 68.7 | 65.8 |
| gi\|84495442\|ref\|ZP_00994561.1\| | Janibacter sp. | | | 55.8 | 55.4 | 37.0 | 36.6 |
| gi\|254182493\|ref\|ZP_04889087.1\| | B.pseudomallei | 72.1 | | 32.3 | | 37.0 | 36.2 |

FIG. 3D- BKD E3 Subunit Homologs

| Acc. No. | Organism | ID%Sc | ID%Pp | ID%Bs | ID%Sa3 | ID%Sa2 | ID%Sa | ID%Sc2 |
|---|---|---|---|---|---|---|---|---|
| gi\|221319573\|ref\|ZP_03600867.1\| | Bacillus subtilis | 41.5 | 34.9 | 100 | 30.5 | 39.5 | 39.7 | 30.3 |
| gi\|221310326\|ref\|ZP_03592173.1\| | Bacillus subtilis | 40.4 | | 99.8 | 30.8 | 38.7 | 38.4 | 30.8 |
| gi\|154686665\|ref\|YP_001421826.1\| | B.amyloliquefaciens | 40.7 | 35.9 | 82.9 | 30.5 | 39.0 | 39.1 | 30.1 |
| gi\|52080944\|ref\|YP_079735.1\| | B.licheniformis | 40.4 | 35.7 | 81.4 | 31.1 | 40.0 | 39.9 | 30.9 |
| gi\|157692912\|ref\|YP_001487374.1\| | B. pumilus | 41.9 | 33.8 | 79.7 | 30.3 | 38.9 | 40.1 | 30.3 |
| gi\|194016987\|ref\|ZP_03055600.1\| | B.pumilus | 41.9 | 34.0 | 79.1 | 29.9 | 38.9 | 40.1 | 29.9 |
| gi\|89099271\|ref\|ZP_01172149.1\| | Bacillus sp. | 44.2 | 34.1 | 78.4 | 29.8 | 39.3 | 41.8 | 29.4 |
| gi\|212638802\|ref\|YP_002315322.1\| | A.flavithermus | 43.3 | 34.8 | 75.5 | 32.0 | 42.1 | 42.1 | 32.0 |
| gi\|149181877\|ref\|ZP_01860366.1\| | Bacillus sp. | 42.5 | 34.7 | 75.3 | 28.5 | 38.1 | 41.6 | 28.2 |
| gi\|239827652\|ref\|YP_002950276.1\| | Geobacillus sp. | 43.2 | 36.3 | 75.1 | 31.3 | 41.2 | 41.7 | 31.1 |
| gi\|255332687\|ref\|ZP_05373686.1\| | Geobacillus sp. | 42.2 | 36.5 | 74.5 | 32.3 | 41.0 | 41.3 | 31.9 |
| gi\|196248840\|ref\|ZP_03147540.1\| | Geobacillus sp. | 42.4 | 35.6 | 74.3 | 32.6 | 41.8 | 41.3 | 32.6 |
| gi\|138895949\|ref\|YP_001126402.1\| | G.thermodenitrificans | 42.2 | 35.6 | 74.3 | 32.8 | 42.1 | 41.1 | 32.6 |
| gi\|56420914\|ref\|YP_148232.1\| | G.kaustophilus | 42.2 | 35.0 | 74.1 | 33.4 | 42.3 | 41.5 | 33.2 |
| gi\|229498331\|ref\|ZP_04392027.1\| | Geobacillus sp. | 42.2 | 35.0 | 73.8 | 33.8 | 42.5 | 41.5 | 33.6 |
| gi\|42558167\|dbj\|BAD11090.1\| | M.thermoacetica | 42.4 | 35.0 | 73.8 | 33.4 | 41.8 | 41.0 | 33.2 |
| gi\|30264238\|ref\|NP_846615.1\| | B.thuringiensis, B.cereus, B. anthracis | 43.0 | 34.7 | 73.8 | 30.4 | 40.2 | 42.3 | 30.9 |
| gi\|42783281\|ref\|NP_980528.1\| | Bacillus cereus | 43.0 | 34.7 | 73.8 | 30.4 | 40.2 | 42.3 | 30.9 |
| gi\|225866145\|ref\|YP_002751523.1\| | Bacillus cereus | 42.8 | 34.7 | 73.8 | 30.7 | 40.4 | 42.0 | 31.1 |
| gi\|152976568\|ref\|YP_001376085.1\| | B. cereus, B. cytotoxicus | 43.4 | 34.5 | 73.8 | 30.0 | 39.5 | 42.0 | 30.0 |
| gi\|229031811\|ref\|ZP_04187799.1\| | Bacillus cereus | 43.0 | 34.7 | 73.6 | 30.2 | 40.2 | 42.3 | 30.7 |
| gi\|222097610\|ref\|YP_002531667.1\| | Bacillus cereus | 43.0 | 34.7 | 73.6 | 30.4 | 40.2 | 42.3 | 30.9 |
| gi\|228987355\|ref\|ZP_04147475.1\| | B.thuringiensis | 43.0 | 34.7 | 73.6 | 30.4 | 40.2 | 42.3 | 30.7 |
| gi\|47569680\|ref\|ZP_00240355.1\| | Bacillus cereus | 43.0 | 34.7 | 73.6 | 30.2 | 40.2 | 42.3 | 30.7 |
| gi\|229174839\|ref\|ZP_04302359.1\| | Bacillus cereus | 43.0 | 34.7 | 73.6 | 30.2 | 40.4 | 42.3 | 30.7 |
| gi\|30022244\|ref\|NP_833875.1\| | B.cereus, B. thuringiensis | 42.8 | 34.7 | 73.6 | 30.5 | 40.4 | 42.0 | 30.9 |
| gi\|229075870\|ref\|ZP_04208846.1\| | Bacillus cereus | 42.8 | 34.7 | 73.4 | 30.3 | 40.4 | 42.0 | 30.7 |
| gi\|228992908\|ref\|ZP_04152832.1\| | B. pseudo-mycoides, B. mycoides | 43.0 | 34.5 | 73.4 | 30.1 | 39.8 | 42.3 | 30.5 |
| gi\|75761047\|ref\|ZP_00741047.1\| | B.thuringiensis, B. cereus | 42.8 | 34.7 | 73.4 | 30.3 | 40.4 | 42.0 | 30.7 |
| gi\|229047859\|ref\|ZP_04193436.1\| | Bacillus cereus | 42.8 | 34.7 | 73.4 | 30.5 | 40.4 | 42.0 | 30.9 |

FIG. 3D-BKD cont'd

FIG. 3D- BKD E3 Subunit Homologs

| | | | | | | | | |
|---|---|---|---|---|---|---|---|---|
| gi\|206971318\|ref\|ZP_03232269.1\| | Bacillus cereus | 42.6 | 34.7 | 73.4 | 30.3 | 40.2 | 41.8 | 30.7 |
| gi\|229013374\|ref\|ZP_04170514.1\| | B. cereus, B.mycoides | 42.3 | 34.7 | 73.2 | 30.5 | 40.6 | 41.6 | 30.5 |
| gi\|163941913\|ref\|YP_001646797.1\| | B.cereus, B. wei-henstephanensis | 42.3 | 34.7 | 73.2 | 30.3 | 40.4 | 41.6 | 30.7 |
| gi\|228922916\|ref\|ZP_04086211.1\| | B.thuringiensis | 42.8 | 34.7 | 73.2 | 30.3 | 40.6 | 42.0 | 30.7 |
| gi\|229086735\|ref\|ZP_04218901.1\| | Bacillus cereus | 43.0 | 34.7 | 73.2 | 30.3 | 40.4 | 42.0 | 30.7 |
| gi\|229019376\|ref\|ZP_04176200.1\| | Bacillus cereus | 42.3 | 34.7 | 73.2 | 30.3 | 40.4 | 41.6 | 30.7 |
| gi\|42558173\|dbj\|BAD11095.1\| | G. thermoca-tenulatus | 42.0 | 35.3 | 72.4 | 33.8 | 42.3 | 40.9 | 33.5 |
| gi\|15615327\|ref\|NP_243630.1\| | B.halodurans | 40.7 | 34.0 | 71.1 | 29.1 | 39.5 | 39.4 | 28.9 |
| gi\|283567957\|gb\|EFC18380.1\| | B.cellulosilyticus | 40.1 | | 69.1 | 27.5 | 36.5 | 38.9 | 27.9 |
| gi\|23099322\|ref\|NP_692788.1\| | O. iheyensis | 38.2 | 33.2 | 68.5 | 30.4 | 36.6 | 37.5 | 30.6 |
| gi\|229556640\|ref\|ZP_04444429.1\| | Listeria grayi | 39.3 | | 68.4 | 29.4 | 37.1 | 38.5 | 30.2 |
| gi\|229543915\|ref\|ZP_04432974.1\| | B.coagulans | 40.4 | | 68.1 | 28.8 | 37.9 | 39.2 | 28.8 |
| gi\|226311955\|ref\|YP_002771849.1\| | B.brevis | 42.6 | | 67.7 | 29.2 | 40.7 | 42.0 | 28.1 |
| gi\|254827631\|ref\|ZP_05232318.1\| | L. monocytogenes | 38.7 | | 66.2 | | 36.2 | 37.9 | 28.7 |
| gi\|163763747\|ref\|ZP_02170807.1\| | B. selenitireducens | 41.2 | 34.6 | 66.2 | 28.1 | 38.3 | 40.6 | |
| gi\|224501686\|ref\|ZP_03669993.1\| | L. monocytogenes | 38.8 | | 66.0 | | 36.2 | 37.9 | 28.7 |
| gi\|126653077\|ref\|ZP_01725212.1\| | Bacillus sp. | 37.2 | | 65.9 | 29.9 | 36.0 | 35.6 | 29.9 |
| gi\|16800476\|ref\|NP_470744.1\| | Listeria innocua | 39.4 | | 65.8 | | 36.3 | 38.5 | 28.9 |
| gi\|47095954\|ref\|ZP_00233557.1\| | L. monocytogenes | 39.0 | | 65.8 | | 36.0 | 38.1 | 28.9 |
| gi\|254932314\|ref\|ZP_05265673.1\| | L. monocytogenes | 38.9 | | 65.8 | | 36.1 | 38.1 | |
| gi\|46907597\|ref\|YP_013986.1\| | Listeria monocytogenes | 38.9 | | 65.8 | | 36.1 | 38.1 | |
| gi\|16803411\|ref\|NP_464896.1\| | Listeria monocytogenes | 38.8 | | 65.8 | | 36.2 | 37.9 | 28.5 |
| gi\|255026809\|ref\|ZP_05298795.1\| | Listeria monocytogenes | 38.8 | | 65.8 | | 36.0 | 37.9 | 28.5 |
| gi\|116872802\|ref\|YP_849583.1\| | L. welshimeri | 38.6 | | 65.8 | 27.5 | 35.3 | 38.0 | 27.7 |
| gi\|254873037\|ref\|ZP_05245747.1\| | Listeria monocytogenes | 38.9 | | 65.6 | | 36.1 | 38.1 | 28.7 |
| gi\|169828955\|ref\|YP_001699113.1\| | L. sphaericus | 37.9 | 33.3 | 65.5 | 29.0 | 36.3 | 36.5 | 29.2 |
| gi\|217964483\|ref\|YP_002350161.1\| | Listeria monocytogenes | 39.2 | | 65.4 | | 36.1 | 38.3 | 28.5 |
| gi\|22773770\|gb\|AAN05019.1\| | Listeria monocytogenes | 38.2 | | 65.1 | | 35.6 | 37.3 | |
| gi\|255522570\|ref\|ZP_05389807.1\| | Listeria monocytogenes | 38.4 | | 64.5 | | 35.8 | 37.5 | |
| gi\|258611750\|ref\|ZP_05711625.1\| | Listeria monocytogenes | 39.3 | | 63.3 | | 35.6 | 39.5 | |
| gi\|56964217\|ref\|YP_175948.1\| | Bacillus clausii | 41.1 | | 63.0 | | 36.3 | 38.5 | |

FIG. 3D-BKD cont'd

FIG. 3D- BKD E3 Subunit Homologs

| | | | | | | | | |
|---|---|---|---|---|---|---|---|---|
| gi\|253576334\|ref\|ZP_04853664.1\| | Paenibacillus sp. | 39.8 | 35.1 | 60.9 | 31.6 | 41.4 | 39.4 | 30.9 |
| gi\|251796331\|ref\|YP_003011062.1\| | P. sp. JDR-2 | 40.2 | 34.6 | 60.5 | 32.0 | 40.0 | 39.9 | 31.6 |
| gi\|261405971\|ref\|YP_003242212.1\| | Geobacillus sp. | 40.6 | | 60.2 | 30.6 | 39.8 | 39.7 | 29.5 |
| gi\|172056955\|ref\|YP_001813415.1\| | E.sibiricum | 39.7 | | 60.0 | | 37.8 | 37.8 | |
| gi\|229916239\|ref\|YP_002884885.1\| | Exiguobacterium sp. | 39.3 | | 56.0 | 28.5 | 37.0 | 38.3 | 30.6 |
| gi\|51893301\|ref\|YP_075992.1\| | S. thermophilum | 41.1 | | 53.3 | 31.5 | 40.5 | 40.8 | 31.3 |
| gi\|257422518\|ref\|ZP_05599508.1\| | E.faecalis | 40.5 | | 53.0 | 29.7 | 33.0 | 38.6 | 29.3 |
| gi\|257085090\|ref\|ZP_05579451.1\| | E.faecalis | 40.5 | | 53.0 | 29.7 | 33.0 | 38.6 | 29.3 |
| gi\|229549918\|ref\|ZP_04438643.1\| | E.faecalis | 40.3 | | 52.7 | 29.7 | 32.8 | 38.4 | 29.3 |
| gi\|257416186\|ref\|ZP_05593180.1\| | E.faecalis | 40.3 | | 52.7 | 29.7 | 33.0 | 38.4 | 29.3 |
| gi\|257082458\|ref\|ZP_05576819.1\| | E.faecalis | 40.0 | | 52.7 | 29.5 | 33.0 | 38.2 | 29.0 |
| gi\|29376215\|ref\|NP_815369.1\| | E.faecalis | 40.0 | | 52.7 | 29.5 | 32.8 | 38.2 | 29.0 |
| gi\|227518847\|ref\|ZP_03948896.1\| | E. faecalis | 40.0 | | 52.7 | 29.5 | 32.8 | 38.2 | 29.0 |
| gi\|229545728\|ref\|ZP_04434453.1\| | E.faecalis | 40.3 | | 52.5 | 29.5 | 32.5 | 38.4 | 29.0 |
| gi\|238856492\|ref\|ZP_04646758.1\| | E.faecalis | 40.3 | | 52.5 | 29.5 | 32.5 | 38.4 | 29.0 |
| gi\|256965032\|ref\|ZP_05569203.1\| | E.faecalis | 40.3 | | 52.5 | 29.5 | 32.5 | 38.4 | 29.0 |
| gi\|256959072\|ref\|ZP_05563243.1\| | E.faecalis | 40.3 | | 52.3 | 29.5 | 32.5 | 38.4 | 29.0 |
| gi\|257086949\|ref\|ZP_05581310.1\| | E.faecalis | 40.3 | | 52.3 | 29.3 | 32.5 | 38.4 | 28.8 |
| gi\|257419388\|ref\|ZP_05596382.1\| | E.faecalis | 40.3 | | 52.3 | 29.5 | 32.5 | 38.4 | 29.0 |
| gi\|255975753\|ref\|ZP_05426339.1\| | E.faecalis | 40.3 | | 52.3 | 29.5 | 32.5 | 38.4 | 29.0 |
| gi\|239631468\|ref\|ZP_04674499.1\| | L.paracasei | 38.4 | | 50.9 | 28.7 | 33.8 | 37.3 | 27.4 |
| gi\|116494932\|ref\|YP_806666.1\| | L.casei | 38.2 | | 50.9 | 28.4 | 34.0 | 37.5 | 27.2 |
| gi\|73662546\|ref\|YP_301327.1\| | S. saprophyticus | 33.5 | 32.1 | 50.8 | 28.3 | 30.5 | 32.5 | 27.8 |
| gi\|191638442\|ref\|YP_001987608.1\| | L.casei | 38.2 | | 50.7 | 28.4 | 33.5 | 37.1 | 27.2 |
| gi\|221635892\|ref\|YP_002523768.1\| | T. roseum | 42.9 | | 49.6 | 32.6 | 39.8 | 42.1 | 32.3 |
| gi\|242373818\|ref\|ZP_04819392.1\| | S.pidermidis | 34.7 | 32.5 | 49.5 | 30.2 | 31.3 | 33.9 | 30.0 |
| gi\|283470797\|emb\|CAQ50008.1\| | S.aureus | 35.2 | | 49.2 | 28.8 | 31.5 | 33.3 | 28.4 |
| gi\|27468117\|ref\|NP_764754.1\| | S.pidermidis | 34.5 | | 49.0 | 28.8 | 30.7 | 34.0 | 28.6 |
| gi\|57866999\|ref\|YP_188656.1\| | S.pidermidis | 34.5 | | 49.0 | 28.6 | 30.7 | 34.0 | 28.4 |
| gi\|228476011\|ref\|ZP_04060719.1\| | S.hominis | 34.9 | | 48.9 | 28.1 | 30.2 | 33.3 | 27.6 |
| gi\|82751123\|ref\|YP_416864.1\| | S. aureus | 35.2 | | 48.9 | 28.6 | 31.5 | 33.3 | 28.2 |

FIG. 3D-BKD cont'd

FIG. 3D- BKD E3 Subunit Homologs

| | | | | | | | | |
|---|---|---|---|---|---|---|---|---|
| gi\|21283200\|ref\|NP_646288.1\| | S. aureus | 34.7 | | 48.9 | 28.6 | 31.5 | 33.3 | 28.2 |
| gi\|15924508\|ref\|NP_372042.1\| | S.aureus | 35.2 | | 48.9 | 28.6 | 31.5 | 33.3 | 28.2 |
| gi\|262051185\|ref\|ZP_06023409.1\| | S. aureus | 34.7 | | 48.9 | 28.6 | 31.5 | 33.3 | 28.2 |
| gi\|227557717\|ref\|ZP_03987764.1\| | S.aureus | 35.2 | | 48.7 | 28.6 | 31.7 | 33.3 | 28.2 |
| gi\|269203148\|ref\|YP_003282417.1\| | S. aureus | 35.2 | | 48.7 | 28.4 | 31.3 | 33.3 | 28.0 |
| gi\|258423172\|ref\|ZP_05686065.1\| | S. aureus | 35.3 | | 48.7 | 29.1 | 31.0 | 33.5 | 28.5 |
| gi\|154253578\|ref\|YP_001414402.1\| | P. lavamentivorans | 40.3 | 35.3 | 48.5 | 30.6 | 40.8 | 40.4 | 30.0 |
| gi\|282919295\|ref\|ZP_06327030.1\| | S. aureus | 35.2 | | 48.5 | 28.4 | 31.7 | 33.3 | 28.0 |
| gi\|49483768\|ref\|YP_040992.1\| | S.aureus | 35.0 | | 48.5 | 28.4 | 31.5 | 33.1 | 28.0 |
| gi\|242242787\|ref\|ZP_04797232.1\| | S.pidermidis | 34.8 | | 48.4 | 28.8 | 30.7 | 33.3 | 28.4 |
| gi\|223043150\|ref\|ZP_03613197.1\| | S. capitis | 33.5 | 31.9 | 48.3 | 29.1 | 31.0 | 33.6 | 29.3 |
| gi\|157273471\|gb\|ABV27370.1\| | C.thermophilum | 44.6 | 33.5 | 48.3 | 32.6 | 38.6 | 43.6 | 31.9 |
| gi\|239946823\|ref\|ZP_04698576.1\| | R. endosymbiont | 34.0 | | 48.2 | 26.8 | 33.7 | 33.9 | 26.5 |
| gi\|239637672\|ref\|ZP_04678644.1\| | S. warneri | 34.2 | | 48.1 | 27.8 | 30.0 | 33.3 | 26.9 |
| gi\|67459662\|ref\|YP_247286.1\| | Rickettsia felis | 34.1 | 32.8 | 48.1 | 28.1 | 34.6 | 33.7 | 27.9 |
| gi\|70726398\|ref\|YP_253312.1\| | S. haemolyticus | 34.9 | | 48.0 | 26.4 | 29.6 | 34.1 | 26.2 |
| gi\|157804177\|ref\|YP_001492726.1\| | R.canadensis | 34.5 | 32.7 | 47.8 | 28.8 | 35.7 | 34.1 | 28.1 |
| gi\|34581168\|ref\|ZP_00142648.1\| | R.sibirica | 33.6 | 33.6 | 47.8 | 28.1 | 35.4 | 33.7 | 27.7 |
| gi\|269929378\|ref\|YP_003321699.1\| | S. thermophilus | 43.4 | | 47.7 | 31.6 | 39.2 | 42.7 | 31.2 |
| gi\|15893162\|ref\|NP_360876.1\| | R.conorii | 33.8 | 33.4 | 47.6 | 27.6 | 35.0 | 33.9 | 27.2 |
| gi\|157826261\|ref\|YP_001493981.1\| | Rickettsia akari | 34.7 | 33.2 | 47.4 | 28.1 | 34.4 | 34.4 | 27.7 |
| gi\|283560797\|gb\|EFC11449.1\| | R. vannielii | 37.5 | 37.4 | 47.4 | 33.1 | 37.2 | 38.0 | 32.5 |
| gi\|86131897\|ref\|ZP_01050494.1\| | D.donghaensis | 40.6 | 35.1 | 47.4 | 28.7 | 38.2 | 39.6 | 28.0 |
| gi\|157827767\|ref\|YP_001496831.1\| | Rickettsia bellii | 35.2 | 34.1 | 47.3 | 27.7 | 35.7 | 34.6 | 27.5 |
| gi\|238650825\|ref\|YP_002916680.1\| | R.peacockii | 33.8 | 33.4 | 47.3 | 27.9 | 35.2 | 33.9 | 27.5 |
| gi\|165933797\|ref\|YP_001650586.1\| | R.rickettsii | 34.1 | 33.4 | 47.3 | 27.7 | 35.2 | 34.1 | 27.3 |
| gi\|157829071\|ref\|YP_001495313.1\| | R.rickettsii | 34.1 | 33.4 | 47.3 | 27.7 | 35.4 | 34.1 | 27.3 |
| gi\|94971330\|ref\|YP_593378.1\| | C. Koribacter | 46.1 | 33.9 | 47.3 | 30.4 | 39.2 | 45.5 | 29.9 |
| gi\|108805341\|ref\|YP_645278.1\| | R.xylanophilus | 41.4 | 37.0 | 47.2 | 32.4 | 39.2 | 40.0 | 32.4 |
| gi\|224476627\|ref\|YP_002634233.1\| | S.carnosus | 36.5 | | 47.2 | 28.6 | 31.4 | 34.9 | 28.0 |
| gi\|91204906\|ref\|YP_537261.1\| | Rickettsia bellii | 34.9 | 34.1 | 47.1 | 27.5 | 35.7 | 34.6 | 27.3 |

FIG. 3D-BKD cont'd

FIG. 3D- BKD E3 Subunit Homologs

| | | | | | | | | |
|---|---|---|---|---|---|---|---|---|
| gi\|157964953\|ref\|YP_001499777.1\| | R.massiliae | 34.1 | 34.1 | 47.1 | 28.3 | 34.7 | 33.9 | 27.7 |
| gi\|229587167\|ref\|YP_002845668.1\| | R.africae | 33.6 | 33.2 | 46.9 | 27.7 | 34.7 | 33.7 | 27.2 |
| gi\|225011931\|ref\|ZP_03702369.1\| | F.bacterium | 38.9 | 33.9 | 46.5 | 29.7 | 35.0 | 37.6 | 29.7 |
| gi\|134298477\|ref\|YP_001111973.1\| | D.reducens | 35.8 | 33.8 | 46.4 | 29.1 | 34.7 | 36.0 | 29.6 |
| gi\|58698764\|ref\|ZP_00373647.1\| | W.endosymbiont | 34.5 | 34.2 | 46.4 | 28.4 | 31.9 | 33.0 | 28.2 |
| gi\|78044229\|ref\|YP_359567.1\| | C.hydrogenoormans | 39.2 | 37.1 | 46.3 | 32.8 | 35.5 | 38.5 | 33.5 |
| gi\|42520210\|ref\|NP_966125.1\| | W.endosymbiont | 34.5 | 34.0 | 46.2 | 28.6 | 31.7 | 33.0 | 28.4 |
| gi\|134298242\|ref\|YP_001111738.1\| | D. reducens | 37.1 | 33.6 | 46.2 | 29.1 | 34.9 | 36.9 | 28.9 |
| gi\|115374465\|ref\|ZP_01461747.1\| | S.aurantiaca | 43.0 | 34.7 | 46.1 | 31.0 | 39.3 | 43.3 | 31.0 |
| gi\|162147726\|ref\|YP_001602187.1\| | G.diazotrophicus | 37.2 | 35.3 | 46.1 | 30.5 | 34.2 | 38.0 | 30.8 |
| gi\|255532889\|ref\|YP_003093261.1\| | P.heparinus | 38.1 | 35.1 | 46.1 | 32.2 | 36.1 | 36.5 | 32.4 |
| gi\|148550590\|ref\|YP_001260029.1\| | S. wittichii | 37.9 | 33.3 | 46.0 | 30.3 | 38.9 | 36.6 | 30.3 |
| gi\|83593213\|ref\|YP_426965.1\| | R.rubrum | 39.1 | 35.3 | 46.0 | 30.8 | 36.7 | 38.1 | 31.0 |
| gi\|163848386\|ref\|YP_001636430.1\| | Chloroflexus sp. | 43.4 | 38.9 | 46.0 | 32.8 | 40.0 | 41.1 | 33.4 |
| gi\|88712280\|ref\|ZP_01106367.1\| | F. bacterium | 41.9 | 32.5 | 45.9 | 29.5 | 36.6 | 40.4 | 29.1 |
| gi\|219848041\|ref\|YP_002462474.1\| | C. aggregans | 42.7 | 38.0 | 45.9 | 33.2 | 40.2 | 40.3 | 33.4 |
| gi\|268317524\|ref\|YP_003291243.1\| | R.marinus | 39.1 | 34.0 | 45.9 | 31.6 | 36.9 | 38.4 | 31.6 |
| gi\|149372793\|ref\|ZP_01891814.1\| | Unid. eubacterium | 42.4 | 34.6 | 45.9 | 29.6 | 38.0 | 40.8 | 29.4 |
| gi\|159901026\|ref\|YP_001547273.1\| | H.aurantiacus | 43.5 | 36.9 | 45.9 | 30.6 | 37.6 | 43.2 | 30.4 |
| gi\|15604637\|ref\|NP_221155.1\| | R.prowazekii | 34.7 | | 45.9 | 27.9 | 33.1 | 35.2 | 27.5 |
| gi\|91218035\|ref\|ZP_01254986.1\| | P. torquis | 38.5 | 33.8 | 45.8 | 29.5 | 36.7 | 36.9 | 31.5 |
| gi\|225677359\|ref\|ZP_03788331.1\| | W. endosymbiont | 34.1 | 34.6 | 45.7 | 28.2 | 31.7 | 32.7 | 28.2 |
| gi\|120436216\|ref\|YP_861902.1\| | G.forsetii | 39.3 | 34.1 | 45.7 | 28.8 | 36.0 | 37.4 | 28.1 |
| gi\|108758911\|ref\|YP_632394.1\| | M.xanthus | 43.4 | 35.1 | 45.7 | 30.3 | 40.5 | 44.1 | 30.1 |
| gi\|209963469\|ref\|YP_002296384.1\| | R. centenum | 38.1 | 36.4 | 45.7 | 31.1 | 38.0 | 37.0 | 30.7 |
| gi\|163754945\|ref\|ZP_02162066.1\| | Kordia algicida | 40.8 | 34.3 | 45.6 | 29.5 | 37.8 | 39.5 | 29.7 |
| gi\|227368731\|ref\|ZP_03852249.1\| | C. gleum | 40.5 | 33.2 | 45.5 | 28.1 | 37.8 | 39.7 | 28.1 |
| gi\|85374056\|ref\|YP_458118.1\| | E.litoralis | 38.6 | 33.2 | 45.5 | 29.4 | 37.5 | 37.8 | 29.5 |
| gi\|86142680\|ref\|ZP_01061119.1\| | L. blandensis | 39.3 | 34.3 | 45.5 | 29.6 | 35.8 | 37.8 | 29.2 |
| gi\|150025783\|ref\|YP_001296609.1\| | F.psychrophilum | 37.1 | 39.4 | 45.4 | 29.5 | 34.1 | 36.1 | 30.1 |
| gi\|86133817\|ref\|ZP_01052399.1\| | Polaribacter sp. | 41.0 | | 45.3 | 28.6 | 36.8 | 40.5 | 27.9 |

FIG. 3D-BKD cont'd

FIG. 3D- BKD E3 Subunit Homologs

| | | | | | | | | |
|---|---|---|---|---|---|---|---|---|
| gi\|149278386\|ref\|ZP_01884523.1\| | Pedobacter sp. | 37.8 | 33.6 | 45.3 | 31.5 | 35.9 | 36.1 | 32.1 |
| gi\|117956078\|gb\|ABK58623.1\| | A. anaerobius | 37.2 | 36.7 | 45.3 | 30.6 | 35.7 | 35.9 | 31.2 |
| gi\|163756970\|ref\|ZP_02164077.1\| | Kordia algicida | 38.7 | 37.7 | 45.3 | 29.6 | 34.0 | 37.2 | 29.9 |
| gi\|228472849\|ref\|ZP_04057606.1\| | C. gingivalis | 39.9 | 33.6 | 45.2 | 29.7 | 36.3 | 38.3 | 28.7 |
| gi\|213963724\|ref\|ZP_03391974.1\| | C.sputigena | 39.8 | 32.7 | 45.2 | 29.9 | 36.6 | 37.8 | 29.5 |
| gi\|163793252\|ref\|ZP_02187228.1\| | alpha proteo-bacterium | 36.1 | | 45.2 | 29.7 | 35.0 | 35.3 | 29.7 |
| gi\|90423993\|ref\|YP_532363.1\| | R. palustris | 38.1 | 33.8 | 45.2 | 30.3 | 35.5 | 38.1 | 29.2 |
| gi\|149372517\|ref\|ZP_01891629.1\| | unidentified eubacterium | 38.9 | 39.3 | 45.2 | 27.5 | 34.4 | 37.4 | 27.9 |
| gi\|148554286\|ref\|YP_001261868.1\| | S. wittichii | 39.7 | 35.3 | 45.2 | 31.8 | 36.0 | 39.5 | 31.5 |
| gi\|260062443\|ref\|YP_003195523.1\| | R.biformata | 40.6 | 34.1 | 45.2 | 30.8 | 36.3 | 39.2 | 30.8 |
| gi\|126663885\|ref\|ZP_01734880.1\| | F.bacterium | 37.5 | 39.5 | 45.2 | 30.2 | 34.5 | 36.1 | 31.1 |
| gi\|89890500\|ref\|ZP_01202010.1\| | F.bacterium | 39.2 | 33.9 | 45.1 | 29.4 | 37.7 | 38.5 | 29.2 |
| gi\|116620040\|ref\|YP_822196.1\| | S.usitatus | 42.3 | 37.2 | 45.1 | 33.0 | 39.6 | 42.0 | 32.1 |
| gi\|134300665\|ref\|YP_001114161.1\| | D.reducens | 39.9 | 33.6 | 45.1 | 29.3 | 36.6 | 39.2 | 28.7 |
| gi\|163788782\|ref\|ZP_02183227.1\| | F. bacterium | 40.5 | 34.2 | 45.1 | 29.8 | 35.6 | 39.3 | 29.2 |
| gi\|504482\|gb\|AAA19188.1\| | K. pneumoniae | 39.3 | 38.6 | 45.0 | 33.4 | 39.9 | 38.2 | 33.2 |
| gi\|1747421\|emb\|CAA57734.1\| | Z.mobilis | 36.9 | 35.8 | 45.0 | 30.8 | 36.3 | 35.2 | 30.5 |
| gi\|56551408\|ref\|YP_162247.1\| | Z.mobilis | 36.6 | 35.8 | 45.0 | 30.6 | 36.5 | 35.2 | 30.3 |
| gi\|206580221\|ref\|YP_002240262.1\| | K.pneumoniae | 38.7 | 37.5 | 44.9 | 32.5 | 40.2 | 37.7 | 32.5 |
| gi\|269916765\|ref\|ZP_06165758.1\| | K.variicola | 38.9 | 37.7 | 44.9 | 32.3 | 40.4 | 37.9 | 32.3 |
| gi\|182678484\|ref\|YP_001832630.1\| | B. indica | 38.5 | 33.3 | 44.9 | 28.1 | 35.4 | 38.6 | 27.3 |
| gi\|83857615\|ref\|ZP_00951143.1\| | C.atlanticus | 40.1 | 32.4 | 44.9 | 29.5 | 37.4 | 38.5 | 29.1 |
| gi\|103486724\|ref\|YP_616285.1\| | S.alaskensis | 39.1 | 35.6 | 44.9 | 31.1 | 37.2 | 39.4 | 30.5 |
| gi\|55980256\|ref\|YP_143553.1\| | T.thermophilus | 38.7 | 39.1 | 44.9 | 31.9 | 40.6 | 38.0 | 31.7 |
| gi\|46200002\|ref\|YP_005669.1\| | T.thermophilus | 39.0 | 39.3 | 44.9 | 31.9 | 40.8 | 38.3 | 31.7 |
| gi\|85708660\|ref\|ZP_01039726.1\| | Erythrobacter sp. | 39.0 | 33.8 | 44.9 | 30.1 | 37.3 | 38.3 | 30.1 |
| gi\|83590598\|ref\|YP_430607.1\| | M. thermoacetica | 37.6 | 37.1 | 44.9 | 32.5 | 37.7 | 35.7 | 32.8 |
| gi\|225181899\|ref\|ZP_03735334.1\| | D.alkaliphilus | 36.9 | 36.0 | 44.8 | 30.1 | 36.6 | 36.1 | 29.5 |
| gi\|51473973\|ref\|YP_067730.1\| | Rickettsia typhi | 34.5 | | 44.8 | 27.3 | 32.9 | 35.0 | 27.1 |
| gi\|227988401\|ref\|ZP_04035495.1\| | M.silvanus | 40.0 | 37.9 | 44.8 | 28.9 | 37.9 | 39.2 | 28.6 |
| gi\|226948961\|ref\|YP_002804052.1\| | C.botulinum | 39.1 | 36.5 | 44.8 | 28.5 | 32.6 | 38.8 | 28.1 |

FIG. 3D- BKD E3 Subunit Homologs

| | | | | | | | | |
|---|---|---|---|---|---|---|---|---|
| gi\|209549207\|ref\|YP_002281124.1\| | R. leguminosarum | 37.9 | 34.4 | 44.8 | 29.8 | 37.1 | 37.6 | 29.5 |
| gi\|190891632\|ref\|YP_001978174.1\| | Rhizobium etli | 37.4 | 34.4 | 44.8 | 29.8 | 37.2 | 37.2 | 29.4 |
| gi\|255037743\|ref\|YP_003088364.1\| | D.fermentans | 38.9 | 33.3 | 44.7 | 29.6 | 35.7 | 38.2 | 29.3 |
| gi\|945058\|gb\|AAB40885.1\| | K.pneumoniae | 38.9 | 38.4 | 44.7 | 32.9 | 40.0 | 38.1 | 32.7 |
| gi\|238893246\|ref\|YP_002917980.1\| | K.pneumoniae | 38.7 | 38.2 | 44.7 | 32.7 | 39.8 | 37.9 | 32.5 |
| gi\|256820981\|ref\|YP_003142260.1\| | C. ochracea | 40.4 | 32.3 | 44.7 | 30.1 | 36.1 | 37.7 | 29.5 |
| gi\|149197721\|ref\|ZP_01874771.1\| | L.araneosa | 39.4 | 40.6 | 44.7 | 29.3 | 34.0 | 37.9 | 30.1 |
| gi\|148657112\|ref\|YP_001277317.1\| | Roseiflexus sp. | 43.6 | 37.0 | 44.7 | 31.1 | 44.6 | 43.1 | 32.1 |
| gi\|156742078\|ref\|YP_001432207.1\| | R. castenholzii | 43.8 | 35.3 | 44.7 | 30.8 | 43.1 | 43.8 | 31.3 |
| gi\|190571293\|ref\|YP_001975651.1\| | W. endosymbiont | 34.6 | 33.5 | 44.6 | 29.1 | 32.2 | 32.6 | 28.6 |
| gi\|218296110\|ref\|ZP_03496879.1\| | T. aquaticus | 38.9 | 39.7 | 44.6 | 32.1 | 38.4 | 38.5 | 32.1 |
| gi\|150024799\|ref\|YP_001295625.1\| | F. psychrophilum | 39.2 | 31.2 | 44.6 | 29.5 | 35.3 | 38.0 | 28.7 |
| gi\|148379595\|ref\|YP_001254136.1\| | C.botulinum A | 39.8 | 36.7 | 44.6 | 28.1 | 33.4 | 39.2 | 28.1 |
| gi\|114704549\|ref\|ZP_01437457.1\| | F.pelagi | 36.6 | 34.2 | 44.6 | 31.4 | 37.4 | 36.6 | 31.2 |
| gi\|86357559\|ref\|YP_469451.1\| | Rhizobium etli | 38.3 | 34.7 | 44.6 | 29.8 | 37.1 | 37.8 | 29.5 |
| gi\|283576749\|gb\|EFC24182.1\| | R.palustris | 35.7 | 34.2 | 44.6 | 28.8 | 36.3 | 35.7 | 28.5 |
| gi\|163789081\|ref\|ZP_02183525.1\| | F. bacterium | 38.1 | 38.9 | 44.5 | 28.5 | 34.1 | 36.7 | 29.2 |
| gi\|197105202\|ref\|YP_002130579.1\| | P. zucineum | 40.8 | 36.7 | 44.5 | 30.5 | 36.1 | 38.6 | 29.9 |
| gi\|196017865\|ref\|XP_002118664.1\| | T.adhaerens | 36.1 | 31.3 | 44.5 | 29.6 | 30.0 | 35.3 | 28.7 |
| gi\|258542309\|ref\|YP_003187742.1\| | A.pasteurianus | 36.6 | | 44.5 | 31.6 | 36.7 | 36.6 | 31.1 |
| gi\|89891405\|ref\|ZP_01202911.1\| | F.bacterium | 37.9 | 39.3 | 44.5 | 27.8 | 36.1 | 37.1 | 27.1 |
| gi\|86749883\|ref\|YP_486379.1\| | R.palustris | 36.3 | 34.4 | 44.5 | 30.1 | 37.1 | 35.9 | 29.9 |
| gi\|88802724\|ref\|ZP_01118251.1\| | P.irgensii | 38.0 | 32.2 | 44.5 | 28.6 | 36.6 | 37.9 | 27.9 |
| gi\|16124597\|ref\|NP_419161.1\| | C. crescentus | 37.6 | 40.9 | 44.5 | 29.7 | 38.5 | 36.2 | 30.2 |
| gi\|150396301\|ref\|YP_001326768.1\| | S.medicae | 37.5 | 31.9 | 44.4 | 28.1 | 37.3 | 37.8 | 28.1 |
| gi\|256821005\|ref\|YP_003142284.1\| | C. ochracea | 38.2 | 39.2 | 44.4 | 29.5 | 34.8 | 38.6 | 29.7 |
| gi\|144898630\|emb\|CAM75494.1\| | M. gryphiswaldense | 36.0 | 33.0 | 44.4 | 28.9 | 35.7 | 36.3 | 28.1 |
| gi\|255535189\|ref\|YP_003095560.1\| | F. bacterium | 39.3 | 34.5 | 44.4 | 29.1 | 36.9 | 38.5 | 28.7 |
| gi\|188580836\|ref\|YP_001924281.1\| | M. populi | 40.0 | 42.7 | 44.4 | 31.4 | 39.1 | 39.4 | 31.4 |
| gi\|225627596\|ref\|ZP_03785633.1\| | Brucella ceti | 35.5 | 33.3 | 44.4 | 29.1 | 36.9 | 36.3 | 28.8 |
| gi\|23502004\|ref\|NP_698131.1\| | B. suis,B. pin-nipedialis, B. neotomae, B. ceti | 35.5 | 33.3 | 44.4 | 29.1 | 36.9 | 36.3 | 28.8 |

FIG. 3D-BKD cont'd

FIG. 3D-BKD cont'd

FIG. 3D- BKD E3 Subunit Homologs

| | | | | | | | | |
|---|---|---|---|---|---|---|---|---|
| gi\|254701869\|ref\|ZP_05163697.1\| | Brucella suis | 35.5 | 33.3 | 44.4 | 29.1 | 36.9 | 36.3 | 28.8 |
| gi\|148559162\|ref\|YP_001259047.1\| | Brucella ovis | 35.5 | 33.3 | 44.4 | 29.1 | 36.7 | 36.3 | 28.8 |
| gi\|116252002\|ref\|YP_767840.1\| | R. leguminosarum | 38.3 | 34.0 | 44.4 | 29.6 | 36.9 | 38.8 | 29.7 |
| gi\|241204529\|ref\|YP_002975625.1\| | R. leguminosarum | 38.0 | 34.0 | 44.4 | 29.6 | 36.7 | 38.6 | 29.5 |
| gi\|227820166\|ref\|YP_002824137.1\| | Rhizobium sp. | 37.7 | 32.2 | 44.4 | 29.5 | 37.6 | 37.8 | 30.2 |
| gi\|168180290\|ref\|ZP_02614954.1\| | C.botulinum | 39.4 | 36.5 | 44.4 | 28.8 | 32.8 | 39.0 | 28.3 |
| gi\|170755477\|ref\|YP_001781267.1\| | C.botulinum | 39.6 | 36.5 | 44.4 | 28.8 | 32.8 | 39.2 | 28.3 |
| gi\|153938916\|ref\|YP_001390971.1\| | C.botulinum F | 39.6 | 36.5 | 44.4 | 28.5 | 32.8 | 39.2 | 28.3 |
| gi\|91977277\|ref\|YP_569936.1\| | R. palustris | 35.4 | 34.8 | 44.4 | 29.9 | 36.6 | 35.3 | 29.3 |
| gi\|269128014\|ref\|YP_003301384.1\| | T. curvata | 40.6 | 35.8 | 44.4 | 31.0 | 40.1 | 40.4 | 31.8 |
| gi\|158317228\|ref\|YP_001509736.1\| | Frankia sp. | 40.0 | 34.2 | 44.3 | 29.6 | 36.2 | 39.7 | 29.4 |
| gi\|126646833\|ref\|ZP_01719343.1\| | Algoriphagus sp. | 38.4 | 34.3 | 44.3 | 30.4 | 34.6 | 37.1 | 30.4 |
| gi\|149184550\|ref\|ZP_01862868.1\| | Erythrobacter sp. | 38.3 | 32.5 | 44.3 | 29.9 | 37.2 | 38.4 | 29.9 |
| gi\|126663835\|ref\|ZP_01734830.1\| | F.bacterium | 39.8 | 32.5 | 44.3 | 30.0 | 36.4 | 38.6 | 29.1 |
| gi\|217966916\|ref\|YP_002352422.1\| | D.turgidum | 39.1 | 37.1 | 44.3 | 29.5 | 36.4 | 38.0 | 29.5 |
| gi\|266629591\|ref\|ZP_06122497.1\| | C. segnis | 36.3 | 40.9 | 44.3 | 30.7 | 37.4 | 35.5 | 30.5 |
| gi\|223934396\|ref\|ZP_03626317.1\| | bacterium | 38.3 | 33.2 | 44.3 | 28.1 | 35.0 | 37.1 | 27.8 |
| gi\|225874414\|ref\|YP_002755873.1\| | A.capsulatum | 42.6 | 36.7 | 44.2 | 29.1 | 37.3 | 41.8 | 29.8 |
| gi\|218529905\|ref\|YP_002420721.1\| | M. chloro-methanicum | 39.7 | 42.3 | 44.2 | 30.9 | 39.2 | 39.0 | 31.0 |
| gi\|254560769\|ref\|YP_003067864.1\| | M.extorquens | 40.0 | 42.5 | 44.2 | 30.8 | 38.9 | 39.2 | 31.4 |
| gi\|17987140\|ref\|NP_539774.1\| | B.melitensis | 35.5 | 33.3 | 44.2 | 29.1 | 36.9 | 36.3 | 28.8 |
| gi\|161619078\|ref\|YP_001592965.1\| | B.suis, B.canis | 35.5 | 33.3 | 44.2 | 29.1 | 36.9 | 36.3 | 28.8 |
| gi\|237815549\|ref\|ZP_04594546.1\| | B.abortus | 35.5 | 33.3 | 44.2 | 29.1 | 36.9 | 36.3 | 28.8 |
| gi\|62290039\|ref\|YP_221832.1\| | B. abortus, B. melitensis | 35.5 | 33.3 | 44.2 | 29.1 | 36.9 | 36.3 | 28.8 |
| gi\|254697485\|ref\|ZP_05159313.1\| | B.abortus | 35.3 | 33.3 | 44.2 | 29.1 | 36.9 | 36.1 | 28.8 |
| gi\|225852626\|ref\|YP_002732859.1\| | B. melitensis | 35.7 | 33.1 | 44.2 | 29.1 | 36.7 | 36.5 | 28.8 |
| gi\|146302403\|ref\|YP_001196994.1\| | F. johnsoniae | 39.8 | 31.8 | 44.2 | 28.4 | 36.2 | 38.8 | 28.0 |
| gi\|187779705\|ref\|ZP_02996178.1\| | C.sporogenes | 40.0 | 35.8 | 44.2 | 29.0 | 32.8 | 39.7 | 27.8 |
| gi\|170761339\|ref\|YP_001787038.1\| | C.botulinum | 39.8 | 36.8 | 44.2 | 28.9 | 32.4 | 38.6 | 29.4 |
| gi\|192291578\|ref\|YP_001992183.1\| | R. palustris | 36.2 | 34.2 | 44.1 | 29.1 | 36.2 | 35.9 | 28.5 |
| gi\|86132778\|ref\|ZP_01051370.1\| | D.donghaensis | 39.3 | 39.1 | 44.1 | | 35.0 | 37.6 | 28.2 |

FIG. 3D-BKD cont'd

FIG. 3D- BKD E3 Subunit Homologs

| | | | | | | | | |
|---|---|---|---|---|---|---|---|---|
| gi\|120401809\|ref\|YP_951638.1\| | M. vanbaalenii | 39.0 | 35.5 | 44.1 | 29.1 | 35.6 | 39.0 | 28.9 |
| gi\|75676005\|ref\|YP_318426.1\| | N.winogradskyi | 38.9 | 35.2 | 44.1 | 29.6 | 36.9 | 38.8 | 29.0 |
| gi\|254449717\|ref\|ZP_05063154.1\| | O. antarcticus | 36.3 | 33.1 | 44.1 | 29.7 | 34.8 | 33.6 | 29.9 |
| gi\|225011764\|ref\|ZP_03702202.1\| | F.bacterium | 38.5 | 39.2 | 44.1 | 28.4 | 33.8 | 38.2 | 28.9 |
| gi\|120436511\|ref\|YP_862197.1\| | G.forsetii | 38.6 | 39.7 | 44.1 | 29.0 | 34.6 | 38.1 | 29.0 |
| gi\|254719190\|ref\|ZP_05181001.1\| | Brucella sp. | 35.7 | 33.4 | 44.1 | 28.8 | 36.9 | 36.5 | 28.6 |
| gi\|213961869\|ref\|ZP_03390135.1\| | C. sputigena Capno | 37.7 | 39.0 | 44.1 | 29.5 | 34.2 | 36.8 | 28.9 |
| gi\|90419627\|ref\|ZP_01227537.1\| | A. mangan-oxydans | 37.4 | 33.8 | 44.0 | 30.4 | 36.1 | 37.5 | 30.6 |
| gi\|110637496\|ref\|YP_677703.1\| | C.hutchinsonii | 40.9 | 32.1 | 44.0 | 30.8 | 35.9 | 39.7 | 31.0 |
| gi\|163851075\|ref\|YP_001639118.1\| | M. extorquens | 39.7 | 42.3 | 44.0 | 30.7 | 39.2 | 39.0 | 30.8 |
| gi\|227821852\|ref\|YP_002825822.1\| | Rhizobium sp. | 37.5 | 32.9 | 44.0 | 29.3 | 36.8 | 37.8 | 29.8 |
| gi\|241890792\|ref\|ZP_04778088.1\| | S. spiritivorum | 38.8 | 37.5 | 44.0 | 29.8 | 35.3 | 37.9 | 28.5 |
| gi\|227538425\|ref\|ZP_03968474.1\| | S.spiritivorum | 38.8 | 37.7 | 44.0 | 30.0 | 35.3 | 37.9 | 28.5 |
| gi\|87199962\|ref\|YP_497219.1\| | N. aromatic-civorans | 39.3 | 33.8 | 44.0 | 31.0 | 36.3 | 39.2 | 31.0 |
| gi\|193215879\|ref\|YP_001997078.1\| | C. thalassium | 37.6 | 33.6 | 43.9 | 29.2 | 33.5 | 36.7 | 29.7 |
| gi\|168184715\|ref\|ZP_02619379.1\| | C. botulinum | 39.8 | 36.5 | 43.9 | 28.3 | 33.2 | 38.4 | 28.5 |
| gi\|39935928\|ref\|NP_948204.1\| | R.palustris | 36.2 | 34.2 | 43.9 | 28.8 | 36.4 | 35.9 | 27.7 |
| gi\|115524625\|ref\|YP_781536.1\| | R.palustris | 37.4 | 35.0 | 43.9 | 31.3 | 36.6 | 37.7 | 30.7 |
| gi\|256824483\|ref\|YP_003148443.1\| | K. sedentarius | 40.7 | 34.3 | 43.9 | 30.5 | 36.8 | 39.7 | 30.3 |
| gi\|86142639\|ref\|ZP_01061078.1\| | L. blandensis | 38.5 | 38.1 | 43.9 | 29.1 | 34.7 | 38.0 | 28.9 |
| gi\|146299889\|ref\|YP_001194480.1\| | F.johnsoniae | 36.8 | 39.6 | 43.9 | 29.1 | 34.4 | 36.7 | 29.5 |
| gi\|254504095\|ref\|ZP_05116246.1\| | L.alexandrii | 37.6 | 32.6 | 43.9 | 29.7 | 37.3 | 37.7 | 29.3 |
| gi\|113473790\|ref\|YP_718053.1\| | Sphingomonas sp. | 39.1 | 34.7 | 43.9 | 31.5 | 37.0 | 38.8 | 31.1 |
| gi\|227538429\|ref\|ZP_03968478.1\| | S. spiritivorum | 38.5 | 34.4 | 43.8 | 31.0 | 36.7 | 37.9 | 31.0 |
| gi\|241890795\|ref\|ZP_04778091.1\| | S. spiritivorum | 38.3 | 34.6 | 43.8 | 31.0 | 36.7 | 37.7 | 31.3 |
| gi\|256380141\|ref\|YP_003103801.1\| | A.mirum | 38.4 | 35.7 | 43.8 | 30.5 | 36.9 | 38.4 | 30.5 |
| gi\|83816057\|ref\|YP_445724.1\| | S.ruber | 35.3 | 33.8 | 43.8 | 31.0 | 35.9 | 35.2 | 31.4 |
| gi\|256112252\|ref\|ZP_05453173.1\| | B.melitensis | 40.5 | 39.9 | 43.8 | 30.4 | 38.3 | 39.7 | 30.3 |
| gi\|256045525\|ref\|ZP_05448408.1\| | B.melitensis | 40.1 | 39.9 | 43.8 | 30.4 | 38.3 | 39.3 | 30.3 |
| gi\|239832015\|ref\|ZP_04680344.1\| | O.intermedium | 35.6 | 32.9 | 43.8 | 29.1 | 36.4 | 36.7 | 28.6 |
| gi\|261749492\|ref\|YP_003257178.1\| | Blattabacterium sp. | 35.4 | 30.3 | 43.7 | 25.8 | 31.1 | 34.2 | 25.8 |

FIG. 3D-BKD cont'd

FIG. 3D- BKD E3 Subunit Homologs

| | | | | | | | | |
|---|---|---|---|---|---|---|---|---|
| gi\|256425217\|ref\|YP_003125870.1\| | C. pinensis | 38.7 | 34.5 | 43.7 | 29.4 | 37.4 | 38.3 | 28.3 |
| gi\|27379889\|ref\|NP_771418.1\| | B. japonicum | 38.4 | 33.6 | 43.7 | 29.1 | 35.7 | 38.7 | 28.1 |
| gi\|220932935\|ref\|YP_002509843.1\| | H.orenii H | 36.5 | 36.3 | 43.7 | 31.2 | 33.2 | 36.9 | 32.1 |
| gi\|163868061\|ref\|YP_001609265.1\| | B.tribocorum | 33.7 | 32.8 | 43.6 | 27.8 | 35.6 | 33.3 | 27.6 |
| gi\|262196889\|ref\|YP_003268098.1\| | H.ochraceum | 41.6 | 35.9 | 43.6 | 30.6 | 38.3 | 40.0 | 30.9 |
| gi\|206901008\|ref\|YP_002250270.1\| | D. thermophilum | 38.0 | 36.7 | 43.6 | 29.7 | 36.8 | 37.2 | 29.0 |
| gi\|110639729\|ref\|YP_679939.1\| | C.hutchinsonii | 37.0 | 39.3 | 43.6 | 30.5 | 33.4 | 37.7 | 29.7 |
| gi\|15966801\|ref\|NP_387154.1\| | S. meliloti | 38.4 | 39.6 | 43.6 | 29.7 | 37.2 | 37.4 | 29.7 |
| gi\|150398133\|ref\|YP_001328600.1\| | S.medicae | 37.7 | 39.5 | 43.6 | 30.4 | 36.4 | 36.8 | 31.0 |
| gi\|163761402\|ref\|ZP_02168476.1\| | H.phototrophica | 39.0 | 39.5 | 43.6 | 29.5 | 36.3 | 38.1 | 30.4 |
| gi\|254717980\|ref\|ZP_05179791.1\| | Brucella sp. | 40.7 | 40.3 | 43.6 | 30.8 | 38.5 | 40.0 | 30.5 |
| gi\|23013388\|ref\|ZP_00053288.1\| | M. magneto-tacticum | 36.5 | 33.0 | 43.6 | 28.5 | 34.3 | 36.4 | 28.1 |
| gi\|255533591\|ref\|YP_003093963.1\| | P.heparinus | 37.1 | 37.8 | 43.6 | 27.6 | 33.3 | 36.5 | 27.4 |
| gi\|153009393\|ref\|YP_001370608.1\| | O.anthropi | 35.5 | 32.8 | 43.6 | 28.9 | 36.3 | 36.7 | 28.7 |
| gi\|256059895\|ref\|ZP_05450081.1\| | B.neotomae | 40.7 | 40.4 | 43.6 | 30.9 | 38.5 | 39.9 | 30.3 |
| gi\|88713490\|ref\|ZP_01107572.1\| | F. bacterium | 38.0 | 38.6 | 43.5 | 28.3 | 33.8 | 37.3 | 28.5 |
| gi\|38489206\|gb\|AAR21288.1\| | B.henselae | 39.1 | 39.9 | 43.5 | 30.2 | 35.8 | 36.5 | 29.9 |
| gi\|269957137\|ref\|YP_003326926.1\| | X.cellulosilytica | 38.2 | 35.1 | 43.5 | 31.3 | 34.8 | 37.0 | 31.9 |
| gi\|149279047\|ref\|ZP_01885181.1\| | Pedobacter sp. | 37.3 | 38.7 | 43.5 | 28.2 | 35.1 | 36.2 | 28.4 |
| gi\|85716519\|ref\|ZP_01047490.1\| | Nitrobacter sp. | 38.4 | 35.2 | 43.5 | 29.1 | 37.5 | 38.7 | 28.4 |
| gi\|188582158\|ref\|YP_001925603.1\| | M. populi | 36.1 | 33.7 | 43.5 | 28.2 | 35.9 | 36.9 | 29.1 |
| gi\|38232984\|ref\|NP_938751.1\| | C. diphtheriae | 37.8 | 34.5 | 43.5 | 29.9 | 33.3 | 37.4 | 29.5 |
| gi\|121602441\|ref\|YP_988852.1\| | B.bacilliformis | 33.7 | 32.1 | 43.4 | 27.3 | 36.0 | 33.9 | 27.1 |
| gi\|241774668\|ref\|ZP_04771989.1\| | A.excentricus | 37.9 | 35.2 | 43.4 | 29.9 | 36.6 | 37.6 | 31.2 |
| gi\|54027239\|ref\|YP_121481.1\| | N.farcinica | 38.2 | 34.2 | 43.4 | 28.8 | 35.9 | 37.3 | 28.6 |
| gi\|83856665\|ref\|ZP_00950194.1\| | C. atlanticus | 37.8 | 38.3 | 43.4 | 27.5 | 34.5 | 37.1 | 28.1 |
| gi\|254819791\|ref\|ZP_05224792.1\| | M. intracellulare | 39.3 | 36.3 | 43.4 | 29.6 | 35.9 | 39.6 | 29.4 |
| gi\|15965203\|ref\|NP_385556.1\| | S. meliloti | 36.9 | 32.4 | 43.4 | 28.7 | 37.3 | 37.6 | 28.9 |
| gi\|88606942\|ref\|YP_504698.1\| | A. phagocytophilum | | | 43.4 | 30.3 | 36.0 | | 29.4 |
| gi\|254561955\|ref\|YP_003069050.1\| | M. extorquens | 35.9 | 33.5 | 43.4 | 28.0 | 36.0 | 36.9 | 28.0 |
| gi\|222146561\|ref\|YP_002549518.1\| | A.vitis | 37.1 | 33.0 | 43.4 | 28.7 | 37.4 | 38.3 | 28.7 |

FIG. 3D- BKD E3 Subunit Homologs

| | | | | | | | | |
|---|---|---|---|---|---|---|---|---|
| gi\|222085880\|ref\|YP_002544411.1\| | A. radiobacter | 37.9 | 34.4 | 43.4 | 28.3 | 37.8 | 38.3 | 28.7 |
| gi\|146341012\|ref\|YP_001206060.1\| | Bradyrhizobium sp. | 38.2 | 35.2 | 43.3 | 28.8 | 36.8 | 37.8 | 27.8 |
| gi\|227382024\|ref\|ZP_03865472.1\| | Kribbella flavida | 68.1 | 36.9 | 43.3 | 30.1 | 47.0 | 67.8 | 30.6 |
| gi\|111019133\|ref\|YP_702105.1\| | R.jostii | 37.4 | 33.8 | 43.3 | 27.6 | 35.9 | 37.6 | 28.2 |
| gi\|49476301\|ref\|YP_034342.1\| | B.henselae | 38.9 | 39.9 | 43.3 | 30.2 | 35.8 | 36.3 | 29.9 |
| gi\|84703802\|ref\|ZP_01017630.1\| | P.bermudensis | 35.8 | 34.2 | 43.3 | 31.3 | 36.8 | 36.2 | 31.1 |
| gi\|167644207\|ref\|YP_001681870.1\| | Caulobacter sp. | 38.1 | 39.8 | 43.3 | 29.9 | 37.9 | 37.7 | 29.5 |
| gi\|217976709\|ref\|YP_002360856.1\| | M.silvestris | 37.1 | 34.5 | 43.3 | 30.3 | 36.6 | 37.0 | 29.7 |
| gi\|114567491\|ref\|YP_754645.1\| | S. wolfei | 35.2 | 38.8 | 43.2 | 31.0 | 35.3 | 34.4 | 31.5 |
| gi\|189501860\|ref\|YP_001957577.1\| | C.Amoebophilus asiaticus | 38.5 | | 43.2 | 28.4 | 33.2 | 37.8 | 28.8 |
| gi\|163852209\|ref\|YP_001640252.1\| | M.extorquens | 35.7 | 33.5 | 43.2 | 28.2 | 35.8 | 36.7 | 28.2 |
| gi\|209885402\|ref\|YP_002289259.1\| | O.carboxidovorans | 37.8 | 34.5 | 43.2 | 29.2 | 36.6 | 38.1 | 28.8 |
| gi\|15828281\|ref\|NP_302544.1\| | M. leprae | 38.5 | 35.2 | 43.2 | 29.1 | 34.9 | 37.5 | 28.7 |
| gi\|226305028\|ref\|YP_002764986.1\| | R.erythropolis | 38.2 | 34.4 | 43.2 | 28.2 | 35.0 | 37.0 | 28.4 |
| gi\|126648610\|ref\|ZP_01721094.1\| | Algoriphagus sp. | 37.5 | 39.7 | 43.2 | 26.8 | 34.1 | 36.5 | 27.2 |
| gi\|110633978\|ref\|YP_674186.1\| | Chelativorans sp. | 37.6 | 34.0 | 43.1 | 28.5 | 35.6 | 37.9 | 28.0 |
| gi\|83311420\|ref\|YP_421684.1\| | M.magneticum | 38.2 | 33.9 | 43.1 | 28.1 | 35.0 | 38.1 | 27.9 |
| gi\|149173322\|ref\|ZP_01851952.1\| | P.maris | 38.7 | 38.2 | 43.1 | 31.4 | 36.5 | 37.3 | 31.4 |
| gi\|254469165\|ref\|ZP_05082570.1\| | Pseudovibrio sp. | 36.5 | 32.6 | 43.1 | 29.3 | 35.4 | 37.4 | 29.3 |
| gi\|226308081\|ref\|YP_002768041.1\| | R.erythropolis | 37.8 | 38.1 | 43.1 | 31.8 | 39.4 | 38.1 | 31.5 |
| gi\|222474880\|ref\|YP_002563295.1\| | A.marginale | | 35.3 | 43.1 | 29.5 | 35.3 | | 28.7 |
| gi\|254994735\|ref\|ZP_05276925.1\| | A. marginale | | 35.3 | 43.1 | 29.1 | 35.3 | | 28.3 |
| gi\|56416512\|ref\|YP_153586.1\| | A.marginale | | 35.5 | 43.1 | 29.7 | 35.5 | | 28.9 |
| gi\|117928144\|ref\|YP_872695.1\| | A.cellulolyticus | 70.7 | 35.3 | 43.1 | 30.8 | 49.1 | 73.4 | 30.1 |
| gi\|229871980\|ref\|ZP_04491566.1\| | S.linguale | 37.9 | 32.8 | 43.1 | 31.4 | 34.1 | 37.2 | 31.2 |
| gi\|117925686\|ref\|YP_866303.1\| | Magnetococcus sp. | 39.9 | 40.6 | 43.1 | 30.8 | 36.8 | 39.4 | 31.2 |
| gi\|211926925\|dbj\|BAG82672.1\| | M. luteolum | 36.7 | 34.5 | 43.0 | 30.0 | 34.9 | 36.2 | 30.5 |
| gi\|209965544\|ref\|YP_002298459.1\| | R. centenum | 40.8 | 42.0 | 43.0 | 31.8 | 38.8 | 41.5 | 31.7 |
| gi\|68537030\|ref\|YP_251735.1\| | C.jeikeium | 37.7 | 36.1 | 43.0 | 28.8 | 35.7 | 37.0 | 29.0 |
| gi\|159039091\|ref\|YP_001538344.1\| | S.arenicola | 68.9 | 35.3 | 43.0 | 29.5 | 46.0 | 69.6 | 29.1 |
| gi\|21674121\|ref\|NP_662186.1\| | C.tepidum | 35.9 | 36.4 | 43.0 | 32.6 | 39.2 | 34.6 | 32.4 |

FIG. 3D-BKD cont'd

FIG. 3D-BKD cont'd

FIG. 3D- BKD E3 Subunit Homologs

| | | | | | | | | |
|---|---|---|---|---|---|---|---|---|
| gi\|13899138\|gb\|AAG12404.1\| | C. tepidum | 35.8 | 36.4 | 43.0 | 32.6 | 39.2 | 34.6 | 32.4 |
| gi\|182414527\|ref\|YP_001819593.1\| | Opitutus terrae | 39.2 | 32.9 | 43.0 | 27.8 | 34.4 | 38.1 | |
| gi\|158423370\|ref\|YP_001524662.1\| | A. caulinodans | 37.1 | 33.8 | 43.0 | 29.1 | 36.9 | 37.4 | 29.0 |
| gi\|227379150\|ref\|ZP_03862608.1\| | Kribbella flavida | 39.0 | 35.5 | 43.0 | 29.9 | 37.5 | 38.0 | 29.4 |
| gi\|256800108\|ref\|ZP_05529732.1\| | S. viridoch-romogenes | 39.7 | 34.6 | 42.9 | 30.0 | 39.0 | 39.0 | 30.4 |
| gi\|282890645\|ref\|ZP_06299168.1\| | P. acanthimoebae | 39.9 | 39.5 | 42.9 | 28.3 | 36.7 | 38.2 | 27.0 |
| gi\|124003513\|ref\|ZP_01688362.1\| | M.marina | 37.9 | 35.6 | 42.9 | 27.3 | 33.4 | 36.6 | 27.3 |
| gi\|114797424\|ref\|YP_760674.1\| | H. neptunium | 36.9 | 35.3 | 42.9 | 30.3 | 35.4 | 36.3 | 30.1 |
| gi\|83858345\|ref\|ZP_00951867.1\| | O. alexandrii | 37.7 | 33.3 | 42.9 | 29.3 | 38.1 | 38.3 | 28.9 |
| gi\|134102127\|ref\|YP_001107788.1\| | S. erythraea | 40.0 | 36.0 | 42.9 | 31.0 | 38.0 | 40.4 | 30.4 |
| gi\|154247817\|ref\|YP_001418775.1\| | X.autotrophicus | 35.4 | 32.5 | 42.9 | 27.9 | 36.4 | 35.7 | 28.2 |
| gi\|240139539\|ref\|YP_002964015.1\| | M.extorquens | 35.7 | 33.5 | 42.8 | 28.0 | 35.8 | 36.9 | 28.0 |
| gi\|218530968\|ref\|YP_002421784.1\| | M.chloromethanicum | 36.1 | 33.7 | 42.8 | 27.8 | 35.8 | 37.1 | 27.8 |
| gi\|114769293\|ref\|ZP_01446919.1\| | alpha proteo-bacterium | 37.3 | 36.5 | 42.8 | 26.7 | 34.4 | 37.2 | 26.3 |
| gi\|226225882\|ref\|YP_002759988.1\| | G.aurantiaca | 38.4 | 37.8 | 42.8 | 31.1 | 36.1 | 37.7 | 30.0 |
| gi\|84687517\|ref\|ZP_01015393.1\| | R. bacterium | 37.4 | 36.5 | 42.8 | 30.6 | 36.4 | 37.5 | 30.2 |
| gi\|91201313\|emb\|CAJ74373.1\| | C. Kuenenia stuttgartiensis | 35.6 | 34.6 | 42.8 | 27.4 | 34.9 | 35.7 | 26.8 |
| gi\|254780675\|ref\|YP_003065088.1\| | C. Liberibacter asiaticus | 35.4 | 31.4 | 42.7 | 29.6 | 34.9 | 35.7 | 29.4 |
| gi\|258541863\|ref\|YP_003187296.1\| | A. pasteurianus | 39.4 | 41.0 | 42.7 | 28.5 | 37.9 | 39.3 | 28.8 |
| gi\|49475371\|ref\|YP_033412.1\| | B.henselae | 34.3 | 32.8 | 42.7 | 27.6 | 35.4 | 33.5 | 27.1 |
| gi\|229537791\|ref\|ZP_04426927.1\| | P. limnophilus | 37.7 | 39.6 | 42.7 | 29.7 | 35.4 | 37.6 | 29.5 |
| gi\|262340991\|ref\|YP_003283846.1\| | Blattabacterium sp. | 36.1 | 31.5 | 42.7 | 27.2 | 30.0 | 35.6 | 26.5 |
| gi\|168701058\|ref\|ZP_02733335.1\| | G.obscuriglobus | 40.5 | 43.0 | 42.7 | 32.6 | 37.0 | 40.2 | 31.6 |
| gi\|42524147\|ref\|NP_969527.1\| | B.bacteriovorus | 41.4 | 38.9 | 42.7 | 32.7 | 35.2 | 41.2 | 30.9 |
| gi\|13470624\|ref\|NP_102193.1\| | M.loti | 37.9 | 33.8 | 42.7 | 29.1 | 37.0 | 38.6 | 29.1 |
| gi\|92117298\|ref\|YP_577027.1\| | N. hamburgensis | 38.9 | 33.0 | 42.6 | 28.4 | 36.5 | 39.2 | 28.1 |
| gi\|49474130\|ref\|YP_032172.1\| | B.quintana | 34.2 | 32.6 | 42.6 | 28.3 | 36.2 | 34.3 | 28.3 |
| gi\|124006662\|ref\|ZP_01691494.1\| | M.marina | 40.4 | 31.9 | 42.6 | 30.6 | 35.7 | 39.2 | 30.2 |
| gi\|119383363\|ref\|YP_914419.1\| | P. denitrificans | 38.4 | 36.1 | 42.6 | 28.5 | 36.2 | 38.5 | 28.3 |
| gi\|126728572\|ref\|ZP_01744387.1\| | S.stellata | 37.4 | 37.5 | 42.6 | 29.7 | 37.8 | 37.5 | 29.7 |
| gi\|163869360\|ref\|YP_001610616.1\| | B.tribocorum | 37.7 | 39.2 | 42.6 | 29.4 | 36.4 | 36.3 | 28.9 |

FIG. 3D-BKD cont'd

FIG. 3D- BKD E3 Subunit Homologs

| | | | | | | | | |
|---|---|---|---|---|---|---|---|---|
| gi\|237786516\|ref\|YP_002907221.1\| | C. kroppen-stedtii | 37.6 | 35.2 | 42.6 | 30.5 | 34.6 | 36.8 | 30.6 |
| gi\|167752125\|ref\|ZP_02424252.1\| | A.putredinis | 37.0 | 36.2 | 42.6 | 32.8 | 34.8 | 37.3 | 31.6 |
| gi\|229209393\|ref\|ZP_04335824.1\| | N.dassonvillei | 42.2 | 34.6 | 42.6 | 30.5 | 38.1 | 41.7 | 30.7 |
| gi\|148255816\|ref\|YP_001240401.1\| | Bradyrhizobium sp. | 37.6 | 34.5 | 42.6 | 28.8 | 36.6 | 37.2 | 28.0 |
| gi\|33114656\|gb\|AAP94898.1\| | A. caulincdans | 38.1 | 34.3 | 42.6 | 28.5 | 37.3 | 38.5 | 28.2 |
| gi\|16125975\|ref\|NP_420539.1\| | C. crescentus | 41.1 | 36.1 | 42.6 | 31.2 | 37.7 | 40.7 | 31.4 |
| gi\|266627788\|ref\|ZP_06120716.1\| | C.segnis | 40.2 | 35.9 | 42.6 | 30.5 | 37.2 | 40.0 | 30.8 |
| gi\|94984461\|ref\|YP_603825.1\| | D.geothermalis | 39.3 | 39.8 | 42.5 | | 37.1 | 37.6 | 29.5 |
| gi\|227408288\|ref\|ZP_03891517.1\| | G.obscurus | 73.5 | | 42.5 | | 46.7 | 75.2 | |
| gi\|114569975\|ref\|YP_756655.1\| | M.maris | 38.8 | 36.4 | 42.5 | 29.2 | 38.3 | 38.2 | 28.8 |
| gi\|163734174\|ref\|ZP_02141615.1\| | R.litoralis | 37.4 | 38.5 | 42.5 | 27.3 | 34.9 | 37.0 | 27.5 |
| gi\|84687125\|ref\|ZP_01015007.1\| | R.bacterium | 33.8 | 33.5 | 42.5 | 28.8 | 36.7 | 33.0 | 28.8 |
| gi\|229861605\|ref\|ZP_04481219.1\| | S. nassauensis | 65.8 | 34.6 | 42.5 | 28.2 | 44.8 | 66.4 | |
| gi\|240850264\|ref\|YP_002971657.1\| | B.grahamii | 34.1 | 31.7 | 42.5 | 29.2 | 35.7 | 33.7 | 28.8 |
| gi\|126463382\|ref\|YP_001044496.1\| | R. sphaeroides | 39.9 | 39.3 | 42.4 | 28.6 | 35.1 | 39.0 | 28.6 |
| gi\|221640453\|ref\|YP_002526715.1\| | R.sphaeroides | 39.9 | 39.3 | 42.4 | 28.6 | 34.9 | 39.0 | 28.6 |
| gi\|58584816\|ref\|YP_198389.1\| | W.endosymbiont | 34.9 | 32.6 | 42.4 | 27.9 | 31.2 | 33.5 | 27.4 |
| gi\|148261805\|ref\|YP_001235932.1\| | A. cryptum | 38.4 | 34.5 | 42.4 | 28.0 | 35.3 | 38.8 | 28.0 |
| gi\|170747426\|ref\|YP_001753686.1\| | M. radiotolerans | 37.2 | 33.9 | 42.4 | 28.8 | 36.2 | 37.9 | 29.4 |
| gi\|254502658\|ref\|ZP_05114809.1\| | L.alexandrii | 39.3 | 41.4 | 42.4 | 28.6 | 36.1 | 38.5 | 28.8 |
| gi\|240851384\|ref\|YP_002972787.1\| | B.grahamii | 38.4 | 38.8 | 42.4 | 29.4 | 36.3 | 37.2 | 29.5 |
| gi\|182680507\|ref\|YP_001834653.1\| | B.indica | 40.3 | 40.3 | 42.4 | 30.3 | 39.1 | 40.2 | 30.5 |
| gi\|227505626\|ref\|ZP_03935675.1\| | C. striatum | 38.9 | 35.0 | 42.3 | 30.4 | 33.7 | 38.0 | 30.2 |
| gi\|280964901\|ref\|ZP_06239412.1\| | Frankia sp. | 64.9 | | 42.3 | | 47.5 | 64.9 | |
| gi\|163760097\|ref\|ZP_02167180.1\| | H.phototrophica | 36.9 | 33.8 | 42.3 | 29.7 | 37.1 | 35.4 | 30.1 |
| gi\|15888759\|ref\|NP_354440.1\| | A.tumefaciens | 36.0 | 33.9 | 42.3 | 31.6 | 36.8 | 36.8 | 31.8 |
| gi\|58578802\|ref\|YP_197014.1\| | E.ruminantium | 32.0 | 32.4 | 42.3 | 26.4 | 30.9 | 31.7 | 26.2 |
| gi\|57238873\|ref\|YP_180009.1\| | E.ruminantium | 32.0 | 32.4 | 42.3 | 26.4 | 30.8 | 31.7 | 26.2 |
| gi\|229488837\|ref\|ZP_04382703.1\| | R. erythropolis | 38.4 | 38.1 | 42.3 | 32.5 | 39.7 | 38.5 | 32.3 |
| gi\|88801370\|ref\|ZP_01116898.1\| | P. irgensii | 38.8 | 36.9 | 42.2 | 30.3 | 35.3 | 37.9 | 30.8 |
| gi\|77464542\|ref\|YP_354046.1\| | R.sphaeroides | 39.9 | 39.5 | 42.2 | 28.6 | 34.9 | 39.0 | 28.6 |

FIG. 3D-BKD cont'd

FIG. 3D- BKD E3 Subunit Homologs

| | | | | | | | | |
|---|---|---|---|---|---|---|---|---|
| gi\|121601923\|ref\|YP_988366.1\| | B.bacilliformis | 38.8 | 38.6 | 42.2 | 29.3 | 35.7 | 36.5 | 29.2 |
| gi\|262378379\|ref\|ZP_06071536.1\| | A. radioresistens | 36.9 | 37.4 | 42.2 | 28.4 | 34.4 | 35.7 | 29.5 |
| gi\|86135035\|ref\|ZP_01053617.1\| | Polaribacter sp. | 37.3 | 36.7 | 42.1 | 28.8 | 33.8 | 37.5 | 29.0 |
| gi\|15835460\|ref\|NP_297219.1\| | C.muridarum | 38.2 | 34.5 | 42.1 | 32.1 | 35.1 | 37.8 | 31.8 |
| gi\|255348937\|ref\|ZP_05380944.1\| | C.trachomatis | 38.2 | 33.8 | 42.1 | 33.4 | 34.1 | 37.6 | 33.5 |
| gi\|15605286\|ref\|NP_220072.1\| | C.trachomatis | 38.0 | 33.8 | 42.1 | 33.4 | 33.9 | 37.4 | 33.5 |
| gi\|227502498\|ref\|ZP_03932547.1\| | C. accolens | 37.6 | 34.3 | 42.1 | 29.5 | 32.0 | 37.0 | 30.1 |
| gi\|146306138\|ref\|YP_001186603.1\| | P.mendocina | 37.6 | 41.2 | 42.1 | 29.0 | 38.2 | 36.4 | 29.7 |
| gi\|256825454\|ref\|YP_003149414.1\| | K. sedentarius | 65.7 | 35.6 | 42.1 | | 47.5 | 65.1 | |
| gi\|254420184\|ref\|ZP_05033908.1\| | Brevundimonas sp. | 39.3 | 36.8 | 42.1 | 28.9 | 37.0 | 38.4 | 30.0 |
| gi\|229869215\|ref\|ZP_04488814.1\| | S.linguale | 36.9 | 37.4 | 42.1 | 27.1 | 35.2 | 35.2 | 26.9 |
| gi\|118589903\|ref\|ZP_01547307.1\| | S.aggregata | 37.6 | 32.4 | 42.1 | 28.8 | 36.6 | 38.1 | 29.1 |
| gi\|255334427\|ref\|ZP_05375343.1\| | H. denitrificans | 33.2 | 34.8 | 42.1 | 32.2 | 36.3 | 33.5 | 30.8 |
| gi\|146277884\|ref\|YP_001168043.1\| | R. sphaeroides | 37.2 | 36.3 | 42.1 | 30.2 | 38.1 | 37.7 | 30.3 |
| gi\|257055153\|ref\|YP_003132985.1\| | S. viridis | 39.4 | 34.3 | 42.1 | 31.8 | 38.3 | 38.8 | 31.2 |
| gi\|229819006\|ref\|YP_002880532.1\| | B.cavernae | 40.9 | 35.7 | 42.0 | 30.7 | 38.9 | 39.8 | 30.0 |
| gi\|146276132\|ref\|YP_001166291.1\| | R.sphaeroides | 40.2 | 38.4 | 42.0 | 28.6 | 35.9 | 39.4 | 28.7 |
| gi\|28211667\|ref\|NP_782611.1\| | C.tetani | 35.0 | 36.6 | 42.0 | 30.3 | 32.2 | 35.6 | 29.2 |
| gi\|187736176\|ref\|YP_001878288.1\| | A.muciniphila | 36.7 | 33.8 | 42.0 | 31.1 | 35.9 | 35.5 | 30.7 |
| gi\|164687626\|ref\|ZP_02211654.1\| | C. bartlettii | 36.4 | 34.1 | 42.0 | 29.8 | 33.9 | 35.4 | 29.0 |
| gi\|262277902\|ref\|ZP_06055695.1\| | alpha prote-obacterium | 40.3 | 41.8 | 42.0 | 26.9 | 34.9 | 39.7 | 27.8 |
| gi\|70725224\|ref\|YP_252138.1\| | S. haemolyticus | 35.7 | 32.9 | 42.0 | | 32.2 | 34.9 | |
| gi\|212639717\|ref\|YP_002316237.1\| | A. flavithermus | 35.7 | 41.9 | 42.0 | 30.6 | 35.7 | 36.1 | 31.3 |
| gi\|255320486\|ref\|ZP_05361667.1\| | A. radioresistens | 36.7 | 37.2 | 41.9 | 28.2 | 34.4 | 35.5 | 29.7 |
| gi\|145595834\|ref\|YP_001160131.1\| | S.tropica | 68.3 | | 41.9 | 30.0 | 44.8 | 68.9 | |
| gi\|166154772\|ref\|YP_001654890.1\| | C.trachomatis | 37.7 | 33.6 | 41.9 | 33.4 | 33.7 | 37.2 | 33.5 |
| gi\|47569036\|ref\|ZP_00239726.1\| | Bacillus cereus | 36.4 | 33.2 | 41.9 | 29.8 | 34.0 | 35.1 | 29.5 |
| gi\|162147213\|ref\|YP_001601674.1\| | G.diazotrophicus | 40.3 | 40.5 | 41.9 | 29.9 | 38.6 | 38.4 | 30.1 |
| gi\|220926289\|ref\|YP_002501591.1\| | M. nodulans | 36.5 | 33.3 | 41.9 | 28.8 | 37.7 | 36.6 | 28.6 |
| gi\|91214555\|ref\|ZP_01251528.1\| | P. torquis | 37.0 | 38.1 | 41.8 | 29.5 | 32.2 | 36.5 | 29.7 |
| gi\|167646717\|ref\|YP_001684380.1\| | Caulobacter sp. | 39.5 | 36.8 | 41.8 | 29.1 | 38.5 | 39.0 | 30.0 |

FIG. 3D-BKD cont'd

FIG. 3D- BKD E3 Subunit Homologs

| | | | | | | | | |
|---|---|---|---|---|---|---|---|---|
| gi\|229207950\|ref\|ZP_04334397.1\| | N.dassonvillei | 67.8 | | 41.8 | | 47.6 | 68.9 | |
| gi\|262279022\|ref\|ZP_06056807.1\| | A.calcoaceticus | 34.8 | 37.2 | 41.8 | 30.5 | 34.4 | 33.1 | 30.8 |
| gi\|260459497\|ref\|ZP_05807752.1\| | M. opportu-nistum | 37.4 | 33.3 | 41.8 | 28.8 | 36.6 | 37.6 | 30.0 |
| gi\|260426921\|ref\|ZP_05780900.1\| | Citreicella sp. | 37.5 | 36.2 | 41.8 | 28.7 | 36.6 | 38.4 | 28.2 |
| gi\|227541609\|ref\|ZP_03971658.1\| | C.glucuronolyticum | 36.3 | 36.6 | 41.8 | 29.3 | 34.0 | 37.1 | 30.0 |
| gi\|227487222\|ref\|ZP_03917538.1\| | C. glucuro-nolyticum | 36.5 | 36.4 | 41.8 | 29.1 | 33.8 | 37.1 | 29.7 |
| gi\|186476477\|ref\|YP_001857947.1\| | B.phymatum | 35.4 | 36.8 | 41.7 | 27.1 | 33.2 | 34.1 | 27.5 |
| gi\|260433388\|ref\|ZP_05787359.1\| | S. lacuscae-rulensis | 37.0 | 37.0 | 41.7 | 30.0 | 36.8 | 37.3 | 29.5 |
| gi\|239983122\|ref\|ZP_04705646.1\| | S.albus | 40.3 | 34.6 | 41.7 | 30.3 | 39.1 | 40.0 | 30.0 |
| gi\|255535729\|ref\|YP_003096100.1\| | F.bacterium | 40.9 | 39.3 | 41.7 | 29.6 | 34.7 | 39.0 | 30.2 |
| gi\|227490119\|ref\|ZP_03920435.1\| | C. pseudo-enitalium | 38.4 | 35.5 | 41.7 | 30.0 | 32.5 | 37.4 | 30.0 |
| gi\|255324216\|ref\|ZP_05365338.1\| | C. tubercul-ostearicum | 38.4 | 35.5 | 41.7 | 29.7 | 32.7 | 37.4 | 30.0 |
| gi\|256370737\|ref\|YP_003108562.1\| | C. Sulciamuelleri | 33.3 | 30.7 | 41.7 | 27.4 | 29.7 | 32.3 | 27.0 |
| gi\|126462382\|ref\|YP_001043496.1\| | R.sphaeroides | 37.3 | 35.4 | 41.6 | 29.5 | 37.1 | 37.2 | 29.8 |
| gi\|221639389\|ref\|YP_002525651.1\| | R.sphaeroides | 37.3 | 35.4 | 41.6 | 30.0 | 37.3 | 37.2 | 30.0 |
| gi\|259419306\|ref\|ZP_05743223.1\| | Silicibacter sp. | 37.0 | 37.0 | 41.6 | 31.3 | 35.6 | 36.6 | 30.8 |
| gi\|254383908\|ref\|ZP_04999255.1\| | Streptomyces sp. | 38.4 | 35.9 | 41.6 | 31.1 | 38.1 | 38.0 | 31.3 |
| gi\|225010838\|ref\|ZP_03701306.1\| | F.bacterium | 39.4 | 39.1 | 41.6 | 28.8 | 35.5 | 38.5 | 29.0 |
| gi\|170743965\|ref\|YP_001772620.1\| | Methylobacterium sp. | 37.2 | 33.8 | 41.6 | 29.4 | 37.5 | 37.2 | 29.9 |
| gi\|271964158\|ref\|YP_003338354.1\| | S. roseum | 65.4 | 33.9 | 41.6 | 30.6 | 49.9 | 66.7 | 29.7 |
| gi\|239826460\|ref\|YP_002949084.1\| | Geobacillus sp. | 37.7 | 42.1 | 41.6 | 31.5 | 36.5 | 38.6 | 31.9 |
| gi\|255331130\|ref\|ZP_05372150.1\| | Geobacillus sp. | 37.4 | 42.3 | 41.6 | 31.9 | 36.3 | 38.4 | 32.3 |
| gi\|49474812\|ref\|YP_032854.1\| | B. quintana | 38.2 | 39.1 | 41.6 | 30.2 | 35.4 | 36.1 | 30.1 |
| gi\|114764577\|ref\|ZP_01443781.1\| | Roseovarius sp. | 37.1 | 36.2 | 41.5 | 29.1 | 35.6 | 37.7 | 28.4 |
| gi\|167562927\|ref\|ZP_02355843.1\| | B.oklahomensis | 36.1 | 36.9 | 41.5 | 27.9 | 34.4 | 35.1 | 27.9 |
| gi\|114327851\|ref\|YP_745008.1\| | G.bethesdensis | 38.2 | 34.7 | 41.5 | 29.2 | 35.6 | 37.8 | 30.0 |
| gi\|260575226\|ref\|ZP_05843226.1\| | Rhodobacter sp. | 37.0 | 36.7 | 41.5 | 30.3 | 37.3 | 37.1 | 30.1 |
| gi\|260555071\|ref\|ZP_05827292.1\| | A. baumannii | 35.3 | 36.3 | 41.5 | 29.9 | 34.6 | 34.0 | 30.3 |
| gi\|21220654\|ref\|NP_626433.1\| | S. coelicolor | 100 | | 41.5 | 28.2 | 45.0 | 91.1 | |
| gi\|256788201\|ref\|ZP_05526632.1\| | S.lividans | 99.8 | | 41.5 | 28.2 | 45.2 | 91.3 | |
| gi\|58040717\|ref\|YP_192681.1\| | G. oxydans | 34.1 | | 41.4 | 29.4 | 35.3 | 34.1 | 28.6 |

FIG. 3D-BKD cont'd

FIG. 3D- BKD E3 Subunit Homologs

| | | | | | | | | |
|---|---|---|---|---|---|---|---|---|
| gi\|77463526\|ref\|YP_353030.1\| | R.sphaeroides | 37.3 | 35.7 | 41.4 | 29.5 | 37.3 | 37.2 | 29.8 |
| gi\|163746639\|ref\|ZP_02153996.1\| | O.indolifex | 37.4 | 36.3 | 41.4 | 30.9 | 36.0 | 37.3 | 30.7 |
| gi\|256832700\|ref\|YP_003161427.1\| | J.denitrificans | 66.0 | 34.9 | 41.4 | | 43.1 | 67.7 | |
| gi\|256667209\|ref\|ZP_05478162.1\| | Streptomyces sp. | 65.2 | 38.0 | 41.4 | | 45.7 | 65.2 | |
| gi\|271962186\|ref\|YP_003336382.1\| | S. roseum | 38.5 | 34.4 | 41.4 | 30.9 | 37.7 | 38.3 | 31.1 |
| gi\|115351445\|ref\|YP_773284.1\| | B.ambifaria | 36.4 | 37.3 | 41.4 | 27.3 | 34.2 | 35.6 | 27.7 |
| gi\|167463418\|ref\|ZP_02328507.1\| | P.larvae | 37.2 | 42.5 | 41.4 | 30.6 | 37.2 | 37.3 | 30.9 |
| gi\|72161398\|ref\|YP_289055.1\| | T.fusca | 66.7 | 34.9 | 41.4 | 27.4 | 46.3 | 67.2 | 26.9 |
| gi\|256767016\|ref\|ZP_05506190.1\| | Streptomyces sp. | 90.9 | | 41.4 | | 44.2 | 93.1 | |
| gi\|194334246\|ref\|YP_002016106.1\| | P.aestuarii | 36.4 | 34.2 | 41.3 | 31.7 | 38.2 | 36.9 | 31.1 |
| gi\|221197769\|ref\|ZP_03570815.1\| | B. multivorans | 36.0 | 38.0 | 41.3 | 27.5 | 34.0 | 35.5 | 27.5 |
| gi\|167570117\|ref\|ZP_02362991.1\| | B.oklahomensis | 36.3 | 37.6 | 41.3 | 27.9 | 34.4 | 35.3 | 27.9 |
| gi\|114328730\|ref\|YP_745887.1\| | G.bethesdensis | 40.3 | 41.5 | 41.3 | 29.2 | 39.2 | 39.0 | 29.0 |
| gi\|94310986\|ref\|YP_584196.1\| | R.metallidurans | 35.5 | 37.5 | 41.3 | 27.7 | 34.2 | 34.7 | 28.1 |
| gi\|83952646\|ref\|ZP_00961376.1\| | R. nubinhibens | 37.8 | 37.6 | 41.3 | 29.5 | 36.8 | 38.4 | 29.7 |
| gi\|77461891\|ref\|YP_351398.1\| | P.fluorescens | 38.5 | 41.0 | 41.3 | 29.7 | 38.1 | 37.7 | 29.8 |
| gi\|254455468\|ref\|ZP_05068897.1\| | C.Pelagibacter sp. | 36.8 | 40.1 | 41.3 | 28.2 | 33.0 | 36.8 | 27.8 |
| gi\|108797611\|ref\|YP_637808.1\| | Mycobacterium sp. | 37.3 | 35.0 | 41.3 | 29.0 | 34.7 | 37.3 | 29.1 |
| gi\|68171860\|ref\|ZP_00545191.1\| | E.chaffeensis | 33.4 | 31.8 | 41.3 | 27.2 | 30.5 | 31.6 | 26.1 |
| gi\|282886664\|ref\|ZP_06295247.1\| | Burkholderia sp. | 35.4 | 37.3 | 41.2 | | 33.8 | 34.0 | |
| gi\|238027574\|ref\|YP_002911805.1\| | B.glumae | 36.1 | 38.0 | 41.2 | 28.6 | 34.6 | 35.6 | 28.1 |
| gi\|159044360\|ref\|YP_001533154.1\| | D. shibae | 36.9 | 35.8 | 41.2 | 28.8 | 37.6 | 36.3 | 29.0 |
| gi\|256391028\|ref\|YP_003112592.1\| | C.acidiphila | 70.7 | 34.1 | 41.2 | 28.0 | 44.6 | 72.9 | 27.9 |
| gi\|163841166\|ref\|YP_001625571.1\| | R.salmoninarum | 62.4 | | 41.2 | | 42.4 | 62.1 | |
| gi\|256391674\|ref\|YP_003113238.1\| | C.acidiphila | 36.9 | 34.6 | 41.2 | 29.4 | 36.7 | 37.0 | 29.4 |
| gi\|84496115\|ref\|ZP_00994969.1\| | Janibacter sp. | 64.8 | 35.1 | 41.2 | 32.4 | 47.0 | 63.4 | |
| gi\|158313616\|ref\|YP_001506124.1\| | Frankia sp. | 64.0 | | 41.2 | | 50.0 | 63.1 | |
| gi\|84503047\|ref\|ZP_01001143.1\| | O.batsensis | 36.0 | 37.0 | 41.1 | 31.5 | 36.9 | 35.7 | 31.0 |
| gi\|254390641\|ref\|ZP_05005855.1\| | S.clavuligerus | 91.0 | | 41.1 | 28.7 | 46.3 | 90.7 | |
| gi\|282871388\|ref\|ZP_06280384.1\| | Streptomyces sp. | 90.3 | | 41.1 | | 45.7 | 93.7 | |
| gi\|182439123\|ref\|YP_001826842.1\| | S.griseus | 90.6 | | 41.1 | | 45.7 | 93.5 | |

FIG. 3D- BKD E3 Subunit Homologs

| | | | | | | | | |
|---|---|---|---|---|---|---|---|---|
| gi\|260459017\|ref\|ZP_05807303.1\| | S. flavogriseus | 91.1 | | 41.1 | | 45.5 | 95.0 | |
| gi\|254377159\|ref\|ZP_04992625.1\| | Streptomyces sp. | 91.9 | | 41.1 | 27.7 | 45.2 | 94.4 | |
| gi\|220912374\|ref\|YP_002487683.1\| | A.chlorophenolicus | 63.9 | 35.0 | 41.1 | | 44.0 | 62.6 | |
| gi\|116670173\|ref\|YP_831106.1\| | Arthrobacter sp. | 63.6 | 35.9 | 41.1 | | 44.6 | 62.4 | |
| gi\|91782999\|ref\|YP_558205.1\| | B.xenovorans | 35.7 | 37.7 | 41.1 | 26.7 | 33.6 | 34.3 | 27.1 |
| gi\|221213150\|ref\|ZP_03586126.1\| | B. multivorans | 36.0 | 37.8 | 41.1 | 27.5 | 34.2 | 35.7 | 27.5 |
| gi\|254476213\|ref\|ZP_05089599.1\| | Ruegeria sp. | 36.3 | 35.9 | 41.1 | 30.0 | 35.6 | 36.4 | 30.0 |
| gi\|272529905\|ref\|ZP_06225360.1\| | Burkholderia sp. | 35.1 | 38.1 | 41.0 | 27.9 | 33.8 | 35.0 | 27.9 |
| gi\|187923634\|ref\|YP_001895276.1\| | B. phytofirmans | 34.9 | 37.1 | 41.0 | 26.9 | 33.2 | 34.2 | 27.3 |
| gi\|254465846\|ref\|ZP_05079257.1\| | R. bacterium | 36.8 | 36.1 | 41.0 | 31.0 | 35.6 | 36.2 | 31.1 |
| gi\|239501823\|ref\|ZP_04661133.1\| | A.baumannii | 35.7 | 36.3 | 41.0 | 30.1 | 35.0 | 34.4 | 30.5 |
| gi\|184158058\|ref\|YP_001846397.1\| | A. baumannii | 35.5 | 36.5 | 41.0 | 30.5 | 34.8 | 34.2 | 30.8 |
| gi\|169796022\|ref\|YP_001713815.1\| | A.baumannii | 35.7 | 36.3 | 41.0 | 30.3 | 35.0 | 34.4 | 30.8 |
| gi\|171317102\|ref\|ZP_02906305.1\| | B.ambifaria | 36.4 | 37.1 | 41.0 | | 34.2 | 35.6 | 27.9 |
| gi\|256780005\|ref\|ZP_05518468.1\| | S. hygroscopicus | 85.5 | | 40.9 | | 46.7 | 89.2 | |
| gi\|239940664\|ref\|ZP_04692601.1\| | S.roseosporus | 90.5 | | 40.9 | | 45.5 | 93.9 | |
| gi\|256676105\|ref\|ZP_05486416.1\| | Streptomyces sp. | 91.3 | | 40.9 | 27.5 | 45.0 | 95.2 | |
| gi\|116325894\|dbj\|BAF35582.1\| | T. vulgaris | 91.1 | | 40.9 | | 45.7 | 93.1 | |
| gi\|15425686\|dbj\|BAB64316.1\| | A.globiformis | 63.9 | 35.9 | 40.9 | | 44.6 | 62.8 | |
| gi\|254252527\|ref\|ZP_04945845.1\| | B.dolosa | 36.0 | 37.8 | 40.9 | 27.5 | 34.0 | 35.7 | 27.5 |
| gi\|76809352\|ref\|YP_333325.1\| | B.pseudomallei | 35.4 | 38.0 | 40.9 | | 34.0 | 35.7 | |
| gi\|167587328\|ref\|ZP_02379716.1\| | B.ubonensis | 36.6 | 37.8 | 40.9 | 27.9 | 34.2 | 36.0 | 27.9 |
| gi\|53719521\|ref\|YP_108507.1\| | B.pseudomallei | 35.4 | 38.2 | 40.9 | | 34.0 | 35.7 | |
| gi\|254460483\|ref\|ZP_05073899.1\| | R. bacterium | 36.3 | 35.7 | 40.9 | 30.8 | 37.2 | 36.9 | 30.8 |
| gi\|15615215\|ref\|NP_243518.1\| | B.halodurans | 39.1 | 41.6 | 40.8 | 31.8 | 33.4 | 39.7 | 32.3 |
| gi\|111224533\|ref\|YP_715327.1\| | Frankia alni | 68.3 | | 40.8 | | 48.7 | 68.8 | |
| gi\|83943205\|ref\|ZP_00955665.1\| | Sulfitobacter sp. | 37.6 | 35.7 | 40.8 | 30.6 | 36.6 | 37.5 | 30.6 |
| gi\|83954340\|ref\|ZP_00963060.1\| | Sulfitobacter sp. | 37.8 | 35.9 | 40.8 | 30.8 | 36.8 | 37.7 | 30.8 |
| gi\|254486772\|ref\|ZP_05099977.1\| | Roseobacter sp. | 38.5 | 35.7 | 40.8 | 30.8 | 37.3 | 38.4 | 30.8 |
| gi\|85705250\|ref\|ZP_01036349.1\| | Roseovarius sp. | 37.0 | 35.9 | 40.8 | 29.3 | 36.8 | 36.9 | 29.1 |
| gi\|99080937\|ref\|YP_613091.1\| | Ruegeria sp. | 37.2 | 36.7 | 40.8 | 29.3 | 35.0 | 37.3 | 29.5 |

FIG. 3D-BKD cont'd

FIG. 3D-BKD cont'd

FIG. 3D- BKD E3 Subunit Homologs

| | | | | | | | | |
|---|---|---|---|---|---|---|---|---|
| gi\|153854089\|ref\|ZP_01995397.1\| | D.longicatena | 36.1 | 33.3 | 40.8 | 26.0 | 35.8 | 36.2 | 25.8 |
| gi\|269794861\|ref\|YP_003314316.1\| | S. keddieii | 65.2 | 36.0 | 40.8 | 29.4 | 43.5 | 66.5 | 29.0 |
| gi\|258510468\|ref\|YP_003183902.1\| | A. acidocaldarius | 39.5 | 43.8 | 40.8 | 29.6 | 36.6 | 39.0 | 30.0 |
| gi\|282853815\|ref\|ZP_06263152.1\| | P. acnes | 38.7 | 35.4 | 40.8 | 29.7 | 36.7 | 37.9 | 29.4 |
| gi\|50842707\|ref\|YP_055934.1\| | P. acnes | 38.5 | 35.4 | 40.8 | 29.7 | 36.5 | 37.7 | 29.2 |
| gi\|161524918\|ref\|YP_001579930.1\| | B. multivorans | 36.0 | 37.6 | 40.8 | 27.5 | 34.2 | 35.5 | 27.5 |
| gi\|89897888\|ref\|YP_514998.1\| | C. felis | 36.6 | 33.2 | 40.8 | 31.2 | 33.0 | 36.0 | 31.6 |
| gi\|1633234\|pdb\|1EBD\|A | | 38.5 | 41.8 | 40.7 | 31.8 | 36.0 | 38.9 | 31.3 |
| gi\|269922609\|ref\|ZP_06171515.1\| | B.subvibrioides | 37.8 | 35.9 | 40.7 | 28.7 | 35.6 | 37.6 | 29.3 |
| gi\|282862249\|ref\|ZP_06271312.1\| | Streptomyces sp. | 89.4 | | 40.7 | | 45.7 | 93.7 | |
| gi\|254386438\|ref\|ZP_05001742.1\| | Streptomyces sp. | 90.8 | | 40.7 | | 44.4 | 93.9 | |
| gi\|83720959\|ref\|YP_443071.1\| | B. thailandensis | 35.4 | 37.8 | 40.7 | | 33.8 | 35.5 | 27.3 |
| gi\|167836810\|ref\|ZP_02463693.1\| | B. thailandensis | 35.4 | 37.3 | 40.7 | | 33.6 | 35.5 | |
| gi\|126726333\|ref\|ZP_01742174.1\| | R. bacterium | 35.9 | 34.3 | 40.7 | 29.5 | 35.7 | 36.2 | 29.5 |
| gi\|227369480\|ref\|ZP_03852989.1\| | C.gleum | 39.8 | 39.4 | 40.7 | 30.6 | 35.1 | 38.2 | 31.5 |
| gi\|114778872\|ref\|ZP_01453671.1\| | M.ferrooxydans | 35.8 | 34.1 | 40.7 | 28.7 | 35.3 | 35.9 | 28.7 |
| gi\|238060348\|ref\|ZP_04605057.1\| | Micromonospora sp. | 69.3 | 36.5 | 40.7 | 30.1 | 45.1 | 70.2 | |
| gi\|15807360\|ref\|NP_296091.1\| | D.radiodurans | 38.2 | 39.1 | 40.6 | 28.8 | 38.5 | 36.7 | 27.8 |
| gi\|118671\|sp\|P11959.2\|DLDH1_BACST | G. stearoth-ermophilus | 37.9 | 41.9 | 40.6 | 31.8 | 35.5 | 39.0 | 31.3 |
| gi\|209520206\|ref\|ZP_03268977.1\| | Burkholderia sp. | 35.1 | 37.7 | 40.6 | 27.9 | 34.0 | 35.0 | 27.9 |
| gi\|56697085\|ref\|YP_167448.1\| | R.pomeroyi | 36.3 | 36.1 | 40.6 | 30.4 | 35.5 | 36.2 | 30.7 |
| gi\|126739324\|ref\|ZP_01755017.1\| | Roseobacter sp. | 36.8 | 35.9 | 40.6 | 30.6 | 35.9 | 36.6 | 30.7 |
| gi\|229240799\|ref\|ZP_04365194.1\| | C.flavigena | 64.1 | 35.9 | 40.6 | | 44.6 | 65.8 | |
| gi\|213959489\|ref\|ZP_03387772.1\| | P.acnes | 38.1 | 35.2 | 40.6 | 29.7 | 36.3 | 37.3 | 29.2 |
| gi\|107022583\|ref\|YP_620910.1\| | B.cenocepacia | 36.0 | 36.9 | 40.6 | 27.7 | 33.8 | 35.8 | 27.7 |
| gi\|170732836\|ref\|YP_001764783.1\| | B.cenocepacia | 36.0 | 37.1 | 40.6 | 27.7 | 33.8 | 35.8 | 27.7 |
| gi\|170700012\|ref\|ZP_02891037.1\| | B.ambifaria | 36.0 | 37.3 | 40.6 | 27.3 | 34.0 | 35.6 | 27.7 |
| gi\|134295584\|ref\|YP_001119319.1\| | B.vietnamiensis | 36.0 | 37.8 | 40.6 | | 34.2 | 36.2 | 27.3 |
| gi\|262185632\|ref\|ZP_06045053.1\| | A. marinum | 63.4 | 34.5 | 40.6 | 30.5 | 41.5 | 64.1 | 30.9 |
| gi\|71082940\|ref\|YP_265659.1\| | C.Pelagibacter ubique | 36.6 | 40.6 | 40.5 | 27.2 | 32.4 | 36.5 | 27.2 |
| gi\|62185502\|ref\|YP_220287.1\| | C.abortus | 36.8 | 32.8 | 40.5 | 30.4 | 34.0 | 36.4 | 30.5 |

FIG. 3D-BKD cont'd

FIG. 3D- BKD E3 Subunit Homologs

| | | | | | | | | |
|---|---|---|---|---|---|---|---|---|
| gi\|254394753\|ref\|ZP_05009830.1\| | S. pristinae-spiralis | 46.3 | | 40.5 | | 82.8 | 46.4 | |
| gi\|73666771\|ref\|YP_302787.1\| | E. canis str. | 31.9 | 31.8 | 40.5 | 26.6 | 29.6 | 31.0 | 25.6 |
| gi\|89068266\|ref\|ZP_01155676.1\| | O.granulosus | 38.1 | 36.2 | 40.5 | 30.8 | 35.5 | 38.0 | 30.3 |
| gi\|114771128\|ref\|ZP_01448568.1\| | alpha prote-obacterium | 34.5 | 34.1 | 40.5 | 26.5 | 34.3 | 35.4 | 26.2 |
| gi\|226312882\|ref\|YP_002772776.1\| | B. brevis | 37.1 | 44.2 | 40.5 | 31.1 | 37.2 | 36.7 | 31.0 |
| gi\|239979067\|ref\|ZP_04701591.1\| | S. albus | 88.7 | | 40.5 | | 44.4 | 92.0 | |
| gi\|15791043\|ref\|NP_280867.1\| | H. salinarum | 35.4 | 45.2 | 40.5 | 30.5 | 38.0 | 35.4 | 30.7 |
| gi\|255264026\|ref\|ZP_05343368.1\| | Thalassiobium sp. | 37.8 | 35.0 | 40.5 | 30.1 | 35.7 | 37.5 | 29.6 |
| gi\|134098222\|ref\|YP_001103883.1\| | S. erythraea | 64.4 | 38.5 | 40.5 | | 44.9 | 64.6 | |
| gi\|256772415\|ref\|ZP_05511589.1\| | Streptomyces sp. | 73.9 | | 40.5 | | 46.2 | 73.6 | |
| gi\|24215586\|ref\|NP_713067.1\| | L. interrogans serovar | 35.0 | 33.6 | 40.5 | 28.6 | 36.0 | 35.5 | 29.8 |
| gi\|152967222\|ref\|YP_001363006.1\| | K.radiotolerans | 65.7 | 37.8 | 40.4 | 30.6 | 45.9 | 66.8 | 30.6 |
| gi\|229498269\|ref\|ZP_04391966.1\| | Geobacillus sp. | 38.1 | 42.1 | 40.4 | 31.3 | 35.7 | 39.0 | 31.0 |
| gi\|149202086\|ref\|ZP_01879059.1\| | Roseovarius sp. | 37.4 | 35.9 | 40.4 | 29.7 | 36.4 | 38.1 | 29.1 |
| gi\|86138789\|ref\|ZP_01057361.1\| | Roseobacter sp. | 36.8 | 36.3 | 40.4 | 30.2 | 35.6 | 36.0 | 30.4 |
| gi\|218289429\|ref\|ZP_03493663.1\| | A.acidocaldarius | 39.3 | 43.6 | 40.4 | 29.6 | 36.6 | 38.8 | 30.0 |
| gi\|78066121\|ref\|YP_368890.1\| | Burkholderia sp. | 36.6 | 37.3 | 40.4 | | 34.0 | 36.2 | 27.5 |
| gi\|206559883\|ref\|YP_002230647.1\| | B. cenocepacia | 35.8 | 37.3 | 40.4 | 27.5 | 33.5 | 36.0 | 27.5 |
| gi\|256782189\|ref\|ZP_05520652.1\| | S.hygroscopicus | 38.7 | 34.4 | 40.3 | 29.4 | 40.9 | 38.4 | 29.9 |
| gi\|91762636\|ref\|ZP_01264601.1\| | C. Pelagiba-cter ubique | 36.8 | 40.3 | 40.3 | 27.4 | 32.2 | 36.8 | 27.4 |
| gi\|86741820\|ref\|YP_482220.1\| | Frankia sp. | 68.3 | | 40.3 | | 49.5 | 69.0 | |
| gi\|119964061\|ref\|YP_947516.1\| | A.aurescens | 60.2 | 35.4 | 40.3 | | 43.7 | 62.5 | |
| gi\|270502433\|ref\|ZP_06219340.1\| | M.aurantiaca | 69.3 | 35.6 | 40.3 | | 44.4 | 69.9 | |
| gi\|253576717\|ref\|ZP_04854044.1\| | Paenibacillus sp. | 39.3 | 40.0 | 40.3 | 32.3 | 36.5 | 39.2 | 32.1 |
| gi\|603923\|gb\|AAA74473.1\| | S.erythraea | 64.0 | 38.2 | 40.3 | | 44.9 | 64.2 | |
| gi\|56419596\|ref\|YP_146914.1\| | G.kaustophilus | 38.3 | 42.1 | 40.2 | 31.5 | 36.0 | 39.3 | 31.3 |
| gi\|138894595\|ref\|YP_001125048.1\| | Geobacillus sp. | 39.1 | 41.5 | 40.2 | 31.8 | 36.3 | 39.7 | 31.5 |
| gi\|254509473\|ref\|ZP_05121540.1\| | R. bacterium | 36.8 | 36.1 | 40.2 | 30.4 | 35.4 | 36.9 | 30.4 |
| gi\|84515557\|ref\|ZP_01002919.1\| | L. vestfoldensis | 36.8 | 37.0 | 40.2 | 30.6 | 36.7 | 36.4 | 30.6 |
| gi\|154685878\|ref\|YP_001421039.1\| | B.amyloliquefaciens | 36.8 | 40.7 | 40.2 | 30.9 | 34.6 | 37.1 | 31.6 |
| gi\|256375489\|ref\|YP_003099149.1\| | Actinosynnema mirum | 63.3 | 36.3 | 40.2 | | 44.6 | 64.2 | |

FIG. 3D- BKD E3 Subunit Homologs

| | | | | | | | | |
|---|---|---|---|---|---|---|---|---|
| gi\|126735612\|ref\|ZP_01751357.1\| | Roseobacter sp. | 36.6 | 35.2 | 40.2 | 31.0 | 35.7 | 36.4 | 30.6 |
| gi\|172041520\|ref\|YP_001801234.1\| | C. urealyticum | 36.8 | 35.3 | 40.2 | 28.5 | 34.7 | 36.8 | 29.5 |
| gi\|88856916\|ref\|ZP_01131568.1\| | marine act-ionbacterium | 61.9 | | 40.1 | | 44.4 | 61.5 | |
| gi\|257055101\|ref\|YP_003132933.1\| | S. viridis | 66.4 | | 40.1 | | 44.7 | 64.8 | |
| gi\|227872932\|ref\|ZP_03991234.1\| | O. sinus | 39.7 | 33.3 | 40.1 | 29.3 | 35.4 | 40.7 | 29.3 |
| gi\|89054211\|ref\|YP_509662.1\| | Jannaschia sp. | 35.6 | 35.1 | 40.1 | 29.0 | 33.8 | 35.3 | 28.8 |
| gi\|4335850\|gb\|AAD17483.1\| | S. seoulensis | 90.3 | | 40.1 | 28.3 | 45.4 | 95.9 | |
| gi\|239991630\|ref\|ZP_04712294.1\| | S.roseosporus | 45.1 | | 40.0 | 29.4 | 80.0 | 46.6 | |
| gi\|239945169\|ref\|ZP_04697106.1\| | S.roseosporus | 45.1 | | 40.0 | 29.4 | 80.0 | 46.6 | |
| gi\|163742744\|ref\|ZP_02150129.1\| | P. gallaeciensis | 36.6 | 36.1 | 40.0 | 30.2 | 35.8 | 36.6 | 29.7 |
| gi\|16078525\|ref\|NP_389344.1\| | Bacillus subtilis | 37.2 | 41.6 | 40.0 | 30.7 | 34.8 | 37.5 | 31.3 |
| gi\|258654230\|ref\|YP_003203386.1\| | N.multipartita | 45.6 | | 39.9 | 31.3 | 42.5 | 45.8 | 32.2 |
| gi\|119716531\|ref\|YP_923496.1\| | Nocardioides sp. | 66.1 | 37.2 | 39.9 | | 46.3 | 66.4 | |
| gi\|50084222\|ref\|YP_045732.1\| | Acinetobacter sp. | 35.7 | 36.4 | 39.8 | 29.9 | 32.7 | 34.3 | 29.9 |
| gi\|283567449\|gb\|EFC17875.1\| | B. cellulosilyticus | 39.4 | 42.1 | 39.8 | 29.7 | 35.7 | 39.9 | 31.0 |
| gi\|163736609\|ref\|ZP_02144028.1\| | P.gallaeciensis | 36.1 | 35.9 | 39.8 | 30.0 | 35.8 | 36.2 | 29.5 |
| gi\|193248363\|dbj\|BAG50251.1\| | A.xylanus | 37.4 | 41.3 | 39.8 | 31.5 | 33.8 | 37.8 | 32.2 |
| gi\|283457790\|ref\|YP_003362381.1\| | R.mucilaginosa | 54.2 | 37.6 | 39.8 | | 40.3 | 56.6 | |
| gi\|255327071\|ref\|ZP_05368147.1\| | R. mucilaginosa | 55.7 | 36.7 | 39.8 | | 40.6 | 57.7 | |
| gi\|269127302\|ref\|YP_003300672.1\| | T.curvata | 63.4 | 35.5 | 39.8 | 30.5 | 50.9 | 64.5 | 30.1 |
| gi\|226362323\|ref\|YP_002780101.1\| | R.opacus | 59.0 | | 39.7 | | 46.9 | 58.8 | |
| gi\|226362063\|ref\|YP_002779841.1\| | R. opacus | 59.1 | | 39.7 | | 43.0 | 58.0 | |
| gi\|239931719\|ref\|ZP_04688672.1\| | S.ghanaensis | 90.9 | | 39.7 | 28.1 | 46.1 | 95.9 | |
| gi\|57833863\|ref\|NP_827200.2\| | S.avermitilis | 91.1 | | 39.7 | | 45.7 | 100 | |
| gi\|170783541\|ref\|YP_001742033.1\| | Arthrobacter sp. | 60.0 | 35.3 | 39.7 | | 43.1 | 60.0 | |
| gi\|257867141\|ref\|ZP_05646794.1\| | E.casseliflavus | 35.7 | 42.6 | 39.6 | 31.6 | 32.7 | 36.1 | 32.7 |
| gi\|257877227\|ref\|ZP_05656880.1\| | E. casseliflavus | 35.9 | 42.6 | 39.6 | 31.6 | 32.7 | 36.4 | 32.7 |
| gi\|89099520\|ref\|ZP_01172395.1\| | Bacillus sp. | 35.8 | 41.9 | 39.6 | 29.3 | 34.3 | 37.2 | 31.2 |
| gi\|149183622\|ref\|ZP_01862040.1\| | Bacillus sp. | 35.1 | 40.6 | 39.6 | 29.4 | 34.4 | 36.3 | 29.8 |
| gi\|29828696\|ref\|NP_823330.1\| | S.avermitilis | 45.0 | | 39.5 | | 100 | 45.7 | |
| gi\|254453675\|ref\|ZP_05067112.1\| | O. antarcticus | 35.9 | 34.8 | 39.5 | 31.6 | 36.0 | 36.2 | 31.5 |

FIG. 3D-BKD cont'd

FIG. 3D-BKD cont'd

FIG. 3D- BKD E3 Subunit Homologs

| | | | | | | | | |
|---|---|---|---|---|---|---|---|---|
| gi\|111020307\|ref\|YP_703279.1\| | R.jostii | 58.9 | 35.8 | 39.5 | | 45.6 | 58.1 | |
| gi\|254439769\|ref\|ZP_05053263.1\| | O.antarcticus | 36.3 | 34.6 | 39.4 | 31.3 | 35.6 | 36.8 | 31.4 |
| gi\|269219454\|ref\|ZP_06163308.1\| | Actinomyces sp. | 60.8 | 34.8 | 39.4 | 29.9 | 44.0 | 61.9 | |
| gi\|260906812\|ref\|ZP_05915134.1\| | B.linens | 62.4 | | 39.4 | | 42.0 | 62.6 | |
| gi\|149200388\|ref\|ZP_01877405.1\| | L.araneosa | 36.8 | 33.7 | 39.4 | 28.2 | 35.5 | 36.2 | 28.7 |
| gi\|56964182\|ref\|YP_175913.1\| | Bacillus clausii | 38.4 | 41.3 | 39.2 | 30.6 | 34.0 | 39.2 | 31.9 |
| gi\|260650589\|emb\|CBG73705.1\| | S.scabiei | 89.8 | | 39.2 | 27.7 | 45.2 | 96.5 | |
| gi\|256816690\|ref\|ZP_05541705.1\| | S. griseoflavus | 90.5 | | 39.2 | 28.3 | 45.9 | 93.9 | |
| gi\|163941709\|ref\|YP_001646593.1\| | B.cereus, B.weihenstephanensis, B.mycoides | 37.6 | 42.5 | 39.2 | 29.7 | 33.3 | 38.5 | 29.2 |
| gi\|257387048\|ref\|YP_003176821.1\| | H. mukohataei | 36.9 | 43.5 | 39.2 | 31.9 | 37.2 | 36.0 | 32.1 |
| gi\|116662165\|ref\|YP_829220.1\| | Arthrobacter sp. | 60.3 | 35.1 | 39.2 | | 43.4 | 59.3 | |
| gi\|55379543\|ref\|YP_137393.1\| | H.marismortui | 37.1 | 44.9 | 39.1 | 30.6 | 38.7 | 37.0 | 31.4 |
| gi\|50954699\|ref\|YP_061987.1\| | Leifsonia xyli | 61.6 | 35.1 | 39.1 | 30.3 | 44.2 | 61.7 | |
| gi\|227823515\|ref\|YP_002827488.1\| | Rhizobium sp. | 35.1 | 57.2 | 39.0 | 30.6 | 37.7 | 35.3 | 31.0 |
| gi\|256801334\|ref\|ZP_05530958.1\| | S.viridochro-mogenes | 91.6 | | 39.0 | 28.4 | 44.8 | 95.7 | |
| gi\|229086534\|ref\|ZP_04218706.1\| | Bacillus cereus | 37.6 | 42.9 | 39.0 | 29.7 | 33.3 | 38.4 | 29.2 |
| gi\|228998751\|ref\|ZP_04158337.1\| | B.mycoides | 38.0 | 43.1 | 39.0 | 30.3 | 34.0 | 38.5 | 29.8 |
| gi\|229162903\|ref\|ZP_04290860.1\| | Bacillus cereus | 38.0 | 42.5 | 39.0 | 29.9 | 33.5 | 38.7 | 29.4 |
| gi\|229006267\|ref\|ZP_04163951.1\| | B.mycoides | 38.0 | 42.9 | 39.0 | 30.3 | 34.0 | 38.3 | 29.8 |
| gi\|228992707\|ref\|ZP_04152633.1\| | B. pseudo-mycoides | 38.0 | 42.9 | 39.0 | 30.3 | 34.0 | 38.3 | 29.8 |
| gi\|229098435\|ref\|ZP_04229379.1\| | Bacillus cereus | 37.8 | 42.7 | 39.0 | 29.7 | 33.5 | 38.1 | 29.2 |
| gi\|229019172\|ref\|ZP_04176005.1\| | Bacillus cereus | 37.8 | 42.7 | 39.0 | 29.7 | 33.5 | 38.4 | 29.2 |
| gi\|222478581\|ref\|YP_002564818.1\| | H.lacusprofundi | 33.1 | 44.2 | 38.9 | 30.8 | 39.6 | 33.9 | 30.4 |
| gi\|110680193\|ref\|YP_683200.1\| | R.denitrificans | 37.0 | 35.2 | 38.9 | 31.0 | 36.4 | 36.9 | 30.6 |
| gi\|149914727\|ref\|ZP_01903257.1\| | Roseobacter sp. | 37.2 | 35.7 | 38.9 | 29.5 | 37.2 | 37.0 | 28.7 |
| gi\|157692139\|ref\|YP_001486601.1\| | B.pumilus | 38.3 | 41.8 | 38.9 | 31.8 | 35.5 | 38.2 | 32.1 |
| gi\|229491122\|ref\|ZP_04384950.1\| | R. erythropolis | 58.4 | 35.9 | 38.9 | 33.3 | 45.0 | 58.4 | 32.6 |
| gi\|111019918\|ref\|YP_702890.1\| | R.jostii | 58.0 | | 38.9 | | 42.6 | 56.4 | |
| gi\|227495207\|ref\|ZP_03925523.1\| | A.coleocanis | 63.1 | | 38.8 | | 41.1 | 62.7 | |
| gi\|228922720\|ref\|ZP_04086018.1\| | B.thuringiensis | 38.2 | 42.5 | 38.8 | 30.1 | 33.8 | 38.8 | 29.6 |
| gi\|152976383\|ref\|YP_001375900.1\| | B.cereus,B.cytotoxicus | 38.0 | 43.5 | 38.8 | 29.5 | 34.0 | 38.5 | 29.2 |

FIG. 3D-BKD cont'd

FIG. 3D- BKD E3 Subunit Homologs

| | | | | | | | | |
|---|---|---|---|---|---|---|---|---|
| gi\|30022058\|ref\|NP_833689.1\| | B.thuringiensis,B.cereus | 38.0 | 42.7 | 38.8 | 29.9 | 33.8 | 38.5 | 29.3 |
| gi\|228966992\|ref\|ZP_04128030.1\| | B.thuringiensis | 37.8 | 42.7 | 38.8 | 29.9 | 33.9 | 38.1 | 29.4 |
| gi\|27381445\|ref\|NP_772974.1\| | B. japonicum | 33.0 | 56.5 | 38.8 | 30.3 | 38.5 | 32.3 | 30.5 |
| gi\|150398027\|ref\|YP_001328494.1\| | S.medicae | 35.7 | 56.5 | 38.7 | 32.1 | 36.9 | 35.8 | 32.3 |
| gi\|256775687\|ref\|ZP_05514150.1\| | S.hygroscopicus | 45.4 | | 38.7 | | 80.9 | 44.9 | |
| gi\|184201087\|ref\|YP_001855294.1\| | K.rhizophila | 57.6 | 37.2 | 38.7 | 29.4 | 41.6 | 58.9 | 28.7 |
| gi\|257068804\|ref\|YP_003155059.1\| | B. faecium | 61.2 | | 38.6 | | 42.1 | 61.2 | |
| gi\|163764130\|ref\|ZP_02171188.1\| | B.selenitireducens | 36.8 | 40.8 | 38.6 | 30.1 | 33.8 | 37.5 | 30.7 |
| gi\|196038740\|ref\|ZP_03106048.1\| | B. cereus | 38.0 | 42.7 | 38.6 | 29.7 | 33.5 | 38.3 | 29.8 |
| gi\|30264041\|ref\|NP_846418.1\| | B. anthracis, B. cereus, B. thuringiensis | 38.0 | 42.7 | 38.6 | 29.7 | 33.8 | 38.5 | 29.8 |
| gi\|42783065\|ref\|NP_980312.1\| | B. cereus, B. thuringiensis | 38.0 | 42.7 | 38.6 | 29.7 | 33.8 | 38.5 | 29.2 |
| gi\|163731374\|ref\|ZP_02138821.1\| | R.litoralis | 37.2 | 35.2 | 38.5 | 31.0 | 36.2 | 37.1 | 30.6 |
| gi\|229541253\|ref\|ZP_04430313.1\| | B.coagulans | 37.3 | 42.9 | 38.4 | 30.3 | 34.7 | 37.7 | 30.5 |
| gi\|222150963\|ref\|YP_002560116.1\| | M.caseolyticus | 36.7 | 41.1 | 38.4 | 31.0 | 34.0 | 37.1 | 31.3 |
| gi\|239636400\|ref\|ZP_04677402.1\| | S. warneri | 37.6 | 40.9 | 38.4 | 28.6 | 34.9 | 37.5 | 29.1 |
| gi\|148272824\|ref\|YP_001222385.1\| | C.michiganensis | 63.0 | 35.7 | 38.4 | 30.2 | 43.3 | 61.0 | 30.2 |
| gi\|258652087\|ref\|YP_003201243.1\| | N.multipartita | 61.2 | | 38.3 | | 43.2 | 61.8 | |
| gi\|461933\|sp\|Q04829.2\|DLDH_HALVO | H.volcanii | 34.8 | 45.7 | 38.3 | 31.2 | 37.4 | 35.8 | 31.2 |
| gi\|226309468\|ref\|YP_002769430.1\| | R.erythropolis | 59.4 | 34.7 | 38.2 | 32.9 | 45.6 | 58.9 | 32.3 |
| gi\|228474296\|ref\|ZP_04059031.1\| | S. hominis | 37.3 | 40.0 | 38.2 | 29.2 | 34.6 | 37.3 | 29.4 |
| gi\|170782016\|ref\|YP_001710348.1\| | C. Michiganensis | 62.8 | 36.8 | 38.2 | 30.0 | 43.5 | 60.6 | 30.0 |
| gi\|227880919\|ref\|ZP_03998781.1\| | H. borinquense | 35.1 | 42.5 | 38.2 | 30.4 | 37.2 | 34.9 | 30.0 |
| gi\|114569260\|ref\|YP_755940.1\| | M. maris | | 53.0 | 38.1 | | 35.8 | | 30.0 |
| gi\|27467712\|ref\|NP_764349.1\| | S.epidermidis | 38.0 | 41.1 | 38.0 | 28.8 | 34.6 | 38.0 | 28.8 |
| gi\|88194795\|ref\|YP_499592.1\| | S. aureus | 37.6 | 40.0 | 38.0 | 29.3 | 33.8 | 37.7 | 29.3 |
| gi\|15924086\|ref\|NP_371620.1\| | S. aureus | 37.8 | 40.0 | 38.0 | 29.3 | 33.8 | 38.0 | 29.7 |
| gi\|87161349\|ref\|YP_493694.1\| | S. aureus | 37.8 | 40.0 | 38.0 | 28.9 | 34.0 | 38.0 | 29.7 |
| gi\|242373317\|ref\|ZP_04818891.1\| | S. epidermidis | 37.8 | 41.1 | 38.0 | 28.6 | 34.6 | 37.7 | 28.6 |
| gi\|229556156\|ref\|ZP_04443945.1\| | Listeria grayi | 36.7 | 41.3 | 37.8 | 30.6 | 33.8 | 38.0 | 30.6 |
| gi\|223043880\|ref\|ZP_03613922.1\| | S. capitis | 37.8 | 40.5 | 37.8 | 28.6 | 34.4 | 37.7 | 28.6 |
| gi\|70726857\|ref\|YP_253771.1\| | S. haemolyticus | 38.3 | 40.0 | 37.8 | 28.4 | 34.0 | 38.4 | 28.6 |

FIG. 3D-BKD cont'd

FIG. 3D- BKD E3 Subunit Homologs

| | | | | | | | | |
|---|---|---|---|---|---|---|---|---|
| gi\|15966688\|ref\|NP_387041.1\| | S. meliloti | 35.3 | 56.6 | 37.8 | 32.1 | 36.9 | 34.5 | 32.1 |
| gi\|126649795\|ref\|ZP_01722031.1\| | Bacillus sp. | 37.1 | 43.2 | 37.7 | 30.8 | 34.9 | 37.4 | 31.9 |
| gi\|167645837\|ref\|YP_001683500.1\| | Caulobacter sp. | | 56.5 | 37.7 | | 36.6 | | |
| gi\|229820355\|ref\|YP_002881881.1\| | B.cavernae | 60.5 | | 37.6 | | 46.8 | 61.0 | |
| gi\|28493469\|ref\|NP_787630.1\| | T. whipplei | 49.2 | 34.2 | 37.5 | | 39.3 | 50.3 | |
| gi\|28572419\|ref\|NP_789199.1\| | T. whipplei | 49.2 | 34.0 | 37.5 | | 39.3 | 50.3 | |
| gi\|169826946\|ref\|YP_001697104.1\| | L.sphaericus | 36.9 | 43.0 | 37.5 | 30.8 | 35.1 | 37.2 | 31.9 |
| gi\|257052876\|ref\|YP_003130709.1\| | H.utahensis | 33.8 | 44.3 | 37.4 | 32.1 | 39.5 | 34.7 | 32.4 |
| gi\|28378764\|ref\|NP_785656.1\| | L. plantarum | 36.2 | 42.3 | 37.4 | 31.3 | 33.7 | 36.7 | 31.2 |
| gi\|150011035\|gb\|ABR57174.1\| | S. xylosus | 38.0 | 40.5 | 37.4 | 28.2 | 34.5 | 38.0 | 28.4 |
| gi\|73663002\|ref\|YP_301783.1\| | S. saprophy-ticus | 38.5 | 40.7 | 37.4 | 28.2 | 34.7 | 38.4 | 28.4 |
| gi\|255292429\|dbj\|BAH89547.1\| | uncultured bacterium | 33.0 | 56.5 | 37.4 | 30.4 | 37.5 | 33.8 | 30.9 |
| gi\|154508739\|ref\|ZP_02044381.1\| | A.odontolyticus | 59.7 | 35.7 | 37.3 | | 42.8 | 61.2 | |
| gi\|224822709\|ref\|ZP_03695826.1\| | N.magadii | 35.6 | 42.0 | 37.3 | 32.8 | 37.0 | 35.5 | 32.0 |
| gi\|83859619\|ref\|ZP_00953139.1\| | O. alexandrii | 35.6 | 52.7 | 37.1 | | 35.2 | 36.3 | |
| gi\|239917833\|ref\|YP_002957391.1\| | M.luteus | 61.0 | 36.1 | 37.1 | 28.4 | 40.6 | 61.2 | |
| gi\|227875545\|ref\|ZP_03993685.1\| | M.mulieris | 55.5 | 33.0 | 36.9 | | 40.7 | 55.8 | |
| gi\|269977210\|ref\|ZP_06184183.1\| | M.mulieris | 55.5 | 33.0 | 36.9 | | 40.7 | 55.8 | |
| gi\|111020366\|ref\|YP_703338.1\| | R.jostii | 56.5 | 37.5 | 36.9 | | 47.1 | 56.9 | |
| gi\|90420467\|ref\|ZP_01228374.1\| | A. mangan-oxydans | | 57.6 | 36.7 | | 37.1 | | |
| gi\|167566999\|ref\|ZP_02359915.1\| | B.oklahomensis | 34.0 | 67.2 | 36.5 | | 36.7 | 34.2 | |
| gi\|167590840\|ref\|ZP_02383228.1\| | B.ubonensis | | 68.0 | 36.5 | 31.6 | 36.1 | | 31.6 |
| gi\|227493838\|ref\|ZP_03924154.1\| | M.curtisii | 56.3 | 33.8 | 36.4 | 29.1 | 41.3 | 56.3 | |
| gi\|163796020\|ref\|ZP_02189983.1\| | alpha prote-obacterium | 34.5 | 60.3 | 36.4 | 30.9 | 37.3 | 34.6 | 32.0 |
| gi\|163857821\|ref\|YP_001632119.1\| | Bordetella petrii | 33.9 | 68.8 | 36.3 | | 36.4 | 34.2 | 29.0 |
| gi\|239833854\|ref\|ZP_04682182.1\| | O.intermedium | | 58.3 | 36.3 | | 36.9 | 33.0 | 31.4 |
| gi\|209546468\|ref\|YP_002278386.1\| | R. legumino-sarum | | 57.9 | 36.2 | 31.2 | 38.5 | 33.5 | 31.6 |
| gi\|84683578\|ref\|ZP_01011481.1\| | R.bacterium | 34.6 | 55.5 | 36.2 | | 37.8 | 34.3 | |
| gi\|260469855\|ref\|ZP_05814003.1\| | M. opportunistum | | 60.4 | 36.2 | | 36.0 | 33.2 | 30.0 |
| gi\|13473766\|ref\|NP_105334.1\| | M. loti | | 60.0 | 36.2 | | 36.8 | | 30.1 |
| gi\|153010875\|ref\|YP_001372089.1\| | O.anthropi | | 57.9 | 36.2 | | 36.5 | | 32.1 |

FIG. 3D-BKD cont'd

FIG. 3D- BKD E3 Subunit Homologs

| | | | | | | | | |
|---|---|---|---|---|---|---|---|---|
| gi\|169627993\|ref\|YP_001701642.1\| | M. abscessus | 57.5 | | 36.1 | 33.9 | 43.8 | 56.4 | |
| gi\|152989284\|ref\|YP_001348351.1\| | P. aeruginosa | 36.1 | 73.3 | 36.0 | 30.6 | 37.6 | 36.6 | 30.8 |
| gi\|70729899\|ref\|YP_259638.1\| | P. fluorescens | | 76.0 | 36.0 | | 34.7 | | |
| gi\|116050197\|ref\|YP_790986.1\| | P. aeruginosa | 36.1 | 73.3 | 35.9 | 30.2 | 37.8 | 36.4 | 30.6 |
| gi\|254240691\|ref\|ZP_04934013.1\| | P.aeruginosa | 36.1 | 73.1 | 35.9 | 30.2 | 37.8 | 36.4 | 30.6 |
| gi\|227496253\|ref\|ZP_03926549.1\| | A.urogenitalis | 60.5 | | 35.8 | | 40.0 | 61.2 | |
| gi\|218891776\|ref\|YP_002440643.1\| | P. aeruginosa | 35.9 | 73.1 | 35.7 | 30.0 | 37.8 | 36.2 | 30.4 |
| gi\|107101696\|ref\|ZP_01365614.1\| | P. aeruginosa | 35.9 | 73.1 | 35.7 | 30.4 | 37.6 | 36.2 | 30.8 |
| gi\|15597446\|ref\|NP_250940.1\| | P.aeruginosa | 35.9 | 73.1 | 35.7 | 30.6 | 37.6 | 36.2 | 31.0 |
| gi\|53723288\|ref\|YP_112273.1\| | B.pseudomallei | 34.5 | 68.7 | 35.7 | | 35.7 | 34.2 | |
| gi\|53716068\|ref\|YP_106528.1\| | B.mallei | 34.5 | 68.2 | 35.7 | | 35.5 | 34.2 | |
| gi\|241554276\|ref\|YP_002979489.1\| | R.leguminosarum | 32.8 | 57.1 | 35.6 | 30.1 | 38.5 | 33.5 | 30.9 |
| gi\|116254748\|ref\|YP_770584.1\| | R.leguminosarum | 33.0 | 57.7 | 35.6 | 30.5 | 37.3 | 33.5 | 31.6 |
| gi\|86360118\|ref\|YP_472007.1\| | Rhizobium etli | 33.4 | 58.4 | 35.6 | 30.5 | 38.5 | 33.6 | 31.3 |
| gi\|126740936\|ref\|ZP_01756620.1\| | Roseobacter sp. | 34.7 | 56.0 | 35.5 | 32.0 | 35.9 | 34.4 | 32.3 |
| gi\|126442365\|ref\|YP_001064181.1\| | B.pseudomallei | 34.3 | 68.5 | 35.5 | | 35.7 | 34.0 | |
| gi\|167908242\|ref\|ZP_02495447.1\| | B.pseudomallei | 34.6 | 68.5 | 35.5 | | 36.2 | 34.0 | |
| gi\|76818035\|ref\|YP_336565.1\| | B. pseudo-allei | 34.3 | 68.5 | 35.5 | | 35.5 | 34.0 | |
| gi\|167725355\|ref\|ZP_02408591.1\| | B. pseudo-allei | 34.6 | 68.5 | 35.5 | | 36.0 | 34.0 | |
| gi\|167579154\|ref\|ZP_02372028.1\| | B. thailandensis | 33.6 | 68.7 | 35.5 | | 37.2 | 33.3 | |
| gi\|83717960\|ref\|YP_440488.1\| | B. thailandensis | 33.4 | 68.7 | 35.5 | | 37.2 | 33.1 | |
| gi\|170701858\|ref\|ZP_02892788.1\| | B. ambifaria | | 68.8 | 35.4 | 30.5 | 37.8 | | 32.3 |
| gi\|104782860\|ref\|YP_609358.1\| | P. entomophila | | 91.7 | 35.4 | | | 36.0 | |
| gi\|172060192\|ref\|YP_001807844.1\| | B. ambifaria | | 68.6 | 35.3 | 30.8 | 37.3 | 32.5 | 31.9 |
| gi\|119387483\|ref\|YP_918517.1\| | P. denitrificans | | 58.4 | 35.3 | | 38.4 | | |
| gi\|77459688\|ref\|YP_349195.1\| | P. fluorescens | | 76.1 | 35.3 | | 34.6 | | |
| gi\|225628959\|ref\|ZP_03786993.1\| | B.ceti, B. pin- nipedialis, B. suis | 33.0 | 57.2 | 35.2 | | 36.8 | | 32.5 |
| gi\|256059274\|ref\|ZP_05449476.1\| | B.neotomae | 33.0 | 57.2 | 35.2 | | 36.8 | | 32.5 |
| gi\|254720463\|ref\|ZP_05182274.1\| | Brucella sp. | | 57.2 | 35.2 | | 36.6 | | 32.7 |
| gi\|115351179\|ref\|YP_773018.1\| | B.ambifaria | | 68.6 | 35.1 | | 37.6 | 32.5 | 31.7 |
| gi\|167840920\|ref\|ZP_02467604.1\| | B.thailandensis | 33.8 | 68.2 | 35.0 | | 36.3 | 34.3 | |

FIG. 3D- BKD E3 Subunit Homologs

| | | | | | | | | |
|---|---|---|---|---|---|---|---|---|
| gi\|23500274\|ref\|NP_699714.1\| | Brucella suis | | 57.0 | 35.0 | | 36.8 | | 32.3 |
| gi\|254702906\|ref\|ZP_05164734.1\| | Brucella suis bv. | 32.8 | 56.7 | 35.0 | | 36.6 | | 32.3 |
| gi\|229591399\|ref\|YP_002873518.1\| | P. fluorescens | 36.0 | 77.6 | 34.9 | | 35.3 | 36.3 | |
| gi\|78065834\|ref\|YP_368603.1\| | Burkholderia sp. | 32.6 | 69.7 | 34.9 | 31.0 | 36.7 | 32.6 | 31.1 |
| gi\|254467522\|ref\|ZP_05080932.1\| | R. bacterium | 33.9 | 56.9 | 34.9 | 33.5 | 36.3 | 34.2 | 33.1 |
| gi\|171320116\|ref\|ZP_02909181.1\| | B.ambifaria | | 69.1 | 34.8 | | 37.8 | 33.0 | |
| gi\|170732569\|ref\|YP_001764516.1\| | B.cenocepacia | | 69.3 | 34.8 | 30.8 | 37.2 | | 32.1 |
| gi\|107022321\|ref\|YP_620648.1\| | B.cenocepacia | | 69.7 | 34.8 | 30.8 | 37.6 | | 32.1 |
| gi\|99082615\|ref\|YP_614769.1\| | Ruegeria sp. | 33.4 | 55.3 | 34.8 | 32.0 | 36.8 | 33.3 | 32.5 |
| gi\|62317612\|ref\|YP_223465.1\| | B.abortus | 33.2 | 57.2 | 34.8 | 31.5 | 36.6 | | 32.3 |
| gi\|148558309\|ref\|YP_001257493.1\| | Brucella ovis | | 56.7 | 34.8 | | 36.6 | | 32.3 |
| gi\|206559592\|ref\|YP_002230353.1\| | B. cenocepacia | | 69.5 | 34.7 | 31.3 | 37.2 | | 31.1 |
| gi\|256111572\|ref\|ZP_05452567.1\| | B.melitensis | | 55.4 | 34.4 | | 36.3 | | 31.5 |
| gi\|254695585\|ref\|ZP_05157413.1\| | B.abortus | | 55.4 | 34.2 | | 36.0 | | 31.3 |
| gi\|157831895\|pdb\|1LVL\|A | | | 98.0 | | | | 35.2 | |
| gi\|56554479\|pdb\|1XDI\|A | | | | | 55.0 | | | 54.9 |
| gi\|280960167\|ref\|ZP_06234743.1\| | Frankia sp. | | | | 59.5 | | | 60.3 |
| gi\|229240529\|ref\|ZP_04364928.1\| | C. flavigena | | | | 60.3 | | | 60.7 |
| gi\|158317672\|ref\|YP_001510180.1\| | Frankia sp. | | | | 60.7 | | | 61.1 |
| gi\|254403159\|ref\|ZP_05018105.1\| | S.sviceus | | | | 95.6 | | | 94.3 |
| gi\|229489632\|ref\|ZP_04383495.1\| | R.erythropolis | | | | 59.0 | | | 58.9 |
| gi\|111220667\|ref\|YP_711461.1\| | Frankia alni | | | | 58.3 | | | 58.7 |
| gi\|29829882\|ref\|NP_824516.1\| | S.avermitilis | | | | 100 | | | 93.9 |
| gi\|227502797\|ref\|ZP_03932846.1\| | C. accolens | | | | 53.8 | | | 53.4 |
| gi\|145294861\|ref\|YP_001137682.1\| | C. glutamicum R | | | | 55.0 | | | 55.2 |
| gi\|54022934\|ref\|YP_117176.1\| | N.farcinica | | | | 56.5 | | | 57.0 |
| gi\|269795840\|ref\|YP_003315295.1\| | S. keddieii | | | | 64.3 | | | 64.6 |
| gi\|255323923\|ref\|ZP_05365049.1\| | C. tubercul-ostearicum | | | | 54.4 | | | 54.0 |
| gi\|271962830\|ref\|YP_003337026.1\| | S. roseum | | | | 64.2 | | | 64.0 |
| gi\|31794483\|ref\|NP_856976.1\| | M. bovis | | | | 55.0 | | | 55.1 |
| gi\|227489858\|ref\|ZP_03920174.1\| | C.pseudoenitalium | | | | 54.3 | | | 53.8 |

FIG. 3D-BKD cont'd

FIG. 3D-BKD cont'd

FIG. 3D- BKD E3 Subunit Homologs

| | | | | | | | | |
|---|---|---|---|---|---|---|---|---|
| gi\|237786113\|ref\|YP_002906818.1\| | C. kroppen-stedtii | | | | 52.6 | | | 53.6 |
| gi\|15610439\|ref\|NP_217820.1\| | M. tuberculosis | | | | 55.0 | | | 54.9 |
| gi\|239917098\|ref\|YP_002956656.1\| | M.luteus | | | | 57.9 | | | 57.5 |
| gi\|170722908\|ref\|YP_001750596.1\| | P. putida | | 91.7 | | | | 35.5 | |
| gi\|262185874\|ref\|ZP_06045295.1\| | A. marinum | | | | 66.6 | | | 68.1 |
| gi\|239943809\|ref\|ZP_04695746.1\| | S.roseosporus | | | | 92.3 | | | 92.9 |
| gi\|229206289\|ref\|ZP_04332745.1\| | N.dassonvillei | | | | 62.4 | | 32.7 | 62.2 |
| gi\|159036439\|ref\|YP_001535692.1\| | S. arenicola | | | | 60.6 | | | 61.2 |
| gi\|260454505\|ref\|ZP_05802903.1\| | S. flavogriseus | | | | 92.9 | | | 93.1 |
| gi\|111023225\|ref\|YP_706197.1\| | R. jostii | | | | 58.2 | | | 57.9 |
| gi\|254389897\|ref\|ZP_05005120.1\| | S.clavuligerus | | | | 87.2 | | | 87.6 |
| gi\|256666100\|ref\|ZP_05477053.1\| | Streptomyces sp. | | | | 59.8 | | | 60.0 |
| gi\|225020595\|ref\|ZP_03709787.1\| | C. matruchotii | | | | 56.2 | | | 56.0 |
| gi\|163841694\|ref\|YP_001626099.1\| | R.salmoninarum | | | | 60.8 | | | 60.6 |
| gi\|117927603\|ref\|YP_872154.1\| | A.cellulolyticus | | | | 59.7 | | | 60.3 |
| gi\|118677\|sp\|P09063.1\|DLDH1_PSEPU | P.putida | | 98.0 | | | | 35.2 | |
| gi\|108798220\|ref\|YP_638417.1\| | Mycobacterium sp. | | | | 55.7 | | | 55.8 |
| gi\|116669824\|ref\|YP_830757.1\| | Arthrobacter sp. | | | | 60.6 | | | 60.8 |
| gi\|255327279\|ref\|ZP_05368353.1\| | R. mucilaginosa | | | | 57.4 | | | 58.9 |
| gi\|259506600\|ref\|ZP_05749502.1\| | C. efficiens | | | | 55.3 | | | 55.3 |
| gi\|25027264\|ref\|NP_737318.1\| | C. efficiens | | | | 55.3 | | | 55.3 |
| gi\|229821413\|ref\|YP_002882939.1\| | B.cavernae | | | | 64.6 | | | 64.6 |
| gi\|119717739\|ref\|YP_924704.1\| | Nocardioides sp. | | | | 67.5 | | | 67.0 |
| gi\|86739409\|ref\|YP_479809.1\| | Frankia sp. | | | | 58.7 | | | 59.5 |
| gi\|50954277\|ref\|YP_061565.1\| | Leifsonia xyli | | | | 55.9 | | | 56.3 |
| gi\|226365732\|ref\|YP_002783515.1\| | R.opacus | | | | 57.9 | | | 57.7 |
| gi\|118473132\|ref\|YP_886107.1\| | M. smegmatis | | | | 57.3 | | | 57.7 |
| gi\|227377910\|ref\|ZP_03861371.1\| | Kribbella flavida | | | | 67.8 | | | 67.4 |
| gi\|257069259\|ref\|YP_003155514.1\| | B. faecium | | | | 60.3 | | | 60.5 |
| gi\|253800346\|ref\|YP_003033347.1\| | acterium tuberculosis | | | | 55.0 | | | 54.9 |
| gi\|227549952\|ref\|ZP_03980001.1\| | C. lipophilo-flavum | | | | 50.4 | | | 50.6 |

FIG. 3D-BKD cont'd

FIG. 3D- BKD E3 Subunit Homologs

| | | | | | | | | |
|---|---|---|---|---|---|---|---|---|
| gi\|84498060\|ref\|ZP_00996857.1\| | Janibacter sp. | | | | 62.5 | | | 63.8 |
| gi\|238062645\|ref\|ZP_04607354.1\| | Micromonospora sp. | | | | 61.0 | | | 61.5 |
| gi\|259417932\|ref\|ZP_05741851.1\| | Silicibacter sp. | 32.5 | 54.2 | | 31.0 | 36.8 | 32.6 | 31.2 |
| gi\|256832074\|ref\|YP_003160801.1\| | J.denitrificans | | | | 58.8 | | | 58.1 |
| gi\|28572194\|ref\|NP_788974.1\| | T.whipplei | | | | 48.0 | | | 48.0 |
| gi\|256814153\|ref\|ZP_05539168.1\| | S.griseoflavus | | | | 95.3 | | | 94.8 |
| gi\|19551918\|ref\|NP_599920.1\| | C.glutamicum | | | | 55.2 | | | 55.5 |
| gi\|167034960\|ref\|YP_001670191.1\| | P.putida | | 96.7 | | | | 35.4 | |
| gi\|265989842\|ref\|ZP_06102399.1\| | B.melitensis | | 56.8 | | | | | |
| gi\|226305568\|ref\|YP_002765528.1\| | R.erythropolis | | | | 59.0 | | | 58.9 |
| gi\|15842894\|ref\|NP_337931.1\| | M. tuberculosis | | | | 55.0 | | | 54.9 |
| gi\|270503359\|ref\|ZP_06220248.1\| | M.aurantiaca | | | | 61.5 | | | 61.7 |
| gi\|239979765\|ref\|ZP_04702289.1\| | S.albus | | | | 92.1 | | | 92.0 |
| gi\|227832367\|ref\|YP_002834074.1\| | C.aurimucosum | | | | 53.3 | | | 53.7 |
| gi\|256804230\|ref\|ZP_05533854.1\| | S. viridochr-omogenes | | | | 94.6 | | | 94.4 |
| gi\|238023735\|ref\|YP_002907967.1\| | B. glumae | | 66.7 | | | 38.3 | | |
| gi\|148553702\|ref\|YP_001261284.1\| | S.wittichii | 35.7 | 58.0 | | | 40.8 | 36.4 | |
| gi\|21223293\|ref\|NP_629072.1\| | S.coelicolor | | | | 93.9 | | | 100 |
| gi\|256676912\|ref\|ZP_05487223.1\| | Streptomyces sp. | | | | 90.8 | | | 91.7 |
| gi\|227505366\|ref\|ZP_03935415.1\| | C striatum | | | | 53.7 | | | 54.2 |
| gi\|227980211\|ref\|ZP_04027474.1\| | T.paurometabola | | | | 57.3 | | | 57.7 |
| gi\|254293979\|ref\|YP_003060002.1\| | Hirschia baltica | | 52.1 | | | | | |
| gi\|83269595\|ref\|YP_418886.1\| | B. melitensis | | 55.4 | | | 36.1 | | 31.3 |
| gi\|50843181\|ref\|YP_056408.1\| | P. acnes | | | | 60.7 | | | 59.8 |
| gi\|256778680\|ref\|ZP_05517143.1\| | S.hygroscopicus | | | | 91.4 | | | 92.9 |
| gi\|145593395\|ref\|YP_001157692.1\| | S.tropica | | | | 60.4 | | | 60.8 |
| gi\|254776713\|ref\|ZP_05218229.1\| | M. avium | | | | 54.7 | | | 55.2 |
| gi\|258651596\|ref\|YP_003200752.1\| | N. multipartita | | | | 60.0 | | | 59.4 |
| gi\|227497391\|ref\|ZP_03927623.1\| | A.urogenitalis | | | | 54.6 | | | 54.4 |
| gi\|88856471\|ref\|ZP_01131129.1\| | marine acti-nobacterium | | | | 55.7 | | | 56.0 |
| gi\|239929279\|ref\|ZP_04686232.1\| | S. ghanaensis | | | | 95.5 | | | 94.8 |

FIG. 3D-BKD cont'd

FIG. 3D- BKD E3 Subunit Homologs

| | | | | | | | | |
|---|---|---|---|---|---|---|---|---|
| gi\|256785601\|ref\|ZP_05524032.1\| | S. lividans | | | | 94.0 | | | 99.6 |
| gi\|252127883\|ref\|ZP_04837278.1\| | C.matruchotii | | | | 56.2 | | | 56.0 |
| gi\|283458569\|ref\|YP_003363202.1\| | R. mucilaginosa | | | | 57.4 | | | 58.9 |
| gi\|213961491\|ref\|ZP_03389769.1\| | P. acnes | | | | 60.9 | | | 60.0 |
| gi\|257054641\|ref\|YP_003132473.1\| | S. viridis | | | | 59.1 | | | 59.7 |
| gi\|254419260\|ref\|ZP_05032984.1\| | Brevundimonas sp. | | 58.3 | | | 36.1 | | |
| gi\|262201735\|ref\|YP_003272943.1\| | G. bronchialis | | | | 56.0 | | | 56.2 |
| gi\|254394273\|ref\|ZP_05009353.1\| | S.pristinaespiralis | | | | 94.9 | | | 93.9 |
| gi\|189022864\|ref\|YP_001932605.1\| | B. abortus | | 54.0 | | | | | |
| gi\|26991093\|ref\|NP_746518.1\| | P. putida | | 98.9 | | | | 35.4 | |
| gi\|182436417\|ref\|YP_001824136.1\| | S.griseus | | | | 92.6 | | | 93.2 |
| gi\|269128375\|ref\|YP_003301745.1\| | T. curvata | | | | 60.7 | | | 60.6 |
| gi\|170781043\|ref\|YP_001709375.1\| | C.michiganensis | | | | 57.6 | | | 57.2 |
| gi\|282868208\|ref\|ZP_06277220.1\| | Streptomyces sp. | | | | 92.3 | | | 92.9 |
| gi\|119962835\|ref\|YP_947178.1\| | A.aurescens | | | | 60.3 | | | 60.3 |
| gi\|254385156\|ref\|ZP_05000488.1\| | Streptomyces sp. | | | | 91.2 | | | 91.4 |
| gi\|145225400\|ref\|YP_001136078.1\| | M.gilvum | | | | 57.0 | | | 56.7 |
| gi\|126433878\|ref\|YP_001069569.1\| | Mycobacterium sp. | | | | 54.9 | | | 55.4 |
| gi\|269955807\|ref\|YP_003325596.1\| | X.cellulosilytica | | | | 63.6 | | | 63.1 |
| gi\|220912080\|ref\|YP_002487389.1\| | A. chloroph-enolicus | | | | 60.8 | | | 61.6 |
| gi\|41409522\|ref\|NP_962358.1\| | M. avium | | | | 54.5 | | | 55.0 |
| gi\|258561245\|ref\|ZP_05707919.1\| | C. genitalium | | | | 52.1 | | | 51.9 |
| gi\|213964806\|ref\|ZP_03393005.1\| | C. amycolatum | | | | 56.5 | | | 56.1 |
| gi\|254245803\|ref\|ZP_04939124.1\| | B.cenocepacia | | 68.4 | | | | | |
| gi\|260647455\|emb\|CBG70560.1 | S.scabiei | | | | 93.0 | | | 92.4 |
| gi\|256380391\|ref\|YP_003104051.1\| | A. mirum | | | | 60.5 | | | 60.7 |
| gi\|260906835\|ref\|ZP_05915157.1\| | B. linens | | | | 60.6 | | | 60.8 |
| gi\|215405316\|ref\|ZP_03417497.1\| | M. tuberculosis | | | | 55.0 | | | 55.1 |
| gi\|240171337\|ref\|ZP_04749996.1\| | M. kansasii | | | | 53.5 | | | 54.3 |
| gi\|28492986\|ref\|NP_787147.1\| | T.whipplei | | | | 48.0 | | | 48.0 |
| gi\|254820221\|ref\|ZP_05225222.1\| | M. intracellulare | | | | 53.5 | | | 54.5 |

FIG. 3D-BKD cont'd

FIG. 3D- BKD E3 Subunit Homologs

| | | | | | | | | |
|---|---|---|---|---|---|---|---|---|
| gi\|229863055\|ref\|ZP_04482668.1\| | S. nassauensis | | | | 58.6 | | | 59.7 |
| gi\|120402625\|ref\|YP_952454.1\| | M. vanbaalenii | | | | 55.4 | | | 55.7 |
| gi\|184201346\|ref\|YP_001855553.1\| | K.rhizophila | | | | 59.6 | | | 59.6 |
| gi\|134102959\|ref\|YP_001108620.1\| | S. erythraea | | | | 57.0 | | | 57.8 |
| gi\|148272170\|ref\|YP_001221731.1\| | C. Michiganensis | | | | 57.8 | | | 57.4 |
| gi\|183981246\|ref\|YP_001849537.1\| | M. marinum | | | | 54.5 | | | 55.1 |
| gi\|256824677\|ref\|YP_003148637.1\| | K.sedentarius | | | | 58.3 | | | 59.1 |
| gi\|256769407\|ref\|ZP_05508581.1\| | Streptomyces sp. | | | | 90.8 | | | 91.4 |
| gi\|269922270\|ref\|ZP_06171177.1\| | B. subvibrioides | | 58.4 | | | 36.5 | | |
| gi\|282861019\|ref\|ZP_06270085.1\| | Streptomyces sp. | | | | 92.3 | | | 93.8 |
| gi\|254233911\|ref\|ZP_04927236.1\| | M.tuberculosis C | | | | 57.7 | | | 57.6 |
| gi\|282855061\|ref\|ZP_06264393.1\| | P. acnes | | | | 60.5 | | | 59.6 |
| gi\|169630735\|ref\|YP_001704384.1\| | M. abscessus | | | | 57.1 | | | 57.9 |
| gi\|38233252\|ref\|NP_939019.1\| | C.diphtheriae | | | | 55.0 | | | 54.6 |
| gi\|152967861\|ref\|YP_001363645.1\| | K.radiotolerans | | | | 66.7 | | | 66.0 |
| gi\|256390018\|ref\|YP_003111582.1\| | C. acidiphila | | | | 65.9 | | | 66.2 |
| gi\|227486987\|ref\|ZP_03917303.1\| | C. glucuron-olyticum | | | | 53.1 | | | 52.7 |
| gi\|72162958\|ref\|YP_290615.1\| | T. fusca | | | | 61.8 | | | 62.2 |
| gi\|227409693\|ref\|ZP_03892909.1\| | G. obscurus | | | | 60.1 | | | 61.6 |
| gi\|118618128\|ref\|YP_906460.1\| | M. ulcerans | | | | 54.9 | | | 55.5 |
| gi\|225686319\|ref\|YP_002734291.1\| | B.melitensis | | 55.4 | | | 36.1 | | 31.3 |
| gi\|148546690\|ref\|YP_001266792.1\| | P.putida F1 | | 100 | | | | 35.2 | |

FIG. 3E: Beta Ketoacyl-ACP Synthase Homologs

| Acc. No. | Organism | ID% Li | ID%Sm | ID%Sa | ID%Ec | ID%Sav |
|---|---|---|---|---|---|---|
| gi\|145886\|gb\|AAA23741.1\| | Escherichia coli | 39.0 | 34.8 | 38.4 | 100 | 33.9 |
| gi\|41365\|emb\|CAA77659.1\| | Escherichia coli | | | 37.7 | 100 | |
| gi\|147302\|gb\|AAB59065.1\| | Escherichia coli | | | | 100 | |
| gi\|157160617\|ref\|YP_001457935.1 | Escherichia coli | 38.3 | 38.1 | 40.3 | 99.7 | 36.4 |
| gi\|209918346\|ref\|YP_002292430.1 | Escherichia coli | 38.3 | 37.8 | 40.3 | 99.7 | 36.7 |
| gi\|82777296\|ref\|YP_403645.1\| | Shigella dysenteriae | 38.0 | 37.8 | 40.3 | 99.7 | 36.7 |
| gi\|24112497\|ref\|NP_707007.1\| | Shigella flexneri, boydii | 38.0 | 37.5 | 39.9 | 99.7 | 36.4 |
| gi\|170768244\|ref\|ZP_02902697.1\| | Escherichia albertii | 38.6 | 37.5 | 40.3 | 98.4 | 37.0 |
| gi\|157146211\|ref\|YP_001453530.1 | Citrobacter koseri | 36.4 | 38.1 | 39.0 | 95.9 | 36.5 |
| gi\|213420096\|ref\|ZP_03353162.1\| | Salmonella enterica | | | | 95.4 | |
| gi\|213616306\|ref\|ZP_03372132.1\| | Salmonella enterica | | | | 95.2 | |
| gi\|218549182\|ref\|YP_002382973.1 | Escherichia fergusonii | 38.6 | 38.4 | 41.5 | 95.0 | 37.9 |
| gi\|62179711\|ref\|YP_216128.1\| | Salmonella enterica | 36.7 | 36.5 | 39.3 | 95.0 | 36.0 |
| gi\|213618903\|ref\|ZP_03372729.1\| | Salmonella enterica | 38.5 | 33.7 | 38.5 | 94.7 | 35.2 |
| gi\|16764548\|ref\|NP_460163.1\| | Salmonella typhimurium | 36.7 | 36.2 | 39.0 | 94.6 | 35.7 |
| gi\|237731023\|ref\|ZP_04561504.1\| | Citrobacter sp. | 36.4 | 37.5 | 40.3 | 94.6 | 36.8 |
| gi\|16760069\|ref\|NP_455686.1\| | Salmonella enterica | 36.4 | 36.5 | 39.3 | 94.6 | 36.3 |
| gi\|56413821\|ref\|YP_150896.1\| | Salmonella enterica | 36.7 | 36.5 | 39.6 | 94.6 | 36.0 |
| gi\|213024868\|ref\|ZP_03339315.1\| | Salmonella enterica | 37.6 | 36.4 | 39.4 | 94.6 | 35.8 |
| gi\|161503721\|ref\|YP_001570833.1 | Salmonella enterica | 37.0 | 37.5 | 39.3 | 94.3 | 36.6 |
| gi\|213418092\|ref\|ZP_03351162.1\| | Salmonella enterica | 37.2 | 35.5 | 39.9 | 94.2 | 34.0 |
| gi\|283833614\|ref\|ZP_06353355.1\| | Citrobacter youngae | 36.1 | 38.1 | 39.9 | 93.7 | 37.0 |
| gi\|283784880\|ref\|YP_003364745.1 | Citrobacter rodentium | 37.0 | 39.3 | 39.9 | 93.7 | 38.2 |
| gi\|261339392\|ref\|ZP_05967250.1\| | E. cancerogenus | 38.6 | 39.0 | 41.2 | 91.5 | 37.3 |
| gi\|213977786\|ref\|ZP_03405045.1\| | Salmonella enterica | | | | 91.4 | |
| gi\|152969643\|ref\|YP_001334752.1 | Klebsiella pneumoniae | 38.0 | 39.3 | 40.3 | 90.2 | 36.7 |
| gi\|260597462\|ref\|YP_003210033.1 | Cronobacter turicensis | 38.0 | 39.3 | 40.6 | 90.2 | 37.7 |
| gi\|146311262\|ref\|YP_001176336.1 | Enterobacter sp. | 37.0 | 39.0 | 39.3 | 89.9 | 37.3 |
| gi\|269919260\|ref\|ZP_06168207.1\| | Klebsiella variicola | 38.3 | 39.6 | 39.9 | 89.9 | 36.4 |
| gi\|206579577\|ref\|YP_002239290.1 | Klebsiella pneumoniae | 38.3 | 39.6 | 40.3 | 89.9 | 36.4 |

FIG. 3E: Beta cont'd

FIG. 3E: Beta Ketoacyl-ACP Synthase Homologs

| | | | | | | |
|---|---|---|---|---|---|---|
| gi\|156934423\|ref\|YP_001438339.1 | Enterobacter sakazakii | 38.0 | 39.3 | 40.6 | 89.0 | 37.7 |
| gi\|157370146\|ref\|YP_001478135.1 | S.proteamaculans | 38.9 | 41.7 | 40.6 | 83.0 | 37.1 |
| gi\|270261343\|ref\|ZP_06189616.1\| | Serratia odorifera | 38.3 | 40.7 | 40.3 | 82.3 | 37.1 |
| gi\|238791861\|ref\|ZP_04635498.1\| | Yersinia intermedia | 38.0 | 38.9 | 38.7 | 81.4 | 34.9 |
| gi\|188534156\|ref\|YP_001907953.1 | Erwinia tasmaniensis | 37.7 | 39.5 | 40.1 | 81.4 | 34.6 |
| gi\|238789114\|ref\|ZP_04632903.1\| | Yersinia frederiksenii | 38.0 | 38.6 | 40.3 | 81.1 | 34.8 |
| gi\|238795964\|ref\|ZP_04639476.1\| | Yersinia mollaretii | 37.7 | 38.9 | 39.6 | 81.1 | 34.3 |
| gi\|22125650\|ref\|NP_669073.1\| | Yersinia pestis | 38.0 | 40.2 | 40.1 | 81.1 | 34.1 |
| gi\|238749671\|ref\|ZP_04611176.1\| | Yersinia rohdei | 38.0 | 39.0 | 40.3 | 80.8 | 35.4 |
| gi\|259908798\|ref\|YP_002649154.1 | Erwinia pyrifoliae | 38.0 | 39.0 | 40.6 | 80.8 | 35.8 |
| gi\|145599132\|ref\|YP_001163208.1 | Y.pestis Pestoides | 38.0 | 40.2 | 39.7 | 80.8 | 33.8 |
| gi\|238783761\|ref\|ZP_04627780.1\| | Yersinia bercovieri | 38.0 | 39.3 | 40.0 | 80.5 | 33.8 |
| gi\|238762189\|ref\|ZP_04623161.1\| | Yersinia kristensenii | 38.3 | 40.3 | 39.7 | 80.5 | 34.8 |
| gi\|258635621\|ref\|ZP_05728383.1\| | Pantoea sp. | 37.0 | 39.5 | 40.4 | 80.4 | 35.4 |
| gi\|238758389\|ref\|ZP_04619566.1\| | Yersinia aldovae | 37.7 | 39.5 | 39.6 | 80.1 | 35.5 |
| gi\|123441939\|ref\|YP_001005922.1 | Yersinia enterocolitica | 37.5 | 40.1 | 39.1 | 80.1 | 34.8 |
| gi\|50120728\|ref\|YP_049895.1\| | P.atrosepticum | 37.7 | 39.2 | 38.7 | 79.5 | 34.3 |
| gi\|227326849\|ref\|ZP_03830873.1\| | P. carotovorum | 38.2 | 38.9 | 39.6 | 79.5 | 34.3 |
| gi\|227111677\|ref\|ZP_03825333.1\| | P.carotovorum | 38.2 | 38.9 | 39.6 | 79.5 | 34.3 |
| gi\|253688882\|ref\|YP_003018072.1 | P. carotovorum | 37.9 | 38.3 | 39.0 | 79.5 | 34.3 |
| gi\|242239025\|ref\|YP_002987206.1 | Dickeya dadantii | 36.7 | 38.7 | 38.8 | 79.5 | 35.8 |
| gi\|238754382\|ref\|ZP_04615738.1\| | Yersinia ruckeri | 38.6 | 39.9 | 39.0 | 79.5 | 34.8 |
| gi\|167427078\|ref\|ZP_02318831.1\| | Y. pestis biovar Mediaevalis | 36.5 | 37.7 | 38.9 | 79.3 | 32.5 |
| gi\|261822064\|ref\|YP_003260170.1 | P.wasabiae | 37.9 | 39.2 | 39.3 | 79.2 | 34.6 |
| gi\|271500130\|ref\|YP_003333155.1 | Dickeya dadantii | 36.7 | 38.4 | 40.1 | 79.2 | 35.4 |
| gi\|238920262\|ref\|YP_002933777.1 | Edwardsiella ictaluri | 37.4 | 39.9 | 39.5 | 78.9 | 34.6 |
| gi\|251789232\|ref\|YP_003003953.1 | Dickeya zeae | 37.3 | 38.1 | 38.5 | 78.9 | 33.6 |
| gi\|269139446\|ref\|YP_003296147.1 | Edwardsiella tarda | 37.1 | 39.5 | 39.7 | 78.6 | 35.2 |
| gi\|85059036\|ref\|YP_454738.1\| | Sodalis glossinidius | 37.3 | 38.1 | 39.0 | 77.3 | 36.6 |
| gi\|261346046\|ref\|ZP_05973690.1\| | Providencia rustigianii | 39.7 | 41.2 | 39.6 | 77.3 | 35.7 |
| gi\|268589214\|ref\|ZP_06123435.1\| | Providencia rettgeri | 37.5 | 39.6 | 39.9 | 77.0 | 35.5 |

FIG. 3E: Beta cont'd

FIG. 3E: Beta Ketoacyl-ACP Synthase Homologs

| | | | | | | |
|---|---|---|---|---|---|---|
| gi\|212712803\|ref\|ZP_03320931.1\| | P.alcalifaciens | 40.0 | 41.2 | 39.3 | 76.7 | 36.4 |
| gi\|183599493\|ref\|ZP_02960986.1\| | Providencia stuartii | 35.5 | 39.0 | 38.3 | 76.0 | 34.9 |
| gi\|227357749\|ref\|ZP_03842098.1\| | Proteus mirabilis | 38.1 | 38.6 | 39.3 | 75.4 | 34.3 |
| gi\|197284744\|ref\|YP_002150616.1 | Proteus mirabilis | 38.1 | 38.6 | 39.3 | 75.4 | 34.3 |
| gi\|226330535\|ref\|ZP_03806053.1\| | Proteus penneri | 36.8 | 36.7 | 38.1 | 74.4 | 34.0 |
| gi\|260773149\|ref\|ZP_05882065.1\| | Vibrio metschnikovii | 40.9 | 43.0 | 40.9 | 73.6 | 36.3 |
| gi\|253989182\|ref\|YP_003040538.1 | Photorhabdus asymbiotica | 39.2 | 37.2 | 39.3 | 73.5 | 34.0 |
| gi\|262393767\|ref\|YP_003285621.1 | Vibrio sp. | 41.7 | 42.4 | 43.2 | 73.5 | 36.5 |
| gi\|262166127\|ref\|ZP_06033864.1\| | Vibrio mimicus | 40.1 | 43.1 | 43.8 | 73.5 | 37.1 |
| gi\|258625448\|ref\|ZP_05720341.1\| | Vibrio mimicus | 39.8 | 42.8 | 43.5 | 73.2 | 36.8 |
| gi\|262404378\|ref\|ZP_06080933.1\| | Vibrio sp. | 38.6 | 42.1 | 42.5 | 73.2 | 36.3 |
| gi\|258621212\|ref\|ZP_05716246.1\| | Vibrio mimicus | 39.2 | 42.4 | 43.5 | 73.2 | 36.6 |
| gi\|260776335\|ref\|ZP_05885230.1\| | Vibrio coralliilyticus | 38.9 | 41.2 | 42.3 | 72.9 | 35.3 |
| gi\|37526725\|ref\|NP_930069.1\| | P. luminescens | 40.1 | 38.3 | 40.6 | 72.6 | 34.6 |
| gi\|269967351\|ref\|ZP_06181412.1\| | Vibrio alginolyticus | 41.8 | 43.0 | 43.1 | 72.6 | 36.7 |
| gi\|28898830\|ref\|NP_798435.1\| | Vibrio parahaemolyticus | 41.8 | 42.7 | 43.5 | 72.6 | 37.0 |
| gi\|229528958\|ref\|ZP_04418348.1\| | Vibrio cholerae | 38.9 | 41.8 | 42.2 | 72.6 | 36.6 |
| gi\|229521935\|ref\|ZP_04411352.1\| | Vibrio cholerae | 38.9 | 41.8 | 42.2 | 72.6 | 36.6 |
| gi\|15642025\|ref\|NP_231657.1\| | Vibrio cholerae | 38.9 | 41.8 | 42.2 | 72.6 | 36.6 |
| gi\|254286853\|ref\|ZP_04961806.1\| | Vibrio cholerae | 39.4 | 41.7 | 42.5 | 72.5 | 36.6 |
| gi\|90413254\|ref\|ZP_01221249.1\| | P. profundum | 38.0 | 38.7 | 42.9 | 72.4 | 36.3 |
| gi\|260896169\|ref\|ZP_05904665.1\| | Vibrio parahaemolyticus | 42.3 | 42.5 | 44.1 | 72.3 | 37.1 |
| gi\|54308386\|ref\|YP_129406.1\| | P.profundum | 38.0 | 38.7 | 42.2 | 72.3 | 35.8 |
| gi\|218709016\|ref\|YP_002416637.1 | Vibrio splendidus | 40.1 | 42.7 | 42.0 | 72.2 | 35.9 |
| gi\|27366283\|ref\|NP_761811.1\| | Vibrio vulnificus | 39.2 | 40.6 | 41.9 | 71.9 | 35.9 |
| gi\|269962042\|ref\|ZP_06176396.1\| | Vibrio harveyi | 39.7 | 42.7 | 43.5 | 71.9 | 36.1 |
| gi\|261253412\|ref\|ZP_05945985.1\| | Vibrio orientalis | 40.1 | 42.4 | 42.9 | 71.9 | 35.3 |
| gi\|163803782\|ref\|ZP_02197637.1\| | Vibrio sp. | 40.7 | 42.9 | 42.8 | 71.6 | 35.6 |
| gi\|284007277\|emb\|CBA72597.1\| | A. nasoniae | 38.6 | 38.2 | 38.4 | 71.6 | 34.0 |
| gi\|89073424\|ref\|ZP_01159948.1\| | Vibrio angustum | 38.3 | 38.5 | 41.4 | 71.5 | 35.0 |
| gi\|209695675\|ref\|YP_002263604.1 | Aliivibrio salmonicida | 38.7 | 39.0 | 41.1 | 71.3 | 34.9 |

FIG. 3E: Beta cont'd

FIG. 3E: Beta Ketoacyl-ACP Synthase Homologs

| | | | | | | |
|---|---|---|---|---|---|---|
| gi\|156975183\|ref\|YP_001446090.1 | Vibrio harveyi | 40.6 | 42.4 | 44.2 | 71.3 | 36.7 |
| gi\|238897668\|ref\|YP_002923347.1 | C. Hamiltonella defensa | 37.0 | 39.5 | 39.0 | 71.3 | 34.0 |
| gi\|59712349\|ref\|YP_205125.1\| | Vibrio fischeri | 38.7 | 39.0 | 41.4 | 71.0 | 35.2 |
| gi\|117617599\|ref\|YP_856773.1\| | Aeromonas hydrophila | 36.7 | 38.1 | 39.2 | 70.5 | 38.1 |
| gi\|153824283\|ref\|ZP_01976950.1\| | Vibrio cholerae | 38.8 | 41.9 | 44.6 | 70.2 | 36.1 |
| gi\|262276049\|ref\|ZP_06053858.1\| | Grimontia hollisae | 38.0 | 40.2 | 41.8 | 70.1 | 35.5 |
| gi\|145299030\|ref\|YP_001141871.1 | Aeromonas salmonicida | 36.2 | 38.4 | 39.8 | 69.9 | 37.7 |
| gi\|269102261\|ref\|ZP_06154958.1\| | P. damselae | 37.5 | 39.6 | 40.6 | 69.7 | 34.4 |
| gi\|94676843\|ref\|YP_588877.1\| | B.cicadellinicola | 37.7 | 39.0 | 39.6 | 69.4 | 34.6 |
| gi\|240949741\|ref\|ZP_04754073.1\| | Actinobacillus minor | 35.9 | 37.2 | 38.3 | 69.4 | 33.1 |
| gi\|270674857\|ref\|ZP_06222661.1\| | Haemophilus influenzae | 39.2 | 42.3 | 41.1 | 69.4 | |
| gi\|153840736\|ref\|ZP_01993357.1\| | Vibrio parahaemolyticus | 42.4 | 43.0 | 45.1 | 69.2 | 36.8 |
| gi\|167623705\|ref\|YP_001673999.1 | Shewanella halifaxensis | 37.0 | 37.6 | 38.1 | 69.0 | 35.0 |
| gi\|167855647\|ref\|ZP_02478405.1\| | Haemophilus parasuis | 36.1 | 38.1 | 37.1 | 68.8 | 32.7 |
| gi\|15603779\|ref\|NP_246853.1\| | Pasteurella multocida | 38.2 | 39.6 | 38.4 | 68.8 | 36.8 |
| gi\|257465222\|ref\|ZP_05629593.1\| | Actinobacillus minor | 36.0 | 36.6 | 38.2 | 68.8 | 32.8 |
| gi\|127512530\|ref\|YP_001093727.1 | Shewanella loihica | 37.2 | 38.0 | 37.2 | 68.7 | 36.6 |
| gi\|219871722\|ref\|YP_002476097.1 | Haemophilus parasuis | 36.3 | 38.3 | 37.0 | 68.6 | 32.5 |
| gi\|71892185\|ref\|YP_277917.1\| | C. Blochmannia pennsylvanicus | 36.9 | 35.9 | 37.4 | 68.5 | 34.0 |
| gi\|260912837\|ref\|ZP_05919323.1\| | Pasteurella dagmatis | 37.5 | 38.4 | 37.7 | 68.5 | 35.2 |
| gi\|170726393\|ref\|YP_001760419.1 | Shewanella woodyi | 36.2 | 38.6 | 38.1 | 68.3 | 36.9 |
| gi\|163752669\|ref\|ZP_02159837.1\| | Shewanella benthica | 37.9 | 38.0 | 39.4 | 68.3 | 35.9 |
| gi\|157962317\|ref\|YP_001502351.1 | Shewanella pealeana | 36.6 | 37.0 | 38.4 | 68.0 | 35.3 |
| gi\|120599246\|ref\|YP_963820.1\| | S.putrefaciens | 36.1 | 37.7 | 37.5 | 68.0 | 35.6 |
| gi\|114047960\|ref\|YP_738510.1\| | Shewanella sp. | 36.0 | 39.4 | 37.5 | 68.0 | 36.6 |
| gi\|251793204\|ref\|YP_003007932.1 | A.aphrophilus | 37.7 | 38.4 | 38.3 | 67.8 | 32.7 |
| gi\|126173946\|ref\|YP_001050095.1 | Shewanella baltica | 37.5 | 37.9 | 38.4 | 67.7 | 35.3 |
| gi\|113970733\|ref\|YP_734526.1\| | Shewanella sp. | 36.3 | 39.1 | 37.8 | 67.7 | 36.2 |
| gi\|114562673\|ref\|YP_750186.1\| | S. frigidimarina | 36.8 | 39.3 | 38.1 | 67.4 | 35.9 |
| gi\|91793647\|ref\|YP_563298.1\| | Shewanella denitrificans | 36.2 | 38.0 | 37.8 | 67.4 | 36.4 |
| gi\|237808939\|ref\|YP_002893379.1 | Tolumonas auensis | 36.2 | 38.4 | 39.4 | 67.4 | 35.9 |

FIG. 3E: Beta cont'd

FIG. 3E: Beta Ketoacyl-ACP Synthase Homologs

| | | | | | | |
|---|---|---|---|---|---|---|
| gi\|119775117\|ref\|YP_927857.1\| | S. amazonensis | 36.8 | 39.6 | 37.5 | 67.4 | 36.9 |
| gi\|212635827\|ref\|YP_002312352.1 | S. piezotolerans | 36.3 | 37.6 | 39.1 | 67.4 | 34.4 |
| gi\|24374316\|ref\|NP_718359.1\| | Shewanella oneidensis | 36.3 | 39.1 | 37.8 | 67.4 | 36.6 |
| gi\|261868801\|ref\|YP_003256723.1 | A.actinomycetemcomitans | 36.4 | 35.6 | 38.0 | 67.2 | 31.8 |
| gi\|152979655\|ref\|YP_001345284.1 | A. succinogenes | 35.5 | 37.3 | 37.5 | 66.9 | 31.1 |
| gi\|261493143\|ref\|ZP_05989678.1\| | M. haemolytica | 36.1 | 37.0 | 38.5 | 66.9 | 32.7 |
| gi\|114774295\|ref\|ZP_01450875.1\| | alpha proteobacterium | 36.1 | 34.2 | 36.4 | 66.7 | 28.9 |
| gi\|254362210\|ref\|ZP_04978325.1\| | M. haemolytica | 35.3 | 37.0 | 38.5 | 66.6 | 32.4 |
| gi\|126643668\|gb\|ABO25835.1\| | Shewanella hanedai | 36.2 | 38.9 | 37.5 | 66.5 | 35.6 |
| gi\|90406887\|ref\|ZP_01215078.1\| | Psychromonas sp. | 37.6 | 39.3 | 40.9 | 66.5 | 35.5 |
| gi\|145641490\|ref\|ZP_01797068.1\| | Haemophilus influenzae | 36.8 | 37.9 | 38.5 | 66.2 | 31.7 |
| gi\|145631278\|ref\|ZP_01787050.1\| | Haemophilus influenzae | 36.2 | 37.3 | 38.5 | 65.9 | 31.7 |
| gi\|46128970\|ref\|ZP_00154722.2\| | Haemophilus influenzae | 36.2 | 37.3 | 38.5 | 65.9 | 31.7 |
| gi\|16272124\|ref\|NP_438327.1\| | Haemophilus influenzae | 36.2 | 37.3 | 38.5 | 65.9 | 31.7 |
| gi\|145637318\|ref\|ZP_01792978.1\| | Haemophilus influenzae | 36.2 | 37.3 | 38.5 | 65.9 | 31.7 |
| gi\|119944845\|ref\|YP_942525.1\| | P. ingrahamii | 39.0 | 40.1 | 38.6 | 65.8 | 34.9 |
| gi\|53733117\|ref\|ZP_00156000.2\| | Haemophilus influenzae | 36.5 | 37.3 | 38.5 | 65.6 | 31.3 |
| gi\|145628455\|ref\|ZP_01784255.1\| | Haemophilus influenzae | 36.2 | 37.3 | 38.2 | 65.6 | 31.7 |
| gi\|145633585\|ref\|ZP_01789313.1\| | Haemophilus influenzae | 36.2 | 37.3 | 38.2 | 65.6 | 30.8 |
| gi\|157375761\|ref\|YP_001474361.1 | Shewanella sediminis | 35.9 | 37.6 | 38.1 | 65.5 | 35.2 |
| gi\|148825575\|ref\|YP_001290328.1 | Haemophilus influenzae | 36.2 | 36.7 | 37.9 | 65.2 | 30.3 |
| gi\|109898441\|ref\|YP_661696.1\| | P. atlantica | 34.0 | 37.5 | 36.6 | 65.0 | 35.3 |
| gi\|32035440\|ref\|ZP_00135406.1\| | A. pleuropneumoniae | 36.5 | 38.7 | 38.0 | 65.0 | 33.0 |
| gi\|190150704\|ref\|YP_001969229.1 | A.pleuropneumoniae | 37.1 | 38.7 | 37.1 | 65.0 | 33.3 |
| gi\|33151937\|ref\|NP_873290.1\| | Haemophilus ducreyi | 35.2 | 36.2 | 35.8 | 64.0 | 31.7 |
| gi\|56460450\|ref\|YP_155731.1\| | Idiomarina loihiensis | 39.1 | 40.2 | 40.5 | 63.8 | 37.8 |
| gi\|239996665\|ref\|ZP_04717189.1\| | Alteromonas macleodii | 33.7 | 36.9 | 37.9 | 63.6 | 34.9 |
| gi\|170718452\|ref\|YP_001783387.1 | Haemophilus somnus | 36.6 | 37.5 | 38.0 | 63.4 | 33.1 |
| gi\|190573057\|ref\|YP_001970902.1 | S.maltophilia | 38.7 | 41.5 | 40.3 | 63.2 | 39.5 |
| gi\|113460311\|ref\|YP_718372.1\| | Haemophilus somnus | 36.6 | 37.5 | 37.7 | 63.1 | 32.8 |
| gi\|254521688\|ref\|ZP_05133743.1\| | Stenotrophomonas sp. | 39.0 | 41.5 | 40.9 | 62.8 | 39.2 |

FIG. 3E: Beta cont'd

FIG. 3E: Beta Ketoacyl-ACP Synthase Homologs

| | | | | | | |
|---|---|---|---|---|---|---|
| gi\|91775860\|ref\|YP_545616.1\| | M.flagellatus | 40.3 | 40.9 | 43.1 | 62.7 | 40.3 |
| gi\|253999097\|ref\|YP_003051160.1 | Methylovorus sp. | 41.8 | 42.5 | 45.0 | 62.7 | 44.0 |
| gi\|33519865\|ref\|NP_878697.1\| | C.Blochmannia floridanus | 36.9 | 38.4 | 39.2 | 62.6 | 33.4 |
| gi\|71275375\|ref\|ZP_00651661.1\| | Xylella fastidiosa | 41.5 | 43.0 | 43.4 | 62.5 | 43.1 |
| gi\|71900529\|ref\|ZP_00682658.1\| | Xylella fastidiosa | 41.2 | 43.3 | 43.4 | 62.5 | 43.1 |
| gi\|15838415\|ref\|NP_299103.1\| | Xylella fastidiosa | 41.5 | 43.0 | 43.4 | 62.2 | 42.8 |
| gi\|52425926\|ref\|YP_089063.1\| | M.succiniciproducens | 38.8 | 39.5 | 39.1 | 62.0 | 30.7 |
| gi\|194364647\|ref\|YP_002027257.1 | S. maltophilia | 39.0 | 41.8 | 39.9 | 62.0 | 39.8 |
| gi\|28198945\|ref\|NP_779259.1\| | Xylella fastidiosa | 41.5 | 43.0 | 43.1 | 61.9 | 42.8 |
| gi\|21230475\|ref\|NP_636392.1\| | Xanthomonas campestris | 39.9 | 42.7 | 42.8 | 61.7 | 41.3 |
| gi\|224817647\|ref\|ZP_03690779.1\| | Thioalkalivibrio sp. | 39.6 | 39.6 | 43.5 | 61.4 | 41.5 |
| gi\|66769531\|ref\|YP_244293.1\| | X. campestris | 39.6 | 42.4 | 42.5 | 61.4 | 41.0 |
| gi\|74317569\|ref\|YP_315309.1\| | T.denitrificans | 42.8 | 41.7 | 41.3 | 61.2 | 40.9 |
| gi\|253996514\|ref\|YP_003048578.1 | Methylotenera mobilis | 41.0 | 42.2 | 45.8 | 61.0 | 37.8 |
| gi\|256822410\|ref\|YP_003146373.1 | Kangiella koreensis | 38.2 | 39.4 | 44.3 | 60.9 | 35.5 |
| gi\|285017420\|ref\|YP_003375131.1 | X. albilineans | 39.4 | 39.9 | 41.7 | 60.9 | 38.7 |
| gi\|78046699\|ref\|YP_362874.1\| | X. campestris | 39.6 | 42.1 | 43.1 | 60.4 | 40.7 |
| gi\|21241878\|ref\|NP_641460.1\| | X.axonopodis | 38.7 | 42.1 | 42.1 | 60.4 | 40.4 |
| gi\|254492066\|ref\|ZP_05105242.1\| | Methylophaga thiooxidans | 41.2 | 41.8 | 43.5 | 60.4 | 38.8 |
| gi\|126666473\|ref\|ZP_01737452.1\| | Marinobacter sp. | 41.3 | 43.4 | 41.2 | 60.3 | 41.2 |
| gi\|149374888\|ref\|ZP_01892661.1\| | Marinobacter algicola | 41.1 | 41.2 | 42.5 | 60.1 | 39.3 |
| gi\|120554298\|ref\|YP_958649.1\| | Marinobacter aquaeolei | 41.8 | 42.5 | 41.5 | 60.1 | 42.5 |
| gi\|58425095\|gb\|AAW74132.1\| | X. oryzae pv. | 39.3 | 41.5 | 42.8 | 60.1 | 40.7 |
| gi\|84622460\|ref\|YP_449832.1\| | X. oryzae pv. | 39.3 | 41.5 | 42.8 | 60.1 | 40.7 |
| gi\|166710962\|ref\|ZP_02242169.1\| | Xanthomonas oryzae | 38.7 | 41.2 | 42.8 | 60.1 | 40.4 |
| gi\|220935080\|ref\|YP_002513979.1 | Thioalkalivibrio sp. | 39.3 | 38.5 | 41.8 | 59.1 | 39.6 |
| gi\|53803724\|ref\|YP_114435.1\| | M. capsulatus | 40.2 | 39.2 | 39.9 | 58.8 | 40.4 |
| gi\|78485055\|ref\|YP_390980.1\| | T. crunogena | 40.1 | 44.3 | 41.8 | 58.6 | 39.6 |
| gi\|254433614\|ref\|ZP_05047122.1\| | Nitrosococcus oceani | 40.4 | 42.0 | 42.2 | 58.6 | 38.7 |
| gi\|77165144\|ref\|YP_343669.1\| | Nitrosococcus oceani | 40.1 | 41.7 | 42.2 | 58.6 | 38.7 |
| gi\|255021126\|ref\|ZP_05293179.1\| | Acidithiobacillus caldus | 38.6 | 38.4 | 40.1 | 58.4 | 41.2 |

FIG. 3E: Beta cont'd

FIG. 3E: Beta Ketoacyl-ACP Synthase Homologs

| | | | | | | |
|---|---|---|---|---|---|---|
| gi\|167949656\|ref\|ZP_02536730.1\| | Endoriftia persephone | 40.7 | 39.9 | 43.7 | 58.1 | 37.6 |
| gi\|261856393\|ref\|YP_003263676.1 | H. neapolitanus | 39.3 | 41.6 | 42.7 | 57.8 | 39.9 |
| gi\|114330490\|ref\|YP_746712.1\| | Nitrosomonas eutropha | 39.8 | 40.9 | 47.0 | 57.5 | 39.9 |
| gi\|114320579\|ref\|YP_742262.1\| | Alkalilimnicola ehrlichii | 36.3 | 39.3 | 42.2 | 57.5 | 40.2 |
| gi\|251827711\|ref\|ZP_04830786.1\| | Gallionella ferruginea | 40.2 | 43.0 | 45.3 | 57.5 | 41.1 |
| gi\|118594893\|ref\|ZP_01552240.1\| | M. bacterium | 40.4 | 41.2 | 43.8 | 57.3 | 39.1 |
| gi\|30249610\|ref\|NP_841680.1\| | Nitrosomonas europaea | 40.4 | 42.1 | 47.3 | 56.9 | 38.7 |
| gi\|88810817\|ref\|ZP_01126074.1\| | Nitrococcus mobilis | 38.9 | 39.5 | 39.1 | 56.9 | 45.2 |
| gi\|121998025\|ref\|YP_001002812.1 | H.halophila | 40.2 | 41.1 | 39.9 | 56.7 | 40.9 |
| gi\|82702201\|ref\|YP_411767.1\| | Nitrosospira multiformis | 41.1 | 43.4 | 46.3 | 56.5 | 40.1 |
| gi\|198283689\|ref\|YP_002220010.1 | A. ferrooxidans | 40.7 | 39.0 | 41.6 | 56.5 | 41.5 |
| gi\|83311453\|ref\|YP_421717.1\| | M. magneticum | 41.8 | 43.6 | 41.2 | 56.4 | 43.5 |
| gi\|241662592\|ref\|YP_002980952.1 | Ralstonia pickettii | 43.0 | 42.6 | 41.1 | 56.3 | 41.6 |
| gi\|241775612\|ref\|ZP_04772895.1\| | A. vinosum | 38.8 | 39.9 | 42.0 | 56.3 | 42.4 |
| gi\|160871931\|ref\|ZP_02062063.1\| | Rickettsiella grylli | 38.7 | 41.3 | 39.4 | 56.3 | 36.3 |
| gi\|224826376\|ref\|ZP_03699478.1\| | Lutiella nitroferrum | 41.3 | 42.3 | 44.4 | 56.3 | 42.1 |
| gi\|255258360\|ref\|ZP_05337720.1\| | S. lithotrophicus | 39.0 | 41.4 | 45.8 | 56.2 | 38.0 |
| gi\|23014672\|ref\|ZP_00054477.1\| | M. magnetotacticum | 41.5 | 43.3 | 40.4 | 56.1 | 43.2 |
| gi\|187928010\|ref\|YP_001898497.1 | Ralstonia pickettii | 43.3 | 42.9 | 40.8 | 56.0 | 41.6 |
| gi\|255061954\|ref\|ZP_05313976.1\| | Nitrosomonas sp. | 40.4 | 40.3 | 46.3 | 55.9 | 39.3 |
| gi\|34498871\|ref\|NP_903086.1\| | C.violaceum | 41.6 | 41.0 | 43.3 | 55.8 | 41.2 |
| gi\|71907643\|ref\|YP_285230.1\| | D. aromatica | 42.3 | 43.8 | 40.6 | 55.5 | 40.7 |
| gi\|117924943\|ref\|YP_865560.1\| | Magnetococcus sp. | 38.3 | 38.8 | 37.6 | 55.2 | 41.0 |
| gi\|221068700\|ref\|ZP_03544805.1\| | C.testosteroni | 40.3 | 42.1 | 47.2 | 54.8 | 41.5 |
| gi\|258542775\|ref\|YP_003188208.1 | A.pasteurianus | 40.3 | 43.4 | 40.4 | 54.7 | 43.4 |
| gi\|217970729\|ref\|YP_002355963.1 | Thauera sp. | 45.3 | 44.8 | 42.3 | 54.7 | 42.2 |
| gi\|153209896\|ref\|ZP_01947533.1\| | Coxiella burnetii | 38.2 | 37.7 | 41.7 | 54.5 | 38.2 |
| gi\|154707060\|ref\|YP_001424921.1 | C. burnetii Dugway | 38.2 | 37.4 | 41.7 | 54.2 | 37.8 |
| gi\|29653835\|ref\|NP_819527.1\| | Coxiella burnetii | 38.2 | 37.4 | 41.7 | 54.2 | 37.8 |
| gi\|161831071\|ref\|YP_001596423.1 | Coxiella burnetii | 38.2 | 37.4 | 41.4 | 54.2 | 37.5 |
| gi\|17545769\|ref\|NP_519171.1\| | Ralstonia solanacearum | 40.4 | 42.2 | 41.7 | 54.2 | 41.9 |

FIG. 3E: Beta cont'd

FIG. 3E: Beta Ketoacyl-ACP Synthase Homologs

| | | | | | | |
|---|---|---|---|---|---|---|
| gi\|264677106\|ref\|YP_003277012.1 | C.testosteroni | 40.3 | 41.8 | 46.3 | 54.2 | 41.8 |
| gi\|78222809\|ref\|YP_384556.1\| | G. metallireducens | 40.5 | 45.7 | 42.4 | 54.0 | 41.5 |
| gi\|103486904\|ref\|YP_616465.1\| | S.alaskensis | 39.2 | 38.4 | 40.1 | 54.0 | 40.5 |
| gi\|225024138\|ref\|ZP_03713330.1\| | Eikenella corrodens | 41.5 | 43.9 | 43.4 | 53.9 | 41.9 |
| gi\|212213023\|ref\|YP_002303959.1 | Coxiella burnetii | 38.2 | 37.4 | 41.4 | 53.9 | 37.5 |
| gi\|77919037\|ref\|YP_356852.1\| | Pelobacter carbinolicus | 43.1 | 44.1 | 43.8 | 53.9 | 43.1 |
| gi\|226939501\|ref\|YP_002794574.1 | L.hongkongensis | 39.1 | 39.9 | 42.2 | 53.9 | 39.3 |
| gi\|83748455\|ref\|ZP_00945477.1\| | Ralstonia solanacearum | 40.4 | 41.9 | 40.8 | 53.9 | 41.9 |
| gi\|121605967\|ref\|YP_983296.1\| | P. naphthalenivorans | 41.4 | 42.0 | 44.9 | 53.7 | 38.9 |
| gi\|241759456\|ref\|ZP_04757560.1\| | Neisseria flavescens | 45.5 | 44.5 | 45.8 | 53.6 | 40.9 |
| gi\|261363906\|ref\|ZP_05976789.1\| | Neisseria mucosa | 42.6 | 45.1 | 43.3 | 53.6 | 41.5 |
| gi\|222055701\|ref\|YP_002538063.1 | Geobacter sp. | 40.7 | 46.3 | 43.8 | 53.5 | 41.2 |
| gi\|261378176\|ref\|ZP_05982749.1\| | Neisseria cinerea | 43.7 | 42.9 | 43.3 | 53.5 | 40.9 |
| gi\|119897914\|ref\|YP_933127.1\| | Azoarcus sp. | 42.8 | 43.6 | 43.5 | 53.4 | 40.3 |
| gi\|254468037\|ref\|ZP_05081443.1\| | beta proteobacterium | 40.4 | 42.3 | 44.0 | 53.3 | 37.7 |
| gi\|225077265\|ref\|ZP_03720464.1\| | Neisseria flavescens | 46.2 | 44.2 | 45.8 | 53.3 | 40.9 |
| gi\|255065806\|ref\|ZP_05317661.1\| | Neisseria sicca | 43.0 | 45.1 | 43.9 | 53.3 | 41.8 |
| gi\|261400594\|ref\|ZP_05986719.1\| | Neisseria lactamica | 44.0 | 43.0 | 44.5 | 53.3 | 39.9 |
| gi\|161621302\|ref\|YP_584576.2\| | Ralstonia metallidurans | 41.5 | 44.2 | 43.1 | 53.3 | 40.9 |
| gi\|93355218\|gb\|ABF09307.1\| | Ralstonia metallidurans | 41.5 | 44.2 | 43.1 | 53.3 | 40.9 |
| gi\|15677747\|ref\|NP_274910.1\| | Neisseria meningitidis | 44.6 | 42.9 | 44.9 | 53.1 | 41.2 |
| gi\|148259289\|ref\|YP_001233416.1 | Acidiphilium cryptum | 38.8 | 42.0 | 39.7 | 53.1 | 41.9 |
| gi\|261393247\|emb\|CAX50870.1\| | Neisseria meningitidis | 44.6 | 42.9 | 44.9 | 53.1 | 41.2 |
| gi\|218767510\|ref\|YP_002342022.1 | Neisseria meningitidis | 44.6 | 42.9 | 44.9 | 53.1 | 41.2 |
| gi\|120609871\|ref\|YP_969549.1\| | Acidovorax avenae | 39.8 | 39.2 | 42.7 | 53.1 | 38.8 |
| gi\|85374551\|ref\|YP_458613.1\| | Erythrobacter litoralis | 39.6 | 38.5 | 42.4 | 53.0 | 44.4 |
| gi\|254670900\|emb\|CBA07454.1\| | Neisseria meningitidis | 41.6 | 38.2 | 42.9 | 53.0 | 37.1 |
| gi\|284799982\|ref\|ZP_05985366.2\| | Neisseria subflava | 45.2 | 44.5 | 46.1 | 53.0 | 40.6 |
| gi\|222832123\|gb\|EEE70600.1\| | Populus trichocarpa | 51.2 | 57.6 | 47.1 | 52.9 | 42.2 |
| gi\|269467947\|gb\|EEZ79682.1\| | uncultured cluster bacterium | 39.3 | 43.2 | 42.4 | 52.8 | 40.4 |
| gi\|238022649\|ref\|ZP_04603075.1\| | Kingella oralis | 42.3 | 43.0 | 42.9 | 52.8 | 41.6 |

FIG. 3E: Beta cont'd

FIG. 3E: Beta Ketoacyl-ACP Synthase Homologs

| | | | | | | |
|---|---|---|---|---|---|---|
| gi\|121634176\|ref\|YP_974421.1\| | Neisseria meningitidis | 44.9 | 42.9 | 44.6 | 52.8 | 41.5 |
| gi\|240122675\|ref\|ZP_04735631.1\| | Neisseria gonorrhoeae | 44.9 | 42.6 | 45.6 | 52.8 | 40.9 |
| gi\|59802462\|ref\|YP_209174.1\| | Neisseria gonorrhoeae | 45.2 | 42.9 | 45.6 | 52.8 | 40.9 |
| gi\|254804268\|ref\|YP_003082489.1 | Neisseria meningitidis | 44.6 | 42.9 | 44.6 | 52.8 | 40.9 |
| gi\|253699784\|ref\|YP_003020973.1 | Geobacter sp. | 44.0 | 46.8 | 45.2 | 52.8 | 42.1 |
| gi\|255057218\|ref\|ZP_05309394.1\| | Geobacter sp. | 43.7 | 46.8 | 43.9 | 52.8 | 42.7 |
| gi\|148556458\|ref\|YP_001264040.1 | Sphingomonas wittichii | 39.4 | 38.6 | 43.2 | 52.7 | 42.9 |
| gi\|260441349\|ref\|ZP_05795165.1\| | Neisseria gonorrhoeae | 45.2 | 42.9 | 45.6 | 52.5 | 40.9 |
| gi\|270492700\|ref\|ZP_06209760.1\| | Acidovorax avenae | 39.5 | 39.2 | 43.0 | 52.5 | 38.8 |
| gi\|160900704\|ref\|YP_001566286.1 | Populus trichocarpa | 41.3 | 41.3 | 46.9 | 52.5 | 40.4 |
| gi\|206559385\|ref\|YP_002230146.1 | B. cenocepacia | 38.5 | 39.8 | 43.0 | 52.5 | 40.7 |
| gi\|134295151\|ref\|YP_001118886.1 | B. vietnamiensis | 37.9 | 39.8 | 41.7 | 52.5 | 39.8 |
| gi\|115351051\|ref\|YP_772890.1\| | Burkholderia ambifaria | 39.1 | 40.4 | 42.4 | 52.5 | 41.0 |
| gi\|254252856\|ref\|ZP_04946174.1\| | Burkholderia dolosa | 39.1 | 40.4 | 42.4 | 52.5 | 41.0 |
| gi\|149186062\|ref\|ZP_01864376.1\| | Erythrobacter sp. | 40.1 | 40.3 | 43.1 | 52.4 | 46.0 |
| gi\|162148846\|ref\|YP_001603307.1 | G.diazotrophicus | 39.8 | 41.8 | 38.4 | 52.3 | 42.5 |
| gi\|209545406\|ref\|YP_002277635.1 | G.diazotrophicus | 39.8 | 41.8 | 38.4 | 52.3 | 42.5 |
| gi\|39996701\|ref\|NP_952652.1\| | G. sulfurreducens | 39.8 | 46.6 | 44.0 | 52.3 | 41.8 |
| gi\|257093139\|ref\|YP_003166780.1 | C. Accumulibacter phosphatis clade | 40.8 | 42.4 | 41.0 | 52.2 | 41.7 |
| gi\|121595583\|ref\|YP_987479.1\| | Diaphorobacter sp. | 40.4 | 42.2 | 45.1 | 52.2 | 40.1 |
| gi\|95929576\|ref\|ZP_01312318.1\| | D. acetoxidans | 42.8 | 45.6 | 44.1 | 52.2 | 39.8 |
| gi\|121610193\|ref\|YP_998000.1\| | V.eiseniae | 38.0 | 39.8 | 43.5 | 52.2 | 40.1 |
| gi\|107022197\|ref\|YP_620524.1\| | B.cenocepacia | 38.2 | 39.5 | 42.7 | 52.2 | 40.7 |
| gi\|78065705\|ref\|YP_368474.1\| | Burkholderia sp. | 38.3 | 40.1 | 43.0 | 52.2 | 40.1 |
| gi\|116689143\|ref\|YP_834766.1\| | B.cenocepacia | 38.2 | 39.5 | 42.7 | 52.2 | 40.7 |
| gi\|53720048\|ref\|YP_109034.1\| | Burkholderia pseudomallei | 39.7 | 40.4 | 41.4 | 52.2 | 41.0 |
| gi\|53725370\|ref\|YP_102326.1\| | Burkholderia mallei | 39.7 | 40.4 | 41.4 | 52.2 | 41.3 |
| gi\|170700228\|ref\|ZP_02891244.1\| | Burkholderia ambifaria | 39.4 | 40.7 | 42.1 | 52.2 | 40.7 |
| gi\|194290166\|ref\|YP_002006073.1 | Cupriavidus taiwanensis | 41.9 | 43.0 | 42.5 | 52.0 | 42.3 |
| gi\|73541952\|ref\|YP_296472.1\| | Ralstonia eutropha | 41.5 | 42.7 | 41.6 | 52.0 | 40.5 |
| gi\|209885009\|ref\|YP_002288866.1 | O.carboxidovorans | 40.9 | 41.6 | 41.6 | 52.0 | 41.4 |

FIG. 3E: Beta cont'd

FIG. 3E: Beta Ketoacyl-ACP Synthase Homologs

| | | | | | | |
|---|---|---|---|---|---|---|
| gi\|89900519\|ref\|YP_522990.1\| | R.ferrireducens | 38.6 | 41.3 | 43.0 | 52.0 | 40.8 |
| gi\|148263932\|ref\|YP_001230638.1 | G.uraniireducens | 41.6 | 47.9 | 42.3 | 52.0 | 41.8 |
| gi\|124265829\|ref\|YP_001019833.1 | Methylibium petroleiphilum | 41.6 | 42.2 | 43.3 | 51.9 | 41.0 |
| gi\|197119479\|ref\|YP_002139906.1 | Geobacter bemidjiensis | 43.4 | 45.9 | 44.5 | 51.9 | 42.1 |
| gi\|209964629\|ref\|YP_002297544.1 | R.centenum | 40.6 | 41.1 | 42.3 | 51.9 | 44.0 |
| gi\|167720572\|ref\|ZP_02403808.1\| | Burkholderia pseudomallei | 39.7 | 40.7 | 41.4 | 51.9 | 41.3 |
| gi\|83719007\|ref\|YP_442252.1\| | B.thailandensis | 38.6 | 39.8 | 41.1 | 51.9 | 40.4 |
| gi\|126453602\|ref\|YP_001067100.1 | Burkholderia pseudomallei | 39.7 | 40.7 | 41.4 | 51.9 | 40.7 |
| gi\|167563541\|ref\|ZP_02356457.1\| | B.oklahomensis | 38.8 | 39.5 | 41.1 | 51.9 | 41.3 |
| gi\|241763838\|ref\|ZP_04761883.1\| | Acidovorax delafieldii | 40.9 | 40.6 | 47.2 | 51.9 | 41.5 |
| gi\|171319462\|ref\|ZP_02908566.1\| | Burkholderia ambifaria | 39.1 | 40.7 | 41.7 | 51.9 | 41.0 |
| gi\|167586618\|ref\|ZP_02379006.1\| | Burkholderia ubonensis | 38.3 | 40.1 | 43.0 | 51.8 | 40.7 |
| gi\|134095267\|ref\|YP_001100342.1 | H.arsenicoxydans | 41.9 | 42.2 | 39.8 | 51.8 | 38.7 |
| gi\|94495939\|ref\|ZP_01302518.1\| | Sphingomonas sp. | 40.5 | 39.0 | 39.4 | 51.7 | 40.9 |
| gi\|113868531\|ref\|YP_727020.1\| | Ralstonia eutropha | 42.0 | 43.3 | 42.8 | 51.7 | 41.7 |
| gi\|54297303\|ref\|YP_123672.1\| | Legionella pneumophila | 38.1 | 37.7 | 44.3 | 51.6 | 37.2 |
| gi\|58038601\|ref\|YP_190565.1\| | Gluconobacter oxydans | 41.5 | 41.1 | 41.4 | 51.6 | 43.4 |
| gi\|56552795\|ref\|YP_163634.1\| | Zymomonas mobilis | 38.0 | 38.5 | 36.6 | 51.6 | 42.9 |
| gi\|75675599\|ref\|YP_318020.1\| | N. winogradskyi | 42.3 | 42.5 | 41.7 | 51.6 | 42.5 |
| gi\|221201338\|ref\|ZP_03574377.1\| | B. multivorans | 38.6 | 39.5 | 42.7 | 51.5 | 40.7 |
| gi\|167570701\|ref\|ZP_02363575.1\| | B.oklahomensis | 38.5 | 39.5 | 40.8 | 51.5 | 41.3 |
| gi\|83593002\|ref\|YP_426754.1\| | Rhodospirillum rubrum | 41.0 | 40.9 | 39.3 | 51.5 | 45.2 |
| gi\|87200379\|ref\|YP_497636.1\| | N.aromaticivorans | 40.1 | 38.2 | 39.8 | 51.4 | 42.0 |
| gi\|54294279\|ref\|YP_126694.1\| | Legionella pneumophila | 38.0 | 38.0 | 44.3 | 51.3 | 36.8 |
| gi\|52841623\|ref\|YP_095422.1\| | Legionella pneumophila | 38.1 | 37.7 | 44.3 | 51.3 | 36.8 |
| gi\|241762467\|ref\|ZP_04760544.1\| | Zymomonas mobilis | 38.0 | 38.5 | 36.6 | 51.3 | 42.9 |
| gi\|260753479\|ref\|YP_003226372.1 | Zymomonas mobilis | 38.0 | 38.5 | 36.6 | 51.3 | 42.9 |
| gi\|91789500\|ref\|YP_550452.1\| | Polaromonas sp. | 41.1 | 41.7 | 44.0 | 51.2 | 40.7 |
| gi\|161525353\|ref\|YP_001580365.1 | B. multivorans | 38.6 | 39.5 | 42.4 | 51.2 | 40.7 |
| gi\|238026604\|ref\|YP_002910835.1 | Burkholderia glumae | 40.7 | 39.6 | 42.7 | 51.2 | 41.7 |
| gi\|145588585\|ref\|YP_001155182.1 | P.necessarius | 41.0 | 42.3 | 41.5 | 51.2 | 38.1 |

FIG. 3E: Beta cont'd

FIG. 3E: Beta Ketoacyl-ACP Synthase Homologs

| | | | | | | |
|---|---|---|---|---|---|---|
| gi\|237745499\|ref\|ZP_04575979.1\| | Oxalobacter formigenes | 38.7 | 40.7 | 42.8 | 51.2 | 41.4 |
| gi\|146329454\|ref\|YP_001210090.1 | Dichelobacter nodosus | 43.1 | 45.7 | 41.9 | 51.1 | 39.9 |
| gi\|144899187\|emb\|CAM76051.1\| | M. gryphiswaldense | 38.3 | 40.4 | 42.6 | 51.1 | 42.7 |
| gi\|148244595\|ref\|YP_001219289.1 | C. Vesicomyosocius okutanii | 38.6 | 40.1 | 38.9 | 50.9 | 37.9 |
| gi\|260220739\|emb\|CBA28601.1\| | C.putative symbiont | 39.8 | 40.4 | 43.9 | 50.9 | 41.9 |
| gi\|187477618\|ref\|YP_785642.1\| | Bordetella avium | 40.2 | 39.6 | 40.8 | 50.9 | 40.1 |
| gi\|167837362\|ref\|ZP_02464245.1\| | B. thailandensis | 38.3 | 38.9 | 41.1 | 50.9 | 40.4 |
| gi\|270156738\|ref\|ZP_06185395.1\| | Legionella longbeachae | 36.3 | 35.1 | 42.7 | 50.6 | 35.9 |
| gi\|56478540\|ref\|YP_160129.1\| | A. aromaticum | 42.0 | 42.8 | 43.2 | 50.6 | 41.2 |
| gi\|27380131\|ref\|NP_771660.1\| | Bradyrhizobium japonicum | 41.3 | 42.1 | 41.7 | 50.6 | 42.9 |
| gi\|33593427\|ref\|NP_881071.1\| | Bordetella pertussis | 41.1 | 41.7 | 39.5 | 50.6 | 41.0 |
| gi\|33602733\|ref\|NP_890293.1\| | B. bronchiseptica | 40.8 | 41.4 | 39.8 | 50.6 | 41.0 |
| gi\|239814396\|ref\|YP_002943306.1 | Variovorax paradoxus | 42.1 | 42.4 | 44.7 | 50.6 | 41.8 |
| gi\|282884806\|ref\|ZP_06293393.1\| | Burkholderia sp. | 40.4 | 39.2 | 43.6 | 50.6 | 39.8 |
| gi\|256757644\|ref\|ZP_05498317.1\| | Thiomonas intermedia | 37.9 | 42.1 | 40.6 | 50.6 | 40.2 |
| gi\|171463184\|ref\|YP_001797297.1 | P.necessarius | 39.0 | 40.8 | 40.9 | 50.6 | 38.5 |
| gi\|118602495\|ref\|YP_903710.1\| | C. Ruthia magnifica | 39.3 | 41.3 | 40.2 | 50.5 | 38.4 |
| gi\|83858236\|ref\|ZP_00951758.1\| | Oceanicaulis alexandrii | 38.5 | 39.7 | 42.0 | 50.5 | 43.4 |
| gi\|220926816\|ref\|YP_002502118.1 | M. nodulans | 40.4 | 40.9 | 41.2 | 50.5 | 41.2 |
| gi\|114704823\|ref\|ZP_01437731.1\| | Fulvimarina pelagi | 40.6 | 42.0 | 41.8 | 50.3 | 41.4 |
| gi\|49475534\|ref\|YP_033575.1\| | Bartonella henselae | 37.2 | 37.2 | 41.1 | 50.3 | 38.2 |
| gi\|33597831\|ref\|NP_885474.1\| | Bordetella parapertussis | 40.5 | 41.1 | 39.8 | 50.3 | 40.7 |
| gi\|163856063\|ref\|YP_001630361.1 | Bordetella petrii | 42.0 | 41.1 | 38.6 | 50.3 | 39.7 |
| gi\|170695409\|ref\|ZP_02886554.1\| | Burkholderia graminis | 40.1 | 38.9 | 43.3 | 50.3 | 40.1 |
| gi\|272528635\|ref\|ZP_06224552.1\| | Burkholderia sp. | 38.6 | 38.0 | 42.4 | 50.3 | 40.1 |
| gi\|152980023\|ref\|YP_001353046.1 | Janthinobacterium sp. | 41.4 | 40.7 | 40.8 | 50.3 | 39.3 |
| gi\|153005599\|ref\|YP_001379924.1 | Anaeromyxobacter sp. | 37.3 | 40.6 | 42.6 | 50.3 | 40.5 |
| gi\|163843048\|ref\|YP_001627452.1 | Brucella suis | 39.1 | 40.4 | 42.0 | 50.2 | 39.5 |
| gi\|39935808\|ref\|NP_948084.1\| | R. palustris | 41.1 | 41.6 | 40.4 | 50.2 | 44.5 |
| gi\|283822743\|ref\|ZP_06349548.1\| | R.vannielii | 43.6 | 43.1 | 41.5 | 50.2 | 42.6 |
| gi\|170744276\|ref\|YP_001772931.1 | Methylobacterium sp. | 39.5 | 40.6 | 40.9 | 50.2 | 40.5 |

FIG. 3E: Beta cont'd

FIG. 3E: Beta Ketoacyl-ACP Synthase Homologs

| | | | | | | |
|---|---|---|---|---|---|---|
| gi\|254499182\|ref\|ZP_05111862.1\| | Legionella drancourtii | 38.4 | 36.9 | 42.6 | 50.0 | 36.1 |
| gi\|187924888\|ref\|YP_001896530.1 | B.phytofirmans | 41.5 | 39.5 | 43.6 | 50.0 | 38.6 |
| gi\|154253363\|ref\|YP_001414187.1 | P. lavamentivorans | 41.9 | 42.2 | 42.5 | 50.0 | 41.6 |
| gi\|154248305\|ref\|YP_001419263.1 | X.autotrophicus | 41.5 | 41.3 | 41.1 | 50.0 | 44.4 |
| gi\|154173643\|ref\|YP_001408846.1 | Campylobacter curvus | 39.0 | 42.4 | 41.9 | 50.0 | 39.5 |
| gi\|86159172\|ref\|YP_465957.1\| | Anaeromyxobacter sp. | 38.7 | 39.6 | 44.1 | 50.0 | 41.5 |
| gi\|92117138\|ref\|YP_576867.1\| | N.hamburgensis | 41.6 | 42.2 | 42.0 | 50.0 | 44.8 |
| gi\|85716273\|ref\|ZP_01047247.1\| | Nitrobacter sp. | 41.9 | 42.5 | 42.3 | 50.0 | 43.6 |
| gi\|114777085\|ref\|ZP_01452105.1\| | M.ferrooxydans | 36.1 | 37.8 | 37.6 | 49.8 | 40.6 |
| gi\|163793228\|ref\|ZP_02187204.1\| | alpha proteobacterium | 41.3 | 39.3 | 39.0 | 49.8 | 42.5 |
| gi\|283843780\|ref\|ZP_06361298.1\| | R. palustris | 42.0 | 41.9 | 40.1 | 49.8 | 44.1 |
| gi\|86749767\|ref\|YP_486263.1\| | R.palustris | 42.3 | 41.9 | 40.1 | 49.8 | 43.5 |
| gi\|91977157\|ref\|YP_569816.1\| | R. palustris | 42.3 | 41.3 | 40.1 | 49.8 | 44.1 |
| gi\|148559178\|ref\|YP_001258755.1 | Brucella ovis | 39.4 | 40.4 | 42.0 | 49.8 | 39.5 |
| gi\|17987463\|ref\|NP_540097.1\| | B.melitensis, B.neotomae, B.ceti, B.abortus, B.pinnipedialis | 39.4 | 40.4 | 42.0 | 49.8 | 39.5 |
| gi\|91784720\|ref\|YP_559926.1\| | B.xenovorans | 41.3 | 40.4 | 43.0 | 49.7 | 39.5 |
| gi\|209517235\|ref\|ZP_03266080.1\| | Burkholderia sp. | 39.5 | 38.6 | 42.4 | 49.7 | 40.1 |
| gi\|260892844\|ref\|YP_003238941.1 | Ammonifex degensii | 43.8 | 48.9 | 45.4 | 49.7 | 43.9 |
| gi\|170750365\|ref\|YP_001756625.1 | M.radiotolerans | 42.5 | 41.8 | 41.8 | 49.7 | 42.5 |
| gi\|240850683\|ref\|YP_002972083.1 | Bartonella grahamii | 36.7 | 37.2 | 41.7 | 49.7 | 37.0 |
| gi\|114327678\|ref\|YP_744835.1\| | G.bethesdensis | 39.1 | 41.1 | 39.2 | 49.7 | 40.7 |
| gi\|158423918\|ref\|YP_001525210.1 | A.caulinodans | 40.7 | 40.6 | 42.3 | 49.5 | 42.7 |
| gi\|167041411\|gb\|ABZ06163.1\| | uncultured marine microorganism | 39.5 | 41.0 | 48.2 | 49.5 | 39.7 |
| gi\|121533809\|ref\|ZP_01665636.1\| | T. carboxydivorans | 42.9 | 46.1 | 49.5 | 49.5 | 41.4 |
| gi\|167041967\|gb\|ABZ06704.1\| | uncultured marine microorganism | 38.6 | 41.4 | 47.8 | 49.5 | 39.1 |
| gi\|115524832\|ref\|YP_781743.1\| | R. palustris | 40.4 | 41.6 | 39.6 | 49.5 | 42.3 |
| gi\|163739612\|ref\|ZP_02147021.1\| | P. gallaeciensis | 42.5 | 39.3 | 42.9 | 49.5 | 42.6 |
| gi\|225852292\|ref\|YP_002732525.1 | B. melitensis | 39.4 | 40.4 | 42.0 | 49.5 | 39.5 |
| gi\|23501664\|ref\|NP_697791.1\| | B. suis, B.canis | 39.4 | 40.4 | 42.0 | 49.5 | 39.5 |
| gi\|13476952\|ref\|NP_108522.1\| | Mesorhizobium loti | 39.6 | 37.8 | 42.9 | 49.5 | 39.9 |
| gi\|260460935\|ref\|ZP_05809185.1\| | M. opportunistum | 39.6 | 38.1 | 42.9 | 49.5 | 39.9 |

FIG. 3E: Beta cont'd

FIG. 3E: Beta Ketoacyl-ACP Synthase Homologs

| | | | | | | |
|---|---|---|---|---|---|---|
| gi\|227424077\|ref\|ZP_03907176.1\| | Denitrovibrio acetiphilus | 42.4 | 42.9 | 43.6 | 49.4 | 40.2 |
| gi\|90424174\|ref\|YP_532544.1\| | R. palustris | 41.7 | 41.9 | 41.4 | 49.4 | 41.6 |
| gi\|49474168\|ref\|YP_032210.1\| | Bartonella quintana | 37.6 | 37.2 | 41.1 | 49.4 | 37.4 |
| gi\|163868459\|ref\|YP_001609668.1 | Bartonella tribocorum | 37.0 | 36.9 | 41.4 | 49.4 | 37.6 |
| gi\|186475593\|ref\|YP_001857063.1 | Burkholderia phymatum | 39.5 | 41.1 | 41.7 | 49.2 | 40.7 |
| gi\|86138659\|ref\|ZP_01057232.1\| | Roseobacter sp. | 40.2 | 39.3 | 42.9 | 49.2 | 42.4 |
| gi\|146341333\|ref\|YP_001206381.1 | Bradyrhizobium sp. | 41.1 | 41.3 | 41.8 | 49.2 | 41.9 |
| gi\|42520798\|ref\|NP_966713.1\| | W. endosymbiont | 39.0 | 41.9 | 42.8 | 49.2 | 36.7 |
| gi\|91215259\|ref\|ZP_01252231.1\| | Psychroflexus torquis | 35.9 | 37.6 | 36.8 | 49.1 | 34.2 |
| gi\|157165417\|ref\|YP_001466309.1 | C. concisus | 38.4 | 42.5 | 40.6 | 49.1 | 38.3 |
| gi\|188581268\|ref\|YP_001924713.1 | M. populi | 40.6 | 40.5 | 41.3 | 49.1 | 40.8 |
| gi\|218530286\|ref\|YP_002421102.1 | M. chloromethanicum | 40.3 | 40.2 | 42.5 | 49.1 | 39.7 |
| gi\|121602417\|ref\|YP_988942.1\| | Bartonella bacilliformis | 36.3 | 38.8 | 40.1 | 49.1 | 36.2 |
| gi\|254442812\|ref\|ZP_05056288.1\| | V. bacterium | 39.1 | 42.7 | 44.9 | 49.0 | 39.7 |
| gi\|58697191\|ref\|ZP_00372602.1\| | Wolbachia sp. | 39.7 | 41.9 | 42.4 | 49.0 | 36.9 |
| gi\|171057302\|ref\|YP_001789651.1 | L. cholodnii SP-6 | 40.1 | 39.5 | 44.1 | 48.9 | 39.3 |
| gi\|115377145\|ref\|ZP_01464359.1\| | Stigmatella aurantiaca | 39.3 | 39.9 | 41.0 | 48.9 | 41.2 |
| gi\|148255980\|ref\|YP_001240565.1 | Bradyrhizobium sp. | 41.1 | 40.9 | 40.9 | 48.9 | 42.1 |
| gi\|239831602\|ref\|ZP_04679931.1\| | O. intermedium | 38.4 | 39.4 | 41.4 | 48.9 | 39.1 |
| gi\|153009846\|ref\|YP_001371061.1 | Ochrobactrum anthropi | 37.3 | 39.1 | 42.0 | 48.9 | 39.2 |
| gi\|220918033\|ref\|YP_002493337.1 | A. dehalogenans | 38.4 | 39.0 | 44.1 | 48.8 | 41.5 |
| gi\|163851478\|ref\|YP_001639521.1 | M. extorquens | 40.3 | 40.2 | 42.5 | 48.8 | 39.7 |
| gi\|240138643\|ref\|YP_002963115.1 | M. extorquens | 40.3 | 40.2 | 42.5 | 48.8 | 39.7 |
| gi\|217976839\|ref\|YP_002360986.1 | Methylocella silvestris | 40.7 | 42.3 | 42.6 | 48.7 | 38.7 |
| gi\|254477647\|ref\|ZP_05091033.1\| | Ruegeria sp. | 42.8 | 38.7 | 45.3 | 48.6 | 42.6 |
| gi\|15964976\|ref\|NP_385329.1\| | Sinorhizobium meliloti | 38.4 | 38.4 | 42.3 | 48.6 | 39.6 |
| gi\|190571413\|ref\|YP_001975771.1 | W. endosymbiont . | 39.1 | 41.1 | 43.0 | 48.6 | 35.6 |
| gi\|163741402\|ref\|ZP_02148793.1\| | P.gallaeciensis | 42.0 | 39.4 | 42.8 | 48.5 | 42.4 |
| gi\|126739444\|ref\|ZP_01755137.1\| | Roseobacter sp. | 41.1 | 38.7 | 42.8 | 48.5 | 41.8 |
| gi\|237747696\|ref\|ZP_04578176.1\| | Oxalobacter formigenes | 38.0 | 40.1 | 44.3 | 48.5 | 41.5 |
| gi\|257460098\|ref\|ZP_05625202.1\| | Campylobacter gracilis | 38.0 | 42.4 | 39.6 | 48.4 | 36.9 |

FIG. 3E: Beta cont'd

FIG. 3E: Beta Ketoacyl-ACP Synthase Homologs

| | | | | | | |
|---|---|---|---|---|---|---|
| gi\|213018811\|ref\|ZP_03334619.1\| | W. endosymbiont | 39.9 | 41.1 | 43.0 | 48.4 | 35.9 |
| gi\|152993625\|ref\|YP_001359346.1 | Sulfurovum sp. | 39.6 | 38.5 | 41.7 | 48.3 | 36.8 |
| gi\|158320485\|ref\|YP_001512992.1 | Alkaliphilus oremlandii | 46.1 | 48.4 | 48.0 | 48.3 | 38.4 |
| gi\|255339139\|ref\|ZP_05379984.1\| | T. mathranii | 41.1 | 44.3 | 50.0 | 48.3 | 37.5 |
| gi\|255253206\|ref\|ZP_05332784.1\| | T.italicus | 41.1 | 44.3 | 50.0 | 48.3 | 37.5 |
| gi\|89069688\|ref\|ZP_01157025.1\| | Oceanicola granulosus | 42.6 | 39.0 | 45.6 | 48.3 | 41.8 |
| gi\|56697342\|ref\|YP_167710.1\| | Ruegeria pomeroyi | 42.8 | 39.0 | 45.0 | 48.3 | 42.7 |
| gi\|150396053\|ref\|YP_001326520.1 | Sinorhizobium medicae | 39.4 | 39.1 | 44.2 | 48.3 | 38.3 |
| gi\|222148216\|ref\|YP_002549173.1 | Agrobacterium vitis | 39.4 | 38.4 | 42.3 | 48.3 | 40.1 |
| gi\|157414625\|ref\|YP_001481881.1 | Campylobacter jejuni | 41.1 | 41.1 | 42.8 | 48.2 | 34.4 |
| gi\|86148946\|ref\|ZP_01067178.1\| | Campylobacter jejuni | 40.8 | 40.8 | 42.5 | 48.2 | 34.4 |
| gi\|88597152\|ref\|ZP_01100387.1\| | Campylobacter jejuni | 41.1 | 40.8 | 42.5 | 48.2 | 34.4 |
| gi\|148926423\|ref\|ZP_01810106.1\| | Campylobacter jejuni | 41.1 | 40.8 | 42.5 | 48.2 | 34.4 |
| gi\|283955753\|ref\|ZP_06373244.1\| | Campylobacter jejuni | 40.8 | 40.5 | 42.5 | 48.2 | 34.4 |
| gi\|57237379\|ref\|YP_178392.1\| | Campylobacter jejuni | 40.8 | 40.5 | 42.8 | 48.2 | 34.3 |
| gi\|163759218\|ref\|ZP_02166304.1\| | Hoeflea phototrophica | 39.9 | 40.9 | 42.6 | 48.2 | 40.3 |
| gi\|254465642\|ref\|ZP_05079053.1\| | R.bacterium | 42.5 | 38.7 | 42.3 | 48.2 | 40.5 |
| gi\|110633499\|ref\|YP_673707.1\| | Chelativorans sp. Mesorhizobium sp. | 40.0 | 42.0 | 43.3 | 48.2 | 41.0 |
| gi\|154149483\|ref\|YP_001407027.1 | Campylobacter hominis | 39.9 | 41.5 | 40.5 | 48.0 | 35.2 |
| gi\|85709151\|ref\|ZP_01040217.1\| | Erythrobacter sp. | 39.0 | 39.8 | 40.4 | 48.0 | 44.7 |
| gi\|118474601\|ref\|YP_891441.1\| | Campylobacter fetus | 39.9 | 40.1 | 44.6 | 48.0 | 38.7 |
| gi\|90419420\|ref\|ZP_01227330.1\| | A. manganoxydans | 42.4 | 39.1 | 43.4 | 48.0 | 43.0 |
| gi\|258514463\|ref\|YP_003190685.1 | D. acetoxidans | 38.3 | 40.3 | 44.1 | 48.0 | 41.8 |
| gi\|167465807\|ref\|ZP_02330896.1\| | Paenibacillus larvae | 41.2 | 44.3 | 47.7 | 48.0 | 40.6 |
| gi\|86151195\|ref\|ZP_01069410.1\| | Campylobacter jejuni | 41.1 | 40.8 | 42.5 | 47.9 | 34.4 |
| gi\|153952312\|ref\|YP_001398621.1 | Campylobacter jejuni | 41.1 | 40.2 | 42.2 | 47.9 | 34.4 |
| gi\|57168466\|ref\|ZP_00367600.1\| | Campylobacter coli | 39.5 | 40.8 | 43.4 | 47.9 | 33.7 |
| gi\|205356022\|ref\|ZP_03222790.1\| | Campylobacter jejuni | 40.5 | 40.2 | 42.8 | 47.9 | 34.3 |
| gi\|78777965\|ref\|YP_394280.1\| | S.denitrificans | 38.1 | 39.3 | 40.4 | 47.9 | 37.1 |
| gi\|189424998\|ref\|YP_001952175.1 | Geobacter lovleyi SZ | 40.4 | 41.8 | 44.1 | 47.9 | 42.6 |
| gi\|115360973\|ref\|YP_778110.1\| | Burkholderia ambifaria | 37.3 | 41.1 | 39.0 | 47.9 | 39.6 |

FIG. 3E: Beta cont'd

FIG. 3E: Beta Ketoacyl-ACP Synthase Homologs

| | | | | | | |
|---|---|---|---|---|---|---|
| gi\|269836406\|ref\|YP_003318634.1 | S.thermophilus | 39.1 | 40.1 | 44.8 | 47.8 | 41.9 |
| gi\|168704647\|ref\|ZP_02736924.1\| | G.obscuriglobus | 37.9 | 39.3 | 37.2 | 47.8 | 40.2 |
| gi\|83856930\|ref\|ZP_00950459.1\| | Croceibacter atlanticus | 38.5 | 37.6 | 36.4 | 47.8 | 34.7 |
| gi\|268678871\|ref\|YP_003303302.1 | S.deleyianum | 36.9 | 39.9 | 42.4 | 47.7 | 36.8 |
| gi\|118587999\|ref\|ZP_01545409.1\| | Stappia aggregata | 40.0 | 41.7 | 44.2 | 47.7 | 44.5 |
| gi\|284048730\|ref\|YP_003399069.1 | A.fermentans | 40.1 | 44.3 | 48.0 | 47.7 | 41.2 |
| gi\|189485607\|ref\|YP_001956548.1 | Termite gp.1 bacterium phylotype | 37.7 | 40.1 | 44.8 | 47.7 | 39.8 |
| gi\|114762843\|ref\|ZP_01442275.1\| | Roseovarius sp. | 43.3 | 39.9 | 44.2 | 47.7 | 41.6 |
| gi\|254419241\|ref\|ZP_05032965.1\| | Brevundimonas sp. | 38.4 | 38.7 | 44.7 | 47.7 | 44.7 |
| gi\|221633599\|ref\|YP_002522825.1 | T. roseum | 39.0 | 40.1 | 44.4 | 47.7 | 44.0 |
| gi\|126736414\|ref\|ZP_01752156.1\| | Roseobacter sp. | 42.4 | 38.7 | 44.7 | 47.6 | 42.2 |
| gi\|227821545\|ref\|YP_002825515.1 | Rhizobium sp. | 39.9 | 39.7 | 43.4 | 47.6 | 39.9 |
| gi\|222085522\|ref\|YP_002544052.1 | Agrobacterium radiobacter | 38.8 | 40.8 | 43.3 | 47.6 | 41.2 |
| gi\|283955195\|ref\|ZP_06372697.1\| | Campylobacter jejuni | 40.3 | 40.8 | 42.2 | 47.6 | 34.1 |
| gi\|57506043\|ref\|ZP_00371966.1\| | C.upsaliensis | 40.1 | 40.9 | 43.4 | 47.6 | 34.0 |
| gi\|222824331\|ref\|YP_002575905.1 | Campylobacter lari | 40.2 | 39.6 | 42.1 | 47.6 | 34.7 |
| gi\|254457001\|ref\|ZP_05070429.1\| | C. bacterium | 37.2 | 39.6 | 40.7 | 47.5 | 37.4 |
| gi\|196231868\|ref\|ZP_03130724.1\| | Chthoniobacter flavus | 38.4 | 41.3 | 43.7 | 47.5 | 41.0 |
| gi\|29840244\|ref\|NP_829350.1\| | Chlamydophila caviae | 35.8 | 35.8 | 40.7 | 47.5 | 38.2 |
| gi\|88714083\|ref\|ZP_01108161.1\| | F.bacterium | 39.2 | 39.3 | 36.9 | 47.5 | 35.6 |
| gi\|254500527\|ref\|ZP_05112678.1\| | Labrenzia alexandrii | 40.3 | 40.8 | 44.4 | 47.4 | 43.3 |
| gi\|206890275\|ref\|YP_002249274.1 | T. yellowstonii | 42.3 | 46.3 | 44.6 | 47.4 | 37.5 |
| gi\|269922519\|ref\|ZP_06171425.1\| | B. subvibrioides | 39.0 | 39.9 | 43.4 | 47.4 | 43.6 |
| gi\|118199814\|gb\|ABK78991.1\| | Francisella tularensis | 40.3 | 40.3 | 41.2 | 47.4 | 35.5 |
| gi\|115360965\|ref\|YP_778102.1\| | Burkholderia ambifaria | 38.2 | 41.5 | 40.1 | 47.4 | 41.0 |
| gi\|254469167\|ref\|ZP_05082572.1\| | Pseudovibrio sp. | 42.6 | 41.9 | 42.9 | 47.3 | 41.6 |
| gi\|99080755\|ref\|YP_612909.1\| | Ruegeria sp. | 41.2 | 39.0 | 42.5 | 47.3 | 43.2 |
| gi\|254510949\|ref\|ZP_05123016.1\| | R. bacterium | 41.9 | 37.9 | 44.5 | 47.3 | 41.6 |
| gi\|58700000\|ref\|ZP_00374563.1\| | W. endosymbiont . | 43.8 | 45.5 | 44.8 | 47.3 | 37.2 |
| gi\|73667190\|ref\|YP_303206.1\| | Ehrlichia canis | 39.8 | 45.0 | 44.1 | 47.3 | 38.6 |
| gi\|251772096\|gb\|EES52666.1\| | L. ferrodiazotrophum | 41.5 | 41.5 | 41.3 | 47.3 | 44.6 |

FIG. 3E: Beta cont'd

FIG. 3E: Beta Ketoacyl-ACP Synthase Homologs

| | | | | | | |
|---|---|---|---|---|---|---|
| gi\|15835128\|ref\|NP_296887.1\| | Chlamydia muridarum | 35.8 | 36.6 | 39.7 | 47.2 | 37.2 |
| gi\|262037549\|ref\|ZP_06011008.1\| | Leptotrichia goodfellowii | 44.1 | 45.6 | 46.5 | 47.2 | 41.2 |
| gi\|149926449\|ref\|ZP_01914710.1\| | Limnobacter sp. | 38.2 | 41.7 | 37.3 | 47.2 | 38.4 |
| gi\|163782791\|ref\|ZP_02177787.1\| | Hydrogenivirga sp. | 42.8 | 43.3 | 43.9 | 47.2 | 40.5 |
| gi\|89890636\|ref\|ZP_01202146.1\| | Flavobacteria bacterium | 36.9 | 37.2 | 34.8 | 47.2 | 34.7 |
| gi\|260063522\|ref\|YP_003196602.1 | Robiginitalea biformata | 37.2 | 39.6 | 36.7 | 47.1 | 36.3 |
| gi\|255659792\|ref\|ZP_05405201.1\| | Mitsuokella multacida | 40.7 | 43.4 | 47.1 | 47.1 | 39.1 |
| gi\|258405537\|ref\|YP_003198279.1 | D.retbaense | 39.8 | 39.2 | 42.9 | 47.1 | 40.4 |
| gi\|219669837\|ref\|YP_002460272.1 | D.hafniense | 40.1 | 42.1 | 46.8 | 47.0 | 43.1 |
| gi\|147678080\|ref\|YP_001212295.1 | P. thermopropionicum | 41.4 | 43.3 | 46.8 | 47.0 | 44.6 |
| gi\|170694827\|ref\|ZP_02885977.1\| | Burkholderia graminis | 39.1 | 39.6 | 41.5 | 47.0 | 40.9 |
| gi\|226313214\|ref\|YP_002773108.1 | Brevibacillus brevis | 42.5 | 44.2 | 50.0 | 47.0 | 40.2 |
| gi\|256750703\|ref\|ZP_05491588.1\| | T.ethanolicus | 42.3 | 44.6 | 49.1 | 47.0 | 37.8 |
| gi\|255257455\|ref\|ZP_05336892.1\| | T.bacterium | 40.2 | 43.4 | 47.5 | 47.0 | 37.5 |
| gi\|167040363\|ref\|YP_001663348.1 | T.bacter sp. | 42.0 | 44.3 | 48.8 | 47.0 | 37.8 |
| gi\|83589795\|ref\|YP_429804.1\| | Moorella thermoacetica | 42.6 | 42.9 | 47.2 | 47.0 | 46.1 |
| gi\|120436685\|ref\|YP_862371.1\| | Gramella forsetii | 37.5 | 38.9 | 36.0 | 47.0 | 32.9 |
| gi\|253573481\|ref\|ZP_04850824.1\| | Paenibacillus sp. | 41.7 | 47.0 | 55.2 | 47.0 | 44.6 |
| gi\|261408038\|ref\|YP_003244279.1 | Geobacillus sp. | 39.9 | 43.8 | 53.6 | 47.0 | 42.0 |
| gi\|259419119\|ref\|ZP_05743036.1\| | Silicibacter sp. | 41.5 | 38.7 | 42.8 | 47.0 | 43.9 |
| gi\|266627934\|ref\|ZP_06120861.1\| | Caulobacter segnis | 39.0 | 40.9 | 43.4 | 47.0 | 44.0 |
| gi\|162329643\|ref\|YP_469062.2\| | Rhizobium etli | 39.3 | 39.1 | 42.3 | 47.0 | 39.9 |
| gi\|149202719\|ref\|ZP_01879691.1\| | Roseovarius sp. | 40.8 | 38.6 | 44.7 | 47.0 | 41.3 |
| gi\|171912977\|ref\|ZP_02928447.1\| | V.spinosum | 41.5 | 41.6 | 42.9 | 46.9 | 42.8 |
| gi\|238019515\|ref\|ZP_04599941.1\| | Veillonella dispar | 41.5 | 43.1 | 44.6 | 46.9 | 37.5 |
| gi\|283851285\|ref\|ZP_06368567.1\| | Desulfovibrio sp. | 37.2 | 38.8 | 40.0 | 46.9 | 39.4 |
| gi\|258545279\|ref\|ZP_05705513.1\| | C. hominis | 41.3 | 42.0 | 42.0 | 46.9 | 40.9 |
| gi\|254293750\|ref\|YP_003059773.1 | Hirschia baltica | 40.7 | 41.6 | 41.0 | 46.9 | 43.5 |
| gi\|114570073\|ref\|YP_756753.1\| | Maricaulis maris | 36.8 | 38.3 | 40.2 | 46.8 | 42.0 |
| gi\|118199821\|gb\|ABK78994.1\| | Francisella tularensis | 41.4 | 41.8 | 41.9 | 46.8 | 35.9 |
| gi\|124515069\|gb\|EAY56580.1\| | Leptospirillum rubarum | 39.5 | 44.2 | 39.0 | 46.7 | 41.6 |

FIG. 3E: Beta cont'd

FIG. 3E: Beta Ketoacyl-ACP Synthase Homologs

| | | | | | | |
|---|---|---|---|---|---|---|
| gi\|227824528\|ref\|ZP_03989360.1\| | Acidaminococcus sp. | 39.9 | 43.2 | 48.0 | 46.7 | 37.8 |
| gi\|58584871\|ref\|YP_198444.1\| | W. endosymbiont | 37.1 | 40.1 | 42.0 | 46.7 | 32.2 |
| gi\|118199832\|gb\|ABK78999.1\| | Francisella tularensis | 40.9 | 40.5 | 40.7 | 46.7 | 35.0 |
| gi\|89895409\|ref\|YP_518896.1\| | D.hafniense | 40.1 | 42.4 | 47.1 | 46.7 | 42.5 |
| gi\|171315866\|ref\|ZP_02905096.1\| | Burkholderia ambifaria | 38.1 | 40.7 | 39.1 | 46.7 | 41.0 |
| gi\|241903018\|ref\|ZP_04787747.1\| | T.brockii | 42.9 | 45.3 | 49.7 | 46.7 | 38.7 |
| gi\|167037702\|ref\|YP_001665280.1 | T.pseudethanolicus | 42.9 | 45.3 | 49.7 | 46.7 | 38.7 |
| gi\|114798802\|ref\|YP_759881.1\| | H. neptunium | 40.2 | 39.4 | 40.7 | 46.7 | 44.8 |
| gi\|260433447\|ref\|ZP_05787418.1\| | S.lacuscaerulensis | 41.6 | 39.6 | 43.1 | 46.7 | 41.8 |
| gi\|119384598\|ref\|YP_915654.1\| | P. denitrificans | 39.5 | 38.0 | 42.9 | 46.7 | 43.3 |
| gi\|86281272\|gb\|ABC90335.1\| | Rhizobium etli | 39.0 | 38.7 | 42.7 | 46.7 | 40.7 |
| gi\|88658133\|ref\|YP_507266.1\| | Ehrlichia chaffeensis | 38.6 | 43.1 | 44.1 | 46.7 | 37.7 |
| gi\|83952158\|ref\|ZP_00960890.1\| | R.nubinhibens | 40.1 | 38.1 | 44.0 | 46.7 | 41.6 |
| gi\|401573\|sp\|P30790.1\|FABH_RHOCA | R.capsulatus | 43.4 | 40.5 | 42.1 | 46.7 | 43.6 |
| gi\|110638295\|ref\|YP_678504.1\| | Cytophaga hutchinsonii | 35.5 | 38.4 | 36.4 | 46.7 | 34.8 |
| gi\|281357315\|ref\|ZP_06243804.1\| | Victivallis vadensis | 38.7 | 41.4 | 40.5 | 46.6 | 40.7 |
| gi\|115314900\|ref\|YP_763623.1\| | F. novicida, F.tularensis | 40.3 | 40.5 | 40.9 | 46.6 | 35.5 |
| gi\|57339706\|gb\|AAW49840.1\| | synthetic construct | 40.3 | 40.5 | 40.9 | 46.6 | 35.5 |
| gi\|56708426\|ref\|YP_170322.1\| | Francisella tularensis | 40.3 | 40.5 | 40.9 | 46.6 | 35.5 |
| gi\|89256465\|ref\|YP_513827.1\| | Francisella tularensis | 39.7 | 40.5 | 40.9 | 46.6 | 35.5 |
| gi\|237802662\|ref\|YP_002887856.1 | Chlamydia trachomatis | 35.8 | 36.6 | 40.0 | 46.6 | 36.6 |
| gi\|255348597\|ref\|ZP_05380604.1\| | Chlamydia trachomatis | 36.1 | 36.6 | 40.0 | 46.6 | 36.6 |
| gi\|260888909\|ref\|ZP_05900172.1\| | Leptotrichia hofstadii | 46.0 | 47.3 | 46.5 | 46.6 | 39.6 |
| gi\|269797759\|ref\|YP_003311659.1 | Veillonella parvula | 41.5 | 43.4 | 44.3 | 46.6 | 37.5 |
| gi\|258594820\|ref\|ZP_05709630.1\| | D.alkaliphilus | 39.0 | 39.8 | 41.2 | 46.6 | 37.1 |
| gi\|118199828\|gb\|ABK78997.1\| | Francisella tularensis | 41.2 | 40.9 | 41.2 | 46.6 | 35.0 |
| gi\|256756761\|ref\|ZP_05497510.1\| | C. papyrosolvens | 37.7 | 44.3 | 44.5 | 46.6 | 33.5 |
| gi\|62185099\|ref\|YP_219884.1\| | Chlamydophila abortus | 35.8 | 35.4 | 40.7 | 46.6 | 37.6 |
| gi\|89898330\|ref\|YP_515440.1\| | Chlamydophila felis | 35.8 | 35.3 | 40.7 | 46.6 | 36.9 |
| gi\|23098659\|ref\|NP_692125.1\| | O. iheyensis | 44.6 | 42.9 | 56.2 | 46.5 | 38.1 |
| gi\|206901562\|ref\|YP_002250658.1 | D. thermophilum | 39.8 | 41.9 | 46.2 | 46.5 | 36.2 |

FIG. 3E: Beta cont'd

FIG. 3E: Beta Ketoacyl-ACP Synthase Homologs

| | | | | | | |
|---|---|---|---|---|---|---|
| gi\|239908630\|ref\|YP_002955372.1 | D.magneticus | 37.4 | 40.1 | 39.9 | 46.5 | 40.4 |
| gi\|220928133\|ref\|YP_002505042.1 | C. cellulolyticum | 39.3 | 43.8 | 45.2 | 46.4 | 34.7 |
| gi\|197105122\|ref\|YP_002130499.1 | P. zucineum | 39.3 | 41.2 | 42.5 | 46.4 | 45.6 |
| gi\|280958462\|ref\|ZP_06233101.1\| | D. aespoeensis | 36.9 | 37.8 | 39.3 | 46.4 | 42.5 |
| gi\|241773807\|ref\|ZP_04771151.1\| | A.excentricus | 41.5 | 39.2 | 43.9 | 46.4 | 41.9 |
| gi\|225166240\|ref\|ZP_03727944.1\| | O. bacterium | 38.6 | 41.8 | 39.8 | 46.4 | 38.8 |
| gi\|163735833\|ref\|ZP_02143262.1\| | Roseobacter litoralis | 42.3 | 37.8 | 43.4 | 46.4 | 42.6 |
| gi\|110680343\|ref\|YP_683350.1\| | R.denitrificans | 43.5 | 37.8 | 42.5 | 46.4 | 43.2 |
| gi\|15888517\|ref\|NP_354198.1\| | A.tumefaciens | 39.8 | 39.4 | 42.3 | 46.4 | 39.9 |
| gi\|254437842\|ref\|ZP_05051336.1\| | O.antarcticus | 42.9 | 38.7 | 43.1 | 46.4 | 42.4 |
| gi\|209548800\|ref\|YP_002280717.1 | R.leguminosarum | 38.8 | 39.4 | 41.4 | 46.4 | 40.0 |
| gi\|229918444\|ref\|YP_002887090.1 | Exiguobacterium sp. | 41.0 | 41.3 | 46.6 | 46.4 | 40.9 |
| gi\|190891217\|ref\|YP_001977759.1 | Rhizobium etli | 38.6 | 38.4 | 42.1 | 46.4 | 41.0 |
| gi\|42523489\|ref\|NP_968869.1\| | B.bacteriovorus | 42.1 | 40.6 | 41.2 | 46.3 | 38.1 |
| gi\|156502571\|ref\|YP_001428636.1 | Francisella tularensis | 40.3 | 40.5 | 40.9 | 46.3 | 35.5 |
| gi\|118199817\|gb\|ABK78992.1\| | Francisella tularensis | 40.3 | 40.5 | 40.9 | 46.3 | 35.5 |
| gi\|15604960\|ref\|NP_219744.1\| | Chlamydia trachomatis | 35.8 | 36.3 | 40.0 | 46.3 | 36.6 |
| gi\|148656735\|ref\|YP_001276940.1 | Roseiflexus sp. | 38.2 | 39.8 | 40.1 | 46.3 | 46.5 |
| gi\|282849033\|ref\|ZP_06258422.1\| | Veillonella parvula | 41.5 | 43.4 | 43.8 | 46.3 | 37.5 |
| gi\|15618218\|ref\|NP_224503.1\| | C. pneumoniae | 37.0 | 37.2 | 43.5 | 46.3 | 36.6 |
| gi\|15896812\|ref\|NP_350161.1\| | C.acetobutylicum | 48.8 | 47.8 | 49.5 | 46.3 | 37.5 |
| gi\|225180927\|ref\|ZP_03734375.1\| | Dethiobacter alkaliphilus | 41.6 | 43.3 | 44.1 | 46.3 | 44.0 |
| gi\|229068831\|ref\|ZP_04202127.1\| | Bacillus cereus | 42.2 | 43.2 | 59.5 | 46.2 | 40.9 |
| gi\|255321896\|ref\|ZP_05363046.1\| | Campylobacter showae | 37.4 | 40.1 | 42.8 | 46.2 | 36.3 |
| gi\|187735136\|ref\|YP_001877248.1 | A. muciniphila | 39.9 | 39.6 | 42.6 | 46.2 | 41.4 |
| gi\|126729746\|ref\|ZP_01745559.1\| | Sagittula stellata | 40.6 | 39.2 | 42.4 | 46.2 | 41.2 |
| gi\|91202495\|emb\|CAJ72134.1\| | C. Kuenenia stuttgartiensis | 38.0 | 40.6 | 43.3 | 46.1 | 36.8 |
| gi\|146296615\|ref\|YP_001180386.1 | C.saccharolyticus | 44.0 | 46.9 | 48.9 | 46.1 | 41.0 |
| gi\|206603809\|gb\|EDZ40289.1\| | Leptospirillum sp. | 40.5 | 44.0 | 38.9 | 46.1 | 42.2 |
| gi\|226227045\|ref\|YP_002761151.1 | G. aurantiaca | 39.8 | 39.3 | 40.6 | 46.1 | 40.5 |
| gi\|182680279\|ref\|YP_001834425.1 | Beijerinckia indica | 40.8 | 39.4 | 43.6 | 46.1 | 38.9 |

FIG. 3E: Beta cont'd

FIG. 3E: Beta Ketoacyl-ACP Synthase Homologs

| | | | | | | |
|---|---|---|---|---|---|---|
| gi\|150390519\|ref\|YP_001320568.1 | A,metalliredigens | 43.6 | 44.3 | 49.5 | 46.1 | 40.0 |
| gi\|20807922\|ref\|NP_623093.1\| | T, tengcongensis | 41.8 | 43.7 | 50.3 | 46.1 | 38.7 |
| gi\|77463166\|ref\|YP_352670.1\| | R,sphaeroides | 43.2 | 37.5 | 42.0 | 46.1 | 41.6 |
| gi\|51246645\|ref\|YP_066529.1\| | D,psychrophila | 39.0 | 39.4 | 40.7 | 46.0 | 36.6 |
| gi\|258510042\|ref\|YP_003183476.1 | A, acidocaldarius | 35.8 | 37.8 | 41.1 | 46.0 | 39.1 |
| gi\|156741784\|ref\|YP_001431913.1 | Roseiflexus castenholzii | 39.7 | 39.4 | 41.3 | 46.0 | 46.5 |
| gi\|229004016\|ref\|ZP_04161820.1\| | Bacillus mycoides | 43.8 | 43.6 | 61.8 | 45.9 | 40.5 |
| gi\|228990257\|ref\|ZP_04150225.1\| | B,pseudomycoides | 43.8 | 43.3 | 61.8 | 45.9 | 40.5 |
| gi\|228996353\|ref\|ZP_04155996.1\| | Bacillus mycoides | 43.8 | 43.6 | 61.8 | 45.9 | 40.5 |
| gi\|229028948\|ref\|ZP_04185047.1\| | Bacillus cereus | 42.2 | 43.2 | 59.5 | 45.9 | 40.9 |
| gi\|229010566\|ref\|ZP_04167768.1\| | B, mycoides, B,cereus | 42.2 | 42.9 | 61.1 | 45.9 | 41.2 |
| gi\|229171921\|ref\|ZP_04299488.1\| | Bacillus cereus | 42.2 | 42.5 | 61.1 | 45.9 | 41.2 |
| gi\|228899858\|ref\|ZP_04064103.1\| | B, thuringiensis, B,cereus | 42.2 | 42.9 | 59.8 | 45.9 | 40.9 |
| gi\|163755950\|ref\|ZP_02163067.1\| | Kordia algicida | 37.9 | 39.8 | 37.8 | 45.9 | 33.2 |
| gi\|256827886\|ref\|YP_003156614.1 | D, baculatum | 35.9 | 36.7 | 40.2 | 45.8 | 39.5 |
| gi\|149371241\|ref\|ZP_01890727.1\| | unidentified eubacterium | 37.7 | 36.7 | 36.5 | 45.8 | 34.2 |
| gi\|134299921\|ref\|YP_001113417.1 | D,reducens | 41.0 | 42.3 | 44.0 | 45.8 | 40.2 |
| gi\|260427652\|ref\|ZP_05781631.1\| | Citreicella sp. | 41.8 | 39.3 | 43.5 | 45.8 | 41.6 |
| gi\|163746486\|ref\|ZP_02153844.1\| | Oceanibulbus indolifex | 42.5 | 39.3 | 41.6 | 45.8 | 43.0 |
| gi\|221639023\|ref\|YP_002525285.1 | R,sphaeroides | 43.6 | 37.9 | 42.0 | 45.8 | 41.2 |
| gi\|116251405\|ref\|YP_767243.1\| | R, leguminosarum | 38.1 | 38.8 | 41.7 | 45.7 | 40.3 |
| gi\|241204021\|ref\|YP_002975117.1 | R, leguminosarum | 38.4 | 38.8 | 41.7 | 45.7 | 39.8 |
| gi\|260589509\|ref\|ZP_05855422.1\| | B, hansenii | 47.4 | 48.8 | 43.5 | 45.7 | 39.7 |
| gi\|126462038\|ref\|YP_001043152.1 | R. sphaeroides | 43.2 | 37.5 | 42.0 | 45.7 | 41.6 |
| gi\|149914951\|ref\|ZP_01903480.1\| | Roseobacter sp. | 39.8 | 39.6 | 42.9 | 45.7 | 42.1 |
| gi\|167627577\|ref\|YP_001678077.1 | Francisella philomiragia | 40.8 | 39.9 | 41.2 | 45.7 | 35.8 |
| gi\|241668144\|ref\|ZP_04755722.1\| | Francisella philomiragia | 40.8 | 40.2 | 41.2 | 45.7 | 35.8 |
| gi\|94264504\|ref\|ZP_01288291.1\| | delta proteobacterium | 38.2 | 42.1 | 41.2 | 45.7 | 37.7 |
| gi\|254495455\|ref\|ZP_05108379.1\| | Polaribacter sp. | 37.0 | 37.5 | 39.0 | 45.7 | 33.8 |
| gi\|269121073\|ref\|YP_003309250.1 | Sebaldella termitidis | 44.0 | 46.4 | 46.5 | 45.7 | 40.3 |
| gi\|86132223\|ref\|ZP_01050818.1\| | Dokdonia donghaensis | 39.9 | 40.5 | 38.1 | 45.7 | 35.9 |

FIG. 3E: Beta cont'd

FIG. 3E: Beta Ketoacyl-ACP Synthase Homologs

| | | | | | | |
|---|---|---|---|---|---|---|
| gi\|126662121\|ref\|ZP_01733120.1\| | Flavobacteria bacterium | 37.6 | 38.7 | 35.5 | 45.6 | 34.1 |
| gi\|146298019\|ref\|YP_001192610.1 | F.johnsoniae | 39.1 | 39.9 | 36.1 | 45.6 | 34.4 |
| gi\|89054275\|ref\|YP_509726.1\| | Jannaschia sp. | 39.8 | 40.1 | 43.4 | 45.6 | 40.3 |
| gi\|210622483\|ref\|ZP_03293188.1\| | Clostridium hiranonis | 45.8 | 44.1 | 48.6 | 45.6 | 43.0 |
| gi\|225849366\|ref\|YP_002729530.1 | S.azorense | 42.7 | 46.4 | 47.9 | 45.6 | 41.5 |
| gi\|114771804\|ref\|ZP_01449197.1\| | alpha proteobacterium | 42.4 | 41.7 | 41.8 | 45.6 | 41.6 |
| gi\|163939075\|ref\|YP_001643959.1 | B.weihenstephanensis | 42.2 | 42.9 | 61.7 | 45.6 | 41.2 |
| gi\|75763553\|ref\|ZP_00743259.1\| | B. thuringiensis, B. cereus | 42.2 | 42.9 | 60.4 | 45.6 | 40.9 |
| gi\|269958623\|ref\|YP_003328410.1 | A. centrale | 39.1 | 39.4 | 38.9 | 45.6 | 38.5 |
| gi\|212639964\|ref\|YP_002316484.1 | A.flavithermus | 42.0 | 42.7 | 61.3 | 45.5 | 39.0 |
| gi\|65318552\|ref\|ZP_00391511.1\| | B.thuringiensis, B. cereus | 42.2 | 43.2 | 60.5 | 45.5 | 40.9 |
| gi\|228906911\|ref\|ZP_04070778.1\| | Bacillus thuringiensis | 42.5 | 43.2 | 59.8 | 45.5 | 40.6 |
| gi\|228913852\|ref\|ZP_04077477.1\| | B. thuringiensis | 42.2 | 43.2 | 60.8 | 45.5 | 40.6 |
| gi\|229095762\|ref\|ZP_04226741.1\| | Bacillus cereus | 41.9 | 42.5 | 60.5 | 45.5 | 40.9 |
| gi\|228919996\|ref\|ZP_04083349.1\| | Bacillus thuringiensis | 41.3 | 42.5 | 60.1 | 45.5 | 41.2 |
| gi\|229183479\|ref\|ZP_04310704.1\| | Bacillus cereus | 42.2 | 43.2 | 60.5 | 45.5 | 40.9 |
| gi\|217967330\|ref\|YP_002352836.1 | Dictyoglomus turgidum | 40.4 | 42.9 | 46.2 | 45.5 | 34.7 |
| gi\|160893366\|ref\|ZP_02074152.1\| | Clostridium sp. | 43.3 | 43.8 | 41.8 | 45.5 | 39.3 |
| gi\|254519776\|ref\|ZP_05131832.1\| | Clostridium sp. | 46.2 | 44.2 | 41.8 | 45.5 | 37.0 |
| gi\|167646995\|ref\|YP_001684658.1 | Caulobacter sp. | 38.7 | 39.0 | 42.1 | 45.5 | 43.8 |
| gi\|27262210\|gb\|AAN87386.1\| | Heliobacillus mobilis, | 40.0 | 42.1 | 45.4 | 45.5 | 41.5 |
| gi\|77920577\|ref\|YP_358392.1\| | Pelobacter carbinolicus | 40.5 | 39.1 | 41.9 | 45.5 | 40.2 |
| gi\|169830823\|ref\|YP_001716805.1 | C. Desulforudis audaxviator | 39.5 | 42.9 | 49.8 | 45.5 | 46.6 |
| gi\|260575263\|ref\|ZP_05843263.1\| | Rhodobacter sp. | 42.4 | 39.0 | 43.2 | 45.4 | 42.4 |
| gi\|218960594\|ref\|YP_001740369.1 | C. Cloacamonas acidaminovorans, | 38.1 | 41.5 | 42.1 | 45.4 | 35.5 |
| gi\|126698775\|ref\|YP_001087672.1 | Clostridium difficile | 44.5 | 44.5 | 50.9 | 45.4 | 39.9 |
| gi\|255655182\|ref\|ZP_05400591.1\| | Clostridium difficile | 44.6 | 44.8 | 51.2 | 45.4 | 39.9 |
| gi\|162452090\|ref\|YP_001614457.1 | Sorangium cellulosum | 39.9 | 40.4 | 38.9 | 45.4 | 41.7 |
| gi\|218288989\|ref\|ZP_03493226.1\| | A. acidocaldarius | 36.9 | 37.8 | 40.4 | 45.4 | 39.1 |
| gi\|222529146\|ref\|YP_002573028.1 | A.thermophilum | 42.7 | 47.2 | 50.5 | 45.3 | 40.1 |
| gi\|220931869\|ref\|YP_002508777.1 | Halothermothrix orenii | 43.3 | 45.2 | 51.4 | 45.3 | 39.6 |

FIG. 3E: Beta cont'd

FIG. 3E: Beta Ketoacyl-ACP Synthase Homologs

| | | | | | | |
|---|---|---|---|---|---|---|
| gi\|30261284\|ref\|NP_843661.1\| | B. thuringiensis, B.anthracis, B. cereus | 42.2 | 43.2 | 61.0 | 45.3 | 40.9 |
| gi\|42780367\|ref\|NP_977614.1\| | Bacillus cereus | 42.2 | 43.2 | 61.3 | 45.3 | 40.6 |
| gi\|196044366\|ref\|ZP_03111602.1\| | Bacillus cereus | 42.2 | 43.2 | 61.0 | 45.3 | 40.9 |
| gi\|56419339\|ref\|YP_146657.1\| | G.kaustophilus | 43.2 | 43.7 | 62.3 | 45.3 | 41.2 |
| gi\|229101860\|ref\|ZP_04232574.1\| | Bacillus cereus | 41.2 | 42.7 | 60.5 | 45.3 | 39.9 |
| gi\|229154843\|ref\|ZP_04282958.1\| | Bacillus cereus | 42.2 | 43.2 | 60.5 | 45.2 | 40.6 |
| gi\|229137964\|ref\|ZP_04266563.1\| | Bacillus cereus | 41.9 | 42.9 | 60.5 | 45.2 | 40.2 |
| gi\|228957549\|ref\|ZP_04119301.1\| | B. cereus, B. thuringiensis | 42.2 | 43.2 | 60.5 | 45.2 | 40.9 |
| gi\|228984348\|ref\|ZP_04144529.1\| | B. thuringiensis | 42.2 | 43.2 | 60.5 | 45.2 | 40.6 |
| gi\|229149480\|ref\|ZP_04277716.1\| | Bacillus cereus | 41.9 | 42.9 | 60.1 | 45.2 | 40.6 |
| gi\|229160233\|ref\|ZP_04288232.1\| | Bacillus cereus | 41.9 | 42.5 | 60.5 | 45.2 | 40.6 |
| gi\|255335033\|ref\|ZP_05375947.1\| | H. denitrificans | 43.2 | 42.8 | 42.1 | 45.2 | 39.8 |
| gi\|254780497\|ref\|YP_003064910.1 | C. Liberibacter asiaticus | 38.4 | 37.9 | 40.4 | 45.2 | 35.3 |
| gi\|146277949\|ref\|YP_001168108.1 | Rsphaeroides | 41.7 | 36.3 | 42.5 | 45.1 | 41.0 |
| gi\|255262421\|ref\|ZP_05341763.1\| | Thalassiobium sp. | 43.0 | 38.1 | 43.5 | 45.1 | 41.3 |
| gi\|254487266\|ref\|ZP_05100471.1\| | Roseobacter sp. | 40.7 | 39.3 | 42.8 | 45.1 | 40.7 |
| gi\|83942552\|ref\|ZP_00955013.1\| | Sulfitobacter sp. | 41.3 | 38.7 | 41.2 | 45.1 | 40.6 |
| gi\|221234369\|ref\|YP_002516805.1 | Caulobacter crescentus | 38.3 | 40.9 | 44.0 | 45.1 | 43.5 |
| gi\|57239299\|ref\|YP_180435.1\| | Ehrlichia ruminantium | 39.1 | 41.6 | 43.5 | 45.1 | 40.5 |
| gi\|254453296\|ref\|ZP_05066733.1\| | O.antarcticus | 42.2 | 38.1 | 42.0 | 45.1 | 42.7 |
| gi\|172058073\|ref\|YP_001814533.1 | E. sibiricum | 42.6 | 43.7 | 49.5 | 45.1 | 38.9 |
| gi\|225012668\|ref\|ZP_03703103.1\| | Flavobacteria bacterium | 35.2 | 36.9 | 34.8 | 45.1 | 33.2 |
| gi\|269926750\|ref\|YP_003323373.1 | T.terrenum | 39.2 | 42.8 | 41.7 | 45.1 | 39.6 |
| gi\|167630230\|ref\|YP_001680729.1 | H. modesticaldum | 37.0 | 39.9 | 43.5 | 45.0 | 41.5 |
| gi\|188996759\|ref\|YP_001931010.1 | Sulfurihydrogenibium sp. | 43.7 | 46.1 | 49.2 | 45.0 | 41.4 |
| gi\|47568377\|ref\|ZP_00239078.1\| | Bacillus cereus | 42.2 | 43.2 | 61.0 | 45.0 | 40.6 |
| gi\|206977706\|ref\|ZP_03238598.1\| | Bacillus cereus | 41.9 | 42.9 | 61.0 | 45.0 | 40.2 |
| gi\|30019328\|ref\|NP_830959.1\| | Bacillus cereus | 42.2 | 43.2 | 61.0 | 45.0 | 40.9 |
| gi\|218232455\|ref\|YP_002365961.1 | Bacillus cereus | 41.9 | 42.9 | 60.7 | 45.0 | 40.6 |
| gi\|218902373\|ref\|YP_002450207.1 | Bacillus cereus | 42.2 | 43.2 | 61.3 | 45.0 | 40.6 |
| gi\|222094902\|ref\|YP_002528962.1 | Bacillus cereus | 42.2 | 43.2 | 61.3 | 45.0 | 40.6 |

FIG. 3E: Beta cont'd

FIG. 3E: Beta Ketoacyl-ACP Synthase Homologs

| | | | | | | |
|---|---|---|---|---|---|---|
| gi\|52079630\|ref\|YP_078421.1\| | Bacillus licheniformis | 42.6 | 41.9 | 58.1 | 45.0 | 38.1 |
| gi\|152990146\|ref\|YP_001355870.1 | Nitratiruptor sp. | 37.4 | 42.9 | 41.2 | 45.0 | 36.8 |
| gi\|83814585\|ref\|YP_444197.1\| | Salinibacter ruber | 40.0 | 40.2 | 39.4 | 44.9 | 42.0 |
| gi\|255530139\|ref\|YP_003090511.1 | Pedobacter heparinus | 35.3 | 37.0 | 38.5 | 44.9 | 32.8 |
| gi\|182415412\|ref\|YP_001820478.1 | Opitutus terrae | 38.6 | 41.1 | 41.5 | 44.9 | 36.9 |
| gi\|257125402\|ref\|YP_003163516.1 | Leptotrichia buccalis | 46.0 | 47.9 | 46.8 | 44.9 | 39.3 |
| gi\|16125618\|ref\|NP_420182.1\| | Caulobacter crescentus | 38.3 | 40.9 | 44.0 | 44.9 | 43.5 |
| gi\|225572697\|ref\|ZP_03781452.1\| | B.hydrogenotrophica | 46.1 | 45.0 | 41.3 | 44.9 | 38.2 |
| gi\|258645859\|ref\|ZP_05733328.1\| | Dialister invisus | 40.7 | 40.7 | 43.5 | 44.9 | 37.5 |
| gi\|124010072\|ref\|ZP_01694733.1\| | Microscilla marina | 35.5 | 36.9 | 37.9 | 44.8 | 36.0 |
| gi\|3006128\|emb\|CAA06179.1\| | T.thermosaccharolyticum | 39.9 | 41.3 | 46.2 | 44.8 | 37.2 |
| gi\|126726951\|ref\|ZP_01742790.1\| | R.bacterium | 40.7 | 39.6 | 41.1 | 44.8 | 40.5 |
| gi\|83953773\|ref\|ZP_00962494.1\| | Sulfitobacter sp. | 41.0 | 38.4 | 41.8 | 44.8 | 40.8 |
| gi\|58617319\|ref\|YP_196518.1\| | Ehrlichia ruminantium | 38.5 | 41.3 | 43.1 | 44.8 | 40.2 |
| gi\|84516336\|ref\|ZP_01003696.1\| | Loktanella vestfoldensis | 39.9 | 38.5 | 44.2 | 44.8 | 40.6 |
| gi\|86142358\|ref\|ZP_01060868.1\| | L. blandensis | 38.2 | 37.2 | 38.4 | 44.8 | 34.8 |
| gi\|150025557\|ref\|YP_001296383.1 | F. psychrophilum | 37.0 | 39.0 | 36.7 | 44.7 | 35.6 |
| gi\|78357471\|ref\|YP_388920.1\| | D.desulfuricans | 41.5 | 41.4 | 42.0 | 44.7 | 41.4 |
| gi\|152974703\|ref\|YP_001374220.1 | Bacillus cereus | 42.5 | 43.0 | 61.3 | 44.7 | 39.6 |
| gi\|229498759\|ref\|ZP_04392452.1\| | Geobacillus sp. | 42.9 | 43.3 | 62.6 | 44.7 | 40.6 |
| gi\|196248032\|ref\|ZP_03146734.1\| | Geobacillus sp. | 44.2 | 44.3 | 62.3 | 44.7 | 39.3 |
| gi\|138894356\|ref\|YP_001124809.1 | G. thermodenitrificans | 44.2 | 44.3 | 62.3 | 44.7 | 39.3 |
| gi\|157691839\|ref\|YP_001486301.1 | Bacillus pumilus | 42.3 | 42.4 | 60.4 | 44.7 | 37.5 |
| gi\|126654340\|ref\|ZP_01726102.1\| | Bacillus sp. | 44.2 | 43.8 | 61.5 | 44.7 | 39.0 |
| gi\|163789349\|ref\|ZP_02183790.1\| | F.bacterium | 36.6 | 38.9 | 37.4 | 44.6 | 34.0 |
| gi\|56416963\|ref\|YP_154037.1\| | Anaplasma marginale | 39.1 | 40.6 | 39.5 | 44.6 | 37.3 |
| gi\|188585983\|ref\|YP_001917528.1 | N.thermophilus | 42.1 | 44.1 | 46.8 | 44.6 | 39.3 |
| gi\|239623103\|ref\|ZP_04666134.1\| | Clostridiales bacterium | 46.1 | 44.7 | 42.1 | 44.6 | 38.0 |
| gi\|261877568\|ref\|ZP_06004173.1\| | Selenomonas noxia | 40.7 | 43.7 | 42.8 | 44.6 | 36.6 |
| gi\|238926912\|ref\|ZP_04658672.1\| | Selenomonas flueggei | 40.4 | 44.0 | 40.4 | 44.6 | 35.7 |
| gi\|85703261\|ref\|ZP_01034365.1\| | Roseovarius sp. | 41.6 | 38.3 | 43.7 | 44.6 | 41.0 |

FIG. 3E: Beta cont'd

FIG. 3E: Beta Ketoacyl-ACP Synthase Homologs

| | | | | | | |
|---|---|---|---|---|---|---|
| gi\|51892586\|ref\|YP_075277.1\| | S. thermophilum | 40.4 | 42.0 | 46.8 | 44.5 | 41.5 |
| gi\|118199812\|gb\|ABK78990.1\| | Francisella tularensis | 41.1 | 41.5 | 41.5 | 44.5 | 35.1 |
| gi\|84687533\|ref\|ZP_01015409.1\| | R. bacterium | 41.1 | 38.5 | 41.4 | 44.5 | 39.8 |
| gi\|197303789\|ref\|ZP_03168825.1\| | Ruminococcus lactaris | 42.5 | 42.8 | 42.3 | 44.5 | 33.7 |
| gi\|219849850\|ref\|YP_002464283.1 | Chloroflexus aggregans | 40.5 | 42.9 | 39.8 | 44.4 | 49.2 |
| gi\|118199824\|gb\|ABK78995.1\| | Francisella tularensis | 41.1 | 41.5 | 41.5 | 44.4 | 34.8 |
| gi\|182679922\|ref\|YP_001834068.1 | Beijerinckia indica | 38.1 | 38.7 | 41.0 | 44.4 | 38.3 |
| gi\|87310854\|ref\|ZP_01092980.1\| | Blastopirellula marina | 37.3 | 40.2 | 44.9 | 44.4 | 40.2 |
| gi\|126648098\|ref\|ZP_01720592.1\| | Algoriphagus sp. | 37.3 | 40.8 | 37.8 | 44.4 | 35.4 |
| gi\|157736556\|ref\|YP_001489239.1 | Arcobacter butzieri | 37.9 | 40.6 | 44.3 | 44.3 | 38.2 |
| gi\|239826277\|ref\|YP_002948901.1 | Geobacillus sp. | 43.8 | 43.2 | 61.7 | 44.3 | 37.5 |
| gi\|217963636\|ref\|YP_002349314.1 | Listeria monocytogenes | 42.1 | 44.0 | 57.8 | 44.3 | 39.2 |
| gi\|116873635\|ref\|YP_850416.1\| | Listeria welshimeri serovar | 40.5 | 42.7 | 57.2 | 44.3 | 38.6 |
| gi\|255520172\|ref\|ZP_05387409.1\| | Listeria monocytogenes | 41.7 | 44.6 | 57.8 | 44.3 | 40.1 |
| gi\|16804241\|ref\|NP_465726.1\| | Listeria monocytogenes | 41.7 | 44.6 | 58.1 | 44.3 | 40.1 |
| gi\|194014985\|ref\|ZP_03053602.1\| | Bacillus pumilus | 42.6 | 42.4 | 60.4 | 44.3 | 37.5 |
| gi\|217978633\|ref\|YP_002362780.1 | Methylocella silvestris | 39.8 | 41.8 | 40.4 | 44.3 | 39.5 |
| gi\|222475329\|ref\|YP_002563746.1 | Anaplasma marginale | 39.1 | 40.3 | 39.2 | 44.3 | 37.0 |
| gi\|125973453\|ref\|YP_001037363.1 | C thermocellum | 41.2 | 41.4 | 45.9 | 44.2 | 34.2 |
| gi\|149922132\|ref\|ZP_01910572.1\| | Plesiocystis pacifica | 36.5 | 37.8 | 42.5 | 44.2 | 39.3 |
| gi\|251797481\|ref\|YP_003012212.1 | Paenibacillus sp. | 39.6 | 43.2 | 50.5 | 44.2 | 40.6 |
| gi\|88802390\|ref\|ZP_01117917.1\| | Polaribacter irgensii | 36.1 | 37.8 | 36.6 | 44.2 | 34.5 |
| gi\|108562621\|ref\|YP_626937.1\| | Helicobacter pylori | 38.8 | 39.4 | 41.2 | 44.2 | 34.3 |
| gi\|84500954\|ref\|ZP_00999189.1\| | Oceanicola batsensis | 42.5 | 38.7 | 41.5 | 44.2 | 40.4 |
| gi\|262193557\|ref\|YP_003264766.1 | Haliangium ochraceum | 39.1 | 39.6 | 40.4 | 44.1 | 41.9 |
| gi\|149199110\|ref\|ZP_01876150.1\| | Lentisphaera araneosa | 38.1 | 40.1 | 44.2 | 44.1 | 32.7 |
| gi\|268318340\|ref\|YP_003292059.1 | Rhodothermus marinus | 41.5 | 39.8 | 41.0 | 44.1 | 40.5 |
| gi\|150015954\|ref\|YP_001308208.1 | Clostridium beijerinckii | 40.4 | 42.6 | 43.0 | 44.1 | 34.1 |
| gi\|34558276\|ref\|NP_908091.1\| | Wolinella succinogenes, | 37.5 | 40.1 | 41.9 | 44.0 | 36.8 |
| gi\|16801369\|ref\|NP_471637.1\| | Listeria innocua | 40.8 | 43.0 | 57.8 | 44.0 | 38.9 |
| gi\|16078198\|ref\|NP_389015.1\| | Bacillus subtilis | 39.3 | 40.3 | 57.8 | 44.0 | 36.5 |

FIG. 3E: Beta cont'd

FIG. 3E: Beta Ketoacyl-ACP Synthase Homologs

| | | | | | | |
|---|---|---|---|---|---|---|
| gi\|169826793\|ref\|YP_001696951.1 | L. sphaericus | 43.8 | 44.4 | 60.8 | 44.0 | 39.0 |
| gi\|229084266\|ref\|ZP_04216549.1\| | Bacillus cereus | 42.9 | 43.0 | 61.8 | 44.0 | 40.2 |
| gi\|261367528\|ref\|ZP_05980411.1\| | S.variabile | 41.9 | 39.4 | 35.2 | 44.0 | 36.5 |
| gi\|126660634\|ref\|ZP_01731736.1\| | Cyanothece sp. | 45.9 | 45.3 | 41.8 | 43.9 | 39.7 |
| gi\|163784248\|ref\|ZP_02179169.1\| | Hydrogenivirga sp. | 41.4 | 50.0 | 48.2 | 43.9 | 42.2 |
| gi\|84701556\|ref\|ZP_01016131.1\| | P.bermudensis | 37.8 | 39.2 | 42.8 | 43.9 | 44.2 |
| gi\|159044269\|ref\|YP_001533063.1 | Dinoroseobacter shibae | 41.3 | 39.3 | 41.7 | 43.9 | 42.3 |
| gi\|34098749\|sp\|Q9RT22.2\|FABH2_DEIRA | | 34.2 | 39.4 | 43.0 | 43.9 | 39.9 |
| gi\|15806945\|ref\|NP_295670.1\| | D. radiodurans | 34.2 | 39.4 | 43.0 | 43.9 | 39.9 |
| gi\|208434152\|ref\|YP_002265818.1 | Helicobacter pylori | 38.8 | 39.7 | 41.2 | 43.9 | 34.3 |
| gi\|210134404\|ref\|YP_002300843.1 | Helicobacter pylori | 38.2 | 39.1 | 41.5 | 43.9 | 34.3 |
| gi\|254778913\|ref\|YP_003057018.1 | Helicobacter pylori | 38.8 | 39.7 | 41.8 | 43.9 | 34.3 |
| gi\|15644831\|ref\|NP_207001.1\| | Helicobacter pylori | 38.8 | 39.7 | 41.8 | 43.9 | 34.3 |
| gi\|207092505\|ref\|ZP_03240292.1\| | Helicobacter pylori | 38.2 | 38.8 | 41.5 | 43.9 | 34.3 |
| gi\|261837651\|gb\|ACX97417.1\| | Helicobacter pylori | 38.8 | 39.4 | 41.8 | 43.9 | 34.3 |
| gi\|109946995\|ref\|YP_664223.1\| | H.acinonychis | 39.0 | 39.1 | 41.5 | 43.9 | 34.0 |
| gi\|119512195\|ref\|ZP_01631285.1\| | Nodularia spumigena | 42.2 | 44.3 | 40.7 | 43.8 | 40.6 |
| gi\|241891899\|ref\|ZP_04779195.1\| | S. spiritivorum | 35.8 | 37.0 | 38.5 | 43.8 | 32.3 |
| gi\|46447354\|ref\|YP_008719.1\| | C. Protochlamydia amoebophila | 40.9 | 40.6 | 40.5 | 43.8 | 38.9 |
| gi\|118199830\|gb\|ABK78998.1\| | F. tularensis . | 42.3 | 41.8 | 43.0 | 43.8 | 35.3 |
| gi\|118199819\|gb\|ABK78993.1\| | F. tularensis . | 40.9 | 40.9 | 42.3 | 43.7 | 35.4 |
| gi\|154685567\|ref\|YP_001420728.1 | B.amyloliquefaciens | 41.0 | 41.0 | 60.4 | 43.7 | 37.0 |
| gi\|218509113\|ref\|ZP_03506991.1\| | Rhizobium etli Brasil | 37.3 | 36.1 | 39.2 | 43.7 | 38.4 |
| gi\|73663107\|ref\|YP_301888.1\| | S.saprophyticus | 38.1 | 38.7 | 79.2 | 43.7 | 39.5 |
| gi\|94984541\|ref\|YP_603905.1\| | D. geothermalis | 41.5 | 42.1 | 44.4 | 43.7 | 41.4 |
| gi\|237735600\|ref\|ZP_04566081.1\| | Mollicutes bacterium | 39.8 | 39.6 | 42.1 | 43.7 | 31.7 |
| gi\|167757321\|ref\|ZP_02429448.1\| | Clostridium ramosum | 39.8 | 39.6 | 42.1 | 43.7 | 31.7 |
| gi\|22298388\|ref\|NP_681635.1\| | T. elongatus | 41.3 | 42.0 | 41.8 | 43.7 | 40.0 |
| gi\|145692849\|gb\|ABP93352.1\| | Helianthus annuus | 41.1 | 41.7 | 38.8 | 43.6 | 39.1 |
| gi\|223934953\|ref\|ZP_03626872.1\| | bacterium Ellin514 | 40.4 | 46.0 | 43.2 | 43.6 | 39.7 |
| gi\|224372473\|ref\|YP_002606845.1 | Nautilia profundicola | 41.5 | 45.4 | 46.0 | 43.6 | 38.9 |

FIG. 3E: Beta cont'd

FIG. 3E: Beta Ketoacyl-ACP Synthase Homologs

| | | | | | | |
|---|---|---|---|---|---|---|
| gi\|213961752\|ref\|ZP_03390018.1\| | C. sputigena Capno. | 37.0 | 38.4 | 37.0 | 43.6 | 33.8 |
| gi\|237756404\|ref\|ZP_04584947.1\| | S. yellowstonense | 41.9 | 46.0 | 49.6 | 43.6 | 39.9 |
| gi\|237669018\|ref\|ZP_04529002.1\| | Clostridium butyricum | 41.7 | 43.2 | 41.2 | 43.6 | 34.1 |
| gi\|188475825\|gb\|ACD50087.1\| | uncultured crenarchaeote | 40.1 | 41.0 | 43.0 | 43.6 | 40.0 |
| gi\|15611258\|ref\|NP_222909.1\| | Helicobacter pylori | 38.5 | 39.1 | 41.5 | 43.6 | 34.9 |
| gi\|188527007\|ref\|YP_001909694.1 | Helicobacter pylori | 38.2 | 39.4 | 41.2 | 43.6 | 34.9 |
| gi\|217034027\|ref\|ZP_03439449.1\| | Helicobacter pylori | 38.5 | 39.4 | 41.5 | 43.6 | 34.9 |
| gi\|217031963\|ref\|ZP_03437465.1\| | Helicobacter pylori | 38.5 | 39.4 | 41.5 | 43.6 | 34.6 |
| gi\|261839063\|gb\|ACX98828.1\| | Helicobacter pylori | 38.2 | 39.7 | 41.2 | 43.6 | 34.6 |
| gi\|225197074\|ref\|ZP_03736211.1\| | D.thiodismutans | 36.4 | 40.1 | 40.0 | 43.6 | 36.9 |
| gi\|255038809\|ref\|YP_003089430.1 | D. fermentans | 38.6 | 39.2 | 37.7 | 43.5 | 37.2 |
| gi\|237751548\|ref\|ZP_04582028.1\| | Helicobacter bilis | 40.7 | 41.6 | 41.2 | 43.5 | 36.3 |
| gi\|283797600\|ref\|ZP_06346753.1\| | Clostridium sp. | 42.8 | 45.0 | 44.0 | 43.5 | 39.9 |
| gi\|186680647\|ref\|YP_001863843.1 | Nostoc punctiforme | 42.5 | 42.0 | 41.0 | 43.5 | 40.6 |
| gi\|160936941\|ref\|ZP_02084305.1\| | Clostridium bolteae | 46.4 | 46.9 | 42.7 | 43.5 | 39.7 |
| gi\|242310112\|ref\|ZP_04809267.1\| | Helicobacter pullorum | 39.0 | 42.6 | 42.8 | 43.4 | 39.2 |
| gi\|229541398\|ref\|ZP_04430458.1\| | Bacillus coagulans | 41.0 | 43.0 | 64.5 | 43.4 | 41.0 |
| gi\|229555813\|ref\|ZP_04443602.1\| | Listeria grayi | 40.5 | 41.3 | 59.7 | 43.4 | 38.9 |
| gi\|169351367\|ref\|ZP_02868305.1\| | Clostridium spiroforme | 39.5 | 39.3 | 43.4 | 43.4 | 32.9 |
| gi\|225387398\|ref\|ZP_03757162.1\| | C.asparagiforme | 45.2 | 46.0 | 42.4 | 43.3 | 36.8 |
| gi\|67922029\|ref\|ZP_00515545.1\| | Crocosphaera watsonii | 44.3 | 43.7 | 42.4 | 43.3 | 39.8 |
| gi\|237737601\|ref\|ZP_04568082.1\| | F.mortiferum | 38.8 | 39.9 | 44.4 | 43.3 | 39.0 |
| gi\|256389598\|ref\|YP_003111162.1 | Catenulispora acidiphila | 38.5 | 38.0 | 42.0 | 43.3 | 61.6 |
| gi\|262068128\|ref\|ZP_06027740.1\| | F. periodonticum | 40.8 | 43.2 | 44.4 | 43.3 | 38.7 |
| gi\|149194089\|ref\|ZP_01871187.1\| | C. mediatlanticus | 41.3 | 45.1 | 44.2 | 43.3 | 38.0 |
| gi\|242278137\|ref\|YP_002990266.1 | Desulfovibrio salexigens | 40.7 | 40.7 | 43.0 | 43.3 | 40.5 |
| gi\|228472864\|ref\|ZP_04057621.1\| | C.gingivalis | 35.0 | 38.1 | 38.1 | 43.3 | 33.3 |
| gi\|118199826\|gb\|ABK78996.1\| | Francisella tularensis | 42.5 | 40.8 | 42.0 | 43.3 | 35.5 |
| gi\|227536202\|ref\|ZP_03966251.1\| | S. spiritivorum | 35.7 | 36.3 | 38.3 | 43.3 | 32.2 |
| gi\|220915128\|ref\|YP_002490432.1 | A. dehalogenans | 33.2 | 35.8 | 32.5 | 43.3 | 37.6 |
| gi\|253681256\|ref\|ZP_04862054.1\| | Clostridium botulinum | 45.1 | 46.0 | 47.1 | 43.2 | 36.2 |

FIG. 3E: Beta cont'd

FIG. 3E: Beta Ketoacyl-ACP Synthase Homologs

| | | | | | | |
|---|---|---|---|---|---|---|
| gi\|163847960\|ref\|YP_001636004.1 | Chloroflexus sp. | 39.6 | 41.8 | 41.4 | 43.2 | 49.8 |
| gi\|118443447\|ref\|YP_877018.1\| | Clostridium novyi | 46.9 | 47.2 | 44.6 | 43.2 | 35.9 |
| gi\|33864261\|ref\|NP_895821.1\| | P. marinus | 43.6 | 42.5 | 38.0 | 43.2 | 39.5 |
| gi\|218778424\|ref\|YP_002429742.1 | D.alkenivorans | 37.6 | 41.1 | 39.5 | 43.2 | 38.2 |
| gi\|254424393\|ref\|ZP_05038111.1\| | Synechococcus sp. | 44.1 | 43.1 | 42.9 | 43.2 | 40.4 |
| gi\|205372924\|ref\|ZP_03225732.1\| | Bacillus coahuilensis | 44.8 | 42.5 | 61.3 | 43.1 | 40.2 |
| gi\|255330343\|ref\|ZP_05371368.1\| | Geobacillus sp. | 42.6 | 44.1 | 62.3 | 43.1 | 38.7 |
| gi\|284037897\|ref\|YP_003387827.1 | Spirosoma linguale | 34.4 | 36.8 | 34.3 | 43.1 | 36.6 |
| gi\|218246636\|ref\|YP_002372007.1 | Cyanothece sp. | 45.6 | 47.3 | 41.3 | 43.0 | 41.2 |
| gi\|257059679\|ref\|YP_003137567.1 | Cyanothece sp. | 45.3 | 47.0 | 41.0 | 43.0 | 40.6 |
| gi\|172036499\|ref\|YP_001803000.1 | Cyanothece sp. | 44.9 | 44.3 | 42.1 | 43.0 | 39.1 |
| gi\|123964629\|gb\|ABM79385.1\| | P. marinus | 43.5 | 42.2 | 38.2 | 43.0 | 39.7 |
| gi\|56964312\|ref\|YP_176043.1\| | Bacillus clausii | 42.6 | 42.2 | 56.1 | 43.0 | 40.9 |
| gi\|237740798\|ref\|ZP_04571279.1\| | Fusobacterium sp. | 40.2 | 42.7 | 44.8 | 43.0 | 38.4 |
| gi\|256673617\|ref\|ZP_05484570.1\| | Streptomyces sp. | 36.9 | 40.1 | 36.6 | 43.0 | 58.0 |
| gi\|254462454\|ref\|ZP_05075870.1\| | R.bacterium | 40.6 | 38.7 | 41.8 | 42.9 | 40.2 |
| gi\|161347559\|ref\|YP_001018650.2 | P. marinus | 43.5 | 42.2 | 38.0 | 42.9 | 39.5 |
| gi\|46579618\|ref\|YP_010426.1\| | Desulfovibrio vulgaris | 37.6 | 39.4 | 40.7 | 42.9 | 44.8 |
| gi\|78044947\|ref\|YP_360282.1\| | C. hydrogenoformans | 39.9 | 44.9 | 46.1 | 42.9 | 38.8 |
| gi\|160933853\|ref\|ZP_02081241.1\| | Clostridium leptum | 35.3 | 36.7 | 40.6 | 42.9 | 36.7 |
| gi\|148240586\|ref\|YP_001225973.1 | Synechococcus sp. | 45.2 | 42.4 | 38.5 | 42.9 | 40.5 |
| gi\|224418697\|ref\|ZP_03656703.1\| | H.canadensis | 40.3 | 44.5 | 42.6 | 42.8 | 39.9 |
| gi\|237753242\|ref\|ZP_04583722.1\| | H.winghamensis | 40.5 | 44.5 | 41.5 | 42.8 | 37.7 |
| gi\|224482649\|gb\|ACN50181.1\| | Annona cherimola | 38.4 | 40.1 | 39.1 | 42.8 | 37.7 |
| gi\|145354437\|ref\|XP_001421491.1 | O.lucimarinus | 44.9 | 42.9 | 37.0 | 42.8 | 33.8 |
| gi\|163814759\|ref\|ZP_02206148.1\| | Coprococcus eutactus | 42.0 | 44.2 | 40.9 | 42.8 | 38.4 |
| gi\|196256129\|ref\|ZP_03154667.1\| | Cyanothece sp. | 42.8 | 41.0 | 40.1 | 42.7 | 39.0 |
| gi\|225874598\|ref\|YP_002756057.1 | A.capsulatum | 40.0 | 41.8 | 42.2 | 42.7 | 40.9 |
| gi\|95929950\|ref\|ZP_01312690.1\| | D.acetoxidans | 41.8 | 42.4 | 42.5 | 42.7 | 37.4 |
| gi\|254302537\|ref\|ZP_04969895.1\| | F.nucleatum | 39.3 | 41.8 | 44.4 | 42.7 | 39.3 |
| gi\|260496875\|ref\|ZP_05815995.1\| | Fusobacterium sp. | 39.3 | 42.1 | 44.9 | 42.7 | 38.4 |

FIG. 3E: Beta cont'd

FIG. 3E: Beta Ketoacyl-ACP Synthase Homologs

| | | | | | | |
|---|---|---|---|---|---|---|
| gi\|237743498\|ref\|ZP_04573979.1\| | Fusobacterium sp. | 39.3 | 42.1 | 45.2 | 42.7 | 38.4 |
| gi\|197120426\|ref\|YP_002132377.1 | Anaeromyxobacter sp. | 33.5 | 35.2 | 33.4 | 42.6 | 38.2 |
| gi\|86156435\|ref\|YP_463220.1\| | A. dehalogenans | 32.9 | 35.4 | 33.0 | 42.6 | 37.9 |
| gi\|159897273\|ref\|YP_001543520.1 | H. aurantiacus | 38.7 | 39.8 | 40.2 | 42.6 | 40.9 |
| gi\|123959989\|gb\|ABM74772.1\| | P. marinus | 43.5 | 43.9 | 39.6 | 42.6 | 36.8 |
| gi\|266620886\|ref\|ZP_06113821.1\| | Clostridium hathewayi | 46.5 | 46.0 | 41.5 | 42.6 | 38.3 |
| gi\|170077150\|ref\|YP_001733788.1 | Synechococcus sp. | 46.9 | 45.1 | 41.7 | 42.6 | 37.4 |
| gi\|283848181\|ref\|ZP_06365591.1\| | Bacillus cellulosilyticus | 40.7 | 39.5 | 40.9 | 42.6 | 36.4 |
| gi\|260435489\|ref\|ZP_05789459.1\| | Synechococcus sp. | 39.7 | 41.2 | 36.7 | 42.5 | 39.3 |
| gi\|88807096\|ref\|ZP_01122608.1\| | Synechococcus sp. | 45.2 | 43.0 | 38.5 | 42.5 | 41.3 |
| gi\|225850316\|ref\|YP_002730550.1 | Persephonella marina | 40.6 | 45.2 | 48.9 | 42.5 | 42.2 |
| gi\|222150853\|ref\|YP_002560006.1 | M.caseolyticus | 39.7 | 39.4 | 63.9 | 42.5 | 38.9 |
| gi\|255611553\|ref\|XP_002539320.1 | Ricinus communis, | 38.0 | 37.7 | 41.3 | 42.5 | 41.8 |
| gi\|161407970\|ref\|YP_001014037.2 | P.marinus | 43.5 | 43.9 | 39.1 | 42.5 | 36.5 |
| gi\|256819304\|ref\|YP_003140583.1 | C.ochracea | 36.7 | 37.8 | 37.6 | 42.5 | 33.8 |
| gi\|149183825\|ref\|ZP_01862223.1\| | Bacillus sp. | 44.3 | 43.1 | 63.7 | 42.4 | 38.2 |
| gi\|218438036\|ref\|YP_002376365.1 | Cyanothece sp. | 42.5 | 42.0 | 40.9 | 42.4 | 39.2 |
| gi\|56750111\|ref\|YP_170812.1\| | S.elongatus | 44.0 | 42.8 | 38.6 | 42.4 | 41.0 |
| gi\|72383338\|ref\|YP_292693.1\| | P.marinus | 43.2 | 43.6 | 39.1 | 42.4 | 37.1 |
| gi\|238925484\|ref\|YP_002939001.1 | Eubacterium rectale | 44.1 | 45.4 | 41.9 | 42.4 | 39.6 |
| gi\|227368579\|ref\|ZP_03852100.1\| | C.gleum | 36.8 | 38.4 | 38.2 | 42.4 | 35.8 |
| gi\|159902691\|ref\|YP_001550035.1 | P.marinus | 43.6 | 43.3 | 37.7 | 42.4 | 38.0 |
| gi\|237741215\|ref\|ZP_04571696.1\| | Fusobacterium sp. | 39.3 | 41.5 | 43.7 | 42.4 | 39.0 |
| gi\|34764081\|ref\|ZP_00144961.1\| | F.nucleatum | 39.3 | 41.5 | 43.7 | 42.4 | 39.0 |
| gi\|15615446\|ref\|NP_243749.1\| | Bacillus halodurans | 39.9 | 41.5 | 57.4 | 42.4 | 39.0 |
| gi\|32444698\|emb\|CAD74700.1\| | Rhodopirellula baltica | 36.9 | 38.0 | 39.3 | 42.4 | 38.9 |
| gi\|161579032\|ref\|NP_867155.2\| | Rhodopirellula baltica | 36.9 | 38.0 | 39.0 | 42.4 | 38.9 |
| gi\|7862174\|gb\|AAF70509.1\| | Glycine max | 42.0 | 40.1 | 39.0 | 42.3 | 35.9 |
| gi\|254430124\|ref\|ZP_05043827.1\| | Cyanobium sp. | 41.9 | 41.8 | 38.0 | 42.3 | 41.5 |
| gi\|153813426\|ref\|ZP_01966094.1\| | Ruminococcus obeum | 43.7 | 43.1 | 42.6 | 42.3 | 39.5 |
| gi\|87301816\|ref\|ZP_01084650.1\| | Synechococcus sp. | 42.5 | 41.2 | 37.0 | 42.3 | 38.2 |

FIG. 3E: Beta cont'd

FIG. 3E: Beta Ketoacyl-ACP Synthase Homologs

| | | | | | | |
|---|---|---|---|---|---|---|
| gi\|195952615\|ref\|YP_002120905.1 | Hydrogenobaculum | 41.6 | 41.8 | 47.1 | 42.3 | 39.2 |
| gi\|268609157\|ref\|ZP_06142884.1\| | R. flavefaciens | 37.6 | 38.5 | 38.0 | 42.2 | 32.8 |
| gi\|256781486\|ref\|ZP_05519949.1\| | S. hygroscopicus | 38.6 | 41.3 | 38.4 | 42.2 | 58.9 |
| gi\|254796979\|ref\|YP_003081816.1 | Neorickettsia risticii | 38.7 | 42.5 | 40.7 | 42.1 | 36.6 |
| gi\|258652256\|ref\|YP_003201412.1 | Nakamurella multipartita | 33.1 | 33.3 | 35.7 | 42.1 | 37.8 |
| gi\|255535508\|ref\|YP_003095879.1 | F.bacterium | 36.7 | 38.7 | 37.9 | 42.1 | 36.1 |
| gi\|116747564\|ref\|YP_844251.1\| | S.fumaroxidans | 37.3 | 37.8 | 39.3 | 42.1 | 37.5 |
| gi\|166364688\|ref\|YP_001656961.1 | Microcystis aeruginosa | 43.5 | 44.3 | 42.6 | 42.1 | 38.5 |
| gi\|188590229\|ref\|YP_001920474.1 | Clostridium botulinum | 46.1 | 46.3 | 40.7 | 42.1 | 38.3 |
| gi\|94986606\|ref\|YP_594539.1\| | Lawsonia intracellularis | 36.7 | 38.6 | 40.2 | 42.1 | 38.2 |
| gi\|257468855\|ref\|ZP_05632949.1\| | Fusobacterium ulcerans | 39.6 | 41.2 | 45.5 | 42.1 | 37.5 |
| gi\|193290706\|gb\|ACF17661.1\| | Capsicum annuum | 39.9 | 39.3 | 38.1 | 42.0 | 38.3 |
| gi\|283782500\|ref\|YP_003373255.1 | Pirellula staleyi | 36.9 | 40.1 | 40.2 | 42.0 | 41.8 |
| gi\|257440483\|ref\|ZP_05616238.1\| | F.prausnitzii | 38.9 | 38.3 | 34.4 | 42.0 | 36.5 |
| gi\|15613327\|ref\|NP_241630.1\| | Bacillus halodurans | 42.4 | 40.9 | 41.2 | 42.0 | 36.3 |
| gi\|1345946\|sp\|Q07510.1\|FABH_SPIOL | Spinacia oleracea, | 40.8 | 38.5 | 40.1 | 42.0 | 36.2 |
| gi\|46198357\|ref\|YP_004024.1\| | Thermus thermophilus | 40.8 | 43.8 | 48.9 | 42.0 | 44.6 |
| gi\|78198353\|gb\|ABB36118.1\| | Synechococcus sp. | 40.4 | 41.4 | 36.7 | 41.9 | 39.3 |
| gi\|161353759\|ref\|YP_382673.2\| | Synechococcus sp. | 40.4 | 41.4 | 36.8 | 41.9 | 39.0 |
| gi\|145300158\|ref\|YP_001142999.1 | Aeromonas salmonicida | 43.2 | 44.5 | 40.3 | 41.9 | 39.3 |
| gi\|598075\|gb\|AAA61348.1\| | Arabidopsis thaliana | 39.4 | 42.1 | 37.5 | 41.9 | 37.1 |
| gi\|88606851\|ref\|YP_504929.1\| | A.phagocytophilum | 41.5 | 42.0 | 39.8 | 41.9 | 39.3 |
| gi\|229208495\|ref\|ZP_04334938.1\| | N.dassonvillei | 36.5 | 39.0 | 36.9 | 41.9 | 36.2 |
| gi\|114567368\|ref\|YP_754522.1\| | Syntrophomonas wolfei | 37.8 | 40.1 | 41.9 | 41.8 | 37.8 |
| gi\|157827729\|ref\|YP_001496793.1 | Rickettsia bellii | 38.8 | 38.6 | 42.0 | 41.8 | 37.5 |
| gi\|228474382\|ref\|ZP_04059117.1\| | Staphylococcus hominis | 40.9 | 41.6 | 87.5 | 41.8 | 38.7 |
| gi\|159026902\|emb\|CAO89153.1\| | Microcystis aeruginosa | 43.8 | 45.6 | 42.3 | 41.8 | 37.9 |
| gi\|227992686\|ref\|ZP_04039751.1\| | Meiothermus ruber | 39.7 | 43.4 | 48.1 | 41.8 | 39.5 |
| gi\|253581842\|ref\|ZP_04859066.1\| | Fusobacterium varium | 39.4 | 41.5 | 45.2 | 41.7 | 37.5 |
| gi\|123965399\|ref\|YP_001010480.1 | P.marinus | 42.9 | 41.5 | 39.6 | 41.7 | 31.9 |
| gi\|19703493\|ref\|NP_603055.1\| | F.nucleatum | 38.6 | 41.5 | 45.4 | 41.7 | 37.8 |

FIG. 3E: Beta cont'd

FIG. 3E: Beta Ketoacyl-ACP Synthase Homologs

| | | | | | | |
|---|---|---|---|---|---|---|
| gi\|257466293\|ref\|ZP_05630604.1\| | F.gonidiaformans | 38.8 | 40.6 | 45.5 | 41.7 | 37.8 |
| gi\|157412492\|ref\|YP_001483358.1 | P. marinus | 42.9 | 40.8 | 40.5 | 41.7 | 34.4 |
| gi\|256371868\|ref\|YP_003109692.1 | A.ferrooxidans | 37.9 | 37.4 | 44.1 | 41.6 | 41.8 |
| gi\|2921213\|gb\|AAC04693.1\| | Perilla frutescens | 40.5 | 41.7 | 37.3 | 41.6 | 35.8 |
| gi\|261404774\|ref\|YP_003241015.1 | Geobacillus sp. | 40.7 | 41.7 | 42.9 | 41.6 | 37.5 |
| gi\|255034412\|ref\|YP_003085033.1 | D.fermentans | 36.7 | 36.2 | 39.1 | 41.6 | 36.2 |
| gi\|149910440\|ref\|ZP_01899081.1\| | Moritella sp. | 42.3 | 44.1 | 44.5 | 41.6 | 40.9 |
| gi\|255037898\|ref\|YP_003088519.1 | D. fermentans | 36.9 | 38.0 | 41.1 | 41.6 | 37.1 |
| gi\|117617513\|ref\|YP_855582.1\| | Aeromonas hydrophila | 42.3 | 44.2 | 40.3 | 41.6 | 39.0 |
| gi\|149277213\|ref\|ZP_01883355.1\| | Pedobacter sp. | 31.9 | 35.3 | 36.0 | 41.6 | 31.4 |
| gi\|162660817\|gb\|EDQ48549.1\| | Physcomitrella patens | 47.5 | 52.6 | 47.2 | 41.6 | 45.6 |
| gi\|226355422\|ref\|YP_002785162.1 | Deinococcus deserti | 41.3 | 41.0 | 42.7 | 41.6 | 39.2 |
| gi\|154484984\|ref\|ZP_02027432.1\| | E.ventriosum | 43.2 | 42.7 | 40.4 | 41.6 | 32.1 |
| gi\|282890064\|ref\|ZP_06298597.1\| | P.acanthamoebae | 37.3 | 38.4 | 41.1 | 41.6 | 38.0 |
| gi\|116626090\|ref\|YP_828246.1\| | Solibacter usitatus | 36.9 | 39.4 | 37.3 | 41.5 | 39.9 |
| gi\|168700782\|ref\|ZP_02733059.1\| | G.obscuriglobus | 38.8 | 36.5 | 41.2 | 41.5 | 38.1 |
| gi\|284928703\|ref\|YP_003421225.1 | cyanobacterium | 44.3 | 44.8 | 41.9 | 41.5 | 36.3 |
| gi\|33860696\|ref\|NP_892257.1\| | P.marinus | 42.6 | 41.8 | 39.3 | 41.5 | 31.8 |
| gi\|187934883\|ref\|YP_001885344.1 | Clostridium botulinum | 46.1 | 45.3 | 40.4 | 41.5 | 36.8 |
| gi\|21674923\|ref\|NP_662988.1\| | Chlorobium tepidum | 41.0 | 43.1 | 38.4 | 41.5 | 37.1 |
| gi\|118578465\|ref\|YP_899715.1\| | Pelobacter propionicus | 35.2 | 40.0 | 36.6 | 41.5 | 37.5 |
| gi\|260645723\|emb\|CBG68814.1\| | Streptomyces scabiei | 35.9 | 33.1 | 35.6 | 41.5 | 39.1 |
| gi\|257452423\|ref\|ZP_05617722.1\| | Fusobacterium sp. | 38.8 | 40.6 | 45.2 | 41.4 | 37.8 |
| gi\|69245725\|ref\|ZP_00603591.1\| | Enterococcus faecium | 54.3 | 55.7 | 37.4 | 41.4 | 35.7 |
| gi\|257885274\|ref\|ZP_05664927.1\| | Enterococcus faecium | 54.3 | 55.4 | 37.4 | 41.4 | 35.7 |
| gi\|218780563\|ref\|YP_002431881.1 | D.alkenivorans | 36.7 | 39.2 | 40.8 | 41.4 | 38.4 |
| gi\|210611735\|ref\|ZP_03289005.1\| | Clostridium nexile | 43.9 | 45.3 | 43.5 | 41.4 | 36.7 |
| gi\|161353819\|ref\|YP_001008548.2 | P. marinus | 42.6 | 42.5 | 39.3 | 41.4 | 34.3 |
| gi\|123197800\|gb\|ABM69441.1\| | P.marinus | 42.6 | 42.5 | 39.0 | 41.4 | 34.3 |
| gi\|254527129\|ref\|ZP_05139181.1\| | P.marinus | 42.6 | 40.8 | 40.8 | 41.4 | 34.5 |
| gi\|160944890\|ref\|ZP_02092117.1\| | F.prausnitzii | 40.2 | 39.3 | 33.0 | 41.4 | 36.0 |

FIG. 3E: Beta cont'd

FIG. 3E: Beta Ketoacyl-ACP Synthase Homologs

| | | | | | | |
|---|---|---|---|---|---|---|
| gi\|256776450\|ref\|ZP_05514913.1\| | S.hygroscopicus | 35.0 | 33.5 | 35.0 | 41.3 | 38.9 |
| gi\|15221522\|ref\|NP_176452.1\| | Arabidopsis thaliana, | 40.1 | 42.2 | 37.8 | 41.3 | 37.1 |
| gi\|209526114\|ref\|ZP_03274646.1\| | Arthrospira maxima | 42.5 | 40.9 | 41.0 | 41.3 | 38.8 |
| gi\|226325382\|ref\|ZP_03800900.1\| | Coprococcus comes | 44.2 | 43.3 | 42.0 | 41.3 | 36.7 |
| gi\|153002884\|ref\|YP_001377209.1 | Anaeromyxobacter sp. | 32.2 | 35.5 | 33.1 | 41.3 | 37.3 |
| gi\|220907907\|ref\|YP_002483218.1 | Cyanothece sp. | 43.5 | 40.4 | 40.4 | 41.3 | 40.0 |
| gi\|226458038\|gb\|EEH55336.1\| | Micromonas pusilla | 39.8 | 41.0 | 35.7 | 41.2 | 35.8 |
| gi\|255523974\|ref\|ZP_05390936.1\| | Ccarboxidivorans | 48.0 | 49.8 | 42.8 | 41.2 | 36.7 |
| gi\|226364666\|ref\|YP_002782448.1 | Rhodococcus opacus | 35.3 | 31.8 | 38.1 | 41.2 | 34.8 |
| gi\|72162373\|ref\|YP_290030.1\| | Thermobifida fusca | 36.1 | 36.5 | 36.3 | 41.2 | 39.3 |
| gi\|163752609\|ref\|ZP_02159787.1\| | Shewanella benthica | 42.0 | 53.6 | 42.3 | 41.2 | 38.8 |
| gi\|91204943\|ref\|YP_537298.1\| | Rickettsia bellii | 38.5 | 38.3 | 41.6 | 41.2 | 37.2 |
| gi\|70726974\|ref\|YP_253888.1\| | S.haemolyticus | 40.1 | 41.3 | 86.6 | 41.2 | 38.4 |
| gi\|224476077\|ref\|YP_002633683.1 | S.carnosus | 40.5 | 39.4 | 81.8 | 41.2 | 41.5 |
| gi\|225620402\|ref\|YP_002721659.1 | B.hyodysenteriae | 39.8 | 40.5 | 37.1 | 41.2 | 36.6 |
| gi\|242260608\|ref\|ZP_04805325.1\| | C cellulovorans | 43.9 | 47.9 | 41.9 | 41.2 | 36.7 |
| gi\|168183683\|ref\|ZP_02618347.1\| | Clostridium botulinum | 44.0 | 48.5 | 41.4 | 41.2 | 34.3 |
| gi\|257069835\|ref\|YP_003156090.1 | B.faecium | 34.3 | 33.2 | 39.1 | 41.1 | 36.8 |
| gi\|257462238\|ref\|ZP_05626655.1\| | Fusobacterium sp. | 37.9 | 39.7 | 46.2 | 41.1 | 37.2 |
| gi\|218888185\|ref\|YP_002437506.1 | Desulfovibrio vulgaris | 35.7 | 35.6 | 39.4 | 41.1 | 44.2 |
| gi\|225569454\|ref\|ZP_03778479.1\| | Clostridium hylemonae | 41.0 | 42.3 | 40.1 | 41.1 | 37.4 |
| gi\|194476780\|ref\|YP_002048959.1 | P.chromatophora | 39.7 | 39.6 | 36.8 | 41.0 | 37.3 |
| gi\|113955327\|ref\|YP_731787.1\| | Synechococcus sp. | 42.5 | 42.3 | 37.2 | 41.0 | 40.3 |
| gi\|167771281\|ref\|ZP_02443334.1\| | A.colihominis | 34.9 | 31.8 | 36.3 | 41.0 | 34.4 |
| gi\|222424441\|dbj\|BAH20176.1\| | Arabidopsis thaliana | 39.8 | 41.9 | 37.5 | 41.0 | 36.8 |
| gi\|256375464\|ref\|YP_003099124.1 | Actinosynnema mirum | 34.5 | 33.5 | 36.5 | 41.0 | 40.9 |
| gi\|218296535\|ref\|ZP_03497263.1\| | Thermus aquaticus | 41.5 | 45.1 | 46.7 | 41.0 | 41.9 |
| gi\|269125884\|ref\|YP_003299254.1 | T.curvata | 36.3 | 36.5 | 37.1 | 41.0 | 39.2 |
| gi\|10120315\|emb\|CAC08184.1\| | Pisum sativum | 42.0 | 40.6 | 39.0 | 41.0 | 34.0 |
| gi\|119488103\|ref\|ZP_01621547.1\| | Lyngbya sp. | 42.0 | 42.9 | 40.7 | 41.0 | 38.5 |
| gi\|186682436\|ref\|YP_001865632.1 | Nostoc punctiforme | 40.6 | 41.0 | 38.9 | 41.0 | 38.0 |

FIG. 3E: Beta cont'd

FIG. 3E: Beta Ketoacyl-ACP Synthase Homologs

| | | | | | | |
|---|---|---|---|---|---|---|
| gi\|78778524\|ref\|YP_396636.1\| | P.marinus | 43.1 | 42.5 | 40.8 | 41.0 | 35.4 |
| gi\|225375180\|ref\|ZP_03752401.1\| | Roseburia inulinivorans | 45.0 | 44.1 | 42.7 | 41.0 | 39.7 |
| gi\|229539030\|ref\|ZP_04428166.1\| | P.limnophilus | 39.8 | 39.9 | 38.6 | 41.0 | 42.2 |
| gi\|17227735\|ref\|NP_484283.1\| | Nostoc sp. | 42.2 | 42.7 | 42.2 | 41.0 | 39.7 |
| gi\|193214393\|ref\|YP_001995592.1 | C.thalassium | 39.3 | 41.9 | 41.0 | 41.0 | 37.5 |
| gi\|148241347\|ref\|YP_001226504.1 | Synechococcus sp. | 40.9 | 41.2 | 37.7 | 40.9 | 39.5 |
| gi\|116055216\|emb\|CAL57612.1\| | Oryza sativa | 44.0 | 42.8 | 37.3 | 40.9 | 35.4 |
| gi\|111022173\|ref\|YP_705145.1\| | Rhodococcus jostii | 35.0 | 31.8 | 37.8 | 40.9 | 36.0 |
| gi\|239946699\|ref\|ZP_04698452.1\| | R.endosymbiont | 38.6 | 40.1 | 41.3 | 40.9 | 36.6 |
| gi\|283846267\|ref\|ZP_06363736.1\| | Bacillus cellulosilyticus | 41.7 | 42.4 | 56.5 | 40.9 | 36.2 |
| gi\|108804216\|ref\|YP_644153.1\| | Rubrobacter x. | 34.6 | 35.4 | 39.3 | 40.9 | 39.3 |
| gi\|284040088\|ref\|YP_003390018.1 | Spirosoma linguale | 37.9 | 37.2 | 41.8 | 40.9 | 39.9 |
| gi\|228477895\|ref\|ZP_04062509.1\| | Streptococcus salivarius | 62.0 | 68.6 | 39.2 | 40.9 | 40.0 |
| gi\|32266180\|ref\|NP_860212.1\| | Helicobacter hepaticus | 37.4 | 37.5 | 41.9 | 40.9 | 35.6 |
| gi\|237797062\|ref\|YP_002864614.1 | Clostridium botulinum | 44.0 | 48.5 | 41.4 | 40.8 | 34.3 |
| gi\|153939948\|ref\|YP_001392959.1 | Clostridium botulinum F | 45.0 | 48.2 | 41.2 | 40.8 | 35.1 |
| gi\|171778057\|ref\|ZP_02919314.1\| | S.infantarius | 62.5 | 71.1 | 41.0 | 40.8 | 36.2 |
| gi\|239934285\|ref\|ZP_04691238.1\| | S.ghanaensis | 38.2 | 38.1 | 37.1 | 40.8 | 64.4 |
| gi\|224540874\|ref\|ZP_03681413.1\| | Catenibacterium mitsuokai | 44.6 | 42.1 | 43.8 | 40.8 | 33.5 |
| gi\|21221679\|ref\|NP_627458.1\| | S. lividans, S. coelicolor | 38.3 | 39.2 | 36.9 | 40.8 | 53.3 |
| gi\|227550564\|ref\|ZP_03980613.1\| | Enterococcus faecium | 54.6 | 55.7 | 38.1 | 40.8 | 36.3 |
| gi\|256783970\|ref\|ZP_05522401.1\| | Streptomyces lividans | 34.8 | 34.8 | 34.7 | 40.8 | 39.2 |
| gi\|94969044\|ref\|YP_591092.1\| | C. Koribacter versatilis | 36.5 | 39.4 | 37.2 | 40.7 | 40.5 |
| gi\|224013337\|ref\|XP_002295320.1 | T.pseudonana | 37.5 | 37.3 | 37.8 | 40.7 | 39.6 |
| gi\|158333843\|ref\|YP_001515015.1 | Acaryochloris marina | 40.7 | 42.1 | 38.5 | 40.7 | 40.9 |
| gi\|254413157\|ref\|ZP_05026929.1\| | M.chthonoplastes | 44.4 | 42.4 | 42.2 | 40.7 | 38.2 |
| gi\|75908941\|ref\|YP_323237.1\| | Anabaena variabilis | 41.3 | 41.6 | 41.6 | 40.7 | 39.1 |
| gi\|78183888\|ref\|YP_376322.1\| | Synechococcus sp. | 40.7 | 41.0 | 35.9 | 40.7 | 39.0 |
| gi\|270260055\|emb\|CBI31890.1\| | Vitis vinifera | 41.5 | 40.9 | 37.5 | 40.7 | 37.1 |
| gi\|162447324\|ref\|YP_001620456.1 | Acholeplasma laidlawii | 44.3 | 42.1 | 45.0 | 40.6 | 36.5 |
| gi\|257054257\|ref\|YP_003132089.1 | S.viridis | 37.7 | 38.0 | 38.8 | 40.6 | 57.9 |

FIG. 3E: Beta Ketoacyl-ACP Synthase Homologs

| | | | | | | |
|---|---|---|---|---|---|---|
| gi\|284030504\|ref\|YP_003380435.1 | Kribbella flavida | 33.5 | 32.6 | 37.4 | 40.6 | 36.7 |
| gi\|262193331\|ref\|YP_003264540.1 | Haliangium ochraceum | 32.9 | 38.0 | 36.9 | 40.6 | 36.8 |
| gi\|56001095\|dbj\|BAD72838.1\| | Staphylococcus aureus | 41.9 | 39.2 | 100 | 40.6 | 39.9 |
| gi\|220913112\|ref\|YP_002488421.1 | A.chlorophenolicus | 34.5 | 31.3 | 38.1 | 40.6 | 36.6 |
| gi\|157804142\|ref\|YP_001492691.1 | Rickettsia canadensis | 38.0 | 39.2 | 41.6 | 40.6 | 35.6 |
| gi\|89098087\|ref\|ZP_01170973.1\| | Bacillus sp. | 42.6 | 41.6 | 61.7 | 40.6 | 37.5 |
| gi\|242242266\|ref\|ZP_04796711.1\| | S.epidermidis | 42.8 | 40.3 | 88.8 | 40.6 | 39.0 |
| gi\|161344761\|ref\|NP_441338.2\| | Synechocystis sp. | 42.6 | 41.0 | 41.5 | 40.6 | 37.6 |
| gi\|86609780\|ref\|YP_478542.1\| | Synechococcus sp. | 42.8 | 41.4 | 39.3 | 40.6 | 38.7 |
| gi\|261250982\|ref\|ZP_05943556.1\| | Vibrio orientalis | 39.9 | 39.3 | 43.0 | 40.6 | 38.1 |
| gi\|110598665\|ref\|ZP_01386930.1\| | C.ferrooxidans | 41.6 | 42.7 | 40.0 | 40.5 | 34.8 |
| gi\|92111312\|gb\|ABE73469.1\| | Elaeis guineensis | 41.7 | 41.3 | 38.4 | 40.5 | 37.0 |
| gi\|256669627\|ref\|ZP_05480780.1\| | Streptomyces sp. | 33.4 | 36.8 | 33.9 | 40.5 | 35.0 |
| gi\|168181072\|ref\|ZP_02615736.1\| | Clostridium botulinum | 44.7 | 48.2 | 41.2 | 40.5 | 35.1 |
| gi\|167759943\|ref\|ZP_02432070.1\| | Clostridium scindens | 41.3 | 41.2 | 36.5 | 40.5 | 36.1 |
| gi\|284034290\|ref\|YP_003384221.1 | Kribbella flavida | 36.5 | 36.9 | 35.0 | 40.5 | 37.0 |
| gi\|189219228\|ref\|YP_001939869.1 | M.infernorum | 37.3 | 41.7 | 40.2 | 40.5 | 36.1 |
| gi\|257888589\|ref\|ZP_05668242.1\| | Enterococcus faecium | 54.6 | 55.7 | 37.7 | 40.5 | 36.3 |
| gi\|257898974\|ref\|ZP_05678627.1\| | Enterococcus faecium | 54.6 | 56.0 | 37.4 | 40.5 | 37.5 |
| gi\|33866778\|ref\|NP_898337.1\| | Synechococcus sp. | 41.1 | 41.9 | 37.5 | 40.5 | 39.0 |
| gi\|153852690\|ref\|ZP_01994127.1\| | Dorea longicatena | 40.6 | 43.0 | 38.3 | 40.5 | 35.9 |
| gi\|238650589\|ref\|YP_002916441.1 | Rickettsia peacockii | 38.0 | 39.6 | 41.6 | 40.4 | 35.9 |
| gi\|34581204\|ref\|ZP_00142684.1\| | Rickettsia sibirica | 38.0 | 39.6 | 41.6 | 40.4 | 35.9 |
| gi\|15893125\|ref\|NP_360839.1\| | R. conorii, R. africae, R.rickettsii | 38.0 | 39.6 | 41.6 | 40.4 | 35.9 |
| gi\|164687309\|ref\|ZP_02211337.1\| | Clostridium bartlettii | 45.4 | 45.4 | 44.6 | 40.4 | 33.6 |
| gi\|21224866\|ref\|NP_630645.1\| | Streptomyces coelicolor | 34.5 | 34.5 | 34.7 | 40.4 | 39.5 |
| gi\|116073936\|ref\|ZP_01471198.1\| | Synechococcus sp. | 42.4 | 41.3 | 35.0 | 40.4 | 41.2 |
| gi\|92111314\|gb\|ABE73470.1\| | Elaeis oleifera | 41.0 | 40.8 | 38.0 | 40.4 | 37.2 |
| gi\|193290708\|gb\|ACF17662.1\| | Capsicum annuum | 41.1 | 40.6 | 37.1 | 40.4 | 37.7 |
| gi\|255577831\|ref\|XP_002529789.1 | Ricinus communis | 39.5 | 40.3 | 39.0 | 40.4 | 37.1 |
| gi\|134098111\|ref\|YP_001103772.1 | S. erythraea | 35.4 | 33.0 | 33.9 | 40.4 | 36.1 |

FIG. 3E: Beta cont'd

FIG. 3E: Beta cont'd

FIG. 3E: Beta Ketoacyl-ACP Synthase Homologs

| | | | | | | |
|---|---|---|---|---|---|---|
| gi\|149178694\|ref\|ZP_01857278.1\| | Planctomyces maris | 39.1 | 42.1 | 41.9 | 40.4 | 39.3 |
| gi\|260901495\|ref\|ZP_05909890.1\| | Vibrio parahaemolyticus | 41.4 | 42.0 | 40.6 | 40.4 | 37.1 |
| gi\|116071499\|ref\|ZP_01468767.1\| | Synechococcus sp. | 40.7 | 40.9 | 36.2 | 40.4 | 39.3 |
| gi\|284053783\|ref\|ZP_06383993.1\| | Arthrospira platensis | 42.4 | 42.7 | 41.0 | 40.4 | 38.9 |
| gi\|225426958\|ref\|XP_002264765.1 | Vitis vinifera | 41.2 | 40.4 | 37.2 | 40.4 | 36.8 |
| gi\|270306639\|emb\|CBI25782.1\| | Vitis vinifera | 41.2 | 40.4 | 37.2 | 40.4 | 36.8 |
| gi\|251795470\|ref\|YP_003010201.1 | Paenibacillus sp. | 39.4 | 40.2 | 40.7 | 40.3 | 34.6 |
| gi\|170757452\|ref\|YP_001783240.1 | Clostridium botulinum | 44.3 | 49.2 | 40.6 | 40.3 | 33.9 |
| gi\|229860988\|ref\|ZP_04480602.1\| | S.nassauensis | 38.6 | 37.9 | 35.3 | 40.3 | 39.3 |
| gi\|218128435\|ref\|ZP_03457239.1\| | Bacteroides eggerthii | 38.4 | 35.0 | 40.2 | 40.3 | 39.9 |
| gi\|86606992\|ref\|YP_475755.1\| | Synechococcus sp. | 41.3 | 41.2 | 38.9 | 40.3 | 37.4 |
| gi\|51473940\|ref\|YP_067697.1\| | Rickettsia typhi | 37.1 | 39.2 | 41.3 | 40.3 | 34.7 |
| gi\|15604605\|ref\|NP_221123.1\| | Rickettsia prowazekii | 37.4 | 38.9 | 41.6 | 40.3 | 35.3 |
| gi\|157964922\|ref\|YP_001499746.1 | Rickettsia massiliae | 37.8 | 39.5 | 42.0 | 40.3 | 36.8 |
| gi\|21282594\|ref\|NP_645682.1\| | Staphylococcus aureus | 41.9 | 39.4 | 99.0 | 40.3 | 39.9 |
| gi\|269940484\|emb\|CBI48861.1\| | Staphylococcus aureus | 41.9 | 39.0 | 98.7 | 40.3 | 39.9 |
| gi\|239636497\|ref\|ZP_04677499.1\| | Staphylococcus warneri | 42.4 | 41.0 | 91.1 | 40.3 | 40.6 |
| gi\|27467595\|ref\|NP_764232.1\| | S. epidermidis | 42.4 | 40.3 | 88.8 | 40.3 | 38.7 |
| gi\|160946932\|ref\|ZP_02094135.1\| | Parvimonas micra | 41.7 | 47.5 | 40.8 | 40.3 | 34.6 |
| gi\|110799885\|ref\|YP_695770.1\| | Clostridium perfringens | 45.7 | 45.1 | 43.8 | 40.2 | 38.9 |
| gi\|168215284\|ref\|ZP_02640909.1\| | Clostridium perfringens | 45.7 | 45.1 | 43.5 | 40.2 | 38.9 |
| gi\|152985725\|ref\|YP_001349750.1 | P.aeruginosa | 31.8 | 30.7 | 31.1 | 40.2 | 35.0 |
| gi\|193211806\|ref\|YP_001997759.1 | Chlorobaculum parvum | 41.4 | 45.0 | 39.0 | 40.2 | 38.0 |
| gi\|78186023\|ref\|YP_374066.1\| | Chlorobium luteolum | 41.6 | 44.2 | 41.8 | 40.2 | 37.2 |
| gi\|118579939\|ref\|YP_901189.1\| | Pelobacter propionicus | 33.3 | 37.1 | 38.5 | 40.2 | 39.1 |
| gi\|168028451\|ref\|XP_001766741.1 | Physcomitrella patens | 39.3 | 38.9 | 39.6 | 40.2 | 37.4 |
| gi\|229059523\|ref\|ZP_04196905.1\| | Bacillus cereus | 38.9 | 36.3 | 40.3 | 40.1 | 32.7 |
| gi\|229166738\|ref\|ZP_04294488.1\| | Bacillus cereus | 39.2 | 36.6 | 40.6 | 40.1 | 33.0 |
| gi\|187777411\|ref\|ZP_02993884.1\| | Clostridium sporogenes | 44.3 | 48.8 | 41.0 | 40.1 | 34.6 |
| gi\|153952755\|ref\|YP_001393520.1 | Clostridium kluyveri | 43.0 | 46.0 | 36.9 | 40.1 | 32.9 |
| gi\|256784687\|ref\|ZP_05523118.1\| | Streptomyces lividans | 38.9 | 39.9 | 39.6 | 40.1 | 58.6 |

FIG. 3E: Beta cont'd

FIG. 3E: Beta Ketoacyl-ACP Synthase Homologs

| | | | | | | |
|---|---|---|---|---|---|---|
| gi\|126645680\|ref\|ZP_01718224.1\| | Algoriphagus sp. | 36.8 | 37.1 | 41.5 | 40.1 | 39.0 |
| gi\|28209898\|ref\|NP_780842.1\| | Clostridium tetani | 43.9 | 44.5 | 40.0 | 40.1 | 34.8 |
| gi\|224436816\|ref\|ZP_03657814.1\| | Helicobacter cinaedi | 37.6 | 39.5 | 41.0 | 40.1 | 35.6 |
| gi\|2921215\|gb\|AAC04694.1\| | Perilla frutescens | 39.3 | 41.5 | 37.0 | 40.1 | 34.9 |
| gi\|116248671\|gb\|ABJ90470.1\| | Jatropha curcas | 40.2 | 40.3 | 37.9 | 40.1 | 36.7 |
| gi\|228002262\|ref\|ZP_04049259.1\| | Brachyspira murdochii | 33.6 | 35.2 | 39.9 | 40.1 | 33.8 |
| gi\|257056080\|ref\|YP_003132912.1 | S.viridis | 33.8 | 35.2 | 40.5 | 40.1 | 40.3 |
| gi\|260438982\|ref\|ZP_05792798.1\| | Butyrivibrio crossotus | 36.5 | 37.4 | 39.6 | 40.1 | 36.1 |
| gi\|282898514\|ref\|ZP_06306504.1\| | Raphidiopsis brookii | 42.3 | 41.9 | 41.9 | 40.1 | 38.2 |
| gi\|28900826\|ref\|NP_800481.1\| | Vibrio parahaemolyticus | 41.0 | 42.0 | 40.9 | 40.1 | 36.8 |
| gi\|262383939\|ref\|ZP_06077075.1\| | Bacteroides sp. | 37.2 | 38.0 | 37.6 | 40.1 | 37.0 |
| gi\|213963558\|ref\|ZP_03391811.1\| | C.sputigena Capno, | 38.8 | 40.2 | 39.9 | 40.1 | 39.3 |
| gi\|262395384\|ref\|YP_003287237.1 | Vibrio sp. | 40.4 | 41.1 | 41.3 | 40.1 | 37.1 |
| gi\|269792710\|ref\|YP_003317614.1 | T.acidaminovorans | 36.0 | 37.2 | 36.6 | 40.1 | 37.4 |
| gi\|239983411\|ref\|ZP_04705935.1\| | Streptomyces albus | 35.1 | 33.1 | 35.3 | 40.1 | 37.8 |
| gi\|194333023\|ref\|YP_002014883.1 | P.aestuarii | 42.4 | 44.0 | 39.8 | 40.1 | 37.4 |
| gi\|218132934\|ref\|ZP_03461738.1\| | B.pectinophilus | 42.4 | 42.7 | 45.4 | 40.0 | 38.2 |
| gi\|167765449\|ref\|ZP_02437562.1\| | Bacteroides stercoris | 38.4 | 35.0 | 40.2 | 40.0 | 39.3 |
| gi\|163791229\|ref\|ZP_02185645.1\| | Carnobacterium sp. | 55.7 | 58.8 | 43.1 | 40.0 | 38.4 |
| gi\|39933000\|gb\|AAR32677.1\| | S.hygroscopicus | 31.5 | 32.3 | 38.6 | 40.0 | 39.2 |
| gi\|254375818\|ref\|ZP_04991295.1\| | Streptomyces sp. | 33.5 | 30.4 | 38.5 | 40.0 | 38.3 |
| gi\|226495781\|ref\|NP_001147105.1 | Zea mays | 40.4 | 42.2 | 39.2 | 39.9 | 36.2 |
| gi\|7381101\|gb\|AAF61399.1\|AF134854_1 | Cuphea hookeriana | 39.4 | 40.5 | 36.9 | 39.9 | 36.8 |
| gi\|194335359\|ref\|YP_002017153.1 | P.phaeoclathratiforme | 40.4 | 42.7 | 39.3 | 39.9 | 36.3 |
| gi\|55822359\|ref\|YP_140800.1\| | S.thermophilus | 61.8 | 68.9 | 36.9 | 39.9 | 39.7 |
| gi\|21224230\|ref\|NP_630009.1\| | Streptomyces coelicolor | 39.2 | 40.3 | 39.6 | 39.9 | 58.6 |
| gi\|281425282\|ref\|ZP_06256195.1\| | Prevotella oris | 42.0 | 40.4 | 37.8 | 39.9 | 38.8 |
| gi\|67459627\|ref\|YP_247251.1\| | Rickettsia felis | 38.8 | 40.1 | 41.6 | 39.9 | 36.2 |
| gi\|257425033\|ref\|ZP_05601460.1\| | Staphylococcus aureus | 41.4 | 39.0 | 99.7 | 39.9 | 39.9 |
| gi\|223042947\|ref\|ZP_03612995.1\| | Staphylococcus capitis | 41.4 | 40.3 | 91.7 | 39.9 | 39.6 |
| gi\|242373144\|ref\|ZP_04818718.1\| | Staphylococcus epidermidis | 41.4 | 40.0 | 90.7 | 39.9 | 39.6 |

FIG. 3E: Beta cont'd

FIG. 3E: Beta Ketoacyl-ACP Synthase Homologs

| | | | | | | |
|---|---|---|---|---|---|---|
| gi\|256667170\|ref\|ZP_05478123.1\| | Streptomyces sp. | 35.2 | 36.3 | 37.3 | 39.9 | 41.3 |
| gi\|254377667\|ref\|ZP_04993127.1\| | Streptomyces sp. | 35.4 | 31.2 | 34.1 | 39.9 | 33.9 |
| gi\|116748377\|ref\|YP_845064.1\| | S.fumaroxidans | 38.6 | 40.5 | 41.1 | 39.9 | 40.8 |
| gi\|282866797\|ref\|ZP_06275834.1\| | Streptomyces sp. | 33.7 | 36.0 | 35.0 | 39.9 | 42.3 |
| gi\|125718732\|ref\|YP_001035865.1 | S. sanguinis | 64.9 | 69.5 | 39.6 | 39.9 | 37.7 |
| gi\|262283264\|ref\|ZP_06061031.1\| | Streptococcus sp. | 65.8 | 69.8 | 40.1 | 39.9 | 40.2 |
| gi\|159039157\|ref\|YP_001538410.1 | Salinispora arenicola | 36.6 | 34.5 | 35.4 | 39.9 | 38.5 |
| gi\|170759774\|ref\|YP_001788947.1 | Clostridium botulinum | 44.0 | 48.2 | 40.0 | 39.9 | 34.9 |
| gi\|1143069\|gb\|AAB61310.1\| | Allium ampeloprasum | 40.4 | 41.1 | 39.2 | 39.8 | 36.0 |
| gi\|225518643\|ref\|ZP_03765587.1\| | 'Nostoc azollae' | 40.5 | 42.0 | 40.7 | 39.8 | 38.5 |
| gi\|87125175\|ref\|ZP_01081021.1\| | Synechococcus sp. | 42.1 | 41.0 | 36.5 | 39.8 | 42.8 |
| gi\|15806944\|ref\|NP_295669.1\| | D.radiodurans | 39.2 | 39.3 | 38.8 | 39.8 | 37.3 |
| gi\|15598529\|ref\|NP_252023.1\| | P.aeruginosa | 38.3 | 37.7 | 37.1 | 39.8 | 50.9 |
| gi\|256825044\|ref\|YP_003149004.1 | Kytococcus sedentarius | 31.5 | 32.2 | 36.5 | 39.8 | 36.8 |
| gi\|229011170\|ref\|ZP_04168363.1\| | Bacillus mycoides | 38.9 | 36.3 | 40.3 | 39.8 | 32.7 |
| gi\|229132700\|ref\|ZP_04261546.1\| | Bacillus cereus | 38.9 | 36.3 | 39.9 | 39.8 | 32.7 |
| gi\|224369606\|ref\|YP_002603770.1 | D. autotrophicum | 36.2 | 39.2 | 35.6 | 39.8 | 36.8 |
| gi\|189345718\|ref\|YP_001942247.1 | Chlorobium limicola | 40.8 | 42.0 | 39.1 | 39.8 | 34.5 |
| gi\|257081562\|ref\|ZP_05575923.1\| | Enterococcus faecalis | 59.0 | 59.8 | 38.5 | 39.8 | 35.5 |
| gi\|256854173\|ref\|ZP_05559538.1\| | Enterococcus faecalis | 59.3 | 59.8 | 38.5 | 39.8 | 36.9 |
| gi\|29377351\|ref\|NP_816505.1\| | Enterococcus faecalis | 59.3 | 60.1 | 38.5 | 39.8 | 36.0 |
| gi\|255974774\|ref\|ZP_05425360.1\| | Enterococcus faecalis | 59.3 | 59.8 | 38.5 | 39.8 | 36.0 |
| gi\|256763447\|ref\|ZP_05504027.1\| | Enterococcus faecalis | 59.3 | 59.8 | 38.5 | 39.8 | 35.8 |
| gi\|256599928\|pdb\|3IL5\|A | (Diethylamino)sulfonyl | 59.3 | 60.1 | 38.5 | 39.8 | 35.8 |
| gi\|167768016\|ref\|ZP_02440069.1\| | Clostridium sp. | 45.6 | 48.1 | 42.1 | 39.8 | 34.8 |
| gi\|218262400\|ref\|ZP_03476880.1\| | P.johnsonii | 37.2 | 37.7 | 37.0 | 39.8 | 38.2 |
| gi\|150009040\|ref\|YP_001303783.1 | Parabacteroides sp., Bacteroides sp., | 36.9 | 38.0 | 37.0 | 39.8 | 37.6 |
| gi\|154494316\|ref\|ZP_02033636.1\| | P.merdae | 37.2 | 37.7 | 37.0 | 39.8 | 38.2 |
| gi\|153832799\|ref\|ZP_01985466.1\| | Vibrio harveyi | 39.5 | 39.9 | 41.6 | 39.8 | 36.8 |
| gi\|229528376\|ref\|ZP_04417767.1\| | Vibrio cholerae | 40.1 | 40.7 | 42.1 | 39.8 | 35.9 |
| gi\|154503820\|ref\|ZP_02040880.1\| | Ruminococcus gnavus | 43.6 | 44.5 | 40.8 | 39.8 | 39.3 |

FIG. 3E: Beta cont'd

FIG. 3E: Beta Ketoacyl-ACP Synthase Homologs

| | | | | | | |
|---|---|---|---|---|---|---|
| gi\|226228575\|ref\|YP_002762681.1 | G.aurantiaca | 32.6 | 35.0 | 36.9 | 39.8 | 35.6 |
| gi\|269967727\|ref\|ZP_06181775.1\| | Vibrio alginolyticus | 41.0 | 41.7 | 40.9 | 39.8 | 37.1 |
| gi\|37676566\|ref\|NP_936962.1\| | Vibrio vulnificus | 41.7 | 41.5 | 42.7 | 39.8 | 37.1 |
| gi\|27366791\|ref\|NP_762318.1\| | Vibrio vulnificus | 41.7 | 41.5 | 42.7 | 39.8 | 37.1 |
| gi\|86740791\|ref\|YP_481191.1\| | Frankia sp. | 36.4 | 38.9 | 38.1 | 39.7 | 57.1 |
| gi\|149190733\|ref\|ZP_01868999.1\| | Vibrio shilonii | 41.7 | 42.1 | 41.7 | 39.7 | 35.2 |
| gi\|160882376\|ref\|ZP_02063379.1\| | Bacteroides sp., B. ovatus | 38.1 | 35.6 | 40.5 | 39.7 | 38.3 |
| gi\|260172015\|ref\|ZP_05758427.1\| | Bacteroides sp. | 38.1 | 35.6 | 40.5 | 39.7 | 38.3 |
| gi\|237712745\|ref\|ZP_04543226.1\| | Bacteroides sp. | 38.1 | 35.6 | 40.5 | 39.7 | 38.3 |
| gi\|153809061\|ref\|ZP_01961729.1\| | Bacteroides caccae | 38.1 | 35.6 | 40.5 | 39.7 | 38.3 |
| gi\|256395928\|ref\|YP_003117492.1 | Catenulispora acidiphila | 31.1 | 32.6 | 37.3 | 39.7 | 37.5 |
| gi\|256816452\|ref\|ZP_05541467.1\| | S.griseoflavus | 32.7 | 32.1 | 38.8 | 39.7 | 37.3 |
| gi\|239931511\|ref\|ZP_04688464.1\| | S. ghanaensis | 32.7 | 31.8 | 38.5 | 39.7 | 37.3 |
| gi\|15824218\|dbj\|BAB69376.1\| | S.avermitilis | 35.5 | 36.7 | 36.2 | 39.7 | 61.9 |
| gi\|148878549\|dbj\|BAC68319.2\| | S.avermitilis | 35.7 | 36.9 | 35.9 | 39.7 | 62.0 |
| gi\|148381542\|ref\|YP_001256083.1 | Clostridium botulinum | 45.3 | 48.5 | 40.9 | 39.7 | 34.8 |
| gi\|6630446\|gb\|AAF19534.1\|AC007190_2 | Arabidopsis thaliana | 38.5 | 40.5 | 36.5 | 39.7 | 35.4 |
| gi\|218195688\|gb\|EEC78115.1\| | Oryza sativa | 41.6 | 44.4 | 39.1 | 39.6 | 37.1 |
| gi\|168034759\|ref\|XP_001769879.1 | Physcomitrella patens | 40.6 | 40.7 | 39.7 | 39.6 | 36.8 |
| gi\|242077378\|ref\|XP_002448625.1 | Sorghum bicolor | 40.8 | 43.1 | 38.6 | 39.6 | 36.2 |
| gi\|7381099\|gb\|AAF61398.1\|AF134853_1 | Cuphea hookeriana | 37.9 | 39.6 | 36.9 | 39.6 | 35.6 |
| gi\|240143418\|ref\|ZP_04742019.1\| | Roseburia intestinalis | 45.6 | 46.7 | 41.2 | 39.6 | 39.4 |
| gi\|169342365\|ref\|ZP_02863431.1\| | Clostridium perfringens | 46.0 | 45.7 | 43.2 | 39.6 | 38.0 |
| gi\|168207994\|ref\|ZP_02633999.1\| | Clostridium perfringens | 46.0 | 45.4 | 43.2 | 39.6 | 37.7 |
| gi\|18310050\|ref\|NP_561984.1\| | Clostridium perfringens | 46.0 | 45.4 | 43.2 | 39.6 | 38.0 |
| gi\|282880852\|ref\|ZP_06289545.1\| | Prevotella timonensis | 41.5 | 38.8 | 40.0 | 39.6 | 38.7 |
| gi\|55820474\|ref\|YP_138916.1\| | S.thermophilus | 61.5 | 68.6 | 38.5 | 39.6 | 39.4 |
| gi\|37523261\|ref\|NP_926638.1\| | Gloeobacter violaceus | 43.2 | 42.7 | 37.3 | 39.6 | 41.5 |
| gi\|139438567\|ref\|ZP_01772083.1\| | Collinsella aerofaciens | 39.2 | 36.5 | 38.1 | 39.6 | 41.7 |
| gi\|227987074\|ref\|ZP_04034171.1\| | Meiothermus silvanus | 40.0 | 43.7 | 46.9 | 39.6 | 39.8 |
| gi\|160882089\|ref\|ZP_02063092.1\| | Bacteroides ovatus | 39.2 | 36.1 | 38.3 | 39.6 | 38.3 |

FIG. 3E: Beta cont'd

FIG. 3E: Beta Ketoacyl-ACP Synthase Homologs

| | | | | | | |
|---|---|---|---|---|---|---|
| gi\|229549007\|ref\|ZP_04437732.1\| | Enterococcus faecalis | 60.3 | 60.9 | 39.1 | 39.6 | 35.6 |
| gi\|229544792\|ref\|ZP_04433517.1\| | Enterococcus faecalis | 60.3 | 60.9 | 39.1 | 39.6 | 36.8 |
| gi\|227519391\|ref\|ZP_03949440.1\| | Enterococcus faecalis | 60.3 | 60.9 | 39.1 | 39.6 | 37.1 |
| gi\|228992126\|ref\|ZP_04152062.1\| | B. pseudomycoides | 40.7 | 39.4 | 40.9 | 39.6 | 33.1 |
| gi\|228998180\|ref\|ZP_04157778.1\| | Bacillus mycoides | 40.3 | 38.8 | 40.6 | 39.6 | 33.4 |
| gi\|225620503\|ref\|YP_002721760.1 | B.hyodysenteriae | 35.4 | 36.5 | 39.1 | 39.6 | 34.2 |
| gi\|229005675\|ref\|ZP_04163379.1\| | Bacillus mycoides | 40.8 | 39.8 | 40.6 | 39.6 | 33.8 |
| gi\|229086073\|ref\|ZP_04218294.1\| | Bacillus cereus | 41.5 | 39.4 | 41.8 | 39.6 | 33.8 |
| gi\|225027945\|ref\|ZP_03717137.1\| | Eubacterium hallii | 43.4 | 42.7 | 38.8 | 39.6 | 36.0 |
| gi\|227536115\|ref\|ZP_03966164.1\| | S.spiritivorum | 40.8 | 41.5 | 40.5 | 39.6 | 40.5 |
| gi\|110802643\|ref\|YP_698458.1\| | Clostridium perfringens | 46.3 | 46.0 | 43.5 | 39.6 | 39.1 |
| gi\|126695493\|ref\|YP_001090379.1 | P. marinus | 41.8 | 39.9 | 38.7 | 39.6 | 33.8 |
| gi\|270293321\|ref\|ZP_06199530.1\| | Streptococcus sp. | 62.8 | 70.8 | 40.1 | 39.6 | 38.7 |
| gi\|270501849\|ref\|ZP_06218765.1\| | M.aurantiaca | 35.5 | 34.9 | 34.4 | 39.6 | 38.2 |
| gi\|229096351\|ref\|ZP_04227324.1\| | Bacillus cereus | 38.5 | 36.7 | 40.9 | 39.5 | 33.0 |
| gi\|229074800\|ref\|ZP_04207815.1\| | Bacillus cereus | 38.5 | 36.7 | 40.9 | 39.5 | 33.0 |
| gi\|1706757\|sp\|P49244.2\|FABH1_CUPWR | Cuphea wrightii, | 38.8 | 39.3 | 37.5 | 39.5 | 35.6 |
| gi\|1345947\|sp\|P49245.1\|FABH2_CUPWR | Cuphea wrightii, | 39.5 | 40.9 | 36.6 | 39.5 | 35.9 |
| gi\|256772528\|ref\|ZP_05511702.1\| | Streptomyces sp. | 36.1 | 37.6 | 37.1 | 39.5 | 42.3 |
| gi\|21234232\|ref\|NP_639843.1\| | Streptomyces coelicolor | 35.8 | 38.5 | 35.9 | 39.5 | 55.1 |
| gi\|254398628\|ref\|ZP_05013654.1\| | S.pristinaespiralis | 36.1 | 35.0 | 36.0 | 39.5 | 36.1 |
| gi\|29828373\|ref\|NP_823007.1\| | S.avermitilis | 35.7 | 34.4 | 37.0 | 39.5 | 37.2 |
| gi\|255971776\|ref\|ZP_05422362.1\| | Enterococcus faecalis | 59.0 | 59.4 | 38.5 | 39.4 | 35.2 |
| gi\|257417056\|ref\|ZP_05594050.1\| | Enterococcus faecalis | 59.0 | 59.8 | 38.2 | 39.4 | 35.7 |
| gi\|158317504\|ref\|YP_001510012.1 | Frankia sp. | 38.0 | 38.5 | 36.9 | 39.4 | 71.9 |
| gi\|282899054\|ref\|ZP_06307035.1\| | C. raciborskii | 42.3 | 41.3 | 41.6 | 39.4 | 38.5 |
| gi\|260896727\|ref\|ZP_05905223.1\| | Vibrio parahaemolyticus | 40.4 | 41.4 | 40.0 | 39.4 | 36.1 |
| gi\|256818879\|ref\|YP_003140158.1 | Capnocytophaga ochracea | 38.8 | 40.8 | 39.1 | 39.4 | 39.3 |
| gi\|269964190\|ref\|ZP_06178483.1\| | Vibrio harveyi | 39.5 | 39.9 | 41.6 | 39.4 | 36.8 |
| gi\|260773918\|ref\|ZP_05882833.1\| | Vibrio metschnikovii | 40.3 | 41.1 | 41.9 | 39.4 | 36.1 |
| gi\|262403795\|ref\|ZP_06080353.1\| | Vibrio sp. | 39.8 | 40.1 | 41.7 | 39.4 | 36.2 |

FIG. 3E: Beta cont'd

FIG. 3E: Beta Ketoacyl-ACP Synthase Homologs

| | | | | | | |
|---|---|---|---|---|---|---|
| gi\|153800751\|ref\|ZP_01955337.1\| | Vibrio cholerae | 40.1 | 40.4 | 42.4 | 39.4 | 36.2 |
| gi\|254226183\|ref\|ZP_04919778.1\| | Vibrio cholerae | 40.1 | 40.4 | 42.4 | 39.4 | 36.2 |
| gi\|121725881\|ref\|ZP_01679181.1\| | Vibrio cholerae | 40.1 | 40.4 | 42.4 | 39.4 | 36.2 |
| gi\|262189646\|ref\|ZP_06048029.1\| | Vibrio cholerae | 40.1 | 40.4 | 42.4 | 39.4 | 36.2 |
| gi\|121585534\|ref\|ZP_01675330.1\| | Vibrio cholerae | 40.1 | 40.4 | 42.4 | 39.4 | 36.2 |
| gi\|254222090\|ref\|ZP_04915964.1\| | Vibrio cholerae | 40.1 | 40.4 | 42.4 | 39.4 | 36.2 |
| gi\|153219887\|ref\|ZP_01951456.1\| | Vibrio cholerae | 40.1 | 40.4 | 42.4 | 39.4 | 36.2 |
| gi\|153215609\|ref\|ZP_01950054.1\| | Vibrio cholerae | 40.1 | 40.4 | 42.4 | 39.4 | 36.2 |
| gi\|153820769\|ref\|ZP_01973436.1\| | Vibrio cholerae | 40.4 | 40.4 | 42.4 | 39.4 | 36.2 |
| gi\|156976915\|ref\|YP_001447821.1 | Vibrio harveyi | 39.5 | 39.9 | 41.6 | 39.4 | 36.8 |
| gi\|153820765\|ref\|ZP_01973432.1\| | Vibrio cholerae | 40.4 | 40.4 | 42.4 | 39.4 | 36.2 |
| gi\|91224653\|ref\|ZP_01259914.1\| | Vibrio alginolyticus | 40.7 | 41.4 | 40.6 | 39.4 | 37.1 |
| gi\|189423489\|ref\|YP_001950666.1 | Geobacter lovleyi | 40.9 | 42.7 | 36.0 | 39.4 | 37.7 |
| gi\|159490266\|ref\|XP_001703101.1 | C.reinhardtii | 37.2 | 35.5 | 33.8 | 39.4 | 35.6 |
| gi\|255693539\|ref\|ZP_05417214.1\| | Bacteroides finegoldii | 38.1 | 35.6 | 40.5 | 39.4 | 38.4 |
| gi\|15596196\|ref\|NP_249690.1\| | P.aeruginosa | 33.0 | 30.3 | 32.0 | 39.4 | 35.0 |
| gi\|149012168\|ref\|ZP_01833277.1\| | S.pneumoniae | 62.5 | 71.4 | 39.4 | 39.4 | 39.5 |
| gi\|225012406\|ref\|ZP_03702842.1\| | Flavobacteria bacterium | 41.8 | 41.0 | 36.6 | 39.4 | 37.4 |
| gi\|85712656\|ref\|ZP_01043702.1\| | Idiomarina baltica | 39.1 | 41.0 | 39.2 | 39.4 | 34.9 |
| gi\|256676289\|ref\|ZP_05486600.1\| | Streptomyces sp. | 32.6 | 30.7 | 39.1 | 39.4 | 38.6 |
| gi\|148906212\|gb\|ABR16262.1\| | Picea sitchensis | 41.5 | 38.6 | 37.3 | 39.4 | 38.7 |
| gi\|90415808\|ref\|ZP_01223741.1\| | marine gamma proteobacterium | 37.6 | 40.4 | 38.5 | 39.3 | 33.4 |
| gi\|222629657\|gb\|EEE61789.1\| | Oryza sativa | 41.6 | 44.4 | 39.1 | 39.3 | 36.8 |
| gi\|38344881\|emb\|CAE01542.2\| | Oryza sativa | 41.6 | 43.4 | 39.1 | 39.3 | 36.8 |
| gi\|115460900\|ref\|NP_001054050.1 | Oryza sativa | 41.6 | 43.4 | 39.1 | 39.3 | 36.8 |
| gi\|226498710\|ref\|NP_001147180.1 | Zea mays | 40.1 | 41.6 | 38.9 | 39.3 | 35.9 |
| gi\|78189621\|ref\|YP_379959.1\| | C.chlorochromatii | 42.8 | 45.1 | 40.2 | 39.3 | 38.5 |
| gi\|282878063\|ref\|ZP_06286868.1\| | Prevotella buccalis | 43.0 | 38.8 | 38.0 | 39.3 | 37.3 |
| gi\|33239610\|ref\|NP_874552.1\| | P. marinus | 41.8 | 42.4 | 36.6 | 39.3 | 36.0 |
| gi\|260777519\|ref\|ZP_05886413.1\| | Vibrio coralliilyticus | 41.0 | 40.8 | 42.2 | 39.3 | 39.3 |
| gi\|116048927\|ref\|YP_792272.1\| | P.aeruginosa | 33.0 | 30.3 | 32.0 | 39.3 | 35.0 |

FIG. 3E: Beta cont'd

FIG. 3E: Beta Ketoacyl-ACP Synthase Homologs

| | | | | | | |
|---|---|---|---|---|---|---|
| gi\|157826224\|ref\|YP_001493944.1 | Rickettsia akari | 37.2 | 38.9 | 40.4 | 39.3 | 35.4 |
| gi\|229827447\|ref\|ZP_04453516.1\| | Abiotrophia defectiva | 38.0 | 38.2 | 42.0 | 39.3 | 31.6 |
| gi\|271968301\|ref\|YP_003342497.1 | S.roseum | 35.9 | 36.8 | 37.6 | 39.2 | 37.7 |
| gi\|145595893\|ref\|YP_001160190.1 | Salinispora tropica | 37.5 | 33.6 | 36.0 | 39.2 | 37.4 |
| gi\|220904878\|ref\|YP_002480190.1 | D.desulfuricans | 35.2 | 34.6 | 38.8 | 39.2 | 41.7 |
| gi\|259046611\|ref\|ZP_05737012.1\| | Granulicatella adiacens | 47.0 | 48.7 | 37.7 | 39.2 | 36.6 |
| gi\|158521861\|ref\|YP_001529731.1 | D. oleovorans | 38.1 | 34.7 | 39.0 | 39.2 | 38.1 |
| gi\|229213591\|ref\|ZP_04339939.1\| | D.peptidovorans | 38.5 | 39.2 | 37.7 | 39.1 | 37.0 |
| gi\|152975916\|ref\|YP_001375433.1 | B. cereus,B. cytotoxicus | 39.7 | 39.7 | 40.9 | 39.1 | 31.7 |
| gi\|256960928\|ref\|ZP_05565099.1\| | Enterococcus faecalis | 58.6 | 59.1 | 38.2 | 39.1 | 35.7 |
| gi\|167753073\|ref\|ZP_02425200.1\| | Alistipes putredinis | 39.3 | 39.4 | 36.2 | 39.1 | 38.7 |
| gi\|34541716\|ref\|NP_906195.1\| | P. gingivalis | 37.3 | 38.3 | 37.6 | 39.1 | 36.7 |
| gi\|163803984\|ref\|ZP_02197805.1\| | Vibrio sp. | 38.9 | 39.9 | 41.6 | 39.1 | 36.5 |
| gi\|146298409\|ref\|YP_001193000.1 | F.johnsoniae | 39.8 | 39.0 | 41.0 | 39.1 | 37.3 |
| gi\|54309186\|ref\|YP_130206.1\| | P.profundum | 39.7 | 39.7 | 41.1 | 39.1 | 37.4 |
| gi\|88608629\|ref\|YP_506508.1\| | Neorickettsia sennetsu | 38.0 | 42.8 | 40.2 | 39.1 | 35.8 |
| gi\|212702203\|ref\|ZP_03310331.1\| | Desulfovibrio piger | 36.1 | 37.9 | 36.0 | 39.1 | 39.8 |
| gi\|218893041\|ref\|YP_002441910.1 | P, aeruginosa | 33.0 | 30.3 | 32.0 | 39.1 | 34.4 |
| gi\|107100440\|ref\|ZP_01364358.1\| | P,aeruginosa | 33.0 | 30.3 | 32.0 | 39.1 | 34.4 |
| gi\|280966815\|ref\|ZP_06241189.1\| | Frankia sp. | 34.0 | 34.9 | 36.8 | 39.0 | 35.9 |
| gi\|145219016\|ref\|YP_001129725.1 | C,phaeovibrioides | 42.2 | 42.8 | 39.6 | 39.0 | 36.0 |
| gi\|281421768\|ref\|ZP_06252767.1\| | Prevotella copri | 41.3 | 38.8 | 39.2 | 39.0 | 38.2 |
| gi\|148988169\|ref\|ZP_01819632.1\| | S,pneumoniae | 62.5 | 71.4 | 39.2 | 39.0 | 39.6 |
| gi\|15900336\|ref\|NP_344940.1\| | S,pneumoniae | 62.5 | 71.4 | 39.2 | 39.0 | 39.6 |
| gi\|149007993\|ref\|ZP_01831550.1\| | S.pneumoniae | 62.2 | 71.1 | 39.2 | 39.0 | 39.6 |
| gi\|148983814\|ref\|ZP_01817133.1\| | S.pneumoniae | 62.2 | 71.7 | 38.9 | 39.0 | 39.3 |
| gi\|261880030\|ref\|ZP_06006457.1\| | Prevotella bergensis | 39.5 | 39.3 | 37.7 | 39.0 | 39.9 |
| gi\|260591204\|ref\|ZP_05856662.1\| | Prevotella veroralis | 40.5 | 39.9 | 39.6 | 39.0 | 39.0 |
| gi\|161511223\|ref\|NP_821784.2\| | S.avermitilis | 35.8 | 37.3 | 35.3 | 39.0 | 61.8 |
| gi\|255085230\|ref\|XP_002505046.1 | Micromonas sp. | 40.1 | 41.7 | 37.6 | 39.0 | 35.0 |
| gi\|163764198\|ref\|ZP_02171256.1\| | B.selenitireducens | 39.9 | 42.2 | 58.5 | 39.0 | 37.8 |

FIG. 3E: Beta cont'd

FIG. 3E: Beta Ketoacyl-ACP Synthase Homologs

| | | | | | | |
|---|---|---|---|---|---|---|
| gi\|154246856\|ref\|YP_001417814.1 | X.autotrophicus | 32.4 | 32.8 | 39.2 | 39.0 | 41.0 |
| gi\|157151320\|ref\|YP_001450975.1 | Streptococcus gordonii | 66.5 | 69.2 | 39.8 | 38.9 | 39.0 |
| gi\|116492621\|ref\|YP_804356.1\| | P. pentosaceus | 45.5 | 46.3 | 37.7 | 38.9 | 34.2 |
| gi\|119716221\|ref\|YP_923186.1\| | Nocardioides sp. | 34.1 | 35.0 | 35.7 | 38.9 | 38.1 |
| gi\|149918052\|ref\|ZP_01906545.1\| | Plesiocystis pacifica | 34.8 | 37.2 | 38.3 | 38.9 | 36.7 |
| gi\|229079052\|ref\|ZP_04211603.1\| | Bacillus cereus | 37.2 | 37.4 | 38.5 | 38.9 | 31.6 |
| gi\|168002625\|ref\|XP_001754014.1 | Physcomitrella patens | 40.7 | 41.4 | 39.6 | 38.9 | 38.8 |
| gi\|226304625\|ref\|YP_002764583.1 | R. erythropolis | 33.0 | 31.7 | 36.8 | 38.9 | 37.3 |
| gi\|256599932\|pdb\|3IL6\|A | | 58.3 | 59.1 | 37.6 | 38.8 | 35.7 |
| gi\|188994053\|ref\|YP_001928305.1 | P.gingivalis | 37.3 | 38.3 | 37.6 | 38.8 | 36.9 |
| gi\|167747174\|ref\|ZP_02419301.1\| | Anaerostipes caccae | 45.6 | 45.0 | 38.7 | 38.8 | 37.5 |
| gi\|262173961\|ref\|ZP_06041638.1\| | Vibrio mimicus | 39.7 | 40.4 | 42.1 | 38.8 | 36.5 |
| gi\|258622628\|ref\|ZP_05717649.1\| | Vibrio mimicus | 40.1 | 40.4 | 42.1 | 38.8 | 36.2 |
| gi\|258623960\|ref\|ZP_05718913.1\| | Vibrio mimicus | 40.1 | 40.4 | 42.0 | 38.8 | 36.2 |
| gi\|227523050\|ref\|ZP_03953099.1\| | Lactobacillus hilgardii | 48.0 | 47.8 | 39.8 | 38.8 | 36.3 |
| gi\|153824369\|ref\|ZP_01977036.1\| | Vibrio cholerae | 39.8 | 40.1 | 41.7 | 38.8 | 35.9 |
| gi\|282861739\|ref\|ZP_06270803.1\| | Streptomyces sp. | 33.2 | 31.4 | 37.5 | 38.8 | 36.6 |
| gi\|156093785\|ref\|XP_001612931.1 | Plasmodium vivax | 39.2 | 36.5 | 37.5 | 38.8 | 34.3 |
| gi\|29349242\|ref\|NP_812745.1\| | Bacteroides sp., B. thetaiotaomicron | 37.2 | 35.3 | 40.2 | 38.8 | 37.4 |
| gi\|29345532\|ref\|NP_809035.1\| | B.thetaiotaomicron | 39.0 | 35.3 | 38.8 | 38.8 | 39.1 |
| gi\|253571679\|ref\|ZP_04849085.1\| | Bacteroides sp. | 39.0 | 35.3 | 38.8 | 38.8 | 39.1 |
| gi\|255011700\|ref\|ZP_05283826.1\| | Bacteroides fragilis | 38.7 | 36.5 | 39.6 | 38.8 | 38.0 |
| gi\|229208849\|ref\|ZP_04335288.1\| | N. dassonvillei | 33.6 | 35.0 | 36.0 | 38.8 | 40.5 |
| gi\|257792616\|ref\|YP_003183222.1 | Eggerthella lenta | 35.5 | 32.5 | 34.8 | 38.8 | 35.1 |
| gi\|168334939\|ref\|ZP_02693058.1\| | Epulopiscium sp. | 45.7 | 48.0 | 43.0 | 38.8 | 36.9 |
| gi\|118477290\|ref\|YP_894441.1\| | B.cereus,B.thuringiensis | 37.2 | 37.7 | 40.3 | 38.7 | 33.0 |
| gi\|166032073\|ref\|ZP_02234902.1\| | Dorea formicigenerans | 42.1 | 42.0 | 37.5 | 38.7 | 35.1 |
| gi\|253575028\|ref\|ZP_04852367.1\| | Paenibacillus sp. | 39.4 | 37.8 | 41.5 | 38.7 | 36.5 |
| gi\|254506635\|ref\|ZP_05118776.1\| | Vibrio parahaemolyticus | 39.5 | 40.5 | 42.2 | 38.7 | 36.6 |
| gi\|252118185\|ref\|ZP_04632613.1\| | P.melaninogenica | 41.5 | 40.2 | 39.3 | 38.7 | 39.9 |
| gi\|260769218\|ref\|ZP_05878151.1\| | Vibrio furnissii | 40.9 | 41.6 | 41.7 | 38.7 | 37.4 |

FIG. 3E: Beta cont'd

FIG. 3E: Beta Ketoacyl-ACP Synthase Homologs

| | | | | | | |
|---|---|---|---|---|---|---|
| gi\|238917644\|ref\|YP_002931161.1 | Eubacterium eligens | 42.3 | 41.2 | 37.8 | 38.7 | 33.9 |
| gi\|77409848\|ref\|ZP_00786484.1\| | S.agalactiae | 62.8 | 65.4 | 39.7 | 38.7 | 35.9 |
| gi\|255533698\|ref\|YP_003094070.1 | Pedobacter heparinus | 38.9 | 41.1 | 38.7 | 38.7 | 39.9 |
| gi\|218961004\|ref\|YP_001740779.1 | C. Cloacamonas acidaminovorans | 38.5 | 40.6 | 37.7 | 38.6 | 38.5 |
| gi\|189425477\|ref\|YP_001952654.1 | Geobacter lovleyi | 37.7 | 38.3 | 39.4 | 38.6 | 38.9 |
| gi\|16078081\|ref\|NP_388898.1\| | Bacillus subtilis | 38.7 | 38.7 | 42.9 | 38.6 | 35.6 |
| gi\|225010290\|ref\|ZP_03700762.1\| | Flavobacteria bacterium | 41.6 | 42.2 | 38.7 | 38.6 | 38.0 |
| gi\|145208329\|gb\|ABP38071.1\| | Brassica juncea | 39.9 | 39.2 | 35.6 | 38.6 | 37.5 |
| gi\|238060432\|ref\|ZP_04605141.1\| | Micromonospora sp. | 36.0 | 33.8 | 35.1 | 38.6 | 37.9 |
| gi\|148262218\|ref\|YP_001228924.1 | G.uraniireducens | 38.3 | 43.8 | 38.7 | 38.6 | 37.0 |
| gi\|189462214\|ref\|ZP_03010999.1\| | Bacteroides coprocola | 40.0 | 36.8 | 37.8 | 38.6 | 38.3 |
| gi\|227529868\|ref\|ZP_03959917.1\| | Lactobacillus vaginalis | 48.9 | 49.4 | 38.8 | 38.6 | 40.2 |
| gi\|111220463\|ref\|YP_711257.1\| | Frankia alni ACN14a, | 36.8 | 36.8 | 33.9 | 38.6 | 37.0 |
| gi\|1653102\|dbj\|BAA18018.1\| | Synechocystis sp. | 41.8 | 39.4 | 42.2 | 38.5 | 37.0 |
| gi\|229196078\|ref\|ZP_04322830.1\| | Bacillus cereus | 37.8 | 36.7 | 40.6 | 38.5 | 33.0 |
| gi\|229017155\|ref\|ZP_04174069.1\| | Bacillus cereus | 37.5 | 37.0 | 40.1 | 38.5 | 32.1 |
| gi\|228914457\|ref\|ZP_04078067.1\| | Bacillus thuringiensis | 37.2 | 36.7 | 40.3 | 38.5 | 33.0 |
| gi\|260583681\|ref\|ZP_05851429.1\| | Granulicatella elegans | 48.3 | 47.4 | 38.1 | 38.5 | 36.4 |
| gi\|256805777\|ref\|ZP_05535401.1\| | S.viridochromogenes | 35.0 | 34.8 | 35.9 | 38.5 | 36.1 |
| gi\|189499167\|ref\|YP_001958637.1 | C.phaeobacteroides | 40.4 | 45.0 | 39.4 | 38.5 | 38.2 |
| gi\|78224463\|ref\|YP_386210.1\| | G.metallireducens | 40.2 | 42.8 | 37.7 | 38.5 | 38.2 |
| gi\|163754508\|ref\|ZP_02161630.1\| | Kordia algicida | 39.3 | 40.2 | 40.4 | 38.5 | 37.7 |
| gi\|227509988\|ref\|ZP_03940037.1\| | Lactobacillus brevis | 47.7 | 47.5 | 39.5 | 38.5 | 37.1 |
| gi\|262164892\|ref\|ZP_06032630.1\| | Vibrio mimicus | 39.8 | 40.7 | 42.4 | 38.5 | 36.2 |
| gi\|227512922\|ref\|ZP_03942971.1\| | Lactobacillus buchneri | 47.7 | 48.5 | 40.3 | 38.5 | 36.7 |
| gi\|90410377\|ref\|ZP_01218393.1\| | P.profundum | 39.4 | 39.9 | 41.1 | 38.5 | 37.4 |
| gi\|54027256\|ref\|YP_121498.1\| | Nocardia farcinica | 33.3 | 32.2 | 34.3 | 38.5 | 36.9 |
| gi\|160890561\|ref\|ZP_02071564.1\| | B. uniformis B. sp. | 38.7 | 35.9 | 39.3 | 38.5 | 39.0 |
| gi\|257865877\|ref\|ZP_05645530.1\| | E.casseliflavus | 58.6 | 59.4 | 40.0 | 38.5 | 38.4 |
| gi\|53715373\|ref\|YP_101365.1\| | Bacteroides sp., B. fragilis, | 39.0 | 36.5 | 39.6 | 38.5 | 37.7 |
| gi\|217959355\|ref\|YP_002337903.1 | Bacillus cereus | 37.8 | 36.0 | 40.6 | 38.5 | 33.2 |

FIG. 3E: Beta cont'd

FIG. 3E: Beta Ketoacyl-ACP Synthase Homologs

| | | | | | | |
|---|---|---|---|---|---|---|
| gi\|228984962\|ref\|ZP_04145131.1\| | Bacillus thuringiensis | 37.8 | 36.0 | 40.6 | 38.5 | 33.2 |
| gi\|222095495\|ref\|YP_002529555.1 | Bacillus cereus Q1 | 37.8 | 35.6 | 40.6 | 38.5 | 33.3 |
| gi\|52143586\|ref\|YP_083243.1\| | Bacillus cereus E33L | 38.8 | 37.0 | 40.6 | 38.5 | 32.6 |
| gi\|42780983\|ref\|NP_978230.1\| | Bacillus cereus | 37.4 | 36.9 | 39.9 | 38.5 | 32.5 |
| gi\|269956923\|ref\|YP_003326712.1 | Xylanimonas cellulosilytica | 32.9 | 34.2 | 39.0 | 38.4 | 35.5 |
| gi\|119358258\|ref\|YP_912902.1\| | C.phaeobacteroides | 43.2 | 43.0 | 37.2 | 38.4 | 36.9 |
| gi\|229029569\|ref\|ZP_04185649.1\| | Bacillus cereus | 37.8 | 37.0 | 40.3 | 38.4 | 33.0 |
| gi\|282860194\|ref\|ZP_06269268.1\| | Prevotella bivia | 39.7 | 41.0 | 39.5 | 38.4 | 38.0 |
| gi\|254405834\|ref\|ZP_05020754.1\| | Streptomyces sviceus | 33.4 | 32.3 | 40.0 | 38.4 | 36.1 |
| gi\|163839848\|ref\|YP_001624253.1 | R.salmoninarum | 30.4 | 31.5 | 34.6 | 38.3 | 34.4 |
| gi\|149277467\|ref\|ZP_01883608.1\| | Pedobacter sp. | 38.6 | 41.1 | 39.0 | 38.3 | 40.2 |
| gi\|124005903\|ref\|ZP_01690741.1\| | Microscilla marina | 38.3 | 38.2 | 37.5 | 38.3 | 38.3 |
| gi\|86742164\|ref\|YP_482564.1\| | Frankia sp. | 34.2 | 35.4 | 35.4 | 38.3 | 36.1 |
| gi\|32470544\|ref\|NP_863215.1\| | S.epidermidis | 39.2 | 39.7 | 43.1 | 38.3 | 32.5 |
| gi\|255326001\|ref\|ZP_05367089.1\| | Rothia mucilaginosa | 32.7 | 32.5 | 34.9 | 38.3 | 33.6 |
| gi\|225863732\|ref\|YP_002749110.1 | Bacillus cereus | 37.2 | 36.7 | 40.6 | 38.3 | 33.0 |
| gi\|125624577\|ref\|YP_001033060.1 | Lactococcus lactis | 92.6 | 63.8 | 41.1 | 38.3 | 38.4 |
| gi\|15672753\|ref\|NP_266927.1\| | Lactococcus lactis | 100 | 63.8 | 41.7 | 38.3 | 39.3 |
| gi\|224535781\|ref\|ZP_03676320.1\| | Bacteroides cellulosilyticus | 38.4 | 35.0 | 39.3 | 38.3 | 38.7 |
| gi\|253702674\|ref\|YP_003023863.1 | Geobacter sp. | 39.6 | 43.8 | 37.8 | 38.3 | 39.2 |
| gi\|153815746\|ref\|ZP_01968414.1\| | Ruminococcus torques | 41.4 | 42.9 | 36.1 | 38.2 | 33.6 |
| gi\|257456999\|ref\|ZP_05622180.1\| | Treponema vincentii | 39.4 | 41.7 | 40.3 | 38.2 | 33.5 |
| gi\|227979876\|ref\|ZP_04027140.1\| | T.paurometabola | 31.9 | 29.3 | 34.9 | 38.2 | 36.5 |
| gi\|42526118\|ref\|NP_971216.1\| | Treponema denticola | 42.0 | 42.0 | 43.6 | 38.2 | 32.1 |
| gi\|239927768\|ref\|ZP_04684721.1\| | S.ghanaensis | 35.0 | 32.6 | 36.3 | 38.2 | 36.7 |
| gi\|229160829\|ref\|ZP_04288820.1\| | Bacillus cereus | 38.2 | 37.0 | 40.3 | 38.2 | 33.0 |
| gi\|256770874\|ref\|ZP_05510048.1\| | Streptomyces sp. | 35.8 | 35.9 | 35.8 | 38.2 | 36.9 |
| gi\|153806688\|ref\|ZP_01959356.1\| | Bacteroides caccae | 39.9 | 36.8 | 40.7 | 38.2 | 40.2 |
| gi\|149277739\|ref\|ZP_01883879.1\| | Pedobacter sp. | 37.5 | 38.7 | 37.5 | 38.2 | 37.5 |
| gi\|228473691\|ref\|ZP_04058441.1\| | C.gingivalis | 38.3 | 36.5 | 38.3 | 38.2 | 35.9 |
| gi\|262275796\|ref\|ZP_06053605.1\| | Grimontia hollisae | 38.2 | 41.5 | 41.7 | 38.2 | 37.8 |

FIG. 3E: Beta cont'd

FIG. 3E: Beta Ketoacyl-ACP Synthase Homologs

| | | | | | | |
|---|---|---|---|---|---|---|
| gi\|227514351\|ref\|ZP_03944400.1\| | Lfermentum | 51.4 | 53.1 | 36.4 | 38.2 | 40.3 |
| gi\|184154786\|ref\|YP_001843126.1 | L.fermentum | 51.1 | 52.8 | 36.1 | 38.2 | 40.3 |
| gi\|254380767\|ref\|ZP_04996133.1\| | Streptomyces sp. | 34.5 | 32.9 | 36.6 | 38.2 | 53.8 |
| gi\|257869163\|ref\|ZP_05648816.1\| | E;gallinarum | 59.9 | 57.3 | 37.1 | 38.2 | 39.0 |
| gi\|196033629\|ref\|ZP_03101041.1\| | Bacillus cereus | 37.8 | 36.0 | 40.3 | 38.1 | 32.9 |
| gi\|229155445\|ref\|ZP_04283554.1\| | Bacillus cereus | 37.8 | 36.0 | 40.3 | 38.1 | 33.2 |
| gi\|229090839\|ref\|ZP_04222067.1\| | Bacillus cereus | 37.8 | 37.0 | 40.6 | 38.1 | 32.6 |
| gi\|228945478\|ref\|ZP_04107829.1\| | Bacillus thuringiensis | 38.1 | 36.7 | 40.9 | 38.1 | 32.6 |
| gi\|228926872\|ref\|ZP_04089938.1\| | Bacillus thuringiensis ; | 37.8 | 36.7 | 40.9 | 38.1 | 32.6 |
| gi\|218902987\|ref\|YP_002450821.1 | Bacillus cereus | 37.8 | 36.7 | 40.9 | 38.1 | 32.6 |
| gi\|154500683\|ref\|ZP_02038721.1\| | Bacteroides capillosus | 38.6 | 35.2 | 39.7 | 38.1 | 39.2 |
| gi\|169335686\|ref\|ZP_02862879.1\| | A; stercorihominis | 39.0 | 41.3 | 42.0 | 38.1 | 34.5 |
| gi\|56460964\|ref\|YP_156245.1\| | Idiomarina loihiensis | 35.9 | 41.0 | 38.2 | 38.1 | 34.5 |
| gi\|254389086\|ref\|ZP_05004316.1\| | S; clavuligerus | 35.3 | 32.6 | 38.5 | 38.1 | 37.0 |
| gi\|239979258\|ref\|ZP_04701782.1\| | Streptomyces albus | 33.5 | 30.8 | 39.1 | 38.1 | 38.3 |
| gi\|34098420\|sp\|Q54206.1\|FABH_STRGA | Streptomyces glaucescens | 32.5 | 32.1 | 38.5 | 38.1 | 36.4 |
| gi\|5454206\|gb\|AAD43621.1\|AC005698_20 | Arabidopsis thaliana | 36.5 | 38.5 | 34.3 | 38.1 | 35.1 |
| gi\|225869910\|ref\|YP_002745857.1 | Streptococcus equi | 64.3 | 69.5 | 39.2 | 38.1 | 38.3 |
| gi\|225869139\|ref\|YP_002745087.1 | Streptococcus equi | 64.6 | 69.8 | 39.2 | 38.1 | 38.3 |
| gi\|254777049\|ref\|ZP_05218565.1\| | Mycobacterium avium | 35.5 | 36.5 | 38.0 | 38.1 | 39.1 |
| gi\|256394324\|ref\|YP_003115888.1 | Catenulispora acidiphila | 32.4 | 34.3 | 34.1 | 38.1 | 34.9 |
| gi\|56182658\|gb\|AAV84077.1\| | Streptomyces echinatus | 32.7 | 32.1 | 37.4 | 38.0 | 37.2 |
| gi\|256767211\|ref\|ZP_05506385.1\| | Streptomyces sp. | 31.7 | 31.0 | 39.0 | 38.0 | 38.3 |
| gi\|283853322\|ref\|ZP_06370571.1\| | Desulfovibrio sp. | 33.4 | 33.1 | 35.2 | 38.0 | 43.7 |
| gi\|282854072\|ref\|ZP_06263409.1\| | P;acnes | 33.9 | 34.6 | 35.8 | 38.0 | 35.2 |
| gi\|229823813\|ref\|ZP_04449882.1\| | Catonella morbi | 39.0 | 40.5 | 35.8 | 38.0 | 32.2 |
| gi\|50842467\|ref\|YP_055694.1\| | P;acnes | 34.2 | 34.9 | 35.8 | 38.0 | 33.2 |
| gi\|238623523\|emb\|CAX48662.1\| | Streptomyces anulatus, | 35.1 | 36.2 | 34.9 | 38.0 | 45.6 |
| gi\|47565554\|ref\|ZP_00236595.1\| | Bacillus cereus | 37.5 | 36.3 | 39.8 | 38.0 | 32.6 |
| gi\|158313116\|ref\|YP_001505624.1 | Frankia sp. | 34.9 | 36.0 | 35.5 | 38.0 | 38.3 |
| gi\|116511580\|ref\|YP_808796.1\| | Lactococcus lactis | 92.6 | 63.8 | 40.8 | 38.0 | 38.4 |

FIG. 3E: Beta cont'd

FIG. 3E: Beta Ketoacyl-ACP Synthase Homologs

| | | | | | | |
|---|---|---|---|---|---|---|
| gi\|281491267\|ref\|YP_003353247.1 | Lactococcus lactis | 99.7 | 63.8 | 41.4 | 38.0 | 39.3 |
| gi\|198274287\|ref\|ZP_03206819.1\| | Bacteroides plebeius | 38.8 | 36.2 | 37.8 | 38.0 | 38.3 |
| gi\|222056786\|ref\|YP_002539148.1 | Geobacter sp. | 37.0 | 41.5 | 38.1 | 37.9 | 36.0 |
| gi\|39995399\|ref\|NP_951350.1\| | G;sulfurreducens | 39.6 | 44.2 | 37.4 | 37.9 | 39.5 |
| gi\|90399279\|emb\|CAJ86191.1\| | Oryza sativa | 38.9 | 41.6 | 36.4 | 37.9 | 35.1 |
| gi\|67078276\|ref\|YP_245896.1\| | Bacillus cereus | 37.2 | 34.9 | 39.0 | 37.9 | 34.1 |
| gi\|222153611\|ref\|YP_002562788.1 | Streptococcus uberis | 62.5 | 70.2 | 39.2 | 37.9 | 36.3 |
| gi\|255532396\|ref\|YP_003092768.1 | Pedobacter heparinus | 36.8 | 39.0 | 37.6 | 37.9 | 39.2 |
| gi\|75763079\|ref\|ZP_00742862.1\| | Bacillus thuringiensis | 36.8 | 37.1 | 39.8 | 37.9 | 32.7 |
| gi\|54026953\|ref\|YP_121195.1\| | Nocardia farcinica | 30.0 | 32.2 | 32.5 | 37.9 | 36.6 |
| gi\|260061399\|ref\|YP_003194479.1 | Robiginitalea biformata | 41.4 | 41.5 | 40.1 | 37.9 | 40.0 |
| gi\|256801564\|ref\|ZP_05531188.1\| | S;viridochromogenes | 32.8 | 32.2 | 39.1 | 37.8 | 37.0 |
| gi\|280961106\|ref\|ZP_06235677.1\| | Frankia sp. | 31.2 | 32.7 | 35.8 | 37.8 | 38.1 |
| gi\|30261869\|ref\|NP_844246.1\| | Bacillus anthracis | 37.5 | 36.3 | 40.6 | 37.8 | 32.9 |
| gi\|49480542\|ref\|YP_036004.1\| | Bacillus thuringiensis | 37.5 | 36.7 | 40.9 | 37.8 | 32.9 |
| gi\|228933154\|ref\|ZP_04096011.1\| | Bacillus thuringiensis | 37.8 | 36.7 | 40.9 | 37.8 | 33.2 |
| gi\|195977549\|ref\|YP_002122793.1 | Streptococcus equi | 64.3 | 69.5 | 38.5 | 37.8 | 38.9 |
| gi\|24380116\|ref\|NP_722071.1\| | Streptococcus mutans | 63.8 | 100 | 39.4 | 37.8 | 39.6 |
| gi\|254996804\|dbj\|BAH87405.1\| | Streptococcus mutans | 63.2 | 98.5 | 39.0 | 37.8 | 39.9 |
| gi\|251783213\|ref\|YP_002997518.1 | S;dysgalactiae | 62.2 | 68.3 | 37.5 | 37.8 | 39.7 |
| gi\|218676470\|ref\|YP_002395289.1 | Vibrio splendidus | 39.6 | 41.1 | 41.6 | 37.8 | 36.8 |
| gi\|88857718\|ref\|ZP_01132361.1\| | P;tunicata | 38.5 | 38.6 | 39.3 | 37.8 | 35.4 |
| gi\|256779668\|ref\|ZP_05518131.1\| | S;hygroscopicus | 32.8 | 30.6 | 37.6 | 37.8 | 38.3 |
| gi\|86739702\|ref\|YP_480102.1\| | Frankia sp. | 35.0 | 36.8 | 38.4 | 37.8 | 40.1 |
| gi\|260650305\|emb\|CBG73421.1\| | Streptomyces scabiei | 33.1 | 30.6 | 39.1 | 37.7 | 36.6 |
| gi\|254382858\|ref\|ZP_04998214.1\| | Streptomyces sp. | 32.5 | 30.5 | 39.0 | 37.7 | 37.6 |
| gi\|167750659\|ref\|ZP_02422786.1\| | Eubacterium siraeum | 33.5 | 36.8 | 38.3 | 37.7 | 31.9 |
| gi\|119961500\|ref\|YP_948164.1\| | Arthrobacter aurescens | 32.4 | 33.2 | 34.9 | 37.7 | 38.6 |
| gi\|77414427\|ref\|ZP_00790579.1\| | S;agalactiae | 62.5 | 68.0 | 40.4 | 37.7 | 36.1 |
| gi\|22536527\|ref\|NP_687378.1\| | S;agalactiae | 62.5 | 68.0 | 40.4 | 37.7 | 36.1 |
| gi\|189463675\|ref\|ZP_03012460.1\| | Bacteroides intestinalis | 38.7 | 35.6 | 38.4 | 37.7 | 38.4 |

FIG. 3E: Beta cont'd

FIG. 3E: Beta Ketoacyl-ACP Synthase Homologs

| | | | | | | |
|---|---|---|---|---|---|---|
| gi\|169628234\|ref\|YP_001701883.1 | Mycobacterium abscessus | 33.3 | 34.1 | 37.0 | 37.7 | 38.1 |
| gi\|260904691\|ref\|ZP_05913013.1\| | Brevibacterium linens | 35.2 | 33.3 | 36.2 | 37.7 | 35.2 |
| gi\|162450872\|ref\|YP_001613239.1 | Sorangium cellulosum | 31.0 | 31.8 | 35.2 | 37.7 | 35.9 |
| gi\|197120356\|ref\|YP_002140783.1 | Geobacter bemidjiensis | 40.3 | 42.7 | 38.1 | 37.6 | 38.5 |
| gi\|282864636\|ref\|ZP_06273691.1\| | Streptomyces sp. | 34.0 | 34.7 | 35.3 | 37.6 | 38.6 |
| gi\|256680394\|ref\|ZP_05490705.1\| | Streptomyces sp. | 34.1 | 32.9 | 36.4 | 37.6 | 36.1 |
| gi\|254399623\|ref\|ZP_05014612.1\| | S;pristinaespiralis | 32.3 | 30.6 | 36.7 | 37.6 | 37.2 |
| gi\|284045611\|ref\|YP_003395951.1 | Conexibacter woesei | 32.8 | 34.4 | 35.5 | 37.6 | 40.3 |
| gi\|113475486\|ref\|YP_721547.1\| | T; erythraeum | 42.2 | 41.1 | 40.1 | 37.6 | 38.5 |
| gi\|255691806\|ref\|ZP_05415481.1\| | Bacteroides finegoldii | 40.5 | 38.3 | 39.1 | 37.6 | 39.6 |
| gi\|256812482\|ref\|ZP_05537497.1\| | S;griseoflavus | 35.3 | 32.9 | 35.1 | 37.6 | 36.4 |
| gi\|239940935\|ref\|ZP_04692872.1\| | S;roseosporus | 33.1 | 31.6 | 37.9 | 37.6 | 36.9 |
| gi\|228952250\|ref\|ZP_04114339.1\| | Bacillus thuringiensis | 37.5 | 36.4 | 39.8 | 37.5 | 32.1 |
| gi\|229069420\|ref\|ZP_04202709.1\| | Bacillus cereus | 37.2 | 36.1 | 39.8 | 37.5 | 32.7 |
| gi\|228958151\|ref\|ZP_04119884.1\| | Bacillus thuringiensis | 36.1 | 36.4 | 38.6 | 37.5 | 32.1 |
| gi\|229150073\|ref\|ZP_04278296.1\| | Bacillus cereus | 37.2 | 36.4 | 39.2 | 37.5 | 32.5 |
| gi\|154685474\|ref\|YP_001420635.1 | B;amyloliquefaciens | 39.6 | 37.2 | 39.6 | 37.5 | 36.3 |
| gi\|259501753\|ref\|ZP_05744655.1\| | Lactobacillus antri | 50.5 | 50.6 | 38.1 | 37.5 | 40.4 |
| gi\|260458304\|ref\|ZP_05806642.1\| | S;flavogriseus | 35.3 | 34.6 | 35.3 | 37.5 | 38.0 |
| gi\|167461795\|ref\|ZP_02326884.1\| | Paenibacillus larvae | 38.1 | 38.1 | 41.3 | 37.5 | 35.3 |
| gi\|111152561\|emb\|CAJ64302.1\| | Frankia alni | 34.3 | 36.0 | 35.1 | 37.5 | 37.7 |
| gi\|182438900\|ref\|YP_001826619.1 | Streptomyces sp. S. griseus | 33.2 | 30.9 | 38.7 | 37.5 | 35.7 |
| gi\|270296338\|ref\|ZP_06202538.1\| | Bacteroides sp. D20 | 38.0 | 34.0 | 39.6 | 37.5 | 38.8 |
| gi\|160892016\|ref\|ZP_02073019.1\| | Bacteroides uniformis | 38.0 | 34.0 | 39.6 | 37.5 | 39.1 |
| gi\|224539051\|ref\|ZP_03679590.1\| | Bacteroides cellulosilyticus | 38.6 | 35.9 | 40.2 | 37.5 | 39.6 |
| gi\|189467270\|ref\|ZP_03016055.1\| | Bacteroides intestinalis | 38.3 | 35.7 | 39.6 | 37.5 | 39.6 |
| gi\|88711698\|ref\|ZP_01105786.1\| | F.bacterium | 39.6 | 39.6 | 39.1 | 37.5 | 37.2 |
| gi\|86148822\|ref\|ZP_01067088.1\| | Vibrio sp. | 39.9 | 40.5 | 41.6 | 37.5 | 36.8 |
| gi\|84394535\|ref\|ZP_00993243.1\| | Vibrio splendidus | 39.9 | 41.1 | 41.9 | 37.5 | 36.8 |
| gi\|284105819\|ref\|ZP_06386223.1\| | Candidatus Poribacteria | 32.7 | 31.1 | 35.2 | 37.5 | 36.6 |
| gi\|196041176\|ref\|ZP_03108471.1\| | Bacillus cereus | 36.8 | 35.6 | 40.3 | 37.5 | 32.9 |

FIG. 3E: Beta cont'd

FIG. 3E: Beta Ketoacyl-ACP Synthase Homologs

| | | | | | | |
|---|---|---|---|---|---|---|
| gi\|11465662\|ref\|NP_053806.1\| | Porphyra purpurea, | 44.8 | 41.3 | 42.8 | 37.4 | 38.5 |
| gi\|41410126\|ref\|NP_962962.1\| | Mycobacterium avium | 34.3 | 35.5 | 37.7 | 37.4 | 38.9 |
| gi\|91217310\|ref\|ZP_01254271.1\| | Psychroflexus torquis | 37.1 | 39.3 | 37.4 | 37.4 | 31.7 |
| gi\|170781992\|ref\|YP_001710324.1 | C.michiganensis | 33.8 | 33.8 | 37.1 | 37.4 | 36.3 |
| gi\|148272800\|ref\|YP_001222361.1 | C.michiganensis | 33.8 | 33.8 | 37.1 | 37.4 | 36.3 |
| gi\|283458207\|ref\|YP_003362825.1 | Rothia mucilaginosa | 32.8 | 32.2 | 34.9 | 37.4 | 33.3 |
| gi\|149371690\|ref\|ZP_01891106.1\| | unidentified eubacterium | 40.4 | 39.3 | 38.3 | 37.4 | 35.7 |
| gi\|91217483\|ref\|ZP_01254442.1\| | Psychroflexus torquis | 37.9 | 39.9 | 37.7 | 37.4 | 36.5 |
| gi\|91792739\|ref\|YP_562390.1\| | Shewanella denitrificans | 38.4 | 40.9 | 39.8 | 37.4 | 38.0 |
| gi\|162139906\|ref\|YP_715823.2\| | Frankia alni ACN14a | 33.7 | 35.4 | 35.1 | 37.4 | 37.3 |
| gi\|256389781\|ref\|YP_003111345.1 | Catenulispora acidiphila | 34.2 | 33.9 | 35.2 | 37.3 | 55.0 |
| gi\|239934031\|ref\|ZP_04690984.1\| | S. ghanaensis | 34.8 | 35.3 | 37.5 | 37.3 | 49.7 |
| gi\|21220855\|ref\|NP_626634.1\| | S. lividans S. coelicolor | 31.9 | 31.1 | 37.2 | 37.3 | 37.5 |
| gi\|152975595\|ref\|YP_001375112.1 | B. cereus, B.cytotoxicus | 39.9 | 39.3 | 40.6 | 37.3 | 33.7 |
| gi\|88801927\|ref\|ZP_01117455.1\| | Polaribacter irgensii | 39.9 | 40.2 | 39.1 | 37.3 | 37.5 |
| gi\|256425897\|ref\|YP_003126550.1 | Chitinophaga pinensis | 40.0 | 40.5 | 37.7 | 37.3 | 37.7 |
| gi\|127513294\|ref\|YP_001094491.1 | Shewanella loihica PV-4 | 39.1 | 41.4 | 40.6 | 37.3 | 38.9 |
| gi\|223043683\|ref\|ZP_03613727.1\| | Staphylococcus capitis | 39.1 | 40.8 | 43.2 | 37.2 | 32.4 |
| gi\|52079504\|ref\|YP_078295.1\| | Bacillus licheniformis | 36.3 | 38.9 | 42.4 | 37.2 | 33.8 |
| gi\|218896802\|ref\|YP_002445213.1 | Bacillus cereus G9842 | 36.8 | 37.1 | 39.5 | 37.2 | 33.0 |
| gi\|229189967\|ref\|ZP_04316975.1\| | Bacillus cereus | 36.5 | 36.4 | 39.8 | 37.2 | 32.7 |
| gi\|229043625\|ref\|ZP_04191332.1\| | Bacillus cereus | 36.5 | 35.8 | 39.2 | 37.2 | 32.1 |
| gi\|229109325\|ref\|ZP_04238922.1\| | Bacillus cereus | 36.8 | 35.8 | 38.9 | 37.2 | 32.1 |
| gi\|218231606\|ref\|YP_002366551.1 | Bacillus cereus | 36.8 | 36.1 | 38.9 | 37.2 | 32.1 |
| gi\|30019904\|ref\|NP_831535.1\| | Bacillus cereus | 35.8 | 36.1 | 38.2 | 37.2 | 31.8 |
| gi\|256832740\|ref\|YP_003161467.1 | Jonesia denitrificans | 33.9 | 32.3 | 38.1 | 37.2 | 35.5 |
| gi\|212551107\|ref\|YP_002309424.1 | C.Azobacteroides pseudotrichonymphae | 37.7 | 38.2 | 35.6 | 37.2 | 39.3 |
| gi\|89889701\|ref\|ZP_01201212.1\| | Flavobacteria bacterium | 38.9 | 40.5 | 35.7 | 37.2 | 38.9 |
| gi\|239945472\|ref\|ZP_04697409.1\| | S.roseosporus | 35.6 | 34.5 | 35.3 | 37.2 | 38.4 |
| gi\|220912954\|ref\|YP_002488263.1 | A.chlorophenolicus | 32.2 | 32.5 | 35.5 | 37.1 | 37.6 |
| gi\|225016820\|ref\|ZP_03706012.1\| | C.methylpentosum | 36.0 | 33.9 | 36.0 | 37.1 | 33.1 |

FIG. 3E: Beta cont'd

FIG. 3E: Beta Ketoacyl-ACP Synthase Homologs

| | | | | | | |
|---|---|---|---|---|---|---|
| gi\|118463479\|ref\|YP_883741.1\| | Mycobacterium avium | 33.9 | 35.2 | 37.7 | 37.1 | 38.9 |
| gi\|170727170\|ref\|YP_001761196.1 | Shewanella woodyi | 39.5 | 41.5 | 41.7 | 37.1 | 38.9 |
| gi\|262201490\|ref\|YP_003272698.1 | Gordonia bronchialis | 34.3 | 34.2 | 37.1 | 37.1 | 36.9 |
| gi\|157374897\|ref\|YP_001473497.1 | Shewanella sediminis | 38.7 | 42.2 | 42.3 | 37.1 | 38.0 |
| gi\|119774664\|ref\|YP_927404.1\| | S.amazonensis | 38.2 | 42.5 | 40.3 | 37.1 | 39.8 |
| gi\|40882377\|dbj\|BAD07381.1\| | Actinoplanes sp. | 35.8 | 35.7 | 37.5 | 37.1 | 40.5 |
| gi\|229172519\|ref\|ZP_04300078.1\| | Bacillus cereus | 34.2 | 34.9 | 40.2 | 37.1 | 32.5 |
| gi\|226311414\|ref\|YP_002771308.1 | Brevibacillus brevis | 37.7 | 38.1 | 43.7 | 37.0 | 36.2 |
| gi\|212690521\|ref\|ZP_03298649.1\| | Bacteroides dorei | 39.6 | 35.9 | 37.2 | 37.0 | 39.3 |
| gi\|150003045\|ref\|YP_001297789.1 | Bacteroides sp., B. vulgatus | 39.6 | 35.9 | 37.2 | 37.0 | 39.3 |
| gi\|50954930\|ref\|YP_062218.1\| | Leifsonia xyli | 37.0 | 36.3 | 35.4 | 37.0 | 35.4 |
| gi\|29832330\|ref\|NP_826964.1\| | S.avermitilis | 30.9 | 30.8 | 38.2 | 37.0 | 37.3 |
| gi\|255058760\|ref\|ZP_05310924.1\| | Geobacter sp. M18 | 38.5 | 43.1 | 37.6 | 37.0 | 38.7 |
| gi\|239944430\|ref\|ZP_04696367.1\| | S.roseosporus | 34.2 | 34.0 | 36.3 | 37.0 | 58.0 |
| gi\|84496776\|ref\|ZP_00995630.1\| | Janibacter sp. | 28.9 | 29.7 | 35.8 | 37.0 | 34.6 |
| gi\|86144163\|ref\|ZP_01062500.1\| | L. blandensis | 38.8 | 38.8 | 38.5 | 37.0 | 38.7 |
| gi\|150026409\|ref\|YP_001297235.1 | F.psychrophilum | 41.9 | 39.9 | 39.4 | 37.0 | 38.8 |
| gi\|83855890\|ref\|ZP_00949419.1\| | Croceibacter atlanticus | 39.1 | 37.7 | 38.8 | 37.0 | 36.0 |
| gi\|237837525\|ref\|XP_002368060.1 | Toxoplasma gondii | 36.0 | 37.7 | 37.8 | 36.9 | 36.2 |
| gi\|221488679\|gb\|EEE26893.1\| | Toxoplasma gondii GT1 | 36.0 | 37.7 | 37.8 | 36.9 | 36.2 |
| gi\|255010621\|ref\|ZP_05282747.1\| | Bacteroides fragilis | 38.1 | 35.9 | 38.7 | 36.9 | 39.8 |
| gi\|117928085\|ref\|YP_872636.1\| | A.cellulolyticus | 33.0 | 31.9 | 34.8 | 36.9 | 38.1 |
| gi\|260170437\|ref\|ZP_05756849.1\| | Bacteroides sp. D2 | 38.3 | 34.5 | 39.1 | 36.9 | 39.6 |
| gi\|182434913\|ref\|YP_001822632.1 | Streptomyces griseus | 35.0 | 34.5 | 35.3 | 36.9 | 37.5 |
| gi\|162453329\|ref\|YP_001615696.1 | Sorangium cellulosum | 33.5 | 34.1 | 32.2 | 36.9 | 37.9 |
| gi\|228907560\|ref\|ZP_04071417.1\| | Bacillus thuringiensis | 36.8 | 38.1 | 38.9 | 36.9 | 33.1 |
| gi\|282870769\|ref\|ZP_06279769.1\| | Streptomyces sp. | 35.3 | 33.9 | 34.9 | 36.9 | 37.7 |
| gi\|269794727\|ref\|YP_003314182.1 | Sanguibacter keddieii | 34.3 | 33.5 | 38.4 | 36.9 | 36.1 |
| gi\|167966704\|ref\|ZP_02548981.1\| | M.tuberculosis | 32.9 | 34.3 | 37.5 | 36.9 | 36.8 |
| gi\|260454041\|ref\|ZP_05802443.1\| | S.flavogriseus | 34.0 | 31.2 | 39.1 | 36.9 | 36.9 |
| gi\|223933990\|ref\|ZP_03625947.1\| | Streptococcus suis | 63.0 | 65.2 | 39.8 | 36.8 | 40.5 |

FIG. 3E: Beta cont'd

FIG. 3E: Beta Ketoacyl-ACP Synthase Homologs

| | | | | | | |
|---|---|---|---|---|---|---|
| gi\|146319461\|ref\|YP_001199173.1 | Streptococcus suis | 63.0 | 65.5 | 39.1 | 36.8 | 40.8 |
| gi\|3170574\|gb\|AAC18104.1\| | S.roseofulvus | 27.5 | 30.0 | 33.3 | 36.8 | 34.1 |
| gi\|256680494\|ref\|ZP_05490805.1\| | Streptomyces sp. | 27.6 | 29.7 | 32.6 | 36.8 | 34.1 |
| gi\|189232044\|emb\|CAP09194.1\| | Streptomyces lydicus | 33.1 | 30.4 | 38.5 | 36.8 | 37.0 |
| gi\|241894768\|ref\|ZP_04782064.1\| | W.paramesenteroides | 45.7 | 43.6 | 34.9 | 36.8 | 34.7 |
| gi\|117920029\|ref\|YP_869221.1\| | Shewanella sp. | 38.3 | 42.8 | 40.3 | 36.8 | 39.8 |
| gi\|24374382\|ref\|NP_718425.1\| | Shewanella oneidensis | 38.3 | 43.4 | 40.3 | 36.8 | 40.4 |
| gi\|239944826\|ref\|ZP_04696763.1\| | S.roseosporus | 33.5 | 35.6 | 35.6 | 36.8 | 37.7 |
| gi\|284991920\|ref\|YP_003410474.1 | G.obscurus | 30.9 | 33.3 | 35.0 | 36.7 | 38.9 |
| gi\|227536920\|ref\|ZP_03966969.1\| | S. spiritivorum | 36.9 | 35.8 | 40.8 | 36.7 | 40.7 |
| gi\|258647983\|ref\|ZP_05735452.1\| | Prevotella tannerae | 40.2 | 39.3 | 37.6 | 36.7 | 36.8 |
| gi\|225016821\|ref\|ZP_03706013.1\| | C.methylpentosum | 34.2 | 34.5 | 37.5 | 36.7 | 35.2 |
| gi\|116671013\|ref\|YP_831946.1\| | Arthrobacter sp. | 33.5 | 33.3 | 36.1 | 36.7 | 36.2 |
| gi\|242372454\|ref\|ZP_04818028.1\| | S. epidermidis | 41.2 | 40.5 | 44.5 | 36.7 | 31.3 |
| gi\|29828832\|ref\|NP_823466.1\| | S.avermitilis | 39.0 | 39.3 | 40.2 | 36.7 | 100 |
| gi\|282867842\|ref\|ZP_06276855.1\| | Streptomyces sp. | 33.2 | 33.9 | 35.3 | 36.7 | 53.9 |
| gi\|182440428\|ref\|YP_001828147.1 | Streptomyces griseus | 33.1 | 33.8 | 35.3 | 36.7 | 53.7 |
| gi\|86131469\|ref\|ZP_01050067.1\| | Dokdonia donghaensis | 39.4 | 42.6 | 39.3 | 36.6 | 38.8 |
| gi\|86134883\|ref\|ZP_01053465.1\| | Polaribacter sp. | 40.0 | 40.6 | 39.0 | 36.6 | 37.7 |
| gi\|237716348\|ref\|ZP_04546829.1\| | Bacteroides sp. | 37.8 | 35.0 | 39.6 | 36.6 | 40.8 |
| gi\|160886057\|ref\|ZP_02067060.1\| | Bacteroides sp. B. ovatus | 39.2 | 35.3 | 38.7 | 36.6 | 39.3 |
| gi\|161508107\|ref\|YP_001578074.1 | Lactobacillus helveticus | 47.4 | 45.7 | 38.2 | 36.6 | 34.0 |
| gi\|254818929\|ref\|ZP_05223930.1\| | M. intracellulare | 35.1 | 36.1 | 36.1 | 36.6 | 37.8 |
| gi\|256377229\|ref\|YP_003100889.1 | Actinosynnema mirum | 30.1 | 30.6 | 32.8 | 36.6 | 39.0 |
| gi\|51209851\|ref\|YP_063515.1\| | Gracilaria tenuistipitata | 42.2 | 41.8 | 39.5 | 36.6 | 33.5 |
| gi\|120437665\|ref\|YP_863351.1\| | Gramella forsetii | 40.5 | 39.8 | 38.4 | 36.6 | 37.9 |
| gi\|221053097\|ref\|XP_002257923.1 | Plasmodium knowlesi | 38.5 | 37.8 | 38.5 | 36.6 | 32.5 |
| gi\|118586424\|ref\|ZP_01543871.1\| | Oenococcus oeni | 47.2 | 47.7 | 36.0 | 36.6 | 36.0 |
| gi\|116491566\|ref\|YP_811110.1\| | Oenococcus oeni | 47.5 | 48.0 | 36.0 | 36.6 | 36.6 |
| gi\|228920574\|ref\|ZP_04083919.1\| | Bacillus thuringiensis | 36.5 | 37.1 | 38.6 | 36.5 | 32.7 |
| gi\|228964858\|ref\|ZP_04125963.1\| | Bacillus thuringiensis | 36.5 | 36.4 | 39.2 | 36.5 | 32.7 |

FIG. 3E: Beta cont'd

FIG. 3E: Beta Ketoacyl-ACP Synthase Homologs

| | | | | | | |
|---|---|---|---|---|---|---|
| gi\|228938982\|ref\|ZP_04101582.1\| | Bacillus thuringiensis | 36.1 | 35.8 | 39.2 | 36.5 | 31.8 |
| gi\|256812692\|ref\|ZP_05537707.1\| | S.griseoflavus | 30.0 | 29.9 | 35.3 | 36.5 | 38.0 |
| gi\|399473\|sp\|P31176.1\|FABH_PORUM | Porphyra purpurea, | 44.2 | 40.6 | 41.9 | 36.5 | 37.5 |
| gi\|239917448\|ref\|YP_002957006.1 | Micrococcus luteus | 33.0 | 34.0 | 32.9 | 36.5 | 35.2 |
| gi\|113969862\|ref\|YP_733655.1\| | Shewanella sp. | 38.6 | 43.1 | 40.0 | 36.4 | 39.8 |
| gi\|120598471\|ref\|YP_963045.1\| | S.putrefaciens | 37.4 | 41.8 | 39.7 | 36.4 | 38.6 |
| gi\|241893564\|ref\|ZP_04780860.1\| | S. spiritivorum | 37.4 | 36.1 | 39.9 | 36.4 | 40.4 |
| gi\|262201496\|ref\|YP_003272704.1 | Gordonia bronchialis | 31.6 | 31.3 | 34.7 | 36.4 | 37.4 |
| gi\|225182094\|ref\|ZP_03735523.1\| | Dethiobacter alkaliphilus | 37.4 | 36.6 | 38.3 | 36.4 | 36.5 |
| gi\|219556365\|ref\|ZP_03535441.1\| | M.tuberculosis | 32.5 | 34.2 | 36.7 | 36.4 | 36.0 |
| gi\|215429362\|ref\|ZP_03427281.1\| | M.tuberculosis | 33.6 | 34.7 | 37.5 | 36.4 | 37.1 |
| gi\|91215448\|ref\|ZP_01252419.1\| | Psychroflexus torquis | 40.1 | 39.5 | 38.5 | 36.3 | 37.2 |
| gi\|53714495\|ref\|YP_100487.1\| | Bacteroides sp., B.fragilis | 38.8 | 35.9 | 37.6 | 36.3 | 39.6 |
| gi\|254399123\|ref\|ZP_05014136.1\| | S.pristinaespiralis | 33.0 | 32.8 | 31.8 | 36.3 | 39.3 |
| gi\|189502112\|ref\|YP_001957829.1 | C.Amoebophilus asiaticus | 39.2 | 37.7 | 36.8 | 36.2 | 38.2 |
| gi\|116617449\|ref\|YP_817820.1\| | L.mesenteroides | 47.9 | 45.2 | 37.6 | 36.2 | 34.5 |
| gi\|240171281\|ref\|ZP_04749940.1\| | Mycobacterium kansasii | 32.9 | 32.9 | 36.7 | 36.2 | 36.3 |
| gi\|126174847\|ref\|YP_001050996.1 | Shewanella baltica | 40.4 | 43.1 | 40.1 | 36.1 | 38.6 |
| gi\|110638026\|ref\|YP_678233.1\| | Cytophaga hutchinsonii | 37.0 | 36.9 | 38.7 | 36.0 | 40.0 |
| gi\|268315683\|ref\|YP_003289402.1 | Rhodothermus marinus | 31.5 | 31.4 | 35.1 | 36.0 | 38.9 |
| gi\|227871709\|ref\|ZP_03990119.1\| | Oribacterium sinus | 37.4 | 37.3 | 35.0 | 36.0 | 32.1 |
| gi\|241896487\|ref\|ZP_04783783.1\| | W.paramesenteroides | 51.4 | 49.5 | 39.9 | 36.0 | 39.2 |
| gi\|239617359\|ref\|YP_002940681.1 | Kosmotoga olearia | 32.4 | 34.9 | 35.6 | 36.0 | 33.6 |
| gi\|254469189\|ref\|ZP_05082594.1\| | Pseudovibrio sp. JE062 | 29.9 | 28.8 | 34.9 | 35.9 | 36.6 |
| gi\|15675602\|ref\|NP_269776.1\| | S. pyogenes | 58.5 | 67.4 | 35.6 | 35.9 | 40.8 |
| gi\|218752172\|ref\|ZP_03530968.1\| | M. tuberculosis | 32.8 | 34.2 | 37.5 | 35.9 | 37.8 |
| gi\|54037100\|sp\|P64117.1\|FABH_TROW8 | Tropheryma whipplei | 34.0 | 35.8 | 34.1 | 35.9 | 31.8 |
| gi\|161486578\|ref\|NP_787381.2\| | Tropheryma whipplei | 33.9 | 35.7 | 34.1 | 35.9 | 31.8 |
| gi\|227431197\|ref\|ZP_03913251.1\| | L.mesenteroides | 47.6 | 44.9 | 37.5 | 35.9 | 34.5 |
| gi\|162316923\|ref\|YP_001107651.2 | S. erythraea | 38.3 | 37.2 | 33.9 | 35.9 | 59.1 |
| gi\|209863938\|gb\|ACI88883.1\| | Streptomyces sp. | 30.7 | 31.5 | 35.4 | 35.8 | 36.1 |

FIG. 3E: Beta cont'd

FIG. 3E: Beta Ketoacyl-ACP Synthase Homologs

| | | | | | | |
|---|---|---|---|---|---|---|
| gi\|77362216\|ref\|YP_341790.1\| | P.haloplanktis | 38.8 | 39.2 | 37.8 | 35.8 | 36.7 |
| gi\|119468644\|ref\|ZP_01611696.1\| | A.bacterium | 36.9 | 37.7 | 37.5 | 35.8 | 37.9 |
| gi\|270290345\|ref\|ZP_06196570.1\| | Pediococcus acidilactici | 44.4 | 43.8 | 38.1 | 35.8 | 36.4 |
| gi\|212634799\|ref\|YP_002311324.1 | S.piezotolerans | 36.1 | 41.9 | 42.0 | 35.8 | 38.2 |
| gi\|157961525\|ref\|YP_001501559.1 | Shewanella pealeana | 37.7 | 43.4 | 41.4 | 35.8 | 37.4 |
| gi\|86475806\|dbj\|BAE78983.1\| | Streptomyces sp. | 33.9 | 36.2 | 34.2 | 35.8 | 40.9 |
| gi\|7416010\|dbj\|BAA93641.1\| | Lactobacillus plantarum | 45.4 | 46.2 | 33.4 | 35.8 | 34.2 |
| gi\|28377469\|ref\|NP_784361.1\| | Lactobacillus plantarum | 45.1 | 46.2 | 33.4 | 35.8 | 34.2 |
| gi\|254555699\|ref\|YP_003062116.1 | Lactobacillus plantarum | 44.5 | 46.2 | 32.8 | 35.8 | 33.9 |
| gi\|54027371\|ref\|YP_121613.1\| | Nocardia farcinica | 32.8 | 32.5 | 34.1 | 35.8 | 36.3 |
| gi\|224025982\|ref\|ZP_03644348.1\| | Bacteroides coprophilus | 37.3 | 34.7 | 38.6 | 35.8 | 37.1 |
| gi\|133914613\|emb\|CAM04726.1\| | S.erythraea | 38.6 | 37.8 | 33.9 | 35.7 | 59.5 |
| gi\|152967288\|ref\|YP_001363072.1 | K.radiotolerans | 30.4 | 31.4 | 34.4 | 35.7 | 39.5 |
| gi\|81428426\|ref\|YP_395426.1\| | Lactobacillus sakei | 50.3 | 50.2 | 37.0 | 35.7 | 35.6 |
| gi\|88854972\|ref\|ZP_01129637.1\| | marine actinobacterium | 36.8 | 35.0 | 35.8 | 35.6 | 33.4 |
| gi\|28476261\|gb\|AAO44350.1\| | Tropheryma whipplei | 33.9 | 35.7 | 34.1 | 35.6 | 31.8 |
| gi\|19746710\|ref\|NP_607846.1\| | S.pyogenes | 58.5 | 67.7 | 35.9 | 35.6 | 40.8 |
| gi\|94994950\|ref\|YP_603048.1\| | S.pyogenes | 58.5 | 67.7 | 35.9 | 35.6 | 40.8 |
| gi\|209559870\|ref\|YP_002286342.1 | S.pyogenes | 58.5 | 67.7 | 35.9 | 35.6 | 41.1 |
| gi\|94991071\|ref\|YP_599171.1\| | S. pyogenes | 58.5 | 67.4 | 35.9 | 35.6 | 40.5 |
| gi\|149369314\|ref\|ZP_01889166.1\| | unidentified eubacterium | 39.8 | 40.9 | 39.9 | 35.6 | 38.0 |
| gi\|167838952\|ref\|ZP_02465729.1\| | B.thailandensis | 29.5 | 30.3 | 33.3 | 35.6 | 35.7 |
| gi\|227544524\|ref\|ZP_03974573.1\| | Lactobacillus reuteri | 46.1 | 47.2 | 35.6 | 35.5 | 36.7 |
| gi\|148544219\|ref\|YP_001271589.1 | Lactobacillus reuteri | 47.0 | 47.9 | 35.9 | 35.5 | 37.0 |
| gi\|114562726\|ref\|YP_750239.1\| | S.frigidimarina | 36.3 | 41.5 | 38.4 | 35.5 | 39.2 |
| gi\|108763242\|ref\|YP_628497.1\| | Myxococcus xanthus | 35.3 | 33.9 | 32.3 | 35.5 | 35.0 |
| gi\|257068834\|ref\|YP_003155089.1 | B.faecium | 36.0 | 34.7 | 35.8 | 35.5 | 35.0 |
| gi\|227971394\|ref\|ZP_04022706.1\| | Lactobacillus reuteri | 46.5 | 48.0 | 36.5 | 35.5 | 36.6 |
| gi\|229241615\|ref\|ZP_04365992.1\| | Cellulomonas flavigena | 33.1 | 32.6 | 37.3 | 35.4 | 38.1 |
| gi\|126662567\|ref\|ZP_01733566.1\| | Flavobacteria bacterium | 40.3 | 40.6 | 38.5 | 35.4 | 38.5 |
| gi\|238760209\|ref\|ZP_04621355.1\| | Yersinia aldovae | 34.0 | 36.6 | 38.0 | 35.3 | 40.4 |

FIG. 3E: Beta cont'd

FIG. 3E: Beta Ketoacyl-ACP Synthase Homologs

| | | | | | | |
|---|---|---|---|---|---|---|
| gi\|189425467\|ref\|YP_001952644.1 | Geobacter lovleyi SZ | 36.2 | 37.2 | 35.4 | 35.3 | 33.2 |
| gi\|50914834\|ref\|YP_060606.1\| | S. pyogenes | 58.5 | 67.7 | 35.9 | 35.3 | 40.8 |
| gi\|260910019\|ref\|ZP_05916702.1\| | Prevotella sp. | 39.9 | 41.9 | 38.2 | 35.3 | 38.7 |
| gi\|116333574\|ref\|YP_795101.1\| | Lactobacillus brevis | 42.4 | 42.5 | 35.8 | 35.3 | 35.1 |
| gi\|146300976\|ref\|YP_001195567.1 | F.johnsoniae | 35.1 | 37.8 | 36.2 | 35.3 | 37.4 |
| gi\|167624480\|ref\|YP_001674774.1 | Shewanella halifaxensis | 38.0 | 43.1 | 41.7 | 35.2 | 37.7 |
| gi\|256800067\|ref\|ZP_05529691.1\| | S.viridochromogenes | 32.1 | 32.9 | 34.3 | 35.1 | 39.1 |
| gi\|163786848\|ref\|ZP_02181296.1\| | F.bacterium | 39.3 | 39.7 | 39.0 | 35.1 | 35.9 |
| gi\|258509115\|ref\|YP_003171866.1 | L. rhamnosus | 45.8 | 46.1 | 37.7 | 35.1 | 35.4 |
| gi\|199597461\|ref\|ZP_03210891.1\| | L.rhamnosus | 45.5 | 45.8 | 37.7 | 35.1 | 35.4 |
| gi\|229553080\|ref\|ZP_04441805.1\| | L.rhamnosus | 45.5 | 46.1 | 37.3 | 35.1 | 35.4 |
| gi\|182411874\|ref\|YP_001816940.1 | Opitutus terrae PB90-1 | 31.6 | 34.9 | 34.4 | 35.1 | 35.2 |
| gi\|148982384\|ref\|ZP_01816740.1\| | Vibrionales bacterium | 35.2 | 37.4 | 42.8 | 35.0 | 33.5 |
| gi\|218262149\|ref\|ZP_03476708.1\| | P.johnsonii | 36.5 | 36.0 | 38.8 | 35.0 | 32.6 |
| gi\|124801164\|ref\|XP_001349620.1 | Plasmodium falciparum, | 36.4 | 37.5 | 38.2 | 35.0 | 30.0 |
| gi\|260178848\|gb\|ACX34097.1\| | synthetic construct | 36.3 | 37.4 | 38.2 | 35.0 | 30.1 |
| gi\|167578697\|ref\|ZP_02371571.1\| | B.thailandensis | 29.2 | 29.2 | 34.0 | 35.0 | 36.6 |
| gi\|83716602\|ref\|YP_440126.1\| | B.thailandensis | 29.2 | 29.2 | 33.6 | 35.0 | 36.3 |
| gi\|33327109\|gb\|AAQ08929.1\| | Streptomyces griseus | 30.0 | 30.9 | 33.9 | 34.9 | 37.0 |
| gi\|194466384\|ref\|ZP_03072371.1\| | Lactobacillus reuteri | 46.4 | 47.3 | 35.6 | 34.9 | 37.0 |
| gi\|70733415\|ref\|YP_263190.1\| | P. fluorescens | 30.6 | 27.5 | 27.3 | 34.9 | 34.7 |
| gi\|254444420\|ref\|ZP_05057896.1\| | V.bacterium | 31.4 | 34.8 | 34.5 | 34.9 | 34.3 |
| gi\|119383421\|ref\|YP_914477.1\| | P. denitrificans | 28.6 | 26.8 | 28.4 | 34.9 | 33.2 |
| gi\|229590654\|ref\|YP_002872773.1 | P.fluorescens | 33.7 | 35.0 | 34.9 | 34.8 | 53.3 |
| gi\|183980900\|ref\|YP_001849191.1 | M.marinum | 34.8 | 35.4 | 37.4 | 34.8 | 35.8 |
| gi\|118616436\|ref\|YP_904768.1\| | M.ulcerans | 34.8 | 35.4 | 37.4 | 34.8 | 35.5 |
| gi\|254379554\|ref\|ZP_04994974.1\| | Streptomyces sp. | 34.1 | 32.6 | 36.0 | 34.8 | 38.0 |
| gi\|153010143\|ref\|YP_001371357.1 | Ochrobactrum anthropi | 31.4 | 31.8 | 33.6 | 34.8 | 39.6 |
| gi\|229820298\|ref\|YP_002881824.1 | Beutenbergia cavernae | 30.2 | 31.2 | 34.7 | 34.8 | 36.2 |
| gi\|90994387\|ref\|YP_536877.1\| | Porphyra yezoensis, | 37.8 | 34.7 | 37.3 | 34.7 | 34.2 |
| gi\|225155982\|ref\|ZP_03724466.1\| | Opitutaceae bacterium | 30.0 | 32.5 | 33.8 | 34.7 | 32.9 |

FIG. 3E: Beta cont'd

FIG. 3E: Beta Ketoacyl-ACP Synthase Homologs

| | | | | | | |
|---|---|---|---|---|---|---|
| gi\|53721521\|ref\|YP_110506.1\| | Burkholderia pseudomallei | 28.9 | 28.9 | 33.6 | 34.7 | 36.9 |
| gi\|228470556\|ref\|ZP_04055413.1\| | P.uenonis | 34.3 | 33.6 | 35.2 | 34.6 | 32.7 |
| gi\|191639059\|ref\|YP_001988225.1 | Lactobacillus casei | 43.0 | 46.0 | 34.5 | 34.6 | 35.1 |
| gi\|57753876\|dbj\|BAD86806.1\| | Streptomyces sp. | 32.5 | 36.2 | 38.5 | 34.6 | 42.4 |
| gi\|184200724\|ref\|YP_001854931.1 | Kocuria rhizophila | 35.1 | 33.4 | 34.8 | 34.5 | 34.0 |
| gi\|116626427\|ref\|YP_828583.1\| | Solibacter usitatus | 29.6 | 32.6 | 29.8 | 34.5 | 31.8 |
| gi\|170016588\|ref\|YP_001727507.1 | Leuconostoc citreum | 43.7 | 45.4 | 35.7 | 34.5 | 36.4 |
| gi\|167588027\|ref\|ZP_02380415.1\| | Burkholderia ubonensis | 29.1 | 30.2 | 32.7 | 34.5 | 37.6 |
| gi\|167565171\|ref\|ZP_02358087.1\| | B.oklahomensis | 28.7 | 29.9 | 33.6 | 34.5 | 36.2 |
| gi\|167572274\|ref\|ZP_02365148.1\| | B.oklahomensis | 28.3 | 29.9 | 33.6 | 34.5 | 36.2 |
| gi\|229496964\|ref\|ZP_04390669.1\| | Propionibacterium sp. | 33.6 | 34.3 | 34.7 | 34.4 | 33.3 |
| gi\|126457853\|ref\|YP_001074692.1 | Burkholderia pseudomallei | 28.6 | 28.6 | 33.3 | 34.4 | 36.6 |
| gi\|227528767\|ref\|ZP_03958816.1\| | Lactobacillus ruminis | 45.3 | 45.1 | 33.0 | 34.3 | 33.8 |
| gi\|13474852\|ref\|NP_106422.1\| | Mesorhizobium loti | 31.9 | 33.0 | 34.3 | 34.3 | 39.8 |
| gi\|260461698\|ref\|ZP_05809944.1\| | M.opportunistum | 32.0 | 32.5 | 35.2 | 34.3 | 40.3 |
| gi\|227533871\|ref\|ZP_03963920.1\| | Lactobacillus paracasei | 42.7 | 46.0 | 34.8 | 34.3 | 35.4 |
| gi\|116495577\|ref\|YP_807311.1\| | Lactobacillus casei | 42.4 | 45.7 | 34.8 | 34.3 | 35.4 |
| gi\|116513956\|ref\|YP_812862.1\| | Lactobacillus delbrueckii | 48.9 | 50.3 | 37.3 | 34.3 | 38.7 |
| gi\|172064810\|ref\|YP_001815522.1 | Burkholderia ambifaria | 29.1 | 30.5 | 31.8 | 34.2 | 36.4 |
| gi\|115360510\|ref\|YP_777647.1\| | Burkholderia ambifaria | 28.8 | 29.9 | 31.2 | 34.2 | 35.5 |
| gi\|13488065\|ref\|NP_085659.1\| | Mesorhizobium loti | 33.8 | 34.0 | 37.5 | 34.0 | 38.5 |
| gi\|104773949\|ref\|YP_618929.1\| | Lactobacillus delbrueckii | 48.9 | 50.3 | 37.0 | 34.0 | 38.4 |
| gi\|227891237\|ref\|ZP_04009042.1\| | Lactobacillus salivarius | 41.7 | 42.7 | 31.0 | 33.9 | 31.7 |
| gi\|256668039\|ref\|ZP_05478992.1\| | Streptomyces sp. AA4. | 33.4 | 33.8 | 36.6 | 33.8 | 37.8 |
| gi\|227526590\|ref\|ZP_03956639.1\| | Lactobacillus ruminis | 47.7 | 49.2 | 35.7 | 33.7 | 36.4 |
| gi\|209883893\|ref\|YP_002287750.1 | O.carboxidovorans | 30.4 | 31.6 | 33.3 | 33.7 | 40.7 |
| gi\|12044307\|gb\|AAG47795.1\|AF311738_11 | Mesorhizobium loti | 30.6 | 34.0 | 34.9 | 33.7 | 40.6 |
| gi\|169402972\|emb\|CAM58805.1\| | Streptomyces sp. | 30.6 | 32.1 | 36.7 | 33.7 | 37.1 |
| gi\|90961428\|ref\|YP_535344.1\| | Lactobacillus salivarius | 46.9 | 48.5 | 38.2 | 33.6 | 33.3 |
| gi\|256827531\|ref\|YP_003151490.1 | Cryptobacterium curtum | 36.3 | 35.1 | 32.9 | 33.6 | 30.6 |
| gi\|254780489\|ref\|YP_003064902.1 | C. Liberibacter asiaticus | 29.4 | 32.0 | 33.8 | 33.6 | 33.5 |

FIG. 3E: Beta cont'd

FIG. 3E: Beta Ketoacyl-ACP Synthase Homologs

| | | | | | | |
|---|---|---|---|---|---|---|
| gi\|227431211\|ref\|ZP_03913265.1\| | L.mesenteroides | 53.1 | 49.4 | 37.0 | 33.5 | 37.0 |
| gi\|90962231\|ref\|YP_536147.1\| | Lactobacillus salivarius | 41.0 | 42.7 | 30.4 | 33.5 | 31.4 |
| gi\|239833331\|ref\|ZP_04681659.1\| | O.intermedium | 31.6 | 31.3 | 34.2 | 33.4 | 39.3 |
| gi\|227823048\|ref\|YP_002827020.1 | Rhizobium sp. | 30.9 | 31.8 | 34.9 | 33.4 | 40.7 |
| gi\|68071527\|ref\|XP_677677.1\| | Plasmodium berghei | 38.0 | 34.8 | 40.2 | 33.4 | 30.6 |
| gi\|70946265\|ref\|XP_742865.1\| | Plasmodium chabaudi | 36.9 | 35.6 | 39.9 | 33.3 | 31.0 |
| gi\|227890517\|ref\|ZP_04008322.1\| | Lactobacillus salivarius | 47.2 | 47.6 | 37.8 | 33.3 | 33.3 |
| gi\|116617436\|ref\|YP_817807.1\| | L.mesenteroides | 52.4 | 49.7 | 36.3 | 33.3 | 37.0 |
| gi\|116493249\|ref\|YP_804984.1\| | P. pentosaceus | 45.1 | 44.8 | 34.5 | 33.2 | 35.9 |
| gi\|171317251\|ref\|ZP_02906449.1\| | Burkholderia ambifaria | 27.1 | 28.0 | 30.8 | 33.2 | 34.5 |
| gi\|187761557\|dbj\|BAG31978.1\| | M. intracellulare | 32.6 | 32.5 | 29.6 | 33.2 | 29.7 |
| gi\|28378361\|ref\|NP_785253.1\| | Lactobacillus plantarum | 40.3 | 41.5 | 33.5 | 33.0 | 34.4 |
| gi\|254387377\|ref\|ZP_05002626.1\| | Streptomyces sp. Mg1 | 32.1 | 31.9 | 34.8 | 33.0 | 35.4 |
| gi\|148558468\|ref\|YP_001257462.1 | Brucella ovis | 31.6 | 32.9 | 34.5 | 33.0 | 38.6 |
| gi\|254819595\|ref\|ZP_05224596.1\| | M. intracellulare | 32.3 | 32.4 | 29.2 | 33.0 | 29.4 |
| gi\|17989124\|ref\|NP_541757.1\| | B. melitensis, B. suis, B.neotomae, B.ceti, B. abortus | 32.9 | 34.4 | 35.7 | 33.0 | 38.6 |
| gi\|163844651\|ref\|YP_001622306.1 | Brucella suis | 32.9 | 34.4 | 35.3 | 33.0 | 38.6 |
| gi\|170016659\|ref\|YP_001727578.1 | Leuconostoc citreum | 50.2 | 49.1 | 37.0 | 32.9 | 35.8 |
| gi\|227892758\|ref\|ZP_04010563.1\| | Lactobacillus ultunensis | 47.8 | 51.9 | 37.1 | 32.9 | 34.9 |
| gi\|227895174\|ref\|ZP_04012979.1\| | Lactobacillus plantarum | 40.0 | 41.5 | 33.5 | 32.7 | 34.9 |
| gi\|115373787\|ref\|ZP_01461080.1\| | Stigmatella aurantiaca | 33.4 | 32.1 | 30.7 | 32.7 | 33.5 |
| gi\|254711696\|ref\|ZP_05173507.1\| | Brucella pinnipedialis | 32.6 | 34.0 | 35.3 | 32.7 | 38.3 |
| gi\|254556571\|ref\|YP_003062988.1 | Lactobacillus plantarum | 40.9 | 41.8 | 33.8 | 32.6 | 34.1 |
| gi\|183983211\|ref\|YP_001851502.1 | M.marinum | 33.3 | 35.0 | 33.8 | 32.6 | 38.0 |
| gi\|159896904\|ref\|YP_001543151.1 | H.aurantiacus | 28.6 | 29.6 | 28.2 | 32.6 | 32.1 |
| gi\|159185988\|ref\|NP_356639.2\| | A.tumefaciens | 31.2 | 31.9 | 35.8 | 32.5 | 38.6 |
| gi\|167721713\|ref\|ZP_02404949.1\| | Burkholderia pseudomallei | 30.8 | 31.7 | 31.1 | 32.4 | 34.3 |
| gi\|53724347\|ref\|YP_104388.1\| | Burkholderia mallei | 30.8 | 32.3 | 31.1 | 32.4 | 34.3 |
| gi\|167913030\|ref\|ZP_02500121.1\| | Burkholderia pseudomallei | 30.8 | 32.3 | 31.2 | 32.4 | 34.3 |
| gi\|53720934\|ref\|YP_109920.1\| | B.pseudomallei, B.mallei | 30.8 | 32.3 | 31.1 | 32.4 | 34.3 |
| gi\|126454553\|ref\|YP_001068177.1 | Burkholderia pseudomallei | 30.8 | 32.0 | 31.1 | 32.4 | 34.3 |

FIG. 3E: Beta cont'd

FIG. 3E: Beta Ketoacyl-ACP Synthase Homologs

| | | | | | | |
|---|---|---|---|---|---|---|
| gi\|255335359\|ref\|ZP_05376271.1\| | H. denitrificans | 31.8 | 31.3 | 34.4 | 32.2 | 39.4 |
| gi\|213385133\|dbj\|BAG84261.1\| | S.griseoviridis | 34.0 | 32.7 | 32.7 | 32.1 | 49.6 |
| gi\|254720493\|ref\|ZP_05182304.1\| | Brucella sp. 83/13 | 32.6 | 34.4 | 35.3 | 32.0 | 38.3 |
| gi\|270291213\|ref\|ZP_06197436.1\| | Pediococcus acidilactici | 46.5 | 45.3 | 34.8 | 32.0 | 36.3 |
| gi\|282856842\|ref\|ZP_06266101.1\| | P. piscolens | 29.3 | 29.5 | 27.9 | 31.9 | 31.3 |
| gi\|227370787\|ref\|ZP_03854283.1\| | C.gleum | 31.8 | 32.6 | 31.3 | 31.9 | 30.1 |
| gi\|282883186\|ref\|ZP_06291785.1\| | Peptoniphilus lacrimalis | 36.4 | 38.6 | 37.4 | 31.8 | 29.6 |
| gi\|54297551\|ref\|YP_123920.1\| | Legionella pneumophila | 28.6 | 29.8 | 29.5 | 31.8 | 28.6 |
| gi\|8896108\|gb\|AAF81236.1\| | Streptomyces griseus | 27.8 | 28.0 | 32.8 | 31.2 | 30.2 |
| gi\|118618820\|ref\|YP_907152.1\| | M. ulcerans | 32.7 | 34.1 | 32.2 | 31.1 | 36.2 |
| gi\|52841859\|ref\|YP_095658.1\| | Legionella pneumophila | 28.6 | 30.1 | 30.4 | 31.0 | 28.9 |
| gi\|148359166\|ref\|YP_001250373.1 | Legionella pneumophila | 28.3 | 29.9 | 29.6 | 30.6 | 28.2 |
| gi\|127512265\|ref\|YP_001093462.1 | Shewanella loihica PV-4 | 31.6 | 28.6 | 29.2 | 30.5 | 30.2 |
| gi\|260655591\|ref\|ZP_05861079.1\| | Jonquetella anthropi | 31.4 | 30.5 | 27.0 | 30.4 | 34.7 |
| gi\|255015999\|ref\|ZP_05288125.1\| | Bacteroides sp. 2_1_7. | 30.6 | 31.6 | 31.0 | 30.4 | 28.5 |
| gi\|127512264\|ref\|YP_001093461.1 | Shewanella loihica PV-4 | 33.1 | 29.6 | 30.5 | 30.3 | 29.1 |
| gi\|170726022\|ref\|YP_001760048.1 | Shewanella woodyi | 29.5 | 30.9 | 33.6 | 30.3 | 29.5 |
| gi\|265765451\|ref\|ZP_06093726.1\| | Bacteroides sp. 2_1_16, | 33.3 | 31.4 | 27.1 | 30.0 | 30.6 |
| gi\|213967602\|ref\|ZP_03395750.1\| | Pseudomonas syringae | 31.7 | 31.7 | 31.6 | 30.0 | 35.1 |
| gi\|28869120\|ref\|NP_791739.1\| | Pseudomonas syringae | 31.7 | 31.7 | 31.1 | 30.0 | 34.0 |
| gi\|87307972\|ref\|ZP_01090115.1\| | Blastopirellula marina | 36.6 | 33.0 | 31.2 | 30.0 | 32.8 |
| gi\|126725808\|ref\|ZP_01741650.1\| | R. bacterium | 27.7 | 28.3 | 31.1 | 29.8 | 30.3 |
| gi\|256842321\|ref\|ZP_05547825.1\| | Parabacteroides sp. | 33.1 | 31.5 | 29.2 | 29.8 | 30.9 |
| gi\|238025840\|ref\|YP_002910071.1 | Burkholderia glumae | 30.5 | 30.5 | 31.2 | 29.8 | 36.1 |
| gi\|265762838\|ref\|ZP_06091406.1\| | Bacteroides sp. | 31.8 | 30.4 | 27.5 | 29.7 | 27.8 |
| gi\|153830082\|ref\|ZP_01982749.1\| | Vibrio cholerae . | 32.5 | 34.0 | 31.8 | 29.4 | 32.1 |
| gi\|91217304\|ref\|ZP_01254265.1\| | Psychroflexus torquis | 30.7 | 31.4 | 31.2 | 29.3 | 29.6 |
| gi\|26991068\|ref\|NP_746493.1\| | Pseudomonas putida | 31.8 | 31.3 | 31.8 | 29.2 | 29.8 |
| gi\|91785679\|ref\|YP_560885.1\| | B.xenovorans | 31.3 | 30.8 | 30.9 | 29.0 | 33.4 |
| gi\|228473378\|ref\|ZP_04058132.1\| | C. gingivalis | 32.0 | 30.6 | 31.6 | 29.0 | 30.3 |
| gi\|218530981\|ref\|YP_002421797.1 | M.chloromethanicum | 32.6 | 30.8 | 30.6 | 29.0 | 34.7 |

FIG. 3E: Beta cont'd

FIG. 3E: Beta Ketoacyl-ACP Synthase Homologs

| | | | | | | |
|---|---|---|---|---|---|---|
| gi\|163852222\|ref\|YP_001640265.1 | M.extorquens | 32.0 | 30.5 | 31.2 | 29.0 | 33.9 |
| gi\|255011327\|ref\|ZP_05283453.1\| | Bacteroides fragilis | 31.8 | 31.4 | 28.6 | 28.9 | 30.4 |
| gi\|150010208\|ref\|YP_001304951.1 | P.distasonis | 31.4 | 28.5 | 29.0 | 28.8 | 30.4 |
| gi\|156972997\|ref\|YP_001443904.1 | Vibrio harveyi | 33.0 | 32.4 | 30.7 | 28.8 | 30.7 |
| gi\|255013317\|ref\|ZP_05285443.1\| | Bacteroides sp. | 32.8 | 33.4 | 31.2 | 28.8 | 29.7 |
| gi\|172064977\|ref\|YP_001815689.1 | Burkholderia ambifaria | 32.4 | 28.5 | 30.9 | 28.8 | 34.3 |
| gi\|240139553\|ref\|YP_002964029.1 | M.extorquens | 32.0 | 30.5 | 30.9 | 28.7 | 34.7 |
| gi\|254561968\|ref\|YP_003069063.1 | M. extorquens | 32.9 | 30.8 | 31.2 | 28.4 | 34.2 |
| gi\|71737752\|ref\|YP_275581.1\| | Pseudomonas syringae | 31.5 | 32.4 | 32.3 | 28.3 | 34.5 |
| gi\|283781629\|ref\|YP_003372384.1 | Pirellula staleyi | 32.8 | 29.1 | 30.6 | 28.2 | 33.6 |
| gi\|262383294\|ref\|ZP_06076430.1\| | Bacteroides | 29.1 | 28.9 | 29.3 | 28.2 | 26.6 |
| gi\|42521903\|ref\|NP_967283.1\| | B.bacteriovorus | 28.3 | 27.9 | 31.0 | 28.2 | 29.9 |
| gi\|170726024\|ref\|YP_001760050.1 | Shewanella woodyi | 32.7 | 31.2 | 30.0 | 28.1 | 31.3 |
| gi\|229589183\|ref\|YP_002871302.1 | P.fluorescens | 32.4 | 29.7 | 31.2 | 28.1 | 31.0 |
| gi\|220928643\|ref\|YP_002505552.1 | C.cellulolyticum | 29.8 | 29.5 | 32.2 | 28.1 | 33.4 |
| gi\|32473839\|ref\|NP_866833.1\| | Rhodopirellula baltica | 33.0 | 29.5 | 31.3 | 28.0 | 33.7 |
| gi\|256842319\|ref\|ZP_05547823.1\| | Parabacteroides sp. | 29.8 | 28.9 | 28.2 | 28.0 | 26.8 |
| gi\|153830088\|ref\|ZP_01982755.1\| | Vibrio cholerae | 31.6 | 31.8 | 30.0 | 27.9 | 29.6 |
| gi\|52142302\|ref\|YP_084527.1\| | Bacillus cereus | 29.7 | 26.6 | 27.8 | 27.8 | 26.4 |
| gi\|30263174\|ref\|NP_845551.1\| | B.cereus,B. anthracis, B. thuringiensis | 29.7 | 26.6 | 28.1 | 27.8 | 26.7 |
| gi\|229092198\|ref\|ZP_04223379.1\| | Bacillus cereus | 29.4 | 26.6 | 27.8 | 27.8 | 26.7 |
| gi\|118478513\|ref\|YP_895664.1\| | B.cereus,B.thuringiensis | 29.7 | 26.9 | 27.8 | 27.8 | 26.4 |
| gi\|49478091\|ref\|YP_037326.1\| | B.thuringiensis,B.cereus | 29.7 | 26.6 | 27.8 | 27.8 | 26.4 |
| gi\|196037767\|ref\|ZP_03105077.1\| | Bacillus cereus | 29.4 | 26.3 | 27.5 | 27.8 | 26.5 |
| gi\|163940889\|ref\|YP_001645773.1 | B.weihenstephanensis | 28.7 | 25.4 | 27.8 | 27.8 | 25.5 |
| gi\|88710984\|ref\|ZP_01105072.1\| | F.bacterium | 31.9 | 27.7 | 31.2 | 27.8 | 27.3 |
| gi\|224539483\|ref\|ZP_03680022.1\| | Bacteroides cellulosilyticus | 28.8 | 27.1 | 28.1 | 27.7 | 23.7 |
| gi\|187925807\|ref\|YP_001897449.1 | B.phytofirmans | 32.4 | 30.8 | 31.8 | 27.6 | 33.1 |
| gi\|167632425\|ref\|ZP_02390752.1\| | Bacillus anthracis | 29.7 | 26.6 | 28.1 | 27.5 | 26.7 |
| gi\|228946840\|ref\|ZP_04109142.1\| | Bacillus thuringiensis | 29.7 | 26.6 | 28.1 | 27.5 | 26.7 |
| gi\|229167884\|ref\|ZP_04295615.1\| | Bacillus cereus AH621 | 28.7 | 25.7 | 27.5 | 27.5 | 25.5 |

FIG. 3E: Beta cont'd

FIG. 3E: Beta Ketoacyl-ACP Synthase Homologs

| | | | | | | |
|---|---|---|---|---|---|---|
| gi\|229173890\|ref\|ZP_04301428.1\| | Bacillus cereus MM3 | 29.1 | 26.3 | 27.8 | 27.5 | 26.1 |
| gi\|255011328\|ref\|ZP_05283454.1\| | Bacteroides fragilis | 29.1 | 28.7 | 29.8 | 27.5 | 27.4 |
| gi\|167034935\|ref\|YP_001670166.1 | Pseudomonas putida | 30.7 | 31.6 | 31.6 | 27.3 | 29.8 |
| gi\|187925809\|ref\|YP_001897451.1 | B. phytofirmans | 32.0 | 33.6 | 30.6 | 27.2 | 31.1 |
| gi\|228921970\|ref\|ZP_04085281.1\| | Bacillus thuringiensis | 29.4 | 25.7 | 27.2 | 27.2 | 26.1 |
| gi\|255012522\|ref\|ZP_05284648.1\| | Bacteroides | 28.2 | 28.0 | 26.3 | 27.1 | 27.1 |
| gi\|242281108\|ref\|YP_002993237.1 | Desulfovibrio salexigens | 30.2 | 30.7 | 31.3 | 27.0 | 30.9 |
| gi\|91785681\|ref\|YP_560887.1\| | B.xenovorans | 31.1 | 31.2 | 31.1 | 26.9 | 29.6 |
| gi\|228995898\|ref\|ZP_04155556.1\| | Bacillus mycoides | 29.1 | 26.0 | 28.7 | 26.9 | 26.2 |
| gi\|228989698\|ref\|ZP_04149680.1\| | B.pseudomycoides | 29.1 | 26.0 | 28.7 | 26.9 | 26.2 |
| gi\|256839039\|ref\|ZP_05544549.1\| | Parabacteroides sp. | 27.9 | 28.0 | 27.2 | 26.8 | 25.7 |
| gi\|254482488\|ref\|ZP_05095727.1\| | marine gamma proteobacterium | 35.4 | 32.2 | 30.5 | 26.8 | 29.5 |
| gi\|229088324\|ref\|ZP_04220174.1\| | Bacillus cereus | 29.4 | 25.4 | 29.1 | 26.6 | 25.6 |
| gi\|150007222\|ref\|YP_001301965.1 | P. distasonis | 30.1 | 32.0 | 26.5 | 26.6 | 30.3 |
| gi\|229589186\|ref\|YP_002871305.1 | P.fluorescens | 35.7 | 33.7 | 31.8 | 25.9 | 33.9 |
| gi\|172064978\|ref\|YP_001815690.1 | Burkholderia ambifaria | 30.9 | 32.5 | 30.0 | 25.5 | 32.4 |
| gi\|189466291\|ref\|ZP_03015076.1\| | Bacteroides intestinalis | 32.6 | 30.4 | 29.2 | 25.5 | 29.3 |
| gi\|238025838\|ref\|YP_002910069.1 | Burkholderia glumae | 30.3 | 31.4 | 28.2 | 25.1 | 33.0 |
| gi\|53712115\|ref\|YP_098107.1\| | Bacteroides fragilis | 32.5 | 31.5 | 30.2 | 24.2 | 27.0 |
| gi\|255007640\|ref\|ZP_05279766.1\| | Bacteroides fragilis | 32.2 | 31.5 | 29.9 | 24.2 | 26.5 |
| gi\|83645204\|ref\|YP_433639.1\| | Hahella chejuensis | 29.9 | 31.7 | 27.5 | 23.7 | 27.8 |
| gi\|66046696\|ref\|YP_236537.1\| | Pseudomonas syringae | 33.4 | 32.6 | 33.7 | | 30.8 |
| gi\|71737685\|ref\|YP_275551.1\| | Pseudomonas syringae | 32.7 | 33.2 | 33.2 | | 30.2 |
| gi\|237799222\|ref\|ZP_04587683.1\| | Pseudomonas syringae | 33.1 | 32.9 | 33.2 | | 30.5 |
| gi\|146335611\|gb\|ABQ23410.1\| | Pseudomonas syringae | 32.7 | 33.2 | 33.2 | | 30.2 |
| gi\|104782831\|ref\|YP_609329.1\| | P.entomophila | 33.4 | 32.8 | 32.5 | | 33.2 |
| gi\|257484931\|ref\|ZP_05638972.1\| | Pseudomonas syringae | 32.7 | 33.2 | 33.2 | | 30.2 |
| gi\|213967571\|ref\|ZP_03395719.1\| | Pseudomonas syringae | 33.4 | 32.6 | 33.2 | | 30.2 |
| gi\|28869152\|ref\|NP_791771.1\| | Pseudomonas syringae | 33.7 | 32.6 | 33.5 | | 30.2 |
| gi\|49205102\|dbj\|BAD24669.1\| | Pseudomonas syringae | 32.7 | 33.2 | 33.3 | | 30.2 |
| gi\|77457751\|ref\|YP_347256.1\| | P.fluorescens | 32.0 | 32.5 | 32.6 | | 30.3 |

FIG. 3E: Beta cont'd

FIG. 3E: Beta Ketoacyl-ACP Synthase Homologs

| | | | | | | |
|---|---|---|---|---|---|---|
| gi\|229591863\|ref\|YP_002873982.1 | P.fluorescens | 31.0 | 32.5 | 32.5 | | 30.8 |
| gi\|148546727\|ref\|YP_001266829.1 | P.putida F1 | 33.2 | 32.9 | 33.5 | | 33.0 |

Calibration curve obtained by linear regression. The triangles represent data (instrument response and concentration) for each level of the standard compound.

FIG. 6A

- pDG2 plasmid sequence:

1 GGGGAATTGT GAGCGGATAA CAATTCCCCT GTAGAAATAA TTTTGTTTAA CTTTAATAAG
61 GAGATATACC ATGGCGCAAC TCACTCTTCT TTTAGTCGGC AATTCCGACG CCATCACGCC
121 ATTACTTGCT AAAGCTGACT TTGAACAACG TTCGCGTCTG CAGATTATTC CTGCGCAGTC
181 AGTTATCGCC AGTGATGCCC GGCCTTCGCA AGCTATCCGC GCCAGTCGTG GGAGTTCAAT
241 GCGCGTGGCC CTGGAGCTGG TGAAAGAAGG TCGAGCGCAA GCCTGTGTCA GTGCCGGTAA
301 TACCGGGGCG CTGATGGGGC TGGCAAAATT ATTACTCAAG CCCCTGGAGG GGATTGAGCG
361 TCCGGCGCTG GTGACGGTAT TACCACATCA GCAAAAGGGC AAAACGGTGG TCCTTGACTT
421 AGGGGCCAAC GTCGATTGTG ACAGCACAAT GCTGGTGCAA TTTGCCATTA TGGGCTCAGT
481 TCTGGCTGAA GAGGTGGTGG AAATTCCCAA TCCTCGCGTG GCGTTGCTCA ATATTGGTGA
541 AGAAGAAGTA AAGGGTCTCG ACAGTATTCG GGATGCCTCA GCGGTGCTTA AAACAATCCC
601 TTCTATCAAT TATATCGGCT ATCTTGAAGC CAATGAGTTG TTAACTGGCA AGACAGATGT
661 GCTGGTTTGT GACGGCTTTA CAGGAAATGT CACATTAAAG ACGATGGAAG GTGTTGTCAG
721 GATGTTCCTT TCTCTGCTGA AATCTCAGGG TGAAGGGAAA AAACGGTCGT GGTGGCTACT
781 GTTATTAAAG CGTTGGCTAC AAAAGAGCCT GACGAGGCGA TTCAGTCACC TCAACCCCGA
841 CCAGTATAAC GGCGCCTGTC TGTTAGGATT GCGCGGCACG GTGATAAAAA GTCATGGTGC
901 AGCCAATCAG CGAGCTTTTG CGGTCGCGAT TGAACAGGCA GTGCAGGCGG TGCAGCGACA
961 AGTTCCTCAG CGAATTGCCG CTCGCCTGGA ATCTGTATAC CCAGCTGGTT TTGAGCTGCT
1021 GGACGGTGGC AAAAGCGGAA CTCTGCGGTA GCAGGACGCT GCCAGCGAAC TCGCAGTTTG
1081 CAAGTGACGG TATATAACCG AAAAGTGACT GAGCGCATAT GTATACGAAG ACTCGAGTCT
1141 GGTAAAGAAA CCGCTGCTGC GAAATTTGAA CGCCAGCACA TGGACTCGTC TACTAGCGCA
1201 GCTTAATTAA CCTAGGCTGC TGCCACCGCT GAGCAATAAC TAGCATAACC CCTTGGGGCC
1261 TCTAAACGGG TCTTGAGGGG TTTTTTGCTG AAACCTCAGG CATTTGAGAA GCACACGGTC
1321 ACACTGCTTC CGGTAGTCAA TAAACCGGTA AACCAGCAAT AGACATAAGC GGCTATTTAA
1381 CGACCCTGCC CTGAACCGAC GACCGGGTCA TCGTGGCCGG ATCTTGCGGC CCCTCGGCTT
1441 GAACGAATTG TTAGACATTA TTTGCCGACT ACCTTGGTGA TCTCGCCTTT CACGTAGTGG
1501 ACAAATTCTT CCAACTGATC TGCGCGCGAG GCCAAGCGAT CTTCTTCTTG TCCAAGATAA
1561 GCCTGTCTAG CTTCAAGTAT GACGGGCTGA TACTGGGCCG GCAGGCGCTC CATTGCCCAG
1621 TCGGCAGCGA CATCCTTCGG CGCGATTTTG CCGGTTACTG CGCTGTACCA AATGCGGGAC
1681 AACGTAAGCA CTACATTTCG CTCATCGCCA GCCCAGTCGG GCGGCGAGTT CCATAGCGTT
1741 AAGGTTTCAT TTAGCGCCTC AAATAGATCC TGTTCAGGAA CCGGATCAAA GAGTTCCTCC
1801 GCCGCTGGAC CTACCAAGGC AACGCTATGT TCTCTTGCTT TTGTCAGCAA GATAGCCAGA
1861 TCAATGTCGA TCGTGGCTGG CTCGAAGATA CCTGCAAGAA TGTCATTGCG CTGCCATTCT
1921 CCAAATTGCA GTTCGCGCTT AGCTGGATAA CGCCACGGAA TGATGTCGTC GTGCACAACA
1981 ATGGTGACTT CTACAGCGCG GAGAATCTCG CTCTCTCCAG GGGAAGCCGA AGTTTCCAAA
2041 AGGTCGTTGA TCAAAGCTCG CCGCGTTGTT TCATCAAGCC TTACGGTCAC CGTAACCAGC
2101 AAATCAATAT CACTGTGTGG CTTCAGGCCG CCATCCACTG CGGAGCCGTA CAAATGTACG
2161 GCCAGCAACG TCGGTTCGAG ATGGCGCTCG ATGACGCCAA CTACCTCTGA TAGTTGAGTC
2221 GATACTTCGG CGATCACCGC TTCCCTCATA CTCTTCCTTT TTCAATATTA TTGAAGCATT
2281 TATCAGGGTT ATTGTCTCAT GAGCGGATAC ATATTTGAAT GTATTTAGAA AAATAAACAA
2341 ATAGCTAGCT CACTCGGTCG CTACGCTCCG GGCGTGAGAC TGCGGCGGGC GCTGCGGACA
2401 CATACAAAGT TACCCACAGA TTCCGTGGAT AAGCAGGGGA CTAACATGTG AGGCAAAACA
2461 GCAGGGCCGC GCCGGTGGCG TTTTTCCATA GGCTCCGCCC TCCTGCCAGA GTTCACATAA
2521 ACAGACGCTT TTCCGGTGCA TCTGTGGGAG CCGTGAGGCT CAACCATGAA TCTGACAGTA
2581 CGGGCGAAAC CCGACAGGAC TTAAAGATCC CCACCGTTTC CGGCGGGTCG CTCCCTCTTG
2641 CGCTCTCCTG TTCCGACCCT GCCGTTTACC GGATACCTGT TCCGCCTTTC TCCCTTACGG
2701 GAAGTGTGGC GCTTTCTCAT AGCTCACACA CTGGTATCTC GGCTCGGTGT AGGTCGTTCG

FIG. 6A cont'd

```
2761 CTCCAAGCTG GGCTGTAAGC AAGAACTCCC CGTTCAGCCC GACTGCTGCG CCTTATCCGG
2821 TAACTGTTCA CTTGAGTCCA ACCCGGAAAA GCACGGTAAA ACGCCACTGG CAGCAGCCAT
2881 TGGTAACTGG GAGTTCGCAG AGGATTTGTT TAGCTAAACA CGCGGTTGCT CTTGAAGTGT
2941 GCGCCAAAGT CCGGCTACAC TGGAAGGACA GATTTGGTTG CTGTGCTCTG CGAAAGCCAG
3001 TTACCACGGT TAAGCAGTTC CCCAACTGAC TTAACCTTCG ATCAAACCAC CTCCCCAGGT
3061 GGTTTTTTCG TTTACAGGGC AAAAGATTAC GCGCAGAAAA AAAGGATCTC AAGAAGATCC
3121 TTTGATCTTT TCTACTGAAC CGCTCTAGAT TTCAGTGCAA TTTATCTCTT CAAATGTAGC
3181 ACCTGAAGTC AGCCCCATAC GATATAAGTT GTAATTCTCA TGTTAGTCAT GCCCCGCGCC
3241 CACCGGAAGG AGCTGACTGG GTTGAAGGCT CTCAAGGGCA TCGGTCGAGA TCCCGGTGCC
3301 TAATGAGTGA GCTAACTTAC ATTAATTGCG TTGCGCTCAC TGCCCGCTTT CCAGTCGGGA
3361 AACCTGTCGT GCCAGCTGCA TTAATGAATC GGCCAACGCG CGGGGAGAGG CGGTTTGCGT
3421 ATTGGGCGCC AGGGTGGTTT TTCTTTTCAC CAGTGAGACG GGCAACAGCT GATTGCCCTT
3481 CACCGCCTGG CCCTGAGAGA GTTGCAGCAA GCGGTCCACG CTGGTTTGCC CCAGCAGGCG
3541 AAAATCCTGT TTGATGGTGG TTAACGGCGG GATATAACAT GAGCTGTCTT CGGTATCGTC
3601 GTATCCCACT ACCGAGATGT CCGCACCAAC GCGCAGCCCG GACTCGGTAA TGGCGCGCAT
3661 TGCGCCCAGC GCCATCTGAT CGTTGGCAAC CAGCATCGCA GTGGGAACGA TGCCCTCATT
3721 CAGCATTTGC ATGGTTTGTT GAAAACCGGA CATGGCACTC CAGTCGCCTT CCCGTTCCGC
3781 TATCGGCTGA ATTTGATTGC GAGTGAGATA TTTATGCCAG CCAGCCAGAC GCAGACGCGC
3841 CGAGACAGAA CTTAATGGGC CCGCTAACAG CGCGATTTGC TGGTGACCCA ATGCGACCAG
3901 ATGCTCCACG CCCAGTCGCG TACCGTCTTC ATGGGAGAAA ATAATACTGT TGATGGGTGT
3961 CTGGTCAGAG ACATCAAGAA ATAACGCCGG AACATTAGTG CAGGCAGCTT CCACAGCAAT
4021 GGCATCCTGG TCATCCAGCG GATAGTTAAT GATCAGCCCA CTGACGCGTT GCGCGAGAAG
4081 ATTGTGCACC GCCGCTTTAC AGGCTTCGAC GCCGCTTCGT TCTACCATCG ACACCACCAC
4141 GCTGGCACCC AGTTGATCGG CGCGAGATTT AATCGCCGCG ACAATTTGCG ACGGCGCGTG
4201 CAGGGCCAGA CTGGAGGTGG CAACGCCAAT CAGCAACGAC TGTTTGCCCG CCAGTTGTTG
4261 TGCCACGCGG TTGGGAATGT AATTCAGCTC CGCCATCGCC GCTTCCACTT TTTCCCGCGT
4321 TTTCGCAGAA ACGTGGCTGG CCTGGTTCAC CACGCGGGAA ACGGTCTGAT AAGAGACACC
4381 GGCATACTCT GCGACATCGT ATAACGTTAC TGGTTTCACA TTCACCACCC TGAATTGACT
4441 CTCTTCCGGG CGCTATCATG CCATACCGCG AAAGGTTTTG CGCCATTCGA TGGTGTCCGG
4501 GATCTCGACG CTCTCCCTTA TGCGACTCCT GCATTAGGAA ATTAATACGA CTCACTATA
(SEQ ID NO:128)
```

FIG. 6B

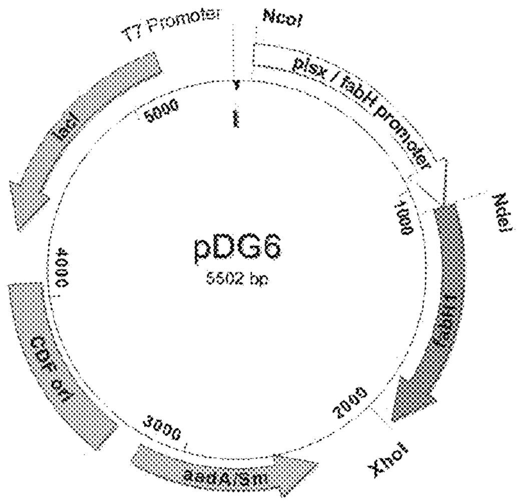

FIG. 6C:

– pDG6 (pCFDuet+*E.coli PfabH*+*B.subtilis fabH1*) plasmid sequence:

ggggaattgtgagcggataacaattcccctgtagaaataattttgtttaactttaataaggagatatacc
atggCGCAACTCACTCTTCTTTTAGTCGGCAATTCCGACGCCATCACGCCATTACTTGCTAAAGCTGACT
TTGAACAACGTTCGCGTCTGCAGATTATTCCTGCGCAGTCAGTTATCGCCAGTGATGCCCGGCCTTCGCA
AGCTATCCGCGCCAGTCGTGGGAGTTCAATGCGCGTGGCCCTGGAGCTGGTGAAAGAAGGTCGAGCGCAA
GCCTGTGTCAGTGCCGGTAATACCGGGGCGCTGATGGGGCTGGCAAAATTATTACTCAAGCCCCTGGAGG
GGATTGAGCGTCCGGCGCTGGTGACGGTATTACCACATCAGCAAAAGGGCAAAACGGTGGTCCTTGACTT
AGGGGCCAACGTCGATTGTGACAGCACAATGCTGGTGCAATTTGCCATTATGGGCTCAGTTCTGGCTGAA
GAGGTGGTGGAAATTCCCAATCCTCGCGTGGCGTTGCTCAATATTGGTGAAGAAGAAGTAAAGGGTCTCG
ACAGTATTCGGGATGCCTCAGCGGTGCTTAAAACAATCCCTTCTATCAATTATATCGGCTATCTTGAAGC
CAATGAGTTGTTAACTGGCAAGACAGATGTGCTGGTTTGTGACGGCTTTACAGGAAATGTCACATTAAAG
ACGATGGAAGGTGTTGTCAGGATGTTCCTTTCTCTGCTGAAATCTCAGGGTGAAGGAAAAAACGGTCGT
GGTGGCTACTGTTATTAAAGCGTTGGCTACAAAAGAGCCTGACGAGGCGATTCAGTCACCTCAACCCCGA
CCAGTATAACGGCGCCTGTCTGTTAGGATTGCGCGGCACGGTGATAAAAAGTCATGGTGCAGCCAATCAG
CGAGCTTTTGCGGTCGCGATTGAACAGGCAGTGCAGGCGGTGCAGCGACAAGTTCCTCAGCGAATTGCCG
CTCGCCTGGAATCTGTATACCCAGCTGGTTTTGAGCTGCTGGACGGTGGCAAAAGCGGAACTCTGCGGTA
GCAGGACGCTGCCAGCGAACTCGCAGTTTGCAAGTGACGGTATATAACCGAAAAGTGACTGAGCGcat*AT*
*GAAAGCTGGCATTCTTGGTGTTGGACGTTACATTCCTGAGAAGGTTTTAACAAATCATGATCTTGAAAAA*
*ATGGTTGAAACTTCTGACGAGTGGATTCGTACAAGAACAGGAATAGAAGAAAGAAGAATCGCAGCAGATG*
*ATGTGTTTTCATCACACATGGCTGTTGCAGCAGCGAAAAATGCGCTGGAACAAGCTGAAGTGGCTGCTGA*
*GGATCTGGATATGATCTTGGTTGCAACTGTTACACCTGATCAGTCATTCCCTACGGTGTCTTGTATGATT*
*CAAGAACAACTCGGCGCGAAGAAAGCGTGTGCTATGGATATCAGCGCGGCTTGTGCGGGCTTCATGTACG*
*GGGTTGTAACCGGTAAACAATTTATTGAATCCGGAACCTACAAGCATGTTCTAGTTGTTGGTGTAGAGAA*
*GCTCTCAAGCATTACCGACTGGGAAGACCGCAATACAGCCGTTCTGTTTGGAGACGGAGCAGGCGCTGCG*
*GTAGTCGGGCCAGTCAGTGATGACAGAGGAATCCTTTCATTTGAACTAGGAGCCGACGGCACAGGCGGTC*
*AGCACTTGTATCTGAATGAAAAACGACATACAATCATGAATGGACGAGAAGTTTTCAAATTTGCAGTCCG*
*CCAAATGGGAGAATCATGCGTAAATGTCATTGAAAAAGCCGGACTTTCAAAAGAGGATGTGGACTTTTTG*
*ATTCCGCATCAGGCGAACATCCGTATCATGGAAGCTGCTCGCGAGCGTTTAGAGCTTCCTGTCGAAAAGA*
*TGTCTAAAACTGTTCATAAATATGGAAATACTTCTGCCGCATCCATTCCGATCTCTCTTGTAGAAGAATT*
*GGAAGCCGGTAAAATCAAAGACGGCGATGTGGTCGTTATGGTAGGGTTCGGCGGAGGACTAACATGGGGC*
*GCCATTGCAATCCGCTGGGGCCGATAAAAAAAAGGTGAGGTGCA*ctcgagtctggtaaagaaaccgctgc
tgcgaaatttgaacgccagcacatggactcgtctactagcgcagcttaattaacctaggctgctgccacc
gctgagcaataactagcataaccccttggggcctctaaacgggtcttgaggggttttttgctgaaacctc
aggcatttgagaagcacacggtcacactgcttccggtagtcaataaaccggtaaaccagcaatagacata
agcggctatttaacgaccctgccctgaaccgacgaccgggtcatcgtggccggatcttgcggcccctcgg
cttgaacgaattgttagacattatttgccgactaccttggtgatctcgcctttcacgtagtggacaaatt
cttccaactgatctgcgcgcgaggccaagcgatcttcttcttgtccaagataagcctgtctagcttcaag
tatgacgggctgatactgggccggcaggcgctccattgcccagtcggcagcgacatccttcggcgcgatt
ttgccggttactgcgctgtaccaaatgcgggacaacgtaagcactacatttcgctcatcgccagcccagt
cgggcggcgagttccatagcgttaaggtttcatttagcgcctcaaatagatcctgttcaggaaccggatc
aaagagttcctccgccgctggacctaccaaggcaacgctatgttctcttgcttttgtcagcaagatagcc
agatcaatgtcgatcgtggctggctcgaagatacctgcaagaatgtcattgcgctgccattctccaaatt
gcagttcgcgcttagctggataacgccacggaatgatgtcgtcgtgcacaacaatggtgacttctacagc
gcggagaatctcgctctctccaggggaagccgaagtttccaaaaggtcgttgatcaaagctcgccgcgtt
gtttcatcaagccttacggtcaccgtaaccagcaaatcaatatcactgtgtggcttcaggccgccatcca
ctgcggagccgtacaaatgtacggccagcaacgtcggttcgagatggcgctcgatgacgccaactacctc

FIG. 6C cont'd tgatagttgagtcgatacttcggcgatcaccgcttccctcatactcttcctttttcaatattattgaagc
atttatcagggttattgtctcatgagcggatacatatttgaatgtatttagaaaaataaacaaatagcta
gctcactcggtcgctacgctccgggcgtgagactgcggcgggcgctgcggacacatacaaagttacccac
agattccgtggataagcaggggactaacatgtgaggcaaaacagcagggccgcgccggtggcgtttttcc
ataggctccgccctcctgccagagttcacataaacagacgcttttccggtgcatctgtgggagccgtgag
gctcaaccatgaatctgacagtacgggcgaaacccgacaggacttaaagatccccaccgtttccggcggg
tcgctccctcttgcgctctcctgttccgaccctgccgtttaccggatacctgttccgcctttctccctta
cgggaagtgtggcgctttctcatagctcacacactggtatctcggctcggtgtaggtcgttcgctccaag
ctgggctgtaagcaagaactccccgttcagcccgactgctgcgccttatccggtaactgttcacttgagt
ccaacccggaaaagcacggtaaaacgccactggcagcagccattggtaactgggagttcgcagaggattt
gtttagctaaacacgcggttgctcttgaagtgtgcgccaaagtccggctacactggaaggacagatttgg
ttgctgtgctctgcgaaagccagttaccacggttaagcagttccccaactgacttaaccttcgatcaaac
cacctccccaggtggtttttttcgtttacagggcaaaagattacgcgcagaaaaaaaggatctcaagaaga
tcctttgatcttttctactgaaccgctctagatttcagtgcaatttatctcttcaaatgtagcacctgaa
gtcagccccatacgatataagttgtaattctcatgttagtcatgccccgcgcccaccggaaggagctgac
tgggttgaaggctctcaagggcatcggtcgagatcccggtgcctaatgagtgagctaacttacattaatt
gcgttgcgctcactgcccgctttccagtcgggaaacctgtcgtgccagctgcattaatgaatcggccaac
gcgcggggagaggcggtttgcgtattgggcgccagggtggtttttcttttcaccagtgagacgggcaaca
gctgattgcccttcaccgcctggccctgagagagttgcagcaagcggtccacgctggtttgccccagcag
gcgaaaatcctgtttgatggtggttaacggcgggatataacatgagctgtcttcggtatcgtcgtatccc
actaccgagatgtccgcaccaacgcgcagcccggactcggtaatggcgcgcattgcgcccagcgccatct
gatcgttggcaaccagcatcgcagtgggaacgatgccctcattcagcatttgcatggtttgttgaaaacc
ggacatggcactccagtcgccttcccgttccgctatcggctgaatttgattgcgagtgagatatttatgc
cagccagccagacgcagacgcgccgagacagaacttaatgggcccgctaacagcgcgatttgctggtgac
ccaatgcgaccagatgctccacgcccagtcgcgtaccgtcttcatgggagaaaataatactgttgatggg
tgtctggtcagagacatcaagaaataacgccggaacattagtgcaggcagcttccacagcaatggcatcc
tggtcatccagcggatagttaatgatcagcccactgacgcgttgcgcgagaagattgtgcaccgccgctt
tacaggcttcgacgccgcttcgttctaccatcgacaccaccacgctggcacccagttgatcggcgcgaga
tttaatcgccgcgacaatttgcgacggcgcgtgcagggccagactggaggtggcaacgccaatcagcaac
gactgtttgcccgccagttgttgtgccacgcggttgggaatgtaattcagctccgccatcgccgcttcca
ctttttcccgcgttttcgcagaaacgtggctggcctggttcaccacgcgggaaacggtctgataagagac
accggcatactctgcgacatcgtataacgttactggtttcacattcaccaccctgaattgactctcttcc
gggcgctatcatgccataccgcgaaaggttttgcgccattcgatggtgtccgggatctcgacgctctccc
ttatgcgactcctgcattaggaaattaatacgactcactata (SEQ ID NO:129)

FIG. 6D

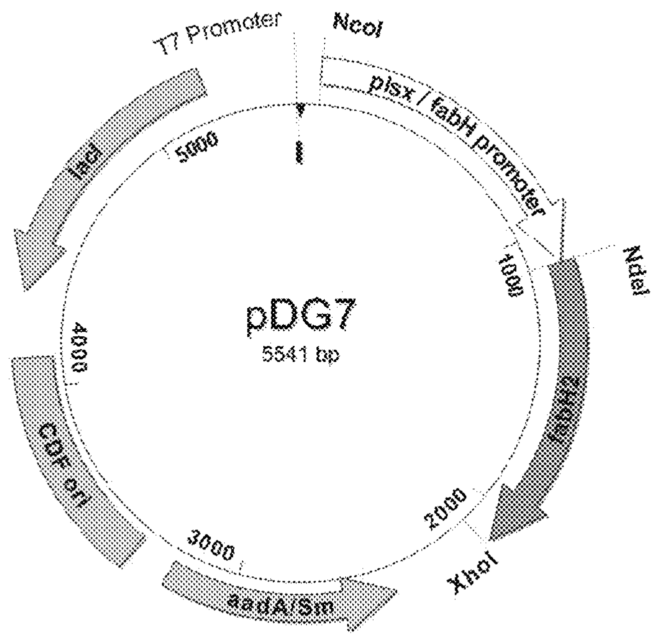

FIG. 6E

- pDG7 plasmid sequence:

```
   1 GGGGAATTGT GAGCGGATAA CAATTCCCCT GTAGAAATAA TTTTGTTTAA CTTTAATAAG
  61 GAGATATACC ATGGCGCAAC TCACTCTTCT TTTAGTCGGC AATTCCGACG CCATCACGCC
 121 ATTACTTGCT AAAGCTGACT TTGAACAACG TTCGCGTCTG CAGATTATTC CTGCGCAGTC
 181 AGTTATCGCC AGTGATGCCC GGCCTTCGCA AGCTATCCGC GCCAGTCGTG GGAGTTCAAT
 241 GCGCGTGGCC CTGGAGCTGG TGAAAGAAGG TCGAGCGCAA GCCTGTGTCA GTGCCGGTAA
 301 TACCGGGGCG CTGATGGGGC TGGCAAAATT ATTACTCAAG CCCCTGGAGG GGATTGAGCG
 361 TCCGGCGCTG GTGACGGTAT TACCACATCA GCAAAAGGGC AAAACGGTGG TCCTTGACTT
 421 AGGGGCCAAC GTCGATTGTG ACAGCACAAT GCTGGTGCAA TTTGCCATTA TGGGCTCAGT
 481 TCTGGCTGAA GAGGTGGTGG AAATTCCCAA TCCTCGCGTG GCGTTGCTCA ATATTGGTGA
 541 AGAAGAAGTA AAGGGTCTCG ACAGTATTCG GGATGCCTCA GCGGTGCTTA AAACAATCCC
 601 TTCTATCAAT TATATCGGCT ATCTTGAAGC CAATGAGTTG TTAACTGGCA AGACAGATGT
 661 GCTGGTTTGT GACGGCTTTA CAGGAAATGT CACATTAAAG ACGATGGAAG GTGTTGTCAG
 721 GATGTTCCTT TCTCTGCTGA AATCTCAGGG TGAAGGGAAA AAACGGTCGT GGTGGCTACT
 781 GTTATTAAAG CGTTGGCTAC AAAAGAGCCT GACGAGGCGA TTCAGTCACC TCAACCCCGA
 841 CCAGTATAAC GGCGCCTGTC TGTTAGGATT GCGCGGCACG GTGATAAAAA GTCATGGTGC
 901 AGCCAATCAG CGAGCTTTTG CGGTCGCGAT TGAACAGGCA GTGCAGGCGG TGCAGCGACA
 961 AGTTCCTCAG CGAATTGCCG CTCGCCTGGA ATCTGTATAC CCAGCTGGTT TTGAGCTGCT
1021 GGACGGTGGC AAAAGCGGAA CTCTGCGGTA GCAGGACGCT GCCAGCGAAC TCGCAGTTTG
1081 CAAGTGACGG TATATAACCG AAAAGTGACT GAGCGCATAT GTCAAAAGCA AAAATTACAG
1141 CTATCGGCAC CTATGCGCCG AGCAGACGTT TAACCAATGC AGATTTAGAA AAGATCGTTG
1201 ATACCTCTGA TGAATGGATC GTTCAGCGCA CAGGAATGAG AGAACGCCGG ATTGCGGATG
1261 AACATCAATT TACCTCTGAT TTATGCATAG AAGCGGTGAA GAATCTCAAG AGCCGTTATA
```

FIG. 6E cont'd

```
1321 AAGGAACGCT TGATGATGTC GATATGATCC TCGTTGCCAC AACCACATCC GATTACGCCT
1381 TTCCGAGTAC GGCATGCCGC GTACAGGAAT ATTTCGGCTG GGAAAGCACC GGCGCGCTGG
1441 ATATTAATGC GACATGCGCC GGGCTGACAT ACGGCCTCCA TTTGGCAAAT GGATTGATCA
1501 CATCTGGCCT TCATCAAAAA ATTCTCGTCA TCGCCGGAGA GACGTTATCA AAGGTAACCG
1561 ATTATACGGA TCGAACGACA TGCGTACTGT TCGGCGATGC CGCGGGTGCG CTGTTAGTAG
1621 AACGAGATGA AGAGACGCCG GGATTTCTTG CGTCTGTACA AGGAACAAGC GGGAACGGCG
1681 GCGATATTTT GTATCGTGCC GGACTGCGAA ATGAAATAAA CGGTGTGCAG CTTGTCGGTT
1741 CCGGAAAAAT GGTGCAAAAC GGACGCGAGG TATATAAATG GGCCGCAAGA ACCGTCCCTG
1801 GCGAATTTGA ACGGCTTTTA CATAAAGCAG GACTCAGCTC CGATGATCTC GATTGGTTTG
1861 TTCCTCACAG CGCCAACTTG CGCATGATCG AGTCAATTTG TGAAAAAACA CCGTTCCCGA
1921 TTGAAAAAAC GCTCACTAGC GTTGAGCACT ACGGAAACAC GTCTTCGGTT TCAATTGTTT
1981 TGGCGCTCGA TCTCGCAGTG AAAGCCGGGA AGCTGAAAAA AGATCAAATC GTTTTGCTTT
2041 TCGGGTTTGG CGGCGGATTA ACCTATACAG GATTGCTTAT TAAATGGGGG ATGTAAAGAT
2101 CTCCTAGGCG TCACTCGAGT CTGGTAAAGA AACCGCTGCT GCGAAATTTG AACGCCAGCA
2161 CATGGACTCG TCTACTAGCG CAGCTTAATT AACCTAGGCT GCTGCCACCG CTGAGCAATA
2221 ACTAGCATAA CCCCTTGGGG CCTCTAAACG GGTCTTGAGG GGTTTTTTGC TGAAACCTCA
2281 GGCATTTGAG AAGCACACGG TCACACTGCT TCCGGTAGTC AATAAACCGG TAAACCAGCA
2341 ATAGACATAA GCGGCTATTT AACGACCCTG CCCTGAACCG ACGACCGGGT CATCGTGGCC
2401 GGATCTTGCG GCCCCTCGGC TTGAACGAAT TGTTAGACAT TATTTGCCGA CTACCTTGGT
2461 GATCTCGCCT TTCACGTAGT GGACAAATTC TTCCAACTGA TCTGCGCGCG AGGCCAAGCG
2521 ATCTTCTTCT TGTCCAAGAT AAGCCTGTCT AGCTTCAAGT ATGACGGGCT GATACTGGGC
2581 CGGCAGGCGC TCCATTGCCC AGTCGGCAGC GACATCCTTC GGCGCGATTT TGCCGGTTAC
2641 TGCGCTGTAC CAAATGCGGG ACAACGTAAG CACTACATTT CGCTCATCGC CAGCCCAGTC
2701 GGGCGGCGAG TTCCATAGCG TTAAGGTTTC ATTTAGCGCC TCAAATAGAT CCTGTTCAGG
2761 AACCGGATCA AAGAGTTCCT CCGCCGCTGG ACCTACCAAG GCAACGCTAT GTTCTCTTGC
2821 TTTTGTCAGC AAGATAGCCA GATCAATGTC GATCGTGGCT GGCTCGAAGA TACCTGCAAG
2881 AATGTCATTG CGCTGCCATT CTCCAAATTG CAGTTCGCGC TTAGCTGGAT AACGCCACGG
2941 AATGATGTCG TCGTGCACAA CAATGGTGAC TTCTACAGCG CGGAGAATCT CGCTCTCTCC
3001 AGGGGAAGCC GAAGTTTCCA AAAGGTCGTT GATCAAAGCT CGCCGCGTTG TTTCATCAAG
3061 CCTTACGGTC ACCGTAACCA GCAAATCAAT ATCACTGTGT GGCTTCAGGC CGCCATCCAC
3121 TGCGGAGCCG TACAAATGTA CGGCCAGCAA CGTCGGTTCG AGATGGCGCT CGATGACGCC
3181 AACTACCTCT GATAGTTGAG TCGATACTTC GGCGATCACC GCTTCCCTCA TACTCTTCCT
3241 TTTTCAATAT TATTGAAGCA TTTATCAGGG TTATTGTCTC ATGAGCGGAT ACATATTTGA
3301 ATGTATTTAG AAAAATAAAC AAATAGCTAG CTCACTCGGT CGCTACGCTC CGGGCGTGAG
3361 ACTGCGGCGG GCGCTGCGGA CACATACAAA GTTACCCACA GATTCCGTGG ATAAGCAGGG
3421 GACTAACATG TGAGGCAAAA CAGCAGGGCC GCGCCGGTGG CGTTTTTCCA TAGGCTCCGC
3481 CCTCCTGCCA GAGTTCACAT AAACAGACGC TTTTCCGGTG CATCTGTGGG AGCCGTGAGG
3541 CTCAACCATG AATCTGACAG TACGGGCGAA ACCCGACAGG ACTTAAAGAT CCCCACCGTT
3601 TCCGGCGGGT CGCTCCCTCT TGCGCTCTCC TGTTCCGACC CTGCCGTTTA CCGGATACCT
3661 GTTCCGCCTT TCTCCCTTAC GGGAAGTGTG GCGCTTTCTC ATAGCTCACA CACTGGTATC
3721 TCGGCTCGGT GTAGGTCGTT CGCTCCAAGC TGGGCTGTAA GCAAGAACTC CCCGTTCAGC
3781 CCGACTGCTG CGCCTTATCC GGTAACTGTT CACTTGAGTC CAACCCGGAA AAGCACGGTA
3841 AAACGCCACT GGCAGCAGCC ATTGGTAACT GGGAGTTCGC AGAGGATTTG TTTAGCTAAA
3901 CACGCGGTTG CTCTTGAAGT GTGCGCCAAA GTCCGGCTAC ACTGGAAGGA CAGATTTGGT
3961 TGCTGTGCTC TGCGAAAGCC AGTTACCACG GTTAAGCAGT TCCCCAACTG ACTTAACCTT
4021 CGATCAAACC ACCTCCCCAG GTGGTTTTTT CGTTTACAGG GCAAAAGATT ACGCGCAGAA
4081 AAAAAGGATC TCAAGAAGAT CCTTTGATCT TTTCTACTGA ACCGCTCTAG ATTTCAGTGC
4141 AATTTATCTC TTCAAATGTA GCACCTGAAG TCAGCCCCAT ACGATATAAG TTGTAATTCT
4201 CATGTTAGTC ATGCCCCGCG CCCACCGGAA GGAGCTGACT GGGTTGAAGG CTCTCAAGGG
4261 CATCGGTCGA GATCCCGGTG CCTAATGAGT GAGCTAACTT ACATTAATTG CGTTGCGCTC
4321 ACTGCCCGCT TTCCAGTCGG GAAACCTGTC GTGCCAGCTG CATTAATGAA TCGGCCAACG
4381 CGCGGGGAGA GGCGGTTTGC GTATTGGGCG CCAGGGTGGT TTTTCTTTTC ACCAGTGAGA
```

FIG. 6E cont'd

```
4441 CGGGCAACAG CTGATTGCCC TTCACCGCCT GGCCCTGAGA GAGTTGCAGC AAGCGGTCCA
4501 CGCTGGTTTG CCCCAGCAGG CGAAAATCCT GTTTGATGGT GGTTAACGGC GGGATATAAC
4561 ATGAGCTGTC TTCGGTATCG TCGTATCCCA CTACCGAGAT GTCCGCACCA ACGCGCAGCC
4621 CGGACTCGGT AATGGCGCGC ATTGCGCCCA GCGCCATCTG ATCGTTGGCA ACCAGCATCG
4681 CAGTGGGAAC GATGCCCTCA TTCAGCATTT GCATGGTTTG TTGAAAACCG GACATGGCAC
4741 TCCAGTCGCC TTCCCGTTCC GCTATCGGCT GAATTTGATT GCGAGTGAGA TATTTATGCC
4801 AGCCAGCCAG ACGCAGACGC GCCGAGACAG AACTTAATGG GCCCGCTAAC AGCGCGATTT
4861 GCTGGTGACC CAATGCGACC AGATGCTCCA CGCCCAGTCG CGTACCGTCT TCATGGGAGA
4921 AAATAATACT GTTGATGGGT GTCTGGTCAG AGACATCAAG AAATAACGCC GGAACATTAG
4981 TGCAGGCAGC TTCCACAGCA ATGGCATCCT GGTCATCCAG CGGATAGTTA ATGATCAGCC
5041 CACTGACGCG TTGCGCGAGA AGATTGTGCA CCGCCGCTTT ACAGGCTTCG ACGCCGCTTC
5101 GTTCTACCAT CGACACCACC ACGCTGGCAC CCAGTTGATC GGCGCGAGAT TTAATCGCCG
5161 CGACAATTTG CGACGGCGCG TGCAGGGCCA GACTGGAGGT GGCAACGCCA ATCAGCAACG
5221 ACTGTTTGCC CGCCAGTTGT TGTGCCACGC GGTTGGGAAT GTAATTCAGC TCCGCCATCG
5281 CCGCTTCCAC TTTTTCCCGC GTTTTCGCAG AAACGTGGCT GGCCTGGTTC ACCACGCGGG
5341 AAACGGTCTG ATAAGAGACA CCGGCATACT CTGCGACATC GTATAACGTT ACTGGTTTCA
5401 CATTCACCAC CCTGAATTGA CTCTCTTCCG GGCGCTATCA TGCCATACCG CGAAAGGTTT
5461 TGCGCCATTC GATGGTGTCC GGGATCTCGA CGCTCTCCCT TATGCGACTC CTGCATTAGG
5521 AAATTAATAC GACTCACTAT A (SEQ ID NO:130)
```

FIG. 6F

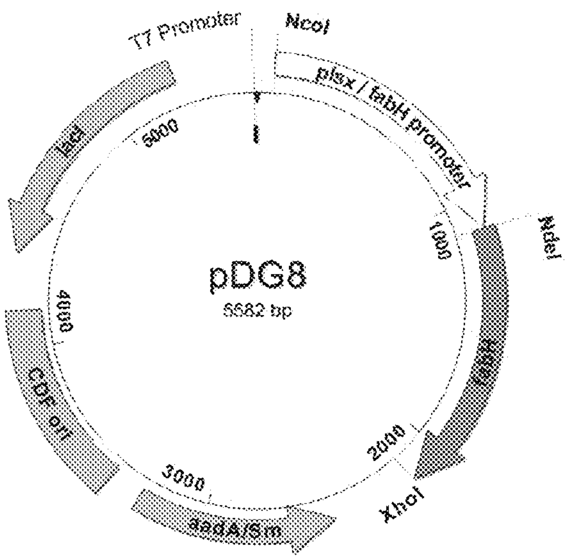

FIG. 6G pDG8 plasmid sequence:

```
 1 GGGGAATTGT GAGCGGATAA CAATTCCCCT GTAGAAATAA TTTTGTTTAA CTTTAATAAG
61 GAGATATACC ATGGCGCAAC TCACTCTTCT TTTAGTCGGC AATTCCGACG CCATCACGCC
```

FIG. 6G cont'd

```
 121 ATTACTTGCT AAAGCTGACT TTGAACAACG TTCGCGTCTG CAGATTATTC CTGCGCAGTC
 181 AGTTATCGCC AGTGATGCCC GGCCTTCGCA AGCTATCCGC GCCAGTCGTG GGAGTTCAAT
 241 GCGCGTGGCC CTGGAGCTGG TGAAAGAAGG TCGAGCGCAA GCCTGTGTCA GTGCCGGTAA
 301 TACCGGGGCG CTGATGGGGC TGGCAAAATT ATTACTCAAG CCCCTGGAGG GGATTGAGCG
 361 TCCGGCGCTG GTGACGGTAT TACCACATCA GCAAAAGGGC AAAACGGTGG TCCTTGACTT
 421 AGGGGCCAAC GTCGATTGTG ACAGCACAAT GCTGGTGCAA TTTGCCATTA TGGGCTCAGT
 481 TCTGGCTGAA GAGGTGGTGG AAATTCCCAA TCCTCGCGTG GCGTTGCTCA ATATTGGTGA
 541 AGAAGAAGTA AAGGGTCTCG ACAGTATTCG GGATGCCTCA GCGGTGCTTA AAACAATCCC
 601 TTCTATCAAT TATATCGGCT ATCTTGAAGC CAATGAGTTG TTAACTGGCA AGACAGATGT
 661 GCTGGTTTGT GACGGCTTTA CAGGAAATGT CACATTAAAG ACGATGGAAG GTGTTGTCAG
 721 GATGTTCCTT TCTCTGCTGA AATCTCAGGG TGAAGGGAAA AAACGGTCGT GGTGGCTACT
 781 GTTATTAAAG CGTTGGCTAC AAAAGAGCCT GACGAGGCGA TTCAGTCACC TCAACCCCGA
 841 CCAGTATAAC GGCGCCTGTC TGTTAGGATT GCGCGGCACG GTGATAAAAA GTCATGGTGC
 901 AGCCAATCAG CGAGCTTTTG CGGTCGCGAT TGAACAGGCA GTGCAGGCGG TGCAGCGACA
 961 AGTTCCTCAG CGAATTGCCG CTCGCCTGGA ATCTGTATAC CCAGCTGGTT TTGAGCTGCT
1021 GGACGGTGGC AAAAGCGGAA CTCTGCGGTA GCAGGACGCT GCCAGCGAAC TCGCAGTTTG
1081 CAAGTGACGG TATATAACCG AAAAGTGACT GAGCGCATAT GTCTAAGATC AAGCCAAGCA
1141 AGGGCGCTCC GTACGCGCGC ATCCTGGGCG TCGGCGGTTA CCGTCCGACC CGTGTGGTGC
1201 CGAACGAGGT GATCCTGGAG AAGATCGACT CTTCCGACGA GTGGATTCGC TCTCGCTCCG
1261 GCATCGAAAC GCGTCACTGG GCGGGTCCGG AAGAAACCGT CGCGGCGATG TCTGTGGAGG
1321 CCTCCGGCAA GGCACTGGCC GACGCCGGTA TCGACGCCTC TCGTATCGGT GCCGTGGTAG
1381 TCTCTACCGT GTCTCACTTC AGCCAGACCC CGGCCATCGC CACCGAGATC GCCGACCGCC
1441 TGGGCACGGA CAAGGCCGCA GCCTTCGACA TCTCTGCCGG CTGCGCGGGC TTCGGCTACG
1501 GTCTGACCCT GGCCAAGGGC ATGGTCGTCG AAGGTTCTGC GGAGTACGTG CTGGTCATCG
1561 GCGTGGAGCG TCTGTCCGAC CTGACCGACC TGGAGGACCG TGCCACGGCC TTCCTGTTCG
1621 GCGACGGCGC TGGTGCGGTC GTGGTCGGCC CGTCCCAGGA GCCGGCAATC GGCCCGACGG
1681 TCTGGGGCTC TGAGGGCGAC AAGGCCGAAA CGATCAAGCA GACCGTTTCC TGGGACCGCT
1741 TCCGTATCGG CGATGTCTCC GAACTGCCGC TGGACTCCGA GGGCAACGTC AAGTTTCCTG
1801 CGATCACGCA GGAGGGCCAG GCGGTGTTCC GCTGGGCCGT GTTCGAGATG GCGAAGGTCG
1861 CGCAGCAGGC GCTGGACGCG GCGGGTATCA GCCCGGACGA CCTGGACGTC TTTATCCCGC
1921 ACCAGGCCAA TGTGCGTATC ATCGACTCTA TGGTGAAAAC CCTGAAGCTG CCGGAGCACG
1981 TCACGGTCGC CCGTGACATC CGCACCACCG GCAACACCTC TGCCGCCTCT ATTCCGCTGG
2041 CGATGGAGCG TCTGCTGGCG ACCGGCGACG CGCGTAGCGG CGACACCGCG CTGGTCATCG
2101 GCTTCGGTGC GGGTCTGGTC TACGCCGCGA CGGTCGTTAC CCTGCCGTAA CCACCTCGAG
2161 TCTGGTAAAG AAACCGCTGC TGCGAAATTT GAACGCCAGC ACATGGACTC GTCTACTAGC
2221 GCAGCTTAAT TAACCTAGGC TGCTGCCACC GCTGAGCAAT AACTAGCATA ACCCCTTGGG
2281 GCCTCTAAAC GGGTCTTGAG GGGTTTTTTG CTGAAACCTC AGGCATTTGA GAAGCACACG
2341 GTCACACTGC TTCCGGTAGT CAATAAACCG GTAAACCAGC AATAGACATA AGCGGCTATT
2401 TAACGACCCT GCCCTGAACC GACGACCGGG TCATCGTGGC CGGATCTTGC GGCCCCTCGG
2461 CTTGAACGAA TTGTTAGACA TTATTTGCCG ACTACCTTGG TGATCTCGCC TTTCACGTAG
2521 TGGACAAATT CTTCCAACTG ATCTGCGCGC GAGGCCAAGC GATCTTCTTC TTGTCCAAGA
2581 TAAGCCTGTC TAGCTTCAAG TATGACGGGC TGATACTGGG CCGGCAGGCG CTCCATTGCC
2641 CAGTCGGCAG CGACATCCTT CGGCGCGATT TTGCCGGTTA CTGCGCTGTA CCAAATGCGG
2701 GACAACGTAA GCACTACATT TCGCTCATCG CCAGCCCAGT CGGGCGGCGA GTTCCATAGC
2761 GTTAAGGTTT CATTTAGCGC CTCAAATAGA TCCTGTTCAG GAACCGGATC AAAGAGTTCC
2821 TCCGCCGCTG GACCTACCAA GGCAACGCTA TGTTCTCTTG CTTTTGTCAG CAAGATAGCC
2881 AGATCAATGT CGATCGTGGC TGGCTCGAAG ATACCTGCAA GAATGTCATT GCGCTGCCAT
2941 TCTCCAAATT GCAGTTCGCG CTTAGCTGGA TAACGCCACG GAATGATGTC GTCGTGCACA
3001 ACAATGGTGA CTTCTACAGC GCGGAGAATC TCGCTCTCTC CAGGGGAAGC CGAAGTTTCC
3061 AAAAGGTCGT TGATCAAAGC TCGCCGCGTT GTTTCATCAA GCCTTACGGT CACCGTAACC
3121 AGCAAATCAA TATCACTGTG TGGCTTCAGG CCGCCATCCA CTGCGGAGCC GTACAAATGT
3181 ACGGCCAGCA ACGTCGGTTC GAGATGGCGC TCGATGACGC CAACTACCTC TGATAGTTGA
```

FIG. 6G cont'd

3241 GTCGATACTT CGGCGATCAC CGCTTCCCTC ATACTCTTCC TTTTTCAATA TTATTGAAGC
3301 ATTTATCAGG GTTATTGTCT CATGAGCGGA TACATATTTG AATGTATTTA GAAAAATAAA
3361 CAAATAGCTA GCTCACTCGG TCGCTACGCT CCGGGCGTGA GACTGCGGCG GGCGCTGCGG
3421 ACACATACAA AGTTACCCAC AGATTCCGTG GATAAGCAGG GGACTAACAT GTGAGGCAAA
3481 ACAGCAGGGC CGCGCCGGTG GCGTTTTTCC ATAGGCTCCG CCCTCCTGCC AGAGTTCACA
3541 TAAACAGACG CTTTTCCGGT GCATCTGTGG GAGCCGTGAG GCTCAACCAT GAATCTGACA
3601 GTACGGGCGA AACCCGACAG GACTTAAAGA TCCCCACCGT TTCCGGCGGG TCGCTCCCTC
3661 TTGCGCTCTC CTGTTCCGAC CCTGCCGTTT ACCGGATACC TGTTCCGCCT TTCTCCCTTA
3721 CGGGAAGTGT GGCGCTTTCT CATAGCTCAC ACACTGGTAT CTCGGCTCGG TGTAGGTCGT
3781 TCGCTCCAAG CTGGGCTGTA AGCAAGAACT CCCCGTTCAG CCCGACTGCT GCGCCTTATC
3841 CGGTAACTGT TCACTTGAGT CCAACCCGGA AAAGCACGGT AAAACGCCAC TGGCAGCAGC
3901 CATTGGTAAC TGGGAGTTCG CAGAGGATTT GTTTAGCTAA ACACGCGGTT GCTCTTGAAG
3961 TGTGCGCCAA AGTCCGGCTA CACTGGAAGG ACAGATTTGG TTGCTGTGCT CTGCGAAAGC
4021 CAGTTACCAC GGTTAAGCAG TTCCCCAACT GACTTAACCT TCGATCAAAC CACCTCCCCA
4081 GGTGGTTTTT TCGTTTACAG GGCAAAAGAT TACGCGCAGA AAAAAAGGAT CTCAAGAAGA
4141 TCCTTTGATC TTTTCTACTG AACCGCTCTA GATTTCAGTG CAATTTATCT CTTCAAATGT
4201 AGCACCTGAA GTCAGCCCCA TACGATATAA GTTGTAATTC TCATGTTAGT CATGCCCCGC
4261 GCCCACCGGA AGGAGCTGAC TGGGTTGAAG GCTCTCAAGG GCATCGGTCG AGATCCCGGT
4321 GCCTAATGAG TGAGCTAACT TACATTAATT GCGTTGCGCT CACTGCCCGC TTTCCAGTCG
4381 GGAAACCTGT CGTGCCAGCT GCATTAATGA ATCGGCCAAC GCGCGGGGAG AGGCGGTTTG
4441 CGTATTGGGC GCCAGGGTGG TTTTTCTTTT CACCAGTGAG ACGGGCAACA GCTGATTGCC
4501 CTTCACCGCC TGGCCCTGAG AGAGTTGCAG CAAGCGGTCC ACGCTGGTTT GCCCCAGCAG
4561 GCGAAAATCC TGTTTGATGG TGGTTAACGG CGGGATATAA CATGAGCTGT CTTCGGTATC
4621 GTCGTATCCC ACTACCGAGA TGTCCGCACC AACGCGCAGC CCGGACTCGG TAATGGCGCG
4681 CATTGCGCCC AGCGCCATCT GATCGTTGGC AACCAGCATC GCAGTGGGAA CGATGCCCTC
4741 ATTCAGCATT TGCATGGTTT GTTGAAAACC GGACATGGCA CTCCAGTCGC CTTCCCGTTC
4801 CGCTATCGGC TGAATTTGAT TGCGAGTGAG ATATTTATGC CAGCCAGCCA GACGCAGACG
4861 CGCCGAGACA GAACTTAATG GGCCCGCTAA CAGCGCGATT TGCTGGTGAC CCAATGCGAC
4921 CAGATGCTCC ACGCCCAGTC GCGTACCGTC TTCATGGGAG AAAATAATAC TGTTGATGGG
4981 TGTCTGGTCA GAGACATCAA GAAATAACGC CGGAACATTA GTGCAGGCAG CTTCCACAGC
5041 AATGGCATCC TGGTCATCCA GCGGATAGTT AATGATCAGC CCACTGACGC GTTGCGCGAG
5101 AAGATTGTGC ACCGCCGCTT TACAGGCTTC GACGCCGCTT CGTTCTACCA TCGACACCAC
5161 CACGCTGGCA CCCAGTTGAT CGGCGCGAGA TTTAATCGCC GCGACAATTT GCGACGGCGC
5221 GTGCAGGGCC AGACTGGAGG TGGCAACGCC AATCAGCAAC GACTGTTTGC CCGCCAGTTG
5281 TTGTGCCACG CGGTTGGGAA TGTAATTCAG CTCCGCCATC GCCGCTTCCA CTTTTTCCCG
5341 CGTTTTCGCA GAAACGTGGC TGGCCTGGTT CACCACGCGG GAAACGGTCT GATAAGAGAC
5401 ACCGGCATAC TCTGCGACAT CGTATAACGT TACTGGTTTC ACATTCACCA CCCTGAATTG
5461 ACTCTCTTCC GGGCGCTATC ATGCCATACC GCGAAAGGTT TTGCGCCATT CGATGGTGTC
5521 CGGGATCTCG ACGCTCTCCC TTATGCGACT CCTGCATTAG GAAATTAATA CGACTCACTA
5581 TA (SEQ ID NO:131)

FIG. 6H

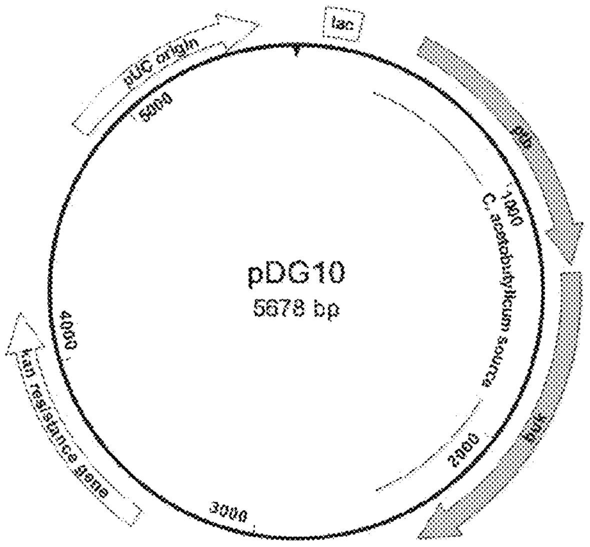

FIG. 6I

-pDG10 plasmid sequence:

```
   1 AGCGCCCAAT ACGCAAACCG CCTCTCCCCG CGCGTTGGCC GATTCATTAA TGCAGCTGGC
  61 ACGACAGGTT TCCCGACTGG AAAGCGGGCA GTGAGCGCAA CGCAATTAAT GTGAGTTAGC
 121 TCACTCATTA GGCACCCCAG GCTTTACACT TTATGCTTCC GGCTCGTATG TTGTGTGGAA
 181 TTGTGAGCGG ATAACAATTT CACACAGGAA ACAGCTATGA CCATGATTAC GCCAAGCTAT
 241 TTAGGTGACG CGTTAGAATA CTCAAGCTAT GCATCAAGCT TGGTACCGAG CTCGGATCCA
 301 CTAGTAACGG CCGCCAGTGT GCTGGAATTC AGGCTTAACT TCATGTGAAA AGTTTGTTAA
 361 AATATAAATG AGCACGTTAA TCATTTAACA TAGATAATTA AATAGTAAAA GGGAGTGTAC
 421 GACCAGTGAT TAAGAGTTTT AATGAAATTA TCATGAAGGT AAAGAGCAAA GAAATGAAAA
 481 AAGTTGCTGT TGCTGTAGCA CAAGACGAGC CAGTACTTGA AGCAGTAAGA GATGCTAAGA
 541 AAAATGGTAT TGCAGATGCT ATTCTTGTTG GAGACCATGA CGAAATCGTG TCAATCGCGC
 601 TTAAAATAGG AATGGATGTA AATGATTTTG AAATAGTAAA CGAGCCTAAC GTTAAGAAAG
 661 CTGCTTTAAA GGCAGTAGAG CTTGTATCAA CTGGAAAAGC TGATATGGTA ATGAAGGGAC
 721 TTGTAAATAC AGCAACTTTC TTAAGATCTG TATTAAACAA AGAAGTTGGA CTTAGAACAG
 781 GAAAAACTAT GTCTCACGTT GCAGTATTTG AAACTGAGAA ATTTGATAGA CTATTATTTT
 841 TAACAGATGT TGCTTTCAAT ACTTATCCTG AATTAAAGGA AAAAATTGAT ATAGTAAACA
 901 ATTCAGTTAA GGTTGCACAT GCAATAGGAA TTGAAAATCC AAAGGTTGCT CCAATTTGTG
 961 CAGTTGAGGT TATAAACCCT AAAATGCCAT CAACACTTGA TGCAGCAATG CTTTCAAAAA
1021 TGAGTGACAG AGGACAAATT AAAGGTTGTG TAGTTGACGG ACCTTTAGCA CTTGATATAG
1081 CTTTATCAGA AGAAGCAGCA CATCATAAGG GAGTAACAGG AGAAGTTGCT GGAAAAGCTG
1141 ATATCTTCTT AATGCCAAAC ATAGAAACAG GAAATGTAAT GTATAAGACT TTAACATATA
1201 CAACTGATTC AAAAAATGGA GGAATCTTAG TTGGAACTTC TGCACCAGTT GTTTTAACTT
1261 CAAGAGCTGA CAGCCATGAA ACAAAAATGA ACTCTATAGC ACTTGCAGCT TTAGTTGCAG
```

FIG. 6I cont'd

1321 GCAATAAATA AATTAAAGTT AAGTGGAGGA ATGTTAACAT GTATAGATTA CTAATAATCA
1381 ATCCTGGCTC GACCTCAACT AAAATTGGTA TTTATGACGA TGAAAAAGAG ATATTTGAGA
1441 AGACTTTAAG ACATTCAGCT GAAGAGATAG AAAAATATAA CACTATATTT GATCAATTTC
1501 AATTCAGAAA GAATGTAATT TTAGATGCGT TAAAAGAAGC AAACATAGAA GTAAGTTCTT
1561 TAAATGCTGT AGTTGGAAGA GGCGGACTCT TAAAGCCAAT AGTAAGTGGA ACTTATGCAG
1621 TAAATCAAAA AATGCTTGAA GACCTTAAAG TAGGAGTTCA AGGTCAGCAT GCGTCAAATC
1681 TTGGTGGAAT TATTGCAAAT GAAATAGCAA AAGAAATAAA TGTTCCAGCA TACATAGTTG
1741 ATCCAGTTGT TGTGGATGAG CTTGATGAAG TTTCAAGAAT ATCAGGAATG GCTGACATTC
1801 CAAGAAAAAG TATATTCCAT GCATTAAATC AAAAAGCAGT TGCTAGAAGA TATGCAAAAG
1861 AAGTTGGAAA AAAATACGAA GATCTTAATT TAATCGTAGT CCACATGGGT GGAGGTACTT
1921 CAGTAGGTAC TCATAAAGAT GGTAGAGTAA TAGAAGTTAA TAATACACTT GATGGAGAAG
1981 GTCCATTCTC ACCAGAAAGA AGTGGTGGAG TTCCAATAGG AGATCTTGTA AGATTGTGCT
2041 TCAGCAACAA ATATACTTAT GAAGAAGTAA TGAAAAAGAT AAACGGCAAA GGCGGAGTTG
2101 TTAGTTACTT AAATACTATC GATTTTAAGG CTGTAGTTGA TAAAGCTCTT GAAGGAGATA
2161 AGAAATGTGC ACTTATATAT GAAGCTTTCA CATTCCAGGT AGCAAAAGAG ATAGGAAAAT
2221 GTTCAACCGT TTTAAAAGGA AATGTAGATG CAATAATCTT AACAGGCGGA ATTGCGTACA
2281 ACGAGCATGT ATGTAATGCC ATAGAGGATA GAGTAAAATT CATAGCACCT GTAGTTAGAT
2341 ATGGTGGAGA AGATGAACTT CTTGCACTTG CAGAAGGTGG ACTTAGAGTT TTAAGAGGAG
2401 AAGAAAAAGC TAAGGAATAC AAATAATAAA GTCATAAATA ATATAATATA ACCAGTACCC
2461 ATGTTTATAA AACTTTTGCC CTATAAACAT GGGTATTGTC CTGAATTCTG CAGATATCCA
2521 TCACACTGGC GGCCGCTCGA GCATGCATCT AGAGGGCCCA ATTCGCCCTA TAGTGAGTCG
2581 TATTACAATT CACTGGCCGT CGTTTTACAA CGTCGTGACT GGGAAAACCC TGGCGTTACC
2641 CAACTTAATC GCCTTGCAGC ACATCCCCCT TTCGCCAGCT GGCGTAATAG CGAAGAGGCC
2701 CGCACCGATC GCCCTTCCCA ACAGTTGCGC AGCCTATACG TACGGCAGTT TAAGGTTTAC
2761 ACCTATAAAA GAGAGAGCCG TTATCGTCTG TTTGTGGATG TACAGAGTGA TATTATTGAC
2821 ACGCCGGGGC GACGGATGGT GATCCCCCTG GCCAGTGCAC GTCTGCTGTC AGATAAAGTC
2881 TCCCGTGAAC TTTACCCGGT GGTGCATATC GGGGATGAAA GCTGGCGCAT GATGACCACC
2941 GATATGGCCA GTGTGCCGGT CTCCGTTATC GGGGAAGAAG TGGCTGATCT CAGCCACCGC
3001 GAAAATGACA TCAAAAACGC CATTAACCTG ATGTTCTGGG GAATATAAAT GTCAGGCATG
3061 AGATTATCAA AAAGGATCTT CACCTAGATC CTTTTCACGT AGAAAGCCAG TCCGCAGAAA
3121 CGGTGCTGAC CCCGGATGAA TGTCAGCTAC TGGGCTATCT GGACAAGGGA AAACGCAAGC
3181 GCAAAGAGAA AGCAGGTAGC TTGCAGTGGG CTTACATGGC GATAGCTAGA CTGGGCGGTT
3241 TTATGGACAG CAAGCGAACC GGAATTGCCA GCTGGGGCGC CCTCTGGTAA GGTTGGGAAG
3301 CCCTGCAAAG TAAACTGGAT GGCTTTCTTG CCGCCAAGGA TCTGATGGCG CAGGGGATCA
3361 AGCTCTGATC AAGAGACAGG ATGAGGATCG TTTCGCATGA TTGAACAAGA TGGATTGCAC
3421 GCAGGTTCTC CGGCCGCTTG GGTGGAGAGG CTATTCGGCT ATGACTGGGC ACAACAGACA
3481 ATCGGCTGCT CTGATGCCGC CGTGTTCCGG CTGTCAGCGC AGGGGCGCCC GGTTCTTTTT
3541 GTCAAGACCG ACCTGTCCGG TGCCCTGAAT GAACTGCAAG ACGAGGCAGC GCGGCTATCG
3601 TGGCTGGCCA CGACGGGCGT TCCTTGCGCA GCTGTGCTCG ACGTTGTCAC TGAAGCGGGA
3661 AGGGACTGGC TGCTATTGGG CGAAGTGCCG GGGCAGGATC TCCTGTCATC TCACCTTGCT
3721 CCTGCCGAGA AAGTATCCAT CATGGCTGAT GCAATGCGGC GGCTGCATAC GCTTGATCCG
3781 GCTACCTGCC CATTCGACCA CCAAGCGAAA CATCGCATCG AGCGAGCACG TACTCGGATG
3841 GAAGCCGGTC TTGTCGATCA GGATGATCTG GACGAAGAGC ATCAGGGGCT CGCGCCAGCC
3901 GAACTGTTCG CCAGGCTCAA GGCGAGCATG CCCGACGGCG AGGATCTCGT CGTGACCCAT
3961 GGCGATGCCT GCTTGCCGAA TATCATGGTG GAAAATGGCC GCTTTTCTGG ATTCATCGAC
4021 TGTGGCCGGC TGGGTGTGGC GGACCGCTAT CAGGACATAG CGTTGGCTAC CCGTGATATT
4081 GCTGAAGAGC TTGGCGGCGA ATGGGCTGAC CGCTTCCTCG TGCTTTACGG TATCGCCGCT
4141 CCCGATTCGC AGCGCATCGC CTTCTATCGC CTTCTTGACG AGTTCTTCTG AATTATTAAC
4201 GCTTACAATT TCCTGATGCG GTATTTTCTC CTTACGCATC TGTGCGGTAT TTCACACCGC
4261 ATCAGGTGGC ACTTTTCGGG GAAATGTGCG CGGAACCCCT ATTTGTTTAT TTTTCTAAAT
4321 ACATTCAAAT ATGTATCCGC TCATGAGACA ATAACCCTGA TAAATGCTTC AATAATAGCA
4381 CGTGAGGAGG GCCACCATGG CCAAGTTGAC CAGTGCCGTT CCGGTGCTCA CCGCGCGCGA

FIG. 6I cont'd

4441 CGTCGCCGGA GCGGTCGAGT TCTGGACCGA CCGGCTCGGG TTCTCCCGGG ACTTCGTGGA
4501 GGACGACTTC GCCGGTGTGG TCCGGGACGA CGTGACCCTG TTCATCAGCG CGGTCCAGGA
4561 CCAGGTGGTG CCGGACAACA CCCTGGCCTG GGTGTGGGTG CGCGGCCTGG ACGAGCTGTA
4621 CGCCGAGTGG TCGGAGGTCG TGTCCACGAA CTTCCGGGAC GCCTCCGGGC CGGCCATGAC
4681 CGAGATCGGC GAGCAGCCGT GGGGGCGGGA GTTCGCCCTG CGCGACCCGG CCGGCAACTG
4741 CGTGCACTTC GTGGCCGAGG AGCAGGACTG ACACGTGCTA AAACTTCATT TTTAATTTAA
4801 AAGGATCTAG GTGAAGATCC TTTTTGATAA TCTCATGACC AAAATCCCTT AACGTGAGTT
4861 TTCGTTCCAC TGAGCGTCAG ACCCCGTAGA AAAGATCAAA GGATCTTCTT GAGATCCTTT
4921 TTTTCTGCGC GTAATCTGCT GCTTGCAAAC AAAAAAACCA CCGCTACCAG CGGTGGTTTG
4981 TTTGCCGGAT CAAGAGCTAC CAACTCTTTT TCCGAAGGTA ACTGGCTTCA GCAGAGCGCA
5041 GATACCAAAT ACTGTTCTTC TAGTGTAGCC GTAGTTAGGC CACCACTTCA AGAACTCTGT
5101 AGCACCGCCT ACATACCTCG CTCTGCTAAT CCTGTTACCA GTGGCTGCTG CCAGTGGCGA
5161 TAAGTCGTGT CTTACCGGGT TGGACTCAAG ACGATAGTTA CCGGATAAGG CGCAGCGGTC
5221 GGGCTGAACG GGGGGTTCGT GCACACAGCC CAGCTTGGAG CGAACGACCT ACACCGAACT
5281 GAGATACCTA CAGCGTGAGC TATGAGAAAG CGCCACGCTT CCCGAAGGGA GAAAGGCGGA
5341 CAGGTATCCG GTAAGCGGCA GGGTCGGAAC AGGAGAGCGC ACGAGGGAGC TTCCAGGGGG
5401 AAACGCCTGG TATCTTTATA GTCCTGTCGG GTTTCGCCAC CTCTGACTTG AGCGTCGATT
5461 TTTGTGATGC TCGTCAGGGG GGCGGAGCCT ATGGAAAAAC GCCAGCAACG CGGCCTTTTT
5521 ACGGTTCCTG GCCTTTTGCT GGCCTTTTGC TCACATGTTC TTTCCTGCGT TATCCCCTGA
5581 TTCTGTGGAT AACCGTATTA CCGCCTTTGA GTGAGCTGAT ACCGCTCGCC GCAGCCGAAC
5641 GACCGAGCGC AGCGAGTCAG TGAGCGAGGA AGCGGAAG (SEQ ID NO:132)

FIG. 6J pLS9-111 plasmid sequence

1 TAGAAAAACT CATCGAGCAT CAAATGAAAC TGCAATTTAT TCATATCAGG ATTATCAATA
61 CCATATTTTT GAAAAAGCCG TTTCTGTAAT GAAGGAGAAA ACTCACCGAG GCAGTTCCAT
121 AGGATGGCAA GATCCTGGTA TCGGTCTGCG ATTCCGACTC GTCCAACATC AATACAACCT
181 ATTAATTTCC CCTCGTCAAA AATAAGGTTA TCAAGTGAGA AATCACCATG AGTGACGACT
241 GAATCCGGTG AGAATGGCAA AAGTTTATGC ATTTCTTTCC AGACTTGTTC AACAGGCCAG
301 CCATTACGCT CGTCATCAAA ATCACTCGCA TCAACCAAAC CGTTATTCAT TCGTGATTGC
361 GCCTGAGCGA GGCGAAATAC GCGATCGCTG TTAAAAGGAC AATTACAAAC AGGAATCGAG
421 TGCAACCGGC GCAGGAACAC TGCCAGCGCA TCAACAATAT TTTCACCTGA ATCAGGATAT
481 TCTTCTAATA CCTGGAACGC TGTTTTTCCG GGGATCGCAG TGGTGAGTAA CCATGCATCA
541 TCAGGAGTAC GGATAAAATG CTTGATGGTC GGAAGTGGCA TAAATTCCGT CAGCCAGTTT
601 AGTCTGACCA TCTCATCTGT AACATCATTG GCAACGCTAC CTTTGCCATG TTTCAGAAAC
661 AACTCTGGCG CATCGGGCTT CCCATACAAG CGATAGATTG TCGCACCTGA TTGCCCGACA
721 TTATCGCGAG CCCATTTATA CCCATATAAA TCAGCATCCA TGTTGGAATT TAATCGCGGC
781 CTCGACGTTT CCCGTTGAAT ATGGCTCATA TTCTTCCTTT TTCAATATTA TTGAAGCATT
841 TATCAGGGTT ATTGTCTCAT GAGCGGATAC ATATTTGAAT GTATTTAGAA AAATAAACAA
901 ATAGGGGTCA GTGTTACAAC CAATTAACCA ATTCTGAACA TTATCGCGAG CCCATTTATA
961 CCTGAATATG GCTCATAACA CCCCTTGTTT GCCTGGCGGC AGTAGCGCGG TGGTCCCACC
1021 TGACCCCATG CCGAACTCAG AAGTGAAACG CCGTAGCGCC GATGGTAGTG TGGGGACTCC
1081 CCATGCGAGA GTAGGGAACT GCCAGGCATC AAATAAAACG AAAGGCTCAG TCGAAAGACT
1141 GGGCCTTTCG CCCGGGCTAA TTAGGGGGTG TCGCCCTTAC GTACGTACTC GATTGACGCC
1201 TAGGAGATCT TTACATCCCC CATTTAATAA GCAATCCTGT ATAGGTTAAT CCGCCGCCAA
1261 ACCCGAAAAG CAAAACGATT TGATCTTTTT TCAGCTTCCC GGCTTTCACT GCGAGATCGA
1321 GCGCCAAAAC AATTGAAACC GAAGACGTGT TTCCGTAGTG CTCAACGCTA GTGAGCGTTT
1381 TTTCAATCGG GAACGGTGTT TTTTCACAAA TTGACTCGAT CATGCGCAAG TTGGCGCTGT

FIG. 6J cont'd

1441 GAGGAACAAA CCAATCGAGA TCATCGGAGC TGAGTCCTGC TTTATGTAAA AGCCGTTCAA
1501 ATTCGCCAGG GACGGTTCTT GCGGCCCATT TATATACCTC GCGTCCGTTT TGCACCATTT
1561 TTCCGGAACC GACAAGCTGC ACACCGTTTA TTTCATTTCG CAGTCCGGCA CGATACAAAA
1621 TATCGCCGCC GTTCCCGCTT GTTCCTTGTA CAGACGCAAG AAATCCCGGC GTCTCTTCAT
1681 CTCGTTCTAC TAACAGCGCA CCCGCGGCAT CGCCGAACAG TACGCATGTC GTTCGATCCG
1741 TATAATCGGT TACCTTTGAT AACGTCTCTC CGGCGATGAC GAGAATTTTT TGATGAAGGC
1801 CAGATGTGAT CAATCCATTT GCCAAATGGA GGCCGTATGT CAGCCCGGCG CATGTCGCAT
1861 TAATATCCAG CGCGCCGGTG CTTTCCCAGC CGAAATATTC CTGTACGCGG CATGCCGTAC
1921 TCGGAAAGGC GTAATCGGAT GTGGTTGTGG CAACGAGGAT CATATCGACA TCATCAAGCG
1981 TTCCTTTATA ACGGCTCTTG AGATTCTTCA CCGCTTCTAT GCATAAATCA GAGGTAAATT
2041 GATGTTCATC CGCAATCCGG CGTTCTCTCA TTCCTGTGCG CTGAACGATC CATTCATCAG
2101 AGGTATCAAC GATCTTTTCT AAATCTGCAT TGGTTAAACG TCTGCTCGGC GCATAGGTGC
2161 CGATAGCTGT AATTTTTGCT TTTGACATAT GTCAGCGAAA GGGCGACACA AAATTTATTC
2221 TAAATGCATA ATAAATACTG ATAACATCTT ATAGTTTGTA TTATATTTTG TATTATCGTT
2281 GACATGTATA ATTTTGATAT CAAAAACTGA TTTTCCCTTT ATTATTTTCG AGATTTATTT
2341 TCTTAATTCT CTTTAACAAA CTAGAAATAT TGTATATACA AAAAATCATA AATAATAGAT
2401 GAATAGTTTA ATTATAGGTG TTCATCAATC GAAAAAGCAA CGTATCTTAT TTAAAGTGCG
2461 TTGCTTTTTT CTCATTTATA AGGTTAAATA ATTCTCATAT ATCAAGCAAA GTGACAGGCG
2521 CCCTTAAATA TTCTGACAAA TGCTCTTTCC CTAAACTCCC CCCATAAAAA AACCCGCCGA
2581 AGCGGGTTTT TACGTTATTT GCGGATTAAC GATTACTCGT TATCAGAACC GCCCAGGGGG
2641 CCCGAGCTTA AGACTGGCCG TCGTTTTACA ACACAGAAAG AGTTTGTAGA AACGCAAAAA
2701 GGCCATCCGT CAGGGGCCTT CTGCTTAGTT TGATGCCTGG CAGTTCCCTA CTCTCGCCTT
2761 CCGCTTCCTC GCTCACTGAC TCGCTGCGCT CGGTCGTTCG GCTGCGGCGA GCGGTATCAG
2821 CTCACTCAAA GGCGGTAATA CGGTTATCCA CAGAATCAGG GGATAACGCA GGAAAGAACA
2881 TGTGAGCAAA AGGCCAGCAA AAGGCCAGGA ACCGTAAAAA GGCCGCGTTG CTGGCGTTTT
2941 TCCATAGGCT CCGCCCCCCT GACGAGCATC ACAAAAATCG ACGCTCAAGT CAGAGGTGGC
3001 GAAACCCGAC AGGACTATAA AGATACCAGG CGTTTCCCCC TGGAAGCTCC CTCGTGCGCT
3061 CTCCTGTTCC GACCCTGCCG CTTACCGGAT ACCTGTCCGC CTTTCTCCCT TCGGGAAGCG
3121 TGGCGCTTTC TCATAGCTCA CGCTGTAGGT ATCTCAGTTC GGTGTAGGTC GTTCGCTCCA
3181 AGCTGGGCTG TGTGCACGAA CCCCCCGTTC AGCCCGACCG CTGCGCCTTA TCCGGTAACT
3241 ATCGTCTTGA GTCCAACCCG GTAAGACACG ACTTATCGCC ACTGGCAGCA GCCACTGGTA
3301 ACAGGATTAG CAGAGCGAGG TATGTAGGCG GTGCTACAGA GTTCTTGAAG TGGTGGCCTA
3361 ACTACGGCTA CACTAGAAGA ACAGTATTTG GTATCTGCGC TCTGCTGAAG CCAGTTACCT
3421 TCGGAAAAAG AGTTGGTAGC TCTTGATCCG GCAAACAAAC CACCGCTGGT AGCGGTGGTT
3481 TTTTTGTTTG CAAGCAGCAG ATTACGCGCA GAAAAAAAGG ATCTCAAGAA GATCCTTTGA
3541 TCTTTTCTAC GGGGTCTGAC GCTCAGTGGA ACGACGCGCG CGTAACTCAC GTTAAGGGAT
3601 TTTGGTCATG AGCTTGCGCC GTCCCGTCAA GTCAGCGTAA TGCTCTGCTT T (SEQ ID NO:133)

FIG. 6K

-pLS9-114 plasmid sequence

1 TTAATAAGAT GATCTTCTTG AGATCGTTTT GGTCTGCGCG TAATCTCTTG CTCTGAAAAC
61 GAAAAAAACCG CCTTGCAGGG CGGTTTTTCG AAGGTTCTCT GAGCTACCAA CTCTTTGAAC
121 CGAGGTAACT GGCTTGGAGG AGCGCAGTCA CCAAAACTTG TCCTTTCAGT TTAGCCTTAA
181 CCGGCGCATG ACTTCAAGAC TAACTCCTCT AAATCAATTA CCAGTGGCTG CTGCCAGTGG
241 TGCTTTTGCA TGTCTTTCCG GGTTGGACTC AAGACGATAG TTACCGGATA AGGCGCAGCG
301 GTCGGACTGA ACGGGGGGTT CGTGCATACA GTCCAGCTTG GAGCGAACTG CCTACCCGGA
361 ACTGAGTGTC AGGCGTGGAA TGAGACAAAC GCGGCCATAA CAGCGGAATG ACACCGGTAA

FIG. 6K cont'd

```
 421 ACCGAAAGGC AGGAACAGGA GAGCGCACGA GGGAGCCGCC AGGGGGAAAC GCCTGGTATC
 481 TTTATAGTCC TGTCGGGTTT CGCCACCACT GATTTGAGCG TCAGATTTCG TGATGCTTGT
 541 CAGGGGGGCG GAGCCTATGG AAAAACGGCT TTGCCGCGGC CCTCTCACTT CCCTGTTAAG
 601 TATCTTCCTG GCATCTTCCA GGAAATCTCC GCCCCGTTCG TAAGCCATTT CCGCTCGCCG
 661 CAGTCGAACG ACCGAGCGTA GCGAGTCAGT GAGCGAGGAA GCGGAATATA TCCTGTATCA
 721 CATATTCTGC TGACGCACCG GTGCAGCCTT TTTTCTCCTG CCACATGAAG CACTTCACTG
 781 ACACCCTCAT CAGTGCCAAC ATAGTAAGCC AGTATACACT CCGCTAGCGC TGAGGTCCCG
 841 CAGCCGAACG ACCGAGCGCA GCGGCGAGAG TAGGGAACTG CCAGGCATCC TGGGCGGTTC
 901 TGATAACGAG TAATCGTTAA TCCGCAAATA ACGTAAAAAC CCGCTTCGGC GGGTTTTTTT
 961 ATGGGGGGAG TTTAGGGAAA GAGCATTTGT CAGAATATTT AAGGGCGCCT GTCACTTTGC
1021 TTGATATATG AGAATTATTT AACCTTATAA ATGAGAAAAA AGCAACGCAC TTTAAATAAG
1081 ATACGTTGCT TTTTCGATTG ATGAACACCT ATAATTAAAC TATTCATCTA TTATTTATGA
1141 TTTTTTGTAT ATACAATATT TCTAGTTTGT TAAAGAGAAT TAAGAAAATA AATCTCGAAA
1201 ATAATAAAGG GAAAATCAGT TTTTGATATC AAAATTATAC ATGTCAACGA TAATACAAAA
1261 TATAATACAA ACTATAAGAT GTTATCAGTA TTTATTATGC ATTTAGAATA CCTTTTGTGT
1321 CGCCCTTGGG GCATATGAAA GCTGGCATTC TTGGTGTTGG ACGTTACATT CCTGAGAAGG
1381 TTTTAACAAA TCATGATCTT GAAAAAATGG TTGAAACTTC TGACGAGTGG ATTCGTACAA
1441 GAACAGGAAT AGAAGAAAGA AGAATCGCAG CAGATGATGT GTTTTCATCA CACATGGCTG
1501 TTGCAGCAGC GAAAAATGCG CTGGAACAAG CTGAAGTGGC TGCTGAGGAT CTGGATATGA
1561 TCTTGGTTGC AACTGTTACA CCTGATCAGT CATTCCCTAC GGTGTCTTGT ATGATTCAAG
1621 AACAACTCGG CGCGAAGAAA GCGTGTGCTA TGGATATCAG CGCGGCTTGT GCGGGCTTCA
1681 TGTACGGGGT TGTAACCGGT AAACAATTTA TTGAATCCGG AACCTACAAG CATGTTCTAG
1741 TTGTTGGTGT AGAGAAGCTC TCAAGCATTA CCGACTGGGA AGACCGCAAT ACAGCCGTTC
1801 TGTTTGGAGA CGGAGCAGGC GCTGCGGTAG TCGGGCCAGT CAGTGATGAC AGAGGAATCC
1861 TTTCATTTGA ACTAGGAGCC GACGGCACAG GCGGTCAGCA CTTGTATCTG AATGAAAAAC
1921 GACATACAAT CATGAATGGA CGAGAAGTTT TCAAATTTGC AGTCCGCCAA ATGGGAGAAT
1981 CATGCGTAAA TGTCATTGAA AAAGCCGGAC TTTCAAAAGA GGATGTGGAC TTTTTGATTC
2041 CGCATCAGGC GAACATCCGT ATCATGGAAG CTGCTCGCGA GCGTTTAGAG CTTCCTGTCG
2101 AAAAGATGTC TAAAACTGTT CATAAATATG GAAATACTTC TGCCGCATCC ATTCCGATCT
2161 CTCTTGTAGA AGAATTGGAA GCCGGTAAAA TCAAAGACGG CGATGTGGTC GTTATGGTAG
2221 GGTTCGGCGG AGGACTAACA TGGGGCGCCA TTGCAATCCG CTGGGGCCGA TAAAAAAAAG
2281 GTGAGGTGCA CACAAGATGA CTAAAAAACG TGTAGTTGTT ACAGGTCTTG GAGCATTATC
2341 TCCACTTGGC AACGACGTCG ATACAAGTTG GAATAACGCA ATCAACGGTG TGTCCGGAAT
2401 CGGTCCGATC ACTCGTGTTG ACGCTGAAGA ATATCCGGCA AAAGTTGCCG CTGAATTAAA
2461 AGATTTTAAT GTTGAAGATT ATATGGATAA AAAAGAAGCC AGAAAAATGG ACCGCTTTAC
2521 ACAATATGCG GTTGTGGCTG CGAAAATGGC GGTTGAAGAT GCTGATCTTA ACATTACCGA
2581 TGAGATCGCG CCGAGAGTCG GTGTTTGGGT AGGCTCCGGT ATCGGAGGAC TTGAAACACT
2641 AGAGTCTCAA TTTGAAATCT TCTTAACAAA AGGCCCAAGA CGGGTAAGCC CGTTTTTCGT
2701 GCCAATGATG ATTCCTGACA TGGCGACAGG CCAGATTTCT ATTGCATTAG GAGCAAAAGG
2761 GGTGAACTCT TGTACGGTTA CAGCATGTGC TACAGGAACG AACTCCATCG GTGACGCGTT
2821 TAAGGTTATT CAGCGCGGTG ATGCAGACGT GATGGTCACA GGCGGAACAG AAGCGCTGCT
2881 GACAAGAATG TCATTCGCCG GCTTTAGTGC CAACAAAGCG CTGTCTACTA ATCCAGATCC
2941 GAAAACAGCG AGCCGCCCGT TTGATAAAAA CCGTGATGGC TTTGTCATGG GGGAAGGTGC
3001 AGGGATTATC GTTCTTGAAG AACTTGAGCA TGCCCTGGCC CGCGGCGCTA AAATTTACGG
3061 AGAAATTGTC GGCTACGGCT CAACCGGAGA CGCTTATCAT ATCACAGCGC CGGCCCAAGA
3121 CGGTGAAGGC GGAGCGAGAG CGATGCAAGA AGCCATTAAA GATGCAGGCA TTGCACCTGA
3181 AGAAATTGAT TACATCAATG CTCACGGGAC AAGCACGTAT TACAACGACA AATACGAAAC
3241 AATGGCGATT AAGACCGTTT TTGGCGAGCA TGCGCATAAA CTTGCGGTAA GCTCTACAAA
3301 ATCGATGACA GGCCACCTCT TAGGAGCAGC CGGCGGTATT GAAGCCATTT TCTCTATCCT
3361 GGCCATTAAA GAAGGCGTGA TTCCGCCGAC AATCAATATT CAAACACCTG ACGAAGAATG
3421 TGATTTGGAT TATGTGCCTG ATGAAGCCCG CAGACAGGAA CTTAATTATG TTCTCAGCAA
3481 CTCATTAGGA TTCGGCGGAC ACAACGCAAC ATTAATCTTT AAAAAATATC AATCATAAGT
```

FIG. 6K cont'd

3541 TTTTTCTCGA AAATTTCATC GTAGTTTCTC TAGTTTTTTA AAAACGAATC CACTATAATA
3601 CTTGAGGGGA GGTGAATTGC TATGGCAGAC ACATTAGAGC GTGTAACGAA AATCATCGTA
3661 GATCGCCTTG GCGTTGATGA AGCAGACGTC AAACTTGAAG CATCTTTCAA GGAAGACTTA
3721 GGTGCTGATT CCCTAGATGT AGTTGAGCTT GTTATGGAAC TTGAAGACGA GTTTGATATG
3781 GAGATTTCTG ACGAAGATGC TGAAAAGATT GCAACAGTCG GCGACGCTGT GAACTACATA
3841 CAAAACCAGC AATAATTAAT TAACCTAGGA AAAAAGGGCG ACACCCCTCA ATTAGCCCGG
3901 GCGAAAGGCC CAGTCTTTCG ACTGAGCCTT TCGTTTTATT TGATGCCTGG CAGTTCCCTA
3961 CTCTCGCATG GGGAGTCCCC ACACTACCAT CGGCGCTACG GCGTTTCACT TCTGAGTTCG
4021 GCATGGGGTC AGGTGGGACC ACCGCGCTAC TGCCGCCAGG CAAACAAGGG GTGTTATGAG
4081 CCATATTCAG GTATAAATGG GCTCGCGATA ATGTTCAGAA TTGGTTAATT GGTTGTAACA
4141 CTGACCCCTA TTTGTTTATT TTTCTAAATA CATTCAAATA TGTATCCGCT CATGAGACAA
4201 TAACCCTGAT AAATGCTTCA ATAATATTGA AAAAGGAAGA ATATGAGTAT TCAACATTTC
4261 CGTGTCGCCC TTATTCCCTT TTTTGCGGCA TTTTGCCTTC CTGTTTTTGC TCACCCAGAA
4321 ACGCTGGTGA AAGTAAAAGA TGCTGAAGAT CAGTTGGGTG CACGAGTGGG TTACATCGAA
4381 CTGGATCTCA ACAGCGGTAA GATCCTTGAG AGTTTTCGCC CCGAAGAACG TTTTCCAATG
4441 ATGAGCACTT TTAAAGTTCT GCTATGTGGC GCGGTATTAT CCCGTATTGA CGCCGGGCAA
4501 GAGCAACTCG GTCGCCGCAT ACACTATTCT CAGAATGACT TGGTTGAGTA CTCACCAGTC
4561 ACAGAAAAGC ATCTTACGGA TGGCATGACA GTAAGAGAAT TATGCAGTGC TGCCATAACC
4621 ATGAGTGATA ACACTGCGGC CAACTTACTT CTGACAACGA TCGGAGGACC GAAGGAGCTA
4681 ACCGCTTTTT TGCACAACAT GGGGGATCAT GTAACTCGCC TTGATCGTTG GGAACCGGAG
4741 CTGAATGAAG CCATACCAAA CGACGAGCGT GACACCACGA TGCCTGTAGC GATGGCAACA
4801 ACGTTGCGCA AACTATTAAC TGGCGAACTA CTTACTCTAG CTTCCCGGCA ACAATTAATA
4861 GACTGGATGG AGGCGGATAA AGTTGCAGGA CCACTTCTGC GCTCGGCCCT TCCGGCTGGC
4921 TGGTTTATTG CTGATAAATC CGGAGCCGGT GAGCGTGGTT CTCGCGGTAT CATCGCAGCG
4981 CTGGGGCCAG ATGGTAAGCC CTCCCGTATC GTAGTTATCT ACACGACGGG GAGTCAGGCA
5041 ACTATGGATG AACGAAATAG ACAGATCGCT GAGATAGGTG CCTCACTGAT TAAGCATTGG
5101 TAAAGGAGGA AAAAAAAATG AGCCATATTC AACGGGAAAC GTCGAGGCCG CGATTAAATT
5161 CCAACATGGA TGCTGATTTA TATGGGTATA AATGGGCTCG CGATAATGTC GGGCAATCAG
5221 GTGCGACAAT CTATCGCTTG TATGGGAAGC CCGATGCGCC AGAGTTGTTT CTGAAACATG
5281 GCAAAGGTAG CGTTGCCAAT GATGTTACAG ATGAGATGGT CAGACTAAAC TGGCTGACGG
5341 AATTTATGCC ACTTCCGACC ATCAAGCATT TTATCCGTAC TCCTGATGAT GCATGGTTAC
5401 TCACCACTGC GATCCCCGGA AAAACAGCGT TCCAGGTATT AGAAGAATAT CCTGATTCAG
5461 GTGAAAATAT TGTTGATGCG CTGGCAGTGT TCCTGCGCCG GTTGCACTCG ATTCCTGTTT
5521 GTAATTGTCC TTTTAACAGC GATCGCGTAT TTCGCCTCGC TCAGGCGCAA TCACGAATGA
5581 ATAACGGTTT GGTTGATGCG AGTGATTTTG ATGACGAGCG TAATGGCTGG CCTGTTGAAC
5641 AAGTCTGGAA AGAAATGCAT AAACTTTTGC CATTCTCACC GGATTCAGTC GTCACTCATG
5701 GTGATTTCTC ACTTGATAAC CTTATTTTTG ACGAGGGGAA ATTAATAGGT TGTATTGATG
5761 TTGGACGAGT CGGAATCGCA GACCGATACC AGGATCTTGC CATCCTATGG AACTGCCTCG
5821 GTGAGTTTTC TCCTTCATTA CAGAAACGGC TTTTTCAAAA ATATGGTATT GATAATCCTG
5881 ATATGAATAA ATTGCAGTTT CATTTGATGC TCGATGAGTT TTTCTAAGG AGGAAAAAAA
5941 AATGGAGAAA AAAATCACTG GATATACCAC CGTTGATATA TCCCAATGGC ATCGTAAAGA
6001 ACATTTTGAG GCATTTCAGT CAGTTGCTCA ATGTACCTAT AACCAGACCG TTCAGCTGGA
6061 TATTACGGCC TTTTTAAAGA CCGTAAAGAA AAATAAGCAC AAGTTTTATC CGGCCTTTAT
6121 TCACATTCTT GCCCGCCTGA TGAATGCTCA TCCGGAGTTC CGTATGGCAA TGAAAGACGG
6181 TGAGCTGGTG ATATGGGATA GTGTTCACCC TTGTTACACC GTTTTCCATG AGCAAACTGA
6241 AACGTTTTCA TCGCTCTGGA GTGAATACCA CGACGATTTC CGGCAGTTTC TACACATATA
6301 TTCGCAAGAT GTGGCGTGTT ACGGTGAAAA CCTGGCCTAT TTCCCTAAAG GGTTTATTGA
6361 GAATATGTTT TTCGTCAGCG CCAATCCCTG GGTGAGTTTC ACCAGTTTTG ATTTAAACGT
6421 GGCCAATATG GACAACTTCT TCGCCCCCGT TTTCACTATG GGCAAATATT ATACGCAAGG
6481 CGACAAGGTG CTGATGCCGC TGGCGATTCA GGTTCATCAT GCCGTCTGTG ATGGCTTCCA
6541 TGTCGGCAGA ATGCTTAATG AATTACAACA GTACTGCGAT GAGTGGCAGG GCGGGGCGTA
6601 AACGCCGAGG AGGAAAAAAA AATGCGCTCA CGCAACTGGT CCAGAACCTT GACCGAACGC

FIG. 6K cont'd

6661 AGCGGTGGTA ACGGCGCAGT GGCGGTTTTC ATGGCTTGTT ATGACTGTTT TTTTGTACAG
6721 TCTATGCCTC GGGCATCCAA GCAGCAAGCG CGTTACGCCG TGGGTCGATG TTTGATGTTA
6781 TGGAGCAGCA ACGATGTTAC GCAGCAGGGC AGTCGCCCTA AAACAAAGTT AGGTGGCTCA
6841 AGTATGGGCA TCATTCGCAC ATGTAGGCTC GGCCCTGACC AAGTCAAATC CATGCGGGCT
6901 GCTCTTGATC TTTTCGGTCG TGAGTTCGGT GACGTAGCCA CCTACTCCCA ACATCAGCCG
6961 GACTCCGATT ACCTCGGGAA CTTGCTCCGT AGTAAGACAT TCATCGCGCT TGCTGCCTTC
7021 GACCAAGAAG CGGTTGTTGG CGCTCTCGCG GCTTACGTTC TGCCCAAGTT TGAGCAGCCG
7081 CGTAGTGAGA TCTATATCTA TGATCTCGCA GTCTCCGGCG AGCACCGGAG GCAGGGCATT
7141 GCCACCGCGC TCATCAATCT CCTCAAGCAT GAGGCCAACG CGCTTGGTGC TTATGTGATC
7201 TACGTGCAAG CAGATTACGG TGACGATCCC GCAGTGGCTC TCTATACAAA GTTGGGCATA
7261 CGGGAAGAAG TGATGCACTT TGATATCGAC CCAAGTACCG CCACCTAAGC (SEQ ID
NO:134)

FIG. 6L pLS9-115 plasmid sequence

1 GGTGGCGGTA CTTGGGTCGA TATCAAAGTG CATCACTTCT TCCCGTATGC CCAACTTTGT
61 ATAGAGAGCC ACTGCGGGAT CGTCACCGTA ATCTGCTTGC ACGTAGATCA CATAAGCACC
121 AAGCGCGTTG GCCTCATGCT TGAGGAGATT GATGAGCGCG GTGGCAATGC CCTGCCTCCG
181 GTGCTCGCCG GAGACTGCGA GATCATAGAT ATAGATCTCA CTACGCGGCT GCTCAAACTT
241 GGGCAGAACG TAAGCCGCGA GAGCGCCAAC AACCGCTTCT TGGTCGAAGG CAGCAAGCGC
301 GATGAATGTC TTACTACGGA GCAAGTTCCC GAGGTAATCG GAGTCCGGCT GATGTTGGGA
361 GTAGGTGGCT ACGTCACCGA ACTCACGACC GAAAAGATCA AGAGCAGCCC GCATGGATTT
421 GACTTGGTCA GGGCCGAGCC TACATGTGCG AATGATGCCC ATACTTGAGC CACCTAACTT
481 TGTTTTAGGG CGACTGCCCT GCTGCGTAAC ATCGTTGCTG CTCCATAACA TCAAACATCG
541 ACCCACGGCG TAACGCGCTT GCTGCTTGGA TGCCCGAGGC ATAGACTGTA CAAAAAAACA
601 GTCATAACAA GCCATGAAAA CCGCCACTGC GCCGTTACCA CCGCTGCGTT CGGTCAAGGT
661 TCTGGACCAG TTGCGTGAGC GCATTTTTTT TTCCTCCTCG GCGTTTACGC CCCGCCCTGC
721 CACTCATCGC AGTACTGTTG TAATTCATTA AGCATTCTGC CGACATGGAA GCCATCACAG
781 ACGGCATGAT GAACCTGAAT CGCCAGCGGC ATCAGCACCT TGTCGCCTTG CGTATAATAT
841 TTGCCCATAG TGAAAACGGG GGCGAAGAAG TTGTCCATAT TGGCCACGTT TAAATCAAAA
901 CTGGTGAAAC TCACCCAGGG ATTGGCGCTG ACGAAAAACA TATTCTCAAT AAACCCTTTA
961 GGGAAATAGG CCAGGTTTTC ACCGTAACAC GCCACATCTT GCGAATATAT GTGTAGAAAC
1021 TGCCGGAAAT CGTCGTGGTA TTCACTCCAG AGCGATGAAA ACGTTTCAGT TTGCTCATGG
1081 AAAACGGTGT AACAAGGGTG AACACTATCC CATATCACCA GCTCACCGTC TTTCATTGCC
1141 ATACGGAACT CCGGATGAGC ATTCATCAGG CGGGCAAGAA TGTGAATAAA GGCCGGATAA
1201 AACTTGTGCT TATTTTTCTT TACGGTCTTT AAAAAGGCCG TAATATCCAG CTGAACGGTC
1261 TGGTTATAGG TACATTGAGC AACTGACTGA AATGCCTCAA AATGTTCTTT ACGATGCCAT
1321 TGGGATATAT CAACGGTGGT ATATCCAGTG ATTTTTTTCT CCATTTTTTT TTCCTCCTTT
1381 AGAAAAACTC ATCGAGCATC AAATGAAACT GCAATTTATT CATATCAGGA TTATCAATAC
1441 CATATTTTTG AAAAAGCCGT TTCTGTAATG AAGGAGAAAA CTCACCGAGG CAGTTCCATA
1501 GGATGGCAAG ATCCTGGTAT CGGTCTGCGA TTCCGACTCG TCCAACATCA ATACAACCTA
1561 TTAATTTCCC CTCGTCAAAA ATAAGGTTAT CAAGTGAGAA ATCACCATGA GTGACGACTG
1621 AATCCGGTGA GAATGGCAAA AGTTTATGCA TTTCTTTCCA GACTTGTTCA ACAGGCCAGC
1681 CATTACGCTC GTCATCAAAA TCACTCGCAT CAACCAAACC GTTATTCATT CGTGATTGCG
1741 CCTGAGCGAG GCGAAATACG CGATCGCTGT TAAAAGGACA ATTACAAACA GGAATCGAGT
1801 GCAACCGGCG CAGGAACACT GCCAGCGCAT CAACAATATT TTCACCTGAA TCAGGATATT
1861 CTTCTAATAC CTGGAACGCT GTTTTTCCGG GGATCGCAGT GGTGAGTAAC CATGCATCAT
1921 CAGGAGTACG GATAAAATGC TTGATGGTCG GAAGTGGCAT AAATTCCGTC AGCCAGTTTA

FIG. 6L cont'd

```
1981 GTCTGACCAT CTCATCTGTA ACATCATTGG CAACGCTACC TTTGCCATGT TTCAGAAACA
2041 ACTCTGGCGC ATCGGGCTTC CCATACAAGC GATAGATTGT CGCACCTGAT TGCCCGACAT
2101 TATCGCGAGC CCATTTATAC CCATATAAAT CAGCATCCAT GTTGGAATTT AATCGCGGCC
2161 TCGACGTTTC CCGTTGAATA TGGCTCATTT TTTTTCCTC CTTTACCAAT GCTTAATCAG
2221 TGAGGCACCT ATCTCAGCGA TCTGTCTATT TCGTTCATCC ATAGTTGCCT GACTCCCCGT
2281 CGTGTAGATA ACTACGATAC GGGAGGGCTT ACCATCTGGC CCCAGCGCTG CGATGATACC
2341 GCGAGAACCA CGCTCACCGG CTCCGGATTT ATCAGCAATA AACCAGCCAG CCGGAAGGGC
2401 CGAGCGCAGA AGTGGTCCTG CAACTTTATC CGCCTCCATC CAGTCTATTA ATTGTTGCCG
2461 GGAAGCTAGA GTAAGTAGTT CGCCAGTTAA TAGTTTGCGC AACGTTGTTG CCATCGCTAC
2521 AGGCATCGTG GTGTCACGCT CGTCGTTTGG TATGGCTTCA TTCAGCTCCG GTTCCCAACG
2581 ATCAAGGCGA GTTACATGAT CCCCCATGTT GTGCAAAAAA GCGGTTAGCT CCTTCGGTCC
2641 TCCGATCGTT GTCAGAAGTA AGTTGGCCGC AGTGTTATCA CTCATGGTTA TGGCAGCACT
2701 GCATAATTCT CTTACTGTCA TGCCATCCGT AAGATGCTTT TCTGTGACTG GTGAGTACTC
2761 AACCAAGTCA TTCTGAGAAT AGTGTATGCG GCGACCGAGT TGCTCTTGCC CGGCGTCAAT
2821 ACGGGATAAT ACCGCGCCAC ATAGCAGAAC TTTAAAAGTG CTCATCATTG GAAAACGTTC
2881 TTCGGGGCGA AAACTCTCAA GGATCTTACC GCTGTTGAGA TCCAGTTCGA TGTAACCCAC
2941 TCGTGCACCC AACTGATCTT CAGCATCTTT TACTTTCACC AGCGTTTCTG GGTGAGCAAA
3001 AACAGGAAGG CAAAATGCCG CAAAAAAGGG AATAAGGGCG ACACGGAAAT GTTGAATACT
3061 CATATTCTTC CTTTTTCAAT ATTATTGAAG CATTTATCAG GGTTATTGTC TCATGAGCGG
3121 ATACATATTT GAATGTATTT AGAAAAATAA ACAAATAGGG GTCAGTGTTA CAACCAATTA
3181 ACCAATTCTG AACATTATCG CGAGCCCATT TATACCTGAA TATGGCTCAT AACACCCCTT
3241 GTTTGCCTGG CGGCAGTAGC GCGGTGGTCC CACCTGACCC CATGCCGAAC TCAGAAGTGA
3301 AACGCCGTAG CGCCGATGGT AGTGTGGGGA CTCCCCATGC GAGAGTAGGG AACTGCCAGG
3361 CATCAAATAA AACGAAAGGC TCAGTCGAAA GACTGGGCCT TTCGCCCGGG CTAATTGAGG
3421 GGTGTCGCCC TTATTCGACT CTATAGTGAA GTTCCTATTC TCTAGAAAGT ATAGGAACTT
3481 CTGAAGTGGG GCATATGTCT AAGATCAAGC CAAGCAAGGG CGCTCCGTAC GCGCGCATCC
3541 TGGGCGTCGG CGGTTACCGT CCGACCCGTG TGGTGCCGAA CGAGGTGATC CTGGAGAAGA
3601 TCGACTCTTC CGACGAGTGG ATTCGCTCTC GCTCCGGCAT CGAAACGCGT CACTGGGCGG
3661 GTCCGGAAGA AACCGTCGCG GCGATGTCTG TGGAGGCCTC CGGCAAGGCA CTGGCCGACG
3721 CCGGTATCGA CGCCTCTCGT ATCGGTGCCG TGGTAGTCTC TACCGTGTCT CACTTCAGCC
3781 AGACCCCGGC CATCGCCACC GAGATCGCCG ACCGCCTGGG CACGGACAAG GCCGCAGCCT
3841 TCGACATCTC TGCCGGCTGC GCGGGCTTCG GCTACGGTCT GACCCTGGCC AAGGGCATGG
3901 TCGTCGAAGG TTCTGCGGAG TACGTGCTGG TCATCGGCGT GGAGCGTCTG TCCGACCTGA
3961 CCGACCTGGA GGACCGTGCC ACGGCCTTCC TGTTCGGCGA CGGCGCTGGT GCGGTCGTGG
4021 TCGGCCCGTC CCAGGAGCCG GCAATCGGCC CGACGGTCTG GGGCTCTGAG GGCGACAAGG
4081 CCGAAACGAT CAAGCAGACC GTTTCCTGGG ACCGCTTCCG TATCGGCGAT GTCTCCGAAC
4141 TGCCGCTGGA CTCCGAGGGC AACGTCAAGT TTCCTGCGAT CACGCAGGAG GGCCAGGCGG
4201 TGTTCCGCTG GGCCGTGTTC GAGATGGCGA AGGTCGCGCA GCAGGCGCTG GACGCGGCGG
4261 GTATCAGCCC GGACGACCTG GACGTCTTTA TCCCGCACCA GGCCAATGTG CGTATCATCG
4321 ACTCTATGGT GAAAACCCTG AAGCTGCCGG AGCACGTCAC GGTCGCCCGT GACATCCGCA
4381 CCACCGGCAA CACCTCTGCC GCCTCTATTC CGCTGGCGAT GGAGCGTCTG CTGGCGACCG
4441 GCGACGCGCG TAGCGGCGAC ACCGCGCTGG TCATCGGCTT CGGTGCGGGT CTGGTCTACG
4501 CCGCGACGGT CGTTACCCTG CCGTAACCAC TCCGTGCCGG ATCACCCCGG TCCGGAACGG
4561 AGAGCAGCAC CGCCCGCCGC CGACGCGGCG GGCCGCCACA CCCTCTGGAC AACAAAGAAG
4621 GAGCGCCGTC ATGGCCGCCA CTCAGGAAGA GATCGTCGCC GGTCTGGCGG AGATCGTGAA
4681 CGAGATCGCC GGCATCCCGG TCGAGGACGT CAAGCTGGAC AAGTCCTTCA CCGACGACCT
4741 GGACGTAGAC TCTCTGAGCA TGGTCGAGGT CGTCGTCGCC GCCGAAGAGC GCTTCGACGT
4801 CAAGATCCCG GACGACGACG TCAAGAACCT GAAAACGGTC GGCGACGCGA CGAAGTACAT
4861 CCTGGACCAC CAGGCCTGAT CCGCCGATAC TCGGGCATGA CCCGCGTACC GGGCAGATCC
4921 GGGCAGACTG CCCCGCCGCC CGGCGGTGGC GCCGTACGAA TCCGTATCCC GTTGGAGAAA
4981 GAATTCCCAT GAGCAGCACC AATCGCACCG TGGTCGTCAC CGGTATCGGC GCAACCACCC
5041 CGCTGGGTGG CGACGCAGCC TCTACCTGGG AGGGTCTGGT CGCGGGTCGT TCCGGCGTCC
```

FIG. 6L cont'd

5101 GTCCGCTGGA GCAGGAGTGG GCTGCCGACC AGGCGGTCCG TATCGCAGCG CCGGCAGCCG
5161 TAGACCCGTC CGAGGTCATC CCGCGTCCGC AGGCACGCCG TCTGGACCGC TCTGCGCAGT
5221 TCGCGCTGAT CGCGGCGCAG GAGGCCTGGA AGGACGCCGG TTACGCCGGC AAGGCGGGCG
5281 AGTCTCCGGC GGAGGACGGT GCGGCTCACG TAGACCCGGA CCGTCTGGGT GCGGTCATCG
5341 CCTCCGGCAT CGGCGGCGTG ACCACGCTGC TGGACCAGTA CGACGTGCTG AAGGAGAAGG
5401 GCGTCCGCCG CGTTTCCCCG CACACCGTCC CGATGCTGAT GCCGAACGGT CCGTCCGCCA
5461 ACGTCGGCCT GGCCGTGGGT GCCCGTGCGG GCGTGCACAC CCCGGTGTCT GCCTGCGCGT
5521 CTGGCGCCGA GGCCATCGGC TACGCCATCG AGATGATCCG CACTGGCCGT GCGGACGTCG
5581 TCGTCGCGGG TGGCACGGAG GCGGCGATCC ACCCGCTGCC GATTGCCGCG TTCGGCAACA
5641 TGATGGCGAT GTCCAAGAAC AACGACGACC CGCAGGGCGC CTCCCGCCCG TTCGACACGG
5701 CGCGTGACGG CTTCGTCCTG GGCGAAGGTG CCGGCGTCCT GGTCCTGGAG TCCGCCGAGC
5761 ATGCGGCAGC GCGCGGTGCC CGCGTCTACG CGGAGGCGGT CGGCCAGGGC ATCTCCGCCG
5821 ACAGCCACGA CATCGTGCAG CCGGAGCCGG AGGGCCGTGG CATCTCCGCA GCGCTGCAAA
5881 ACCTGCTGGA CGGCAACGAC CTGGACCCGG CCGAGATCGT GCACGTCAAC GCGCACGCCA
5941 CCTCTACCCC GGCAGGTGAC ATCGCCGAGC TGAAGGCGCT GCGCAAGGTC CTGGGCGACG
6001 ACGTAGACCA CATGGCCGTC AGCGGCACCA AGTCTATGAC CGGTCACCTG CTGGGTGGCG
6061 CTGGCGGCGT GGAGTCCGTG GCGACCGTGC TGGCGCTGTA CCACCGTGTG GCTCCGCCGA
6121 CCATCAACGT CGAGAACCTG GACCCGGAGG CCGAGGCCAA CGCGGACATC GTCCGCGGTG
6181 AGGCCCGCAA GCTGCCGGTG GAGGGCCGTA TCGCCGCGCT GAACGACTCT TTCGGCTTCG
6241 GCGGTCACAA CGTGGTGCTG GCGTTCCGTT CTGTCTGATT AATTAACCTA GGAAAATGAA
6301 GTGAAGTTCC TATACTTTCT AGAGAATAGG AACTTCTATA GTGAGTCGAA TAAGGGCGAC
6361 ACAAAATTTA TTCTAAATGC ATAATAAATA CTGATAACAT CTTATAGTTT GTATTATATT
6421 TTGTATTATC GTTGACATGT ATAATTTTGA TATCAAAAAC TGATTTTCCC TTTATTATTT
6481 TCGAGATTTA TTTTCTTAAT TCTCTTTAAC AAACTAGAAA TATTGTATAT ACAAAAAATC
6541 ATAAATAATA GATGAATAGT TTAATTATAG GTGTTCATCA ATCGAAAAAG CAACGTATCT
6601 TATTTAAAGT GCGTTGCTTT TTTCTCATTT ATAAGGTTAA ATAATTCTCA TATATCAAGC
6661 AAAGTGACAG GCGCCCTTAA ATATTCTGAC AAATGCTCTT TCCCTAAACT CCCCCCATAA
6721 AAAAACCCGC CGAAGCGGGT TTTTACGTTA TTTGCGGATT AACGATTACT CGTTATCAGA
6781 ACCGCCCAGG GGGCCCGAGC TTAAGACTGG CCGTCGTTTT ACAACACAGA AAGAGTTTGT
6841 AGAAACGCAA AAAGGCCATC CGTCAGGGGC CTTCTGCTTA GTTTGATGCC TGGCAGTTCC
6901 CTACTCTCGC CTTCCGCTTC CTCGCTCACT GACTCGCTGC GCTCGGTCGT TCGGCTGCGG
6961 CGAGCGGTAT CAGCTCACTC AAAGGCGGTA ATACGGTTAT CCACAGAATC AGGGGATAAC
7021 GCAGGAAAGA ACATGTGAGC AAAAGGCCAG CAAAAGGCCA GGAACCGTAA AAAGGCCGCG
7081 TTGCTGGCGT TTTTCCATAG GCTCCGCCCC CCTGACGAGC ATCACAAAAA TCGACGCTCA
7141 AGTCAGAGGT GGCGAAACCC GACAGGACTA TAAAGATACC AGGCGTTTCC CCCTGGAAGC
7201 TCCCTCGTGC GCTCTCCTGT TCCGACCCTG CCGCTTACCG GATACCTGTC CGCCTTTCTC
7261 CCTTCGGGAA GCGTGGCGCT TTCTCATAGC TCACGCTGTA GGTATCTCAG TTCGGTGTAG
7321 GTCGTTCGCT CCAAGCTGGG CTGTGTGCAC GAACCCCCCG TTCAGCCCGA CCGCTGCGCC
7381 TTATCCGGTA ACTATCGTCT TGAGTCCAAC CCGGTAAGAC ACGACTTATC GCCACTGGCA
7441 GCAGCCACTG GTAACAGGAT TAGCAGAGCG AGGTATGTAG GCGGTGCTAC AGAGTTCTTG
7501 AAGTGGTGGG CTAACTACGG CTACACTAGA AGAACAGTAT TTGGTATCTG CGCTCTGCTG
7561 AAGCCAGTTA CCTTCGGAAA AAGAGTTGGT AGCTCTTGAT CCGGCAAACA AACCACCGCT
7621 GGTAGCGGTG GTTTTTTTGT TTGCAAGCAG CAGATTACGC GCAGAAAAAA AGGATCTCAA
7681 GAAGATCCTT TGATCTTTTC TACGGGGTCT GACGCTCAGT GGAACGACGC GCGCGTAACT
7741 CACGTTAAGG GATTTTGGTC ATGAGCTTGC GCCGTCCCGT CAAGTCAGCG TAATGCTCTG
7801 CTTA (SEQ ID NO:135)

FIG. 7:

pKZ4 plasmid sequence:

tcgcgacgcgaggctggatggccttccccattatgattcttctcgcttccggcggcatcgggatgcccgc
gttgcaggccatgctgtccaggcaggtagatgacgaccatcagggacagcttcaaggatcgctcgcggct
cttaccagcctaacttcgatcactggaccgctgatcgtcacggcgatttatgccgcctcggcgagcacat
ggaacgggttggcatggattgtaggcgccgccctataccttgtctgcctccccgcgttgcgtcgcggtgc
atggagccgggccacctcgacctgaatggaagccggcggcacctcgctaacggattcaccactccaagaa
ttggagccaatcaattcttgcggagaactgtgaatgcgcaaaccaacccttggcagaacatatccatcgc
gtccgccatctccagcagccgcacgcggcgcatctcgggcagcgttgggtcctggccacgggtgcgcatg
atcgtgctcctgtcgttgaggacccggctaggctggcggggttgccttactggttagcagaatgaatcac
cgatacgcgagcgaacgtgaagcgactgctgctgcaaaacgtctgcgacctgagcaacaacatgaatggt
cttcggtttccgtgtttcgtaaagtctggaaacgcggaagtcagcgccctgcaccattatgttccggatc
tgcatcgcaggatgctgctggctaccctgtggaacacctacatctgtattaacgaagcgctggcattgac
cctgagtgatttttctctggtcccgccgcatccataccgccagttgtttaccctcacaacgttccagtaa
ccgggcatgttcatcatcagtaacccgtatcgtgagcatcctctctcgtttcatcggtatcattaccccc
atgaacagaaatcccccttacacggaggcatcagtgaccaaacaggaaaaaaccgcccttaacatggccc
gctttatcagaagccagacattaacgcttctggagaaactcaacgagctggacgcggatgaacaggcaga
catctgtgaatcgcttcacgaccacgctgatgagctttaccgcagctgcctcgcgcgtttcggtgatgac
ggtgaaaacctctgacacatgcagctcccggagacggtcacagcttgtctgtaagcggatgccgggagca
gacaagcccgtcagggcgcgtcagcgggtgttggcgggtgtcggggcgcagccatgacccagtcacgtag
cgatagcggagtgtatactggcttaactatgcggcatcagagcagattgtactgagagtgcaccatatgc
ggtgtgaaataccgcacagatgcgtaaggagaaaataccgcatcaggcgctcttccgcttcctcgctcac
tgactcgctgcgctcggtcgttcggctgcggcgagcggtatcagctcactcaaaggcggtaatacggtta
tccacagaatcaggggataacgcaggaaagaacatgtgagcaaaaggccagcaaaaggccaggaaccgta
aaaaggccgcgttgctggcgtttttccataggctccgcccccctgacgagcatcacaaaaatcgacgctc
aagtcagaggtggcgaaacccgacaggactataaagataccaggcgtttccccctggaagctccctcgtg
cgctctcctgttccgaccctgccgcttaccggatacctgtccgcctttctcccttcgggaagcgtggcgc
tttctcatagctcacgctgtaggtatctcagttcggtgtaggtcgttcgctccaagctgggctgtgtgca
cgaaccccccgttcagcccgaccgctgcgccttatccggtaactatcgtcttgagtccaacccggtaaga
cacgacttatcgccactggcagcagccactggtaacaggattagcagagcgaggtatgtaggcggtgcta
cagagttcttgaagtggtggcctaactacggctacactagaaggacagtatttggtatctgcgctctgct
gaagccagttaccttcggaaaaagagttggtagctcttgatccggcaaacaaaccaccgctggtagcggt
ggtttttttgtttgcaagcagcagattacgcgcagaaaaaaaggatctcaagaagatcctttgatctttt
ctacggggtctgacgctcagtggaacgaaaactcacgttaagggattttggtcatgagattatcaaaaag
gatcttcacctagatccttttaaattaaaaatgaagttttaaatcaatctaaagtatatatgagtaaact
tggtctgacagttaccaatgcttaatcagtgaggcacctatctcagcgatctgtctatttcgttcatcca
tagttgcctgactccccgtcgtgtagataactacgatacgggagggcttaccatctggccccagtgctgc
aatgataccgcgagacccacgctcaccggctccagatttatcagcaataaaccagccagccggaagggcc
gagcgcagaagtggtcctgcaactttatccgcctccatccagtctattaattgttgccgggaagctagag
taagtagttcgccagttaatagtttgcgcaacgttgttgccattgctgcaggcatcgtggtgtcacgctc
gtcgtttggtatggcttcattcagctccggttcccaacgatcaaggcgagttacatgatcccccatgttg
tgcaaaaaagcggttagctccttcggtcctccgatcgttgtcagaagtaagttggccgcagtgttatcac
tcatggttatggcagcactgcataattctcttactgtcatgccatccgtaagatgcttttctgtgactgg
tgagtactcaaccaagtcattctgagaatagtgtatgcggcgaccgagttgctcttgcccggcgtcaaca
cgggataataccgcgccacatagcagaactttaaaagtgctcatcattggaaaacgttcttcggggcgaa
aactctcaaggatcttaccgctgttgagatccagttcgatgtaacccactcgtgcacccaactgatcttc
agcatcttttactttcaccagcgtttctgggtgagcaaaaacaggaaggcaaaatgccgcaaaaaaggga
ataagggcgacacggaaatgttgaatactcatactcttcctttttcaatattattgaagcatttatcagg
gttattgtctcatgagcggatacatatttgaatgtatttagaaaaataaacaaataggggttccgcgcac

FIG. 7 cont'd atttccccgaaaagtgccacctgacgtcttaattaaTCAGGAGAGCGTTCACCGACAAACAACAGATAAA
ACGAAAGGCCCAGTCTTTCGACTGAGCCTTTCGTTTTATTTGATGCCTGGCAGTTCCCTACTCTCGCATG
GGGAGACCCCACACTACCATCGGCGCTACGGCGTTTCACTTCTGAGTTCGGCATGGGGTCAGGTGGGACC
ACCGCGCTACTGCCGCCAGGCAAATTCTGTTTTATCAGACCGCTTCTGCGTTCTGATTTAATCTGTATCA
GGCTGAAAATCTTCTCTCATCCGCCAAAACAGCCAAGCTGGAGACCGTTTAAACTCAATGATGATGATGA
TGATGGTCGACGGCGCTATTCAGATCCTCTTCTGAGATGAGTTTTTGTTCGGGCCCAAGCTTCGAATTCt
*cagatatgcaaggcgtggcccaacgcgcgtagggcggcttcttgcaccgcttcacccaacgtggggtggg*
*catgaatggtgccggccacatcttccaggcacgcgcccatctccagcgattgggcaaacgcggtggacag*
*ctcggagaccgccacgccaaccgcctgccaacccacgatcaggtggttgtcacggcgcgccaccacccgc*
*acgaaaccgctttcgactccaggctcatggcccggccattggcggcaaacgggaactgcgcgacgatgc*
*agtccagggcctgctggctggcttgttccggggtcttgccgaccaccaccacttccgggtcggtaaagca*
*cacggcggcaatcgctgccggctcgaagcgtcgggccttgccggcgatgatttcggcgaccatctcgcct*
*tgggccatggcccggtgcgccagcatcggttcgccagcgacgtcgccaatggcccagacgttgtgcatgc*
*tggtatgacagcgctcgtcgatggcaatggcggtgccgttcatcttcaggtccaggcattccaggttgaa*
*gcccttggtgcgtggccggcggcccacggccaccagtacctgatcggcttcaagacgcagttgcccaccc*
*ttgccgtcgctggccagcaggcagccattttcgtagccctcgacgctgtggcccaggtgcaacgcgatgc*
*ccagtttcttcagcgactcggccaccggggcggtcaattcgctgtcgtaggtcggcaggatgcgttcgcg*
*cgcttccaccacactcacctgtgcacccagcttgcgataggcaatgcccagctccaggccgatatagcca*
*ccgccgaccaccaccaggtgttgcggcagggctttcggcgccagggcttcggtcgaggaaatcaccgggc*
*cacccagcggcagcatcggcagttcgacactggtggaaccggtcgccagcaacagatgctcgcactggat*
*acgctggccatcgacctcgacctgcttgccgtccagtaccttggcccagccatgcaccactttcaccccg*
*tgctttttcagcaaggcggcaacaccggtggtcagacggtcgacaatgccgtccttccaggtgacgctct*
*ggccgatgtccaggcgcggcgaagccacgctgatgcccagcggcgagggttcggtaaagcgcgaggcttg*
*gtgaaactgctcggccacgtggatcagcgccttggacgggatgcagccgatgttcaggcaggtgccgccc*
*agtgcctggccttccaccagtacggtaggaatgcccagttgcccggcgcggatggctgctacatagccgc*
*cagggccgccgccgatgatcaacagggtagtctggataatctgttgcatgctcactccacgaacaggcag*
*gcgggttgttcgagcaggccacgcacggcctggatgaacagggcggcgtccatgccatcgaccacgcggt*
*ggtcgaacgagctggacaggttcatcatcttgcgcacgacgatctggccatcaatcaccaccggtcgttc*
*gaccatgcggttgaccccgacgattgccacttccggggtgttgaccaccggcgtgctgacaatgccaccc*
*aaggcgccgaggctggtcagggtgatggtcgagccggacagctcctcgcggctggccttgttgttacgtg*
*cagcgttggccaggcgcgaaatctcgccggcattggcccacaggctgcccgcttcggcgtggcgcagcac*
*gggtaccatcaggccgttgtcaccctgggtggcaatgcccacatgcaccgcgccatggcgggtgatgatc*
*tgcgcttcgtcgtcgtaggtcgcgttgatctgcgggaagtcacgcagcgccacgacgagggcgcgcacca*
*ggaatggcagcaaggtcagtttgccgcggctgtcgccgtgcttgctgttgagttgctggcgcagggcttc*
*cagggcggtgacgtcgatttcctcgacataactgaagtgcgcgacccggcgtttggcgtcctgcatgcgc*
*tgggcgatcttgcggcgcaggccgatcaccggcacctgctcgctgtcggtgcgcttggcataaccatcag*
*gtgcttgcccggcattgctttgcggcttgctcatgaaggcgtcgaggtcttcgtgcagaatgcgcccggc*
*cgggccgctaccatgcacataacgcagttcgataccggcgtccagggcgcgtttgcgcacggccggcgag*
*gccagcggcttgtcgcccggctggcgcggcacgatgggcgcagcttcgtggttggcgggcgcctggtaca*
*cggcgggttttacgtctttctgcggttccggcttggctgcaatcggggcggccggggcctctaccggttt*
*tggctgaggcacgtccacatggttgccgctgccttccacttcgatgcggatcagttcgctaccgaccgcc*
*atcacttccccgggctggccacccagggccaacaccttgccgctgaccggcgaggggatttccacggtgg*
*ccttgtcggtcatgacgtcggccaccacctggtcctcggcgatgatgtcgccgaccttgacgaaccattc*
*caccaactcgacctgcgcgatgccttcgccaatgtccggcatcttgatgacgtgcgtgcccattcagacc*
*tccatgacctttttcagtgccgcacctacccgcgaagggccggggaagtaagcccattcctgtgcgtgag*
*ggtagggggtgtcccagccggtgacgcgctcgatcggcgcctccaggtggtggaagcagtgctcctgcac*
*cagcgacaccagctcggcaccgaagccgcaggtgcgggtggcctcgtgcaccaccacgcaacggccagtc*
*tttttcaccgactcgacgatagtgtccaggtccagcggccacaggctgcgcaggtcgatcacttcggcat*
*cgacgccgctttcttcggcggccacctgggccacgtacaccgtggtgccgtaagtcagtacggtcacgtc*
*attgccagggcgggtaatggcggccttgtccagcggtacggtgtaatagccgtcgggcacggcgctgtgc*
*gggtgcttcgaccatggggttacagggcggtcgtggtggccatcgaacgggccgttgtacagacgtttgg*
*gctccaggaagattaccgggtcgtcgcattcgatcgaggcaatcagcaggcctttggcgtcataagggtt*

FIG. 7 cont'd ggacggcatcacggtgcgcaggccgcagacctgggtgaacatcgcttccgggctctggctgtgagtctgg
ccgccatagatgccgccgccgcaaggcatgcgcagggtcagcggggcaatgaactcgccggccgaccggt
aacgcaggcgggccagctcggagacgatctggtcggaggccgggtagaagtagtcggcgaactggatctc
caccaccgggcgcaggccataggcgcccatgcctacggcggtaccgacgatgccgctctcggagatgggc
gcgtcgaacacgcgcgatttgccgtacttgttctgcaggccttcggtgcagcggaacacgccgccgaagt
aaccgacgtcctggccgtacaccaccacattgtcgtcgcgctcaagcatgacatccatggccgagcgcag
ggcctggatcatggtcatggtagtggtggccatggcggtttccgggttgatgctgttgttgtggtcgttc
atcTCAaaccccccagttcctggcgttgacggcgcaggtgttcgggcatctccttgtacacatcctcgaac
atcgaggcggcgctcgggatgtgcccgttagccagggtgccgtactgctcggcttctttctgtgcggcaa
tcaccgcagcttcgagctcggccgtgacggcttggtgttcttcttcggaccagtggccgatcttgatcag
gtgctgcttcaggcgggcgatcgggtcacccagcgggaagtggctccagtcatcggcagggcggtacttg
gaggggtcgtccgacgtcgagtgcgggccggcacggtaggtgacccactcgatcaggcttgggcccaggc
cgcggcgggcgcgctcggcagcccagcgcgaggcggcgtacacggcgacgaagtcgttgccgtcaacccg
cagcgaggcaatgccgcagcccacgccacggccggcgaaggtggtcgactcgccaccggcgatggcctgg
aaggtagaaatcgcccactggttgttgaccacattgaggatcaccggggcgcggtaaacgtgggcaaagg
tgagggcggtgtggaagtccgactcggcggtggctccgtcaccgatccacgccgaagcaatcttggtatc
gcccttgatcgccgaggccatggcccagccgactgcctgcacgaactgggtcgccaggttgccgctgatg
gtgaagaagccggcttcgcgcaccgagtacatgatcggcaactggcggcccttgaggggtcgcgctcgt
tggacagcagttggcagatcatctcgaccagcgatacgtcgcgggccatcaggatgctttgctggcggta
ggtcgggaagcacatgtcggtgcggttcagcgccagcgcctggccactgccgatggcttcttcgcccagg
ctttgcatgtagaaggacatcttcttctggcgctgggcaaccaccatgcggctgtcgaagatccgcgtct
tgagcatggcgcgcatgccttgacgaaggatctgtgggtcgatgtcttcggcccaggggccttgcgcatc
accttgctcgtcgagcacgcggaccaggctgtaggacaggtcggcagtgtcggcagcatcgacatcgatc
gcgggtttacgggcttgacctgcatcgttgaggcgcaggtaggaaaaatcggtctggcagcctggccggc
cggtgggctcgggcacatgcaaacgcagggggggcgtactcgttcatGGATCCATGGTTTATTCCTCCTTA
TTTAATCGATACATTAATATATACCTCTTTAATTTTTAATAATAAAGTTAATCGATAATTCCGGTCGAGT
GCCCACACAGATTGTCTGATAAATTGTTAAAGAGCAGTGCCGCTTCGCTTTTTCTCAGCGGCGCTGTTTC
CTGTGTGAAATTGTTATCCGCTCACAATTCCACACATTATACGAGCCGGATGATTAATTGTCAACAGCTC
ATTTCAGAATATTTGCCAGAACCGTTATGATGTCGGCGCAAAAAACATTATCCAGAACGGGAGTGCGCCT
TGAGCGACACGAATTATGCAGTGATTTACGACCTGCACAGCCATACCACAGCTTCCGATGGCTGCCTGAC
GCCAGAAGCATTGGTGCACCGTGCAGTCGATGATAAGCTGTCAAACCAGATCAATTCGCGCTAACTCACA
TTAATTGCGTTGCGCTCACTGCCCGCTTTCCAGTCGGGAAACCTGTCGTGCCAGCTGCATTAATGAATCG
GCCAACGCGCGGGGAGAGGCGGTTTGCGTATTGGGCGCCAGGGTGGTTTTTCTTTTCACCAGTGAGACGG
GCAACAGCTGATTGCCCTTCACCGCCTGGCCCTGAGAGAGTTGCAGCAAGCGGTCCACGCTGGTTTGCCC
CAGCAGGCGAAAATCCTGTTTGATGGTGGTTGACGGCGGGATATAACATGAGCTGTCTTCGGTATCGTCG
TATCCCACTACCGAGATATCCGCACCAACGCGCAGCCCGGACTCGGTAATGGCGCGCATTGCGCCCAGCG
CCATCTGATCGTTGGCAACCAGCATCGCAGTGGGAACGATGCCCTCATTCAGCATTTGCATGGTTTGTTG
AAAACCGGACATGGCACTCCAGTCGCCTTCCCGTTCCGCTATCGGCTGAATTTGATTGCGAGTGAGATAT
TTATGCCAGCCAGCCAGACGCAGACGCGCCGAGACAGAACTTAATGGGCCCGCTAACAGCGCGATTTGCT
GGTGACCCAATGCGACCAGATGCTCCACGCCCAGTCGCGTACCGTCTTCATGGGAGAAAATAATACTGTT
GATGGGTGTCTGGTCAGAGACATCAAGAAATAACGCCGGAACATTAGTGCAGGCAGCTTCCACAGCAATG
GCATCCTGGTCATCCAGCGGATAGTTAATGATCAGCCCACTGACGCGTTGCGCGAGAAGATTGTGCACCG
CCGCTTTACAGGCTTCGACGCCGCTTCGTTCTACCATCGACACCACCACGCTGGCACCCAGTTGATCGGC
GCGAGATTTAATCGCCGCGACAATTTGCGACGGCGCGTGCAGGGCCAGACTGGAGGTGGCAACGCCAATC
AGCAACGACTGTTTGCCCGCCAGTTGTTGTGCCACGCGGTTGGGAATGTAATTCAGCTCCGCCATCGCCG
CTTCCACTTTTTCCCGCGTTTTCGCAGAAACGTGGCTGGCCTGGTTCACCACGCGGGAAACGGTCTGATA
AGAGACACCGGCATACTCTGCGACATCGTATAACGTTACTGGTTTCACATTCACCACCCTGAATTGACTC
TCTTCCGGGCGCTATCATGCCATACCGCGAAAGGTTTTGCACCATTCGATGGTGTCAACGTAAATGCATG
CCGCTTCGCCTTCGCGCGCGAATTGATCTGCTGCCTCGCGCGTTTCGGTGATGACGGTGAAAACCTCTGA
CACATGCAGCTCCCGGAGACGGTCACAGCTTGTCTGTAAGCGGATGCCGGGAGCAGACAAGCCCGTCAGG
GCGCGTCAGCGGGTGTTGGCGGggccggcc (SEQ ID NO:136)

FIG. 8 pGL10.173b vector backbone sequence:

tcgcgacgcgaggctggatggccttccccattatgattcttctcgcttccggcggcatcgggatgcccgc
gttgcaggccatgctgtccaggcaggtagatgacgaccatcagggacagcttcaaggatcgctcgcggct
cttaccagcctaacttcgatcactggaccgctgatcgtcacggcgatttatgccgcctcggcgagcacat
ggaacgggttggcatggattgtaggcgccgccctataccttgtctgcctccccgcgttgcgtcgcggtgc
atggagccgggccacctcgacctgaatggaagccggcggcacctcgctaacggattcaccactccaagaa
ttggagccaatcaattcttgcggagaactgtgaatgcgcaaaccaacccttggcagaacatatccatcgc
gtccgccatctccagcagccgcacgcggcgcatctcgggcagcgttgggtcctggccacgggtgcgcatg
atcgtgctcctgtcgttgaggacccggctaggctggcggggttgccttactggttagcagaatgaatcac
cgatacgcgagcgaacgtgaagcgactgctgctgcaaaacgtctgcgacctgagcaacaacatgaatggt
cttcggtttccgtgtttcgtaaagtctggaaacgcggaagtcagcgccctgcaccattatgttccggatc
tgcatcgcaggatgctgctggctaccctgtggaacacctacatctgtattaacgaagcgctggcattgac
cctgagtgatttttctctggtcccgccgcatccataccgccagttgtttaccctcacaacgttccagtaa
ccgggcatgttcatcatcagtaacccgtatcgtgagcatcctctctcgtttcatcggtatcattaccccc
atgaacagaaatcccccttacacggaggcatcagtgaccaaacaggaaaaaaccgcccttaacatggccc
gctttatcagaagccagacattaacgcttctggagaaactcaacgagctggacgcggatgaacaggcaga
catctgtgaatcgcttcacgaccacgctgatgagctttaccgcagctgcctcgcgcgtttcggtgatgac
ggtgaaaacctctgacacatgcagctcccggagacggtcacagcttgtctgtaagcggatgccgggagca
gacaagcccgtcagggcgcgtcagcgggtgttggcgggtgtcggggcgcagccatgacccagtcacgtag
cgatagcggagtgtatactggcttaactatgcggcatcagagcagattgtactgagagtgcaccatatgc
ggtgtgaaataccgcacagatgcgtaaggagaaaataccgcatcaggcgctcttccgcttcctcgctcac
tgactcgctgcgctcggtcgttcggctgcggcgagcggtatcagctcactcaaaggcggtaatacggtta
tccacagaatcaggggataacgcaggaaagaacatgtgagcaaaaggccagcaaaaggccaggaaccgta
aaaaggccgcgttgctggcgtttttccataggctccgcccccctgacgagcatcacaaaaatcgacgctc
aagtcagaggtggcgaaacccgacaggactataaagataccaggcgtttccccctggaagctccctcgtg
cgctctcctgttccgaccctgccgcttaccggatacctgtccgcctttctcccttcgggaagcgtggcgc
tttctcatagctcacgctgtaggtatctcagttcggtgtaggtcgttcgctccaagctgggctgtgtgca
cgaaccccccgttcagcccgaccgctgcgccttatccggtaactatcgtcttgagtccaacccggtaaga
cacgacttatcgccactggcagcagccactggtaacaggattagcagagcgaggtatgtaggcggtgcta
cagagttcttgaagtggtggcctaactacggctacactagaaggacagtatttggtatctgcgctctgct
gaagccagttaccttcggaaaaagagttggtagctcttgatccggcaaacaaaccaccgctggtagcggt
ggtttttttgtttgcaagcagcagattacgcgcagaaaaaaaggatctcaagaagatcctttgatctttt
ctacggggtctgacgctcagtggaacgaaaactcacgttaagggattttggtcatgagattatcaaaaag
gatcttcacctagatccttttaaattaaaaatgaagttttaaatcaatctaaagtatatatgagtaaact
tggtctgacagttaccaatgcttaatcagtgaggcacctatctcagcgatctgtctatttcgttcatcca
tagttgcctgactccccgtcgtgtagataactacgatacgggagggcttaccatctggccccagtgctgc
aatgataccgcgagacccacgctcaccggctccagatttatcagcaataaaccagccagccggaagggcc
gagcgcagaagtggtcctgcaactttatccgcctccatccagtctattaattgttgccgggaagctagag
taagtagttcgccagttaatagtttgcgcaacgttgttgccattgctgcaggcatcgtggtgtcacgctc
gtcgtttggtatggcttcattcagctccggttcccaacgatcaaggcgagttacatgatcccccatgttg
tgcaaaaaagcggttagctccttcggtcctccgatcgttgtcagaagtaagttggccgcagtgttatcac
tcatggttatggcagcactgcataattctcttactgtcatgccatccgtaagatgcttttctgtgactgg
tgagtactcaaccaagtcattctgagaatagtgtatgcggcgaccgagttgctcttgcccggcgtcaaca
cgggataataccgcgccacatagcagaactttaaaagtgctcatcattggaaaacgttcttcggggcgaa
aactctcaaggatcttaccgctgttgagatccagttcgatgtaacccactcgtgcacccaactgatcttc
agcatcttttactttcaccagcgtttctgggtgagcaaaaacaggaaggcaaaatgccgcaaaaaaggga
ataagggcgacacggaaatgttgaatactcatactcttcctttttcaatattattgaagcatttatcagg
gttattgtctcatgagcggatacatatttgaatgtatttagaaaaataaacaaataggggttccgcgcac

FIG. 8 cont'd atttccccgaaaagtgccacctgacgtcttaattaaTCAGGAGAGCGTTCACCGACAAACAACAGATAAA
ACGAAAGGCCCAGTCTTTCGACTGAGCCTTTCGTTTTATTTGATGCCTGGCAGTTCCCTACTCTCGCATG
GGGAGACCCCACACTACCATCGGCGCTACGGCGTTTCACTTCTGAGTTCGGCATGGGGTCAGGTGGGACC
ACCGCGCTACTGCCGCCAGGCAAATTCTGTTTTATCAGACCGCTTCTGCGTTCTGATTTAATCTGTATCA
GGCTGAAAATCTTCTCTCATCCGCCAAAACAGCCAAGCTGGAGACCGTTTAAACTCAATGATGATGATGA
TGATGGTCGACGGCGCTATTCAGATCCTCTTCTGAGATGAGTTTTTGTTCGGGCCCAAGCTTCG (EcoRI
) AATTCCCATATGGTACCAGCTGCAGATCTCGAGCTCG (BamHI) GATCCATGGTTTATTCCTCCTTATT
TAATCGATACATTAATATATACCTCTTTAATTTTTAATAATAAAGTTAATCGATAATTCCGGTCGAGTGC
CCACACAGATTGTCTGATAAATTGTTAAAGAGCAGTGCCGCTTCGCTTTTTCTCAGCGGCGCTGTTTCCT
GTGTGAAATTGTTATCCGCTCACAATTCCACACATTATACGAGCCGGATGATTAATTGTCAACAGCTCAT
TTCAGAATATTTGCCAGAACCGTTATGATGTCGGCGCAAAAAACATTATCCAGAACGGGAGTGCGCCTTG
AGCGACACGAATTATGCAGTGATTTACGACCTGCACAGCCATACCACAGCTTCCGATGGCTGCCTGACGC
CAGAAGCATTGGTGCACCGTGCAGTCGATGATAAGCTGTCAAACCAGATCAATTCGCGCTAACTCACATT
AATTGCGTTGCGCTCACTGCCCGCTTTCCAGTCGGGAAACCTGTCGTGCCAGCTGCATTAATGAATCGGC
CAACGCGCGGGGAGAGGCGGTTTGCGTATTGGGCGCCAGGGTGGTTTTTCTTTTCACCAGTGAGACGGGC
AACAGCTGATTGCCCTTCACCGCCTGGCCCTGAGAGAGTTGCAGCAAGCGGTCCACGCTGGTTTGCCCCA
GCAGGCGAAAATCCTGTTTGATGGTGGTTGACGGCGGGATATAACATGAGCTGTCTTCGGTATCGTCGTA
TCCCACTACCGAGATATCCGCACCAACGCGCAGCCCGGACTCGGTAATGGCGCGCATTGCGCCCAGCGCC
ATCTGATCGTTGGCAACCAGCATCGCAGTGGGAACGATGCCCTCATTCAGCATTTGCATGGTTTGTTGAA
AACCGGACATGGCACTCCAGTCGCCTTCCCGTTCCGCTATCGGCTGAATTTGATTGCGAGTGAGATATTT
ATGCCAGCCAGCCAGACGCAGACGCGCCGAGACAGAACTTAATGGGCCCGCTAACAGCGCGATTTGCTGG
TGACCCAATGCGACCAGATGCTCCACGCCCAGTCGCGTACCGTCTTCATGGGAGAAAATAATACTGTTGA
TGGGTGTCTGGTCAGAGACATCAAGAAATAACGCCGGAACATTAGTGCAGGCAGCTTCCACAGCAATGGC
ATCCTGGTCATCCAGCGGATAGTTAATGATCAGCCCACTGACGCGTTGCGCGAGAAGATTGTGCACCGCC
GCTTTACAGGCTTCGACGCCGCTTCGTTCTACCATCGACACCACCACGCTGGCACCCAGTTGATCGGCGC
GAGATTTAATCGCCGCGACAATTTGCGACGGCGCGTGCAGGGCCAGACTGGAGGTGGCAACGCCAATCAG
CAACGACTGTTTGCCCGCCAGTTGTTGTGCCACGCGGTTGGGAATGTAATTCAGCTCCGCCATCGCCGCT
TCCACTTTTTCCCGCGTTTTCGCAGAAACGTGGCTGGCCTGGTTCACCACGCGGGAAACGGTCTGATAAG
AGACACCGGCATACTCTGCGACATCGTATAACGTTACTGGTTTCACATTCACCACCCTGAATTGACTCTC
TTCCGGGCGCTATCATGCCATACCGCGAAAGGTTTTGCACCATTCGATGGTGTCAACGTAAATGCATGCC
GCTTCGCCTTCGCGCGCGAATTGATCTGCTGCCTCGCGCGTTTCGGTGATGACGGTGAAAACCTCTGACA
CATGCAGCTCCCGGAGACGGTCACAGCTTGTCTGTAAGCGGATGCCGGGAGCAGACAAGCCCGTCAGGGC
GCGTCAGCGGGTGTTGGCGGgccggcc (SEQ ID NO:137)

FIG. 9: Sequences of the Disclosure

**AAR_7942 sequence, SEQ ID NO:158 - *Synechococcus elongatus* PCC7942 Synpcc7942_1594 DNA**

```
   1 atgttcggtc ttatcggtca tctcaccagt ttggagcagg cccgcgacgt ttctcgcagg
  61 atgggctacg acgaatacgc cgatcaagga ttggagtttt ggagtagcgc tcctcctcaa
 121 atcgttgatg aaatcacagt caccagtgcc acaggcaagg tgattcacgg tcgctacatc
 181 gaatcgtgtt tcttgccgga aatgctggcg gcgcgccgct tcaaaacagc cacgcgcaaa
 241 gttctcaatg ccatgtccca tgcccaaaaa cacggcatcg acatctcggc cttggggggc
 301 tttacctcga ttattttcga gaatttcgat ttggccagtt tgcggcaagt gcgcgacact
 361 accttggagt ttgaacggtt caccaccggc aatactcaca cggcctacgt aatctgtaga
 421 caggtggaag ccgctgctaa aacgctgggc atcgacatta cccaagcgac agtagcggtt
 481 gtcggcgcga ctggcgatat cggtagcgct gtctgccgct ggctcgacct caaactgggt
 541 gtcggtgatt tgatcctgac ggcgcgcaat caggagcgtt tggataacct gcaggctgaa
 601 ctcggccggg gcaagattct gcccttggaa gccgctctgc cggaagctga ctttatcgtg
 661 tgggtcgcca gtatgcctca gggcgtagtg atcgacccag caaccctgaa gcaaccctgc
 721 gtcctaatcg acgggggcta ccccaaaaac ttgggcagca aagtccaagg tgagggcatc
 781 tatgtcctca atggcggggt agttgaacat tgcttcgaca tcgactggca gatcatgtcc
 841 gctgcagaga tggcgcggcc cgagcgccag atgtttgcct gctttgccga ggcgatgctc
 901 ttggaatttg aaggctggca tactaacttc tcctggggcc gcaaccaaat cacgatcgag
 961 aagatggaag cgatcggtga ggcatcggtg cgccacggct tccaaccctt ggcattggca
1021 atttga (SEQ ID NO:138)
```

**SEQ ID NO:159 - *Synechococcus elongatus* PCC7942 Synpcc7942_1594 protein (YP_400611)**

```
   1 MFGLIGHLTS LEQARDVSRR MGYDEYADQG LEFWSSAPPQ IVDEITVTSA TGKVIHGRYI
  61 ESCFLPEMLA ARRFKTATRK VLNAMSHAQK HGIDISALGG FTSIIFENFD LASLRQVRDT
 121 TLEFERFTTG NTHTAYVICR QVEAAAKTLG IDITQATVAV VGATGDIGSA VCRWLDLKLG
 181 VGDLILTARN QERLDNLQAE LGRGKILPLE AALPEADFIV WVASMPQGVV IDPATLKQPC
 241 VLIDGGYPKN LGSKVQGEGI YVLNGGVVEH CFDIDWQIMS AAEMARPERQ MFACFAEAML
 301 LEFEGWHTNF SWGRNQITIE KMEAIGEASV RHGFQPLALA I (SEQ ID NO:139)
```

SEQ ID NO:160 – Nucleotide sequence of plasmid pCL-Ptrc-carB_'tesA

```
CACTATACCAATTGAGATGGGCTAGTCAATGATAATTACTAGTCCTTTTCCTTTGAGTTGTGGGTATCTG
TAAATTCTGCTAGACCTTTGCTGGAAAACTTGTAAATTCTGCTAGACCCTCTGTAAATTCCGCTAGACCT
TTGTGTGTTTTTTTTGTTTATATTCAAGTGGTTATAATTTATAGAATAAAGAAAGAATAAAAAAAGATAA
AAAGAATAGATCCCAGCCCTGTGTATAACTCACTACTTTAGTCAGTTCCGCAGTATTACAAAAGGATGTC
GCAAACGCTGTTTGCTCCTCTACAAAACAGACCTTAAAACCCTAAAGGCgtcGGCATCCGCTTACAGACA
AGCTGTGACCGTCTCCGGGAGCTGCATGTGTCAGAGGTTTTCACCGTCATCACCGAAACGCGCGAGGCAG
CAGATCAATTCGCGCGCGAAGGCGAAGCGGCATGCATTTACGTTGACACCATCGAATGGTGCAAAACCTT
TCGCGGTATGGCATGATAGCGCCCGGAAGAGAGTCAATTCAGGGTGGTGAATGTGAAACCAGTAACGTTA
TACGATGTCGCAGAGTATGCCGGTGTCTCTTATCAGACCGTTTCCCGCGTGGTGAACCAGGCCAGCCACG
TTTCTGCGAAAACGCGGGAAAAAGTGGAAGCGGCGATGGCGGAGCTGAATTACATTCCCAACCGCGTGGC
ACAACAACTGGCGGGCAAACAGTCGTTGCTGATTGGCGTTGCCACCTCCAGTCTGGCCCTGCACGCGCCG
TCGCAAATTGTCGCGGCGATTAAATCTCGCGCCGATCAACTGGGTGCCAGCGTGGTGGTGTCGATGGTAG
AACGAAGCGGCGTCGAAGCCTGTAAAGCGGCGGTGCACAATCTTCTCGCGCAACGCGTCAGTGGGCTGAT
CATTAACTATCCGCTGGATGACCAGGATGCCATTGCTGTGGAAGCTGCCTGCACTAATGTTCCGGCGTTA
TTTCTTGATGTCTCTGACCAGACACCCATCAACAGTATTATTTTCTCCCATGAAGACGGTACGCGACTGG
GCGTGGAGCATCTGGTCGCATTGGGTCACCAGCAAATCGCGCTGTTAGCGGGCCCATTAAGTTCTGTCTC
```

FIG. 9 cont'd

GGCGCGTCTGCGTCTGGCTGGCTGGCATAAATATCTCACTCGCAATCAAATTCAGCCGATAGCGGAACGG
GAAGGCGACTGGAGTGCCATGTCCGGTTTTCAACAAACCATGCAAATGCTGAATGAGGGCATCGTTCCCA
CTGCGATGCTGGTTGCCAACGATCAGATGGCGCTGGGCGCAATGCGCGCCATTACCGAGTCCGGGCTGCG
CGTTGGTGCGGATATCTCGGTAGTGGGATACGACGATACCGAAGACAGCTCATGTTATATCCCGCCGTtA
ACCACCATCAAACAGGATTTTCGCCTGCTGGGGCAAACCAGCGTGGACCGCTTGCTGCAACTCTCTCAGG
GCCAGGCGGTGAAGGGCAATCAGCTGTTGCCCGTCTCACTGGTGAAAAGAAAAACCACCCTGGCGCCCAA
TACGCAAACCGCCTCTCCCCGCGCGTTGGCCGATTCATTAATGCAGCTGGCACGACAGGTTTCCCGACTG
GAAAGCGGGCAGTGAGCGCAACGCAATTAATGTaAGTTAGCGCGAATTGATCTGGTTTGACAGCTTATCA
TCGACTGCACGGTGCACCAATGCTTCTGGCGTCAGGCAGCCATCGGAAGCTGTGGTATGGCTGTGCAGGT
CGTAAATCACTGCATAATTCGTGTCGCTCAAGGCGCACTCCCGTTCTGGATAATGTTTTTTGCGCCGACA
TCATAACGGTTCTGGCAAATATTCTGAAATGAGCTGTTGACAATTAATCATCCGGCTCGTATAATGTGTG
GAATTGTGAGCGGATAACAATTTCACACAGGAAACAGCGCCGCTGAGAAAAAGCGAAGCGGCACTGCTCT
TTAACAATTTATCAGACAATCTGTGTGGGCACTCGACCGGAATTATCGATTAACTTTATTATTAAAAATT
AAAGAGGTATATATTAATGTATCGATTAAATAAGGAGGAATAAACCATGACCAGCGATGTTCACGACGCC
ACAGACGGCGTCACCGAAACCGCACTCGACGACGAGCAGTCGACCCGCCGCATCGCCGAGCTGTACGCCA
CCGATCCCGAGTTCGCCGCCGCCGCACCGTTGCCCGCCGTGGTCGACGCGGCGCACAAACCCGGGCTGCG
GCTGGCAGAGATCCTGCAGACCCTGTTCACCGGCTACGGTGACCGCCCGGCGCTGGGATACCGCGCCCGT
GAACTGGCCACCGACGAGGGCGGGCGCACCGTGACGCGTCTGCTGCCGCGGTTCGACACCCTCACCTACG
CCCAGGTGTGGTCGCGCGTGCAAGCGGTCGCCGCGGCCCTGCGCCACAACTTCGCGCAGCCGATCTACCC
CGGCGACGCCGTCGCGACGATCGGTTTCGCGAGTCCCGATTACCTGACGCTGGATCTCGTATGCGCCTAC
CTGGGCCTCGTGAGTGTTCCGCTGCAGCACAACGCACCGGTCAGCCGGCTCGCCCCGATCCTGGCCGAGG
TCGAACCGCGGATCCTCACCGTGAGCGCCGAATACCTCGACCTCGCAGTCGAATCCGTGCGGGACGTCAA
CTCGGTGTCGCAGCTCGTGGTGTTCGACCATCACCCCGAGGTCGACGACCACCGCGACGCACTGGCCCGC
GCGCGTGAACAACTCGCCGGCAAGGGCATCGCCGTCACCACCCTGGACGCGATCGCCGACGAGGGCGCCG
GGCTGCCGGCCGAACCGATCTACACCGCCGACCATGATCAGCGCCTCGCGATGATCCTGTACACCTCGGG
TTCCACCGGCGCACCCAAGGGTGCGATGTACACCGAGGCGATGGTGGCGCGGCTGTGGACCATGTCGTTC
ATCACGGGTGACCCCACGCCGGTCATCAACGTCAACTTCATGCCGCTCAACCACCTGGGCGGGCGCATCC
CCATTTCCACCGCCGTGCAGAACGGTGGAACCAGTTACTTCGTACCGGAATCCGACATGTCCACGCTGTT
CGAGGATCTCGCGCTGGTGCGCCCGACCGAACTCGGCCTGGTTCCGCGCGTCGCCGACATGCTCTACCAG
CACCACCTCGCCACCGTCGACCGCCTGGTCACGCAGGGCGCCGACGAACTGACCGCCGAGAAGCAGGCCG
GTGCCGAACTGCGTGAGCAGGTGCTCGGCGGACGCGTGATCACCGGATTCGTCAGCACCGCACCGCTGGC
CGCGGAGATGAGGGCGTTCCTCGACATCACCCTGGGCGCACACATCGTCGACGGCTACGGGCTCACCGAG
ACCGGCGCCGTGACACGCGACGGTGTGATCGTGCGGCCACCGGTGATCGACTACAAGCTGATCGACGTTC
CCGAACTCGGCTACTTCAGCACCGACAAGCCCTACCCGCGTGGCGAACTGCTGGTCAGGTCGCAAACGCT
GACTCCCGGGTACTACAAGCGCCCCGAGGTCACCGCGAGCGTCTTCGACCGGGACGGCTACTACCACACC
GGCGACGTCATGGCCGAGACCGCACCCGACCACCTGGTGTACGTGGACCGTCGCAACAACGTCCTCAAAC
TCGCGCAGGGCGAGTTCGTGGCGGTCGCCAACCTGGAGGCGGTGTTCTCCGGCGCGGCGCTGGTGCGCCA
GATCTTCGTGTACGGCAACAGCGAGCGCAGTTTCCTTCTGGCCGTGGTGGTCCCGACGCCGGAGGCGCTC
GAGCAGTACGATCCGGCCGCGCTCAAGGCCGCGCTGGCCGACTCGCTGCAGCGCACCGCACGCGACGCCG
AACTGCAATCCTACGAGGTGCCGGCCGATTTCATCGTCGAGACCGAGCCGTTCAGCGCCGCCAACGGGCT
GCTGTCGGGTGTCGGAAAACTGCTGCGGCCCAACCTCAAAGACCGCTACGGGCAGCGCCTGGAGCAGATG
TACGCCGATATCGCGGCCACGCAGGCCAACCAGTTGCGCGAACTGCGGCGCGCGGCCGCCACACAACCGG
TGATCGACACCCTCACCCAGGCCGCTGCCACGATCCTCGGCACCGGGAGCGAGGTGGCATCCGACGCCCA
CTTCACCGACCTGGGCGGGGATTCCCTGTCGGCGCTGACACTTTCGAACCTGCTGAGCGATTTCTTCGGT
TTCGAAGTTCCCGTCGGCACCATCGTGAACCCGGCCACCAACCTCGCCCAACTCGCCCAGCACATCGAGG
CGCAGCGCACCGCGGGTGACCGCAGGCCGAGTTTCACCACCGTGCACGGCGCGGACGCCACCGAGATCCG
GGCGAGTGAGCTGACCCTGGACAAGTTCATCGACGCCGAAACGCTCCGGGCCGCACCGGGTCTGCCCAAG
GTCACCACCGAGCCACGGACGGTGTTGCTCTCGGGCGCCAACGGCTGGCTGGGCCGGTTCCTCACGTTGC
AGTGGCTGGAACGCCTGGCACCTGTCGGCGGCACCCTCATCACGATCGTGCGGGGCCGCGACGACGCCGC
GGCCCGCGCACGGCTGACCCAGGCCTACGACACCGATCCCGAGTTGTCCCGCCGCTTCGCCGAGCTGGCC
GACCGCCACCTGCGGGTGGTCGCCGGTGACATCGGCGACCCGAATCTGGGCCTCACACCCGAGATCTGGC
ACCGGCTCGCCGCCGAGGTCGACCTGGTGGTGCATCCGGCAGCGCTGGTCAACCACGTGCTCCCCTACCG

FIG. 9 cont'd

GCAGCTGTTCGGCCCCAACGTCGTGGGCACGGCCGAGGTGATCAAGCTGGCCCTCACCGAACGGATCAAG
CCCGTCACGTACCTGTCCACCGTGTCGGTGGCCATGGGGATCCCCGACTTCGAGGAGGACGGCGACATCC
GGACCGTGAGCCCGGTGCGCCCGCTCGACGGCGGATACGCCAACGGCTACGGCAACAGCAAGTGGGCCGG
CGAGGTGCTGCTGCGGGAGGCCCACGATCTGTGCGGGCTGCCCGTGGCGACGTTCCGCTCGGACATGATC
CTGGCGCATCCGCGCTACCGCGGTCAGGTCAACGTGCCAGACATGTTCACGCGACTCCTGTTGAGCCTCT
TGATCACCGGCGTCGCGCCGCGGTCGTTCTACATCGGAGACGGTGAGCGCCCGCGGGCGCACTACCCCGG
CCTGACGGTCGATTTCGTGGCCGAGGCGGTCACGACGCTCGGCGCGCAGCAGCGCGAGGGATACGTGTCC
TACGACGTGATGAACCCGCACGACGACGGGATCTCCCTGGATGTGTTCGTGGACTGGCTGATCCGGGCGG
GCCATCCGATCGACCGGGTCGACGACTACGACGACTGGGTGCGTCGGTTCGAGACCGCGTTGACCGCGCT
TCCCGAGAAGCGCCGCGCACAGACCGTACTGCCGCTGCTGCACGCGTTCCGCGCTCCGCAGGCACCGTTG
CGCGGCGCACCCGAACCCACGGAGGTGTTCCACGCCGCGGTGCGCACCGCGAAGGTGGGCCCGGGAGACA
TCCCGCACCTCGACGAGGCGCTGATCGACAAGTACATACGCGATCTGCGTGAGTTCGGTCTGATCTGAGA
ATTCTAGATCTGATCGTTGCGGGCGGGGCGAGAGTCTCGCCCCGCCCGCGACCGCGGTGAAAATACGAGA
ATATTATTTGTATTGATCTCCTAGGCGGGGTACCGTATTTTGGATGATAACGAGGCGCAAAAAATGGCGG
ACACGTTATTGATTCTGGGTGATAGCCTGAGCGCCGGGTATCGAATGTCTGCCAGCGCGGCCTGGCCTGC
CTTGTTGAATGATAAGTGGCAGAGTAAAACGTCGGTAGTTAATGCCAGCATCAGCGGCGACACCTCGCAA
CAAGGACTGGCGCGCCTTCCGGCTCTGCTGAAACAGCATCAGCCGCGTTGGGTGCTGGTTGAACTGGGCG
GCAATGACGGTTTGCGTGGTTTTCAGCCACAGCAAACCGAGCAAACGCTGCGCCAGATTTTGCAGGATGT
CAAAGCCGCCAACGCTGAACCATTGTTAATGCAAATACGTCTGCCTGCAAACTATGGTCGCCGTTATAAT
GAAGCCTTTAGCGCCATTTACCCCAAACTCGCCAAAGAGTTTGATGTTCCGCTGCTGCCCTTTTTTATGG
AAGAGGTCTACCTCAAGCCACAATGGATGCAGGATGACGGTATTCATCCCAACCGCGACGCCCAGCCGTT
TATTGCCGACTGGATGGCGAAGCAGTTGCAGCCTTTAGTAAATCATGACTCATAAcctaggggtaccgct
agcgagctctctagaGAAGCTTGGGCCCGAACAAAAACTCATCTCAGAAGAGGATCTGAATAGCGCCGTC
GACCATCATCATCATCATCATTGAGTTTAAACGGTCTCCAGCTTGGCTGTTTTGGCGGATGAGAGAAGAT
TTTCAGCCTGATACAGATTAAATCAGAACGCAGAAGCGGTCTGATAAAACAGAATTTGCCTGGCGGCAGT
AGCGCGGTGGTCCCACCTGACCCCATGCCGAACTCAGAAGTGAAACGCCGTAGCGCCGATGGTAGTGTGG
GGTCTCCCCATGCGAGAGTAGGGAACTGCCAGGCATCAAATAAAACGAAAGGCTCAGTCGAAAGACTGGG
CCTTTCGTTTTATCTGTTGTTTGTCGGTGAACGCTCTCCTgacGCCTGATGCGGTATTTTCTCCTTACGC
ATCTGTGCGGTATTTCACACCGCATATGGTGCACTCTCAGTACAATCTGCTCTGATGCCGCATAGTTAAG
CCAGCCCCGACACCCGCCAACACCCGCTGACGAGCTTAGTAAAGCCCTCGCTAGATTTTAATGCGGATGT
TGCGATTACTTCGCCAACTATTGCGATAACAAGAAAAAGCCAGCCTTTCATGATATATCTCCCAATTTGT
GTAGGGCTTATTATGCACGCTTAAAAATAATAAAAGCAGACTTGACCTGATAGTTTGGCTGTGAGCAATT
ATGTGCTTAGTGCATCTAACGCTTGAGTTAAGCCGCGCCGCGAAGCGGCGTCGGCTTGAACGAATTGTTA
GACATTATTTGCCGACTACCTTGGTGATCTCGCCTTTCACGTAGTGGACAAATTCTTCCAACTGATCTGC
GCGCGAGGCCAAGCGATCTTCTTCTTGTCCAAGATAAGCCTGTCTAGCTTCAAGTATGACGGGCTGATAC
TGGGCCGGCAGGCGCTCCATTGCCCAGTCGGCAGCGACATCCTTCGGCGCGATTTTGCCGGTTACTGCGC
TGTACCAAATGCGGGACAACGTAAGCACTACATTTCGCTCATCGCCAGCCCAGTCGGGCGGCGAGTTCCA
TAGCGTTAAGGTTTCATTTAGCGCCTCAAATAGATCCTGTTCAGGAACCGGATCAAAGAGTTCCTCCGCC
GCTGGACCTACCAAGGCAACGCTATGTTCTCTTGCTTTTGTCAGCAAGATAGCCAGATCAATGTCGATCG
TGGCTGGCTCGAAGATACCTGCAAGAATGTCATTGCGCTGCCATTCTCCAAATTGCAGTTCGCGCTTAGC
TGGATAACGCCACGGAATGATGTCGTCGTGCACAACAATGGTGACTTCTACAGCGCGGAGAATCTCGCTC
TCTCCAGGGGAAGCCGAAGTTTCCAAAAGGTCGTTGATCAAAGCTCGCCGCGTTGTTTCATCAAGCCTTA
CGGTCACCGTAACCAGCAAATCAATATCACTGTGTGGCTTCAGGCCGCCATCCACTGCGGAGCCGTACAA
ATGTACGGCCAGCAACGTCGGTTCGAGATGGCGCTCGATGACGCCAACTACCTCTGATAGTTGAGTCGAT
ACTTCGGCGATCACCGCTTCCCTCATGATGTTTAACTTTGTTTTAGGGCGACTGCCCTGCTGCGTAACAT
CGTTGCTGCTCCATAACATCAAACATCGACCCACGGCGTAACGCGCTTGCTGCTTGGATGCCCGAGGCAT
AGACTGTACCCCAAAAAAACAGTCATAACAAGCCATGAAAACCGCCACTGCGCCGTTACCACCGCTGCGT
TCGGTCAAGGTTCTGGACCAGTTGCGTGAGCGCATACGCTACTTGCATTACAGCTTACGAACCGAACAGG
CTTATGTCCACTGGGTTCGTGCCTTCATCCGTTTCCACGGTGTGCGTCACCCGGCAACCTTGGGCAGCAG
CGAAGTCGAGGCATTTCTGTCCTGGCTGGCGAACGAGCGCAAGGTTTCGGTCTCCACGCATCGTCAGGCA
TTGGCGGCCTTGCTGTTCTTCTACGGCAAGGTGCTGTGCACGGATCTGCCCTGGCTTCAGGAGATCGGAA
GACCTCGGCCGTCGCGGCGCTTGCCGGTGGTGCTGACCCCGGATGAAGTGGTTCGCATCCTCGGTTTTCT

FIG. 9 cont'd

GGAAGGCGAGCATCGTTTGTTCGCCCAGCTTCTGTATGGAACGGGCATGCGGATCAGTGAGGGTTTGCAA
CTGCGGGTCAAGGATCTGGATTTCGATCACGGCACGATCATCGTGCGGGAGGGCAAGGGCTCCAAGGATC
GGGCCTTGATGTTACCCGAGAGCTTGGCACCCAGCCTGCGCGAGCAGGGGAATTAATTCCCACGGGTTTT
GCTGCCCGCAAACGGGCTGTTCTGGTGTTGCTAGTTTGTTATCAGAATCGCAGATCCGGCTTCAGCCGGT
TTGCCGGCTGAAAGCGCTATTTCTTCCAGAATTGCCATGATTTTTTCCCCACGGGAGGCGTCACTGGCTC
CCGTGTTGTCGGCAGCTTTGATTCGATAAGCAGCATCGCCTGTTTCAGGCTGTCTATGTGTGACTGTTGA
GCTGTAACAAGTTGTCTCAGGTGTTCAATTTCATGTTCTAGTTGCTTTGTTTTACTGGTTTCACCTGTTC
TATTAGGTGTTACATGCTGTTCATCTGTTACATTGTCGATCTGTTCATGGTGAACAGCTTTGAATGCACC
AAAAACTCGTAAAAGCTCTGATGTATCTATCTTTTTTACACCGTTTTCATCTGTGCATATGGACAGTTTT
CCCTTTGATATGTAACGGTGAACAGTTGTTCTACTTTTGTTTGTTAGTCTTGATGCTTCACTGATAGATA
CAAGAGCCATAAGAACCTCAGATCCTTCCGTATTTAGCCAGTATGTTCTCTAGTGTGGTTCGTTGTTTTT
GCGTGAGCCATGAGAACGAACCATTGAGATCATACTTACTTTGCATGTCACTCAAAAATTTTGCCTCAAA
ACTGGTGAGCTGAATTTTTGCAGTTAAAGCATCGTGTAGTGTTTTTCTTAGTCCGTTATGTAGGTAGGAA
TCTGATGTAATGGTTGTTGGTATTTTGTCACCATTCATTTTTATCTGGTTGTTCTCAAGTTCGGTTACGA
GATCCATTTGTCTATCTAGTTCAACTTGGAAAATCAACGTATCAGTCGGGCGGCCTCGCTTATCAACCAC
CAATTTCATATTGCTGTAAGTGTTTAAATCTTTACTTATTGGTTTCAAAACCCATTGGTTAAGCCTTTTA
AACTCATGGTAGTTATTTTCAAGCATTAACATGAACTTAAATTCATCAAGGCTAATCTCTATATTTGCCT
TGTGAGTTTTCTTTTGTGTTAGTTCTTTTAATAACCACTCATAAATCCTCATAGAGTATTTGTTTTCAAA
AGACTTAACATGTTCCAGATTATATTTTATGAATTTTTTTAACTGGAAAAGATAAGGCAATATCTCTTCA
CTAAAAACTAATTCTAATTTTTCGCTTGAGAACTTGGCATAGTTTGTCCACTGGAAAATCTCAAAGCCTT
TAACCAAAGGATTCCTGATTTCCACAGTTCTCGTCATCAGCTCTCTGGTTGCTTTAGCTAATACACCATA
AGCATTTTCCCTACTGATGTTCATCATCTGAGCGTATTGGTTATAAGTGAACGATACCGTCCGTTCTTTC
CTTGTAGGGTTTTCAATCGTGGGGTTGAGTAGTGCCACACAGCATAAAATTAGCTTGGTTTCATGCTCCG
TTAAGTCATAGCGACTAATCGCTAGTTCATTTGCTTTGAAAACAACTAATTCAGACATACATCTCAATTG
GTCTAGGTGATTTTAAT (SEQ ID NO:140)

**TER *Euglena gracilis* (Q5EU90)without N-terminal transit peptide**

Amino acid sequence (SEQ ID NO:141)

```
  1 vpqmaegfsg eatsawaaag pqwaaplvaa assalalwww aarrsvrrpl aalaelptav
 61 thlappmamf tttakviqpk irgficttth pigcekrvqe eiayarahpp tspgpkrvlv
121 igcstgygls tritaafgyq aatlgvflag pptkgrpaaa gwyntvafek aaleaglyar
181 slngdafdst tkartveaik rdlgtvdlvv ysiaapkrtd patgvlhkac lkpigatytn
241 rtvntdkaev tdvsiepasp eeiadtvkvm ggedwelwiq alseagvlae gaktvaysyi
301 gpemtwpvyw sgtigeakkd vekaakritq qygcpaypvv akalvtqass aipvvplyic
361 llyrvmkekg thegcieqmv rllttklype ngapivdeag rvrvddwema edvqqavkdl
421 wsqvstanlk disdfagyqt eflrlfgfgi dgvdydqpvd veadlpsaaq q
```

fadA (YP026272)

Nucleotide sequence (SEQ ID NO:142)

```
  1 atggaacagg ttgtcattgt cgatgcaatt cgcaccccga tgggccgttc gaagggcggt
 61 gcttttcgta acgtgcgtgc agaagatctc tccgctcatt taatgcgtag cctgctggcg
121 cgtaacccgg cgctggaagc ggcggccctc gacgatattt actggggttg tgtgcagcag
181 acgctggagc agggttttaa tatcgcccgt aacgcggcgc tgctggcaga agtaccacac
241 tctgtcccgg cggttaccgt taatcgcttg tgtggttcat ccatgcaggc actgcatgac
301 gcagcacgaa tgatcatgac tggcgatgcg caggcatgtc tggttggcgg cgtggagcat
361 atgggccatg tgccgatgag tcacggcgtc gattttcacc ccggcctgag ccgcaatgtc
421 gccaaagcgg cgggcatgat gggcttaacg gcagaaatgc tggcgcgtat gcacggtatc
481 agccgtgaaa tgcaggatgc ctttgccgcg cggtcacacg cccgcgcctg ggccgccacg
541 cagtcggccg catttaaaaa tgaaatcatc ccgaccggtg gtcacgatgc cgacggcgtc
```

FIG. 9 cont'd

```
 601 ctgaagcagt ttaattacga cgaagtgatt cgcccggaaa ccaccgtgga agccctcgcc
 661 acgctgcgtc cggcgtttga tccagtaaac ggtatggtaa cggcgggcac atcttctgca
 721 ctttccgatg gcgcagctgc catgctggtg atgagtgaaa gccgcgccca tgaattaggt
 781 cttaagccgc gcgctcgtgt gcgttcgatg gcggtcgttg gttgtgaccc atcgattatg
 841 ggttacggcc cggttccggc ctcgaaactg gcgctgaaaa aagcggggct ttctgccagc
 901 gatatcggcg tgtttgaaat gaacgaagcc tttgccgcgc agatcctgcc atgtattaaa
 961 gatctgggac taattgagca gattgacgag aagatcaacc tcaacggtgg cgcgatcgcg
1021 ctgggtcatc cgctgggttg ttccggtgcg cgtatcagca ccacgctgct gaatctgatg
1081 gaacgcaaag acgttcagtt tggtctggcg acgatgtgta tcggtctggg tcagggtatt
1141 gcgacggtgt ttgagcgggt ttaa
```

Amino acid sequence (SEQ ID NO:143)

```
  1 meqvvivdai rtpmgrskgg afrnvraedl sahlmrslla rnpaleaaal ddiywgcvqq
 61 tleqgfniar naallaevph svpavtvnrl cgssmqalhd aarmimtgda qaclvggveh
121 mghvpmshgv dfhpglsrnv akaagmmglt aemlarmhgi sremqdafaa rsharawaat
181 qsaafkneii ptgghdadgv lkqfnydevi rpettveala tlrpafdpvn gmvtagtssa
241 lsdgaaamlv msesrahelg lkprarvrsm avvgcdpsim gygpvpaskl alkkaglsas
301 digvfemnea faaqilpcik dlglieqide kinlnggaia lghplgcsga risttllnlm
361 erkdvqfgla tmciglgqgi atvferv
```

fadB (NP_416843)

Nucleotide sequence (SEQ ID NO:144)

```
   1 atgctttaca aaggcgacac cctgtacctt gactggctgg aagatggcat tgccgaactg
  61 gtatttgatg ccccaggttc agttaataaa ctcgacactg cgaccgtcgc cagcctcggc
 121 gaggccatcg gcgtgctgga acagcaatca gatctaaaag ggctgctgct gcgttcgaac
 181 aaagcagcct ttatcgtcgg tgctgatatc accgaatttt tgtccctgtt cctcgttcct
 241 gaagaacagt taagtcagtg gctgcacttt gccaatagcg tgtttaatcg cctggaagat
 301 ctgccggtgc cgaccattgc tgccgtcaat ggctatgcgc tgggcggtgg ctgcgaatgc
 361 gtgctggcga ccgattatcg tctggcgacg ccggatctgc gcatcggtct gccggaaacc
 421 aaactgggca tcatgcctgg ctttggcggt tctgtacgta tgccacgtat gctgggcgct
 481 gacagtgcgc tggaaatcat tgccgccggt aaagatgtcg gcgcggatca ggcgctgaaa
 541 atcggtctgg tggatggcgt agtcaaagca gaaaaactgg ttgaaggcgc aaaggcggtt
 601 ttacgccagg ccattaacgg cgacctcgac tggaaagcaa aacgtcagcc gaagctggaa
 661 ccactaaaac tgagcaagat tgaagccacc atgagcttca ccatcgctaa agggatggtc
 721 gcacaaacag cggggaaaca ttatccggcc cccatcaccg cagtaaaaac cattgaagct
 781 gcggcccgtt ttggtcgtga agaagcctta aacctggaaa acaaaagttt tgtcccgctg
 841 gcgcatacca acgaagcccg cgcactggtc ggcattttcc ttaacgatca atatgtaaaa
 901 ggcaaagcga agaaactcac caaagacgtt gaaaccccga aacaggccgc ggtgctgggt
 961 gcaggcatta tgggcggcgg catcgcttac cagtctgcgt ggaaaggcgt gccggttgtc
1021 atgaaagata tcaacgacaa gtcgttaacc ctcggcatga ccgaagccgc gaaactgctg
1081 aacaagcagc ttgagcgcgg caagatcgat ggtctgaaac tggctggcgt gatctccaca
1141 atccacccaa cgctcgacta cgccggattt gaccgcgtgg atattgtggt agaagcggtt
1201 gttgaaaacc cgaaagtgaa aaaagccgta ctggcagaaa ccgaacaaaa agtacgccag
1261 gataccgtgc tggcgtctaa cacttcaacc attcctatca gcgaactggc caacgcgctg
1321 gaacgcccgg aaaacttctg cggcatgcac ttctttaacc cggtccaccg aatgccgttg
1381 gtagaaatta ttcgcggcga gaaaagctcc gacgaaacca tcgcgaaagt tgtcgcctgg
1441 gcgagcaaga tgggcaagac gccgattgtg gttaacgact gccccggctt ctttgttaac
1501 cgcgtgctgt tcccgtattt cgccggtttc agccagctgc tgcgcgacgg cgcggatttc
1561 cgcaagatcg acaaagtgat ggaaaaacag tttggctggc cgatgggccc ggcatatctg
```

FIG. 9 cont'd

```
1621 ctggacgttg tgggcattga taccgcgcat cacgctcagg ctgtcatggc agcaggcttc
1681 ccgcagcgga tgcagaaaga ttaccgcgat gccatcgacg cgctgtttga tgccaaccgc
1741 tttggtcaga agaacggcct cggtttctgg cgttataaag aagacagcaa aggtaagccg
1801 aagaaagaag aagacgccgc cgttgaagac ctgctggcag aagtgagcca gccgaagcgc
1861 gatttcagcg aagaagagat tatcgcccgc atgatgatcc cgatggtcaa cgaagtggtg
1921 cgctgtctgg aggaaggcat tatcgccact ccggcggaag cggatatggc gctggtctac
1981 ggcctgggct tccctccgtt ccacggcggc gcgttccgct ggctggacac cctcggtagc
2041 gcaaaatacc tcgatatggc acagcaatat cagcacctcg gcccgctgta tgaagtgccg
2101 gaaggtctgc gtaataaagc gcgtcataac gaaccgtact atcctccggt tgagccagcc
2161 cgtccggttg gcgacctgaa aacggcttaa
```

Amino acid sequence (SEQ ID NO:145)

```
  1 mlykgdtlyl dwledgiael vfdapgsvnk ldtatvaslg eaigvleqqs dlkglllrsn
 61 kaafivgadi teflslflvp eeqlsqwlhf ansvfnrled lpvptiaavn gyalgggcec
121 vlatdyrlat pdlriglpet klgimpgfgg svrmprmlga dsaleiiaag kdvgadqalk
181 iglvdgvvka eklvegakav lrqaingdld wkakrqpkle plklskieat msftiakgmv
241 aqtagkhypa pitavktiea aarfgreeal nlenksfvpl ahtnearalv giflndqyvk
301 gkakkltkdv etpkqaavlg agimgggiay qsawkgvpvv mkdindkslt lgmteaakll
361 nkqlergkid glklagvist ihptldyagf drvdivveav venpkvkkav laeteqkvrq
421 dtvlasntst ipiselanal erpenfcgmh ffnpvhrmpl veiirgekss detiakvvaw
481 askmgktpiv vndcpgffvn rvlfpyfagf sqllrdgadf rkidkvmekq fgwpmgpayl
541 ldvvgidtah haqavmaagf pqrmqkdyrd aidalfdanr fgqknglgfw rykedskgkp
601 kkeedaaved llaevsqpkr dfseeeiiar mmipmvnevv rcleegiiat paeadmalvy
661 glgfppfhgg afrwldtlgs akyldmaqqy qhlgplyevp eglrnkarhn epyyppvepa
721 rpvgdlkta
```

fadI (NP_416844)

Nucleotide sequence (SEQ ID NO:146)

```
   1 atgggtcagg ttttaccgct ggttacccgc cagggcgatc gtatcgccat tgttagcggt
  61 ttacgtacgc cttttgcccg tcaggcgacg gcttttcatg gcattcccgc ggttgattta
 121 gggaagatgg tggtaggcga actgctggca cgcagcgaga tccccgccga agtgattgaa
 181 caactggtct ttggtcaggt cgtacaaatg cctgaagccc ccaacattgc gcgtgaaatt
 241 gttctcggta cgggaatgaa tgtacatacc gatgcttaca gcgtcagccg cgcttgcgct
 301 accagtttcc aggcagttgc aaacgtcgca gaaagcctga tggcgggaac tattcgagcg
 361 gggattgccg gtggggcaga ttcctcttcg gtattgccaa ttggcgtcag taaaaaactg
 421 gcgcgcgtgc tggttgatgt caacaaagct cgtaccatga gccagcgact gaaactcttc
 481 tctcgcctgc gtttgcgcga cttaatgccc gtaccacctg cggtagcaga atattctacc
 541 ggcttgcgga tgggcgacac cgcagagcaa atggcgaaaa cctacggcat cacccgagaa
 601 cagcaagatg cattagcgca ccgttcgcat cagcgtgccg ctcaggcatg gtcagacgga
 661 aaactcaaag aagaggtgat gactgccttt atccctcctt ataaacaacc gcttgtcgaa
 721 gacaacaata ttcgcggtaa ttcctcgctt gccgattacg caaagctgcg cccggcgttt
 781 gatcgcaaac acggaacggt aacggcggca aacagtacgc cgctgaccga tggcgcggca
 841 gcggtgatcc tgatgactga atcccgggcg aaagaattag ggctggtgcc gctggggtat
 901 ctgcgcagct acgcatttac tgcgattgat gtctggcagg acatgttgct cggtccagcc
 961 tggtcaacac cgctggcgct ggagcgtgcc ggtttgacga tgagcgatct gacattgatc
1021 gatatgcacg aagcctttgc agctcagacg ctggcgaata ttcagttgct gggtagtgaa
1081 cgttttgctc gtgaagcact ggggcgtgca catgccactg gcgaagtgga cgatagcaaa
1141 tttaacgtgc ttggcggttc gattgcttac gggcatccct tcgcggcgac cggcgcgcgg
1201 atgattaccc agacattgca tgaacttcgc cgtcgcggcg gtggatttgg tttagttacc
```

FIG. 9 cont'd

```
1261 gcctgtgctg ccggtgggct tggcgcggca atggttctgg aggcggaata a
```

Amino acid sequence (SEQ ID NO:147)

```
  1 mgqvlplvtr qgdriaivsg lrtpfarqat afhgipavdl gkmvvgella rseipaevie
 61 qlvfgqvvqm peapniarei vlgtgmnvht daysvsraca tsfqavanva eslmagtira
121 giaggadsss vlpigvskkl arvlvdvnka rtmsqrlklf srlrlrdlmp vppavaeyst
181 glrmgdtaeq maktygitre qqdalahrsh qraaqawsdg klkeevmtaf ippykqplve
241 dnnirgnssl adyaklrpaf drkhgtvtaa nstpltdgaa avilmtesra kelglvplgy
301 lrsyaftaid vwqdmllgpa wstplalera gltmsdltli dmheafaaqt laniqllgse
361 rfarealgra hatgevddsk fnvlggsiay ghpfaatgar mitqtlhelr rrgggfglvt
421 acaagglgaa mvleae
```

fadJ (NP_416843)

Nucleotide sequence (SEQ ID NO:148)

```
   1 atggaaatga catcagcgtt taccettaat gttcgtctgg acaacattgc cgttatcacc
  61 atcgacgtac cgggtgagaa aatgaatacc ctgaaggcgg agtttgcctc gcaggtgcgc
 121 gccattatta agcaactccg tgaaaacaaa gagttgcgag gcgtggtgtt tgtctccgct
 181 aaaccggaca acttcattgc tggcgcagac atcaacatga tcggcaactg caaaacggcg
 241 caagaagcgg aagctctggc gcggcagggc caacagttga tggcggagat tcatgctttg
 301 cccattcagg ttatcgcggc tattcatggc gcttgcctgg gtggtgggct ggagttggcg
 361 ctggcgtgcc acggtcgcgt ttgtactgac gatcctaaaa cggtgctcgg tttgcctgaa
 421 gtacaacttg gattgttacc cggttcaggc ggcacccagc gtttaccgcg tctgataggc
 481 gtcagcacag cattagagat gatcctcacc ggaaaacaac ttcgggcgaa acaggcatta
 541 aagctggggc tggtggatga cgttgttccg cactccattc tgctggaagc cgctgttgag
 601 ctggcaaaga aggagcgccc atcttcccgc cctctacctg tacgcgagcg tattctggcg
 661 gggccgttag gtcgtgcgct gctgttcaaa atggtcggca agaaaacaga acacaaaact
 721 caaggcaatt atccggcgac agaacgcatc ctggaggttg ttgaaacggg attagcgcag
 781 ggcaccagca gcggttatga cgccgaagct cgggcgtttg gcgaactggc gatgacgcca
 841 caatcgcagg cgctgcgtag tatctttttt gccagtacgg acgtgaagaa agatcccggc
 901 agtgatgcgc cgcctgcgcc attaaacagc gtggggattt taggtggtgg cttgatgggc
 961 ggcggtattg cttatgtcac tgcttgtaaa gcggggattc cggtcagaat taaagatatc
1021 aacccgcagg gcataaatca tgcgctgaag tacagttggg atcagctgga gggcaaagtt
1081 cgccgtcgtc atctcaaagc cagcgaacgt gacaaacagc tggcattaat ctccggaacg
1141 acggactatc gcggctttgc ccatcgcgat ctgattattg aagcggtgtt tgaaaatctc
1201 gaattgaaac aacagatggt ggcggaagtt gagcaaaatt gcgccgctca taccatcttt
1261 gcttcgaata cgtcatcttt accgattggt gatatcgccg ctcacgccac gcgacctgag
1321 caagttatcg gcctgcattt cttcagtccg gtggaaaaaa tgccgctggt ggagattatt
1381 cctcatgcgg ggacatcggc gcaaaccatc gctaccacag taaaactggc gaaaaaacag
1441 ggtaaaacgc caattgtcgt gcgtgacaaa gccggttttt acgtcaatcg catcttagcg
1501 ccttacatta atgaagctat ccgcatgttg acccaaggtg aacgggtaga gcacattgat
1561 gccgcgctag tgaaatttgg ttttccggta ggcccaatcc aacttttgga tgaggtagga
1621 atcgacaccg ggactaaaat tattcctgta ctggaagccg cttatggaga acgttttagc
1681 gcgcctgcaa atgttgtttc ttcaattttg aacgacgatc gcaaaggcag aaaaaatggc
1741 cgggtttct atctttatgg tcagaaaggg cgtaaaagca aaaaacaggt cgatcccgcc
1801 atttacccgc tgattggcac acaagggcag ggcgaatct ccgcaccgca ggttgctgaa
1861 cggtgtgtga tgttgatgct gaatgaagca gtacgttgtg ttgatgagca ggttatccgt
1921 agcgtgcgtg acggggatat tggcgcggta tttggcattg gttttccgcc atttctcggt
1981 ggaccgttcc gctatatcga ttctctcggc gcgggcgaag tggttgcaat aatgcaacga
2041 cttgccacgc agtatggttc ccgttttacc ccttgcgagc gtttggtcga gatgggcgcg
```

FIG. 9 cont'd 2101 cgtggggaaa gtttttggaa aacaactgca actgacctgc aataa

Amino Acid sequence (SEQ ID NO:149)

```
  1 memtsaftln vrldniavit idvpgekmnt lkaefasqvr aiikqlrenk elrgvvfvsa
 61 kpdnfiagad inmignckta qeaealarqg qqlmaeihal piqviaaihg aclggglela
121 lachgrvctd dpktvlglpe vqlgllpgsg gtqrlprlig vstalemilt gkqlrakqal
181 klglvddvvp hsilleaave lakkerpssr plpvrerila gplgrallfk mvgkktehkt
241 qgnypateri levvetglaq gtssgydaea rafgelamtp qsqalrsiff astdvkkdpg
301 sdappaplns vgilgggimg ggiayvtack agipvrikdi npqginhalk yswdqlegkv
361 rrrhlkaser dkqlalisgt tdyrgfahrd liieavfenl elkqqmvaev eqncaahtif
421 asntssipig diaahatrpe qviglhffsp vekmplveii phagtsaqti attvklakkq
481 gktpivvrdk agfyvnrila pyineairml tqgervehid aalvkfgfpv gpiqlldevg
541 idtgtkiipv leaaygerfs apanvvssil nddrkgrkng rgfylygqkg rkskkqvdpa
601 iypligtqgq grisapqvae rcvmlmlnea vrcvdeqvir svrdgdigav fgigfppflg
661 gpfryidslg agevvaimqr latqygsrft pcerlvemga rgesfwktta tdlq
```

fabI (NP_415804)

Nucleotide sequence (SEQ ID NO:150)

```
  1 atgggttttc tttccggtaa gcgcattctg gtaaccggtg ttgccagcaa actatccatc
 61 gcctacggta tcgctcaggc gatgcaccgc gaaggagctg aactggcatt cacctaccag
121 aacgacaaac tgaaaggccg cgtagaagaa tttgccgctc aattgggttc tgacatcgtt
181 ctgcagtgcg atgttgcaga agatgccagc atcgacacca tgttcgctga actggggaaa
241 gtttggccga aatttgacgg tttcgtacac tctattggtt ttgcacctgg cgatcagctg
301 gatggtgact atgttaacgc cgttacccgt gaaggcttca aaattgccca cgacatcagc
361 tcctacagct tcgttgcaat ggcaaaagct tgccgctcca tgctgaatcc gggttctgcc
421 ctgctgaccc tttcctacct tggcgctgag cgcgctatcc cgaactacaa cgttatgggt
481 ctggcaaaag cgtctctgga agcgaacgtg cgctatatgg cgaacgcgat gggtccggaa
541 ggtgtgcgtg ttaacgccat ctctgctggt ccgatccgta ctctggcggc ctccggtatc
601 aaagacttcc gcaaaatgct ggctcattgc gaagccgtta ccccgattcg ccgtaccgtt
661 actattgaag atgtgggtaa ctctgcggca ttcctgtgct ccgatctctc tgccggtatc
721 tccggtgaag tggtccacgt tgacggcggt ttcagcattg ctgcaatgaa cgaactcgaa
781 ctgaaataa
```

Amino acid sequence (SEQ ID NO:151)

```
  1 mgflsgkril vtgvasklsi aygiaqamhr egaelaftyq ndklkgrvee faaqlgsdiv
 61 lqcdvaedas idtmfaelgk vwpkfdgfvh sigfapgdql dgdyvnavtr egfkiahdis
121 sysfvamaka crsmlnpgsa lltlsylgae raipnynvmg lakasleanv rymanamgpe
181 gvrvnaisag pirtlaasgi kdfrkmlahc eavtpirrtv tiedvgnsaa flcsdlsagi
241 sgevvhvdgg fsiaamnele lk
```

tesB (NP_414986)

Nucleotide sequence (SEQ ID NO:152)

```
  1 atgagtcagg cgctaaaaaa tttactgaca ttgttaaatc tggaaaaaat tgaggaagga
 61 ctctttcgcg gccagagtga agatttaggt ttacgccagg tgtttggcgg ccaggtcgtg
121 ggtcaggcct tgtatgctgc aaaagagacc gtccctgaag agcggctggt acattcgttt
181 cacagctact ttcttcgccc tggcgatagt aagaagccga ttatttatga tgtcgaaacg
```

FIG. 9 cont'd

```
241 ctgcgtgacg gtaacagctt cagcgcccgc cgggttgctg ctattcaaaa cggcaaaccg
301 atttttttata tgactgcctc tttccaggca ccagaagcgg gtttcgaaca tcaaaaaaca
361 atgccgtccg cgccagcgcc tgatggcctc ccttcggaaa cgcaaatcgc ccaatcgctg
421 gcgcacctgc tgccgccagt gctgaaagat aaattcatct gcgatcgtcc gctggaagtc
481 cgtccggtgg agtttcataa cccactgaaa ggtcacgtcg cagaaccaca tcgtcaggtg
541 tggatccgcg caaatggtag cgtgccggat gacctgcgcg ttcatcagta tctgctcggt
601 tacgcttctg atcttaactt cctgccggta gctctacagc cgcacggcat cggttttctc
661 gaaccgggga ttcagattgc caccattgac cattccatgt ggttccatcg cccgtttaat
721 ttgaatgaat ggctgctgta tagcgtggag agcacctcgg cgtccagcgc acgtggcttt
781 gtgcgcggtg agttttatac ccaagacggc gtactggttg cctcgaccgt tcaggaaggg
841 gtgatgcgta atcacaatta a
```

Amino acid sequence (SEQ ID NO:153)

```
  1 msqalknllt llnlekieeg lfrgqsedlg lrqvfggqvv gqalyaaket vpeerlvhsf
 61 hsyflrpgds kkpiiydvet lrdgnsfsar rvaaiqngkp ifymtasfqa peagfehqkt
121 mpsapapdgl psetqiaqsl ahllppvlkd kficdrplev rpvefhnplk ghvaephrqv
181 wirangsvpd dlrvhqyllg yasdlnflpv alqphgigfl epgiqiatid hsmwfhrpfn
241 lnewllysve stsassargf vrgefytqdg vlvastvqeg vmrnhn
```

Acr1_Acinetobacter (YP_047869)

Nucleotide sequence (SEQ ID NO:154)

```
  1 TTGATATCAA TCAGGGAAAA ACGCGTGAAC AAAAAACTTG AAGCTCTCTT CCGAGAGAAT
 61 GTAAAAGGTA AAGTGGCTTT GATCACTGGT GCATCTAGTG GAATCGGTTT GACGATTGCA
121 AAAAGAATTG CTGCGGCAGG TGCTCATGTA TTATTGGTTG CCCGAACCCA AGAAACACTG
181 GAAGAAGTGA AAGCTGCAAT TGAACAGCAA GGGGGACAGG CCTCTATTTT TCCTTGTGAC
241 CTGACTGACA TGAATGCGAT TGACCAGTTA TCACAACAAA TTATGGCCAG TGTCGATCAT
301 GTCGATTTCC TGATCAATAA TGCAGGGCGT TCGATTCGCC GTGCCGTACA CGAGTCGTTT
361 GATCGCTTCC ATGATTTTGA ACGCACCATG CAGCTGAATT ACTTTGGTGC GGTACGTTTA
421 GTGTTAAATT TACTGCCACA TATGATTAAG CGTAAAAATG GCCAGATCAT CAATATCAGC
481 TCTATTGGTG TATTGGCCAA TGCGACCCGT TTTTCTGCTT ATGTCGCGTC TAAAGCTGCG
541 CTGGATGCCT TCAGTCGCTG TCTTTCAGCC GAGGTACTCA AGCATAAAAT CTCAATTACC
601 TCGATTTATA TGCCATTGGT GCGTACCCCA ATGATCGCAC CCACCAAAAT TTATAAATAC
661 GTGCCCACGC TTTCCCCAGA AGAAGCCGCA GATCTCATTG TCTACGCCAT TGTGAAACGT
721 CCAAAACGTA TTGCGACGCA CTTGGGTCGT CTGGCGTCAA TTACCTATGC CATCGCACCA
781 GACATCAATA ATATTCTGAT GTCGATTGGA TTTAACCTAT TCCCAAGCTC AACGGCTGCA
841 CTGGGTGAAC AGGAAAAATT GAATCTGCTA CAACGTGCCT ATGCCCGCTT GTTCCCAGGC
901 GAACACTGGT AA
```

Amino acid sequence (SEQ ID NO:155)

```
  1 misirekrvn kklealfren vkgkvalitg assgigltia kriaaagahv llvartqetl
 61 eevkaaieqq ggqasifpcd ltdmnaidql sqqimasvdh vdflinnagr sirravhesf
121 drfhdfertm qlnyfgavrl vlnllphmik rkngqiinis sigvlanatr fsayvaskaa
181 ldafsrclsa evlkhkisit siymplvrtp miaptkiyky vptlspeeaa dlivyaivkr
241 pkriathlgr lasityaiap dinnilmsig fnlfpsstaa lgeqeklnll qrayarlfpg
301 ehw
```

FIG. 9 cont'd

*C. acetobutylicum* phosphotransbutyrylase

>gi|457633|gb|AAA75486.1| phosphotransbutyrylase [Clostridium acetobutylicum]
MIKSFNEIIMKVKSKEMKKVAVAVAQDEPVLEAVRDAKKNGIADAILVGDHDEIVSIALKIGMDVNDFEI
VNEPNVKKAALKAVELVSTGKADILMNGLVNTATFLKICILNKEVGLRTGKIMSHVAVFETETSDRLSFL
TDVAFNTYPELKEKIDIVNNSVKVAHAIGIVNPKVAPICAVEVINPKMPSTLDAAMLSKMSDRGQIKGCV
VDGPLALDIALSEEAAHHKGVTGEVAGKADIFLMPNIETGNVMYKTLTYTTDSKNGGILVGTSAPVVLTS
RADSHETKMNSIALAA (SEQ ID NO:156)

*C. acetobutylicum* butyrate kinase

>gi|484480|pir||JN0795 butyrate kinase (EC 2.7.2.7) - Clostridium acetobutylicum (strain NCIMB 8052)
MSYKLLIINPGSTSTKIGVYEGEKELFEETLRHTNEEIKRYDTIYDQFEFRKEVILNVLKEKNFDIKTLS
AIVGRGGMLRPVEGGTYAVNDAMVEDLKVGVQGPHASNLGGIIAKSIGDELNIPSFIVDPVVTDELADVA
RLSGVPELPRKSKFHALNQKAVAKRYGKESGQGYENLNLVVVHMGGGVSVGAHNHGKVVDVNNALDGDGP
FSPERAGSVPIGDLVKMCFSGKYSEAEVYGKAVGKGGFVGYLNTNDVKGVIDKMEEGDKECESIYKAFVY
QISKAIGEMSVVLEGKVDQIIFTGGIAYSPTLVPDLKAKVEWIAPVTVYPGEDELLALAQGAIRVLDGEE
QAKVY (SEQ ID NO:157)

SURFACTANT AND CLEANING COMPOSITIONS COMPRISING MICROBIALLY PRODUCED BRANCHED FATTY ALCOHOLS

CROSS REFERENCE TO RELATED APPLICATIONS

This application claims the benefit of U.S. Provisional Patent Application No. 61/304,448, filed Feb. 14, 2010, and U.S. Provisional Patent Application No. 61/324,310, filed Apr. 15, 2010, the entire contents of which are hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 415,467 bytes ASCII (Text) file named "707643_ST25" created Apr. 11, 2011.

BACKGROUND OF THE INVENTION

Fatty alcohols have many commercial uses. Worldwide annual sales of fatty alcohols and their derivatives are in excess of US$1 billion. Fatty alcohols are used in diverse industries. For example, they are used in the cosmetic and food industries as emulsifiers, emollients, and thickeners. Due to their amphiphilic nature, fatty alcohols can be formulated or be used per se as nonionic surfactants, which are useful in personal care and household products, for example, in detergents. In addition, fatty alcohols are used in waxes, gums, resins, pharmaceutical salves and lotions, lubricating oil additives, textile antistatic and finishing agents, plasticizers, cosmetics, industrial solvents, and solvents for fats.

One major use for fatty alcohols is in cleaning compositions. On the other hand, fatty alcohols find applicability as surfactants, which are, for example, capable of enhancing oil recovery and/or engine performance. Conventional surfactants comprise molecules having at least one water-solublizing substituent or moiety (e.g., hydrophilic group) and at least one oleophilic substituent or moiety (e.g., hydrophobic group). Examples of hydrophilic groups include, without limitation, carboxylate, sulfate, sulfonate, amine oxide, or polyoxyethylene. Examples of the hydrophobic groups include, without limitation, alkyl, alkenyl, or alkaryl hydrophobes, which typically contain about 10 to about 20 carbon atoms.

Surfactants are typically regarded as the major force behind cleaning products' ability to break up stains, solubilize dirt and soil, and/or prevent their redeposition to surfaces. As such, surfactants are also referred to as wetting agents and foamers, which lower the surface tension of the medium in which they are dissolved. Capable of lowering the interfacial tension between two media or interfaces (e.g., air/water, water/oil, or oil/solid interfaces), surfactants play a key role, and are often the most important component in detergents. Conventional detergent compositions contain mixtures of various surfactants in order to remove different types of soils and stains from surfaces.

The earliest utilized source of hydrophobe groups were natural fats and oils, which were converted into soaps (e.g., carboxylate hydrophile) using base via saponification processes. Coconut and palm oils are to this day used to manufacture soaps and alkylsulfate surfactants. As edible oils became more scarce, it has become increasingly prevalent to manufacture detergents from petrochemicals, using processes such as the Zeigler process to convert petroleum derived ethylene to fatty alcohols. For example, ethylene has been converted into alkyl benzene sulfonate surfactants, which are commonly found in today's detergents and cleaning compositions.

Fatty alcohols can also served as starting materials in the preparation of surfactants and of other cleaning composition ingredients including, for example, alkyl sulfates, fatty ether sulfates, fatty alcohol sulfates, fatty phosphate esters, alkylbenzyl dimethylammonium salts, fatty amine oxides, alkyl polyglucosides, and alkyl glyceryl ether sulfonates. Among these, alkyl sulfates are commonly known due to the ease of their manufacture as well as their improved solubility and surfactant characteristics over traditional soap-based surfactants. However, long-chain alkyl surfactants have less than optimal performance as surfactants or as component(s) of detergents at low temperatures (e.g., about 50° C. or lower, about 30° C. or lower).

While there have been isolated reports that branching, especially towards the middle part of the long-chain alkyl, can reduce solubility of the surfactant, others have described that, in commercial practices, branching in fatty alcohols is highly desirable. See, e.g., R. G. Laughlin, The Aqueous Phase Behavior of Surfactants," Academic Press, N.Y., (1994), at page 347; but see, Finger et al., Detergent alcohols—the effect of alcohol structure and molecular weight on surfactant properties, J. Amer. Oil Chemicals Society, Vol. 44:525 (1967); Technical Bulletin, Shell Chemical Co., SC:164-80. In addition, K. R. Wormuth, et al., Langmuir, vol 7 (1991): 2048-2053, describes the technical advantages observed with a number of branched alkyl sulfates, especially with the "branched Guerbet" type, derived from the highly branched "Exxal" alcohols (Exxon). Phase studies have established a lipophilic ranking (i.e., a hydrophobicity ranking) if highly branched/double tail>methyl branched>linear. Furthermore, patents and applications, including, for example, U.S. Pat. No. 6,008,181 indicates that certain branched or multi-branched fatty alcohol derivatives exhibit improved cleaning capacity, especially at lower temperatures.

Branched fatty alcohols and various precursors are known to have additional preferred properties such as considerably lower melting points, which can in turn confer lower pour points when made into industrial chemicals, as compared to linear alcohols of comparable molecular weights. They are also known to confer substantially lower volatility and vapor pressure, and improved stability against oxidation and rancidity than their linear counterparts. These additional preferred properties, in addition to making branched materials desirable surfactants, make them particularly suited as components or feedstocks for cosmetic and pharmaceutical applications, as components of plasticizers for making synthetic resins, as solvents for solutions for printing ink and specialty inks, or as industrial lubricants.

Those added preferred properties can be alternatively obtained from unsaturated fatty alcohols and precursors. But unsaturation promotes oxidation, leading to short shelf lives and corrosion. Thus desirable properties, e.g., lower melting points, pour points, volatility, and vapor pressure and improved oxidative stability, are better achieved via branching.

Obtaining branched materials from crude petroleum requires a significant financial investment as well as consumes a great deal of energy. It is also an inefficient process because frequently it is necessary to crack the long chain hydrocarbons in crude petroleum to produce smaller monomers, which only then become useful as raw materials for manufacturing complex specialty chemicals. Furthermore, it is commonplace in the petrochemical industry to obtain branched chemicals, such as branched alcohols and aldehydes, by isomerization of straight-chain hydrocarbons. Expensive catalysts are typically required for isomerization, thus increasing manufacturing cost. The catalysts often then become undesirable contaminants that are removed from the finished products, adding yet further cost to the processes.

Obtaining specialty chemicals such as branched alcohols or derivatives from crude petroleum also drains the dwindling resource of petroleum, in addition to the cost and problems associated with exploring, extracting, transporting, and refining. One estimate of world petroleum consumption is 30 billion barrels per year. By some estimates, it is predicted that at current production levels, the world's petroleum reserves could be depleted before 2050.

Finally, processing and manufacturing of surfactants and/or detergents from petroleum inevitably releases greenhouse gases (e.g., in the form of carbon dioxide) and other forms of air pollution (e.g., carbon monoxide, sulfur dioxide, etc.). The accumulation of greenhouse gases in the atmosphere can lead to increase global warming, causing local pollutions and spillage as well as global environmental detriments.

Thus, although it is possible to obtain branched fatty alcohols and derivatives from natural oils and petroleum, it would be desirable to produce these branched materials from other sources, such as directly from biomass.

SUMMARY OF THE INVENTION

The invention provides a surfactant composition and a cleaning composition comprising one or more microbially produced branched fatty alcohols, branched fatty alcohol precursors, or branched fatty alcohol derivatives thereof.

The invention provides a surfactant composition comprising about 0.001 wt. % to about 100 wt. % of one or more microbially produced branched fatty alcohols or branched alcohol derivatives thereof.

The invention also provides a liquid cleaning composition comprising (a) about 0.1 wt. % to about 50 wt. % of one or more microbially produced branched fatty alcohols or derivatives thereof, or about 0.1 wt. % to about 50 wt. % of a surfactant comprising one or more microbially produced branched fatty alcohols or derivatives thereof, (b) about 1 wt. % to about 30 wt. % of one or more co-surfactants, (c) about 0 wt. % to about 10 wt. % of one or more detergency builders, (d) 0 wt. % to about 2 wt. % of one or more enzymes, (e) about 0 wt. % to about 15 wt. % of one or more chelating agents, (f) about 0 wt. % to about 20 wt. % of one or more hydrotropes, (g), about 0 wt. % to about 1.0 wt. % of one or more organic sequestering agents, and (h) about 0.1 wt. % to about 98 wt. % of a solvent system. In some embodiments, the liquid cleaning composition further comprises one or more suitable adjuncts.

The invention further provides a solid cleaning composition comprising (a) about 0.1 wt. % to about 50 wt. % of one or more microbially produced branched fatty alcohols or derivatives thereof, or about 0.1 wt. % to about 50 wt. % of a surfactant comprising one or more microbially produced branched fatty alcohols or derivatives thereof, (b) about 1 wt. % to about 30 wt. % of one or more co-surfactants, (c) about 1 wt. % to about 60 wt. % of one or more detergency builders, (d) about 0 wt. % to about 2 wt. % of one or more enzymes, (e) about 0 wt. % to about 20 wt. % of one or more hydrotropes, (f) about 10 wt. % to about 35 wt. % of one or more filler salts, (g) about 0 wt. % to about 15 wt. % of one or more chelating agents, and (g) about 0.01 wt. % to about 1 wt. % of one or more organic sequestering agents. In certain embodiments, the solid cleaning composition further comprises one or more suitable adjuncts.

In particular embodiments, the invention pertains to a household cleaning composition comprising (a) about 0.1 wt. % to about 50 wt. % of one or more microbially produced branched fatty alcohols and/or derivatives thereof, or about 0.1 wt. % to about 50 wt. % of a surfactant comprising one or more microbially produced fatty alcohols and/or derivatives thereof; (b) about 1 wt. % to about 30 wt. % of one or more co-surfactants; (c) about 0 wt. % to about 30 wt. % of one or more detergency builders; (d) about 0 wt. % to about 2.0 wt. % of one or more suitable detersive enzymes; (e) about 0 wt. % to about 15 wt. % one or more chelating agents; (f) about 0 wt. % to about 20 wt. % of one or more hydrotropes, (g) about 0 to about 15 wt. % of one or more rheology modifier; (h) about 0 wt. % to about 1.0 wt. % of one or more organic sequestering agents; and (i) various other adjuncts such as, for example, one or more of bleaching agents, additional enzymes, suds suppressors, dispersants, lime-soap dispersants, soil suspension and anti-redeposition agents, and corrosion inhibitors. In an exemplary embodiment, a laundry composition can also comprise softening agents, fragrances, bleach systems, dyes or colorants, preservatives, germicides, fungicides, fabric care benefit agents, gelling agents, anti-deposition agents, and other detersive adjuncts Such a household cleaning composition can be a liquid, which further comprises water and/or a suitable aqueous carrier or solvent. Liquid compositions can be in a "concentrated" form, the density of which can range from, for example, about 400 to about 1,200 g/L, when measured at 200° C. For example, the water content of a typical concentrated liquid detergent is less than about 40 wt. %, or less than about 30 wt. %. Alternatively, a household cleaning composition can be a solid, for example, in the form of a tablet, a bar, a powder or a granule. Granular compositions can also be in a "compact" form, which is best reflected by density and, in terms of composition, by the amount of inorganic filler salt. Inorganic filler salts are conventional ingredients of solid cleaning compositions, present in substantial amounts, varying from, for example, about 10 wt. % to about 35 wt. %. Suitable filler salts include, for example, alkali and alkaline-earth metal salts of sulfates and chlorides. An exemplary filler salt is sodium sulfate.

In another embodiment, the invention provides a personal or beauty care cleaning or treatment composition comprising (a) about 0.1 wt. % to about 50 wt. % of one or more microbially produced branched fatty alcohols and/or derivatives thereof, or about 0.1 wt. % to about 50 wt. % of a surfactant comprising one or more microbially produced branched fatty alcohols and/or derivatives thereof; (b) about 0.001 wt. % to about 30 wt. % of one or more co-surfactants; (c) about 0 wt. % to about 30 wt. % of one or more detergency builders; (d) about 0 wt. % to about 2.0 wt. % of one or more suitable detersive enzymes; (e) about 0 wt. % to about 15 wt. % one or more chelating agents; (f) about 0 wt. % to about 20 wt. % of one or more hydrotropes, (g) about 0 to about 15 wt. % of one or more rheology modifier; (h) about 0 wt. % to about 1.0 wt. % of one or more organic sequestering agents; and (i) various other adjuncts such as, for example, one or more of conditioner, silicone, fragrances, silica particles, cationic cellose or guar polymers, silicone microemulsion stabilizers, fatty amphiphiles, germicides, fungicides, anti-dandruff agents, pearlescent agents, foam boosters, pediculocides, pH adjusting agents, UV absorbers, sunscreens, skin active agents, vitamins, minerals, herbal/fruit/food extracts, sphingolipids, sensory indicators, suspension agents, and mixtures thereof.

BRIEF DESCRIPTION OF THE DRAWINGS

FIG. 2A lists representative homologs of BKD E1 alpha subunit, their amino acid sequences and polynucleotide sequences, as well as amino acid sequence motifs of suitable BKD E1 alpha subunit homologs and variants. FIG. 2B lists representative homologs of BKD E1 beta subunit, their amino acid sequences and polynucleotide sequences, as well as amino acid sequence motifs of suitable BKD E1 beta subunit homologs and variants. FIG. 2C lists representative homologs of BKD E2 subunit, their amino acid sequences and polypeptide sequences, as well as amino acid sequence motifs of suitable BKD E2 subunit homologs and variants. FIG. 2D lists representative homologs of BKD E3 subunit homologs and variants, as well as amino acid sequence motifs of suitable BKD E3 subunit homologs and variants. FIG. 2E lists representative homologs of beta ketoacyl-ACP synthase homologs, their amino acid sequences and polynucleotide sequences, as well as amino acid sequences of suitable beta keto-acyl-ACP synthase homologs and variants.

FIG. 3A is a table of BKD E1 alpha subunit homologs. FIG. 3B is a table of BKD E1 beta subunit homologs. FIG. 3C is a table of BKD E2 subunit homologs. FIG. 3D if a table of BKD E3 subunit homologs. FIG. 3E is a table of beta ketoacyl-ACP synthase homologs. These tables also present % identity in reference to the sequences of various organisms. For example, "ID % Pp" indicates that the identity listed in the column below are in reference to a *P. putida* gene encoding that subunit. "ID % Bs" refers to the identity to a *B. subtilis* gene encoding that subunit. "ID % Sc" and "ID % Sc2" refer to identity to a first and second *S. coelicolor* genes encoding that subunit, respectively. "ID % Sa" and "ID % Sa2" refer to identity to a first and a second *S. avermitilis* genes encoding that subunit, respectively.

FIG. 6A is a listing of nucleotide sequence of the pDG2 plasmid. FIG. 6B depicts a map of the pDG6 plasmid. FIG. 6C is a listing of nucleotide sequence of the pDG6 plasmid, constructed by inserting *B. subtilis* fabH1 into pDG2, comprising *E. coli* PfabH1 (promoter) and *B. subtilis* fabH1. The *B. subtilis* fabH1 insert is in upper case italic letters. FIG. 6D depicts a map of the pDG7 plasmid. FIG. 6E is a listing of nucleotide sequence of the pDG7 plasmid, constructed by inserting a *B. subtilis* fabH2 into pDG2, comprising *E. coli* PfabH1 (promoter) and *B. subtilis* fabH2. FIG. 6F depicts a map of the pDG8 plasmid. FIG. 6G is a listing of nucleotide sequence of pDG8 plasmid, constructed by inserting *S. coelicolor* fabH into pDG2, comprising *E. coli* PfabH1 (promoter) and *S. coelicolor* fabH. FIG. 6H is a plasmid map of the pDG10 plasmid. FIG. 6I is listing of nucleotide sequence of the pDG10 plasmid, comprising a *C. acetobutylicum* ptb_buk insert. FIG. 6J is a listing of nucleotide sequence of the pLS9-111 plasmid. FIG. 6K is a listing of nucleotide sequence of the pLS9-114 plasmid. FIG. 6L is a listing of nucleotide sequence of the pLS9-115 plasmid.

FIG. 7 is a listing of nucleotide sequence of the pKZ4 plasmid having a pGL10.173B vector backbone and a polynucleotide insert encoding a BKD complex from *Pseudomonas putida*. The *P. putida* genes encoding a BKD complex are shown in lower case italic letters.

FIG. 8 is a listing of nucleotide sequence of the pGL10.173B vector backbone, which contains the BamHI and EcoRI sites to which the *Pseudomonas putida* bkd genes (operon) were inserted. The BamHI and EcoRI restriction sites are marked.

FIG. 9 is a listing of additional nucleotide and amino acid sequences of the disclosure.

DETAILED DESCRIPTION OF THE INVENTION

Figure 1A:
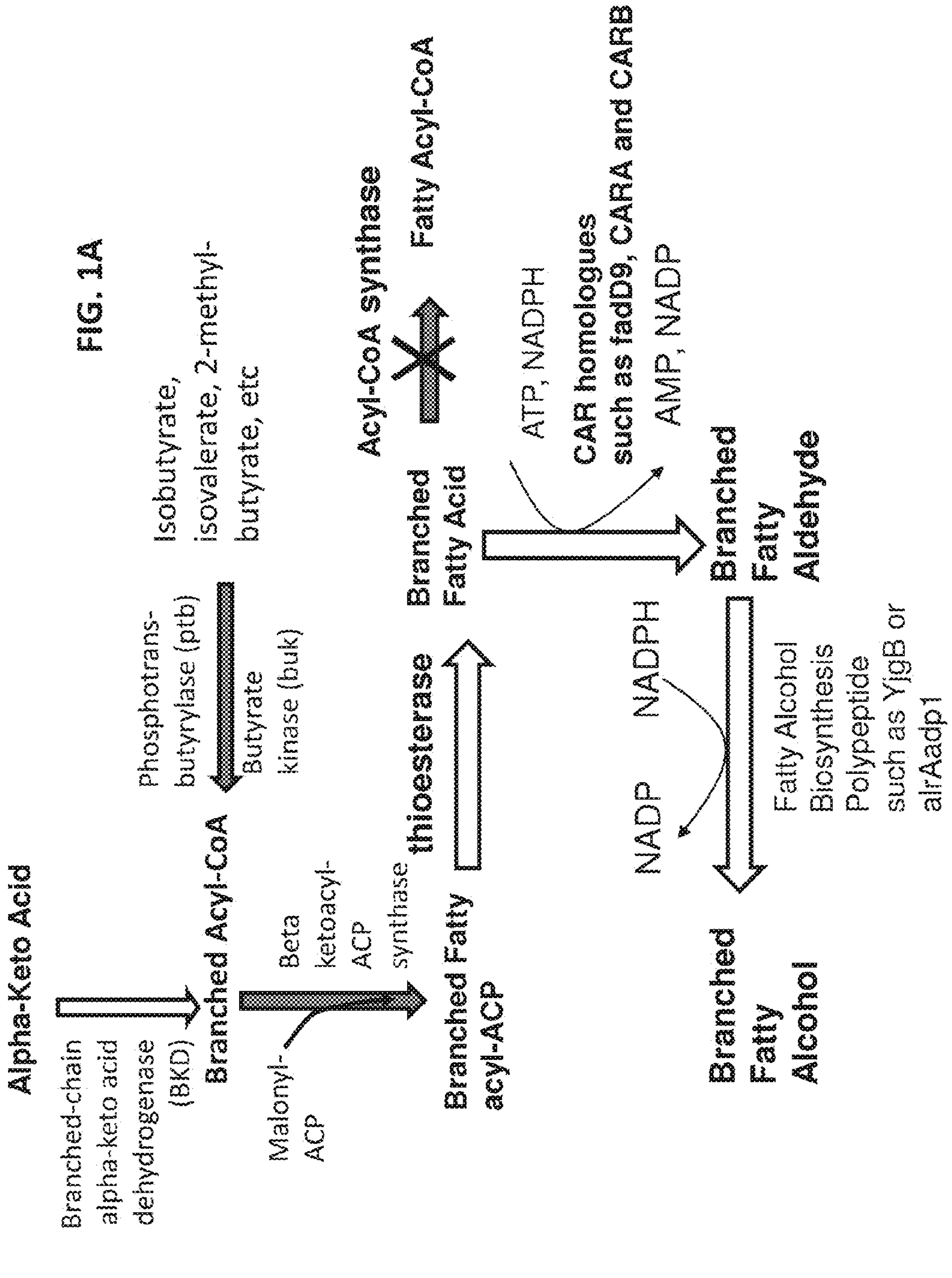
FIG. 1A and FIG. 1B are schematics of two exemplary alternative pathways for producing branched fatty alcohols using recombinant microbial host cells.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein, including GenBank database sequences, are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DEFINITIONS

Throughout the specification, a reference may be made using an abbreviated gene name or polypeptide name, but it is understood that such an abbreviated gene or polypeptide name represents the genus of genes or polypeptides. Such gene names include all genes encoding the same polypeptide and homologous polypeptides having the same physiological function. Polypeptide names include all polypeptides and homologous polypeptides that have the same activity (e.g., that catalyze the same fundamental chemical reaction).

Unless otherwise indicated, the accession numbers referenced herein are derived from the NCBI database (National Center for Biotechnology Information) maintained by the National Institute of Health, U.S.A. Unless otherwise indicated, the accession numbers are as provided in the database as of December 2009.

EC numbers are established by the Nomenclature Committee of the International Union of Biochemistry and Molecular Biology (NC-IUBMB) (available at www.chem.qmul.ac.uk/iubmb/enzyme/). The EC numbers referenced herein are derived from the KEGG Ligand database, maintained by the Kyoto Encyclopedia of Genes and Genomics, sponsored in part by the University of Tokyo. Unless otherwise indicated, the EC numbers are as provided in the database as of October 2008.

The articles "a" and "an" are used herein to refer to one or to more than one (i.e., to at least one) of the grammatical object of the article. By way of example, "an element" means one element or more than one element.

The term "about" is used herein to mean a value±20% of a given numerical value. Thus, "about 60%" means a value of between 60±(20% of 60) (i.e., between 48 and 70).

The term "alkyl" is used herein to mean a straight chain or a branched chain hydrocarbon residue having from about 6 carbon atoms to about 26 carbon atoms and in the context of the present specification is used interchangeably with the term "fatty."

As used herein, the term "alcohol dehydrogenase" (EC 1.1.1.*) refers to a polypeptide capable of catalyzing the conversion of a fatty aldehyde to an alcohol (e.g., fatty alcohol). In certain embodiments, these enzymes can also be referred to as fatty aldehyde recutases, oxidoreductases, or aldo-keto reductases. Additionally, one of ordinary skill in the art will appreciate that some alcohol dehydrogenases will catalyze other reactions as well. For example, some alcohol dehydrogenases will accept other substrates in addition to fatty aldehydes. Such non-specific alcohol dehydrogenases are, therefore, also included in this definition. Nucleic acid sequences encoding alcohol dehydrogenases are known in the art, and such alcohol dehydrogenases are publicly available. Exemplary GenBank Accession Numbers are provided in Table 8 herein.

As used herein, the term "attenuate" means to weaken, reduce, or diminish. For example, a polypeptide can be attenuated by modifying the polypeptide to reduce its activity (e.g., by modifying a nucleotide sequence that encodes the polypeptide) or its expression level.

As used herein, the term "biomass" refers to any biological material from which a carbon source is derived. In some instances, a biomass is processed into a carbon source, which is suitable for bioconversion. In other instances, the biomass may not require further processing into a carbon source. The carbon source can be converted into a fatty alcohol. One exemplary source of biomass is plant matter or vegetation. For example, corn, sugar cane, or switchgrass can be used as biomass. Another non-limiting example of biomass is metabolic wastes, such as animal matter, for example cow manure. In addition, biomass may include algae and other marine plants. Biomass also includes waste products from industry, agriculture, forestry, and households. Examples of such waste products that can be used as biomass are fermentation waste, ensilage, straw, lumber, sewage, garbage, cellulosic urban waste, and food leftovers. Biomass also includes carbon sources such as carbohydrates (e.g., monosaccharides, disaccharides, or polysaccharides).

As used herein, the phrase "carbon source" refers to a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino acids, peptides, and gases (e.g., CO and $CO_2$). These include, for example, various monosaccharides, such as glucose, fructose, mannose, and galactose; oligosaccharides, such as fructo-oligosaccharide and galacto-oligosaccharide; polysaccharides such as xylose and arabinose; disaccharides, such as sucrose, maltose, and turanose; cellulosic material, such as methyl cellulose and sodium carboxymethyl cellulose; saturated or unsaturated fatty acid esters, such as succinate, lactate, and acetate; alcohols, such as ethanol, methanol, and glycerol, or mixtures thereof. The carbon source can also be a product of photosynthesis, including, but not limited to, glucose. A preferred carbon source is biomass. Another preferred carbon source is glucose.

A nucleotide sequence is "complementary" to another nucleotide sequence if each of the bases of the two sequences matches (i.e., is capable of forming Watson-Crick base pairs). The term "complementary strand" is used herein interchangeably with the term "complement". The complement of a nucleic acid strand can be the complement of a coding strand or the complement of a non-coding strand.

As used herein, the term "conditions sufficient to allow expression" means any conditions that allow a host cell to produce a desired product, such as a polypeptide or fatty alcohol described herein. Suitable conditions include, for example, fermentation conditions. Fermentation conditions can comprise many parameters, such as temperature ranges, levels of aeration, and media composition. Each of these conditions, individually and in combination, allows the host cell to grow. Exemplary culture media include broths or gels. Generally, the medium includes a carbon source, such as glucose, fructose, cellulose, or the like, that can be metabolized by a host cell directly. In addition, enzymes can be used in the medium to facilitate the mobilization (e.g., the depolymerization of starch or cellulose to fermentable sugars) and subsequent metabolism of the carbon source.

To determine if conditions are sufficient to allow expression, a host cell can be cultured, for example, for about 4, 8, 12, 24, 36, or 48 hours. During and/or after culturing, samples can be obtained and analyzed to determine if the conditions allow expression. For example, the host cells in the sample or the medium in which the host cells were grown can be tested for the presence of a desired product. When testing for the presence of a product, assays, such as TLC, HPLC, GC/FID, GC/MS, LC/MS, and MS, can be used.

It is understood that the polypeptides described herein may have additional conservative or non-essential amino acid substitutions, which do not have a substantial effect on the polypeptide functions. Whether or not a particular substitution will be tolerated (i.e., will not adversely affect desired biological properties, such as carboxylic acid reductase activity) can be determined as described in Bowie et al., *Science,* 247: 1306-1310 (1990). A "conservative amino acid substitution" refers to the replacement of one amino acid residue with another amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine).

As used herein, "control element" means a transcriptional and/or a translational control element. Control elements include promoters and enhancers, such as ribosome binding sequences. The term "promoter element," "promoter," or "promoter sequence" refers to a DNA sequence that functions as a switch that activates the expression of a gene. If the gene is activated, it is said to be transcribed or participating in transcription. Transcription involves the synthesis of mRNA from the gene. A promoter, therefore, serves as a transcriptional regulatory element and also provides a site for initiation of transcription of the gene into mRNA. Control elements interact specifically with cellular proteins involved in transcription (Maniatis et al., *Science,* 236: 1237 (1987)).

As used herein, the term "detergent" refers broadly to agents and materials that are useful in cleaning applications or as cleaning aids. This term is thus used interchangeably with the term "cleaning composition." The term encompasses materials and agents that comprise various surfactants at various percentages by weight or by volume, as well as suitable additives, and are capable of emulsifying stains in a cleaning matrix. A detergent can take the physical form of, for example, a liquid, a paste, a gel, a bar, a powder, a tablet, or a granule. Granular compositions can also be in "compact" form, whereas liquid compositions can be in "concentrate" form.

As used herein, detergent compositions include articles and compositions of cleaning and/or treatment. As used herein, the term "cleaning and/or treatment composition" includes, unless otherwise indicated, tablet, granular, or power-form all-purpose or "heavy duty" washing agents, especially laundry detergents; liquid, gel, or paste-form all-purpose washing agents, especially the so-called heavy-duty liquid types; liquid fine-fabric detergents; hand dishwashing agents, or light duty dishwashing agents, especially those of the high-foaming type; machine dishwashing agents, including the various tablets, granular, liquid and rinse-aid types for household and institutional use. The compositions can also be in unit dose packages, including those known in the art and those that are water soluble, water insoluble and/or water permeable.

As used herein, detergent composition also include personal or beauty care products in the form of skin and hair care compositions including, for example, conditioning treatments, cleansing products, such as hair and/or scalp shampoos, body washes, hand cleaners, water-less hand sanitizers/cleansers, facial cleansers, and the like.

As used herein, the term "fatty acid" means a carboxylic acid having the formula RCOOH. R represents an aliphatic group, preferably an alkyl group. R can comprise about 4 or more carbon atoms. In some embodiments, the fatty acid comprises between about 4 and about 22 carbon atoms. Fatty acids can be saturated, monounsaturated, or polyunsaturated. In addition, fatty acids can comprise a straight or branched chain. The branched chains may have one or more points of branching. In addition, the branched chains may include cyclic branches. In a preferred embodiment, the fatty acid is made from a fatty acid biosynthetic pathway.

As used herein, the term "fatty acid biosynthetic pathway" means a biosynthetic pathway that produces fatty acids. The fatty acid biosynthetic pathway includes fatty acid enzymes that can be engineered, as described herein, to produce fatty acids, and in some embodiments can be expressed with additional enzymes to produce fatty acids having desired carbon chain characteristics.

As used herein, the term "fatty acid derivative" means products made in part from the fatty acid biosynthetic pathway of the production host organism. "Fatty acid derivative" also includes products made in part from acyl-ACP or acyl-ACP derivatives. The fatty acid biosynthetic pathway includes fatty acid synthase enzymes which can be engineered as described herein to produce fatty acid derivatives, and in some examples can be expressed with additional enzymes to produce fatty acid derivatives having desired carbon chain characteristics. Exemplary fatty acid derivatives include, for example, fatty acids, acyl-CoA, fatty aldehyde, short and long chain alcohols, hydrocarbons, fatty alcohols, and esters (e.g., waxes, fatty acid esters, or fatty esters), although due to their separate and industrial utilities and depending the sources from which they derive, hydrocarbons can sometimes be grouped into a separate "hydrocarbon" category.

As used herein, the term "fatty acid derivative enzyme" means any enzyme that may be expressed or overexpressed in the production of fatty acid derivatives. These enzymes may be part of the fatty acid biosynthetic pathway. Non-limiting examples of fatty acid derivative enzymes include fatty acid synthases, thioesterases, acyl-CoA synthases, acyl-CoA reductases, alcohol dehydrogenases, alcohol acyltransferases, fatty alcohol-forming acyl-CoA reductases, carboxylic acid reductases (e.g., fatty acid reductases), acyl-ACP reductases, fatty acid hydroxylases, acyl-CoA desaturases, acyl-ACP desaturases, acyl-CoA oxidases, acyl-CoA dehydrogenases, ester synthases, and/or alkane biosynthetic polypeptides, etc. Fatty acid derivative enzymes can convert a substrate into a fatty acid derivative. In some examples, the substrate may be a fatty acid derivative that the fatty acid derivative enzyme converts into a different fatty acid derivative.

As used herein, "fatty acid enzyme" means any enzyme involved in fatty acid biosynthesis. Fatty acid enzymes can be expressed or overexpressed in host cells to produce fatty acids. Non-limiting examples of fatty acid enzymes include fatty acid synthases and thioesterases.

As used herein, "fatty aldehyde" means an aldehyde having the formula RCHO characterized by an unsaturated carbonyl group (C=O). In a preferred embodiment, the fatty aldehyde is any aldehyde made from a fatty acid or fatty acid derivative. In one embodiment, the R group is at least about 1, 2, 3, 4, 5, 6, 7, 8, 9, 10, 11, 12, 13, 14, 15, 16, 17, 18, 19, 20, 21, 22, 23, 24, 25, or 26 carbons in length, or is a value between any two of the foregoing values.

R can be straight or branched chain. The branched chains may have one or more points of branching. In addition, the branched chains may include cyclic branches.

Furthermore, R can be saturated or unsaturated. If unsaturated, the R can have one or more points of unsaturation.

In one embodiment, the fatty aldehyde is produced biosynthetically.

Fatty aldehydes have many uses. For example, fatty aldehydes can be used to produce many specialty chemicals. For example, fatty aldehydes are used to produce polymers, resins, dyes, flavorings, plasticizers, perfumes, pharmaceuticals, and other chemicals. Some are used as solvents, preservatives, or disinfectants. Some natural and synthetic compounds, such as vitamins and hormones, are aldehydes.

The terms "fatty aldehyde biosynthetic polypeptide", "carboxylic acid reductase", and "CAR" are used interchangeably herein.

As used herein, "fatty alcohol" means an alcohol having the formula ROH. In a preferred embodiment, the fatty alcohol is any alcohol made from a fatty acid or fatty acid derivative. In one embodiment, the R group is at least about 5, 6, 7, 8, 9, 10, 11, 12, 13, 14, 15, 16, 17, 18, 19, 20, 21, 22, 23, 24, 25, or 26 carbons in length, or is a value between any two of the foregoing values. Typically, the fatty alcohol comprises an R group that is 6 to 26 carbons in length. Preferably, the fatty alcohol comprises an R group that is 8, 10, 12, 14, 16, or 18 carbons in length.

R can be straight or branched chain. The branched chains may have one or more points of branching. In addition, the branched chains may include cyclic branches. In a particular embodiment, the fatty alcohol of the present invention comprises one or more points of branching.

Furthermore, R can be saturated or unsaturated. If unsaturated, the R can have one or more points of unsaturation.

In one embodiment, the branched fatty alcohol is produced biosynthetically.

Fatty alcohols have many uses. For example, fatty alcohols can be used to produce various specialty chemicals. As such, fatty alcohols are used as a biofuel; as solvents for fats, waxes, gums, and resins; in pharmaceutical salves, emollients, and lotions; as lubricating-oil additives; in detergents and emulsifiers; as textile antistatic and finishing agents; as plasticizers; as nonionic surfactants; in cosmetics, e.g., as thickeners.

The term "fatty alcohol derivative" refers to a compound derived from a fatty alcohol. The fatty alcohol derivative can include the oxygen atom derived from the fatty alcohol, or, in some embodiments, does not include the aforesaid oxygen atom, in, for example, fatty amine oxides. For example, a fatty amide, which also can be referred to as an alkyl amide, refers to a compound comprising an amide group and a hydrocarbon residue having about 6 carbon atoms or more, wherein the hydrocarbon residue is bonded to the carbonyl group of the amide group or to the nitrogen atom of the amide group. In some embodiments, the hydrocarbon residue of the fatty alcohol is bonded to the carbonyl group of the amide group or to the nitrogen atom of the amide group. In some embodiments, the hydrocarbon residue is saturated. In other embodiments, the hydrocarbon residue is monounsaturated. In further embodiments, the hydrocarbon residue is polyunsaturated. In certain other embodiments, the hydrocarbon residue can be a straight-chain residue. In certain further embodiments, the hydrocarbon residue can contain one or more points of branching.

Branched fatty alcohols have particularly beneficial properties as compared to their corresponding straight-chain isomers (i.e., isomers of the same molecular weight). For example, branched fatty alcohols tend to have considerably lower melting points when compared to their corresponding straight-chain isomers. Lower melting points confer lower pour points. In addition, branched fatty alcohols tend to substantially lower volatility and vapor pressure, and improved stability against oxidation and rancidity, as compared to their corresponding straight-chain isomers. These beneficial properties render particular suitability of using branched fatty alcohols and/or derivatives thereof as components or feedstocks for cosmetic and pharmaceutical applications, as components of plasticizers for synthetic resins, as solvents for solutions for printing ink and specialty inks, or as industrial lubricants. These materials are also well suited as components of surfactants that have good low-temperature detersive performance. As such, they are especially desirable as ingredients of various household and/or personal care cleaning/treatment compositions wherein low washing temperatures are preferred.

As used herein, "fraction of modern carbon" or "$f_M$" has the same meaning as defined by National Institute of Standards and Technology (NIST) Standard Reference Materials (SRMs) 4990B and 4990C, known as oxalic acids standards HOxI and HOxII, respectively. The fundamental definition relates to 0.95 times the $^{14}C/^{12}C$ isotope ratio HOxI (referenced to AD 1950). This is roughly equivalent to decay-corrected pre-Industrial Revolution wood. For the current living biosphere (plant material), $f_M$ is approximately 1.1.

"Gene knockout", as used herein, refers to a procedure by which a gene encoding a target protein is modified or inactivated so as to reduce or eliminate the function of the intact protein. Inactivation of the gene may be performed by general methods such as mutagenesis by UV irradiation or treatment with N-methyl-N'-nitro-N-nitrosoguanidine, site-directed mutagenesis, homologous recombination, insertion-deletion mutagenesis, or "Red-driven integration" (Datsenko et al., *Proc. Natl. Acad. Sci. USA,* 97: 6640-45 (2000)). For example, in one embodiment, a construct is introduced into a host cell, such that it is possible to select for homologous recombination events in the host cell. One of skill in the art can readily design a knock-out construct including both positive and negative selection genes for efficiently selecting transfected cells that undergo a homologous recombination event with the construct. The alteration in the host cell may be obtained, for example, by replacing through a single or double crossover recombination a wild type DNA sequence by a DNA sequence containing the alteration. For convenient selection of transformants, the alteration may, for example, be a DNA sequence encoding an antibiotic resistance marker or a gene complementing a possible auxotrophy of the host cell. Mutations include, but are not limited to, deletion-insertion mutations. An example of such an alteration includes a gene disruption (i.e., a perturbation of a gene) such that the product that is normally produced from this gene is not produced in a functional form. This could be due to a complete deletion, a deletion and insertion of a selective marker, an insertion of a selective marker, a frameshift mutation, an in-frame deletion, or a point mutation that leads to premature termination. In some instances, the entire mRNA for the gene is absent. In other situations, the amount of mRNA produced varies.

Calculations of "homology" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence that is aligned for comparison purposes is at least about 30%, preferably at least about 40%, more preferably at least about 50%, even more preferably at least about 60%, and even more preferably at least about 70%, at least about 80%, at least about 90%, or about 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein, amino acid or nucleic acid "identity" is equivalent to amino acid or nucleic acid "homology"). The percent identity between the two sequences is a function of the number of identical positions shared by the sequences, taking into account the number of gaps and the length of each gap, which need to be introduced for optimal alignment of the two sequences.

The comparison of sequences and determination of percent homology between two sequences can be accomplished using a mathematical algorithm. In a preferred embodiment, the percent homology between two amino acid sequences is determined using the Needleman and Wunsch (1970), *J. Mol. Biol.* 48:444 453, algorithm that has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent homology between two nucleotide sequences is determined using the GAP program in the GCG software package, using a NWSgapdna. CMP matrix and a gap weight of about 40, 50, 60, 70, or 80 and a length weight of about 1, 2, 3, 4, 5, or 6. A particularly preferred set of parameters (and the one that should be used if the practitioner is uncertain about which parameters should be applied to determine if a molecule is within a homology limitation of the claims) are a Blossum 62 scoring matrix with a gap penalty of 12, a gap extend penalty of 4, and a frameshift gap penalty of 5.

Other methods for aligning sequences for comparison are well known in the art. Various programs and alignment algorithms are described in, for example, Smith & Waterman, *Adv. Appl. Math.* 2:482, 1981; Pearson & Lipman, *Proc. Natl. Acad. Sci. USA* 85:2444, 1988; Higgins & Sharp, *Gene* 73:237 244, 1988; Higgins & Sharp, *CABIOS* 5:151-153, 1989; Corpet et al., *Nucleic Acids Research* 16:10881-10890, 1988; Huang et al., *CABIOS* 8:155-165, 1992; and Pearson et al., *Methods in Molecular Biology* 24:307-331, 1994. and Altschul et al., *J. Mol. Biol.* 215:403-410, 1990.

As used herein, a "host cell" is a cell used to produce a product described herein (e.g., a branched fatty alcohol described herein). A host cell can be modified to express or overexpress selected genes or to have attenuated expression of selected genes. Non-limiting examples of host cells include plant, animal, human, bacteria, yeast, or filamentous fungi cells.

As used herein, the term "hybridizes under low stringency, medium stringency, high stringency, or very high stringency conditions" describes conditions for hybridization and washing. Guidance for performing hybridization reactions can be found, for example, in Current Protocols in Molecular Biology, John Wiley & Sons, N.Y. (1989), 6.3.1-6.3.6. Aqueous and nonaqueous methods are described in that reference, and either method can be used. An example of hybridization conditions referred to herein are as follows: 1) low stringency hybridization conditions in 6× sodium chloride/sodium citrate (SSC) at about 45° C., followed by two washes in 0.2× SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2.×SSC, 0.1% SDS at 65° C.; and 4) very high stringency hybridization conditions in 0.5M sodium phosphate, 7% SDS at 65° C., followed by one or more washes at 0.2×SSC, 1% SDS at 65° C. Very high stringency conditions of 4) are the preferred conditions unless otherwise specified.

The term "isolated" as used herein with respect to nucleic acids, such as DNA or RNA, refers to molecules separated from other DNAs or RNAs, respectively, that are present in the natural source of the nucleic acid. Moreover, by an "isolated nucleic acid" is meant to include nucleic acid fragments, which are not naturally occurring as fragments and would not be found in the natural state. The term "isolated" is also used herein to refer to polypeptides, which are isolated from other cellular proteins, and is meant to encompass both purified and recombinant polypeptides. The term "isolated" as used herein also refers to a nucleic acid or peptide that is substantially free of cellular material, viral material, or culture medium when produced by recombinant DNA techniques. The term "isolated" as used herein also refers to a nucleic acid or peptide that is substantially free of chemical precursors or other chemicals when chemically synthesized.

As used herein, the "level of expression of a gene in a cell" refers to the level of mRNA, pre-mRNA nascent transcript(s), transcript processing intermediates, mature mRNA(s), and degradation products encoded by the gene in the cell.

As used herein, the term "microorganism" means prokaryotic and eukaryotic microbial species from the domains Archaea, Bacteria, and Eucarya, the latter including yeast and filamentous fungi, protozoa, algae, or higher Protista. The terms "microbial cells" (i.e., cells from microbes) and "microbes" are used interchangeably and refer to cells or small organisms that can only be seen with the aid of a microscope.

As used herein, the term "nucleic acid" refers to polynucleotides, such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides, ESTs, chromosomes, cDNAs, mRNAs, and rRNAs.

As used herein, the term "operably linked" means that selected nucleotide sequence (e.g., encoding a polypeptide described herein) is in proximity to a promoter to allow the promoter to regulate expression of the selected DNA. In addition, the promoter is located upstream of the selected nucleotide sequence in terms of the direction of transcription and translation. By "operably linked" is meant that a nucleotide sequence and a regulatory sequence(s) are connected in such a way as to permit gene expression when the appropriate molecules (e.g., transcriptional activator proteins) are bound to the regulatory sequence(s).

The term "or" is used herein to mean, and is used interchangeably with, the term "and/or," unless context clearly indicates otherwise.

As used herein, "overexpress" means to express or cause to be expressed a nucleic acid or polypeptide in a cell at a greater concentration than is normally expressed in a corresponding wild-type cell. For example, a polypeptide can be "overexpressed" in a recombinant host cell when the polypeptide is present in a greater concentration in the recombinant host cell compared to its concentration in a non-recombinant host cell of the same species.

As used herein, "partition coefficient" or "P" is defined as the equilibrium concentration of a compound in an organic phase divided by the concentration at equilibrium in an aqueous phase (e.g., fermentation broth). In one embodiment of a bi-phasic system described herein, the organic phase is formed by the fatty aldehyde or fatty alcohol during the production process. However, in some examples, an organic phase can be provided, such as by providing a layer of octane, to facilitate product separation. When describing a two phase system, the partition characteristics of a compound can be described as log P. For example, a compound with a log P of 1 would partition 10:1 to the organic phase:aqueous phase. A compound with a log P of −1 would partition 1:10 to the organic phase:aqueous phase. By choosing an appropriate fermentation broth and organic phase, a branched fatty aldehyde or branched fatty alcohol with a high log P value can separate into the organic phase even at very low concentrations in the fermentation vessel.

As used herein, the term "purify," "purified," or "purification" means the removal or isolation of a molecule from its environment by, for example, isolation or separation. "Substantially purified" molecules are at least about 60% free, preferably at least about 75% free, and more preferably at least about 90% free from other components with which they are associated. As used herein, these terms also refer to the removal of contaminants from a sample. For example, the removal of contaminants can result in an increase in the percentage of branched fatty aldehyde or branched fatty alcohol in a sample. For example, when branched fatty alcohols are produced in a host cell, the branched fatty alcohols can be purified by the removal of host cell proteins, or by simply separating and removing linear fatty alcohols that are produced during the same process. After purification, the percentage of branched fatty alcohols in the sample is increased.

The terms "purify," "purified," and "purification" do not require absolute purity. They are relative terms. Thus, for example, when branched fatty alcohols are produced in host cells, a purified branched fatty alcohol is one that is substantially separated from other cellular components (e.g., nucleic acids, polypeptides, lipids, carbohydrates, or other compounds, such as, for example, linear fatty alcohols). In another example, a purified branched fatty alcohol preparation is one in which the branched fatty alcohol is substantially free from contaminants, such as those that might be present following fermentation. In some embodiments, a branched fatty alcohol is purified when at least about 50% by weight of a sample is composed of the branched fatty alcohol. In other embodiments, a branched fatty alcohol is purified when at least about 60%, 70%, 80%, 85%, 90%, 92%, 95%, 98%, or 99% or more by weight of a sample is composed of the branched fatty alcohol.

As used herein, the term "recombinant polypeptide" refers to a polypeptide that is produced by recombinant DNA techniques, wherein generally DNA encoding the expressed protein or RNA is transferred into a suitable expression vector and that is in turn used to transform a host cell to produce the polypeptide or RNA.

As used herein, the term "substantially identical" (or "substantially homologous") is used to refer to a first amino acid or nucleotide sequence that contains a sufficient number of identical or equivalent (e.g., with a similar side chain, such as involving conservative amino acid substitutions) amino acid residues or nucleotides to a second amino acid or nucleotide sequence such that the first and second amino acid or nucleotide sequences have similar activities.

As used herein, the term "surfactants" refers broadly to surface active agents. These agents are typically amphipathic molecules comprising both hydrophilic and hydrophobic moieties that partition preferentially at the interface between fluid phases with different degrees of polarity and hydrogen bonding, such as, for example, an oil/water interface, or an air/water interface. Surfactants are capable of reducing surface and interfacial tension and forming microemulsions. These characteristics confer detergency, emulsifying, foaming and dispersing traits, making them some of the most versatile process chemicals.

Surfactants can be natural or synthetic in origin. Surfactants from natural origin can be derived from, for example, vegetable or animal sources. Surfactants derived from synthetic origin are typically those derived from petroleum.

There are many types of surfactants, including, for example, anionic surfactants, cationic surfactants, non-ionic surfactants, and amphoteric/zwitterionic surfactants, each with distinct characteristics.

The hydrophobic end of an anionic surfactant is negatively charged in solution. As a result, they have good cleaning properties and high sudding potentials, which make them particularly effective as some of the most widely used types of surfactants in, for example, laundry detergents, dishwashing liquids, and shampoos. Known anionic surfactants include, for example, alkyl sulfates, alkyl ethoxylate sulfates, and soaps.

The hydrophobic end of a cationic surfactant is positively charged in solution. Three types of cationic surfactants are the most commonly known. The first type is the esterquat, which is widely included in, for example, fabric treatment agents or softeners and in detergents with built-in softeners. This is because esterquat is capable of adding softness to fabrics. The second type is a mono alkyl quaternary system, which is found in many household cleaners due to its disinfecting and/or sanitizing properties.

Non-ionic surfactants do not have an electrical charge in solution, making them resistant to water hardness deactivation. They are typically excellent grease removers. The most commonly used non-ionic surfactants are ethers or derivatives of fatty alcohols.

Amphoteric/zwitterionic surfactants are milder than the other types of surfactants, making them particularly suitable for use in personal or beauty care cleaning/treatment products. They may contain two oppositely-charged groups. While the positive charge is typically conferred by ammonium, the source of the negative charge can vary. For example, the negative charge can be conferred by carboxylate, sulfate, sulfonate, or a combination thereof. They can be anionic (e.g., negatively charged), cationic (e.g., positively charged) or non-ionic (e.g., no charge) in solution, depending on the acidity or pH of the solution. They have good compatibility with the other types of surfactants and are well known for being soluble and effective in the presence of high concentrations of electrolytes, acids and alkalis. An example of an amphoteric/zwitterionic surfactant is an alkyl betaine.

In typical applications, different types of surfactants are blended or otherwise used together to achieve an array of desirable properties.

As used herein, the term "synthase" means an enzyme that catalyzes a synthesis process. As used herein, the term synthase includes synthases, synthetases, and ligases.

As used herein, the term "transfection" means the introduction of a nucleic acid (e.g., via an expression vector) into a recipient cell by nucleic acid-mediated gene transfer.

As used herein, "transformation" refers to a process in which a cell's genotype is changed as a result of the cellular uptake of exogenous DNA or RNA. This may result in the transformed cell expressing a recombinant form of an RNA or polypeptide. In the case of antisense expression from the transferred gene, the expression of a naturally-occurring form of the polypeptide is disrupted.

As used herein, a "transport protein" is a polypeptide that facilitates the movement of one or more compounds in and/or out of a cellular organelle and/or a cell.

As used herein, a "variant" of polypeptide X refers to a polypeptide having the amino acid sequence of peptide X in which one or more amino acid residues is altered. The variant may have conservative changes or nonconservative changes. Guidance in determining which amino acid residues may be substituted, inserted, or deleted without affecting biological activity may be found using computer programs well known in the art, for example, LASERGENE software (DNASTAR).

The term "variant," when used in the context of a polynucleotide sequence, may encompass a polynucleotide sequence related to that of a gene or the coding sequence thereof. This definition may also include, for example, "allelic," "splice," "species," or "polymorphic" variants. A splice variant may have significant identity to a reference polynucleotide, but will generally have a greater or fewer number of polynucleotides due to alternative splicing of exons during mRNA processing. The corresponding polypeptide may possess additional functional domains or an absence of domains. Species variants are polynucleotide sequences that vary from one species to another. The resulting polypeptides generally will have significant amino acid sequence identity relative to each other. A polymorphic variant is a variation in the polynucleotide sequence of a particular gene between individuals of a given species.

As used herein, the term "vector" refers to a nucleic acid molecule capable of transporting another nucleic acid to which it has been linked. One type of useful vector is an episome (i.e., a nucleic acid capable of extra-chromosomal replication). Useful vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids," which refer generally to circular double stranded DNA loops that, in their vector form, are not bound to the chromosome. In the present specification, "plasmid" and "vector" are used interchangeably, as the plasmid is the most commonly used form of vector. However, also included are such other forms of expression vectors that serve equivalent functions and that become known in the art subsequently hereto.

Surfactants and Cleaning Compositions Comprising a Microbially Produced Branched Fatty Alcohol or a Branched Fatty Alcohol Derivative Thereof The invention provides a surfactant composition comprising one or more microbially produced branched chain fatty alcohols and/or derivatives thereof. The invention further provides a detergent/cleaning composition, such as, for example, a household cleaning composition or a personal or beauty care cleaning composition, comprising such a surfactant.

In one aspect, the invention features a surfactant composition comprising branched chain fatty alcohols and/or derivatives thereof produced by microbes. In some embodiments, the microbially produced branched fatty alcohol and/or derivative thereof is produced by a host cell expressing genes encoding at least one subunit of a branched-chain alpha-keto acid dehydrogenase polypeptide. The host cell expresses genes encoding at least two subunits of a branched-chain alpha-keto acid dehydrogenase polypeptide. For example, the host cell expresses a set of genes encoding the first subunit and a second subunit of a branched-chain alpha-keto acid dehydrogenase polypeptide. In certain embodiments, the host cell expresses a third gene encoding the second subunit of a branched-chain alpha-keto acid dehydrogenase polypeptide. In some embodiments, the first and second polypeptides have branched-chain alpha-keto acid decarboxylase activity, and the third polypeptide has lipoamide acyltransferase activity. In further embodiments, the host cell expresses a fourth gene encoding the third subunit of a branched-chain alpha-keto acid dehydrogenase polypeptide. In some embodiments, the fourth polypeptide has lipoamide dehydrogenase activity.

In some embodiments, the microbially produced branched fatty alcohol and/or derivative thereof is produced by a host cell expressing a gene encoding a beta ketoacyl-ACP synthase polypeptide. In certain embodiments, the beta ketoacyl-ACP synthase polypeptide has FabH activity. In certain embodiments the beta ketoacyl-ACP synthase has specificity for branched-chain acyl-CoA substrates.

In some embodiments, the microbially produced branched fatty alcohol and/or derivative thereof is produced by a host cell expressing a set of genes encoding at least one subunit of a branched-chain alpha-keto acid dehydrogenase complex. Specifically, the microbially produced branched fatty alcohol and/or derivative thereof is produced by a host cell expressing a first gene encoding a first polypeptide comprising the amino acid sequence that is any one of SEQ ID NOs:1, 3, 5, 7, 9, 11, 13, and 15, or one that has at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% sequence identity to the amino acid sequence of any one of SEQ ID NOs: 1, 3, 5, 7, 9, 11, 13, and 15, or a variant thereof; a second gene encoding a second polypeptide comprising an amino acid sequence of any one of SEQ ID NOs:24, 26, 28, 30, 32, 34, 36, and 38, or one that has at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% sequence identity to the amino acid sequence of any one of SEQ ID NOs:24, 26, 28, 30, 32, 34, 36, and 38, or a variant thereof. In certain embodiments, the host cell also expresses a third gene encoding a third polypeptide comprising the amino acid sequence of any one of SEQ ID NOs:47, 49, 51, 53, 55, 57, 59, and 61, or one that has at least 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% sequence identity to the amino acid sequence of any one of SEQ ID NOs:47, 49, 51, 53, 55, 57, 59, and 61, or a variant thereof. In some embodiments, the branched fatty aldehyde, branched fatty alcohol, or a derivative thereof is isolated from the host cell, for example, isolated from the extracellular environment of the host cell. In some embodiments, the branched fatty aldehyde, branched fatty alcohol, or the derivative thereof is spontaneously secreted, completely or partially, from the host cell. In alternative embodiments, the branched fatty aldehyde, branched fatty alcohol, or the derivative thereof is transported into the extracellular environment. In further embodiments, the branched fatty aldehyde, branched fatty alcohol, or the derivative thereof is passively transported or spontaneously secreted into the extracellular environment.

The first polypeptide comprises the amino acid sequence of any one of SEQ ID NOs:1, 3, 5, 7, 9, 11, 13, and 15, with one or more amino acid substitutions, additions, insertions, or deletions, the second polypeptide comprises the amino acid sequence of any one of SEQ ID NOs: 24, 26, 28, 30, 32, 34, 36, and 38, wherein the first and second polypeptides together have alpha-keto acid decarboxylase activity. In certain embodiments, the first polypeptide comprises one or more or all of the amino acid sequence motifs selected from SEQ ID NOs:17-23. The second polypeptide comprises one or more or all of the amino acid sequence motifs selected from SEQ ID NOs:40-46. In some embodiments, the third polypeptide comprises an amino acid sequence of any one of SEQ ID NOs: 47, 49, 51, 53, 55, 57, 59, and 61, with one or more amino acid substitutions, additions, insertions, or deletions, wherein the third polypeptide has lipoamide acyltransferase activity. The third polypeptide comprises one or more or all of the amino acid sequence motifs selected from SEQ ID NOs: 63-68. In some embodiments, the first, second and third polypeptides are capable of catalyzing the conversion of alpha-keto acids to branched acyl-CoAs. It is within the capacity of those skilled in the art to devise a suitable enzymatic assay using the appropriate substrates. Examples of such assays are described herein.

In some embodiments, the first, second, and third polypeptides independently comprises 1 or more, 5 or more, 10 or more, 15 or more, 20 or more, 30 or more, 40 or more, 50 or more, or 100 or more of the following conservative amino acid substitutions: replacement of an aliphatic amino acid, such as alanine, valine, leucine, and isoleucine, with another aliphatic amino acid; replacement of a serine with a threonine; replacement of a threonine with a serine; replacement of an acidic residue, such as aspartic acid and glutamic acid, with another acidic residue; replacement of a residue bearing an amide group, such as asparagine and glutamine, with another residue bearing an amide group; exchange of a basic residue, such as lysine and arginine, with another basic residue; and replacement of an aromatic residue, such as phenylalanine and tyrosine, with another aromatic residue. In some embodiments, the first and second polypeptides independently comprises about 1, 2, 3, 4, 5, 6, 7, 8, 9, 10, 15, 20, 30, 40, 50, 60, 70, 80, 90, 100, 200, or more amino acid substitutions, additions, insertions, or deletions. In some embodiments, the third polypeptide comprises about 1, 2, 3, 4, 5, 6, 7, 8, 9, 10, 15, 20, 30, 40, 50, 60, 70, 80, 90, 100, 200, or more amino acid substitutions, additions, insertions, or deletions. In some embodiments, the first and second polypeptides have branched-chain alpha-keto acid decarboxylase activity and the third polypeptide has lipoamide acyltransferase activity. In some embodiments, the first, second and third polypeptides are capable of catalyzing the conversion of branched alpha-keto acids to branched acyl-CoAs.

In certain embodiments, the microbially produced branched fatty alcohol and/or derivative thereof is produced by a host cell expressing a fourth gene encoding a fourth polypeptide comprising the amino acid sequence of any one of SEQ ID NOs:69, 71, 73, 75, 77, 79, 81, and 83, or one that has at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% sequence identity to the amino acid sequence of any one of SEQ ID NOs:69, 71, 73, 75, 77, 79, 81, and 83, or a variant thereof. In some embodiments, the branched fatty aldehyde, branched fatty alcohol, or a derivative thereof is isolated from the host cell, for example, from the extracellular environment. In certain embodiments, the branched fatty aldehyde, branched fatty alcohol, or the derivative thereof is spontaneously secreted, partially or completely, into the extracellular environment. In other embodiments, the branched fatty aldehyde, branched fatty alcohol, or the derivative thereof is transported into the extracellular environment. In certain embodiments, the branched fatty aldehyde, branched fatty alcohol or the derivative thereof is passively transported into the extracellular environment.

The fourth polypeptide comprises the amino acid sequence of any one of SEQ ID NOs:69, 71, 73, 75, 77, 79, 81, and 83, with one or more amino acid substitutions, additions, insertions, or deletions, and the polypeptide has lipoamide dehydrogenase activity. In certain embodiments, the fourth polypeptide comprises one or more or all of amino acid sequence motifs selected from SEQ ID NOs:85-89. In some embodiments, the fourth polypeptide comprises 1 or more, 5 or more, 10 or more, 15 or more, 20 or more, 30 or more, 40 or more, 50 or more, or 100 or more of the following conservative amino acid substitutions: replacement of an aliphatic amino acid, such as alanine, valine, leucine, and isoleucine, with another aliphatic amino acid; replacement of a serine with a threonine; replacement of a threonine with a serine; replacement of an acidic residue, such as aspartic acid and glutamic acid, with another acidic residue; replacement of a residue bearing an amide group, such as asparagine and glutamine, with another residue bearing an amide group; exchange of a basic residue, such as lysine and arginine, with another basic residue; and replacement of an aromatic residue, such as phenylalanine and tyrosine, with another aromatic residue. In some embodiments, the fourth polypeptide comprises about 1, 2, 3, 4, 5, 6, 7, 8, 9, 10, 15, 20, 30, 40, 50, 60, 70, 80, 90, 100, 200, or more amino acid substitutions, additions, insertions, or deletions. In some embodiments, the fourth polypeptide has lipoamide dehydrogenase activity. In some embodiments, the first, second, third and fourth polypeptides have branched chain alpha-keto acid decarboxylase and/or lipoamide acyltransferase and/or lipoamide dehydrogenase activity. In some embodiments, the first, second, third and fourth polypeptides, optionally forming a complex, are capable of catalyzing the conversion alpha-keto acids to branched-chain acyl-CoAs.

In certain embodiments, the microbially produced branched fatty alcohol and/or derivative thereof is produced by a host cell further expressing a gene encoding a beta-ketoacyl ACP synthase comprising the amino acid sequence of any one of SEQ ID NOs: 90, 92, 94, 96, 98, 100, 102, 104, 106, 108, 110, 112, 114, 116, 118, and 120, or one that has at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% sequence identity to the amino acid sequence of any one of SEQ ID NOs:90, 92, 94, 96, 98, 100, 102, 104, 106, 108, 110, 112, 114, 116, 118, and 120, or a variant thereof. In some embodiments, the branched fatty aldehyde, branched fatty alcohol, or a derivative thereof is isolated from the host cell, for example, from the extracellular environment. In certain embodiments, the branched fatty aldehyde, branched fatty alcohol, or the derivative thereof is spontaneously secreted, partially or completely, into the extracellular environment. In other embodiments, the branched fatty aldehyde, branched fatty alcohol, or the derivative thereof is transported into the extracellular environment. In certain embodiments, the branched fatty aldehyde, branched fatty alcohol, or the derivative thereof is passively transported into the extracellular environment.

The beta ketoacyl-ACP synthase polypeptide comprises the amino acid sequence of any one of SEQ ID NOs:90, 92, 94, 96, 98, 100, 102, 104, 106, 108, 110, 112, 114, 116, 118, and 120, with one or more amino acid substitutions, additions, insertions, or deletions. In some embodiments, the beta ketoacyl-ACP synthase polypeptide comprises one or more or all of amino acid sequence motifs selected from SEQ ID NOs:122-127. In some embodiments, the polypeptide has FabH activity. In certain embodiments, the beta ketoacyl-ACP synthase polypeptide has specificity for branched-chain fatty acyl-CoA substrates. In certain embodiments, the polypeptide is capable of catalyzing the condensation reaction between a branched acyl-CoA and malonyl-ACP. It is within the capacity of those skilled in the art to devise a suitable enzymatic assay using the appropriate substrates in order to distinguish those polypeptides having sequence homology to the beta-ketoacyl-ACP synthase polypeptides herein but are not suitable or does not have specificity for branched-chain substrates. Two examples of such enzymatic assays are described herein.

The beta ketoacyl-ACP synthase polypeptide can comprise 1 or more, 5 or more, 10 or more, 15 or more, 20 or more, 30 or more, 40 or more, 50 or more, or 100 or more of the following conservative amino acid substitutions: replacement of an aliphatic amino acid, such as alanine, valine, leucine, and isoleucine, with another aliphatic amino acid; replacement of a serine with a threonine; replacement of a threonine with a serine; replacement of an acidic residue, such as aspartic acid and glutamic acid, with another acidic residue; replacement of a residue bearing an amide group, such as asparagine and glutamine, with another residue bearing an amide group; exchange of a basic residue, such as lysine and arginine, with another basic residue; and replacement of an aromatic residue, such as phenylalanine and tyrosine, with another aromatic residue. In some embodiments, the polypeptide comprises about 1, 2, 3, 4, 5, 6, 7, 8, 9, 10, 15, 20, 30, 40, 50, 60, 70, 80, 90, 100, 200 or more amino acid substitutions, additions, insertions, or deletions. In some embodiments, the polypeptide has FabH activity. In some embodiments, the polypeptide has specificity for branched-chain acyl-CoAs. In some embodiments, the polypeptide is capable of catalyzing the condensation of a branched acyl-CoA and malonyl-ACP.

In certain embodiments, the first polypeptide comprises an amino acid sequence motif of any one of or one or more or all of SEQ ID NOs:17-23, wherein the first polypeptide is of about 200 to about 800 amino acid residues in length, or about 300 to about 700 amino acid residues in length, or about 400 to about 600 amino acids in length. In some embodiments, the second polypeptide comprises an amino acid sequence motif of any one of or one or more or all of SEQ ID NOs:40-46, wherein the second polypeptide is about 200 to about 800 amino acid residues in length, or about 300 to about 700 amino acid residues in length, or about 400 to about 600 amino acid residues in length. In some embodiments, the third polypeptide comprises an amino acid sequence motif of any one of or one or more or all of SEQ ID NOs:63-68, wherein the first polypeptide is of about 200 to about 800 amino acid residues in length, or about 300 to about 700 amino acid residues in length, or about 400 to about 600 amino acid residues in length. In some embodiments, the first, second and optionally the third polypeptides are capable of catalyzing the conversion of alpha-keto acid substrates to branched acyl-CoAs.

In certain embodiments, the microbially produced branched fatty alcohol and/or derivative thereof is produced by a host cell further expressing a gene encoding a fatty aldehyde biosynthesis polypeptide selected from those listed in the Table 6, or a variant thereof. In some embodiments, the fatty aldehyde biosynthesis polypeptide comprises the amino acid sequence of an enzyme listed in Table 6, with one or more amino acid substitutions, additions, insertions, or deletions, and the polypeptide has carboxylic acid reductase activity. In some embodiments, the polypeptide has fatty acid reductase activity. In some embodiments, the fatty aldehyde biosynthesis polypeptide comprises one or more of the following conservative amino acid substitutions. In some embodiments, the fatty aldehyde biosynthesis polypeptide has about 1, 2, 3, 4, 5, 6, 7, 8, 9, 10, 15, 20, 30, 40, 50, 60, 70, 80, 90, 100, or more amino acid substitutions, additions, insertions, or deletions. In some embodiments, the polypeptide has carboxylic acid reductase activity. In some embodiments, the polypeptide has fatty acid reductase activity.

In some embodiments, the branched fatty alcohol or a derivative thereof is isolated from the host cell, for example, from the extracellular environment. In some embodiments, the branched fatty alcohol or the derivative thereof is spontaneously secreted, partially or completely, from the host cell. In alternative embodiments, the branched fatty alcohol or the derivative thereof is transported into the extracellular environment. In other embodiments, the branched fatty alcohol or the derivative thereof is passively transported into the extracellular environment.

In some embodiments, the microbially produced branched fatty alcohol and/or derivative thereof is produced by a host cell wherein a gene encoding a fatty acid synthase is modified. For example, modifying the expression of a gene encoding a fatty acid synthase includes expressing a gene encoding a fatty acid synthase in the host cell and/or increasing the expression or activity of an endogenous fatty acid synthase in the host cell. Alternatively, modifying the expression of a gene encoding a fatty acid synthase includes attenuating a gene encoding a fatty acid synthase in the host cell and/or decreasing the expression or activity of an endogenous fatty acid synthase in the host cell. In some embodiments, the fatty acid synthase is a thioesterase. In particular embodiments, the thioesterase is encoded by tesA, tesA without leader sequence, tesB, fatB, fatB2, fatB3, fatA, or fatA1.

In some embodiments, the microbially produced branched fatty alcohol and/or derivative thereof is produced by a host cell expressing a gene encoding a fatty alcohol biosynthesis polypeptide. The fatty alcohol biosynthesis polypeptide is, for example, an alcohol dehydrogenase. In particular embodiments, the fatty alcohol biosynthesis polypeptide is one selected from the enzymes listed in Table 8, or a variant thereof.

In certain other embodiments, the microbially produced branched fatty alcohol and/or derivative thereof is produced by a host cell expressing a gene encoding another aldehyde biosynthetic polypeptide or an acyl-ACP reductase polypeptide comprising the amino acid sequence of any of the enzymes listed in Table 7, or a variant thereof. In some embodiments, the branched fatty alcohol or derivative thereof is isolated from the host cell, for example, from the extracellular environment. In certain embodiments, the branched fatty alcohol or derivative thereof is spontaneously secreted, partially or completely, from the host cell. In alternative embodiments, the branched fatty alcohol or derivative thereof is transported into the extracellular environment. In other embodiments, the branched fatty alcohol or derivative thereof is passively transported into the extracellular environment.

The acyl-ACP reductase polypeptide, for example, comprises the amino acid sequence of an enzyme selected from those listed in Table 7, with one or more amino acid substitutions, additions, insertions, or deletions, and the polypeptide has reductase activity. In certain embodiments, the polypeptide is capable of catalyzing the conversion of a suitable biological substrate into an aldehyde. The acyl-ACP reductase polypeptide, for example, comprises one or more conservative amino acid substitutions, or has about 1, 2, 3, 4, 5, 6, 7, 8, 9, 10, 15, 20, 30, 40, 50, 60, 70, 80, 90, 100, 150, or more amino acid substitutions, additions, insertions, or deletions. In some embodiments, the polypeptide has reductase activity. In some embodiments, the polypeptide is capable of catalyzing the conversion of a suitable biological substrate into an aldehyde.

In any of the above-described embodiments, the microbially produced branched fatty alcohol and/or derivative thereof is produced by a host cell, which is genetically engineered to express an attenuated level of a fatty acid degradation enzyme relative to a wild type host cell. For example, the host cell is genetically engineered to express an attenuated level of an acyl-CoA synthase relative to a wild type host cell. In particular embodiments, the host cell expresses an attenuated level of an acyl-CoA synthase encoded by fadD, fadK, BH3103, yhfL, Pfl-4354, EAV15023, fadD1, fadD2, RPC_4074, fadDD35, fadDD22, faa3p or the gene encoding the protein ZP_01644857. In certain embodiments, the genetically engineered host cell comprises a knockout of one or more genes encoding a fatty acid degradation enzyme, such as the aforementioned acyl-CoA synthase genes. In certain embodiments, the host cell is genetically engineered to express, relative to a wild type host cell, a decreased level of at least one of a gene encoding an acyl-CoA dehydrogenase, a gene encoding an outer membrane protein receptor, and a gene encoding a transcriptional regulator of fatty acid biosynthesis. In some embodiments, the gene encoding an acyl-CoA dehydrogenase is fadE. In some embodiments, the gene encoding an outer membrane protein receptor is tonA (also known as fhuA). Yet in other embodiments, the gene encoding a transcriptional regulator of fatty acid biosynthesis is fabR.

In yet other embodiments, the microbially produced branched fatty alcohol and/or derivative thereof is produced by a host cell, which is genetically engineered to express an attenuated level of a dehydratase/isomerase enzyme, such as an enzyme encoded by fabA or by a gene listed in Table 1 or Table 2. In some embodiments, the host cell comprises a knockout of fabA or a gene listed in Table 1 or Table 2. In other embodiments, the microbially produced branched fatty alcohol and/or derivative thereof is produced by a host cell, which is genetically engineered to express an attenuated level of an endogenous ketoacyl-ACP synthase, such as an enzyme encoded by fabB or by a gene listed in Table 3 or Table 4. In certain embodiments, the host cell comprises a knockout of fabB or a gene listed in Table 3 or Table 4. In yet other embodiments, the host cell is genetically engineered to express a modified level of a gene encoding a desaturase enzyme, such as desA.

In certain embodiments, the branched-chain alpha-keto acid dehydrogenase complex polypeptides, the beta ketoacyl-ACP synthase polypeptide, the aldehyde biosynthesis polypeptide, the fatty acid synthase, the acyl-ACP reductase, the alcohol biosynthesis polypeptide, and the fatty acid degradation enzyme polypeptide are each independently obtained from a bacterium, a plant, an insect, a yeast, a fungus, or a mammal. For example, each of the above-mentioned polypeptides is from a mammalian cell, plant cell, insect cell, yeast cell, fungus cell, filamentous fungi cell, bacterial cell, or any other organism described herein. In certain embodiments, the branched-chain alpha-keto acid dehydrogenase complex polypeptides can be from a bacterium that uses branched amino acids as carbon source, including, for example, *Pseudomonas putida* or a *Bacillus subtilis*. In certain embodiments, the branched-chain alpha-keto acid dehydrogenase complex polypeptide can be from a bacterium that comprises branched fatty acids in its phospholipids, including, for example, a *Legionella, Stenotrophomonas, Alteromonas, Flavobacterium, Myxococcus, Bacteroides, Micrococcus, Staphylococcus, Bacillus, Clostridium, Listeria, Lactococcus*, or *Streptomyces bacterium*. In some embodiments, the bacterium is a *Leginella pneumophila, Stenotrophomonas maltophilia, Alteromonas macleodii, Flabobacterium phsychrophilum, Myxococcus Xanthus, Bacteroides thetaiotaomicron, Macrococcus luteus, Staphylococcus aureus, Clostridium thermocellum, Listeria monocytogenes, Streptomyces lividans, Streptomyces coelicolor, Streptomyces glaucescens, Streptococcus pneumoniae, Streptomyces peucetius, Streptococcus pyogenes, Escherichia coli, Escherichia coli* K-12, *Lactococcus lactis* ssp. *Lactis, Mycobacterium tuberculosis, Enterococcus tuberculosis, Bacillus subtilis, Lactobacillus plantarum*. In certain embodiments, suitable fatty aldehyde biosynthesis polypeptides, fatty alcohol biosynthesis polypeptides, acyl-ACP reductases, and other polypeptides of the invention can be from a mycobacterium selected from the group consisting of *Mycobacterium smegmatis, Mycobacterium abscessus, Mycobacterium avium, Mycobacterium bovis, Mycobacterium tuberculosis, Mycobacterium leprae, Mycobacterium marinum*, and *Mycobacterium ulcerans*. In other embodiments, the bacterium is *Nocardia* sp. NRRL 5646, *Nocardia farcinica, Streptomyces griseus, Salinispora arenicola*, or *Clavibacter michiganenesis*. In certain further embodiments, the polypeptide of the invention is derived from a cyanobacterium, including, for example, *Synechococcus elongatus* PCC7942, *Synechocystis* sp. PCC6803, *Cyanothece* sp. ATCC51142, *Prochlorococcus marinus* subsp. *pastoris* str. CCMP 1986 PMM0533, *Gloeobacter violaceus* PCC7421, *Nostoc punctiforme* PCC73102, *Anabaena variabilis* ATCC29413, *Synechococcus elongatus* PCC6301, and *Nostoc* sp. PCC 7120, *Microcoleus chthonoplastes* PCC7420, *Arthrospira maxima* CS-328, *Lyngbya* sp. PCC8106, *Nodularia spumigena* CCY9414, *Trichodesmium erythraeum* IMS101, *Microcystis aeruginosa, Nostoc azollae, Anabaena variabilis, Crocophaera watsonii, Thermosynechococcus elongatus, Gloeobacer violaceus, Cyanobium*, or *Prochlorococcus marinus*.

In some embodiments, the microbially produced branched fatty alcohol and/or derivative thereof is produced by a host cell cultured in the presence of at least one biological substrate for the branched-chain alpha-keto acid dehydrogenase polypeptides, the beta ketoacyl-ACP synthase polypeptide, the aldehyde biosynthesis polypeptide, the acyl-ACP reductase, and/or the alcohol biosynthesis polypeptide. Suitable substrate for the branched-chain alpha-keto acid dehydrogenase polypeptides can include, without limitation, 2-oxo-isovalerate, 2-oxo-isobutyrate, or 2-oxo-3-methyl-valerate.

In another aspect, the invention features a surfactant or detergent composition comprising a microbially produced branched fatty alcohol or a derivative thereof. In some embodiments, the microbially produced branched fatty alcohol and/or derivative thereof is produced by a host cell expressing a first polynucleotide that hybridizes to a complement of a nucleotide sequence of any one of SEQ ID NOs:2, 4, 6, 8, 10, 12, 14, and 16, or to a fragment thereof, and a second polynucleotide that hybridizes to a complement of a second polynucleotide sequence of any one of SEQ ID NOs: 25, 27, 29, 31, 33, 35, 37, and 39. In certain embodiments, the microbially produced branched fatty alcohol and/or derivative thereof is produced by a host cell expressing a third polynucleotide that hybridizes to a complement of a third nucleotide sequence of any one of SEQ ID NOs:48, 50, 52, 54, 56, 58, 60, and 62, or to a fragment thereof, wherein the first and second polynucleotides encode the first and second polypeptides having branched-chain alpha-keto acid decarboxylase activity, and wherein the third polynucleotide encodes a polypeptide having lipoamide acyltransferase activity. In some embodiments, the first and the second polypeptides, optionally forming a single subunit, optionally together with the third polypeptide, are capable of catalyzing the conversion of branched-chain alpha-keto acids to branched acyl-CoAs.

The first polynucleotide hybridizes under low stringency, medium stringency, high stringency, or very high stringency conditions, to a complement of the nucleotide sequence of any one of SEQ ID NOs:2, 4, 6, 8, 10, 12, 14, and 16, or to a fragment thereof. The second polynucleotide hybridizes under low stringency, medium stringency, high stringency, or very high stringency conditions, to a complement of the nucleotide sequence of any one of SEQ ID NOs: 25, 27, 29, 31, 33, 35, 37, and 39, or to a fragment thereof. The third polynucleotide hybridizes under low stringency, medium stringency, high stringency, or very high stringency conditions, to a complement of the nucleotide sequence of any one of SEQ ID NOs: 48, 50, 52, 54, 56, 58, 60, and 62.

In some embodiments, the microbially produced branched fatty alcohol and/or derivative thereof is produced by a host cell expressing a fourth polynucleotide that hybridizes to a complement of a nucleotide sequence of any one of SEQ ID NOs:70, 72, 74, 76, 78, 80, 82, and 84, or to a fragment thereof, wherein the fourth polynucleotide encodes a polypeptide having lipoamide dehydrogenase activity. In some embodiments, the first, second, and optionally the third and/or fourth polypeptides are capable of catalyzing the conversion of branched-chain alpha-keto acids into branched acetyl-CoAs.

In some embodiments, the microbially produced branched fatty alcohol and/or derivative thereof is produced by a host cell expressing a polynucleotide that hybridizes to a complement of a nucleotide sequence of any one of SEQ ID NOs:91, 93, 95, 97, 99, 101, 103, 105, 107, 109, 111, 113, 115, 117, 119, and 121, or to a fragment thereof, wherein the polynucleotide encodes a polypeptide having beta ketoacyl-ACP synthase activity. In some embodiments, the polypeptide is capable of catalyzing the condensation of a branched acyl-CoA with malonyl-ACP. In some embodiments, the polypeptide has FabH activity. In some embodiments, the polypeptide has specificity for branched acyl-CoA substrates. The polynucleotide hybridizes under low stringency, medium stringency, high stringency, or very high stringency conditions, to a complement of the nucleotide sequence of any one of SEQ ID NOs:91, 93, 95, 97, 99, 101, 103, 105, 107, 109, 111, 113, 115, 117, 119, and 121, or to a fragment thereof.

In some embodiments, the branched fatty aldehyde, branched fatty alcohol, or derivative thereof is isolated from the host cell, for example, from the extracellular environment. In certain embodiments, the branched fatty aldehyde, branched fatty alcohol, or derivative thereof is spontaneously secreted, partially or completely, from the host cell. In alternative embodiments, the branched fatty aldehyde, branched fatty alcohol, or derivative thereof is transported into the extracellular environment. In other embodiments, the branched fatty aldehyde, branched fatty alcohol, or derivative thereof is passively transported into the extracellular environment.

In certain embodiments, the microbially produced branched fatty alcohol and/or derivative thereof is produced by a host cell expressing a polynucleotide that hybridizes to a complement of the nucleotide sequence encoding a fatty aldehyde biosynthesis polypeptide listed in Table 6, or to a fragment thereof, wherein the polynucleotide encodes a polypeptide having carboxylic acid reductase activity. In some embodiments, the polypeptide has fatty acid reductase activity.

In some embodiments, the microbially produced branched fatty alcohol and/or derivative thereof is produced by a host cell, wherein the gene encoding a fatty acid synthase is modified. In certain embodiments, modifying the expression of a gene encoding a fatty acid synthase includes expressing a gene encoding a fatty acid synthase in the host cell and/or increasing the expression or activity of an endogenous fatty acid synthase in the host cell. In alternate embodiments, modifying the expression of a gene encoding a fatty acid synthase includes attenuating a gene encoding a fatty acid synthase in the host cell and/or decreasing the expression or activity of an endogenous fatty acid synthase in the host cell. In some embodiments, the fatty acid synthase is a thioesterase. In particular embodiments, the thioesterase is encoded by tesA, tesA without leader sequence, tesB, fatB, fatB2, fatB3, fatA, or fatA1.

In some embodiments, the microbially produced branched fatty alcohol and/or derivative thereof is produced by a host cell expressing a gene encoding a fatty alcohol biosynthesis polypeptide. For example, the fatty alcohol biosynthesis polypeptide is an alcohol dehydrogenase. In particular embodiments, the fatty alcohol biosynthesis polypeptide is one selected from those listed in Table 8, or a variant thereof.

In any of the above-described embodiments, the microbially produced branched fatty alcohol and/or derivative thereof is produced by a host cell, which is genetically engineered to express an attenuated level of a fatty acid degradation enzyme relative to a wild type host cell. In some embodiments, the host cell is genetically engineered to express an attenuated level of an acyl-CoA synthase relative to a wild type host cell. In particular embodiments, the host cell expresses an attenuated level of an acyl-CoA synthase encoded by fadD, fadK, BH3103, yhfL, Pfl-4354, EAV15023, fadD1, fadD2, RPC_4074, fadDD35, fadDD22, faa3p or the gene encoding the protein ZP_01644857. In certain embodiments, the genetically engineered host cell comprises a knockout of one or more genes encoding a fatty acid degradation enzyme, such as the aforementioned acyl-CoA synthase genes. In certain embodiments, the host cell is genetically engineered to express, relative to a wild type host cell, a decreased level of at least one of a gene encoding an acyl-CoA dehydrogenase, a gene encoding an outer membrane protein receptor, and a gene encoding a transcriptional regulator of fatty acid biosynthesis. In some embodiments, the gene encoding an acyl-CoA dehydrogenase is fadE. In some embodiments, the gene encoding an outer membrane protein receptor is tonA (also known as fhuA). Yet in other embodiments, the gene encoding a transcriptional regulator of fatty acid biosynthesis is fabR.

In yet other embodiments, the microbially produced branched fatty alcohol and/or derivative thereof is produced by a host cell, which is genetically engineered to express an attenuated level of a dehydratase/isomerase enzyme, such as an enzyme encoded by fabA or by a gene listed in Table 1 or Table 2. In some embodiments, the host cell comprises a knockout of fabA or a gene listed in Table 1 or Table 2. In other embodiments, the host cell is genetically engineered to express an attenuated level of a ketoacyl-ACP synthase, such as an enzyme encoded by fabB or by a gene listed in Table 3 or Table 4. In certain embodiments, the host cell comprises a knockout of fabB or a gene listed in Table 3 or Table 4. In yet other embodiments, the host cell is genetically engineered to express a modified level of a gene encoding a desaturase enzyme, such as desA.

In some embodiments, the branched fatty alcohol or a derivative thereof is isolated from the host cell, for example, from the extracellular environment. In certain embodiments, the branched fatty alcohol or the derivative thereof is spontaneously secreted, partially or completely, from the host cell. In alternative embodiments, the branched fatty alcohol or the derivative thereof is transported into the extracellular environment. In other embodiments, the branched fatty alcohol or the derivative thereof is passively transported into the extracellular environment.

In some embodiments, the microbially produced branched fatty alcohol and/or derivative thereof is produced by a host cell expressing a polynucleotide that hybridizes to a complement of a nucleotide sequence encoding an acyl-ACP reductases selected from those listed in Table 7, or to a fragment thereof, wherein the polynucleotide encodes a polypeptide having reductase activity. The polynucleotide hybridizes under low stringency, medium stringency, high stringency, or very high stringency conditions, to a complement of the nucleotide sequence encoding an acyl-ACP reductases selected from those listed in Table 7, or to a fragment thereof.

In some embodiments, the microbially produced branched fatty alcohol and/or derivative thereof is produced by a host cell expressing a gene encoding a fatty alcohol biosynthesis polypeptide in the host cell. For example, the fatty alcohol biosynthesis polypeptide is an alcohol dehydrogenase. In particular embodiments, the fatty alcohol biosynthesis polypeptide is one selected from those listed in Table 8, or a variant thereof.

In any of the above-described embodiments, the microbially produced branched fatty alcohol and/or derivative thereof is produced by a host cell, which is genetically engineered to express an attenuated level of a fatty acid degradation enzyme relative to a wild type host cell. In some embodiments, the host cell is genetically engineered to express an attenuated level of an acyl-CoA synthase relative to a wild type host cell. In particular embodiments, the host cell expresses an attenuated level of an acyl-CoA synthase encoded by fadD, fadK, BH3103, yhfL, Pfl-4354, EAV15023, fadD1, fadD2, RPC__4074, fadDD35, fadDD22, faa3p or the gene encoding the protein ZP__01644857. In certain embodiments, the genetically engineered host cell comprises a knockout of one or more genes encoding a fatty acid degradation enzyme, such as the aforementioned acyl-CoA synthase genes. In certain embodiments, the host cell is genetically engineered to express, relative to a wild type host cell, a decreased level of at least one of a gene encoding an acyl-CoA dehydrogenase, a gene encoding an outer membrane protein receptor, and a gene encoding a transcriptional regulator of fatty acid biosynthesis. In some embodiments, the gene encoding an acyl-CoA dehydrogenase is fadE. In some embodiments, the gene encoding an outer membrane protein receptor is tonA (also known as fhuA). Yet in other embodiments, the gene encoding a transcriptional regulator of fatty acid biosynthesis is fabR.

In yet other embodiments, the microbially produced branched fatty alcohol and/or derivative thereof is produced by a host cell, which is genetically engineered to express an attenuated level of a dehydratase/isomerase enzyme, such as an enzyme encoded by fabA or by a gene listed in Table 1 or Table 2. In some embodiments, the host cell comprises a knockout of fabA or a gene listed in Table 1 or Table 2. In other embodiments, the host cell is genetically engineered to express an attenuated level of a ketoacyl-ACP synthase, such as an enzyme encoded by fabB or by a gene listed in Table 3 or Table 4. In certain embodiments, the host cell comprises a knockout of fabB or a gene listed in Table 3 or Table 4. In yet other embodiments, the host cell is genetically engineered to express a modified level of a gene encoding a desaturase enzyme, such as desA.

In some embodiments, the branched fatty alcohol or derivative thereof is isolated from the host cell, e.g., from the extracellular environment. In certain embodiments, the branched fatty alcohol or derivative thereof is spontaneously secreted, partially or completely, from the host cell. In alternative embodiments, the branched fatty alcohol or derivative thereof is transported into the extracellular environment. In other embodiments, the branched fatty alcohol or derivative thereof is passively transported into the extracellular environment.

In some embodiments, the branched-chain alpha-keto acid dehydrogenase complex, the beta ketoacyl-ACP synthase polypeptide, the aldehyde biosynthesis polypeptide, the fatty acid synthase, the acyl-ACP reductase, the alcohol biosynthesis polypeptide, and the fatty acid degradation enzyme polypeptide are each independently from a bacterium, a plant, an insect, a yeast, a fungus, or a mammal. For example, the branched-chain alpha-keto acid dehydrogenase complex polypeptides can be from a bacterium that uses branched amino acids as carbon source, including, for example, *Pseudomonas putida*, or *Bacillus subtilis*. In another example, the branched-chain alpha-keto acid dehydrogenase complex polypeptide can be from a bacterium that comprises branched fatty acids in its phospholipids, including, for example, a *Legionella, Stenotrophomonas, Alteromonas, Flavobacterium, Myxococcus, Bccteroides, Micrococcus, Staphylococcus, Bacillus, Clostridium, Listeria, Lactococcus*, or *Streptomyces bacterium*. In some embodiments, the bacterium is a *Leginella pneumophila, Stenotrophomonas maltophilia, Alteromonas macleodii, Flabobacterium phsychrophilum, Myxococcus Xanthus, Bacteroides thetaiotaomicron, Macrococcus luteus, Staphylococcus aureus, Clostridium thermocellum, Listeria monocytogenes, Streptomyces lividans, Streptomyces coelicolor, Streptomyces glaucescens, Streptococcus pneumoniae, Streptomyces peucetius, Streptococcus pyogenes, Escherichia coli, Escherichia coli* K-12, *Lactococcus lactis* ssp. *Lactis, Mycobacterium tuberculosis, Enterococcus tuberculosis, Bacillus subtilis, Lactobacillus plantarum*. In some embodiments, suitable fatty aldehyde biosynthesis polypeptides, fatty alcohol biosynthesis polypeptides, acyl-ACP reductases, and other polypeptides of the invention can be from a mycobacterium selected from the group consisting of *Mycobacterium smegmatis, Mycobacterium abscessus, Mycobacterium avium, Mycobacterium bovis, Mycobacterium tuberculosis, Mycobacterium leprae, Mycobacterium marinum*, and *Mycobacterium ulcerans*. In other embodiments, the bacterium is *Nocardia* sp. NRRL 5646, *Nocardia farcinica, Streptomyces griseus, Salinispora arenicola*, or *Clavibacter michiganenesis*. In yet further embodiments, the polypeptide of the invention is derived from a cyanobacterium, including, for example, *Synechococcus elongatus* PCC7942, *Synechocystis* sp. PCC6803, *Cyanothece* sp. ATCC51142, *Prochlorococcus marinus* subsp. *pastoris* str. CCMP1986 PMM0533, *Gloeobacter violaceus* PCC7421, *Nostoc punctiforme* PCC73102, *Anabaena variabilis* ATCC29413, *Synechococcus elongatus* PCC6301, and *Nostoc* sp. PCC 7120, *Microcoleus chthonoplastes* PCC7420, *Arthrospira maxima* CS-328, *Lyngbya* sp. PCC8106, *Nodularia spumigena* CCY9414, *Trichodesmium erythraeum* IMS101, *Microcystis aeruginosa, Nostoc azollae, Anabaena variabilis, Crocophaera watsonii, Thermosynechococcus elongatus, Gloeobacer violaceus, Cyanobium*, or *Prochlorococcus marinus*.

In some embodiments, the microbially produced branched fatty alcohol and/or derivative thereof is produced by a host cell cultured in the presence of at least one biological substrate for the branched-chain alpha-keto acid dehydrogenase polypeptides, the beta ketoacyl-ACP synthase polypeptide, the aldehyde biosynthesis polypeptide, the acyl-ACP reductase, or the alcohol biosynthesis polypeptide. In some embodiments, the host cell is cultured under conditions that allow the expression of the branched-chain alpha-keto acid dehydrogenase polypeptides, the beta ketoacyl-ACP synthase, the aldehyde biosynthesis polypeptide, the acyl-ACP reductase, and/or the alcohol biosynthesis polypeptide. In particular embodiments, the host cell is cultured under conditions that allow the production of branched fatty alcohols or derivatives thereof.

In some embodiments, the microbially produced branched fatty alcohol and/or derivative thereof is produced by a host cell cultured in the presence of at least one biological substrate for the branched-chain alpha-keto acid dehydrogenase complex, the aldehyde biosynthesis polypeptide, the alcohol biosynthesis polypeptide, and/or the acyl-ACP reductase polypeptide. Accordingly, the host cell is cultured under conditions that allow expression of branched-chain alpha-keto acid dehydrogenase complex, the aldehyde biosynthesis polypeptide, the alcohol biosynthesis polypeptide, and/or the acyl-ACP reductase polypeptide.

In some embodiments, the branched fatty alcohol or derivative thereof is isolated from the host cell, e.g., from the extracellular environment. In some embodiments, the branched fatty alcohol or derivative thereof is spontaneously secreted, partially or completely, from the host cell. In alternative embodiments, the branched fatty alcohol or derivative thereof is transported into the extracellular environment. In other embodiments, the branched fatty alcohol or derivative thereof is passively transported into the extracellular environment.

In another aspect, the invention features a surfactant or detergent composition comprising a microbially produced branched fatty alcohol or a derivative thereof. In certain embodiments, the microbially produced branched fatty alcohol and/or derivative thereof is produced by a host cell expressing one or more recombinant vectors comprising at least the E1 alpha and beta subunits of a branched-chain alpha-keto acid dehydrogenase. In certain embodiments, the recombinant vector further comprises an E2 subunit of a branched-chain alpha-keto acid dehydrogenase. The subunits can be introduced into the host cell in separate vectors or together in a single vector. For example, the vector can comprise a first polynucleotide sequence having at least about 30%, e.g., at least about 35%, at least about 40%, at least about 45%, at least about 50%, at least about 55%, at least about 60%, at least about 65%, at least about 70%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity sequence identity to a polynucleotide sequence listed in FIG. 2A, and a second polynucleotide sequence having at least about 30%, e.g., at least about 35%, at least about 40%, at least about 45%, at least about 50%, at least about 55%, at least about 60%, at least about 65%, at least about 70%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity sequence identity to a polynucleotide sequence listed in FIG. 2B. In another example, the vector can further comprise a third polynucleotide having at least about 30%, e.g., at least about 35%, at least about 40%, at least about 45%, at least about 50%, at least about 55%, at least about 60%, at least about 65%, at least about 70%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity sequence identity to a polynucleotide sequence listed in FIG. 2C. The polynucleotides encoding the alpha and beta subunits of the E1 subunit can be linked and constitute a single operon, or they may be separately introduced into a vector and/or into a host cell. Likewise, the polynucleotides encoding the E1 subunit and the polynucleotide encoding the E2 subunit can be linked and constitute a single operon, or they may be separately introduced into a vector and/or into a host cell. For example, a first vector can comprise a first polynucleotide sequence having at least about 30%, e.g., at least about 35%, at least about 40%, at least about 45%, at least about 50%, at least about 55%, at least about 60%, at least about 65%, at least about 70%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity sequence identity to a polynucleotide sequence listed in FIG. 2A, and a second vector can comprise a second polynucleotide having at least about 30%, e.g., at least about 35%, at least about 40%, at least about 45%, at least about 50%, at least about 55%, at least about 60%, at least about 65%, at least about 70%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity sequence identity to a polynucleotide sequence listed in FIG. 2B.

In some embodiment, the nucleotide sequence of the first polynucleotide has at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% sequence identity to the nucleotide sequence of any one of SEQ ID NOs: 2, 4, 6, 8, 10, 12, 14 and 16; the second polynucleotide has at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% sequence identity to the nucleotide sequence of any one of SEQ ID NOs: 25, 27, 29, 31, 33, 35, 37, and 39; and the nucleotide sequence of the third polynucleotide has at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% sequence identity to the nucleotide sequence of any one of SEQ ID NOs: 48, 50, 52, 54, 56, 58, 60, and 62. In some embodiment, the nucleotide sequence of the first polynucleotide is any one of SEQ ID NOs: 2, 4, 6, 8, 10, 12, 14 and 16, the nucleotide sequence of the second polynucleotide is any one of SEQ ID NOs: 25, 27, 29, 31, 33, 35, 37, and 39, and the nucleotide sequence of the third polynucleotide, when present, is any one of SEQ ID NOs: 48, 50, 52, 54, 56, 58, 60, and 62.

In some embodiment, each of the vectors above, or another vector can comprise a fourth polynucleotide sequence having at least about 30%, e.g., at least about 35%, at least about 40%, at least about 45%, at least about 50%, at least about 55%, at least about 60%, at least about 65%, at least about 70%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to a polynucleotide sequence listed in FIG. 2D. In certain embodiments, the nucleotide sequence of the fourth polynucleotide has at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% sequence identity to the nucleotide sequence of any one of SEQ ID NOs:70, 72, 74, 76, 78, 80, 82, and 84. In some embodiments, the nucleotide sequence of the fourth polynucleotide is any one of SEQ ID NOs:70, 72, 74, 76, 78, 80, 82, and 84.

In some embodiments, each of the vectors above, or another vector can be introduced into the host cell wherein the vector comprises a beta-ketoacyl ACP synthase nucleotide that has at least about 30%, e.g., at least about 35%, at least about 40%, at least about 45%, at least about 50%, at least about 55%, at least about 60%, at least about 65%, at least about 70%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to a polynucleotide sequence listed in FIG. 2E. In certain embodiments, the nucleotide sequence of the beta-ketoacyl ACP synthase nucleotide has at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% sequence identity to the nucleotide sequence of any one of SEQ ID NOs:91, 93, 95, 97, 99, 101, 103, 105, 107, 109, 111, 113, 115, 117, 119, and 121. In some embodiments, the nucleotide sequence of beta-ketoacyl ACP synthase nucleotide is SEQ ID NOs: 91, 93, 95, 97, 99, 101, 103, 105, 107, 109, 111, 113, 115, 117, 119, and 121.

In yet another embodiment, an individual vector comprising a beta-ketoacyl-ACP synthase nucleotide that has at least about 30%, e.g., at least about 35%, at least about 40%, at least about 45%, at least about 50%, at least about 55%, at least about 60%, at least about 65%, at least about 70%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to a polynucleotide sequence listed in FIG. 2E can be introduced into a suitable host cell, independent of whether one or more other vectors comprising one or more subunits of a branched-chain alpha-keto acid dehydrogenase is introduced into the same cell. For example, the host cell can suitably be one that expresses an endogenous branched-chain alpha-keto acid dehydrogenase, or one or more subunits thereof.

In some embodiments, the branched fatty aldehyde, branched fatty alcohol, or derivative thereof is isolated from the host cell, for example, from the extracellular environment. In some embodiments, the branched fatty aldehyde, branched fatty alcohol or derivative thereof is spontaneously secreted, partially or completely, from the host cell. In alternative embodiments, the branched fatty aldehyde, branched fatty alcohol or derivative thereof is transported into the extracellular environment. In other embodiments, the branched fatty aldehyde, branched fatty alcohol, or derivative thereof is passively transported into the extracellular environment.

The recombinant vector can further comprises a promoter operably linked to the nucleotide sequence. In certain embodiments, the promoter is a developmentally-regulated, an organelle-specific, a tissue-specific, an inducible, a constitutive, or a cell-specific promoter.

In other embodiments, the recombinant vector comprises at least one sequence selected from the group consisting of (a) a regulatory sequence operatively coupled to the nucleotide sequence; (b) a selection marker operatively coupled to the nucleotide sequence; (c) a marker sequence operatively coupled to the nucleotide sequence; (d) a purification moiety operatively coupled to the nucleotide sequence; (e) a secretion sequence operatively coupled to the nucleotide sequence; and (f) a targeting sequence operatively coupled to the nucleotide sequence.

In some embodiments, the recombinant vector is a plasmid.

In some embodiments, the host cell expresses a polypeptide encoded by the recombinant vector. In some embodiments, the nucleotide sequence is stably incorporated into the genomic DNA of the host cell, and the expression of the nucleotide sequence is under the control of a regulated promoter region. In an exemplary embodiment, one or more of the polynucleotides encoding a branched-chain alpha-keto acid dehydrogenase polypeptide, a beta ketoacyl-ACP synthase polypeptide, a fatty aldehyde biosynthesis polypeptide, a fatty alcohol biosynthesis polypeptide, and/or an acyl-ACP reductase of the invention can be stably incorporated into the genomic DNA of the host cell, and the expression of the polynucleotide sequence is under the control of a regulated promoter region.

In some embodiment, an above-described vector or another vector can be introduced into the host cell wherein the vector comprises a fatty aldehyde biosynthesis polynucleotide having at least about 70% sequence identity to a nucleotide sequence encoding an enzyme listed in Table 6.

In some embodiments, the microbially produced branched fatty alcohol and/or derivative thereof is produced by a host cell wherein the expression of a gene encoding a fatty acid synthase is modified. In certain embodiments, modifying the expression of a gene encoding a fatty acid synthase includes expressing a gene encoding a fatty acid synthase in the host cell and/or increasing the expression or activity of an endogenous fatty acid synthase in the host cell. In alternate embodiments, modifying the expression of a gene encoding a fatty acid synthase includes attenuating a gene encoding a fatty acid synthase in the host cell and/or decreasing the expression or activity of an endogenous fatty acid synthase in the host cell. In some embodiments, the fatty acid synthase is a thioesterase. In particular embodiments, the thioesterase is encoded by tesA, tesA without leader sequence, tesB, fatB, fatB2, fatB3, fatA, or fatA1.

In some embodiments, the microbially produced branched fatty alcohol and/or derivative thereof is produced by a host cell expressing a gene encoding a fatty alcohol biosynthesis polypeptide. For example, the fatty alcohol biosynthesis polypeptide is an alcohol dehydrogenase. In particular embodiments, the fatty alcohol biosynthesis polypeptide comprises the amino acid sequence of an enzyme listed in Table 8, or a variant thereof.

In any of the embodiments described above, the microbially produced branched fatty alcohol and/or derivative thereof is produced by a host cell, which is genetically engineered to express an attenuated level of a fatty acid degradation enzyme relative to a wild type host cell. In some embodiments, the host cell is genetically engineered to express an attenuated level of an acyl-CoA synthase relative to a wild type host cell. In particular embodiments, the host cell expresses an attenuated level of an acyl-CoA synthase encoded by fadD, fadK, BH3103, yhfL, Pfl-4354, EAV15023, fadD1, fadD2, RPC_4074, fadDD35, fadDD22, faa3p or the gene encoding the protein ZP_01644857. In certain embodiments, the genetically engineered host cell comprises a knockout of one or more genes encoding a fatty acid degradation enzyme, such as the aforementioned acyl-CoA synthase genes. In certain embodiments, the host cell is genetically engineered to express, relative to a wild type host cell, a decreased level of at least one of a gene encoding an acyl-CoA dehydrogenase, a gene encoding an outer membrane protein receptor, and a gene encoding a transcriptional regulator of fatty acid biosynthesis. In some embodiments, the gene encoding an acyl-CoA dehydrogenase is fadE. In some embodiments, the gene encoding an outer membrane protein receptor is tonA (also known as fhuA). Yet in other embodiments, the gene encoding a transcriptional regulator of fatty acid biosynthesis is fabR.

In yet other embodiments, the microbially produced branched fatty alcohol and/or derivative thereof is produced by a host cell, which is genetically engineered to express an attenuated level of a dehydratase/isomerase enzyme, such as an enzyme encoded by fabA or by a gene listed in Table 1 or Table 2. In some embodiments, the host cell comprises a knockout of fabA or a gene listed in Table 1 or Table 2. In other embodiments, the host cell is genetically engineered to express an attenuated level of a ketoacyl-ACP synthase, such as an enzyme encoded by fabB or by a gene listed in Table 3 or Table 4. In certain embodiments, the host cell comprises a knockout of fabB or a gene listed in Table 3 or Table 4. In yet other embodiments, the host cell is genetically engineered to express a modified level of a gene encoding a desaturase enzyme, such as desA.

In certain other embodiments, any of the vectors comprising the E1 alpha, E1 beta, and/or optionally E2 and/or optionally E3 subunits of a branched-chain alpha-keto acid dehydrogenase complex or another vector can be introduced into the host cell wherein the vector further comprises an acyl-ACP reductase polynucleotide having at least about 70% sequence identity to a nucleotide sequence encoding an enzyme listed in Table 7.

In some embodiments, the host cell is cultured in the presence of at least one biological substrate for the branched-chain alpha-keto acid dehydrogenase complex, the aldehyde biosynthesis polypeptide, the alcohol biosynthesis polypeptide, and/or the acyl-ACP reductase polypeptide. In certain embodiments, the host cell is cultured under conditions that are sufficient for expressing a branched-chain alpha-keto acid dehydrogenase complex, an aldehyde biosynthesis polypeptide, an alcohol biosynthesis polypeptide, and/or an acyl-ACP reductase polypeptide. In certain other embodiments, the host cell is cultured under conditions that allow the production of branched fatty alcohols or derivatives thereof.

In some embodiments, the microbially produced branched fatty alcohol and/or derivative thereof is produced by a host cell cultured in the presence of at least one biological substrate for the branched-chain alpha-keto acid dehydrogenase complex, the aldehyde biosynthesis polypeptide, the alcohol biosynthesis polypeptide, and/or the acyl-ACP reductase polypeptide. Accordingly, the host cell is cultured under conditions that allow expression of branched-chain alpha-keto acid dehydrogenase complex, the aldehyde biosynthesis polypeptide, the alcohol biosynthesis polypeptide, and/or the acyl-ACP reductase polypeptide.

In some embodiments, the branched fatty alcohol or derivative thereof is isolated from the host cell, for example, from the extracellular environment. In some embodiments, the branched fatty alcohol or derivative thereof is secreted from the host cell. In alternative embodiments, the branched fatty alcohol or derivative thereof is transported into the extracellular environment. In other embodiments, the branched fatty alcohol or derivative thereof is passively transported into the extracellular environment.

In any of the aspects of the invention described herein, the host cell can be selected from the group consisting of a mammalian cell, plant cell, insect cell, yeast cell, fungus cell, filamentous fungi cell, and bacterial cell. In some embodiments, the host cell is a Gram-positive bacterial cell. In other embodiments, the host cell is a Gram-negative bacterial cell. In some embodiments, the host cell is selected from the genus *Escherichia, Bacillus, Lactobacillus, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Stenotrophamonas, Schizosaccharomyces, Yarrowia*, or *Streptomyces.*

In certain embodiments, the host cell is a *Bacillus lentus* cell, a *Bacillus brevis* cell, a *Bacillus stearothermophilus* cell, a *Bacillus licheniformis* cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, a *Bacillus subtilis* cell, or a *Bacillus amyloliquefaciens* cell.

In other embodiments, the host cell is a *Trichoderma koningii* cell, a *Trichoderma viride* cell, a *Trichoderma reesei* cell, a *Trichoderma longibrachiatum* cell, an *Aspergillus awamori* cell, an *Aspergillus fumigates* cell, an *Aspergillus foetidus* cell, an *Aspergillus nidulans* cell, an *Aspergillus niger* cell, an *Aspergillus oryzae* cell, a *Humicola insolens* cell, a *Humicola lanuginose* cell, a *Rhodococcus opacus* cell, a *Rhizomucor miehei* cell, or a *Mucor michei* cell.

In yet other embodiments, the host cell is a *Streptomyces lividans* cell or a *Streptomyces murinus* cell.

In yet other embodiments, the host cell is an *Actinomycetes* cell.

In some embodiments, the host cell is a *Saccharomyces cerevisiae* cell.

In particular embodiments, the host cell is a cell from an eukaryotic plant, algae, cyanolacterium, green-sulfur bacterium, green non-sulfur bacterium, purple sulfur bacterium, purple non-sulfur bacterium, extremophile, yeast, fungus, engineered organisms thereof, or a synthetic organism. In some embodiments, the host cell is light dependent or fixes carbon. In some embodiments, the host cell is light dependent or fixes carbon. In some embodiments, the host cell has autotrophic activity. In some embodiments, the host cell has photoautotrophic activity, such as in the presence of light. In some embodiments, the host cell is heterotrophic or mixotrophic in the absence of light. In certain embodiments, the host cell is a cell from *Avabidopsis thaliana, Panicum virgatum, Miscanthus giganteus, Zea mays, Botryococcuse braunii, Chlamydomonas reinhardtii, Dunaliela salina, Synechococcus* Sp. PCC 7002, *Synechococcus* Sp. PCC 7942, *Synechocystis* Sp. PCC 6803, *Thermosynechococcus elongates* BP-1, *Chlorobium tepidum, Chloroflexus auranticus, Chromatiumm vinosum, Rhodospirillum rubrum, Rhodobacter capsulatus, Rhodopseudomonas palusris, Clostridium ljungdahlii, Clostridiuthermocellum, Penicillium chrysogenum, Pichia pastoris, Saccharomyces cerevisiae, Schizosaccharomyces pombe, Pseudomonas fluorescens*, or *Zymomonas mobilis.*

In other embodiments, the host cell is a CHO cell, a COS cell, a VERO cell, a BHK cell, a HeLa cell, a Cv1 cell, an MDCK cell, a 293 cell, a 3T3 cell, or a PC12 cell.

In yet other embodiments, the host cell is an *E. coli* cell. In certain embodiments, the *E. coli* cell is a strain B, a strain C, a strain K, or a strain W *E. coli* cell.

In further embodiments, the host cell can be genetically engineered to express an attenuated level of a dehydratase/isomerase enzyme. For example, an *E. coli* cell is chosen as a suitable host cell, wherein one or more of the endogenous dehydratase/isomerase enzymes such as those listed in Table 1 below can be attenuated or knocked out.

TABLE 1

*E. coli* dehydratase/isomerase enzymes

| Gene | Name | Polynucleotide Acc. No. | Polypeptide Acc. No. |
|---|---|---|---|
| fabA | beta-hydroxydecanoyl thioester dehydrase | GU072596.1 | ACY27485.1 |
| fabZ | (3R)-hydroxymyristol acyl carrier protein dehydratase | GU072604 | ACY27493.1 |
| cysM | cysteine synthase B | CP001637.1 | ACX38914 |
| maoC | fused aldehyde dehydrogenase/ enoyl-CoA hydratase | CP001637 | ACX39905.1 |

Other dehydratase/isomerase enzymes encoded by a gene listed below in Table 2 can also be attenuated or knocked from an organism comprising such a gene.

TABLE 2

Other dehydatase/isomerase enzymes

| Organism | Accession No. |
|---|---|
| *Shigella* sp. D9 | ZP_05432652 |
| *Citrobacter youngae* ATCC 29220 | ZP_04561391.1 |
| *Salmonella enterica* | YP_001570967.1 |
| *Escherichia fergusonii* ATCC 35469 | YP_002382254.1 |
| *Klebsiella pneumoniae* NTUH-K2044 | YP_002918743.1 |
| *Enterobacter cancerogenus* ATCC 35316 | ZP_03281954.1 |
| *Cronobacter turicensis* | CBA29728.1 |
| *Erwinia pyrifoliae* Ep1/96 | YP_002649242.1 |
| *Pectobacterium carotovorum* subsp. *carotovorum* PC1 | YP_003018119.1 |
| *Dickeya dadantii* Ech703 | YP_002987184.1 |
| *Edwardsiella ictaluri* 93-146 | YP_002932813.1 |
| *Providencia alcalifaciens* DSM 30120 | ZP_03317956.1 |
| *Yersinia kristensenii* ATCC 33638 | ZP_04624337.1 |
| *Photorhabdus asymbiotica* | YP_003041580.1 |
| *Pantoea* sp. At-9b | ZP_05728924.1 |
| *Actinobacillus succinogenes* 130Z | YP_001344737.1 |
| *Mannheimia succiniciproducens* MBEL55E | YP_088386.1 |
| *Pasteurella multocida* subsp. *multocida* str. Pm70 | NP_245421.1 |
| *Haemophilus somnus* 129PT | YP_719117.1 |
| *Proteus mirabilis* HI4320 | YP_002150544.1 |
| *Sodalis glossinidius* str. 'morsitans' | YP_454706.1 |
| *Candidatus Blochmannia pennsylvanicus* str. BPEN | YP_277927.1 |
| *Aggregatibacter aphrophilus* NJ8700 | YP_003007342.1 |
| *Vibrio cholerae* MZO-3 | ZP_01958381.1 |
| *Baumannia cicadellinicola* str. Hc (*Homalodisca coagulata*) | YP_588853.1 |
| *Vibrionales* bacterium SWAT-3 | ZP_01815187.1 |
| *Aliivibrio salmonicida* LFI1238 | YP_002262988.1 |
| *Aeromonas salmonicida* subsp. *salmonicida* A449 | YP_001141819.1 |
| *Wigglesworthia glossinidia* endosymbiont of *Glossina brevipalpis* | NP_871303.1 |
| *Glaciecola* sp. HTCC2999 | ZP_03560821.1 |
| *Alteromonas macleodii* ATCC 27126 | ZP_04714556.1 |

In other embodiments, the host cell is genetically engineered to express an attenuated level of an endogenous ketoacyl-ACP synthase. For example, an *E. coli* cell is used as a suitable host cell, wherein one or more of the ketoacyl-ACP genes listed in Table 3 below can be attenuated or knocked out.

TABLE 3

*E. coli* ketoacyl-ACP synthase enzymes

| Gene | Name | Polynucleotide Acc. No. | Polypeptide Acc. No. |
|---|---|---|---|
| fabB | B-ketoacyl synthase/ 3-oxoacyl-[acyl-carrier-protein] synthase I | GU072597.1 | ACY27486.1 |
| fabF | 3-oxoacyl-[acyl-carrier-protein] synthase II | GU072598.1 | ACY27487 |
| fadJ | fused enoyl-CoA hydratase and epimerase/isomerase/ 3-hydroxyacyl-CoA dehydrogenase | CP001637.1 | ACX38989.1 |
| xerC | site-specific tyrosine recombinase | CP001637.1 | ACX41768.1 |
| yqeF | predicted acyltransferase | CP001637.1 | ACX38529.1 |
| murQ | predicted PTS component | CP001637.1 | ACX38907.1 |

Other endogenous ketoacyl-ACP synthases, such as the ones listed in Table 4, can be attenuated or knocked out from an organism comprising such an enzyme.

TABLE 4

Other ketoacyl-ACP synthases

| Organism | Accession No. |
|---|---|
| *Shigella boydii* CDC 3083-94 | YP_001881145.1 |
| *Escherichia fergusonii* ATCC 35469 | YP_002382013.1 |
| *Salmonella enterica* subsp. *arizonae* | YP_001569590.1 |
| *Citrobacter* sp. 30_2 | ZP_04562837.1 |
| *Klebsiella pneumoniae* subsp. *pneumoniae* MGH 78578 | YP_001336360.1 |
| *Pectobacterium carotovorum* subsp. *carotovorum* WPP14 | ZP_03831287.1 |
| *Enterobacter cancerogenus* ATCC 35316 | ZP_03283474.1 |
| *Pantoea* sp. At-9b | ZP_05730617.1 |
| *Cronobacter turicensis* | CBA32510.1 |
| *Dickeya dadantii* Ech586 | ZP_05723897.1 |
| *Erwinia tasmaniensis* Et1/99 | YP_001907100.1 |
| *Serratia proteamaculans* 568 | YP_001479594.1 |
| *Edwardsiella ictaluri* 93-146 | YP_002934130.1 |
| *Sodalis glossinidius* str. 'morsitans' | YP_455303.1 |
| *Yersinia aldovae* ATCC 35236 | ZP_04620215.1 |
| *Providencia stuartii* ATCC 25827 | ZP_02961167.1 |
| *Photorhabdus asymbiotica* | YP_003040275.1 |
| *Proteus mirabilis* HI4320 | YP_002151524.1 |
| *Candidatus Blochmannia pennsylvanicus* str. BPEN | YP_278005.1 |
| *Glaciecola* sp. HTCC2999 | ZP_03561088.1 |
| *Vibrio cholerae* V51 | ZP_04919940.1 |
| *Wigglesworthia glossinidia* endosymbiont of *Glossina brevipalpis* | NP_871411.1 |
| *Tolumonas auensis* DSM 9187 | YP_002892770.1 |
| *Actinobacillus pleuropneumoniae* serovar 1 str. 4074 | ZP_00134992.2 |
| *Aggregatibacter aphrophilus* NJ8700 | YP_003007711.1 |
| *Pseudoalteromonas tunicata* D2 | ZP_01135065.1 |
| *Vibrionales* bacterium SWAT-3 | ZP_01816638.1 |
| *Pasteurella multocida* subsp. *multocida* str. Pm70 | NP_245276.1 |
| *Mannheimia succiniciproducens* MBEL55E | YP_088783.1 |
| *Haemophilus somnus* 129PT | YP_718877.1 |
| *Shewanella loihica* PV-4 | YP_001094535.1 |
| *Aliivibrio salmonicida* LFI1238 | YP_002262558.1 |

In yet other embodiments, the host cell is genetically engineered to express a modified level of a gene encoding a desaturase enzyme, such as desA.

In certain embodiments, the microorganism is genetically engineered to express a modified level (including, e.g., to attenuate or knock out or to express or overexpress) of a gene encoding a fatty aldehyde biosynthesis polypeptide. In some embodiments, the fatty aldehyde biosynthesis polypeptide comprises an amino acid sequence that has at least 70% sequence identity to an enzyme listed in Table 6.

In certain embodiments, the microorganism is genetically engineered to express a modified level of a fatty acid synthase in the host cell. An exemplary fatty acid synthase is a thioesterase encoded by, for example, tesA, tesA without leader sequence, tesB, fatB, fatB2, fatB3, fatA, or fatA1.

In certain embodiments, the microorganism is genetically engineered to express a modified level of gene encoding a fatty alcohol biosynthesis polypeptide. For example, the fatty alcohol biosynthesis polypeptide is an alcohol dehydrogenase. In particular embodiments, the fatty alcohol biosynthesis polypeptide comprises an amino acid sequence that has at least 70% sequence identity to an enzyme listed in Table 8.

Branched-Chain Alpha-Keto Acid Dehydrogenase Complex (BKD Complex) and Beta Ketoacyl-ACP Synthase The methods described herein can be used to produce branched fatty alcohols and/or derivatives, for example, from alpha keto acids. The oxidative decarboxylation step, which converts the alpha keto acids to the corresponding branched-chain acyl-CoA involves a branched-chain α-keto acid dehydrogenase complex (bkd; EC 1.2.4.4.) (Denoya et al., *J. Bacteria* 177:3504 (1995)), which consists of E1 alpha/beta (decarboxylase), E2 (dihydrolipoyl transacylase), and E3 (dihydrolipoyl dehydrogenase) subunits. Any microorganism that possesses branched-chain fatty acids, and/or grows on branched-chain amino acids can be used as a source to isolate bkd genes for expression in host cells, for example, *E. coli*. Furthermore, *E. coli* has the E3 component as part of its pyruvate dehydrogenase complex (lpd, EC 1.8.1.4, GenBank accession NP_414658). Thus, branched fatty alcohols and/or derivatives can be made by heterologously expressing only the E1 alpha/beta and E2 bkd genes. Furthermore, certain of the host cells, including *E. coli*, can produce branched products when only the E1 alpha/beta is expressed without co-expression of the E2 bkd gene.

On the other hand, microorganisms that endogenously express a suitable beta-ketoacyl ACP synthase can be engineered to express or overexpress at least the first (E1) subunit of a branched-chain alpha keto acid dehydrogenase complex, optionally also the second (E2) and/or the third (E3) subunits of that complex to produce the desirable branched fatty alcohols and/or derivatives thereof. The endogenous beta-ketoacyl ACP synthase can be overexpressed, or can be modified such that it is attenuated or deleted, and a heterologous beta-ketoacyl ACP synthase gene can be expressed in its place.

In a further embodiment, microorganisms that endogenously express at least the first (E1) subunit of a branched-chain alpha keto acid dehydrogenase complex, and optionally also the second (E2) and/or the third (E3) subunits of that complex, can be engineered to express or overexpress a beta-ketoacyl ACP synthase. For example, the endogenous genes encoding the subunits of the branched-chain alpha keto acid dehydrogenase complex can be overexpressed, or can be modified such that they are attenuated or deleted and a gene encoding one or more subunits of a heterologous branched-chain alpha keto acid dehydrogenase complex can be expressed in the host cell.

Substrates for Branched Fatty Alcohol Production

The branched fatty alcohols and/or derivatives, as well as the surfactant compositions comprising them, can be produced from, for example, branched fatty aldehydes, which themselves can be produced from an appropriate substrate. While not wishing to be bound by theory, it is believed that the branched fatty aldehyde biosynthetic polypeptides described herein produce branched fatty aldehydes from substrates via a reduction mechanism. In some instances, the substrate is a branched fatty acid derivative, and a fatty aldehyde having particular branching patterns and carbon chain length can be produced from a branched fatty acid derivative having those characteristics. The branched fatty aldehyde can then be converted into the desired branched fatty alcohol in a reaction catalyzed by a fatty alcohol biosynthesis polypeptide.

Alternatively, a suitable acyl-ACP reductases can be employed to convert a branched acyl-ACP into a fatty aldehyde, which can in turn be converted into a branched fatty alcohol in a reaction catalyzed by a fatty alcohol biosynthesis polypeptide.

Accordingly, each step within a biosynthetic pathway that leads to the production of a branched fatty acid derivative substrate can be modified to produce or overproduce the branched substrate of interest. For example, known genes involved in the fatty acid biosynthetic pathway or the fatty aldehyde biosynthesis pathway can be expressed, overexpressed, or attenuated in host cells to produce a desired substrate (see, e.g., International Publication WO 2008/119082, the disclosure of which is incorporated by reference).

Synthesis of Branched Fatty Alcohols and Substrates

Fatty acid synthase (FAS) is a group of polypeptides that catalyze the initiation and elongation of acyl chains (Marrakchi et al., *Biochemical Society,* 30: 1050-1055 (2002)). The acyl carrier protein (ACP) along with the enzymes in the FAS pathway control the length, degree of saturation, and branching of the fatty acid derivatives produced. The fatty acid biosynthetic pathway involves the precursors acetyl-CoA and malonyl-CoA. The steps in this pathway are catalyzed by enzymes of the fatty acid biosynthesis (fab) and acetyl-CoA carboxylase (acc) gene families (see, e.g., Heath et al., *Prog. Lipid Res.,* 40(6): 467-97 (2001)).

Host cells can be engineered to express fatty acid derivative substrates by recombinantly expressing or overexpressing one or more fatty acid synthase genes, such as acetyl-CoA and/or malonyl-CoA synthase genes. For example, to increase acetyl-CoA production, one or more of the following genes can be expressed in a host cell: pdh (a multienzyme complex comprising aceEF (which encodes the E1p dehydrogenase component, the E2p dihydrolipoamide acyltransferase component of the pyruvate and 2-oxoglutarate dehydrogenase complexes, and lpd), panK, fabH, fabB, fabD, fabG, acpP, and fabF. Exemplary GenBank accession numbers for these genes are: pdh (BAB34380, AAC73227, AAC73226), panK (also known as CoA, AAC76952), aceEF (AAC73227, AAC73226), fabH (AAC74175), fabB (P0A953), fabD (AAC74176), fabG (AAC74177), acpP (AAC74178), and fabF (AAC74179). Additionally, the expression levels of fadE, gpsA, ldhA, pflb, adhE, pta, poxB, ackA, and/or ackB can be attenuated or knocked-out in an engineered host cell by transformation with conditionally replicative or non-replicative plasmids containing null or deletion mutations of the corresponding genes or by substituting promoter or enhancer sequences. Exemplary GenBank accession numbers for these genes are: fadE (AAC73325), gspA (AAC76632), ldhA (AAC74462), pflb (AAC73989), adhE (AAC74323), pta (AAC75357), poxB (AAC73958), ackA (AAC75356), and ackB (BAB81430). The resulting host cells will have increased acetyl-CoA production levels when grown in an appropriate environment.

Malonyl-CoA overexpression can be affected by introducing accABCD (e.g., accession number AAC73296, EC 6.4.1.2) into a host cell. Fatty acid production can be further increased by introducing into the host cell a DNA sequence encoding a lipase (e.g., accession numbers CAA89087, CAA98876).

In addition, inhibiting PlsB can lead to an increase in the levels of long chain acyl-ACP, which will inhibit early steps in the pathway (e.g., accABCD, fabH, and fabI). The plsB (e.g., accession number AAC77011) D311E mutation can be used to increase the amount of available fatty acids.

In addition, a host cell can be engineered to overexpress a sfa gene (suppressor of fabA, e.g., accession number AAN79592) to increase production of monounsaturated fatty acids (Rock et al., *J. Bacteriology,* 178: 5382-5387 (1996)).

The chain length of a fatty acid derivative substrate can be selected for by modifying the expression of selected thioesterases. Thioesterase influences the chain length of fatty acids produced. Hence, host cells can be engineered to express, overexpress, have attenuated expression, or not to express one or more selected thioesterases to increase the production of a preferred fatty acid derivative substrate. For example, $C_{10}$ fatty acids can be produced by expressing a thioesterase that has a preference for producing $C_{10}$ fatty acids and attenuating thioesterases that have a preference for producing fatty acids other than $C_{10}$ fatty acids (e.g., a thioesterase which prefers to produce $C_{14}$ fatty acids). This would result in a relatively homogeneous population of fatty acids that have a carbon chain length of 10. In other instances, $C_{14}$ fatty acids can be produced by attenuating endogenous thioesterases that produce non-$C_{14}$ fatty acids and expressing the thioesterases that have a preference for $C_{14}$-ACP. In some situations, $C_{12}$ fatty acids can be produced by expressing thioesterases that have a preference for $C_{12}$-ACP and attenuating thioesterases that preferentially produce non-$C_{12}$ fatty acids. Acetyl-CoA, malonyl-CoA, and fatty acid overproduction can be verified using methods known in the art, for example, by using radioactive precursors, HPLC, or GC-MS subsequent to cell lysis. Non-limiting examples of thioesterases that can be used in the methods described herein are listed in Table 5.

TABLE 5

Thioesterases

| Accession Number | Source Organism | Gene |
|---|---|---|
| AAC73596 | *E. coli* | tesA without leader sequence |
| AAC73555 | *E. coli* | tesB |
| Q41635, AAA34215 | *Umbellularia california* | fatB |
| AAC49269 | *Cuphea hookeriana* | fatB2 |
| Q39513; AAC72881 | *Cuphea hookeriana* | fatB3 |
| Q39473, AAC49151 | *Cinnamonum camphorum* | fatB |
| CAA85388 | *Arabidopsis thaliana* | fatB [M141T]* |
| NP 189147; NP 193041 | *Arabidopsis thaliana* | fatA |
| CAC39106 | *Bradyrhiizobium japonicum* | fatA |
| AAC72883 | *Cuphea hookeriana* | fatA |
| AAL79361 | *Helianthus annus* | fatA1 |

*Mayer et al., *BMC Plant Biology*, 7: 1-11 (2007)

In certain embodiments, a host cell, which is used to produce branched fatty alcohols and/or derivatives herein, can be engineered to express or overexpress one of more fatty aldehyde biosynthetic polypeptides. Alternatively, the host cell can be engineered to express an attenuated level of an endogenous fatty aldehyde biosynthetic polypeptide. In other instances, a fatty aldehyde biosynthetic polypeptide, a variant, or a fragment thereof is expressed in a host cell that contains a naturally occurring mutation that results in an increased level of branched fatty aldehyde substrate in the host cell or of branched fatty alcohol produced by the host cell. In some instances, a branched fatty aldehyde is produced by expressing a fatty aldehyde biosynthesis gene, for example, a carboxylic acid reductases gene, encoding a protein listed in Table 6, below, as well as a polynucleotide variant there. In some instances, the fatty aldehyde biosynthesis gene encodes one of the enzymes listed in Table 6 below.

TABLE 6

Fatty Aldehyde Biosynthesis Genes

| Name/Organism | Accession No. |
|---|---|
| *Nocardia* sp. NRRL 5646 | >gi\|40796035\|gb\|AAR91681.1\| |
| *Mycobacterium tuberculosis* H37Rv | >gi\|15609727\|ref\|NP_217106.1 |
| *Mycobacterium smegmatis* str. MC2 155 | >gi\|118174788\|gb\|ABK75684.1\| |
| *Mycobacterium smegmatis* str. MC2 155 | >gi\|118469671\|ref\|YP_889972.1\| |
| FadD9 | uniprot\|A0PPD8\|A0PPD8_MYCUA |
| *Tsukamurella paurometabola* DSM 20162 | >gi\|227980601\|ref\|ZP_04027864.1\| |
| *Cyanobium* sp. PCC 7001 | >gi\|254431429\|ref\|ZP_05045132.1\| |
| Putative acyl-CoA dehydrogenase | >uniprot\|A0QIB5\|A0QIB5_MYCA1 |
| NAD dependent epimerase/ dehydratase | >uniprot\|A0QWI7\|A0QWI7_MYCS2 |
| *Mycobacterium intracellulare* ATCC13950 | >gi\|254819907\|ref\|ZP_05224908.1\| |
| Putative long-chain fattyacid-CoA ligase | >uniprot\|A0R484\|A0R484_MYCS2 |
| *Mycobacterium kansasii* ATCC 12478 | >gi\|240173202\|ref\|ZP_04751860.1\| |
| Probable fatty-acid-CoA ligase fadD9 | >uniprot\|A1KLT8\|A1KLT8_MYCBP |
| *Mycobacterium intracellulare* ATCC13950 | >gi\|254822803\|ref\|ZP_05227804.1\| |
| Fatty-acid-CoA ligase fadD9 | >uniprot\|A1QUM2\|A1QUM2_MYCTF |
| Thioester reductase domain | >uniprot\|A1T887\|A1T887_MYCVP |
| Thioester reductase domain | >uniprot\|A1UFA8\|A1UFA8_MYCSK |
| *Mycobacterium avium* subsp. ATCC 25291 | >gi\|254775919\|ref\|ZP_05217435.1\| |
| Thioester reductase domain | >uniprot\|A3PYW9\|A3PYW9_MYCSJ |
| *Mycobacterium leprae* Br4923 | >gi\|219932734\|emb\|CAR70557.1\| |
| Putative acyl-CoA synthetase | >uniprot\|A5CM59\|A5CM59_CLAM3 |
| Thioester reductase domain | >uniprot\|A8M8D3\|A8M8D3_SALAI |
| Probable fatty-acid-CoA ligase FadD | >uniprot\|B1MCR9\|B1MCR9_MYCAB |
| Probable fatty-acid-CoA ligase FadD | >uniprot\|B1MCS0\|B1MCS0_MYCAB |
| Putative fatty-acid-CoA ligase | >uniprot\|B1MDX4\|B1MDX4_MYCAB |
| Probable fatty-acid-coa ligase FadD | >uniprot\|B1MLD7\|B1MLD7_MYCAB |
| Putative carboxylic acid reductase | >uniprot\|B1VMZ4\|B1VMZ4_STRGG |
| Fatty-acid-CoA ligase FadD9_1 | >uniprot\|B2HE95\|B2HE95_MYCMM |
| Fatty-acid-CoA ligase FadD9 | >uniprot\|B2HN69\|B2HN69_MYCMM |
| Putative Acyl-CoA synthetase | >uniprot\|O69484\|O69484_MYCLE |
| Probable peptide synthetase nrp | >uniprot\|Q10896\|Q10896_MYCTU |
| Putative carboxylic acid reductase | >uniprot\|Q5YY80\|Q5YY80_NOCFA |
| ATP/NADPH-dependent carboxylic acid reductase | >uniprot\|Q6RKB1\|Q6RKB1_9NOCA |
| FadD9 | >uniprot\|Q741P9\|Q741P9_MYCPA |
| Substrate--CoA ligase, putative | >uniprot\|Q7D6X4\|Q7D6X4_MYCTU |
| Probable fatty-acid-coa ligase fadd9 | >uniprot\|Q7TY99\|Q7TY99_MYCBO |
| Putative acyl-CoA synthetase | >uniprot\|Q9CCT4\|Q9CCT4_MYCLE |
| Putative uncharacterized protein | >uniprot\|Q54JK0\|Q54JK0_DICDI |
| Putative non-ribosomal peptide synthetase | >uniprot\|Q2MFQ3\|Q2MFQ3_STRRY |
| *Mycobacterium tuberculosis* EAS054 | >gi\|215431545\|ref\|ZP_03429464.1\| |
| *Mycobacterium tuberculosis* GM 1503 | >gi\|218754327\|ref\|ZP_03533123.1\| |
| *Mycobacterium tuberculosis* T85 | >gi\|215446840\|ref\|ZP_03433592.1\| |
| *Mycobacterium tuberculosis* T17 | >gi\|219558593\|ref\|ZP_03537669.1\| |
| *Mycobacterium intracellulare* ATCC13950 | >gi\|254819907\|ref\|ZP_05224908.1\| |

In certain embodiments, a host cell, which is used to produce branched tatty alcohols and/or derivatives herein, can be engineered to express or overexpress one or more acyl-ACP reductases polypeptides, variants, or fragments thereof to achieve an improved production of one or more desirable branched fatty alcohols or derivatives. Alternatively, a host cell can be engineered to express an attenuated level of an endogenous acyl-ACP reductase. Non-limiting examples of suitable acyl-ACP reductases are listed in Table 7 below:

TABLE 7

Acyl-ACP Reductase Polypeptides

| Organism | Accession No. |
|---|---|
| *Synechococcus elongatus* PCC7942 | Synpcc7942_1594 (YP_400611) |
| *Synechocystis* sp. | sll0209 (NP_442146) |
| *Cyanothece* sp. ATCC51142 | cce_1430 (YP_001802846) |
| *Prochlorococcus marinus* subsp. *pastoris* str. | CCMP1986 PMM0533 (NP_892651) |
| *Gloeobacter violaceus* | PCC7421 NP_96091 (gll3145) |
| *Nostoc punctiforme* | PCC73102 ZP_00108837 (Npun02004176) |
| *Anabaena variabilis* | ATCC29413 YP_323044 (Ava_2534) |
| *Synechococcus elongatus* | PCC6301 YP_170761 (syc0051_d) |
| *Nostoc* sp. | PCC 7120 alr5284 (NP_489324) |
| *Prochlorococcus marinus* subsp. *pastoris* str. | CCMP1986 PMM0533 (NP_892651) |

In certain embodiments, a host cell, which is used to produce fatty alcohols and/or derivatives herein, can be further engineered to express or overexpress one or more fatty alcohol biosynthesis polypeptides, variants, or fragments thereof in order to achieve an improved production of one or more desirable branched fatty alcohols or derivatives. Alternatively, a host cell can be engineered to express an attenuated level of an endogenous fatty alcohol biosynthesis polypeptide. Non limiting examples of suitable fatty alcohol biosynthesis polypeptides are listed in Table 8 below:

TABLE 8

Fatty Alcohol Biosynthesis/Alcohol Dehydrogenase Polypeptide

| Name | GenBank Accession No. | Name | GenBank Accession No. | Name | GenBank Accession No. |
|---|---|---|---|---|---|
| ygjB | NP_418690 | YggP | YP_026187 | YciK | NP_415787 |
| yahK | NP_414859 | YiaY | YP_026233 | YgfF | NP_417378 |
| adhP | NP_415995 | FucO | NP_417279 | YghA | NP_417476 |
| ydjL | NP_416290 | EutG | NP_416948 | YjgI | NP_418670 |
| ydjJ | NP_416288 | YqhD | NP_417484 | YdfG | NP_416057 |
| idnD | NP_418688 | AdhE | NP_415757 | YgcW | NP_417254 |
| Tdh | NP_418073 | dkgB | NP_414743 | UcpA | NP_416921 |
| yjjN | NP_418778 | YdjG | NP_416285 | EntA | NP_415128 |
| rspB | NP_416097 | YeaE | NP_416295 | FolM | NP_416123 |
| gatD | NP_416594 | dkgA | NP_417485 | HdhA | NP_416136 |
| yphC | NP_417040 | YajO | NP_414953 | HcaB | NP_417036 |
| yhdH | NP_417719 | YghZ | NP_417474 | SrlD | NP_417185 |
| ycjQ | NP_415829 | Tas | NP_417311 | KduD | NP_417319 |
| yncB | NP_415966 | YdhF | YP_025305 | IdnO | NP_418687 |
| Qor | NP_418475 | YdbC | NP_415924 | FabG | NP_415611 |
| frmA | NP_414890 | ybbO | NP_415026 | FabI | NP_415804 |
| ybdR | NP_415141 | yohF | NP_416641 | YdjA | NP_416279 |

In some instances, a host cell, which can be used to produce branched fatty alcohols and/or derivatives herein, is genetically engineered to increase the level of branched fatty acids in the host cell relative to a corresponding wild-type host cell. For example, the host cell can be genetically engineered to express a reduced level of an acyl-CoA synthase relative to a wild-type host cell. In one embodiment, the level of expression of one or more genes (e.g., an acyl-CoA synthase gene) is reduced by genetically engineering a "knock out" host cell. Any known acyl-CoA synthase gene can be reduced or knocked out in a host cell. Non-limiting examples of acyl-CoA synthase genes include fadD, fadK, BH3103, yhfL, Pfl-4354, EAV15023, fadD1, fadD2, RPC_4074, fadDD35, fadDD22, faa3p or the gene encoding the protein ZP_01644857. Specific examples of acyl-CoA synthase genes include fadDD35 from *M. tuberculosis* H37Rv [NP_217021], fadDD22 from *M. tuberculosis* H37Rv [NP_217464], fadD from *E. coli* [NP_416319], fadK from *E. coli* [YP_416216], fadD from *Acinetobacter* sp. ADP1 [YP_045024], fadD from *Haemophilus influenza* RdkW20 [NP_438551], fadD from *Rhodopseudomonas palustris* Bis B18 [YP_533919], BH3101 from *Bacillus halodurans* C-125 [NP_243969], Pfl-4354 from *Pseudomonas fluorescens* Pfo-1 [YP_350082], EAV15023 from *Comamonas testosterone* KF-1 [ZP_01520072], yhfL from *B. subtilis* [NP_388908], fadD1 from *P. aeruginosa* PAO1 [NP_251989], fadD1 from *Ralstonia solanacearum* GM1 1000 [NP_520978], fadD2 from *P. aeruginosa* PAO1 [NP_251990], the gene encoding the protein ZP_01644857 from *Stenotrophomonas maltophilia* R551-3, faa3p from *Saccharomyces cerevisiae* [NP_012257], faa1p from *Saccharomyces cerevisiae* [NP_014962], lcfA from *Bacillus subtilis* [CAA99571], or those described in Shockey et al., *Plant. Physiol.*, 129: 1710-1722 (2002); Caviglia et al., *J. Biol. Chem.*, 279: 1163-1169 (2004); Knoll et al., *J. Biol. Chem.*, 269(23): 16348-56 (1994); Johnson et al., *J. Biol. Chem.*, 269: 18037-18046 (1994); and Black et al., *J. Biol. Chem.* 267: 25513-25520 (1992).

Production of Branched Precursors

Branched fatty alcohols and derivatives can be produced from branched fatty aldehydes containing one or more branched points, using branched acyl-ACPs as substrates for a fatty aldehyde biosynthesis polypeptide or an acyl-ACP reductase polypeptide as described herein. The first step in forming branched fatty alcohol precursors is the production of the corresponding alpha-keto acids by a branched-chain amino acid aminotransferase. Host cells may endogenously include genes encoding such enzymes or such genes can be recombinantly introduced. *E. coli*, for example, endogenously expresses such an enzyme, IlvE (EC 2.6.1.42; GenBank accession YP_026247). In host cells where no branched-chain amino acid aminotransferase are expressed, an *E. coli* IlvE or any other branched-chain amino acid aminotransferase (e.g., IlvE from *Lactococcus lactic* (GenBank accession AAF34406), IlvE from *Pseudomonas putida* (GenBank accession NP_745648), or IlvE from *Streptomyces coelicolor* (GenBank accession NP_629657)), can be introduced.

In another embodiment, the production of alpha-keto acids can be achieved using the methods described in Park et al., PNAS, 104:7797-7802 (2007) and Atsumi et al., *Nature,* 451: 86-89 (2008). For example, 2-ketoisovalerate can be produced by overexpressing the genes encoding IlvI, IlvH, IlvH mutant, IlvB, IlvN, IlvGM, IlvC, or IlvD. Alternatively, 2-keto-3-methyl-valerate can be produced by overexpressing the genes encoding IlvA and IlvI, IlvH (or AlsS of *Bacillus subtilis*), IlvC, IlvD, or their homologs. 2-keto-4-methyl-pentanoate can also be produced by overexpressing the genes encoding IlvI, IlvH, IlvC, IlvD and LeuA, LeuB, LeuC, LeuD, or their homologs.

In another example, isobutyryl-CoA can be made in a host cell, for example in *E. coli*, through the coexpression of a crotonyl-CoA reductase (Ccr, EC 1.6.5.5, 1.1.1.1) and isobutyryl-CoA mutase (large subunit IcmA, EC 5.4.99.2; small subunit IcmB, EC 5.4.99.2) (Han and Reynolds, *J. Bacteriol.,* 179: 5157 (1997)). Crotonyl-CoA is an intermediate in fatty acid biosynthesis in *E. coli* and other microorganisms. Non-limiting examples of ccr and icm genes from selected microorganisms are listed in Table 9.

TABLE 9 ccr and icm Genes from Selected Microorganisms

| Organism | Gene | GenBank Accession # |
|---|---|---|
| *Streptomyces coelicolor* | Ccr | NP_630556 |
|  | icmA | NP_629554 |
|  | icmB | NP_630904 |
| *Streptomyces cinnamonensis* | Ccr | AAD53915 |
|  | icmA | AAC08713 |
|  | icmB | AJ246005 |

Formation of Branched Cyclic Fatty Alcohols and Derivatives

Branched cyclic fatty alcohols can be produced from suitable alpha keto acids using branched cyclic fatty acid derivatives such as a branched cyclic acyl-ACP as substrates. To produce branched cyclic fatty acid derivative substrates, genes that provide cyclic precursors (e.g., the ans, chc, and plm gene families) can be introduced into a host cell and expressed to allow initiation of fatty acid biosynthesis from branched cyclic precursors. For example, to convert a host cell, such as *E. coli*, into one capable of synthesizing co-cyclic fatty acids (cyFA), a gene that provides the cyclic precursor cyclohexylcarbonyl-CoA (CHC-CoA) (Cropp et al., *Nature Biotech.,* 18: 980-983 (2000)) can be introduced and expressed in the host cell. Non-limiting examples of genes that provide CHC-CoA in *E. coli* include: ansJ, ansK, ansL, chcA, and ansM from the ansatrienin gene cluster of *Streptomyces collinus* (Chen et al., *Eur. J. Biochem.,* 261: 98-107 (1999)) or plmJ, plmK, plmL, chcA, and plmM from the phoslactomycin B gene cluster of *Streptomyces* sp. HK803 (Palaniappan et al., *J. Biol. Chem.,* 278: 35552-35557 (2003)) together with the chcB gene (Patton et al., *Biochem.,* 39: 7595-7604 (2000)) from *S. collinus, S. avermitilis,* or *S. coelicolor* (see Table 10). The genes listed in Table 10 can then be expressed to allow initiation and elongation of co-cyclic fatty acids. Alternatively, the homologous genes can be isolated from microorganisms that make cyFA and expressed in a host cell (e.g., *E. coli*).

TABLE 10

Genes for the Synthesis of CHC-CoA

| Organism | Gene | GenBank Accession No. |
|---|---|---|
| *Streptomyces collinus* | ansJK | U72144* |
|  | ansL |  |
|  | chcA |  |
|  | ansM |  |
|  | chcB | AF268489 |
| *Streptomyces* sp. HK803 | pmlJK | AAQ84158 |
|  | pmlL | AAQ84159 |
|  | chcA | AAQ84160 |
|  | pmlM | AAQ84161 |
| *Streptomyces coelicolor* | chcB/caiD | NP_629292 |
| *Streptomyces avermitilis* | chcB/caiD | NP_629292 |

*Only chcA is annotated in GenBank entry U72144; ansJKLM are according to Chen et al. (*Eur. J. Biochem.*, 261: 98-107 (1999)).

Genes fabH, acp, and fabF allow initiation and elongation of co-cyclic fatty acids because they have broad substrate specificity. If the coexpression of any of these genes with the genes listed in Table 10 does not yield cyFA, then fabH, acp, and/or fabF homologs from microorganisms that make cyFAs (e.g., those listed in Table 11) can be isolated (e.g., by using degenerate PCR primers or heterologous DNA sequence probes) and coexpressed.

TABLE 11

Non-Limiting Examples of Microorganisms Containing ω-cyclic Fatty Acids

| Organism | Reference |
|---|---|
| *Curtobacterium pusillum* | ATCC19096 |
| *Alicyclobacillus acidoterrestris* | ATCC49025 |
| *Alicyclobacillus acidocaldarius* | ATCC27009 |
| *Alicyclobacillus cycloheptanicus** | Moore, *J Org. Chem.*, 62: 2173 (1997) |

*Uses cycloheptylcarbonyl-CoA and not cyclohexylcarbonyl-CoA as precursor for cyFA biosynthesis.

Branched Fatty Alcohol Saturation Levels

The degree of saturation in branched fatty acid derivative substrates, such as, for example, a branched acyl-ACP, (which can then be converted into branched fatty aldehydes and then branched fatty alcohols as described herein) can be controlled by regulating the degree of saturation of fatty acid intermediates. For example, the sfa, gns, and fab families of genes can be expressed or overexpressed to control the saturation of a branched acyl-ACP. In certain embodiments, the host cells can be engineered to reduce the expression of an sfa, gns, or fab gene and control the level of saturated substrates vs. unsaturated substrates, which in turn affects the production level of saturated branched fatty alcohols or derivatives vs. unsaturated branched fatty alcohols or derivatives.

In some instances, a host cell can be engineered to express an attenuated level of a dehydratase/isomerase and/or a ketoacyl-ACP synthase. For example, a host cell can be engineered to express a decreased level of fabA and/or fabB. In some instances, the host cell can be cultured or grown in the presence of unsaturated fatty acids. In some instances, the host cell can be engineered to express or overexpress a gene encoding a desaturases enzyme. One non-limiting example of a desaturases is *B. subtilis* DesA (AF037430). Other genes encoding desaturases are known in the art can be introduced or used in the host cell and methods described herein, such as desaturases that use acyl-ACPs, including, for example, hexadecanoyl-ACP or octadecanoyl-ACP.

In some embodiments, those cells can be engineered to produce unsaturated fatty acids by engineering the production host to overexpress fabB or by growing the production host at low temperatures (e.g., less than 37° C.). FabB has preference to cis-δ3decenoyl-ACP and results in unsaturated fatty acid production in *E. coli*. Overexpression of fabB results in the production of a significant percentage of unsaturated fatty acids (de Mendoza et al., *J. Biol. Chem.,* 258: 2098-2101 (1983)). The gene fabB may be inserted into and expressed in host cells not naturally having the gene. These unsaturated fatty acids can then be used as intermediates in host cells that are engineered to produce branched and unsaturated fatty acid derivative substrates, such as branched and unsaturated fatty aldehydes, which can in turn be converted into branched and unsaturated fatty alcohols and derivatives.

In other instances, a repressor of fatty acid biosynthesis, for example, fabB (GenBank accession NP_418398), can be deleted, which will also result in increased unsaturated fatty acid production in *E. coli* (Zhang et al., *J. Biol. Chem.,* 277: 15558 (2002)). Similar deletions may be made in other host cells. A further increase in unsaturated fatty acids may be achieved, for example, by overexpressing fabM (trans-2, cis-3-decenoyl-ACP isomerase, GenBank accession DAA05501) and controlled expression of fabK (trans-2-enoyl-ACP reductase II, GenBank accession NP_357969) from *Streptococcus pneumoniae* (Marrakchi et al., *J. Biol. Chem.,* 277: 44809 (2002)), while deleting *E. coli* fabI (trans-2-enoyl-ACP reductase, GenBank accession NP_415804). In some examples, the endogenous fabF gene can be attenuated, thus increasing the percentage of palmitoleate (C16:1) produced.

Production of Genetic Variants

Variants can be naturally occurring or created in vitro. In particular, such variants can be created using genetic engineering techniques, such as site directed mutagenesis, random chemical mutagenesis, Exonuclease III deletion procedures, or standard cloning techniques. Alternatively, such variants, fragments, analogs, or derivatives can be created using chemical synthesis or modification procedures.

Methods of making variants are well known in the art. These include procedures in which nucleic acid sequences obtained from natural isolates are modified to generate nucleic acids that encode polypeptides having characteristics that enhance their value in industrial or laboratory applications. In such procedures, a large number of variant sequences having one or more nucleotide differences with respect to the sequence obtained from the natural isolate are generated and characterized. Typically, these nucleotide differences result in amino acid changes with respect to the polypeptides encoded by the nucleic acids from the natural isolates.

For example, variants can be created using error prone PCR (see, e.g., Leung et al., *Technique,* 1: 11-15 (1989); and Caldwell et al., *PCR Methods Applic.,* 2: 28-33 (1992)). In error prone PCR, PCR is performed under conditions where the copying fidelity of the DNA polymerase is low, such that a high rate of point mutations is obtained along the entire length of the PCR product. Briefly, in such procedures, nucleic acids to be mutagenized (e.g., a fatty aldehyde biosynthetic polynucleotide sequence) are mixed with PCR primers, reaction buffer, $MgCl_2$, $MnCl_2$, Taq polymerase, and an appropriate concentration of dNTPs for achieving a high rate of point mutation along the entire length of the PCR product. For example, the reaction can be performed using 20 fmoles of nucleic acid to be mutagenized (e.g., a fatty aldehyde biosynthetic polynucleotide sequence), 30 pmole of each PCR primer, a reaction buffer comprising 50 mM KCl, 10 mM Tris HCl (pH 8.3), and 0.01% gelatin, 7 mM $MgCl_2$, 0.5 mM $MnCl_2$, 5 units of Taq polymerase, 0.2 mM dGTP, 0.2 mM dATP, 1 mM dCTP, and 1 mM dTTP. PCR can be performed for 30 cycles of 94° C. for 1 min, 45° C. for 1 min, and 72° C. for 1 min. However, it will be appreciated that these parameters can be varied as appropriate. The mutagenized nucleic acids are then cloned into an appropriate vector and the activities of the polypeptides encoded by the mutagenized nucleic acids are evaluated.

Variants can also be created using oligonucleotide directed mutagenesis to generate site-specific mutations in any cloned DNA of interest. Oligonucleotide mutagenesis is described in, for example, Reidhaar-Olson et al., *Science,* 241: 53-57 (1988).

Variants can also be generated by assembly PCR, which involves the assembly of a PCR product from a mixture of small DNA fragments. A large number of different PCR reactions occur in parallel in the same vial, with the products of one reaction priming the products of another reaction. Assembly PCR is described in, e.g., U.S. Pat. No. 5,965,408.

Still another method of generating variants is sexual PCR mutagenesis, wherein forced homologous recombination occurs between DNA molecules of different, but highly related, DNA sequence in vitro as a result of random fragmentation of the DNA molecule based on sequence homology. This is followed by fixation of the crossover by primer extension in a PCR reaction. Sexual PCR mutagenesis is described in, for example, Stemmer, *Proc. Natl. Acad. Sci. USA,* 91: 10747-10751 (1994).

Variants can also be created by in vivo mutagenesis. In some embodiments, random mutations in a nucleic acid sequence are generated by propagating the sequence in a bacterial strain, such as an *E. coli* strain, which carries mutations in one or more of the DNA repair pathways. Such "mutator" strains have a higher random mutation rate than that of a wild-type strain. Propagating a DNA sequence (e.g., a BKD polynucleotide sequence, a beta acyl-ACP synthase polynucleotide sequence, a fatty aldehyde biosynthesis polynucleotide sequence, or a fatty alcohol biosynthesis polynucleotide sequence) in one of these strains will eventually generate random mutations within the DNA. Mutator strains suitable for use for in vivo mutagenesis are described in, for example, International Publication WO 91/016427.

Variants can also be generated using cassette mutagenesis. In cassette mutagenesis, a small region of a double stranded DNA molecule is replaced with a synthetic oligonucleotide "cassette" that differs from the native sequence. The oligonucleotide often contains a completely and/or partially randomized native sequence.

Recursive ensemble mutagenesis can also be used to generate variants. Recursive ensemble mutagenesis is an algorithm for protein engineering (i.e., protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described in, for example, Arkin et al., *Proc. Natl. Acad. Sci. USA,* 89: 7811-7815 (1992).

In some embodiments, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described in, for example, Delegrave et al., *Biotech. Res.,* 11: 1548-1552 (1993). Random and site-directed mutagenesis are described in, for example, Arnold, *Curr. Opin. Biotech.,* 4: 450-455 (1993).

In some embodiments, variants are created using shuffling procedures wherein portions of a plurality of nucleic acids that encode distinct polypeptides are fused together to create chimeric nucleic acid sequences that encode chimeric polypeptides as described in, for example, U.S. Pat. Nos. 5,965,408 and 5,939,250.

Polynucleotide variants also include nucleic acid analogs. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine and 5-methyl-2'-deoxycytidine or 5-bromo-2'-deoxycytidine for deoxycytidine. Modifications of the sugar moiety include modification of the 2' hydroxyl of the ribose sugar to form 2'-halo, 2'-O-methyl or 2'-O-allyl sugars. The deoxyribose phosphate backbone can be modified to produce morpholino nucleic acids, in which each base moiety is linked to a six-membered, morpholino ring, or peptide nucleic acids, in which the deoxyphosphate backbone is replaced by a pseudopeptide backbone and the four bases are retained. (See, e.g., Summerton et al., *Antisense Nucleic Acid Drug Dev.,* 7: 187-195 (1997); and Hyrup et al., *Bioorgan. Med. Chem.,* 4: 5-23 (1996)). In addition, the deoxyphosphate backbone can be replaced with, for example, a phosphorothioate or phosphorodithioate backbone, a phosphoroamidite, or an alkyl phosphotriester backbone.

Production of Polypeptide Variants

Conservative substitutions are those that substitute an amino acid in a polypeptide by another amino acid of similar characteristics. Common conservative substitutions include, without limitation: replacing an aliphatic amino acid, such as alanine, valine, leucine, and isoleucine, with another aliphatic amino acid; replacing a serine with a threonine or vice versa; replacing an acidic residue, such as aspartic acid and glutamic acid, with another acidic residue; replacing a residue bearing an amide group, such as asparagine and glutamine, with another residue bearing an amide group; replacing a basic residue, such as lysine and arginine, with another basic residue; and replacing an aromatic residue, such as phenylalanine and tyrosine, with another aromatic residue.

Other polypeptide variants are those in which one or more amino acid residues include a substituent group. Still other polypeptide variants are those in which the polypeptide is associated with another compound, such as a compound to increase the half-life of the polypeptide (e.g., polyethylene glycol).

Additional polypeptide variants are those in which additional amino acids are fused to the polypeptide, such as a leader sequence, a secretory sequence, a proprotein sequence, or a sequence which facilitates purification, enrichment, or stabilization of the polypeptide.

In some instances, the polypeptide variants described herein retain the same biological function as a polypeptide from which they are derived (e.g., retain branched-chain alpha keto acid dehydrogenase activity, retain beta ketoyacyl ACP synthase activity, such as FabH activity, or retain fatty aldehyde biosynthetic activity, such as carboxylic acid or fatty acid reductase activity) and have amino acid sequences substantially identical thereto.

In other instances, the polypeptide variants have at least about 50%, at least about 55%, at least about 60%, at least about 65%, at least about 70%, at least about 75%, at least about 80%, at least about 85%, at least about 90%, at least about 95%, or more than about 95% homology to an amino acid sequence from which they are derived. In another embodiment, the polypeptide variants include a fragment comprising at least about 5, 10, 15, 20, 25, 30, 35, 40, 50, 75, 100, or 150 consecutive amino acids thereof.

The polypeptide variants or fragments thereof can be obtained by isolating nucleic acids encoding them using techniques described herein or by expressing synthetic nucleic acids encoding them. Alternatively, polypeptide variants or fragments thereof can be obtained through biochemical enrichment or purification procedures. The sequence of polypeptide variants or fragments can be determined by proteolytic digestion, gel electrophoresis, and/or microsequencing. The sequence of the polypeptide variants or fragments can then be compared to the amino acid sequence from which it is derived using any of the programs described herein.

The polypeptide variants and fragments thereof can be assayed for enzymatic activity. For example, the polypeptide variants or fragments can be contacted with a substrate under conditions that allow the polypeptide variants or fragments to function. A decrease in the level of the substrate or an increase in the level of the desired product can be measured to determine its activity.

Modifications to Increase Conversion of Branched Substrates to Branched Fatty Alcohol Host cells can be engineered using known polypeptides to produce branched fatty alcohols from branched substrate, including, for example, a branched fatty acid, a branched fatty acid derivative, a branched acyl-CoA, or a branched acyl-CoA derivative substrate. For example, one method of making branched fatty alcohols involves increasing the expression of, or expressing more active forms of fatty alcohol forming acyl-CoA reductases (encode by a gene such as acr1 from FAR, EC 1.2.1.50/1.1.1) or acyl-CoA reductases (EC 1.2.1.50) and alcohol dehydrogenase (EC 1.1.1.1).

The host cell can also be, for example, modified or engineered, such that it expresses or overexpresses at least one (E1) subunit of a branched-chain alpha keto acid dehydrogenase complex, and a beta ketoacyl-ACP synthase. The host cell can be further engineered such that it expresses or overexpresses a fatty aldehyde biosynthesis polypeptide and/or a fatty alcohol biosynthesis polypeptide. Alternatively, the host cell can be engineered such that it expresses or overexpresses an acyl-ACP reductase polypeptide and a fatty alcohol biosynthesis polypeptide.

In certain embodiments, the gene encoding the subunits of branched-chain alpha keto acid dehydrogenase complex can be derived from a bacterium, a plant, an insect, a yeast, a fungus, or a mammal. For example, the subunits of the branched-chain alpha keto acid dehydrogenase complex can be derived from a bacterium that uses branched amino acids as carbon source, including, for example, *Pseudomonas putida* or *Bacillus subtilis*. In another example, the branched-chain alpha-keto acid dehydrogenase complex polypeptide can be from a bacterium that comprises branched fatty acids in its phospholipids, including, e.g., a *Legionella, Stenotrophomonas, Alteromonas, Flavobacterium, Myxococcus, Bccteroides, Micrococcus, Staphylococcus, Bacillus, Clostridium, Listeria, Lactococcus*, or *Streptomyces*. In some embodiments, the bacterium is a *Leginella pneumophila, Stenotrophomonas maltophilia, Alteromonas macleodii, Flabobacterium phsychrophilum, Myxococcus Xanthus, Bacteroides thetaiotaomicron, Macrococcus luteus, Staphylococcus aureus, Clostridium thermocellum, Listeria monocytogenes, Streptomyces lividans, Streptomyces coelicolor, Streptomyces glaucescens, Streptococcus pneumoniae, Streptomyces peucetius, Streptococcus pyogenes, Escherichia coli, Escherichia coli* K-12, *Lactococcus lactis* ssp. *Lactis, Mycobacterium tuberculosis, Enterococcus tuberculosis, Bacillus subtilis, Lactobacillus plantarum*. In some embodiments, suitable fatty aldehyde biosynthesis polypeptides, fatty alcohol biosynthesis polypeptides, acyl-ACP reductases, and other polypeptides of the invention can be from a mycobacterium selected from *Mycobacterium smegmatis, Mycobacterium abscessus, Mycobacterium avium, Mycobacterium bovis, Mycobacterium tuberculosis, Mycobacterium leprae, Mycobacterium marinum*, or *Mycobacterium ulcerans*. In other embodiments, the bacterium is *Nocardia* sp. NRRL 5646, *Nocardia farcinica, Streptomyces griseus, Salinispora arenicola*, or *Clavibacter michiganenesis*. In yet further embodiments, the polypeptide of the invention is derived from a cyanobacterium, including, for example, *Synechococcus elongatus* PCC7942, *Synechocystis* sp. PCC6803, *Cyanothece* sp. ATCC51142, *Prochlorococcus marinus* subsp. *pastoris* str. CCMP1986 PMM0533, *Gloeobacter violaceus* PCC7421, *Nostoc punctiforme* PCC73102, *Anabaena variabilis* ATCC29413, *Synechococcus elongatus*

PCC6301, and *Nostoc* sp. PCC 7120, *Microcoleus chthonoplastes* PCC7420, *Arthrospira maxima* CS-328, *Lyngbya* sp. PCC8106, *Nodularia spumigena* CCY9414, *Trichodesmium erythraeum* IMS101, *Microcystis aeruginosa, Nostoc azollae, Anabaena variabilis, Crocophaera watsonii, Thermosynechococcus elongatus, Gloeobacer violaceus, Cyanobium*, or *Prochlorococcus marinus.*

Genetic Engineering of Host Cells to Produce Branched Fatty Alcohols

Various host cells can be used to produce branched fatty alcohols, as described herein. A host cell can be any prokaryotic or eukaryotic cell. For example, the host cell can be bacterial cells (such as *E. coli*), insect cells, yeast, or mammalian cells (such as Chinese hamster ovary cells (CHO) cells, COS cells, VERO cells, BHK cells, HeLa cells, Cv1 cells, MDCK cells, 293 cells, 3T3 cells, or PC12 cells). Other exemplary host cells include cells from the members of the genus *Escherichia, Bacillus, Lactobacillus, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Schizosaccharomyces, Yarrowia*, or *Streptomyces*. Yet other exemplary host cells can be a *Bacillus lentus* cell, a *Bacillus brevis* cell, a *Bacillus stearothermophilus* cell, a *Bacillus licheniformis* cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, a *Bacillus subtilis* cell, a *Bacillus amyloliquefaciens* cell, a *Trichoderma koningii* cell, a *Trichoderma viride* cell, a *Trichoderma reesei* cell, a *Trichoderma longibrachiatum* cell, an *Aspergillus awamori* cell, an *Aspergillus fumigates* cell, an *Aspergillus foetidus* cell, an *Aspergillus nidulans* cell, an *Aspergillus niger* cell, an *Aspergillus oryzae* cell, a *Humicola insolens* cell, a *Humicola lanuginose* cell, a *Rhizomucor miehei* cell, a *Mucor michei* cell, a *Streptomyces lividans* cell, a *Streptomyces murinus* cell, or an *Actinomycetes* cell. Host cells can also be cyanobacterial cells such as, for example, *Synechoccus* sp., *Synechoccus elongatus*, or *Synechocystis* sp. cells.

In a preferred embodiment, the host cell is an *E. coli* cell, a *Saccharomyces cerevisiae* cell, or a *Bacillus subtilis* cell. For example, the host cell can be one from *E. coli* strain B, C, K, or W. Other suitable host cells are known to those skilled in the art.

Various methods well known in the art can be used to genetically engineer host cells to produce branched fatty alcohols. The methods can include the use of vectors, preferably expression vectors, containing a nucleic acid encoding the first (E1 alpha/beta) subunit of a branched-chain alpha keto acid dehydrogenase, and optionally also the second (E2) and/or the third (E3) subunit of that enzyme, and/or a beta ketoacyl-ACP synthase, and/or a fatty aldehyde biosynthetic polypeptide, and/or an alcohol dehydrogenase, and/or an acyl-ACP reductases, described herein, polypeptide variant, or a fragment thereof. Those skilled in the art will appreciate a variety of viral vectors (for example, retroviral vectors, lentiviral vectors, adenoviral vectors, and adeno-associated viral vectors) and non-viral vectors can be used in the methods described herein.

The recombinant expression vectors can include polynucleotides described herein in a form suitable for expression in a host cell. The recombinant expression vectors can include one or more control sequences, selected on the basis of the host cell to be used for expression. The control sequence is operably linked to the nucleic acid sequence to be expressed. Such control sequences are described, for example, in Goeddel, Gene Expression Technology: Methods in Enzymology 185, Academic Press, San Diego, Calif. (1990). Control sequences include those that direct constitutive expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors described herein can be introduced into host cells to produce polypeptides, including fusion polypeptides, encoded by the nucleic acids as described herein.

In some embodiments, recombinant expression vectors can be designed for expression of a gene encoding a first (E1 alpha/beta) subunit, and optionally a second (E2) and/or a third (E3) subunit of a branched-chain alpha-keto acid dehydrogenase (or variant) and/or a gene encoding a beta-ketoacyl ACP synthase (or variant), and/or a gene encoding a fatty aldehyde biosynthesis polypeptide (or variant), and/or a gene encoding an alcohol dehydrogenase (or variant), and/or a gene encoding an acyl-ACP reductases (or variant) in a suitable host cell. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example, by using T7 promoter regulatory sequences and T7 polymerase.

Expression of genes encoding polypeptides in prokaryotes, for example, *E. coli*, is most often carried out with vectors containing constitutive or inducible promoters directing the expression of either fusion or non-fusion polypeptides. Fusion vectors add a number of amino acids to a polypeptide encoded therein, usually to the amino terminus of the recombinant polypeptide. Such fusion vectors typically serve three purposes: (1) to increase expression of the recombinant polypeptide; (2) to increase the solubility of the recombinant polypeptide; and (3) to aid in the purification of the recombinant polypeptide by acting as a ligand in affinity purification. Often, in fusion expression vectors, a proteolytic cleavage site is introduced at the junction of the fusion moiety and the recombinant polypeptide. This enables separation of the recombinant polypeptide from the fusion moiety after purification of the fusion polypeptide. Examples of such enzymes, and their cognate recognition sequences, include Factor Xa, thrombin, and enterokinase. Exemplary fusion expression vectors include pGEX (Pharmacia Biotech Inc.; Smith et al., *Gene,* 67: 31-40 (1988)), pMAL (New England Biolabs, Beverly, Mass.), and pRITS (Pharmacia, Piscataway, N.J.), which fuse glutathione S-transferase (GST), maltose E binding protein, or protein A, respectively, to the target recombinant polypeptide.

Examples of inducible, non-fusion *E. coli* expression vectors include pTrc (Amann et al., *Gene,* 69: 301-315 (1988)) and pET 11d (Studier et al., Gene Expression Technology: Methods in Enzymology 185, Academic Press, San Diego, Calif. (1990), pp. 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident X, prophage harboring a T7 gn1 gene under the transcriptional control of the lacUV 5 promoter.

One strategy to maximize expression is to express the polypeptide in a host cell with an impaired capacity to proteolytically cleave the recombinant polypeptide (see Gottesman, Gene Expression Technology: Methods in Enzymology 185, Academic Press, San Diego, Calif. (1990), pp. 119-128). Another strategy is to alter the nucleic acid sequence to be inserted into an expression vector so that the individual codons for each amino acid are those preferentially utilized in the host cell (Wada et al., *Nucleic Acids Res.,* 20: 2111-18 (1992)). These strategies can be carried out by standard DNA synthesis techniques.

In another embodiment, the host cell is a yeast cell, and the expression vector is a yeast expression vector. Examples of vectors for expression in yeast *S. cerevisiae* include pYepSec1 (Baldari et al., *EMBO J.,* 6: 229-234 (1987)), pMFa (Kurjan et al., *Cell,* 30: 933-943 (1982)), pJRY88 (Schultz et al., *Gene,* 54: 113-123 (1987)), pYES2 (Invitrogen Corporation, San Diego, Calif.), and picZ (Invitrogen Corp, San Diego, Calif.).

Alternatively, polypeptides described herein can be expressed in insect cells using baculovirus expression vectors. Available baculovirus vectors include, for example, the pAc series (Smith et al., *Mol. Cell. Biol.,* 3: 2156-2165 (1983)) and the pVL series (Lucklow et al., *Virology,* 170: 31-39 (1989)).

In yet another embodiment, the polypeptides described herein can be expressed in mammalian cells using a mammalian expression vector. Examples of mammalian expression vectors include pCDM8 (Seed, *Nature,* 329: 840 (1987)) and pMT2PC (Kaufman et al., *EMBO J.,* 6: 187-195 (1987)). When used in mammalian cells, the expression vector's control functions can be provided by viral regulatory elements. Commonly used promoters include those derived from polyoma, Adenovirus 2, cytomegalovirus, and Simian Virus 40. Other suitable expression systems for both prokaryotic and eukaryotic cells are described in chapters 16-17 of Sambrook et al., eds., Molecular Cloning: A Laboratory Manual. $2^{nd}$, ed., Cold Spring Harbor Laboratory, Cold Spring Harbor Laboratory Press, Cold Spring Harbor, N.Y., 1989.

Vectors can be introduced into prokaryotic or eukaryotic cells via conventional transformation or transfection techniques. As used herein, the terms "transformation" and "transfection" refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

It is known that, depending upon the expression vector and transformation technique used, only a small fraction of bacterial cells will take-up and replicate the expression vector. In order to identify and select these transformants, a gene that encodes a selectable marker (e.g., resistance to antibiotics) can be introduced into the host cells along with the gene of interest. Selectable markers include those that confer resistance to drugs, such as ampicillin, kanamycin, chloramphenicol, or tetracycline. Nucleic acids encoding a selectable marker can be introduced into a host cell on the same vector as that encoding a polypeptide described herein or can be introduced on a separate vector. Cells stably transfected with the introduced nucleic acid can be identified by drug selection (e.g., cells that have incorporated the selectable marker gene will survive, while the other cells die).

It is known that, depending upon the expression vector and transfection technique used, only a small fraction of mammalian cells may integrate the foreign DNA into their genome. In order to identify and select these integrants, a gene that encodes a selectable marker (e.g., resistance to antibiotics) can be introduced into the host cells along with the gene of interest. Preferred selectable markers include those which confer resistance to drugs, such as G418, hygromycin, and methotrexate. Nucleic acids encoding a selectable marker can be introduced into a host cell on the same vector as that encoding a polypeptide described herein or can be introduced on a separate vector. Cells stably transfected with the introduced nucleic acid can be identified by drug selection (e.g., cells that have incorporated the selectable marker gene will survive, while the other cells die).

Transport Proteins

Transport proteins can export or excrete polypeptides and organic compounds (e.g., branched fatty alcohols) out of a host cell. A number of transport and efflux proteins can be modified to selectively secrete particular types of compounds such as branched fatty alcohols.

Non-limiting examples of suitable transport proteins are ATP-Binding Cassette (ABC) transport proteins, efflux proteins, and fatty acid transporter proteins (FATP). Additional suitable transport proteins include the ABC transport proteins from organisms such as *Caenorhabditis elegans, Arabidopsis thalania, Alkaligenes eutrophus*, or *Rhodococcus erythropolis*. Exemplary ABC transport proteins include, without limitation, CER5, AtMRP5, AmiS2, and AtPGP1. Host cells can also be chosen for their endogenous ability to secrete organic compounds. The efficiency of organic compound production and secretion into the host cell environment (e.g., culture medium, fermentation broth) can be expressed as a ratio of intracellular product to extracellular product. For example, the ratio can be about 5:1, 4:1, 3:1, 2:1, 1:1, 1:2, 1:3, 1:4, or 1:5.

Fermentation

The production and isolation of branched fatty alcohols can be enhanced by employing beneficial fermentation techniques. One method for maximizing production while reducing costs is increasing the percentage of the carbon source that is converted to the branched fatty alcohol products.

During normal cellular lifecycles, carbon is used in cellular functions such as producing lipids, saccharides, proteins, organic acids, and nucleic acids. Reducing the amount of carbon necessary for growth-related activities can increase the efficiency of carbon source conversion to product. This can be achieved by, for example, first growing host cells to a desired density (for example, a density achieved at the peak of the log phase of growth). At such a point, replication checkpoint genes can be harnessed to stop the growth of cells. Specifically, quorum sensing mechanisms (reviewed in Camilli et al., *Science,* 311: 1113 (2006); Venturi *FEMS Microbio. Rev.,* 30: 274-291 (2006); and Reading et al., *FEMS Microbiol. Lett.,* 254: 1-11 (2006)) can be used to activate checkpoint genes, such as p53, p21, or other checkpoint genes.

Genes that can be activated to stop cell replication and/or growth in *E. coli* include umuDC genes. The overexpression of umuDC genes stops the progression from stationary phase to exponential growth (Murli et al., *J. Bact.,* 182: 1127 (2000)). UmuC is a DNA polymerase that can carry out translesion synthesis over non-coding lesions—the mechanistic basis of most UV and chemical mutagenesis. The umuDC gene products are involved in the process of translesion synthesis and also serve as a DNA sequence damage checkpoint. The umuDC gene products include UmuC, UmuD, umuD', $UmuD'_2C$, $UmuD'_2$, and $UmuD_2$. Simultaneously, product-producing genes can be activated, thus minimizing the need for replication and maintenance pathways to be used while a fatty aldehyde is being made. Host cells can also be engineered to express umuC and umuD from *E. coli* in pBAD24 under the prpBCDE promoter system through de novo synthesis of this gene with the appropriate end-product production genes.

The percentage of input carbons converted to branched fatty alcohols can be a cost driver. The more efficient the process is (i.e., the higher the percentage of input carbons converted to branched fatty alcohols), the less expensive the process will be. For oxygen-containing carbon sources (e.g., glucose and other carbohydrate based sources), the oxygen must be released in the form of carbon dioxide. For every 2 oxygen atoms released, a carbon atom is also released leading to a maximal theoretical metabolic efficiency of approximately 34% (w/w) (for fatty acid derived products). This figure, however, changes for other organic compounds and carbon sources. Typical efficiencies in the literature are approximately less than 5%. Host cells engineered to produce fatty alcohols can have greater than about 1, 3, 5, 10, 15, 20, 25, and 30% efficiency. In one example, host cells can exhibit an efficiency of about 10% to about 25%. In other examples, such host cells can exhibit an efficiency of about 25% to about 30%. In other examples, host cells can exhibit greater than 30% efficiency.

The host cell can be additionally engineered to express recombinant cellulosomes, such as those described in International Publication WO 2008/100251. These cellulosomes can allow the host cell to use cellulosic material as a carbon source. For example, the host cell can be additionally engineered to express invertases (EC 3.2.1.26) so that sucrose can be used as a carbon source. Similarly, the host cell can be engineered using the teachings described in U.S. Pat. Nos. 5,000,000; 5,028,539; 5,424,202; 5,482,846; and 5,602,030, so that the host cell can assimilate carbon efficiently and use cellulosic materials as carbon sources.

In one example, the fermentation chamber can enclose a fermentation that is undergoing a continuous reduction. In this instance, a stable reductive environment can be created. The electron balance can be maintained by the release of carbon dioxide (in gaseous form). Efforts to augment the NAD/H and NADP/H balance can also facilitate in stabilizing the electron balance. The availability of intracellular NADPH can also be enhanced by engineering the host cell to express an NADH:NADPH transhydrogenase. The expression of one or more NADH:NADPH transhydrogenases converts the NADH produced in glycolysis to NADPH, which can enhance the production of fatty alcohols.

For small scale production, the engineered host cells can be (a) grown in batches of, for example, about 100 mL, 500 mL, 1 L, 2 L, 5 L, or 10 L, (b) fermented, and (c) induced to express desired bkd genes, beta-ketoacyl ACP synthase genes, fatty aldehyde biosynthesis genes, alcohol dehydrogenase genes, and/or acyl-ACP reductases genes, based on the specific genes encoded in the appropriate plasmids. For large scale production, the engineered host cells can be (a) grown in batches of about 10 L, 100 L, 1000 L, 10,000 L, 100,000 L, 1,000,000 L, or larger, (b) fermented, and (c) induced to express the desired bkd genes, beta-ketoacyl ACP synthase genes, fatty aldehyde biosynthesis genes, alcohol dehydrogenase genes, and/or acyl-ACP reductases genes based on the specific genes encoded in the plasmids or incorporated into the host cell's genome.

For example, a suitable production host, such as an *E. coli*, harboring plasmids containing the desired genes or having the genes integrated in its chromosome can be incubated in a suitable reactor, for example a 1 L reactor, for 20 hours at 37° C. in an M9 medium supplemented with 2% glucose, carbenicillin, and chloramphenicol. When the $OD_{600}$ of the culture reaches 0.9, the production host can be induced with IPTG alcohol After incubation, the spent media can be extracted and the organic phase can be examined for the presence of branched fatty alcohols using GC-MS.

In some instances, after the first hour of induction, aliquots of no more than about 10% of the total cell volume can be removed each hour and allowed to sit without agitation to allow the branched fatty alcohols to rise to the surface and undergo a spontaneous phase separation or precipitation. The branched fatty alcohol component can then be collected, and the aqueous phase returned to the reaction chamber. The reaction chamber can be operated continuously. When the $OD_{600}$ drops below 0.6, the cells can be replaced with a new batch grown from a seed culture.

Producing Branched Fatty Alcohols and Derivatives Using Cell-Free Methods

In some embodiments, branched fatty alcohols can be produced using a purified polypeptide (e.g., a branched-chain alpha keto acid dehydrogenase complex polypeptide) described herein and a substrate (e.g., an alpha keto acid, malonyl-CoA, 2-oxo-isovalerate, 2-oxo-isobutylrate, 2-oxo-3-methyl-valerate. 2-oxo-isocaproate, 2-oxoglutarate, 2-oxo-pentanoate, 3-methyl-2-oxobutanoate, 3-methyl-2-oxopentanoate, 4-methyl-2-oxopentanoate, or pyruvate) produced, for example, by a method described herein. For example, a host cell can be engineered to express a branched-chain alpha keto acid dehydrogenase polypeptide or the E1 (alpha and beta), and optionally, the E2 and/or the E3 subunits thereof, or variants as described herein. The host cell can be cultured under conditions sufficient to allow expression of the polypeptide. Cell free extracts can then be generated using known methods, including, for example, cell lysis using detergents or sonication. The expressed polypeptides can be purified. Thereafter, substrates described herein can be added to the cell free extracts and maintained under conditions to allow conversion of the substrates (e.g., alpha keto acids, such as 2-oxo-isovalerate, 2-oxo-isobutylrate, 2-oxo-3-methyl-valerate. 2-oxo-isocaproate, 2-oxoglutarate, 2-oxopentanoate, 3-methyl-2-oxobutanoate, 3-methyl-2-oxopentanoate, 4-methyl-2-oxopentanoate, or pyruvate) to branched chain acyl-CoAs, which can then be converted into branched fatty aldehydes and branched fatty alcohols. The branched fatty alcohols can then be separated and purified using known techniques.

Post-Production Processing

Depending on the intended use of the branched fatty alcohols produced in accordance with the methods here, post-production processing may or may not be necessary. As such, in certain industrial applications, the produced branched fatty alcohols and/or derivatives may be suitably used per se as surfactants. Moreover, such surfactants can be directly blended or formulated into suitable cleaning compositions.

The branched fatty alcohols produced during fermentation can be separated from the fermentation media, using any known technique for separating fatty alcohols from aqueous media. One exemplary separation process is a two phase (bi-phasic) separation process, which involves fermenting the genetically engineered host cells under conditions sufficient to produce a branched fatty alcohol, allowing it to collect in an organic phase, and separating the organic phase from the aqueous fermentation broth. This method can be practiced in both a batch and continuous fermentation processes.

Bi-phasic separation uses the relative immiscibility of fatty alcohols to facilitate separation. Immiscible refers to the relative inability of a compound to dissolve in water and is defined by the compound's partition coefficient. One of ordinary skill in the art will appreciate that by choosing a fermentation broth and organic phase, such that the branched fatty alcohol being produced has a high log P value, the branched fatty alcohol can separate into the organic phase, even at very low concentrations, in the fermentation vessel.

The branched fatty alcohols produced by the methods described herein can be relatively immiscible in the fermentation broth and the cytoplasm. Therefore, the branched fatty alcohol can collect in an organic phase either intracellularly or extracellularly. The collection of the products in the organic phase can lessen the impact of the branched fatty alcohol on cellular function and can allow the host cell to produce more product.

The branched fatty alcohol can thus be produced as a homogeneous compounds wherein at least about 60%, 70%, 80%, 90%, or 95% of the branched fatty alcohols produced will have carbon chain lengths that vary by less than about 6 carbons, less than about 4 carbons, or less than about 2 carbons. These compounds can also be produced with a relatively uniform degree of saturation. They can be used per se as surfactants or can be formulated into suitable cleaning compositions. They can also be used as fuels, fuel additives, starting materials for production of other chemical compounds (e.g., polymers, surfactants, plastics, textiles, solvents, adhesives, etc.), or personal care additives. These compounds can also be used as feedstock for subsequent reactions, for example, hydrogenation, catalytic cracking (e.g., via hydrogenation, pyrolysis, or both), and can be dehydrated to make other products. In particular, these branched products confer low volatility, beneficial low-temperature properties, as well as oxidative stability, making them ideal for low temperature applications such as in household cleaning compositions and personal and beauty care products.

In some embodiments, the branched fatty alcohols produced using methods described herein can contain between about 50% and about 90% carbon, or between about 5% and about 25% hydrogen. In other embodiments, the branched fatty alcohols produced using methods described herein can contain between about 65% and about 85% carbon, or between about 10% and about 15% hydrogen.

In some embodiments, the branched fatty alcohols produced in accordance with the disclosure herein comprises a $C_6$-$C_{26}$ branched fatty alcohol. In some embodiments, the branched fatty alcohol comprises a $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, or a $C_{26}$ branched fatty alcohol. In particular embodiments, the branched fatty alcohol is a $C_6$, $C_8$, $C_{10}$, $C_{12}$, $C_{13}$, $C_{14}$, $C_{15}$, $C_{16}$, $C_{17}$, or $C_{18}$ branched fatty alcohol. In certain embodiments, the hydroxyl group of the branched fatty alcohol is in the primary ($C_1$) position. In certain embodiment, the branched fatty alcohol is an iso-fatty alcohol or an anteiso-fatty alcohol. In exemplary embodiments, the branched fatty alcohol is selected from iso-$C_{7:0}$, iso-$C_{8:0}$, iso-$C_{10:0}$, iso-$C_{11:0}$, iso-$C_{12:0}$, iso-$C_{13:0}$, iso-$C_{14:0}$, iso-$C_{15:0}$, iso-$C_{16:0}$, iso-$C_{17:0}$, iso-$C_{18:0}$, iso-$C_{19:0}$, anteiso-$C_{7:0}$, anteiso-$C_{8:0}$, anteiso-$C_{9:0}$, anteiso-$C_{10:0}$, anteiso-$C_{11:0}$, anteiso-$C_{12:0}$, anteiso-$C_{13:0}$, anteiso-$C_{14:0}$, anteiso-$C_{15:0}$, anteiso-$C_{16:0}$, anteiso-$C_{17:0}$, anteiso-$C_{18:0}$, and anteiso-$C_{19:0}$ fatty alcohol.

In certain embodiments, the fatty alcohol product can comprise straight chain fatty alcohols. In other embodiments, the branched fatty alcohols produced by the host cells described herein can comprise one or more points of branching. In certain embodiments, the branched fatty alcohols produced by the host cells as described herein can comprise one or more cyclic moieties.

In some embodiments, the branched fatty alcohols can be unsaturated branched fatty alcohols. For example, the branched fatty alcohols produced in accordance with the present description can be monounsaturated branched fatty alcohols. In certain embodiments, the unsaturated branched fatty alcohol can be a C6:1, C7:1, C8:1, C9:1, C10:1, C11:1, C12:1, C13:1, C14:1, C15:1, C16:1, C17:1, C18:1, C19:1, C20:1, C21:1, C22:1, C23:1, C24:1, C25:1, or a C26:1 unsaturated branched fatty alcohol. In other embodiments, the branched fatty alcohol is unsaturated at the omega-7 position. In certain embodiments, the unsaturated branched fatty alcohol comprises a cis double bond.

In some embodiments, branched fatty alcohols are produced at a relative yield to a straight-chain fatty alcohol at about 20%, for example, at about 25%, 30%, 35%, 40%, 45%, 50%, 55%, 60%, or higher. In an exemplary embodiment, the total amount of branched fatty alcohols produced is estimated to about 45% to about 50% relative to the amount of straight-chain fatty alcohols produced by a host cell.

In any of the aspects described herein, the production yield of fatty alcohols, including branched fatty alcohols and straight chain fatty alcohol, is about 1 mg/L, 5 mg/L, 10 mg/L, 15 mg/L, 20 mg/L, 25 mg/L, about 50 mg/L, about 75 mg/L, about 100 mg/L, about 125 mg/L, about 150 mg/L, about 175 mg/L, about 200 mg/L, about 225 mg/L, about 250 mg/L, about 275 mg/L, about 300 mg/L, about 325 mg/L, about 350 mg/L, about 375 mg/L, about 400 mg/L, about 425 mg/L, about 450 mg/L, about 475 mg/L, about 500 mg/L, about 525 mg/L, about 550 mg/L, about 575 mg/L, about 600 mg/L, about 625 mg/L, about 650 mg/L, about 675 mg/L, about 700 mg/L, about 725 mg/L, about 750 mg/L, about 775 mg/L, about 800 mg/L, about 825 mg/L, about 850 mg/L, about 875 mg/L, about 900 mg/L, about 925 mg/L, about 950 mg/L, about 975 mg/L, about 1000 g/L, about 1050 mg/L, about 1075 mg/L, about 1100 mg/L, about 1125 mg/L, about 1150 mg/L, about 1175 mg/L, about 1200 mg/L, about 1225 mg/L, about 1250 mg/L, about 1275 mg/L, about 1300 mg/L, about 1325 mg/L, about 1350 mg/L, about 1375 mg/L, about 1400 mg/L, about 1425 mg/L, about 1450 mg/L, about 1475 mg/L, about 1500 mg/L, about 1525 mg/L, about 1550 mg/L, about 1575 mg/L, about 1600 mg/L, about 1625 mg/L, about 1650 mg/L, about 1675 mg/L, about 1700 mg/L, about 1725 mg/L, about 1750 mg/L, about 1775 mg/L, about 1800 mg/L, about 1825 mg/L, about 1850 mg/L, about 1875 mg/L, about 1900 mg/L, about 1925 mg/L, about 1950 mg/L, about 1975 mg/L, about 2000 mg/L, or more.

In another aspect, the branched fatty alcohol produced in accordance with the present invention is produced by culturing a host cell described herein in a medium having a low level of iron, under conditions sufficient to produce a branched fatty alcohol. In particular embodiments, the medium contains less than about 500 μM iron, less than about 400 μM iron, less than about 300 μM iron, less than about 200 μM iron, less than about 150 μM iron, less than about 100 μM iron, less than about 90 μM iron, less than about 80 μM iron, less than about 70 μM iron, less than about 60 μM iron, less than about 50 μM iron, less than about 40 μM iron, less than about 30 μM iron, less than about 20 μM iron, less than about 10 μM iron, or less than about 5 μM iron. In certain embodiments, the medium does not contain iron.

Bioproducts (e.g., surfactants and cleaning compositions) comprising microbially produced branched fatty alcohols and/or derivatives, produced using the fatty acid biosynthetic pathway, have not been produced from renewable sources and, as such, are new compositions of matter. These new bioproducts can be distinguished from organic compounds derived from petrochemical carbon on the basis of dual carbon-isotopic fingerprinting or $^{14}C$ dating. Additionally, the specific source of biosourced carbon (e.g., glucose vs. glycerol) can be determined by dual carbon-isotopic fingerprinting (see, e.g., U.S. Pat. No. 7,169,588, which is herein incorporated by reference).

The ability to distinguish bioproducts from petroleum based organic compounds is beneficial in tracking these materials in commerce. Organic compounds or chemicals comprising both biologically based and petroleum based carbon isotope profiles may be distinguished from organic compounds and chemicals made only of petroleum based materials. Hence, the surfactants and cleaning compositions of the present invention be followed in commerce on the basis of their unique carbon isotope profile.

Surfactants or cleaning compositions produced in accordance with the present disclosure can be distinguished from petroleum-derived compounds by comparing the stable carbon isotope ratio ($^{13}C/^{12}C$) of each. The $^{13}C/^{12}C$ ratio in a given bioproduct is a consequence of the $^{13}C/^{12}C$ ratio in atmospheric carbon dioxide at the time the carbon dioxide is fixed. It also reflects the precise metabolic pathway. Regional variations also occur. Petroleum, $C_3$ plants (the broadleaf), $C_4$ plants (the grasses), and marine carbonates all show significant differences in $^{13}C/^{12}C$ and the corresponding $\delta^{13}C$ values. Moreover, lipid matter of $C_3$ and $C_4$ plants analyze differently than materials derived from the carbohydrate components of the same plants as a consequence of the metabolic pathway.

Within the precision of measurement, $^{13}C$ shows large variations due to isotopic fractionation effects, the most significant of which for bioproducts is the photosynthetic mechanism. The major cause of differences in the carbon isotope ratio in plants is closely associated with differences in the pathway of photosynthetic carbon metabolism in the plants, particularly the reaction occurring during the primary carboxylation (i.e., the initial fixation of atmospheric $CO_2$). Two large classes of vegetation are those that incorporate the "$C_3$" (or Calvin-Benson) photosynthetic cycle and those that incorporate the "$C_4$" (or Hatch-Slack) photosynthetic cycle.

In $C_3$ plants, the primary $CO_2$ fixation/carboxylation reaction involves the enzyme ribulose-1,5-diphosphate carboxylase, and the first stable product is a 3-carbon compound. $C_3$ plants, such as hardwoods and conifers, are dominant in the temperate climate zones.

In $C_4$ plants, an additional carboxylation reaction involving phosphoenol-pyruvate carboxylase, is the primary carboxylation reaction. The first stable carbon compound is a 4-carbon acid that is subsequently decarboxylated. The $CO_2$ thus released is refixed by the $C_3$ cycle. Examples of $C_4$ plants are tropical grasses, corn, and sugar cane.

Both $C_4$ and $C_3$ plants exhibit a range of $^{13}C/^{12}C$ isotopic ratios, but typical values are about −7 to about −13 per mil for $C_4$ plants and about −19 to about −27 per mil for $C_3$ plants (see, e.g., Stuiver et al., *Radiocarbon,* 19: 355 (1977)). Coal and petroleum fall generally in this latter range. The $^{13}C$ measurement scale was originally defined by a zero set by Pee Dee Belemnite (PDB) limestone, where values are given in parts per thousand deviations from this material. The "$\delta^{13}C$" values are expressed in parts per thousand (per mil), abbreviated, ‰, and are calculated as follows:

$$\delta^{13}C(‰)=[(^{13}C/^{12}C)_{sample}-(^{13}C/^{12}C)_{standard}]/(^{13}C/^{12}C)_{standard}\times 1000$$

Since the PDB reference material (RM) has been exhausted, a series of alternative RMs have been developed in cooperation with the IAEA, USGS, NIST, and other selected international isotope laboratories. Notations for the per mil deviations from PDB is $\delta^{13}C$. Measurements are made on $CO_2$ by high precision stable ratio mass spectrometry (IRMS) on molecular ions of masses 44, 45, and 46.

The branched fatty alcohol and derivative compositions as well as the surfactants or cleaning compositions described herein include bioproducts produced by any of the methods described herein. The surfactants and cleaning compositions can have a $\delta^{13}C$ of about −28 or greater, about −27 or greater, −20 or greater, −18 or greater, −15.4 or greater, −15 or greater, −13 or greater, −10 or greater, or −8 or greater. A surfactant or cleaning composition so produced can have a $\delta^{13}C$ of about −30 to about −15, about −27 to about −19, about −25 to about −21, about −15 to about −5, about −15.4 to about −10.9, about −13.92 to about −13.84, about −13 to about −7, or about −13 to about −10. For example it can have a $\delta^{13}C$ of about −10, −11, −12, or −12.3.

The surfactants or cleaning compositions herein can also be distinguished from petroleum-derived compounds by comparing the amount of $^{14}C$ in each compound. Because $^{14}C$ has a nuclear half life of 5730 years, petroleum based chemicals containing "older" carbon can be distinguished from bioproducts which contain "newer" carbon (see, e.g., Currie, "Source Apportionment of Atmospheric Particles," *Characterization of Environmental Particles*, J. Buffle and H. P. van Leeuwen, Eds., 1 of Vol. I of the IUPAC Environmental Analytical Chemistry Series (Lewis Publishers, Inc.) (1992), pp. 3-74).

The basic assumption in radiocarbon dating is that the constancy of $^{14}C$ concentration in the atmosphere leads to the constancy of $^{14}C$ in living organisms. But because of atmospheric nuclear testing since 1950 and the burning of fossil fuel since 1850, $^{14}C$ has acquired a second, geochemical time characteristic. Its concentration in atmospheric $CO_2$, and hence in the living biosphere, approximately doubled at the peak of nuclear testing, in the mid-1960s. It has since been gradually returning to the steady-state cosmogenic (atmospheric) baseline isotope rate ($^{14}C/^{12}C$) of about $1.2\times10^{-12}$, with an approximate relaxation "half-life" of 7-10 years. (This latter half-life is not to be taken literally; rather, the detailed atmospheric nuclear input/decay function to trace the variation of atmospheric and biospheric $^{14}C$ since the onset of the nuclear age should be used).

It is this latter biospheric $^{14}C$ time characteristic that holds out the promise of annual dating of recent biospheric carbon. $^{14}C$ can be measured by accelerator mass spectrometry (AMS), with results given in units of "fraction of modern carbon" ($f_M$). $f_M$ is defined by National Institute of Standards and Technology (NIST) Standard Reference Materials (SRMs) 4990B and 4990C. As used herein, "fraction of modern carbon" or "$f_M$" has the same meaning as defined by National Institute of Standards and Technology (NIST) Standard Reference Materials (SRMs) 4990B and 4990C, known as oxalic acids standards HOxI and HOxII, respectively. The fundamental definition relates to 0.95 times the $^{14}C/^{12}C$ isotope ratio HOxI (referenced to AD 1950). This is roughly equivalent to decay-corrected pre-Industrial Revolution wood. For the current living biosphere (plant material), $f_M$ is approximately 1.1.

The invention provides surfactants or cleaning compositions, having an $f_M$ $^{14}C$ of at least about 1. An exemplary surfactant has an $f_M$ $^{14}C$ of at least about 1.01, of at least about 1.5, an $f_M$ $^{14}C$ of about 1 to about 1.5, an $f_M$ $^{14}C$ of about 1.04 to about 1.18, or an $f_M$ $^{14}C$ of about 1.111 to about 1.124. Likewise, an exemplary cleaning composition has an $f_M$ $^{14}C$ of at least about 1.01, of at least about 1.5, an $f_M$ $^{14}C$ of about 1 to about 1.5, an $f_M$ $^{14}C$ of about 1.04 to about 1.18, or an $f_M$ $^{14}C$ of about 1.111 to about 1.124.

Another measurement of $^{14}C$ is known as the percent of modern carbon, pMC. For an archaeologist or geologist using $^{14}C$ dates, AD 1950 equals "zero years old". This also represents 100 pMC. "Bomb carbon" in the atmosphere reached almost twice the normal level in 1963 at the peak of thermonuclear weapons testing. Its distribution within the atmosphere has been approximated since its appearance, showing values that are greater than 100 pMC for plants and animals living since AD 1950. It has gradually decreased over time with today's value being near 107.5 pMC. This means that a fresh biomass material, such as corn, would give a $^{14}C$ signature near 107.5 pMC. Petroleum based compounds will have a pMC value of zero. Combining fossil carbon with present day carbon will result in a dilution of the present day pMC content. By presuming 107.5 pMC represents the $^{14}C$ content of present day biomass materials and 0 pMC represents the $^{14}C$ content of petroleum based products, the measured pMC value for that material will reflect the proportions of the two component types. For example, a material derived 100% from present day soybeans would give a radiocarbon signature near 107.5 pMC. If that material was diluted 50% with petroleum based products, it would give a radiocarbon signature of approximately 54 pMC.

A biologically based carbon content is derived by assigning "100%" equal to 107.5 pMC and "0%" equal to 0 pMC. For example, a sample measuring 99 pMC will give an equivalent biologically based carbon content of 93%. This value is referred to as the mean biologically based carbon result and assumes all the components within the analyzed material originated either from present day biological material or petroleum based material.

A surfactant or a cleaning composition comprising branched fatty alcohols and/or derivatives described herein can have a pMC of at least about 50, 60, 70, 75, 80, 85, 90, 95, 96, 97, 98, 99, or 100. In other instances, such a surfactant or cleaning composition can have a pMC of between about 50 and about 100; between about 60 and about 100; between about 70 and about 100; between about 80 and about 100; between about 85 and about 100; between about 87 and about 98; or between about 90 and about 95. In yet other instances, it can have a pMC of about 90, 91, 92, 93, 94, or 94.2.

Accordingly the present invention is drawn to a branched fatty alcohol or a derivative thereof produced by an engineered microbial host cell. The engineered microbial host cell expresses: (a) a first gene encoding a first polypeptide having at least about 85% sequence identity to the amino acid sequence of any one of SEQ ID NOs: 1, 3, 5, 7, 9, 11, 13 and 15, or of a variant thereof; and (b) a second gene encoding a second polypeptide having at least about 85% sequence identity to the amino acid sequence of any one or SEQ ID NOs:24, 26, 28, 30, 32, 34, 36, and 38, or of a variant thereof, and is cultured in the presence of one or more biological substrates of the first and second polypeptides. In some embodiments, the microbial host cell is engineered to express a third gene encoding a third polypeptide comprising an amino acid sequence having at least an about 85% sequence identity to the amino acid sequence of any one of SEQ ID NOs:47, 49, 51, 53, 55, 57, 59, and 61, or of a variant thereof. In some embodiments, the microbial host cell is engineered to express a fourth gene encoding a fourth polypeptide comprising an amino acid sequence having at least an about 85% sequence identity to the amino acid sequence of any one of SEQ ID NO:69, 71, 73, 75, 77, 79, 81, and 83, or of a variant thereof. In any of the above embodiments, the microbial host cell is engineered to express a beta-ketoacyl ACP synthase gene in the host cell, wherein the beta-ketoacyl ACP gene encodes a polypeptide comprising an amino acid sequence having at least about 85% sequence identity to the amino acid sequence of any one of SEQ ID NOs:90, 92, 94, 96, 98, 100, 102, 104, 106, 108, 110, 112, 114, 116, 118, and 120, or of a variant thereof. The beta-ketoacyl ACP synthase is, for example, a FabH that has specificity for branched-chain acyl-CoA substrates. In any of the embodiments above, the microbial host cell is engineered to express a fatty aldehyde biosynthesis polypeptide, or a variant thereof. In any of the embodiments above, the microbial host cell is engineered to express an acyl-ACP reductase polypeptide or a variant thereof, to modify the expression of a gene encoding a fatty acid synthase, which comprise expressing a gene encoding a thioesterase in the microbial host cell, to express a gene encoding an alcohol dehydrogenase or a variant thereof, and/or to express an attenuated level of a fatty acid degradation enzyme relative to a wild type host cell. The fatty acid degradation enzyme is, for example, an acyl-CoA synthase.

Branched Fatty Alcohol Derivatives

A derivative of the branched fatty alcohol produced in accordance to the methods described herein can be produced by converting the isolated branched fatty alcohol into a branched fatty alcohol derivative thereof. The branched fatty alcohol derivative can be any suitable branched fatty alcohol derivative selected from, for example, a branched fatty ether sulfate, a branched fatty phosphate ester, an alkylbenzyldimethyl-ammonium chloride, a branched fatty amine oxide, a branched fatty alcohol sulfate, a branched alkyl polyglucoside, a branched alkyl glyceryl ether sulfonate, and a branched ethoxylated fatty alcohol. Typically, the branched fatty alcohol derivative comprises an alkyl group that is about 6 to about 26 carbons in length. Preferably, the branched fatty alcohol comprises an alkyl group that is about 7, 8, 9, 10, 11, 12, 13, 14, 15, 16, 17, or 18 carbons in length. In certain embodiments, the alkyl group comprises one or more points of branching. In this regard, the number of carbons in the alkyl group refers to the hydrocarbon group derived from the branched fatty alcohol, and not to any carbon atoms added in the preparation of the branched fatty alcohol derivative, such as polyethoxy groups and the like.

As used herein, the term "fatty ether sulfate" is the same as "alkyl ether sulfate" wherein the alkyl residue is a fatty residue, and denotes a compound of the structure: $RO(CH_2CH_2O)_n—SO_3H$, wherein R is a $C_6$-$C_{26}$ alkyl group as defined herein, and n is an integer of 1 to about 50. Fatty ether sulfate can also refer to the salt denoted by $RO(CH_2CH_2O)_nSO_3X$, where n and R are as defined above and X is a cation. An exemplary fatty ether sulfate salt is a sodium salt, for example, $RO(CH_2CH_2O)_nSO_3Na$. In an exemplary embodiment, the R group comprises one or more points of branching.

As used herein, the term "fatty alcohol sulfate" denotes a compound of the structure: $ROSO_3H$ wherein R is a $C_8$-$C_{26}$ alkyl group. Fatty alcohol sulfate can also refer to the salt of the above structure, denoted by $ROSO_3X$ where R is as defined above and X is a cation. An exemplary fatty alcohol sulfate salt is a sodium salt, for example, $ROSO_3Na$. In an exemplary embodiment, the R group comprises one or more points of branching.

As used herein, the term "fatty phosphate ester" is the same as "alkyl phosphate ester" wherein the alkyl residue is a fatty residue, and denotes a compound of the structure:

$$ROP(O)(OH)_2$$

As used herein, alkylbenzyldimethylammonium chlorides have the structure:

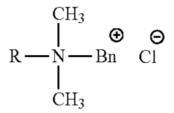

wherein R is a $C_8$-$C_{26}$ alkyl group as defined herein. For example, the alkyl group of R comprises one or more points of branching.

As used herein, the term "fatty amine oxide" is the same as "alkyl amine oxide" wherein the alkyl residue is a fatty residue as defined herein, and denotes a compound of the structure:

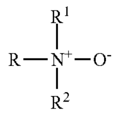

wherein R is a $C_8$-$C_{26}$ alkyl group as defined herein and wherein $R^1$ and $R^2$ are $C_1$-$C_{26}$ alkyl groups, preferably $C_1$-$C_6$ alkyl groups. Preferably the alkyl groups of R, $R^1$ and $R^2$ each independently comprises one or more points of branching.

Alkyl polyglucosides have the structure: $RO(C_nH_{2n}O)_tZ_x$ wherein R is a $C_8$-$C_{26}$ alkyl group, preferably comprising one or more points of branching, Z is a glucose residue, n is 2 or 3, t is from 0 to 10, and x is from about 1 to 10, preferably from about 1.5 to 4.

Alkyl glyceryl ether sulfonates have the structure:

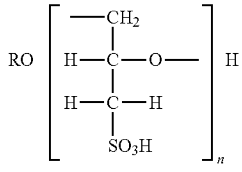

wherein R is a $C_8$-$C_{26}$ alkyl group as defined herein, preferably comprising one or more points of branching, and n is an integer from 1 to 4, for example, 1, 2, 3, or 4.

As used herein, the term "fatty alcohol alkoxylate" is the same as "alkoxylated fatty alcohol" and denotes a compound of the structure: $RO(CH_2CH_2)_nOH$ wherein R is a $C_8$-$C_{26}$ alkyl group as defined herein and n is an integer from 1 to about 50. Preferably R comprises one or more points of branching.

The branched fatty alcohol derivatives can be produced by any suitable method, many of which are known in the art. See, e.g., "Handbook on Soaps, Detergents, and Acid Slurry," $2^{nd}$ ed., NIIR Board, Asia Pacific Business Press, Inc., Delhi, India.

In one embodiment, the branched fatty alcohol derivative is an ethoxylated branched fatty alcohol, which is also known in the art as a branched fatty alcohol ethoxylate, and has a structure as described herein. Preferably, the ethoxylated branched fatty alcohol contains from about 1 to about 50 moles of ethylene oxide per mole of branched fatty alcohol.

Surfactants or Detersive Surfactants

A surfactant composition of the present invention can comprise about 0.001 wt. % to about 100 wt. % of microbially produced branched fatty alcohols and/or derivatives thereof. Preferably, a surfactant composition is a blend of a microbially produced branched fatty alcohol and/or derivative in combination with one or more other surfactants and/or surfactant systems that have been derived from similar (e.g., microbially derived) or different sources (e.g., synthetic, petroleum-derived). Those other surfactants and/or surfactant systems can confer additional desirable properties. In some embodiments, the one or more other surfactants and/or surfactant systems that are blended with the microbially produced branched fatty alcohols and/or derivatives can comprise linear or branched fatty alcohol derivatives, or they can be other types of surfactants such as, cationic surfactants, anionic surfactants and/or amphoteric/zwitterionic surfactants. These other surfactants and/or surfactants systems are collectively referred to as "co-surfactants" herein. For example, a surfactant composition of the invention can be a blend of a microbially produced branched fatty alcohol and/or derivative composition prepared in accordance with the disclosure herein, and a cationic surfactant derived from a petrochemical source, and the resulting surfactant composition only has good cleaning properties but also contributes certain disinfecting and/sanitizing benefits.

The cleaning composition of the invention can comprise, in addition to the microbially produced branched fatty alcohols and/or derivatives, or the surfactants comprising such branched materials and/or derivatives, co-surfactants selected from nonionic surfactants, anionic surfactants, cationic surfactants, ampholytic surfactants, squitterionic surfactants, semi-polar nonionic surfactants, and mixtures thereof. When present, the total amount of surfactants, including the microbially produced branched fatty alcohols and/or derivatives thereof, and the co-surfactants, is typically present at a level of about 0.1 wt. % or higher (e.g., about 1.0 wt. % or higher, about 10 wt. % or higher, about 25 wt. % or higher, about 50 wt. % or higher, about 70 wt. % or higher). For example, the total amount of surfactant in a cleaning composition can vary from about 0.1 wt. % to about 80 wt. % (e.g., from about 0.1 wt. % to about 40 wt. %, from about 0.1 wt % to about 12 wt. %, from about 1.0 wt. % to about 50 wt. %, or from about 5 wt. % to about 40 wt. %).

Various known surfactants can be suitable co-surfactants. In some embodiments, the co-surfactant can comprise an anionic surfactant. In certain embodiments, the amount of one or more anionic surfactants in the cleaning composition can be, for example, about 1 wt. % or more (e.g., about 5 wt. % or more, about 10 wt. % or more, about 20 wt. % or more, about 30 wt. % or more, about 40 wt. % or more). For example, the amount of one or more anionic surfactants in the cleaning composition can vary from about 1 wt. % to about 40 wt. %. Suitable anionic surfactants include, for example, linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl esters, alkyl- or alkenylsuccinic acid or soap. In some embodiments, an anionic surfactant is, for example, a $C_{10}$-$C_{18}$ alkyl alkoxy ester ($AE_xS$), wherein x is from 1-30. Other suitable anionic surfactants can be found in International Publication WO98/39403, Surface Active Agents and Detergents (Vol. 1, & II, by Schwartz, Perry and Berch), and U.S. Pat. Nos. 3,929,678, 6,020,303, 6,060,443, 6,008,181, International Publications WO 99/05243, WO 99/05242 and WO 99/05244, the relevant disclosures of which are incorporated herein by reference.

In another embodiment, the co-surfactant can comprise a cationic surfactant. Suitable cationic surfactants include, for example, those having long-chain hydrocarbyl groups. Examples include ammonium surfactants such as alkyltrimethylammonium halogenides, and surfactants having the formula $[R^2(OR^3)y][R^4(OR^3)y]_2R^5N{+}X^-$, wherein $R^2$ is an alkyl or alkyl benzyl group having from about 8 to about 18 carbon atoms in the alkyl chain, each $R^3$ is independently selected from the group consisting of $—CH_2CH_2—$, $CH_2CH(CH_3)—$, $CH_2(CH(CH_2OH))—$, $CH_2CH_2CH_2—$, and mixtures thereof; each $R^4$ is selected from the group consisting of $C_1$-$C_4$ alkyl, $C_1$-$C_4$ hydroxyalkyl, benzyl ring structures formed by joining the two $R^4$ groups, $—CH_2CHOH—$ $CHOHCOR^6CHOHCH_2OH$ wherein $R^6$ is any hexose or hexose polymer having a molecular weight less than about 1,000, and hydrogen, when y is not 0; $R^5$ is the same as $R^4$ or is an alkyl chain wherein the total number of carbon atoms of $R^2$ plus $R^5$ is not more than about 18; each y is from 0 to about 10 and the sum of the y values is from 0 to about 15; and X is any compatible anion.

Certain quaternary ammonium surfactant may also be suitable as cationic co-surfactants, and examples of those are described in International Publication WO 98/39403. Examples of suitable quaternary ammonium compounds include coconut trimethyl ammonium chloride or bromide; coconut methyl dihydroxyethyl ammonium chloride or bromide; decyl triethyl ammonium chloride; decyl di methyl hydroxyethyl ammonium chloride or bromide; $C_{12-15}$ dimethyl hydroxyethyl ammonium chloride or bromide; coconut dimethyl hydroxyethyl ammonium chloride or bromide; myristyl trimethyl ammonium methyl sulphate; lauryl dimethyl benzyl ammonium chloride or bromide; lauryl di methyl (ethenoxy) 4 ammonium chloride or bromide. Other cationic surfactants have been described in U.S. Pat. Nos. 4,228,044, 4,228,042, 4,239,660 4,260,529 6,136,769, 6,004,922, 6,022,844, and 6,221,825, International Publications WO 98/35002, WO 98/35003, WO 98/35004, WO 98/35005, WO 98/35006, and WO 00/47708, as well as European Patent Application EP 000,224. When included herein, the surfactant/detergent and the cleaning/treatment compositions of the present invention can comprise, for example, from about 0.2 wt. % to about 25 wt. %, preferably from about 1 wt. % to about 8 wt. % by weight of cationic surfactants.

In certain embodiments, co-surfactants can comprise nonionic surfactants. Polyethylene, polypropylene, and polybutylene oxide condensates of alkyl phenols are suitable, with the polyethylene oxide condensates being preferred. They include the condensation products of alkyl phenols having an alkyl group having about 6 to about 14 carbon atoms, preferably from about 8 to about 14 carbon atoms, in either a straight-chain or branched-chain configuration, with alkylene oxide. In particular embodiments, the ethylene oxide is present in an amount of from about 2 to about 25 moles (e.g., from about 3 to about 15 moles) of ethylene oxide per mole of alkyl phenol. Commercially available nonionic surfactants of this type include Igepal™ C0-630 (The GAF Corp.), Triton™ X-45, X-114, X-100 and X-102 (Dow Chemicals). These surfactants are commonly referred to as alkylphenol alkoxylates (e.g., alkyl phenol ethoxylates).

Moreover, condensation products of primary and secondary aliphatic alcohols with from about 1 to about 25 moles of ethylene oxide are suitable nonionic co-surfactants. The alkyl chain of the aliphatic alcohol can be straight or branched, primary or secondary, and generally can contain about 8 to about 22 (e.g., about 8 to about 20, or about 10 to about 18) carbon atoms with about 2 to about 10 moles (e.g., about 2 to about 5 moles) of ethylene oxide per mole of alcohol present in the condensation products. Examples of commercially available nonionic surfactants of this type include Tergitol™ 15-S-9, Tergitol™ 24-L-6 NMW (Union Carbide); Neodol™ 45-9, Neodol™ 23-3, Neodol™ 45-7, Neodol™ 45-5 (Shell Chemical), Kyro™ EOB (Procter & Gamble), and Genapol LA 030 or 050 (Hoechst).

Further examples of nonionic co-surfactants include $C_{12}$-$C_{18}$ alkyl ethoxylates (e.g., NEODOL® nonionic surfactants (Shell)), $C_6$-$C_{12}$ alkyl phenol alkoxylates wherein the alkoxylate units are a mixture of ethyleneoxy and propyleneoxy units, $C_{12}$-$C_{18}$ alcohol and $C_6$-$C_{12}$ alkyl phenol condensates with ethylene oxide/propylene oxide block alkyl polyamine ethoxylates (e.g., PLURONIC® (BASF)), $C_{14}$-$C_{22}$ mid-chain branched alcohols as described in U.S. Pat. No. 6,150,322, $C_{14}$-$C_{22}$ mid-chain branched alkyl alkoxylates, $BAE_x$, wherein x is from 1-30, as described in U.S. Pat. Nos. 6,153,577, 6,020,303 and 6,093,856, alkylpolysaccharides as described in U.S. Pat. No. 4,565,647, alkylpolyglycosides as described in U.S. Pat. No. 4,483,780 and U.S. Pat. No. 4,483,779, polyhydroxy detergent acid amides as described in U.S. Pat. No. 5,332,528, or ether capped poly(oxyalkylated) alcohol surfactants as described in U.S. Pat. No. 6,482,994 and International Publication WO 01/42408.

Semi-polar nonionic surfactants can also be suitable. They include, e.g., water-soluble amine oxides containing 1 alkyl moiety of from about 10 to about 18 carbon atoms and 2 moieties selected from alkyl or hydroxyalkyl moieties containing about 1 to about 3 carbon atoms, water-soluble phosphine oxides containing 1 alkyl moiety of about 10 to about 18 carbon atoms and 2 moieties selected from alkyl or hydroxyalkyl moieties containing about 1 to about 3 carbon atoms; and water-soluble sulfoxides containing 1 alkyl moiety of about 10 to about 18 carbon atoms and a moiety selected from alkyl or hydroxyalkyl moieties of about 1 to about 3 carbon atoms. Semi-polar nonionic surfactants have been described in, e.g., International Publication WO 01/32816, U.S. Pat. Nos. 4,681,704 and 4,133,779.

Moreover, alkylpolysaccharides, such as those described in U.S. Pat. No. 4,565,647, having a hydrophobic group containing about 6 to about 30 carbon atoms (e.g., from about 10 to about 16 carbon atoms) and a polysaccharide, can also be suitable semi-polar nonionic co-surfactants. Others have been described in, for example, International Publication WO 98/39403. When included herein, the cleaning/treatment compositions of the present invention can comprise, for example, about 0.2 wt. % or more (e.g., about 1 wt. % or more, about 5 wt. % or more, or about 8 wt. % or more) of such semi-polar nonionic surfactants. For example, the cleaning compositions of the invention can comprise about 0.2 wt. % to about 15 wt. % (e.g., about 1 wt. % to about 10 wt. %) of semi-polar nonionic surfactants.

In certain embodiments, the co-surfactants comprises ampholytic surfactants. Ampholytic surfactants can be broadly described as aliphatic derivatives of secondary or tertiary amines, or aliphatic derivatives of heterocyclic secondary and tertiary amines in which the aliphatic radical can be straight- or branched-chain. One of the aliphatic substituents can contain at least about 8 carbon atoms (e.g., from about 8 to about 18 carbon atoms), and at least another contains an anionic water-solubilizing group, e.g. carboxy, sulfonate, or sulfate. Ampholytica surfactants have been described in, for example, U.S. Pat. No. 3,929,678. When included therein, a cleaning composition of the invention can comprise, for example, about 0.2 wt. % to about 15 wt. % (e.g., about 1 wt. % to about 10 wt. %) of ampholytic surfactants.

In certain other embodiments, especially in personal care cleaning/treatment compositions, zwitterionic surfactants are included as co-surfactants. These surfactants can be broadly described as derivatives of secondary and tertiary amines, derivatives of heterocyclic secondary and tertiary amines, or derivatives of quaternary ammonium, quaternary phosphonium or tertiary sulfonium compounds. Zwitterionic surfactants have been described in, for example, U.S. Pat. No. 3,929,678. When included therein, a surfactant/detergent or cleaning/treatment composition of the invention can comprise, for example, about 0.2 wt. % to about 15 wt. % (e.g., about 1 wt. % to about 10 wt. %) of zwitterionic surfactants.

In further embodiments, primary or tertiary amines can be included as co-surfactants. Suitable primary amines include amines according to the formula $R^1NH_2$ wherein $R^1$ is a $C_6$-$C_{12}$, preferably $C_6$-$C_{10}$, alkyl chain; or $R_4X(CH_2)n$, wherein X is —O—, —C(O)NH— or —NH—, $R^4$ is a $C_6$-$C_{12}$ alkyl chain, n is between 1 to 5 (e.g., 3). The alkyl chain of $R^1$ can be straight or branched, and can be interrupted with up to 12, but preferably less than 5 ethylene oxide moieties. Preferred amines include n-alkyl amines, selected from, for example, 1-hexylamine, 1-octylamine, 1-decylamine and laurylamine, $C_8$-$C_{10}$ oxypropylamine, octyloxypropylamine, 2-ethylhexyl-oxypropylamine, lauryl amido propylamine or amido propylamine. Suitable tertiary amines include those having the formula $R^1R^2R^3N$ wherein $R^1$ and $R^2$ are $C_1$-$C_8$ alkylchains, $R^3$ is either a $C_6$-$C_{12}$, preferably $C_6$-$C_{10}$, alkyl chain, or $R^3$ is $R^4X(CH_2)n$, whereby X is —O—, —C(O)NH— or —NH—, $R^4$ is a $C_4$-$C_{12}$, n is between 1 and 5 (e.g., 2, 3, or 4), $R^5$ is H or $C_1$-$C_2$ alkyl, and x is between 1 and 6. $R^3$ and $R^4$ may be linear or branched. The alkyl chain of $R^3$ can be interrupted with up to 12, but preferably less than 5, ethylene oxide moieties. Preferred tertiary amines include, for example, 1-hexylamine, 1-octylamine, 1-decylamine, 1-dodecylamine, n-dodecyldimethylamine, bishydroxyethylcoconutalkylamine, oleylamine(7)ethoxylated, lauryl amido propylamine, and cocoamido propylamine. Other useful detersive surfactants have been described in the prior art, for example, in U.S. Pat. Nos. 3,664,961, 3,919,678, 4,222,905, and 4,239,659.

In some embodiments, the detergent/cleaning composition of the invention comprises greater than about 5 wt. % anionic surfactant and/or less than about 25 wt. % nonionic surfactant. For example, the composition comprises greater than about 10 wt. % anionic surfactants. In another example, the composition comprises less than 15%, more preferably, less than 12% nonionic surfactants.

The total amount of surfactants included in a cleaning composition of the invention is typically about 0.1 wt. % or more (e.g., about 1 wt. % or more, about 10 wt. % or more, about 25 wt. % or more, about 50 wt. % or more, about 60 wt. % or more, about 70 wt. % or more). An exemplary cleaning composition of the invention comprises about 0.1 wt. % to about 80 wt. % total surfactants (e.g., about 1 wt. % to about 50 wt. %, about 10 wt. % to about 40 wt. %, about 20 wt. % to about 35 wt. %) of total surfactants, including the microbially produced branched fatty alcohols and/or derivatives thereof and co-surfactants.

One criteria based on which to the type(s) and amount(s) of surfactants to be included in cleaning compositions can be determined is compatibility with the enzyme components present in the cleaning compositions. For example, in liquid or gel compositions, the cleaning composition (including all the surfactants, which are, for example, pre-formulated into a surfactant package) is prepared such that it promotes, or at least does not degrade, the stability of any enzyme in the cleaning composition.

A surfactant composition of the present invention, or a surfactant package, which can be formulated and subsequently included in a cleaning composition, can be in any form, for example, a liquid; a solid such as a powder, granules, agglomerate, paste, tablet, pouches, bar; a gel; an emulsion; or in a suitable form to be delivered in dual-compartment containers. The composition can also be formulated into a spray or foam detergent, premoistened wipes (e.g., the cleaning composition in combination with a nonwoven material as described, for example, in U.S. Pat. No. 6,121,165), dry wipes (e.g., a cleaning composition in combination with a nonwoven material, activated with water by a consumer, as described, for example, in U.S. Pat. No. 5,980,931), and other homogeneous or multiphase consumer cleaning product forms.

Cleaning Compositions

Surfactant compositions comprising branched fatty alcohols and/or derivatives thereof, e.g., sulfate, alkoxylated or alkoxylated sulfate derivatives, are particularly suitable as soil detachment-promoting ingredients of laundry detergents, dishwashing liquids and powders, and various other cleaning compositions. They exhibit good dissolving power especially when faced with greasy soils, and it is particular advantageous that they display the outstanding soil-detaching power even at low washing temperatures.

The branched fatty alcohol/derivative compositions of the present invention can be included or blended into a surfactant package as described above, which comprises about 0.0001 wt. % to about 100 wt. % of one or more branched fatty alcohols and/or derivatives produced by a genetically engineered host cell or microbe. That surfactant package can then be blended into a cleaning composition to impart detergency and cleaning power to the cleaning composition. In alternative embodiments, the branched fatty alcohols and/or derivatives thereof produced by the host cell or microbe can be blended into a cleaning composition directly, in an amount of about 0.001 wt. % or more (e.g., about 0.001 wt. % or more, about 0.1 wt. % or more, about 1 wt. % or more, about 10 wt. % or more, about 20 wt. % or more, or about 40 wt. % or more) based on the total weight of the cleaning composition. For example, the branched fatty alcohols and/or derivatives thereof can be blended into a composition in an amount of about 0.001 wt. % to about 50 wt. % (e.g., about 0.01 wt. % to about 45 wt. %, about 0.1 wt. % to about 40 wt. %, about 1 wt. % to about 35 wt. %). Accordingly, a cleaning composition of the present invention, in either a solid form (e.g., a tablet, granule, powder, or compact), or a liquid form (e.g., a fluid, gel, paste, emulsion, or concentrate) can comprise about 0.001 wt. % to about 50 wt. % of microbially produced branched fatty alcohols and/or derivatives thereof. For example, a cleaning composition of the invention can comprise about 0.5 wt. % to about 44 wt. % of microbially produced branched fatty alcohols and/or derivatives thereof. Preferably, the cleaning composition comprises about 1 wt. % to about 30 wt. % of microbially produced branched fatty alcohols and/or derivatives.

Alternatively, a cleaning composition of the present invention can comprise about 0.001 wt. % to about 80 wt. % of a surfactant package formulated to comprise about 0.001 wt. % to about 100 wt. % of microbially produced branched fatty alcohols and/or derivatives. For example, a cleaning composition of the present invention can comprise about 0.1 wt. % to about 50 wt. % of such a surfactant package. The surfactant package can comprise other surfactants (i.e., co-surfactants), which can include surfactants derived from similar (e.g., microbially-produced surfactant) or different sources (e.g., petroleum-derived surfactants). In a particular embodiment, however, the surfactant package can comprise mostly or exclusively of branched fatty alcohols and/or derivatives produced by a host cell or a microbe as described herein.

Industrial Cleaning Compositions, Household Cleaning Compositions & Personal Care Cleaning Compositions In certain embodiments, the cleaning composition of the present invention is a liquid or solid laundry detergent composition. In some embodiments, the cleaning composition is a hard surface cleaning composition, wherein the hard surface cleaning composition preferably impregnates a nonwoven substrate. As used herein, “impregnate” means that the hard surface cleaning composition is placed in contact with a nonwoven substrate such that at least a portion of the nonwoven substrate is penetrated by the hard surface cleaning composition. For example, the hard surface cleaning composition preferably saturates the nonwoven substrate. In other embodiments, the cleaning composition of the present invention is a car care composition, which is useful for cleaning various surfaces such as hard wood, tile, ceramic, plastic, leather, metal, and/or glass. In some embodiments, the cleaning composition is a dish-washing composition, such as, for example, a liquid hand dishwashing composition, a solid automatic dishwashing composition, a liquid automatic dishwashing composition, and a tab/unit dose form automatic dishwashing composition.

In further embodiments, the cleaning composition can be used in industrial environments for cleaning of various equipment, machinery, and for use in oil drilling operations. For example, the cleaning composition of the present invention can be particularly suited in environments wherein it comes into contact with free hardness and in compositions that require hardness tolerant surfactant systems, such as when used to aid oil drilling.

In some embodiments, the cleaning composition of the invention can be formulated into personal or pet care compositions such as shampoos, body washes, or liquid or solid soaps.

Common cleaning adjuncts applicable to most cleaning compositions, including, household cleaning compositions, and personal care compositions and the like, include builders, enzymes, polymers, suds boosters, suds suppressors (antifoam), dyes, fillers, germicides, hydrotropes, anti-oxidants, perfumes, pro-perfumes, enzyme stabilizing agents, pigments, and the like. In some embodiments, the cleaning composition is a liquid cleaning composition, wherein the composition comprises one or more selected from solvents, chelating agents, dispersants, and water. In other embodiments, the cleaning composition is a solid, wherein the composition further comprises, for example, an inorganic filler salt. Inorganic filler salts are conventional ingredients of solid cleaning compositions, present in substantial amounts, varying from, for example, about 10 wt. % to about 35 wt. %. Suitable filler salts include, for example, alkali and alkaline-earth metal salts of sulfates and chlorides. An exemplary filler salt is sodium sulfate.

Household cleaning compositions, including, e.g., laundry detergents and household surface cleaners typically comprise certain additional, in some embodiments, more specialized, ingredients or cleaning adjuncts selected from one or more of: bleaches, bleach activators, catalytic materials, suds boosters, suds suppressors (antifoams), diverse active ingredients or specialized materials such as dispersant polymers (e.g., dispersant polymers sold by BASF or Dow Chemicals), silver-care, anti-tarnish and/or anti-corrosion agents, dyes, germicides, alkalinity sources, hydrotropes, anti-oxidants, enzyme stabilizing agents, pro-perfumes, perfumes, solubilizing agents, carriers, processing aids, pigments, and, for liquid formulations, solvents, chelating agents, dye transfer inhibiting agents, dispersants, brighteners, dyes, structure elasticizing agents, fabric softeners, anti-abrasion agents, hydrotropes, processing aids, and other fabric care agents. The cleaning adjuncts particularly useful for household cleaning compositions and the levels of use have been described in, e.g., U.S. Pat. Nos. 5,576,282, 6,306,812 and 6,326,348. A comprehensive list of suitable laundry or other household cleaning adjuncts is, e.g., in International Publication WO 99/05245.

Personal/pet or beauty care cleaning compositions including, e.g., shampoos, facial cleansers, hand sanitizers, body-wash, and the like, can also comprise, in some embodiments, other more specialized adjuncts, including, for example, conditioning agents such as vitamines, silicone, silicone emulsion stabilizing components, cationic cellulose or polymers such as Guar polymers, anti-dandruff agents, antibacterial agents, dispersed gel network phase, suspending agents, viscosity modifiers, dyes, non-volatile solvents or diluents (water soluble or insoluble), foam boosters, pediculocides, pH adjusting agents, perfumes, preservatives, chelants, proteins, skin active agents, sunscreens, UV absorbers, and minerals, herbal/fruit/food extracts, sphingolipids derivatives or synthetic derivatives and clay.

Common Adjuncts (1) Enzymes

Various known detersive enzymes can be blended into a cleaning composition of the present invention. Suitable enzymes include, e.g., proteases, amylases, lipases, cellulases, pectinases, mannases, arabinases, galactanases, xylanases, oxidases (e.g., laccases), peroxidases, and/or mixtures thereof. They can provide enhanced cleaning performance and/or fabric care benefits. In general, just as the selection of the type and amount of surfactants to be formulated into a cleaning composition should take account of the enzymes therein, the types of enzyme chosen to be included in the composition should take account of the other components in the composition (including the surfactants). Considerations may include, e.g., the pH-optimum of the overall composition, the presence of absence of enzyme stabilization agents, etc. The enzymes should be present in the cleaning compositions in effective amounts.

Suitable proteases include those of animal, vegetable or microbial origin. Microbial origin is preferred. Chemically modified or engineered mutants (e.g., those described in International Publications WO 92/19729, 98/20115, 98/20116, and 98/34946) can also be included. Suitable proteases can be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (as described in International Publications WO 89/06279 and WO 05/103244). Other suitable serine proteases include those from *Micrococcineae* sp. and those from *Cellulonas* sp. and variants thereof as, e.g., described in International Publication WO05/052146. Examples of trypsin-like proteases include trypsin (e.g. of porcine or bovine origin) and *Fusarium* proteases such as those described in International Publications WO 89/06270 and WO 94/25583. Many proteases are commercially available, including, e.g., Alcalase™, Savinase™, Primase™, Duralase™, Esperase™, Coronase™, Polarzyme™, Kannase™ (Novozymes A/S), Maxatase™, Maxacal™, Maxapem™, Properase™, Purafect™, Purafect Prime™, Purafect OxPO, FNA, FN2, FN3, and FN4 (Genencor Int'l Inc.).

Suitable lipases include those of bacterial or fungal origin. For example, suitable lipases can be derived from yeast, from genera such as *Candida, Kluyvermyces, pichia, Saccharomyces, Schizosaccharomyces*, or *Yarrowia*, or derived from a filamentous fungus, such as *Acremonium, Aspergillus, Aureobasidum, Cryptococcus, Filobasidium, Fusarium, Humicolar, Magnaporthe, Mucor, Myceliophthora, Neocallimasix, Neurospora, Paecilomyces, Penicillium, Piromyces, Schizophyllum, Talaromyces, thermoascus, Thielavia, Tolypocladium, Thermomyces* or *Trichoderma*. Many chemically modified lipases are also suitable, including, for example, those from *Humicola*, (e.g., a modified lipase from *H. lanuginosa* as described in EP 258 068 and 305 216, a modified lipase from *H. insolens* as described in International Publication WO 96/13580), those from *Pseudomonas* (e.g., a modified lipase from *P. alcaligenes*, or from *P. pseudoalcaligenes* as described in EP 218 272, a modified lipase from *P. cepacia* as described in EP 331 376, a modified lipase from *P. stutzeri* as described in GB 1,372,034, a modified lipase from *P. fluoresces* or *Pseudomonas* sp. strain SD 705, as described in International Publications WO 95/06720 and WO96/27002, a modified lipase from *P. wisconsinensis* as described in International Publication WO 96/12012), those from *Bacillus* (e.g. a modified lipase from *B. subtilis* as described in Dartois et al. Biochemica et Biophysica Acta, 1131, 253-360 (1993)), a modified lipase from *B. stearothermophilus* as described in JP Application 64/744992, a modified lipase from *B. pumilus* as described in International Publication WO 91/16422. Other examples are lipase variants include those described in International Publications WO 92/05249, WO 94/01541, WO 95/35381, WO 96/00292, WO 95/30744, WO 94/25578, WO 95/14783, WO 95/22615, WO 97/04079, WO 97/07202, and EP 407 225 and 260 105.

A number of lipase enzymes, which can be included in a cleaning composition of the invention, are commercially available. They include Lipolase™, Lipolase™ Ultra and Lipex™ (Novozymes A/S). Suitable amylases ($\alpha$ and/or $\beta$) include those of bacterial or fungal origin. Chemically modified or engineered mutant amylases can also be suitably included in a cleaning composition of the invention. Amylases include, for example, $\alpha$-amylases obtained from *Bacillus* (for example, from a special strain of *B. licheniformis* as described GB Patent 1,296,839). Various mutant amylases, which can be suitably included in a cleaning composition, have been described in International Publications WO 94/02597, WO 94/18314, WO 96/23873, and WO 97/43424. A number of amylases, which can be included in a cleaning composition of the present invention, are commercially available. They include Duramyl™, Termamyl™, Stainzyme™, Stainzyme Ultra™, Stainzyme Plus™, Fungamyl™ and BAN™ (Novozymes A/S), Rapidase™ and Purastar™ (Genencor Int'l Inc.).

Suitable cellulases include those of bacterial or fungal origin. Chemically modified or engineered mutant cellulases can also be suitably included in a cleaning composition of the invention. Cellulases include, for example, those obtained from the genera *Bacillus, Pseudomonas, Humicola* (e.g., from *Humicola insolens*), *Fusarium* (e.g., from *Fusarium oxysporum*), *Thielavia, Acremonium, Myceliophthora*, as described in U.S. Pat. Nos. 4,435,307, 5,648,263, 5,691,178, 5,776,757, and International Publication WO 89/09259. Especially suitable cellulases are the alkaline or neutral cellulases that impart color care benefits. Examples of such cellulases include those described in EP 0 495 257, 0 531 372, and International Publications WO 96/11262, WO 96/29397, and WO 98/08940. A number of cellulases, especially those that provide added color care benefits, are commercially available, which can be included in a cleaning composition of the invention, especially in, for example, a laundry detergent composition. Commercially available cellulases include, e.g., Renozyme™, Celluclean™, Endolase™, Celluzyme™, and Carezyme™ (Novozymes A/S), Clazinase™, and Puradax HA™ (Genencor International Inc.), and KAC-500 (B)™ (Kao Corporation).

Suitable peroxidases/oxidases include those of plant, bacterial or fungal origin. Chemically modified or engineered mutant peroxidases/oxidases can also be suitably included in a cleaning composition of the invention. Useful peroxidases include, for example, those obtained from the genera *Coprinus* (e.g., a periosidase from *C. cinereus* and variants thereof as described in International Publications WO 93/24618, WO 95/10602, and WO 98/15257). Commercially available peroxidases include, for example, Guardzyme™ (Novozymes A/S).

Suitable enzymes described above can be present in a cleaning composition of the present invention at levels of about 0.00001 wt. % or higher (e.g., about 0.01 wt % or higher, about 0.1 wt. % or higher, about 0.5 wt. % or higher, or about 1 wt. % or higher). For example, one or more such enzymes can be present in a cleaning composition of the invention in an amount of about 0.00001 wt. % to about 2 wt. % (e.g., about 0.0001 wt. % to about 1 wt. %, about 0.001 wt. % to about 0.5 wt. %) based on the total weight of the cleaning composition. In certain embodiments, the enzyme(s) can be present or used at very low levels, for example, at about 0.001 wt. % or lower. In alternative embodiments, enzyme(s) can be formulated, for example, into a heavier duty laundry detergent composition, at about 0.1 wt. % and higher, for example, at about 0.5 wt. % or higher.

2) Enzyme Stabilizers

In certain embodiments, the cleaning composition of the present invention, which comprises one or more enzymes, further comprises one or more enzyme stabilizers. For example, the enzymes employed in the cleaning composition can be stabilized by the presence of water-soluble sources of calcium and/or magnesium ions in the finished compositions that provide such ions to the enzymes. Known stabilizing agents include, for example, a polyol such as propylene glycol or a glycerol, a sugar or a sugar alcohol, a lactic acid, a boric acid, a boric acid derivative such as an aromatic borate ester, a phenyl boronic acid derivative such as a 4-formylphenyl boronic acid. The enzyme stabilizers can be incorporated into the cleaning composition according to known methods, such as, for example, those described in International Publications WO 92/19709 and WO 92/19708.

3) Builders

Cleaning compositions of the present invention optionally comprise one or more detergent builders or builder systems. When a builder is used, the subject composition can comprise, e.g., at least about 1 wt. % (e.g., at least about 1 wt. %, at least about 5 wt. %, at least about 10 wt. %, at least about 20 wt. %, at least about 30 wt. %, at least about 40 wt. %, at least about 50 wt. %, or more) of one or more builders. For example, a solid cleaning composition of the present invention can comprise, e.g., about 1 wt. % to about 60 wt. % (e.g., about 5 wt. % to about 50 wt. %, about 10 wt. % to about 40 wt. %, about 15 wt. % to about 30 wt. %) of one or more builders or a builder system. For example, a liquid cleaning composition of the present invention can comprise about 0 wt. % to about 10 wt. % of one or more detergency builders.

Various known builder materials can be used, including, e.g., aluminosilicate materials, silicates, polycarboxylates, alkyl- or alkenyl-succinic acid, and fatty acids, materials such as ethylenediamine tetraacetate, diethylene triamine pentamethyleneacetate, metal ion sequestrants such as aminopolyphosphonates, particularly ethylenediamine tetramethylene phosphonic acid and diethylene tramine pentamethylenephosphonic acid. Particularly, builder materials such as calcium sequestrant materials, precipitating materials, calcium ion-exchange materials, polycarboxylate materials, citrate builder, succinic acid builders, aminocarboxylates, and mixtures thereof are preferred.

Examples of calcium sequestrant builder materials include alkali metal polyphosphates, such as sodium tripolyphosphate and organic sequestrants, and ethylene diamine tetraacetic acid. Examples of precipitating builder materials include sodium orthophosphate and sodium carbonate.

Examples of calcium ion-exchange builder materials include the water-insoluble crystalline or amorphous aluminosilicates, of which zeolites are the best known, e.g., zeolite A, zeolite B (also known as zeolite P), zeolite C, zeolite X, zeolite Y, and also the zeolite P-type as described in, e.g., EP 0 384 070.

Of particular importance are citrate builders, including, for example, citric acid and soluble salts thereof (particularly sodium salt), are polycarboxylate builders of particular importance for heavy duty liquid detergent formulations due to their availability from renewable resources and their biodegradability. Oxydisuccinates are also especially useful in such compositions and combinations. Useful succinic acid builders can also be $C_5$-$C_{20}$ alkyl and alkenyl succinic acids and salts thereof, including laurylsuccinate, myristylsuccinate, palmitylsuccinate, 2-dodecenylsuccinate, 2-pentadecenylsuccinate. with dodecenylsuccinic acid being particularly preferred.

Suitable polycarboxylate builders include, for example, cyclic compounds, particularly alicyclic compounds, such as those described in U.S. Pat. Nos. 3,308,067, 3,723,322, 3,835,163; 3,923,679; 4,102,903, 4,120,874, 4,144,226, and 4,158,635.

Ether hydroxypolycarboxylates, copolymers of maleic anhydride with ethylene or vinyl methyl ether, 1,3,5-trihydroxy benzene-2,4,6-trisulphonic acid, and carboxymethyl oxysuccinic acid, various alkali metal, ammonium, and substituted ammonium salts of poly acetic acids such as ethylenediamine tetraacetic acid and nitrilotriacetic acid, and polycarboxylates such as mellitic acid, succinic acid, oxydisuccinic acid, polymaleic acid, benzene 1,3,5-tricarboxylic acid, carboxymethyloxy-succinic acid, and soluble salts thereof can be used as builders. Other nitrogen-containing, phospho-free aminocarboxylates are sometimes used. Specific examples include ethylene diamine disuccinic acid and salts thereof (ethylene diamine disuccinates, EDDS), ethylene diamine tetraacetic acid and salts thereof (ethylene diamine tetraacetates, EDTA), and diethylene triamine penta acetic acid and salts thereof (diethylene triamine penta acetates, DTPA). In particular embodiments of a liquid composition, 3,3-dicarboxy-4-oxa-1,6-hexanedioates and related compounds as described in U.S. Pat. No. 4,566,984 can be suitable.

4) Chelating Agents

Cleaning compositions of the present invention can optionally comprise one or a mixture of more than one copper, iron and/or manganese chelating agents. When such an agent is used, the subject cleaning composition can comprise, for example, about 0.005 wt. % or more (e.g., about 0.01 wt. % or more, about 1 wt. % or more, about 5 wt. % or more, about 10 wt. % or more) chelating agents. For example, a cleaning composition of the invention comprises about 0.005 wt. % to about 15 wt. % (e.g., about 0.01 wt. % to about 12 wt. %, about 0.1 wt. % to about 10 wt. %, about 1 wt. % to about 8 wt. %, about 2 wt. % to about 6 wt. %) chelating agents.

Suitable chelating agents include, e.g., amino carboxylates, amino phosphonates, polyfunctionally-substituted aromatic chelating agents, or mixtures, which are capable of removing copper, iron, or manganese ions from washing mixtures by forming soluble chelates.

Amino carboxylates include, for example, ethylenediaminetetracetates, N-hydroxyethylethylenediamintriacetates, nitrilotriacetates, ethylenediamine tetraproprionates, triethylenetetraamine-hexacetates, diethylenetriamine penta-acetates, and ethanoldiglycines, alkali metal, ammonium, and substituted ammonium salts thereof.

Amino phosphonates are selectively used in cleaning compositions because they increase the amount of total phosphorus. For some applications wherein the amount of total phosphorus in a cleaning composition is limited, amino phosphonates may not be a suitable chelating agent or should be used in low amounts. Amino phosphonates include, e.g., ethylenediamine tetrakis (methylenephosphonates). The amino phosphonates preferably do not contain alkyl or alkenyl groups with more than about 6 carbon atoms.

Suitable polyfunctionally-substituted aromatic chelating agents have been described in, e.g., U.S. Pat. No. 3,812,044. Exemplary polyfunctionally-substituted aromatic chelating agents include a dihydroxydisulfobenzene, such as a 1,2-dihydroxy-3,5-disulfobenzene.

In some embodiments, biodegradable chelators can be included in a cleaning composition of the invention. An exemplary biodegradable chelator is ethylenediamine disuccinate ("EDDS"), especially the [S,S] isomer as described in U.S. Pat. No. 4,704,233.

The compositions herein may also contain water-soluble methyl glycine diacetic acid (MGDA) salts (or acid form) as a chelant or co-builder useful with, for example, insoluble builders such as zeolites, layered silicates and the like.

5) Hydrotropes

Hydrotropes can be optionally included in cleaning compositions of the present invention to improve the physical and chemical stability of the compositions. Suitable hydrotropes include sulfonated hydrotropes, which include, for example, alkyl aryl sulfonates, or alkyl aryl sulfonic acids. Alkyl aryl sulfonates can be sodium, potassium, calcium, or ammonium xylene sulfonates; sodium, potassium, calcium, or ammonium toluene sulfonates; sodium, potassium, calcium, or ammonium euraene sulfonates; sodium, potassium, calcium, or ammonium substituted or unsubstituted naphthalene sulfonates, and mixtures thereof. Preferred among these are the sodium salts. Alkyl aryl sulfonic acids can be xylenesulfonic acid, toluenesulfonic acid, cumenesulfonic acid, substituted or unsubstituted naphthalenesulfonic acid, or salts thereof. In certain embodiments, a mixture of xylenesulfonic acid and p-toluene sulfonate can be used.

If present, a cleaning composition of the present invention comprises hydrotropes in an amount of about 0.01 wt. % or more (e.g., about 0.02 wt. % or more, about 0.05 wt. % or more, about 0.1 wt. % or more, about 1 wt. % or more, about 5 wt. % or more, about 10 wt. % or more, or about 15 wt. % or more). On the other hand, a cleaning composition of the present invention comprises hydrotropes in an amount of no more bout 20 wt. % (e.g., no more than about 20 wt. %, no more than about 15 wt. %, no more than about 10 wt. %, no more than about 5 wt. %, no more than about 1 wt. %). In certain embodiments, the cleaning composition can comprise hydrotropes in an amount of about 0.01 wt. % to about 20 wt. % (e.g., about 0.02 wt. % to about 18 wt. %, about 0.05 wt. % to about 15 wt. %, about 0.1 wt. % to about 10 wt. %, about 1 wt. % to about 5 wt. %), based on the total weight of the cleaning composition.

6) Rheology Modifier

A cleaning composition of the present invention, when in the form of a liquid, can suitably comprise a rheology modifier to provide a matrix that is "shear-thinning". A shear-thinning fluid, as it is understood by those skilled in the art, is a fluid the viscosity of which decreases as shear is applied. Thus, at rest, for example, during storage or shipping of a composition, the liquid matrix of the composition preferably has a relatively high viscosity. When shear is applied to the composition, however, such as in the act of pouring or squeezing the composition from its container, the viscosity of the matrix is lowered to the extent that dispensing of the fluid product is easily and readily accomplished.

Various materials that are capable of forming shear-thinning fluids when combined with water or other aqueous liquids are known. One type of useful structuring agent for this purpose comprises non-polymeric (except for conventional alkoxylation) crystalline hydroxy-functional materials that can form thread-like structuring systems throughout the liquid matrix when crystallized within the matrix in situ. Such materials include, e.g., crystalline hydroxyl-containing fatty acids, fatty esters, or fatty waxes. Specific examples of crystalline hydroxyl-containing rheology modifiers include castor oil and derivatives. Preferred are hydrogenated castor oil derivatives such as hydrogenated castor oil and hydrogenated castor wax. A number of these materials are commercially available, including, for example, THIXCIN® (Elementis Specialties), 1,4-di-O-benzyl-D-Threitol in the R,R, and S,S forms and any mixtures, optically active or not, and others described in, for example, U.S. Pat. No. 6,080,708 and International Publication WO 02/40627.

Suitable polymeric rheology modifiers include those of the polyacrylate, polysaccharide or polysaccharide derivative type. Polysaccharide derivatives typically used as rheology modifiers comprise polymeric gum materials. Such gums include pectine, alginate, arabinogalactan, carrageenan, gellan gum, xanthan gum and guar gum. Another suitable rheology modifier is a combination of a solvent and a polycarboxylate polymer. The solvent can be, for example, an alkylene glycol, more preferably dipropy glycol. For example, the solvent can comprise a mixture of dipropyleneglycol and 1,2-propanediol, with a ratio of dipropyleneglycol to 1,2-propanediol being about 3:1 to about 1:3 (e.g., about 1:1). The polycarboxylate polymer can be, e.g., a polyacrylate, polymethacrylate, or mixtures thereof. The polyacrylate can be a copolymer of unsaturated mono- or di-carbonic acid and 1-30C alkyl ester of the (meth) acrylic acid, or a polyacrylate of unsaturated mono- or di-carbonic acid and 1-30C alkyl ester of the (meth) acrylic acid. Some of these polymers are commercially available, for example, under the tradename Carbopol® Aqua 30 (Lubrizol, Wickliffe, Ohio).

The rheology modifiers can be present at a level of about 0.5 wt. % to about 15 wt. % (e.g., about 1 wt. % to about 12 wt. %, about 2 wt. % to about 9 wt. %), based on the total weight of the cleaning composition. The polycarboxylate polymer is suitably present at a level of about 0.1 wt. % to about 10 wt. % (e.g., about 1 wt. % to about 8 wt. %, about 1.5% to about 6 wt. %, about 2 wt. % to about 5 wt. %) in the cleaning composition.

6) Solvents or Solvent Systems

A cleaning composition of the invention can be in a liquid form, wherein one or more suitable solvents or solvent systems are included. Suitable solvents include water, lipophilic fluids, or organic solvents. Examples of suitable lipophilic fluids include siloxanes, other types of silicones, hydrocarbons, glycol ethers, glycerine derivatives such as glycerine ethers, perfluorinated amines, perfluorinated and hydrofluoroether solvents, low-volatility nonfluorinated organic solvents, diol solvents, other environmentally-friendly solvents and mixtures. Particularly suitable solvents include low molecular weight primary and secondary alcohols, such as methanol, ethanol, propanil, or isopropanol. Monohydric alcohols, e.g., polyols containing about 2 to about 6 carbon atoms, and/or about 2 to about 6 hydroxy groups (e.g., propylene glycol, ethylene glycol, glycerin, and 1,2-propanediol) are also suitable.

Solvents can be absent, for example, from anhydrous solid embodiments of the cleaning compositions of the invention. But in a liquid cleaning composition, they are typically present at levels of bout 0.1 wt. % to about 98 wt. % (e.g., about 1 wt. % to about 90 wt. %, about 10 wt. % to about 80 wt. %, about 20 wt. % to about 75 wt. %).

7) Organic Sequestering Agent

A cleaning composition of the invention can optionally comprise about 0.01 wt. % to about 1.0 wt. % of an organic sequestering agent. Non-limiting example of organic sequestering agent include nitriloacetic acid, EDTA, organic phosphonates, sodium citrate, sodium tartrate monosuccinate, sodium tartrate disuccinate, and mixture thereof.

Certain adjuncts are particularly suitable for laundry/household cleaning applications as compared to for personal/beauty care cleaning compositions, while other adjuncts are vise versa. Certain adjuncts are categorized and described below as particularly suitable for the former or the latter, but that categorization is not meant to be exclusive in that adjuncts that are suitable for laundry/household cleaning compositions can be included in personal/beauty care cleaning compositions and vise versa as appropriate.

Adjuncts Particularly Suitable for Laundry/Household Applications

1) Bleach System

A bleach system suitable for use herein can contain one or more bleaching agents. Suitable bleaching agents include, e.g., catalytic metal complexes, activated peroxygen sources, bleach activators, bleach boosters, photobleaches, bleaching enzymes, free radical initiators, and hyohalite bleaches. Suitable activated peroxygen sources include, e.g., preformed peracids, a hydrogen peroxide source with a bleach activator, or a mixture thereof. Suitable preformed peracids include, e.g., percarboxylic acids and salts, percarbonic acids and salts, perimidic acids and salts, peroxymonosulfuric acids and salts, and mixtures thereof. Suitable sources of hydrogen peroxide include, e.g., perborate compounds, percarbonate compounds, perphosphate compounds and mixtures. Suitable types and levels of activated peroxygen sources are described in, e.g., U.S. Pat. Nos. 5,576,282, 6,306,812, and 6,326,348.

A household cleaning composition of the invention can optionally comprise photobleach, which can be, for example, a xanthene dye photobleach, a photo-initiator, or mixtures thereof. Suitable photobleaches can also catalytic photobleaches and photo-initiators. In certain embodiments, catalytic photobleaches are selected from the group consisting of water soluble phthalocyanines of the formula:

$$[Me]_q-[PC]-[Q1]_r^{+}\ As^{-} \quad \text{or} \quad [Me]_q-[PC]-[Q2]_r$$

wherein: PC is the phthalocyanine ring system; Me is Zn; Fe(II); Ca; Mg; Na; K; Al—$Z_1$; Si(IV); P(V); Ti(IV); Ge(IV); Cr(VI); Ga(III); Zr(IV); In(III); Sn(IV) or Hf(VI); $Z_1$ is a halide; sulfate; nitrate; carboxylate; alkanolate; or hydroxyl ion; q is 0; 1 or 2; r is 1 to 4; Q1 is a sulfur or carboxyl group; or a radical of the formula: $—SO_2X_2—R_1—X_3^+$; $—O—R_1—X_3^+$; or $—(CH_2)$, $—Y_1^+$; in which $R_1$ is a branched or unbranched $C_1$-$C_8$ alkylene; or 1,3- or 1,4-phenylene; $X_2$ is —NH—; or —N—$C_1$-$C_5$ alkyl; $X_3^+$ is a group of the formula:

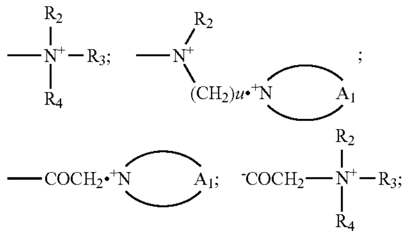

or, in the case where $R_1$═$C_1$-$C_5$ alkylene, also a group of the formula:

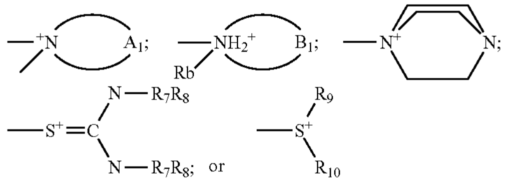

$Y_1^+$ is a group of the formula:

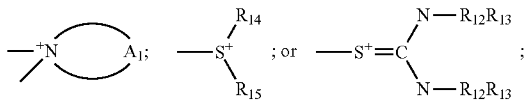

wherein t is 0 or 1; $R_2$ and $R_3$ independently of one another are $C_1$-$C_6$ alkyl; $R_4$ is $C_1$-$C_5$ alkyl; $C_5$-$C_7$ cycloalkyl or $NR_7R_8$; $R_5$ and $R_6$ independently of one another are $C_1$-$C_5$ alkyl; $R_7$ and $R_8$ independently of one another are hydrogen or $C_1$-$C_5$ alkyl; $R_9$ and $R_{10}$ independently of one another are unsubstituted $C_1$-$C_6$ alkyl or $C_1$-$C_6$ alkyl substituted by hydroxyl, cyano, carboxyl, carb-$C_1$-$C_6$ alkoxy, $C_1$-$C_6$ alkoxy, phenyl, naphthyl or pyridyl; u is from 1 to 6; $A_1$ is a unit which completes an aromatic 5- to 7-membered nitrogen heterocycle, which may where appropriate also contain one or two further nitrogen atoms as ring members, and $B_1$ is a unit which completes a saturated 5- to 7-membered nitrogen heterocycle, which may where appropriate also contain 1 to 2 nitrogen, oxygen and/or sulfur atoms as ring members; Q2 is hydroxyl; $C_1$-$C_{22}$ alkyl; branched $C_3$-$C_{22}$ alkyl; $C_2$-$C_{22}$ alkenyl; branched $C_3$-$C_{22}$ alkenyl and mixtures thereof; $C_1$-$C_{22}$ alkoxy; a sulfo or carboxyl radical; a radical of the formula:

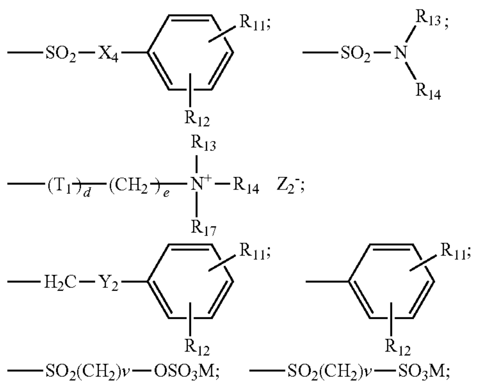

-continued

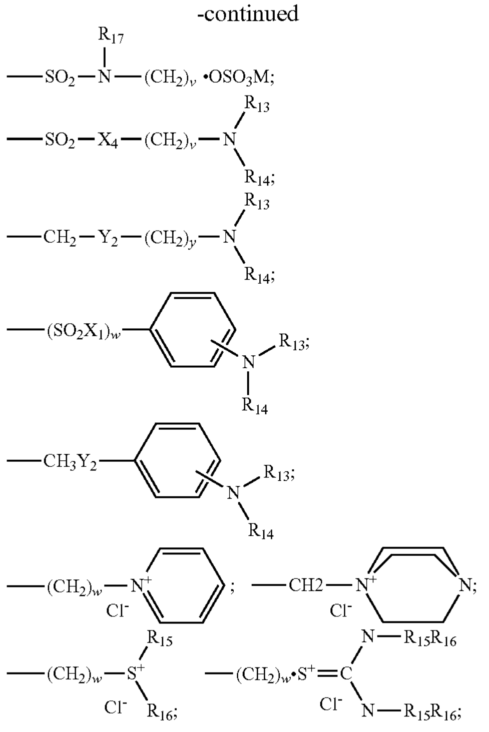

a branched alkoxy radical of the formula:

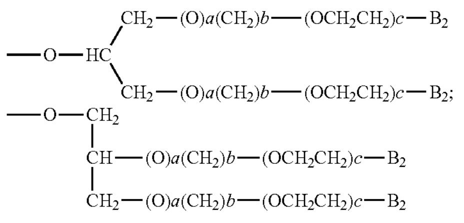

an alkylethyleneoxy unit of the formula: -$(T_1)$d—$(CH_2)_b$ $(OCH_2CH_2)$e—$B_3$; or an ester of the formula: $COOR_{18}$, wherein $B_2$ is hydrogen; hydroxyl; $C_1$-$C_{30}$ alkyl; $C_1$-$C_{30}$ alkoxy; —$CO_2H$; —$CH_2COOH$; —$SO_3$-$M_1OSO_3$-$M_1$; —$PO_3^{2-}M_1$; —$OPO_3^{2-}M_1$; and mixtures thereof; $B_3$ is hydrogen; hydroxyl; —COOH; —$SO_3$-$M_1$; —$OSO_3$-$M_1$ or $C_1$-$C_6$ alkoxy; $M_1$ is a water-soluble cation; $T_1$ is —O—; or —NH—; $X_1$ and $X_4$ independently of one another are —O—; —NH— or —N—$C_1$-$C_5$alkyl; $R_{11}$ and $R_{12}$ independently of one another are hydrogen; a sulfo group and salts thereof; a carboxyl group and salts thereof or a hydroxyl group; at least one of the radicals $R_{11}$ and $R_{12}$ being a sulfo or carboxyl group or salts thereof, $Y_2$ is —O—; —S—; —NH— or —N—$C_1$-$C_5$alkyl; $R_{13}$ and $R_{14}$ independently of one another are hydrogen; $C_1$-$C_6$ alkyl; hydroxy-$C_1$-$C_6$ alkyl; cyano-$C_1$-$C_6$ alkyl; sulfo-$C_1$-$C_6$ alkyl; carboxy or halogen-$C_1$-$C_6$ alkyl; unsubstituted phenyl or phenyl substituted by halogen, $C_1$-$C_4$ alkyl or $C_1$-$C_4$ alkoxy; sulfo or carboxyl or $R_{13}$ and $R_{14}$ together with the nitrogen atom to which they are bonded form a saturated 5- or 6-membered heterocyclic ring which may additionally also contain a nitrogen or oxygen atom as a ring member; $R_{15}$ and $R_{16}$ independently of one another are $C_1$-$C_6$ alkyl or aryl-$C_1$-$C_6$ alkyl radicals; $R_{17}$ is hydrogen; an unsubstituted $C_1$-$C_6$ alkyl or $C_1$-$C_6$ alkyl substituted by halogen, hydroxyl, cyano, phenyl, carboxyl, carb-$C_1$-$C_6$ alkoxy or $C_1$-$C_6$ alkoxy;

$R_{18}$ is $C_1$-$C_{22}$ alkyl; branched $C_3$-$C_{22}$ alkyl; $C_1$-$C_{22}$ alkenyl or branched $C_3$-$C_{22}$ alkenyl; $C_3$-$C_{22}$ glycol; $C_1$-$C_{22}$ alkoxy; branched $C_3$-$C_{22}$ alkoxy; and mixtures thereof; M is hydrogen; or an alkali metal ion or ammonium ion, $Z_2^-$ is a chlorine; bromine; alkylsulfate or arylsulfate ion; a is 0 or 1; b is from 0 to 6; c is from 0 to 100; d is 0; or 1; e is from 0 to 22; v is an integer from 2 to 12; w is 0 or 1; and A" is an organic or inorganic anion, and s is equal to r in cases of monovalent anions $A^-$ and less than or equal to r in cases of polyvalent anions, it being necessary for $A_s^-$ to compensate the positive charge; where, when r is not equal to 1, the radicals $Q_1$ can be identical or different, and where the phthalocyanine ring system may also comprise further solubilising groups.

Other suitable catalytic photobleaches include xanthene dyes, sulfonated zinc phthalocyanine, sulfonated aluminium phthalocyanine, Eosin Y, Phoxine B, Rose Bengal, C.I. Food Red 14, and mixtures. In some embodiment, a photobleach can be a mixture of sulfonated zinc phthalocyanine and sulfonated aluminium phthalocyanine, wherein the weight ratio of sulfonated zinc phthalocyanine to sulfonated aluminium phthalocyanine is greater than 1, greater than 1 but less than about 100, or from 1 to about 4.

Suitable photo-initiators include, e.g., aromatic 1,4-quinones such as anthraquinones and naphthoquinones; alpha amino ketones, particularly those containing benzoyl moieties; alphahydroxy ketones, particularly alpha-hydroxy acetophenones; phosphorus-containing photoinitiators, including monoacyl, bisacyl and trisacyl phosphine oxide and sulphides; dialkoxy acetophenones; alpha-haloacetophenones; trisacyl phosphine oxides; benzoin and benzoin based photoinitiators; and mixtures thereof. Photo-initiators can, e.g., be 2-ethyl anthraquinone; Vitamin K3; 2-sulphate-anthraquinone; 2-methyl 1-[4-phenyl]-2-morpholinopropan-1-one (Irgacure® 907); (2-benzyl-2-dimethyl amino-1-(4-morpholinophenyl)-butan-1-one (Irgacure® 369); (1-[4-(2-hydroxyethoxy)-phenyl]-2 hydroxy-2-methyl-1-propan-1-one) (Irgacure® 2959); 1-hydroxy-cyclohexyl-phenyl-ketone (Irgacure® 184) (Ciba); oligo[2-hydroxy 2-methyl-1-[4(1-methyl)-phenyl]propanone (Esacure® KIP 150) (Lamberti); 2-4-6-(trimethyl-benzoyl)diphenyl-phosphine oxide, bis(2,4,6-trimethylbenzoyl)-phenyl-phosphine oxide (Irgacure® 819); (2,4,6 trimethyl benzoyl)phenyl phosphinic acid ethyl ester (Lucirin® TPO-L (BASF)); and mixtures thereof.

A number of photobleaches are commercially available, including those described above, from, e.g., Aldrich; Frontier Scientific; Ciba; BASF; Lamberti S.p.A; Dayglo Color Corporation; Organic Dyestuffs Corp.

2) Pearlescent Agents

Pearlescent agents are optional but commonly included ingredients of a number of household cleaners, especially, e.g., in hard surface cleaners. They are typically crystalline or glassy solids, transparent or translucent compounds capable of reflecting and/or refracting light to produce a pearlescent effects. For example, they are crystalline particles insoluble in the composition in which they are incorporated. Preferably the pearlescent agents have the shape of thin plates or spheres (which are generally spherical). As commonly practiced in the art, particle sizes are measured across the largest diameter of spheres. Plate-like particles are defined as those wherein the two dimensions of the particle (length and width) are at least 5 times the third dimension (depth or thickness). Other crystal shapes like cubes or needles typically do not display pearlescent effect and thus are not used as pearlescent agents.

Suitable pearlescent agents have D0.99 (sometimes referred to as D99) volume particle size of less than 50 μm. Preferably the pearlescent agents have D0.99 of less than 40 μm, e.g., less than 30 μm. More preferably the particles have volume particle size of greater than 1 μm. The D0.99 is a measure of particle size relating to particle size distribution and meaning in this instance that 99% of the particles have volume particle size of less than 50 μm. Volume particle size and particle size distribution can be measured using conventional methods and equipment, such as, e.g., a Hydro 2000G (Malvern Instruments). The choice of a particle size needs to balance the ease of distribution vs. the efficacy of the pearlescent agent because the smaller the particles, the easier they are suspended, but the lower the efficacy.

Liquid compositions containing less water and more organic solvents will typically have a refractive index that is higher in comparison to the more aqueous compositions. In these compositions, pearlescent agents with high refractive index are preferably included because otherwise the pearlescent agents do not impart sufficient visual perlescence even when introduced at high levels (e.g., more than about 3 wt. %). In liquid compositions containing less water and more organic solvents, the pearlescent agent is preferably one having a refractive index of more than 1.41 (e.g., more than 1.8, more than 2.0. In some embodiments, the difference in refractive index between the pearlescent agent and the cleaning composition or medium, to which pearlescent agent is added, is at least 0.02, or at least 0.2, or at least 0.6.

A liquid cleaning composition may comprise about 0.01 wt. % or more (e.g., about 0.02 wt. % or more, about 0.05 wt. % or more, about 0.1 wt. % or more, about 0.5 wt. % or more, about 1.0 wt. % or more, about 1.5 wt. % or more) of one or more pearlescent agents. Typically, however, the liquid composition comprises no more than about 2 wt. % (e.g., no more than about 1.5 wt. %, no more than about 1.0 wt. %, no more than about 0.5 wt. %) of one or more pearlescent agents. For example, a liquid cleaning composition herein comprises about 0.01 wt. % to about 2.0 wt. % (e.g., about 0.1 wt. % to about 1.5 wt. %) of pearlescent agents.

Suitable pearlescent agents may be organic or inorganic. Organic pearlescent agents include, e.g., monoester and/or diester of alkylene glycols, propylene glycol, diethylene glycol, dipropylene glycol, methylene glycol or tetraethylene glycol with fatty acids containing 6 to 22, preferably about 12 to about 18 carbon atoms, e.g., caproic acid, caprylic acid, 2-ethyhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, arachic acid, gadoleic acid, behenic acid, erucic acid, and mixtures.

Inorganic pearlescent agents include mica, metal oxide coated mica, silica coated mica, bismuth oxychloride coated mica, bismuth oxychloride, myristyl myristate, glass, metal oxide coated glass, guanine, glitter, and mixtures thereof.

Organic pearlescent agent such as ethylene glycol mono stearate and ethylene glycol distearate provide pearlescence, but typically only when the composition is in motion. Hence only when the composition is poured will the composition exhibit pearlescence. Inorganic pearlescent materials are preferred as the provide both dynamic and static pearlescence. By dynamic pearlescence it is meant that the composition exhibits a pearlescent effect when the composition is in motion. By static pearlescence it is meant that the composition exhibits pearlescence when the composition is static.

Inorganic pearlescent agents are available as a powder, or as a slurry of the powder in an appropriate suspending agent. Suitable suspending agents include ethylhexyl hydroxystearate, hydrogenated castor oil. The powder or slurry of the powder can be added to the composition without the need for any additional process steps.

Optionally, co-crystallizing agents can be used to enhance the crystallization of the organic pearlescent agents. Suitable co-crystallizing agents include but are not limited to fatty acids and/or fatty alcohols having a linear or branched, optionally hydroxyl substituted, alkyl group containing from about 12 to about 22, preferably from about 16 to about 22, and more preferably from about 18 to 20 carbon atoms, such as palmitic acid, linoleic acid, stearic acid, oleic acid, ricinoleic acid, behenyl acid, cetearyl alcohol, hydroxystearyl alcohol, behenyl alcohol, linolyl alcohol, linolenyl alcohol, and mixtures thereof.

3) Perfumes/Fragrances

The term "perfume" as used herein encompasses individual perfume ingredients as well as perfume accords. The perfume ingredients are often premixed to form a perfume accord prior to adding to a cleaning composition. As used herein, the term "perfume" can also include perfume microencapsulates. Perfume microcapsules comprise perfume raw materials encapsulated within a capsule made with materials selected from urea and formaldehyde; melamine and formaldehyde; phenol and formaldehyde; gelatine; polyurethane; polyamides; cellulose ethers; cellulose esters; polymethacrylate; and mixtures thereof. Encapsulation techniques are known and described in, for example, "Microencapsulation": methods and industrial applications, Benita & Simon, eds. (Marcel Dekker, Inc., 1996).

The perfume ingredients that can be included in a cleaning composition can include various natural and synthetic chemicals. Exemplary perfume ingredients include aldehydes, ketones, esters, natural extracts, natural essences and the like.

Industrial cleaning compositions often do not comprise perfume ingredients. However, perfume ingredients are commonly found in household and personal care cleaning compositions. When present, the level of perfume or perfume accord is, e.g., present in an amount of about 0.0001 wt. % or more (e.g., about 0.01 wt. % or more, about 0.1 wt. % or more, about 0.5 wt. % or more, about 2 wt. % or more), based on the total weight of the cleaning composition. For example, the level of perfume or perfume accord can be present in an amount of about 0.0001 wt. % to about 10 wt. % (e.g., about 0.01 wt. % to about 5 wt. %, about 0.1 wt. % to about 2 wt. %, preferably about 0.02 wt. % to about 0.8 wt. %, or about 0.003 wt. % to about 0.6 wt. %), by weight of the detergent composition. The level of perfume ingredients in a perfume accord, if one exists, is typically from about 0.0001 wt. % to about 99 wt. % by weight of the perfume accord. Exemplary perfume ingredients and perfume accords are disclosed in, for example, U.S. Pat. Nos. 5,445,747, 5,500,138, 5,531,910, 6,491,840, and 6,903,061.

4) Dyes, Colorants, and Preservatives

The cleaning compositions herein can optionally contain dyes, colorants, and/or preservatives, or contain one or more, or none of these components. The dyes, colorants and/or preservatives can be naturally occurring or slightly processed from natural materials, or they can be synthetic. For example, natural-occurring preservatives include benzyl alcohol, potassium sorbate and bisabalol, sodium benzoate, and 2-phenoxyethanol. Synthetic preservatives can be selected from, for example, mildewstate or bacteriostate, methyl, ethyl, and propyl parabens, bisguamidine components (e.g., Dantagard™ and/or Glydant™ (Lonza Group)). Midewstate or bacteriostate compounds include, without limitation, KATHON® GC, a 5-chloro-3-methyl-4-isothiazolin-3-one, KATHON® ICP, a 2-methyl-4-isothiazolin-4-one, and a blend thereof, and KATHON® 886, a 5-chloro-2-methyl-4-isothiazolin-3-one (Dow Chemicals); BRONOPOL, a 2-bromo-2-nitropropane 1,3 diol (Boots, Co. Ltd.); DOWICIDE™ A, a 1,2-benzoisothiazolin-3-one (Dow Chemicals); and IRGASAN® DP 200, a 2,4,4'-trichloro-2-hydroxydiphenylether (Ciba-Geigy, AG).

Dyes and colorants include synthetic dyes such as Liquitint® Yellow or Blue or natural plant yes or pigments, such as natural yellow, orange, red, and/or brown pigment, such as carotenoids, including, for example, beta-carotene and lycopene. The composition can additionally contain fluorescent whitening agents or bluing agents. Certain dyes can be light sensitive, including for example Acid Blue 145 (Crompton), Hidacid® blue (Hilton, Davis, Knowles & Triconh); Pigment Green No. 7, FD&C Green No. 7, Acid Blue 1, Acid Blue 80, Acid Violet 48, and Acid Yellow 17 (Sandoz Corp.); D&C Yellow No. 10 (Warner Jenkinson).

If present, dyes or colorants are, e.g., present in an amount of about 0.001 wt. % or more (e.g., about 0.002 wt. % or more, 0.01 wt. % or more, 0.05 wt. % or more, 0.1 wt. % or more; 0.5 wt. % or more). Usually, dyes and colorants are present, if at all, in an amount of no more than about 1 wt. % (e.g., no more than about 0.8 wt. %, no more than about 0.5 wt. %, no more than about 0.2 wt. %, no more than about 0.1 wt. %, no more than about 0.01 wt. %). For example, dyes and colorants can be present in a cleaning composition herein in an amount of about 0.001 wt. % to about 1 wt. % (e.g., about 0.01 wt. % to about 0.4 wt. %).

5) Fabric Care Benefit Agents

A household cleaning composition can be a laundry detergent, wherein a preferred optional ingredient can be a fabric care benefit agent. As used herein, "fabric care benefit agent" refers to any material that can provide fabric care benefits such as fabric softening, color protection, pill/fuzz reduction, anti-abrasion, anti-wrinkle, and the like to garments and fabrics, particularly on cotton and cotton-rich garments and fabrics, when an adequate amount of the material is present on the garment/fabric. Non-limiting examples of fabric care benefit agents include cationic surfactants, silicones, poly olefin waxes, latexes, oily sugar derivatives, cationic polysaccharides, polyurethanes and mixtures. Suitable silicones include, e.g., silicone fluids such as poly(di)alkyl siloxanes, especially polydimethyl siloxanes and cyclic silicones.

Polydimethyl siloxane derivatives include, e.g., organofunctional silicones. One embodiment of functional silicone are the ABn type silicones, as described in U.S. Pat. Nos. 6,903,061, 6,833,344, and International Publication WO02/018528. A number of silicones are commercially available, including, e.g., Waro™ and Silsoft™ 843 (GE Silicones). Functionalized silicones or copolymers with one or more different types of functional groups such as amino, alkoxy, alkyl, phenyl, polyether, acrylate, silicon hydride, mercaptopropyl, carboxylic acid, quaternized nitrogen are also suitable as fabric care benefit agents. A number of these are commercially available including, e.g., SM2125, Silwet 7622 (GE Silicones), DC8822, PP-5495, DC-5562 (Dow Chemicals), KF-888, KF-889 (Shin Etsu Silicones); Ultrasil® SW-12, Ultrasil® DW-18, Ultrasil® DW-AV, Ultrasil® Q-Plus, Ultrasil® Ca-I, Ultrasil® CA-2, Ultrasil® SA-I, Ultrasil® PE-100 (Noveon Inc.), Pecosil® CA-20, Pecosil® SM-40, Pecosil® PAN-150 (Phoenix Chemical). Oily sugar derivatives suitable as fabric care benefit agents were described in International Publication WO 98/16538. Olean® is a commercial brand for certain oily sugar derivatives marketed by The Procter and Gamble Co.

Many dispersible polyolefins can be used to provide fabric care benefits. The polyolefins can be in the form of waxes, emulsions, dispersions, or suspensions. Preferably, the polyolefin is a polyethylene, polypropylene, or a mixture. The polyolefin can be partially modified to contain various functional groups, such as carboxyl, alkylamide, sulfonic acid or amide groups. For example, the polyolefin is partially carboxyl modified or oxidized.

Polymer latex can also be used to provide fabric care benefits in a water based cleaning composition. Non-limiting examples of polymer latexes include those described in, e.g., International Publication WO 02/018451. Additional non-limiting examples include the monomers used in producing polymer latexes, such as 100% or pure butylacrylate, butylacrylate and butadiene mixtures with at least 20 wt. % of butylacrylate, butylacrylate and less than 20 wt. % of other monomers excluding butadiene, alkylacrylate with an alkyl carbon chain at or greater than $C_6$, alkylacrylate with an alkyl carbon chain at or greater than $C_6$ and less than 50 wt. % of other monomers, or a third monomer added into monomer systems above.

Cationic surfactants are also useful in this invention. Examples of cationic surfactants have been described in, e.g., U.S. Patent Publication US2005/0164905.

Fatty acids can also be used as fabric care benefit agents. When deposited on fabrics, fatty acids or soaps thereof, provide fabric care benefits (e.g., softness, shape retention) to laundry fabrics. Useful fatty acids (or soaps, such as alkali metal soaps) are the higher fatty acids containing from about 8 to about 24 carbon atoms, more preferably from about 12 to about 18 carbon atoms. Soaps can be made by direct saponification of fats and oils or by the neutralization of free fatty acids. Particularly useful are the sodium and potassium salts of the mixtures of fatty acids derived from coconut oil and tallow. Fatty acids can be from natural or synthetic origin, both saturated and unsaturated with linear or branched chains.

Color care agents are another type of fabric care benefit agent that can be suitably included in a cleaning composition. Examples include metallo catalysts for color maintenance, such as those described in International Publication WO 98/39403.

Fabric care benefit agents, when present in a household cleaning composition such as a laundry detergent composition, can suitably be present at a level of up to about 30 wt. % (e.g., up to about 20 wt. %, up to about 15 wt. %, up to about 10 wt. %, up to about 5 wt. %, up to about 2 wt. %), based on the total weight of the cleaning composition. For example, a cleaning composition of the invention comprises about 1 wt. % to about 20 wt. % (e.g., about 2 wt. % to about 15 wt. %, about 5 wt. % to about 10 wt. %) of one or more fabric care benefit agents.

6) Deposition Aid

As used herein, "deposition aid" refers to any cationic polymer or combination of cationic polymers that significantly enhance the deposition of the fabric care benefit agent onto the fabric during laundering. An effective deposition aid typically has a strong binding capability with the water insoluble fabric care benefit agents via physical forces such as van der Waals forces or non-covalent chemical bonds such as hydrogen bonding and/or ionic bonding.

An exemplary deposition aid is a cationic or amphoteric polymer. Amphoteric polymers have a net cationic charge. The cationic charge density of the polymer can range from about 0.05 milliequivalents/g to about 6 milliequivalents/g. The charge density is calculated by dividing the number of net charge per repeating unit by the molecular weight of the repeating unit. Nonlimiting examples of deposition aids include cationic polysaccharides, chitosan and its derivatives, and cationic synthetic polymers. Specific deposition aids include, e.g., cationic hydroxy ethyl cellulose, cationic starch, cationic guar derivatives, and mixtures. Certain deposition aids are commercially available, including, e.g., the JR 30M, JR 400, JR 125, LR 400 and LK 400 polymers (Amerchol Corp.), Celquat® H200, Celquat® L-200, and the Cato® starch (National Starch and Chemical Co.), and Jaguar Cl 3 and Jaguar Excel (Rhodia, Inc.).

7) Fabric Substantive and Hueing Dye

Dyes can be included in a cleaning composition of the invention, e.g., a laundry detergent. Conventionally, dyes include certain types of acid, basic, reactive, disperse, direct, vat, sulphur or solvent dyes. For inclusion in cleaning compositions, direct dyes, acid dyes, and reactive dyes are preferred. Direct dyes are water-soluble dyes taken up directly by fibers from an aqueous solution containing an electrolyte, presumably due to selective adsorption. In the Color Index system, direct dye refers to various planar, highly conjugated molecular structures that contain one or more anionic sulfonate group. Acid dyes are water soluble anionic dyes that are applied from an acidic solution. Reactive dyes are those containing reactive groups capable of forming covalent linkages with certain portions of the molecules of natural or synthetic fibers. Suitable fabric substantive dyes that can be included in a cleaning composition include, e.g., an azo compound, stilbenes, oxazines and phthalocyanines.

Hueing dyes are another type of dyes that may be present in a household cleaning composition of the invention. Such dyes have been found to exhibit good tinting efficiency during a laundry wash cycle without exhibiting excessive undesirable build up during laundering. Typically, a hueing dye is included in the laundry detergent composition in an amount sufficient to provide a tinting effect to fabric washed in a solution containing the detergent. In one embodiment, the detergent composition comprises, e.g., about 0.0001 wt. % to about 0.05 wt. % (e.g., about 0.001 wt. % to about 0.01 wt. %) of a hueing dye.

8) Dye Transfer Inhibitors

A household cleaning composition of the invention, e.g., a laundry detergent composition, can comprise one or more compounds for inhibiting dye transfer from one fabric to another of solubilized and suspended dyes encountered during fabric laundering operations involving colored fabrics. Exemplary dye transfer inhibitors include polymeric dye transfer inhibiting agents, which are capable of complexing or absorbing the fugitive dyes washed out of dyed fabrics before the dyes have an opportunity to become attached to other articles in the wash. Polymeric dye transfer agents are described in, e.g., International Publication WO 98/39403. Modified polyethyleneimine polymers, such as those described in International Publication WO 00/05334, which are water-soluble or dispersible, modified polyamines can also be used. Other exemplary dye transfer inhibiting agents include, e.g., polyvinylpyrridine N-oxide (PVNO), polyvinyl pyrrolidone (PVP), polyvinyl imidazole, N-vinyl-pyrrolidone and N-vinylimidazole copolymers (PVPVI), copolymers thereof, and mixtures. The amount of dye transfer inhibiting agents in the cleaning composition can be, e.g., about 0.01 wt. % to about 10 wt. % (e.g., about 0.02 wt. % to about 5 wt. %, about 0.03 wt. % to about 2 wt. %).

9) Optional Ingredients

Unless specified herein below, an "effective amount" of a particular adjunct or ingredient is preferably present in an amount of about 0.01 wt. % or more (e.g., about 0.1 wt. % or more, about 0.5 wt. % or more, about 1.0 wt. % or more, about 2.0 wt. % or more), based on the total weight of the detergent composition. Optional adjuncts are usually presented in an amount of no more than about 20 wt. % (e.g., no more than about 15 wt. %, no more than about 10 wt. %, no more than about 5 wt. %, or no more than about 1 wt. %).

Examples of other suitable cleaning adjuncts, one or more of which may be included in a cleaning composition, include, e.g., effervescent systems comprising hydrogen peroxide and catalase; optical brighteners or fluorescers; soil release polymers; dispersants; suds suppressors; photoactivators; hydrolysable surfactants; preservatives; anti-oxidants; anti-shrinkage agents; gelling agents (e.g., amidoamines, amidoamine oxides, gellan gums); anti-wrinkle agents; germicides; fungicides; color speckles; antideposition agents such as celluose derivatives, colored beads, spheres or extrudates; sunscreens; fluorinated compounds; clays; luminescent agents or chemiluminescent agents; anti-corrosion and/or appliance protectant agents; alkalinity sources or other pH adjusting agents; solubilizing agents; processing aids; pigments; free radical scavengers, and mixtures. Suitable materials and effective amounts are described in, e.g., U.S. Pat. Nos. 5,705,464, 5,710,115, 5,698,504, 5,695,679, 5,686,014 and 5,646,101. Mixtures of the above components can be made in any proportion.

10) Encapsulated Composition

A cleaning composition, such as a household cleaning composition including a laundry detergent, a dishwashing liquid, or a surface cleaning composition, of the present invention can optionally be encapsulated within a water soluble film. The water-soluble film can be made from polyvinyl alcohol or other suitable variations, carboxy methyl cellulose, cellulose derivatives, starch, modified starch, sugars, PEG, waxes, or combinations thereof.

In certain embodiment the water-soluble film may comprise other adjuncts such as copolymer of vinyl alcohol and a carboxylic acid, the advantages of which have been described in, for example, U.S. Pat. No. 7,022,656. An exemplary benefit of such encapsulation practice is the improvement of the shelf-life of the pouched composition. Another exemplary advantage is that this practice provides improved cold water (e.g., less than 10° C.) solubility to the cleaning composition. The level of the co-polymer in the film material is at least about 60 wt. % (e.g., about 65 wt. %, about 70 wt. %, about 80 wt. %) by weight. The polymer can have any average molecular weight, preferably about 1,000 daltons to 1,000,000 daltons (e.g., about 10,000 daltons to about 300,000 daltons, about 15,000 daltons to 200,000 daltons, about 20,000 daltons to 150,000 daltons). In certain embodiments, the copolymer present in the film is about 60% to about 98% hydrolysed (e.g., about 80% to 95% hydrolysed), to improve the dissolution of the material. In certain embodiments, the copolymer comprises about 0.1 mol % to about 30 mol % (e.g., about 1 mol % to about 6 mol %) of carboxylic acid. In certain embodiments, the water-soluble film comprises additional co-monomers, including, for example, sulfonates and ethoxylates such as 2-acrylamido-2-methyl-1-propane sulphonic acid. In further embodiments, the film can also comprise other ingredients, including, for example, plasticizers, for example, glycerol, ethylene glycol, diethyleneglycol, propane diol, 2-methyl-1,3-propane diol, sorbitol, and mixtures thereof, additional water, disintegrating aids, fillers, anti-foaming agents, emulsifying/dispersing agents, and/or anti-blocking agents. It may be useful that the pouch or water-soluble film itself comprises a detergent additive to be delivered to the wash water, for example organic polymeric soil release agents, dispersants, dye transfer inhibitors. Optionally the surface of the film of the pouch may be dusted with fine powder to reduce the coefficient of friction. Sodium aluminosilicate, silica, talc and amylose are examples of suitable fine powders. Certain water-soluble films are commercially available, for example, those marketed under the tradename M8630™ (Mono-Sol).

Adjuncts Particularly Suitable for Personal Care Applications

1) Hair Conditioning Agents

Cleaning compositions of the invention can comprise, in some embodiments such as, for example, in personal or beauty care applications, certain known conditioning agents. An exemplary conditioning agent especially suitable for personal care compositions such as shampoos, is a silicone or a silicone-containing material. Such materials can be selected from, e.g., non-volatile silicones, siloxane gums and resins, aminofunctional silicones, quaternary silicones, and mixtures thereof with each other and with volatile silicones. Examples of these silicone polymers have been disclosed, for example, in U.S. Pat. No. 6,316,541.

Silicone oils are flowable silicone materials having a viscosity as measured at 25° C. of less than about 50,000 centistokes (e.g., less than about 30,000 centistokes). For example, silicone oils typically have a viscosity of about 5 centistokes to about 50,000 centistokes (e.g., about 10 centistokes to about 30,000 centistokes). Suitable silicone oils include polyalkyl siloxanes, polyaryl siloxanes, polyalkylaryl siloxanes, polyether siloxane copolymers, and mixtures. Other insoluble, non-volatile silicone fluids having hair conditioning properties can also be used. Methods of making microemulsions of silicone particles are described in the art, including, e.g., the technique described in U.S. Pat. No. 6,316,541. The silicone may, e.g., be a liquid at ambient temperatures, so as to be of a suitable viscosity to enable the material itself to be readily emulsified to the required particle size of about 0.15 microns or less.

The amount of silicone incorporated into a cleaning composition of the invention may depend on the type of composition and the particular silicone materials used. A preferred amount is about 0.01 wt. % to about 10 wt. %, although these limits are not absolute. The lower limit is determined by the minimum level to achieve acceptable conditioning for a target consumer group and the upper limit by the maximum level to avoid making the hair and/or skin unacceptably greasy. The activity of the microemulsion can be adjusted accordingly to achieve the desired amount of silicone or a lower level of the preformed microemulsion can be added.

The microemulsion of silicone oil may be further stabilized by sodium lauryl sulfate or sodium lauryl ether sulfate with 1-10 moles of ethoxylation. Additional emulsifier, preferably chosen from anionic, cationic, nonionic, amphoteric and zwitterionic surfactants, and mixtures thereof may be present. The amount of emulsifier will typically be in the ratio of about 1:1 to about 1:7 parts by weight of the silicone, although larger amounts of emulsifier can be used, e.g., in about 5:1 parts by weight of the silicone or more. Use of these emulsifiers may be necessary to maintain clarity of the microemulsion if the microemulsion is diluted prior to addition to the personal care cleaning composition. The same detersive surfactants in the cleaning composition can also serve as the emulsifier in the preformed microemulsion.

The silicone microemulsion may be further stabilized using an emulsion polymerization process. A suitable emulsion polymerization process has been described by, for example, U.S. Pat. No. 6,316,541. A typical emulsifier is TEA dodecyl benzene sulfonate which is formed in the process when triethanolamine (TEA) is used to neutralize the dodecyl benzene sulfonic acid used as the emulsion polymerization catalyst. It has been found that selection of the anionic counterion, typically an amine, and/or selection of the alkyl or alkenyl group in the sulfonic acid catalyst can further improve the stability of the microemulsion in the shampoo composition. Examples of preferred amines include, without limitation, triisopropanol amine, diisopropanol amine, and aminomethyl propanol.

2) Pearlescent Agents

Pearlescent agents, such as those described herein above can be suitably included in a personal care cleaning composition such as a shampoo. They are defined, for the purpose of the present disclosure, as materials which impart to a composition the appearance of mother of pearl. Pearlescence is produced by specular reflection of light. Light reflected from pearl platelets or spheres as they lie essentially parallel to each other at different levels in the composition creates a sense of depth and luster. Some light is reflected off the pearlescent agent, and the remainder will pass through the agent, which may pass directly through or be refracted. Reflected, refracted light produces a different colour, brightness and luster.

3) Cationic Cellulose or Guar Polymer

Cleaning compositions of the present invention can further contain a cationic polymer to aid the deposition of the silicone oil component and enhance conditioning performance. Non limiting examples of such polymers are described in the CTFA Cosmetic Ingredient Dictionary, 3rd ed, Estrin, Crosley, & Haynes eds., (The Cosmetic, Toiletry, and Fragrance Association, Inc., Washington, D.C. (1982)). Suitable cationic polymers include polysaccharide polymers, such as cationic cellulose derivatives, for example, salts of hydroxyethyl cellulose reacted with trimethyl ammonium substituted epoxide, referred to in the industry (CTFA) as Polyquaternium 10, as well as Polymer LR, JR, JP and KG series polymers (Amerchol Corp.). Other suitable cationic cellulose polymers includes the polymeric quaternary ammonium salts of hydroxyethyl cellulose reacted with lauryl dimethyl ammonium-substituted epoxide referred to in the industry (CTFA) as Polyquaternium 24, available under the tradename Polymer LM-200 (Amerchol Corp). Suitable cationic guar polymers include cationic guar gum derivatives, such as guar hydroxypropyltrimonium chloride, and those described in, for example, U.S. Pat. No. 5,756,720. Certain of these polymers are commercially available, including, for example, Jaguar® Excel (Rhodia Corp.).

When used, the cationic polymers herein are either soluble in the cleaning composition or are soluble in a complex coacervate phase in the cleaning composition formed by the cationic polymer and the anionic, amphoteric and/or zwitterionic detersive surfactant component described hereinbefore. Complex coacervates of the cationic polymer can also be formed with other charged materials in the composition.

Concentrations of the cationic polymer in the composition can range from about 0.01 wt. % to about 3 wt. % (e.g., about 0.05 wt. % to about 2 wt. %, about 0.1 wt. % to about 1 wt. %). Suitable cationic polymers have cationic charge densities of at least about 0.4 meq/gm (e.g., at least about 0.6 meq/gm). Suitable cationic polymers have cationic charge densities of no more than about 5 meq/gm, at the pH of intended use of the cleaning composition. In an exemplary personal care cleaning composition, such as, for example, a shampoo, which generally has a pH range of about 3 to about 9 (e.g., about 4 to about 8). As used herein, “cationic charge density” of a polymer refers to the ratio of the number of positive charges on the polymer to the molecular weight of the polymer. The average molecular weight of suitable cationic guars and cellulose polymers is typically at least about 800,000 daltons. For example, suitable cationic polymers, which can be included in a cleaning composition of the present invention, is one of sufficiently high cationic charge density to effectively enhance deposition efficiency of the solid particle components in the cleaning composition. Cationic polymers comprising cationic cellulose polymers and cationic guar derivatives with cationic charge densities of at least about 0.5 meq/gm and preferably less than about 7 meq/gm are suitable.

Preferably, the deposition polymers give good clarity and adequate flocculation on dilution with water during use, especially when suitable electrolytes including, e.g., sodium chloride, sodium benzoate, magnesium chloride, and magnesium sulfate, are added.

4) Perfumes/Fragrances

Just as perfumes or perfume accords are typically included in a household cleaning composition of the invention, perfumes or perfume accords as described herein (e.g., supra) are often included in a personal care cleaning composition, such as a shampoo or a bodywash composition. The perfume ingredients, which optionally can be formulated into a perfume accord prior to blending or formulating the cleaning composition, can be obtained from a wide variety of natural or synthetic sources. They include, without limitation, aldehydes, ketones, esters, and the like. They also include, for example, natural extracts and essences, which can include complex mixtures of ingredients, such as orange oils, lemon oils, rose extracts, lavender, musk, patchouli, balsamic essence, sandalwood oil, pine oil, cedar, and the like. The amount of perfume to be included in a cleaning composition of the invention can vary, for example, from about 0.0001 wt. % to about 2 wt. % (e.g., about 0.01 wt. % to about 1.0 wt. %, about 0.1 wt. % to about 0.5 wt. %), based on the total weight of the cleaning composition.

5) Sensory Indicators—Silica Particles

Optionally, in a personal care cleaning composition of the invention, various sensory indicators can be included. These agents provide a change in sensory feel after an appropriate usage time, allowing for easy and precise recognition for the appropriate time of washing. For example, these agents are particularly suitable for cleaning compositions such as hand cleansers. An exemplary type of sensory indicators are silica particles. The properties of the silica particle may be adjusted to provide the desired end point in time.

Various silica particles are commercially available, including, for example, those made and distributed by INEOS Silicas Ltd. These particles have also been described in, for example, U.S. Pat. No. 6,165,510, U.S. Patent Publication 2003/0044442.

Silica particles can be present in an amount that can initially be felt by hands when starting washing with the cleaning composition. In one embodiment, the amount of silica particles is about 0.05 wt. % to about 8 wt. %. In some embodiments, suitable silica particles can have an initial average diameter of about 50 μm to about 600 μm (e.g., about 180 to about 420 μm). In some embodiments, silica particles can further comprise color or pigment on the surface. In other embodiments, suitable silica particles diminish in size and cannot be felt by users during washing before about 5 min, about 2 min, about 30 sec, about 25 sec, about 20 sec, about 15 sec, about 10 sec, about 5 sec, about 5 to about 30 sec, or about 10 to about 30 sec.

Silica particles can also, in addition to providing sensory indications, improve the dispensing of the cleaning composition. For example, by including these particles, the cleaning composition, such as a liquid hand cleaner or a shampoo, may achieve a desirable thickness such that it is easier to be dispensed with a pump.

It is often desirable to regulate the viscosity of a composition comprising silica particles, however. Addition of glycerin has been found to be an effective approach to achieve this regulation. Glycerin is typically added to a composition comprising silica particles in an amount of at least about 1 wt. % (e.g., about 2 wt. %, about 2.5 wt. %, about 3 wt. %, about 4 wt. %, about 5 wt. %, or about 6 wt. %), based on the total weight of the cleaning composition. In some embodiments, glycerin is added in an amount of less than about 10 wt. % (e.g., less than about 8 wt. %, less than about 6 wt. %, less than about 4 wt. %, less than about 2 wt. %). The addition of glycerin may, in certain embodiments, help prevent clogging of pumps.

6) Suspension Agents—Viscosity Control

Cleaning compositions of the invention can also include a suspending agent that allows the particulate matters therein, e.g., the silica particles, to remain suspended. Suspending agents are materials that are capable of increasing the ability of the composition to suspend material. Examples of suspending agents include, e.g., synthetic structuring agents, polymeric gums, polysaccharides, pectin, alginate, arabinogalactan, carrageen, gellan gum, xanthum gum, guar gum, rhamsan gum, furcellaran gum, and other natural gum. An exemplary synthetic structuring agent is a polyacrylate. An exemplary acrylate aqueous solution used to form a stable suspension of the solid particles is manufactured by Lubrizol as CARBOPOL™ resins, also known as CARBOMER™, which are hydrophilic high molecular weight, crosslinked acrylic acid polymers. Other polymers suitable as suspension agents include, e.g., CARBOPOL™ Aqua 30, CARBOPOL™ 940 and CARBOPOL™ 934.

The suspending agents can be used alone or in combination. The amount of suspending agent can be any amount that provides for a desired level of suspending ability. In certain embodiment, the suspending agent is present in an amount of about 0.01 wt. % to about 15 wt. % (e.g., about 0.1 wt. % to about 12 wt. %, about 1 wt. % to about 10 wt. %, about 2 wt % to about 5 wt. %) by weight of the cleaning composition.

7) Other Suitable Adjuncts

A number of other adjuncts can be suitable for inclusion in a personal care cleaning composition. Those include, for example, thickeners, such as hydroxylethyl cellulose derivatives (e.g., Methocel™ products, Dow Chemicals; Natrosol® products, Aqualon Ashland; Carbopol™ products, Lubrizol).

Stability enhancers can also be included as suitable adjuncts. They are typically nonionic surfactants, including those having an hydrophilic-lipophilic balance range of about 9-18. These surfactants can be straight chained or branched chained, and they typically containing various levels of ethoxylation/propoxylation. The nonionic surfactants useful in the present invention are preferably formed from a fatty alcohol, a fatty acid, or a glyceride with a $C_3$ to $C_{24}$ carbon chain, preferably a $C_{12}$ to $C_{18}$ carbon chain derivatized to yield a Hydrophilic-Lipophilic Balance (HLB) of at least 9. HLB is understood to mean the balance between the size and strength of the hydrophilic group and the size and strength of the lipophilic group of the surfactant. Suitable adjuncts for personal care cleaning compositions can also include various vitamins, including, for example, vitamin B complex; including thiamine, nicotinic acid, biotin, pantothenic acid, choline, riboflavin, vitamin B6, vitamin B12, pyridoxine, inositol, carnitine, vitamins A, C, D, E, K, and their derivatives.

Further suitable adjuncts may include one or more materials such as antimicrobial agents, antifungal agents, antidandruff agents, dyes, foam boosters, pediculocides, pH adjusting agents, preservatives, proteins, skin active agents, sunscreens, UV absorbers, minerals, herbal/fruit/food extracts, sphingolipid derivatives or synthetic derivatives, and clay.

Examples of Preferred Embodiments

Surfactant compositions of the invention can be formulated or used without substantial post-production processing. This is especially the case if the surfactant composition is applied in industrial settings, for example, in oil industry for oil recovery applications. Because typically minimum purity specification is required in such settings, it is potentially possible to use whole-cell broths. Surfactants comprising microbially-produced branched fatty alcohols and derivatives prepared in accordance with the methods herein are relatively more selective, as compared with conventional chemical surfactants. As such, they are required in small quantities, and effective under a broad range of oil and reservoir conditions. They are also more environmentally friendly in protection of coastal areas from additional damage inflicted by synthetic chemicals, because they are readily biodegradable and have lower toxicity than synthetic surfactants. Potentially an about 30% or more increase in total oil recovery from underground sandstone can be achieved using surfactants comprising microbially produced fatty alcohols and derivatives such as those described herein.

Microbially-produced fatty alcohols, including branched fatty alcohols and derivatives thereof such as those described herein, are also more anaerobic, halotolerant and thermotolerant as compared to their petroleum-derived counterparts, making surfactants comprising these fatty alcohols particularly useful for in situ enhanced oil recovery. These surfactants are potent reducers of oil viscosity, making it vastly easier to pump heavy oils from underground sandstone as well as through commercial pipelines for long distances. Microbially-produced fatty alcohols and derivatives and surfactants comprising these materials can also be used to desludge crude oil storage tanks. The branched fatty alcohols and derivates described herein also have improved low temperature properties, and are thus particularly suited for application in low temperature environments such as in the deep sea.

Potentially, suitable host cells can be engineered such that the culture broth not only provide suitable surfactants but also provides biodegradation of hydrocarbons, resulting in microbial remediation of hydrocarbon- and crude oil-contaminated soils. Furthermore, the branched fatty alcohols, derivatives thereof, as well as the surfactants comprising these materials can be used to manage and emulsify hydrocarbon-water mixtures. This capacity to effectively emulsify oil/water mixtures can be utilized in oil spill management.

With more extensive post-production processing, surfactants comprising the branched fatty alcohols and derivatives as described herein can be particularly suitable as food additives or in the health care and cosmetic industries. The branching of these molecules confer added oxidative stability and significantly decreased volatility and vapor pressure. They are also useful as ingredients in various household and personal and/or pet care cleaning compositions, with particular advantages at lower washing temperatures.

In certain embodiments, the invention features a surfactant composition comprising about 0.001 wt. % to about 100 wt. % (e.g., about 0.01 wt. % to about 80 wt. %, about 0.1 wt. % to about 70 wt. %, about 1 wt. % to about 60 wt. %, about 5 wt. % to about 50 wt. %) of one or more microbially produced branched fatty alcohols and/or derivatives thereof. An exemplary surfactant composition of the invention comprises about 0.1 wt. % to about 50 wt. % of microbially produced branched fatty alcohols and/or derivatives thereof. The surfactant composition of the present invention can further comprise one or more other co-surfactants, derived from similar origins (e.g., microbially produced) or different origins (e.g., chemically synthesized, derived from petroleum sources).

In another aspect, the invention pertains to a cleaning composition comprising one or more surfactants comprising branched fatty alcohols and derivatives produced in accordance with the methods described herein. The inventive cleaning composition can be formulated as a solid cleaning composition or as a liquid cleaning composition.

In certain embodiment, the invention provides a cleaning composition comprising about 0.1 wt. % to about 50 wt. % (e.g., about 0.1 wt. % to about 50 wt. %, about 0.5 wt. % to about 45 wt. %, about 1 wt. % to about 40 wt. %, about 5 wt. % to about 35 wt. %, about 10 wt. % to about 30 wt. %) of one or more microbially produced branched fatty alcohols and/or derivatives thereof. An exemplary cleaning composition comprises about 1 wt. % to about 40 wt. % of microbially produced branched fatty alcohols and/or derivatives thereof. In another embodiment, the composition comprises about 2 wt. % to about 20 wt. % of microbially produced branched fatty alcohols and/or derivatives thereof.

In one embodiment, the invention features a liquid cleaning composition comprising (a) about 0.1 wt. % to about 50 wt. % (e.g., about 0.1 wt. % to about 50 wt. %, about 0.5 wt. % to about 45 wt. %, about 1 wt. % to about 40 wt. %, about 5 wt. % to about 35 wt. %, about 10 wt. % to about 30 wt. %) of one or more microbially produced branched fatty alcohols and/or derivatives thereof, (b) about 1 wt. % to about 30 wt. % (e.g., about 2 wt. % to about 25 wt. %, about 5 wt. % to about 20 wt. %) of one or more co-surfactant, (c) about 0 wt. % to about 10 wt. % (e.g., about 0 wt. % to about 10 wt. %, about 0 wt. % to about 8 wt. %, about 0 wt. % to about 5 wt. %, about 0 wt. % to about 2 wt. %) of one or more detergency builders, (d) about 0 wt. % to about 2.0 wt. % (e.g., about 0.0001 wt % to about 1.5 wt. %, about 0.001 wt. % to about 1 wt. %, about 0.01 wt. % to about 0.8 wt. %) of one or more enzymes; (e) about 0 wt. % to about 15 wt. % (e.g., about 0 wt. % to about 12 wt. %, about 0 wt. % to about 10 wt. %, about 0 wt. % to about 8 wt. %, about 0 wt. % to about 5 wt. %) of one or more chelating agents; (f) about 0 wt. % to about 20 wt. % (about 0 wt. % to about 15 wt. %, about 0 wt. % to about 10 wt %, about 0 wt. % to about 5 wt. %) of one or more hydrotropes; (g) about 0 to about 15 wt. % (e.g., about 0 wt. % to about 10 wt. %, about 0 wt. % to about 8 wt. %, about 0 wt. % to about 5 wt. %) of one or more rheology modifiers; (h) about 0 wt % to about 1.0 wt. % (e.g., about 0 wt. % to about 0.8 wt. %, about 0 wt. % to about 0.5 wt. %, about 0 wt. % to about 0.2 wt. %) of one or more organic sequestering agents; and (i) about 0.1 wt. % to about 98 wt. % (e.g., about 0.1 wt. % to about 95 wt. %, about 1 wt. % to about 90 wt. %, about 10 wt. % to about 85 wt. %) of a solvent system comprising water or other suitable solvents.

In another embodiment, the invention features a solid detergent composition comprising (a) about 0.1 wt. % to about 50 wt. % of one or more microbially produced fatty alcohols and/or derivatives thereof, (b) about 1 wt. % to about 30 wt. % of one or more co-surfactants, (c) about 1 wt. % to about 60 wt. % of one or more detergency builders, (d) about 0 wt. % to about 2.0 wt. % of one or more enzymes, (e) about 0 wt. % to about 20 wt. % of one or more hydrotropes, (f) about 10 wt. % to about 35 wt. % of one or more filler salts, (f) about 0 wt. % to about 15 wt. % of one or more chelating agents, and (g) about 0.01 wt. % to about 1 wt. % of one or more organic sequestering agents.

When the cleaning composition is a solid (e.g., a particulate, a granule, a tablet), the composition herein can be in any solid form, such as a granular composition or for example a tablet, flake, extrudate, agglomerate, or granule-containing composition. Alternatively, the detergent composition can be a powder. The composition herein can be made by methods such as dry-mixing, agglomerating, compaction, spray drying of various ingredients comprised in the composition herein, or a combination thereof. The composition herein preferably has a bulk density of from about 300 g/L, 350 g/L, or 450 g/L to 1500 g/L, 1000 g/L, or 850 g/L.

In certain embodiments, a liquid cleaning composition of the present invention is formulated such that during use, the wash water will have a pH of between about 6.5 and about 11.0 (e.g., between about 6.5 to about 11, between about 7.0 to about 8.5).

In one embodiment, the invention provides a dishwashing detergent composition. The dishwashing detergent composition can be formulated for use in hand washing of dishes or for use in automatic dishwashers. A skilled person will appreciate that a detergent composition formulated for use in automatic dishwashers should contain suitable antifoaming agents in order to prevent excessive foaming of the detergent composition within the dishwasher. However, foaming may be desirable when hand washing dishes. Antifoaming agents are known. For example, various silicone antifoam compounds can be used, including a variety of relatively high molecular weight polymers containing siloxane units and hydrocarbyl groups of various types. Other suitable antifoam agents include monocarboxylic fatty acids and soluble salts thereof, high molecular weight fatty esters (e.g., fatty acid triglycerides), fatty acid esters of monovalent alcohols, aliphatic $C_{18}$-$C_{40}$ ketones (e.g., stearone), N-alkylated amino triazines (e.g., tri- to hexa-alkylmelamine or di- to tetra-alkyldiamine chlortriazines), propylene oxide, bis-stearic acid amide, and monostearyl di-alkali metal (e.g., sodium, potassium, lithium) phosphate and phosphate esters, amine oxides, alkanolamides, betaines, and mixtures thereof.

In addition the dishwashing detergents can optionally comprise one or more enzymes, gelling agents, abrasive materials, fragrances, solubility enhancers, antideposition agents, e.g., cellulose derivatives. Abrasive materials can be, e.g., pumice, sand, feldspar, corn meal, or mixtures. Antideposition agent can be present in an exemplary cleaning composition in an amount of about 0.1 wt. % to about 5 wt. % (e.g., about 0.1 wt. % to about 2 wt. %).

In certain embodiments, the invention provides a laundry detergent composition comprising, in addition to the microbially produced branched fatty alcohols and/or derivatives thereof as described herein, the co-surfactants and the builders, optionally one or more enzymes, gelling agents, fragrances, antideposition agents, brighteners, anticaking agents, pearlescent agents, fabric softeners, bleach systems, dyes or colorants, preservatives, fabric care benefit agents, hueing dyes, soil release polymers, photoactivators, hydrolysable surfactants, anti-shrinkage agents, anti-wrinkle agents, germicides, fungicides, color speckles, colored beads, fluorinated compounds, etc.

In certain embodiments, the invention further provides a solid surface cleaning composition. In addition to the microbially produced branched fatty alcohols and/or derivatives thereof as described herein, the co-surfactants and the builders, the surface cleaning composition can further comprise one or more of the optional ingredients including, without limitation, one or more enzymes, gelling agents, fragrances, antideposition agents, pearlescent agents, soil release polymers, germicides, abrasive materials, fungicides and mixtures thereof.

In certain embodiments, the invention also provide a personal and/or pet care cleaning composition comprising one or more microbially produced branched fatty alcohols and/or derivatives thereof, builders, and co-surfactants. Optionally, additional components can be included in the personal and/or pet care cleaning composition, including, for example, conditioners, silicones, silica particles, cationic cellulose or guar polymers, silicone microemulsion stabilizers, enzymes, fatty amphiphiles, germicides, fungicides, anti-dandruff agents, pearlescent agents, foam boosters, pediculocides, pH adjusting agents, UV absorbers, sunscreens, skin active agents, vitamins, minerals, herbal/fruit/food extracts, sphingolipids, sensory indicators, suspension agents, and mixtures thereof.

The invention further provides a method for cleaning a substrate, such as fibers, fabrics, hard surfaces, skin, hair, etc., by contacting the substrate with the cleaning composition of the invention and water. Agitation is preferably provided to enhance cleaning. Suitable means for providing agitation include rubbing by hand or with a brush, sponge, cloth, mop, or other cleaning device, automatic laundry machines, automatic dishwashers, and the like.

EXAMPLES

The invention is further illustrated by the following examples. The examples are provided for illustrative purposes only. They are not to be construed as limiting the scope or content of the invention in any way.

Although particular methods are described, one of ordinary skill in the art will understand that other, similar methods also can be used. In general, standard laboratory practices were used, unless otherwise stipulated. For example, standard laboratory practices were used for: cloning; manipulation and sequencing of nucleic acids; purification and analysis of proteins; and other molecular biological and biochemical techniques. Such techniques are explained in detail in standard laboratory manuals, such as Sambrook et al., *Molecular Cloning: A Laboratory Manual,* 3rd ed., vol. 1-3, Cold Spring Harbor, N.Y. (2000), and Ausubel et al., *Current Protocols in Molecular Biology*, Greene Publ. Assoc. & Wiley-Intersciences (1989).

Example 1

Constructing *E. coli* MG1655 ΔfadE_ΔtonA AAR:kan

This example describes the construction of a genetically engineered microorganism in which the expression of a fatty acid degradation enzyme is attenuated.

The fadE gene of *E. coli* MG1655 was deleted using the lambda red system described by Datsenko et al., *Proc. Natl. Acad. Sci. USA* 97: 6640-6645 (2000), with the following modifications:

The following two primers were used to create the deletion of fadE:

```
Del-fadE-F                           (SEQ ID NO: 158)
5'-AAAAACAGCAACAATGTGAGCTTTGTTGTAATTATATTGTAAACAT

ATTGATTCCGGGGATCCGTCGACC;
and

Del-fadE-R                           (SEQ ID NO: 159)
5'-AAACGGAGCCTTTCGGCTCCGTTATTCATTTACGCGGCTTCAACTT

TCCTGTAGGCTGGAGCTGCTTC
```

The Del-fadE-F and Del-fadE-R primers were used to amplify the kanamycin resistance ($Km^R$) cassette from plasmid pKD13 by PCR. The PCR product was then used to transform electrocompetent *E. coli* MG1655 cells containing pKD46 that had been previously induced with arabinose for 3-4 hours. Following a 3-hour outgrowth in SOC medium at 37° C., the cells were plated on Luria agar plates containing 50 μg/ml of Kanamycin. Resistant colonies were identified and isolated after an overnight incubation at 37° C. Disruption of the fadE gene was confirmed in some of the colonies by PCR amplification using primers fadE-L2 and fadE-R1, which were designed to flank the *E. coli* fadE gene.

The fadE deletion confirmation primers were:

```
                                     (SEQ ID NO: 160)
fadE-L2   5'-CGGGCAGGTGCTATGACCAGGAC;
and

                                     (SEQ ID NO: 161)
fadE-R1   5'-CGCGGCGTTGACCGGCAGCCTGG
```

After the fadE deletion was confirmed, a single colony was used to remove the $Km^R$ marker using the pCP20 plasmid as described by Datsenko et al., supra. The resulting MG1655 *E. coli* strain with the fadE gene deleted and the $Km^R$ marker removed was named *E. coli* MG1655 ΔfadE, or *E. coli* MG 1655 D1.

Furthermore, the expression of an outer membrane protein receptor for ferrichrome, colicin M, or phages T1, T5, and phi80 are attenuated.

The tonA gene of *E. coli* MG1655, which encodes a ferrichrome outer membrane transporter (GenBank Accession No. NP_414692), was deleted from strain *E. coli* MG1655 D1 of Example 1, using the lambda red system according to Datsenko et al., supra, but with the following modifications:

The primers used to create the deletion of tonA were:

```
Del-tonA-F                           (SEQ ID NO: 162)
5'-ATCATTCTCGTTTACGTTATCATTCACTTTACATCAGAGATATACC

AATGATTCCGGGGATCCGTCGACC;
and

Del-tonA-R                           (SEQ ID NO: 163)
5'-GCACGGAAATCCGTGCCCCAAAAGAGAAATTAGAAACGGAAG

GTTGCGG TTGTAGGCTGGAGCTGCTTC
```

The Del-tonA-F and Del-tonA-R primers were used to amplify the kanamycin resistance ($Km^R$) cassette from plasmid pKD13 by PCR. The PCR product obtained in this way was used to transform electrocompetent *E. coli* MG1655 D1 cells of Example 1 containing pKD46, which cells had been previously induced with arabinose for 3-4 h. Following a 3-hour outgrowth in SOC medium at 37° C., cells were plated on Luria agar plates containing 50 μg/ml of kanamycin. Resistant colonies were identified and isolated after an overnight incubation at 37° C. Disruption of the tonA gene was confirmed in some of the colonies by PCR amplification using primers flanking the *E. coli* tonA gene: tonA-verF and tonA-verR:.

```
tonA-verF                (SEQ ID NO: 164)
5'-CAACAGCAACCTGCTCAGCAA;
and

tonA-verR                (SEQ ID NO: 165)
5'-AAGCTGGAGCAGCAAAGCGTT
```

After the tonA deletion was confirmed, a single colony was used to remove the $Km^R$ marker using the pCP20 plasmid as described by Datsenko et al., supra. The resulting MG1655 *E.*

*coli* strain having fadE and tonA gene deletions was named *E. coli* MG1655 ΔfadE_ΔtonA, or *E. coli* MG1655 DV2

The aar gene encoding *Synechococcus elongatus* PCC_Synpcc7942__1594 enzyme is integrated into the chromosome with the kanamycin marker directly after the aar sequence.

Example 2

Expression of BKD Homologs and FabH in *E. coli*

A branched chain alpha-keto acid dehydrogenase complex from *Pseudomonas putida* and a FabH from *Bacillus subtilis* were used to generate two *E. coli* plasmids for expression. First, the *Pseudomonas putida* BKD operon was PCT-amplified from *Pseudomonas putida* F1 genomic DNA. The following primers were used:

```
P.p.BKDFUsion_F:                    (SEQ ID NO: 166)
5'-ATAAACCATGGATCCATGAACGAGTACGCCCC-3'

P.pBKDFusion_R:                     (SEQ ID NO: 167)
5'-CCAAGCTTCGAATTCTCAGATATGCAAGGCGTG-3'
```

Using these primers, *Pseudomonas putida* Pput__1450 (GenBank Accession No. A5W0E08), Pput__1451 (GenBank Accession No. A5W0E9), Pput__1452 (GenBank Accession No. A5W0F0), and Pput__1453 (A5W0F1) were amplified. The PCR product was then cloned into vector pGL10.173B (See, FIG. 8), a plasmid with a pBR322 backbone and a pTrc promoter to drive gene expression. The PCR product was cloned into pGL between BamHI and EcoRI restriction sites. Correct insertion of the PCR product was verified by diagnostic restriction digests. The resulting plasmid was named "pKZ4." (See, FIG. 7)

To clone *E. coli* PfabH promoter-*B. subtilis* fabH1 into a pACYC vector, insert of pDG6 (pCFDuet-*E. coli* PfabH promoter-*B. subtilis* fabH1) was subcloned into pACYC vector using NcoI and AvrII restriction sites. The resulting plasmid was named pDG6 (pCFDuet+*E. coli* PfabH+*B. subtilis* fabH1). (See, FIG. 6B and FIG. 6C)

*E. coli* strain MG1655 ΔfadE_ΔtonA, AAR:kan was transformed with pKZ4 and pDG6 (pCFDuet+*E. coli* PfabH+*B. subtilis* fabH1). The strain was evaluated for production of branched chain materials using shake flask fermentation. Shake flask fermentation was carried out using Che-9 media. Specifically, cultures of *E. coli* MG1655 ΔfadE_ΔtonA AAR:kan without plasmids or carrying individual plasmids were used as controls. Seed cultures of *E. coli* MG1655 ΔfadE_ΔtonA AAR:kan, *E. coli* MG1655 ΔfadE_ΔtonA AAR:kan+pKZ4, *E. coli* MG1655 ΔfadE_ΔtonA AAR:kan+pDG6, and *E. coli* MG1655 ΔfadE_ΔtonA AAR:kan+pKZ4+pDG6 were grown in LB broths supplemented with the appropriate antibiotics. After 4 hours of growth, the cultures were diluted 1:25 in Che-92NBT medium+appropriate selection marker and grown overnight. The cultures were then diluted in 4NBT to a final $OD_{600}$~0.2. After 6 h of growth, IPTG was added to a final concentration of 1 mM. At 24 h post-induction, 1 mL of culture was extracted with 0.5 mL of methyl tert-butyl ether (MTBE) and subjected to GC/MS analysis. The analysis revealed the production of iso-$C_{14:0}$, iso-$C_{15:0}$, anteiso-$C_{15:0}$, iso-$C_{16:0}$, iso-$C_{17:0}$, and anteiso-$C_{17:0}$ fatty alcohols. (See, FIG. 4A).

Example 3

Quantification and Identification of Branched Fatty Alcohols

Instrumentation:

The instrument is an Agilent 5975B MSD system equipped with a 30 m×0.25 mm (0.10 μm film) DB-5 column. The mass spectrometer was equipped with an electron impact ionization source. Two GC/MS programs were utilized.

GC/MS program #1: The temperature of the column is held isothermal at 90° C. for 5 min, then is raised to 300° C. with a 25° C./min ramp, and finally stays at 300° C. for 1.6 min. The total run time is 15 min. With this program, the inlet temperature is hold at 300° C. The injector is set at splitless mode. 1 μL of sample is injected for every injection. The carrier gas (helium) is released at 1.0 mL/min. The source temperature of the mass spectrometer is held at 230° C.

GC/MS program #2: The temperature of the column is held isothermal at 100° C. for 3 min, then is raised to 320° C. with 20° C./min, and finally stays isothermal at 320° C. for 5 min. The total run time is 19 min. The injector is set at splitless mode. 1 μl, of sample is injected for every injection. The carrier gas (helium) is released at 1.2 mL/min. The ionization source temperature is set at 230° C.

Figure 4A:
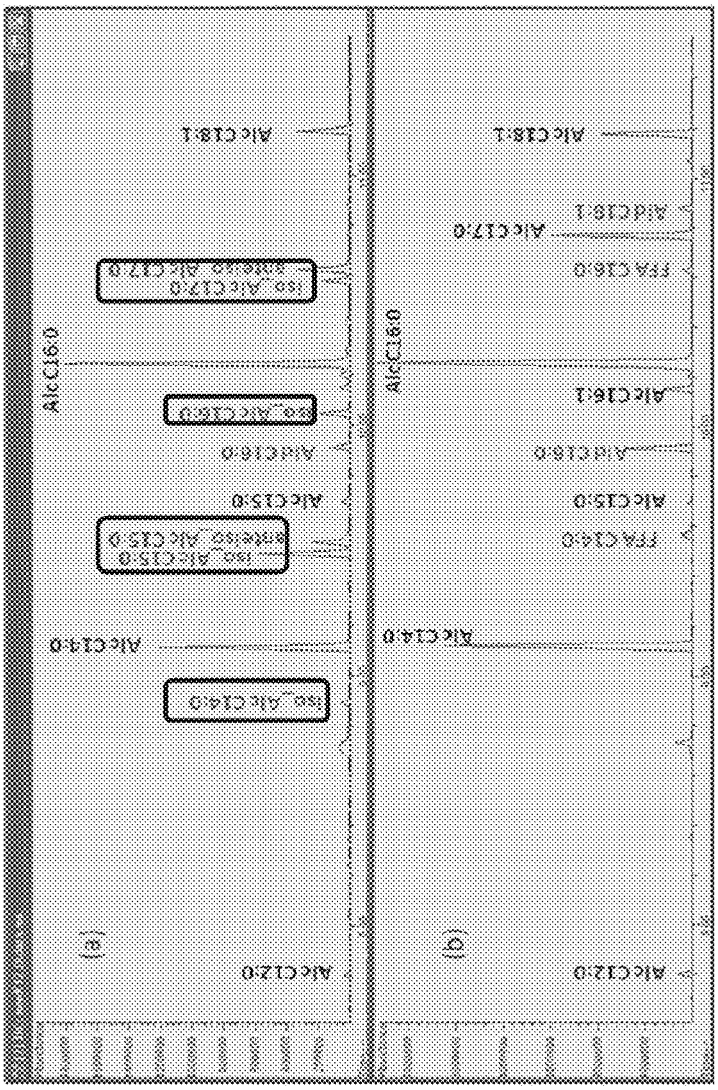
FIG. 4A depicts a GC/MS trace of branched fatty alcohol production of strain MG1655_ΔtonA AAR:kan transformed with a pGL10 vector containing *P. putida* Pput1450, Pput1451, Pput1452 and Pput1453 inserts, and with *B. subtilis* fabH1. The figure indicates the production of iso-$C_{14:0}$, iso-$C_{15:0}$, anteiso-$C_{15:0}$, iso-$C_{16:0}$, iso-$C_{17:0}$ and anteiso-$C_{17:0}$ branched fatty alcohols.

Samples:

Extracts containing fatty alcohols by the engineered *E. coli* strains were analyzed on GC/MS. In FIG. 4A chromatograms of the extracts from the mutant strains are compared to those from control strains which only produce straight chain fatty alcohols. The branched fatty alcohol produced are listed: iso-$C_{14:0}$, iso-$C_{15:0}$, anteiso-$C_{15:0}$, iso-$C_{16:0}$, iso-$C_{17:0}$, and anteiso-$C_{17:0}$.

In FIG. 4A top panel, a GC/MS chromatogram of extract from strain *E. coli* MG1655 ΔfadE ΔtonA AAR:kan+pKZ4+pDG6 (a) and of control strain *E. coli* MG1655 ΔfadE ΔtonA AAR:kan+pBR322+pCFDuet(b). Both chromatograms were obtained with GC/MS program #2. Compared to the control strain, mutant strain produces branched-chain fatty alcohols, and the peaks representing the branched fatty alcohols are boxed.

Figure 5:
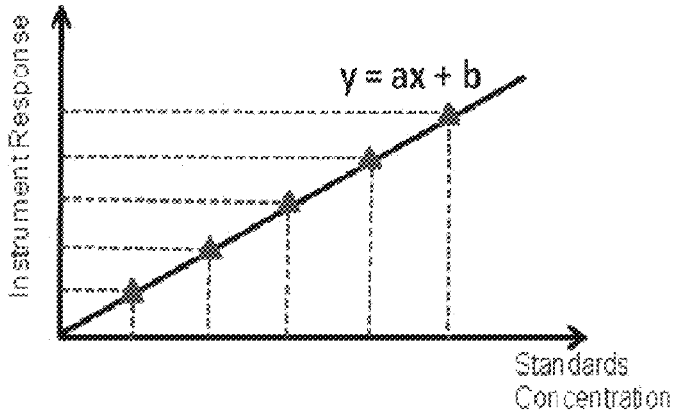
FIG. 5 is a representative calibration curve obtained by linear regression, which was used in the semi-quantitative measurement of the amount of branched fatty alcohol yield relative to the amount of straight-chain fatty alcohol yield.

GC/MS Semi-Quantitative Analysis:

In addition to the qualitative analysis, semi-quantitative analysis was performed to obtain the ratio between the branched chain compounds and the straight chain isomers. Due to the lack of commercially available standards for branched fatty alcohols, accurate quantitation for the branched chain compounds was challenging. However, by using straight chain standard with the same functional group, the relative quantity or yield of branched-chain fatty alcohols in relation to the yield of their straight-chain counterpart (isomers) were estimated semi-quantitatively. Standard curve quantitation method was applied, wherein standard mixtures with different concentrations were analyzed by the same GC/MS program as the samples. After data acquisition, the instrument response (total ion current) was plotted against the concentrations of the standards. Linear calibration curves were obtained. (See, FIG. 5). The concentration of branched alcohols in a given sample was calculated according to Equation 1: y=ax+b, wherein y is the instrument response for a particular compound in a sample. Slope a and intercept b for this calibration curve were determined by the linear regression of all calibration levels of standard fatty alcohols (FIG. 4A lower panel)×(the concentration of the branched fatty alcohol product in the sample). Accordingly, the relative concentration of branched fatty alcohols in the production mixture was calculated.

The table below lists the compounds used as standards to quantify different branched fatty alcohol compounds.

| Alcohol in sample | Standard used for quantitation |
|---|---|
| Iso-Alc $C_{15:0}$ | Alc $C_{15:0}$ |
| Anteiso-Alc $C_{15:0}$ | Alc $C_{15:0}$ |
| Alc $C_{15:0}$ | Alc $C_{15:0}$ |
| Ald $C_{16:0}$ | Alc $C_{15:0}$ |
| Alc $C_{16:0}$ | Alc $C_{15:0}$ |

Once the titers were obtained for all the fatty alcohol compounds, the ratio between the production of branched chain fatty alcohols and the production of straight chain isomers were calculated according to equation 2:

$$\text{Percentage production} = \frac{\text{Total branched chain products in mg/L}}{\text{Total straight chain products in mg/L}} \times 100\%$$

Using this method, we were able to semi-quantitatively estimate the amount of branched fatty alcohol yield relative to the straight-chain fatty alcohol yield to be about 48%.

Example 4

Production of Branched Acyl-CoA Precursors

An *E. coli* strain, MG1655(DE3) ΔfadE::FRT ΔfabH::cat/pDG6 was created, which was tested for its ability to utilize branched-chain substrate molecules to create branched-chain fatty precursors of branched fatty alcohols in vivo.

The strain MG1655(DE3) ΔfadE::FRT ΔfabH::cat/pDG6 was constructed as follows:

A region of the *E. coli* fabH gene described in Lai, et al., 2003, J. Biol. Chem. 278(51): 59494, was replaced by an antibiotic resistance gene. This deletion was performed in a strain that was complemented for fabH by the plasmid pDG6 carrying the *B. subtilis* fabH1 gene.

Initially, the pDG2 plasmid was constructed. The pCDF-Duet-1 vector was purchased from Novagen/EMD Biosciences. The vector carries the CloDF13 replicon, lacI gene and streptomycin/spectinomycin resistance gene (aadA).

The C-terminal portion of the plsX gene, which contains an internal promoter for the downstream fabH gene, was amplified from *E. coli* MG1655 genomic DNA using primers 5'-TGAATTCCATGGCGCAACTCACTCT-TCTTTTAGTCG-3' (SEQ ID NO:168) and 5'-CAGTAC-CTCGAGTCTTCGTATACATATGCGCT CAGTCAC-3' (SEQ ID NO:169). These primers introduced NcoI and XhoI restriction sites near the ends, as well as an internal NdeI site.

Both the plsX insert and pCDFDuet-1 vector were digested with restriction enzymes NcoI and XhoI. The cut vector was treated with Antarctic phosphatase. The insert was ligated into the vector and transformed into chemically competent TOP10 cells. Clones were screened by DNA sequencing. See, FIG. 6A.

Then a pDG6 plasmid was constructed using the pDG2 plasmid. The fabH1 gene from *Bacillus subtilis* strain 168 was amplified from plasmid pLS9-114 (see, FIG. 6K) using primers 5'-CCTTGGGGCATATGAAAGCTG-3' (SEQ ID NO:170) and 5'-TTTAGTCATCTCGAGTGCACCTCAC-CTTT-3' (SEQ ID NO:171). These primers introduced or included NdeI and XhoI restriction sites.

Both the fabH1 insert and pDG2 vector were digested with restriction enzymes NdeI and XhoI. The cut vector was treated with Antarctic phosphatase. The insert was ligated into the vector and transformed into chemically competent TOP10 cells. Clones were screened by DNA sequencing. See, FIG. 6B and FIG. 6C.

Then, the cat chloramphenicol resistance gene was amplified from template plasmid pKD3 using primers 5'-GCCA-CATTGCCGCGCCAAACGAAACC GTTTCAACCATG-GCATATGAATATCCTCCTTAGTTCCTATTCCG-3' (SEQ ID NO: 172) and 5'-CGCCCCAGATTTCACGTAT-TGATCGGCTACGCTTAATGCAT GTGTAGGCTG-GAGCTGCTTC-3' (SEQ ID NO:173) which added 50 bp nucleotide ends that are homologous to the *E. coli* fabH gene. This linear PCR product was used to inactivate the *E. coli* fabH gene.

Strain MG1655(DE3) ΔfadE::FRT was first transformed with plasmid pKD46 encoding the lambda red recombinase genes. MG1655(DE3) ΔfadE::FRT/pKD46 was then transformed with plasmid pDG6. Finally, MG1655(DE3) ΔfadE::FRT/pKD46+pDG6 was induced for expression of the recombinase genes by addition of 10 mM arabinose and transformed with the linear PCR product as described in Datsenko et al. (supra). Colonies were selected on LB plates containing 30 μg/mL chloramphenicol and screened using colony PCR with primers 5'-TTGACACGTC TAAC-CCTGGC-3' (SEQ ID NO:174) and 5'-CTGTCCAGGGAA-CACAAATG C-3' (SEQ ID NO:175).

A number of other constructs comprising pDG7, and pDG8 were also constructed following the approach as above. The plasmids are prepared as follows.

The plasmid pDG7 was prepared from pDG2 with *B. subtilis* fabH2 insert. The fabH2 gene from *Bacillus subtilis* strain 168 was amplified from plasmid pLS9-111 (see, FIG. 6J) using primers 5'-TTGTGTCGCCCTTTCGCTG-3'(SEQ ID NO:176) and 5'-CTTACGTACGTACTCGAGTGACGC-3' (SEQ ID NO:177). These primers introduced or included NdeI and XhoI restriction sites.

Both the fabH2 insert and pDG2 vector were digested with restriction enzymes NdeI and XhoI. The cut vector was treated with Antarctic phosphatase. The insert was ligated into the vector and transformed into chemically competent TOP10 cells. Clones were screened by DNA sequencing. See, FIG. 6D and FIG. 6E.

The plasmid pDG8 was prepared from pDG2 with *S. coelicolor* fabH insert. The fabH gene from *Streptomyces coelicolor* was amplified from plasmid pLS9-115 (see, FIG. 6L) using primers 5'-AAGTGGGGCATATGTCTAAGATC-3' (SEQ ID NO:178) and 5'-GTGATCCGGCTCGAGGTGGT-TAC-3' (SEQ ID NO:179). These primers introduced or included NdeI and XhoI restriction sites.

Both the fabH insert and pDG2 vector were digested with restriction enzymes NdeI and XhoI. The cut vector was treated with Antarctic phosphatase. The insert was ligated into the vector and transformed into chemically competent TOP10 cells. Clones were screened by DNA sequencing. See, FIG. 6F and FIG. 6G.

The plasmid pDG10 was prepared using pCR-Blunt vector, which was purchased from Invitrogen, with *C. acetobutylicum* ptb_buk operon insert, wherein the ptb part represents the gene encoding *C. acetobutylicum* phosphotransbutyrylase (GenBank Accession AAA75486.1, SEQ ID NO:156), and the buk part represents the gene encoding *C. acetobutylicum* butyrate kinase (GenBank Accession JN0795, SEQ ID NO:157). The buk_ptb operon was amplified from *Clostridium acetobutylicum* genomic DNA (ATCC 824) using primers 5'-CTTAACTTCATGTGAAAAGTTTGT-3' (SEQ ID NO:180) and 5'-ACAATACCCATGTTTAT-AGGGCAA-3' (SEQ ID NO:181). The PCR product was ligated into the pCR Blunt vector following the manufacturer's instructions. Colonies were verified by DNA sequencing. See, FIG. 6H and FIG. 6I.

*E. coli* strains were transformed with pDG10, and OP-180 plasmid comprising *E. coli* thioesterase gene tesA under the control of the Ptrc promoter and independently also one of the pDG6, pDG7 and pDG8 plasmids as described above.

Figure 1B:
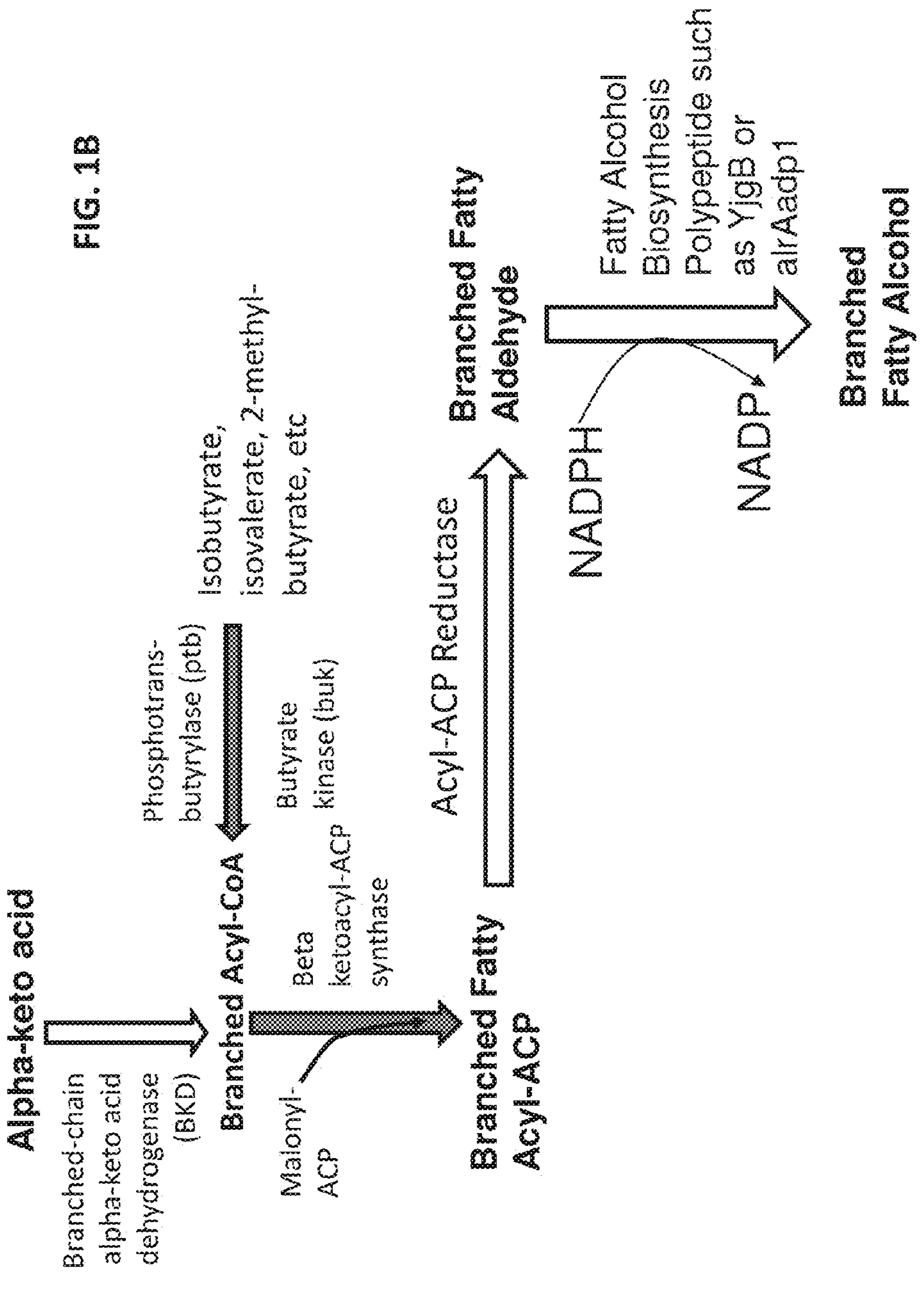
Figure 4B:
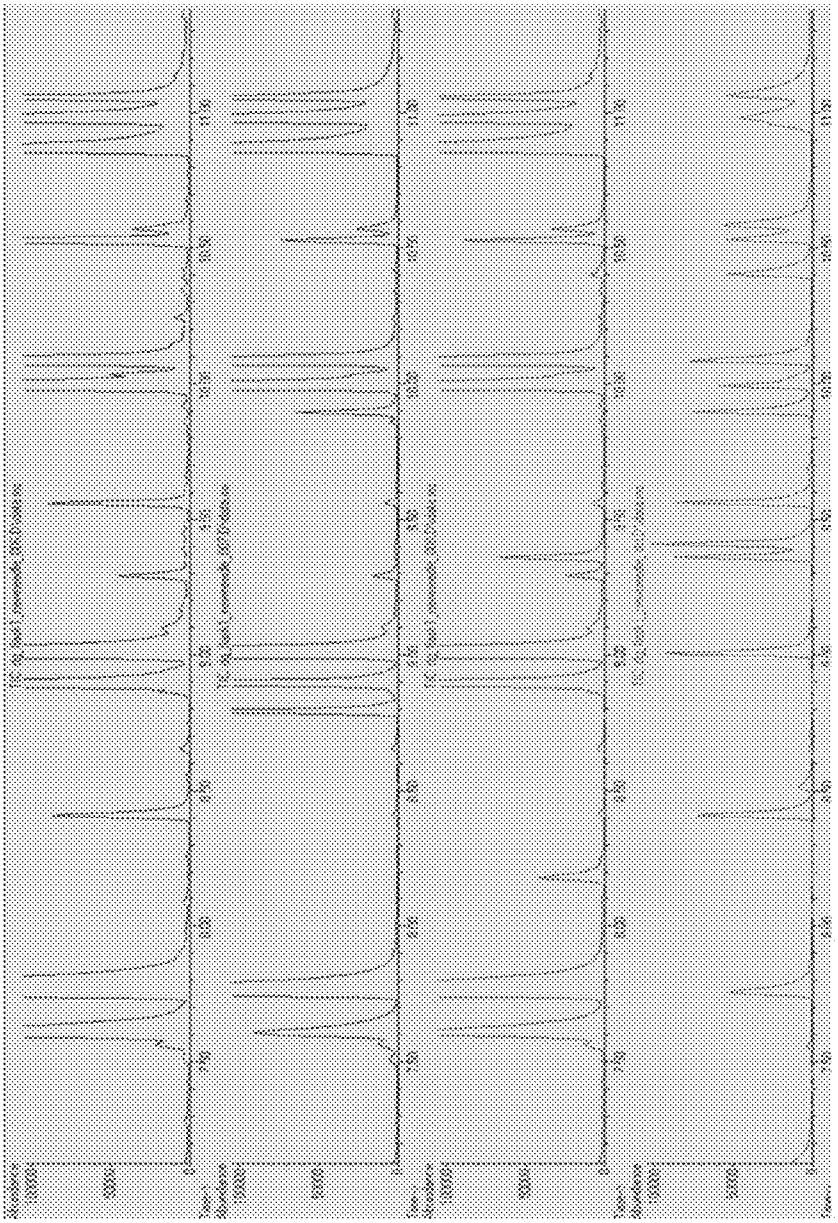
FIG. 4B depicts the production of branched fatty acyl-CoA precursors by feeding branched substrates isobutyrate and isovalerate to an engineered *E. coli* strain comprising the pDG10 and an OP-180 plasmids, the latter plasmid contained teas under the control of a Ptrc promoter.

These strains were fed branched molecules isobutyrate, which resulted in iso-$C_{14:0}$ and iso-$C_{16:0}$ branched acyl-CoA precursors. Independently they were fed branched molecule isovalerate, which resulted in iso-$C_{13:0}$ and iso-$C_{15:0}$ branched acyl-CoA precursors. See, FIG. 4B. These precursors can then be incorporated into the branched fatty alcohol pathways as described herein and depicted in FIG. 1A and FIG. 1B.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of making a surfactant composition using branched chain fatty alcohols produced in a recombinant host cell, the method comprising, (a) obtaining a recombinant host cell genetically modified to comprise (i) a polynucleotide encoding a branched chain alpha-keto acid dehydrogenase (BKD) complex, (ii) a polynucleotide encoding a polypeptide having beta-ketoacyl-ACP synthase (FabH) activity that utilizes a branched acyl-CoA molecule as a substrate, and (iii) a polynucleotide encoding a fatty aldehyde biosynthesis polypeptide selected from an acyl-ACP reductase (AAR) that utilizes a branched fatty acyl-ACP as a substrate, and a carboxylic acid reductase (CAR) that utilizes a branched fatty acid as a substrate when a thioesterase is present;

(b) culturing the recombinant host cell in the presence of a carbon source under conditions effective to express the polynucleotides and produce branched chain fatty alcohols that are secreted into the extracellular environment of the host cell;

(c) collecting the branched chain fatty alcohols; and (d) blending the branched chain fatty alcohols to make a surfactant composition.

2. The method of claim 1, further comprising a polypeptide having fatty alcohol biosynthesis activity.

3. The method of claim 2, wherein said polypeptide having fatty alcohol biosynthesis activity is an alcohol dehydrogenase (EC 1.1.1.1).

4. The method of claim 1, wherein the branched chain fatty alcohols include one or more of saturated or unsaturated C 12, C 14 and C 16 fatty alcohols.

* * * * *

SEQUENCE LISTING

<160> NUMBER OF SEQ ID NOS: 181

<210> SEQ ID NO 1
<211> LENGTH: 330
<212> TYPE: PRT
<213> ORGANISM: Bacillus subtilis

<400> SEQUENCE: 1

Met Ser Thr Asn Arg His Gln Ala Leu Gly Leu Thr Asp Gln Glu Ala
1 5 10 15

Val Asp Met Tyr Arg Thr Met Leu Leu Ala Arg Lys Ile Asp Glu Arg
20 25 30

Met Trp Leu Leu Asn Arg Ser Gly Lys Ile Pro Phe Val Ile Ser Cys
35 40 45

Gln Gly Gln Glu Ala Ala Gln Val Gly Ala Ala Phe Ala Leu Asp Arg
50 55 60

Glu Met Asp Tyr Val Leu Pro Tyr Tyr Arg Asp Met Gly Val Val Leu
65 70 75 80

Ala Phe Gly Met Thr Ala Lys Asp Leu Met Met Ser Gly Phe Ala Lys
85 90 95

Ala Ala Asp Pro Asn Ser Gly Gly Arg Gln Met Pro Gly His Phe Gly
100 105 110

Gln Lys Lys Asn Arg Ile Val Thr Gly Ser Ser Pro Val Thr Thr Gln
115 120 125

Val Pro His Ala Val Gly Ile Ala Leu Ala Gly Arg Met Glu Lys Lys
130 135 140

Asp Ile Ala Ala Phe Val Thr Phe Gly Glu Gly Ser Ser Asn Gln Gly
145 150 155 160

Asp Phe His Glu Gly Ala Asn Phe Ala Ala Val His Lys Leu Pro Val
165 170 175

Ile Phe Met Cys Glu Asn Asn Lys Tyr Ala Ile Ser Val Pro Tyr Asp
180 185 190

Lys Gln Val Ala Cys Glu Asn Ile Ser Asp Arg Ala Ile Gly Tyr Gly
195 200 205

Met Pro Gly Val Thr Val Asn Gly Asn Asp Pro Leu Glu Val Tyr Gln
210 215 220

Ala Val Lys Glu Ala Arg Glu Arg Ala Arg Arg Gly Glu Gly Pro Thr
225 230 235 240

Leu Ile Glu Thr Ile Ser Tyr Arg Leu Thr Pro His Ser Ser Asp Asp
245 250 255

Asp Asp Ser Ser Tyr Arg Gly Arg Glu Glu Val Glu Glu Ala Lys Lys
260 265 270

Ser Asp Pro Leu Leu Thr Tyr Gln Ala Tyr Leu Lys Glu Thr Gly Leu
275 280 285

```
Leu Ser Asp Glu Ile Glu Gln Thr Met Leu Asp Glu Ile Met Ala Ile
    290                 295                 300

Val Asn Glu Ala Thr Asp Glu Ala Glu Asn Ala Pro Tyr Ala Ala Pro
305                 310                 315                 320

Glu Ser Ala Leu Asp Tyr Val Tyr Ala Lys
                325                 330


<210> SEQ ID NO 2
<211> LENGTH: 993
<212> TYPE: DNA
<213> ORGANISM: Bacillus subtilis

<400> SEQUENCE: 2

ctacttcgca taaacataat caagcgctga ctcaggagct gcatatgggg cgttctccgc      60

ttcatccgtc gcttcattta cgattgccat aatttcatcc agcatggttt gttctatctc     120

atcggacagc aggcctgttt cctttaagta agcttgataa gtaagcaggg gatcactttt     180

tttcgcttcc tctacttctt cacggcctct gtagctgctg tcatcgtcat cactggaatg     240

tggtgtaagg cggtaagaaa tcgtttcaat taatgtcggg ccttctcctc tgcgtgccct     300

ttcgcgtgct tctttaaccg cttgataaac ttccagcgga tcatttccat tcacagttac     360

gccaggcatc ccatagccta tggcacggtc ggaaatgttc tcacatgcga cttgcttatc     420

gtaaggcact gagattgcgt atttgttgtt ttcacacatg aaaataaccg gcagcttatg     480

gacagcggca aagtttgccc cttcatggaa atcgccttgg tttgaagacc cttccccgaa     540

tgtaacaaag gctgcgatat cctttttctc catacgtccc gcaagcgcaa taccgactgc     600

gtgcggcact tgcgttgtaa ccggagatga tcccgtcaca atgcggtttt tcttttgtcc     660

gaaatgtccc ggcatctggc ggcctcctga gttcggatct gctgcttttg caaacccgga     720

catcattaag tcctttgctg tcatgccaaa cgcgagcacg acacccatgt ctctgtagta     780

cggcaataca taatccattt cacggtcaag tgcgaaagcc gctcctacct gtgctgcttc     840

ctgtccttga caagagatta caaatggaat tttgccagaa cggtttaaca gccacattct     900

ttcatcgatt tttcttgcta acagcatggt tctatacata tcaacggctt cctgatcagt     960

cagccctagt gcttgatgtc ggtttgtact cat                                  993


<210> SEQ ID NO 3
<211> LENGTH: 406
<212> TYPE: PRT
<213> ORGANISM: Streptomyces avermitilis

<400> SEQUENCE: 3

Met Thr Val Glu Ser Thr Ala Ala Arg Lys Pro Arg Arg Ser Ala Gly
1               5                   10                  15

Thr Lys Ser Ala Ala Ala Lys Arg Thr Ser Pro Gly Ala Lys Lys Ser
            20                  25                  30

Pro Ser Thr Thr Gly Ala Glu His Glu Leu Ile Gln Leu Leu Thr Pro
        35                  40                  45

Asp Gly Arg Arg Val Lys Asn Pro Glu Tyr Asp Ala Tyr Val Ala Asp
    50                  55                  60

Ile Thr Pro Glu Glu Leu Arg Gly Leu Tyr Arg Asp Met Val Leu Ser
65                  70                  75                  80

Arg Arg Phe Asp Ala Glu Ala Thr Ser Leu Gln Arg Gln Gly Glu Leu
                85                  90                  95

Gly Leu Trp Ala Ser Met Leu Gly Gln Glu Ala Ala Gln Ile Gly Ser
```

```
            100                 105                 110

Gly Arg Ala Thr Arg Asp Asp Asp Tyr Val Phe Pro Thr Tyr Arg Glu
        115                 120                 125

His Gly Val Ala Trp Cys Arg Gly Val Asp Pro Thr Asn Leu Leu Gly
    130                 135                 140

Met Phe Arg Gly Val Asn Asn Gly Gly Trp Asp Pro Asn Ser Asn Asn
145                 150                 155                 160

Phe His Leu Tyr Thr Ile Val Ile Gly Ser Gln Thr Leu His Ala Thr
                165                 170                 175

Gly Tyr Ala Met Gly Ile Ala Lys Asp Gly Ala Asp Ser Ala Val Ile
            180                 185                 190

Ala Tyr Phe Gly Asp Gly Ala Ser Ser Gln Gly Asp Val Ala Glu Ser
        195                 200                 205

Phe Thr Phe Ser Ala Val Tyr Asn Ala Pro Val Val Phe Phe Cys Gln
    210                 215                 220

Asn Asn Gln Trp Ala Ile Ser Glu Pro Thr Glu Lys Gln Thr Arg Val
225                 230                 235                 240

Pro Leu Tyr Gln Arg Ala Gln Gly Tyr Gly Phe Pro Gly Val Arg Val
                245                 250                 255

Asp Gly Asn Asp Val Leu Ala Cys Leu Ala Val Thr Lys Trp Ala Leu
            260                 265                 270

Glu Arg Ala Arg Arg Gly Glu Gly Pro Thr Leu Val Glu Ala Phe Thr
        275                 280                 285

Tyr Arg Met Gly Ala His Thr Thr Ser Asp Asp Pro Thr Lys Tyr Arg
    290                 295                 300

Ala Asp Glu Glu Arg Glu Ala Trp Glu Ala Lys Asp Pro Ile Leu Arg
305                 310                 315                 320

Leu Arg Thr Tyr Leu Glu Ala Ser Asn His Ala Asp Glu Gly Phe Phe
                325                 330                 335

Ala Glu Leu Glu Val Glu Ser Glu Ala Leu Gly Arg Arg Val Arg Glu
            340                 345                 350

Val Val Arg Ala Met Pro Asp Pro Asp His Phe Ala Ile Phe Glu Asn
        355                 360                 365

Val Tyr Ala Asp Gly His Ala Leu Val Asp Glu Glu Arg Ala Gln Phe
    370                 375                 380

Ala Ala Tyr Gln Ala Ser Phe Thr Thr Glu Pro Asp Gly Gly Ser Ala
385                 390                 395                 400

Ala Gly Gln Gly Gly Asn
                405
```

<210> SEQ ID NO 4
<211> LENGTH: 1221
<212> TYPE: DNA
<213> ORGANISM: Streptomyces avermitilis

<400> SEQUENCE: 4

```
gtgaccgtgg agagcactgc cgcgcgaaag ccgcgacgca gcgccggtac gaagagcgcc      60

gcagccaagc gcaccagccc cggcgccaag aagtcaccga gcacgaccgg cgccgagcac     120

gagctgattc agctgctcac gcccgacggc cggcgggtga agaaccccga gtacgacgcg     180

tacgtcgcgg acatcacccc cgaagagctg cgcggtctgt accgggacat ggtgctgagc     240

cgccgcttcg acgcagaggc cacctccctg caacgccagg gcgagctggg cctgtgggcc     300

tcgatgctcg ggcaggaggc cgcccagatc ggctcgggcc gggccacccg tgacgacgac     360
```

-continued

```
tacgtcttcc cgacctaccg cgagcacggc gtcgcctggt gccgcggggt cgaccccacc    420

aacctgctcg gcatgttccg cggcgtgaac aacggcggct gggatcccaa cagcaacaac    480

ttccacctct acacgatcgt catcggctcg cagacgctgc acgccaccgg ctacgccatg    540

ggtatcgcca aggacggcgc cgactcggcc gtgatcgcgt acttcggtga cggcgcctcc    600

agccagggtg acgtcgccga atcgttcacc ttctccgcgg tctacaacgc ccctgtcgtc    660

ttcttctgcc agaacaacca gtgggcgatc tccgagccca ccgagaagca gacccgcgtc    720

ccgctctacc agcgcgcgca gggctacggc ttcccgggcg tccgcgtcga cggcaacgac    780

gtactggcct gcctcgccgt caccaagtgg gccctcgagc gggcccgccg gggcgagggg    840

cccacgttgg tcgaggcgtt cacgtaccgc atgggcgcgc acaccacctc cgacgacccg    900

accaagtacc gggccgacga ggagcgcgag gcgtgggagg cgaaggaccc gatcctgcgt    960

ctgcgcacgt atctcgaggc ctcaaaccac gcggacgagg gattcttcgc ggaactcgag   1020

gtggagagcg aggcgttggg aaggcgagtg cgcgaagtgg tgcgtgccat gccggacccg   1080

gaccacttcg ccatcttcga gaacgtgtac gcggacgggc atgcgctcgt cgacgaggag   1140

cgggcgcagt tcgccgccta ccaggcgtcg ttcacgacgg agcctgacgg cggctccgcc   1200

gcgggacagg ggggtaactg a                                             1221
```

<210> SEQ ID NO 5
<211> LENGTH: 410
<212> TYPE: PRT
<213> ORGANISM: Pseudomonas putida

<400> SEQUENCE: 5

```
Met Asn Glu Tyr Ala Pro Leu Arg Leu His Val Pro Glu Pro Thr Gly
1               5                   10                  15

Arg Pro Gly Cys Gln Thr Asp Phe Ser Tyr Leu Arg Leu Asn Asp Ala
            20                  25                  30

Gly Gln Ala Arg Lys Pro Ala Ile Asp Val Asp Ala Ala Asp Thr Ala
        35                  40                  45

Asp Leu Ser Tyr Ser Leu Val Arg Val Leu Asp Glu Gln Gly Asp Ala
    50                  55                  60

Gln Gly Pro Trp Ala Glu Asp Ile Asp Pro Gln Ile Leu Arg Gln Gly
65                  70                  75                  80

Met Arg Ala Met Leu Lys Thr Arg Ile Phe Asp Ser Arg Met Val Val
                85                  90                  95

Ala Gln Arg Gln Lys Lys Met Ser Phe Tyr Met Gln Ser Leu Gly Glu
            100                 105                 110

Glu Ala Ile Gly Ser Gly Gln Ala Leu Ala Leu Asn Arg Thr Asp Met
        115                 120                 125

Cys Phe Pro Thr Tyr Arg Gln Gln Ser Ile Leu Met Ala Arg Asp Val
    130                 135                 140

Ser Leu Val Glu Met Ile Cys Gln Leu Leu Ser Asn Glu Arg Asp Pro
145                 150                 155                 160

Leu Lys Gly Arg Gln Leu Pro Ile Met Tyr Ser Val Arg Glu Ala Gly
                165                 170                 175

Phe Phe Thr Ile Ser Gly Asn Leu Ala Thr Gln Phe Val Gln Ala Val
            180                 185                 190

Gly Trp Ala Met Ala Ser Ala Ile Lys Gly Asp Thr Lys Ile Ala Ser
        195                 200                 205

Ala Trp Ile Gly Asp Gly Ala Thr Ala Glu Ser Asp Phe His Thr Ala
    210                 215                 220
```

-continued

```
Leu Thr Phe Ala His Val Tyr Arg Ala Pro Val Ile Leu Asn Val Val
225                 230                 235                 240

Asn Asn Gln Trp Ala Ile Ser Thr Phe Gln Ala Ile Ala Gly Gly Glu
                245                 250                 255

Ser Thr Thr Phe Ala Gly Arg Gly Val Gly Cys Gly Ile Ala Ser Leu
            260                 265                 270

Arg Val Asp Gly Asn Asp Phe Val Ala Val Tyr Ala Ala Ser Arg Trp
        275                 280                 285

Ala Ala Glu Arg Ala Arg Arg Gly Leu Gly Pro Ser Leu Ile Glu Trp
    290                 295                 300

Val Thr Tyr Arg Ala Gly Pro His Ser Thr Ser Asp Asp Pro Ser Lys
305                 310                 315                 320

Tyr Arg Pro Ala Asp Asp Trp Ser His Phe Pro Leu Gly Asp Pro Ile
                325                 330                 335

Ala Arg Leu Lys Gln His Leu Ile Lys Ile Gly His Trp Ser Glu Glu
            340                 345                 350

Glu His Gln Ala Val Thr Ala Glu Leu Glu Ala Ala Val Ile Ala Ala
        355                 360                 365

Gln Lys Glu Ala Glu Gln Tyr Gly Thr Leu Ala Asn Gly His Ile Pro
    370                 375                 380

Ser Ala Ala Ser Met Phe Glu Asp Val Tyr Lys Glu Met Pro Glu His
385                 390                 395                 400

Leu Arg Arg Gln Arg Gln Glu Leu Gly Val
                405                 410


<210> SEQ ID NO 6
<211> LENGTH: 1233
<212> TYPE: DNA
<213> ORGANISM: Pseudomonas putida

<400> SEQUENCE: 6

tcaaaccccc agttcctggc gttgacggcg caggtgttcg ggcatctcct tgtacacatc      60

ctcgaacatc gaggcggcgc tcgggatgtg cccgttagcc agggtgccgt actgctcggc     120

ttctttctgt gcggcaatca ccgcagcttc gagctcggcc gtgacggctt ggtgttcttc     180

ttcggaccag tggccgatct tgatcaggtg ctgcttcagg cgggcgatcg ggtcacccag     240

cgggaagtgg ctccagtcat cggcagggcg gtacttggag ggtcgtccg acgtcgagtg     300

cgggccggca cggtaggtga cccactcgat caggcttggg cccaggccgc ggcgggcgcg     360

ctcggcagcc cagcgcgagg cggcgtacac ggcgacgaag tcgttgccgt caacccgcag     420

cgaggcaatg ccgcagccca cgccacggcc ggcgaaggtg gtcgactcgc caccggcgat     480

ggcctggaag gtagaaatcg cccactggtt gttgaccaca ttgaggatca ccggggcgcg     540

gtaaacgtgg gcaaaggtga gggcggtgtg gaagtccgac tcggcggtgg ctccgtcacc     600

gatccacgcc gaagcaatct tggtatcgcc cttgatcgcc gaggccatgg cccagccgac     660

tgcctgcacg aactgggtcg ccaggttgcc gctgatggtg aagaagccgg cttcgcgcac     720

cgagtacatg atcggcaact ggcggccctt gagggggtcg cgctcgttgg acagcagttg     780

gcagatcatc tcgaccagcg atacgtcgcg ggccatcagg atgctttgct ggcggtaggt     840

cgggaagcac atgtcggtgc ggttcagcgc cagcgcctgg ccactgccga tggcttcttc     900

gcccaggctt tgcatgtaga aggacatctt cttctggcgc tgggcaacca ccatgcggct     960

gtcgaagatc cgcgtcttga gcatggcgcg catgccttga cgaaggatct gtgggtcgat    1020
```

-continued

```
gtcttcggcc caggggcctt gcgcatcacc ttgctcgtcg agcacgcgga ccaggctgta   1080

ggacaggtcg gcagtgtcgg cagcatcgac atcgatcgcg ggtttacggg cttgacctgc   1140

atcgttgagg cgcaggtagg aaaaatcggt ctggcagcct ggccggccgg tgggctcggg   1200

cacatgcaaa cgcagggggg cgtactcgtt cat                               1233
```

<210> SEQ ID NO 7
<211> LENGTH: 331
<212> TYPE: PRT
<213> ORGANISM: Listeria monocytogenes

<400> SEQUENCE: 7

```
Met Thr Leu Lys Glu Ala Gly Leu Thr Glu Asp Lys Leu Ile Lys Met
1               5                   10                  15

Tyr Glu Thr Met Leu Met Ala Arg Arg Leu Asp Glu Arg Met Trp Leu
            20                  25                  30

Leu Asn Arg Ser Gly Lys Ile Pro Phe Thr Ile Ser Gly Gln Gly Gln
        35                  40                  45

Glu Thr Ala Gln Ile Gly Ala Ala Phe Ala Phe Asp Leu Asp Lys Asp
    50                  55                  60

Tyr Ala Leu Pro Tyr Tyr Arg Asp Leu Ala Val Val Leu Ala Phe Gly
65                  70                  75                  80

Met Thr Ala Lys Asp Ile Met Leu Ser Ala Phe Ala Lys Ala Glu Asp
                85                  90                  95

Pro Asn Ser Gly Gly Arg Gln Met Pro Ala His Phe Gly Gln Lys Ser
            100                 105                 110

Asn Arg Ile Val Thr Gln Ser Ser Pro Val Thr Thr Gln Phe Pro His
        115                 120                 125

Ala Ala Gly Ile Gly Leu Ala Ala Lys Met Ala Gly Asp Glu Ile Ala
    130                 135                 140

Ile Tyr Ala Ser Thr Gly Glu Gly Ser Ser Asn Gln Gly Asp Phe His
145                 150                 155                 160

Glu Gly Ile Asn Phe Ala Ser Val His Lys Leu Pro Val Val Phe Val
                165                 170                 175

Ile His Asn Asn Gln Tyr Ala Ile Ser Val Pro Ala Ser Lys Gln Tyr
            180                 185                 190

Ala Ala Glu Lys Leu Ser Asp Arg Ala Ile Gly Tyr Gly Ile Pro Gly
        195                 200                 205

Glu Arg Val Asp Gly Thr Asn Met Gly Glu Val Tyr Ala Ala Phe Lys
    210                 215                 220

Arg Ala Ala Asp Arg Ala Arg Asn Gly Glu Gly Pro Thr Leu Ile Glu
225                 230                 235                 240

Thr Val Ser Tyr Arg Phe Thr Pro His Ser Ser Asp Asp Asp Asp Ser
                245                 250                 255

Ser Tyr Arg Ser Arg Glu Glu Val Asn Glu Ala Lys Gly Lys Asp Pro
            260                 265                 270

Leu Thr Ile Phe Gln Thr Glu Leu Leu Glu Glu Gly Tyr Leu Thr Glu
        275                 280                 285

Glu Lys Ile Ala Glu Ile Glu Lys Asn Ile Ala Lys Glu Val Asn Glu
    290                 295                 300

Ala Thr Asp Tyr Ala Glu Ser Ala Ala Tyr Ala Glu Pro Glu Ser Ser
305                 310                 315                 320

Leu Leu Tyr Val Tyr Asp Glu Glu Ala Asn Ser
                325                 330
```

-continued

<210> SEQ ID NO 8
<211> LENGTH: 996
<212> TYPE: DNA
<213> ORGANISM: Listeria monocytogenes

<400> SEQUENCE: 8
atgactttaa aagaagcagg tttaacagaa gataaattaa ttaaaatgta tgaaacaatg 60
ctaatggcaa gaagactaga cgagcgtatg tggttgctga accgttctgg gaaaattcct 120
ttcaccattt ctggacaagg acaagaaacg gcacaaattg gcgcagcgtt tgcctttgat 180
ttagataaag attacgcatt accatattac cgtgatttag cggtggtgtt agcatttggg 240
atgacagcga aagatattat gttatccgcg ttcgctaaag cagaggatcc aaactctggt 300
ggacgtcaaa tgccagctca ttttggtcaa aaatcaaatc gcatcgtgac acaaagttca 360
ccagtaacaa cgcagttccc gcatgcagca ggtattggtc ttgcagcgaa aatggccggt 420
gatgagattg caatttatgc ttcaacgggt gaaggatctt ctaaccaagg agatttccat 480
gaaggaatca acttcgcatc tgtacataag ttgccagttg ttttcgtgat tcacaataac 540
caatatgcca tttccgttcc agcatcgaaa caatatgctg cagaaaaact atccgaccga 600
gcaatcggtt atggtatccc aggggaacgt gtggatggca caaatatggg tgaagtatac 660
gcggcattta aacgtgcagc agatcgtgca agaaacggcg agggccccac tttaattgaa 720
acagtttctt accgattcac accgcactct tctgatgatg atgacagcag ttatcgttcc 780
agagaagaag tgaacgaagc aaaaggaaaa gatccactga caattttcca aacagaatta 840
ctcgaagaag gttacttaac agaagaaaaa atcgctgaaa tcgaaaaaaa tattgcaaaa 900
gaagttaacg aagcaaccga ttacgcggaa agtgcagcat acgctgaacc agaatcatct 960
ttactttatg tatatgatga agaagcgaat agctga 996

<210> SEQ ID NO 9
<211> LENGTH: 381
<212> TYPE: PRT
<213> ORGANISM: Streptomyces avermitilis

<400> SEQUENCE: 9

Met Thr Val Met Glu Gln Arg Gly Ala Tyr Arg Pro Thr Pro Pro Pro
1 5 10 15

Ala Trp Gln Pro Arg Thr Asp Pro Ala Pro Leu Leu Pro Asp Ala Leu
20 25 30

Pro His Arg Val Leu Gly Thr Glu Ala Ala Ala Glu Ala Asp Pro Leu
35 40 45

Leu Leu Arg Arg Leu Tyr Ala Glu Leu Val Arg Gly Arg Arg Tyr Asn
50 55 60

Thr Gln Ala Thr Ala Leu Thr Lys Gln Gly Arg Leu Ala Val Tyr Pro
65 70 75 80

Ser Ser Thr Gly Gln Glu Ala Cys Glu Val Ala Ala Ala Leu Val Leu
85 90 95

Glu Glu Arg Asp Trp Leu Phe Pro Ser Tyr Arg Asp Thr Leu Ala Ala
100 105 110

Val Ala Arg Gly Leu Asp Pro Val Gln Ala Leu Thr Leu Leu Arg Gly
115 120 125

Asp Trp His Thr Gly Tyr Asp Pro Arg Glu His Arg Ile Ala Pro Leu
130 135 140

Cys Thr Pro Leu Ala Thr Gln Leu Pro His Ala Val Gly Leu Ala His
145 150 155 160

```
Ala Ala Arg Leu Lys Gly Asp Asp Val Val Ala Leu Ala Leu Val Gly
                165                 170                 175

Asp Gly Gly Thr Ser Glu Gly Asp Phe His Glu Ala Leu Asn Phe Ala
            180                 185                 190

Ala Val Trp Gln Ala Pro Val Val Phe Leu Val Gln Asn Asn Gly Phe
        195                 200                 205

Ala Ile Ser Val Pro Leu Ala Lys Gln Thr Ala Ala Pro Ser Leu Ala
    210                 215                 220

His Lys Ala Val Gly Tyr Gly Met Pro Gly Arg Leu Val Asp Gly Asn
225                 230                 235                 240

Asp Ala Ala Ala Val His Glu Val Leu Ser Asp Ala Val Ala His Ala
                245                 250                 255

Arg Ala Gly Gly Gly Pro Thr Leu Val Glu Ala Val Thr Tyr Arg Ile
            260                 265                 270

Asp Ala His Thr Asn Ala Asp Asp Ala Thr Arg Tyr Arg Gly Asp Ser
        275                 280                 285

Glu Val Glu Ala Trp Arg Ala His Asp Pro Ile Ala Leu Leu Glu His
    290                 295                 300

Glu Leu Thr Glu Arg Gly Leu Leu Asp Glu Asp Gly Ile Arg Ala Ala
305                 310                 315                 320

Arg Glu Asp Ala Glu Ala Met Ala Ala Asp Leu Arg Ala Arg Met Asn
                325                 330                 335

Gln Asp Pro Ala Leu Asp Pro Met Asp Leu Phe Ala His Val Tyr Ala
            340                 345                 350

Glu Pro Thr Pro Gln Leu Arg Glu Gln Glu Ala Gln Leu Arg Ala Glu
        355                 360                 365

Leu Ala Ala Glu Ala Asp Gly Pro Gln Gly Val Gly Arg
    370                 375                 380
```

<210> SEQ ID NO 10
<211> LENGTH: 1146
<212> TYPE: DNA
<213> ORGANISM: Streptomyces avermitilis

<400> SEQUENCE: 10

```
atgacggtca tggagcagcg gggcgcttac cggcccacac cgccgcccgc ctggcagccc      60

cgcaccgacc ccgcgccact gctgcccgac gcgctgcccc accgcgtcct gggcaccgag     120

gcggccgcgg aggccgaccc gctactgctg cgccgcctgt acgcggagct ggtgcgcggc     180

cgccgctaca acacgcaggc cacggctctc accaagcagg gccggctcgc cgtctacccg     240

tcgagcacgg gccaggaggc ctgcgaggtc gccgccgcgc tcgtgctgga ggagcgcgac     300

tggctcttcc ccagctaccg ggacaccctc gccgccgtcg cccgcggcct cgatcccgtc     360

caggcgctca ccctcctgcg cggcgactgg cacaccgggt acgacccccg tgagcaccgc     420

atcgcgcccc tgtgcacccc tctcgcgacc cagctcccgc acgccgtcgg cctcgcgcac     480

gccgcccgcc tcaagggcga cgacgtggtc gcgctcgccc tggtcggcga cggcggcacc     540

agcgagggcg acttccacga ggcactgaac ttcgccgccg tctggcaggc gccggtcgtc     600

ttcctcgtgc agaacaacgg cttcgccatc tccgtcccgc tcgccaagca gaccgccgcc     660

ccgtcgctgg cccacaaggc cgtcggctac gggatgccgg gccgcctggt cgacggcaac     720

gacgcggcgg ccgtgcacga ggtcctcagc gacgccgtgg cccacgcgcg cgcgggaggg     780

gggccgacgc tcgtggaggc ggtgacctac cgcatcgacg cccacaccaa cgccgacgac     840
```

-continued gcgacgcgct accgggggga ctccgaggtg gaggcctggc gcgcgcacga cccgatcgcg 900
ctcctggagc acgagttgac cgaacgcggg ctgctcgacg aggacggcat ccgggccgcc 960
cgcgaggacg ccgaggcgat ggccgcggac ctgcgcgcac gcatgaacca ggatccggcc 1020
ctggacccca tggacctgtt cgcccatgtg tatgccgagc ccacccccca gctgcgggag 1080
caggaagccc agttgcgggc cgagctggca gcggaggccg acgggcccca aggagtcggc 1140
cgatga 1146

<210> SEQ ID NO 11
<211> LENGTH: 384
<212> TYPE: PRT
<213> ORGANISM: Micrococcus luteus

<400> SEQUENCE: 11

Met Thr Leu Val Asp His Thr Arg Pro Thr Gly Gly Gln Ser Ala Gly
1 5 10 15

Ser Pro Pro Pro Ala Gly Pro Ala Glu Ala Val Met Leu Gln Val Leu
20 25 30

Asp Thr Glu Gly Arg Arg Arg Pro Gln Pro Glu Leu Asp Pro Trp Ile
35 40 45

Glu Asp Val Asp Ala Ala Ala Leu Ala Ala Leu Tyr Arg Gln Met Ala
50 55 60

Val Val Arg Arg Leu Asp Val Glu Ala Thr His Leu Gln Arg Gln Gly
65 70 75 80

Glu Leu Ala Leu Trp Pro Pro Leu Leu Gly Gln Glu Ala Ala Gln Val
85 90 95

Gly Ser Ala Val Ala Leu Arg Pro Asp Asp Phe Val Phe Pro Ser Tyr
100 105 110

Arg Glu Asn Gly Val Ala Leu Leu Arg Gly Val Pro Ala Leu Asp Leu
115 120 125

Leu Arg Val Trp Arg Gly Ser Thr Phe Ser Ser Trp Asp Pro Asn Glu
130 135 140

Thr Arg Val Ala Thr Gln Gln Ile Ile Ile Gly Ala Gln Ala Leu His
145 150 155 160

Ala Val Gly Tyr Ala Met Gly Val Gln Arg Asp Gln Ala Asp Val Ala
165 170 175

Thr Ile Val Tyr Phe Gly Asp Gly Ala Thr Ser Gln Gly Asp Val Asn
180 185 190

Glu Ala Met Val Phe Ser Ala Ser Tyr Gln Ala Pro Val Val Phe Phe
195 200 205

Cys Gln Asn Asn His Trp Ala Ile Ser Glu Pro Val Arg Leu Gln Thr
210 215 220

Arg Arg Ser Ile Ala Asp Arg Pro Trp Gly Phe Gly Ile Pro Ser Met
225 230 235 240

Arg Val Asp Gly Asn Asp Val Leu Ala Val Leu Ala Ala Thr Arg Ala
245 250 255

Ala Val Glu Arg Ala Ala Asp Gly Gly Gly Pro Thr Phe Val Glu Ala
260 265 270

Val Thr Tyr Arg Met Gly Pro His Thr Thr Ala Asp Asp Pro Thr Arg
275 280 285

Tyr Arg Asp Asp Ala Glu Leu Glu Ala Trp Lys Ala Arg Asp Pro Leu
290 295 300

Thr Arg Val Glu Ala His Leu Arg Thr Leu Asp Val Asp Val Asp Ala
305 310 315 320

Val Leu Ala Gln Ala Gln Ala Glu Ala Asp Glu Leu Ala Ala Glu Val
325 330 335

Arg Arg Ala Leu Glu Ala Leu Glu Glu Asp Gly Ala Asp Arg Leu Phe
340 345 350

Asp Glu Ile Tyr Ala Glu Pro His Gln Glu Leu Glu Arg Gln Arg Arg
355 360 365

Glu His Ala Leu Tyr Leu Gln Gln Phe Asp Asp Glu Glu Ala Gly Ala
370 375 380

<210> SEQ ID NO 12
<211> LENGTH: 1155
<212> TYPE: DNA
<213> ORGANISM: Micrococcus luteus

<400> SEQUENCE: 12
gtgaccctcg tggaccacac ccgtcccacc ggcggacagt ccgccggctc tccgcccccg 60
gcgggcccgg ccgaggccgt gatgctccag gtgctcgaca cggagggccg ccgccgtccg 120
cagccggagc tcgacccgtg gatcgaggac gtcgacgccg ccgccctcgc cgcgctgtac 180
cgccagatgg ccgtggtccg tcgcctcgac gtcgaggcca cgcacctgca gcgtcagggc 240
gagctggccc tgtggccgcc gctgctgggc caggaggccg cccaggtggg ctccgccgtc 300
gcgctgcgcc cggacgactt cgtcttcccg tcctaccgcg agaacggcgt ggccctgctg 360
cgcggcgtcc ccgcgctgga cctgctgcgg gtgtggcgcg gctccacgtt ctcgagctgg 420
gacccgaacg agacgcgggt ggccacccag cagatcatca tcggcgcgca ggccctgcac 480
gccgtcggct acgcgatggg cgtccagcgg gaccaggcgg acgtcgccac gatcgtctac 540
ttcggcgacg gcgccacgag ccagggcgac gtcaacgagg ccatggtctt cagcgcctcc 600
taccaggcgc ccgtggtgtt cttctgccag aacaaccact gggccatctc cgagcccgtg 660
cgcctgcaga cccgccgcag catcgcggac cgcccgtggg gcttcggcat cccgtcgatg 720
cgcgtggacg gcaacgacgt cctggccgtg ctcgccgcaa cccgcgccgc cgtcgagcgc 780
gcggccgacg gggcggcccc cacgttcgtc gaggccgtca cctaccgcat gggtccacac 840
accaccgcgg acgaccccac ccgctaccgg gacgacgccg agctcgaggc ctggaaggcc 900
cgtgacccgc tgacccgcgt ggaggcgcac ctgcgcaccc tcgacgtgga cgtggacgcc 960
gtgcttgcac aggcccaggc cgaggccgac gagctggcag cggaggtccg ccgtgccctc 1020
gaggcgctcg aggaggacgg cgcggacagg ctcttcgacg agatctacgc ggagccccac 1080
caggagctcg agcggcagcg ccgcgagcac gccctctacc tgcagcagtt cgacgacgag 1140
gaggcgggcg cgtga 1155

<210> SEQ ID NO 13
<211> LENGTH: 330
<212> TYPE: PRT
<213> ORGANISM: Staphylococcus aureus

<400> SEQUENCE: 13

Met Ile Asp Tyr Lys Ser Leu Gly Leu Ser Glu Glu Asp Leu Lys Val
1 5 10 15

Ile Tyr Lys Trp Met Asp Leu Gly Arg Lys Ile Asp Glu Arg Leu Trp
20 25 30

Leu Leu Asn Arg Ala Gly Lys Ile Pro Phe Val Val Ser Gly Gln Gly
35 40 45

Gln Glu Ala Thr Gln Ile Gly Met Ala Tyr Ala Leu Glu Glu Gly Asp

```
    50                  55                  60

Ile Thr Ala Pro Tyr Tyr Arg Asp Leu Ala Phe Val Thr Tyr Met Gly
65                  70                  75                  80

Ile Ser Ala Tyr Asp Thr Phe Leu Ser Ala Phe Gly Lys Lys Asp Asp
                85                  90                  95

Val Asn Ser Gly Gly Lys Gln Met Pro Ser His Phe Ser Ser Arg Ala
            100                 105                 110

Lys Asn Ile Leu Ser Gln Ser Ser Pro Val Ala Thr Gln Ile Pro His
        115                 120                 125

Ala Val Gly Ala Ala Leu Ala Leu Lys Met Asp Gly Lys Lys Lys Ile
    130                 135                 140

Ala Thr Ala Thr Val Gly Glu Gly Ser Ser Asn Gln Gly Asp Phe His
145                 150                 155                 160

Glu Gly Leu Asn Phe Ala Gly Val His Lys Leu Pro Phe Val Cys Val
                165                 170                 175

Ile Ile Asn Asn Lys Tyr Ala Ile Ser Val Pro Asp Ser Leu Gln Tyr
            180                 185                 190

Ala Ala Glu Lys Leu Ser Asp Arg Ala Leu Gly Tyr Gly Ile His Gly
        195                 200                 205

Glu Gln Val Asp Gly Asn Asp Pro Leu Ala Met Tyr Lys Ala Met Lys
    210                 215                 220

Glu Ala Arg Asp Arg Ala Ile Ser Gly Gln Gly Ser Thr Leu Ile Glu
225                 230                 235                 240

Ala Val Thr Ser Arg Met Thr Ala His Ser Ser Asp Asp Asp Asp Gln
                245                 250                 255

Tyr Arg Thr Lys Glu Glu Arg Glu Ala Leu Lys Lys Ala Asp Cys Asn
            260                 265                 270

Glu Lys Phe Lys Lys Glu Leu Leu Ser Ala Gly Ile Ile Asp Asp Ala
        275                 280                 285

Trp Leu Ala Glu Ile Glu Ala Glu His Lys Asp Ile Ile Asn Lys Ala
    290                 295                 300

Thr Lys Ala Ala Glu Asp Ala Pro Tyr Pro Ser Val Glu Glu Ala Tyr
305                 310                 315                 320

Ala Phe Val Tyr Glu Glu Gly Ser Leu Asn
                325                 330


<210> SEQ ID NO 14
<211> LENGTH: 993
<212> TYPE: DNA
<213> ORGANISM: Staphylococcus aureus

<400> SEQUENCE: 14

ttagttaaga ctcccttctt cgtacacaaa tgcataggct tcttcgacac ttggatatgg      60

cgcgtcttca gcagcctttg tcgctttatt gatgatgtct ttatgctccg cttctatttc     120

tgccaaccaa gcatcatcga taatgccagc tgaaagcaac tctttttga actttcatt      180

gcagtcagct tttttaagcg cttcacgctc ttctttcgta cgatattggt cgtcatcatc     240

tgatgaatga gctgtcatac gacttgttac tgcttcaatc aaagttgaac cttgaccaga     300

aatagctcga tctcttgctt ctttcatcgc tttatacatt gctaatggat cattaccatc     360

tacttgttca ccatgtatac cgtaaccaag tgctctatcc gataattttt cagctgcgta     420

ttgtaatgaa tcaggtactg aaattgcata tttattattt ataatgacac atacaaaagg     480

aagtttgtgt acacccgcga agtttaaacc ttcatggaag tcaccttggt ttgagctacc     540
```

-continued

```
ttcaccaaca gttgctgttg caattttctt cttaccatcc atttttaaag ctaaagcagc    600

accaacagca tggggtattt gagttgctac cggtgaactt tgagacaaaa tattcttagc    660

tctactacta aagtgtgatg gcatttgttt tccaccagag ttaacatcgt ctttctttcc    720

aaacgctgat aaaaacgtat catacgctga gatacccata taagtaacga aagctagatc    780

tctataataa ggcgctgtaa tatcaccttc ttctaatgcg tatgccatcc caatctgagt    840

tgcttcttgt ccttgaccac ttacaacaaa tggaatttta cctgcacggt tcaataacca    900

cagtctttca tctatttttc tacctaaatc catccattta tatattactt ttaggtcttc    960

ttcgctaagg cctaatgatt tataatcaat cat                                  993
```

<210> SEQ ID NO 15
<211> LENGTH: 331
<212> TYPE: PRT
<213> ORGANISM: Streptococcus mutans

<400> SEQUENCE: 15

```
Met Ala Arg Lys Ile Leu Glu Val Ile Ile Ala Met Leu Ser Lys Lys
1               5                   10                  15

Gln Tyr Leu Asp Met Phe Leu Lys Met Gln Arg Ile Arg Asp Val Asp
            20                  25                  30

Thr Lys Leu Asn Lys Leu Val Arg Arg Gly Phe Val Gln Gly Met Thr
        35                  40                  45

His Phe Ser Val Gly Glu Glu Ala Ala Ser Val Gly Ala Ile Gln Gly
    50                  55                  60

Leu Thr Asp Gln Asp Ile Ile Phe Ser Asn His Arg Gly His Gly Gln
65                  70                  75                  80

Thr Ile Ala Lys Gly Ile Asp Ile Pro Ala Met Phe Ala Glu Leu Ala
                85                  90                  95

Gly Lys Ala Thr Gly Ser Ser Lys Gly Arg Gly Gly Ser Met His Leu
            100                 105                 110

Ala Asn Leu Glu Lys Gly Asn Tyr Gly Thr Asn Gly Ile Val Gly Gly
        115                 120                 125

Gly Tyr Ala Leu Ala Val Gly Ala Ala Leu Thr Gln Gln Tyr Asp Asn
    130                 135                 140

Thr Gly Asn Ile Val Val Ala Phe Ser Gly Asp Ser Ala Thr Asn Glu
145                 150                 155                 160

Gly Ser Phe His Glu Ser Val Asn Leu Ala Ala Val Trp Asn Leu Pro
                165                 170                 175

Val Ile Phe Phe Ile Ile Asn Asn Arg Tyr Gly Ile Ser Thr Asp Ile
            180                 185                 190

Asn Tyr Ser Thr Lys Ile Ser His Leu Tyr Leu Arg Ala Asp Ala Tyr
        195                 200                 205

Gly Ile Pro Gly His Tyr Val Glu Asp Gly Asn Asp Val Ile Ala Val
    210                 215                 220

Tyr Glu Lys Met Gln Glu Val Ile Asp Tyr Val Arg Ser Gly Asn Gly
225                 230                 235                 240

Pro Ala Leu Val Glu Val Glu Ser Tyr Arg Trp Phe Gly His Ser Thr
                245                 250                 255

Ala Asp Ala Gly Ala Tyr Arg Thr Lys Glu Glu Val Asp Ala Trp Lys
            260                 265                 270

Ala Lys Asp Pro Leu Lys Lys Tyr Arg Thr Tyr Leu Thr Glu Asn Lys
        275                 280                 285

Ile Ala Thr Asp Glu Glu Leu Asp Met Ile Glu Lys Glu Val Ala Gln
```

-continued

```
    290                 295                 300

Glu Ile Glu Asp Ala Val Lys Phe Ala Gln Asp Ser Pro Glu Pro Glu
305                 310                 315                 320

Leu Ser Val Ala Phe Glu Asp Val Trp Val Asp
                325                 330
```

<210> SEQ ID NO 16
<211> LENGTH: 996
<212> TYPE: DNA
<213> ORGANISM: Streptococcus mutans

<400> SEQUENCE: 16

```
atggcaagaa aaattttgga ggtcattata gcaatgttat ctaaaaaaca atatttggat      60

atgtttttaa aaatgcagcg tatccgtgat gtcgatacaa aactcaataa attagttcgt     120

cgtggtttcg tacaaggtat gacacacttt tcagtaggag aagaggcggc ttcggttggt     180

gcgattcaag gcttgactga tcaggatatt atcttttcaa atcaccgtgg acatggtcaa     240

accattgcaa aagggattga cattcctgct atgtttgcag aattagccgg taaggcaacg     300

ggttcttcaa aaggtcgtgg tggttctatg cacttggcaa atcttgaaaa aggaaactat     360

gggaccaatg gtattgttgg cgggggttat gccttagcag tcggtgctgc tttgacacag     420

caatatgaca atacgggaaa tattgttgtc gccttttcag gagactcggc aactaatgaa     480

ggctctttcc atgagtctgt taatttggca gctgtctgga atttaccggt tatcttcttt     540

attattaata atcgttatgg tatctcaaca gatatcaatt attctactaa gatttcacat     600

ctttatttac gtgctgatgc ttatggtatt cctggacatt atgttgaaga tggtaatgat     660

gtcattgcag tttatgaaaa aatgcaggaa gtcattgatt atgtgcgttc aggaaatggg     720

ccagctcttg ttgaagtgga atcttatcgt tggttcggac attctactgc tgatgcagga     780

gcttaccgta caaaagaaga agtagatgct tggaaagcta aagatcctct caagaaatac     840

cgcacttatc taacagaaaa taagattgca acagatgagg aacttgatat gattgaaaaa     900

gaagtcgcac aggaaattga ggatgcagtg aaatttgccc aagatagccc tgaaccagag     960

ctttctgtag cttttgaaga tgtttgggta gattag                               996
```

<210> SEQ ID NO 17
<211> LENGTH: 16
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Ser or Gln
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be Gln or Glu
<220> FEATURE:
<221> NAME/KEY: MISC_FEATURE
<222> LOCATION: (8)..(10)
<223> OTHER INFORMATION: Xaa can be any amino acid
<220> FEATURE:
<221> NAME/KEY: MISC_FEATURE
<222> LOCATION: (11)..(11)
<223> OTHER INFORMATION: Xaa can be Gly or Ala
<220> FEATURE:
<221> NAME/KEY: MISC_FEATURE
<222> LOCATION: (12)..(12)
<223> OTHER INFORMATION: Xaa can be any amino acid
<220> FEATURE:
<221> NAME/KEY: MISC_FEATURE
<222> LOCATION: (13)..(13)
<223> OTHER INFORMATION: Xaa can be Gly or Ala
<220> FEATURE:
<221> NAME/KEY: MISC_FEATURE
<222> LOCATION: (14)..(14)
<223> OTHER INFORMATION: Xaa can be any amino acid
<220> FEATURE:
<221> NAME/KEY: MISC_FEATURE
<222> LOCATION: (15)..(15)
<223> OTHER INFORMATION: Xaa can be Val or Ala
<220> FEATURE:
<221> NAME/KEY: MISC_FEATURE
<222> LOCATION: (16)..(16)
<223> OTHER INFORMATION: Xaa can be Leu or Thr

<400> SEQUENCE: 17

```
Xaa Xaa Xaa Gly Xaa Glu Ala Xaa Xaa Xaa Xaa Xaa Xaa Xaa Xaa Xaa
1               5                   10                  15
```

<210> SEQ ID NO 18
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa can be Leu or Phe
<220> FEATURE:
<221> NAME/KEY: MISC_FEATURE
<222> LOCATION: (6)..(6)
<223> OTHER INFORMATION: Xaa can be any amino acid

<400> SEQUENCE: 18

```
Asp Xaa Xaa Xaa Pro Xaa Tyr Arg
1               5
```

<210> SEQ ID NO 19
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Ser or Thr
<220> FEATURE:
<221> NAME/KEY: MISC_FEATURE
<222> LOCATION: (3)..(4)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be His or Gln
<220> FEATURE:
<221> NAME/KEY: MISC_FEATURE
<222> LOCATION: (7)..(7)
<223> OTHER INFORMATION: Xaa can be Thr or Val
<220> FEATURE:
<221> NAME/KEY: MISC_FEATURE
<222> LOCATION: (9)..(9)
<223> OTHER INFORMATION: Xaa can be any amino acid
<220> FEATURE:
<221> NAME/KEY: MISC_FEATURE
<222> LOCATION: (11)..(11)

<223> OTHER INFORMATION: Xaa can be Ala or Gly

<400> SEQUENCE: 19

Xaa Gln Xaa Xaa Xaa Ala Xaa Gly Xaa Ala Xaa
1 5 10

<210> SEQ ID NO 20
<211> LENGTH: 20
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Lys or Gly
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (3)..(3)
<223> OTHER INFORMATION: Xaa can be Thr or Asp
<220> FEATURE:
<221> NAME/KEY: MISC_FEATURE
<222> LOCATION: (4)..(5)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be Ala or Val
<220> FEATURE:
<221> NAME/KEY: MISC_FEATURE
<222> LOCATION: (7)..(7)
<223> OTHER INFORMATION: Xaa can be any amino acid
<220> FEATURE:
<221> NAME/KEY: MISC_FEATURE
<222> LOCATION: (8)..(8)
<223> OTHER INFORMATION: Xaa can be Ala or Val
<220> FEATURE:
<221> NAME/KEY: MISC_FEATURE
<222> LOCATION: (9)..(10)
<223> OTHER INFORMATION: Xaa can be any amino acid
<220> FEATURE:
<221> NAME/KEY: MISC_FEATURE
<222> LOCATION: (12)..(12)
<223> OTHER INFORMATION: Xaa can be Glu or Asp
<220> FEATURE:
<221> NAME/KEY: MISC_FEATURE
<222> LOCATION: (14)..(17)
<223> OTHER INFORMATION: Xaa can be any amino acid
<220> FEATURE:
<221> NAME/KEY: MISC_FEATURE
<222> LOCATION: (18)..(18)
<223> OTHER INFORMATION: Xaa can be Gly or Ser
<220> FEATURE:
<221> NAME/KEY: MISC_FEATURE
<222> LOCATION: (20)..(20)
<223> OTHER INFORMATION: Xaa can be Phe or Val

<400> SEQUENCE: 20

Xaa Xaa Xaa Xaa Xaa Xaa Xaa Xaa Xaa Xaa Gly Xaa Gly Xaa Xaa Xaa
1 5 10 15

Xaa Xaa Asp Xaa
20

<210> SEQ ID NO 21
<211> LENGTH: 21
<212> TYPE: PRT
<213> ORGANISM: Artificial sequence
<220> FEATURE:
<223> OTHER INFORMATION: Synthetic polypeptide
<220> FEATURE:

-continued

<221> NAME/KEY: MISC_FEATURE
<222> LOCATION: (2)..(2)
<223> OTHER INFORMATION: Xaa can be Ala or Ser
<220> FEATURE:
<221> NAME/KEY: MISC_FEATURE
<222> LOCATION: (3)..(3)
<223> OTHER INFORMATION: Xaa can be His or Ala
<220> FEATURE:
<221> NAME/KEY: MISC_FEATURE
<222> LOCATION: (5)..(6)
<223> OTHER INFORMATION: Xaa can be any amino acid
<220> FEATURE:
<221> NAME/KEY: MISC_FEATURE
<222> LOCATION: (7)..(7)
<223> OTHER INFORMATION: Xaa can be Leu or Ala
<220> FEATURE:
<221> NAME/KEY: MISC_FEATURE
<222> LOCATION: (10)..(10)
<223> OTHER INFORMATION: Xaa can be any amino acid
<220> FEATURE:
<221> NAME/KEY: MISC_FEATURE
<222> LOCATION: (11)..(11)
<223> OTHER INFORMATION: Xaa can be Leu or Phe
<220> FEATURE:
<221> NAME/KEY: MISC_FEATURE
<222> LOCATION: (12)..(14)
<223> OTHER INFORMATION: Xaa can be any amino acid
<220> FEATURE:
<221> NAME/KEY: MISC_FEATURE
<222> LOCATION: (17)..(18)
<223> OTHER INFORMATION: Xaa can be any amino acid

<400> SEQUENCE: 21

```
Phe Xaa Xaa Val Xaa Xaa Xaa Pro Val Xaa Xaa Xaa Xaa Xaa Asn Asn
1               5                   10                  15

Xaa Xaa Ala Ile Ser
            20
```

<210> SEQ ID NO 22
<211> LENGTH: 16
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Lys or Arg
<220> FEATURE:
<221> NAME/KEY: MISC_FEATURE
<222> LOCATION: (2)..(2)
<223> OTHER INFORMATION: Xaa can be Gly or Ala
<220> FEATURE:
<221> NAME/KEY: MISC_FEATURE
<222> LOCATION: (3)..(3)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be Cys or Tyr
<220> FEATURE:
<221> NAME/KEY: MISC_FEATURE
<222> LOCATION: (6)..(6)
<223> OTHER INFORMATION: Xaa can be Phe or Gly
<220> FEATURE:
<221> NAME/KEY: MISC_FEATURE
<222> LOCATION: (7)..(7)
<223> OTHER INFORMATION: Xaa can be any amino acid
<220> FEATURE:
<221> NAME/KEY: MISC_FEATURE
<222> LOCATION: (8)..(8)
<223> OTHER INFORMATION: Xaa can be Ala or Pro
<220> FEATURE:
<221> NAME/KEY: MISC_FEATURE
<222> LOCATION: (9)..(9)
<223> OTHER INFORMATION: Xaa can be Ser or Gly
<220> FEATURE:
<221> NAME/KEY: MISC_FEATURE
<222> LOCATION: (10)..(11)
<223> OTHER INFORMATION: Xaa can be any amino acid

<400> SEQUENCE: 22

Xaa Xaa Xaa Gly Xaa Xaa Xaa Xaa Xaa Xaa Xaa Val Asp Gly Asn Asp
1               5                   10                  15

<210> SEQ ID NO 23
<211> LENGTH: 31
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be His or Arg
<220> FEATURE:
<221> NAME/KEY: MISC_FEATURE
<222> LOCATION: (4)..(4)
<223> OTHER INFORMATION: Xaa can be Ala or Arg
<220> FEATURE:
<221> NAME/KEY: MISC_FEATURE
<222> LOCATION: (6)..(6)
<223> OTHER INFORMATION: Xaa can be any amino acid
<220> FEATURE:
<221> NAME/KEY: MISC_FEATURE
<222> LOCATION: (9)..(9)
<223> OTHER INFORMATION: Xaa can be any amino acid
<220> FEATURE:
<221> NAME/KEY: MISC_FEATURE
<222> LOCATION: (11)..(11)
<223> OTHER INFORMATION: Xaa can be any amino acid
<220> FEATURE:
<221> NAME/KEY: MISC_FEATURE
<222> LOCATION: (13)..(14)
<223> OTHER INFORMATION: Xaa can be any amino acid
<220> FEATURE:
<221> NAME/KEY: MISC_FEATURE
<222> LOCATION: (15)..(15)
<223> OTHER INFORMATION: Xaa can be Ser or Thr
<220> FEATURE:
<221> NAME/KEY: MISC_FEATURE
<222> LOCATION: (18)..(20)
<223> OTHER INFORMATION: Xaa can be any amino acid
<220> FEATURE:
<221> NAME/KEY: MISC_FEATURE
<222> LOCATION: (22)..(24)
<223> OTHER INFORMATION: Xaa can be any amino acid
<220> FEATURE:
<221> NAME/KEY: MISC_FEATURE
<222> LOCATION: (27)..(29)
<223> OTHER INFORMATION: Xaa can be any amino acid

<400> SEQUENCE: 23

Xaa Ala Arg Xaa Gly Xaa Gly Pro Xaa Leu Xaa Glu Xaa Xaa Xaa Tyr
1               5                   10                  15

Arg Xaa Xaa Xaa His Xaa Xaa Xaa Asp Asp Xaa Xaa Xaa Tyr Arg
            20                  25                  30

<210> SEQ ID NO 24
<211> LENGTH: 327
<212> TYPE: PRT
<213> ORGANISM: Bacillus subtillis

<400> SEQUENCE: 24

Met Ser Val Met Ser Tyr Ile Asp Ala Ile Asn Leu Ala Met Lys Glu
1               5                   10                  15

Glu Met Glu Arg Asp Ser Arg Val Phe Val Leu Gly Glu Asp Val Gly
            20                  25                  30

-continued

```
Arg Lys Gly Gly Val Phe Lys Ala Thr Ala Gly Leu Tyr Glu Gln Phe
        35                  40                  45

Gly Glu Glu Arg Val Met Asp Thr Pro Leu Ala Glu Ser Ala Ile Ala
    50                  55                  60

Gly Val Gly Ile Gly Ala Ala Met Tyr Gly Met Arg Pro Ile Ala Glu
65                  70                  75                  80

Met Gln Phe Ala Asp Phe Ile Met Pro Ala Val Asn Gln Ile Ile Ser
                85                  90                  95

Glu Ala Ala Lys Ile Arg Tyr Arg Ser Asn Asn Asp Trp Ser Cys Pro
            100                 105                 110

Ile Val Val Arg Ala Pro Tyr Gly Gly Gly Val His Gly Ala Leu Tyr
        115                 120                 125

His Ser Gln Ser Val Glu Ala Ile Phe Ala Asn Gln Pro Gly Leu Lys
    130                 135                 140

Ile Val Met Pro Ser Thr Pro Tyr Asp Ala Lys Gly Leu Leu Lys Ala
145                 150                 155                 160

Ala Val Arg Asp Glu Asp Pro Val Leu Phe Phe Glu His Lys Arg Ala
                165                 170                 175

Tyr Arg Leu Ile Lys Gly Glu Val Pro Ala Asp Asp Tyr Val Leu Pro
            180                 185                 190

Ile Gly Lys Ala Asp Val Lys Arg Glu Gly Asp Asp Ile Thr Val Ile
        195                 200                 205

Thr Tyr Gly Leu Cys Val His Phe Ala Leu Gln Ala Ala Glu Arg Leu
    210                 215                 220

Glu Lys Asp Gly Ile Ser Ala His Val Val Asp Leu Arg Thr Val Tyr
225                 230                 235                 240

Pro Leu Asp Lys Glu Ala Ile Ile Glu Ala Ala Ser Lys Thr Gly Lys
                245                 250                 255

Val Leu Leu Val Thr Glu Asp Thr Lys Glu Gly Ser Ile Met Ser Glu
            260                 265                 270

Val Ala Ala Ile Ile Ser Glu His Cys Leu Phe Asp Leu Asp Ala Pro
        275                 280                 285

Ile Lys Arg Leu Ala Gly Pro Asp Ile Pro Ala Met Pro Tyr Ala Pro
    290                 295                 300

Thr Met Glu Lys Tyr Phe Met Val Asn Pro Asp Lys Val Glu Ala Ala
305                 310                 315                 320

Met Arg Glu Leu Ala Glu Phe
                325
```

<210> SEQ ID NO 25
<211> LENGTH: 984
<212> TYPE: DNA
<213> ORGANISM: Bacillus subtillis

<400> SEQUENCE: 25

```
ttaaaactcc gctaattctc tcatcgccgc ttccacttta tcagggttga ccataaagta      60

tttttccatt gtcggcgcat aaggcatagc cggaatatca ggacctgcaa gccgtttgat     120

cggcgcgtct aagtcgaaca gacaatgctc ggatataatt gcggctactt cgctcatgat     180

gctgccttct tttgtatctt ctgtgaccaa aagaaccttt ccagttttgg acgcagcttc     240

gatgatggct tctttatcaa gcgggtaaac tgttcttaaa tccaccacat gcgctgaaat     300

gccatctttt tcgagacgtt ctgcagcttg taaggcgaag tggacacaca ggccgtatgt     360

gatcactgtg atgtcgtcgc cttccctttt tacgtccgcc ttgccgattg gcaggacata     420
```

```
atcatcagcc ggaacctcgc cctttatcag acggtatgcc cgcttgtgct caaaaaacag    480

cacggggtct tcgtcacgaa ctgcggcttt taagagccct ttcgcgtcat atggtgttga    540

tggcatgaca attttcagtc cgggctggtt ggcgaaaatt gcttcgactg attgagaatg    600

atacagggct ccgtgcacgc ctccgccgta tggcgctctg acgacaatcg gacagctcca    660

gtcattgttg ctgcggtagc ggattttagc cgcttcagaa ataatttggt tgactgccgg    720

cataatgaaa tcagcaaact gcatttcagc aatcggtctc attccgtaca ttgccgctcc    780

gataccgact cctgcgattg cagattcagc aagcggcgta tccataacgc gctcttcccc    840

aaattgttca tagagtcccg ctgtcgcttt aaacacaccg ccttttcttc ctacatcttc    900

cccaaggacg aaaacgcgag aatctcgttc catttcttct ttcatcgcca aattgattgc    960

atcaatatat gacattactg acat                                            984
```

<210> SEQ ID NO 26
<211> LENGTH: 325
<212> TYPE: PRT
<213> ORGANISM: Streptomyces avermitilis

<400> SEQUENCE: 26

```
Met Ala Glu Lys Met Ala Ile Ala Lys Ala Ile Asn Glu Ser Leu Arg
1               5                   10                  15

Lys Ala Leu Glu Ser Asp Pro Lys Val Leu Ile Met Gly Glu Asp Val
            20                  25                  30

Gly Lys Leu Gly Gly Val Phe Arg Val Thr Asp Gly Leu Gln Lys Asp
        35                  40                  45

Phe Gly Glu Glu Arg Val Ile Asp Thr Pro Leu Ala Glu Ser Gly Ile
    50                  55                  60

Val Gly Thr Ala Ile Gly Leu Ala Leu Arg Gly Tyr Arg Pro Val Val
65                  70                  75                  80

Glu Ile Gln Phe Asp Gly Phe Val Phe Pro Ala Tyr Asp Gln Ile Val
                85                  90                  95

Thr Gln Leu Ala Lys Met His Ala Arg Ala Leu Gly Lys Ile Lys Leu
            100                 105                 110

Pro Val Val Val Arg Ile Pro Tyr Gly Gly Gly Ile Gly Ala Val Glu
        115                 120                 125

His His Ser Glu Ser Pro Glu Ala Leu Phe Ala His Val Ala Gly Leu
    130                 135                 140

Lys Val Val Ser Pro Ser Asn Ala Ser Asp Ala Tyr Trp Met Met Gln
145                 150                 155                 160

Gln Ala Ile Gln Ser Asp Asp Pro Val Ile Phe Phe Glu Pro Lys Arg
                165                 170                 175

Arg Tyr Trp Asp Lys Gly Glu Val Asn Val Glu Ala Ile Pro Asp Pro
            180                 185                 190

Leu His Lys Ala Arg Val Val Arg Glu Gly Thr Asp Leu Thr Leu Ala
        195                 200                 205

Ala Tyr Gly Pro Met Val Lys Val Cys Gln Glu Ala Ala Ala Ala Ala
    210                 215                 220

Glu Glu Glu Gly Lys Ser Leu Glu Val Val Asp Leu Arg Ser Met Ser
225                 230                 235                 240

Pro Ile Asp Phe Asp Ala Val Gln Ala Ser Val Glu Lys Thr Arg Arg
                245                 250                 255

Leu Val Val Val His Glu Ala Pro Val Phe Leu Gly Thr Gly Ala Glu
            260                 265                 270
```

Ile Ala Ala Arg Ile Thr Glu Arg Cys Phe Tyr His Leu Glu Ala Pro
        275                 280                 285

Val Leu Arg Val Gly Gly Tyr His Ala Pro Tyr Pro Pro Ala Arg Leu
    290                 295                 300

Glu Glu Glu Tyr Leu Pro Gly Leu Asp Arg Val Leu Asp Ala Val Asp
305                 310                 315                 320

Arg Ser Leu Ala Tyr
                325

<210> SEQ ID NO 27
<211> LENGTH: 978
<212> TYPE: DNA
<213> ORGANISM: Streptomyces avermitilis

<400> SEQUENCE: 27
atggccgaga agatggcgat cgccaaggcg atcaacgagt cgctgcgcaa ggccctggag 60
tccgacccca aggttctgat catgggtgag gacgtcggca agctcggtgg cgtcttccgc 120
gtcaccgacg gcctgcagaa ggacttcggc gaggagcggg tcatcgacac cccgctcgcc 180
gagtcgggca tcgtcggcac ggcgatcggt ctcgccctgc gcggctaccg cccggtggtg 240
gagatccagt tcgacggctt cgtcttcccg gcgtacgacc agatcgtcac gcagctcgcg 300
aagatgcacg cgcgggcgct cggcaagatc aagctccccg ttgtcgtccg catcccgtac 360
ggcggcggca tcggcgccgt cgagcaccac tccgagtccc ccgaggcgct cttcgcgcac 420
gtggcgggcc tcaaggtggt ctccccgtcc aacgcgtcgg acgcgtactg gatgatgcag 480
caggccatcc agagcgacga cccggtgatc ttcttcgagc cgaagcggcg ctactgggac 540
aagggcgagg tcaacgtcga ggcgatcccc gacccgctgc acaaggcccg tgtggtgcgt 600
gagggcaccg acctgacgct cgccgcgtac ggcccgatgg tgaaggtctg ccaggaggcc 660
gcggccgccg ccgaggagga gggcaagtcc ctggaggtcg tcgacctgcg ctccatgtcg 720
ccgatcgact tcgacgccgt ccaggcctcc gtcgagaaga cccgccgtct ggtcgtggtg 780
cacgaggcgc cggtgttcct gggcacgggc gcggagatcg ccgcccgcat cacggagcgc 840
tgcttctacc acctggaggc acccgtgctg agggtcggcg gctaccacgc cccgtatccg 900
ccggcgcgtc tggaagagga gtaccttccg ggccttgacc gggtgctcga tgccgtcgac 960
cgctcgctgg cgtactga 978

<210> SEQ ID NO 28
<211> LENGTH: 410
<212> TYPE: PRT
<213> ORGANISM: Pseudomonas putida

<400> SEQUENCE: 28

Met Asn Glu Tyr Ala Pro Leu Arg Leu His Val Pro Glu Pro Thr Gly
1               5                   10                  15

Arg Pro Gly Cys Gln Thr Asp Phe Ser Tyr Leu Arg Leu Asn Asp Ala
            20                  25                  30

Gly Gln Ala Arg Lys Pro Ala Ile Asp Val Asp Ala Ala Asp Thr Ala
        35                  40                  45

Asp Leu Ser Tyr Ser Leu Val Arg Val Leu Asp Glu Gln Gly Asp Ala
    50                  55                  60

Gln Gly Pro Trp Ala Glu Asp Ile Asp Pro Gln Ile Leu Arg Gln Gly
65                  70                  75                  80

Met Arg Ala Met Leu Lys Thr Arg Ile Phe Asp Ser Arg Met Val Val

-continued

```
                85                  90                  95

Ala Gln Arg Gln Lys Lys Met Ser Phe Tyr Met Gln Ser Leu Gly Glu
            100                 105                 110

Glu Ala Ile Gly Ser Gly Gln Ala Leu Ala Leu Asn Arg Thr Asp Met
        115                 120                 125

Cys Phe Pro Thr Tyr Arg Gln Gln Ser Ile Leu Met Ala Arg Asp Val
    130                 135                 140

Ser Leu Val Glu Met Ile Cys Gln Leu Leu Ser Asn Glu Arg Asp Pro
145                 150                 155                 160

Leu Lys Gly Arg Gln Leu Pro Ile Met Tyr Ser Val Arg Glu Ala Gly
                165                 170                 175

Phe Phe Thr Ile Ser Gly Asn Leu Ala Thr Gln Phe Val Gln Ala Val
            180                 185                 190

Gly Trp Ala Met Ala Ser Ala Ile Lys Gly Asp Thr Lys Ile Ala Ser
        195                 200                 205

Ala Trp Ile Gly Asp Gly Ala Thr Ala Glu Ser Asp Phe His Thr Ala
    210                 215                 220

Leu Thr Phe Ala His Val Tyr Arg Ala Pro Val Ile Leu Asn Val Val
225                 230                 235                 240

Asn Asn Gln Trp Ala Ile Ser Thr Phe Gln Ala Ile Ala Gly Gly Glu
                245                 250                 255

Ser Thr Thr Phe Ala Gly Arg Gly Val Gly Cys Gly Ile Ala Ser Leu
            260                 265                 270

Arg Val Asp Gly Asn Asp Phe Val Ala Val Tyr Ala Ala Ser Arg Trp
        275                 280                 285

Ala Ala Glu Arg Ala Arg Arg Gly Leu Gly Pro Ser Leu Ile Glu Trp
    290                 295                 300

Val Thr Tyr Arg Ala Gly Pro His Ser Thr Ser Asp Asp Pro Ser Lys
305                 310                 315                 320

Tyr Arg Pro Ala Asp Asp Trp Ser His Phe Pro Leu Gly Asp Pro Ile
                325                 330                 335

Ala Arg Leu Lys Gln His Leu Ile Lys Ile Gly His Trp Ser Glu Glu
            340                 345                 350

Glu His Gln Ala Val Thr Ala Glu Leu Glu Ala Ala Val Ile Ala Ala
        355                 360                 365

Gln Lys Glu Ala Glu Gln Tyr Gly Thr Leu Ala Asn Gly His Ile Pro
    370                 375                 380

Ser Ala Ala Ser Met Phe Glu Asp Val Tyr Lys Glu Met Pro Glu His
385                 390                 395                 400

Leu Arg Arg Gln Arg Gln Glu Leu Gly Val
                405                 410
```

<210> SEQ ID NO 29
<211> LENGTH: 1233
<212> TYPE: DNA
<213> ORGANISM: Pseudomonas putida

<400> SEQUENCE: 29

```
tcaaaccccc agttcctggc gttgacggcg caggtgttcg ggcatctcct tgtacacatc      60

ctcgaacatc gaggcggcgc tcgggatgtg cccgttagcc agggtgccgt actgctcggc     120

ttctttctgt gcggcaatca ccgcagcttc gagctcggcc gtgacggctt ggtgttcttc     180

ttcggaccag tggccgatct tgatcaggtg ctgcttcagg cgggcgatcg ggtcacccag     240

cgggaagtgg ctccagtcat cggcagggcg gtacttggag ggtcgtccg acgtcgagtg      300
```

-continued

```
cgggccggca cggtaggtga cccactcgat caggcttggg cccaggccgc ggcgggcgcg    360

ctcggcagcc cagcgcgagg cggcgtacac ggcgacgaag tcgttgccgt caacccgcag    420

cgaggcaatg ccgcagccca cgccacggcc ggcgaaggtg gtcgactcgc caccggcgat    480

ggcctggaag gtagaaatcg cccactggtt gttgaccaca ttgaggatca ccggggcgcg    540

gtaaacgtgg gcaaaggtga gggcggtgtg gaagtccgac tcggcggtgg ctccgtcacc    600

gatccacgcc gaagcaatct tggtatcgcc cttgatcgcc gaggccatgg cccagccgac    660

tgcctgcacg aactgggtcg ccaggttgcc gctgatggtg aagaagccgg cttcgcgcac    720

cgagtacatg atcggcaact ggcggccctt gagggggtcg cgctcgttgg acagcagttg    780

gcagatcatc tcgaccagcg atacgtcgcg ggccatcagg atgctttgct ggcggtaggt    840

cgggaagcac atgtcggtgc ggttcagcgc cagcgcctgg ccactgccga tggcttcttc    900

gcccaggctt tgcatgtaga aggacatctt cttctggcgc tgggcaacca ccatgcggct    960

gtcgaagatc cgcgtcttga gcatggcgcg catgccttga cgaaggatct gtgggtcgat   1020

gtcttcggcc caggggcctt gcgcatcacc ttgctcgtcg agcacgcgga ccaggctgta   1080

ggacaggtcg gcagtgtcgg cagcatcgac atcgatcgcg ggtttacggg cttgacctgc   1140

atcgttgagg cgcaggtagg aaaaatcggt ctggcagcct ggccggccgg tgggctcggg   1200

cacatgcaaa cgcagggggg cgtactcgtt cat                                1233
```

<210> SEQ ID NO 30
<211> LENGTH: 327
<212> TYPE: PRT
<213> ORGANISM: Listeria monocytogenes

<400> SEQUENCE: 30

```
Met Pro Val Ile Ser Tyr Ile Asp Ala Ile Thr Met Ala Leu Lys Glu
1               5                   10                  15

Glu Met Glu Arg Asp Asp Lys Val Phe Ile Leu Gly Glu Asp Val Gly
            20                  25                  30

Lys Lys Gly Gly Val Phe Lys Ala Thr Ala Gly Leu Tyr Asp Glu Phe
        35                  40                  45

Gly Glu Asp Arg Val Leu Asp Thr Pro Leu Ala Glu Ser Ala Ile Ala
    50                  55                  60

Gly Val Gly Ile Gly Ala Ala Met Tyr Gly Tyr Arg Pro Val Ala Glu
65                  70                  75                  80

Met Gln Phe Ala Asp Phe Ile Met Pro Ala Val Asn Gln Ile Ile Ser
                85                  90                  95

Glu Ala Ala Arg Ile Arg Tyr Arg Ser Asn Asn Asp Trp Ser Cys Pro
            100                 105                 110

Met Val Ile Arg Ala Pro Phe Gly Gly Gly Val His Gly Ala Leu Tyr
        115                 120                 125

His Ser Gln Ser Val Glu Lys Val Phe Phe Gly Gln Pro Gly Leu Lys
    130                 135                 140

Ile Val Val Pro Ser Ser Pro Tyr Asp Ala Lys Gly Leu Leu Lys Ala
145                 150                 155                 160

Ala Ile Arg Asp Asn Asp Pro Val Leu Phe Phe Glu His Lys Arg Ala
                165                 170                 175

Tyr Arg Leu Leu Lys Gly Glu Val Pro Glu Thr Asp Tyr Ile Val Pro
            180                 185                 190

Ile Gly Glu Ala Asn Val Val Arg Glu Gly Asp Asp Ile Thr Val Ile
        195                 200                 205
```

Thr Tyr Gly Leu Ala Val Gln Phe Ala Gln Gln Ala Ala Glu Arg Leu
    210                 215                 220

Ala Ala Glu Gly Val Glu Ala His Ile Leu Asp Leu Arg Thr Ile Tyr
225                 230                 235                 240

Pro Leu Asp Gln Glu Ala Ile Ile Glu Ala Thr Lys Lys Thr Gly Lys
                245                 250                 255

Val Leu Leu Val Thr Glu Asp Asn Lys Gln Gly Ser Ile Ile Ser Glu
            260                 265                 270

Val Ala Ala Ile Ile Ser Glu His Cys Leu Phe Asp Leu Asp Ala Pro
        275                 280                 285

Ile Ala Arg Leu Ala Gly Pro Asp Thr Pro Ala Met Pro Phe Ala Pro
    290                 295                 300

Thr Met Glu Lys His Phe Met Ile Asn Pro Asp Lys Val Ala Asp Ala
305                 310                 315                 320

Met Lys Glu Leu Ala Glu Phe
                325

<210> SEQ ID NO 31
<211> LENGTH: 984
<212> TYPE: DNA
<213> ORGANISM: Listeria monocytogenes

<400> SEQUENCE: 31
atgccagtca tttcatatat tgatgcaata accatggcgc ttaaagaaga aatggagcgc      60
gatgataaag tatttatttt aggagaagat gttgggaaaa aaggtggcgt atttaaagcg     120
actgctggtc tatatgacga atttggtgaa gacagagtac ttgatacacc acttgctgaa     180
tctgccattg ccggagttgg aattggcgcg gcgatgtatg gctaccgccc agttgcagaa     240
atgcaatttg ctgactttat tatgccagct gtcaaccaaa tcatttcaga agctgccaga     300
attcggtacc gttctaataa cgattggtct tgtccaatgg ttattcgcgc accttttggc     360
ggcggggtac acggggcact ttaccattca caatctgttg aaaaagtgtt tttcggacaa     420
cctggtttga aaatcgttgt tccttcttca ccatatgatg caaaagggct tttaaaagcg     480
gcgattcgcg ataatgatcc agtgcttttc tttgagcata aacgtgcgta ccgcttgcta     540
aaaggcgaag tgccagaaac tgattatatc gttccaatcg gcgaagcaaa tgttgttcgt     600
gaaggtgatg atattacagt aattacttac ggacttgcgg ttcaatttgc ccaacaagca     660
gcagaacgtt tagcagcgga aggcgtagaa gcacatattc ttgatttacg gacaatctat     720
ccactagacc aagaagcaat tattgaagca acgaaaaaaa caggtaaagt acttcttgta     780
acggaagata acaaacaagg aagtattatc agtgaagtgg cagcaatcat ttcggagcat     840
tgtttatttg acttagacgc accgattgct agactcgcag gacctgatac cccagcgatg     900
ccttttgctc caacaatgga aaaacatttt atgatcaatc cagataaagt ggcggatgca     960
atgaaagaat tagcggaatt ttag                                            984

<210> SEQ ID NO 32
<211> LENGTH: 334
<212> TYPE: PRT
<213> ORGANISM: Streptomyces avermitilis

<400> SEQUENCE: 32

Met Thr Thr Val Ala Leu Lys Pro Ala Thr Met Ala Gln Ala Leu Thr
1               5                   10                  15

Arg Ala Leu Arg Asp Ala Met Ala Ala Asp Pro Ala Val His Val Met

```
            20                  25                  30

Gly Glu Asp Val Gly Thr Leu Gly Gly Val Phe Arg Val Thr Asp Gly
        35                  40                  45

Leu Ala Lys Glu Phe Gly Glu Asp Arg Cys Thr Asp Thr Pro Leu Ala
    50                  55                  60

Glu Ala Gly Ile Leu Gly Thr Ala Val Gly Met Ala Met Tyr Gly Leu
65                  70                  75                  80

Arg Pro Val Val Glu Met Gln Phe Asp Ala Phe Ala Tyr Pro Ala Phe
                85                  90                  95

Glu Gln Leu Ile Ser His Val Ala Arg Met Arg Asn Arg Thr Arg Gly
            100                 105                 110

Ala Met Pro Leu Pro Ile Thr Ile Arg Val Pro Tyr Gly Gly Gly Ile
        115                 120                 125

Gly Gly Val Glu His His Ser Asp Ser Ser Glu Ala Tyr Tyr Met Ala
    130                 135                 140

Thr Pro Gly Leu His Val Val Thr Pro Ala Thr Val Ala Asp Ala Tyr
145                 150                 155                 160

Gly Leu Leu Arg Ala Ala Ile Ala Ser Asp Asp Pro Val Val Phe Leu
                165                 170                 175

Glu Pro Lys Arg Leu Tyr Trp Ser Lys Asp Ser Trp Asn Pro Asp Glu
            180                 185                 190

Pro Gly Thr Val Glu Pro Ile Gly Arg Ala Val Val Arg Arg Ser Gly
        195                 200                 205

Arg Ser Ala Thr Leu Ile Thr Tyr Gly Pro Ser Leu Pro Val Cys Leu
    210                 215                 220

Glu Ala Ala Glu Ala Ala Arg Ala Glu Gly Trp Asp Leu Glu Val Val
225                 230                 235                 240

Asp Leu Arg Ser Leu Val Pro Phe Asp Asp Glu Thr Val Cys Ala Ser
                245                 250                 255

Val Arg Arg Thr Gly Arg Ala Val Val Val His Glu Ser Gly Gly Tyr
            260                 265                 270

Gly Gly Pro Gly Gly Glu Ile Ala Ala Arg Ile Thr Glu Arg Cys Phe
        275                 280                 285

His His Leu Glu Ala Pro Val Leu Arg Val Ala Gly Phe Asp Ile Pro
    290                 295                 300

Tyr Pro Pro Pro Met Leu Glu Arg His His Leu Pro Gly Val Asp Arg
305                 310                 315                 320

Ile Leu Asp Ala Val Gly Arg Leu Gln Trp Glu Ala Gly Ser
                325                 330


<210> SEQ ID NO 33
<211> LENGTH: 1005
<212> TYPE: DNA
<213> ORGANISM: Streptomyces avermitilis

<400> SEQUENCE: 33

atgaccaccg ttgccctcaa gccggccacc atggcgcagg cactcacacg cgcgttgcgt      60

gacgccatgg ccgccgaccc cgccgtccac gtgatgggcg aggacgtcgg cacgctcggc     120

ggggtcttcc gggtcaccga cggctcgcc aaggagttcg gcgaggaccg ctgcacggac     180

acgccgctcg ccgaggcagg catcctcggc acggccgtcg gcatggcgat gtacgggctg     240

cggccggtcg tcgagatgca gttcgacgcg ttcgcgtacc cggcgttcga gcagctcatc     300

agccatgtcg cgcggatgcg caaccgcacc cgcggggcga tgccgctgcc gatcaccatc     360
```

-continued

```
cgtgtcccct acggcggcgg aatcggcgga gtcgaacacc acagcgactc ctccgaggcg    420

tactacatgg cgactccggg gctccatgtc gtcacgcccg ccacggtcgc cgacgcgtac    480

gggctgctgc gcgccgccat cgcctccgac gacccggtcg tcttcctgga gcccaagcgg    540

ctgtactggt cgaaggactc ctggaacccg gacgagccgg ggaccgttga accgataggc    600

cgcgcggtgg tgcggcgctc gggccggagc gccacgctca tcacgtacgg gccttccctg    660

cccgtctgcc tggaggcggc cgaggcggcc cgggccgagg gctgggacct cgaagtcgtc    720

gatctgcgct ccctggtgcc cttcgacgac gagacggtgt gcgcgtcggt gcgccggacc    780

ggacgcgccg tcgtcgtgca cgagtcgggt ggttacggcg gcccgggcgg ggagatcgcc    840

gcgcggatca ccgagcgctg cttccaccat ctggaggcgc cggtgctgcg cgtcgccggg    900

ttcgacatcc cgtatccgcc gccgatgctg gagcgccatc atctgcccgg tgtcgaccgg    960

atcctggacg cggtggggcg gcttcagtgg gaggcgggga gctga                   1005
```

<210> SEQ ID NO 34
<211> LENGTH: 355
<212> TYPE: PRT
<213> ORGANISM: Micrococcus luteus

<400> SEQUENCE: 34

```
Met Ser Glu Arg Met Thr Phe Gly Arg Ala Ile Asn Arg Gly Leu His
1               5                   10                  15

Arg Ala Leu Ala Asp Asp Pro Lys Val Leu Leu Met Gly Glu Asp Ile
            20                  25                  30

Gly Ala Leu Gly Gly Val Phe Arg Ile Thr Asp Gly Leu Gln Ala Glu
        35                  40                  45

Phe Gly Glu Asp Arg Val Leu Asp Thr Pro Leu Ala Glu Ser Gly Ile
    50                  55                  60

Val Gly Thr Ala Ile Gly Leu Ala Met Arg Gly Tyr Arg Pro Val Val
65                  70                  75                  80

Glu Ile Gln Phe Asp Gly Phe Val Tyr Pro Ala Phe Asp Gln Ile Val
                85                  90                  95

Ala Asn Leu Ala Lys Leu Arg Ala Arg Thr Arg Gly Ala Val Pro Met
            100                 105                 110

Pro Val Thr Ile Arg Ile Pro Phe Gly Gly Gly Ile Gly Ser Pro Glu
        115                 120                 125

His His Ser Glu Ser Pro Glu Ala Tyr Phe Leu His Thr Ala Gly Leu
    130                 135                 140

Arg Val Val Ser Pro Ser Ser Pro Gln Glu Gly Tyr Asp Leu Ile Arg
145                 150                 155                 160

Ala Ala Ile Ala Ser Glu Asp Pro Val Val Tyr Leu Glu Pro Lys Arg
                165                 170                 175

Arg Tyr His Asp Lys Gly Asp Val Asp Leu Gly Val Ala Ile Pro Pro
            180                 185                 190

Met Ser Pro Ala Arg Ile Leu Arg Glu Gly Arg Asp Ala Thr Leu Val
        195                 200                 205

Ala Tyr Gly Pro Leu Val Lys Thr Ala Leu Gln Ala Ala Glu Val Ala
    210                 215                 220

Ala Glu Glu Gly Val Glu Val Glu Val Val Asp Leu Arg Ser Leu Ser
225                 230                 235                 240

Pro Leu Asp Thr Gly Leu Val Glu Ser Ser Val Arg Arg Thr Gly Arg
                245                 250                 255

Leu Val Val Ala His Glu Ala Ser Arg Thr Gly Gly Leu Gly Ala Glu
```

```
            260                 265                 270

Leu Val Ala Thr Val Ala Glu Arg Ala Phe His Trp Leu Glu Ala Pro
        275                 280                 285

Pro Val Arg Val Thr Gly Met Asp Val Pro Tyr Pro Pro Ser Lys Leu
    290                 295                 300

Glu His Leu His Leu Pro Asp Leu Asp Arg Ile Leu Asp Gly Leu Asp
305                 310                 315                 320

Arg Ala Leu Gly Arg Pro Asn Ser Leu Asp Ser Val Asp Ala Phe Ala
                325                 330                 335

Ala Pro Glu Thr Ala Glu Gln Phe Leu Ala Ala Gln Asn Ala Gly Glu
            340                 345                 350

Glu Thr Arg
        355


<210> SEQ ID NO 35
<211> LENGTH: 1068
<212> TYPE: DNA
<213> ORGANISM: Micrococcus luteus

<400> SEQUENCE: 35

gtgagcgagc gcatgacctt cggccgtgcg atcaaccgcg gcctgcaccg tgccctggcc     60

gacgacccca aggtcctgct catgggcgag gacatcggcg ccctcggcgg cgtgttccgc    120

atcaccgacg gcctgcaggc cgagttcggc gaggaccggg tgctcgacac cccgctggcc    180

gagtccggca tcgtgggcac ggccatcggc ctggcgatgc gcggctaccg gcccgtcgtc    240

gagatccagt tcgacggctt cgtgtacccg gcgttcgacc agatcgtggc gaacctggcc    300

aagctgcgcg cccgcacccg cggcgccgtg ccgatgccgg tgaccatccg catccccttc    360

ggcggcggca tcggctcccc ggagcaccac tccgagtcgc ccgaggccta cttcctgcac    420

accgcgggtc tgcgcgtggt ctccccgtcc tccccgcagg aggggtacga cctcatccgc    480

gccgcgatcg cctcggagga cccggtggtc tacctcgagc ccaagcgtcg ctaccacgac    540

aagggcgacg tggacctggg cgtcgcgatc ccgccgatga gcccggcccg catcctgcgc    600

gagggccgtg acgccacgct cgtggcctac ggcccgctcg tgaagaccgc cctgcaggcc    660

gccgaggtgg cggccgagga gggtgtcgag gtcgaggtgg tcgacctgcg cagcctgtcc    720

ccgctggaca ccggcctcgt cgagtcctcg gtgcggcgca ccggtcggct cgtcgtggcg    780

cacgaggcct cccgcacggg cggcctcggc gccgagctcg tggccacggt ggccgagcgc    840

gcgttccatt ggctcgaggc cccgccggtg cgcgtcaccg gcatggacgt gccctacccg    900

ccgtccaagc tcgagcacct gcacctgccg gacctcgacc gcatcctcga cggcctggac    960

cgtgctctgg gccggccgaa ttcgctggac tccgtggacg cgttcgccgc ccccgagacc   1020

gccgagcagt tcctcgccgc ccagaacgcc ggggaggaga cccgatga                1068


<210> SEQ ID NO 36
<211> LENGTH: 327
<212> TYPE: PRT
<213> ORGANISM: Staphylococcus aureus

<400> SEQUENCE: 36

Met Ala Lys Leu Ser Tyr Leu Glu Ala Ile Arg Gln Ala Gln Asp Leu
1               5                   10                  15

Ala Leu Gln Gln Asn Lys Asp Val Phe Ile Leu Gly Glu Asp Val Gly
            20                  25                  30

Lys Lys Gly Gly Val Phe Gly Thr Thr Gln Gly Leu Gln Gln Gln Tyr
```

-continued

```
        35                  40                  45

Gly Glu Asp Arg Val Ile Asp Thr Pro Leu Ala Glu Ser Asn Ile Val
    50                  55                  60

Gly Thr Ala Ile Gly Ala Ala Met Val Gly Lys Arg Pro Ile Ala Glu
65                  70                  75                  80

Ile Gln Phe Ala Asp Phe Ile Leu Pro Ala Thr Asn Gln Ile Ile Ser
                85                  90                  95

Glu Ala Ala Lys Met Arg Tyr Arg Ser Asn Asn Asp Trp Gln Cys Pro
            100                 105                 110

Leu Thr Ile Arg Ala Pro Phe Gly Gly Gly Val His Gly Gly Leu Tyr
        115                 120                 125

His Ser Gln Ser Ile Glu Ser Ile Phe Ala Ser Ser Pro Gly Leu Thr
    130                 135                 140

Ile Val Ile Pro Ser Thr Pro Tyr Asp Ala Lys Gly Leu Leu Leu Ser
145                 150                 155                 160

Ser Ile Glu Ser Asn Asp Pro Val Leu Tyr Phe Glu His Lys Lys Ala
                165                 170                 175

Tyr Arg Phe Leu Lys Glu Glu Val Pro Glu Glu Tyr Tyr Thr Val Pro
            180                 185                 190

Leu Gly Lys Ala Asp Val Lys Arg Glu Gly Glu Asp Leu Thr Val Phe
        195                 200                 205

Cys Tyr Gly Leu Met Val Asn Tyr Cys Leu Gln Ala Ala Asp Ile Leu
    210                 215                 220

Ala Ala Asp Gly Ile Asn Val Glu Val Val Asp Leu Arg Thr Val Tyr
225                 230                 235                 240

Pro Leu Asp Lys Glu Thr Ile Ile Asp Arg Ala Lys Asn Thr Gly Lys
                245                 250                 255

Val Leu Leu Val Thr Glu Asp Asn Leu Glu Gly Ser Ile Met Ser Glu
            260                 265                 270

Val Ser Ala Ile Ile Ala Glu His Cys Leu Phe Asp Leu Asp Thr Pro
        275                 280                 285

Ile Met Arg Leu Ala Ala Pro Asp Val Pro Ser Met Pro Phe Ser Pro
    290                 295                 300

Val Leu Glu Asn Glu Ile Met Met Asn Pro Glu Lys Ile Leu Asn Lys
305                 310                 315                 320

Met Arg Glu Leu Ala Glu Phe
                325


<210> SEQ ID NO 37
<211> LENGTH: 984
<212> TYPE: DNA
<213> ORGANISM: Staphylococcus aureus

<400> SEQUENCE: 37

ctagaattct gctaattcac gcattttatt taagattttt tctggattca tcataatttc      60

attttctaat acaggagaaa atggcataga tggtacatct ggagcagcta aacgcatgat     120

tggtgtatct aaatcgaaca agcaatgctc tgcaataatc gctgacactt ctgacataat     180

actaccttct aaattatctt cagttacaag taaaacttta cctgtatttt tagcacgatc     240

aataattgtt tctttatcta atggataaac agttcgtaaa tcaacgactt caacgttgat     300

accgtctgca gctaaaatat ccgctgcttg taaacaataa ttgaccatta atccataaca     360

aaatactgtt aaatcttcac cttcacgttt aacatctgct tttcctaaag gtacagtgta     420

atattcttct ggcacttctt cctttaagaa acgataagct tttttatgct caaagtacaa     480
```

```
tactggatca tttgattcga tagatgataa taaaagccct ttagcatcat acggtgtgga    540

aggaataaca attgttaaac ctggtgatga agcaaatata ctttcaatac tttgtgaatg    600

atatagtcct ccgtgaacac cgccaccaaa tggtgcacga atcgttaatg ggcattgcca    660

atcattattt gaacgataac gcattttcgc agcttcacta ataatttgat ttgtcgcagg    720

taaaataaaa tctgcaaatt gaatttctgc aattggtctt ttacctacca tagctgcacc    780

aatggcagtt ccaacaatat ttgactcagc taatggcgta tcgataactc tgtcttcacc    840

atattgttgt tgtagtcctt gagtagtacc aaatacgcca cctttttac caacatcttc    900

accaagaata aacacatctt tattttgttg taatgctaag tcttgtgcct ggcgtatcgc    960

ctctaaataa gataatttag ccat                                           984


<210> SEQ ID NO 38
<211> LENGTH: 337
<212> TYPE: PRT
<213> ORGANISM: Streptococcus mutans

<400> SEQUENCE: 38

Met Arg Arg Lys Arg Tyr Met Ser Glu Thr Lys Val Val Ala Leu Arg
1               5                   10                  15

Glu Ala Ile Asn Leu Ala Met Ser Glu Glu Met Arg Lys Asp Glu Lys
            20                  25                  30

Ile Ile Leu Met Gly Glu Asp Val Gly Ile Tyr Gly Gly Asp Phe Gly
        35                  40                  45

Thr Ser Val Gly Met Leu Ala Glu Phe Gly Glu Lys Arg Val Lys Asp
    50                  55                  60

Thr Pro Ile Ser Glu Ala Ala Ile Ala Gly Ser Ala Val Gly Ala Ala
65                  70                  75                  80

Gln Thr Gly Leu Arg Pro Ile Val Asp Leu Thr Phe Met Asp Phe Val
                85                  90                  95

Thr Ile Ala Met Asp Ala Ile Val Asn Gln Gly Ala Lys Ala Asn Tyr
            100                 105                 110

Met Phe Gly Gly Gly Leu Lys Thr Pro Val Thr Phe Arg Val Ala Ser
        115                 120                 125

Gly Ser Gly Ile Gly Ser Ala Ala Gln His Ser Gln Ser Leu Glu Ala
    130                 135                 140

Trp Leu Thr His Ile Pro Gly Ile Lys Val Val Ala Pro Gly Thr Val
145                 150                 155                 160

Asn Asp Ala Lys Ala Leu Leu Lys Ser Ala Ile Arg Asp Asn Asn Ile
                165                 170                 175

Val Ile Phe Met Glu Pro Lys Ala Leu Tyr Gly Lys Lys Glu Glu Val
            180                 185                 190

Asn Leu Asp Pro Asp Phe Tyr Ile Pro Leu Gly Lys Gly Glu Ile Lys
        195                 200                 205

Arg Glu Gly Thr Asp Val Thr Ile Val Ser Tyr Gly Arg Met Leu Glu
    210                 215                 220

Arg Val Leu Lys Ala Ala Glu Glu Val Ala Ala Glu Asp Ile Ser Val
225                 230                 235                 240

Glu Val Val Asp Pro Arg Thr Leu Ile Pro Leu Asp Lys Asp Leu Ile
                245                 250                 255

Ile Asn Ser Val Lys Lys Thr Gly Lys Val Ile Leu Val Asn Asp Ala
            260                 265                 270

Tyr Lys Thr Gly Gly Phe Ile Gly Glu Ile Ala Ser Val Ile Thr Glu
```

-continued

```
        275                 280                 285

Ser Glu Ala Phe Asp Tyr Leu Asp Ala Pro Val Leu Arg Leu Ala Ser
    290                 295                 300

Glu Asp Val Pro Val Pro Tyr Ser His Val Leu Glu Thr Ala Ile Leu
305                 310                 315                 320

Pro Asp Val Ala Lys Ile Lys Glu Ala Ile Tyr Lys Gln Val Arg Lys
                325                 330                 335

Arg


<210> SEQ ID NO 39
<211> LENGTH: 1014
<212> TYPE: DNA
<213> ORGANISM: Streptococcus mutans

<400> SEQUENCE: 39

atgaggagaa agagatatat gtcagaaaca aaagtagtag ccttacggga agctatcaat      60

cttgctatga gcgaggaaat gcgtaaggac gaaaaaatta ttttgatggg tgaagatgtc     120

ggtatttatg gtggtgactt tggaacttct gttggtatgc tggctgaatt tggtgaaaag     180

cgtgttaaag ataccoctat ttcagaagca gccattgcag gatctgcagt aggtgccgct     240

caaactggac ttcgtcctat tgttgatttg acctttatgg actttgtgac tattgccatg     300

gatgctattg ttaatcaagg tgctaaagcc aattatatgt ttggcggcgg acttaaaacg     360

cctgtaacct ttcgtgtggc ctcaggctca ggtatcggct cagcagcgca gcattctcag     420

tcactagaag cttggttaac tcatattccg ggaatcaagg tggttgcgcc tggcacagtc     480

aatgatgcta aagccttgct caaatctgct attcgtgata ataatatcgt tattttcatg     540

gaaccaaaag cgctttatgg caaaaaagaa gaggtcaatt tagatcctga tttttatatt     600

ccgcttggta aaggcgaaat taagcgcgag ggaacagatg ttaccattgt gtcttatggt     660

cgtatgctgg aacgcgttct caaagccgct gaggaagtgg cggctgaaga tatcagtgtt     720

gaagttgttg acccgcgtac ccttattccg cttgataaag acttaattat taattctgtg     780

aaaaagacgg gtaaggttat cctagttaat gatgcttata aaacaggtgg tttcattggt     840

gaaatagcat cagtgattac tgaaagcgaa gcatttgatt atttagatgc accagtgctt     900

cgtctcgctt ctgaggatgt gcctgttccc tattctcatg ttctcgaaac agccatttta     960

ccagatgtgg caaaaattaa agaagctatc tataaacaag tcaggaaaag atag          1014


<210> SEQ ID NO 40
<211> LENGTH: 21
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (3)..(3)
<223> OTHER INFORMATION: Xaa can be Val or Ile
<220> FEATURE:
<221> NAME/KEY: MISC_FEATURE
<222> LOCATION: (4)..(4)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be Gln or Glu
<220> FEATURE:
```

<221> NAME/KEY: MISC_FEATURE
<222> LOCATION: (10)..(11)
<223> OTHER INFORMATION: Xaa can be any amino acid
<220> FEATURE:
<221> NAME/KEY: MISC_FEATURE
<222> LOCATION: (16)..(16)
<223> OTHER INFORMATION: Xaa can be Arg or Lys
<220> FEATURE:
<221> NAME/KEY: MISC_FEATURE
<222> LOCATION: (17)..(17)
<223> OTHER INFORMATION: Xaa can be any amino acid
<220> FEATURE:
<221> NAME/KEY: MISC_FEATURE
<222> LOCATION: (19)..(19)
<223> OTHER INFORMATION: Xaa can be any amino acid

<400> SEQUENCE: 40

Val Xaa Xaa Xaa Gly Xaa Asp Val Gly Xaa Xaa Gly Gly Val Phe Xaa
1 5 10 15

Xaa Thr Xaa Gly Ile
20

<210> SEQ ID NO 41
<211> LENGTH: 16
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Tyr or Phe
<220> FEATURE:
<221> NAME/KEY: MISC_FEATURE
<222> LOCATION: (3)..(3)
<223> OTHER INFORMATION: Xaa can be Glu or Lys
<220> FEATURE:
<221> NAME/KEY: MISC_FEATURE
<222> LOCATION: (4)..(4)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be Cys or Val
<220> FEATURE:
<221> NAME/KEY: MISC_FEATURE
<222> LOCATION: (7)..(7)
<223> OTHER INFORMATION: Xaa can be any amino acid
<220> FEATURE:
<221> NAME/KEY: MISC_FEATURE
<222> LOCATION: (9)..(9)
<223> OTHER INFORMATION: Xaa can be Ala or Thr
<220> FEATURE:
<221> NAME/KEY: MISC_FEATURE
<222> LOCATION: (11)..(11)
<223> OTHER INFORMATION: Xaa can be Leu or Ile
<220> FEATURE:
<221> NAME/KEY: MISC_FEATURE
<222> LOCATION: (12)..(12)
<223> OTHER INFORMATION: Xaa can be Ala or Ser
<220> FEATURE:
<221> NAME/KEY: MISC_FEATURE
<222> LOCATION: (14)..(14)
<223> OTHER INFORMATION: Xaa can be Ala or Ser
<220> FEATURE:
<221> NAME/KEY: MISC_FEATURE
<222> LOCATION: (15)..(15)
<223> OTHER INFORMATION: Xaa can be Ala or Gly

<400> SEQUENCE: 41

Xaa Gly Xaa Xaa Arg Xaa Xaa Asp Xaa Pro Xaa Xaa Glu Xaa Xaa Ile
1 5 10 15

<210> SEQ ID NO 42

<211> LENGTH: 15
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (3)..(3)
<223> OTHER INFORMATION: Xaa can be Ala or Glu
<220> FEATURE:
<221> NAME/KEY: MISC_FEATURE
<222> LOCATION: (4)..(4)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be Arg or Tyr
<220> FEATURE:
<221> NAME/KEY: MISC_FEATURE
<222> LOCATION: (7)..(7)
<223> OTHER INFORMATION: Xaa can be any amino acid
<220> FEATURE:
<221> NAME/KEY: MISC_FEATURE
<222> LOCATION: (10)..(10)
<223> OTHER INFORMATION: Xaa can be Ile or Val
<220> FEATURE:
<221> NAME/KEY: MISC_FEATURE
<222> LOCATION: (11)..(11)
<223> OTHER INFORMATION: Xaa can be Ala or Val
<220> FEATURE:
<221> NAME/KEY: MISC_FEATURE
<222> LOCATION: (13)..(13)
<223> OTHER INFORMATION: Xaa can be any amino acid

<400> SEQUENCE: 42

```
Gly Thr Xaa Xaa Xaa Gly Xaa Arg Pro Xaa Xaa Glu Xaa Gln Phe
1               5                   10                  15
```

<210> SEQ ID NO 43
<211> LENGTH: 19
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa can be Cys or Tyr
<220> FEATURE:
<221> NAME/KEY: MISC_FEATURE
<222> LOCATION: (5)..(5)
<223> OTHER INFORMATION: Xaa can be Val or Ile
<220> FEATURE:
<221> NAME/KEY: MISC_FEATURE
<222> LOCATION: (6)..(6)
<223> OTHER INFORMATION: Xaa can be any amino acid
<220> FEATURE:
<221> NAME/KEY: MISC_FEATURE
<222> LOCATION: (7)..(7)
<223> OTHER INFORMATION: Xaa can be Ala or Gly
<220> FEATURE:
<221> NAME/KEY: MISC_FEATURE
<222> LOCATION: (8)..(10)
<223> OTHER INFORMATION: Xaa can be any amino acid
<220> FEATURE:
<221> NAME/KEY: MISC_FEATURE
<222> LOCATION: (13)..(13)
<223> OTHER INFORMATION: Xaa can be any amino acid
<220> FEATURE:
<221> NAME/KEY: MISC_FEATURE
<222> LOCATION: (15)..(15)
<223> OTHER INFORMATION: Xaa can be any amino acid
<220> FEATURE:
<221> NAME/KEY: MISC_FEATURE
<222> LOCATION: (18)..(18)
<223> OTHER INFORMATION: Xaa can be any amino acid
<220> FEATURE:

-continued

```
<221> NAME/KEY: MISC_FEATURE
<222> LOCATION: (19)..(19)
<223> OTHER INFORMATION: Xaa can be Phe or Tyr

<400> SEQUENCE: 43

Pro Xaa Gly Gly Xaa Xaa Xaa Xaa Xaa Xaa His Ser Xaa Ser Xaa Glu
1               5                   10                  15

Ala Xaa Xaa


<210> SEQ ID NO 44
<211> LENGTH: 13
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Glu or Asp
<220> FEATURE:
<221> NAME/KEY: MISC_FEATURE
<222> LOCATION: (5)..(5)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be Phe or Tyr
<220> FEATURE:
<221> NAME/KEY: MISC_FEATURE
<222> LOCATION: (7)..(7)
<223> OTHER INFORMATION: Xaa can be any amino acid
<220> FEATURE:
<221> NAME/KEY: MISC_FEATURE
<222> LOCATION: (9)..(9)
<223> OTHER INFORMATION: Xaa can be His or Pro
<220> FEATURE:
<221> NAME/KEY: MISC_FEATURE
<222> LOCATION: (12)..(12)
<223> OTHER INFORMATION: Xaa can be any amino acid

<400> SEQUENCE: 44

Xaa Asp Pro Val Xaa Xaa Xaa Glu Xaa Lys Arg Xaa Tyr
1               5                   10


<210> SEQ ID NO 45
<211> LENGTH: 12
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be His or Glu
<220> FEATURE:
<221> NAME/KEY: MISC_FEATURE
<222> LOCATION: (3)..(3)
<223> OTHER INFORMATION: Xaa can be Ile or Val
<220> FEATURE:
<221> NAME/KEY: MISC_FEATURE
<222> LOCATION: (7)..(7)
<223> OTHER INFORMATION: Xaa can be Thr or Ser
<220> FEATURE:
<221> NAME/KEY: MISC_FEATURE
<222> LOCATION: (8)..(9)
<223> OTHER INFORMATION: Xaa can be any amino acid
<220> FEATURE:
<221> NAME/KEY: MISC_FEATURE
<222> LOCATION: (11)..(11)
<223> OTHER INFORMATION: Xaa can be any amino acid

<400> SEQUENCE: 45

Xaa Val Xaa Asp Leu Arg Xaa Xaa Xaa Pro Xaa Asp
```

-continued 1 5 10

<210> SEQ ID NO 46
<211> LENGTH: 19
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa can be Leu or Phe
<220> FEATURE:
<221> NAME/KEY: MISC_FEATURE
<222> LOCATION: (5)..(5)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be Asp or His
<220> FEATURE:
<221> NAME/KEY: MISC_FEATURE
<222> LOCATION: (8)..(8)
<223> OTHER INFORMATION: Xaa can be Asp or Glu
<220> FEATURE:
<221> NAME/KEY: MISC_FEATURE
<222> LOCATION: (11)..(12)
<223> OTHER INFORMATION: Xaa can be any amino acid
<220> FEATURE:
<221> NAME/KEY: MISC_FEATURE
<222> LOCATION: (14)..(14)
<223> OTHER INFORMATION: Xaa can be Leu or Val
<220> FEATURE:
<221> NAME/KEY: MISC_FEATURE
<222> LOCATION: (15)..(15)
<223> OTHER INFORMATION: Xaa can be any amino acid
<220> FEATURE:
<221> NAME/KEY: MISC_FEATURE
<222> LOCATION: (17)..(17)
<223> OTHER INFORMATION: Xaa can be any amino acid
<220> FEATURE:
<221> NAME/KEY: MISC_FEATURE
<222> LOCATION: (18)..(18)
<223> OTHER INFORMATION: Xaa can be His or Asp

<400> SEQUENCE: 46

Glu Xaa Cys Xaa Xaa Xaa Leu Xaa Ala Pro Xaa Xaa Arg Xaa Xaa Gly
1 5 10 15

Xaa Xaa Pro

<210> SEQ ID NO 47
<211> LENGTH: 424
<212> TYPE: PRT
<213> ORGANISM: Bacillus subtillis

<400> SEQUENCE: 47

Met Ala Ile Glu Gln Met Thr Met Pro Gln Leu Gly Glu Ser Val Thr
1 5 10 15

Glu Gly Thr Ile Ser Lys Trp Leu Val Ala Pro Gly Asp Lys Val Asn
20 25 30

Lys Tyr Asp Pro Ile Ala Glu Val Met Thr Asp Lys Val Asn Ala Glu
35 40 45

Val Pro Ser Ser Phe Thr Gly Thr Ile Thr Glu Leu Val Gly Glu Glu
50 55 60

Gly Gln Thr Leu Gln Val Gly Glu Met Ile Cys Lys Ile Glu Thr Glu
65 70 75 80

```
Gly Ala Asn Pro Ala Glu Gln Lys Gln Glu Gln Pro Ala Ala Ser Glu
                85                  90                  95

Ala Ala Glu Asn Pro Val Ala Lys Ser Ala Gly Ala Ala Asp Gln Pro
            100                 105                 110

Asn Lys Lys Arg Tyr Ser Pro Ala Val Leu Arg Leu Ala Gly Glu His
        115                 120                 125

Gly Ile Asp Leu Asp Gln Val Thr Gly Thr Gly Ala Gly Gly Arg Ile
    130                 135                 140

Thr Arg Lys Asp Ile Gln Arg Leu Ile Glu Thr Gly Gly Val Gln Glu
145                 150                 155                 160

Gln Asn Pro Glu Glu Leu Lys Thr Ala Ala Pro Ala Pro Lys Ser Ala
                165                 170                 175

Ser Lys Pro Glu Pro Lys Glu Glu Thr Ser Tyr Pro Ala Ser Ala Ala
            180                 185                 190

Gly Asp Lys Glu Ile Pro Val Thr Gly Val Arg Lys Ala Ile Ala Ser
        195                 200                 205

Asn Met Lys Arg Ser Lys Thr Glu Ile Pro His Ala Trp Thr Met Met
    210                 215                 220

Glu Val Asp Val Thr Asn Met Val Ala Tyr Arg Asn Ser Ile Lys Asp
225                 230                 235                 240

Ser Phe Lys Lys Thr Glu Gly Phe Asn Leu Thr Phe Phe Ala Phe Phe
                245                 250                 255

Val Lys Ala Val Ala Gln Ala Leu Lys Glu Phe Pro Gln Met Asn Ser
            260                 265                 270

Met Trp Ala Gly Asp Lys Ile Ile Gln Lys Lys Asp Ile Asn Ile Ser
        275                 280                 285

Ile Ala Val Ala Thr Glu Asp Ser Leu Phe Val Pro Val Ile Lys Asn
    290                 295                 300

Ala Asp Glu Lys Thr Ile Lys Gly Ile Ala Lys Asp Ile Thr Gly Leu
305                 310                 315                 320

Ala Lys Lys Val Arg Asp Gly Lys Leu Thr Ala Asp Asp Met Gln Gly
                325                 330                 335

Gly Thr Phe Thr Val Asn Asn Thr Gly Ser Phe Gly Ser Val Gln Ser
            340                 345                 350

Met Gly Ile Ile Asn Tyr Pro Gln Ala Ala Ile Leu Gln Val Glu Ser
        355                 360                 365

Ile Val Lys Arg Pro Val Val Met Asp Asn Gly Met Ile Ala Val Arg
    370                 375                 380

Asp Met Val Asn Leu Cys Leu Ser Leu Asp His Arg Val Leu Asp Gly
385                 390                 395                 400

Leu Val Cys Gly Arg Phe Leu Gly Arg Val Lys Gln Ile Leu Glu Ser
                405                 410                 415

Ile Asp Glu Lys Thr Ser Val Tyr
            420
```

<210> SEQ ID NO 48
<211> LENGTH: 1275
<212> TYPE: DNA
<213> ORGANISM: Bacillus subtillis

<400> SEQUENCE: 48

```
ttagtaaaca gatgtcttct cgtcaatcga ttctaaaatt tgtttcactc gtccgaggaa      60

tcgtccgcac acgagaccgt caagcactct gtgatctaat gacaggcaca gattaaccat     120
```

-continued

```
gtctctgaca gcaatcatgc cattgtccat gacaaccggg cgtttgacga tggattctac    180

ttgaagaatc gcagcctgag ggtagttgat aatgcccatc gactgaacag acccgaacga    240

acctgtgttg ttgacggtaa acgtgcctcc ctgcatgtca tctgcagtga gttttccgtc    300

tcttactttt ttagctaggc cggtaatgtc tttcgcaatg cctttaattg ttttttcatc    360

agcgttttta atcaccggaa caaataaaga atcctctgtg gcaactgcaa ttgaaatatt    420

gatatccttt ttctgaataa ttttgtcccc cgcccacatg ctattcattt gcgggaattc    480

ttttaacgcc tgagcgaccg cttttacaaa aaaggcgaag aacgttaaat taaagccttc    540

tgtcttctta aaagaatctt ttatactgtt gcgatatgca accatatttg tgacgtcgac    600

ttccatcatc gtccaagcat gcggaatttc tgttttgctt cgcttcatat tggaagcaat    660

tgcttttctt acacctgtga cagggatttc tttatcaccg gctgcagacg caggatatga    720

cgtctcttct tttggctcag gttttgatgc agacttcggt gcaggagctg ctgttttcag    780

ctcctcagga ttctgttctt gcacgccgcc tgtttcaatt aagcgctgaa tatcttttcg    840

tgtgatgcgc ccgccggcac cagttcctgt cacttgatcg aggtcaatgc cgtgctctcc    900

ggccaaacgg agaacagctg gcgagtagcg ctttttattg ggctgatcgg ctgctccagc    960

actttttgca acagggttct cagcggcttc tgatgctgct ggctgttctt gttttgttc    1020

agccggattc gcgccttctg tttcaatttt gcaaatcatt tctccgactt gcagggtttg   1080

gccttcttct cccacaagct ctgttatcgt accagtaaaa gaagacggaa cctctgcatt   1140

taccttatct gtcatgactt ccgcgatcgg atcgtatttg ttcactttat caccgggggc   1200

gacaagccat ttgctgatcg tcccctctgt tacgctttct ccaagctgcg gcatcgtcat   1260

ttgttcaatt gccat                                                    1275
```

<210> SEQ ID NO 49
<211> LENGTH: 462
<212> TYPE: PRT
<213> ORGANISM: Streptomyces avermitilis

<400> SEQUENCE: 49

```
Met Thr Glu Ala Ser Val Arg Glu Phe Lys Met Pro Asp Val Gly Glu
1               5                   10                  15

Gly Leu Thr Glu Ala Glu Ile Leu Lys Trp Tyr Val Gln Pro Gly Asp
            20                  25                  30

Thr Val Thr Asp Gly Gln Val Val Cys Glu Val Glu Thr Ala Lys Ala
        35                  40                  45

Ala Val Glu Leu Pro Ile Pro Tyr Asp Gly Val Val Arg Glu Leu Arg
    50                  55                  60

Phe Pro Glu Gly Thr Thr Val Asp Val Gly Gln Val Ile Ile Ala Val
65                  70                  75                  80

Asp Val Ala Gly Asp Ala Pro Val Ala Glu Ile Pro Val Pro Ala Gln
                85                  90                  95

Glu Ala Pro Val Gln Glu Glu Pro Lys Pro Glu Gly Arg Lys Pro Val
            100                 105                 110

Leu Val Gly Tyr Gly Val Ala Glu Ser Ser Thr Lys Arg Arg Pro Arg
        115                 120                 125

Lys Ser Ala Pro Ala Ser Glu Pro Ala Ala Glu Gly Thr Tyr Phe Ala
    130                 135                 140

Ala Thr Val Leu Gln Gly Ile Gln Gly Glu Leu Asn Gly His Gly Ala
145                 150                 155                 160

Val Lys Gln Arg Pro Leu Ala Lys Pro Pro Val Arg Lys Leu Ala Lys
```

```
                165                 170                 175

Asp Leu Gly Val Asp Leu Ala Thr Ile Thr Pro Ser Gly Pro Asp Gly
            180                 185                 190

Val Ile Thr Arg Glu Asp Val His Ala Ala Val Ala Pro Pro Pro Pro
        195                 200                 205

Ala Pro Gln Pro Val Gln Thr Pro Ala Ala Pro Ala Pro Ala Pro Val
    210                 215                 220

Ala Ala Tyr Asp Thr Ala Arg Glu Thr Arg Val Pro Val Lys Gly Val
225                 230                 235                 240

Arg Lys Ala Thr Ala Ala Ala Met Val Gly Ser Ala Phe Thr Ala Pro
                245                 250                 255

His Val Thr Glu Phe Val Thr Val Asp Val Thr Arg Thr Met Lys Leu
            260                 265                 270

Val Glu Glu Leu Lys Gln Asp Lys Glu Phe Thr Gly Leu Arg Val Asn
        275                 280                 285

Pro Leu Leu Leu Ile Ala Lys Ala Leu Leu Val Ala Ile Lys Arg Asn
    290                 295                 300

Pro Asp Ile Asn Ala Ser Trp Asp Glu Ala Asn Gln Glu Ile Val Leu
305                 310                 315                 320

Lys His Tyr Val Asn Leu Gly Ile Ala Ala Ala Thr Pro Arg Gly Leu
                325                 330                 335

Ile Val Pro Asn Ile Lys Asp Ala His Ala Lys Thr Leu Pro Gln Leu
            340                 345                 350

Ala Glu Ser Leu Gly Glu Leu Val Ser Thr Ala Arg Glu Gly Lys Thr
        355                 360                 365

Ser Pro Thr Ala Met Gln Gly Gly Thr Val Thr Ile Thr Asn Val Gly
    370                 375                 380

Val Phe Gly Val Asp Thr Gly Thr Pro Ile Leu Asn Pro Gly Glu Ser
385                 390                 395                 400

Ala Ile Leu Ala Val Gly Ala Ile Lys Leu Gln Pro Trp Val His Lys
                405                 410                 415

Gly Lys Val Lys Pro Arg Gln Val Thr Thr Leu Ala Leu Ser Phe Asp
            420                 425                 430

His Arg Leu Val Asp Gly Glu Leu Gly Ser Lys Val Leu Ala Asp Val
        435                 440                 445

Ala Ala Ile Leu Glu Gln Pro Lys Arg Leu Ile Thr Trp Ala
    450                 455                 460


<210> SEQ ID NO 50
<211> LENGTH: 1389
<212> TYPE: DNA
<213> ORGANISM: Streptomyces avermitilis

<400> SEQUENCE: 50

atgactgagg cgtccgtgcg tgagttcaag atgcccgatg tgggtgaggg actcaccgag      60

gccgagatcc tcaagtggta cgtccagccc ggcgacaccg tcaccgacgg ccaggtcgtc     120

tgcgaggtcg agaccgcgaa ggcggccgtg gaactcccca ttccgtacga cggtgtcgta     180

cgcgaactcc gtttccccga ggggacgacg gtggacgtgg gacaggtgat catcgcggtg     240

gacgtggccg gcgacgcacc ggtggcggag atccccgtgc ccgcgcagga ggctccggtc     300

caggaggagc ccaagcccga gggccgcaag cccgtcctcg tgggctacgg ggtggccgag     360

tcctccacca agcgccgtcc gcgcaagagc gcgccggcga gcgagcccgc tgcggagggc     420

acgtacttcg cagcgaccgt tctccagggc atccagggcg agctgaacgg acacggcgcg     480
```

-continued

```
gtgaagcagc gtccgctggc gaagccgccg gtgcgcaagc tggccaagga cctgggcgtc    540

gacctcgcga cgatcacgcc gtcgggcccc gacggcgtca tcacgcgcga ggacgtgcac    600

gcggcggtgg cgccaccgcc gccggcaccc cagcccgtgc agacgcccgc tgccccggcc    660

ccggcgccgg tggccgcgta cgacacggct cgtgagaccc gtgtccccgt caagggcgtc    720

cgcaaggcga cggcggcggc gatggtcggc tcggcgttca cggcgccgca cgtcacggag    780

ttcgtgacgg tggacgtgac gcgcacgatg aagctggtcg aggagctgaa gcaggacaag    840

gagttcaccg gcctgcgggt gaacccgctg ctcctcatcg ccaaggcgct cctggtcgcg    900

atcaagcgga acccggacat caacgcgtcc tgggacgagg cgaaccagga gatcgtcctc    960

aagcactatg tgaacctggg catcgcggcg gccaccccgc gcggtctgat cgtcccgaac   1020

atcaaggacg cccacgccaa gacgctgccg caactggccg agtcactggg tgagttggtg   1080

tcgacggccc gcgagggcaa gacgtccccg acggccatgc agggcggcac ggtcacgatc   1140

acgaacgtcg gcgtcttcgg cgtcgacacg ggcacgccga tcctcaaccc cggcgagtcc   1200

gcgatcctcg cggtcggcgc gatcaagctc cagccgtggg tccacaaggg caaggtcaag   1260

ccccgacagg tcaccacgct ggcgctcagc ttcgaccatc gcctggtcga cggcgagctg   1320

ggctccaagg tgctggccga cgtggcggcg atcctggagc agccgaagcg gctgatcacc   1380

tgggcctag                                                            1389


<210> SEQ ID NO 51
<211> LENGTH: 423
<212> TYPE: PRT
<213> ORGANISM: Pseudomonas putida

<400> SEQUENCE: 51

Met Gly Thr His Val Ile Lys Met Pro Asp Ile Gly Glu Gly Ile Ala
1               5                   10                  15

Gln Val Glu Leu Val Glu Trp Phe Val Lys Val Gly Asp Ile Ile Ala
            20                  25                  30

Glu Asp Gln Val Val Ala Asp Val Met Thr Asp Lys Ala Thr Val Glu
        35                  40                  45

Ile Pro Ser Pro Val Ser Gly Lys Val Leu Ala Leu Gly Gly Gln Pro
    50                  55                  60

Gly Glu Val Met Ala Val Gly Ser Glu Leu Ile Arg Ile Glu Val Glu
65                  70                  75                  80

Gly Ser Gly Asn His Val Asp Val Pro Gln Pro Lys Pro Val Glu Ala
                85                  90                  95

Pro Ala Ala Pro Ile Ala Ala Lys Pro Glu Pro Gln Lys Asp Val Lys
            100                 105                 110

Pro Ala Val Tyr Gln Ala Pro Ala Asn His Glu Ala Ala Pro Ile Val
        115                 120                 125

Pro Arg Gln Pro Gly Asp Lys Pro Leu Ala Ser Pro Ala Val Arg Lys
    130                 135                 140

Arg Ala Leu Asp Ala Gly Ile Glu Leu Arg Tyr Val His Gly Ser Gly
145                 150                 155                 160

Pro Ala Gly Arg Ile Leu His Glu Asp Leu Asp Ala Phe Met Ser Lys
                165                 170                 175

Pro Gln Ser Asn Ala Gly Gln Ala Pro Asp Gly Tyr Ala Lys Arg Thr
            180                 185                 190

Asp Ser Glu Gln Val Pro Val Ile Gly Leu Arg Arg Lys Ile Ala Gln
        195                 200                 205
```

```
Arg Met Gln Asp Ala Lys Arg Arg Val Ala His Phe Ser Tyr Val Glu
    210                 215                 220

Glu Ile Asp Val Thr Ala Leu Glu Ala Leu Arg Gln Gln Leu Asn Ser
225                 230                 235                 240

Lys His Gly Asp Ser Arg Gly Lys Leu Thr Leu Leu Pro Phe Leu Val
                245                 250                 255

Arg Ala Leu Val Val Ala Leu Arg Asp Phe Pro Gln Ile Asn Ala Thr
            260                 265                 270

Tyr Asp Asp Glu Ala Gln Ile Ile Thr Arg His Gly Ala Val His Val
        275                 280                 285

Gly Ile Ala Thr Gln Gly Asp Asn Gly Leu Met Val Pro Val Leu Arg
    290                 295                 300

His Ala Glu Ala Gly Ser Leu Trp Ala Asn Ala Gly Glu Ile Ser Arg
305                 310                 315                 320

Leu Ala Asn Ala Ala Arg Asn Asn Lys Ala Ser Arg Glu Glu Leu Ser
                325                 330                 335

Gly Ser Thr Ile Thr Leu Thr Ser Leu Gly Ala Leu Gly Gly Ile Val
            340                 345                 350

Ser Thr Pro Val Val Asn Thr Pro Glu Val Ala Ile Val Gly Val Asn
        355                 360                 365

Arg Met Val Glu Arg Pro Val Val Ile Asp Gly Gln Ile Val Val Arg
    370                 375                 380

Lys Met Met Asn Leu Ser Ser Ser Phe Asp His Arg Val Val Asp Gly
385                 390                 395                 400

Met Asp Ala Ala Leu Phe Ile Gln Ala Val Arg Gly Leu Leu Glu Gln
                405                 410                 415

Pro Ala Cys Leu Phe Val Glu
            420
```

<210> SEQ ID NO 52
<211> LENGTH: 1272
<212> TYPE: DNA
<213> ORGANISM: Pseudomonas putida

<400> SEQUENCE: 52

```
tcactccacg aacaggcagg cgggttgttc gagcaggcca cgcacggcct ggatgaacag      60

ggcggcgtcc atgccatcga ccacgcggtg gtcgaacgag ctggacaggt tcatcatctt     120

gcgcacgacg atctggccat caatcaccac cggtcgttcg accatgcggt tgaccccgac     180

gattgccact tccggggtgt tgaccaccgg cgtgctgaca atgccaccca aggcgccgag     240

gctggtcagg gtgatggtcg agccggacag ctcctcgcgg ctggccttgt tgttacgtgc     300

agcgttggcc aggcgcgaaa tctcgccggc attggcccac aggctgcccg cttcggcgtg     360

gcgcagcacg ggtaccatca ggccgttgtc accctgggtg gcaatgccca catgcaccgc     420

gccatggcgg gtgatgatct gcgcttcgtc gtcgtaggtc gcgttgatct gcgggaagtc     480

acgcagcgcc acgacgaggg cgcgcaccag gaatggcagc aaggtcagtt tgccgcggct     540

gtcgccgtgc ttgctgttga gttgctggcg cagggcttcc agggcggtga cgtcgatttc     600

ctcgacataa ctgaagtgcg cgacccggcg tttggcgtcc tgcatgcgct gggcgatctt     660

gcggcgcagg ccgatcaccg gcacctgctc gctgtcggtg cgcttggcat aaccatcagg     720

tgcttgcccg gcattgcttt gcggcttgct catgaaggcg tcgaggtctt cgtgcagaat     780

gcgcccggcc gggccgctac catgcacata acgcagttcg ataccggcgt ccagggcgcg     840
```

-continued

```
tttgcgcacg gccggcgagg ccagcggctt gtcgcccggc tggcgcggca cgatgggcgc    900

agcttcgtgg ttggcgggcg cctggtacac ggcgggtttt acgtctttct gcggttccgg    960

cttggctgca atcggggcgg ccggggcctc taccggtttt ggctgaggca cgtccacatg   1020

gttgccgctg ccttccactt cgatgcggat cagttcgcta ccgaccgcca tcacttcccc   1080

gggctggcca cccagggcca acaccttgcc gctgaccggc gaggggattt ccacggtggc   1140

cttgtcggtc atgacgtcgg ccaccacctg gtcctcggcg atgatgtcgc cgaccttgac   1200

gaaccattcc accaactcga cctgcgcgat gccttcgcca atgtccggca tcttgatgac   1260

gtgcgtgccc at                                                       1272


<210> SEQ ID NO 53
<211> LENGTH: 416
<212> TYPE: PRT
<213> ORGANISM: Listeria monocytogenes

<400> SEQUENCE: 53

Met Ala Val Glu Lys Ile Thr Met Pro Lys Leu Gly Glu Ser Val Thr
1               5                   10                  15

Glu Gly Thr Ile Ser Ser Trp Leu Val Lys Pro Gly Asp Thr Val Glu
            20                  25                  30

Lys Tyr Asp Ala Ile Ala Glu Val Leu Thr Asp Lys Val Thr Ala Glu
        35                  40                  45

Ile Pro Ser Ser Phe Ser Gly Thr Ile Lys Glu Ile Leu Ala Glu Glu
    50                  55                  60

Asp Glu Thr Leu Glu Val Gly Glu Val Ile Cys Thr Ile Glu Thr Glu
65                  70                  75                  80

Glu Ala Ser Ser Ser Glu Pro Val Val Glu Ala Glu Gln Thr Glu Pro
                85                  90                  95

Lys Thr Pro Glu Lys Gln Glu Thr Lys Gln Val Lys Leu Ala Glu Ala
            100                 105                 110

Pro Ala Ser Gly Arg Phe Ser Pro Ala Val Leu Arg Ile Ala Gly Glu
        115                 120                 125

Asn Asn Ile Asp Leu Ser Thr Val Glu Gly Thr Gly Lys Gly Gly Arg
    130                 135                 140

Ile Thr Arg Lys Asp Leu Leu Gln Val Ile Glu Asn Gly Pro Val Ala
145                 150                 155                 160

Pro Lys Arg Glu Glu Val Lys Ser Ala Pro Gln Glu Lys Glu Ala Thr
                165                 170                 175

Pro Asn Pro Val Arg Ser Ala Ala Gly Asp Arg Glu Ile Pro Ile Asn
            180                 185                 190

Gly Val Arg Lys Ala Ile Ala Lys His Met Ser Val Ser Lys Gln Glu
        195                 200                 205

Ile Pro His Ala Trp Met Met Val Glu Val Asp Ala Thr Gly Leu Val
    210                 215                 220

Arg Tyr Arg Asn Thr Val Lys Asp Ser Phe Lys Lys Glu Glu Gly Tyr
225                 230                 235                 240

Ser Leu Thr Tyr Phe Ala Phe Phe Ile Lys Ala Val Ala Gln Ala Leu
                245                 250                 255

Lys Glu Phe Pro Gln Leu Asn Ser Thr Trp Ala Gly Asp Lys Ile Ile
            260                 265                 270

Glu His Ala Asn Ile Asn Ile Ser Ile Ala Ile Ala Ala Gly Asp Leu
        275                 280                 285

Leu Tyr Val Pro Val Ile Lys Asn Ala Asp Glu Lys Ser Ile Lys Gly
```

-continued

```
    290                 295                 300

Ile Ala Arg Glu Ile Ser Glu Leu Ala Gly Lys Ala Arg Asn Gly Lys
305                 310                 315                 320

Leu Ser Gln Ala Asp Met Glu Gly Gly Thr Phe Thr Val Asn Ser Thr
                325                 330                 335

Gly Ser Phe Gly Ser Val Gln Ser Met Gly Ile Ile Asn His Pro Gln
            340                 345                 350

Ala Ala Ile Leu Gln Val Glu Ser Ile Val Lys Arg Pro Val Ile Ile
        355                 360                 365

Asp Asp Met Ile Ala Val Arg Asp Met Val Asn Leu Cys Leu Ser Ile
    370                 375                 380

Asp His Arg Ile Leu Asp Gly Leu Leu Ala Gly Lys Phe Leu Gln Ala
385                 390                 395                 400

Ile Lys Ala Asn Val Glu Lys Ile Ser Lys Glu Asn Thr Ala Leu Tyr
                405                 410                 415
```

<210> SEQ ID NO 54
<211> LENGTH: 1251
<212> TYPE: DNA
<213> ORGANISM: Listeria monocytogenes

<400> SEQUENCE: 54

```
gtggcagttg aaaaaatcac catgcccaaa ttaggggaaa gtgtaacaga aggaacgatt     60

agttcatggt tagttaaacc aggcgataca gtagaaaaat atgatgctat cgcggaagtt    120

ttaacagata aagtaacagc tgaaatccca tcatccttta gtggcactat caaagaaatt    180

ttagcagagg aagatgaaac actagaagta ggcgaagtta tttgtaccat cgaaacagaa    240

gaggctagta gttcagagcc tgtagttgaa gcagaacaaa cagaaccaaa aactccagaa    300

aaacaagaaa caaaacaagt gaaattagca gaagcaccag ccagtggaag attttcacca    360

gcggtactgc gtattgctgg agaaaacaat attgatttat caaccgtaga aggcacaggt    420

aaaggtggcc gaattacaag aaaagattta cttcaagtaa ttgaaaatgg tccagtagct    480

ccgaaacgcg aggaagtgaa gtctgctcca caagaaaaag aagcgacgcc aaatcctgta    540

cgttcagcag caggtgacag agaaatccca atcaatggtg taagaaaagc gattgctaaa    600

catatgagcg tgagtaaaca agaaattccg catgcttgga tgatggtgga agtagatgca    660

actggtcttg ttcgctatcg taatacagtt aaagacagct ttaaaaaaga agaaggttat    720

tcattaactt atttcgcctt tttcatcaaa gccgttgcac aagcattgaa agaattcccg    780

caacttaaca gcacgtgggc aggcgataaa attattgagc atgcgaatat caatatttcg    840

attgcgattg cagctggcga tttattgtat gtgccagtta ttaaaaatgc ggacgaaaaa    900

tccattaaag gtattgctcg cgaaataagt gaactagctg gaaaagcgcg taatggtaaa    960

ctgagccaag ccgatatgga aggtgggact ttcactgtaa atagtactgg ttcatttggc   1020

tctgttcaat caatggggat tattaaccac ccacaagccg ctattcttca agtggaatcc   1080

attgttaagc gcccagtcat tattgacgat atgattgctg tacgagatat ggtcaaccta   1140

tgtctatcca tcgatcatcg tattttagac ggcttactag caggtaaatt cttacaagca   1200

attaaagcca atgtcgaaaa gatttctaaa gaaaatacag cgttgtatta a             1251
```

<210> SEQ ID NO 55
<211> LENGTH: 455
<212> TYPE: PRT
<213> ORGANISM: Streptomyces avermitilis

<400> SEQUENCE: 55

```
Met Ala Gln Val Leu Glu Phe Lys Leu Pro Asp Leu Gly Glu Gly Leu
1               5                   10                  15

Thr Glu Ala Glu Ile Val Arg Trp Leu Val Gln Val Gly Asp Val Val
            20                  25                  30

Ala Ile Asp Gln Pro Val Val Glu Val Glu Thr Ala Lys Ala Met Val
        35                  40                  45

Glu Val Pro Cys Pro Tyr Gly Gly Val Val Thr Ala Arg Phe Gly Glu
    50                  55                  60

Glu Gly Thr Glu Leu Pro Val Gly Ser Pro Leu Leu Thr Val Ala Val
65                  70                  75                  80

Gly Ala Pro Ser Ser Val Pro Ala Ala Ser Ser Leu Ser Gly Ala Thr
                85                  90                  95

Ser Ala Ser Ser Ala Ser Ser Val Ser Ser Asp Asp Gly Glu Ser Ser
            100                 105                 110

Gly Asn Val Leu Val Gly Tyr Gly Thr Ser Ala Ala Pro Ala Arg Arg
        115                 120                 125

Arg Arg Val Arg Pro Gly Gln Ala Ala Pro Val Val Thr Ala Thr Ala
    130                 135                 140

Ala Ala Ala Ala Thr Arg Val Ala Ala Pro Glu Arg Ser Asp Gly Pro
145                 150                 155                 160

Val Pro Val Ile Ser Pro Leu Val Arg Arg Leu Ala Arg Glu Asn Gly
                165                 170                 175

Leu Asp Leu Arg Ala Leu Ala Gly Ser Gly Pro Asp Gly Leu Ile Leu
            180                 185                 190

Arg Ser Asp Val Glu Gln Ala Leu Arg Ala Ala Pro Thr Pro Ala Pro
        195                 200                 205

Thr Pro Thr Met Pro Pro Ala Pro Thr Pro Ala Pro Thr Pro Ala Ala
    210                 215                 220

Ala Pro Arg Gly Thr Arg Ile Pro Leu Arg Gly Val Arg Gly Ala Val
225                 230                 235                 240

Ala Asp Lys Leu Ser Arg Ser Arg Arg Glu Ile Pro Asp Ala Thr Cys
                245                 250                 255

Trp Val Asp Ala Asp Ala Thr Ala Leu Met His Ala Arg Val Ala Met
            260                 265                 270

Asn Ala Thr Gly Gly Pro Lys Ile Ser Leu Ile Ala Leu Leu Ala Arg
        275                 280                 285

Ile Cys Thr Ala Ala Leu Ala Arg Phe Pro Glu Leu Asn Ser Thr Val
    290                 295                 300

Asp Met Asp Ala Arg Glu Val Val Arg Leu Asp Gln Val His Leu Gly
305                 310                 315                 320

Phe Ala Ala Gln Thr Glu Arg Gly Leu Val Val Pro Val Val Arg Asp
                325                 330                 335

Ala His Ala Arg Asp Ala Glu Ser Leu Ser Ala Glu Phe Ala Arg Leu
            340                 345                 350

Thr Glu Ala Ala Arg Thr Gly Thr Leu Thr Pro Gly Glu Leu Thr Gly
        355                 360                 365

Gly Thr Phe Thr Leu Asn Asn Tyr Gly Val Phe Gly Val Asp Gly Ser
    370                 375                 380

Thr Pro Ile Ile Asn His Pro Glu Ala Ala Met Leu Gly Val Gly Arg
385                 390                 395                 400

Ile Ile Pro Lys Pro Trp Val His Glu Gly Glu Leu Ala Val Arg Gln
                405                 410                 415
```

```
Val Val Gln Leu Ser Leu Thr Phe Asp His Arg Val Cys Asp Gly Gly
            420                 425                 430

Thr Ala Gly Gly Phe Leu Arg Tyr Val Ala Asp Cys Val Glu Gln Pro
        435                 440                 445

Ala Val Leu Leu Arg Thr Leu
    450                 455


<210> SEQ ID NO 56
<211> LENGTH: 1368
<212> TYPE: DNA
<213> ORGANISM: Streptomyces avermitilis

<400> SEQUENCE: 56

atggcccagg tgctcgagtt caagctcccc gacctcgggg agggcctgac cgaggccgag      60

atcgtccgct ggctggtgca ggtcggcgac gtcgtggcga tcgaccagcc ggtcgtcgag     120

gtggagacgg ccaaggcgat ggtcgaggtg ccgtgcccct acgggggcgt ggtcaccgcc     180

cgcttcggcg aggagggcac ggaactgccc gtgggctcac cgctgttgac ggtggctgtc     240

ggagctccgt cctcggtgcc cgcggcgtcc tcgctgtccg gggcgacatc ggcgtcctcc     300

gcgtcctcgg tgtcatcgga cgacggcgag tcgtccggca acgtcctggt cggatacggc     360

acgtcggccg cgcccgcgcg ccggcggagg gtgcggccgg gccaggcggc acccgtggtg     420

acggcaactg ccgccgcggc cgccacgcgc gtggcggctc ccgagcggag cgacggcccc     480

gtgcccgtga tctccccgct ggtccgcagg ctcgcccggg agaacggcct ggatctgcgg     540

gcgctggcgg gctccgggcc cgacgggctg atcctgaggt cggacgtcga gcaggcgctg     600

cgcgccgcgc ccactcctgc ccccaccccg accatgcctc cggctcccac tcctgccccc     660

acccccgccg cggcaccccg cggcacccgc atccccctcc gaggggtccg cggtgccgtc     720

gccgacaaac tctcccgcag ccggcgtgag atccccgacg cgacctgctg ggtggacgcc     780

gacgccacgg cactcatgca cgcgcgcgtg gcgatgaacg cgaccggcgg cccgaagatc     840

tccctcatcg cgctgctcgc caggatctgc accgccgcac tggcccgctt ccccgagctc     900

aactccaccg tcgacatgga cgcccgcgag gtcgtacggc tcgaccaggt gcacctgggc     960

ttcgccgcgc agaccgaacg gggctcgtc gtcccggtcg tgcgggacgc gcacgcgcgg    1020

gacgccgagt cgctcagcgc cgagttcgcg cggctgaccg aggccgcccg gaccggcacc    1080

ctcacacccg gggaactgac cggcggcacc ttcacgttga acaactacgg ggtgttcggc    1140

gtcgacggtt ccacgccgat catcaaccac cccgaggcgg ccatgctggg cgtcggccgc    1200

atcatcccca agccgtgggt gcacgagggc gagctggcgg tgcggcaggt cgtccagctc    1260

tcgctcacct tcgaccaccg ggtgtgcgac ggcggcacgg caggcggttt cctgcgctac    1320

gtggcggact gcgtggaaca gccggcggtg ctgctgcgca ccctgtag                  1368


<210> SEQ ID NO 57
<211> LENGTH: 355
<212> TYPE: PRT
<213> ORGANISM: Micrococcus luteus

<400> SEQUENCE: 57

Met Ser Glu Arg Met Thr Phe Gly Arg Ala Ile Asn Arg Gly Leu His
1               5                   10                  15

Arg Ala Leu Ala Asp Asp Pro Lys Val Leu Leu Met Gly Glu Asp Ile
            20                  25                  30

Gly Ala Leu Gly Gly Val Phe Arg Ile Thr Asp Gly Leu Gln Ala Glu
```

-continued

```
        35                  40                  45

Phe Gly Glu Asp Arg Val Leu Asp Thr Pro Leu Ala Glu Ser Gly Ile
    50                  55                  60

Val Gly Thr Ala Ile Gly Leu Ala Met Arg Gly Tyr Arg Pro Val Val
65                  70                  75                  80

Glu Ile Gln Phe Asp Gly Phe Val Tyr Pro Ala Phe Asp Gln Ile Val
                85                  90                  95

Ala Asn Leu Ala Lys Leu Arg Ala Arg Thr Arg Gly Ala Val Pro Met
            100                 105                 110

Pro Val Thr Ile Arg Ile Pro Phe Gly Gly Gly Ile Gly Ser Pro Glu
        115                 120                 125

His His Ser Glu Ser Pro Glu Ala Tyr Phe Leu His Thr Ala Gly Leu
    130                 135                 140

Arg Val Val Ser Pro Ser Ser Pro Gln Glu Gly Tyr Asp Leu Ile Arg
145                 150                 155                 160

Ala Ala Ile Ala Ser Glu Asp Pro Val Val Tyr Leu Glu Pro Lys Arg
                165                 170                 175

Arg Tyr His Asp Lys Gly Asp Val Asp Leu Gly Val Ala Ile Pro Pro
            180                 185                 190

Met Ser Pro Ala Arg Ile Leu Arg Glu Gly Arg Asp Ala Thr Leu Val
        195                 200                 205

Ala Tyr Gly Pro Leu Val Lys Thr Ala Leu Gln Ala Ala Glu Val Ala
    210                 215                 220

Ala Glu Glu Gly Val Glu Val Glu Val Val Asp Leu Arg Ser Leu Ser
225                 230                 235                 240

Pro Leu Asp Thr Gly Leu Val Glu Ser Ser Val Arg Arg Thr Gly Arg
                245                 250                 255

Leu Val Val Ala His Glu Ala Ser Arg Thr Gly Gly Leu Gly Ala Glu
            260                 265                 270

Leu Val Ala Thr Val Ala Glu Arg Ala Phe His Trp Leu Glu Ala Pro
        275                 280                 285

Pro Val Arg Val Thr Gly Met Asp Val Pro Tyr Pro Pro Ser Lys Leu
    290                 295                 300

Glu His Leu His Leu Pro Asp Leu Asp Arg Ile Leu Asp Gly Leu Asp
305                 310                 315                 320

Arg Ala Leu Gly Arg Pro Asn Ser Leu Asp Ser Val Asp Ala Phe Ala
                325                 330                 335

Ala Pro Glu Thr Ala Glu Gln Phe Leu Ala Ala Gln Asn Ala Gly Glu
            340                 345                 350

Glu Thr Arg
        355


<210> SEQ ID NO 58
<211> LENGTH: 1068
<212> TYPE: DNA
<213> ORGANISM: Micrococcus luteus

<400> SEQUENCE: 58

gtgagcgagc gcatgacctt cggccgtgcg atcaaccgcg gcctgcaccg tgccctggcc      60

gacgacccca aggtcctgct catgggcgag gacatcggcg ccctcggcgg cgtgttccgc     120

atcaccgacg gcctgcaggc cgagttcggc gaggaccggg tgctcgacac cccgctggcc     180

gagtccggca tcgtgggcac ggccatcggc ctggcgatgc gcggctaccg gcccgtcgtc     240

gagatccagt tcgacggctt cgtgtacccg gcgttcgacc agatcgtggc gaacctggcc     300
```

```
aagctgcgcg cccgcacccg cggcgccgtg ccgatgccgg tgaccatccg catccccttc    360

ggcggcggca tcggctcccc ggagcaccac tccgagtcgc ccgaggccta cttcctgcac    420

accgcgggtc tgcgcgtggt ctccccgtcc tccccgcagg aggggtacga cctcatccgc    480

gccgcgatcg cctcggagga cccggtggtc tacctcgagc ccaagcgtcg ctaccacgac    540

aagggcgacg tggacctggg cgtcgcgatc ccgccgatga gcccggcccg catcctgcgc    600

gagggccgtg acgccacgct cgtggcctac ggcccgctcg tgaagaccgc cctgcaggcc    660

gccgaggtgg cggccgagga gggtgtcgag gtcgaggtgg tcgacctgcg cagcctgtcc    720

ccgctggaca ccggcctcgt cgagtcctcg gtgcggcgca ccggtcggct cgtcgtggcg    780

cacgaggcct cccgcacggg cggcctcggc gccgagctcg tggccacggt ggccgagcgc    840

gcgttccatt ggctcgaggc cccgccggtg cgcgtcaccg gcatggacgt gccctacccg    900

ccgtccaagc tcgagcacct gcacctgccg gacctcgacc gcatcctcga cggcctggac    960

cgtgctctgg gccggccgaa ttcgctggac tccgtggacg cgttcgccgc ccccgagacc   1020

gccgagcagt tcctcgccgc ccagaacgcc ggggaggaga cccgatga                1068


<210> SEQ ID NO 59
<211> LENGTH: 424
<212> TYPE: PRT
<213> ORGANISM: Staphylococcus aureus

<400> SEQUENCE: 59

Met Glu Ile Thr Met Pro Lys Leu Gly Glu Ser Val His Glu Gly Thr
1               5                   10                  15

Ile Glu Gln Trp Leu Val Ser Val Gly Asp His Ile Asp Glu Tyr Glu
            20                  25                  30

Pro Leu Cys Glu Val Ile Thr Asp Lys Val Thr Ala Glu Val Pro Ser
        35                  40                  45

Thr Ile Ser Gly Thr Ile Thr Glu Ile Leu Val Glu Ala Gly Gln Thr
    50                  55                  60

Val Ala Ile Asp Thr Ile Ile Cys Lys Ile Glu Thr Ala Asp Glu Lys
65                  70                  75                  80

Thr Asn Glu Thr Thr Glu Glu Ile Gln Ala Lys Val Asp Glu His Thr
                85                  90                  95

Gln Lys Ser Thr Lys Lys Ala Ser Ala Thr Val Glu Gln Thr Phe Thr
            100                 105                 110

Ala Lys Gln Asn Gln Pro Arg Asn Asn Gly Arg Phe Ser Pro Val Val
        115                 120                 125

Phe Lys Leu Ala Ser Glu His Asp Ile Asp Leu Ser Gln Val Val Gly
    130                 135                 140

Ser Gly Phe Glu Gly Arg Val Thr Lys Lys Asp Ile Met Ser Val Ile
145                 150                 155                 160

Glu Asn Gly Gly Thr Thr Ala Gln Ser Asp Lys Gln Val Gln Thr Lys
                165                 170                 175

Ser Thr Ser Val Asp Thr Ser Ser Asn Gln Ser Ser Glu Asp Asn Ser
            180                 185                 190

Glu Asn Ser Thr Ile Pro Val Asn Gly Val Arg Lys Ala Ile Ala Gln
        195                 200                 205

Asn Met Val Asn Ser Val Thr Glu Ile Pro His Ala Trp Met Met Ile
    210                 215                 220

Glu Val Asp Ala Thr Asn Leu Val Asn Thr Arg Asn His Tyr Lys Asn
225                 230                 235                 240
```

```
Ser Phe Lys Asn Lys Glu Gly Tyr Asn Leu Thr Phe Phe Ala Phe Phe
                245                 250                 255

Val Lys Ala Val Ala Asp Ala Leu Lys Ala Tyr Pro Leu Leu Asn Ser
            260                 265                 270

Ser Trp Gln Gly Asn Glu Ile Val Leu His Lys Asp Ile Asn Ile Ser
        275                 280                 285

Ile Ala Val Ala Asp Glu Asn Lys Leu Tyr Val Pro Val Ile Lys His
    290                 295                 300

Ala Asp Glu Lys Ser Ile Lys Gly Ile Ala Arg Glu Ile Asn Thr Leu
305                 310                 315                 320

Ala Thr Lys Ala Arg Asn Lys Gln Leu Thr Thr Glu Asp Met Gln Gly
                325                 330                 335

Gly Thr Phe Thr Val Asn Asn Thr Gly Thr Phe Gly Ser Val Ser Ser
            340                 345                 350

Met Gly Ile Ile Asn His Pro Gln Ala Ala Ile Leu Gln Val Glu Ser
        355                 360                 365

Ile Val Lys Lys Pro Val Val Ile Asn Asp Met Ile Ala Ile Arg Ser
    370                 375                 380

Met Val Asn Leu Cys Ile Ser Ile Asp His Arg Ile Leu Asp Gly Leu
385                 390                 395                 400

Gln Thr Gly Lys Phe Met Asn His Ile Lys Gln Arg Ile Glu Gln Tyr
                405                 410                 415

Thr Leu Glu Asn Thr Asn Ile Tyr
            420
```

<210> SEQ ID NO 60
<211> LENGTH: 1275
<212> TYPE: DNA
<213> ORGANISM: Staphylococcus aureus

<400> SEQUENCE: 60

```
ctaatatata tttgtatttt ctaaagtata ctgttcgata cgctgtttaa tatgattcat     60

aaatttacca gtttgtaaac catctaaaat gcgatgatct attgaaatac ataaatttac    120

catacttcga attgcaatca tatcattaat tactactggc tttttaacga ttgattctac    180

ttgtaatatc gctgcttgag ggtgatttat aatccccatt gatgatactg aaccaaatgt    240

accagtatta ttaactgtaa atgttccacc ttgcatatct tcagttgtca attgcttatt    300

acgcgctttt gttgctaaag tattaatttc tctagctata cctttgattg acttttcgtc    360

tgcatgctta atcacaggta cgtataattt attttcatca gcaacagcaa ttgaaatatt    420

aatgtcttta tgtaagacaa tttcatttcc ttgccagcta ctatttaata aaggatatgc    480

ttttaaagca tctgctacag cttttacaaa gaaagcaaag aacgttagat tatatccttc    540

tttattttta aagctgtttt tataatgatt tctcgtattc acaagatttg tagcatctac    600

ttcaatcatc atccatgcat gtggaatctc tgttacacta ttaaccatat tttgcgcaat    660

tgctttacgc acaccattta ctggtattgt gctgttttca ctattgtctt cagatgattg    720

gttacttgat gtatctactg atgttgattt tgtttgaact tgtttgtcag attgagctgt    780

ggtaccacca ttttcaataa ctgacattat atccttctta gttacacgac cttcaaatcc    840

actacctaca acttgtgata aatcaatgtc atgctctgaa gcgagtttaa atacaacagg    900

tgaaaagcga ccattattac gaggttgatt ttgtttagca gtaaatgtct gttccactgt    960

tgcactagct tttttagtag atttctgagt atgctcatcc acttttgctt gtatctcttc   1020
```

```
agttgtttca tttgtctttt catcagcagt ttcaatttta cagataattg tatcaatagc   1080

tactgtctgc cccgcttcaa ctaaaatttc tgtaattgtt cctgatatcg tggaagggac   1140

ttcagctgtc actttatctg taataacttc acataatggt tcatattcat caatatgatc   1200

accaacagaa actaaccatt gttcaatggt accttcatga acactctcac ctaacttagg   1260

cattgttatt tccat                                                    1275


<210> SEQ ID NO 61
<211> LENGTH: 455
<212> TYPE: PRT
<213> ORGANISM: Streptococcus mutans

<400> SEQUENCE: 61

Met Ala Val Glu Ile Ile Met Pro Lys Leu Gly Val Asp Met Gln Glu
1               5                   10                  15

Gly Glu Ile Ile Glu Trp Lys Lys Gln Glu Gly Asp Glu Val Lys Glu
            20                  25                  30

Gly Glu Ile Leu Leu Glu Ile Met Ser Asp Lys Thr Asn Met Glu Ile
        35                  40                  45

Glu Ala Glu Asp Ser Gly Val Leu Leu Lys Ile Val Lys Gly Asn Gly
    50                  55                  60

Gln Val Val Pro Val Thr Glu Val Ile Gly Tyr Ile Gly Gln Ala Gly
65                  70                  75                  80

Glu Val Leu Glu Ile Ala Asp Val Pro Ala Ser Thr Val Pro Lys Glu
                85                  90                  95

Asn Ser Ala Ala Pro Ala Glu Lys Thr Lys Ala Met Ser Ser Pro Thr
            100                 105                 110

Val Ala Ala Ala Pro Gln Gly Lys Ile Arg Ala Thr Pro Ala Ala Arg
        115                 120                 125

Lys Ala Ala Arg Asp Leu Gly Val Asn Leu Asn Gln Val Ser Gly Thr
    130                 135                 140

Gly Ala Lys Gly Arg Val His Lys Glu Asp Val Glu Ser Phe Lys Ala
145                 150                 155                 160

Ala Gln Pro Lys Ala Thr Pro Leu Ala Arg Lys Ile Ala Ile Asp Lys
                165                 170                 175

Gly Ile Asp Leu Ala Ser Val Ser Gly Thr Gly Phe Gly Gly Lys Ile
            180                 185                 190

Ile Lys Glu Asp Ile Leu Asn Leu Phe Glu Ala Ala Gln Pro Val Asn
        195                 200                 205

Asp Val Ser Asp Pro Ala Lys Glu Ala Ala Ala Leu Pro Glu Gly Val
    210                 215                 220

Glu Val Ile Lys Met Ser Ala Met Arg Lys Ala Val Ala Lys Ser Met
225                 230                 235                 240

Val Asn Ser Tyr Leu Thr Ala Pro Thr Phe Thr Leu Asn Tyr Asp Ile
                245                 250                 255

Asp Met Thr Glu Met Ile Ala Leu Arg Lys Lys Leu Ile Asp Pro Ile
            260                 265                 270

Met Glu Lys Thr Gly Phe Lys Val Ser Phe Thr Asp Leu Ile Gly Leu
        275                 280                 285

Ala Val Val Lys Thr Leu Met Lys Pro Glu His Arg Tyr Leu Asn Ala
    290                 295                 300

Ser Leu Ile Asn Asp Ala Thr Glu Ile Glu Leu His Gln Phe Val Asn
305                 310                 315                 320

Leu Gly Ile Ala Val Gly Leu Asp Glu Gly Leu Leu Val Pro Val Val
```

-continued

```
            325                 330                 335

His Gly Ala Asp Lys Met Ser Leu Ser Asp Phe Val Ile Ala Ser Lys
            340                 345                 350

Asp Val Ile Lys Lys Ala Gln Thr Gly Lys Leu Lys Ala Thr Glu Met
        355                 360                 365

Ser Gly Ser Thr Phe Ser Ile Thr Asn Leu Gly Met Phe Gly Thr Lys
    370                 375                 380

Thr Phe Asn Pro Ile Ile Asn Gln Pro Asn Ser Ala Ile Leu Gly Val
385                 390                 395                 400

Gly Ala Thr Ile Gln Thr Pro Thr Val Val Asp Gly Glu Ile Lys Ile
                405                 410                 415

Arg Pro Ile Met Ala Leu Cys Leu Thr Ile Asp His Arg Leu Val Asp
            420                 425                 430

Gly Met Asn Gly Ala Lys Phe Met Val Asp Leu Lys Lys Leu Met Glu
        435                 440                 445

Asn Pro Phe Thr Leu Leu Ile
    450                 455


<210> SEQ ID NO 62
<211> LENGTH: 1368
<212> TYPE: DNA
<213> ORGANISM: Streptococcus mutans

<400> SEQUENCE: 62

atggcagtcg aaattattat gcctaaactt ggtgttgata tgcaggaagg cgaaatcatc      60

gagtggaaaa aacaagaagg tgatgaggtc aaagaagggg agatcctcct tgagattatg     120

tctgacaaga ccaatatgga aatcgaagct gaggattcag gtgtcctgct taagattgtt     180

aaaggaaatg gtcaagttgt tcctgtaact gaggtcattg gttatattgg tcaagcaggt     240

gaagttcttg aaatagctga tgttcctgca agtacagttc ctaaagaaaa tagtgcagca     300

cctgctgaaa aaacaaaagc aatgtcttct ccgacagttg cagcagcccc tcaaggaaag     360

attcgagcaa caccagcagc tcgtaaggcg gctcgtgatc tgggagttaa cctgaatcag     420

gtttcaggga caggcgctaa aggccgtgtt cacaaggaag atgttgaaag ctttaaagca     480

gctcagccta aagcaacacc attagctagg aaaattgcta tagataaagg tattgatcta     540

gccagtgtct caggaacagg ttttggcggc aaaattatca aggaagatat tttaaatctg     600

tttgaggcag ctcagcctgt taatgatgtg tcagatcctg ctaaagaagc agctgcctta     660

ccagagggtg ttgaagtcat taagatgtct gccatgcgta aggcagtggc taaaagcatg     720

gtcaattctt acctgacagc tccaactttt actctcaatt atgacattga catgactgag     780

atgattgcgt tgcgtaaaaa gttaattgat cctatcatgg aaaaaacagg ttttaaagtt     840

agcttcacag atttgattgg tctggcagtc gtaaaaacct taatgaaacc agaacatcgt     900

tacctcaatg cttcactcat taatgacgcg actgagattg aacttcatca atttgttaac     960

cttggtatcg ccgttggact tgatgaagga ctgttagtac ctgttgttca tggtgcagat    1020

aagatgagct tgtcagattt tgttatagct tcaaaggatg tcattaagaa agctcagacc    1080

ggtaaattaa aagccactga aatgtctggt tcaacctttt ccattacaaa cttggggatg    1140

tttggcacta agactttcaa ccccattatc aatcagccaa attcggctat tttgggtgta    1200

ggagcaacta tccaaacgcc aactgttgtg gatggtgaaa ttaagattcg tccaatcatg    1260

gcactgtgct tgaccatcga tcaccgcttg gttgatggca tgaacggcgc taagttcatg    1320

gttgatctta aaaaactgat ggaaaatcca tttacattat tgatttga                 1368
```

<210> SEQ ID NO 63
<211> LENGTH: 14
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa can be Leu or Arg
<220> FEATURE:
<221> NAME/KEY: MISC_FEATURE
<222> LOCATION: (5)..(5)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be Arg or Leu
<220> FEATURE:
<221> NAME/KEY: MISC_FEATURE
<222> LOCATION: (8)..(10)
<223> OTHER INFORMATION: Xaa can be any amino acid
<220> FEATURE:
<221> NAME/KEY: MISC_FEATURE
<222> LOCATION: (12)..(12)
<223> OTHER INFORMATION: Xaa can be any amino acid
<220> FEATURE:
<221> NAME/KEY: MISC_FEATURE
<222> LOCATION: (13)..(13)
<223> OTHER INFORMATION: Xaa can be Asp or Glu

<400> SEQUENCE: 63

```
Pro Xaa Val Xaa Xaa Xaa Ala Xaa Xaa Xaa Gly Xaa Xaa Leu
1               5                   10
```

<210> SEQ ID NO 64
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Gly or Pro
<220> FEATURE:
<221> NAME/KEY: MISC_FEATURE
<222> LOCATION: (2)..(2)
<223> OTHER INFORMATION: Xaa can be Ser or Thr
<220> FEATURE:
<221> NAME/KEY: MISC_FEATURE
<222> LOCATION: (4)..(4)
<223> OTHER INFORMATION: Xaa can be Ala or Pro
<220> FEATURE:
<221> NAME/KEY: MISC_FEATURE
<222> LOCATION: (5)..(5)
<223> OTHER INFORMATION: Xaa can be any amino acid
<220> FEATURE:
<221> NAME/KEY: MISC_FEATURE
<222> LOCATION: (7)..(7)
<223> OTHER INFORMATION: Xaa can be any amino acid

<400> SEQUENCE: 64

```
Xaa Xaa Gly Xaa Xaa Gly Xaa Ile
1               5
```

<210> SEQ ID NO 65
<211> LENGTH: 16
<212> TYPE: PRT

<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Val or Ile
<220> FEATURE:
<221> NAME/KEY: MISC_FEATURE
<222> LOCATION: (3)..(3)
<223> OTHER INFORMATION: Xaa can be Leu or Val
<220> FEATURE:
<221> NAME/KEY: MISC_FEATURE
<222> LOCATION: (4)..(4)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be Leu or Val
<220> FEATURE:
<221> NAME/KEY: MISC_FEATURE
<222> LOCATION: (8)..(8)
<223> OTHER INFORMATION: Xaa can be any amino acid
<220> FEATURE:
<221> NAME/KEY: MISC_FEATURE
<222> LOCATION: (9)..(9)
<223> OTHER INFORMATION: Xaa can be Ala or Lys
<220> FEATURE:
<221> NAME/KEY: MISC_FEATURE
<222> LOCATION: (11)..(12)
<223> OTHER INFORMATION: Xaa can be any amino acid
<220> FEATURE:
<221> NAME/KEY: MISC_FEATURE
<222> LOCATION: (13)..(13)
<223> OTHER INFORMATION: Xaa can be Leu or Met
<220> FEATURE:
<221> NAME/KEY: MISC_FEATURE
<222> LOCATION: (14)..(15)
<223> OTHER INFORMATION: Xaa can be any amino acid
<220> FEATURE:
<221> NAME/KEY: MISC_FEATURE
<222> LOCATION: (16)..(16)
<223> OTHER INFORMATION: Xaa can be Ala or Ser

<400> SEQUENCE: 65

```
Xaa Pro Xaa Xaa Gly Xaa Arg Xaa Xaa Ala Xaa Xaa Xaa Xaa Xaa Xaa
1               5                   10                  15
```

<210> SEQ ID NO 66
<211> LENGTH: 13
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa can by Gly or Ser
<220> FEATURE:
<221> NAME/KEY: MISC_FEATURE
<222> LOCATION: (4)..(4)
<223> OTHER INFORMATION: Xaa can be any amino acid
<220> FEATURE:
<221> NAME/KEY: MISC_FEATURE
<222> LOCATION: (6)..(7)
<223> OTHER INFORMATION: Xaa can be any amino acid
<220> FEATURE:
<221> NAME/KEY: MISC_FEATURE
<222> LOCATION: (8)..(8)
<223> OTHER INFORMATION: Xaa can be Asn or Ser
<220> FEATURE:
<221> NAME/KEY: MISC_FEATURE
<222> LOCATION: (9)..(9)
<223> OTHER INFORMATION: Xaa can be any amino acid
<220> FEATURE:
<221> NAME/KEY: MISC_FEATURE
<222> LOCATION: (11)..(11)

<223> OTHER INFORMATION: Xaa can be any amino acid
<220> FEATURE:
<221> NAME/KEY: MISC_FEATURE
<222> LOCATION: (12)..(12)
<223> OTHER INFORMATION: Xaa can be Phe or Leu

<400> SEQUENCE: 66

Gly Xaa Thr Xaa Thr Xaa Xaa Xaa Xaa Gly Xaa Xaa Gly
1 5 10

<210> SEQ ID NO 67
<211> LENGTH: 19
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be any amino acid
<220> FEATURE:
<221> NAME/KEY: MISC_FEATURE
<222> LOCATION: (7)..(7)
<223> OTHER INFORMATION: Xaa can be Ile or Met
<220> FEATURE:
<221> NAME/KEY: MISC_FEATURE
<222> LOCATION: (8)..(8)
<223> OTHER INFORMATION: Xaa can be Leu or Val
<220> FEATURE:
<221> NAME/KEY: MISC_FEATURE
<222> LOCATION: (9)..(9)
<223> OTHER INFORMATION: Xaa can be any amino acid
<220> FEATURE:
<221> NAME/KEY: MISC_FEATURE
<222> LOCATION: (11)..(12)
<223> OTHER INFORMATION: Xaa can be any amino acid
<220> FEATURE:
<221> NAME/KEY: MISC_FEATURE
<222> LOCATION: (13)..(13)
<223> OTHER INFORMATION: Xaa can be Ile or Met
<220> FEATURE:
<221> NAME/KEY: MISC_FEATURE
<222> LOCATION: (14)..(16)
<223> OTHER INFORMATION: Xaa can be any amino acid
<220> FEATURE:
<221> NAME/KEY: MISC_FEATURE
<222> LOCATION: (18)..(18)
<223> OTHER INFORMATION: Xaa can be any amino acid

<400> SEQUENCE: 67

Asn Xaa Pro Glu Xaa Ala Xaa Xaa Xaa Val Xaa Xaa Xaa Xaa Xaa Xaa
1 5 10 15

Pro Xaa Val

<210> SEQ ID NO 68
<211> LENGTH: 12
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (3)..(3)
<223> OTHER INFORMATION: Xaa can be Leu or Ser
<220> FEATURE:
<221> NAME/KEY: MISC_FEATURE
<222> LOCATION: (4)..(4)
<223> OTHER INFORMATION: Xaa can be Ser or Thr
<220> FEATURE:
<221> NAME/KEY: MISC_FEATURE
<222> LOCATION: (6)..(6)
<223> OTHER INFORMATION: Xaa can be Asp or Leu
<220> FEATURE:
<221> NAME/KEY: MISC_FEATURE
<222> LOCATION: (9)..(9)
<223> OTHER INFORMATION: Xaa can be Val or Leu
<220> FEATURE:
<221> NAME/KEY: MISC_FEATURE
<222> LOCATION: (10)..(10)
<223> OTHER INFORMATION: Xaa can be any amino acid

<400> SEQUENCE: 68

```
Leu Xaa Xaa Xaa Phe Xaa His Arg Xaa Xaa Asp Gly
1               5                   10
```

<210> SEQ ID NO 69
<211> LENGTH: 457
<212> TYPE: PRT
<213> ORGANISM: Bacillus subtillis

<400> SEQUENCE: 69

```
Met Ala Thr Glu Tyr Asp Val Val Ile Leu Gly Gly Gly Thr Gly Gly
1               5                   10                  15

Tyr Val Ala Ala Ile Arg Ala Ala Gln Leu Gly Leu Lys Thr Ala Val
            20                  25                  30

Val Glu Lys Glu Lys Leu Gly Gly Thr Cys Leu His Lys Gly Cys Ile
        35                  40                  45

Pro Ser Lys Ala Leu Leu Arg Ser Ala Glu Val Tyr Arg Thr Ala Arg
    50                  55                  60

Glu Ala Asp Gln Phe Gly Val Glu Thr Ala Gly Val Ser Leu Asn Phe
65                  70                  75                  80

Glu Lys Val Gln Gln Arg Lys Gln Ala Val Val Asp Lys Leu Ala Ala
                85                  90                  95

Gly Val Asn His Leu Met Lys Lys Gly Lys Ile Asp Val Tyr Thr Gly
            100                 105                 110

Tyr Gly Arg Ile Leu Gly Pro Ser Ile Phe Ser Pro Leu Pro Gly Thr
        115                 120                 125

Ile Ser Val Glu Arg Gly Asn Gly Glu Glu Asn Asp Met Leu Ile Pro
    130                 135                 140

Lys Gln Val Ile Ile Ala Thr Gly Ser Arg Pro Arg Met Leu Pro Gly
145                 150                 155                 160

Leu Glu Val Asp Gly Lys Ser Val Leu Thr Ser Asp Glu Ala Leu Gln
                165                 170                 175

Met Glu Glu Leu Pro Gln Ser Ile Ile Ile Val Gly Gly Gly Val Ile
            180                 185                 190

Gly Ile Glu Trp Ala Ser Met Leu His Asp Phe Gly Val Lys Val Thr
        195                 200                 205

Val Ile Glu Tyr Ala Asp Arg Ile Leu Pro Thr Glu Asp Leu Glu Ile
    210                 215                 220

Ser Lys Glu Met Glu Ser Leu Leu Lys Lys Lys Gly Ile Gln Phe Ile
225                 230                 235                 240

Thr Gly Ala Lys Val Leu Pro Asp Thr Met Thr Lys Thr Ser Asp Asp
                245                 250                 255

Ile Ser Ile Gln Ala Glu Lys Asp Gly Glu Thr Val Thr Tyr Ser Ala
            260                 265                 270
```

-continued

```
Glu Lys Met Leu Val Ser Ile Gly Arg Gln Ala Asn Ile Glu Gly Ile
        275                 280                 285

Gly Leu Glu Asn Thr Asp Ile Val Thr Glu Asn Gly Met Ile Ser Val
    290                 295                 300

Asn Glu Ser Cys Gln Thr Lys Glu Ser His Ile Tyr Ala Ile Gly Asp
305                 310                 315                 320

Val Ile Gly Gly Leu Gln Leu Ala His Val Ala Ser His Glu Gly Ile
                325                 330                 335

Ile Ala Val Glu His Phe Ala Gly Leu Asn Pro His Pro Leu Asp Pro
            340                 345                 350

Thr Leu Val Pro Lys Cys Ile Tyr Ser Ser Pro Glu Ala Ala Ser Val
        355                 360                 365

Gly Leu Thr Glu Asp Glu Ala Lys Ala Asn Gly His Asn Val Lys Ile
    370                 375                 380

Gly Lys Phe Pro Phe Met Ala Ile Gly Lys Ala Leu Val Tyr Gly Glu
385                 390                 395                 400

Ser Asp Gly Phe Val Lys Ile Val Ala Asp Arg Asp Thr Asp Asp Ile
                405                 410                 415

Leu Gly Val His Met Ile Gly Pro His Val Thr Asp Met Ile Ser Glu
            420                 425                 430

Ala Gly Leu Ala Lys Val Leu Asp Ala Thr Pro Trp Glu Val Gly Gln
        435                 440                 445

Thr Ile Ser Pro Ala Ser Asn Ala Phe
    450                 455
```

<210> SEQ ID NO 70
<211> LENGTH: 1374
<212> TYPE: DNA
<213> ORGANISM: Bacillus subtillis

<400> SEQUENCE: 70

```
tcagaaagcg ttggatgcgg gtgaaatcgt ttgcccgacc tcccacggtg ttgcgtccag     60

cactttggca agacccgctt cagaaatcat gtcggtgaca tgcgggccaa tcatatgaac    120

gccgagaata tcatctgtat ctcggtcagc cacgattttg acaaaaccgt cgctttcacc    180

gtatacaagc gcttttccaa tcgccataaa tgggaacttg ccgattttga cattatgccc    240

gttcgccttt gcttcgtctt cggttaagcc gacactggca gcttcagggc ttgagtaaat    300

gcacttcggc acaagcgtcg gatcaagcgg atgcggattg agacctgcaa aatgctcaac    360

agcaataatt ccctcatgtg aagcaacgtg agctaactgc aggccaccga ttacgtctcc    420

gattgcataa atatgagatt ccttcgtttg gcagctttca ttgactgaaa tcatgccatt    480

ttcagtaaca atatcggtgt tctctaggcc gatgccttcg atatttgcct gtctgccgat    540

ggaaacaagc attttctcag cagaataggt aacggtttct ccgtcttttt ccgcttgtat    600

gctgatatcg tctgatgttt ttgtcattgt gtcaggcagc acttttgccc ctgttatgaa    660

ctggatgcct tttttcttaa gaagactttc catttctttt gaaatctcta gatcttcagt    720

cggcaatatg cgatccgcgt attcaataac cgttacctta acgccaaaat catgaagcat    780

agacgcccat tcgataccga taacccctcc gccgacaatg atgattgact gtggcagctc    840

ctccatttgg agcgcctcat ctgaagtcag tacagactta ccgtccactt caagacccgg    900

aagcattctc ggtcttgatc ctgttgcaat gatcacttgt ttcgggatca gcatgtcatt    960

ttcttcgcca tttccccgct caacagaaat tgttcccggc agcggagaga agattgacgg   1020

tccaaggata cgtccatatc cggtgtacac gtcaattttt cctttttca ttaaatgatt   1080
```

```
tacacccgct gcaagcttat caacaacggc ttgcttacgc tgctgcactt tttcaaagtt   1140

gagggacacg ccagccgttt ccactccgaa ttgatcggct tcacgagctg tccggtatac   1200

ctctgcgctt ctaagcagcg ctttactcgg gatacagcct ttatgcagac atgttccccc   1260

gagtttttcc ttttccacaa cggctgtttt taagccgagc tgagcggctc tgatggccgc   1320

aacataaccg ccggtaccgc cgcccagaat gactacgtca tactcagttg ccat         1374


<210> SEQ ID NO 71
<211> LENGTH: 462
<212> TYPE: PRT
<213> ORGANISM: Streptomyces avermitilis

<400> SEQUENCE: 71

Met Ala Asn Asp Ala Ser Thr Val Phe Asp Leu Val Ile Leu Gly Gly
1               5                   10                  15

Gly Ser Gly Gly Tyr Ala Ala Ala Leu Arg Gly Ala Gln Leu Gly Leu
            20                  25                  30

Asp Val Ala Leu Ile Glu Lys Asp Lys Val Gly Gly Thr Cys Leu His
        35                  40                  45

Arg Gly Cys Ile Pro Thr Lys Ala Leu Leu His Ala Gly Glu Ile Ala
    50                  55                  60

Asp Gln Ala Arg Glu Ser Glu Gln Phe Gly Val Lys Ala Thr Phe Glu
65                  70                  75                  80

Gly Ile Asp Val Pro Ala Val His Lys Tyr Lys Asp Gly Val Ile Ser
                85                  90                  95

Gly Leu Tyr Lys Gly Leu Gln Gly Leu Ile Ala Ser Arg Lys Val Thr
            100                 105                 110

Tyr Ile Glu Gly Glu Gly Arg Leu Ser Ser Pro Thr Ser Val Asp Val
        115                 120                 125

Asn Gly Gln Arg Val Gln Gly Arg His Val Leu Leu Ala Thr Gly Ser
    130                 135                 140

Val Pro Lys Ser Leu Pro Gly Leu Ala Ile Asp Gly Asn Arg Ile Ile
145                 150                 155                 160

Ser Ser Asp His Ala Leu Val Leu Asp Arg Val Pro Glu Ser Ala Ile
                165                 170                 175

Val Leu Gly Gly Gly Val Ile Gly Val Glu Phe Ala Ser Ala Trp Lys
            180                 185                 190

Ser Phe Gly Ala Asp Val Thr Val Ile Glu Gly Leu Lys His Leu Val
        195                 200                 205

Pro Val Glu Asp Glu Asn Ser Ser Lys Leu Leu Glu Arg Ala Phe Arg
    210                 215                 220

Lys Arg Gly Ile Lys Phe Asn Leu Gly Thr Phe Phe Ser Lys Ala Glu
225                 230                 235                 240

Tyr Thr Gln Asn Gly Val Lys Val Thr Leu Ala Asp Gly Lys Glu Phe
                245                 250                 255

Glu Ala Glu Val Leu Leu Val Ala Val Gly Arg Gly Pro Val Ser Gln
            260                 265                 270

Gly Leu Gly Tyr Glu Glu Gln Gly Val Ala Met Asp Arg Gly Tyr Val
        275                 280                 285

Leu Val Asp Glu Tyr Met Arg Thr Asn Val Pro Thr Ile Ser Ala Val
    290                 295                 300

Gly Asp Leu Val Pro Thr Leu Gln Leu Ala His Val Gly Phe Ala Glu
305                 310                 315                 320
```

```
Gly Ile Leu Val Ala Glu Arg Leu Ala Gly Leu Lys Thr Val Pro Ile
                325                 330                 335

Asp Tyr Asp Gly Val Pro Arg Val Thr Tyr Cys His Pro Glu Val Ala
            340                 345                 350

Ser Val Gly Ile Thr Glu Ala Lys Ala Lys Glu Ile Tyr Gly Ala Asp
        355                 360                 365

Lys Val Val Ala Leu Lys Tyr Asn Leu Ala Gly Asn Gly Lys Ser Lys
    370                 375                 380

Ile Leu Asn Thr Ala Gly Glu Ile Lys Leu Val Gln Val Lys Asp Gly
385                 390                 395                 400

Ala Val Val Gly Val His Met Val Gly Asp Arg Met Gly Glu Gln Val
                405                 410                 415

Gly Glu Ala Gln Leu Ile Tyr Asn Trp Glu Ala Leu Pro Ala Glu Val
            420                 425                 430

Ala Gln Leu Ile His Ala His Pro Thr Gln Asn Glu Ala Met Gly Glu
        435                 440                 445

Ala His Leu Ala Leu Ala Gly Lys Pro Leu His Ser His Asp
    450                 455                 460
```

<210> SEQ ID NO 72
<211> LENGTH: 1389
<212> TYPE: DNA
<213> ORGANISM: Streptomyces avermitilis

<400> SEQUENCE: 72

```
tcagtcgtgc gagtgcagcg gcttgcccgc gagggccagg tgggcctcgc ccatcgcttc      60
gttctgcgtc gggtgggcgt ggatgagctg ggcgacctcg gccggcagcg cctcccagtt     120
gtagatcagc tgggcttcgc cgacctgctc gcccatacgg tcaccgacca tgtggacgcc     180
gaccacggca ccgtccttca cctggacgag cttgatctcg cccgcggtgt tgaggatctt     240
gctcttgccg ttgcccgcca ggttgtactt cagagcgacg accttgtccg cgccgtagat     300
ctccttggcc ttggcctcgg tgatgcccac ggaggcgacc tcggggtggc agtacgtcac     360
ccgcggcacg ccgtcgtagt cgatcgggac ggtcttcaga ccggccagac gctccgccac     420
caggatgccc tcggcgaagc cgacgtgcgc gagctggagc gtcgggacca ggtcaccgac     480
ggcggagatg gtcgggacgt tcgtccgcat gtactcgtcg accaggacgt agccgcggtc     540
catggcgacg ccctgctcct cgtagccgag gccctgcgag accgggccgc ggccgacggc     600
gacgagcagg acctcggcct cgaactcctt gccgtcggcg agggtgacct tgacaccgtt     660
ctgggtgtac tcggccttcg agaagaaggt gcccaggttg aacttgatgc cgcgcttgcg     720
gaacgcgcgc tcaagaagct tggaggagtt ctcgtcctcg accgggacga ggtgcttgag     780
gccctcgatc accgtcacgt cggctccgaa ggacttccac gcggaggcga actcgacgcc     840
gatgacgccg ccgccgagca cgatcgcgga ctccgggacg cggtccagga ccagcgcgtg     900
gtcggaggag atgatgcggt tgccgtcgat cgccaggccc ggcagcgact tcggcacgga     960
gccggtcgcc aggagcacgt ggcggccctg gacgcgctgg ccgttcacgt cgacggaggt    1020
cggggaggac agacggccct caccctcgat gtacgtcacc ttgcgggagg cgatcagccc    1080
ctgcagaccc ttgtacaggc ccgagatgac cccgtccttg tacttgtgga cggccggtac    1140
gtcgatgccc tcgaaggtgg ccttgacgcc gaactgctcg ctctcgcggg cctggtcggc    1200
gatctcgccc gcgtgcagca gcgccttggt ggggatgcac ccacggtgca ggcaggtacc    1260
gccgaccttg tccttctcga tcagggcgac gtccaggccc agctgcgctc cgcgcagggc    1320
```

```
cgcggcgtaa ccaccgctac caccgccgag gatcactagg tcgaaaacgg tgctggcgtc   1380

gttcgccac                                                           1389


<210> SEQ ID NO 73
<211> LENGTH: 459
<212> TYPE: PRT
<213> ORGANISM: Pseudomonas putida

<400> SEQUENCE: 73

Met Gln Gln Ile Ile Gln Thr Thr Leu Leu Ile Ile Gly Gly Gly Pro
1               5                   10                  15

Gly Gly Tyr Val Ala Ala Ile Arg Ala Gly Gln Leu Gly Ile Pro Thr
            20                  25                  30

Val Leu Val Glu Gly Gln Ala Leu Gly Gly Thr Cys Leu Asn Ile Gly
        35                  40                  45

Cys Ile Pro Ser Lys Ala Leu Ile His Val Ala Glu Gln Phe His Gln
    50                  55                  60

Ala Ser Arg Phe Thr Glu Pro Ser Pro Leu Gly Ile Ser Val Ala Ser
65                  70                  75                  80

Pro Arg Leu Asp Ile Gly Gln Ser Val Thr Trp Lys Asp Gly Ile Val
                85                  90                  95

Asp Arg Leu Thr Thr Gly Val Ala Ala Leu Leu Lys Lys His Gly Val
            100                 105                 110

Lys Val Val His Gly Trp Ala Lys Val Leu Asp Gly Lys Gln Val Glu
        115                 120                 125

Val Asp Gly Gln Arg Ile Gln Cys Glu His Leu Leu Leu Ala Thr Gly
    130                 135                 140

Ser Thr Ser Val Glu Leu Pro Met Leu Pro Leu Gly Gly Pro Val Ile
145                 150                 155                 160

Ser Ser Thr Glu Ala Leu Ala Pro Lys Ala Leu Pro Gln His Leu Val
                165                 170                 175

Val Val Gly Gly Gly Tyr Ile Gly Leu Glu Leu Gly Ile Ala Tyr Arg
            180                 185                 190

Lys Leu Gly Ala Gln Val Ser Val Val Glu Ala Arg Glu Arg Ile Leu
        195                 200                 205

Pro Thr Tyr Asp Ser Glu Leu Thr Ala Pro Val Ala Glu Ser Leu Lys
    210                 215                 220

Lys Leu Gly Ile Ala Leu His Leu Gly His Ser Val Glu Gly Tyr Glu
225                 230                 235                 240

Asn Gly Cys Leu Leu Ala Ser Asp Gly Lys Gly Gly Gln Leu Arg Leu
                245                 250                 255

Glu Ala Asp Gln Val Leu Val Ala Val Gly Arg Arg Pro Arg Thr Lys
            260                 265                 270

Gly Phe Asn Leu Glu Cys Leu Asp Leu Lys Met Asn Gly Thr Ala Ile
        275                 280                 285

Ala Ile Asp Glu Arg Cys His Thr Ser Met His Asn Val Trp Ala Ile
    290                 295                 300

Gly Asp Val Ala Gly Glu Pro Met Leu Ala His Arg Ala Met Ala Gln
305                 310                 315                 320

Gly Glu Met Val Ala Glu Ile Ile Ala Gly Lys Ala Arg Arg Phe Glu
                325                 330                 335

Pro Ala Ala Ile Ala Ala Val Cys Phe Thr Asp Pro Glu Val Val Val
            340                 345                 350

Val Gly Lys Thr Pro Glu Gln Ala Ser Gln Gln Ala Leu Asp Cys Ile
```

```
        355                 360                 365

Val Ala Gln Phe Pro Phe Ala Ala Asn Gly Arg Ala Met Ser Leu Glu
    370                 375                 380

Ser Lys Ser Gly Phe Val Arg Val Val Ala Arg Arg Asp Asn His Leu
385                 390                 395                 400

Ile Val Gly Trp Gln Ala Val Gly Val Ala Val Ser Glu Leu Ser Thr
                405                 410                 415

Ala Phe Ala Gln Ser Leu Glu Met Gly Ala Cys Leu Glu Asp Val Ala
            420                 425                 430

Gly Thr Ile His Ala His Pro Thr Leu Gly Glu Ala Val Gln Glu Ala
        435                 440                 445

Ala Leu Arg Ala Leu Gly His Ala Leu His Ile
    450                 455
```

<210> SEQ ID NO 74
<211> LENGTH: 1380
<212> TYPE: DNA
<213> ORGANISM: Pseudomonas putida

<400> SEQUENCE: 74

```
tcagatatgc aaggcgtggc ccaacgcgcg tagggcggct tcttgcaccg cttcacccaa     60

cgtggggtgg gcatgaatgg tgccggccac atcttccagg cacgcgccca tctccagcga    120

ttgggcaaac gcggtggaca gctcggagac cgccacgcca accgcctgcc aacccacgat    180

caggtggttg tcacggcgcg ccaccacccg cacgaaaccg cttttcgact ccaggctcat    240

ggcccggcca ttggcggcaa acgggaactg cgcgacgatg cagtccaggg cctgctggct    300

ggcttgttcc ggggtcttgc cgaccaccac cacttccggg tcggtaaagc acacggcggc    360

aatcgctgcc ggctcgaagc gtcgggcctt gccggcgatg atttcggcga ccatctcgcc    420

ttgggccatg gcccggtgcg ccagcatcgg ttcgccagcg acgtcgccaa tggcccagac    480

gttgtgcatg ctggtatgac agcgctcgtc gatggcaatg gcggtgccgt tcatcttcag    540

gtccaggcat tccaggttga agcccttggt gcgtggccgg cggcccacgg ccaccagtac    600

ctgatcggct tcaagacgca gttgcccacc cttgccgtcg ctggccagca ggcagccatt    660

ttcgtagccc tcgacgctgt ggcccaggtg caacgcgatg cccagtttct tcagcgactc    720

ggccaccggg gcggtcaatt cgctgtcgta ggtcggcagg atgcgttcgc gcgcttccac    780

cacactcacc tgtgcaccca gcttgcgata ggcaatgccc agctccaggc cgatatagcc    840

accgccgacc accaccaggt gttgcggcag ggctttcggc gccagggctt cggtcgagga    900

aatcaccggg ccacccagcg gcagcatcgg cagttcgaca ctggtggaac cggtcgccag    960

caacagatgc tcgcactgga tacgctggcc atcgacctcg acctgcttgc cgtccagtac   1020

cttggcccag ccatgcacca ctttcacccc gtgctttttc agcaaggcgg caacaccggt   1080

ggtcagacgg tcgacaatgc cgtccttcca ggtgacgctc tggccgatgt ccaggcgcgg   1140

cgaagccacg ctgatgccca gcggcgaggg ttcggtaaag cgcgaggctt ggtgaaactg   1200

ctcggccacg tggatcagcg ccttggacgg gatgcagccg atgttcaggc aggtgccgcc   1260

cagtgcctgg ccttccacca gtacggtagg aatgcccagt tgcccggcgc ggatggctgc   1320

tacatagccg ccagggccgc cgccgatgat caacagggta gtctggataa tctgttgcat   1380
```

<210> SEQ ID NO 75
<211> LENGTH: 475
<212> TYPE: PRT
<213> ORGANISM: Listeria monocytogenes

<400> SEQUENCE: 75

Met Ala Lys Glu Tyr Asp Val Val Ile Leu Gly Gly Gly Thr Gly Gly
1 5 10 15

Tyr Val Ala Ala Ile Gln Ala Ala Lys Asn Gly Gln Lys Val Ala Val
20 25 30

Val Glu Lys Gly Lys Val Gly Gly Thr Cys Leu His Arg Gly Cys Ile
35 40 45

Pro Thr Lys Ala Leu Leu Arg Ser Ala Glu Val Leu Gln Thr Val Lys
50 55 60

Lys Ala Ser Glu Phe Gly Ile Ser Val Glu Gly Thr Ala Gly Ile Asn
65 70 75 80

Phe Leu Gln Ala Gln Glu Arg Lys Gln Ala Ile Val Asp Gln Leu Glu
85 90 95

Lys Gly Ile His Gln Leu Phe Lys Gln Gly Lys Ile Asp Leu Phe Val
100 105 110

Gly Thr Gly Thr Ile Leu Gly Pro Ser Ile Phe Ser Pro Thr Ala Gly
115 120 125

Thr Ile Ser Val Glu Phe Glu Asp Gly Ser Glu Asn Glu Met Leu Ile
130 135 140

Pro Lys Asn Leu Ile Ile Ala Thr Gly Ser Lys Pro Arg Thr Leu Ser
145 150 155 160

Gly Leu Thr Ile Asp Glu Glu His Val Leu Ser Ser Asp Gly Ala Leu
165 170 175

Asn Leu Glu Thr Leu Pro Lys Ser Ile Ile Ile Val Gly Gly Gly Val
180 185 190

Ile Gly Met Glu Trp Ala Ser Met Met His Asp Phe Gly Val Glu Val
195 200 205

Thr Val Leu Glu Tyr Ala Asp Arg Ile Leu Pro Thr Glu Asp Lys Glu
210 215 220

Val Ala Lys Glu Leu Ala Arg Leu Tyr Lys Lys Lys Lys Leu Asn Met
225 230 235 240

His Thr Ser Ala Glu Val Gln Ala Ala Ser Tyr Lys Lys Thr Asp Thr
245 250 255

Gly Val Glu Ile Lys Ala Ile Ile Lys Gly Glu Glu Gln Thr Phe Thr
260 265 270

Ala Asp Lys Ile Leu Val Ser Val Gly Arg Ser Ala Thr Thr Glu Asn
275 280 285

Ile Gly Leu Gln Asn Thr Asp Ile Ala Thr Glu Asn Gly Phe Ile Gln
290 295 300

Val Asn Asp Phe Tyr Gln Thr Lys Glu Ser His Ile Tyr Ala Ile Gly
305 310 315 320

Asp Cys Ile Pro Thr Ile Gln Leu Ala His Val Ala Met Glu Glu Gly
325 330 335

Thr Ile Ala Ala Asn His Ile Ala Gly Lys Ala Ala Glu Lys Leu Asp
340 345 350

Tyr Asp Leu Val Pro Arg Cys Ile Tyr Thr Ser Thr Glu Ile Ala Ser
355 360 365

Val Gly Ile Thr Glu Glu Gln Ala Lys Glu Arg Gly His Glu Val Lys
370 375 380

Lys Gly Lys Phe Phe Phe Arg Gly Ile Gly Lys Ala Leu Val Tyr Gly
385 390 395 400

Glu Ser Asp Gly Phe Ile Lys Ile Ile Ala Asp Lys Lys Thr Asp Asp

```
                405                 410                 415

Ile Leu Gly Val Ser Met Ile Gly Pro His Val Thr Asp Met Ile Ser
            420                 425                 430

Glu Ala Ala Leu Ala Gln Val Leu Asn Ala Thr Pro Trp Glu Val Gly
        435                 440                 445

Asn Thr Ile His Pro His Pro Thr Leu Ser Glu Ser Phe Arg Glu Ala
    450                 455                 460

Ala Leu Ala Val Asp Gly Asn Ala Ile His Gly
465                 470                 475
```

<210> SEQ ID NO 76
<211> LENGTH: 1428
<212> TYPE: DNA
<213> ORGANISM: Listeria monocytogenes

<400> SEQUENCE: 76

```
gtggcaaaag aatatgatgt agttattctt ggcggaggaa ctggcggtta cgttgcagca     60

attcaagcag ctaagaatgg ccagaaagta gccgtcgttg aaaaagggaa agttggagga    120

acgtgtcttc accgtgggtg tattccaacg aaagcgttat tacgttcagc ggaagttcta    180

caaacggtaa aaaaagcaag tgaatttggt atttctgtag aaggaactgc cggaatcaat    240

tttttacaag cacaagaacg aaaacaagca atagtagatc aattagaaaa aggtattcac    300

caattattta aacaagggaa aattgacttg tttgttggaa cgggaactat tttgggacca    360

tcaatttttt caccaacagc tggaacaatt tcagttgaat tcgaagatgg ttctgaaaat    420

gaaatgctaa ttcctaaaaa cttaattatc gcaactgggt ccaaaccgcg cacattaagc    480

ggtttaacaa tcgatgagga acatgtttta tcatctgacg gcgcgcttaa cctagaaact    540

ttaccaaaat caattattat tgttggcggt ggggttatcg gaatggaatg ggcttcgatg    600

atgcatgatt tcggtgtaga agttacggtg ctagaatatg cagaccgaat tttgccaaca    660

gaagataaag aagtggccaa agaattagca agactttata aaaagaaaaa attaaacatg    720

catacatctg ctgaagttca agcagctagt tataaaaaaa cagatactgg tgtggaaatt    780

aaagcaatca ttaaaggcga agagcagact ttcacagcag ataaaattct tgtttcagtt    840

ggtcgttctg ctactacaga aaacatcggc ttacaaaata cagatatcgc gaccgaaaac    900

ggctttatcc aagtaaatga tttttaccaa acaaaagaaa gtcacatcta tgcgattgga    960

gactgcattc caacgattca actcgcgcac gttgcaatgg aagaaggaac aattgcagcc   1020

aaccatattg ccggaaaagc agccgaaaaa cttgactacg acttagttcc ccgctgtatt   1080

tatacttcta cagaaatcgc aagtgtcggt atcacagaag aacaagcaaa agaacggggt   1140

catgaagtga aaaaaggcaa attcttcttc cgtggtatcg ggaaagcgct cgtttacgga   1200

gaatcagatg gcttcattaa aattattgca gataaaaaaa cagacgatat cttaggcgtg   1260

agcatgattg gaccacacgt tacggacatg attagcgaag ccgctttagc acaagtttta   1320

aatgcaacgc cgtgggaagt gggcaacacg attcacccgc acccaacttt atcagaaagt   1380

tttagagaag ctgcccttgc tgtggatggc aatgcaattc acggttaa                1428
```

<210> SEQ ID NO 77
<211> LENGTH: 478
<212> TYPE: PRT
<213> ORGANISM: Streptomyces avermitilis

<400> SEQUENCE: 77

```
Met Glu Asn Met Asn Thr Pro Asp Val Ile Val Ile Gly Gly Gly Thr
```

-continued

```
1               5                   10                  15

Gly Gly Tyr Ser Ala Ala Leu Arg Ala Ala Ala Leu Gly Leu Thr Val
            20                  25                  30

Val Leu Ala Glu Arg Asp Lys Val Gly Gly Thr Cys Leu His Arg Gly
        35                  40                  45

Cys Ile Pro Ser Lys Ala Met Leu His Ala Ala Glu Leu Val Asp Gly
    50                  55                  60

Ile Ala Glu Ala Arg Glu Arg Trp Gly Val Lys Ala Thr Leu Asp Asp
65                  70                  75                  80

Ile Asp Trp Pro Ala Leu Val Ala Thr Arg Asp Asp Ile Val Thr Arg
                85                  90                  95

Asn His Arg Gly Val Glu Ala His Leu Ala His Ala Arg Val Arg Val
            100                 105                 110

Val Arg Gly Ser Ala Arg Leu Thr Gly Pro Arg Ser Val Arg Val Glu
        115                 120                 125

Gly Ala Pro Asp Asp Leu Pro Gly Gly Ala Gly Asp Phe Thr Ala Arg
    130                 135                 140

Arg Gly Ile Val Leu Ala Thr Gly Ser Arg Pro Arg Thr Leu Pro Gly
145                 150                 155                 160

Leu Val Pro Asp Gly Arg Arg Val Val Thr Ser Asp Asp Ala Leu Phe
                165                 170                 175

Ala Pro Gly Leu Pro Arg Ser Val Leu Val Leu Gly Gly Gly Ala Ile
            180                 185                 190

Gly Val Glu Tyr Ala Ser Phe His Arg Ser Met Gly Ala Glu Val Thr
        195                 200                 205

Leu Val Glu Ala Ala Asp Arg Ile Val Pro Leu Glu Asp Val Asp Val
    210                 215                 220

Ser Arg His Leu Thr Arg Gly Leu Lys Lys Arg Gly Ile Asp Val Arg
225                 230                 235                 240

Ala Gly Ala Arg Leu Leu Asp Ala Glu Leu Leu Glu Ala Gly Val Arg
                245                 250                 255

Ala Arg Val Arg Thr Val Arg Gly Glu Ile Arg Thr Leu Glu Ala Glu
            260                 265                 270

Arg Leu Leu Val Ala Val Gly Arg Ala Pro Val Thr Asp Gly Leu Asp
        275                 280                 285

Leu Ala Ala Ala Gly Leu Ala Thr Asp Glu Arg Gly Phe Val Thr Pro
    290                 295                 300

Ser Asp Trp Asp Arg Leu Glu Thr Ala Val Pro Gly Ile His Val Val
305                 310                 315                 320

Gly Asp Leu Leu Pro Pro Pro Ser Leu Gly Leu Ala His Ala Ser Phe
                325                 330                 335

Ala Glu Gly Leu Ser Val Ala Glu Thr Leu Ala Gly Leu Pro Ser Ala
            340                 345                 350

Pro Val Asp Tyr Ala Ala Val Pro Arg Val Thr Tyr Ser Ser Pro Gln
        355                 360                 365

Thr Ala Ser Val Gly Leu Gly Glu Ala Glu Ala Arg Ala Arg Gly His
    370                 375                 380

Glu Val Asp Val Asn Thr Met Pro Leu Thr Ala Val Ala Lys Gly Met
385                 390                 395                 400

Val His Gly Arg Gly Gly Met Val Lys Val Val Ala Glu Glu Gly Gly
                405                 410                 415

Gly Gln Val Leu Gly Val His Leu Val Gly Pro His Val Ser Glu Met
            420                 425                 430
```

Ile Ala Glu Ser Gln Leu Ile Val Gly Trp Asp Ala Gln Pro Ser Asp
435 440 445

Val Ala Arg His Ile His Ala His Pro Thr Leu Ser Glu Ala Val Gly
450 455 460

Glu Thr Phe Leu Thr Leu Ala Gly Arg Gly Leu His Gln Gln
465 470 475

<210> SEQ ID NO 78
<211> LENGTH: 1437
<212> TYPE: DNA
<213> ORGANISM: Streptomyces avermitilis

<400> SEQUENCE: 78
gtggagaaca tgaacacacc ggacgtcatc gtcatcggag gcggcaccgg cggctacagc 60
gccgccctgc gcgccgccgc cctcggtctg accgtggtgc tcgccgagcg ggacaaggtc 120
ggcggaacct gtctgcaccg tggctgcatt ccgagcaagg cgatgctgca cgccgcagaa 180
ctggtcgacg gcatcgccga ggcgcgcgag cgctgggggg tgaaggccac gctggacgac 240
atcgactggc ctgcgctcgt cgccacgcgc gacgacatag tgacgcgcaa ccaccgcggc 300
gtggaggcgc acctcgccca cgcgcgcgtg cgcgtcgtcc ggggcagtgc ccggctgacc 360
ggtccgcgca gcgtccgcgt cgagggtgct ccggacgacc tgccgggcgg cgcgggcgac 420
ttcaccgcgc gccggggcat cgtcctggcg accggctcac ggccgcgtac gctcccgggg 480
ctcgtgccgg acgggcggcg cgtggtgacg agcgacgacg cgctgttcgc gcccggcctc 540
ccccgctccg tgctggtcct gggcggcggt gcgatcgggg tcgagtacgc ctcgttccac 600
cgctccatgg gtgcggaggt cactctcgtc gaggccgccg accggatcgt gccgctcgaa 660
gacgtcgacg tcagccgtca tctgacgcgc ggtctgaaga agcgcggcat cgatgtgcgg 720
gcgggggcgc ggctgctcga cgccgaactc ctggaggcgg gggtacgcgc gcgcgtacgc 780
accgtgcggg gcgagatccg cacactggag gccgagcggc tcctggtggc ggtcgggcgg 840
gcgccggtca ccgacgggct ggacctggcc gccgcgggcc tggcgacgga cgagcggggt 900
tttgtgacgc cgtccgactg ggaccgtctg gagaccgcgg tgcccggcat ccacgtggtg 960
ggcgacctgc tgccaccgcc gtccctggga ctggcccacg cgtcgttcgc cgagggcctg 1020
tcggtggccg agacgctggc cgggctgccg tccgcgcccg tggactacgc ggccgtgccc 1080
cgggtcacgt actcgtcgcc gcagaccgcc tccgtggggc tgggcgaggc ggaggcacgc 1140
gcgcgtggac acgaggtgga cgtcaacacg atgccgctga ccgccgtcgc caagggcatg 1200
gtccacggcc ggggcgggat ggtgaaggtc gtcgccgagg agggcggcgg gcaggtgctc 1260
ggcgtgcatc tggtgggccc ccacgtgtcc gagatgatcg ccgagagcca gctgatcgtc 1320
ggctgggacg cacagccctc cgacgtggcc cggcacatcc acgcgcaccc cacgctgtcc 1380
gaggcggtcg gcgaaacgtt tctcacgctc gcgggacggg ggctgcatca gcagtga 1437

<210> SEQ ID NO 79
<211> LENGTH: 476
<212> TYPE: PRT
<213> ORGANISM: Micrococcus luteus

<400> SEQUENCE: 79

Met Thr Glu Glu Asn Ser Thr Phe Ile Pro Ser Leu Thr Ile Ile Gly
1 5 10 15

Gly Gly Pro Gly Gly Tyr Glu Ala Ala Met Val Ala Ala Lys Leu Gly
20 25 30

-continued

```
Ala Arg Val Thr Leu Val Glu Arg Gln Gly Val Gly Gly Ala Ala Val
        35                  40                  45

Leu Thr Asp Val Val Pro Ser Lys Thr Leu Ile Ala Ala Ala Asp Ser
    50                  55                  60

Met Arg Arg Val Gly Ala Ser Val Asp Leu Gly Val Asp Leu Gly Gly
65                  70                  75                  80

Ala Glu Val His Ala Asp Met Gly Arg Val Gly His Arg Ile Leu Asn
                85                  90                  95

Leu Ala His Glu Gln Ser Ser Asp Ile Arg Ala Gly Leu Glu Arg Val
            100                 105                 110

Gly Val Arg Val Ile Asp Gly Val Gly Arg Val Val Gly Pro His Glu
        115                 120                 125

Val Ser Val Arg Ala Leu Asp Asp Ala Asp Ala Gly Ala Glu Pro Glu
    130                 135                 140

Ile Ile Thr Ser Asp Ala Ile Leu Val Ala Val Gly Ala Ser Pro Arg
145                 150                 155                 160

Glu Leu Pro Thr Ala Val Pro Asp Gly Glu Arg Ile Phe Asn Trp Lys
                165                 170                 175

Gln Val Tyr Asn Leu Lys Glu Leu Pro Glu His Leu Ile Val Val Gly
            180                 185                 190

Ser Gly Val Thr Gly Ala Glu Phe Ala Ser Ala Tyr Asn Arg Leu Gly
        195                 200                 205

Ala Lys Val Thr Leu Val Ser Ser Arg Asp Arg Val Leu Pro Gly Glu
    210                 215                 220

Asp Ala Asp Ala Ala Glu Leu Leu Glu Lys Val Phe Glu Gly Asn Gly
225                 230                 235                 240

Leu Arg Val Val Ser Arg Ser Arg Ala Glu Ser Val Glu Arg Thr Glu
                245                 250                 255

Thr Gly Val Arg Val His Leu Ser Gly Glu Gly Ala Glu Asp Thr Pro
            260                 265                 270

Ser Ile Glu Gly Ser His Ala Leu Val Ala Val Gly Gly Val Pro Asn
        275                 280                 285

Thr Ala Gly Leu Gly Leu Asp Asp Val Gly Val Lys Leu Ala Asp Ser
    290                 295                 300

Gly His Val Leu Val Asp Gly Val Ser Arg Thr Ser Val Pro Ser Ile
305                 310                 315                 320

Tyr Ala Ala Gly Asp Cys Thr Gly Lys Leu Ala Leu Ala Ser Val Ala
                325                 330                 335

Ala Met Gln Gly Arg Ile Ala Val Ala His Leu Leu Gly Asp Ala Leu
            340                 345                 350

Lys Pro Leu Arg Pro His Leu Leu Ala Ser Asn Ile Phe Thr Ser Pro
        355                 360                 365

Glu Ile Ala Thr Val Gly Val Ser Gln Ala Gln Val Asp Ser Gly Gln
    370                 375                 380

Tyr Gln Ala Asp Val Leu Arg Leu Asp Phe His Thr Asn Pro Arg Ala
385                 390                 395                 400

Lys Met Ser Gly Ala Glu Glu Gly Phe Val Lys Ile Phe Ala Arg Gln
                405                 410                 415

Gly Ser Gly Thr Val Ile Gly Gly Val Val Val Ser Pro Arg Ala Ser
            420                 425                 430

Glu Leu Ile Tyr Ala Leu Ala Leu Ala Val Thr His Lys Leu His Val
        435                 440                 445
```

Asp Asp Leu Ala Asp Thr Phe Thr Val Tyr Pro Ser Met Ser Gly Ser
    450                 455                 460

Ile Ala Glu Ala Ala Arg Arg Leu His Val Arg Val
465                 470                 475

<210> SEQ ID NO 80
<211> LENGTH: 1431
<212> TYPE: DNA
<213> ORGANISM: Micrococcus luteus

<400> SEQUENCE: 80
gtgaccgagg aaaacagcac cttcatcccg tccctgacca tcatcggcgg cggcccccggc 60 ggctacgagg ccgccatggt ggccgcgaag ctgggcgccc gcgtgaccct ggtcgagcgc 120
cagggggtgg gcggcgcggc cgtcctcacg gacgtggtcc cctccaagac gctgatcgcc 180
gccgccgact cgatgcgccg cgtgggcgcc tccgtggacc tgggggtcga cctcggcggg 240
gccgaggtcc acgcggacat gggccgggtc ggccaccgca tcctgaacct ggcccacgag 300
cagtcctcgg acatccgcgc gggcctcgag cgggtcggtg tccgggtgat cgacggcgtg 360
ggccgcgtcg tcggccccca cgaggtgtcc gtccgcgccc tcgacgacgc cgacgccggc 420
gccgagcccg agatcatcac ctcggacgcg atcctcgtgg ccgtcggcgc gagtccccgg 480
gagctgccca ccgccgtccc ggacggcgag cggatcttca actggaagca ggtctacaac 540
ctcaaggagc tgcccgagca cctgatcgtc gtgggctccg gcgtcaccgg cgccgagttc 600
gcctcggcct acaaccgcct cggcgccaag gtcaccctcg tctcctcgcg cgaccgcgtg 660
ctccccggcg aggacgccga cgccgcagag ctgctcgaga aggtcttcga gggcaacggc 720
ctcagggttg tctcccgctc ccgggccgag tcggtcgagc ggaccgagac cggcgtgcgc 780
gtgcacctct ccggcgaggg ggccgaagac accccgtcga tcgagggctc ccacgcgctg 840
gtggccgtcg gcggcgtgcc gaacacggcg ggcctcggcc tcgacgacgt gggcgtgaag 900
ctggccgact ccggccacgt gctcgtggac ggcgtctccc gcacgtccgt gccgagcatc 960
tacgcggcgg gcgactgcac gggcaagctc gccctcgcct cggtggcggc catgcagggg 1020
cgcatcgccg tggcccacct gctcggcgac gccctcaagc cgctgcgccc gcacctgctg 1080
gcctcgaaca tcttcacctc gccggagatc gccaccgtgg gcgtctcgca ggcgcaggtg 1140
gactccggcc agtaccaggc ggacgtgctg cgactggact tccacaccaa cccccgcgcc 1200
aagatgtccg gcgcggagga ggggttcgtg aagatcttcg cgcgtcaggg ctccggcacc 1260
gtgatcggcg gcgtggtggt ctcgccgcgc gcctccgagc tgatctacgc gctcgcgctc 1320
gcggtcacgc acaagttgca cgtggacgac ctcgcggaca ccttcaccgt gtacccgtcc 1380
atgtccgggt cgatcgcgga ggcggcgcgc cgcctccatg tgcgggtgtg a 1431

<210> SEQ ID NO 81
<211> LENGTH: 473
<212> TYPE: PRT
<213> ORGANISM: Staphylococcus aureus

<400> SEQUENCE: 81

Met Ser Glu Lys Gln Tyr Asp Leu Val Val Leu Gly Gly Gly Thr Ala
1               5                   10                  15

Gly Tyr Val Ala Ala Ile Arg Ala Ser Gln Leu Gly Lys Lys Val Ala
            20                  25                  30

Ile Val Glu Arg Gln Leu Leu Gly Gly Thr Cys Leu His Lys Gly Cys
        35                  40                  45

-continued

```
Ile Pro Thr Lys Ser Leu Leu Lys Ser Ala Glu Val Phe Gln Thr Val
    50                  55                  60

Lys Gln Ala Ala Met Phe Gly Val Asp Val Lys Asp Ala Asn Val Asn
65                  70                  75                  80

Phe Glu Asn Met Leu Ala Arg Lys Glu Asp Ile Ile Asn Gln Met Tyr
                85                  90                  95

Gln Gly Val Lys His Leu Met Gln His Asn His Ile Asp Ile Tyr Asn
            100                 105                 110

Gly Thr Gly Arg Ile Leu Gly Thr Ser Ile Phe Ser Pro Gln Ser Gly
        115                 120                 125

Thr Ile Ser Val Glu Tyr Glu Asp Gly Glu Ser Asp Leu Leu Pro Asn
    130                 135                 140

Gln Phe Val Leu Ile Ala Thr Gly Ser Ser Pro Ala Glu Leu Pro Phe
145                 150                 155                 160

Leu Ser Phe Asp His Asp Lys Ile Leu Ser Ser Asp Asp Ile Leu Ser
                165                 170                 175

Leu Lys Thr Leu Pro Ser Ser Ile Gly Ile Ile Gly Gly Gly Val Ile
            180                 185                 190

Gly Met Glu Phe Ala Ser Leu Met Ile Asp Leu Gly Val Asp Val Thr
        195                 200                 205

Val Ile Glu Ala Gly Glu Arg Ile Leu Pro Thr Glu Ser Lys Gln Ala
    210                 215                 220

Ser Gln Leu Leu Lys Lys Ser Leu Ser Ala Arg Gly Val Lys Phe Tyr
225                 230                 235                 240

Glu Gly Ile Lys Leu Ser Glu Asn Asp Ile Asn Val Asn Glu Asp Gly
                245                 250                 255

Val Thr Phe Glu Ile Ser Ser Asp Ile Ile Lys Val Asp Lys Val Leu
            260                 265                 270

Leu Ser Ile Gly Arg Lys Pro Asn Thr Ser Asp Ile Gly Leu Asn Asn
        275                 280                 285

Thr Lys Ile Lys Leu Ser Thr Ser Gly His Ile Leu Thr Asn Glu Phe
    290                 295                 300

Gln Gln Thr Glu Asp Lys His Ile Tyr Ala Ala Gly Asp Cys Ile Gly
305                 310                 315                 320

Lys Leu Gln Leu Ala His Val Gly Ser Lys Glu Gly Val Val Ala Val
                325                 330                 335

Asp His Met Phe Glu Gly Asn Pro Ile Pro Val Asn Tyr Asn Met Met
            340                 345                 350

Pro Lys Cys Ile Tyr Ser Gln Pro Glu Ile Ala Ser Ile Gly Leu Asn
        355                 360                 365

Ile Glu Gln Ala Lys Ala Glu Gly Met Lys Val Lys Ser Phe Lys Val
    370                 375                 380

Pro Phe Lys Ala Ile Gly Lys Ala Val Ile Asp Ser His Asp Ala Asn
385                 390                 395                 400

Glu Gly Tyr Ser Glu Met Val Ile Asp Gln Ser Thr Glu Glu Ile Val
                405                 410                 415

Gly Ile Asn Met Ile Gly Pro His Val Thr Glu Leu Ile Asn Glu Ala
            420                 425                 430

Ser Leu Leu Gln Phe Met Asn Gly Ser Ala Leu Glu Leu Gly Leu Thr
        435                 440                 445

Thr His Ala His Pro Ser Ile Ser Glu Val Leu Met Glu Leu Gly Leu
    450                 455                 460

Lys Ala Glu Ser Arg Ala Ile His Val
```

465 470

<210> SEQ ID NO 82
<211> LENGTH: 1422
<212> TYPE: DNA
<213> ORGANISM: Staphylococcus aureus

<400> SEQUENCE: 82
ttatacgtga atagctctac tttctgcttt caatcctaat tccatcaaca cttcagagat 60
ggaaggatgt gcgtgtgttg ttagtcctaa ttctaatgcc gagccattca tgaactgtaa 120
cagtgatgcc tcattaatca attctgttac atgtggacca atcatattaa tacccacaat 180
ttcttcagtt gattgatcaa tcaccatttc gctataccct tcgtttgcgt catggctatc 240
aatcactgct ttaccaattg ctttaaatgg tactttaaaa cttttaactt tcattccctc 300
tgcctttgct tgttcaatgt ttaaaccgat agaagcaatt tcaggttgtg aataaataca 360
cttaggcatc atgttatagt ttactgggat tgggttcccc tcaaacatat gatcaacagc 420
cacaacacct tcttttgatc caacatgtgc caattgtaat tttcctatac aatcaccagc 480
tgcataaata tgtttatctt cagtttgttg aaattcgttc gttaaaatat gtcctgatgt 540
agaaagtttt attttagtgt tgtttaaacc aatatctgat gtgttaggtt ttctaccaat 600
cgatagcaac actttatcta ctttaattat gtctgaagaa atttcaaacg taacaccatc 660
ttcgttaaca tttatatcat tttcagaaag ttttattccc tcatagaatt taacaccacg 720
tgctgacaat gatttttta atagttgtga agcttgttta ctttcagttg gtaaaattct 780
ttcacctgct tctataactg ttacgtcaac acctaaatct atcatcaatg atgcaaattc 840
cattccgata acaccaccac caataatacc aatacttgat ggtaacgtct ttaatgataa 900
tatatcatcg ctagataaaa ttttatcatg atcaaatgat aagaatggca actctgcagg 960
cgaagaacca gttgcaatta atacaaattg gttgggtaat aagtctgatt caccatcttc 1020
atattcgaca gaaattgtgc cactttgagg tgaaaatata gatgtaccta gaatacgtcc 1080
cgtgccatta taaatgtcaa tgtgattgtg ttgcattaaa tgctttacac cttgatacat 1140
ttgattaata atgtcttctt ttcgtgccaa catattttca aaattaacat tagcatcttt 1200
gacatcaacg ccaaacattg ctgcctgttt tactgtttga aatacttcag cagatttaag 1260
cagcgattta gtaggaatac aacctttatg gagacaagta cctcctaata gttgtcgttc 1320
tactattgcc actttcttac ctaattgaga cgcacgtatc gcagcaacat atcctgcagt 1380
acctccaccg agaacgacta aatcatattg tttctctgac at 1422

<210> SEQ ID NO 83
<211> LENGTH: 581
<212> TYPE: PRT
<213> ORGANISM: Streptococcus mutans

<400> SEQUENCE: 83

Met Ala Val Glu Ile Ile Met Pro Lys Leu Gly Val Asp Met Gln Glu
1 5 10 15

Gly Glu Ile Ile Glu Trp Lys Lys Gln Glu Gly Asp Glu Val Lys Glu
20 25 30

Gly Asp Ile Leu Leu Glu Ile Met Ser Asp Lys Thr Asn Met Glu Ile
35 40 45

Glu Ala Glu Asp Ser Gly Val Leu Leu Lys Ile Val Lys Gly Asn Gly
50 55 60

Gln Val Val Pro Val Thr Glu Val Ile Gly Tyr Ile Gly Ser Ala Gly

-continued

```
65                  70                  75                  80

Glu Thr Ile Glu Thr Asn Ala Ala Pro Ala Ala Ser Ala Asp Asp Leu
                85                  90                  95

Lys Ala Ala Gly Leu Glu Val Pro Asp Thr Leu Gly Glu Ser Ala Ala
            100                 105                 110

Pro Ala Ala Gln Lys Thr Pro Leu Ala Asp Asp Glu Tyr Asp Met Ile
        115                 120                 125

Val Val Gly Gly Gly Pro Ala Gly Tyr Tyr Ala Ala Ile Arg Gly Ala
    130                 135                 140

Gln Leu Gly Gly Lys Val Ala Ile Val Glu Lys Ser Glu Phe Gly Gly
145                 150                 155                 160

Thr Cys Leu Asn Lys Gly Cys Ile Pro Thr Lys Thr Tyr Leu Lys Asn
                165                 170                 175

Ala Glu Ile Leu Asp Gly Ile Lys Ile Ala Ala Gly Arg Gly Ile Asn
            180                 185                 190

Phe Ala Ser Thr Asn Tyr Thr Ile Asp Met Asp Lys Thr Val Ala Phe
        195                 200                 205

Lys Asp Thr Val Val Lys Thr Leu Thr Ser Gly Val Gln Gly Leu Leu
    210                 215                 220

Lys Ala Asn Lys Val Thr Ile Phe Asn Gly Leu Gly Gln Val Asn Pro
225                 230                 235                 240

Asp Lys Thr Val Thr Val Gly Ser Glu Thr Ile Lys Gly His Asn Ile
                245                 250                 255

Ile Leu Ala Thr Gly Ser Lys Val Ser Arg Ile Asn Ile Pro Gly Ile
            260                 265                 270

Asp Ser Pro Leu Val Leu Thr Ser Asp Asp Ile Leu Asp Leu Arg Glu
        275                 280                 285

Ile Pro Lys Ser Leu Ala Val Met Gly Gly Gly Val Val Gly Ile Glu
    290                 295                 300

Leu Gly Leu Val Tyr Ala Ser Tyr Gly Thr Glu Val Thr Val Ile Glu
305                 310                 315                 320

Met Ala Asp Arg Ile Ile Pro Ala Met Asp Lys Glu Val Ser Leu Glu
                325                 330                 335

Leu Gln Lys Ile Leu Ser Lys Lys Gly Met Asn Ile Lys Thr Ser Val
            340                 345                 350

Gly Val Ala Glu Ile Val Glu Ala Asn Asn Gln Leu Thr Leu Lys Leu
        355                 360                 365

Asn Asp Gly Ser Glu Val Val Ala Glu Lys Ala Leu Leu Ser Ile Gly
    370                 375                 380

Arg Val Pro Gln Leu Ser Gly Leu Glu Asn Leu Asn Leu Glu Leu Glu
385                 390                 395                 400

Arg Gly Arg Ile Lys Val Asp Asp Tyr Gln Glu Thr Ser Ile Ser Gly
                405                 410                 415

Ile Tyr Ala Pro Gly Asp Val Asn Gly Arg Lys Met Leu Ala His Ala
            420                 425                 430

Ala Tyr Arg Met Gly Glu Val Ala Ala Glu Asn Ala Ile Trp Gly Asn
        435                 440                 445

Val Arg Lys Ala Asn Leu Lys Tyr Thr Pro Ala Ala Val Tyr Thr His
    450                 455                 460

Pro Glu Val Ala Met Cys Gly Ile Thr Glu Glu Gln Ala Arg Gln Glu
465                 470                 475                 480

Tyr Gly Asn Val Leu Val Gly Lys Ser Ser Phe Ser Gly Asn Gly Arg
                485                 490                 495
```

```
Ala Ile Ala Ser Asn Glu Ala Gln Gly Phe Val Lys Val Val Ala Asp
            500                 505                 510

Ala Lys Tyr His Glu Ile Leu Gly Val His Ile Ile Gly Pro Ala Ala
        515                 520                 525

Ala Glu Met Ile Asn Glu Ala Ser Thr Ile Met Glu Asn Glu Leu Thr
    530                 535                 540

Val Asp Glu Leu Leu Arg Ser Ile His Gly His Pro Thr Phe Ser Glu
545                 550                 555                 560

Val Met Tyr Glu Ala Phe Ala Asp Val Leu Gly Glu Ala Ile His Asn
                565                 570                 575

Pro Pro Lys Arg Arg
            580


<210> SEQ ID NO 84
<211> LENGTH: 1746
<212> TYPE: DNA
<213> ORGANISM: Streptococcus mutans

<400> SEQUENCE: 84

atggcagtcg aaattattat gcctaaactc ggtgttgata tgcaggaagg cgaaatcatc     60

gagtggaaaa aacaagaagg tgatgaggtc aaagaagggg atatcctcct tgaaatcatg    120

tctgacaaga ccaatatgga aattgaagct gaggattcag gtgtcctgct caaaattgtt    180

aaaggaaatg gtcaagttgt ccctgtgact gaggtcattg gttatattgg ttctgctggt    240

gaaacgattg aaacaaatgc agcgccagca gcttcagctg atgatctcaa agcagcgggt    300

cttgaagttc ctgatacttt aggcgagtca gcagcaccag cagctcaaaa aactccgctt    360

gctgatgatg agtatgatat gattgtcgtt ggtggtggtc ctgctggtta ttatgctgct    420

attcgcggtg cacaattggg cggcaaggtt gctatcgtcg aaaaatcaga atttggaggg    480

acttgtttaa ataaaggctg cattccaact aaaacttatc ttaagaatgc tgaaatcctt    540

gatggcatca aaattgcagc gggtcgcggt attaattttg cttcaaccaa ctataccatt    600

gacatggaca aaacggttgc ctttaaagat accgttgtta aacattgac aagtggggtt    660

cagggtcttc ttaaagccaa taaagtgact attttcaatg gtctcggtca ggttaatcct    720

gataagacag tgactgtcgg ttcggaaacg attaaaggac ataatattat ccttgcaaca    780

ggttcaaaag tgtctcgtat taatattccg ggaattgatt cacctcttgt tttaacatcg    840

gatgatattc ttgatcttcg tgaaattcca aagtcacttg ctgttatggg cggtggtgtt    900

gtcggcattg aactcggtct tgtttacgct tcctatggta cagaagtgac tgttattgaa    960

atggctgatc gcattattcc tgctatggac aaggaagtat cgcttgaact gcaaaaaatt   1020

ctatccaaga aaggaatgaa cattaagact tctgttggtg tggctgaaat tgttgaagct   1080

aacaatcaat taacgctgaa actcaatgac ggctctgaag ttgtggctga aaaggccctg   1140

ctttctattg gtcgtgtccc acaattaagc ggtttagaaa atcttaatct ggaacttgaa   1200

cgcggtcgca tcaaagtgga cgattatcag gaaacctcta tttcaggtat ttatgccccg   1260

ggtgatgtta atggaagaaa gatgttagcg catgctgcct atcgtatggg tgaagtagct   1320

gccgaaaatg ctatctgggg aaatgttcgt aaggctaacc tgaaatatac accagcagct   1380

gtttacaccc atccagaggt tgctatgtgc ggtattactg aagaacaagc ccgtcaagaa   1440

tatggaaacg tcttagttgg gaaatcctct ttttcaggaa atggacgtgc gatcgcttct   1500

aatgaagcac aaggatttgt caaagttgtc gcagatgcta aataccatga aattcttgga   1560
```

```
gtccatatta ttggaccagc agctgctgag atgattaatg aagcctcaac gattatggaa   1620

aatgagttga cggttgatga gctgctacgt tctattcatg gccatcctac cttctcggag   1680

gttatgtatg aagcctttgc agacgtcctt ggcgaagcta tccataaccc gccaaagcgt   1740

cgttaa                                                              1746


<210> SEQ ID NO 85
<211> LENGTH: 17
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Ile or Val
<220> FEATURE:
<221> NAME/KEY: MISC_FEATURE
<222> LOCATION: (4)..(4)
<223> OTHER INFORMATION: Xaa can be Ala or Thr
<220> FEATURE:
<221> NAME/KEY: MISC_FEATURE
<222> LOCATION: (5)..(5)
<223> OTHER INFORMATION: Xaa can be Ser or Cys
<220> FEATURE:
<221> NAME/KEY: MISC_FEATURE
<222> LOCATION: (6)..(6)
<223> OTHER INFORMATION: Xaa can be Val or Leu
<220> FEATURE:
<221> NAME/KEY: MISC_FEATURE
<222> LOCATION: (7)..(8)
<223> OTHER INFORMATION: Xaa can be any amino acid
<220> FEATURE:
<221> NAME/KEY: MISC_FEATURE
<222> LOCATION: (9)..(9)
<223> OTHER INFORMATION: Xaa can be Gly or Asp
<220> FEATURE:
<221> NAME/KEY: MISC_FEATURE
<222> LOCATION: (11)..(11)
<223> OTHER INFORMATION: Xaa can be Val or Ile
<220> FEATURE:
<221> NAME/KEY: MISC_FEATURE
<222> LOCATION: (13)..(13)
<223> OTHER INFORMATION: Xaa can be Thr or Ser
<220> FEATURE:
<221> NAME/KEY: MISC_FEATURE
<222> LOCATION: (15)..(15)
<223> OTHER INFORMATION: Xaa can be Ala or Thr
<220> FEATURE:
<221> NAME/KEY: MISC_FEATURE
<222> LOCATION: (16)..(16)
<223> OTHER INFORMATION: Xaa can be Met or Leu
<220> FEATURE:
<221> NAME/KEY: MISC_FEATURE
<222> LOCATION: (17)..(17)
<223> OTHER INFORMATION: Xaa can be Ile or Leu

<400> SEQUENCE: 85

Xaa Gly Gly Xaa Xaa Xaa Xaa Xaa Xaa Cys Xaa Pro Xaa Lys Xaa Xaa
1               5                   10                  15

Xaa


<210> SEQ ID NO 86
<211> LENGTH: 17
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Leu or Ile
<220> FEATURE:
```

<221> NAME/KEY: MISC_FEATURE
<222> LOCATION: (5)..(5)
<223> OTHER INFORMATION: Xaa can be Gly or Ser
<220> FEATURE:
<221> NAME/KEY: MISC_FEATURE
<222> LOCATION: (6)..(6)
<223> OTHER INFORMATION: Xaa can be any amino acid
<220> FEATURE:
<221> NAME/KEY: MISC_FEATURE
<222> LOCATION: (7)..(7)
<223> OTHER INFORMATION: Xaa can be Ser or Pro
<220> FEATURE:
<221> NAME/KEY: MISC_FEATURE
<222> LOCATION: (8)..(9)
<223> OTHER INFORMATION: Xaa can be any amino acid
<220> FEATURE:
<221> NAME/KEY: MISC_FEATURE
<222> LOCATION: (11)..(11)
<223> OTHER INFORMATION: Xaa can be Ala or Pro
<220> FEATURE:
<221> NAME/KEY: MISC_FEATURE
<222> LOCATION: (12)..(12)
<223> OTHER INFORMATION: Xaa can be Asp or Gly
<220> FEATURE:
<221> NAME/KEY: MISC_FEATURE
<222> LOCATION: (13)..(15)
<223> OTHER INFORMATION: Xaa can be any amino acid
<220> FEATURE:
<221> NAME/KEY: MISC_FEATURE
<222> LOCATION: (16)..(16)
<223> OTHER INFORMATION: Xaa can be Asp or Leu

<400> SEQUENCE: 86

```
Xaa Ala Thr Gly Xaa Xaa Xaa Xaa Xaa Leu Xaa Xaa Xaa Xaa Xaa Xaa
1               5                   10                  15

Gly
```

<210> SEQ ID NO 87
<211> LENGTH: 12
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Val or Ile
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa can be Gly or Ser
<220> FEATURE:
<221> NAME/KEY: MISC_FEATURE
<222> LOCATION: (6)..(6)
<223> OTHER INFORMATION: Xaa can be any amino acid
<220> FEATURE:
<221> NAME/KEY: MISC_FEATURE
<222> LOCATION: (7)..(7)
<223> OTHER INFORMATION: Xaa can be Ile or Thr
<220> FEATURE:
<221> NAME/KEY: MISC_FEATURE
<222> LOCATION: (9)..(9)
<223> OTHER INFORMATION: Xaa can be any amino acid
<220> FEATURE:
<221> NAME/KEY: MISC_FEATURE
<222> LOCATION: (11)..(11)
<223> OTHER INFORMATION: Xaa can be any amino acid
<220> FEATURE:
<221> NAME/KEY: MISC_FEATURE
<222> LOCATION: (12)..(12)
<223> OTHER INFORMATION: Xaa can be Ala or Gly

<400> SEQUENCE: 87

Xaa Xaa Gly Xaa Gly Xaa Xaa Gly Xaa Glu Xaa Xaa
1 5 10

<210> SEQ ID NO 88
<211> LENGTH: 14
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(7)
<223> OTHER INFORMATION: Xaa can be any amino acid
<220> FEATURE:
<221> NAME/KEY: MISC_FEATURE
<222> LOCATION: (8)..(8)
<223> OTHER INFORMATION: Xaa can be Ala or Val
<220> FEATURE:
<221> NAME/KEY: MISC_FEATURE
<222> LOCATION: (9)..(9)
<223> OTHER INFORMATION: Xaa can be any amino acid
<220> FEATURE:
<221> NAME/KEY: MISC_FEATURE
<222> LOCATION: (12)..(13)
<223> OTHER INFORMATION: Xaa can be any amino acid
<220> FEATURE:
<221> NAME/KEY: MISC_FEATURE
<222> LOCATION: (14)..(14)
<223> OTHER INFORMATION: Xaa can be Pro or Gly

<400> SEQUENCE: 88

Thr Xaa Xaa Xaa Xaa Xaa Xaa Xaa Xaa Gly Asp Xaa Xaa Xaa
1 5 10

<210> SEQ ID NO 89
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Ile or Val
<220> FEATURE:
<221> NAME/KEY: MISC_FEATURE
<222> LOCATION: (2)..(2)
<223> OTHER INFORMATION: Xaa can be Gly or Ala
<220> FEATURE:
<221> NAME/KEY: MISC_FEATURE
<222> LOCATION: (3)..(4)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be Phe or Ile
<220> FEATURE:
<221> NAME/KEY: MISC_FEATURE
<222> LOCATION: (6)..(6)
<223> OTHER INFORMATION: Xaa can be Thr or His
<220> FEATURE:
<221> NAME/KEY: MISC_FEATURE
<222> LOCATION: (7)..(7)
<223> OTHER INFORMATION: Xaa can be any amino acid
<220> FEATURE:
<221> NAME/KEY: MISC_FEATURE
<222> LOCATION: (8)..(8)
<223> OTHER INFORMATION: Xaa can be Tyr or His
<220> FEATURE:
<221> NAME/KEY: MISC_FEATURE
<222> LOCATION: (10)..(10)
<223> OTHER INFORMATION: Xaa can be Ser or Thr
<220> FEATURE:
<221> NAME/KEY: MISC_FEATURE

```
<222> LOCATION: (11)..(11)
<223> OTHER INFORMATION: Xaa can be Gln or Leu

<400> SEQUENCE: 89

Xaa Xaa Xaa Xaa Xaa Xaa Xaa Xaa Pro Xaa Xaa
1               5                   10


<210> SEQ ID NO 90
<211> LENGTH: 317
<212> TYPE: PRT
<213> ORGANISM: Escherichia coli

<400> SEQUENCE: 90

Met Tyr Thr Lys Ile Ile Gly Thr Gly Ser Tyr Leu Pro Glu Gln Val
1               5                   10                  15

Arg Thr Asn Ala Asp Leu Glu Lys Met Val Asp Thr Ser Asp Glu Trp
            20                  25                  30

Ile Val Thr Arg Thr Gly Ile Arg Glu Arg His Ile Ala Ala Gln Asn
        35                  40                  45

Glu Thr Val Ser Thr Met Gly Phe Glu Ala Ala Thr Arg Ala Ile Glu
    50                  55                  60

Met Ala Gly Ile Glu Lys Asp Gln Ile Gly Leu Ile Val Val Ala Thr
65                  70                  75                  80

Thr Ser Ala Thr His Ala Phe Pro Ser Ala Ala Cys Gln Ile Gln Ser
                85                  90                  95

Met Leu Gly Ile Lys Gly Cys Pro Ala Phe Asp Val Ala Ala Ala Cys
            100                 105                 110

Ala Gly Phe Thr Tyr Ala Leu Ser Val Ala Asp Gln Tyr Val Lys Ser
        115                 120                 125

Gly Ala Val Lys Tyr Ala Leu Val Val Gly Ser Asp Val Leu Ala Arg
    130                 135                 140

Thr Cys Asp Pro Thr Asp Arg Gly Thr Ile Ile Ile Phe Gly Asp Gly
145                 150                 155                 160

Ala Gly Ala Ala Val Leu Ala Ala Ser Glu Glu Pro Gly Ile Ile Ser
                165                 170                 175

Thr His Leu His Ala Asp Gly Ser Tyr Gly Glu Leu Leu Thr Leu Pro
            180                 185                 190

Asn Ala Asp Arg Val Asn Pro Glu Asn Ser Ile His Leu Thr Met Ala
        195                 200                 205

Gly Asn Glu Val Phe Lys Val Ala Val Thr Glu Leu Ala His Ile Val
    210                 215                 220

Asp Glu Thr Leu Ala Ala Asn Asn Leu Asp Arg Ser Gln Leu Asp Trp
225                 230                 235                 240

Leu Val Pro His Gln Ala Asn Leu Arg Ile Ile Ser Ala Thr Ala Lys
                245                 250                 255

Lys Leu Gly Met Ser Met Asp Asn Val Val Val Thr Leu Asp Arg His
            260                 265                 270

Gly Asn Thr Ser Ala Ala Ser Val Pro Cys Ala Leu Asp Glu Ala Val
        275                 280                 285

Arg Asp Gly Arg Ile Lys Pro Gly Gln Leu Val Leu Leu Glu Ala Phe
    290                 295                 300

Gly Gly Gly Phe Thr Trp Gly Ser Ala Leu Val Arg Phe
305                 310                 315


<210> SEQ ID NO 91
<211> LENGTH: 954
```

<212> TYPE: DNA
<213> ORGANISM: Escherichia coli

<400> SEQUENCE: 91
atgtatacga agattattgg tactggcagc tatctgcccg aacaagtgcg gacaaacgcc 60
gatttggaaa aaatggtgga cacctctgac gagtggattg tcactcgtac cggtatccgc 120
gaacgccaca ttgccgcgca aaacgaaacc gtttcaacca tgggctttga agcggcgaca 180
cgcgcaattg agatggcggg cattgagaaa gaccagattg gcctgatcgt tgtggcaacg 240
acttctgcta cgcacgcttt cccgagcgca gcttgtcaga ttcaaagcat gctgggcatt 300
aaaggttgcc cggcatttga cgttgcagca gcctgcgcag gtttcaccta tgcattaagc 360
gtagccgatc aatacgtgaa atctggggcg gtgaagtatg ctctggtcgt cggttccgat 420
gtactggcgc gcacctgcga tccaaccgat cgtgggacta ttattatttt tggcgatggc 480
gcgggcgctg cggtgctggc tgcctctgaa gagccgggaa tcatctccac ccatctgcat 540
gccgacggta gctatggtga gttgctgacg ctgcctaatg ctgaccgtgt gaatccagag 600
aattcaattc atctgacgat ggcgggcaac gaagtcttca aggttgcggt aacggaactg 660
gcgcacatcg ttgatgagac gctggcggca aataatcttg accgttctca actggactgg 720
ctggttccgc atcaggctaa cctgcgtatt atcagtgcaa cggcgaaaaa actcggtatg 780
tctatggaca atgtcgtggt gacgctggat cgccacggta atacctctgc ggcctctgtc 840
ccgtgcgcgc tggatgaagc tgtacgcgac gggcgcatta agccggggca gttggttctg 900
cttgaagcct ttggcggtgg attcacctgg ggctccgcgc tggttcgttt ctag 954

<210> SEQ ID NO 92
<211> LENGTH: 317
<212> TYPE: PRT
<213> ORGANISM: Escherichia coli

<400> SEQUENCE: 92

Met Tyr Thr Lys Ile Ile Gly Thr Gly Ser Tyr Leu Pro Glu Gln Val
1 5 10 15

Arg Thr Asn Ala Asp Leu Glu Lys Met Val Asp Thr Ser Asp Glu Trp
20 25 30

Ile Val Thr Arg Thr Gly Ile Arg Glu Arg His Ile Ala Ala Pro Asn
35 40 45

Glu Thr Val Ser Thr Met Gly Phe Glu Ala Ala Thr Arg Ala Ile Glu
50 55 60

Met Ala Gly Ile Glu Lys Asp Gln Ile Gly Leu Ile Val Val Ala Thr
65 70 75 80

Thr Ser Ala Thr His Ala Phe Pro Ser Ala Ala Cys Gln Ile Gln Ser
85 90 95

Met Leu Gly Ile Lys Gly Cys Pro Ala Phe Asp Val Ala Ala Ala Cys
100 105 110

Ala Gly Phe Thr Tyr Ala Leu Ser Val Ala Asp Gln Tyr Val Lys Ser
115 120 125

Gly Ala Val Lys Tyr Ala Leu Val Val Gly Ser Asp Val Leu Ala Arg
130 135 140

Thr Cys Asp Pro Thr Asp Arg Gly Thr Ile Ile Ile Phe Gly Asp Gly
145 150 155 160

Ala Gly Ala Ala Val Leu Ala Ala Ser Glu Glu Pro Gly Ile Ile Ser
165 170 175

Thr His Leu His Ala Asp Gly Ser Tyr Gly Glu Leu Leu Thr Leu Pro

```
            180                 185                 190

Asn Ala Asp Arg Val Asn Pro Glu Asn Ser Ile His Leu Thr Met Ala
        195                 200                 205

Gly Asn Glu Val Phe Lys Val Ala Val Thr Glu Leu Ala His Ile Val
    210                 215                 220

Asp Glu Thr Leu Thr Ala Asn Asn Leu Asp Arg Ser Gln Leu Asp Trp
225                 230                 235                 240

Leu Val Pro His Gln Ala Asn Leu Arg Ile Ile Ser Ala Thr Ala Lys
                245                 250                 255

Lys Leu Gly Met Ser Met Asp Asn Val Val Val Thr Leu Asp Arg His
            260                 265                 270

Gly Asn Thr Ser Ala Ala Ser Val Pro Cys Ala Leu Asp Glu Ala Val
        275                 280                 285

Arg Asp Gly Arg Ile Lys Pro Gly Gln Leu Val Leu Leu Glu Ala Phe
    290                 295                 300

Gly Gly Gly Phe Thr Trp Gly Ser Ala Leu Val Arg Phe
305                 310                 315


<210> SEQ ID NO 93
<211> LENGTH: 954
<212> TYPE: DNA
<213> ORGANISM: Escherichia coli

<400> SEQUENCE: 93

atgtatacga agattattgg tactggcagc tatctgcccg aacaagtgcg gacaaacgcc      60

gatttggaaa aaatggtgga cacctctgac gagtggattg tcactcgtac cggtatccgc     120

gaacgccaca ttgccgcgcc aaacgaaacc gtttcaacca tgggctttga agcggcgaca     180

cgcgcaattg agatggcggg cattgagaaa gaccagattg gcctgatcgt tgtggcaacg     240

acttctgcta cgcacgcttt cccgagcgca gcttgtcaga ttcaaagcat gttgggcatt     300

aaaggttgcc cggcatttga cgttgcagca gcctgcgcag gtttcaccta tgcattaagc     360

gtagccgatc aatacgtgaa atctggggcg gtgaagtatg ctctggtcgt cggttccgat     420

gtactggcgc gcacctgcga tccaaccgat cgtgggacta ttattatttt tggcgatggc     480

gcgggcgctg cggtgctggc tgcctctgaa gagccgggaa tcatctccac ccatctgcat     540

gccgacggta gttatggtga attgctgacg ctgccaaacg ccgaccgcgt gaatccagag     600

aattcaattc atctgacgat ggcgggcaac gaagtcttca aggttgcggt aacggaactg     660

gcgcacatcg ttgatgagac gctgacggcg aataatcttg accgttctca actggactgg     720

ctggttccgc atcaggctaa cctgcgtatt atcagtgcaa cggcgaaaaa actcggtatg     780

tcgatggaca atgtcgtggt gacgctggat cgccacggta atacctctgc ggcctctgtc     840

ccgtgcgcgc tggatgaagc tgtacgcgac gggcgcatta agccggggca gttggttctg     900

cttgaagcct ttggcggtgg attcacctgg ggctccgcgc tggttcgttt ctag           954


<210> SEQ ID NO 94
<211> LENGTH: 312
<212> TYPE: PRT
<213> ORGANISM: Bacillus subtilis

<400> SEQUENCE: 94

Met Lys Ala Gly Ile Leu Gly Val Gly Arg Tyr Ile Pro Glu Lys Val
1               5                   10                  15

Leu Thr Asn His Asp Leu Glu Lys Met Val Glu Thr Ser Asp Glu Trp
            20                  25                  30
```

```
Ile Arg Thr Arg Thr Gly Ile Glu Glu Arg Arg Ile Ala Ala Asp Asp
        35                  40                  45

Val Phe Ser Ser His Met Ala Val Ala Ala Ala Lys Asn Ala Leu Glu
    50                  55                  60

Gln Ala Glu Val Ala Ala Glu Asp Leu Asp Met Ile Leu Val Ala Thr
65                  70                  75                  80

Val Thr Pro Asp Gln Ser Phe Pro Thr Val Ser Cys Met Ile Gln Glu
                85                  90                  95

Gln Leu Gly Ala Lys Lys Ala Cys Ala Met Asp Ile Ser Ala Ala Cys
            100                 105                 110

Ala Gly Phe Met Tyr Gly Val Val Thr Gly Lys Gln Phe Ile Glu Ser
        115                 120                 125

Gly Thr Tyr Lys His Val Leu Val Val Gly Val Glu Lys Leu Ser Ser
    130                 135                 140

Ile Thr Asp Trp Glu Asp Arg Asn Thr Ala Val Leu Phe Gly Asp Gly
145                 150                 155                 160

Ala Gly Ala Ala Val Val Gly Pro Val Ser Asp Asp Arg Gly Ile Leu
                165                 170                 175

Ser Phe Glu Leu Gly Ala Asp Gly Thr Gly Gly Gln His Leu Tyr Leu
            180                 185                 190

Asn Glu Lys Arg His Thr Ile Met Asn Gly Arg Glu Val Phe Lys Phe
        195                 200                 205

Ala Val Arg Gln Met Gly Glu Ser Cys Val Asn Val Ile Glu Lys Ala
    210                 215                 220

Gly Leu Ser Lys Glu Asp Val Asp Phe Leu Ile Pro His Gln Ala Asn
225                 230                 235                 240

Ile Arg Ile Met Glu Ala Ala Arg Glu Arg Leu Glu Leu Pro Val Glu
                245                 250                 255

Lys Met Ser Lys Thr Val His Lys Tyr Gly Asn Thr Ser Ala Ala Ser
            260                 265                 270

Ile Pro Ile Ser Leu Val Glu Glu Leu Glu Ala Gly Lys Ile Lys Asp
        275                 280                 285

Gly Asp Val Val Val Met Val Gly Phe Gly Gly Gly Leu Thr Trp Gly
    290                 295                 300

Ala Ile Ala Ile Arg Trp Gly Arg
305                 310
```

<210> SEQ ID NO 95
<211> LENGTH: 939
<212> TYPE: DNA
<213> ORGANISM: Bacillus subtilis

<400> SEQUENCE: 95

```
atgaaagctg gaatacttgg tgttggacgt tacattcctg agaaggtttt aacaaatcat      60

gatcttgaaa aaatggttga aacttctgac gagtggattc gtacaagaac aggaatagaa     120

gaaagaagaa tcgcagcaga tgatgtgttt tcatcacata tggctgttgc agcagcgaaa     180

aatgcgctgg aacaagctga agtggctgct gaggatctgg atatgatctt ggttgcaact     240

gttacacctg atcagtcatt ccctacggtc tcttgtatga ttcaagaaca actcggcgcg     300

aagaaagcgt gtgctatgga tatcagcgcg gcttgtgcgg gcttcatgta cggggttgta     360

accggtaaac aatttattga atccggaacc tacaagcatg ttctagttgt tggtgtagag     420

aagctctcaa gcattaccga ctgggaagac cgcaatacag ccgttctgtt tggagacgga     480
```

-continued

```
gcaggcgctg cggtagtcgg gccagtcagt gatgacagag gaatcctttc atttgaacta    540

ggagccgacg gcacaggcgg tcagcacttg tatctgaatg aaaaacgaca tacaatcatg    600

aatggacgag aagttttcaa atttgcagtc cgccaaatgg gagaatcatg cgtaaatgtc    660

attgaaaaag ccggactttc aaaagaggat gtcgactttt tgattccgca tcaggcgaac    720

atccgtatca tggaagctgc tcgcgagcgt ttagagcttc ctgtcgaaaa gatgtctaaa    780

actgttcata aatatggaaa tacttctgcc gcatccattc cgatctctct tgtagaagaa    840

ttggaagccg gtaaaatcaa agacggcgat gtggtcgtta tggtagggtt cggcggagga    900

ctaacatggg gcgccattgc aatccgctgg ggccgataa                            939


<210> SEQ ID NO 96
<211> LENGTH: 335
<212> TYPE: PRT
<213> ORGANISM: Streptomyces avermitilis

<400> SEQUENCE: 96

Met Ser Gly Gly Arg Ala Ala Val Ile Thr Gly Ile Gly Gly Tyr Val
1               5                   10                  15

Pro Pro Asp Leu Val Thr Asn Asp Asp Leu Ala Gln Arg Leu Asp Thr
            20                  25                  30

Ser Asp Ala Trp Ile Arg Ser Arg Thr Gly Ile Ala Glu Arg His Val
        35                  40                  45

Ile Ala Pro Gly Thr Ala Thr Ser Asp Leu Ala Val Glu Ala Gly Leu
    50                  55                  60

Arg Ala Leu Lys Ser Ala Gly Asp Glu His Val Asp Ala Val Val Leu
65                  70                  75                  80

Ala Thr Thr Thr Pro Asp Gln Pro Cys Pro Ala Thr Ala Pro Gln Val
                85                  90                  95

Ala Ala Arg Leu Gly Leu Gly Gln Val Pro Ala Phe Asp Val Ala Ala
            100                 105                 110

Val Cys Ser Gly Phe Leu Phe Gly Leu Ala Thr Ala Ser Gly Leu Ile
        115                 120                 125

Ala Ala Gly Val Ala Asp Lys Val Leu Leu Val Ala Ala Asp Ala Phe
    130                 135                 140

Thr Thr Ile Ile Asn Pro Glu Asp Arg Thr Thr Ala Val Ile Phe Ala
145                 150                 155                 160

Asp Gly Ala Gly Ala Val Val Leu Arg Ala Gly Ala Ala Asp Glu Pro
                165                 170                 175

Gly Ala Val Gly Pro Leu Val Leu Gly Ser Asp Gly Glu Leu Ser His
            180                 185                 190

Leu Ile Glu Val Pro Ala Gly Gly Ser Arg Gln Arg Ser Ser Gly Pro
        195                 200                 205

Thr Thr Asp Pro Asp Asp Gln Tyr Phe Arg Met Leu Gly Arg Asp Thr
    210                 215                 220

Tyr Arg His Ala Val Glu Arg Met Thr Asp Ala Ser Gln Arg Ala Ala
225                 230                 235                 240

Glu Leu Ala Asp Trp Arg Ile Asp Asp Val Asp Arg Phe Ala Ala His
                245                 250                 255

Gln Ala Asn Ala Arg Ile Leu Asp Ser Val Ala Glu Arg Leu Gly Val
            260                 265                 270

Pro Ala Glu Arg Gln Leu Thr Asn Ile Ala Arg Val Gly Asn Thr Gly
        275                 280                 285

Ala Ala Ser Ile Pro Leu Leu Leu Ser Gln Ala Ala Ala Ala Gly Arg
```

```
    290                 295                 300

Leu Gly Ala Gly His Arg Val Leu Leu Thr Ala Phe Gly Gly Gly Leu
305                 310                 315                 320

Ser Trp Gly Ala Gly Thr Leu Val Trp Pro Glu Val Gln Pro Val
                325                 330                 335


<210> SEQ ID NO 97
<211> LENGTH: 1008
<212> TYPE: DNA
<213> ORGANISM: Streptomyces avermitilis

<400> SEQUENCE: 97

atgagcggcg gacgcgcggc ggtgatcacc gggatcgggg gctatgtgcc tcccgatctg      60

gtgaccaacg acgatctggc ccagcggctc gacacctccg acgcgtggat ccgctcgcgc     120

accgggatcg ccgagcggca tgtgatcgcg cccggcaccg cgacctccga cctggcggtg     180

gaggccggac tgcgggccct gaagtcggcg ggcgacgagc acgtggacgc ggtcgtcctg     240

gccaccacga cgcccgacca gccctgcccg gcgaccgccc cgcaggtggc cgcacggctg     300

ggactcgggc aggtgccggc gttcgacgtg gccgccgtct gctccggctt cctgttcggc     360

ctcgccaccg cgtccgggct gatcgcggcc ggggtggcgg acaaggtcct gctggtcgcc     420

gccgacgcgt tcaccacgat catcaacccc gaggaccgca ccacggccgt catcttcgcg     480

gacggcgcgg gcgcggtggt gctgcgcgcg ggcgccgccg acgagccggg ggccgtcggc     540

ccgctggtgc tcggcagcga cggcgagctg agccatctca tcgaggtgcc ggcgggcggc     600

tcgcgccagc gctcgtccgg ccccacgacc gacccggacg accagtactt ccggatgctc     660

ggccgggaca cctaccggca cgcggtggag cggatgaccg atgcgtccca gcgggcggcc     720

gaactggccg actggcggat cgacgacgtc gaccggttcg cggcgcacca ggccaacgcc     780

cgcatcctcg actcggtcgc ggaacgtctc ggggtccccg ccgaacggca gttgaccaac     840

atcgcccggg tcggcaacac cggcgccgcc tcgatcccgc tgcttctgtc gcaggcggcc     900

gcggccggcc ggctcggcgc cggcaccgg gtgctcctga ccgcgttcgg cgggggcctg     960

tcctggggcg cggggactct ggtctggccg gaggtccagc cggtctga                 1008


<210> SEQ ID NO 98
<211> LENGTH: 313
<212> TYPE: PRT
<213> ORGANISM: Straphylococcus aureus

<400> SEQUENCE: 98

Met Asn Val Gly Ile Lys Gly Phe Gly Ala Tyr Ala Pro Glu Lys Ile
1               5                   10                  15

Ile Asp Asn Ala Tyr Phe Glu Gln Phe Leu Asp Thr Ser Asp Glu Trp
            20                  25                  30

Ile Ser Lys Met Thr Gly Ile Lys Glu Arg His Trp Ala Asp Asp Asp
        35                  40                  45

Gln Asp Thr Ser Asp Leu Ala Tyr Glu Ala Ser Val Lys Ala Ile Ala
    50                  55                  60

Asp Ala Gly Ile Gln Pro Glu Asp Ile Asp Met Ile Ile Val Ala Thr
65                  70                  75                  80

Ala Thr Gly Asp Met Pro Phe Pro Thr Val Ala Asn Met Leu Gln Glu
                85                  90                  95

Arg Leu Gly Thr Gly Lys Val Ala Ser Met Asp Gln Leu Ala Ala Cys
            100                 105                 110
```

-continued

```
Ser Gly Phe Met Tyr Ser Met Ile Thr Ala Lys Gln Tyr Val Gln Ser
        115                 120                 125

Gly Asp Tyr His Asn Ile Leu Val Val Gly Ala Asp Lys Leu Ser Lys
    130                 135                 140

Ile Thr Asp Leu Thr Asp Arg Ser Thr Ala Val Leu Phe Gly Asp Gly
145                 150                 155                 160

Ala Gly Ala Val Ile Ile Gly Glu Val Ser Glu Gly Arg Gly Ile Ile
                165                 170                 175

Ser Tyr Glu Met Gly Ser Asp Gly Thr Gly Gly Lys His Leu Tyr Leu
            180                 185                 190

Asp Lys Asp Thr Gly Lys Leu Lys Met Asn Gly Arg Glu Val Phe Lys
        195                 200                 205

Phe Ala Val Arg Ile Met Gly Asp Ala Ser Thr Arg Val Val Glu Lys
    210                 215                 220

Ala Asn Leu Thr Ser Asp Asp Ile Asp Leu Phe Ile Pro His Gln Ala
225                 230                 235                 240

Asn Ile Arg Ile Met Glu Ser Ala Arg Glu Arg Leu Gly Ile Ser Lys
                245                 250                 255

Asp Lys Met Ser Val Ser Val Asn Lys Tyr Gly Asn Thr Ser Ala Ala
            260                 265                 270

Ser Ile Pro Leu Ser Ile Asp Gln Glu Leu Lys Asn Gly Lys Leu Lys
        275                 280                 285

Asp Asp Asp Thr Ile Val Leu Val Gly Phe Gly Gly Gly Leu Thr Trp
    290                 295                 300

Gly Ala Met Thr Ile Lys Trp Gly Lys
305                 310
```

<210> SEQ ID NO 99
<211> LENGTH: 942
<212> TYPE: DNA
<213> ORGANISM: Straphylococcus aureus

<400> SEQUENCE: 99

```
ctattttccc cattttattg tcattgcgcc ccaagttagg ccgccaccga atccgacaag      60

aacaattgta tcatcatctt tgagtttacc attttttaat tcttgatcga tacttaaagg     120

tattgacgca gctgaagtat ttccatattt atttacagaa acactcattt tgtcttttga     180

aatacctaag cgttctctag ctgattccat aattctaata ttagcttgat gaggaataaa     240

taaatctata tcatctgatg ttaaattcgc tttttcaact acacgtgttg atgcatcacc     300

cataattcta acagcaaatt taaatacttc tcgaccattc attttcagtt taccagtatc     360

tttatctaaa tataaatgtt taccacctgt gccatcagaa cccatttcat aacttataat     420

acctctgcct tctgaaactt caccgatgat aaccgcacct gcaccatctc caaatagaac     480

tgcagtagaa cggtcagtta aatctgttat tttagataat ttatctgcac cgacaactaa     540

aatattatga taatctccag attgaacata ttgtttagct gtaatcattg aatacataaa     600

tccagaacat gctgcaagtt gatccataga ggcaactttg cccgtcccta aacgttcttg     660

taacatattt gcgacagttg gaaatggcat atctccagtt gctgtggcaa caattatcat     720

atctatatct tcgggctgaa taccagcgtc agcgattgct tttacacttg cttcatatgc     780

taaatctgaa gtatcttgat cgtcatctgc ccaatgtctt tctttaattc cagtcatctt     840

agaaatccat tcatcagatg tatctaaaaa ttgctcaaaa taggcattgt caataatctt     900

ttctggtgca tatgcaccaa aacctttaat acccacgttc at                        942
```

<210> SEQ ID NO 100
<211> LENGTH: 325
<212> TYPE: PRT
<213> ORGANISM: Streptococcus mutans

<400> SEQUENCE: 100

Met Thr Phe Ala Lys Ile Ser Gln Ala Ala Tyr Tyr Val Pro Ser Gln
1               5                   10                  15

Val Val Thr Asn Asp Asp Leu Ser Lys Ile Met Asp Thr Ser Asp Glu
            20                  25                  30

Trp Ile Thr Ser Arg Thr Gly Ile Arg Glu Arg Arg Ile Ser Gln Ser
        35                  40                  45

Glu Asp Thr Ser Asp Leu Ala Ser Gln Val Ala Lys Glu Leu Leu Lys
    50                  55                  60

Lys Ala Ser Leu Lys Ala Lys Glu Ile Asp Phe Ile Ile Val Ala Thr
65                  70                  75                  80

Ile Thr Pro Asp Ala Met Met Pro Ser Thr Ala Ala Cys Val Gln Ala
                85                  90                  95

Lys Ile Gly Ala Val Asn Ala Phe Ala Phe Asp Leu Thr Ala Ala Cys
            100                 105                 110

Ser Gly Phe Ile Phe Ala Leu Ser Ala Ala Glu Lys Met Ile Lys Ser
        115                 120                 125

Gly Gln Tyr Gln Lys Gly Leu Val Ile Gly Ala Glu Val Leu Ser Lys
    130                 135                 140

Ile Ile Asp Trp Ser Asp Arg Thr Thr Ala Val Leu Phe Gly Asp Gly
145                 150                 155                 160

Ala Gly Gly Val Leu Leu Glu Ala Asp Ser Ser Glu His Phe Leu Phe
                165                 170                 175

Glu Ser Ile His Ser Asp Gly Ser Arg Gly Glu Ser Leu Thr Ser Gly
            180                 185                 190

Glu His Ala Val Ser Ser Pro Phe Ser Gln Val Asp Lys Lys Asp Asn
        195                 200                 205

Cys Phe Leu Lys Met Asp Gly Arg Ala Ile Phe Asp Phe Ala Ile Arg
    210                 215                 220

Asp Val Ser Lys Ser Ile Ser Met Leu Ile Arg Lys Ser Asp Met Pro
225                 230                 235                 240

Val Glu Ala Ile Asp Tyr Phe Leu Leu His Gln Ala Asn Ile Arg Ile
                245                 250                 255

Leu Asp Lys Met Ala Lys Lys Ile Gly Ala Asp Arg Glu Lys Phe Pro
            260                 265                 270

Ala Asn Met Met Lys Tyr Gly Asn Thr Ser Ala Ala Ser Ile Pro Ile
        275                 280                 285

Leu Leu Ala Glu Cys Val Glu Asn Gly Thr Ile Glu Leu Asn Gly Ser
    290                 295                 300

His Thr Val Leu Leu Ser Gly Phe Gly Gly Gly Leu Thr Trp Gly Ser
305                 310                 315                 320

Leu Ile Val Lys Ile
                325

<210> SEQ ID NO 101
<211> LENGTH: 978
<212> TYPE: DNA
<213> ORGANISM: Streptococcus mutans

<400> SEQUENCE: 101

-continued

```
atgacttttg caaagattag tcaagcagca tattatgtac catcacaggt tgtcaccaat      60

gatgatttat ctaaaataat ggataccagt gatgaatgga ttacaagtcg tacgggaata     120

agagagcgcc gtattagtca atccgaagat accagtgact tagccagtca ggtggccaaa     180

gaacttttaa aaaaagcctc attaaaggcg aaagagattg attttattat tgttgctaca     240

attactccgg atgcaatgat gccatcaaca gctgcttgtg tccaagcgaa aattggtgca     300

gtgaatgctt ttgctttcga tttaactgcc gcctgcagtg gatttatttt tgcactttca     360

gctgcggaaa aaatgattaa atccggtcag taccagaaag gtttagttat cggtgcagaa     420

gttctatcta aaatcatcga ttggtcggat cgaacaacag ctgttctttt tggagatgga     480

gctggcggtg ttcttttaga agcagattct tctgaacatt ttttatttga atctattcat     540

tcagatggca gtcgtggtga aagtttgaca tcaggtgaac acgctgtttc gtcacccttt     600

tcacaggttg ataaaaaaga taactgtttt ctaaaaatgg atggtcgagc tatatttgac     660

tttgctattc gtgatgtgtc aaaaagtatt tcgatgctca ttaggaagtc agatatgcct     720

gtagaagcga ttgattattt cttattacat caggctaata ttcgtatttt ggataaaatg     780

gctaaaaaaa ttggcgctga tagagaaaaa tttcctgcta atatgatgaa gtatggtaat     840

accagtgcag caagtattcc tattttatta gccgaatgtg tcgaaaatgg aactatagag     900

ctaaatggtt cacacactgt tctcctgagc gggttcggtg gggtttgac atggggcagt     960

ttaattgtta aaatttag                                                   978


<210> SEQ ID NO 102
<211> LENGTH: 325
<212> TYPE: PRT
<213> ORGANISM: Lactococcus lactis

<400> SEQUENCE: 102

Met Thr Phe Ala Lys Ile Thr Gln Val Ala His Tyr Val Pro Glu Asn
1               5                   10                  15

Val Val Ser Asn Asp Asp Leu Ser Lys Ile Met Asp Thr Asn Asp Glu
            20                  25                  30

Trp Ile Tyr Ser Arg Thr Gly Ile Lys Asn Arg His Ile Ser Thr Gly
        35                  40                  45

Glu Asn Thr Ser Asp Leu Ala Ala Lys Val Ala Lys Gln Leu Ile Ser
    50                  55                  60

Asp Ser Asn Leu Ser Pro Glu Thr Ile Asp Phe Ile Ile Val Ala Thr
65                  70                  75                  80

Val Thr Pro Asp Ser Leu Met Pro Ser Thr Ala Ala Arg Val Gln Ala
                85                  90                  95

Gln Val Gly Ala Val Asn Ala Phe Ala Tyr Asp Leu Thr Ala Ala Cys
            100                 105                 110

Ser Gly Phe Val Phe Ala Leu Ser Thr Ala Glu Lys Leu Ile Ser Ser
        115                 120                 125

Gly Ala Tyr Gln Arg Gly Leu Val Ile Gly Ala Glu Val Phe Ser Lys
    130                 135                 140

Val Ile Asp Trp Ser Asp Arg Ser Thr Ala Val Leu Phe Gly Asp Gly
145                 150                 155                 160

Ala Ala Gly Val Leu Ile Glu Ala Gly Ala Ser Gln Pro Leu Ile Ile
                165                 170                 175

Ala Glu Lys Met Gln Thr Asp Gly Ser Arg Gly Asn Ser Leu Leu Ser
            180                 185                 190

Ser Tyr Ala Asp Ile Gln Thr Pro Phe Ala Ser Val Ser Tyr Glu Ser
```

-continued

```
        195                 200                 205

Ser Asn Leu Ser Met Glu Gly Arg Ala Ile Phe Asp Phe Ala Val Arg
    210                 215                 220

Asp Val Pro Lys Asn Ile Gln Ala Thr Leu Glu Lys Ala Asn Leu Ser
225                 230                 235                 240

Ala Glu Glu Val Asp Tyr Tyr Leu Leu His Gln Ala Asn Ser Arg Ile
                245                 250                 255

Leu Asp Lys Met Ala Lys Lys Leu Gly Val Thr Arg Gln Lys Phe Leu
            260                 265                 270

Gln Asn Met Gln Glu Tyr Gly Asn Thr Ser Ala Ala Ser Ile Pro Ile
        275                 280                 285

Leu Leu Ser Glu Ser Val Lys Asn Gly Ile Phe Ser Leu Asp Gly Gln
    290                 295                 300

Thr Lys Val Val Leu Thr Gly Phe Gly Gly Gly Leu Thr Trp Gly Thr
305                 310                 315                 320

Ala Ile Ile Asn Leu
                325


<210> SEQ ID NO 103
<211> LENGTH: 978
<212> TYPE: DNA
<213> ORGANISM: Lactococcus lactis

<400> SEQUENCE: 103

atgacttttg cgaaaattac gcaagtggca cactatgtgc ctgaaaatgt ggtatctaat      60

gatgacttgt ccaaaataat ggatactaat gatgaatgga tttacagtcg gacagggatt     120

aaaaatcgcc atatttcaac tggagagaac acctcagact tagcagctaa agttgctaag     180

cagttgatta gcgattcaaa tttaagccca gaaacgattg acttcatcat tgttgctaca     240

gtaactccgg actcattgat gccttcaacc gcggcacggg ttcaagctca agtaggagca     300

gttaatgctt ttgcttacga tttgactgcg gcttgttcag gctttgtctt tgctctatca     360

acagcggaaa aattaatttc ctcaggagca tatcaacgag ggcttgtcat tggcgcagaa     420

gtcttttcaa aagtaattga ttggtcagac cgatcaactg ctgttctttt cggagatgga     480

gctgctggtg tgcttattga agctggcgcg agtcaacctc tgattattgc tgaaaaaatg     540

caaacagatg gaagtcgtgg gaacagttta ctttctagtt atgctgacat ccaaactcca     600

tttgcctctg tttcatacga aagttcaaac ttgagtatgg aagggcgagc aatttttgat     660

tttgccgtac gtgatgttcc taaaaatatc caggcaactt tagaaaaagc taatttgtct     720

gctgaagaag tagattatta tctccttcat caagcgaatt caagaatcct tgataaaatg     780

gctaaaaagc ttggtgtgac gcgccaaaag ttccttcaaa atatgcaaga atatggtaac     840

acatcggcag caagtatccc tatattgttg tcagaatccg taaaaaatgg tatatttagt     900

ttggacggtc aaacaaaagt cgtcttgaca ggatttggcg gtggcctcac ttggggtaca     960

gcaattatta atttataa                                                   978


<210> SEQ ID NO 104
<211> LENGTH: 317
<212> TYPE: PRT
<213> ORGANISM: Leginonella pneumophila

<400> SEQUENCE: 104

Met Lys Asn Ala Val Ile Ser Gly Thr Gly Ser Tyr Ser Pro Glu Arg
1               5                   10                  15
```

```
Gln Met Thr Asn Ala Glu Leu Glu Thr Met Leu Asp Thr Ser Asp Glu
            20                  25                  30

Trp Ile Val Thr Arg Thr Gly Ile Ser Ser Arg Ser Val Ala Gln Glu
        35                  40                  45

His Glu Thr Thr Ser Tyr Met Ala Ser Arg Ala Ala Glu Gln Ala Leu
    50                  55                  60

Glu Ala Ser Gly Leu Asp Ala Glu Glu Ile Asp Leu Ile Leu Val Ala
65                  70                  75                  80

Thr Cys Thr Pro Asp Tyr Phe Phe Pro Ser Val Ala Cys His Val Gln
                85                  90                  95

His Ala Leu Gly Ile Lys Arg Pro Ile Pro Ala Phe Asp Ile Gly Ala
            100                 105                 110

Ala Cys Ser Gly Phe Val Tyr Ala Met Asp Val Ala Lys Gln Tyr Ile
        115                 120                 125

Ala Thr Gly Ala Ala Lys His Val Leu Val Val Gly Ser Glu Ser Met
    130                 135                 140

Ser Arg Ala Val Asp Trp Thr Asp Arg Ser Ile Cys Val Leu Phe Gly
145                 150                 155                 160

Asp Gly Ala Gly Ala Val Val Leu Ser Ala Ser Asp Arg Gln Gly Ile
                165                 170                 175

Met Gly Ser Val Leu His Ser Ala Tyr Asp Ser Asp Lys Leu Leu Val
            180                 185                 190

Leu Arg Asn Ser Thr Phe Glu Gln Asp Arg Ala Thr Ile Gly Met Arg
        195                 200                 205

Gly Asn Glu Val Phe Lys Ile Ala Val Asn Ile Met Gly Asn Ile Val
    210                 215                 220

Asp Glu Val Leu Glu Ala Ser His Leu Lys Lys Ser Asp Ile Asp Trp
225                 230                 235                 240

Leu Ile Pro His Gln Ala Asn Ile Arg Ile Ile Gln Ala Ile Ala Lys
                245                 250                 255

Lys Leu Ser Leu Pro Met Ser His Val Ile Val Thr Ile Gly Asn Gln
            260                 265                 270

Gly Asn Thr Ser Ala Ala Ser Ile Pro Leu Ala Leu Asp Tyr Ser Ile
        275                 280                 285

Lys Asn Asn Gln Ile Lys Arg Asp Glu Ile Leu Leu Ile Glu Ser Phe
    290                 295                 300

Gly Gly Gly Met Thr Trp Gly Ala Met Val Ile Arg Tyr
305                 310                 315
```

<210> SEQ ID NO 105
<211> LENGTH: 954
<212> TYPE: DNA
<213> ORGANISM: Leginonella pneumophila

<400> SEQUENCE: 105

```
atgaaaaatg ctgttattag tggcactgga agttactctc cagagagaca aatgactaat      60

gctgaactgg aaaccatgct tgatactagc gatgaatgga tagttaccag gactggtatt     120

agtagtcgta gtgttgctca agaacatgaa acaacatctt atatggcctc cagagcagca     180

gagcaagcac tagaggcatc aggccttgat gctgaagaaa ttgatttgat attagtagca     240

acatgtaccc cggattattt ttttcctagc gttgcctgtc acgtacaaca tgctttagga     300

atcaaaagac ctattccggc ttttgacatt ggagctgcat gcagcggttt tgtttatgcg     360

atggatgtag cgaaacaata cattgctaca ggggctgcca aacacgttct tgtcgtaggc     420
```

-continued

```
agcgagagca tgtcaagagc ggtagattgg actgatcgtt ctatttgtgt cttattcgga    480

gatggcgcag gcgctgttgt tttaagcgca agtgatcgcc aagggattat gggtagtgtt    540

ttacattctg cctatgactc tgataaatta ctagtccttc gtaattcaac ttttgaacaa    600

gatcgtgcaa cgattggaat gcgaggtaat gaggtattta aaattgctgt taatattatg    660

ggtaatattg ttgatgaagt gttagaagca agtcatttaa aaaaatctga tattgattgg    720

ctgatacctc atcaagccaa tatacgcatt atacaagcca tagctaaaaa attatctctt    780

cctatgtcac atgttattgt tacaattggt aaccaaggca acacatcggc tgcttctatt    840

cccttagcac ttgattattc tattaaaaat aatcagatta aagggatga aatattatta    900

attgaatcct ttggtggtgg aatgacctgg ggcgctatgg ttattcgtta ctaa          954
```

<210> SEQ ID NO 106
<211> LENGTH: 312
<212> TYPE: PRT
<213> ORGANISM: Listeria monocytogenes

<400> SEQUENCE: 106

```
Met Asn Ala Gly Ile Leu Gly Val Gly Lys Tyr Val Pro Glu Lys Ile
1               5                   10                  15

Val Thr Asn Phe Asp Leu Glu Lys Ile Met Asp Thr Ser Asp Glu Trp
            20                  25                  30

Ile Arg Thr Arg Thr Gly Ile Glu Glu Arg Arg Ile Ala Arg Asp Asp
        35                  40                  45

Glu Tyr Thr His Asp Leu Ala Tyr Glu Ala Ala Lys Val Ala Ile Glu
    50                  55                  60

Asn Ala Gly Leu Thr Pro Asp Asp Ile Asp Leu Phe Ile Val Ala Thr
65                  70                  75                  80

Val Thr Gln Glu Ala Thr Phe Pro Ser Val Ala Asn Ile Ile Gln Asp
                85                  90                  95

Arg Leu Gly Ala Thr Asn Ala Ala Gly Met Asp Val Glu Ala Ala Cys
            100                 105                 110

Ala Gly Phe Thr Phe Gly Val Val Thr Ala Ala Gln Phe Ile Lys Thr
        115                 120                 125

Gly Ala Tyr Lys Asn Ile Val Val Val Gly Ala Asp Lys Leu Ser Lys
    130                 135                 140

Ile Thr Asn Trp Asp Asp Arg Ala Thr Ala Val Leu Phe Gly Asp Gly
145                 150                 155                 160

Ala Gly Ala Val Val Met Gly Pro Val Ser Asp Asp His Gly Leu Leu
                165                 170                 175

Ser Phe Asp Leu Gly Ser Asp Gly Ser Gly Gly Lys Tyr Leu Asn Leu
            180                 185                 190

Asp Glu Asn Lys Lys Ile Tyr Met Asn Gly Arg Glu Val Phe Arg Phe
        195                 200                 205

Ala Val Arg Gln Met Gly Glu Ala Ser Leu Arg Val Leu Glu Arg Ala
    210                 215                 220

Gly Leu Glu Lys Glu Glu Leu Asp Leu Leu Ile Pro His Gln Ala Asn
225                 230                 235                 240

Ile Arg Ile Met Glu Ala Ser Arg Glu Arg Leu Asn Leu Pro Glu Glu
                245                 250                 255

Lys Leu Met Lys Thr Val His Lys Tyr Gly Asn Thr Ser Ser Ser Ser
            260                 265                 270

Ile Ala Leu Ala Leu Val Asp Ala Val Glu Glu Gly Arg Ile Lys Asp
        275                 280                 285
```

```
Asn Asp Asn Val Leu Leu Val Gly Phe Gly Gly Gly Leu Thr Trp Gly
    290                 295                 300

Ala Leu Ile Ile Arg Trp Gly Lys
305                 310
```

<210> SEQ ID NO 107
<211> LENGTH: 939
<212> TYPE: DNA
<213> ORGANISM: Listeria monocytogenes

<400> SEQUENCE: 107

```
atgaacgcag gaattttagg agtaggtaaa tacgtacctg aaaaaatagt aacaaatttt      60

gatttagaaa aaataatgga tacatccgat gagtggattc gtactcgaac tggtattgaa     120

gaaagaagaa ttgctcgtga tgacgaatat acgcacgact tagcatacga agcagcaaag     180

gtagctattg agaatgctgg gcttacacca gatgacattg acttatttat tgttgccact     240

gtgacgcagg aagcgacttt tccatccgtt gcgaatatta ttcaagaccg tttaggagca     300

acaaatgctg cgggtatgga cgtggaagcg gcatgtgccg gttttacttt tggcgtagta     360

actgcagcac aatttattaa aacaggggca tacaagaata tcgtcgtagt tggtgcggat     420

aaattatcta aaatcactaa ctgggatgat cgcgcaacag ccgtattatt tggtgatgga     480

gcgggagccg ttgttatggg tccggtttct gatgaccatg gactactttc gtttgactta     540

ggctcagatg gatctggcgg caaatacttg aacttagatg aaaataagaa gatttatatg     600

aatggacgtg aagtgttccg ttttgcagtt cgccaaatgg gagaagcttc gttacgagta     660

cttgaacgtg ctggacttga aaaagaagaa ttggatttac taattcctca ccaagcaaat     720

atccgtatca tggaagcttc tcgcgagcgt ttgaatttac cggaagaaaa actgatgaaa     780

acagtgcata aatacggtaa tacttcgtca tcttctattg ctcttgcgct agttgatgca     840

gtcgaagaag gacgcattaa agataatgac aatgtcctgc ttgttggctt tggcggcgga     900

ctaacatggg gcgccctaat cattcgttgg ggtaagtaa                            939
```

<210> SEQ ID NO 108
<211> LENGTH: 325
<212> TYPE: PRT
<213> ORGANISM: Bacillus subtilis subsp. subtilis str. 168

<400> SEQUENCE: 108

```
Met Ser Lys Ala Lys Ile Thr Ala Ile Gly Thr Tyr Ala Pro Ser Arg
1               5                   10                  15

Arg Leu Thr Asn Ala Asp Leu Glu Lys Ile Val Asp Thr Ser Asp Glu
            20                  25                  30

Trp Ile Val Gln Arg Thr Gly Met Arg Glu Arg Arg Ile Ala Asp Glu
        35                  40                  45

His Gln Phe Thr Ser Asp Leu Cys Ile Glu Ala Val Lys Asn Leu Lys
    50                  55                  60

Ser Arg Tyr Lys Gly Thr Leu Asp Asp Val Asp Met Ile Leu Val Ala
65                  70                  75                  80

Thr Thr Thr Ser Asp Tyr Ala Phe Pro Ser Thr Ala Cys Arg Val Gln
                85                  90                  95

Glu Tyr Phe Gly Trp Glu Ser Thr Gly Ala Leu Asp Ile Asn Ala Thr
            100                 105                 110

Cys Ala Gly Leu Thr Tyr Gly Leu His Leu Ala Asn Gly Leu Ile Thr
        115                 120                 125
```

-continued

```
Ser Gly Leu His Gln Lys Ile Leu Val Ile Ala Gly Glu Thr Leu Ser
    130                 135                 140

Lys Val Thr Asp Tyr Thr Asp Arg Thr Thr Cys Val Leu Phe Gly Asp
145                 150                 155                 160

Ala Ala Gly Ala Leu Leu Val Glu Arg Asp Glu Glu Thr Pro Gly Phe
                165                 170                 175

Leu Ala Ser Val Gln Gly Thr Ser Gly Asn Gly Gly Asp Ile Leu Tyr
            180                 185                 190

Arg Ala Gly Leu Arg Asn Glu Ile Asn Gly Val Gln Leu Val Gly Ser
        195                 200                 205

Gly Lys Met Val Gln Asn Gly Arg Glu Val Tyr Lys Trp Ala Ala Arg
    210                 215                 220

Thr Val Pro Gly Glu Phe Glu Arg Leu Leu His Lys Ala Gly Leu Ser
225                 230                 235                 240

Ser Asp Asp Leu Asp Trp Phe Val Pro His Ser Ala Asn Leu Arg Met
                245                 250                 255

Ile Glu Ser Ile Cys Glu Lys Thr Pro Phe Pro Ile Glu Lys Thr Leu
            260                 265                 270

Thr Ser Val Glu His Tyr Gly Asn Thr Ser Ser Val Ser Ile Val Leu
        275                 280                 285

Ala Leu Asp Leu Ala Val Lys Ala Gly Lys Leu Lys Lys Asp Gln Ile
    290                 295                 300

Val Leu Leu Phe Gly Phe Gly Gly Gly Leu Thr Tyr Thr Gly Leu Leu
305                 310                 315                 320

Ile Lys Trp Gly Met
                325


<210> SEQ ID NO 109
<211> LENGTH: 978
<212> TYPE: DNA
<213> ORGANISM: Bacillus subtilis subsp. subtilis str. 168

<400> SEQUENCE: 109

atgtcaaaag caaaaattac agctatcggc acctatgcgc cgagcagacg tttaaccaat      60

gcagatttag aaaagatcgt tgatacctct gatgaatgga tcgttcagcg cacaggaatg     120

agagaacgcc ggattgcgga tgaacatcaa tttacctctg atttatgcat agaagcggtg     180

aagaatctca agagccgtta taaaggaacg cttgatgatg tcgatatgat cctcgttgcc     240

acaaccacat ccgattacgc ctttccgagt acggcatgcc gcgtacagga atatttcggc     300

tgggaaagca ccggcgcgct ggatattaat gcgacatgcg ccgggctgac atacggcctc     360

catttggcaa atggattgat cacatctggc cttcatcaaa aaattctcgt catcgccgga     420

gagacgttat caaaggtaac cgattatacc gatcgaacga catgcgtact gttcggcgat     480

gccgcgggtg cgctgttagt agaacgagat gaagagacgc cgggatttct tgcgtctgta     540

caaggaacaa gcgggaacgg cggcgatatt ttgtatcgtg ccggactgcg aaatgaaata     600

aacggtgtgc agcttgtcgg ttccggaaaa atggtgcaaa acggacgcga ggtatataaa     660

tgggccgcaa gaaccgtccc tggcgaattt gaacggcttt tacataaagc aggactcagc     720

tccgatgatc tcgattggtt tgttcctcac agcgccaact tgcgcatgat cgagtcaatt     780

tgtgaaaaaa caccgttccc gattgaaaaa acgctcacta gtgttgagca ctacggaaac     840

acgtcttcgg tttcaattgt tttggcgctc gatctcgcag tgaaagccgg gaagctgaaa     900

aaagatcaaa tcgttttgct tttcgggttt ggcggcggat taacctatac aggattgctt     960
```

attaaatggg ggatgtaa 978

<210> SEQ ID NO 110
<211> LENGTH: 331
<212> TYPE: PRT
<213> ORGANISM: Myxococcus xanthus

<400> SEQUENCE: 110

```
Met Arg Tyr Ala Gln Ile Leu Ser Thr Gly Arg Tyr Val Pro Glu Lys
1               5                   10                  15

Val Leu Thr Asn Ala Asp Val Glu Lys Ile Leu Gly Glu Lys Val Asp
            20                  25                  30

Glu Trp Leu Gln Gln Asn Val Gly Ile Arg Glu Arg His Met Met Ala
        35                  40                  45

Asp Asp Gln Ala Thr Ser Asp Leu Cys Val Gly Ala Ala Arg Gln Ala
    50                  55                  60

Leu Glu Arg Ala Gly Thr Lys Pro Glu Glu Leu Asp Leu Ile Ile Ile
65                  70                  75                  80

Ala Thr Asp Thr Pro Asp Tyr Leu Ser Pro Ala Thr Ala Ser Val Val
                85                  90                  95

Gln Ala Lys Leu Gly Ala Val Asn Ala Gly Thr Tyr Asp Leu Asn Cys
            100                 105                 110

Ala Cys Ala Gly Trp Val Thr Ala Leu Asp Val Gly Ser Lys Thr Ile
        115                 120                 125

Ala Ala Asp Asp Ser Tyr Gln Arg Ile Leu Val Val Gly Ala Tyr Gly
    130                 135                 140

Met Ser Arg Tyr Ile Asn Trp Lys Asp Lys Lys Thr Ala Thr Leu Phe
145                 150                 155                 160

Ala Asp Gly Ala Gly Ala Val Val Leu Gly Ala Gly Asp Thr Pro Gly
                165                 170                 175

Phe Met Gly Ala Lys Leu Leu Ala Asn Gly Glu Tyr His Asp Ala Leu
            180                 185                 190

Gly Val Tyr Thr Gly Gly Thr Asn Arg Pro Ala Thr Ala Glu Ser Leu
        195                 200                 205

Glu Leu Thr Gly Gly Lys Pro Ala Val Gln Phe Val Arg Lys Phe Pro
    210                 215                 220

Ala Thr Phe Asn Thr Glu Arg Trp Pro Met Leu Leu Asp Gln Leu Leu
225                 230                 235                 240

Lys Arg Gln Asn Leu Lys Leu Asp Asp Val Lys Gln Phe Val Phe Thr
                245                 250                 255

Gln Leu Asn Leu Arg Thr Ile Glu Ala Thr Met Lys Ile Leu Gly Gln
            260                 265                 270

Pro Met Glu Lys Ala His Tyr Thr Met Asp Lys Trp Gly Tyr Thr Gly
        275                 280                 285

Ser Ala Cys Ile Pro Met Thr Leu Asp Asp Ala Val Val Gln Gly Lys
    290                 295                 300

Val Gln Arg Gly Asp Leu Val Ala Leu Cys Ala Ser Gly Gly Gly Leu
305                 310                 315                 320

Ala Met Ala Ser Ala Leu Tyr Arg Trp Thr Ala
                325                 330
```

<210> SEQ ID NO 111
<211> LENGTH: 996
<212> TYPE: DNA
<213> ORGANISM: Myxococcus xanthus

<400> SEQUENCE: 111

```
atgcgatacg cccagattct ctccactggc cgctacgtcc ccgagaaggt cctcaccaac      60

gctgacgtcg agaagattct cggtgagaag gtggatgagt ggctccagca gaacgtgggc     120

attcgcgaac gccacatgat ggcggatgac caggccacct ccgacctctg cgtgggcgcc     180

gcccgccagg cgctggagcg cgcgggcacg aagccggagg aactggacct catcatcatc     240

gccaccgata ccccggacta tctcagcccc gccacggcct ccgtggtgca ggcgaagctg     300

ggcgcggtga acgccggcac ctacgacctc aactgcgcgt gcgcgggctg ggtgacggcg     360

ctggacgtgg gctcgaagac gattgccgcg gatgacagct accagcgcat cctcgtcgtg     420

ggcgcctacg gcatgtcgcg ctacatcaac tggaaggaca agaagaccgc caccctgttc     480

gcggacggcg cgggcgcggt cgtgctgggc gcgggtgaca cgcccggctt catgggcgcg     540

aagctgctgg ccaacggcga gtaccacgac gcgctgggtg tctacaccgg cggtacgaac     600

cgcccggcca ccgcggagtc gctggagctc acgggcggca agcccgcggt gcagttcgtc     660

cgcaagttcc cggcgacgtt caacaccgag cgctggccca tgctgctgga ccagctcctc     720

aagcggcaga acctgaagct ggacgacgtg aagcagttcg tcttcacgca gctcaacctg     780

cgcaccatcg aagccaccat gaagatcctg ggccagccga tggagaaggc ccactacacc     840

atggacaagt ggggctacac cggttcggcc tgcatcccga tgacgctgga tgacgcggtg     900

gtgcagggca aggtgcagcg cggcgacctg gtggccctgt gtgccagcgg cggcgggctc     960

gccatggcct ccgccctcta ccgctggacg gcctga                               996
```

<210> SEQ ID NO 112
<211> LENGTH: 325
<212> TYPE: PRT
<213> ORGANISM: Stenotrophomonas maltophilia

<400> SEQUENCE: 112

```
Met Ser Lys Arg Ile Tyr Ser Arg Ile Ala Gly Thr Gly Ser Tyr Leu
1               5                   10                  15

Pro Glu Lys Val Leu Thr Asn Ala Asp Leu Glu Lys Met Val Glu Thr
            20                  25                  30

Ser Asp Glu Trp Ile Gln Ser Arg Thr Gly Ile Arg Glu Arg His Ile
        35                  40                  45

Ala Ala Glu Gly Glu Thr Thr Ser Asp Leu Gly Tyr Asn Ala Ala Leu
    50                  55                  60

Arg Ala Leu Glu Ala Ala Gly Ile Asp Ala Ser Gln Leu Asp Met Ile
65                  70                  75                  80

Val Val Gly Thr Thr Thr Pro Asp Leu Ile Phe Pro Ser Thr Ala Cys
                85                  90                  95

Leu Ile Gln Ala Lys Leu Gly Val Ala Gly Cys Pro Ala Phe Asp Val
            100                 105                 110

Asn Ala Ala Cys Ser Gly Phe Val Phe Ala Leu Gly Val Ala Asp Lys
        115                 120                 125

Phe Ile Arg Ser Gly Asp Cys Arg Tyr Val Leu Val Ile Gly Ala Glu
    130                 135                 140

Thr Leu Thr Arg Met Val Asp Trp Asn Asp Arg Thr Thr Cys Val Leu
145                 150                 155                 160

Phe Gly Asp Gly Ala Gly Ala Val Val Leu Lys Ala Asp Glu Glu Thr
                165                 170                 175

Gly Ile Leu Ser Thr His Leu His Ser Asp Gly Ser Lys Lys Glu Leu
            180                 185                 190
```

```
Leu Trp Asn Pro Val Gly Val Ser Thr Gly Phe Lys Gly Gly Ala Asn
        195                 200                 205

Gly Gly Gly Thr Ile Asn Met Lys Gly Asn Asp Val Phe Lys Tyr Ala
    210                 215                 220

Val Lys Ala Leu Asp Ser Val Val Asp Glu Thr Leu Ala Ala Asn Gly
225                 230                 235                 240

Leu Asp Lys Ser Asp Leu Asp Trp Leu Ile Pro His Gln Ala Asn Leu
                245                 250                 255

Arg Ile Ile Glu Ala Thr Ala Lys Arg Leu Asp Met Ser Met Glu Gln
            260                 265                 270

Val Val Val Thr Val Asp Gln His Gly Asn Thr Ser Ser Gly Ser Val
        275                 280                 285

Pro Leu Ala Leu Asp Ala Ala Val Arg Ser Gly Lys Val Glu Arg Gly
    290                 295                 300

Gln Leu Leu Leu Leu Glu Ala Phe Gly Gly Gly Phe Thr Trp Gly Ser
305                 310                 315                 320

Ala Leu Leu Arg Tyr
                325
```

<210> SEQ ID NO 113
<211> LENGTH: 978
<212> TYPE: DNA
<213> ORGANISM: Stenotrophomonas maltophilia

<400> SEQUENCE: 113

```
atgagcaagc ggatctattc gaggatcgcg ggcaccggta gctatttgcc ggaaaaagtc      60

ctgaccaacg ccgacctgga aaaaatggtc gaaacctcgg atgagtggat ccagtcgcgc     120

accggcattc gtgaacggca catcgcggcc gaaggcgaaa ccaccagcga tctcggctac     180

aacgccgcgc tgcgcgcact tgaagcggcc ggcatcgacg cttcgcagct cgacatgatc     240

gtggtcggta cgaccacccc tgaccttatt ttcccgtcca ccgcgtgcct gatccaggcc     300

aagctcggtg tggccggatg ccccgccttc gacgtcaacg cggcctgttc gggtttcgtg     360

ttcgcgctgg gcgtggccga caaattcatc cgttccggcg actgccggta cgtgctggtg     420

atcggcgccg aaacgctgac ccgcatggtt gactggaacg atcgcaccac ctgcgtgctg     480

ttcggtgatg gtgccggcgc cgtcgtgctc aaggccgacg aagagaccgg catcctcagc     540

acccacctgc attccgatgg cagcaagaag gagctgttgt ggaacccggt gggtgtctcg     600

accggtttca agggcggcgc caacggtggt ggcactatca acatgaaggg caacgatgtg     660

ttcaagtacg ccgtcaaggc gctggactcg gtcgtggacg agaccttggc tgcgaacggc     720

ctggacaagt ccgacctgga ttggctgatt ccgcaccagg ccaacctacg catcatcgaa     780

gccacggcca agcgcctgga catgtcgatg gaacaggtcg tggtcacggt tgatcagcac     840

ggcaacacct cgtccggctc ggtgccgctg gcgctggacg ctgcagtgcg atcgggcaag     900

gtcgagcgcg gccagctgct gttgctggaa gccttcggcg gcggcttcac ctggggttcg     960

gccctgctgc gctattga                                                   978
```

<210> SEQ ID NO 114
<211> LENGTH: 334
<212> TYPE: PRT
<213> ORGANISM: Bacteroides vulgatus

<400> SEQUENCE: 114

```
Met Glu Lys Ile Asn Ala Val Ile Thr Gly Val Gly Gly Tyr Val Pro
```

-continued 1 5 10 15

Asp Tyr Val Leu Thr Asn Glu Glu Ile Ser Arg Met Val Asp Thr Asn
20 25 30

Asp Glu Trp Ile Met Thr Arg Ile Gly Val Lys Glu Arg Arg Ile Leu
35 40 45

Asn Glu Glu Gly Leu Gly Thr Ser Tyr Met Ala Arg Lys Ala Ala Lys
50 55 60

Gln Leu Met Gln Lys Thr Ala Ser Asn Pro Asp Asp Ile Asp Ala Val
65 70 75 80

Ile Val Ala Thr Thr Thr Pro Asp Tyr His Phe Pro Ser Thr Ala Ser
85 90 95

Ile Leu Cys Asp Lys Leu Gly Leu Lys Asn Ala Phe Ala Phe Asp Leu
100 105 110

Gln Ala Ala Cys Cys Gly Phe Leu Tyr Leu Met Glu Thr Ala Ala Ser
115 120 125

Leu Ile Ala Ser Gly Arg His Lys Lys Ile Ile Ile Val Gly Ala Asp
130 135 140

Lys Met Ser Ser Met Val Asn Tyr Gln Asp Arg Ala Thr Cys Pro Ile
145 150 155 160

Phe Gly Asp Gly Ala Ala Ala Cys Met Val Glu Ala Thr Thr Glu Asp
165 170 175

Tyr Gly Ile Met Asp Ser Ile Leu Arg Thr Asp Gly Lys Gly Leu Pro
180 185 190

Phe Leu His Met Lys Ala Gly Gly Ser Val Cys Pro Pro Ser Tyr Phe
195 200 205

Thr Val Asp His Lys Met His Tyr Leu Tyr Gln Glu Gly Arg Thr Val
210 215 220

Phe Lys Tyr Ala Val Ser Asn Met Ser Asp Ile Thr Ala Thr Ile Ala
225 230 235 240

Glu Lys Asn Gly Leu Asn Lys Asp Asn Ile Asp Trp Val Ile Pro His
245 250 255

Gln Ala Asn Leu Arg Ile Ile Asp Ala Val Ala Ser Arg Leu Glu Val
260 265 270

Pro Leu Glu Lys Val Met Ile Asn Ile Gln Arg Tyr Gly Asn Thr Ser
275 280 285

Gly Ala Thr Leu Pro Leu Cys Leu Trp Asp Tyr Glu Lys Gln Leu Lys
290 295 300

Lys Gly Asp Asn Leu Ile Phe Thr Ala Phe Gly Ala Gly Phe Thr Tyr
305 310 315 320

Gly Ala Val Tyr Val Lys Trp Gly Tyr Asp Gly Ser Lys Arg
325 330

<210> SEQ ID NO 115
<211> LENGTH: 1005
<212> TYPE: DNA
<213> ORGANISM: Bacteroides vulgatus

<400> SEQUENCE: 115
atggaaaaaa taaatgcagt aataacagga gtcggtggat atgtaccaga ttatgtcttg 60
actaacgaag agatttcaag aatggtagat accaatgatg aatggattat gactcgaatc 120
ggagttaaag aaagacgtat tctgaatgaa gaaggattag gtacatcgta tatggcgcgt 180
aaggctgcca aacaactgat gcagaaaaca gcttctaatc cggatgacat tgatgcagta 240
atcgtagcaa ctactactcc tgactatcat ttcccttcca ctgcttctat cctgtgtgat 300

```
aagctgggat tgaaaaatgc atttgcattt gatttgcagg ctgcctgctg cggctttttg    360

tatttaatgg aaactgctgc ttcacttatc gcatcgggaa gacataaaaa gattattatt    420

gtcggtgcag ataagatgtc atctatggta aactaccagg atcgtgcaac ttgccctatc    480

tttggtgatg gtgcagcagc atgtatggtg gaagctacta cagaagatta tggtattatg    540

gattctattc ttcgtacaga tggtaaggga cttccttttc ttcacatgaa agccggtggt    600

tctgtatgtc ctccttctta tttcactgtt gatcataaga tgcattatct ttatcaggaa    660

ggaagaacag tatttaaata tgctgtttcc aatatgtcgg atattacagc gactattgcc    720

gaaaagaatg gtttgaataa agataaatatc gactgggtaa ttcctcatca ggctaatctg    780

cgtattattg atgcggtagc ctctcgcttg gaagttccct tggaaaaggt aatgattaat    840

attcagcgat atggtaatac cagtggtgct acacttccgt tgtgtctttg ggattacgaa    900

aagcagctga agaaaggaga taacctgata tttacagctt tcggcgcagg ttttacctat    960

ggagccgttt atgtgaaatg gggttacgat ggtagtaaga gataa                   1005
```

<210> SEQ ID NO 116
<211> LENGTH: 325
<212> TYPE: PRT
<213> ORGANISM: Clostridium acetobutylicum

<400> SEQUENCE: 116

```
Met Asn Ser Val Glu Ile Ile Gly Thr Gly Ser Tyr Val Pro Glu Lys
1               5                   10                  15

Ile Val Thr Asn Glu Asp Met Ser Lys Ile Val Asp Thr Ser Asp Glu
            20                  25                  30

Trp Ile Ser Ser Arg Thr Gly Ile Lys Glu Arg Arg Ile Ser Ile Asn
        35                  40                  45

Glu Asn Thr Ser Asp Leu Gly Ala Lys Ala Ala Leu Arg Ala Ile Glu
    50                  55                  60

Asp Ser Asn Ile Lys Pro Glu Glu Ile Asp Leu Ile Ile Val Ala Thr
65                  70                  75                  80

Thr Ser Pro Asp Ser Tyr Thr Pro Ser Val Ala Cys Ile Val Gln Glu
                85                  90                  95

Lys Ile Gly Ala Lys Asn Ala Ala Cys Phe Asp Leu Asn Ala Ala Cys
            100                 105                 110

Thr Gly Phe Ile Phe Ala Leu Asn Thr Ala Ser Gln Phe Ile Lys Thr
        115                 120                 125

Gly Glu Tyr Lys Thr Ala Leu Val Val Gly Thr Glu Val Leu Ser Lys
    130                 135                 140

Ile Leu Asp Trp Gln Asp Arg Gly Thr Cys Val Leu Phe Gly Asp Gly
145                 150                 155                 160

Ala Gly Ala Val Ile Ile Arg Gly Gly Asp Glu Asn Gly Ile Ile Lys
                165                 170                 175

Ala Cys Leu Gly Ser Asp Gly Thr Gly Lys Asp Phe Leu His Cys Pro
            180                 185                 190

Ala Thr Asn Val Ile Asn Pro Phe Ser Asp Glu Lys Gly Leu Ala Ser
        195                 200                 205

Ser Lys Ile Ser Met Asn Gly Arg Glu Val Phe Lys Phe Ala Val Lys
    210                 215                 220

Val Met Val Ser Ser Val Lys Lys Val Ile Glu Asp Ser Gly Leu Asn
225                 230                 235                 240

Ile Glu Asp Ile Asp Tyr Ile Val Pro His Gln Ala Asn Ile Arg Ile
```

-continued

```
            245                 250                 255

Ile Glu Phe Ala Ala Lys Lys Leu Gly Leu Ser Met Asp Lys Phe Phe
            260                 265                 270

Ile Asn Leu Gln Asn Tyr Gly Asn Thr Ser Gly Ala Thr Ile Pro Leu
        275                 280                 285

Ala Ile Asp Glu Met Asn Lys Lys Gly Leu Leu Lys Arg Gly Ala Lys
    290                 295                 300

Ile Val Val Val Gly Phe Gly Gly Gly Leu Thr Trp Gly Ser Met Val
305                 310                 315                 320

Leu Lys Trp Thr Lys
                325


<210> SEQ ID NO 117
<211> LENGTH: 978
<212> TYPE: DNA
<213> ORGANISM: Clostridium acetobutylicum

<400> SEQUENCE: 117

gtgaatagtg ttgagattat agggactgga agctatgtcc cagaaaaaat agttactaat      60

gaagatatgt ctaagatagt tgatactagt gatgagtgga tatcatcaag aacaggtata     120

aaggaaagaa gaatatctat aaacgaaaat acatcagatt taggtgctaa agctgcctta     180

agggcaatag aggactcaaa cataaaacca gaagaaatag atttaataat agttgcaact     240

acaagtccag actcatatac tccatccgta gcttgtattg ttcaggagaa gataggtgcc     300

aaaaatgctg cctgttttga tttgaatgcg gcatgtactg gatttatatt tgctcttaat     360

acggcatctc agtttataaa aacaggagag tataaaacag ctcttgtagt aggaacagag     420

gtactatcaa agatacttga ttggcaagat agaggtacat gtgtactttt tggagatggt     480

gcaggtgcgg taattataag aggcggagat gaaaacggaa ttattaaagc atgtcttggt     540

tcagatggta cgggaaaaga cttcttgcat tgtccagcga ctaatgtgat aaatccattt     600

tcggatgaaa aaggtttagc aagcagtaag atttctatga atggaagaga agtctttaaa     660

tttgcagtta aggtaatggt aagctcagtt aaaaaggtta tagaagatag tggactaaat     720

atagaagaca ttgattatat agtacctcat caggctaaca ttagaataat agagtttgca     780

gctaaaaaac ttggattaag tatggacaaa ttttttataa acctacaaaa ctatggaaat     840

acatctggag cgactatacc actggcaata gatgaaatga ataaaaaagg cttgcttaaa     900

agaggtgcta aaatagttgt agttggtttt ggtggaggac ttacttgggg ttccatggtt     960

cttaaatgga ctaaataa                                                   978


<210> SEQ ID NO 118
<211> LENGTH: 332
<212> TYPE: PRT
<213> ORGANISM: Flavobacterium johnsoniae

<400> SEQUENCE: 118

Met Asn Thr Ile Thr Ala Ala Ile Thr Ala Val Gly Gly Tyr Val Pro
1               5                   10                  15

Asp Phe Val Leu Ser Asn Lys Val Leu Glu Thr Met Val Asp Thr Asn
            20                  25                  30

Asp Glu Trp Ile Thr Thr Arg Thr Gly Ile Lys Glu Arg Arg Ile Leu
        35                  40                  45

Lys Asp Ala Asp Lys Gly Thr Ser Tyr Leu Ala Ile Gln Ala Ala Gln
    50                  55                  60
```

-continued

```
Asp Leu Ile Ala Lys Ala Asn Ile Asp Pro Leu Glu Ile Asp Met Val
65                  70                  75                  80

Ile Met Ala Thr Ala Thr Pro Asp Met Met Val Ala Ser Thr Gly Val
                85                  90                  95

Tyr Val Ala Thr Glu Ile Gly Ala Val Asn Ala Phe Ala Tyr Asp Leu
            100                 105                 110

Gln Ala Ala Cys Ser Ser Phe Leu Tyr Gly Met Ser Thr Ala Ala Ala
        115                 120                 125

Tyr Val Gln Ser Gly Arg Tyr Lys Lys Val Leu Leu Ile Gly Ala Asp
    130                 135                 140

Lys Met Ser Ser Ile Val Asp Tyr Thr Asp Arg Ala Thr Cys Ile Ile
145                 150                 155                 160

Phe Gly Asp Gly Ala Gly Ala Val Leu Phe Glu Pro Asn Tyr Glu Gly
                165                 170                 175

Leu Gly Leu Gln Asp Glu Tyr Leu Arg Ser Asp Gly Val Gly Arg Asp
            180                 185                 190

Phe Leu Lys Ile Pro Ala Gly Gly Ser Leu Ile Pro Ala Ser Glu Asp
        195                 200                 205

Thr Val Lys Asn Arg Gln His Asn Ile Met Gln Asp Gly Lys Thr Val
    210                 215                 220

Phe Lys Tyr Ala Val Thr Asn Met Ala Asp Ala Ser Glu Leu Ile Leu
225                 230                 235                 240

Gln Arg Asn Asn Leu Thr Asn Gln Asp Val Asp Trp Leu Val Pro His
                245                 250                 255

Gln Ala Asn Lys Arg Ile Ile Asp Ala Thr Ala Gly Arg Leu Glu Leu
            260                 265                 270

Glu Glu Ser Lys Val Leu Val Asn Ile Glu Arg Tyr Gly Asn Thr Thr
        275                 280                 285

Ser Gly Thr Leu Pro Leu Val Leu Ser Asp Phe Glu Asn Gln Phe Lys
    290                 295                 300

Lys Gly Asp Asn Ile Ile Leu Ala Ala Phe Gly Gly Gly Phe Thr Trp
305                 310                 315                 320

Gly Ser Ile Tyr Leu Lys Trp Ala Tyr Asp Lys Lys
                325                 330
```

<210> SEQ ID NO 119
<211> LENGTH: 999
<212> TYPE: DNA
<213> ORGANISM: Flavobacterium johnsoniae

<400> SEQUENCE: 119

```
atgaatacaa tcacagccgc aattaccgct gttggaggct acgttccaga ctttgtgctt      60

tcaaacaaag tgttggaaac aatggtagat accaatgacg aatggattac cactcgtaca     120

ggaattaaag aaagaagaat tcttaaagat gctgataaag gtacatctta ccttgccata     180

caagcagcac aggatttaat agcaaaagct aatattgatc ctcttgaaat tgatatggtt     240

attatggcaa ctgcaacacc agatatgatg gtagcttcaa caggagttta tgttgcaaca     300

gaaattggag ctgttaatgc atttgcatac gatttgcagg cagcttgttc aagtttctta     360

tacggaatgt ctactgctgc ggcttatgta caatctggaa gatataaaaa agttctttta     420

attggtgccg ataaaatgtc atcaattgta gattacacag acagagcaac ttgtattatt     480

tttggtgatg gagcaggggc agttttgttt gagccaaatt acgaaggtct tggtctgcaa     540

gacgaatatt taagaagtga tggtgtagga cgcgattttc ttaaaatacc agctggagga     600
```

```
tctttaattc cagcttcaga agatactgta aaaaacagac aacacaatat tatgcaggat    660

ggtaaaacag tttttaaata tgctgtaacc aatatggctg atgccagcga actaatcttg    720

caaagaaaca atttaactaa tcaggatgtt gattggttag tgcctcacca ggcaaacaaa    780

cgcatcatcg atgcaactgc aggaagacta gagttagaag agtctaaagt actagttaat    840

atcgaaagat atggtaatac aacttcagga acattacctt tggtattaag cgattttgaa    900

aatcaattca aaaaaggaga taatattatt ttagcagcat ttggaggtgg attcacttgg    960

ggatctattt acctaaaatg ggcttacgat aagaaataa                           999


<210> SEQ ID NO 120
<211> LENGTH: 350
<212> TYPE: PRT
<213> ORGANISM: Micrococcus luteus

<400> SEQUENCE: 120

Met Thr Val Thr Leu Lys Gln His Glu Arg Pro Ala Ala Ser Arg Ile
1               5                   10                  15

Val Ala Val Gly Ala Tyr Arg Pro Ala Asn Leu Val Pro Asn Glu Asp
            20                  25                  30

Leu Ile Gly Pro Ile Asp Ser Ser Asp Glu Trp Ile Arg Gln Arg Thr
        35                  40                  45

Gly Ile Val Thr Arg Gln Arg Ala Thr Ala Glu Glu Thr Val Pro Val
    50                  55                  60

Met Ala Val Gly Ala Ala Arg Glu Ala Leu Glu Arg Ala Gly Leu Gln
65                  70                  75                  80

Gly Ser Asp Leu Asp Ala Val Ile Val Ser Thr Val Thr Phe Pro His
                85                  90                  95

Ala Thr Pro Ser Ala Ala Ala Leu Val Ala His Glu Ile Gly Ala Thr
            100                 105                 110

Pro Ala Pro Ala Tyr Asp Val Ser Ala Ala Cys Ala Gly Tyr Cys Tyr
        115                 120                 125

Gly Val Ala Gln Ala Asp Ala Leu Val Arg Ser Gly Thr Ala Arg His
    130                 135                 140

Val Leu Val Val Gly Val Glu Arg Leu Ser Asp Val Val Asp Pro Thr
145                 150                 155                 160

Asp Arg Ser Ile Ser Phe Leu Leu Gly Asp Gly Ala Gly Ala Val Ile
                165                 170                 175

Val Ala Ala Ser Asp Glu Pro Gly Ile Ser Pro Ser Val Trp Gly Ser
            180                 185                 190

Asp Gly Glu Arg Trp Ser Thr Ile Ser Met Thr His Ser Gln Leu Glu
        195                 200                 205

Leu Arg Asp Ala Val Glu His Ala Arg Thr Thr Gly Asp Ala Ser Ala
    210                 215                 220

Ile Thr Gly Ala Glu Gly Met Leu Trp Pro Thr Leu Arg Gln Asp Gly
225                 230                 235                 240

Pro Ser Val Phe Arg Trp Ala Val Trp Ser Met Ala Lys Val Ala Arg
                245                 250                 255

Glu Ala Leu Asp Ala Ala Gly Val Glu Pro Glu Asp Leu Ala Ala Phe
            260                 265                 270

Ile Pro His Gln Ala Asn Met Arg Ile Ile Asp Glu Phe Ala Lys Gln
        275                 280                 285

Leu Lys Leu Pro Glu Ser Val Val Val Ala Arg Asp Ile Ala Asp Ala
    290                 295                 300
```

```
Gly Asn Thr Ser Ala Ala Ser Ile Pro Leu Ala Met His Arg Leu Leu
305                 310                 315                 320

Glu Glu Asn Pro Glu Leu Ser Gly Gly Leu Ala Leu Gln Ile Gly Phe
                325                 330                 335

Gly Ala Gly Leu Val Tyr Gly Ala Gln Val Val Arg Leu Pro
            340                 345                 350


<210> SEQ ID NO 121
<211> LENGTH: 979
<212> TYPE: DNA
<213> ORGANISM: Micrococcus luteus

<400> SEQUENCE: 121

atgaccgtca ccctgaagca gcacgagcgc cccgcggcca gccgcatcgt ggccgtgggc     60

gcctaccgcc cggcgaacct ggtcccgaac gaggacctca tcggccccat cgactcgtcg    120

gacgagtgga tccgccagcg caccggcatc gtcacacgcc agcgcgccac ggcggaggag    180

accgtgcccg tcatggccgt gggcgccgcc cgggaggccc tcgagcgggc cggcctgcag    240

ggctcggacc tggacgccgt gatcgtctcg accgtcacct tcccgcacgc cacccccctcg   300

gccgcggccc tcgtggcgca cgagatcggc gccaccccgg cgcccgccta cgacgtctcc    360

gccgcgtgcg ccggctactg ctacggcgtg gcccaggccg acgcgctcgt gcgctccggc    420

accgcgcggc acgtgctcgt ggtcggcgtc gagcgcctct ccgacgtcgt ggatcccacg    480

gaccgctcca tctccttcct gctgggcgac ggcgcgggcg ccgtgatcgt cgcggcctcg    540

gacgagccgg gcatctcccc ctcggtgtgg ggctcggacg gggagcgctg gtccacgatc    600

tccatgacgc actcgcagct ggagctgcgc gatgccgtgg agcacgcccg caccacgggc    660

gacgcctcgg cgatcaccgg cgcagagggg atgctctggc ccacgctgcg ccaggacggg    720

ccctccgtct tccgttgggc cgtgtggtcg atggcgaagg tggcccgcga ggcccttgac    780

gccgcgggcg tggagcccga ggacctcgcc gcgttcatcc cgcaccaggc caacatgcgg    840

atcatcgacg agttcgccaa gcagctgaag ctgccggagt ccgtcgtcgt ggcccgggac    900

atcgcggacg ccggcaacac gtcggccgcg tccatcccgc tggccatgca ccggctgctg    960

gaggagaacc ccgagctct                                                 979


<210> SEQ ID NO 122
<211> LENGTH: 17
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (3)..(3)
<223> OTHER INFORMATION: Xaa can be Asn or Ser
<220> FEATURE:
<221> NAME/KEY: MISC_FEATURE
<222> LOCATION: (5)..(5)
<223> OTHER INFORMATION: Xaa can be Ala or Glu
<220> FEATURE:
<221> NAME/KEY: MISC_FEATURE
<222> LOCATION: (8)..(9)
<223> OTHER INFORMATION: Xaa can be any amino acid
<220> FEATURE:
<221> NAME/KEY: MISC_FEATURE
<222> LOCATION: (10)..(10)
<223> OTHER INFORMATION: Xaa can be Met or Arg
<220> FEATURE:
<221> NAME/KEY: MISC_FEATURE
<222> LOCATION: (14)..(14)
<223> OTHER INFORMATION: Xaa can be any amino acid
<220> FEATURE:
```

<221> NAME/KEY: MISC_FEATURE
<222> LOCATION: (15)..(15)
<223> OTHER INFORMATION: Xaa can be Asn or Glu
<220> FEATURE:
<221> NAME/KEY: MISC_FEATURE
<222> LOCATION: (17)..(17)
<223> OTHER INFORMATION: Xaa can be Arg or His

<400> SEQUENCE: 122

Asp Thr Xaa Asp Xaa Trp Ile Xaa Xaa Xaa Thr Gly Ile Xaa Xaa Arg
1               5                   10                  15

Xaa

<210> SEQ ID NO 123
<211> LENGTH: 18
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Ser or Ala
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (4)..(5)
<223> OTHER INFORMATION: Xaa can be any amino acid
<220> FEATURE:
<221> NAME/KEY: MISC_FEATURE
<222> LOCATION: (7)..(7)
<223> OTHER INFORMATION: Xaa can be Ala or Val
<220> FEATURE:
<221> NAME/KEY: MISC_FEATURE
<222> LOCATION: (9)..(9)
<223> OTHER INFORMATION: Xaa can be Ala or Ser
<220> FEATURE:
<221> NAME/KEY: MISC_FEATURE
<222> LOCATION: (12)..(14)
<223> OTHER INFORMATION: Xaa can be any amino acid
<220> FEATURE:
<221> NAME/KEY: MISC_FEATURE
<222> LOCATION: (15)..(15)
<223> OTHER INFORMATION: Xaa can be Met or Leu
<220> FEATURE:
<221> NAME/KEY: MISC_FEATURE
<222> LOCATION: (16)..(17)
<223> OTHER INFORMATION: Xaa can be any amino acid

<400> SEQUENCE: 123

Xaa Xaa Asp Xaa Xaa Ala Xaa Cys Xaa Gly Phe Xaa Xaa Xaa Xaa Xaa
1               5                   10                  15

Xaa Ala

<210> SEQ ID NO 124
<211> LENGTH: 15
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (3)..(3)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be Ala or Ile
<220> FEATURE:
<221> NAME/KEY: MISC_FEATURE
<222> LOCATION: (6)..(6)
<223> OTHER INFORMATION: Xaa can be Ile or Val
<220> FEATURE:
<221> NAME/KEY: MISC_FEATURE
<222> LOCATION: (7)..(7)
<223> OTHER INFORMATION: Xaa can be any amino acid
<220> FEATURE:
<221> NAME/KEY: MISC_FEATURE
<222> LOCATION: (9)..(9)
<223> OTHER INFORMATION: Xaa can be Ala or Gly
<220> FEATURE:
<221> NAME/KEY: MISC_FEATURE
<222> LOCATION: (13)..(13)
<223> OTHER INFORMATION: Xaa can be Ala or Gly
<220> FEATURE:
<221> NAME/KEY: MISC_FEATURE
<222> LOCATION: (14)..(14)
<223> OTHER INFORMATION: Xaa can be Gly or Ala
<220> FEATURE:
<221> NAME/KEY: MISC_FEATURE
<222> LOCATION: (15)..(15)
<223> OTHER INFORMATION: Xaa can be Ala or Val

<400> SEQUENCE: 124

```
Asp Arg Xaa Thr Xaa Xaa Xaa Phe Xaa Asp Gly Ala Xaa Xaa Xaa
1               5                   10                  15
```

<210> SEQ ID NO 125
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (5)..(5)
<223> OTHER INFORMATION: Xaa can be any amino acid
<220> FEATURE:
<221> NAME/KEY: MISC_FEATURE
<222> LOCATION: (8)..(8)
<223> OTHER INFORMATION: Xaa can be Met or Leu

<400> SEQUENCE: 125

```
His Gln Ala Asn Xaa Arg Ile Xaa
1               5
```

<210> SEQ ID NO 126
<211> LENGTH: 19
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (4)..(4)
<223> OTHER INFORMATION: Xaa can be Gly or Ser
<220> FEATURE:
<221> NAME/KEY: MISC_FEATURE
<222> LOCATION: (8)..(8)
<223> OTHER INFORMATION: Xaa can be Val or Ile
<220> FEATURE:
<221> NAME/KEY: MISC_FEATURE
<222> LOCATION: (10)..(11)
<223> OTHER INFORMATION: Xaa can be any amino acid
<220> FEATURE:
<221> NAME/KEY: MISC_FEATURE
<222> LOCATION: (12)..(12)
<223> OTHER INFORMATION: Xaa can be Ile or Leu
<220> FEATURE:
<221> NAME/KEY: MISC_FEATURE
<222> LOCATION: (13)..(18)
<223> OTHER INFORMATION: Xaa can be any amino acid

<400> SEQUENCE: 126

```
Gly Asn Thr Xaa Ala Ala Ser Xaa Pro Xaa Xaa Xaa Xaa Xaa Xaa Xaa
1               5                   10                  15

Xaa Xaa Gly


<210> SEQ ID NO 127
<211> LENGTH: 13
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Ile or Val
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (4)..(5)
<223> OTHER INFORMATION: Xaa can be any amino acid
<220> FEATURE:
<221> NAME/KEY: MISC_FEATURE
<222> LOCATION: (10)..(10)
<223> OTHER INFORMATION: Xaa can be Leu or Phe
<220> FEATURE:
<221> NAME/KEY: MISC_FEATURE
<222> LOCATION: (11)..(11)
<223> OTHER INFORMATION: Xaa can be Thr or Ser

<400> SEQUENCE: 127

Xaa Xaa Leu Xaa Xaa Phe Gly Gly Gly Xaa Xaa Trp Gly
1               5                   10


<210> SEQ ID NO 128
<211> LENGTH: 4559
<212> TYPE: DNA
<213> ORGANISM: Artificial sequence
<220> FEATURE:
<223> OTHER INFORMATION: pDG2 plasmid

<400> SEQUENCE: 128

ggggaattgt gagcggataa caattcccct gtagaaataa ttttgtttaa ctttaataag     60

gagatatacc atggcgcaac tcactcttct tttagtcggc aattccgacg ccatcacgcc    120

attacttgct aaagctgact ttgaacaacg ttcgcgtctg cagattattc ctgcgcagtc    180

agttatcgcc agtgatgccc ggccttcgca agctatccgc gccagtcgtg ggagttcaat    240

gcgcgtggcc ctggagctgg tgaaagaagg tcgagcgcaa gcctgtgtca gtgccggtaa    300

taccggggcg ctgatggggc tggcaaaatt attactcaag cccctggagg ggattgagcg    360

tccggcgctg gtgacggtat taccacatca gcaaaagggc aaaacggtgg tccttgactt    420

aggggccaac gtcgattgtg acagcacaat gctggtgcaa tttgccatta tgggctcagt    480

tctggctgaa gaggtggtgg aaattcccaa tcctcgcgtg gcgttgctca atattggtga    540

agaagaagta aagggtctcg acagtattcg ggatgcctca gcggtgctta aaacaatccc    600

ttctatcaat tatatcggct atcttgaagc caatgagttg ttaactggca agacagatgt    660

gctggtttgt gacggcttta caggaaatgt cacattaaag acgatggaag gtgttgtcag    720

gatgttcctt tctctgctga aatctcaggg tgaagggaaa aaacggtcgt ggtggctact    780

gttattaaag cgttggctac aaaagagcct gacgaggcga ttcagtcacc tcaaccccga    840

ccagtataac ggcgcctgtc tgttaggatt gcgcggcacg gtgataaaaa gtcatggtgc    900

agccaatcag cgagcttttg cggtcgcgat tgaacaggca gtgcaggcgg tgcagcgaca    960
```

-continued

```
agttcctcag cgaattgccg ctcgcctgga atctgtatac ccagctggtt ttgagctgct   1020
ggacggtggc aaaagcggaa ctctgcggta gcaggacgct gccagcgaac tcgcagtttg   1080
caagtgacgg tatataaccg aaaagtgact gagcgcatat gtatacgaag actcgagtct   1140
ggtaaagaaa ccgctgctgc gaaatttgaa cgccagcaca tggactcgtc tactagcgca   1200
gcttaattaa cctaggctgc tgccaccgct gagcaataac tagcataacc ccttggggcc   1260
tctaaacggg tcttgagggg ttttttgctg aaacctcagg catttgagaa gcacacggtc   1320
acactgcttc cggtagtcaa taaaccggta aaccagcaat agacataagc ggctatttaa   1380
cgaccctgcc ctgaaccgac gaccgggtca tcgtggccgg atcttgcggc ccctcggctt   1440
gaacgaattg ttagacatta tttgccgact accttggtga tctcgccttt cacgtagtgg   1500
acaaattctt ccaactgatc tgcgcgcgag gccaagcgat cttcttcttg tccaagataa   1560
gcctgtctag cttcaagtat gacgggctga tactgggccg gcaggcgctc cattgcccag   1620
tcggcagcga catccttcgg cgcgattttg ccggttactg cgctgtacca aatgcgggac   1680
aacgtaagca ctacatttcg ctcatcgcca gcccagtcgg gcggcgagtt ccatagcgtt   1740
aaggtttcat ttagcgcctc aaatagatcc tgttcaggaa ccggatcaaa gagttcctcc   1800
gccgctggac ctaccaaggc aacgctatgt tctcttgctt ttgtcagcaa gatagccaga   1860
tcaatgtcga tcgtggctgg ctcgaagata cctgcaagaa tgtcattgcg ctgccattct   1920
ccaaattgca gttcgcgctt agctggataa cgccacggaa tgatgtcgtc gtgcacaaca   1980
atggtgactt ctacagcgcg gagaatctcg ctctctccag gggaagccga agtttccaaa   2040
aggtcgttga tcaaagctcg ccgcgttgtt tcatcaagcc ttacggtcac cgtaaccagc   2100
aaatcaatat cactgtgtgg cttcaggccg ccatccactg cggagccgta caaatgtacg   2160
gccagcaacg tcggttcgag atggcgctcg atgacgccaa ctacctctga tagttgagtc   2220
gatacttcgg cgatcaccgc ttccctcata ctcttccttt ttcaatatta ttgaagcatt   2280
tatcagggtt attgtctcat gagcggatac atatttgaat gtatttagaa aaataaacaa   2340
atagctagct cactcggtcg ctacgctccg ggcgtgagac tgcggcgggc gctgcggaca   2400
catacaaagt tacccacaga ttccgtggat aagcagggga ctaacatgtg aggcaaaaca   2460
gcagggccgc gccggtggcg tttttccata ggctccgccc tcctgccaga gttcacataa   2520
acagacgctt ttccggtgca tctgtgggag ccgtgaggct caaccatgaa tctgacagta   2580
cgggcgaaac ccgacaggac ttaaagatcc ccaccgtttc cggcgggtcg ctccctcttg   2640
cgctctcctg ttccgaccct gccgtttacc ggatacctgt tccgcctttc tcccttacgg   2700
gaagtgtggc gctttctcat agctcacaca ctggtatctc ggctcggtgt aggtcgttcg   2760
ctccaagctg ggctgtaagc aagaactccc cgttcagccc gactgctgcg ccttatccgg   2820
taactgttca cttgagtcca acccggaaaa gcacggtaaa acgccactgg cagcagccat   2880
tggtaactgg gagttcgcag aggatttgtt tagctaaaca cgcggttgct cttgaagtgt   2940
gcgccaaagt ccggctacac tggaaggaca gatttggttg ctgtgctctg cgaaagccag   3000
ttaccacggt taagcagttc cccaactgac ttaaccttcg atcaaaccac ctccccaggt   3060
ggtttttcg tttacagggc aaaagattac gcgcagaaaa aaaggatctc aagaagatcc   3120
tttgatcttt tctactgaac cgctctagat ttcagtgcaa tttatctctt caaatgtagc   3180
acctgaagtc agccccatac gatataagtt gtaattctca tgttagtcat gccccgcgcc   3240
caccggaagg agctgactgg gttgaaggct ctcaagggca tcggtcgaga tcccggtgcc   3300
```

-continued taatgagtga gctaacttac attaattgcg ttgcgctcac tgcccgcttt ccagtcggga 3360
aacctgtcgt gccagctgca ttaatgaatc ggccaacgcg cggggagagg cggtttgcgt 3420
attgggcgcc agggtggttt ttcttttcac cagtgagacg ggcaacagct gattgccctt 3480
caccgcctgg ccctgagaga gttgcagcaa gcggtccacg ctggtttgcc ccagcaggcg 3540
aaaatcctgt ttgatggtgg ttaacggcgg gatataacat gagctgtctt cggtatcgtc 3600
gtatcccact accgagatgt ccgcaccaac gcgcagcccg gactcggtaa tggcgcgcat 3660
tgcgcccagc gccatctgat cgttggcaac cagcatcgca gtgggaacga tgccctcatt 3720
cagcatttgc atggtttgtt gaaaaccgga catggcactc cagtcgcctt cccgttccgc 3780
tatcggctga atttgattgc gagtgagata tttatgccag ccagccagac gcagacgcgc 3840
cgagacagaa cttaatgggc ccgctaacag cgcgatttgc tggtgaccca atgcgaccag 3900
atgctccacg cccagtcgcg taccgtcttc atgggagaaa ataatactgt tgatgggtgt 3960
ctggtcagag acatcaagaa ataacgccgg aacattagtg caggcagctt ccacagcaat 4020
ggcatcctgg tcatccagcg gatagttaat gatcagccca ctgacgcgtt gcgcgagaag 4080
attgtgcacc gccgctttac aggcttcgac gccgcttcgt tctaccatcg acaccaccac 4140
gctggcaccc agttgatcgg cgcgagattt aatcgccgcg acaatttgcg acggcgcgtg 4200
cagggccaga ctggaggtgg caacgccaat cagcaacgac tgtttgcccg ccagttgttg 4260
tgccacgcgg ttgggaatgt aattcagctc cgccatcgcc gcttccactt tttcccgcgt 4320
tttcgcagaa acgtggctgg cctggttcac cacgcgggaa acggtctgat aagagacacc 4380
ggcatactct gcgacatcgt ataacgttac tggtttcaca ttcaccaccc tgaattgact 4440
ctcttccggg cgctatcatg ccataccgcg aaaggttttg cgccattcga tggtgtccgg 4500
gatctcgacg ctctccctta tgcgactcct gcattaggaa attaatacga ctcactata 4559

<210> SEQ ID NO 129
<211> LENGTH: 5502
<212> TYPE: DNA
<213> ORGANISM: Artificial sequence
<220> FEATURE:
<223> OTHER INFORMATION: pDG6 plasmid

<400> SEQUENCE: 129
ggggaattgt gagcggataa caattcccct gtagaaataa ttttgtttaa ctttaataag 60
gagatatacc atggcgcaac tcactcttct tttagtcggc aattccgacg ccatcacgcc 120
attacttgct aaagctgact ttgaacaacg ttcgcgtctg cagattattc ctgcgcagtc 180
agttatcgcc agtgatgccc ggccttcgca agctatccgc gccagtcgtg ggagttcaat 240
gcgcgtggcc ctggagctgg tgaaagaagg tcgagcgcaa gcctgtgtca gtgccggtaa 300
taccggggcg ctgatggggc tggcaaaatt attactcaag cccctggagg ggattgagcg 360
tccggcgctg gtgacggtat taccacatca gcaaaagggc aaaacggtgg tccttgactt 420
aggggccaac gtcgattgtg acagcacaat gctggtgcaa tttgccatta tgggctcagt 480
tctggctgaa gaggtggtgg aaattcccaa tcctcgcgtg gcgttgctca atattggtga 540
agaagaagta aagggtctcg acagtattcg ggatgcctca gcggtgctta aaacaatccc 600
ttctatcaat tatatcggct atcttgaagc caatgagttg ttaactggca agacagatgt 660
gctggtttgt gacggcttta caggaaatgt cacattaaag acgatggaag gtgttgtcag 720
gatgttcctt tctctgctga aatctcaggg tgaagggaaa aaacggtcgt ggtggctact 780
gttattaaag cgttggctac aaaagagcct gacgaggcga ttcagtcacc tcaaccccga 840

-continued

```
ccagtataac ggcgcctgtc tgttaggatt gcgcggcacg gtgataaaaa gtcatggtgc    900
agccaatcag cgagcttttg cggtcgcgat tgaacaggca gtgcaggcgg tgcagcgaca    960
agttcctcag cgaattgccg ctcgcctgga atctgtatac ccagctggtt ttgagctgct   1020
ggacggtggc aaaagcggaa ctctgcggta gcaggacgct gccagcgaac tcgcagtttg   1080
caagtgacgg tatataaccg aaaagtgact gagcgcatat gaaagctggc attcttggtg   1140
ttggacgtta cattcctgag aaggttttaa caaatcatga tcttgaaaaa atggttgaaa   1200
cttctgacga gtggattcgt acaagaacag gaatagaaga aagaagaatc gcagcagatg   1260
atgtgttttc atcacacatg gctgttgcag cagcgaaaaa tgcgctggaa caagctgaag   1320
tggctgctga ggatctggat atgatcttgg ttgcaactgt tacacctgat cagtcattcc   1380
ctacggtgtc ttgtatgatt caagaacaac tcggcgcgaa gaaagcgtgt gctatggata   1440
tcagcgcggc ttgtgcgggc ttcatgtacg gggttgtaac cggtaaacaa tttattgaat   1500
ccggaaccta caagcatgtt ctagttgttg gtgtagagaa gctctcaagc attaccgact   1560
gggaagaccg caatacagcc gttctgtttg gagacggagc aggcgctgcg gtagtcgggc   1620
cagtcagtga tgacagagga atcctttcat ttgaactagg agccgacggc acaggcggtc   1680
agcacttgta tctgaatgaa aaacgacata caatcatgaa tggacgagaa gttttcaaat   1740
ttgcagtccg ccaaatggga gaatcatgcg taaatgtcat tgaaaaagcc ggactttcaa   1800
aagaggatgt ggactttttg attccgcatc aggcgaacat ccgtatcatg gaagctgctc   1860
gcgagcgttt agagcttcct gtcgaaaaga tgtctaaaac tgttcataaa tatggaaata   1920
cttctgccgc atccattccg atctctcttg tagaagaatt ggaagccggt aaaatcaaag   1980
acggcgatgt ggtcgttatg gtagggttcg gcggaggact aacatggggc gccattgcaa   2040
tccgctgggg ccgataaaaa aaaggtgagg tgcactcgag tctggtaaag aaaccgctgc   2100
tgcgaaattt gaacgccagc acatggactc gtctactagc gcagcttaat taacctaggc   2160
tgctgccacc gctgagcaat aactagcata accccttggg gcctctaaac gggtcttgag   2220
gggttttttg ctgaaacctc aggcatttga gaagcacacg gtcacactgc ttccggtagt   2280
caataaaccg gtaaaccagc aatagacata agcggctatt taacgaccct gccctgaacc   2340
gacgaccggg tcatcgtggc cggatcttgc ggcccctcgg cttgaacgaa ttgttagaca   2400
ttatttgccg actaccttgg tgatctcgcc tttcacgtag tggacaaatt cttccaactg   2460
atctgcgcgc gaggccaagc gatcttcttc ttgtccaaga taagcctgtc tagcttcaag   2520
tatgacgggc tgatactggg ccggcaggcg ctccattgcc cagtcggcag cgacatcctt   2580
cggcgcgatt ttgccggtta ctgcgctgta ccaaatgcgg gacaacgtaa gcactacatt   2640
tcgctcatcg ccagcccagt cgggcggcga gttccatagc gttaaggttt catttagcgc   2700
ctcaaataga tcctgttcag gaaccggatc aaagagttcc tccgccgctg gacctaccaa   2760
ggcaacgcta tgttctcttg cttttgtcag caagatagcc agatcaatgt cgatcgtggc   2820
tggctcgaag atacctgcaa gaatgtcatt gcgctgccat tctccaaatt gcagttcgcg   2880
cttagctgga taacgccacg gaatgatgtc gtcgtgcaca acaatggtga cttctacagc   2940
gcggagaatc tcgctctctc caggggaagc cgaagtttcc aaaaggtcgt tgatcaaagc   3000
tcgccgcgtt gtttcatcaa gccttacggt caccgtaacc agcaaatcaa tatcactgtg   3060
tggcttcagg ccgccatcca ctgcggagcc gtacaaatgt acggccagca acgtcggttc   3120
gagatggcgc tcgatgacgc caactacctc tgatagttga gtcgatactt cggcgatcac   3180
```

cgcttccctc atactcttcc tttttcaata ttattgaagc atttatcagg gttattgtct 3240
catgagcgga tacatatttg aatgtattta gaaaaataaa caaatagcta gctcactcgg 3300
tcgctacgct ccgggcgtga gactgcggcg ggcgctgcgg acacatacaa agttacccac 3360
agattccgtg gataagcagg ggactaacat gtgaggcaaa acagcagggc cgcgccggtg 3420
gcgtttttcc ataggctccg ccctcctgcc agagttcaca taaacagacg cttttccggt 3480
gcatctgtgg gagccgtgag gctcaaccat gaatctgaca gtacgggcga aacccgacag 3540
gacttaaaga tccccaccgt ttccggcggg tcgctccctc ttgcgctctc ctgttccgac 3600
cctgccgttt accggatacc tgttccgcct ttctccctta cgggaagtgt ggcgctttct 3660
catagctcac acactggtat ctcggctcgg tgtaggtcgt tcgctccaag ctgggctgta 3720
agcaagaact ccccgttcag cccgactgct gcgccttatc cggtaactgt tcacttgagt 3780
ccaacccgga aagcacggt aaaacgccac tggcagcagc cattggtaac tgggagttcg 3840
cagaggattt gtttagctaa acacgcggtt gctcttgaag tgtgcgccaa agtccggcta 3900
cactggaagg acagatttgg ttgctgtgct ctgcgaaagc cagttaccac ggttaagcag 3960
ttccccaact gacttaacct tcgatcaaac cacctcccca ggtggttttt tcgtttacag 4020
ggcaaaagat tacgcgcaga aaaaaaggat ctcaagaaga tcctttgatc ttttctactg 4080
aaccgctcta gatttcagtg caatttatct cttcaaatgt agcacctgaa gtcagcccca 4140
tacgatataa gttgtaattc tcatgttagt catgccccgc gcccaccgga aggagctgac 4200
tgggttgaag gctctcaagg gcatcggtcg agatcccggt gcctaatgag tgagctaact 4260
tacattaatt gcgttgcgct cactgcccgc tttccagtcg ggaaacctgt cgtgccagct 4320
gcattaatga atcggccaac gcgcggggag aggcggtttg cgtattgggc gccagggtgg 4380
tttttctttt caccagtgag acgggcaaca gctgattgcc cttcaccgcc tggccctgag 4440
agagttgcag caagcggtcc acgctggttt gccccagcag gcgaaaatcc tgtttgatgg 4500
tggttaacgg cgggatataa catgagctgt cttcggtatc gtcgtatccc actaccgaga 4560
tgtccgcacc aacgcgcagc ccggactcgg taatggcgcg cattgcgccc agcgccatct 4620
gatcgttggc aaccagcatc gcagtgggaa cgatgccctc attcagcatt tgcatggttt 4680
gttgaaaacc ggacatggca ctccagtcgc cttcccgttc cgctatcggc tgaatttgat 4740
tgcgagtgag atatttatgc cagccagcca gacgcagacg cgccgagaca gaacttaatg 4800
ggcccgctaa cagcgcgatt tgctggtgac ccaatgcgac cagatgctcc acgcccagtc 4860
gcgtaccgtc ttcatgggag aaaataatac tgttgatggg tgtctggtca gagacatcaa 4920
gaaataacgc cggaacatta gtgcaggcag cttccacagc aatggcatcc tggtcatcca 4980
gcggatagtt aatgatcagc ccactgacgc gttgcgcgag aagattgtgc accgccgctt 5040
tacaggcttc gacgccgctt cgttctacca tcgacaccac cacgctggca cccagttgat 5100
cggcgcgaga tttaatcgcc gcgacaattt gcgacggcgc gtgcagggcc agactggagg 5160
tggcaacgcc aatcagcaac gactgtttgc ccgccagttg ttgtgccacg cggttgggaa 5220
tgtaattcag ctccgccatc gccgcttcca ctttttcccg cgttttcgca gaaacgtggc 5280
tggcctggtt caccacgcgg gaaacggtct gataagagac accggcatac tctgcgacat 5340
cgtataacgt tactggtttc acattcacca ccctgaattg actctcttcc gggcgctatc 5400
atgccatacc gcgaaaggtt ttgcgccatt cgatggtgtc cgggatctcg acgctctccc 5460
ttatgcgact cctgcattag gaaattaata cgactcacta ta 5502

<210> SEQ ID NO 130
<211> LENGTH: 5541
<212> TYPE: DNA
<213> ORGANISM: Artificial sequence
<220> FEATURE:
<223> OTHER INFORMATION: pDG7 plasmid

<400> SEQUENCE: 130

```
ggggaattgt gagcggataa caattcccct gtagaaataa ttttgtttaa ctttaataag     60

gagatatacc atggcgcaac tcactcttct tttagtcggc aattccgacg ccatcacgcc    120

attacttgct aaagctgact ttgaacaacg ttcgcgtctg cagattattc ctgcgcagtc    180

agttatcgcc agtgatgccc ggccttcgca agctatccgc gccagtcgtg ggagttcaat    240

gcgcgtggcc ctggagctgg tgaaagaagg tcgagcgcaa gcctgtgtca gtgccggtaa    300

taccggggcg ctgatggggc tggcaaaatt attactcaag cccctggagg ggattgagcg    360

tccggcgctg gtgacggtat taccacatca gcaaaagggc aaaacggtgg tccttgactt    420

aggggccaac gtcgattgtg acagcacaat gctggtgcaa tttgccatta tgggctcagt    480

tctggctgaa gaggtggtgg aaattcccaa tcctcgcgtg gcgttgctca atattggtga    540

agaagaagta aagggtctcg acagtattcg ggatgcctca gcggtgctta aaacaatccc    600

ttctatcaat tatatcggct atcttgaagc caatgagttg ttaactggca agacagatgt    660

gctggtttgt gacggcttta caggaaatgt cacattaaag acgatggaag gtgttgtcag    720

gatgttcctt tctctgctga aatctcaggg tgaagggaaa aaacggtcgt ggtggctact    780

gttattaaag cgttggctac aaaagagcct gacgaggcga ttcagtcacc tcaaccccga    840

ccagtataac ggcgcctgtc tgttaggatt gcgcggcacg gtgataaaaa gtcatggtgc    900

agccaatcag cgagcttttg cggtcgcgat tgaacaggca gtgcaggcgg tgcagcgaca    960

agttcctcag cgaattgccg ctcgcctgga atctgtatac ccagctggtt ttgagctgct   1020

ggacggtggc aaaagcggaa ctctgcggta gcaggacgct gccagcgaac tcgcagtttg   1080

caagtgacgg tatataaccg aaaagtgact gagcgcatat gtcaaaagca aaaattacag   1140

ctatcggcac ctatgcgccg agcagacgtt taaccaatgc agatttagaa aagatcgttg   1200

atacctctga tgaatggatc gttcagcgca caggaatgag agaacgccgg attgcggatg   1260

aacatcaatt tacctctgat ttatgcatag aagcggtgaa gaatctcaag agccgttata   1320

aaggaacgct tgatgatgtc gatatgatcc tcgttgccac aaccacatcc gattacgcct   1380

ttccgagtac ggcatgccgc gtacaggaat atttcggctg ggaaagcacc ggcgcgctgg   1440

atattaatgc gacatgcgcc gggctgacat acggcctcca tttggcaaat ggattgatca   1500

catctggcct tcatcaaaaa attctcgtca tcgccggaga gacgttatca aaggtaaccg   1560

attatacgga tcgaacgaca tgcgtactgt tcggcgatgc cgcgggtgcg ctgttagtag   1620

aacgagatga agagacgccg ggatttcttg cgtctgtaca aggaacaagc gggaacggcg   1680

gcgatatttt gtatcgtgcc ggactgcgaa atgaaataaa cggtgtgcag cttgtcggtt   1740

ccggaaaaat ggtgcaaaac ggacgcgagg tatataaatg ggccgcaaga accgtccctg   1800

gcgaatttga acggctttta cataaagcag gactcagctc cgatgatctc gattggtttg   1860

ttcctcacag cgccaacttg cgcatgatcg agtcaatttg tgaaaaaaca ccgttcccga   1920

ttgaaaaaac gctcactagc gttgagcact acggaaacac gtcttcggtt tcaattgttt   1980

tggcgctcga tctcgcagtg aaagccggga agctgaaaaa agatcaaatc gttttgcttt   2040

tcgggtttgg cggcggatta acctatacag gattgcttat taaatggggg atgtaaagat   2100
```

-continued ctcctaggcg tcactcgagt ctggtaaaga aaccgctgct gcgaaatttg aacgccagca 2160
catggactcg tctactagcg cagcttaatt aacctaggct gctgccaccg ctgagcaata 2220
actagcataa ccccttgggg cctctaaacg ggtcttgagg ggttttttgc tgaaacctca 2280
ggcatttgag aagcacacgg tcacactgct tccggtagtc aataaaccgg taaaccagca 2340
atagacataa gcggctattt aacgaccctg ccctgaaccg acgaccgggt catcgtggcc 2400
ggatcttgcg gcccctcggc ttgaacgaat tgttagacat tatttgccga ctaccttggt 2460
gatctcgcct ttcacgtagt ggacaaattc ttccaactga tctgcgcgcg aggccaagcg 2520
atcttcttct tgtccaagat aagcctgtct agcttcaagt atgacgggct gatactgggc 2580
cggcaggcgc tccattgccc agtcggcagc gacatccttc ggcgcgattt tgccggttac 2640
tgcgctgtac caaatgcggg acaacgtaag cactacattt cgctcatcgc cagcccagtc 2700
gggcggcgag ttccatagcg ttaaggtttc atttagcgcc tcaaatagat cctgttcagg 2760
aaccggatca aagagttcct ccgccgctgg acctaccaag gcaacgctat gttctcttgc 2820
ttttgtcagc aagatagcca gatcaatgtc gatcgtggct ggctcgaaga tacctgcaag 2880
aatgtcattg cgctgccatt ctccaaattg cagttcgcgc ttagctggat aacgccacgg 2940
aatgatgtcg tcgtgcacaa caatggtgac ttctacagcg cggagaatct cgctctctcc 3000
aggggaagcc gaagtttcca aaaggtcgtt gatcaaagct cgccgcgttg tttcatcaag 3060
ccttacggtc accgtaacca gcaaatcaat atcactgtgt ggcttcaggc cgccatccac 3120
tgcggagccg tacaaatgta cggccagcaa cgtcggttcg agatggcgct cgatgacgcc 3180
aactacctct gatagttgag tcgatacttc ggcgatcacc gcttccctca tactcttcct 3240
ttttcaatat tattgaagca tttatcaggg ttattgtctc atgagcggat acatatttga 3300
atgtatttag aaaaataaac aaatagctag ctcactcggt cgctacgctc cgggcgtgag 3360
actgcggcgg gcgctgcgga cacatacaaa gttacccaca gattccgtgg ataagcaggg 3420
gactaacatg tgaggcaaaa cagcagggcc gcgccggtgg cgtttttcca taggctccgc 3480
cctcctgcca gagttcacat aaacagacgc ttttccggtg catctgtggg agccgtgagg 3540
ctcaaccatg aatctgacag tacgggcgaa acccgacagg acttaaagat ccccaccgtt 3600
tccggcgggt cgctccctct tgcgctctcc tgttccgacc ctgccgttta ccggatacct 3660
gttccgcctt tctcccttac gggaagtgtg gcgctttctc atagctcaca cactggtatc 3720
tcggctcggt gtaggtcgtt cgctccaagc tgggctgtaa gcaagaactc cccgttcagc 3780
ccgactgctg cgccttatcc ggtaactgtt cacttgagtc caacccggaa aagcacggta 3840
aaacgccact ggcagcagcc attggtaact gggagttcgc agaggatttg tttagctaaa 3900
cacgcggttg ctcttgaagt gtgcgccaaa gtccggctac actggaagga cagatttggt 3960
tgctgtgctc tgcgaaagcc agttaccacg gttaagcagt tccccaactg acttaacctt 4020
cgatcaaacc acctccccag gtggtttttt cgtttacagg gcaaaagatt acgcgcagaa 4080
aaaaaggatc tcaagaagat cctttgatct tttctactga accgctctag atttcagtgc 4140
aatttatctc ttcaaatgta gcacctgaag tcagccccat acgatataag ttgtaattct 4200
catgttagtc atgccccgcg cccaccggaa ggagctgact gggttgaagg ctctcaaggg 4260
catcggtcga gatcccggtg cctaatgagt gagctaactt acattaattg cgttgcgctc 4320
actgcccgct ttccagtcgg gaaacctgtc gtgccagctg cattaatgaa tcggccaacg 4380
cgcggggaga ggcggtttgc gtattgggcg ccagggtggt ttttcttttc accagtgaga 4440
cgggcaacag ctgattgccc ttcaccgcct ggccctgaga gagttgcagc aagcggtcca 4500
cgctggtttg ccccagcagg cgaaaatcct gtttgatggt ggttaacggc gggatataac 4560
atgagctgtc ttcggtatcg tcgtatccca ctaccgagat gtccgcacca acgcgcagcc 4620
cggactcggt aatggcgcgc attgcgccca gcgccatctg atcgttggca accagcatcg 4680
cagtgggaac gatgccctca ttcagcattt gcatggtttg ttgaaaaccg gacatggcac 4740
tccagtcgcc ttcccgttcc gctatcggct gaatttgatt gcgagtgaga tatttatgcc 4800
agccagccag acgcagacgc gccgagacag aacttaatgg gcccgctaac agcgcgattt 4860
gctggtgacc caatgcgacc agatgctcca cgcccagtcg cgtaccgtct tcatgggaga 4920
aaataatact gttgatgggt gtctggtcag agacatcaag aaataacgcc ggaacattag 4980
tgcaggcagc ttccacagca atggcatcct ggtcatccag cggatagtta atgatcagcc 5040
cactgacgcg ttgcgcgaga agattgtgca ccgccgcttt acaggcttcg acgccgcttc 5100
gttctaccat cgacaccacc acgctggcac ccagttgatc ggcgcgagat ttaatcgccg 5160
cgacaatttg cgacggcgcg tgcagggcca gactggaggt ggcaacgcca atcagcaacg 5220
actgtttgcc cgccagttgt tgtgccacgc ggttgggaat gtaattcagc tccgccatcg 5280
ccgcttccac tttttcccgc gttttcgcag aaacgtggct ggcctggttc accacgcggg 5340
aaacggtctg ataagagaca ccggcatact ctgcgacatc gtataacgtt actggtttca 5400
cattcaccac cctgaattga ctctcttccg ggcgctatca tgccataccg cgaaaggttt 5460
tgcgccattc gatggtgtcc gggatctcga cgctctccct tatgcgactc ctgcattagg 5520
aaattaatac gactcactat a 5541

<210> SEQ ID NO 131
<211> LENGTH: 5582
<212> TYPE: DNA
<213> ORGANISM: Artificial sequence
<220> FEATURE:
<223> OTHER INFORMATION: pDG8 plasmid

<400> SEQUENCE: 131
ggggaattgt gagcggataa caattcccct gtagaaataa ttttgtttaa ctttaataag 60
gagatatacc atggcgcaac tcactcttct tttagtcggc aattccgacg ccatcacgcc 120
attacttgct aaagctgact ttgaacaacg ttcgcgtctg cagattattc ctgcgcagtc 180
agttatcgcc agtgatgccc ggccttcgca agctatccgc gccagtcgtg ggagttcaat 240
gcgcgtggcc ctggagctgg tgaaagaagg tcgagcgcaa gcctgtgtca gtgccggtaa 300
taccggggcg ctgatggggc tggcaaaatt attactcaag cccctggagg ggattgagcg 360
tccggcgctg gtgacggtat taccacatca gcaaaagggc aaaacggtgg tccttgactt 420
aggggccaac gtcgattgtg acagcacaat gctggtgcaa tttgccatta tgggctcagt 480
tctggctgaa gaggtggtgg aaattcccaa tcctcgcgtg gcgttgctca atattggtga 540
agaagaagta aagggtctcg acagtattcg ggatgcctca gcggtgctta aacaatccc 600 ttctatcaat tatatcggct atcttgaagc caatgagttg ttaactggca agacagatgt 660
gctggtttgt gacggcttta caggaaatgt cacattaaag acgatggaag gtgttgtcag 720
gatgttcctt tctctgctga aatctcaggg tgaagggaaa aaacggtcgt ggtggctact 780
gttattaaag cgttggctac aaaagagcct gacgaggcga ttcagtcacc tcaaccccga 840
ccagtataac ggcgcctgtc tgttaggatt gcgcggcacg gtgataaaaa gtcatggtgc 900
agccaatcag cgagcttttg cggtcgcgat tgaacaggca gtgcaggcgg tgcagcgaca 960

-continued

```
agttcctcag cgaattgccg ctcgcctgga atctgtatac ccagctggtt ttgagctgct   1020
ggacggtggc aaaagcggaa ctctgcggta gcaggacgct gccagcgaac tcgcagtttg   1080
caagtgacgg tatataaccg aaaagtgact gagcgcatat gtctaagatc aagccaagca   1140
agggcgctcc gtacgcgcgc atcctgggcg tcggcggtta ccgtccgacc cgtgtggtgc   1200
cgaacgaggt gatcctggag aagatcgact cttccgacga gtggattcgc tctcgctccg   1260
gcatcgaaac gcgtcactgg gcgggtccgg aagaaaccgt cgcggcgatg tctgtggagg   1320
cctccggcaa ggcactggcc gacgccggta tcgacgcctc tcgtatcggt gccgtggtag   1380
tctctaccgt gtctcacttc agccagaccc cggccatcgc caccgagatc gccgaccgcc   1440
tgggcacgga caaggccgca gccttcgaca tctctgccgg ctgcgcgggc ttcggctacg   1500
gtctgaccct ggccaagggc atggtcgtcg aaggttctgc ggagtacgtg ctggtcatcg   1560
gcgtggagcg tctgtccgac ctgaccgacc tggaggaccg tgccacggcc ttcctgttcg   1620
gcgacggcgc tggtgcggtc gtggtcggcc cgtcccagga gccggcaatc ggcccgacgg   1680
tctggggctc tgagggcgac aaggccgaaa cgatcaagca gaccgtttcc tgggaccgct   1740
tccgtatcgg cgatgtctcc gaactgccgc tggactccga gggcaacgtc aagtttcctg   1800
cgatcacgca ggagggccag gcggtgttcc gctgggccgt gttcgagatg gcgaaggtcg   1860
cgcagcaggc gctggacgcg gcgggtatca gcccggacga cctggacgtc tttatcccgc   1920
accaggccaa tgtgcgtatc atcgactcta tggtgaaaac cctgaagctg ccggagcacg   1980
tcacggtcgc ccgtgacatc cgcaccaccg gcaacacctc tgccgcctct attccgctgg   2040
cgatggagcg tctgctggcg accggcgacg cgcgtagcgg cgacaccgcg ctggtcatcg   2100
gcttcggtgc gggtctggtc tacgccgcga cggtcgttac cctgccgtaa ccacctcgag   2160
tctggtaaag aaaccgctgc tgcgaaattt gaacgccagc acatggactc gtctactagc   2220
gcagcttaat taacctaggc tgctgccacc gctgagcaat aactagcata accccttggg   2280
gcctctaaac gggtcttgag gggttttttg ctgaaacctc aggcatttga gaagcacacg   2340
gtcacactgc ttccggtagt caataaaccg gtaaaccagc aatagacata agcggctatt   2400
taacgaccct gccctgaacc gacgaccggg tcatcgtggc cggatcttgc ggcccctcgg   2460
cttgaacgaa ttgttagaca ttatttgccg actaccttgg tgatctcgcc tttcacgtag   2520
tggacaaatt cttccaactg atctgcgcgc gaggccaagc gatcttcttc ttgtccaaga   2580
taagcctgtc tagcttcaag tatgacgggc tgatactggg ccggcaggcg ctccattgcc   2640
cagtcggcag cgacatcctt cggcgcgatt ttgccggtta ctgcgctgta ccaaatgcgg   2700
gacaacgtaa gcactacatt tcgctcatcg ccagcccagt cgggcggcga gttccatagc   2760
gttaaggttt catttagcgc ctcaaataga tcctgttcag gaaccggatc aaagagttcc   2820
tccgccgctg gacctaccaa ggcaacgcta tgttctcttg cttttgtcag caagatagcc   2880
agatcaatgt cgatcgtggc tggctcgaag atacctgcaa gaatgtcatt gcgctgccat   2940
tctccaaatt gcagttcgcg cttagctgga taacgccacg gaatgatgtc gtcgtgcaca   3000
acaatggtga cttctacagc gcggagaatc tcgctctctc caggggaagc cgaagtttcc   3060
aaaaggtcgt tgatcaaagc tcgccgcgtt gtttcatcaa gccttacggt caccgtaacc   3120
agcaaatcaa tatcactgtg tggcttcagg ccgccatcca ctgcggagcc gtacaaatgt   3180
acggccagca acgtcggttc gagatggcgc tcgatgacgc caactacctc tgatagttga   3240
gtcgatactt cggcgatcac cgcttccctc atactcttcc tttttcaata ttattgaagc   3300
atttatcagg gttattgtct catgagcgga tacatatttg aatgtattta gaaaaataaa   3360
```

-continued

```
caaatagcta gctcactcgg tcgctacgct ccgggcgtga gactgcggcg ggcgctgcgg   3420
acacatacaa agttacccac agattccgtg gataagcagg ggactaacat gtgaggcaaa   3480
acagcagggc cgcgccggtg gcgtttttcc ataggctccg ccctcctgcc agagttcaca   3540
taaacagacg cttttccggt gcatctgtgg gagccgtgag gctcaaccat gaatctgaca   3600
gtacgggcga aacccgacag gacttaaaga tccccaccgt ttccggcggg tcgctccctc   3660
ttgcgctctc ctgttccgac cctgccgttt accggatacc tgttccgcct ttctccctta   3720
cgggaagtgt ggcgctttct catagctcac acactggtat ctcggctcgg tgtaggtcgt   3780
tcgctccaag ctgggctgta agcaagaact ccccgttcag cccgactgct gcgccttatc   3840
cggtaactgt tcacttgagt ccaacccgga aaagcacggt aaaacgccac tggcagcagc   3900
cattggtaac tgggagttcg cagaggattt gtttagctaa acacgcggtt gctcttgaag   3960
tgtgcgccaa agtccggcta cactggaagg acagatttgg ttgctgtgct ctgcgaaagc   4020
cagttaccac ggttaagcag ttccccaact gacttaacct tcgatcaaac cacctcccca   4080
ggtggttttt tcgtttacag ggcaaaagat tacgcgcaga aaaaaaggat ctcaagaaga   4140
tcctttgatc ttttctactg aaccgctcta gatttcagtg caatttatct cttcaaatgt   4200
agcacctgaa gtcagcccca tacgatataa gttgtaattc tcatgttagt catgccccgc   4260
gcccaccgga aggagctgac tgggttgaag gctctcaagg gcatcggtcg agatcccggt   4320
gcctaatgag tgagctaact tacattaatt gcgttgcgct cactgcccgc tttccagtcg   4380
ggaaacctgt cgtgccagct gcattaatga atcggccaac gcgcggggag aggcggtttg   4440
cgtattgggc gccagggtgg tttttctttt caccagtgag acgggcaaca gctgattgcc   4500
cttcaccgcc tggccctgag agagttgcag caagcggtcc acgctggttt gccccagcag   4560
gcgaaaatcc tgtttgatgg tggttaacgg cgggatataa catgagctgt cttcggtatc   4620
gtcgtatccc actaccgaga tgtccgcacc aacgcgcagc ccggactcgg taatggcgcg   4680
cattgcgccc agcgccatct gatcgttggc aaccagcatc gcagtgggaa cgatgccctc   4740
attcagcatt tgcatggttt gttgaaaacc ggacatggca ctccagtcgc cttcccgttc   4800
cgctatcggc tgaatttgat tgcgagtgag atatttatgc cagccagcca gacgcagacg   4860
cgccgagaca gaacttaatg ggcccgctaa cagcgcgatt tgctggtgac ccaatgcgac   4920
cagatgctcc acgcccagtc gcgtaccgtc ttcatgggag aaaataatac tgttgatggg   4980
tgtctggtca gagacatcaa gaaataacgc cggaacatta gtgcaggcag cttccacagc   5040
aatggcatcc tggtcatcca gcggatagtt aatgatcagc ccactgacgc gttgcgcgag   5100
aagattgtgc accgccgctt tacaggcttc gacgccgctt cgttctacca tcgacaccac   5160
cacgctggca cccagttgat cggcgcgaga tttaatcgcc gcgacaattt gcgacggcgc   5220
gtgcagggcc agactggagg tggcaacgcc aatcagcaac gactgtttgc ccgccagttg   5280
ttgtgccacg cggttgggaa tgtaattcag ctccgccatc gccgcttcca ctttttcccg   5340
cgttttcgca gaaacgtggc tggcctggtt caccacgcgg gaaacggtct gataagagac   5400
accggcatac tctgcgacat cgtataacgt tactggtttc acattcacca ccctgaattg   5460
actctcttcc gggcgctatc atgccatacc gcgaaaggtt ttgcgccatt cgatggtgtc   5520
cgggatctcg acgctctccc ttatgcgact cctgcattag gaaattaata cgactcacta   5580
ta                                                                  5582
```

<210> SEQ ID NO 132

<211> LENGTH: 5678
<212> TYPE: DNA
<213> ORGANISM: Artificial sequence
<220> FEATURE:
<223> OTHER INFORMATION: pDG10 plasmid

<400> SEQUENCE: 132
agcgcccaat acgcaaaccg cctctccccg cgcgttggcc gattcattaa tgcagctggc 60
acgacaggtt tcccgactgg aaagcgggca gtgagcgcaa cgcaattaat gtgagttagc 120
tcactcatta ggcaccccag gctttacact ttatgcttcc ggctcgtatg ttgtgtggaa 180
ttgtgagcgg ataacaattt cacacaggaa acagctatga ccatgattac gccaagctat 240
ttaggtgacg cgttagaata ctcaagctat gcatcaagct tggtaccgag ctcggatcca 300
ctagtaacgg ccgccagtgt gctggaattc aggcttaact tcatgtgaaa agtttgttaa 360
aatataaatg agcacgttaa tcatttaaca tagataatta aatagtaaaa gggagtgtac 420
gaccagtgat taagagtttt aatgaaatta tcatgaaggt aaagagcaaa gaaatgaaaa 480
aagttgctgt tgctgtagca caagacgagc cagtacttga agcagtaaga gatgctaaga 540
aaaatggtat tgcagatgct attcttgttg gagaccatga cgaaatcgtg tcaatcgcgc 600
ttaaaatagg aatggatgta aatgattttg aaatagtaaa cgagcctaac gttaagaaag 660
ctgctttaaa ggcagtagag cttgtatcaa ctggaaaagc tgatatggta atgaagggac 720
ttgtaaatac agcaactttc ttaagatctg tattaaacaa agaagttgga cttagaacag 780
gaaaaactat gtctcacgtt gcagtatttg aaactgagaa atttgataga ctattatttt 840
taacagatgt tgctttcaat acttatcctg aattaaagga aaaaattgat atagtaaaca 900
attcagttaa ggttgcacat gcaataggaa ttgaaaatcc aaaggttgct ccaatttgtg 960
cagttgaggt tataaaccct aaaatgccat caacacttga tgcagcaatg ctttcaaaaa 1020
tgagtgacag aggacaaatt aaaggttgtg tagttgacgg acctttagca cttgatatag 1080
ctttatcaga agaagcagca catcataagg gagtaacagg agaagttgct ggaaaagctg 1140
atatcttctt aatgccaaac atagaaacag gaaatgtaat gtataagact ttaacatata 1200
caactgattc aaaaaatgga ggaatcttag ttggaacttc tgcaccagtt gttttaactt 1260
caagagctga cagccatgaa acaaaaatga actctatagc acttgcagct ttagttgcag 1320
gcaataaata aattaaagtt aagtggagga atgttaacat gtatagatta ctaataatca 1380
atcctggctc gacctcaact aaaattggta tttatgacga tgaaaaagag atatttgaga 1440
agactttaag acattcagct gaagagatag aaaaatataa cactatattt gatcaatttc 1500
aattcagaaa gaatgtaatt ttagatgcgt taaaagaagc aaacatagaa gtaagttctt 1560
taaatgctgt agttggaaga ggcggactct taaagccaat agtaagtgga acttatgcag 1620
taaatcaaaa aatgcttgaa gaccttaaag taggagttca aggtcagcat gcgtcaaatc 1680
ttggtggaat tattgcaaat gaaatagcaa aagaaataaa tgttccagca tacatagttg 1740
atccagttgt tgtggatgag cttgatgaag tttcaagaat atcaggaatg gctgacattc 1800
caagaaaaag tatattccat gcattaaatc aaaaagcagt tgctagaaga tatgcaaaag 1860
aagttggaaa aaaatacgaa gatcttaatt taatcgtagt ccacatgggt ggaggtactt 1920
cagtaggtac tcataaagat ggtagagtaa tagaagttaa taatacactt gatggagaag 1980
gtccattctc accagaaaga agtggtggag ttccaatagg agatcttgta agattgtgct 2040
tcagcaacaa atatacttat gaagaagtaa tgaaaaagat aaacggcaaa ggcggagttg 2100
ttagttactt aaatactatc gattttaagg ctgtagttga taaagctctt gaaggagata 2160

```
agaaatgtgc acttatatat gaagctttca cattccaggt agcaaaagag ataggaaaat   2220
gttcaaccgt tttaaaagga aatgtagatg caataatctt aacaggcgga attgcgtaca   2280
acgagcatgt atgtaatgcc atagaggata gagtaaaatt catagcacct gtagttagat   2340
atggtggaga agatgaactt cttgcacttg cagaaggtgg acttagagtt ttaagaggag   2400
aagaaaaagc taaggaatac aaataataaa gtcataaata atataatata accagtaccc   2460
atgtttataa aacttttgcc ctataaacat gggtattgtc ctgaattctg cagatatcca   2520
tcacactggc ggccgctcga gcatgcatct agagggccca attcgcccta tagtgagtcg   2580
tattacaatt cactggccgt cgttttacaa cgtcgtgact gggaaaaccc tggcgttacc   2640
caacttaatc gccttgcagc acatccccct ttcgccagct ggcgtaatag cgaagaggcc   2700
cgcaccgatc gcccttccca acagttgcgc agcctatacg tacggcagtt taaggtttac   2760
acctataaaa gagagagccg ttatcgtctg tttgtggatg tacagagtga tattattgac   2820
acgccggggc gacggatggt gatccccctg gccagtgcac gtctgctgtc agataaagtc   2880
tcccgtgaac tttacccggt ggtgcatatc ggggatgaaa gctggcgcat gatgaccacc   2940
gatatggcca gtgtgccggt ctccgttatc ggggaagaag tggctgatct cagccaccgc   3000
gaaaatgaca tcaaaaacgc cattaacctg atgttctggg gaatataaat gtcaggcatg   3060
agattatcaa aaaggatctt cacctagatc cttttcacgt agaaagccag tccgcagaaa   3120
cggtgctgac cccggatgaa tgtcagctac tgggctatct ggacaaggga aaacgcaagc   3180
gcaaagagaa agcaggtagc ttgcagtggg cttacatggc gatagctaga ctgggcggtt   3240
ttatggacag caagcgaacc ggaattgcca gctggggcgc cctctggtaa ggttgggaag   3300
ccctgcaaag taaactggat ggctttcttg ccgccaagga tctgatggcg caggggatca   3360
agctctgatc aagagacagg atgaggatcg tttcgcatga ttgaacaaga tggattgcac   3420
gcaggttctc cggccgcttg ggtggagagg ctattcggct atgactgggc acaacagaca   3480
atcggctgct ctgatgccgc cgtgttccgg ctgtcagcgc aggggcgccc ggttcttttt   3540
gtcaagaccg acctgtccgg tgccctgaat gaactgcaag acgaggcagc gcggctatcg   3600
tggctggcca cgacgggcgt tccttgcgca gctgtgctcg acgttgtcac tgaagcggga   3660
agggactggc tgctattggg cgaagtgccg gggcaggatc tcctgtcatc tcaccttgct   3720
cctgccgaga aagtatccat catggctgat gcaatgcggc ggctgcatac gcttgatccg   3780
gctacctgcc cattcgacca ccaagcgaaa catcgcatcg agcgagcacg tactcggatg   3840
gaagccggtc ttgtcgatca ggatgatctg gacgaagagc atcaggggct cgcgccagcc   3900
gaactgttcg ccaggctcaa ggcgagcatg cccgacggcg aggatctcgt cgtgacccat   3960
ggcgatgcct gcttgccgaa tatcatggtg gaaaatggcc gcttttctgg attcatcgac   4020
tgtggccggc tgggtgtggc ggaccgctat caggacatag cgttggctac ccgtgatatt   4080
gctgaagagc ttggcggcga atgggctgac cgcttcctcg tgctttacgg tatcgccgct   4140
cccgattcgc agcgcatcgc cttctatcgc cttcttgacg agttcttctg aattattaac   4200
gcttacaatt tcctgatgcg gtattttctc cttacgcatc tgtgcggtat ttcacaccgc   4260
atcaggtggc acttttcggg gaaatgtgcg cggaacccct atttgtttat ttttctaaat   4320
acattcaaat atgtatccgc tcatgagaca ataaccctga taaatgcttc aataatagca   4380
cgtgaggagg gccaccatgg ccaagttgac cagtgccgtt ccggtgctca ccgcgcgcga   4440
cgtcgccgga gcggtcgagt tctggaccga ccggctcggg ttctcccggg acttcgtgga   4500
```

-continued ggacgacttc gccggtgtgg tccgggacga cgtgaccctg ttcatcagcg cggtccagga 4560
ccaggtggtg ccggacaaca ccctggcctg ggtgtgggtg cgcggcctgg acgagctgta 4620
cgccgagtgg tcggaggtcg tgtccacgaa cttccgggac gcctccgggc cggccatgac 4680
cgagatcggc gagcagccgt gggggcggga gttcgccctg cgcgacccgg ccggcaactg 4740
cgtgcacttc gtggccgagg agcaggactg acacgtgcta aaacttcatt tttaatttaa 4800
aaggatctag gtgaagatcc tttttgataa tctcatgacc aaaatccctt aacgtgagtt 4860
ttcgttccac tgagcgtcag accccgtaga aaagatcaaa ggatcttctt gagatccttt 4920
ttttctgcgc gtaatctgct gcttgcaaac aaaaaaacca ccgctaccag cggtggtttg 4980
tttgccggat caagagctac caactctttt tccgaaggta actggcttca gcagagcgca 5040
gataccaaat actgttcttc tagtgtagcc gtagttaggc caccacttca agaactctgt 5100
agcaccgcct acatacctcg ctctgctaat cctgttacca gtggctgctg ccagtggcga 5160
taagtcgtgt cttaccgggt tggactcaag acgatagtta ccggataagg cgcagcggtc 5220
gggctgaacg gggggttcgt gcacacagcc cagcttggag cgaacgacct acaccgaact 5280
gagataccta cagcgtgagc tatgagaaag cgccacgctt cccgaaggga gaaaggcgga 5340
caggtatccg gtaagcggca gggtcggaac aggagagcgc acgagggagc ttccaggggg 5400
aaacgcctgg tatctttata gtcctgtcgg gtttcgccac ctctgacttg agcgtcgatt 5460
tttgtgatgc tcgtcagggg ggcggagcct atggaaaaac gccagcaacg cggccttttt 5520
acggttcctg gccttttgct ggccttttgc tcacatgttc tttcctgcgt tatcccctga 5580
ttctgtggat aaccgtatta ccgcctttga gtgagctgat accgctcgcc gcagccgaac 5640
gaccgagcgc agcgagtcag tgagcgagga agcggaag 5678

<210> SEQ ID NO 133
<211> LENGTH: 3651
<212> TYPE: DNA
<213> ORGANISM: Artificial sequence
<220> FEATURE:
<223> OTHER INFORMATION: pLS9-111 plasmid

<400> SEQUENCE: 133
tagaaaaact catcgagcat caaatgaaac tgcaatttat tcatatcagg attatcaata 60
ccatattttt gaaaaagccg tttctgtaat gaaggagaaa actcaccgag gcagttccat 120
aggatggcaa gatcctggta tcggtctgcg attccgactc gtccaacatc aatacaacct 180
attaatttcc cctcgtcaaa aataaggtta tcaagtgaga aatcaccatg agtgacgact 240
gaatccggtg agaatggcaa aagtttatgc atttctttcc agacttgttc aacaggccag 300
ccattacgct cgtcatcaaa atcactcgca tcaaccaaac cgttattcat tcgtgattgc 360
gcctgagcga ggcgaaatac gcgatcgctg ttaaaaggac aattacaaac aggaatcgag 420
tgcaaccggc gcaggaacac tgccagcgca tcaacaatat tttcacctga atcaggatat 480
tcttctaata cctggaacgc tgtttttccg gggatcgcag tggtgagtaa ccatgcatca 540
tcaggagtac ggataaaatg cttgatggtc ggaagtggca taaattccgt cagccagttt 600
agtctgacca tctcatctgt aacatcattg gcaacgctac ctttgccatg tttcagaaac 660
aactctggcg catcgggctt cccatacaag cgatagattg tcgcacctga ttgcccgaca 720
ttatcgcgag cccatttata cccatataaa tcagcatcca tgttggaatt taatcgcggc 780
ctcgacgttt cccgttgaat atggctcata ttcttccttt ttcaatatta ttgaagcatt 840
tatcagggtt attgtctcat gagcggatac atatttgaat gtatttagaa aaataaacaa 900

-continued

```
atagggtca gtgttacaac caattaacca attctgaaca ttatcgcgag cccatttata    960
cctgaatatg gctcataaca ccccttgttt gcctggcggc agtagcgcgg tggtcccacc  1020
tgaccccatg ccgaactcag aagtgaaacg ccgtagcgcc gatggtagtg tggggactcc  1080
ccatgcgaga gtagggaact gccaggcatc aaataaaacg aaaggctcag tcgaaagact  1140
gggcctttcg cccgggctaa ttagggggtg tcgcccttac gtacgtactc gattgacgcc  1200
taggagatct ttacatcccc catttaataa gcaatcctgt ataggttaat ccgccgccaa  1260
acccgaaaag caaaacgatt tgatcttttt tcagcttccc ggctttcact gcgagatcga  1320
gcgccaaaac aattgaaacc gaagacgtgt ttccgtagtg ctcaacgcta gtgagcgttt  1380
tttcaatcgg gaacggtgtt ttttcacaaa ttgactcgat catgcgcaag ttggcgctgt  1440
gaggaacaaa ccaatcgaga tcatcggagc tgagtcctgc tttatgtaaa agccgttcaa  1500
attcgccagg gacggttctt gcggcccatt tatatacctc gcgtccgttt tgcaccattt  1560
ttccggaacc gacaagctgc acaccgttta tttcatttcg cagtccggca cgatacaaaa  1620
tatcgccgcc gttcccgctt gttccttgta cagacgcaag aaatcccggc gtctcttcat  1680
ctcgttctac taacagcgca cccgcggcat cgccgaacag tacgcatgtc gttcgatccg  1740
tataatcggt tacctttgat aacgtctctc cggcgatgac gagaattttt tgatgaaggc  1800
cagatgtgat caatccattt gccaaatgga ggccgtatgt cagcccggcg catgtcgcat  1860
taatatccag cgcgccggtg ctttcccagc cgaaatattc ctgtacgcgg catgccgtac  1920
tcggaaaggc gtaatcggat gtggttgtgg caacgaggat catatcgaca tcatcaagcg  1980
ttcctttata acggctcttg agattcttca ccgcttctat gcataaatca gaggtaaatt  2040
gatgttcatc cgcaatccgg cgttctctca ttcctgtgcg ctgaacgatc cattcatcag  2100
aggtatcaac gatcttttct aaatctgcat tggttaaacg tctgctcggc gcataggtgc  2160
cgatagctgt aatttttgct tttgacatat gtcagcgaaa gggcgacaca aaatttattc  2220
taaatgcata ataaatactg ataacatctt atagtttgta ttatattttg tattatcgtt  2280
gacatgtata attttgatat caaaaactga ttttcccttt attattttcg agatttattt  2340
tcttaattct ctttaacaaa ctagaaatat tgtatataca aaaaatcata aataatagat  2400
gaatagttta attataggtg ttcatcaatc gaaaaagcaa cgtatcttat ttaaagtgcg  2460
ttgctttttt ctcatttata aggttaaata attctcatat atcaagcaaa gtgacaggcg  2520
cccttaaata ttctgacaaa tgctctttcc ctaaactccc cccataaaaa aacccgccga  2580
agcgggtttt tacgttattt gcggattaac gattactcgt tatcagaacc gcccaggggg  2640
cccgagctta agactggccg tcgttttaca acacagaaag agtttgtaga aacgcaaaaa  2700
ggccatccgt caggggcctt ctgcttagtt tgatgcctgg cagttcccta ctctcgcctt  2760
ccgcttcctc gctcactgac tcgctgcgct cggtcgttcg gctgcggcga gcggtatcag  2820
ctcactcaaa ggcggtaata cggttatcca cagaatcagg ggataacgca ggaaagaaca  2880
tgtgagcaaa aggccagcaa aaggccagga accgtaaaaa ggccgcgttg ctggcgtttt  2940
tccataggct ccgcccccct gacgagcatc acaaaaatcg acgctcaagt cagaggtggc  3000
gaaacccgac aggactataa agataccagg cgtttccccc tggaagctcc ctcgtgcgct  3060
ctcctgttcc gaccctgccg cttaccggat acctgtccgc ctttctccct tcgggaagcg  3120
tggcgctttc tcatagctca cgctgtaggt atctcagttc ggtgtaggtc gttcgctcca  3180
agctgggctg tgtgcacgaa ccccccgttc agcccgaccg ctgcgcctta tccggtaact  3240
```

-continued

```
atcgtcttga gtccaacccg gtaagacacg acttatcgcc actggcagca gccactggta   3300

acaggattag cagagcgagg tatgtaggcg gtgctacaga gttcttgaag tggtgggcta   3360

actacggcta cactagaaga acagtatttg gtatctgcgc tctgctgaag ccagttacct   3420

tcggaaaaag agttggtagc tcttgatccg gcaaacaaac caccgctggt agcggtggtt   3480

tttttgtttg caagcagcag attacgcgca gaaaaaaagg atctcaagaa gatcctttga   3540

tcttttctac ggggtctgac gctcagtgga acgacgcgcg cgtaactcac gttaagggat   3600

tttggtcatg agcttgcgcc gtcccgtcaa gtcagcgtaa tgctctgctt t            3651
```

<210> SEQ ID NO 134
<211> LENGTH: 7310
<212> TYPE: DNA
<213> ORGANISM: Artificial sequence
<220> FEATURE:
<223> OTHER INFORMATION: pLS9-114 plasmid

<400> SEQUENCE: 134

```
ttaataagat gatcttcttg agatcgtttt ggtctgcgcg taatctcttg ctctgaaaac     60

gaaaaaaccg ccttgcaggg cggtttttcg aaggttctct gagctaccaa ctctttgaac    120

cgaggtaact ggcttggagg agcgcagtca ccaaaacttg tcctttcagt ttagccttaa    180

ccggcgcatg acttcaagac taactcctct aaatcaatta ccagtggctg ctgccagtgg    240

tgcttttgca tgtctttccg ggttggactc aagacgatag ttaccggata aggcgcagcg    300

gtcggactga acggggggtt cgtgcataca gtccagcttg gagcgaactg cctacccgga    360

actgagtgtc aggcgtggaa tgagacaaac gcggccataa cagcggaatg acaccggtaa    420

accgaaaggc aggaacagga gagcgcacga gggagccgcc agggggaaac gcctggtatc    480

tttatagtcc tgtcgggttt cgccaccact gatttgagcg tcagatttcg tgatgcttgt    540

caggggggcg gagcctatgg aaaaacggct ttgccgcggc cctctcactt ccctgttaag    600

tatcttcctg gcatcttcca ggaaatctcc gccccgttcg taagccattt ccgctcgccg    660

cagtcgaacg accgagcgta gcgagtcagt gagcgaggaa gcggaatata tcctgtatca    720

catattctgc tgacgcaccg gtgcagcctt ttttctcctg ccacatgaag cacttcactg    780

acaccctcat cagtgccaac atagtaagcc agtatacact ccgctagcgc tgaggtcccg    840

cagccgaacg accgagcgca gcggcgagag tagggaactg ccaggcatcc tgggcggttc    900

tgataacgag taatcgttaa tccgcaaata acgtaaaaac ccgcttcggc gggttttttt    960

atgggggggag tttagggaaa gagcatttgt cagaatattt aagggcgcct gtcactttgc  1020

ttgatatatg agaattattt aaccttataa atgagaaaaa agcaacgcac tttaaataag   1080

atacgttgct tttcgattg atgaacacct ataattaaac tattcatcta ttatttatga    1140

ttttttgtat atacaatatt tctagtttgt taaagagaat taagaaaata aatctcgaaa   1200

ataataaagg gaaaatcagt ttttgatatc aaaattatac atgtcaacga taatacaaaa   1260

tataatacaa actataagat gttatcagta tttattatgc atttagaata ccttttgtgt   1320

cgcccttggg gcatatgaaa gctggcattc ttggtgttgg acgttacatt cctgagaagg   1380

ttttaacaaa tcatgatctt gaaaaaatgg ttgaaacttc tgacgagtgg attcgtacaa   1440

gaacaggaat agaagaaaga agaatcgcag cagatgatgt gttttcatca cacatggctg   1500

ttgcagcagc gaaaaatgcg ctggaacaag ctgaagtggc tgctgaggat ctggatatga   1560

tcttggttgc aactgttaca cctgatcagt cattccctac ggtgtcttgt atgattcaag   1620

aacaactcgg cgcgaagaaa gcgtgtgcta tggatatcag cgcggcttgt gcgggcttca   1680
```

-continued

```
tgtacggggt tgtaaccggt aaacaattta ttgaatccgg aacctacaag catgttctag   1740
ttgttggtgt agagaagctc tcaagcatta ccgactggga agaccgcaat acagccgttc   1800
tgtttggaga cggagcaggc gctgcggtag tcgggccagt cagtgatgac agaggaatcc   1860
tttcatttga actaggagcc gacggcacag gcggtcagca cttgtatctg aatgaaaaac   1920
gacatacaat catgaatgga cgagaagttt tcaaatttgc agtccgccaa atgggagaat   1980
catgcgtaaa tgtcattgaa aaagccggac tttcaaaaga ggatgtggac tttttgattc   2040
cgcatcaggc gaacatccgt atcatggaag ctgctcgcga gcgtttagag cttcctgtcg   2100
aaaagatgtc taaaactgtt cataaatatg gaaatacttc tgccgcatcc attccgatct   2160
ctcttgtaga agaattggaa gccggtaaaa tcaaagacgg cgatgtggtc gttatggtag   2220
ggttcggcgg aggactaaca tggggcgcca ttgcaatccg ctggggccga taaaaaaaag   2280
gtgaggtgca cacaagatga ctaaaaaacg tgtagttgtt acaggtcttg gagcattatc   2340
tccacttggc aacgacgtcg atacaagttg gaataacgca atcaacggtg tgtccggaat   2400
cggtccgatc actcgtgttg acgctgaaga atatccggca aaagttgccg ctgaattaaa   2460
agattttaat gttgaagatt atatggataa aaaagaagcc agaaaaatgg accgctttac   2520
acaatatgcg gttgtggctg cgaaaatggc ggttgaagat gctgatctta acattaccga   2580
tgagatcgcg ccgagagtcg gtgtttgggt aggctccggt atcggaggac ttgaaacact   2640
agagtctcaa tttgaaatct tcttaacaaa aggcccaaga cgggtaagcc cgtttttcgt   2700
gccaatgatg attcctgaca tggcgacagg ccagatttct attgcattag gagcaaaagg   2760
ggtgaactct tgtacggtta cagcatgtgc tacaggaacg aactccatcg gtgacgcgtt   2820
taaggttatt cagcgcggtg atgcagacgt gatggtcaca ggcggaacag aagcgctgct   2880
gacaagaatg tcattcgccg gctttagtgc caacaaagcg ctgtctacta atccagatcc   2940
gaaaacagcg agccgcccgt ttgataaaaa ccgtgatggc tttgtcatgg gggaaggtgc   3000
agggattatc gttcttgaag aacttgagca tgccctggcc cgcggcgcta aaatttacgg   3060
agaaattgtc ggctacggct caaccggaga cgcttatcat atcacagcgc cggcccaaga   3120
cggtgaaggc ggagcgagag cgatgcaaga agccattaaa gatgcaggca ttgcacctga   3180
agaaattgat tacatcaatg ctcacgggac aagcacgtat tacaacgaca aatacgaaac   3240
aatggcgatt aagaccgttt ttggcgagca tgcgcataaa cttgcggtaa gctctacaaa   3300
atcgatgaca ggccacctct taggagcagc cggcggtatt gaagccattt tctctatcct   3360
ggccattaaa gaaggcgtga ttccgccgac aatcaatatt caaacacctg acgaagaatg   3420
tgatttggat tatgtgcctg atgaagcccg cagacaggaa cttaattatg ttctcagcaa   3480
ctcattagga ttcggcggac acaacgcaac attaatcttt aaaaaatatc aatcataagt   3540
tttttctcga aaatttcatc gtagtttctc tagtttttta aaaacgaatc cactataata   3600
cttgagggga ggtgaattgc tatggcagac acattagagc gtgtaacgaa aatcatcgta   3660
gatcgccttg gcgttgatga agcagacgtc aaacttgaag catctttcaa ggaagactta   3720
ggtgctgatt ccctagatgt agttgagctt gttatggaac ttgaagacga gtttgatatg   3780
gagatttctg acgaagatgc tgaaaagatt gcaacagtcg gcgacgctgt gaactacata   3840
caaaaccagc aataattaat taacctagga aaaaagggcg acacccctca attagcccgg   3900
gcgaaaggcc cagtctttcg actgagcctt tcgttttatt tgatgcctgg cagttcccta   3960
ctctcgcatg gggagtcccc acactaccat cggcgctacg gcgtttcact tctgagttcg   4020
```

-continued

```
gcatggggtc aggtgggacc accgcgctac tgccgccagg caaacaaggg gtgttatgag   4080
ccatattcag gtataaatgg gctcgcgata atgttcagaa ttggttaatt ggttgtaaca   4140
ctgaccccta tttgtttatt tttctaaata cattcaaata tgtatccgct catgagacaa   4200
taaccctgat aaatgcttca ataatattga aaaaggaaga atatgagtat tcaacatttc   4260
cgtgtcgccc ttattccctt ttttgcggca ttttgccttc ctgtttttgc tcacccagaa   4320
acgctggtga aagtaaaaga tgctgaagat cagttgggtg cacgagtggg ttacatcgaa   4380
ctggatctca acagcggtaa gatccttgag agttttcgcc ccgaagaacg ttttccaatg   4440
atgagcactt ttaaagttct gctatgtggc gcggtattat cccgtattga cgccgggcaa   4500
gagcaactcg gtcgccgcat acactattct cagaatgact tggttgagta ctcaccagtc   4560
acagaaaagc atcttacgga tggcatgaca gtaagagaat tatgcagtgc tgccataacc   4620
atgagtgata acactgcggc caacttactt ctgacaacga tcggaggacc gaaggagcta   4680
accgcttttt tgcacaacat gggggatcat gtaactcgcc ttgatcgttg ggaaccggag   4740
ctgaatgaag ccataccaaa cgacgagcgt gacaccacga tgcctgtagc gatggcaaca   4800
acgttgcgca aactattaac tggcgaacta cttactctag cttcccggca acaattaata   4860
gactggatgg aggcggataa agttgcagga ccacttctgc gctcggccct tccggctggc   4920
tggtttattg ctgataaatc cggagccggt gagcgtggtt ctcgcggtat catcgcagcg   4980
ctggggccag atggtaagcc ctcccgtatc gtagttatct acacgacggg gagtcaggca   5040
actatggatg aacgaaatag acagatcgct gagataggtg cctcactgat taagcattgg   5100
taaaggagga aaaaaaaatg agccatattc aacgggaaac gtcgaggccg cgattaaatt   5160
ccaacatgga tgctgattta tatgggtata aatgggctcg cgataatgtc gggcaatcag   5220
gtgcgacaat ctatcgcttg tatgggaagc ccgatgcgcc agagttgttt ctgaaacatg   5280
gcaaaggtag cgttgccaat gatgttacag atgagatggt cagactaaac tggctgacgg   5340
aatttatgcc acttccgacc atcaagcatt ttatccgtac tcctgatgat gcatggttac   5400
tcaccactgc gatccccgga aaaacagcgt tccaggtatt agaagaatat cctgattcag   5460
gtgaaaatat tgttgatgcg ctggcagtgt tcctgcgccg gttgcactcg attcctgttt   5520
gtaattgtcc ttttaacagc gatcgcgtat ttcgcctcgc tcaggcgcaa tcacgaatga   5580
ataacggttt ggttgatgcg agtgattttg atgacgagcg taatggctgg cctgttgaac   5640
aagtctggaa agaaatgcat aaacttttgc cattctcacc ggattcagtc gtcactcatg   5700
gtgatttctc acttgataac cttatttttg acgaggggaa attaataggt tgtattgatg   5760
ttggacgagt cggaatcgca gaccgatacc aggatcttgc catcctatgg aactgcctcg   5820
gtgagttttc tccttcatta cagaaacggc tttttcaaaa atatggtatt gataatcctg   5880
atatgaataa attgcagttt catttgatgc tcgatgagtt tttctaaagg aggaaaaaaa   5940
aatggagaaa aaaatcactg gatataccac cgttgatata tcccaatggc atcgtaaaga   6000
acattttgag gcatttcagt cagttgctca atgtacctat aaccagaccg ttcagctgga   6060
tattacggcc tttttaaaga ccgtaaagaa aaataagcac aagttttatc cggcctttat   6120
tcacattctt gcccgcctga tgaatgctca tccggagttc cgtatggcaa tgaaagacgg   6180
tgagctggtg atatgggata gtgttcaccc ttgttacacc gttttccatg agcaaactga   6240
aacgttttca tcgctctgga gtgaatacca cgacgatttc cggcagtttc tacacatata   6300
ttcgcaagat gtggcgtgtt acggtgaaaa cctggcctat ttccctaaag ggtttattga   6360
gaatatgttt ttcgtcagcg ccaatccctg ggtgagtttc accagttttg atttaaacgt   6420
```

```
ggccaatatg gacaacttct tcgcccccgt tttcactatg ggcaaatatt atacgcaagg   6480
cgacaaggtg ctgatgccgc tggcgattca ggttcatcat gccgtctgtg atggcttcca   6540
tgtcggcaga atgcttaatg aattacaaca gtactgcgat gagtggcagg gcggggcgta   6600
aacgccgagg aggaaaaaaa aatgcgctca cgcaactggt ccagaacctt gaccgaacgc   6660
agcggtggta acggcgcagt ggcggttttc atggcttgtt atgactgttt ttttgtacag   6720
tctatgcctc gggcatccaa gcagcaagcg cgttacgccg tgggtcgatg tttgatgtta   6780
tggagcagca acgatgttac gcagcagggc agtcgcccta aaacaaagtt aggtggctca   6840
agtatgggca tcattcgcac atgtaggctc ggccctgacc aagtcaaatc catgcgggct   6900
gctcttgatc ttttcggtcg tgagttcggt gacgtagcca cctactccca acatcagccg   6960
gactccgatt acctcgggaa cttgctccgt agtaagacat tcatcgcgct tgctgccttc   7020
gaccaagaag cggttgttgg cgctctcgcg gcttacgttc tgcccaagtt tgagcagccg   7080
cgtagtgaga tctatatcta tgatctcgca gtctccggcg agcaccggag gcagggcatt   7140
gccaccgcgc tcatcaatct cctcaagcat gaggccaacg cgcttggtgc ttatgtgatc   7200
tacgtgcaag cagattacgg tgacgatccc gcagtggctc tctatacaaa gttgggcata   7260
cgggaagaag tgatgcactt tgatatcgac ccaagtaccg ccacctaagc              7310
```

<210> SEQ ID NO 135
<211> LENGTH: 7804
<212> TYPE: DNA
<213> ORGANISM: Artificial sequence
<220> FEATURE:
<223> OTHER INFORMATION: pLS9-115 plasmid

<400> SEQUENCE: 135

```
ggtggcggta cttgggtcga tatcaaagtg catcacttct tcccgtatgc ccaactttgt     60
atagagagcc actgcgggat cgtcaccgta atctgcttgc acgtagatca cataagcacc    120
aagcgcgttg gcctcatgct tgaggagatt gatgagcgcg gtggcaatgc cctgcctccg    180
gtgctcgccg gagactgcga gatcatagat atagatctca ctacgcggct gctcaaactt    240
gggcagaacg taagccgcga gagcgccaac aaccgcttct tggtcgaagg cagcaagcgc    300
gatgaatgtc ttactacgga gcaagttccc gaggtaatcg gagtccggct gatgttggga    360
gtaggtggct acgtcaccga actcacgacc gaaaagatca agagcagccc gcatggattt    420
gacttggtca gggccgagcc tacatgtgcg aatgatgccc atacttgagc cacctaactt    480
tgttttaggg cgactgccct gctgcgtaac atcgttgctg ctccataaca tcaaacatcg    540
acccacggcg taacgcgctt gctgcttgga tgcccgaggc atagactgta caaaaaaaca    600
gtcataacaa gccatgaaaa ccgccactgc gccgttacca ccgctgcgtt cggtcaaggt    660
tctggaccag ttgcgtgagc gcattttttt ttcctcctcg gcgtttacgc cccgccctgc    720
cactcatcgc agtactgttg taattcatta agcattctgc cgacatggaa gccatcacag    780
acggcatgat gaacctgaat cgccagcggc atcagcacct tgtcgccttg cgtataatat    840
ttgcccatag tgaaaacggg ggcgaagaag ttgtccatat tggccacgtt taaatcaaaa    900
ctggtgaaac tcacccaggg attggcgctg acgaaaaaca tattctcaat aaacccttta    960
gggaaatagg ccaggttttc accgtaacac gccacatctt gcgaatatat gtgtagaaac   1020
tgccggaaat cgtcgtggta ttcactccag agcgatgaaa acgtttcagt ttgctcatgg   1080
aaaacggtgt aacaagggtg aacactatcc catatcacca gctcaccgtc tttcattgcc   1140
```

-continued

```
atacggaact ccggatgagc attcatcagg cgggcaagaa tgtgaataaa ggccggataa   1200
aacttgtgct tatttttctt tacggtcttt aaaaaggccg taatatccag ctgaacggtc   1260
tggttatagg tacattgagc aactgactga aatgcctcaa aatgttcttt acgatgccat   1320
tgggatatat caacggtggt atatccagtg attttttct ccattttttt ttcctccttt    1380
agaaaaactc atcgagcatc aaatgaaact gcaatttatt catatcagga ttatcaatac   1440
catatttttg aaaaagccgt ttctgtaatg aaggagaaaa ctcaccgagg cagttccata   1500
ggatggcaag atcctggtat cggtctgcga ttccgactcg tccaacatca atacaaccta   1560
ttaatttccc ctcgtcaaaa ataaggttat caagtgagaa atcaccatga gtgacgactg   1620
aatccggtga gaatggcaaa agtttatgca tttctttcca gacttgttca acaggccagc   1680
cattacgctc gtcatcaaaa tcactcgcat caaccaaacc gttattcatt cgtgattgcg   1740
cctgagcgag gcgaaatacg cgatcgctgt taaaaggaca attacaaaca ggaatcgagt   1800
gcaaccggcg caggaacact gccagcgcat caacaatatt ttcacctgaa tcaggatatt   1860
cttctaatac ctggaacgct gtttttccgg ggatcgcagt ggtgagtaac catgcatcat   1920
caggagtacg gataaaatgc ttgatggtcg gaagtggcat aaattccgtc agccagttta   1980
gtctgaccat ctcatctgta acatcattgg caacgctacc tttgccatgt ttcagaaaca   2040
actctggcgc atcgggcttc ccatacaagc gatagattgt cgcacctgat tgcccgacat   2100
tatcgcgagc ccatttatac ccatataaat cagcatccat gttggaattt aatcgcggcc   2160
tcgacgtttc ccgttgaata tggctcattt tttttcctc ctttaccaat gcttaatcag    2220
tgaggcacct atctcagcga tctgtctatt tcgttcatcc atagttgcct gactccccgt   2280
cgtgtagata actacgatac gggagggctt accatctggc cccagcgctg cgatgatacc   2340
gcgagaacca cgctcaccgg ctccggattt atcagcaata aaccagccag ccggaagggc   2400
cgagcgcaga agtggtcctg caactttatc cgcctccatc cagtctatta attgttgccg   2460
ggaagctaga gtaagtagtt cgccagttaa tagtttgcgc aacgttgttg ccatcgctac   2520
aggcatcgtg gtgtcacgct cgtcgtttgg tatggcttca ttcagctccg gttcccaacg   2580
atcaaggcga gttacatgat cccccatgtt gtgcaaaaaa gcggttagct ccttcggtcc   2640
tccgatcgtt gtcagaagta agttggccgc agtgttatca ctcatggtta tggcagcact   2700
gcataattct cttactgtca tgccatccgt aagatgcttt tctgtgactg gtgagtactc   2760
aaccaagtca ttctgagaat agtgtatgcg gcgaccgagt tgctcttgcc cggcgtcaat   2820
acgggataat accgcgccac atagcagaac tttaaaagtg ctcatcattg gaaaacgttc   2880
ttcggggcga aaactctcaa ggatcttacc gctgttgaga tccagttcga tgtaacccac   2940
tcgtgcaccc aactgatctt cagcatcttt tactttcacc agcgtttctg ggtgagcaaa   3000
aacaggaagg caaaatgccg caaaaaaggg aataagggcg acacggaaat gttgaatact   3060
catattcttc ctttttcaat attattgaag catttatcag ggttattgtc tcatgagcgg   3120
atacatattt gaatgtattt agaaaaataa acaaataggg gtcagtgtta caaccaatta   3180
accaattctg aacattatcg cgagcccatt tatacctgaa tatggctcat aacacccctt   3240
gtttgcctgg cggcagtagc gcggtggtcc cacctgaccc catgccgaac tcagaagtga   3300
aacgccgtag cgccgatggt agtgtgggga ctccccatgc gagagtaggg aactgccagg   3360
catcaaataa aacgaaaggc tcagtcgaaa gactgggcct ttcgcccggg ctaattgagg   3420
ggtgtcgccc ttattcgact ctatagtgaa gttcctattc tctagaaagt ataggaactt   3480
ctgaagtggg gcatatgtct aagatcaagc caagcaaggg cgctccgtac gcgcgcatcc   3540
```

-continued

```
tgggcgtcgg cggttaccgt ccgacccgtg tggtgccgaa cgaggtgatc ctggagaaga   3600
tcgactcttc cgacgagtgg attcgctctc gctccggcat cgaaacgcgt cactgggcgg   3660
gtccggaaga aaccgtcgcg gcgatgtctg tggaggcctc cggcaaggca ctggccgacg   3720
ccggtatcga cgcctctcgt atcggtgccg tggtagtctc taccgtgtct cacttcagcc   3780
agaccccggc catcgccacc gagatcgccg accgcctggg cacggacaag gccgcagcct   3840
tcgacatctc tgccggctgc gcgggcttcg gctacggtct gaccctggcc aagggcatgg   3900
tcgtcgaagg ttctgcggag tacgtgctgg tcatcggcgt ggagcgtctg tccgacctga   3960
ccgacctgga ggaccgtgcc acggccttcc tgttcggcga cggcgctggt gcggtcgtgg   4020
tcggcccgtc ccaggagccg gcaatcggcc cgacggtctg ggctctgag ggcgacaagg   4080
ccgaaacgat caagcagacc gtttcctggg accgcttccg tatcggcgat gtctccgaac   4140
tgccgctgga ctccgagggc aacgtcaagt ttcctgcgat cacgcaggag ggccaggcgg   4200
tgttccgctg ggccgtgttc gagatggcga aggtcgcgca gcaggcgctg gacgcggcgg   4260
gtatcagccc ggacgacctg gacgtcttta tcccgcacca ggccaatgtg cgtatcatcg   4320
actctatggt gaaaaccctg aagctgccgg agcacgtcac ggtcgcccgt gacatccgca   4380
ccaccggcaa cacctctgcc gcctctattc cgctggcgat ggagcgtctg ctggcgaccg   4440
gcgacgcgcg tagcggcgac accgcgctgg tcatcggctt cggtgcgggt ctggtctacg   4500
ccgcgacggt cgttaccctg ccgtaaccac tccgtgccgg atcaccccgg tccggaacgg   4560
agagcagcac cgcccgccgc cgacgcggcg ggccgccaca ccctctggac aacaaagaag   4620
gagcgccgtc atggccgcca ctcaggaaga gatcgtcgcc ggtctggcgg agatcgtgaa   4680
cgagatcgcc ggcatcccgg tcgaggacgt caagctggac aagtccttca ccgacgacct   4740
ggacgtagac tctctgagca tggtcgaggt cgtcgtcgcc gccgaagagc gcttcgacgt   4800
caagatcccg gacgacgacg tcaagaacct gaaaacggtc ggcgacgcga cgaagtacat   4860
cctggaccac caggcctgat ccgccgatac tcgggcatga cccgcgtacc gggcagatcc   4920
gggcagactg ccccgccgcc cggcggtggc gccgtacgaa tccgtatccc gttggagaaa   4980
gaattcccat gagcagcacc aatcgcaccg tggtcgtcac cggtatcggc gcaaccaccc   5040
cgctgggtgg cgacgcagcc tctacctggg agggtctggt cgcgggtcgt tccggcgtcc   5100
gtccgctgga gcaggagtgg gctgccgacc aggcggtccg tatcgcagcg ccggcagccg   5160
tagacccgtc cgaggtcatc ccgcgtccgc aggcacgccg tctggaccgc tctgcgcagt   5220
tcgcgctgat cgcggcgcag gaggcctgga aggacgccgg ttacgccggc aaggcgggcg   5280
agtctccggc ggaggacggt gcggctcacg tagacccgga ccgtctgggt gcggtcatcg   5340
cctccggcat cggcggcgtg accacgctgc tggaccagta cgacgtgctg aaggagaagg   5400
gcgtccgccg cgtttccccg cacaccgtcc cgatgctgat gccgaacggt ccgtccgcca   5460
acgtcggcct ggccgtgggt gcccgtgcgg gcgtgcacac cccggtgtct gcctgcgcgt   5520
ctggcgccga ggccatcggc tacgccatcg agatgatccg cactggccgt gcggacgtcg   5580
tcgtcgcggg tggcacggag gcggcgatcc acccgctgcc gattgccgcg ttcggcaaca   5640
tgatggcgat gtccaagaac aacgacgacc cgcagggcgc ctcccgcccg ttcgacacgg   5700
cgcgtgacgg cttcgtcctg ggcgaaggtg ccggcgtcct ggtcctggag tccgccgagc   5760
atgcggcagc gcgcggtgcc cgcgtctacg cggaggcggt cggccagggc atctccgccg   5820
acagccacga catcgtgcag ccggagccgg agggccgtgg catctccgca gcgctgcaaa   5880
```

acctgctgga cggcaacgac ctggacccgg ccgagatcgt gcacgtcaac gcgcacgcca 5940
cctctacccc ggcaggtgac atcgccgagc tgaaggcgct gcgcaaggtc ctgggcgacg 6000
acgtagacca catggccgtc agcggcacca agtctatgac cggtcacctg ctgggtggcg 6060
ctggcggcgt ggagtccgtg gcgaccgtgc tggcgctgta ccaccgtgtg gctccgccga 6120
ccatcaacgt cgagaacctg gacccggagg ccgaggccaa cgcggacatc gtccgcggtg 6180
aggcccgcaa gctgccggtg gagggccgta tcgccgcgct gaacgactct ttcggcttcg 6240
gcggtcacaa cgtggtgctg gcgttccgtt ctgtctgatt aattaaccta ggaaaatgaa 6300
gtgaagttcc tatactttct agagaatagg aacttctata gtgagtcgaa taagggcgac 6360
acaaaattta ttctaaatgc ataataaata ctgataacat cttatagttt gtattatatt 6420
ttgtattatc gttgacatgt ataattttga tatcaaaaac tgattttccc tttattattt 6480
tcgagattta ttttcttaat tctctttaac aaactagaaa tattgtatat acaaaaaatc 6540
ataaataata gatgaatagt ttaattatag gtgttcatca atcgaaaaag caacgtatct 6600
tatttaaagt gcgttgcttt ttctcattt ataaggttaa ataattctca tatatcaagc 6660
aaagtgacag gcgcccttaa atattctgac aaatgctctt tccctaaact ccccccataa 6720
aaaaacccgc cgaagcgggt ttttacgtta tttgcggatt aacgattact cgttatcaga 6780
accgcccagg gggcccgagc ttaagactgg ccgtcgtttt acaacacaga aagagtttgt 6840
agaaacgcaa aaaggccatc cgtcaggggc cttctgctta gtttgatgcc tggcagttcc 6900
ctactctcgc cttccgcttc ctcgctcact gactcgctgc gctcggtcgt tcggctgcgg 6960
cgagcggtat cagctcactc aaaggcggta atacggttat ccacagaatc aggggataac 7020
gcaggaaaga acatgtgagc aaaaggccag caaaaggcca ggaaccgtaa aaaggccgcg 7080
ttgctggcgt ttttccatag gctccgcccc cctgacgagc atcacaaaaa tcgacgctca 7140
agtcagaggt ggcgaaaccc gacaggacta taaagatacc aggcgtttcc ccctggaagc 7200
tccctcgtgc gctctcctgt tccgaccctg ccgcttaccg gatacctgtc cgcctttctc 7260
ccttcgggaa gcgtggcgct ttctcatagc tcacgctgta ggtatctcag ttcggtgtag 7320
gtcgttcgct ccaagctggg ctgtgtgcac gaaccccccg ttcagcccga ccgctgcgcc 7380
ttatccggta actatcgtct tgagtccaac ccggtaagac acgacttatc gccactggca 7440
gcagccactg gtaacaggat tagcagagcg aggtatgtag gcggtgctac agagttcttg 7500
aagtggtggg ctaactacgg ctacactaga agaacagtat ttggtatctg cgctctgctg 7560
aagccagtta ccttcggaaa aagagttggt agctcttgat ccggcaaaca aaccaccgct 7620
ggtagcggtg gtttttttgt ttgcaagcag cagattacgc gcagaaaaaa aggatctcaa 7680
gaagatcctt tgatcttttc tacggggtct gacgctcagt ggaacgacgc gcgcgtaact 7740
cacgttaagg gattttggtc atgagcttgc gccgtcccgt caagtcagcg taatgctctg 7800
ctta 7804

<210> SEQ ID NO 136
<211> LENGTH: 10460
<212> TYPE: DNA
<213> ORGANISM: Artificial sequence
<220> FEATURE:
<223> OTHER INFORMATION: pKZ4 plasmid

<400> SEQUENCE: 136
tcgcgacgcg aggctggatg gccttcccca ttatgattct tctcgcttcc ggcggcatcg 60
ggatgcccgc gttgcaggcc atgctgtcca ggcaggtaga tgacgaccat cagggacagc 120
ttcaaggatc gctcgcggct cttaccagcc taacttcgat cactggaccg ctgatcgtca 180
cggcgattta tgccgcctcg gcgagcacat ggaacgggtt ggcatggatt gtaggcgccg 240
ccctatacct tgtctgcctc cccgcgttgc gtcgcggtgc atggagccgg gccacctcga 300
cctgaatgga agccggcggc acctcgctaa cggattcacc actccaagaa ttggagccaa 360
tcaattcttg cggagaactg tgaatgcgca aaccaaccct tggcagaaca tatccatcgc 420
gtccgccatc tccagcagcc gcacgcggcg catctcgggc agcgttgggt cctggccacg 480
ggtgcgcatg atcgtgctcc tgtcgttgag gacccggcta ggctggcggg gttgccttac 540
tggttagcag aatgaatcac cgatacgcga gcgaacgtga agcgactgct gctgcaaaac 600
gtctgcgacc tgagcaacaa catgaatggt cttcggtttc cgtgtttcgt aaagtctgga 660
aacgcggaag tcagcgccct gcaccattat gttccggatc tgcatcgcag gatgctgctg 720
gctaccctgt ggaacaccta catctgtatt aacgaagcgc tggcattgac cctgagtgat 780
ttttctctgg tcccgccgca tccataccgc cagttgttta ccctcacaac gttccagtaa 840
ccgggcatgt tcatcatcag taacccgtat cgtgagcatc ctctctcgtt tcatcggtat 900
cattaccccc atgaacagaa atccccctta cacggaggca tcagtgacca aacaggaaaa 960
aaccgccctt aacatggccc gctttatcag aagccagaca ttaacgcttc tggagaaact 1020
caacgagctg gacgcggatg aacaggcaga catctgtgaa tcgcttcacg accacgctga 1080
tgagctttac cgcagctgcc tcgcgcgttt cggtgatgac ggtgaaaacc tctgacacat 1140
gcagctcccg gagacggtca cagcttgtct gtaagcggat gccgggagca gacaagcccg 1200
tcagggcgcg tcagcgggtg ttggcgggtg tcggggcgca gccatgaccc agtcacgtag 1260
cgatagcgga gtgtatactg gcttaactat gcggcatcag agcagattgt actgagagtg 1320
caccatatgc ggtgtgaaat accgcacaga tgcgtaagga gaaaataccg catcaggcgc 1380
tcttccgctt cctcgctcac tgactcgctg cgctcggtcg ttcggctgcg gcgagcggta 1440
tcagctcact caaaggcggt aatacggtta tccacagaat caggggataa cgcaggaaag 1500
aacatgtgag caaaaggcca gcaaaaggcc aggaaccgta aaaaggccgc gttgctggcg 1560
tttttccata ggctccgccc ccctgacgag catcacaaaa atcgacgctc aagtcagagg 1620
tggcgaaacc cgacaggact ataaagatac caggcgtttc cccctggaag ctccctcgtg 1680
cgctctcctg ttccgaccct gccgcttacc ggatacctgt ccgcctttct cccttcggga 1740
agcgtggcgc tttctcatag ctcacgctgt aggtatctca gttcggtgta ggtcgttcgc 1800
tccaagctgg gctgtgtgca cgaacccccc gttcagcccg accgctgcgc cttatccggt 1860
aactatcgtc ttgagtccaa cccggtaaga cacgacttat cgccactggc agcagccact 1920
ggtaacagga ttagcagagc gaggtatgta ggcggtgcta cagagttctt gaagtggtgg 1980
cctaactacg gctacactag aaggacagta tttggtatct gcgctctgct gaagccagtt 2040
accttcggaa aaagagttgg tagctcttga tccggcaaac aaaccaccgc tggtagcggt 2100
ggtttttttg tttgcaagca gcagattacg cgcagaaaaa aaggatctca agaagatcct 2160
ttgatctttt ctacggggtc tgacgctcag tggaacgaaa actcacgtta agggattttg 2220
gtcatgagat tatcaaaaag gatcttcacc tagatccttt taaattaaaa atgaagtttt 2280
aaatcaatct aaagtatata tgagtaaact tggtctgaca gttaccaatg cttaatcagt 2340
gaggcaccta tctcagcgat ctgtctattt cgttcatcca tagttgcctg actccccgtc 2400
gtgtagataa ctacgatacg ggagggctta ccatctggcc ccagtgctgc aatgataccg 2460

-continued

```
cgagacccac gctcaccggc tccagattta tcagcaataa accagccagc cggaagggcc   2520
gagcgcagaa gtggtcctgc aactttatcc gcctccatcc agtctattaa ttgttgccgg   2580
gaagctagag taagtagttc gccagttaat agtttgcgca acgttgttgc cattgctgca   2640
ggcatcgtgg tgtcacgctc gtcgtttggt atggcttcat tcagctccgg ttcccaacga   2700
tcaaggcgag ttacatgatc ccccatgttg tgcaaaaaag cggttagctc cttcggtcct   2760
ccgatcgttg tcagaagtaa gttggccgca gtgttatcac tcatggttat ggcagcactg   2820
cataattctc ttactgtcat gccatccgta agatgctttt ctgtgactgg tgagtactca   2880
accaagtcat tctgagaata gtgtatgcgg cgaccgagtt gctcttgccc ggcgtcaaca   2940
cgggataata ccgcgccaca tagcagaact ttaaaagtgc tcatcattgg aaaacgttct   3000
tcggggcgaa aactctcaag gatcttaccg ctgttgagat ccagttcgat gtaacccact   3060
cgtgcaccca actgatcttc agcatctttt actttcacca gcgtttctgg gtgagcaaaa   3120
acaggaaggc aaaatgccgc aaaaaaggga ataagggcga cacggaaatg ttgaatactc   3180
atactcttcc tttttcaata ttattgaagc atttatcagg gttattgtct catgagcgga   3240
tacatatttg aatgtattta gaaaaataaa caaatagggg ttccgcgcac atttccccga   3300
aaagtgccac ctgacgtctt aattaatcag gagagcgttc accgacaaac aacagataaa   3360
acgaaaggcc cagtctttcg actgagcctt tcgttttatt tgatgcctgg cagttcccta   3420
ctctcgcatg gggagacccc acactaccat cggcgctacg gcgtttcact tctgagttcg   3480
gcatggggtc aggtgggacc accgcgctac tgccgccagg caaattctgt tttatcagac   3540
cgcttctgcg ttctgattta atctgtatca ggctgaaaat cttctctcat ccgccaaaac   3600
agccaagctg gagaccgttt aaactcaatg atgatgatga tgatggtcga cggcgctatt   3660
cagatcctct tctgagatga gtttttgttc gggcccaagc ttcgaattct cagatatgca   3720
aggcgtggcc caacgcgcgt agggcggctt cttgcaccgc ttcacccaac gtggggtggg   3780
catgaatggt gccggccaca tcttccaggc acgcgcccat ctccagcgat tgggcaaacg   3840
cggtggacag ctcggagacc gccacgccaa ccgcctgcca acccacgatc aggtggttgt   3900
cacggcgcgc caccacccgc acgaaaccgc ttttcgactc caggctcatg gcccggccat   3960
tggcggcaaa cgggaactgc gcgacgatgc agtccagggc ctgctggctg gcttgttccg   4020
gggtcttgcc gaccaccacc acttccgggt cggtaaagca cacggcggca atcgctgccg   4080
gctcgaagcg tcgggccttg ccggcgatga tttcggcgac catctcgcct tgggccatgg   4140
cccggtgcgc cagcatcggt tcgccagcga cgtcgccaat ggcccagacg ttgtgcatgc   4200
tggtatgaca gcgctcgtcg atggcaatgg cggtgccgtt catcttcagg tccaggcatt   4260
ccaggttgaa gcccttggtg cgtggccggc ggcccacggc caccagtacc tgatcggctt   4320
caagacgcag ttgcccaccc ttgccgtcgc tggccagcag gcagccattt tcgtagccct   4380
cgacgctgtg gcccaggtgc aacgcgatgc ccagtttctt cagcgactcg gccaccgggg   4440
cggtcaattc gctgtcgtag gtcggcagga tgcgttcgcg cgcttccacc acactcacct   4500
gtgcacccag cttgcgatag gcaatgccca gctccaggcc gatatagcca ccgccgacca   4560
ccaccaggtg ttgcggcagg gctttcggcg ccagggcttc ggtcgaggaa atcaccgggc   4620
cacccagcgg cagcatcggc agttcgacac tggtggaacc ggtcgccagc aacagatgct   4680
cgcactggat acgctggcca tcgacctcga cctgcttgcc gtccagtacc ttggcccagc   4740
catgcaccac tttcaccccg tgctttttca gcaaggcggc aacaccggtg gtcagacggt   4800
cgacaatgcc gtccttccag gtgacgctct ggccgatgtc caggcgcggc gaagccacgc   4860
```

-continued

```
tgatgcccag cggcgagggt tcggtaaagc gcgaggcttg gtgaaactgc tcggccacgt   4920
ggatcagcgc cttggacggg atgcagccga tgttcaggca ggtgccgccc agtgcctggc   4980
cttccaccag tacggtagga atgcccagtt gcccggcgcg gatggctgct acatagccgc   5040
cagggccgcc gccgatgatc aacagggtag tctggataat ctgttgcatg ctcactccac   5100
gaacaggcag gcgggttgtt cgagcaggcc acgcacggcc tggatgaaca gggcggcgtc   5160
catgccatcg accacgcggt ggtcgaacga gctggacagg ttcatcatct tgcgcacgac   5220
gatctggcca tcaatcacca ccggtcgttc gaccatgcgg ttgaccccga cgattgccac   5280
ttccggggtg ttgaccaccg gcgtgctgac aatgccaccc aaggcgccga ggctggtcag   5340
ggtgatggtc gagccggaca gctcctcgcg gctggccttg ttgttacgtg cagcgttggc   5400
caggcgcgaa atctcgccgg cattggccca caggctgccc gcttcggcgt ggcgcagcac   5460
gggtaccatc aggccgttgt caccctgggt ggcaatgccc acatgcaccg cgccatggcg   5520
ggtgatgatc tgcgcttcgt cgtcgtaggt cgcgttgatc tgcgggaagt cacgcagcgc   5580
cacgacgagg gcgcgcacca ggaatggcag caaggtcagt ttgccgcggc tgtcgccgtg   5640
cttgctgttg agttgctggc gcagggcttc cagggcggtg acgtcgattt cctcgacata   5700
actgaagtgc gcgacccggc gtttggcgtc ctgcatgcgc tgggcgatct tgcggcgcag   5760
gccgatcacc ggcacctgct cgctgtcggt gcgcttggca taaccatcag gtgcttgccc   5820
ggcattgctt tgcggcttgc tcatgaaggc gtcgaggtct tcgtgcagaa tgcgcccggc   5880
cgggccgcta ccatgcacat aacgcagttc gataccggcg tccagggcgc gtttgcgcac   5940
ggccggcgag gccagcggct tgtcgcccgg ctggcgcggc acgatgggcg cagcttcgtg   6000
gttggcgggc gcctggtaca cggcgggttt tacgtctttc tgcggttccg gcttggctgc   6060
aatcggggcg gccggggcct ctaccggttt tggctgaggc acgtccacat ggttgccgct   6120
gccttccact tcgatgcgga tcagttcgct accgaccgcc atcacttccc cgggctggcc   6180
acccagggcc aacaccttgc cgctgaccgg cgaggggatt tccacggtgg ccttgtcggt   6240
catgacgtcg gccaccacct ggtcctcggc gatgatgtcg ccgaccttga cgaaccattc   6300
caccaactcg acctgcgcga tgccttcgcc aatgtccggc atcttgatga cgtgcgtgcc   6360
cattcagacc tccatgacct ttttcagtgc cgcacctacc cgcgaagggc cggggaagta   6420
agcccattcc tgtgcgtgag ggtagggggt gtcccagccg gtgacgcgct cgatcggcgc   6480
ctccaggtgg tggaagcagt gctcctgcac cagcgacacc agctcggcac cgaagccgca   6540
ggtgcgggtg gcctcgtgca ccaccacgca acggccagtc tttttcaccg actcgacgat   6600
agtgtccagg tccagcggcc acaggctgcg caggtcgatc acttcggcat cgacgccgct   6660
ttcttcggcg gccacctggg ccacgtacac cgtggtgccg taagtcagta cggtcacgtc   6720
attgccaggg cgggtaatgg cggccttgtc cagcggtacg gtgtaatagc cgtcgggcac   6780
ggcgctgtgc gggtgcttcg accatggggt tacagggcgg tcgtggtggc catcgaacgg   6840
gccgttgtac agacgtttgg gctccaggaa gattaccggg tcgtcgcatt cgatcgaggc   6900
aatcagcagg cctttggcgt cataagggtt ggacggcatc acggtgcgca ggccgcagac   6960
ctgggtgaac atcgcttccg ggctctggct gtgagtctgg ccgccataga tgccgccgcc   7020
gcaaggcatg cgcagggtca gcggggcaat gaactcgccg gccgaccggt aacgcaggcg   7080
ggccagctcg gagacgatct ggtcggaggc cgggtagaag tagtcggcga actggatctc   7140
caccaccggg cgcaggccat aggcgcccat gcctacggcg gtaccgacga tgccgctctc   7200
```

-continued

```
ggagatgggc gcgtcgaaca cgcgcgattt gccgtacttg ttctgcaggc cttcggtgca   7260
gcggaacacg ccgccgaagt aaccgacgtc ctggccgtac accaccacat tgtcgtcgcg   7320
ctcaagcatg acatccatgg ccgagcgcag ggcctggatc atggtcatgg tagtggtggc   7380
catggcggtt tccgggttga tgctgttgtt gtggtcgttc atctcaaacc cccagttcct   7440
ggcgttgacg gcgcaggtgt tcgggcatct ccttgtacac atcctcgaac atcgaggcgg   7500
cgctcgggat gtgcccgtta gccagggtgc cgtactgctc ggcttctttc tgtgcggcaa   7560
tcaccgcagc ttcgagctcg gccgtgacgg cttggtgttc ttcttcggac cagtggccga   7620
tcttgatcag gtgctgcttc aggcgggcga tcgggtcacc cagcgggaag tggctccagt   7680
catcggcagg gcggtacttg gaggggtcgt ccgacgtcga gtgcgggccg gcacggtagg   7740
tgacccactc gatcaggctt gggcccaggc cgcggcgggc gcgctcggca gcccagcgcg   7800
aggcggcgta cacggcgacg aagtcgttgc cgtcaacccg cagcgaggca atgccgcagc   7860
ccacgccacg gccggcgaag gtggtcgact cgccaccggc gatggcctgg aaggtagaaa   7920
tcgcccactg gttgttgacc acattgagga tcaccggggc gcggtaaacg tgggcaaagg   7980
tgagggcggt gtggaagtcc gactcggcgg tggctccgtc accgatccac gccgaagcaa   8040
tcttggtatc gcccttgatc gccgaggcca tggcccagcc gactgcctgc acgaactggg   8100
tcgccaggtt gccgctgatg gtgaagaagc cggcttcgcg caccgagtac atgatcggca   8160
actggcggcc cttgaggggg tcgcgctcgt tggacagcag ttggcagatc atctcgacca   8220
gcgatacgtc gcgggccatc aggatgcttt gctggcggta ggtcgggaag cacatgtcgg   8280
tgcggttcag cgccagcgcc tggccactgc cgatggcttc ttcgcccagg ctttgcatgt   8340
agaaggacat cttcttctgg cgctgggcaa ccaccatgcg gctgtcgaag atccgcgtct   8400
tgagcatggc gcgcatgcct tgacgaagga tctgtgggtc gatgtcttcg gcccaggggc   8460
cttgcgcatc accttgctcg tcgagcacgc ggaccaggct gtaggacagg tcggcagtgt   8520
cggcagcatc gacatcgatc gcgggtttac gggcttgacc tgcatcgttg aggcgcaggt   8580
aggaaaaatc ggtctggcag cctggccggc cggtgggctc gggcacatgc aaacgcaggg   8640
gggcgtactc gttcatggat ccatggttta ttcctcctta tttaatcgat acattaatat   8700
atacctcttt aatttttaat aataaagtta atcgataatt ccggtcgagt gcccacacag   8760
attgtctgat aaattgttaa agagcagtgc cgcttcgctt tttctcagcg gcgctgtttc   8820
ctgtgtgaaa ttgttatccg ctcacaattc cacacattat acgagccgga tgattaattg   8880
tcaacagctc atttcagaat atttgccaga accgttatga tgtcggcgca aaaaacatta   8940
tccagaacgg gagtgcgcct tgagcgacac gaattatgca gtgatttacg acctgcacag   9000
ccataccaca gcttccgatg gctgcctgac gccagaagca ttggtgcacc gtgcagtcga   9060
tgataagctg tcaaaccaga tcaattcgcg ctaactcaca ttaattgcgt tgcgctcact   9120
gcccgctttc cagtcgggaa acctgtcgtg ccagctgcat taatgaatcg gccaacgcgc   9180
ggggagaggc ggtttgcgta ttgggcgcca gggtggtttt tcttttcacc agtgagacgg   9240
gcaacagctg attgcccttc accgcctggc cctgagagag ttgcagcaag cggtccacgc   9300
tggtttgccc cagcaggcga aaatcctgtt tgatggtggt tgacggcggg atataacatg   9360
agctgtcttc ggtatcgtcg tatcccacta ccgagatatc cgcaccaacg cgcagcccgg   9420
actcggtaat ggcgcgcatt gcgcccagcg ccatctgatc gttggcaacc agcatcgcag   9480
tgggaacgat gccctcattc agcatttgca tggtttgttg aaaaccggac atggcactcc   9540
agtcgccttc ccgttccgct atcggctgaa tttgattgcg agtgagatat ttatgccagc   9600
```

cagccagacg cagacgcgcc gagacagaac ttaatgggcc cgctaacagc gcgatttgct 9660
ggtgacccaa tgcgaccaga tgctccacgc ccagtcgcgt accgtcttca tgggagaaaa 9720
taatactgtt gatgggtgtc tggtcagaga catcaagaaa taacgccgga acattagtgc 9780
aggcagcttc cacagcaatg gcatcctggt catccagcgg atagttaatg atcagcccac 9840
tgacgcgttg cgcgagaaga ttgtgcaccg ccgctttaca ggcttcgacg ccgcttcgtt 9900
ctaccatcga caccaccacg ctggcaccca gttgatcggc gcgagattta atcgccgcga 9960
caatttgcga cggcgcgtgc agggccagac tggaggtggc aacgccaatc agcaacgact 10020
gtttgcccgc cagttgttgt gccacgcggt tgggaatgta attcagctcc gccatcgccg 10080
cttccacttt ttcccgcgtt ttcgcagaaa cgtggctggc ctggttcacc acgcgggaaa 10140
cggtctgata agagacaccg gcatactctg cgacatcgta taacgttact ggtttcacat 10200
tcaccaccct gaattgactc tcttccgggc gctatcatgc cataccgcga aaggttttgc 10260
accattcgat ggtgtcaacg taaatgcatg ccgcttcgcc ttcgcgcgcg aattgatctg 10320
ctgcctcgcg cgtttcggtg atgacggtga aaacctctga cacatgcagc tcccggagac 10380
ggtcacagct tgtctgtaag cggatgccgg gagcagacaa gcccgtcagg gcgcgtcagc 10440
gggtgttggc ggggccggcc 10460

<210> SEQ ID NO 137
<211> LENGTH: 5544
<212> TYPE: DNA
<213> ORGANISM: Artificial sequence
<220> FEATURE:
<223> OTHER INFORMATION: pGL10.173b vector backbone

<400> SEQUENCE: 137
tcgcgacgcg aggctggatg gccttcccca ttatgattct tctcgcttcc ggcggcatcg 60
ggatgcccgc gttgcaggcc atgctgtcca ggcaggtaga tgacgaccat cagggacagc 120
ttcaaggatc gctcgcggct cttaccagcc taacttcgat cactggaccg ctgatcgtca 180
cggcgattta tgccgcctcg gcgagcacat ggaacgggtt ggcatggatt gtaggcgccg 240
ccctatacct tgtctgcctc cccgcgttgc gtcgcggtgc atggagccgg gccacctcga 300
cctgaatgga agccggcggc acctcgctaa cggattcacc actccaagaa ttggagccaa 360
tcaattcttg cggagaactg tgaatgcgca aaccaaccct tggcagaaca tatccatcgc 420
gtccgccatc tccagcagcc gcacgcggcg catctcgggc agcgttgggt cctggccacg 480
ggtgcgcatg atcgtgctcc tgtcgttgag gacccggcta ggctggcggg gttgccttac 540
tggttagcag aatgaatcac cgatacgcga gcgaacgtga agcgactgct gctgcaaaac 600
gtctgcgacc tgagcaacaa catgaatggt cttcggtttc cgtgtttcgt aaagtctgga 660
aacgcggaag tcagcgccct gcaccattat gttccggatc tgcatcgcag gatgctgctg 720
gctaccctgt ggaacaccta catctgtatt aacgaagcgc tggcattgac cctgagtgat 780
ttttctctgg tcccgccgca tccataccgc cagttgttta ccctcacaac gttccagtaa 840
ccgggcatgt tcatcatcag taacccgtat cgtgagcatc ctctctcgtt tcatcggtat 900
cattaccccc atgaacagaa atccccctta cacggaggca tcagtgacca aacaggaaaa 960
aaccgccctt aacatggccc gctttatcag aagccagaca ttaacgcttc tggagaaact 1020
caacgagctg gacgcggatg aacaggcaga catctgtgaa tcgcttcacg accacgctga 1080
tgagctttac cgcagctgcc tcgcgcgttt cggtgatgac ggtgaaaacc tctgacacat 1140

-continued gcagctcccg gagacggtca cagcttgtct gtaagcggat gccgggagca gacaagcccg 1200
tcagggcgcg tcagcgggtg ttggcgggtg tcggggcgca gccatgaccc agtcacgtag 1260
cgatagcgga gtgtatactg gcttaactat gcggcatcag agcagattgt actgagagtg 1320
caccatatgc ggtgtgaaat accgcacaga tgcgtaagga gaaaataccg catcaggcgc 1380
tcttccgctt cctcgctcac tgactcgctg cgctcggtcg ttcggctgcg gcgagcggta 1440
tcagctcact caaaggcggt aatacggtta tccacagaat caggggataa cgcaggaaag 1500
aacatgtgag caaaaggcca gcaaaaggcc aggaaccgta aaaaggccgc gttgctggcg 1560
tttttccata ggctccgccc ccctgacgag catcacaaaa atcgacgctc aagtcagagg 1620
tggcgaaacc cgacaggact ataaagatac caggcgtttc cccctggaag ctccctcgtg 1680
cgctctcctg ttccgaccct gccgcttacc ggatacctgt ccgcctttct cccttcggga 1740
agcgtggcgc tttctcatag ctcacgctgt aggtatctca gttcggtgta ggtcgttcgc 1800
tccaagctgg gctgtgtgca cgaacccccc gttcagcccg accgctgcgc cttatccggt 1860
aactatcgtc ttgagtccaa cccggtaaga cacgacttat cgccactggc agcagccact 1920
ggtaacagga ttagcagagc gaggtatgta ggcggtgcta cagagttctt gaagtggtgg 1980
cctaactacg gctacactag aaggacagta tttggtatct gcgctctgct gaagccagtt 2040
accttcggaa aaagagttgg tagctcttga tccggcaaac aaaccaccgc tggtagcggt 2100
ggtttttttg tttgcaagca gcagattacg cgcagaaaaa aaggatctca agaagatcct 2160
ttgatctttt ctacggggtc tgacgctcag tggaacgaaa actcacgtta agggattttg 2220
gtcatgagat tatcaaaaag gatcttcacc tagatccttt taaattaaaa atgaagtttt 2280
aaatcaatct aaagtatata tgagtaaact tggtctgaca gttaccaatg cttaatcagt 2340
gaggcaccta tctcagcgat ctgtctattt cgttcatcca tagttgcctg actccccgtc 2400
gtgtagataa ctacgatacg ggagggctta ccatctggcc ccagtgctgc aatgataccg 2460
cgagacccac gctcaccggc tccagattta tcagcaataa accagccagc cggaagggcc 2520
gagcgcagaa gtggtcctgc aactttatcc gcctccatcc agtctattaa ttgttgccgg 2580
gaagctagag taagtagttc gccagttaat agtttgcgca acgttgttgc cattgctgca 2640
ggcatcgtgg tgtcacgctc gtcgtttggt atggcttcat tcagctccgg ttcccaacga 2700
tcaaggcgag ttacatgatc ccccatgttg tgcaaaaaag cggttagctc cttcggtcct 2760
ccgatcgttg tcagaagtaa gttggccgca gtgttatcac tcatggttat ggcagcactg 2820
cataattctc ttactgtcat gccatccgta agatgctttt ctgtgactgg tgagtactca 2880
accaagtcat tctgagaata gtgtatgcgg cgaccgagtt gctcttgccc ggcgtcaaca 2940
cgggataata ccgcgccaca tagcagaact ttaaaagtgc tcatcattgg aaaacgttct 3000
tcggggcgaa aactctcaag gatcttaccg ctgttgagat ccagttcgat gtaacccact 3060
cgtgcaccca actgatcttc agcatctttt actttcacca gcgtttctgg gtgagcaaaa 3120
acaggaaggc aaaatgccgc aaaaaaggga ataagggcga cacggaaatg ttgaatactc 3180
atactcttcc tttttcaata ttattgaagc atttatcagg gttattgtct catgagcgga 3240
tacatatttg aatgtattta gaaaaataaa caaatagggg ttccgcgcac atttccccga 3300
aaagtgccac ctgacgtctt aattaatcag gagagcgttc accgacaaac aacagataaa 3360
acgaaaggcc cagtctttcg actgagcctt tcgttttatt tgatgcctgg cagttcccta 3420
ctctcgcatg gggagacccc acactaccat cggcgctacg gcgtttcact tctgagttcg 3480
gcatggggtc aggtgggacc accgcgctac tgccgccagg caaattctgt tttatcagac 3540

-continued

```
cgcttctgcg ttctgattta atctgtatca ggctgaaaat cttctctcat ccgccaaaac   3600

agccaagctg gagaccgttt aaactcaatg atgatgatga tgatggtcga cggcgctatt   3660

cagatcctct tctgagatga gtttttgttc gggcccaagc ttcgaattcc catatggtac   3720

cagctgcaga tctcgagctc ggatccatgg tttattcctc cttatttaat cgatacatta   3780

atatatacct ctttaatttt taataataaa gttaatcgat aattccggtc gagtgcccac   3840

acagattgtc tgataaattg ttaaagagca gtgccgcttc gctttttctc agcggcgctg   3900

tttcctgtgt gaaattgtta tccgctcaca attccacaca ttatacgagc cggatgatta   3960

attgtcaaca gctcatttca gaatatttgc cagaaccgtt atgatgtcgg cgcaaaaaac   4020

attatccaga acgggagtgc gccttgagcg acacgaatta tgcagtgatt tacgacctgc   4080

acagccatac cacagcttcc gatggctgcc tgacgccaga agcattggtg caccgtgcag   4140

tcgatgataa gctgtcaaac cagatcaatt cgcgctaact cacattaatt gcgttgcgct   4200

cactgcccgc tttccagtcg ggaaacctgt cgtgccagct gcattaatga atcggccaac   4260

gcgcggggag aggcggtttg cgtattgggc gccagggtgg tttttctttt caccagtgag   4320

acgggcaaca gctgattgcc cttcaccgcc tggccctgag agagttgcag caagcggtcc   4380

acgctggttt gccccagcag gcgaaaatcc tgtttgatgg tggttgacgg cgggatataa   4440

catgagctgt cttcggtatc gtcgtatccc actaccgaga tatccgcacc aacgcgcagc   4500

ccggactcgg taatggcgcg cattgcgccc agcgccatct gatcgttggc aaccagcatc   4560

gcagtgggaa cgatgccctc attcagcatt tgcatggttt gttgaaaacc ggacatggca   4620

ctccagtcgc cttcccgttc cgctatcggc tgaatttgat tgcgagtgag atatttatgc   4680

cagccagcca gacgcagacg cgccgagaca gaacttaatg ggcccgctaa cagcgcgatt   4740

tgctggtgac ccaatgcgac cagatgctcc acgcccagtc gcgtaccgtc ttcatgggag   4800

aaaataatac tgttgatggg tgtctggtca gagacatcaa gaaataacgc cggaacatta   4860

gtgcaggcag cttccacagc aatggcatcc tggtcatcca gcggatagtt aatgatcagc   4920

ccactgacgc gttgcgcgag aagattgtgc accgccgctt tacaggcttc gacgccgctt   4980

cgttctacca tcgacaccac cacgctggca cccagttgat cggcgcgaga tttaatcgcc   5040

gcgacaattt gcgacggcgc gtgcagggcc agactggagg tggcaacgcc aatcagcaac   5100

gactgtttgc ccgccagttg ttgtgccacg cggttgggaa tgtaattcag ctccgccatc   5160

gccgcttcca ctttttcccg cgttttcgca gaaacgtggc tggcctggtt caccacgcgg   5220

gaaacggtct gataagagac accggcatac tctgcgacat cgtataacgt tactggtttc   5280

acattcacca ccctgaattg actctcttcc gggcgctatc atgccatacc gcgaaaggtt   5340

ttgcaccatt cgatggtgtc aacgtaaatg catgccgctt cgccttcgcg cgcgaattga   5400

tctgctgcct cgcgcgtttc ggtgatgacg gtgaaaacct ctgacacatg cagctcccgg   5460

agacggtcac agcttgtctg taagcggatg ccgggagcag acaagcccgt cagggcgcgt   5520

cagcgggtgt tggcggggcc ggcc                                          5544
```

<210> SEQ ID NO 138
<211> LENGTH: 1026
<212> TYPE: DNA
<213> ORGANISM: Synechococcus elongatus

<400> SEQUENCE: 138

```
atgttcggtc ttatcggtca tctcaccagt ttggagcagg cccgcgacgt ttctcgcagg     60
```

-continued

```
atgggctacg acgaatacgc cgatcaagga ttggagtttt ggagtagcgc tcctcctcaa    120

atcgttgatg aaatcacagt caccagtgcc acaggcaagg tgattcacgg tcgctacatc    180

gaatcgtgtt tcttgccgga aatgctggcg gcgcgccgct tcaaaacagc cacgcgcaaa    240

gttctcaatg ccatgtccca tgcccaaaaa cacggcatcg acatctcggc cttggggggc    300

tttacctcga ttattttcga gaatttcgat ttggccagtt tgcggcaagt gcgcgacact    360

accttggagt ttgaacggtt caccaccggc aatactcaca cggcctacgt aatctgtaga    420

caggtggaag ccgctgctaa aacgctgggc atcgacatta cccaagcgac agtagcggtt    480

gtcggcgcga ctggcgatat cggtagcgct gtctgccgct ggctcgacct caaactgggt    540

gtcggtgatt tgatcctgac ggcgcgcaat caggagcgtt tggataacct gcaggctgaa    600

ctcggccggg gcaagattct gcccttggaa gccgctctgc cggaagctga ctttatcgtg    660

tgggtcgcca gtatgcctca gggcgtagtg atcgacccag caaccctgaa gcaaccctgc    720

gtcctaatcg acggggggcta ccccaaaaac ttgggcagca aagtccaagg tgagggcatc    780

tatgtcctca atggcggggt agttgaacat tgcttcgaca tcgactggca gatcatgtcc    840

gctgcagaga tggcgcggcc cgagcgccag atgtttgcct gctttgccga ggcgatgctc    900

ttggaatttg aaggctggca tactaacttc tcctggggcc gcaaccaaat cacgatcgag    960

aagatggaag cgatcggtga ggcatcggtg cgccacggct tccaaccctt ggcattggca   1020

atttga                                                              1026
```

```
<210> SEQ ID NO 139
<211> LENGTH: 341
<212> TYPE: PRT
<213> ORGANISM: Synechococcus elongatus

<400> SEQUENCE: 139

Met Phe Gly Leu Ile Gly His Leu Thr Ser Leu Glu Gln Ala Arg Asp
1               5                   10                  15

Val Ser Arg Arg Met Gly Tyr Asp Glu Tyr Ala Asp Gln Gly Leu Glu
            20                  25                  30

Phe Trp Ser Ser Ala Pro Pro Gln Ile Val Asp Glu Ile Thr Val Thr
        35                  40                  45

Ser Ala Thr Gly Lys Val Ile His Gly Arg Tyr Ile Glu Ser Cys Phe
    50                  55                  60

Leu Pro Glu Met Leu Ala Ala Arg Arg Phe Lys Thr Ala Thr Arg Lys
65                  70                  75                  80

Val Leu Asn Ala Met Ser His Ala Gln Lys His Gly Ile Asp Ile Ser
                85                  90                  95

Ala Leu Gly Gly Phe Thr Ser Ile Ile Phe Glu Asn Phe Asp Leu Ala
            100                 105                 110

Ser Leu Arg Gln Val Arg Asp Thr Thr Leu Glu Phe Glu Arg Phe Thr
        115                 120                 125

Thr Gly Asn Thr His Thr Ala Tyr Val Ile Cys Arg Gln Val Glu Ala
    130                 135                 140

Ala Ala Lys Thr Leu Gly Ile Asp Ile Thr Gln Ala Thr Val Ala Val
145                 150                 155                 160

Val Gly Ala Thr Gly Asp Ile Gly Ser Ala Val Cys Arg Trp Leu Asp
                165                 170                 175

Leu Lys Leu Gly Val Gly Asp Leu Ile Leu Thr Ala Arg Asn Gln Glu
            180                 185                 190

Arg Leu Asp Asn Leu Gln Ala Glu Leu Gly Arg Gly Lys Ile Leu Pro
```

```
        195                 200                 205

Leu Glu Ala Ala Leu Pro Glu Ala Asp Phe Ile Val Trp Val Ala Ser
    210                 215                 220

Met Pro Gln Gly Val Val Ile Asp Pro Ala Thr Leu Lys Gln Pro Cys
225                 230                 235                 240

Val Leu Ile Asp Gly Gly Tyr Pro Lys Asn Leu Gly Ser Lys Val Gln
                245                 250                 255

Gly Glu Gly Ile Tyr Val Leu Asn Gly Gly Val Val Glu His Cys Phe
            260                 265                 270

Asp Ile Asp Trp Gln Ile Met Ser Ala Ala Glu Met Ala Arg Pro Glu
        275                 280                 285

Arg Gln Met Phe Ala Cys Phe Ala Glu Ala Met Leu Leu Glu Phe Glu
    290                 295                 300

Gly Trp His Thr Asn Phe Ser Trp Gly Arg Asn Gln Ile Thr Ile Glu
305                 310                 315                 320

Lys Met Glu Ala Ile Gly Glu Ala Ser Val Arg His Gly Phe Gln Pro
                325                 330                 335

Leu Ala Leu Ala Ile
            340


<210> SEQ ID NO 140
<211> LENGTH: 10097
<212> TYPE: DNA
<213> ORGANISM: Artificial sequence
<220> FEATURE:
<223> OTHER INFORMATION: pCL-Ptrc-carB_'tesA plasmid

<400> SEQUENCE: 140

cactatacca attgagatgg gctagtcaat gataattact agtccttttc ctttgagttg      60

tgggtatctg taaattctgc tagacctttg ctggaaaact tgtaaattct gctagaccct     120

ctgtaaattc cgctagacct ttgtgtgttt tttttgttta tattcaagtg gttataattt     180

atagaataaa gaaagaataa aaaaagataa aaagaataga tcccagccct gtgtataact     240

cactacttta gtcagttccg cagtattaca aaaggatgtc gcaaacgctg tttgctcctc     300

tacaaaacag accttaaaac cctaaaggcg tcggcatccg cttacagaca agctgtgacc     360

gtctccggga gctgcatgtg tcagaggttt tcaccgtcat caccgaaacg cgcgaggcag     420

cagatcaatt cgcgcgcgaa ggcgaagcgg catgcattta cgttgacacc atcgaatggt     480

gcaaaacctt tcgcggtatg gcatgatagc gcccggaaga gagtcaattc agggtggtga     540

atgtgaaacc agtaacgtta tacgatgtcg cagagtatgc cggtgtctct tatcagaccg     600

tttcccgcgt ggtgaaccag gccagccacg tttctgcgaa aacgcgggaa aaagtggaag     660

cggcgatggc ggagctgaat tacattccca accgcgtggc acaacaactg gcgggcaaac     720

agtcgttgct gattggcgtt gccacctcca gtctggccct gcacgcgccg tcgcaaattg     780

tcgcggcgat taaatctcgc gccgatcaac tgggtgccag cgtggtggtg tcgatggtag     840

aacgaagcgg cgtcgaagcc tgtaaagcgg cggtgcacaa tcttctcgcg caacgcgtca     900

gtgggctgat cattaactat ccgctggatg accaggatgc cattgctgtg gaagctgcct     960

gcactaatgt tccggcgtta tttcttgatg tctctgacca gacacccatc aacagtatta    1020

ttttctccca tgaagacggt acgcgactgg gcgtggagca tctggtcgca ttgggtcacc    1080

agcaaatcgc gctgttagcg ggcccattaa gttctgtctc ggcgcgtctg cgtctggctg    1140

gctggcataa atatctcact cgcaatcaaa ttcagccgat agcggaacgg gaaggcgact    1200
```

-continued

```
ggagtgccat gtccggtttt caacaaacca tgcaaatgct gaatgagggc atcgttccca   1260
ctgcgatgct ggttgccaac gatcagatgg cgctgggcgc aatgcgcgcc attaccgagt   1320
ccgggctgcg cgttggtgcg gatatctcgg tagtgggata cgacgatacc gaagacagct   1380
catgttatat cccgccgtta accaccatca aacaggattt tcgcctgctg gggcaaacca   1440
gcgtggaccg cttgctgcaa ctctctcagg gccaggcggt gaagggcaat cagctgttgc   1500
ccgtctcact ggtgaaaaga aaaaccaccc tggcgcccaa tacgcaaacc gcctctcccc   1560
gcgcgttggc cgattcatta atgcagctgg cacgacaggt ttcccgactg gaaagcgggc   1620
agtgagcgca acgcaattaa tgtaagttag cgcgaattga tctggtttga cagcttatca   1680
tcgactgcac ggtgcaccaa tgcttctggc gtcaggcagc catcggaagc tgtggtatgg   1740
ctgtgcaggt cgtaaatcac tgcataattc gtgtcgctca aggcgcactc ccgttctgga   1800
taatgttttt tgcgccgaca tcataacggt tctggcaaat attctgaaat gagctgttga   1860
caattaatca tccggctcgt ataatgtgtg gaattgtgag cggataacaa tttcacacag   1920
gaaacagcgc cgctgagaaa aagcgaagcg gcactgctct ttaacaattt atcagacaat   1980
ctgtgtgggc actcgaccgg aattatcgat taactttatt attaaaaatt aaagaggtat   2040
atattaatgt atcgattaaa taaggaggaa taaaccatga ccagcgatgt tcacgacgcc   2100
acagacggcg tcaccgaaac cgcactcgac gacgagcagt cgacccgccg catcgccgag   2160
ctgtacgcca ccgatcccga gttcgccgcc gccgcaccgt tgcccgccgt ggtcgacgcg   2220
gcgcacaaac ccgggctgcg gctggcagag atcctgcaga ccctgttcac cggctacggt   2280
gaccgcccgg cgctgggata ccgcgcccgt gaactggcca ccgacgaggg cgggcgcacc   2340
gtgacgcgtc tgctgccgcg gttcgacacc ctcacctacg cccaggtgtg gtcgcgcgtg   2400
caagcggtcg ccgcggccct gcgccacaac ttcgcgcagc cgatctaccc cggcgacgcc   2460
gtcgcgacga tcggtttcgc gagtcccgat tacctgacgc tggatctcgt atgcgcctac   2520
ctgggcctcg tgagtgttcc gctgcagcac aacgcaccgg tcagccggct cgccccgatc   2580
ctggccgagg tcgaaccgcg gatcctcacc gtgagcgccg aatacctcga cctcgcagtc   2640
gaatccgtgc gggacgtcaa ctcggtgtcg cagctcgtgg tgttcgacca tcaccccgag   2700
gtcgacgacc accgcgacgc actggcccgc gcgcgtgaac aactcgccgg caagggcatc   2760
gccgtcacca ccctggacgc gatcgccgac gagggcgccg ggctgccggc cgaaccgatc   2820
tacaccgccg accatgatca gcgcctcgcg atgatcctgt acacctcggg ttccaccggc   2880
gcacccaagg gtgcgatgta caccgaggcg atggtggcgc ggctgtggac catgtcgttc   2940
atcacgggtg accccacgcc ggtcatcaac gtcaacttca tgccgctcaa ccacctgggc   3000
gggcgcatcc ccatttccac cgccgtgcag aacggtggaa ccagttactt cgtaccggaa   3060
tccgacatgt ccacgctgtt cgaggatctc gcgctggtgc gcccgaccga actcggcctg   3120
gttccgcgcg tcgccgacat gctctaccag caccacctcg ccaccgtcga ccgcctggtc   3180
acgcagggcg ccgacgaact gaccgccgag aagcaggccg gtgccgaact gcgtgagcag   3240
gtgctcggcg gacgcgtgat caccggattc gtcagcaccg caccgctggc cgcggagatg   3300
agggcgttcc tcgacatcac cctgggcgca cacatcgtcg acggctacgg gctcaccgag   3360
accggcgccg tgacacgcga cggtgtgatc gtgcggccac cggtgatcga ctacaagctg   3420
atcgacgttc ccgaactcgg ctacttcagc accgacaagc cctacccgcg tggcgaactg   3480
ctggtcaggt cgcaaacgct gactcccggg tactacaagc gccccgaggt caccgcgagc   3540
gtcttcgacc gggacggcta ctaccacacc ggcgacgtca tggccgagac cgcacccgac   3600
```

-continued

```
cacctggtgt acgtggaccg tcgcaacaac gtcctcaaac tcgcgcaggg cgagttcgtg   3660
gcggtcgcca acctggaggc ggtgttctcc ggcgcggcgc tggtgcgcca gatcttcgtg   3720
tacggcaaca gcgagcgcag tttccttctg gccgtggtgg tcccgacgcc ggaggcgctc   3780
gagcagtacg atccggccgc gctcaaggcc gcgctggccg actcgctgca gcgcaccgca   3840
cgcgacgccg aactgcaatc ctacgaggtg ccggccgatt tcatcgtcga gaccgagccg   3900
ttcagcgccg ccaacgggct gctgtcgggt gtcggaaaac tgctgcggcc caacctcaaa   3960
gaccgctacg ggcagcgcct ggagcagatg tacgccgata tcgcggccac gcaggccaac   4020
cagttgcgcg aactgcggcg cgcggccgcc acacaaccgg tgatcgacac cctcacccag   4080
gccgctgcca cgatcctcgg caccgggagc gaggtggcat ccgacgccca cttcaccgac   4140
ctgggcgggg attccctgtc ggcgctgaca ctttcgaacc tgctgagcga tttcttcggt   4200
ttcgaagttc ccgtcggcac catcgtgaac ccggccacca acctcgccca actcgcccag   4260
cacatcgagg cgcagcgcac cgcgggtgac cgcaggccga gtttcaccac cgtgcacggc   4320
gcggacgcca ccgagatccg ggcgagtgag ctgaccctgg acaagttcat cgacgccgaa   4380
acgctccggg ccgcaccggg tctgcccaag gtcaccaccg agccacggac ggtgttgctc   4440
tcgggcgcca acggctggct gggccggttc ctcacgttgc agtggctgga acgcctggca   4500
cctgtcggcg gcaccctcat cacgatcgtg cggggccgcg acgacgccgc ggcccgcgca   4560
cggctgaccc aggcctacga caccgatccc gagttgtccc gccgcttcgc cgagctggcc   4620
gaccgccacc tgcgggtggt cgccggtgac atcggcgacc cgaatctggg cctcacaccc   4680
gagatctggc accggctcgc cgccgaggtc gacctggtgg tgcatccggc agcgctggtc   4740
aaccacgtgc tcccctaccg gcagctgttc ggccccaacg tcgtgggcac ggccgaggtg   4800
atcaagctgg ccctcaccga acggatcaag cccgtcacgt acctgtccac cgtgtcggtg   4860
gccatgggga tccccgactt cgaggaggac ggcgacatcc ggaccgtgag cccggtgcgc   4920
ccgctcgacg gcggatacgc caacggctac ggcaacagca agtgggccgg cgaggtgctg   4980
ctgcgggagg cccacgatct gtgcgggctg cccgtggcga cgttccgctc ggacatgatc   5040
ctggcgcatc cgcgctaccg cggtcaggtc aacgtgccag acatgttcac gcgactcctg   5100
ttgagcctct tgatcaccgg cgtcgcgccg cggtcgttct acatcggaga cggtgagcgc   5160
ccgcgggcgc actaccccgg cctgacggtc gatttcgtgg ccgaggcggt cacgacgctc   5220
ggcgcgcagc agcgcgaggg atacgtgtcc tacgacgtga tgaacccgca cgacgacggg   5280
atctccctgg atgtgttcgt ggactggctg atccgggcgg gccatccgat cgaccgggtc   5340
gacgactacg acgactgggt gcgtcggttc gagaccgcgt tgaccgcgct tcccgagaag   5400
cgccgcgcac agaccgtact gccgctgctg cacgcgttcc gcgctccgca ggcaccgttg   5460
cgcggcgcac ccgaacccac ggaggtgttc cacgccgcgg tgcgcaccgc gaaggtgggc   5520
ccgggagaca tcccgcacct cgacgaggcg ctgatcgaca agtacatacg cgatctgcgt   5580
gagttcggtc tgatctgaga attctagatc tgatcgttgc gggcggggcg agagtctcgc   5640
cccgcccgcg accgcggtga aaatacgaga atattatttg tattgatctc ctaggcgggg   5700
taccgtattt tggatgataa cgaggcgcaa aaaatggcgg acacgttatt gattctgggt   5760
gatagcctga gcgccgggta tcgaatgtct gccagcgcgg cctggcctgc cttgttgaat   5820
gataagtggc agagtaaaac gtcggtagtt aatgccagca tcagcggcga cacctcgcaa   5880
caaggactgg cgcgccttcc ggctctgctg aaacagcatc agccgcgttg ggtgctggtt   5940
```

```
gaactgggcg gcaatgacgg tttgcgtggt tttcagccac agcaaaccga gcaaacgctg   6000
cgccagattt tgcaggatgt caaagccgcc aacgctgaac cattgttaat gcaaatacgt   6060
ctgcctgcaa actatggtcg ccgttataat gaagccttta gcgccattta ccccaaactc   6120
gccaaagagt ttgatgttcc gctgctgccc tttttttatgg aagaggtcta cctcaagcca   6180
caatggatgc aggatgacgg tattcatccc aaccgcgacg cccagccgtt tattgccgac   6240
tggatggcga agcagttgca gcctttagta aatcatgact cataacctag ggtaccgct   6300
agcgagctct ctagagaagc ttgggcccga acaaaaactc atctcagaag aggatctgaa   6360
tagcgccgtc gaccatcatc atcatcatca ttgagtttaa acggtctcca gcttggctgt   6420
tttggcggat gagagaagat tttcagcctg atacagatta aatcagaacg cagaagcggt   6480
ctgataaaac agaatttgcc tggcggcagt agcgcggtgg tcccacctga ccccatgccg   6540
aactcagaag tgaaacgccg tagcgccgat ggtagtgtgg ggtctcccca tgcgagagta   6600
gggaactgcc aggcatcaaa taaaacgaaa ggctcagtcg aaagactggg cctttcgttt   6660
tatctgttgt ttgtcggtga acgctctcct gacgcctgat gcggtatttt ctccttacgc   6720
atctgtgcgg tatttcacac cgcatatggt gcactctcag tacaatctgc tctgatgccg   6780
catagttaag ccagccccga cacccgccaa cacccgctga cgagcttagt aaagccctcg   6840
ctagatttta atgcggatgt tgcgattact tcgccaacta ttgcgataac aagaaaaagc   6900
cagcctttca tgatatatct cccaatttgt gtagggctta ttatgcacgc ttaaaaataa   6960
taaaagcaga cttgacctga tagtttggct gtgagcaatt atgtgcttag tgcatctaac   7020
gcttgagtta agccgcgccg cgaagcggcg tcggcttgaa cgaattgtta gacattattt   7080
gccgactacc ttggtgatct cgcctttcac gtagtggaca aattcttcca actgatctgc   7140
gcgcgaggcc aagcgatctt cttcttgtcc aagataagcc tgtctagctt caagtatgac   7200
gggctgatac tgggccggca ggcgctccat tgcccagtcg gcagcgacat ccttcggcgc   7260
gattttgccg gttactgcgc tgtaccaaat gcgggacaac gtaagcacta catttcgctc   7320
atcgccagcc cagtcgggcg gcgagttcca tagcgttaag gtttcattta gcgcctcaaa   7380
tagatcctgt tcaggaaccg gatcaaagag ttcctccgcc gctggaccta ccaaggcaac   7440
gctatgttct cttgcttttg tcagcaagat agccagatca atgtcgatcg tggctggctc   7500
gaagatacct gcaagaatgt cattgcgctg ccattctcca aattgcagtt cgcgcttagc   7560
tggataacgc cacggaatga tgtcgtcgtg cacaacaatg gtgacttcta cagcgcggag   7620
aatctcgctc tctccagggg aagccgaagt ttccaaaagg tcgttgatca aagctcgccg   7680
cgttgtttca tcaagcctta cggtcaccgt aaccagcaaa tcaatatcac tgtgtggctt   7740
caggccgcca tccactgcgg agccgtacaa atgtacggcc agcaacgtcg gttcgagatg   7800
gcgctcgatg acgccaacta cctctgatag ttgagtcgat acttcggcga tcaccgcttc   7860
cctcatgatg tttaactttg ttttagggcg actgccctgc tgcgtaacat cgttgctgct   7920
ccataacatc aaacatcgac ccacggcgta acgcgcttgc tgcttggatg cccgaggcat   7980
agactgtacc ccaaaaaaac agtcataaca agccatgaaa accgccactg cgccgttacc   8040
accgctgcgt tcggtcaagg ttctggacca gttgcgtgag cgcatacgct acttgcatta   8100
cagcttacga accgaacagg cttatgtcca ctgggttcgt gccttcatcc gtttccacgg   8160
tgtgcgtcac ccggcaacct tgggcagcag cgaagtcgag gcatttctgt cctggctggc   8220
gaacgagcgc aaggtttcgg tctccacgca tcgtcaggca ttggcggcct tgctgttctt   8280
ctacggcaag gtgctgtgca cggatctgcc ctggcttcag gagatcggaa gacctcggcc   8340
```

```
gtcgcggcgc ttgccggtgg tgctgacccc ggatgaagtg gttcgcatcc tcggttttct   8400

ggaaggcgag catcgtttgt tcgcccagct tctgtatgga acgggcatgc ggatcagtga   8460

gggtttgcaa ctgcgggtca aggatctgga tttcgatcac ggcacgatca tcgtgcggga   8520

gggcaagggc tccaaggatc gggccttgat gttacccgag agcttggcac ccagcctgcg   8580

cgagcagggg aattaattcc cacgggtttt gctgcccgca aacgggctgt tctggtgttg   8640

ctagtttgtt atcagaatcg cagatccggc ttcagccggt ttgccggctg aaagcgctat   8700

ttcttccaga attgccatga tttttcccc acgggaggcg tcactggctc ccgtgttgtc   8760

ggcagctttg attcgataag cagcatcgcc tgtttcaggc tgtctatgtg tgactgttga   8820

gctgtaacaa gttgtctcag gtgttcaatt tcatgttcta gttgctttgt tttactggtt   8880

tcacctgttc tattaggtgt tacatgctgt tcatctgtta cattgtcgat ctgttcatgg   8940

tgaacagctt tgaatgcacc aaaaactcgt aaaagctctg atgtatctat ctttttaca   9000

ccgttttcat ctgtgcatat ggacagtttt ccctttgata tgtaacggtg aacagttgtt   9060

ctacttttgt ttgttagtct tgatgcttca ctgatagata caagagccat aagaacctca   9120

gatccttccg tatttagcca gtatgttctc tagtgtggtt cgttgttttt gcgtgagcca   9180

tgagaacgaa ccattgagat catacttact ttgcatgtca ctcaaaaatt ttgcctcaaa   9240

actggtgagc tgaatttttg cagttaaagc atcgtgtagt gtttttctta gtccgttatg   9300

taggtaggaa tctgatgtaa tggttgttgg tattttgtca ccattcattt ttatctggtt   9360

gttctcaagt tcggttacga gatccatttg tctatctagt tcaacttgga aaatcaacgt   9420

atcagtcggg cggcctcgct tatcaaccac caatttcata ttgctgtaag tgtttaaatc   9480

tttacttatt ggtttcaaaa cccattggtt aagcctttta aactcatggt agttattttc   9540

aagcattaac atgaacttaa attcatcaag gctaatctct atatttgcct tgtgagtttt   9600

cttttgtgtt agttctttta ataaccactc ataaatcctc atagagtatt tgttttcaaa   9660

agacttaaca tgttccagat tatattttat gaattttttt aactggaaaa gataaggcaa   9720

tatctcttca ctaaaaacta attctaattt ttcgcttgag aacttggcat agtttgtcca   9780

ctggaaaatc tcaaagcctt taaccaaagg attcctgatt tccacagttc tcgtcatcag   9840

ctctctggtt gctttagcta atacaccata agcattttcc ctactgatgt tcatcatctg   9900

agcgtattgg ttataagtga acgataccgt ccgttctttc cttgtagggt tttcaatcgt   9960

ggggttgagt agtgccacac agcataaaat tagcttggtt tcatgctccg ttaagtcata  10020

gcgactaatc gctagttcat ttgctttgaa aacaactaat tcagacatac atctcaattg  10080

gtctaggtga ttttaat                                                 10097
```

<210> SEQ ID NO 141
<211> LENGTH: 471
<212> TYPE: PRT
<213> ORGANISM: Euglena gracilis

<400> SEQUENCE: 141

```
Val Pro Gln Met Ala Glu Gly Phe Ser Gly Glu Ala Thr Ser Ala Trp
1               5                   10                  15

Ala Ala Ala Gly Pro Gln Trp Ala Ala Pro Leu Val Ala Ala Ala Ser
            20                  25                  30

Ser Ala Leu Ala Leu Trp Trp Trp Ala Ala Arg Arg Ser Val Arg Arg
        35                  40                  45

Pro Leu Ala Ala Leu Ala Glu Leu Pro Thr Ala Val Thr His Leu Ala
```

-continued

```
    50                  55                  60

Pro Pro Met Ala Met Phe Thr Thr Thr Ala Lys Val Ile Gln Pro Lys
65                  70                  75                  80

Ile Arg Gly Phe Ile Cys Thr Thr Thr His Pro Ile Gly Cys Glu Lys
                85                  90                  95

Arg Val Gln Glu Glu Ile Ala Tyr Ala Arg Ala His Pro Pro Thr Ser
            100                 105                 110

Pro Gly Pro Lys Arg Val Leu Val Ile Gly Cys Ser Thr Gly Tyr Gly
        115                 120                 125

Leu Ser Thr Arg Ile Thr Ala Ala Phe Gly Tyr Gln Ala Ala Thr Leu
    130                 135                 140

Gly Val Phe Leu Ala Gly Pro Pro Thr Lys Gly Arg Pro Ala Ala Ala
145                 150                 155                 160

Gly Trp Tyr Asn Thr Val Ala Phe Glu Lys Ala Ala Leu Glu Ala Gly
                165                 170                 175

Leu Tyr Ala Arg Ser Leu Asn Gly Asp Ala Phe Asp Ser Thr Thr Lys
            180                 185                 190

Ala Arg Thr Val Glu Ala Ile Lys Arg Asp Leu Gly Thr Val Asp Leu
        195                 200                 205

Val Val Tyr Ser Ile Ala Ala Pro Lys Arg Thr Asp Pro Ala Thr Gly
    210                 215                 220

Val Leu His Lys Ala Cys Leu Lys Pro Ile Gly Ala Thr Tyr Thr Asn
225                 230                 235                 240

Arg Thr Val Asn Thr Asp Lys Ala Glu Val Thr Asp Val Ser Ile Glu
                245                 250                 255

Pro Ala Ser Pro Glu Glu Ile Ala Asp Thr Val Lys Val Met Gly Gly
            260                 265                 270

Glu Asp Trp Glu Leu Trp Ile Gln Ala Leu Ser Glu Ala Gly Val Leu
        275                 280                 285

Ala Glu Gly Ala Lys Thr Val Ala Tyr Ser Tyr Ile Gly Pro Glu Met
    290                 295                 300

Thr Trp Pro Val Tyr Trp Ser Gly Thr Ile Gly Glu Ala Lys Lys Asp
305                 310                 315                 320

Val Glu Lys Ala Ala Lys Arg Ile Thr Gln Gln Tyr Gly Cys Pro Ala
                325                 330                 335

Tyr Pro Val Val Ala Lys Ala Leu Val Thr Gln Ala Ser Ser Ala Ile
            340                 345                 350

Pro Val Val Pro Leu Tyr Ile Cys Leu Leu Tyr Arg Val Met Lys Glu
        355                 360                 365

Lys Gly Thr His Glu Gly Cys Ile Glu Gln Met Val Arg Leu Leu Thr
    370                 375                 380

Thr Lys Leu Tyr Pro Glu Asn Gly Ala Pro Ile Val Asp Glu Ala Gly
385                 390                 395                 400

Arg Val Arg Val Asp Asp Trp Glu Met Ala Glu Asp Val Gln Gln Ala
                405                 410                 415

Val Lys Asp Leu Trp Ser Gln Val Ser Thr Ala Asn Leu Lys Asp Ile
            420                 425                 430

Ser Asp Phe Ala Gly Tyr Gln Thr Glu Phe Leu Arg Leu Phe Gly Phe
        435                 440                 445

Gly Ile Asp Gly Val Asp Tyr Asp Gln Pro Val Asp Val Glu Ala Asp
    450                 455                 460

Leu Pro Ser Ala Ala Gln Gln
465                 470
```

<210> SEQ ID NO 142
<211> LENGTH: 1164
<212> TYPE: DNA
<213> ORGANISM: Escherichia coli

<400> SEQUENCE: 142

```
atggaacagg ttgtcattgt cgatgcaatt cgcaccccga tgggccgttc gaagggcggt     60

gcttttcgta acgtgcgtgc agaagatctc tccgctcatt taatgcgtag cctgctggcg    120

cgtaacccgg cgctggaagc ggcggccctc gacgatattt actggggttg tgtgcagcag    180

acgctggagc agggttttaa tatcgcccgt aacgcggcgc tgctggcaga agtaccacac    240

tctgtcccgg cggttaccgt taatcgcttg tgtggttcat ccatgcaggc actgcatgac    300

gcagcacgaa tgatcatgac tggcgatgcg caggcatgtc tggttggcgg cgtggagcat    360

atgggccatg tgccgatgag tcacggcgtc gattttcacc ccggcctgag ccgcaatgtc    420

gccaaagcgg cgggcatgat gggcttaacg gcagaaatgc tggcgcgtat gcacggtatc    480

agccgtgaaa tgcaggatgc ctttgccgcg cggtcacacg cccgcgcctg ggccgccacg    540

cagtcggccg catttaaaaa tgaaatcatc ccgaccggtg gtcacgatgc cgacggcgtc    600

ctgaagcagt ttaattacga cgaagtgatt cgcccggaaa ccaccgtgga agccctcgcc    660

acgctgcgtc cggcgtttga tccagtaaac ggtatggtaa cggcgggcac atcttctgca    720

ctttccgatg gcgcagctgc catgctggtg atgagtgaaa gccgcgccca tgaattaggt    780

cttaagccgc gcgctcgtgt gcgttcgatg gcggtcgttg gttgtgaccc atcgattatg    840

ggttacggcc cggttccggc ctcgaaactg gcgctgaaaa aagcggggct ttctgccagc    900

gatatcggcg tgtttgaaat gaacgaagcc tttgccgcgc agatcctgcc atgtattaaa    960

gatctgggac taattgagca gattgacgag aagatcaacc tcaacggtgg cgcgatcgcg   1020

ctgggtcatc cgctgggttg ttccggtgcg cgtatcagca ccacgctgct gaatctgatg   1080

gaacgcaaag acgttcagtt tggtctggcg acgatgtgta tcggtctggg tcagggtatt   1140

gcgacggtgt ttgagcgggt ttaa                                          1164
```

<210> SEQ ID NO 143
<211> LENGTH: 387
<212> TYPE: PRT
<213> ORGANISM: Escherichia coli

<400> SEQUENCE: 143

```
Met Glu Gln Val Val Ile Val Asp Ala Ile Arg Thr Pro Met Gly Arg
1               5                   10                  15

Ser Lys Gly Gly Ala Phe Arg Asn Val Arg Ala Glu Asp Leu Ser Ala
            20                  25                  30

His Leu Met Arg Ser Leu Leu Ala Arg Asn Pro Ala Leu Glu Ala Ala
        35                  40                  45

Ala Leu Asp Asp Ile Tyr Trp Gly Cys Val Gln Gln Thr Leu Glu Gln
    50                  55                  60

Gly Phe Asn Ile Ala Arg Asn Ala Ala Leu Leu Ala Glu Val Pro His
65                  70                  75                  80

Ser Val Pro Ala Val Thr Val Asn Arg Leu Cys Gly Ser Ser Met Gln
                85                  90                  95

Ala Leu His Asp Ala Ala Arg Met Ile Met Thr Gly Asp Ala Gln Ala
            100                 105                 110

Cys Leu Val Gly Gly Val Glu His Met Gly His Val Pro Met Ser His
```

```
        115                 120                 125

Gly Val Asp Phe His Pro Gly Leu Ser Arg Asn Val Ala Lys Ala Ala
    130                 135                 140

Gly Met Met Gly Leu Thr Ala Glu Met Leu Ala Arg Met His Gly Ile
145                 150                 155                 160

Ser Arg Glu Met Gln Asp Ala Phe Ala Ala Arg Ser His Ala Arg Ala
                165                 170                 175

Trp Ala Ala Thr Gln Ser Ala Ala Phe Lys Asn Glu Ile Ile Pro Thr
            180                 185                 190

Gly Gly His Asp Ala Asp Gly Val Leu Lys Gln Phe Asn Tyr Asp Glu
        195                 200                 205

Val Ile Arg Pro Glu Thr Thr Val Glu Ala Leu Ala Thr Leu Arg Pro
    210                 215                 220

Ala Phe Asp Pro Val Asn Gly Met Val Thr Ala Gly Thr Ser Ser Ala
225                 230                 235                 240

Leu Ser Asp Gly Ala Ala Ala Met Leu Val Met Ser Glu Ser Arg Ala
                245                 250                 255

His Glu Leu Gly Leu Lys Pro Arg Ala Arg Val Arg Ser Met Ala Val
            260                 265                 270

Val Gly Cys Asp Pro Ser Ile Met Gly Tyr Gly Pro Val Pro Ala Ser
        275                 280                 285

Lys Leu Ala Leu Lys Lys Ala Gly Leu Ser Ala Ser Asp Ile Gly Val
    290                 295                 300

Phe Glu Met Asn Glu Ala Phe Ala Ala Gln Ile Leu Pro Cys Ile Lys
305                 310                 315                 320

Asp Leu Gly Leu Ile Glu Gln Ile Asp Glu Lys Ile Asn Leu Asn Gly
                325                 330                 335

Gly Ala Ile Ala Leu Gly His Pro Leu Gly Cys Ser Gly Ala Arg Ile
            340                 345                 350

Ser Thr Thr Leu Leu Asn Leu Met Glu Arg Lys Asp Val Gln Phe Gly
        355                 360                 365

Leu Ala Thr Met Cys Ile Gly Leu Gly Gln Gly Ile Ala Thr Val Phe
    370                 375                 380

Glu Arg Val
385


<210> SEQ ID NO 144
<211> LENGTH: 2190
<212> TYPE: DNA
<213> ORGANISM: Escherichia coli

<400> SEQUENCE: 144

atgctttaca aaggcgacac cctgtacctt gactggctgg aagatggcat tgccgaactg      60

gtatttgatg ccccaggttc agttaataaa ctcgacactg cgaccgtcgc cagcctcggc     120

gaggccatcg gcgtgctgga acagcaatca gatctaaaag ggctgctgct gcgttcgaac     180

aaagcagcct ttatcgtcgg tgctgatatc accgaatttt tgtccctgtt cctcgttcct     240

gaagaacagt taagtcagtg gctgcacttt gccaatagcg tgtttaatcg cctggaagat     300

ctgccggtgc cgaccattgc tgccgtcaat ggctatgcgc tgggcggtgg ctgcgaatgc     360

gtgctggcga ccgattatcg tctggcgacg ccggatctgc gcatcggtct gccggaaacc     420

aaactgggca tcatgcctgg ctttggcggt tctgtacgta tgccacgtat gctgggcgct     480

gacagtgcgc tggaaatcat tgccgccggt aaagatgtcg gcgcggatca ggcgctgaaa     540
```

-continued

```
atcggtctgg tggatggcgt agtcaaagca gaaaaactgg ttgaaggcgc aaaggcggtt    600

ttacgccagg ccattaacgg cgacctcgac tggaaagcaa aacgtcagcc gaagctggaa    660

ccactaaaac tgagcaagat tgaagccacc atgagcttca ccatcgctaa agggatggtc    720

gcacaaacag cggggaaaca ttatccggcc cccatcaccg cagtaaaaac cattgaagct    780

gcggcccgtt ttggtcgtga agaagcctta aacctggaaa acaaaagttt tgtcccgctg    840

gcgcatacca acgaagcccg cgcactggtc ggcattttcc ttaacgatca atatgtaaaa    900

ggcaaagcga agaaactcac caaagacgtt gaaaccccga aacaggccgc ggtgctgggt    960

gcaggcatta tgggcggcgg catcgcttac cagtctgcgt ggaaaggcgt gccggttgtc   1020

atgaaagata tcaacgacaa gtcgttaacc ctcggcatga ccgaagccgc gaaactgctg   1080

aacaagcagc ttgagcgcgg caagatcgat ggtctgaaac tggctggcgt gatctccaca   1140

atccacccaa cgctcgacta cgccggattt gaccgcgtgg atattgtggt agaagcggtt   1200

gttgaaaacc cgaaagtgaa aaaagccgta ctggcagaaa ccgaacaaaa agtacgccag   1260

gataccgtgc tggcgtctaa cacttcaacc attcctatca gcgaactggc caacgcgctg   1320

gaacgcccgg aaaacttctg cgggatgcac ttctttaacc cggtccaccg aatgccgttg   1380

gtagaaatta ttcgcggcga gaaaagctcc gacgaaacca tcgcgaaagt tgtcgcctgg   1440

gcgagcaaga tgggcaagac gccgattgtg gttaacgact gccccggctt ctttgttaac   1500

cgcgtgctgt tcccgtattt cgccggtttc agccagctgc tgcgcgacgg cgcggatttc   1560

cgcaagatcg acaaagtgat ggaaaaacag tttggctggc cgatgggccc ggcatatctg   1620

ctggacgttg tgggcattga taccgcgcat cacgctcagg ctgtcatggc agcaggcttc   1680

ccgcagcgga tgcagaaaga ttaccgcgat gccatcgacg cgctgtttga tgccaaccgc   1740

tttggtcaga agaacggcct cggtttctgg cgttataaag aagacagcaa aggtaagccg   1800

aagaaagaag aagacgccgc cgttgaagac ctgctggcag aagtgagcca gccgaagcgc   1860

gatttcagcg aagaagagat tatcgcccgc atgatgatcc cgatggtcaa cgaagtggtg   1920

cgctgtctgg aggaaggcat tatcgccact ccggcggaag cggatatggc gctggtctac   1980

ggcctgggct tccctccgtt ccacggcggc gcgttccgct ggctggacac cctcggtagc   2040

gcaaaatacc tcgatatggc acagcaatat cagcacctcg gcccgctgta tgaagtgccg   2100

gaaggtctgc gtaataaagc gcgtcataac gaaccgtact atcctccggt tgagccagcc   2160

cgtccggttg gcgacctgaa aacggcttaa                                    2190
```

<210> SEQ ID NO 145
<211> LENGTH: 729
<212> TYPE: PRT
<213> ORGANISM: Escherichia coli

<400> SEQUENCE: 145

```
Met Leu Tyr Lys Gly Asp Thr Leu Tyr Leu Asp Trp Leu Glu Asp Gly
1               5                   10                  15

Ile Ala Glu Leu Val Phe Asp Ala Pro Gly Ser Val Asn Lys Leu Asp
            20                  25                  30

Thr Ala Thr Val Ala Ser Leu Gly Glu Ala Ile Gly Val Leu Glu Gln
        35                  40                  45

Gln Ser Asp Leu Lys Gly Leu Leu Leu Arg Ser Asn Lys Ala Ala Phe
    50                  55                  60

Ile Val Gly Ala Asp Ile Thr Glu Phe Leu Ser Leu Phe Leu Val Pro
65                  70                  75                  80
```

```
Glu Glu Gln Leu Ser Gln Trp Leu His Phe Ala Asn Ser Val Phe Asn
                85                  90                  95

Arg Leu Glu Asp Leu Pro Val Pro Thr Ile Ala Ala Val Asn Gly Tyr
            100                 105                 110

Ala Leu Gly Gly Gly Cys Glu Cys Val Leu Ala Thr Asp Tyr Arg Leu
        115                 120                 125

Ala Thr Pro Asp Leu Arg Ile Gly Leu Pro Glu Thr Lys Leu Gly Ile
    130                 135                 140

Met Pro Gly Phe Gly Gly Ser Val Arg Met Pro Arg Met Leu Gly Ala
145                 150                 155                 160

Asp Ser Ala Leu Glu Ile Ile Ala Ala Gly Lys Asp Val Gly Ala Asp
                165                 170                 175

Gln Ala Leu Lys Ile Gly Leu Val Asp Gly Val Val Lys Ala Glu Lys
            180                 185                 190

Leu Val Glu Gly Ala Lys Ala Val Leu Arg Gln Ala Ile Asn Gly Asp
        195                 200                 205

Leu Asp Trp Lys Ala Lys Arg Gln Pro Lys Leu Glu Pro Leu Lys Leu
    210                 215                 220

Ser Lys Ile Glu Ala Thr Met Ser Phe Thr Ile Ala Lys Gly Met Val
225                 230                 235                 240

Ala Gln Thr Ala Gly Lys His Tyr Pro Ala Pro Ile Thr Ala Val Lys
                245                 250                 255

Thr Ile Glu Ala Ala Ala Arg Phe Gly Arg Glu Glu Ala Leu Asn Leu
            260                 265                 270

Glu Asn Lys Ser Phe Val Pro Leu Ala His Thr Asn Glu Ala Arg Ala
        275                 280                 285

Leu Val Gly Ile Phe Leu Asn Asp Gln Tyr Val Lys Gly Lys Ala Lys
    290                 295                 300

Lys Leu Thr Lys Asp Val Glu Thr Pro Lys Gln Ala Ala Val Leu Gly
305                 310                 315                 320

Ala Gly Ile Met Gly Gly Gly Ile Ala Tyr Gln Ser Ala Trp Lys Gly
                325                 330                 335

Val Pro Val Val Met Lys Asp Ile Asn Asp Lys Ser Leu Thr Leu Gly
            340                 345                 350

Met Thr Glu Ala Ala Lys Leu Leu Asn Lys Gln Leu Glu Arg Gly Lys
        355                 360                 365

Ile Asp Gly Leu Lys Leu Ala Gly Val Ile Ser Thr Ile His Pro Thr
    370                 375                 380

Leu Asp Tyr Ala Gly Phe Asp Arg Val Asp Ile Val Val Glu Ala Val
385                 390                 395                 400

Val Glu Asn Pro Lys Val Lys Lys Ala Val Leu Ala Glu Thr Glu Gln
                405                 410                 415

Lys Val Arg Gln Asp Thr Val Leu Ala Ser Asn Thr Ser Thr Ile Pro
            420                 425                 430

Ile Ser Glu Leu Ala Asn Ala Leu Glu Arg Pro Glu Asn Phe Cys Gly
        435                 440                 445

Met His Phe Phe Asn Pro Val His Arg Met Pro Leu Val Glu Ile Ile
    450                 455                 460

Arg Gly Glu Lys Ser Ser Asp Glu Thr Ile Ala Lys Val Val Ala Trp
465                 470                 475                 480

Ala Ser Lys Met Gly Lys Thr Pro Ile Val Val Asn Asp Cys Pro Gly
                485                 490                 495

Phe Phe Val Asn Arg Val Leu Phe Pro Tyr Phe Ala Gly Phe Ser Gln
```

-continued

```
            500                 505                 510

Leu Leu Arg Asp Gly Ala Asp Phe Arg Lys Ile Asp Lys Val Met Glu
        515                 520                 525

Lys Gln Phe Gly Trp Pro Met Gly Pro Ala Tyr Leu Leu Asp Val Val
    530                 535                 540

Gly Ile Asp Thr Ala His His Ala Gln Ala Val Met Ala Ala Gly Phe
545                 550                 555                 560

Pro Gln Arg Met Gln Lys Asp Tyr Arg Asp Ala Ile Asp Ala Leu Phe
                565                 570                 575

Asp Ala Asn Arg Phe Gly Gln Lys Asn Gly Leu Gly Phe Trp Arg Tyr
            580                 585                 590

Lys Glu Asp Ser Lys Gly Lys Pro Lys Lys Glu Glu Asp Ala Ala Val
        595                 600                 605

Glu Asp Leu Leu Ala Glu Val Ser Gln Pro Lys Arg Asp Phe Ser Glu
    610                 615                 620

Glu Glu Ile Ile Ala Arg Met Met Ile Pro Met Val Asn Glu Val Val
625                 630                 635                 640

Arg Cys Leu Glu Glu Gly Ile Ile Ala Thr Pro Ala Glu Ala Asp Met
                645                 650                 655

Ala Leu Val Tyr Gly Leu Gly Phe Pro Pro Phe His Gly Gly Ala Phe
            660                 665                 670

Arg Trp Leu Asp Thr Leu Gly Ser Ala Lys Tyr Leu Asp Met Ala Gln
        675                 680                 685

Gln Tyr Gln His Leu Gly Pro Leu Tyr Glu Val Pro Glu Gly Leu Arg
    690                 695                 700

Asn Lys Ala Arg His Asn Glu Pro Tyr Tyr Pro Pro Val Glu Pro Ala
705                 710                 715                 720

Arg Pro Val Gly Asp Leu Lys Thr Ala
                725


<210> SEQ ID NO 146
<211> LENGTH: 1311
<212> TYPE: DNA
<213> ORGANISM: Escherichia coli

<400> SEQUENCE: 146

atgggtcagg ttttaccgct ggttacccgc cagggcgatc gtatcgccat tgttagcggt      60

ttacgtacgc cttttgcccg tcaggcgacg gcttttcatg gcattcccgc ggttgattta     120

gggaagatgg tggtaggcga actgctggca cgcagcgaga tccccgccga agtgattgaa     180

caactggtct ttggtcaggt cgtacaaatg cctgaagccc ccaacattgc gcgtgaaatt     240

gttctcggta cgggaatgaa tgtacatacc gatgcttaca gcgtcagccg cgcttgcgct     300

accagtttcc aggcagttgc aaacgtcgca gaaagcctga tggcgggaac tattcgagcg     360

gggattgccg gtggggcaga ttcctcttcg gtattgccaa ttggcgtcag taaaaaactg     420

gcgcgcgtgc tggttgatgt caacaaagct cgtaccatga gccagcgact gaaactcttc     480

tctcgcctgc gtttgcgcga cttaatgccc gtaccacctg cggtagcaga atattctacc     540

ggcttgcgga tgggcgacac cgcagagcaa atggcgaaaa cctacggcat cacccgagaa     600

cagcaagatg cattagcgca ccgttcgcat cagcgtgccg ctcaggcatg gtcagacgga     660

aaactcaaag aagaggtgat gactgccttt atccctcctt ataaacaacc gcttgtcgaa     720

gacaacaata ttcgcggtaa ttcctcgctt gccgattacg caaagctgcg cccggcgttt     780

gatcgcaaac acggaacggt aacggcggca aacagtacgc cgctgaccga tggcgcggca     840
```

-continued

```
gcggtgatcc tgatgactga atcccgggcg aaagaattag ggctggtgcc gctggggtat    900

ctgcgcagct acgcatttac tgcgattgat gtctggcagg acatgttgct cggtccagcc    960

tggtcaacac cgctggcgct ggagcgtgcc ggtttgacga tgagcgatct gacattgatc   1020

gatatgcacg aagcctttgc agctcagacg ctggcgaata ttcagttgct gggtagtgaa   1080

cgttttgctc gtgaagcact ggggcgtgca catgccactg gcgaagtgga cgatagcaaa   1140

tttaacgtgc ttggcggttc gattgcttac gggcatccct tcgcggcgac cggcgcgcgg   1200

atgattaccc agacattgca tgaacttcgc cgtcgcggcg gtggatttgg tttagttacc   1260

gcctgtgctg ccggtgggct tggcgcggca atggttctgg aggcggaata a            1311
```

<210> SEQ ID NO 147
<211> LENGTH: 436
<212> TYPE: PRT
<213> ORGANISM: Escherichia coli

<400> SEQUENCE: 147

```
Met Gly Gln Val Leu Pro Leu Val Thr Arg Gln Gly Asp Arg Ile Ala
1               5                   10                  15

Ile Val Ser Gly Leu Arg Thr Pro Phe Ala Arg Gln Ala Thr Ala Phe
            20                  25                  30

His Gly Ile Pro Ala Val Asp Leu Gly Lys Met Val Val Gly Glu Leu
        35                  40                  45

Leu Ala Arg Ser Glu Ile Pro Ala Glu Val Ile Glu Gln Leu Val Phe
    50                  55                  60

Gly Gln Val Val Gln Met Pro Glu Ala Pro Asn Ile Ala Arg Glu Ile
65                  70                  75                  80

Val Leu Gly Thr Gly Met Asn Val His Thr Asp Ala Tyr Ser Val Ser
                85                  90                  95

Arg Ala Cys Ala Thr Ser Phe Gln Ala Val Ala Asn Val Ala Glu Ser
            100                 105                 110

Leu Met Ala Gly Thr Ile Arg Ala Gly Ile Ala Gly Gly Ala Asp Ser
        115                 120                 125

Ser Ser Val Leu Pro Ile Gly Val Ser Lys Lys Leu Ala Arg Val Leu
    130                 135                 140

Val Asp Val Asn Lys Ala Arg Thr Met Ser Gln Arg Leu Lys Leu Phe
145                 150                 155                 160

Ser Arg Leu Arg Leu Arg Asp Leu Met Pro Val Pro Pro Ala Val Ala
                165                 170                 175

Glu Tyr Ser Thr Gly Leu Arg Met Gly Asp Thr Ala Glu Gln Met Ala
            180                 185                 190

Lys Thr Tyr Gly Ile Thr Arg Glu Gln Gln Asp Ala Leu Ala His Arg
        195                 200                 205

Ser His Gln Arg Ala Ala Gln Ala Trp Ser Asp Gly Lys Leu Lys Glu
    210                 215                 220

Glu Val Met Thr Ala Phe Ile Pro Pro Tyr Lys Gln Pro Leu Val Glu
225                 230                 235                 240

Asp Asn Asn Ile Arg Gly Asn Ser Ser Leu Ala Asp Tyr Ala Lys Leu
                245                 250                 255

Arg Pro Ala Phe Asp Arg Lys His Gly Thr Val Thr Ala Ala Asn Ser
            260                 265                 270

Thr Pro Leu Thr Asp Gly Ala Ala Ala Val Ile Leu Met Thr Glu Ser
        275                 280                 285
```

```
Arg Ala Lys Glu Leu Gly Leu Val Pro Leu Gly Tyr Leu Arg Ser Tyr
    290                 295                 300

Ala Phe Thr Ala Ile Asp Val Trp Gln Asp Met Leu Leu Gly Pro Ala
305                 310                 315                 320

Trp Ser Thr Pro Leu Ala Leu Glu Arg Ala Gly Leu Thr Met Ser Asp
                325                 330                 335

Leu Thr Leu Ile Asp Met His Glu Ala Phe Ala Ala Gln Thr Leu Ala
            340                 345                 350

Asn Ile Gln Leu Leu Gly Ser Glu Arg Phe Ala Arg Glu Ala Leu Gly
        355                 360                 365

Arg Ala His Ala Thr Gly Glu Val Asp Asp Ser Lys Phe Asn Val Leu
    370                 375                 380

Gly Gly Ser Ile Ala Tyr Gly His Pro Phe Ala Ala Thr Gly Ala Arg
385                 390                 395                 400

Met Ile Thr Gln Thr Leu His Glu Leu Arg Arg Arg Gly Gly Gly Phe
                405                 410                 415

Gly Leu Val Thr Ala Cys Ala Ala Gly Gly Leu Gly Ala Ala Met Val
            420                 425                 430

Leu Glu Ala Glu
        435
```

<210> SEQ ID NO 148
<211> LENGTH: 2145
<212> TYPE: DNA
<213> ORGANISM: Escherichia coli

<400> SEQUENCE: 148

```
atggaaatga catcagcgtt tacccttaat gttcgtctgg acaacattgc cgttatcacc      60

atcgacgtac cgggtgagaa aatgaatacc ctgaaggcgg agtttgcctc gcaggtgcgc     120

gccattatta agcaactccg tgaaaacaaa gagttgcgag gcgtggtgtt tgtctccgct     180

aaaccggaca acttcattgc tggcgcagac atcaacatga tcggcaactg caaaacggcg     240

caagaagcgg aagctctggc gcggcagggc caacagttga tggcggagat tcatgctttg     300

cccattcagg ttatcgcggc tattcatggc gcttgcctgg gtggtgggct ggagttggcg     360

ctggcgtgcc acggtcgcgt ttgtactgac gatcctaaaa cggtgctcgg tttgcctgaa     420

gtacaacttg gattgttacc cggttcaggc ggcacccagc gtttaccgcg tctgataggc     480

gtcagcacag cattagagat gatcctcacc ggaaaacaac ttcgggcgaa acaggcatta     540

aagctggggc tggtggatga cgttgttccg cactccattc tgctggaagc cgctgttgag     600

ctggcaaaga aggagcgccc atcttcccgc cctctacctg tacgcgagcg tattctggcg     660

gggccgttag gtcgtgcgct gctgttcaaa atggtcggca agaaaacaga acacaaaact     720

caaggcaatt atccggcgac agaacgcatc ctggaggttg ttgaaacggg attagcgcag     780

ggcaccagca gcggttatga cgccgaagct cgggcgtttg gcgaactggc gatgacgcca     840

caatcgcagg cgctgcgtag tatctttttt gccagtacgg acgtgaagaa agatcccggc     900

agtgatgcgc cgcctgcgcc attaaacagc gtggggattt taggtggtgg cttgatgggc     960

ggcggtattg cttatgtcac tgcttgtaaa gcggggattc cggtcagaat taaagatatc    1020

aacccgcagg gcataaatca tgcgctgaag tacagttggg atcagctgga gggcaaagtt    1080

cgccgtcgtc atctcaaagc cagcgaacgt gacaaacagc tggcattaat ctccggaacg    1140

acggactatc gcggctttgc ccatcgcgat ctgattattg aagcggtgtt tgaaaatctc    1200

gaattgaaac aacagatggt ggcggaagtt gagcaaaatt gcgccgctca taccatcttt    1260
```

```
gcttcgaata cgtcatcttt accgattggt gatatcgccg ctcacgccac gcgacctgag   1320

caagttatcg gcctgcattt cttcagtccg gtggaaaaaa tgccgctggt ggagattatt   1380

cctcatgcgg ggacatcggc gcaaaccatc gctaccacag taaaactggc gaaaaaacag   1440

ggtaaaacgc caattgtcgt gcgtgacaaa gccggttttt acgtcaatcg catcttagcg   1500

ccttacatta atgaagctat ccgcatgttg acccaaggtg aacgggtaga gcacattgat   1560

gccgcgctag tgaaatttgg ttttccggta ggcccaatcc aacttttgga tgaggtagga   1620

atcgacaccg ggactaaaat tattcctgta ctggaagccg cttatggaga acgttttagc   1680

gcgcctgcaa atgttgtttc ttcaattttg aacgacgatc gcaaaggcag aaaaaatggc   1740

cggggtttct atctttatgg tcagaaaggg cgtaaaagca aaaaacaggt cgatcccgcc   1800

atttacccgc tgattggcac acaagggcag gggcgaatct ccgcaccgca ggttgctgaa   1860

cggtgtgtga tgttgatgct gaatgaagca gtacgttgtg ttgatgagca ggttatccgt   1920

agcgtgcgtg acggggatat tggcgcggta tttggcattg gttttccgcc atttctcggt   1980

ggaccgttcc gctatatcga ttctctcggc gcgggcgaag tggttgcaat aatgcaacga   2040

cttgccacgc agtatggttc ccgttttacc ccttgcgagc gtttggtcga gatgggcgcg   2100

cgtggggaaa gtttttggaa aacaactgca actgacctgc aataa                   2145
```

<210> SEQ ID NO 149
<211> LENGTH: 714
<212> TYPE: PRT
<213> ORGANISM: Escherichia coli

<400> SEQUENCE: 149

```
Met Glu Met Thr Ser Ala Phe Thr Leu Asn Val Arg Leu Asp Asn Ile
1               5                   10                  15

Ala Val Ile Thr Ile Asp Val Pro Gly Glu Lys Met Asn Thr Leu Lys
            20                  25                  30

Ala Glu Phe Ala Ser Gln Val Arg Ala Ile Ile Lys Gln Leu Arg Glu
        35                  40                  45

Asn Lys Glu Leu Arg Gly Val Val Phe Val Ser Ala Lys Pro Asp Asn
    50                  55                  60

Phe Ile Ala Gly Ala Asp Ile Asn Met Ile Gly Asn Cys Lys Thr Ala
65                  70                  75                  80

Gln Glu Ala Glu Ala Leu Ala Arg Gln Gly Gln Gln Leu Met Ala Glu
                85                  90                  95

Ile His Ala Leu Pro Ile Gln Val Ile Ala Ala Ile His Gly Ala Cys
            100                 105                 110

Leu Gly Gly Gly Leu Glu Leu Ala Leu Ala Cys His Gly Arg Val Cys
        115                 120                 125

Thr Asp Asp Pro Lys Thr Val Leu Gly Leu Pro Glu Val Gln Leu Gly
    130                 135                 140

Leu Leu Pro Gly Ser Gly Gly Thr Gln Arg Leu Pro Arg Leu Ile Gly
145                 150                 155                 160

Val Ser Thr Ala Leu Glu Met Ile Leu Thr Gly Lys Gln Leu Arg Ala
                165                 170                 175

Lys Gln Ala Leu Lys Leu Gly Leu Val Asp Asp Val Val Pro His Ser
            180                 185                 190

Ile Leu Leu Glu Ala Ala Val Glu Leu Ala Lys Lys Glu Arg Pro Ser
        195                 200                 205

Ser Arg Pro Leu Pro Val Arg Glu Arg Ile Leu Ala Gly Pro Leu Gly
```

-continued

```
    210                 215                 220

Arg Ala Leu Leu Phe Lys Met Val Gly Lys Lys Thr Glu His Lys Thr
225                 230                 235                 240

Gln Gly Asn Tyr Pro Ala Thr Glu Arg Ile Leu Glu Val Val Glu Thr
                245                 250                 255

Gly Leu Ala Gln Gly Thr Ser Ser Gly Tyr Asp Ala Glu Ala Arg Ala
            260                 265                 270

Phe Gly Glu Leu Ala Met Thr Pro Gln Ser Gln Ala Leu Arg Ser Ile
        275                 280                 285

Phe Phe Ala Ser Thr Asp Val Lys Lys Asp Pro Gly Ser Asp Ala Pro
    290                 295                 300

Pro Ala Pro Leu Asn Ser Val Gly Ile Leu Gly Gly Gly Leu Met Gly
305                 310                 315                 320

Gly Gly Ile Ala Tyr Val Thr Ala Cys Lys Ala Gly Ile Pro Val Arg
                325                 330                 335

Ile Lys Asp Ile Asn Pro Gln Gly Ile Asn His Ala Leu Lys Tyr Ser
            340                 345                 350

Trp Asp Gln Leu Glu Gly Lys Val Arg Arg Arg His Leu Lys Ala Ser
        355                 360                 365

Glu Arg Asp Lys Gln Leu Ala Leu Ile Ser Gly Thr Thr Asp Tyr Arg
    370                 375                 380

Gly Phe Ala His Arg Asp Leu Ile Ile Glu Ala Val Phe Glu Asn Leu
385                 390                 395                 400

Glu Leu Lys Gln Gln Met Val Ala Glu Val Glu Gln Asn Cys Ala Ala
                405                 410                 415

His Thr Ile Phe Ala Ser Asn Thr Ser Ser Leu Pro Ile Gly Asp Ile
            420                 425                 430

Ala Ala His Ala Thr Arg Pro Glu Gln Val Ile Gly Leu His Phe Phe
        435                 440                 445

Ser Pro Val Glu Lys Met Pro Leu Val Glu Ile Ile Pro His Ala Gly
    450                 455                 460

Thr Ser Ala Gln Thr Ile Ala Thr Thr Val Lys Leu Ala Lys Lys Gln
465                 470                 475                 480

Gly Lys Thr Pro Ile Val Val Arg Asp Lys Ala Gly Phe Tyr Val Asn
                485                 490                 495

Arg Ile Leu Ala Pro Tyr Ile Asn Glu Ala Ile Arg Met Leu Thr Gln
            500                 505                 510

Gly Glu Arg Val Glu His Ile Asp Ala Ala Leu Val Lys Phe Gly Phe
        515                 520                 525

Pro Val Gly Pro Ile Gln Leu Leu Asp Glu Val Gly Ile Asp Thr Gly
    530                 535                 540

Thr Lys Ile Ile Pro Val Leu Glu Ala Ala Tyr Gly Glu Arg Phe Ser
545                 550                 555                 560

Ala Pro Ala Asn Val Val Ser Ser Ile Leu Asn Asp Asp Arg Lys Gly
                565                 570                 575

Arg Lys Asn Gly Arg Gly Phe Tyr Leu Tyr Gly Gln Lys Gly Arg Lys
            580                 585                 590

Ser Lys Lys Gln Val Asp Pro Ala Ile Tyr Pro Leu Ile Gly Thr Gln
        595                 600                 605

Gly Gln Gly Arg Ile Ser Ala Pro Gln Val Ala Glu Arg Cys Val Met
    610                 615                 620

Leu Met Leu Asn Glu Ala Val Arg Cys Val Asp Glu Gln Val Ile Arg
625                 630                 635                 640
```

Ser Val Arg Asp Gly Asp Ile Gly Ala Val Phe Gly Ile Gly Phe Pro
645 650 655

Pro Phe Leu Gly Gly Pro Phe Arg Tyr Ile Asp Ser Leu Gly Ala Gly
660 665 670

Glu Val Val Ala Ile Met Gln Arg Leu Ala Thr Gln Tyr Gly Ser Arg
675 680 685

Phe Thr Pro Cys Glu Arg Leu Val Glu Met Gly Ala Arg Gly Glu Ser
690 695 700

Phe Trp Lys Thr Thr Ala Thr Asp Leu Gln
705 710

<210> SEQ ID NO 150
<211> LENGTH: 789
<212> TYPE: DNA
<213> ORGANISM: Escherichia coli

<400> SEQUENCE: 150
atgggttttc tttccggtaa gcgcattctg gtaaccggtg ttgccagcaa actatccatc 60
gcctacggta tcgctcaggc gatgcaccgc gaaggagctg aactggcatt cacctaccag 120
aacgacaaac tgaaaggccg cgtagaagaa tttgccgctc aattgggttc tgacatcgtt 180
ctgcagtgcg atgttgcaga agatgccagc atcgacacca tgttcgctga actggggaaa 240
gtttggccga aatttgacgg tttcgtacac tctattggtt ttgcacctgg cgatcagctg 300
gatggtgact atgttaacgc cgttacccgt gaaggcttca aaattgccca cgacatcagc 360
tcctacagct tcgttgcaat ggcaaaagct tgccgctcca tgctgaatcc gggttctgcc 420
ctgctgaccc tttcctacct tggcgctgag cgcgctatcc cgaactacaa cgttatgggt 480
ctggcaaaag cgtctctgga agcgaacgtg cgctatatgg cgaacgcgat gggtccggaa 540
ggtgtgcgtg ttaacgccat ctctgctggt ccgatccgta ctctggcggc ctccggtatc 600
aaagacttcc gcaaaatgct ggctcattgc gaagccgtta ccccgattcg ccgtaccgtt 660
actattgaag atgtgggtaa ctctgcggca ttcctgtgct ccgatctctc tgccggtatc 720
tccggtgaag tggtccacgt tgacggcggt ttcagcattg ctgcaatgaa cgaactcgaa 780
ctgaaataa 789

<210> SEQ ID NO 151
<211> LENGTH: 262
<212> TYPE: PRT
<213> ORGANISM: Escherichia coli

<400> SEQUENCE: 151

Met Gly Phe Leu Ser Gly Lys Arg Ile Leu Val Thr Gly Val Ala Ser
1 5 10 15

Lys Leu Ser Ile Ala Tyr Gly Ile Ala Gln Ala Met His Arg Glu Gly
20 25 30

Ala Glu Leu Ala Phe Thr Tyr Gln Asn Asp Lys Leu Lys Gly Arg Val
35 40 45

Glu Glu Phe Ala Ala Gln Leu Gly Ser Asp Ile Val Leu Gln Cys Asp
50 55 60

Val Ala Glu Asp Ala Ser Ile Asp Thr Met Phe Ala Glu Leu Gly Lys
65 70 75 80

Val Trp Pro Lys Phe Asp Gly Phe Val His Ser Ile Gly Phe Ala Pro
85 90 95

Gly Asp Gln Leu Asp Gly Asp Tyr Val Asn Ala Val Thr Arg Glu Gly

-continued

```
            100                 105                 110

Phe Lys Ile Ala His Asp Ile Ser Ser Tyr Ser Phe Val Ala Met Ala
        115                 120                 125

Lys Ala Cys Arg Ser Met Leu Asn Pro Gly Ser Ala Leu Leu Thr Leu
    130                 135                 140

Ser Tyr Leu Gly Ala Glu Arg Ala Ile Pro Asn Tyr Asn Val Met Gly
145                 150                 155                 160

Leu Ala Lys Ala Ser Leu Glu Ala Asn Val Arg Tyr Met Ala Asn Ala
                165                 170                 175

Met Gly Pro Glu Gly Val Arg Val Asn Ala Ile Ser Ala Gly Pro Ile
            180                 185                 190

Arg Thr Leu Ala Ala Ser Gly Ile Lys Asp Phe Arg Lys Met Leu Ala
        195                 200                 205

His Cys Glu Ala Val Thr Pro Ile Arg Arg Thr Val Thr Ile Glu Asp
    210                 215                 220

Val Gly Asn Ser Ala Ala Phe Leu Cys Ser Asp Leu Ser Ala Gly Ile
225                 230                 235                 240

Ser Gly Glu Val Val His Val Asp Gly Gly Phe Ser Ile Ala Ala Met
                245                 250                 255

Asn Glu Leu Glu Leu Lys
            260


<210> SEQ ID NO 152
<211> LENGTH: 861
<212> TYPE: DNA
<213> ORGANISM: Escherichia coli

<400> SEQUENCE: 152

atgagtcagg cgctaaaaaa tttactgaca ttgttaaatc tggaaaaaat tgaggaagga      60

ctctttcgcg gccagagtga agatttaggt ttacgccagg tgtttggcgg ccaggtcgtg     120

ggtcaggcct tgtatgctgc aaaagagacc gtccctgaag agcggctggt acattcgttt     180

cacagctact ttcttcgccc tggcgatagt aagaagccga ttatttatga tgtcgaaacg     240

ctgcgtgacg gtaacagctt cagcgcccgc cgggttgctg ctattcaaaa cggcaaaccg     300

atttttata tgactgcctc tttccaggca ccagaagcgg gtttcgaaca tcaaaaaaca     360

atgccgtccg cgccagcgcc tgatggcctc ccttcggaaa cgcaaatcgc ccaatcgctg     420

gcgcacctgc tgccgccagt gctgaaagat aaattcatct gcgatcgtcc gctggaagtc     480

cgtccggtgg agtttcataa cccactgaaa ggtcacgtcg cagaaccaca tcgtcaggtg     540

tggatccgcg caaatggtag cgtgccggat gacctgcgcg ttcatcagta tctgctcggt     600

tacgcttctg atcttaactt cctgccggta gctctacagc cgcacggcat cggttttctc     660

gaaccgggga ttcagattgc caccattgac cattccatgt ggttccatcg cccgtttaat     720

ttgaatgaat ggctgctgta tagcgtggag agcacctcgg cgtccagcgc acgtggcttt     780

gtgcgcggtg agttttatac ccaagacggc gtactggttg cctcgaccgt tcaggaaggg     840

gtgatgcgta atcacaatta a                                               861


<210> SEQ ID NO 153
<211> LENGTH: 286
<212> TYPE: PRT
<213> ORGANISM: Escherichia coli

<400> SEQUENCE: 153

Met Ser Gln Ala Leu Lys Asn Leu Leu Thr Leu Leu Asn Leu Glu Lys
```

-continued

```
1               5                   10                  15

Ile Glu Glu Gly Leu Phe Arg Gly Gln Ser Glu Asp Leu Gly Leu Arg
            20                  25                  30

Gln Val Phe Gly Gly Gln Val Val Gly Gln Ala Leu Tyr Ala Ala Lys
        35                  40                  45

Glu Thr Val Pro Glu Glu Arg Leu Val His Ser Phe His Ser Tyr Phe
    50                  55                  60

Leu Arg Pro Gly Asp Ser Lys Lys Pro Ile Ile Tyr Asp Val Glu Thr
65                  70                  75                  80

Leu Arg Asp Gly Asn Ser Phe Ser Ala Arg Arg Val Ala Ala Ile Gln
            85                  90                  95

Asn Gly Lys Pro Ile Phe Tyr Met Thr Ala Ser Phe Gln Ala Pro Glu
            100                 105                 110

Ala Gly Phe Glu His Gln Lys Thr Met Pro Ser Ala Pro Ala Pro Asp
        115                 120                 125

Gly Leu Pro Ser Glu Thr Gln Ile Ala Gln Ser Leu Ala His Leu Leu
    130                 135                 140

Pro Pro Val Leu Lys Asp Lys Phe Ile Cys Asp Arg Pro Leu Glu Val
145                 150                 155                 160

Arg Pro Val Glu Phe His Asn Pro Leu Lys Gly His Val Ala Glu Pro
            165                 170                 175

His Arg Gln Val Trp Ile Arg Ala Asn Gly Ser Val Pro Asp Asp Leu
            180                 185                 190

Arg Val His Gln Tyr Leu Leu Gly Tyr Ala Ser Asp Leu Asn Phe Leu
        195                 200                 205

Pro Val Ala Leu Gln Pro His Gly Ile Gly Phe Leu Glu Pro Gly Ile
    210                 215                 220

Gln Ile Ala Thr Ile Asp His Ser Met Trp Phe His Arg Pro Phe Asn
225                 230                 235                 240

Leu Asn Glu Trp Leu Leu Tyr Ser Val Glu Ser Thr Ser Ala Ser Ser
            245                 250                 255

Ala Arg Gly Phe Val Arg Gly Glu Phe Tyr Thr Gln Asp Gly Val Leu
            260                 265                 270

Val Ala Ser Thr Val Gln Glu Gly Val Met Arg Asn His Asn
        275                 280                 285
```

<210> SEQ ID NO 154
<211> LENGTH: 912
<212> TYPE: DNA
<213> ORGANISM: Acinetobacter sp. ADP1

<400> SEQUENCE: 154

```
ttgatatcaa tcagggaaaa acgcgtgaac aaaaaacttg aagctctctt ccgagagaat     60

gtaaaaggta aagtggcttt gatcactggt gcatctagtg gaatcggttt gacgattgca    120

aaaagaattg ctgcggcagg tgctcatgta ttattggttg cccgaaccca agaaacactg    180

gaagaagtga aagctgcaat tgaacagcaa gggggacagg cctctatttt tccttgtgac    240

ctgactgaca tgaatgcgat tgaccagtta tcacaacaaa ttatggccag tgtcgatcat    300

gtcgatttcc tgatcaataa tgcagggcgt tcgattcgcc gtgccgtaca cgagtcgttt    360

gatcgcttcc atgattttga acgcaccatg cagctgaatt actttggtgc ggtacgttta    420

gtgttaaatt tactgccaca tatgattaag cgtaaaaatg gccagatcat caatatcagc    480

tctattggtg tattggccaa tgcgacccgt ttttctgctt atgtcgcgtc taaagctgcg    540
```

-continued

```
ctggatgcct tcagtcgctg tctttcagcc gaggtactca agcataaaat ctcaattacc    600

tcgatttata tgccattggt gcgtacccca atgatcgcac ccaccaaaat ttataaatac    660

gtgcccacgc tttccccaga agaagccgca gatctcattg tctacgccat tgtgaaacgt    720

ccaaaacgta ttgcgacgca cttgggtcgt ctggcgtcaa ttacctatgc catcgcacca    780

gacatcaata atattctgat gtcgattgga tttaacctat tcccaagctc aacggctgca    840

ctgggtgaac aggaaaaatt gaatctgcta caacgtgcct atgcccgctt gttcccaggc    900

gaacactggt aa                                                        912
```

```
<210> SEQ ID NO 155
<211> LENGTH: 303
<212> TYPE: PRT
<213> ORGANISM: Acinetobacter sp. ADP1

<400> SEQUENCE: 155

Met Ile Ser Ile Arg Glu Lys Arg Val Asn Lys Lys Leu Glu Ala Leu
1               5                   10                  15

Phe Arg Glu Asn Val Lys Gly Lys Val Ala Leu Ile Thr Gly Ala Ser
            20                  25                  30

Ser Gly Ile Gly Leu Thr Ile Ala Lys Arg Ile Ala Ala Ala Gly Ala
        35                  40                  45

His Val Leu Leu Val Ala Arg Thr Gln Glu Thr Leu Glu Glu Val Lys
    50                  55                  60

Ala Ala Ile Glu Gln Gln Gly Gly Gln Ala Ser Ile Phe Pro Cys Asp
65                  70                  75                  80

Leu Thr Asp Met Asn Ala Ile Asp Gln Leu Ser Gln Gln Ile Met Ala
                85                  90                  95

Ser Val Asp His Val Asp Phe Leu Ile Asn Asn Ala Gly Arg Ser Ile
            100                 105                 110

Arg Arg Ala Val His Glu Ser Phe Asp Arg Phe His Asp Phe Glu Arg
        115                 120                 125

Thr Met Gln Leu Asn Tyr Phe Gly Ala Val Arg Leu Val Leu Asn Leu
    130                 135                 140

Leu Pro His Met Ile Lys Arg Lys Asn Gly Gln Ile Ile Asn Ile Ser
145                 150                 155                 160

Ser Ile Gly Val Leu Ala Asn Ala Thr Arg Phe Ser Ala Tyr Val Ala
                165                 170                 175

Ser Lys Ala Ala Leu Asp Ala Phe Ser Arg Cys Leu Ser Ala Glu Val
            180                 185                 190

Leu Lys His Lys Ile Ser Ile Thr Ser Ile Tyr Met Pro Leu Val Arg
        195                 200                 205

Thr Pro Met Ile Ala Pro Thr Lys Ile Tyr Lys Tyr Val Pro Thr Leu
    210                 215                 220

Ser Pro Glu Glu Ala Ala Asp Leu Ile Val Tyr Ala Ile Val Lys Arg
225                 230                 235                 240

Pro Lys Arg Ile Ala Thr His Leu Gly Arg Leu Ala Ser Ile Thr Tyr
                245                 250                 255

Ala Ile Ala Pro Asp Ile Asn Asn Ile Leu Met Ser Ile Gly Phe Asn
            260                 265                 270

Leu Phe Pro Ser Ser Thr Ala Ala Leu Gly Glu Gln Glu Lys Leu Asn
        275                 280                 285

Leu Leu Gln Arg Ala Tyr Ala Arg Leu Phe Pro Gly Glu His Trp
    290                 295                 300
```

```
<210> SEQ ID NO 156
<211> LENGTH: 296
<212> TYPE: PRT
<213> ORGANISM: Clostridium acetobutylicum

<400> SEQUENCE: 156

Met Ile Lys Ser Phe Asn Glu Ile Ile Met Lys Val Lys Ser Lys Glu
1               5                   10                  15

Met Lys Lys Val Ala Val Ala Val Ala Gln Asp Glu Pro Val Leu Glu
            20                  25                  30

Ala Val Arg Asp Ala Lys Lys Asn Gly Ile Ala Asp Ala Ile Leu Val
        35                  40                  45

Gly Asp His Asp Glu Ile Val Ser Ile Ala Leu Lys Ile Gly Met Asp
    50                  55                  60

Val Asn Asp Phe Glu Ile Val Asn Glu Pro Asn Val Lys Lys Ala Ala
65                  70                  75                  80

Leu Lys Ala Val Glu Leu Val Ser Thr Gly Lys Ala Asp Ile Leu Met
                85                  90                  95

Asn Gly Leu Val Asn Thr Ala Thr Phe Leu Lys Ile Cys Ile Leu Asn
            100                 105                 110

Lys Glu Val Gly Leu Arg Thr Gly Lys Thr Met Ser His Val Ala Val
        115                 120                 125

Phe Glu Thr Glu Thr Ser Asp Arg Leu Ser Phe Leu Thr Asp Val Ala
    130                 135                 140

Phe Asn Thr Tyr Pro Glu Leu Lys Glu Lys Ile Asp Ile Val Asn Asn
145                 150                 155                 160

Ser Val Lys Val Ala His Ala Ile Gly Ile Val Asn Pro Lys Val Ala
                165                 170                 175

Pro Ile Cys Ala Val Glu Val Ile Asn Pro Lys Met Pro Ser Thr Leu
            180                 185                 190

Asp Ala Ala Met Leu Ser Lys Met Ser Asp Arg Gly Gln Ile Lys Gly
        195                 200                 205

Cys Val Val Asp Gly Pro Leu Ala Leu Asp Ile Ala Leu Ser Glu Glu
    210                 215                 220

Ala Ala His His Lys Gly Val Thr Gly Glu Val Ala Gly Lys Ala Asp
225                 230                 235                 240

Ile Phe Leu Met Pro Asn Ile Glu Thr Gly Asn Val Met Tyr Lys Thr
                245                 250                 255

Leu Thr Tyr Thr Thr Asp Ser Lys Asn Gly Gly Ile Leu Val Gly Thr
            260                 265                 270

Ser Ala Pro Val Val Leu Thr Ser Arg Ala Asp Ser His Glu Thr Lys
        275                 280                 285

Met Asn Ser Ile Ala Leu Ala Ala
    290                 295


<210> SEQ ID NO 157
<211> LENGTH: 355
<212> TYPE: PRT
<213> ORGANISM: Clostridium acetobutylicum

<400> SEQUENCE: 157

Met Ser Tyr Lys Leu Leu Ile Ile Asn Pro Gly Ser Thr Ser Thr Lys
1               5                   10                  15

Ile Gly Val Tyr Glu Gly Glu Lys Glu Leu Phe Glu Glu Thr Leu Arg
            20                  25                  30
```

```
His Thr Asn Glu Glu Ile Lys Arg Tyr Asp Thr Ile Tyr Asp Gln Phe
        35                  40                  45

Glu Phe Arg Lys Glu Val Ile Leu Asn Val Leu Lys Glu Lys Asn Phe
    50                  55                  60

Asp Ile Lys Thr Leu Ser Ala Ile Val Gly Arg Gly Gly Met Leu Arg
65                  70                  75                  80

Pro Val Glu Gly Gly Thr Tyr Ala Val Asn Asp Ala Met Val Glu Asp
                85                  90                  95

Leu Lys Val Gly Val Gln Gly Pro His Ala Ser Asn Leu Gly Gly Ile
            100                 105                 110

Ile Ala Lys Ser Ile Gly Asp Glu Leu Asn Ile Pro Ser Phe Ile Val
        115                 120                 125

Asp Pro Val Val Thr Asp Glu Leu Ala Asp Val Ala Arg Leu Ser Gly
    130                 135                 140

Val Pro Glu Leu Pro Arg Lys Ser Lys Phe His Ala Leu Asn Gln Lys
145                 150                 155                 160

Ala Val Ala Lys Arg Tyr Gly Lys Glu Ser Gly Gln Gly Tyr Glu Asn
                165                 170                 175

Leu Asn Leu Val Val Val His Met Gly Gly Gly Val Ser Val Gly Ala
            180                 185                 190

His Asn His Gly Lys Val Val Asp Val Asn Asn Ala Leu Asp Gly Asp
        195                 200                 205

Gly Pro Phe Ser Pro Glu Arg Ala Gly Ser Val Pro Ile Gly Asp Leu
    210                 215                 220

Val Lys Met Cys Phe Ser Gly Lys Tyr Ser Glu Ala Glu Val Tyr Gly
225                 230                 235                 240

Lys Ala Val Gly Lys Gly Gly Phe Val Gly Tyr Leu Asn Thr Asn Asp
                245                 250                 255

Val Lys Gly Val Ile Asp Lys Met Glu Glu Gly Asp Lys Glu Cys Glu
            260                 265                 270

Ser Ile Tyr Lys Ala Phe Val Tyr Gln Ile Ser Lys Ala Ile Gly Glu
        275                 280                 285

Met Ser Val Val Leu Glu Gly Lys Val Asp Gln Ile Ile Phe Thr Gly
    290                 295                 300

Gly Ile Ala Tyr Ser Pro Thr Leu Val Pro Asp Leu Lys Ala Lys Val
305                 310                 315                 320

Glu Trp Ile Ala Pro Val Thr Val Tyr Pro Gly Glu Asp Glu Leu Leu
                325                 330                 335

Ala Leu Ala Gln Gly Ala Ile Arg Val Leu Asp Gly Glu Glu Gln Ala
            340                 345                 350

Lys Val Tyr
        355
```

<210> SEQ ID NO 158
<211> LENGTH: 70
<212> TYPE: DNA
<213> ORGANISM: Artificial sequence
<220> FEATURE:
<223> OTHER INFORMATION: Synthetic primer

<400> SEQUENCE: 158
aaaaacagca acaatgtgag ctttgttgta attatattgt aaacatattg attccgggga     60
tccgtcgacc                                                            70

<210> SEQ ID NO 159

-continued

<211> LENGTH: 68
<212> TYPE: DNA
<213> ORGANISM: Artificial sequence
<220> FEATURE:
<223> OTHER INFORMATION: Synthetic primer

<400> SEQUENCE: 159
aaacggagcc tttcggctcc gttattcatt tacgcggctt caactttcct gtaggctgga 60
gctgcttc 68

<210> SEQ ID NO 160
<211> LENGTH: 23
<212> TYPE: DNA
<213> ORGANISM: Artificial sequence
<220> FEATURE:
<223> OTHER INFORMATION: Synthetic primer

<400> SEQUENCE: 160
cgggcaggtg ctatgaccag gac 23

<210> SEQ ID NO 161
<211> LENGTH: 23
<212> TYPE: DNA
<213> ORGANISM: Artificial sequence
<220> FEATURE:
<223> OTHER INFORMATION: Synthetic primer

<400> SEQUENCE: 161
cgcggcgttg accggcagcc tgg 23

<210> SEQ ID NO 162
<211> LENGTH: 70
<212> TYPE: DNA
<213> ORGANISM: Artificial sequence
<220> FEATURE:
<223> OTHER INFORMATION: Synthetic primer

<400> SEQUENCE: 162
atcattctcg tttacgttat cattcacttt acatcagaga tataccaatg attccgggga 60
tccgtcgacc 70

<210> SEQ ID NO 163
<211> LENGTH: 69
<212> TYPE: DNA
<213> ORGANISM: Artificial sequence
<220> FEATURE:
<223> OTHER INFORMATION: Synthetic primer

<400> SEQUENCE: 163
gcacggaaat ccgtgcccca aaagagaaat tagaaacgga aggttgcggt tgtaggctgg 60
agctgcttc 69

<210> SEQ ID NO 164
<211> LENGTH: 21
<212> TYPE: DNA
<213> ORGANISM: Artificial sequence
<220> FEATURE:
<223> OTHER INFORMATION: Synthetic primer

<400> SEQUENCE: 164
caacagcaac ctgctcagca a 21

<210> SEQ ID NO 165
<211> LENGTH: 21

<212> TYPE: DNA
<213> ORGANISM: Artificial sequence
<220> FEATURE:
<223> OTHER INFORMATION: Synthetic primer

<400> SEQUENCE: 165
aagctggagc agcaaagcgt t 21

<210> SEQ ID NO 166
<211> LENGTH: 32
<212> TYPE: DNA
<213> ORGANISM: Artificial sequence
<220> FEATURE:
<223> OTHER INFORMATION: Synthetic primer

<400> SEQUENCE: 166
ataaaccatg gatccatgaa cgagtacgcc cc 32

<210> SEQ ID NO 167
<211> LENGTH: 33
<212> TYPE: DNA
<213> ORGANISM: Artificial sequence
<220> FEATURE:
<223> OTHER INFORMATION: Synthetic primer

<400> SEQUENCE: 167
ccaagcttcg aattctcaga tatgcaaggc gtg 33

<210> SEQ ID NO 168
<211> LENGTH: 36
<212> TYPE: DNA
<213> ORGANISM: Artificial sequence
<220> FEATURE:
<223> OTHER INFORMATION: Synthetic primer

<400> SEQUENCE: 168
tgaattccat ggcgcaactc actcttcttt tagtcg 36

<210> SEQ ID NO 169
<211> LENGTH: 39
<212> TYPE: DNA
<213> ORGANISM: Artificial sequence
<220> FEATURE:
<223> OTHER INFORMATION: Synthetic primer

<400> SEQUENCE: 169
cagtacctcg agtcttcgta tacatatgcg ctcagtcac 39

<210> SEQ ID NO 170
<211> LENGTH: 21
<212> TYPE: DNA
<213> ORGANISM: Artificial sequence
<220> FEATURE:
<223> OTHER INFORMATION: Synthetic primer

<400> SEQUENCE: 170
ccttggggca tatgaaagct g 21

<210> SEQ ID NO 171
<211> LENGTH: 29
<212> TYPE: DNA
<213> ORGANISM: Artificial sequence
<220> FEATURE:
<223> OTHER INFORMATION: Synthetic primer

<400> SEQUENCE: 171
tttagtcatc tcgagtgcac ctcaccttt 29

<210> SEQ ID NO 172
<211> LENGTH: 70
<212> TYPE: DNA
<213> ORGANISM: Artificial sequence
<220> FEATURE:
<223> OTHER INFORMATION: Synthetic primer

<400> SEQUENCE: 172
gccacattgc cgcgccaaac gaaaccgttt caaccatggc atatgaatat cctccttagt 60
tcctattccg 70

<210> SEQ ID NO 173
<211> LENGTH: 61
<212> TYPE: DNA
<213> ORGANISM: Artificial sequence
<220> FEATURE:
<223> OTHER INFORMATION: Synthetic primer

<400> SEQUENCE: 173
cgccccagat ttcacgtatt gatcggctac gcttaatgca tgtgtaggct ggagctgctt 60
c 61

<210> SEQ ID NO 174
<211> LENGTH: 20
<212> TYPE: DNA
<213> ORGANISM: Artificial sequence
<220> FEATURE:
<223> OTHER INFORMATION: Synthetic primer

<400> SEQUENCE: 174
ttgacacgtc taaccctggc 20

<210> SEQ ID NO 175
<211> LENGTH: 21
<212> TYPE: DNA
<213> ORGANISM: Artificial sequence
<220> FEATURE:
<223> OTHER INFORMATION: Synthetic primer

<400> SEQUENCE: 175
ctgtccaggg aacacaaatg c 21

<210> SEQ ID NO 176
<211> LENGTH: 19
<212> TYPE: DNA
<213> ORGANISM: Artificial sequence
<220> FEATURE:
<223> OTHER INFORMATION: Synthetic primer

<400> SEQUENCE: 176
ttgtgtcgcc ctttcgctg 19

<210> SEQ ID NO 177
<211> LENGTH: 24
<212> TYPE: DNA
<213> ORGANISM: Artificial sequence
<220> FEATURE:
<223> OTHER INFORMATION: Synthetic primer

<400> SEQUENCE: 177
cttacgtacg tactcgagtg acgc 24

-continued

```
<210> SEQ ID NO 178
<211> LENGTH: 23
<212> TYPE: DNA
<213> ORGANISM: Artificial sequence
<220> FEATURE:
<223> OTHER INFORMATION: Synthetic primer

<400> SEQUENCE: 178

aagtggggca tatgtctaag atc                                          23


<210> SEQ ID NO 179
<211> LENGTH: 23
<212> TYPE: DNA
<213> ORGANISM: Artificial sequence
<220> FEATURE:
<223> OTHER INFORMATION: Synthetic primer

<400> SEQUENCE: 179

gtgatccggc tcgaggtggt tac                                          23


<210> SEQ ID NO 180
<211> LENGTH: 24
<212> TYPE: DNA
<213> ORGANISM: Artificial sequence
<220> FEATURE:
<223> OTHER INFORMATION: Synthetic primer

<400> SEQUENCE: 180

cttaacttca tgtgaaaagt ttgt                                         24


<210> SEQ ID NO 181
<211> LENGTH: 24
<212> TYPE: DNA
<213> ORGANISM: Artificial sequence
<220> FEATURE:
<223> OTHER INFORMATION: Synthetic primer

<400> SEQUENCE: 181

acaataccca tgtttatagg gcaa                                         24
```